US012448399B2

(12) United States Patent
Medina et al.

(10) Patent No.: US 12,448,399 B2
(45) Date of Patent: Oct. 21, 2025

(54) CEREBLON-BASED KRAS DEGRADING PROTACS AND USES RELATED THERETO

(71) Applicant: Arvinas Operations, Inc., New Haven, CT (US)

(72) Inventors: Jesus Raul Medina, Gilbertsville, PA (US); Hanqing Dong, Madison, CT (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

(21) Appl. No.: 18/424,488

(22) Filed: Jan. 26, 2024

(65) Prior Publication Data

US 2024/0287101 A1 Aug. 29, 2024

Related U.S. Application Data

(60) Provisional application No. 63/592,814, filed on Oct. 24, 2023, provisional application No. 63/486,528, filed on Feb. 23, 2023, provisional application No. 63/481,672, filed on Jan. 26, 2023.

(51) Int. Cl.

| | |
|---|---|
| ***C07D 519/00*** | (2006.01) |
| ***A61K 31/519*** | (2006.01) |
| ***A61K 31/55*** | (2006.01) |
| ***A61P 35/00*** | (2006.01) |

(52) U.S. Cl.

CPC .......... *C07D 519/00* (2013.01); *A61K 31/519* (2013.01); *A61K 31/55* (2013.01); *A61P 35/00* (2018.01)

(58) Field of Classification Search

CPC .... C07D 519/00; A61K 31/519; A61K 31/55; A61P 35/00

See application file for complete search history.

(56) References Cited

U.S. PATENT DOCUMENTS

| | | | |
|---|---|---|---|
| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Deshaies et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh et al. |
| 9,500,653 | B2 | 11/2016 | Crews et al. |
| 9,632,089 | B2 | 4/2017 | Crews et al. |
| 10,093,631 | B2 | 10/2018 | Warrell, Jr. et al. |
| 10,646,488 | B2 | 5/2020 | Liu et al. |
| 10,857,140 | B2 | 12/2020 | McCormick et al. |
| 10,994,015 | B2 | 5/2021 | Crew et al. |
| 11,052,154 | B2 | 7/2021 | Miyamoto et al. |
| 11,065,231 | B2 | 7/2021 | Crew et al. |
| 11,161,841 | B2 | 11/2021 | Crew et al. |
| 11,236,068 | B2 | 2/2022 | Malhotra et al. |
| 11,242,344 | B2 | 2/2022 | Blaquiere et al. |
| 11,274,093 | B2 | 3/2022 | Li et al. |
| 11,279,689 | B2 | 3/2022 | Li et al. |
| 11,358,959 | B2 | 6/2022 | Li et al. |
| 11,458,123 | B2 | 10/2022 | Crew et al. |
| 11,707,452 | B2 | 7/2023 | Crew et al. |
| 11,912,699 | B2 | 2/2024 | Crew et al. |
| 12,036,209 | B2 | 7/2024 | Crew et al. |
| 12,053,469 | B2 | 8/2024 | Araujo et al. |
| 2006/0128632 | A1 | 6/2006 | Sharma et al. |
| 2008/0051432 | A1 | 2/2008 | Zhang |
| 2008/0214501 | A1 | 9/2008 | Pan et al. |
| 2008/0269140 | A1 | 10/2008 | Wang et al. |
| 2009/0298843 | A1 | 12/2009 | Kloog et al. |
| 2010/0056555 | A1 | 3/2010 | Horak et al. |
| 2010/0203012 | A1 | 8/2010 | Laurent et al. |
| 2011/0195043 | A1 | 8/2011 | Sun et al. |
| 2012/0270800 | A1 | 10/2012 | Verdine et al. |
| 2014/0235629 | A1 | 8/2014 | Bartberger et al. |
| 2014/0243372 | A1 | 8/2014 | Rew |
| 2014/0302523 | A1 | 10/2014 | Crews et al. |
| 2014/0356322 | A1 | 12/2014 | Crews et al. |
| 2015/0239900 | A1 | 8/2015 | Li et al. |
| 2015/0291562 | A1 | 10/2015 | Crew et al. |
| 2015/0344473 | A1 | 12/2015 | Du et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0136230 | A1 | 5/2016 | Campos et al. |
| 2016/0214972 | A1 | 7/2016 | Jin et al. |
| 2016/0243247 | A1 | 8/2016 | Bradner et al. |
| 2016/0264627 | A1 | 9/2016 | Henning et al. |
| 2016/0272639 | A1 | 9/2016 | Crew et al. |
| 2016/0368911 | A1 | 12/2016 | Campos et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0307614 | A1 | 10/2017 | Crews et al. |
| 2017/0327469 | A1 | 11/2017 | Crew et al. |
| 2018/0015087 | A1 | 1/2018 | Liu et al. |
| 2018/0072711 | A1 | 3/2018 | Crew et al. |

(Continued)

FOREIGN PATENT DOCUMENTS

| | | | |
|---|---|---|---|
| AU | 2019377130 | A1 | 7/2020 |
| AU | 20191377130 | A1 | 7/2020 |

(Continued)

OTHER PUBLICATIONS

Hyun, S., "Small-molecule inhibitors and degraders tareting KRAS-driven cancers." International Journal of Molecular Sciences 22.22 (2021): 12142.*

(Continued)

*Primary Examiner* — John S Kenyon
*Assistant Examiner* — Sara Elizabeth Bell
(74) *Attorney, Agent, or Firm* — Hoxie & Associates LLC

(57) ABSTRACT

Provided herein are compounds that target KRas and are thus useful in the treatment of cancer.

66 Claims, 9 Drawing Sheets

(56) References Cited

U.S. PATENT DOCUMENTS

| | | | |
|---|---|---|---|
| 2018/0099940 | A1 | 4/2018 | Crew et al. |
| 2018/0125821 | A1 | 5/2018 | Crew et al. |
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |
| 2018/0319775 | A1 | 11/2018 | Li et al. |
| 2018/0334454 | A1 | 11/2018 | Lanman et al. |
| 2018/0353501 | A1 | 12/2018 | Crew et al. |
| 2019/0315732 | A1 | 10/2019 | Crew et al. |
| 2021/0220475 | A1 | 7/2021 | Crew et al. |
| 2021/0238193 | A1 | 8/2021 | Mainolfi et al. |
| 2021/0315896 | A1 | 10/2021 | Araujo et al. |
| 2022/0064696 | A1 | 3/2022 | Robers et al. |
| 2022/0112192 | A1 | 4/2022 | Li et al. |
| 2022/0112204 | A1 | 4/2022 | Fan et al. |
| 2022/0177531 | A1 | 6/2022 | Koide et al. |
| 2022/0213101 | A1 | 7/2022 | Lanman et al. |
| 2022/0370416 | A1 | 11/2022 | Chu et al. |
| 2022/0402907 | A1 | 12/2022 | Crew et al. |
| 2023/0002371 | A1 | 1/2023 | Chan et al. |
| 2023/0086457 | A1 | 3/2023 | Berlin et al. |
| 2023/0097358 | A1 | 3/2023 | Araujo et al. |
| 2023/0099344 | A1 | 3/2023 | Araujo et al. |
| 2023/0321253 | A1 | 10/2023 | Lv et al. |
| 2024/0043448 | A1 | 2/2024 | Bharathan et al. |
| 2024/0059712 | A1 | 2/2024 | Lv et al. |
| 2024/0059713 | A1 | 2/2024 | LV et al. |
| 2024/0067647 | A1 | 2/2024 | Chaves et al. |
| 2024/0083913 | A1 | 3/2024 | Bharathan et al. |
| 2024/0091204 | A1 | 3/2024 | Crew et al. |
| 2024/0217962 | A1 | 7/2024 | Crew et al. |
| 2024/0287068 | A1 | 8/2024 | Lanman et al. |
| 2024/0287101 | A1 | 8/2024 | Medina |
| 2024/0294527 | A1 | 9/2024 | Luo et al. |
| 2024/0360152 | A1 | 10/2024 | Araujo et al. |
| 2024/0376127 | A1 | 11/2024 | Wang et al. |
| 2024/0382599 | A1 | 11/2024 | Crew et al. |

FOREIGN PATENT DOCUMENTS

| | | | |
|---|---|---|---|
| CN | 1844118 | | 10/2006 |
| CN | 110885332 | A | 3/2007 |
| CN | 103688176 | A | 3/2014 |
| CN | 110291087 | A | 9/2019 |
| CN | 110612297 | A | 12/2019 |
| CN | 110741004 | A | 1/2020 |
| CN | 115785199 | A | 3/2023 |
| CN | 1155785199 | A | 3/2023 |
| CN | 116375742 | A | 7/2023 |
| CN | 116731206 | A | 9/2023 |
| CN | 116768858 | A | 9/2023 |
| CN | 116891514 | A | 10/2023 |
| CN | 117285590 | A | 12/2023 |
| CN | 117917416 | A | 4/2024 |
| CN | 118496300 | A | 8/2024 |
| CN | 118666870 | A | 9/2024 |
| CN | 118725012 | A | 10/2024 |
| CN | 118772176 | A | 10/2024 |
| CN | 118791505 | A | 10/2024 |
| CN | 118846070 | A | 10/2024 |
| EP | 2985285 | A1 | 2/2016 |
| EP | 3980046 | A1 | 4/2022 |
| JP | 2004525889 | A | 8/2004 |
| JP | 2010-502627 | A | 1/2010 |
| JP | 2016-532656 | A | 10/2016 |
| JP | 2018-533611 | A | 11/2018 |
| JP | 2020-504741 | A | 2/2020 |
| JP | 2022505835 | A | 1/2022 |
| JP | 2022509830 | A | 1/2022 |
| JP | 2022512742 | A | 2/2022 |
| JP | 2022513360 | A | 2/2022 |
| JP | 7061800 | B2 | 5/2022 |
| KR | 20240159370 | A | 11/2024 |
| RU | 2008112221 | | 10/2009 |
| RU | 2448101 | C2 | 4/2012 |
| RU | 2011121567 | | 10/2012 |
| RU | 2012138709 | | 3/2014 |
| TW | 202124374 | A | 7/2021 |
| TW | 202206423 | A | 2/2022 |
| TW | 202210465 | A | 3/2022 |
| WO | 1998003502 | | 1/1998 |
| WO | 2000066119 | | 11/2000 |
| WO | 2002066512 | | 8/2002 |
| WO | 2002100845 | | 12/2002 |
| WO | 2005097791 | | 10/2005 |
| WO | 2006069063 | | 6/2006 |
| WO | 2006113942 | | 10/2006 |
| WO | 2007101347 | | 9/2007 |
| WO | 2007106670 | | 9/2007 |
| WO | 2007115289 | | 10/2007 |
| WO | 2007130626 | | 11/2007 |
| WO | 2008011392 | | 1/2008 |
| WO | 2008014236 | | 1/2008 |
| WO | 2008109057 | | 9/2008 |
| WO | 2008128121 | | 10/2008 |
| WO | 2008128171 | | 10/2008 |
| WO | 2008134679 | | 11/2008 |
| WO | 2009006567 | | 1/2009 |
| WO | 2009015254 | | 1/2009 |
| WO | 2009060292 | | 5/2009 |
| WO | 2010107485 | | 9/2010 |
| WO | 2010141805 | | 12/2010 |
| WO | 2011008260 | | 1/2011 |
| WO | 2012003281 | | 1/2012 |
| WO | 2012007409 | | 1/2012 |
| WO | 2012040527 | | 3/2012 |
| WO | 2012061683 | A2 | 5/2012 |
| WO | 2012078559 | | 6/2012 |
| WO | 2012090104 | | 7/2012 |
| WO | 2013071035 | | 5/2013 |
| WO | 2013071039 | | 5/2013 |
| WO | 2013106643 | A2 | 7/2013 |
| WO | 2013106646 | | 7/2013 |
| WO | 2013170147 | | 11/2013 |
| WO | 2013175417 | | 11/2013 |
| WO | 2013178570 | | 12/2013 |
| WO | 2014011712 | | 1/2014 |
| WO | 2014020502 | | 2/2014 |
| WO | 2014025759 | | 2/2014 |
| WO | 2014038606 | | 3/2014 |
| WO | 2014047024 | | 3/2014 |
| WO | 2014055461 | | 4/2014 |
| WO | 2014074658 | | 5/2014 |
| WO | 2014100065 | | 6/2014 |
| WO | 2014100071 | | 6/2014 |
| WO | 2014107713 | | 7/2014 |
| WO | 2014108452 | | 7/2014 |
| WO | 2014123418 | | 8/2014 |
| WO | 2014134201 | | 9/2014 |
| WO | 2014151863 | | 9/2014 |
| WO | 2015000868 | | 1/2015 |
| WO | 2015006524 | | 1/2015 |
| WO | 2015054572 | A1 | 4/2015 |
| WO | 2015097621 | | 7/2015 |
| WO | 2015160845 | | 10/2015 |
| WO | 2016105518 | | 6/2016 |
| WO | 2016118666 | | 7/2016 |
| WO | 2016146985 | | 9/2016 |
| WO | 2016169989 | | 10/2016 |
| WO | 2016172134 | | 10/2016 |
| WO | 2016197114 | | 12/2016 |
| WO | 2017011590 | | 1/2017 |
| WO | 2017024318 | A1 | 2/2017 |
| WO | 2017024319 | A1 | 2/2017 |
| WO | 2017030814 | A1 | 2/2017 |
| WO | 2017046036 | | 3/2017 |
| WO | 2017058807 | | 4/2017 |
| WO | 2017079267 | | 5/2017 |

(56) References Cited

FOREIGN PATENT DOCUMENTS

| | | | |
|---|---|---|---|
| WO | 2017161119 | | 9/2017 |
| WO | 2017172979 | | 10/2017 |
| WO | 2017185036 | | 10/2017 |
| WO | 2017197051 | | 11/2017 |
| WO | 2017201161 | A1 | 11/2017 |
| WO | 2017223452 | A1 | 12/2017 |
| WO | 2018102725 | A1 | 6/2018 |
| WO | 2018119448 | A1 | 6/2018 |
| WO | WO 2018/102067 | A2 | 6/2018 |
| WO | WO 2018/119441 | A1 | 6/2018 |
| WO | 2018140809 | A1 | 8/2018 |
| WO | 2018148440 | | 8/2018 |
| WO | 2018218070 | | 11/2018 |
| WO | 2018218071 | | 11/2018 |
| WO | 2019195201 | | 10/2019 |
| WO | 2019195609 | A2 | 10/2019 |
| WO | WO 2020/118066 | A1 | 6/2020 |
| WO | WO 2020/173935 | A1 | 9/2020 |
| WO | WO 2021/041671 | A1 | 3/2021 |
| WO | WO 2021/051034 | A1 | 3/2021 |
| WO | WO 2021/081212 | A1 | 4/2021 |
| WO | WO 2021/107160 | A1 | 6/2021 |
| WO | WO 2021/108683 | A1 | 6/2021 |
| WO | WO 2021/119343 | A1 | 6/2021 |
| WO | WO 2021/194879 | A1 | 9/2021 |
| WO | 2021207172 | A1 | 10/2021 |
| WO | WO 2022/015375 | A1 | 1/2022 |
| WO | WO 2022/047260 | A1 | 3/2022 |
| WO | WO 2022/060836 | A1 | 3/2022 |
| WO | WO 2022/066646 | A1 | 3/2022 |
| WO | WO 2022/076917 | A1 | 4/2022 |
| WO | WO 2022/078414 | A1 | 4/2022 |
| WO | WO 2022/081655 | A1 | 4/2022 |
| WO | WO 2022/081928 | A1 | 4/2022 |
| WO | WO 2022/087335 | A1 | 4/2022 |
| WO | WO 2022/098625 | A1 | 5/2022 |
| WO | WO 2022/105855 | A1 | 5/2022 |
| WO | WO 2022/105857 | A1 | 5/2022 |
| WO | WO 2022/105859 | A1 | 5/2022 |
| WO | WO 2022/111513 | A1 | 6/2022 |
| WO | WO 2022/111521 | A1 | 6/2022 |
| WO | WO 2022/132200 | A1 | 6/2022 |
| WO | WO 2022/133038 | A1 | 6/2022 |
| WO | WO 2022/148421 | A1 | 7/2022 |
| WO | WO 2022/148422 | A1 | 7/2022 |
| WO | WO 2022/150628 | A1 | 7/2022 |
| WO | WO 2022/156761 | A1 | 7/2022 |
| WO | WO 2022/173032 | A1 | 8/2022 |
| WO | WO 2022/173678 | A1 | 8/2022 |
| WO | WO 2022/173870 | A1 | 8/2022 |
| WO | WO 2022/184178 | A1 | 9/2022 |
| WO | WO 2022/187688 | A1 | 9/2022 |
| WO | WO 2022/192790 | A1 | 9/2022 |
| WO | WO 2022/192794 | A1 | 9/2022 |
| WO | WO 2022/198112 | A1 | 9/2022 |
| WO | WO 2022/212611 | A1 | 10/2022 |
| WO | WO 2022/216762 | A1 | 10/2022 |
| WO | WO 2022/221739 | A1 | 10/2022 |
| WO | 2022/228568 | A1 | 11/2022 |
| WO | WO 2022/228576 | A1 | 11/2022 |
| WO | WO 2022/232318 | A1 | 11/2022 |
| WO | WO 2022/232320 | A1 | 11/2022 |
| WO | WO 2022/232331 | A1 | 11/2022 |
| WO | WO 2022/232332 | A1 | 11/2022 |
| WO | WO 2022/251296 | A1 | 12/2022 |
| WO | WO 2022/251576 | A1 | 12/2022 |
| WO | WO 2022/251588 | A1 | 12/2022 |
| WO | WO 2022/256459 | A1 | 12/2022 |
| WO | WO 2022/260482 | A1 | 12/2022 |
| WO | WO 2022/261210 | A1 | 12/2022 |
| WO | WO 2022/262686 | A1 | 12/2022 |
| WO | WO 2022/262838 | A1 | 12/2022 |
| WO | WO 2022/266206 | A1 | 12/2022 |
| WO | WO 2022/266248 | A1 | 12/2022 |
| WO | WO 2022/266249 | A1 | 12/2022 |
| WO | WO 2022/269008 | A1 | 12/2022 |
| WO | WO 2022/269508 | A1 | 12/2022 |
| WO | WO 2022/269525 | A1 | 12/2022 |
| WO | WO 2022/271823 | A1 | 12/2022 |
| WO | WO 2023/278600 | A1 | 1/2023 |
| WO | WO 2023/280026 | A1 | 1/2023 |
| WO | WO 2023/280237 | A1 | 1/2023 |
| WO | WO 2023/284537 | A1 | 1/2023 |
| WO | WO 2023/284881 | A1 | 1/2023 |
| WO | WO 2023/014006 | A1 | 2/2023 |
| WO | WO 2023/018809 | A1 | 2/2023 |
| WO | WO 2023/018810 | A1 | 2/2023 |
| WO | WO 2023/018812 | A1 | 2/2023 |
| WO | WO 2023/020347 | A1 | 2/2023 |
| WO | WO 2023/020521 | A1 | 2/2023 |
| WO | WO 2023/025832 | A1 | 3/2023 |
| WO | WO 2023/046135 | A1 | 3/2023 |
| WO | 2023/061463 | A1 | 4/2023 |
| WO | WO 2023/077441 | A1 | 5/2023 |
| WO | WO 2023/081476 | A1 | 5/2023 |
| WO | WO 2023/097194 | A2 | 6/2023 |
| WO | WO 2023/097227 | A1 | 6/2023 |
| WO | WO 2023/098832 | A1 | 6/2023 |
| WO | WO 2023/099592 | A1 | 6/2023 |
| WO | WO 2023/099608 | A1 | 6/2023 |
| WO | WO 2023/099620 | A1 | 6/2023 |
| WO | WO 2023/099623 | A1 | 6/2023 |
| WO | WO 2023/099624 | A1 | 6/2023 |
| WO | WO 2023/114733 | A1 | 6/2023 |
| WO | WO 2023/116934 | A1 | 6/2023 |
| WO | WO 2023/130012 | A1 | 7/2023 |
| WO | WO 2023/138524 | A1 | 7/2023 |
| WO | WO 2023/141570 | A2 | 7/2023 |
| WO | WO 2023/150706 | A1 | 8/2023 |
| WO | WO 2023/152255 | A1 | 8/2023 |
| WO | WO 2023/154766 | A1 | 8/2023 |
| WO | WO 2023/159086 | A1 | 8/2023 |
| WO | WO 2023/159087 | A1 | 8/2023 |
| WO | WO 2023/172737 | A1 | 9/2023 |
| WO | 2023193085 | A1 | 10/2023 |
| WO | WO 2023/185864 | A1 | 10/2023 |
| WO | WO 2023/194310 | A1 | 10/2023 |
| WO | WO 2023/199180 | A1 | 10/2023 |
| WO | WO 2023/214627 | A1 | 11/2023 |
| WO | WO 2023/215906 | A1 | 11/2023 |
| WO | WO 2023/217148 | A1 | 11/2023 |
| WO | WO 2023/220421 | A1 | 11/2023 |
| WO | WO 2023/225302 | A1 | 11/2023 |
| WO | WO 2023/230190 | A1 | 11/2023 |
| WO | WO 2023/232776 | A1 | 12/2023 |
| WO | WO 2023/240188 | A1 | 12/2023 |
| WO | WO 2023/240189 | A1 | 12/2023 |
| WO | WO 2023/246777 | A1 | 12/2023 |
| WO | WO 2024/008068 | A1 | 1/2024 |
| WO | WO 2024/009191 | A1 | 1/2024 |
| WO | WO 2024/017392 | A1 | 1/2024 |
| WO | WO 2024/019103 | A1 | 1/2024 |
| WO | WO 2024/034591 | A1 | 2/2024 |
| WO | WO 2024/034593 | A1 | 2/2024 |
| WO | WO 2024/036270 | A1 | 2/2024 |
| WO | WO 2024/040109 | A2 | 2/2024 |
| WO | WO 2024/041621 | A1 | 2/2024 |
| WO | WO 2024/044334 | A2 | 2/2024 |
| WO | WO 2024/044667 | A2 | 2/2024 |
| WO | WO 2024/050742 | A1 | 3/2024 |
| WO | WO 2024/054625 | A2 | 3/2024 |
| WO | WO 2024/054647 | A1 | 3/2024 |
| WO | WO 2024/054926 | A1 | 3/2024 |
| WO | WO 2024/056005 | A1 | 3/2024 |
| WO | WO 2024/076670 | A2 | 4/2024 |
| WO | WO 2024/076672 | A1 | 4/2024 |
| WO | WO 2024/076674 | A1 | 4/2024 |
| WO | 2024/118960 | A1 | 6/2024 |
| WO | WO 2024/118926 | A1 | 6/2024 |
| WO | WO 2024/118966 | A1 | 6/2024 |
| WO | WO 2024/119278 | A1 | 6/2024 |
| WO | WO 2024/120433 | A1 | 6/2024 |
| WO | WO 2024/123913 | A1 | 6/2024 |
| WO | WO 2024/131777 | A1 | 6/2024 |

(56) References Cited

FOREIGN PATENT DOCUMENTS

| | | | |
|---|---|---|---|
| WO | WO 2024/149214 | A1 | 7/2024 |
| WO | WO 2024/149819 | A1 | 7/2024 |
| WO | WO 2024/152247 | A1 | 7/2024 |
| WO | 2024/188209 | A1 | 9/2024 |
| WO | 2024/188281 | A1 | 9/2024 |
| WO | 2024/193698 | A1 | 9/2024 |
| WO | 2024/199266 | A1 | 10/2024 |
| WO | 2024/206766 | A1 | 10/2024 |
| WO | 2024/207892 | A1 | 10/2024 |
| WO | 2024/208305 | A1 | 10/2024 |
| WO | 2024/209717 | | 10/2024 |
| WO | 2024/213122 | A1 | 10/2024 |
| WO | 2024/215754 | A1 | 10/2024 |
| WO | 2024/218686 | A1 | 10/2024 |
| WO | 2024/227091 | A1 | 10/2024 |
| WO | 2024/229442 | A1 | 11/2024 |
| WO | 2024/229444 | A2 | 11/2024 |
| WO | 2024/229447 | A1 | 11/2024 |
| WO | 2024/230707 | A1 | 11/2024 |
| WO | 2024/230734 | A1 | 11/2024 |
| WO | 2024/233838 | A1 | 11/2024 |
| WO | 2024/234360 | A1 | 11/2024 |
| WO | 2024/235225 | A1 | 11/2024 |
| WO | 2024/236452 | A1 | 11/2024 |
| WO | 2024/238343 | A1 | 11/2024 |
| WO | 2024/238633 | A2 | 11/2024 |
| WO | 2024254404 | | 12/2024 |
| WO | 2024261257 | A1 | 12/2024 |
| WO | 2024263586 | A1 | 12/2024 |
| WO | 2025006704 | A1 | 1/2025 |
| WO | 2025006753 | A2 | 1/2025 |
| WO | 2025006783 | A2 | 1/2025 |
| WO | 2025006962 | A1 | 1/2025 |
| WO | 2025010415 | A1 | 1/2025 |

OTHER PUBLICATIONS

U.S. Appl. No. 16/375,643, filed Apr. 4, 2019, 2019-0315732 A1, Oct. 17, 2019, U.S. Pat. No. 11,161,841, Nov. 2, 2021, Andrew P. Crew.

U.S. Appl. No. 17/360,699, filed Jun. 28, 2021, 2022-0402907 A1, Dec. 22, 2022, Andrew P. Crew.

U.S. Appl. No. 17/223,551, filed Apr. 6, 2021, 2022-0370416 A1, Nov. 24, 2022, Ling Chu.

Arvinas, "Pioneering Today with a different kind of medicine; Transforming Tomorrow for patients who need us." Jan. 2024.

Jesus R. Medina, "Discovery of Potent, Selective, and Efficacious KRAS-Targeted PROTAC Degraders," 6th Targeted Protein Degradation (TPD) Summit, October 31, 2023, Boston, MA.

Katie Smith, PhD, "KRAS-Targeted PROTAC Degraders are Broadly Efficacious Against KRAS-Dependent Tumor Models," American Association for Cancer Research® (AACR) Special Conference: Targeting RAS, March 8, 2023, Philadelphia, PA.

Adachi et al., "Epithelial-to-Mesenchymai Transition is a Cause of Both Intrinsic and Acquired Resistance to KRAS G12C Inhibitor in KRAS G12C-Mutant Non-Small Cell Lung Cancer," *Clinical Cancer Research* 26(22):5962-5973 (2020).

Adachi et al., "Escaping KRAS: Gaining Autonomy and Resistance to KRAS Inhibition in KRAS Mutant Cancers," *Cancers* 13(20):5081 (2021).

Akhave et al., "The Next Generation of KRAS Targeting: Reasons for Excitement and Concern," *Molecular Cancer Therapeutics* 11(21):1645-1651 (2022).

Anonymour "First Ebola vaccine approved," *Nature Biotechnology* 38(1):6 (2020).

Bannoura et al., "Targeting KRAS in pancreatic cancer: new drugs on the horizon," *Cancer and Metastasis Reviews* 40(3):819-835 (2021).

Bear et al., "Biochemical and functional characterization of mutant KRAS epitopes validates this oncoprotein for immunological targeting," *Nature Communications* 12(1):4365 (2021).

Boileve et al., "Codon-specific KRAS mutations predict survival in advanced pancreatic cancer," *ESMO Gastrointestinal Oncology* 3, Issue C, 1-10 (2024).

Bond et al., "Targeted Degradation of Oncogenic $KRAS^{G12C}$ by VHL-Recruiting PROTACs," *ACS Central Science* 6(8):1367-1375 (2020).

Boumelha et al., "Facts and Hopes on RAS Inhibitors and Cancer Immunotherapy," *Clinical Cancer Research* OF1-OF9 (2023).

Briere et al, "The $KRAS^{G12C}$ Inhibitor MRTX849 Reconditions the Tumor Immune Microenvironment and Sensitizes Tumors to Checkpoint Inhibitor Therapy," *Molecular Cancer Therapeutics* 20(6):975-985 (2021).

Bryant et al., "Combination of ERK and autophagy inhibition as a treatment approach for pancreatic cancer." *Nature Medicine* 25(4):628-640 (2019).

Canon et al., "The Clinical KRAS(G12C) inhibitor AMG 510 drives anti-tumour immunity," *Nature* 575(7781):217-223 (2019).

Cascetta et al., "KRAS in NSCLC: State ef the Art and Future Perspectives," *Cancers* 14(21):5430 (2022).

Chen et al., "Small-Molecule Inhibitors Directly Targeting KRAS as Anticancer Therapeutics," *Journal of Medicinal Chemistry* 63(23):14404-14424 (2020).

Chen et al., "Synthesis of Adagrasib (MRTX849), a Covalent KRASG12C Inhibitor Drug for the Treatment of Cancer," *Organic Letters* 6(25):944-949 (2023).

Cheng et al., "Targeting PIKfyve-driven lipid homeostasis as a metabolic vulnerability in pancreatic cancer," bioRxiv https://doi.org/10.1101/2024.03.18.58558 (2024).

Christensen et al., "Targeting $Kras^{g12c}$-mutant cancer with a mutation-specific inhibitor," *Journal of Internal Medicine* 288(2):183-191 (2020).

Cook et al., "The origins and genetic interactions of KRAS mutations are allele- and tissue-specific." *Nature Communications* 12. Article 1808 (2021).

Douglass et al., "Bispecific antibodies targeting mutant RAS neoantigens," *Science Immunology* 6(57):eabd5515 (2021).

Faber et al., "Exploring the differences in the tumor microenvironment and immuno-oncologic targets in pancreatic ductal adenocarcinomas (PDAC) according to KRAS mutational status," *ESMO Gastrointestinal Oncology* 4, Issue C, 100042 (2024).

Fedele et al., "SHP2 inhibition diminishes $KRAS^{G12C}$ cycling and promotes tumor microenvironment remodeling," *Journal of Experimental Medicine* 218(1):e20201414 (2020).

Grimster, "Covalent PROTACs: the best of both worlds?" *RSC Medicinal Chemistry* 12(9):1452-1458 (2021).

Herzberg et al., "KRAS: Druggable at Last," *The Oncologist* 28(4):283-286 (2023).

Holderfield et al., "Concurrent inhibition of oncogenic and wild-type RAS-GTP for cancer therapy," *Nature* 629:919-926 (2024).

Hunter et al., "Biochemical and Structural Analysis of Common Cancer-Associated KRAS Mutations," *Molecular Cancer Research* 13(9):1325-1335 (2015).

Ischenko et al., "KRAS drives immune evasion in a genetic model of pancreatic cancer," *Nature Communications* 12, Article 1482 (2021).

Ji et al., "Discovery of Prodrug of MRTX1133 as an Oral Therapy for Cancers with $KRAS^{G12D}$ Mutation," *ACS Omega* 7(8):7211-7221 (2023).

Jiang et al., "Translational and Therapeutic Evaluation of RAS-GTP Inhibition by RMC-6236 in RAS-Driven Cancers," *Cancer Discovery* 14(6):994-1017 (2024).

Kemp et al., "Efficacy of a Small Molecule Inhibitor of $Kras^{G12D}$ in Immunocompetent Models of Pancreatic Cancer," *Cancer Discovery* 13(2):298-311 (2022).

Kessler et al., "Drugging all RAS isoforms with one pocket," *Future Medicinal Chemistry* 12(21):1911-1923 (2020).

Ketcham et al., "Design and Discovery of MRTX0902, a Potent, Selective, Brain-Penetrant, and Orally Bioavailable Inhibitor of the SOS1:KRAS Protein-Protein Interaction," *Journal of Medicinal Chemistry* 65(14):9678-9690 (2022).

Lamarche et al., "Identification of TN0155, an Allosteric SHP2 Inhibitor for the Treatment of Cancer," *Journal of Medicinal Chemistry* 63(22):13578-13594 (2020).

(56) References Cited

OTHER PUBLICATIONS

Lee et al., "Comprehensive pan-cancer genomic landscape of KRAS altered cancers and real-world outcomes in solid tumors," *npj Precision Oncology* 6. Article 91 (2022).
Lietman et al., "More to the RAS Story: KRAS$^{G12C}$ Inhibition, Resistance Mechanisms, and Moving Beyond KRAS$^{G12C}$," *American Society of Clinical Oncology Educational Book* 42:205-217 (2022).
Liu et al., "Mutant KRAS Drives Immune Evasion by Sensitizing Cytotoxic T-Cells to Activation-Induced Cell Death in Colorectal Cancer," *Advanced Science* 10:2203757 (2023).
Luo et al., "Profiling of diverse tumor types establishes the broad utility of VHL-based ProTaCs and triages candidate ubiquitin ligases," *iScience* 25(3):103985 (2022).
Luo et al., "Adagrasib Treatment After Sotbrasib-Related Hepatotoxicity in Patients With KRAS$^{G12C}$ -Mutated Non-Small Cell Lung Cancer: A Case Series and Literature Review," *JCO Precision Oncology* 8:e2300644 (2024).
Lv et al., "Modulation of the Proteostasis Network Promotes Tumor Resistance to Oncogenic KRAS Inhibitors," *Science* 381 (6662):eabn4180 (2023).
Lyon et al., "Expedient Access to Underexplored Chemical Space: Deoxygenative C(sp3)-C(sp3) Cross-Coupling," *Journal of the American Chemical Society* 14(145):7736-7742 (2023).
Mainardi, "With a little help from my T friends: T cells increase efficacy of KRAS (G12D) inhibitors," *Cell Reports Medicine* 4:100950 (2023).
Massafra et al., "Proteolysis-Targeting Chimeras Enhance T Cell Bispecific Antibody-Driven T Cell Activation and Effector Function through increased MHC Class I Antigen Presentation in Cancer Cells," *The Journal of Immunology* 207(2):493-504 (2021).
McCarthy et al., "Discovery of High-Affinity Noncovalent Allosteric KRAS Inhibitors That Disrupt Effector Binding," *ACS Omega* 4(2):2921-2930 (2019).
Nakajima et al., "FDA Approval Summary: Sotorasib for KRAS G12C-Mutated Metastatic NSCLC," *Clinical Cancer Research* 28(8):1482-1486 (2022).
Nakayama et al., "Characterisation of a novel KRAS G12C inhibitor ASP2453 that shows potent anti-tumour activity in KRAS G12C-mutated preclinical models," *British Journal of Cancer* 126(5):744-753 (2022).
Nusrat et al., "The Clinical Implications of KRAS Mutations and Variant Allele Frequencies in Pancreatic Ductal Adenocarcinoma," *Journal of Clinical Medicine* 13(7):2103 (2024).
Poole et al., "Therapeutic high affinity T cell receptor targeting a KRAS$^{G12D}$ cancer neoantigen," *Nature Communications* 13(1):5333 (2022).
Prior et al., "The Frequency of Ras Mutations in Cancer," *Cancer Research* 80(14):2969-2974 (2020).
Quintanilha et al., "Tomor Mutational Burden in Real-World Patients With Pancreatic Cancer: Genomic Alterations and Predictive Value for Immune Checkpoint Inhibitor Effectiveness," *JCO Precision Oncology* 7(7):e2300092 (2023).
Salmón et al., "Kras oncogene ablation prevents resistance in advanced lung adenocarcinoma," *Journal of Clinical Investigation* 133(7):e164413 (2023).
Shetu et al., "Small-Molecule RAS Inhibitors as Anticancer Agents: Discovery, Development, and Mechanistic Studies," *International Journal of Molecular Sciences* 23(7):3706 (2022).
Sideris et al., "The Role of KRAS in Endometrial Cancer: A Mini-Review" *Anticancer Research* 39(2):533-539 (2019).
Singhal et al., "Targeting KRAS in cancer," *Nature Medicine* 30(4):969-983 (2024).
Snead et al., "Development of Adagrasib's Commercial Manufacturing Route," *Organic Process Research & Development* 3(27):530-538 (2023).
Stickler et al., "Targeting KRAS in pancreatic cancer," *Oncology Research* 32(5):799-805 (2024).
Tanaka et al., "Clinical Acquired Resistance to KRAS$^{G12C}$ Inhibition through a Novel KRAS Switch-II Pocket Mutation and Polyclonal Alterations Converging on RAS-MAPK Reactivation," *Cancer Discovery* 11(8):1913-1922 (2021).
Vasta et al., "KRAS is vulnerable to reversible switch-II pocket engagement in cells," bioRxiv doi: https:/doi.org/10.1101/2021.10.15.464544 (2021).
Vasta et al., "KRAS Is vulnerable to reversible switch-II pocket engagement in cells," *Nature Chemical Biology* 18(6):596-604 (2022).
Volak et al., "Industry Perspective on the Pharmacokinetic and ADME Characterization of Heterobifunctional Protein Degraders," *Drug Metabolism and Disposition* 52(7), DMD-AR-2022-001154 (2023).
Wang et al., "Identification of MRTX1133, a Noncovalent, Potent, and Selective KRAS$^{G12D}$ Inhibitor," *Journal of Medicinal Chemistry* 65(4):3123-3133 (2022).
Wasko et al., "Tumor-selective activity of RAS-GTP inhibition in pancreatic cancer," *Nature* 629:927-936 (2024).
White, "Blockade of RAF and autophagy is the one-two punch to take out Ras," *PNAS* 116(10):3965-3967 (2019).
Wolters-Eisfeld et al., "Unmasking metabolic dependencies in pancreatic cancer: aberrant polyamine synthesis as a promising new therapeutic target," *Signal Transduction and Targeted Therapy 8*, Article 410 (2023).
Yang et al., "Autophagy Is Critical for Pancreatic Tumor Growth and Progression in Tumors with p53 Alterations," *Cancer Discovery* 4(8):905-913 (2014).
Zeng et al., "Exploring Targeted Degradation Strategy for Oneogenvic KRAS$^{G12C}$," *Cell Chemical Biology* 27(1):19-31.e1-e6 (2020).
Zhang et al., "A covalent inhibitor of K-Ras(G12C) induces MHC class I presentation of haptenated peptide neoepitopes targetable by immunotherapy," *Cancer Cell* 40(9):1060-1069.e7 (2022).
Zhang et al., "Chemoselective Covalent Modification of K-Ras(G12R) with a Small Molecule Electrophile," *Journal of the American Chemical Society* 144(35):15916-15921 (2022).
Zhou et al., "Impact of KRAS mutation on the tumor microenvironment in colorectal cancer," *International Journal of Biological Sciences* 20(5):1947-1964 (2024).
Zhu et al., "Targeting KRAS mutant cancers: from druggable therapy to drug resistance," *Molecular Cancer* 21 (1):159 (2022).
Cao et al., "Clinicopathologic features, concurrent genomic alterations, and clinical outcomes of patients with KRAS G12D mutations in resected lung adenocarcinoma," *European Journal of Cancer* 202:113985 (2024).
Chen et al., "PCC0208023, a potent SHP2 allosteric inhibitor, imparts an antitumor effect against KRAS mutant colorectal cancer," *Toxicology and Applied Pharmacology* 398:115019 (2020).
Escher et al., "RAS Degraders: The New Frontier for RAS Driven Cancers," *Molecular Therapy* 31(7):1904-1919 (2023).
Ghosh et al., "An Updated Review on KRAS Mutation in Lung Cancer (NSCLC) and Its Effects on Human Health," *Applied Biochemistry and Biotechnology* 1-18 (2023).
Hallin et al., "Anti-tumor efficacy of a potent and selective non-covalent KRAS$^{G12D}$ inhibitor," *Nature Medicine* 28(10):2171-2182 (2022).
Hansen et al., "The reactivity-driven biochemical mechanism of covalent KRAS$^{G12C}$ inhibitors," *Nature Structural & Molecular Biology* 25(6):454-462 (2018).
He et al., "Design of Small Molecule Autophagy Modulators: A Promising Druggable Strategy," *Journal of Medicinal Chemistry* 61(11):4656-4687 (2018).
Hong et al., Trial in Progress: A phase 1b study of sotorasib, a specific and irreversible KRAS$^{G12C}$ inhibitor, as monotherapy in non-small cell lung cancer (NSCLC) with brain metastasis and in combination with other anticancer therapies in advanced solid tumors (CodeBreak 101)—2021 ASCO Annual Meeting I—Abstract.
Horie et al., "Pan-Cancer Comparative and Integrative Analyses of Driver Alterations Using Japanese and International Genomic Databases", *Cancer Discovery* 14(5):786-803 (2024).

(56) References Cited

OTHER PUBLICATIONS

Huang et al., "Inhibition of ADAM9 promotes the selective degradation of KRAS and sensitizes pancreatic cancers to chemotherapy," *Nature Cancer* 5(3):400-419 (2024).
Kessler et al., "The hanging heart: How KRAS lures its prey to the membrane", PNAS 117(43):26556-26558 (2020).
Kirschner et al., "Targeting KRAS Diversity: Covalent Modulation of G12X and Beyond in Cancer Therapy," Journal of Medicinal Chemistry 67(8):6044-6051 (2024).
Klein et al., "Addicted to proteostasis: How KRAS-driven cancers acquire resistance to clinical KRAS inhibitors," *Cell Chemical Biology* 30(11):1334-1336 (2023).
Leonhardt et al., "KRAS degradation averts PDAC chemoresistance," *Nature Cancer* 5:375-377 (2024).
Li et al., "Discovery of KRas G12C-IN-3 and Pomalidomide-based PROTACs as degraders of endogenous KRAS G12C with potent anticancer activity," Bioorganic Chemistry 117:105447 (2021).
Li et al., "First Report of Safety/Efficacy of Sotorasib in Combination with Pembrolizumab or Atezolizumab in Advanced KRAS p.G12C NSCLC", *Journal of Thoracic Oncology* 17(9):S10-S11 (2022).
McNamara et al., "Preclinical efficacy of RAF/MEK clamp avutometinib in combination with FAK inhibition in low grade serous ovarian cancer," *Gynecologic Oncology* 183:133-140 (2024).
Melief, "T-Cell Immunotherapy against Mutant KRAS for Pancreatic Cancer", *The New England Journal of Medicine* 386(22):2143-2144 (2022).
Mugarza et al., "Therapeutic $KRAS^{G12C}$ inhibition drives effective interferon-mediated antitumor immunity in immunogenic lung cancers", *Science Advances* 8:3abm8780 (2022).
Passaro et al., "Setting the Benchmark for $KRAS^{G12C}$-Mutated NSCLC", *The New England Journal of Medicine* 387(2):180-183 (2022).
Perurena et al., "Combinatorial strategies to target RAS-driven cancers," *Nature Reviews Cancer* 24:316-337 (2024).
Ramharter et al., "One Atom Makes All the Difference: Getting a Foot in the Door between SOS1 and KRAS," *Journal of Medicinal Chemistry* 64(10):6569-6580 (2021).
Sahin et al., "Targeting KRAS Oncogene for Patients With Colorectal Cancer: A New Step Toward Precision Medicine," *JCO Oncology Practice* OP2300787 (2024).
Wang et al., "Identification of MRTX1133, a Noncovalent, Potent, and Selective $KRAS^{G12D}$ Inhibitor," *Journal of Medicinal Chemistry* 65(4):S1-S195 (2022)—Supporting Information.
Wang et al., "Annual review of KRAS inhibitors in 2022," *European Journal of Medicinal Chemistry* 249:115124 (2023).
Wang et al., "Exploration of efficacy of different therapy regimens for advanced NSCLC patients with KRAS mutation in the first-line treatment," *Clinical and Translational Oncology* (2024).
Xiao et al., "KRAS G12C Inhibitors in the Treatment of Metastatic Colorectal Cancer," *Clinical Colorectal Cancer* 23(3):199-206 (2024); doi: https://doi.org/10.1016/j.clcc.2024.05.004—Abstract.
Zhou et al., "Discovery of the First-in-Class Agonist-Based SOS1 PROTACs Effective in Human Cancer Cells Harboring Various KRAS Mutations," *Journal of Medicinal Chemistry* 65(5):3923-3942 (2022).
English Abstract of Chinese Publication No. 11846070A, 1 page, retrieved from European Patent Office website on Jan. 17, 2025.
English Abstract of Chinese Publication No. 118496300A, 1 page, retrieved from European Patent Office website on Jan. 17, 2025.
English Abstract of Chinese Publication No. 118666870A, 1 page, retrieved from European Patent Office website on Jan. 17, 2025.
English Abstract of Chinese Publication No. 118725012A, 1 page, retrieved from European Patent Office website on Jan. 17, 2025.
English Abstract of Chinese Publication No. 118772176A, 1 page, retrieved from European Patent Office website on Jan. 17, 2025.
English Abstract of Chinese Publication No. 118791505A, 1 page, retrieved from European Patent Office website on Jan. 17, 2025.
Troup et al., "Current Strategies for the Design of PROTAC Linkers: A Critical Review," Explor Target Antitumor Ther., vol. 1, p. 273-312, (2020).
"Arvinas' KRAS G12D-targeting PROTAC May Provide a Significant Advance in Treatment for Multiple Cancers," Arvinas Operations, Inc., 4 pages.
Bar-Sagi, D., "The Sos (Son of sevenless) Protein," Trends Endocrinol Metab., vol. 5 , No. 4, p. 165-169, (1994); Abstract only.
Boriack-Sjodin et al., "The Structural Basis of the Activation of Ras by Sos," Nature, vol. 394, No. 6691, p. 337-343, (1998); Abstract Only.
Cacace, A., "Heterobifunctional Degrader Molecules that Lead to the Clearance of Pathologic Proteins in Neurodegeneration," Alzheimer's Association International Conference, Denver, Colorado and Online, Jul. 26-30, 2021, 15 pages.
Campbell et al., "Distinct Patterns of Somatic Genome Alterations in Lung Adenocarcinomas and Squamous Cell Carcinomas," Nat Genet., vol. 48, No. 6, p. 607-616, (2016).
International Search Report and Written Opinion dated Jun. 24, 2021 for PCT/US2021/025935.
International Search Report and Written Opinion for PCT/US2019/025878, dated Oct. 15, 2019.
Ito et al., "Regional Polysterism in the GTP-bound Form of the Human c-Ha-Ras Protein," Biochemistry, vol. 36, No. 30, p. 9109-9119, (1997); Abstract Only.
Land et al., "Tumorigenic Conversion of Primary Embryo Fibroblasts Requires At Least Two Cooperating Oncogenes," Nature, vol. 304, No. 5927, p. 596-602, (1983); Abstract Only.
Lu et al., "GTP Binding and Oncogenic Mutations May Attenuate Hypervariable Region (HVR)-Catalytic Domain Interactions in Small GTPase K-Ras4B, Exposing the Effector Binding Site," The Journal of Biological Chemistry, vol. 290, No. 48, p. 28887-28900, (2015).
Medina, J.R., "Discovery of Potent, Selective, and Efficacious KRAS-Targeted PROTAC Degraders," PBSS Conference, 25 pages, Sep. 25, 2024.
Medina, J.R., "PROTAC Protein Degrader Molecules: Challenging the Perceived Limits of Small Molecule Drug Discovery," Presentation, Arvinas Operations, Inc., 18 pages, Nov. 2020.
Milburn et al., "Molecular Switch for Signal Transduction: Structural Differences Between Active and Inactive Forms of Protooncogenic Ras Proteins," Science, vol. 247, No. 4945, p. 939-945, (1990); Abstract Only.
Newbold et al., "Fibroblast Immortality is a Prerequisite for Transformation by EJ c-Ha-ras Oncogene," Nature, vol. 304, No. 5927, p. 648-651, (1983); Abstract only.
Nnadi et al., "Novel K-Ras G12C Switch-II Covalent Binders Destabilize Ras and Accelerate Nucleotide Exchange," J Chem Inf Model., vol. 58, No. 2, p. 464-471, (2018).
Ostrem et al., "K-Ras(G12C) Inhibitors Allosterically Control GTP Affinity and Effector Interactions," Nature, vol. 503, No. 7477, p. 548-551, (2013).
Sakamoto, et al., "Development of Protacs to target cancer-promoting proteins for ubiquitination and degradation," Mol cell Proteomics. 2(12), Dec. 2003, 1350-1358.
Sakamoto, et al., "Protacs: chimeric molecules that target proteins to the Skp I -Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Scharovsky, et al., "Inhibition of ras oncogene: a novel approach to antineoplastic therapy", (2000), Journal of Biomedical Science. 7(4) 292-298.
Schiedel, M., et al., "Chemically Induced Degradation of Sirtuin 2 (Sirt2) by a Proteolysis Targeting Chimera (PROTAC) Based on Sirtuin Rean-anging Ligands (SirReals)," J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., "Targeted intracellular protein degradation induced by a small molecule: En route to chemical proteomics," Bioorg. Med. Chem. Lett. 18 (2008) 5904-5908.

(56) References Cited

OTHER PUBLICATIONS

Schwinn et al., "CRISPR-mediated Tagging of Endogenous Proteins with a Luminescent Peptide," ACS Chem Biol., vol. 13, No. 2, p. 467-474, (2018).
Shangary et al., "Temporal activation of p53 by a specific MDM2 inhibitor is selectively toxic to tumors and leads to complete tumor growth inhabitation," PNAS USA, vol. 105, p. 3933-3938, (2008).
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Smith, K., "PROTAC Degraders to Target KRAS G12C & Beyond," Presentation, Arvinas Operations, Inc., 25 pages, Feb. 25, 2021.
Stanton, et al., (2018) "Chemically induced proximity in biology and medicine." Science 359(6380).
Stewart, Scott G et al., "Efforts toward elucidating Thalidomide's molecular target: An Expedient Synthesis or the first Thalidomide Biotin Analogue" Org. Biomol., Chem., 8, 4059-4062.
Stoppler, Melissa Conrad. , Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, B. et al., "BET protein proteolysis targeting chimera (PROTAC) exerts potent lethal activity against mantle cell lymphoma cells." Leukemia 32, 343-352 (2018).
Sun, D, et al., "Discovery of AMG 232, a potent, selective, and orally bioavailable MDM2-p53 inhibitor in clinical development," J Med Chem. Feb. 2014 1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity," J. Med. Chem. 53, 3306-3318 (2011).
Toure, et al., (2016) "Small-Molecule PROTACS: New Approaches to Protein Degradation." Angew Chem Int Ed Engl 55(6): 1966-1973.
Turk, B. E., "Binding of thalidomide to alphal-acid glycoprotein may be involved in its inhibition of tumor necrosis factor alpha production," Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP," ACS Chem. Biol., 8(4), 725-732 (2013).
Van Molle, et al., "Dissecting fragment-based lead discovery at the von Hippel-Lindau protein:hypoxia inducible factor la protein-protein interface," Chem Biol. 19(10), Oct. 26, 2012, 1300-1312.
Vassilev, et al., "In vivo activation or the p53 pathway by small-molecule antagonists or MDM2", Science 303, Feb. 6, 2004, 844-848.
Vazquez, A. et al., "The genetics of the p53 pathway, apoptosis and cancer therapy," Nat. Rev. Drug. Dis., 7, 979-982 (2008).
Vu, B. et al. "Discovery of RG7112: a small-molecule MDM2 inhibitor in clinical development," ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Winter, et al., "Phthalimide Conjugation as a strategy for in vivo target protein degradation," Science, 2015 vol. 348 (6241), pp. 1376-1381 [Pub online: May 21, 2015].
Yao, Z. et al., "Tumors with class 3 BRAF mutants are sensitive to the inhibition of activated RAS.," Nature 548, 234-238 (2017).
Zeng, M., et al., "Potent and Selective Covalent Quinazoline Inhibitors of KRAS G12C," Cell Chemical Biology, 24, 1005-1016, (2017).
Zengerle, et al., "Selective Small Molecule Induced Degradation of the BET Bromodomain Protein," ACS Chemical Biology, Jun. 2, 2015, vol. 10, pp. 1770-1777.
Zhang B. et al., "Small-molecule MDM2-p53 inhibitors: recent advances," Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhao et al., "Small-molecule inhibitors of the MDM2-p53 protein-protein interaction (MDM2 inhibitors) in clinical trials for cancer treatment," J. Med. Chem., vol. 58, p. 1038-1052, (2015).
Zhou, B., et al. "Discovery of a Small-Molecule Degrader of Bromodomain and Extra-Terminal (BET) Proteins with Picomolar Cellular Potencies and Capable of Achieving Tumor Regression," J Med Chem. 61(2), 462-481 (2018) (DOI:10.1021/acs.jmedchem.6b01816) (2017).
Pierre et al., "Understanding SOS (Son of Sevenless)," Biochem Pharmacol., vol. 82, No. 9, p. 1049-1056, (2011); Abstract Only.
Prior et al., "A Comprehensive Survey of Ras Mutations in Cancer," Cancer Res., vol. 72, No. 10, p. 2457-2467, (2012).
Rudolph et al., "Selective Inhibition of Mutant Ras Protein Through Covalent Binding," Agnew Chem Int Ed Engl., vol. 53, No. 15, p. 3777-3779, (2014); Abstract Only.
Ryan et al., "Vertical Pathway Inhibition Overcomes Adaptive Feedback Resistance to KRASG12C Inhibition," Clin Cancer Res., vol. 26, No. 7, p. 1633-1643, (2020).
Scheffzek et al., "The Ras-RasGAP Complex: Structural Basis for GTPase Activation and its Loss in Oncogenic Ras Mutants," Science, vol. 277, No. 5324, p. 333-338, (1997); Abstract Only.
Simanshu et al., "RAS Proteins and Their Regulators in Human Disease," Cell., vol. 170, No. 1, p. 17-33, (2017).
Spencer-Smith et al., "Direct Inhibition of RAS: Quest for the Holy Grail?," Semin Cancer Biol., vol. 54, p. 138-148, (2019).
Stewart et al., "Pumping the Brakes on RAS—Negative Regulators and Death Effectors of RAS," Journal of Cell Science, vol. 133, No. jcs238865, 10 pages, (2020).
Xue et al., "Rapid Non-uniform Adaptation to Conformation-specific KRAS(G12C) Inhibition," Nature, vol. 577, No. 7790, p. 421-425, (2020).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in HIC-I alpha by pVHL", Nature 417, Jun. 27, 2002, 975-978.
Huang Jit, et al. (2018) "A Chemoproteomic Approach to Query the Degradable Kinome Using a Multi-kinase Degrader." Cell Chem Biol 25(1):88-99 e86.
Huang, et al., (2016) "Drugging the undruggables: exploring the ubiquitin system for drug development." Cell Res 26 (4):484-498.
Hughes, et al., (2017) "Molecular recognition of ternary complexes: a new dimension in the structure-guided design of chemical degraders. " Essays Biochem 61(5):505-516.
Ivan, M., et al., "HIFa Targeted for VHL-Mediated Destruction by Proline Hydroxylation: Implications for 02 Sensing," Science, vol. 292, No. 5516, pp. 464-468, 2001.
Jang, E.R. et al., "Targeted Degradation of Proteins by PROTACs, " Curr. Protoc. Chem. Biol., 2010, vol. 2, No. 2, pp. 7187.
Kim, K.S., "Discovery of tetrahydroisoquinoline-based bivalent heterodimeric IAP antagonists", Bioorg. Med. Chem. Lett. 24(21), 5022-5029 (2014).
Knickelbein, K., et al., Mutant KRAS as a critical determinant of the therapeutic response of colorectal cancer, Genes Dis. Mar. 2015; 2(1):4-12.
Knott, Edward (1955). "Compounds containing sulphur chromophores. Part I. The action of bases on heterocyclic sulphide quarterary salts", Journal of The Chemical Society (resumed). 10.1039/jr9550000916. 949-954.
Kronke, et al., "Lenalidomide Causes Selective Degradation of IKZFI and IKZF3 in Multiple Myeloma Cells," Science 343, 301-305 (2014).
Lai, A.C., et al., "Modular PROTAC Design for the Degradation of Oncogenic BCR-ABL" Angew Chem Int Ed Engl 55, 807-810 (2016).
Lai, et al., (2017) "Induced protein degradation: an emerging drug discovery paradigm." Nat Rev Drug Discov 16 (2): 101-114.
Lala, et al., "Role of nitric oxide in tumor progression: Lessons from experimental tumors", Cancer and Metastasis Reviews 17:91-106 (1998).

(56) References Cited

OTHER PUBLICATIONS

Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Ilydrocarbon Receptor by the PROTAC Approach: A Useful Chemical Genetic Tool", ChemBioChem vol. 8, Issue 17, pp. 2058-2062, Nov. 23, 2007.
Levine, et al., "Targeting the androgen receptor with steroid conjugates," J. Med. Chem., vol. 57., No. 20. pp. 8224 8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", org. Biomol. Chem. 2013, 11, 4757-4763.
Lopez-Girona, A. et al., "Cereblon is a direct protein target for immunomodulatory and antiproliferative activities of lenalidomide and pomalidomide," Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins," Science 343, 305-309 (2014).
Luo, J. et al. "A genome-wide RNAi screen identifies multiple synthetic lethal interactions with the Ras oncogene", Cell 137, 835-848 doi:S0092-8674(09)00529-7 [pil] 10.1016/j.cell.2009.05.006 (2009).
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the Vhl E3 ubiquitin ligase to induce self-degradation." Nat Commun 8(1):830 1-13.
Mannhold R., et al., "IAP antagonists: promising candidates for cancer therapy", Drug Discov. Today, 15 (5-6), 210-219 (2010).
Martinez-Iacaci, L., et al., "RAS transformation causes sustained activation of epidermal growth factor receptor and elevation of mitogen-activated protein kinase in human mammary epithelial cells", Int. J. Cancer (2000), 88(1), 44-52.
Medline Plus Trusted Health Information for You, www.nlm.nih.gov/medlineplus/cancer.html pp. 1-10, (2007).
Min, Jung-hyun, et al., "Structure of an HIV-I-alpha pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., " Amino-Substituted Thalodomide Analogs: Potent Inhibitors of TNF-a Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138 144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer"; Journal of Medicinal Chemistry 2004, 47, 4417-4426.
Ostrem et al., "Direct small-molecule inhibitors of KRAS: from structural insights to mechanism-based design", Nat Rev Drug Discov. Nov. 2016;15(11):771-785.
Ottis P, et al. (2017) "Assessing Different E3 Ligases for Small Molecule Induced Protein Ubiquitination and Degradation " ACS Chem Biol 12(10):2570-2578.
Ottis, et al., (2017) "Proteolysis-Targeting Chimeras: Induced Protein Degradation as a Therapeutic Strategy." ACS Chem Biol 12(4):892-898.
Pan, Ting, et al., A recombinant chimeric protein specifically induces mutant KRAS degradation and potently inhibits pancreatic tumor growth, Oncotarget, vol. 7, No. 28, p. 44299-44309.
Perez, HL," Discovery of potent heterodimeric antagonists of inhibitor of apoptosis proteins (IAPs) with sustained antitumor activity", J. Med. Chem. 58(3), 1556-1562 (2015).
Powell, C. E. et al. Chemically Induced Degradation of Anaplastic Lymphoma Kinase (ALK). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." Curr Opin Chem Biol 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." Angew Chem Ed Engl 56(21):5738-5743.
Rew, Y, et al., "Discovery of a potent and selective 4-amidobenzoic acid inhibitor of the MDM2-p53 interaction", . 1 Med Chem. Dec. 2014 10499-10511. doi: 10.1021(jm501550p. Epub Dec. 4, 2014. PubMed PMID: 25384157.
Rotili, D., et al., "Photoactivable peptides for identifying enzyme-substrate and protein-protein interactions", Chem Commun (Carob) 47(5), Feb. 2011, 1488-1490.
Ruchelman, A., et al., Isosteric analogs of lenalidominde and pomalidomide: Synthesis and biological activity Bioorganic & Medicinal Chemistry Letters 23 (2013) 360-365.
U.S. Appl. No. 18/729,843, Jan. 20, 2023, Medina.
Ahn, et al., "HIF-lalpha peptide derivatives with modifications at the hydroxyproline residue as activators of HIF-lalpha," Bioorg Med Chem Lett. 19(15), 2009, 4403-4405.
Ardecky, R.J, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).
Ashby, M.N. (1998), "CaaX converting enzymes", Current Opinion in Lipidology. 9 (2) 99-102.
Bargagna-Mohan et al., "Use of PROTACS as molecular probes of angiogenesis", Bioorg. Med. Chem. Left. 15 (11) 2005, 2724-2727.
Bondeson et al., "Catalytic in vivo protein knockdown by small-molecule PROTACS", National Chem Biol. 11(8) Aug. 2015, 611-617.
Bondeson et al., "Lessons in PROTAC Design from Selective Degradation with a Promiscuous Warhead." Cell Chem Biol 25(1):78-87 e75, (2018).
Bondeson et al., "Targeted Protein Degradation by Small Molecules." Annu Rev Pharmacol Toxicol, vol. 57, p. 107-123, (2017).
Bos, J. L., "ras oncogenes in human cancer: a review", Cancer Res 49, 4682-4689 (1989).
Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIFla", Angew Chem Int Ed Engl.51(46), Nov. 12, 2012, 11463-11467.
Buckley, et al., "Targeting the von Hippel-Lindau E3 ubiquitin ligase using small molecules to disrupt the VHL/HIF-la interaction", Journal of the American Chemical Society, Feb. 27, 2012, 134(10): 4465-4468.

(56) References Cited

OTHER PUBLICATIONS

Burslem GM, et al. (2018) "The Advantages of Targeted Protein Degradation Over Inhibition: An RTK Case Study." Cell Chem Biol 25(1):67-77 e63.
Burslem, et al., (2017) "Small-Molecule Modulation of Protein Homeostasis." Chem Rev 1 17(17): 11269-11301.
Capitosti, S., et al., "Thalidomide analogues demonstrate dual inhibition of both angiogenesis and prostate cancer" Bioorganic & Medicinal Chemistry 12, (2004) 327-336.
Carmony et al., "PROTAC-Induced Proteolytic Targeting", Methods Mol. Biol., vol. 832, pp. 627-638, (2012).
CAS Registry No. 1004933-70-3, which entered STN on Feb. 21, 2008.
CAS Registry No. 1226974-40-8, indexed in the Registry file on STN CAS Online Jun. 4, 2010.
CAS Registry No. 871986-52-6 entered STN Jan. 16, 2006.
Chan, et al., (2018) "Impact of Target Warhead and Linkage Vector on Inducing Protein Degradation: Comparison of Bromodomain and Extra-Terminal (BET) Degraders Derived from Triazolodiazepine (JQI) and Tetrahydroquinoline (IBET726) Bet Inhibitor Scaffolds." J Med Chem 61(2):504-513.
Chene, P., et al., "Inhibiting the p53-MDM2 interaction: an important target for cancer therapy" Nat. Rev. Cancer (2003), 3, 102-109.
Churcher I (2018) "Protac-Induced Protein Degradation in Drug Discovery: Breaking the Rules or Just Making New Ones?" J Med Chem 61(2): 444-452.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antogonists of inhibitors of apoptosis proteins based on thiazole amide isosteres", Bioorg. Med. Chem. Lett., 20(7), 2229-2233 (2010).
Collins, MA., et al., "Kras as a key oncogene and therapeutic target in pancreatic cancer", Frontiers in Physiol. Jan. 21, 2014: 4:407.
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11 pp. 677-692; Nov. 21, 2008.
Crew AP, el al. (2018) "Identification and Characterization of Von Ilippel-Lindau-Recruiting Proteolysis Targeting Chimeras (PROTACs) of TANK-Binding Kinase 1." J Med Chem 61(2):583-598.
Crews, C. M., "Targeting the undruggable proteome: the small molecules or my dreams", Chem Biol 17, 551-555, doi:S1074-5521 (10)00196-1 [pii] 10.1016/j. chembi01.2010.05.011 (2010).
Cromm, et al., (2017) "Targeted Protein Degradation: from Chemical Biology to Drug Discovery." Cell Chem Biol 24 (9): 1181-1190.
Cyrus, et al., "Jostling for position: optimizing linker location in the design of estrogen receptor-targeting PROTACs," Chem Med Chem. 5(7), Jul. 5, 2010, 979-985.
Cyrus, K. et al., "Impact of Linker Length on the Activity of PROTACs, " Mol. Biosyst., 2011, vol. 7, No. 2, pp. 359-364.
Cyrus, K. et al., "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 65(14):5979-83. doi: 10.1021/jm400487c. Epub Jul. 16, 2013. PubMed PMID: 23808545 (J. Med. Chem. (2013) 56, 5979-5983 Ding, et al.).
Dixon, S. J. et al., "Identifying druggable disease-modifying gene products",. Curr Opin Chem Biol 13, 549-555, doi: S1367-5931 (09)00107-0 [pil] 10.1016/j. cbpa.2009.08.003 (2009).
Fischer, et al., "Structure of the DDB I-DRBN E3 Ubiquitin ligase in complex with thalidomide", Nature, vol. 000, pp. 1-5 (2014).
Flygare, .I.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes" , Pro. Natl. Acad Sci, vol. 92, pp. 9117-9121, 1995.
Hallin et al., "The KRASG12C Inhibitor MRTX849 Provides Insight Toward Therapeutic Susceptibility of KRAS-Mutant Cancers in Mouse Models and Patients," Cancer Discov., vol. 10, No. 1, p. 54-71, (2020).
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hong et al., "KRASG12C Inhibition with Sotorasib in Advanced Solid Tumors," New England Journal of Medicine 383 (13): 1207-1217 (2020).
Long et al., "Evaluation of KRAS inhibitor-directed therapies for pancreatic cancer treatment," Frontiers in Oncology 14:1402128 (2024).
Lu et al., "Safety and Efficacy of D-1 553 in Patients with KRAS G12C Mutated Non-Small Cell Lung Cancer: A Phase 1 Trial", Journal of Thoracic Oncology 17(9S): S11 (2022); Abstract Only.
Rodriguez-Gonzalez, A., "Targeting Steroid Hormone Receptors for Ubiquitination and Degradation in Breast and Prostate Cancer," Oncogene, vol. 27, p. 7201-7211, (2008).

* cited by examiner

CEREBLON-BASED KRAS DEGRADING PROTACS AND USES RELATED THERETO

CROSS-REFERENCE TO RELATED APPLICATIONS

This application is claims priority to U.S. Provisional Application Ser. No. 63/592,814 filed Oct. 24, 2023, U.S. Provisional Application Ser. No. 63/486,528 filed Feb. 23, 2023, and U.S. Provisional Application Ser. No. 63/481,672, filed Jan. 26, 2023, which are hereby incorporated herein by reference in their entireties.

BACKGROUND

E3 ubiquitin ligases like Cereblon confer substrate specificity for ubiquitination, and therefore are more attractive therapeutic targets than general proteasome inhibitors due to their specificity for certain protein substrates. Bifunctional compounds, such as those described in U.S. Patent Application Publication Nos. 2015/0291562 and 2014/0356322 (both incorporated herein by reference), function to recruit endogenous proteins to an E3 ubiquitin ligase for ubiquitination and degradation. In particular, these publications describe bifunctional or proteolysis targeting chimeric compounds (PROTAC® protein degraders), which find utility as modulators of targeted ubiquitination of a variety of polypeptides and proteins, which are then degraded via the proteasome system. These bifunctional compounds function to recruit endogenous proteins to an E3 ubiquitin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

The Kirsten rat sarcoma (KRAS) gene is an oncogene encoding KRas, which is a small GTPase signal transduction protein. Ras proteins associate with the plasma membrane, and act as switches in the transduction of extracellular signals to intracellular response, thereby regulating, e.g., cell division. Numerous activating or gain-of-function mutations of the KRas gene are known, and in fact, KRas is the most frequently mutated gene in cancer. Gain-in-function KRas mutations are found in approximately 30% of all human cancers, including, e.g., pancreatic cancer (>80%), colon cancer (approximately 40-50%), lung cancer (approximately 30-50%), non-small cell lung cancer, biliary tract malignancies, endometrial cancer, cervical cancer, bladder cancer, liver cancer, myeloid leukemia, and breast cancer. These activating mutations impair the ability of KRas to switch between active and inactive states. Key roles for mutant KRas have been established in initiation, maintenance, progression, and metastasis of various cancers, and mutations are frequently correlated with poor prognosis and increased resistance to chemotherapy and biological therapies, including, e.g., therapies that target epidermal growth factor receptor. However, despite its key role and high rates prevalence in cancer, there is an absence of effective therapies that directly target this oncogene, leading to it being considered "undruggable."

Thus, an ongoing need exists in the art for effective treatments for disease associated with overexpression, aggregation, and/or overactivation of KRas.

SUMMARY

Provided herein are compounds that target KRas and are thus useful in the treatment of cancer.

Provided herein are compounds of any one of Formula I-IV:

(I)

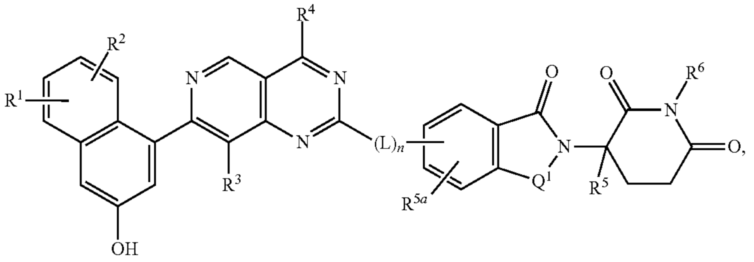

(II)

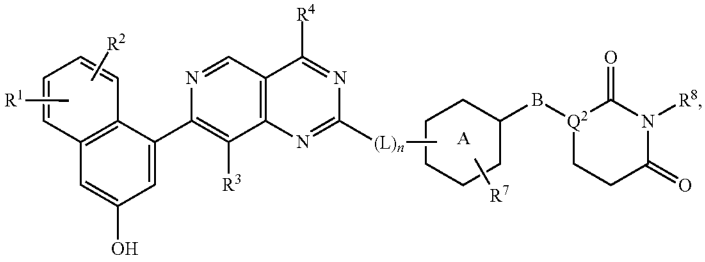

-continued
(III)
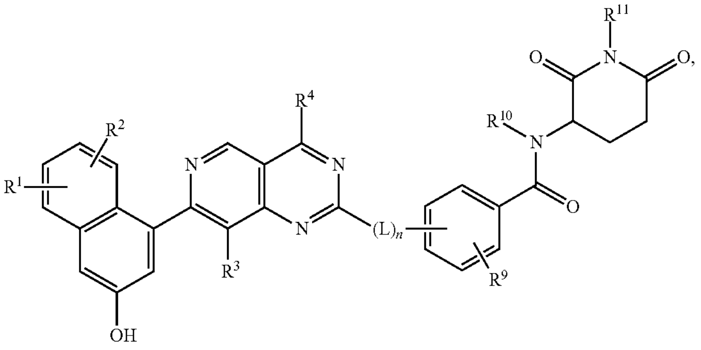
or
(IV)
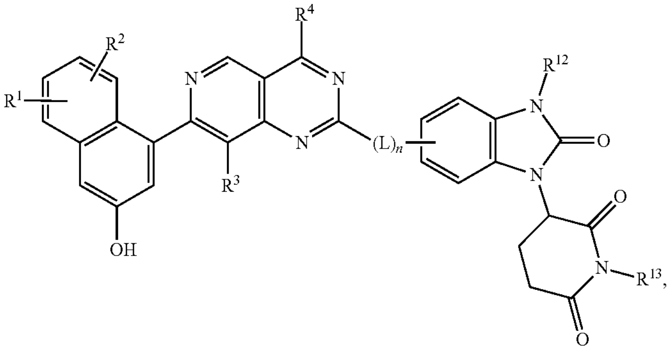
or a pharmaceutically acceptable salt thereof, wherein the variables are defined herein.
Also provided herein are compounds of Formula V and VI:
(V)
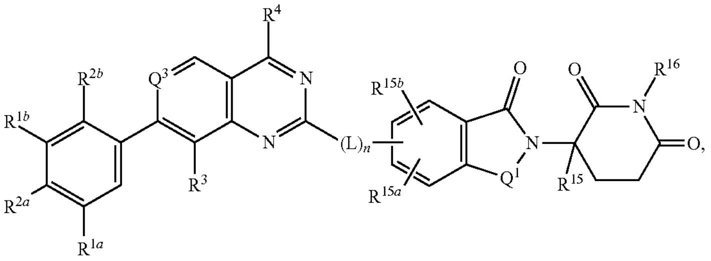
and
(VI)
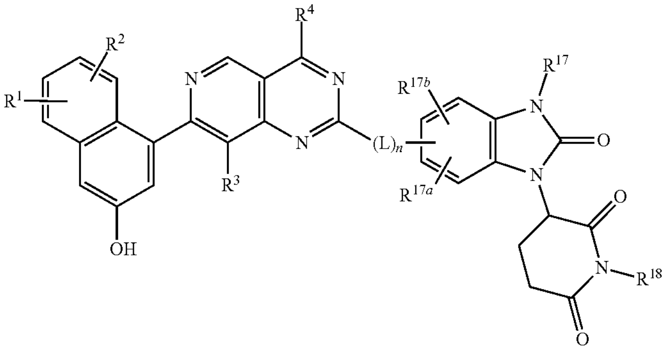
or a pharmaceutically acceptable salt thereof.
In an aspect, provided herein are compounds of Formula AI or AIV:

(AI)

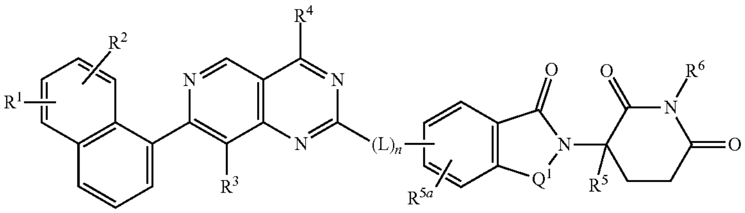

or (AIV)

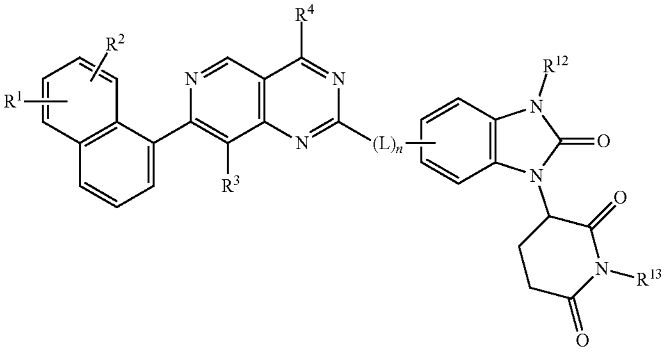

or a pharmaceutically acceptable salt thereof.

In another aspect, provided herein is a compound of Formula VII:

(VII)

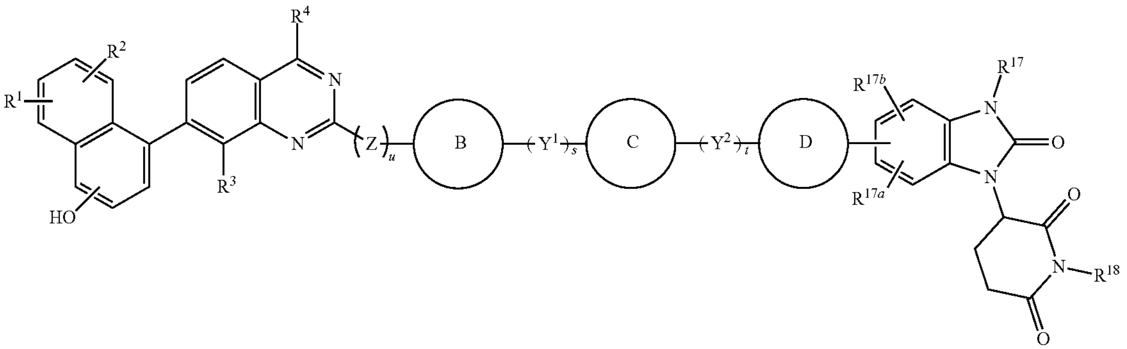

or a pharmaceutically acceptable salt thereof.

In embodiments, the compound of Formula I has a structure of Formula IA:

(IA)

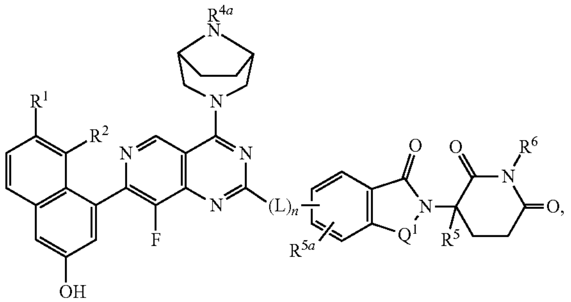

or a pharmaceutically acceptable salt thereof.

In embodiments, the compound of Formula I has a structure of Formula IB:

(IB)

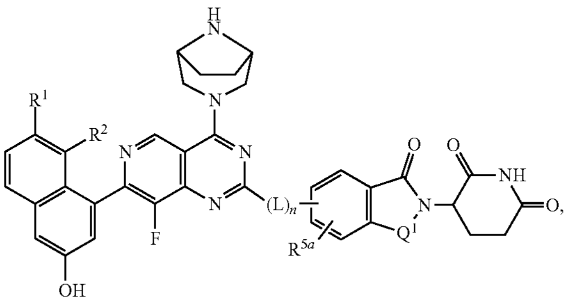

or a pharmaceutically acceptable salt thereof.

In embodiments, the compound of Formula I has a structure of Formula IB-i:

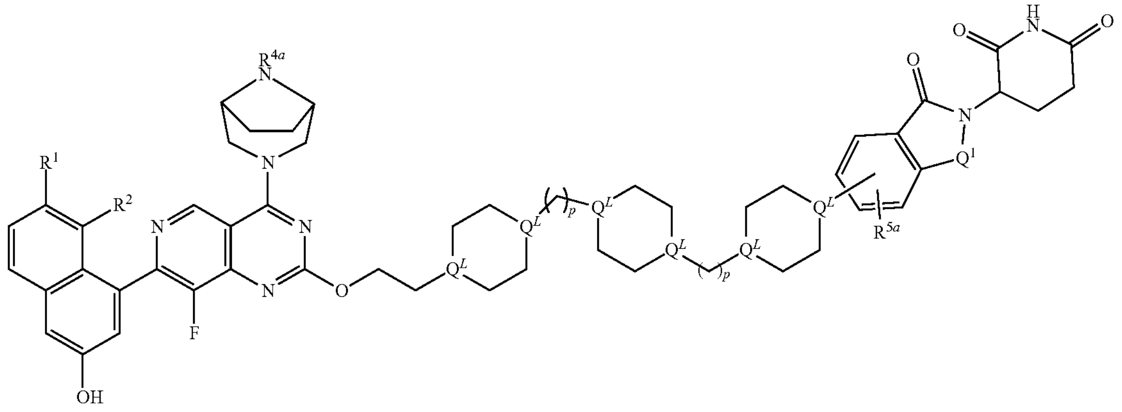

or a pharmaceutically acceptable salt thereof.

In embodiments, the compound of Formula II has a structure of Formula IIA:

(IIA)

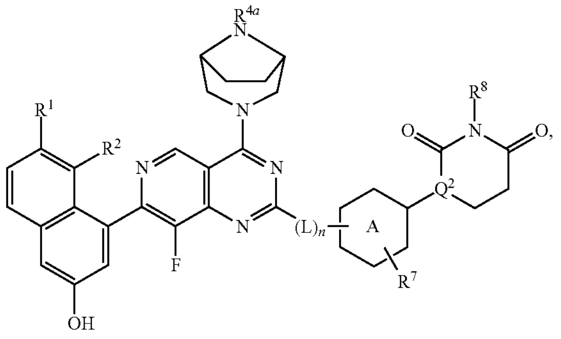

or a pharmaceutically acceptable salt thereof.

In embodiments, the compound of Formula II has a structure of Formula IIB:

(IIB)

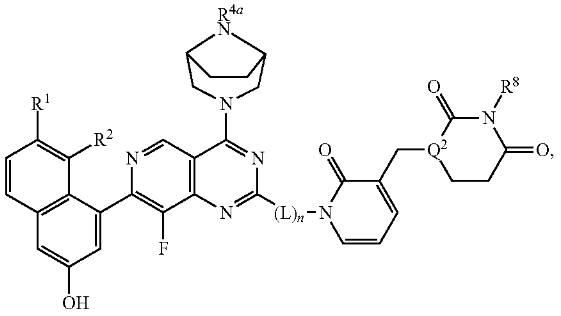

or a pharmaceutically acceptable salt thereof.

In embodiments, the compound of Formula III has a structure of Formula IIIA:

(IIIA)

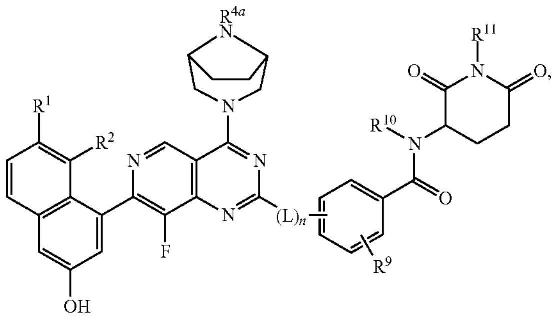

or a pharmaceutically acceptable salt thereof.

In embodiments, the compound of Formula IV has a structure of Formula IVA:

(IVA)

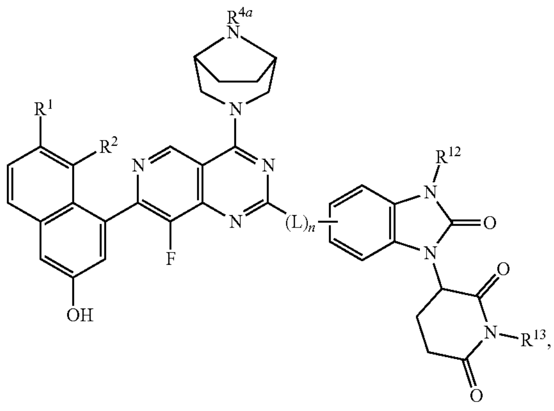

or a pharmaceutically acceptable salt thereof.

In embodiments, the compound of Formula V has a structure of Formula VA:

(VA)

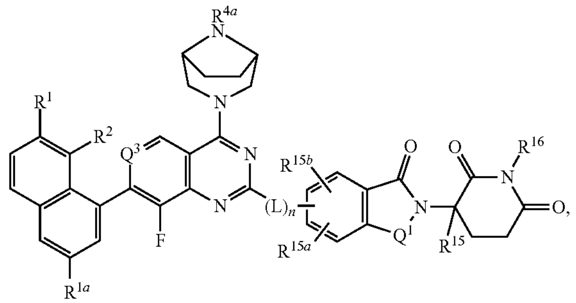

or a pharmaceutically acceptable salt thereof.

In embodiments, the compound of Formula VI has a structure of Formula VIA:

(VIA)

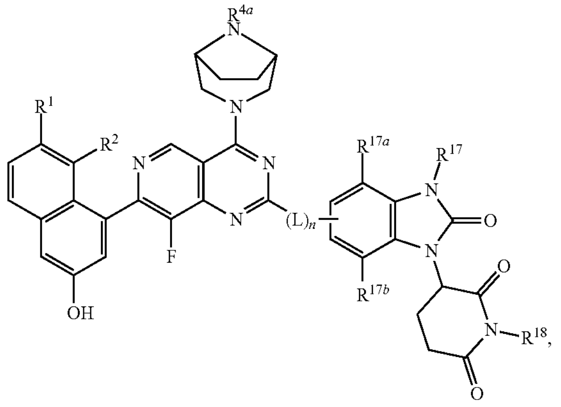

or a pharmaceutically acceptable salt thereof.

In yet another aspect, provided herein is a compound of Formula IVB:

(IVB)

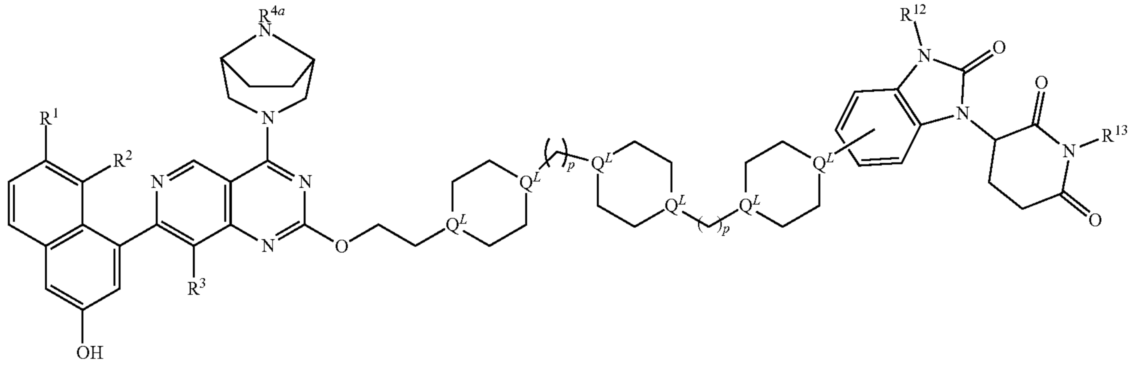

or a pharmaceutically acceptable salt thereof.

Also provided herein are methods of treating or ameliorating a disease state or condition that are modulated through or causally related to the target protein, e.g., KRas.

Additionally, provided herein are methods comprising treating a disease or disorder in a subject, comprising administering to a subject an effective amount of a compound disclosed herein, or a therapeutically effective amount of a pharmaceutical composition disclosed herein.

In embodiments, the disease or disorder is cancer.

Also provided herein are methods for regulating KRas protein activity comprising administering to a subject an effective amount of any of the compounds disclosed herein or a pharmaceutical salt thereof, or a pharmaceutical composition comprising any of the compounds disclosed herein, and a pharmaceutically acceptable carrier.

Also provided herein are methods for regulating cereblon protein activity comprising administering to a subject an effective amount of any of compounds disclosed herein or a pharmaceutical salt thereof, or a pharmaceutical composition comprising any of the compounds disclosed herein, and a pharmaceutically acceptable carrier.

Also provided herein are methods of degrading a target protein in a cell comprising contacting the cell with an effective amount of any of the compounds disclosed herein or a pharmaceutically acceptable salt thereof, or a pharmaceutical composition comprising any of the compounds disclosed herein, and a pharmaceutically acceptable carrier.

BRIEF DESCRIPTION OF THE DRAWINGS

The accompanying drawings, which are incorporated into and form a part of the specification, illustrate several embodiments of the present disclosure and, together with the description, help explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure.

pERK suppression in AsPC-1 spheroids treated with E3-inactive Compound 69 overtime.

Figure 1:
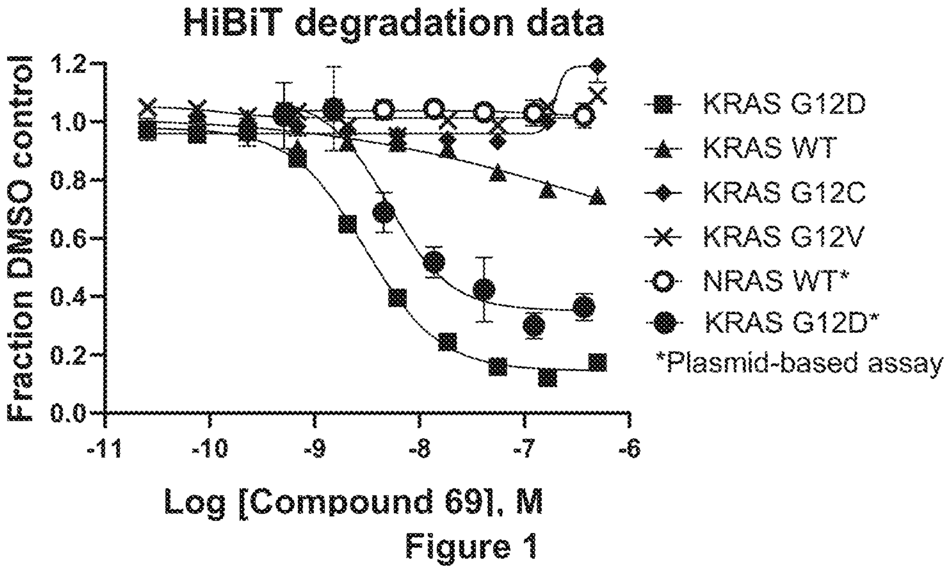
FIG. 1 illustrates the HiBiT degradation of various KRAS cells treated with Compound 69.
Figure 2:
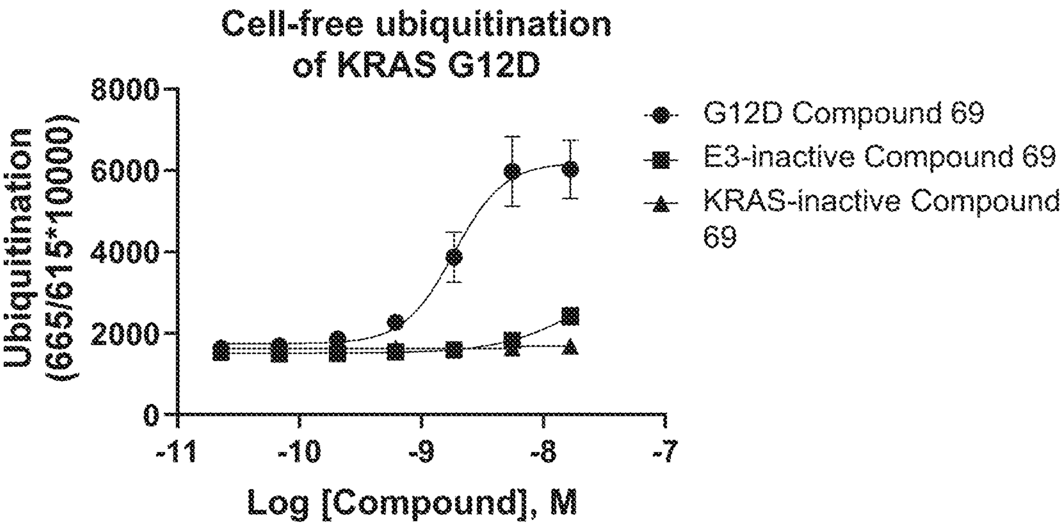
FIG. 2 illustrates the cell-free ubiquitination of KRAS G12D treated with a compound in accordance with one or more embodiments of the present disclosure.
Figure 3A:
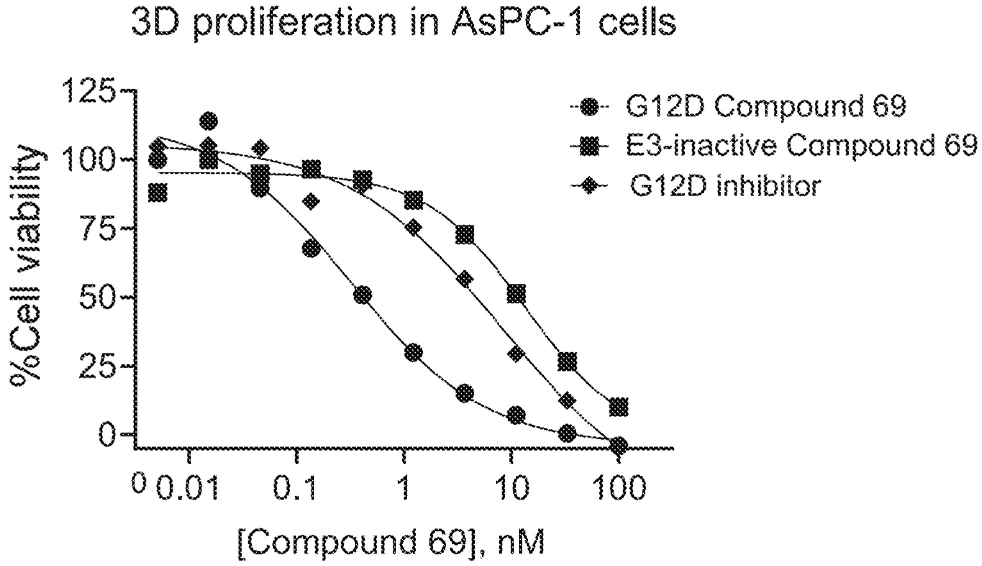
FIGS. 3A and 3B (A) Proliferation in AsPC-1 cells treated with G12D Compound 69, E3-inactive Compound 69, and a control. (B) Proliferation in various cell types treated with active Compound 69.
Figure 3B:
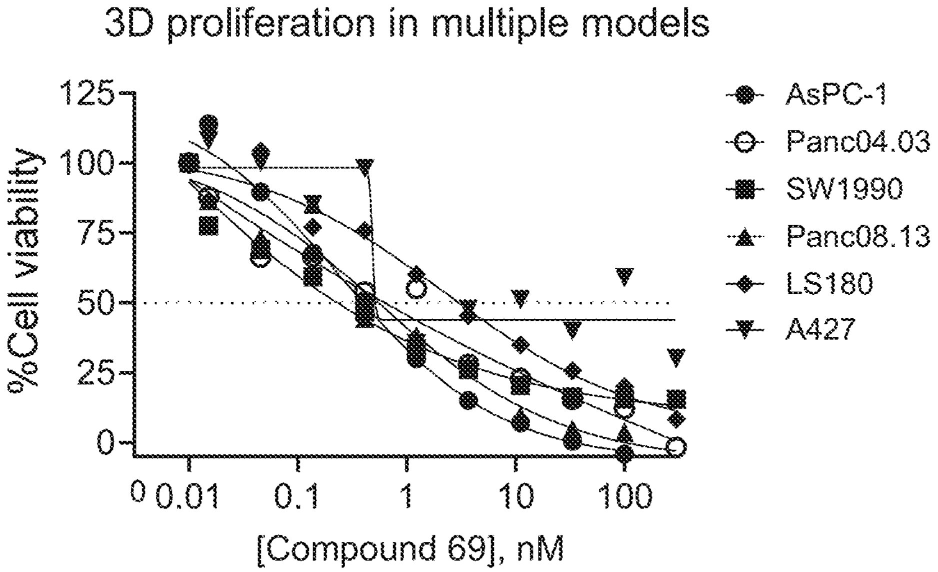
Figure 4A:
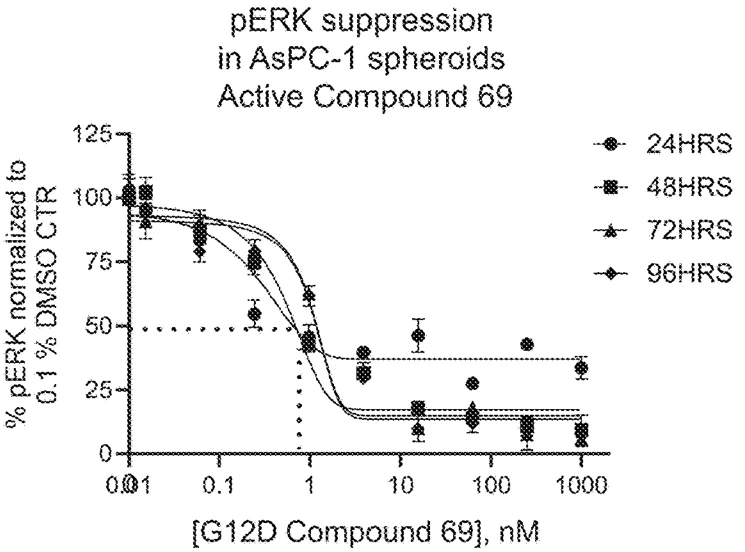
FIGS. 4A and 4B (A) pERK suppression in AsPC-1 spheroids treated with G12D Compound 69 over time. (B)
Figure 4B:
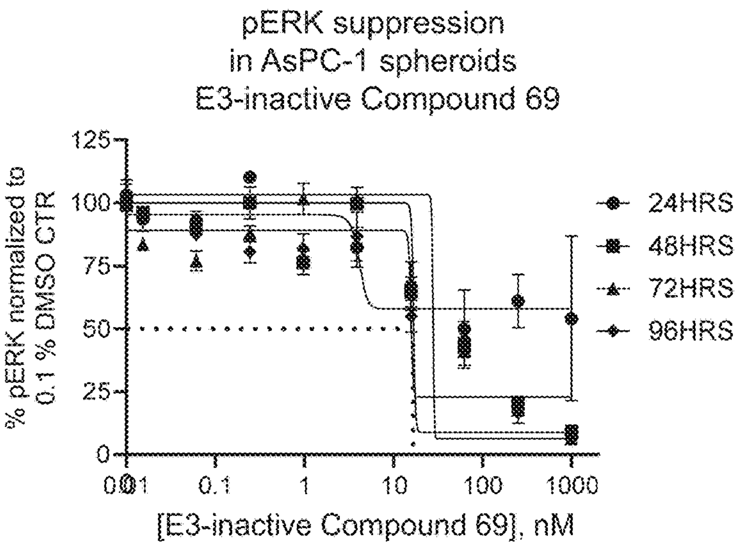
Figure 5:
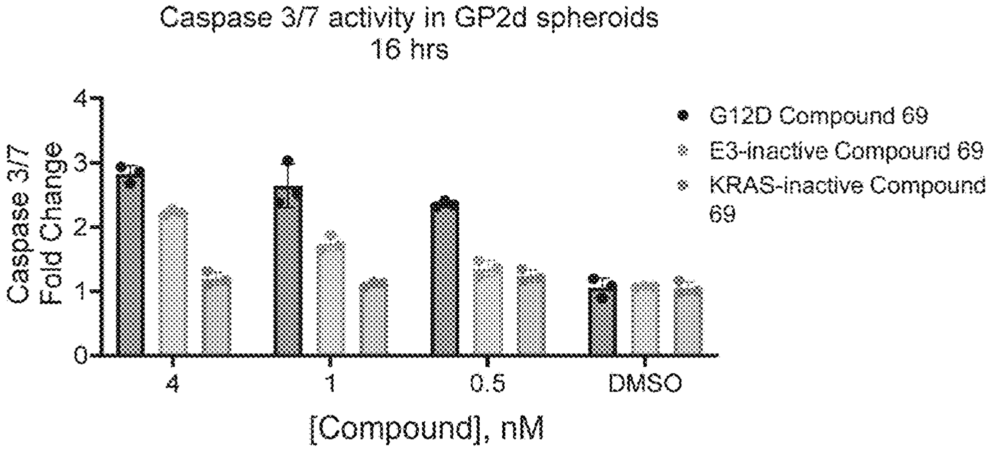

FIG. 5 illustrates caspase 3/7 activity in GP2d spheroids treated with G12D Compound 69, E3-inactive Compound 69 and KRAS-inactive Compound 69 after 16 hours.

Figure 6A:
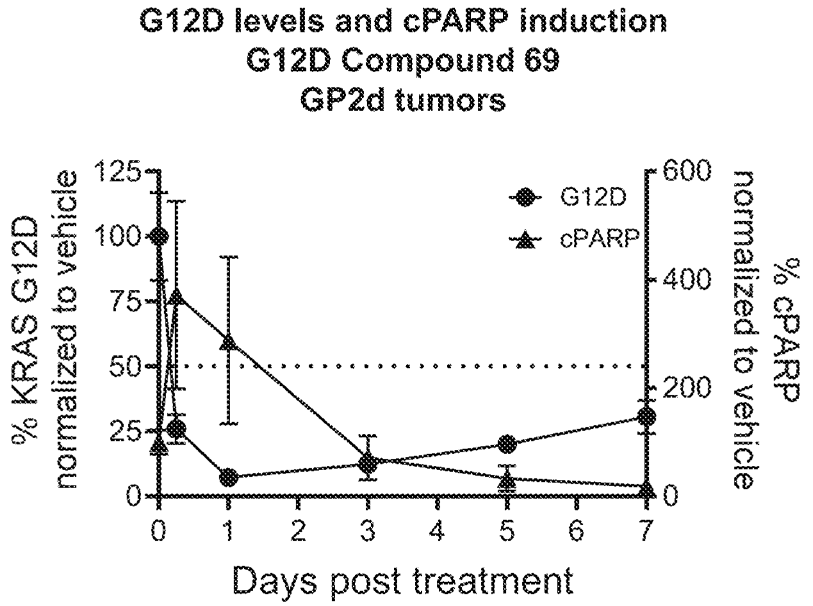
Figure 6B:
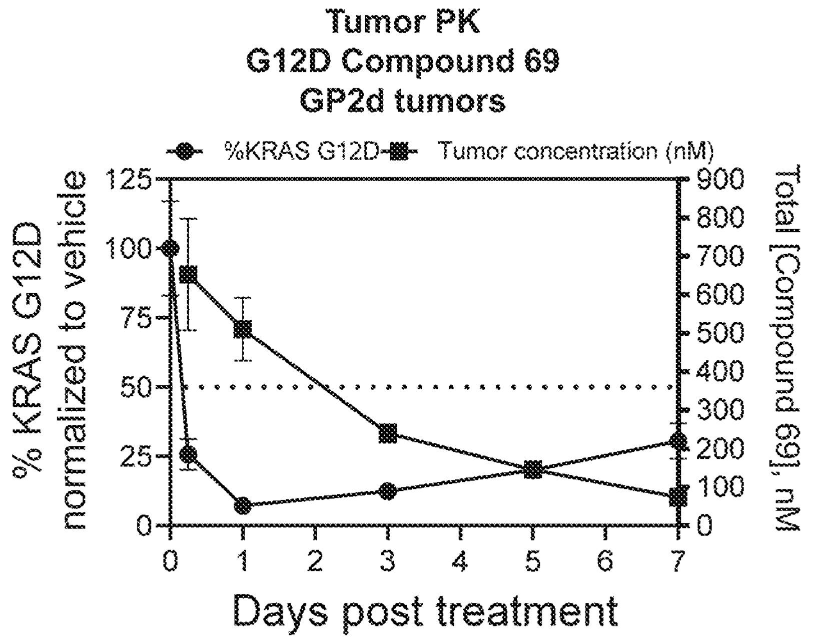

FIGS. 6A and 6B (A) KRAS levels and cPARP induction in GP2d tumors treated with a single dose of G12D Compound 69. (B) Tumor concentration and KRAS levels in GP2d tumors treated with a single dose of G12D Compound 69.

Figure 7A:
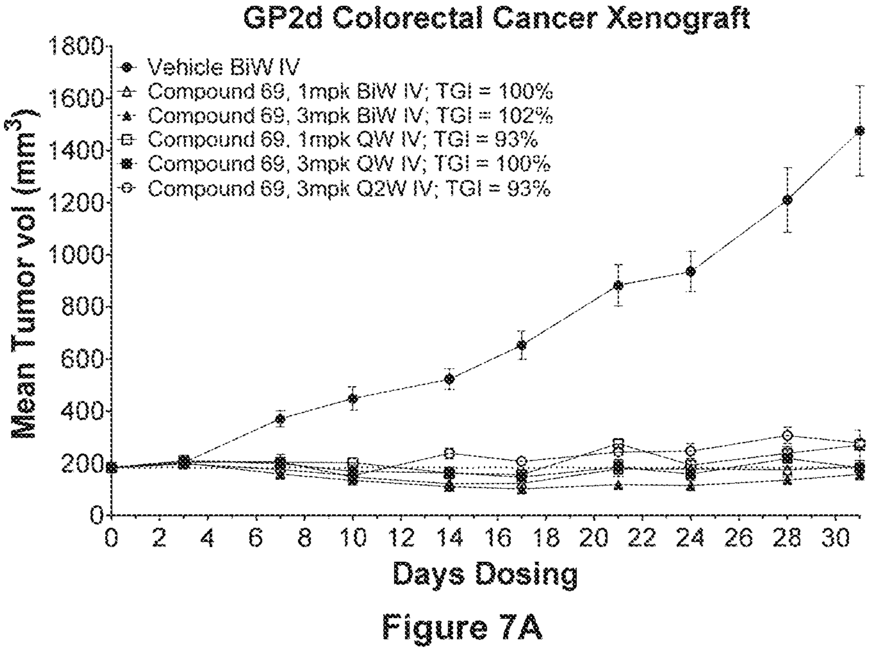
Figure 7B:
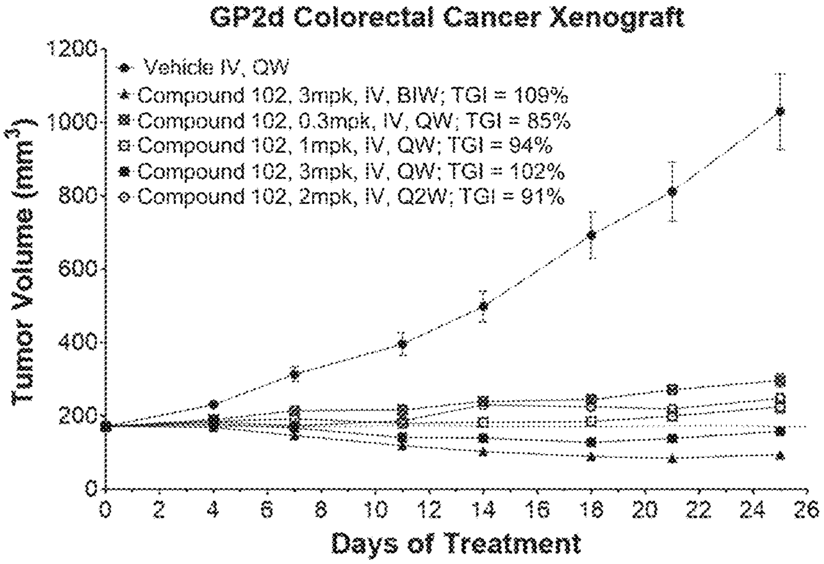

FIGS. 7A and 7B (A) is a graph of GP2d tumor growth volumes after treatment with vehicle or Compound 69. (B) XB is a graph of GP2d tumor growth volumes after treatment with vehicle or Compound 102.

Figure 8:
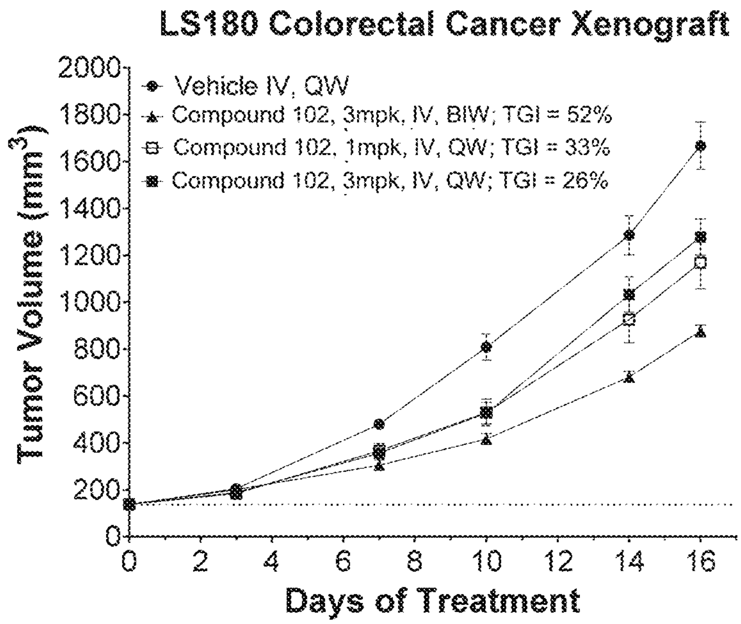

FIG. 8 is a graph of LS180 tumor growth volumes after treatment with vehicle or Compound 102.

Figure 9A:
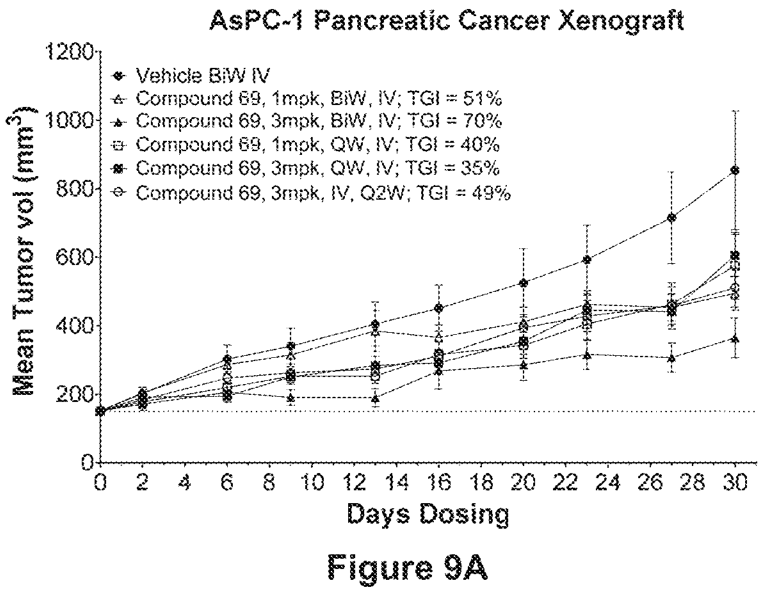
Figure 9B:
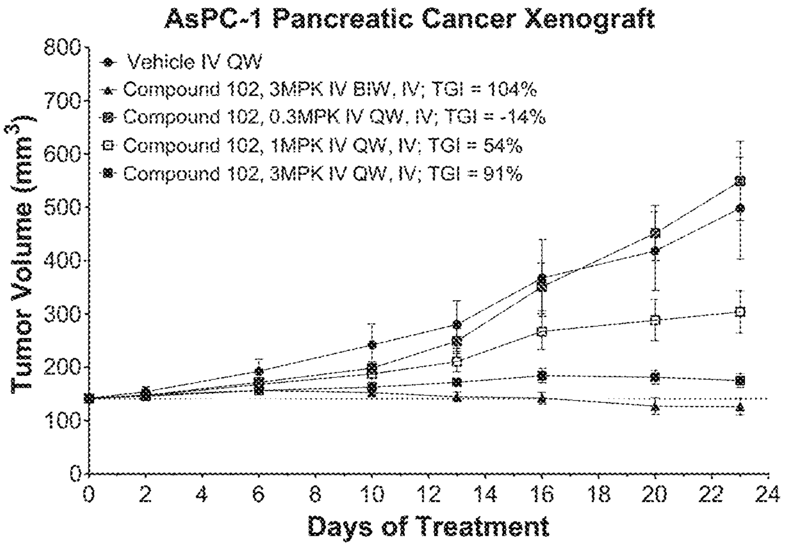

FIG. 9A and FIG. 9B (A) is a graph of AsPC-1 tumor growth volumes after treatment with vehicle or Compound 69. (B) is a graph of AsPC-1 tumor growth volumes after treatment with vehicle or Compound 102.

Figure 10A:
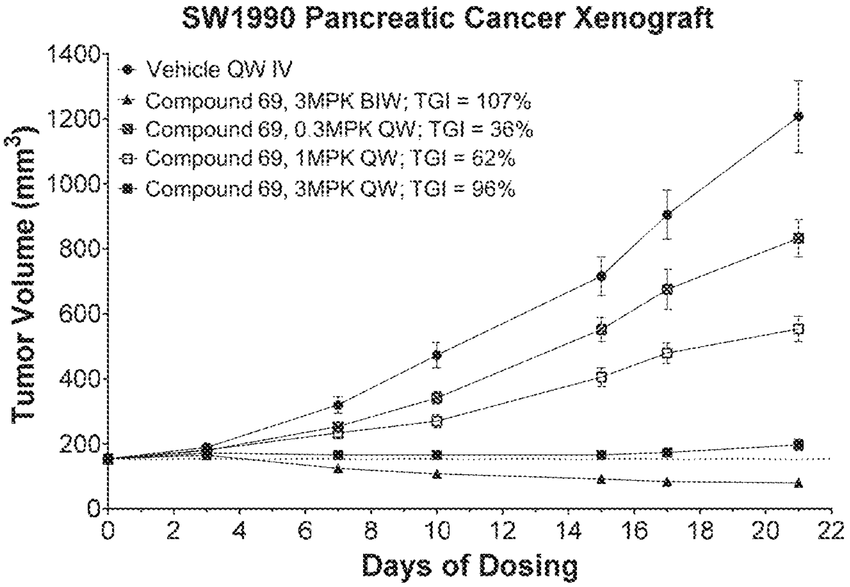
Figure 10B:
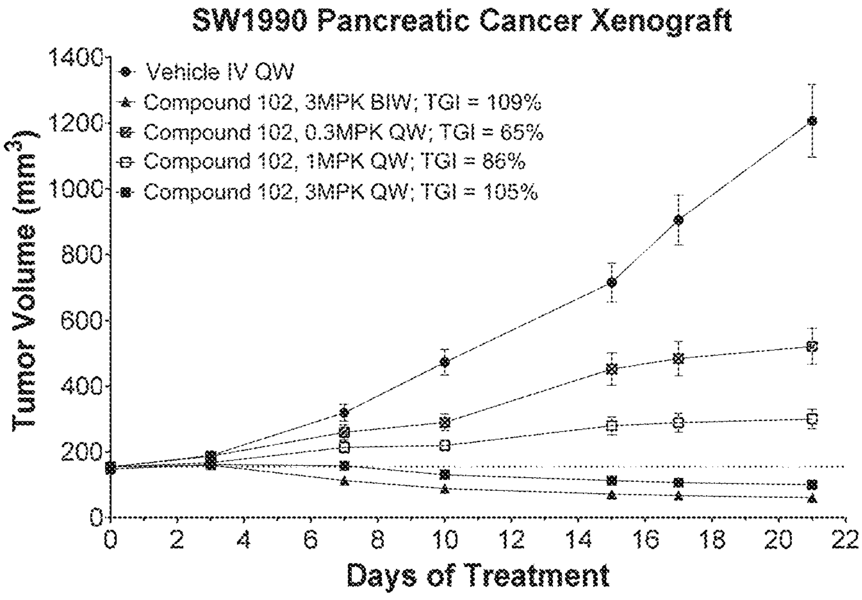

FIGS. 10A and 10B (A) is a graph of SW1990 tumor growth volumes after treatment with vehicle or Compound 69. (B) is a graph of SW1990 tumor growth volumes after treatment with vehicle or Compound 102.

Figure 11:
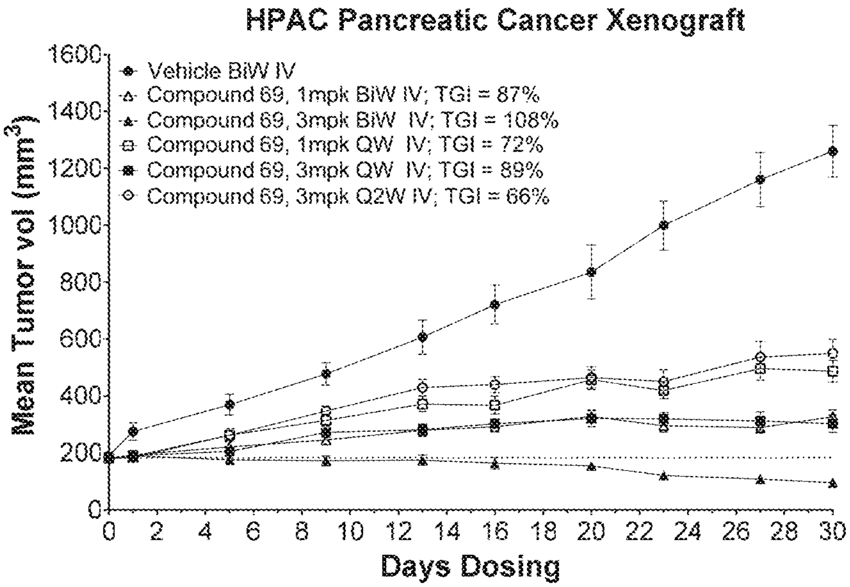

FIG. 11 is a graph of HPAC tumor growth volumes after treatment with vehicle or Compound 69.

Figure 12:
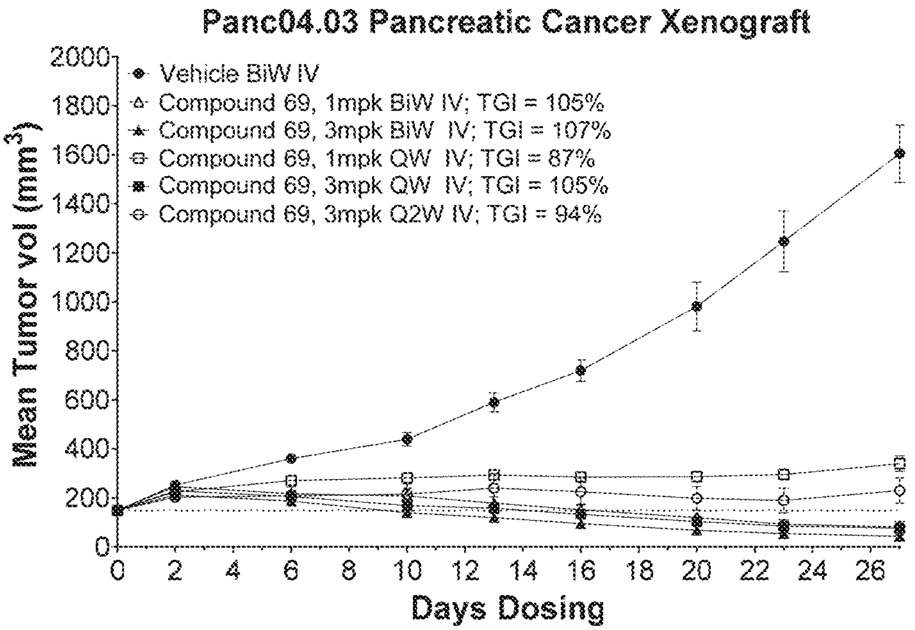

FIG. 12 is a graph of Panc04.03 tumor growth volumes after treatment with vehicle or Compound 69.

DETAILED DESCRIPTION

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

Specific compounds of the present invention may be identified in the present specification by chemical name and/or chemical structure. In the event of any conflict between the chemical name and chemical structure, the chemical structure will control.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, 1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises alleviating the symptoms of cancer.

As used herein, the term "prevent" or "prevention" means no disorder or disease development if none had occurred, or no further disorder or disease development if there had already been development of the disorder or disease. Also considered is the ability of one to prevent some or all the symptoms associated with the disorder or disease.

As used herein, the term "cell" is meant to refer to a cell that is in vitro, ex vivo, or in vivo. In embodiments, an ex vivo cell can be part of a tissue sample excised from an organism such as a mammal. In embodiments, an in vitro cell can be a cell in a cell culture. In embodiments, an in vivo cell is a cell living in an organism such as a mammal.

As used herein, the term "subject" refers to a human or a non-human mammal. Non-human mammals include, for example, livestock and pets, such as ovine, bovine, porcine, canine, feline and marine mammals. Preferably the subject is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition, or carrier, such as a liquid or solid filler, stabilizer, dispersing agent, suspending agent, diluent, excipient, thickening agent, solvent or encapsulating material, involved in carrying or transporting a compound useful within the disclosure within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure and are physiologically acceptable to the subject. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_{1-6}$ alkyl include ethyl, methyl, isopropyl, isobutyl, n-pentyl, and n-hexyl.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In embodiments, cycloalkyl refers to $C_{3-10}$ cycloalkyl. In another embodiment, cycloalkyl refers to $C_{3-6}$ cycloalkyl.

As used herein, the term "heterocycloalkyl" means a non-aromatic carbocyclic system containing 1, 2, 3, or 4 heteroatoms independently selected from N, O, and S and having 1, 2, or 3 rings wherein such rings may be fused, wherein fused is defined above. The term "heterocycloalkyl" includes unsaturated compounds such as dihydropyridinyl, dihydropyridazinyl, dihydropyrimidinyl, and dihydropyrazinyl. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1] heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In embodiments, heterocycloalkyl refers to 3-12 membered heterocycloalkyl. In embodiments, heterocycloalkyl refers to 6-12 membered heterocycloalkyl. In embodiments, heterocycloalkyl refers to 3-10 membered heterocycloalkyl. In embodiments, heterocycloalkyl refers to 6-8 membered heterocycloalkyl. In embodiments, heterocycloalkyl refers to 6-membered heterocycloalkyl. In embodiments, heterocycloalkyl refers to 7-membered heterocycloalkyl. In embodiments, heterocycloalkyl refers to 9-membered heterocycloalkyl. In embodiments, heterocycloalkyl refers to 9-membered heterocycloalkyl.

A 6-membered heterocycloalkyl ring is a heteroaryl group having six ring atoms wherein one or more (e.g., 1, 2, or 3) ring atoms are independently selected from N, O, and S.

Exemplary 6-membered ring heterocycloalkyls include piperidinyl, piperazinyl, dioxanyl thianyl, dithianyl, morpholinyl, thiomorpholinyl, and dihydropyridinyl.

A 7-membered heterocycloalkyl ring is a heteroaryl group having seven ring atoms wherein one or more (e.g., 1, 2 or 3) ring atoms are independently selected from N, O and S.

Exemplary 7-membered ring heterocycloalkyls include azepinyl, oxepanyl, thiepanyl, oxathiepanyl, diazaspiro[3.3]heptanyl, and azaspiro[3.3]heptanyl.

A 9-membered heterocycloalkyl ring is a heterocycloalkyl group having nine ring atoms wherein one or more (e.g., 1, 2 or 3) ring atoms are independently selected from N, O and S. Exemplary 9-membered ring heterocycloalkyls are 2-azaspiro[3.5]nonanyl and 2,7-diazaspiro[3.5]nonanyl.

An 11-membered heterocycloalkyl ring is a heteroaryl group having eleven ring atoms wherein one or more (e.g., 1, 2, or 3) ring atoms are independently selected from N, O and S.

Exemplary 11-membered ring heterocycloalkyls include 3,9-diazaspiro[5.5]undecanyl and 3-azaspiro[5.5]undecanyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated, or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In embodiments, aryl groups have from six to ten carbon atoms. In embodiments, aryl groups have from six to sixteen carbon atoms. In embodiments, the aryl group has six to ten carbon atoms.

As used herein, the term "heteroaryl" means an aromatic carbocyclic system containing 1, 2, 3, or 4 heteroatoms independently selected from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In embodiment, heteroaryl is 5-10 membered heteroaryl. In embodiments, heteroaryl is 5-7 membered heteroaryl. In embodiments, heteroaryl is 6-7 membered heteroaryl. In embodiments, heteroaryl is 6-membered heteroaryl.

A 5-membered heteroaryl ring is a heteroaryl group having five ring atoms wherein one or more (e.g., 1, 2, or 3) ring atoms are independently selected from N, O and S. Exemplary 5-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A 6-membered heteroaryl ring is a heteroaryl group having six ring atoms wherein one or more (e.g., 1, 2, or 3) ring atoms are independently selected from N, O, and S. Exemplary 6-membered ring heteroaryls are pyridyl, pyrazinyl, pyrimidinyl, triazinyl, isoindolyl, and pyridazinyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

The term "independently selected" is used herein to indicate that, for a variable which occurs in more than one location in a genus, the identity of the variable is determined separately in each instance. For example, if $R^x$ appears as a substituent on two different atoms, the two instances of $R^x$ may be the same moiety, or different moieties. The same is true if a single atom is substituted with more than one instance of $R^x$. The identity of $R^x$ in each instance is determined independently of the identity of the other(s).

Compounds

Provided herein are compounds that target Kras and are thus useful in the treatment of cancer.

In particular, provided herein are compounds of any one of Formula I-IV:

(I)

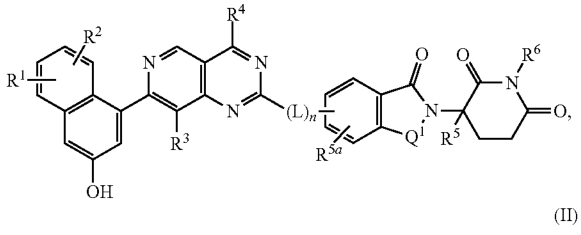

(II)

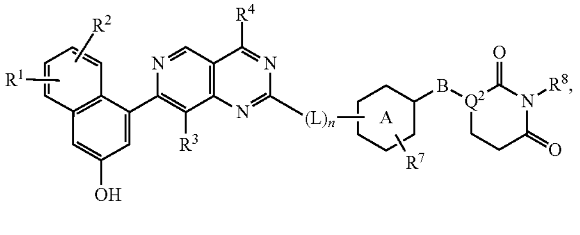

-continued (III)

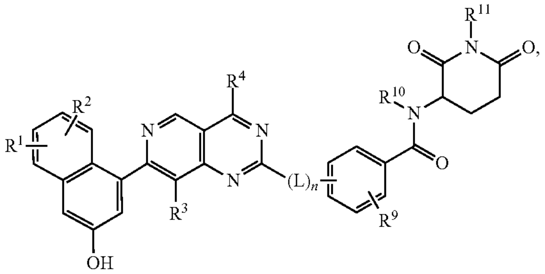

or (IV)

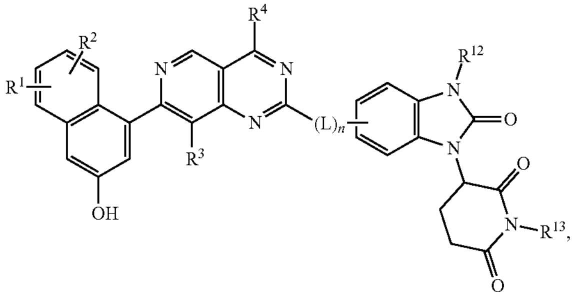

or a pharmaceutically acceptable salt thereof, wherein:

$Q^1$ is selected from $C(R^{14})_2$, C(O), and $NR^{14}$;

$Q^2$ is $CR^{14}$ or N;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with $R^{4a}$;

$R^{4a}$ is selected from H, $C_{1-6}$ alkyl, $C_{1-6}$ alkoxy, and $C_{1-6}$ haloalkyl;

$R^{5a}$, $R^5$, $R^6$, $R^8$, $R^{10}$, $R^{11}$, $R^{12}$, $R^{13}$, and $R^{14}$ are each independently selected from H, halo, $C_{1-6}$ alkyl, $C_{1-6}$ alkoxy, and $C_{1-6}$ haloalkyl;

$R^7$ is selected from H, =O, halo, $C_{1-6}$ alkyl, $C_{1-6}$ alkoxy, and $C_{1-6}$ haloalkyl;

$R^9$ is selected from H, halo, $C_{1-6}$ alkyl, and $C_{1-6}$ alkoxy;

Ring A is selected from phenyl, 6-membered heteroaryl, $C_6$ cycloalkyl, and 6-membered heterocycloalkyl;

B is a bond or $C_{1-6}$ alkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10. In embodiments of Formulae I-IV, $Q^1$ is $C(R^{14})_2$ or C(O);

$Q^2$ is N;

$R^1$ and $R^2$ are each independently selected from H, halo, $C_{1-6}$ alkyl, $C_{2-6}$ alkenyl, and $C_{2-6}$ alkynyl;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{5a}$, $R^5$, $R^6$, $R^8$, $R^{10}$, $R^{11}$, $R^{12}$, $R^{13}$, and $R^{14}$ are each independently selected from H, halo, $C_{1-6}$ alkyl, and $C_{1-6}$ alkoxy;

$R^7$ is selected from H, =O, halo, $C_{1-6}$ alkyl, and $C_{1-6}$ alkoxy;

$R^9$ is selected from H, halo, $C_{1-6}$ alkyl, and $C_{1-6}$ alkoxy;

Ring A is selected from phenyl, 6-membered heteroaryl, and 6-membered heterocycloalkyl;

B is a bond or $C_{1-6}$ alkyl;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formulae I-IV, $Q^1$ is $C(R^{14})_2$ or C(O);

$Q^2$ is N;

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{5a}$, $R^5$, $R^6$, $R^8$, $R^{10}$, $R^{11}$, $R^{12}$, $R^{13}$, and $R^{14}$ are each independently selected from H, halo, $C_{1-6}$ alkyl, and $C_{1-6}$ alkoxy;

$R^7$ is selected from H, =O, halo, $C_{1-6}$ alkyl, and $C_{1-6}$ alkoxy;

$R^9$ is selected from H, halo, $C_{1-6}$ alkyl, and $C_{1-6}$ alkoxy;

Ring A is phenyl or 6-membered heterocycloalkyl;

B is a bond or $C_{1-6}$ alkyl;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In an embodiment, the compound has a structure of Formula I, (I)

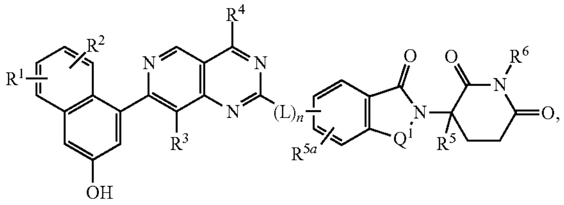

or a pharmaceutically acceptable salt thereof, wherein:

$Q^1$ is $C(R^{14})_2$ or C(O);

$R^1$ and $R^2$ are each independently selected from halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In another embodiment, the compound has a structure of Formula II, (II)

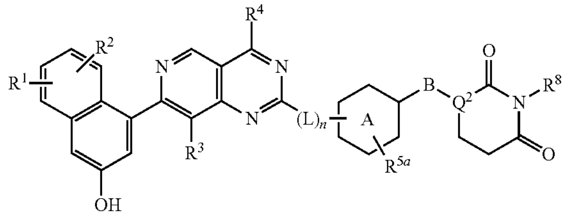

or a pharmaceutically acceptable salt thereof, wherein:

$Q^2$ is N;

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^8$ and $R^{14}$ are each independently selected from H, halo, $C_{1-6}$ alkyl, and $C_{1-6}$ alkoxy;

$R^7$ is selected from H, =O, halo, $C_{1-6}$ alkyl, and $C_{1-6}$ alkoxy;

Ring A is phenyl or 6-membered heterocycloalkyl;

B is a bond or $C_{1-6}$ alkyl;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In yet another embodiment, the compound has a structure of Formula III, (III)

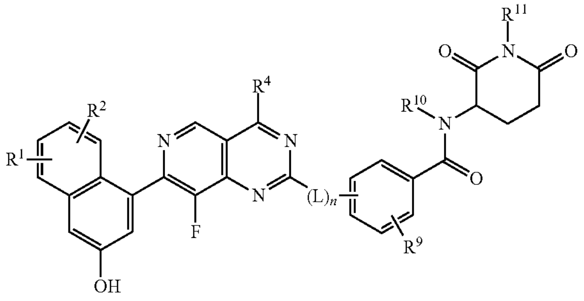

or a pharmaceutically acceptable salt thereof, wherein:

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{10}$ and $R^{11}$ are each independently selected from H, halo, $C_{1-6}$ alkyl, and $C_{1-6}$ alkoxy;

$R^9$ is selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In still another embodiment, the compound has a structure of Formula IV, (IV)

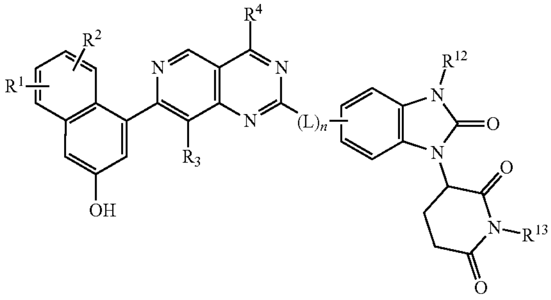

or a pharmaceutically acceptable salt thereof, wherein:

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{12}$ and $R^{13}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6. Also provided herein are compounds of Formula V and VI:

(V)

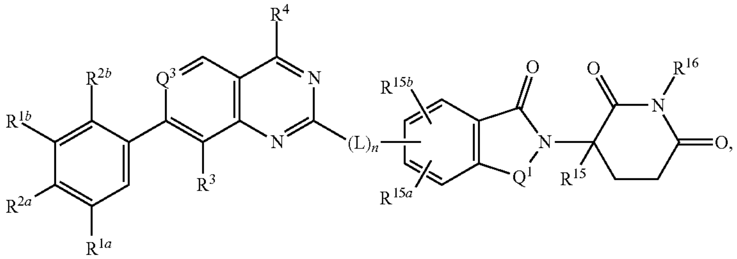

and (VI)

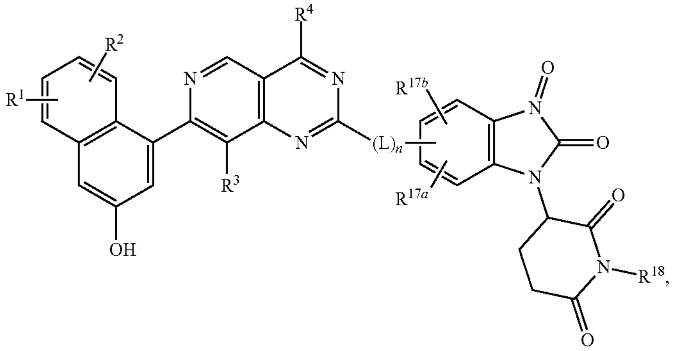

or a pharmaceutically acceptable salt thereof, wherein:

$Q^1$ is selected from $C(R^{14})_2$, C(O), and $NR^{14}$;

$Q^3$ is $CR^{14}$ or N;

$R^{1a}$ and $R^{2a}$ are each independently selected from OH, H, and halo;

$R^{1b}$ and $R^{2b}$ are each independently selected from halo and $C_{3-6}$ cycloalkyl, or $R^{1b}$ and $R^{2b}$, together with the phenyl to which they attach, form $C_{8-12}$ aryl, wherein $C_{8-12}$ aryl is optionally substituted with $R^1$ and $R^2$;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with 1 or 2 $R^{4a}$;

each $R^{4a}$ is independently selected from H, OH, $C_{1-6}$ alkyl, $C_{1-6}$ alkoxy, and $C_{1-6}$ haloalkyl;

$R^{14}$, $R^{15a}$, $R^{15b}$, $R^{15}$, $R^{16}$, $R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, 8, 9, or 10.

In an embodiment, the compound has a structure of Formula V, (V)

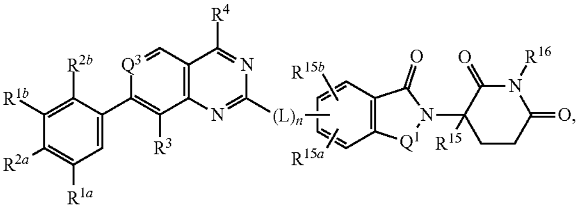

or a pharmaceutically acceptable salt thereof, wherein:

$Q^1$ is $C(R^{14})_2$ or C(O);

$Q^3$ is CH or N;

$R^{1a}$ and $R^{2a}$ are each independently selected from H, OH, and halo;

$R^{1b}$ and $R^{2b}$, together with the phenyl to which they attach, form naphthyl substituted with $R^1$ and $R^2$;

$R^1$ and $R^2$ are each independently selected from H, halo, $C_{1-3}$ alkyl, $C_{3-5}$ cycloalkyl and C≡CH;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with 1 or 2 $R^{4a}$; each $R^{4a}$ is independently selected from H, OH, and $C_{1-6}$ alkyl;

$R^{14}$, $R^{15}$, and $R^{16}$ are each independently selected from H, halo, $C_{1-3}$ alkyl, and $C_{1-3}$ alkoxy;

$R^{15a}$ and $R^{15b}$ are each independently selected from halo, $C_{1-3}$ alkyl, and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In another embodiment, the compound has a structure of Formula VI, (VI)

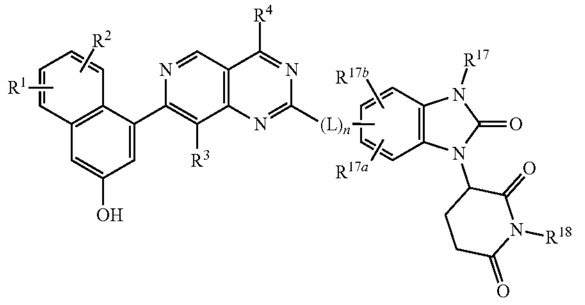

or a pharmaceutically acceptable salt thereof,
wherein:

$R^1$ and $R^2$ are each independently selected from H, halo, $C_{1-3}$ alkyl, $C_{3-5}$ cycloalkyl, and $C{\equiv}CH$;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with 1 or 2 $R^{4a}$;

each $R^{4a}$ is independently selected from H, OH, and $C_{1-6}$ alkyl;

$R^{17a}$, $R^{17b}$, $R^{17}$, and $R^{18}$ are each independently selected from H, halo, $C_{1-3}$ alkyl, and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

wherein:

$Q^1$ is selected from $C(R^{14})_2$, C(O), and $NR^{14}$;

$Q^2$ is $CR^{14}$ or N;

$R^1$ and $R^2$ are each independently halo or $C_{2-6}$ alkynyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with $R^{4a}$;

$R^{4a}$ is selected from H, $C_{1-6}$ alkyl, $C_{1-6}$ alkoxy, and $C_{1-6}$ haloalkyl;

$R^{5a}$, $R^5$, $R^6$, $R^{12}$, $R^{13}$, and $R^{14}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In an aspect, provided herein is a compound of Formula AI or AIV:

(AI)

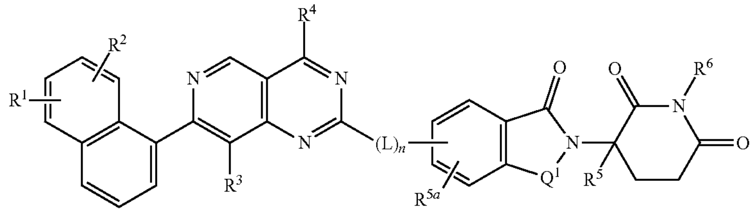

or (AIV)

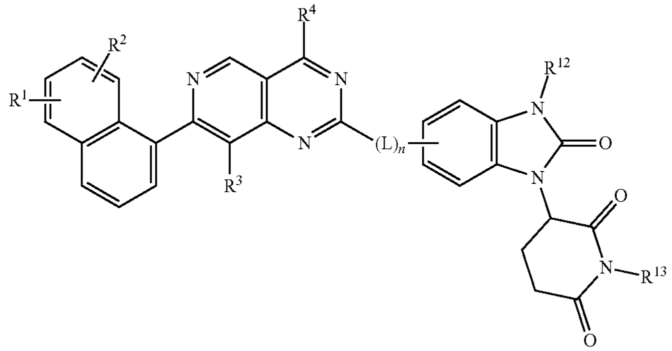

or a pharmaceutically acceptable salt thereof,

In another aspect, provided herein is a compound of Formula VII:

(VII)

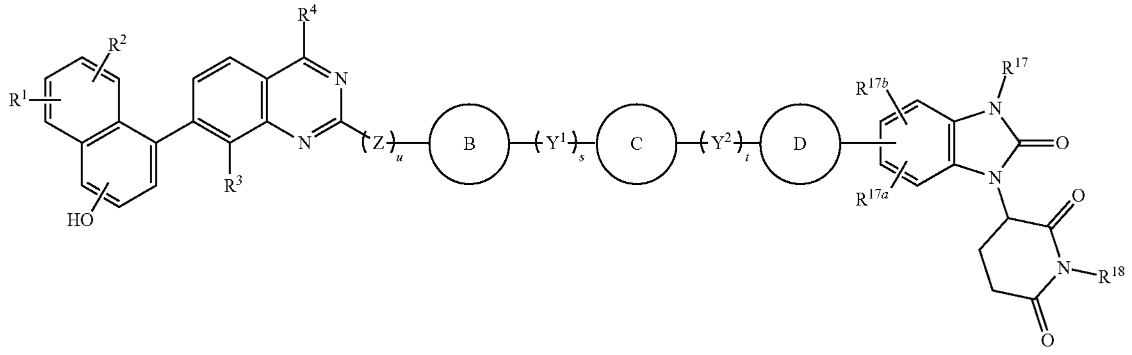

or a pharmaceutically acceptable salt thereof, wherein:

Ring B and Ring C are each independently selected from 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl;

Ring D is selected from a bond, $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl, provided that when Ring D is a bond, then $Y^2$ is also a bond and t is 0;

$Y^1$ and $Y^2$ are each independently selected from a bond, O, C(O), N(H), N($C_{1-6}$ alkyl), $C_{1-6}$ alkyl, $C_{1-6}$ haloalkyl, and $C_{1-6}$ alkoxy;

Z is selected from N(H), N($C_{1-6}$ alkyl), $C_{1-6}$ alkyl, $C_{1-6}$ haloalkyl, and $C_{1-6}$ alkoxy;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with $R^{4a}$;

$R^{4a}$ is selected from H, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

s and t are each independently 0, 1, 2, or 3; and u is 1 or 2.

In embodiments of Formula I-VI:

$Q^1$ is $C(R^{14})_2$ or C(O);

$Q^2$ is N;

$Q^3$ is $CR^{14}$ or N;

$R^{1a}$ and $R^{2a}$ are each independently selected from OH, H, and halo;

$R^{1b}$ and $R^{2b}$, together with the phenyl to which they attach, form $C_{8-12}$ aryl, wherein the $C_{8-12}$ aryl is optionally substituted with $R^1$ and $R^2$;

$R^1$ and $R^2$ are each independently selected from H, halo, $C_{1-6}$ alkyl, $C_{3-6}$ cycloalkyl, $C_{2-6}$ alkenyl, and $C_{2-6}$ alkynyl;

$R^3$ is selected from H, halo, and CN;

$R^4$ is selected from $C_{3-11}$ cycloalkyl and 3-10 membered heterocycloalkyl, wherein $C_{3-11}$ cycloalkyl and 3-10 membered heterocycloalkyl are optionally substituted with 1 or 2 $R^{4a}$;

each $R^{4a}$ is independently selected from H, OH, and $C_{1-6}$ alkyl;

$R^{5a}$, $R^5$, $R^6$, $R^8$, $R^{10}$, $R^{11}$, $R^{12}$, $R^{13}$, $R^{14}$, $R^{15a}$, $R^{15b}$, $R^{15}$, $R^{16}$, $R^{17a}$, $R^{17b}$, $R^{17}$, and $R^{18}$ are each independently selected from H, halo, $C_{1-6}$ alkyl and $C_{1-6}$ alkoxy;

$R^7$ is selected from H, =O, halo, $C_{1-6}$ alkyl, and $C_{1-6}$ alkoxy;

$R^9$ is selected from H, halo, $C_{1-6}$ alkyl, and $C_{1-6}$ alkoxy;

Ring A is selected from phenyl, 6-membered heteroaryl, and 6-membered heterocycloalkyl;

B is a bond or $C_{1-6}$ alkyl;

each L is independently selected from $C_{1-6}$ alkyl, $C_{1-6}$ haloalkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula I-VI:

$Q^1$ is $C(R^{14})_2$ or C(O);

$Q^2$ is N;

$Q^3$ is $CR^{14}$ or N;

$R^{1a}$ and $R^{2a}$ are each independently selected from H, OH, and halo;

$R^{1b}$ and $R^{2b}$, together with the phenyl to which they attach, form naphthyl substituted with $R^1$ and $R^2$;

$R^1$ and $R^2$ are each independently selected from H, halo, $C_{1-3}$ alkyl, $C_{3-5}$ cycloalkyl and C≡CH;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with 1 or 2 $R^{4a}$;

each $R^{4a}$ is independently selected from H, OH, and $C_{1-6}$ alkyl;

$R^{5a}$, $R^5$, $R^6$, $R^8$, $R^{10}$, $R^{11}$, $R^{12}$, $R^{13}$, $R^{14}$, $R^{15a}$, $R^{15b}$, $R^{15}$, $R^{16}$, $R^{17a}$, $R^{17b}$, $R^{17}$, and $R^{18}$ are each independently selected from H, halo, $C_{1-3}$ alkyl and $C_{1-3}$ alkoxy;

$R^7$ is selected from H, =O, halo, $C_{1-6}$ alkyl, and $C_{1-6}$ alkoxy;

$R^9$ is selected from H, halo, $C_{1-6}$ alkyl, and $C_{1-6}$ alkoxy;

Ring A is phenyl or 6-membered heterocycloalkyl;

B is a bond or $C_{1-6}$ alkyl;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments of Formula I, $Q^1$ is $C(R^{14})_2$ or C(O);

$R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula I, $Q^1$ is $C(R^{14})_2$ or C(O);

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments of Formula II, $Q^2$ is N;

$R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^7$ is selected from H, =O, halo, $C_{1-6}$ alkyl, and $C_{1-6}$ alkoxy;

$R^8$ is selected from H, $C_{1-6}$ alkyl, and $C_{1-6}$ alkoxy;

Ring A is selected from phenyl, 6-membered heteroaryl, and 6-membered heterocycloalkyl;

B is a bond or $C_{1-6}$ alkyl;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula II, $Q^2$ is N;

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^7$ is selected from H, =O, halo, $C_{1-6}$ alkyl, and $C_{1-6}$ alkoxy;

$R^8$ is selected from H, $C_{1-6}$ alkyl, and $C_{1-6}$ alkoxy;

Ring A is phenyl or 6-membered heterocycloalkyl;

B is a bond or $C_{1-6}$ alkyl;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments of Formula III, $R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^9$ is selected from H, halo, $C_{1-6}$ alkyl, and $C_{1-6}$ alkoxy;

$R^{10}$ and $R^{11}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula III, $R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^9$ is selected from H, halo, $C_{1-6}$ alkyl, and $C_{1-6}$ alkoxy;

$R^{10}$ and $R^{11}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments of Formula IV, $R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IV, $R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments of Formula IV:

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{12}$ and $R^{13}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments of Formula V:

$Q^1$ is $C(R^{14})_2$ or C(O);

$Q^3$ is $CR^{14}$ or N;

$R^{1a}$ and $R^{2a}$ are each independently selected from OH, H, and halo;

$R^{1b}$ and $R^{2b}$, together with the phenyl to which they attach, form $C_{8-12}$ aryl, wherein the $C_{8-12}$ aryl is optionally substituted with $R^1$ and $R^2$;

$R^1$ and $R^2$ are each independently selected from H, halo, $C_{1-6}$ alkyl, $C_{3-6}$ cycloalkyl, $C_{2-6}$ alkenyl, and $C_{2-6}$ alkynyl;

$R^3$ is selected from H, halo, and CN;

$R^4$ is selected from $C_{3-11}$ cycloalkyl and 3-10 membered heterocycloalkyl, wherein $C_{3-11}$ cycloalkyl and 3-10 membered heterocycloalkyl are optionally substituted with 1 or 2 $R^{4a}$;

each $R^{4a}$ is independently selected from H, OH, and $C_{1-6}$ alkyl;

$R^{14}$, $R^{15a}$, $R^{15b}$, $R^{15}$, and $R^{16}$, are each independently selected from H, halo, $C_{1-6}$ alkyl and $C_{1-6}$ alkoxy;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, or 8.

In embodiments of Formula V:

$Q^1$ is $C(R^{14})_2$ or C(O);

$Q^3$ is CH or N;

$R^{1a}$ and $R^{2a}$ are each independently selected from H, OH, and halo;

$R^{1b}$ and $R^{2b}$, together with the phenyl to which they attach, form naphthyl substituted with $R^1$ and $R^2$;

$R^1$ and $R^2$ are each independently selected from H, halo, $C_{1-3}$ alkyl, $C_{3-5}$ cycloalkyl and C≡CH;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with 1 or 2 $R^{4a}$;

each $R^{4a}$ is independently selected from H, OH, and $C_{1-6}$ alkyl;

$R^{14}$, $R^{15a}$, $R^{15b}$, $R^{15}$, and $R^{16}$, are each independently selected from H, halo, $C_{1-6}$ alkyl and $C_{1-6}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 5-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In embodiments of Formula VI:

$R^1$ and $R^2$ are each independently selected from H, halo, $C_{1-6}$ alkyl, $C_{3-6}$ cycloalkyl, $C_{2-6}$ alkenyl, and $C_{2-6}$ alkynyl;

$R^3$ is selected from H, halo, and CN;

$R^4$ is selected from $C_{3-11}$ cycloalkyl and 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{17a}$, $R^{17b}$, $R^{17}$, and $R^{18}$ are each independently selected from H, halo, $C_{1-6}$ alkyl and $C_{1-6}$ alkoxy;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, or 8.

In embodiments of Formula VI:

$R^1$ and $R^2$ are each independently selected from H, halo, $C_{1-3}$ alkyl, and C≡CH;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{17a}$, $R^{17b}$, $R^{17}$, and $R^{18}$ are each independently selected from H, halo, $C_{1-3}$ alkyl and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 5-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In embodiments of Formula VI:

$R^1$ and $R^2$ are each independently selected from H, halo, $C_{1-3}$ alkyl, $C_{3-5}$ cycloalkyl, and C≡CH;

$R^3$ is H or halo;

$R^4$ is selected from $C_{6-8}$ cycloalkyl and 6-8 membered heterocycloalkyl, wherein $C_{6-8}$ cycloalkyl and 6-8 membered heterocycloalkyl are optionally substituted with 1 or 2 $R^{4a}$;

each $R^{4a}$ is independently selected from H, OH, and $C_{1-6}$ alkyl;

$R^{17a}$, $R^{17b}$, $R^{17}$, and $R^{18}$ are each independently selected from H, halo, $C_{1-3}$ alkyl, and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), 5-12 membered heterocycloalkyl, and 6-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In embodiments of Formula AI, $Q^1$ is $C(R^{14})_2$ or C(O);

$R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula AI, $Q^1$ is $C(R^{14})_2$ or C(O);

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments of Formula AIV, $R^1$ and $R^2$ are each independently selected from H, halo, $C_{1-6}$ alkyl, and C≡CH;

$R^3$ is selected from H, halo, and CN;

$R^4$ is $C_{3-11}$ cycloalkyl or 3-10 membered heterocycloalkyl, wherein $C_{3-11}$ cycloalkyl and 3-10 membered heterocycloalkyl are optionally substituted with $R^{4a}$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula AIV, $R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments of Formula AIV:

$R^1$ and $R^2$ are each independently selected from H, halo, $C_{1-6}$ alkyl, and C≡CH;

$R^3$ is selected from H, halo, and CN;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^{12}$ and $R^{13}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments of Formula VII, Ring B and Ring C are each independently selected from 3-6 membered heterocycloalkyl and 5- or 6-membered heteroaryl, wherein 3-6 membered heterocycloalkyl is optionally substituted with halo, CN, and $C_{1-6}$ alkyl;

Ring D is selected from a bond, 3-6 membered heterocycloalkyl, and 5- or 6-membered heteroaryl, wherein 3-6 membered heterocycloalkyl is optionally substituted with halo, CN, and $C_{1-6}$ alkyl, provided that when Ring D is a bond, then $Y^2$ is also a bond and t is 0;

$Y^1$ and $Y^2$ are each independently selected from a bond, O, C(O), N(H), N($C_{1-6}$ alkyl), $C_{1-6}$ alkyl, $C_{1-6}$ haloalkyl, and $C_{1-6}$ alkoxy;

Z is selected from N(H), N($C_{1-6}$ alkyl), $C_{1-6}$ alkyl, $C_{1-6}$ haloalkyl, and $C_{1-6}$ alkoxy;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is 6-8 membered heterocycloalkyl, optionally substituted with $R^{4a}$;

$R^{4a}$ is selected from H, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

s and t are each independently 0, 1, 2, or 3; and u is 1 or 2.

In embodiments of Formula VII, Ring B and Ring C are each independently 3-6 membered heterocycloalkyl optionally substituted with halo, CN, and $C_{1-6}$ alkyl;

Ring D is a bond or 3-6 membered heterocycloalkyl optionally substituted with halo, CN, and $C_{1-6}$ alkyl, provided that when Ring D is a bond, then $Y^2$ is also a bond and t is 0;

$Y^1$ and $Y^2$ are each independently selected from a bond, O, C(O), N(H), N($C_{1-6}$ alkyl), $C_{1-6}$ alkyl, $C_{1-6}$ haloalkyl, and $C_{1-6}$ alkoxy;

Z is selected from N(H), N($C_{1-6}$ alkyl), $C_{1-6}$ alkyl, $C_{1-6}$ haloalkyl, and $C_{1-6}$ alkoxy;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is 6-8 membered heterocycloalkyl, optionally substituted with $R^{4a}$;

$R^{4a}$ is selected from H, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

s and t are each independently 0, 1, 2, or 3; and u is 1 or 2.

In embodiments of Formula VII, Ring B and Ring C are each independently 3-6 membered heterocycloalkyl optionally substituted with halo, CN, and $C_{1-6}$ alkyl;

Ring D is 3-6 membered heterocycloalkyl optionally substituted with halo, CN, and $C_{1-6}$ alkyl;

$Y^1$ and $Y^2$ are each independently selected from a bond, O, C(O), N(H), and $C_{1-6}$ alkyl;

Z is selected from N(H) and $C_{1-6}$ alkyl;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^3$ is selected from H, halo, CN, $C_{1-6}$ alkyl, $C_{1-6}$ alkoxy, and $C_{1-6}$ haloalkyl;

$R^4$ is 6-8 membered heterocycloalkyl, optionally substituted with $R^{4a}$;

$R^{4a}$ is selected from H, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

s and t are each independently 0, 1, or 2; and u is 1.

In embodiments of Formula VII, Ring B, Ring C, and Ring D are each independently 5- or 6-membered heterocycloalkyl optionally substituted with halo, CN, and $C_{1-6}$ alkyl.

In embodiments of Formulae I-VI, $R^4$ is bridged 8-membered heterocycloalkyl optionally substituted with $R^{4a}$.

In embodiments of Formulae I-VI, $R^4$ is:

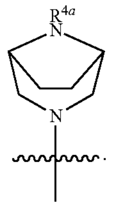

In embodiments of Formulae I-IV, $R^6$ is H.

In embodiments of Formulae I-IV, $R^8$ is H.

In embodiments of Formulae I-IV, $R^{11}$ is H.

In embodiments of Formulae I-IV, $R^{13}$ is H.

In embodiments of Formulae I-IV, $R^{15}$ is H.

In embodiments of Formulae I-IV, $R^{16}$ is H.

In embodiments of Formulae I-IV $R^6$, $R^8$, $R^{11}$, and $R^{13}$ are each H.

In embodiments of Formulae I-IV, $R^{15}$ and $R^{16}$ are each H.

In embodiments of Formula V, $R^4$ is a 6-7 membered heterocycloalkyl optionally substituted with 1 or 2 $R^{4a}$.

In embodiments, the compounds of Formula I have a structure of Formula IA:

(IA)

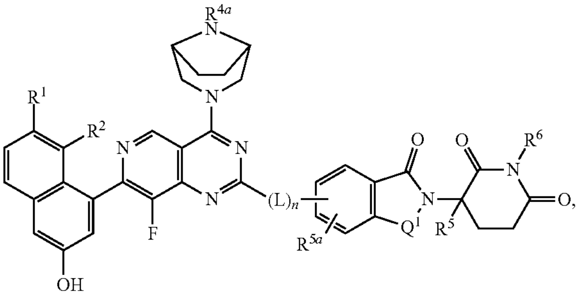

or a pharmaceutically acceptable salt thereof, wherein:

$Q^1$ is selected from $C(R^{14})_2$, C(O), and $NR^{14}$;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^{4a}$ is selected from H, $C_{1-6}$ alkyl, $C_{1-6}$ alkoxy, and $C_{1-6}$ haloalkyl;

$R^{5a}$, $R^5$, $R^6$, and $R^{14}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IA, $Q^1$ is $C(R^{14})_2$ or C(O);

$R^1$ and $R^2$ are each independently selected from H, halo, $C_{1-6}$ alkyl, and C≡CH;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IA, $Q^1$ is $C(R^{14})_2$ or C(O);

$R^1$ and $R^2$ are each independently selected from H, halo, $C_{1-6}$ alkyl, and C≡CH;

$R^{4a}$ is H or $C_{1-6}$ alkyl;

$R^{5a}$, $R^5$, $R^6$, and $R^{14}$ are each independently selected from H, halo, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 5-12 membered heterocycloalkyl, and 6-7 membered heteroaryl, wherein 5-12 membered heterocycloalkyl is optionally substituted with halo, CN, and $C_{1-6}$ alkyl; and n is 1, 2, 3, 4, 5, or 6.

In embodiments, the compounds of Formula I have a structure of Formula IB:

(IB)

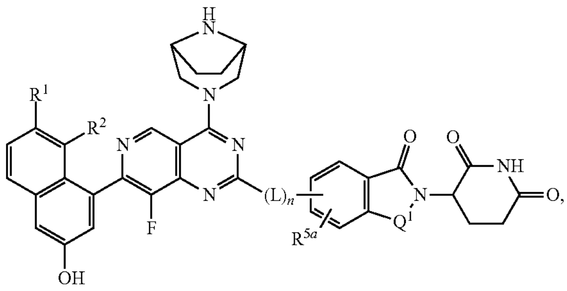

or a pharmaceutically acceptable salt thereof, wherein:

$Q^1$ is selected from $C(R^{14})_2$, C(O), and $NR^{14}$;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^{5a}$ and $R^{14}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IB, $Q^1$ is $CH_2$ or C(O);

$R^1$ and $R^2$ are each independently selected from H, halo, $C_{1-6}$ alkyl, and C≡CH;

$R^{5a}$ is independently selected from H, halo, and $C_{1-6}$ alkyl;

each L is independently selected from $C_{1-6}$ alkyl, $C_{1-6}$ alkoxy, O, and 5-12 membered heterocycloalkyl, wherein 5-12 membered heterocycloalkyl is optionally substituted with halo, CN, and $C_{1-6}$ alkyl; and n is 4, 5, or 6.

In embodiments of Formula IB, n is 6, and each L forms the following linker: ($C_{1-6}$ alkoxy)-(6-12 membered heterocycloalkyl)-($C_{1-6}$ alkyl)-(6-12 membered heterocycloalkyl)-($C_{1-6}$ alkyl)-(6-membered heterocycloalkyl).

In embodiments of Formula IB, n is 6, and each L forms the following linker: ($C_{1-6}$ alkoxy)-(6-membered heterocycloalkyl)-($C_{1-6}$ alkyl)-(6-membered heterocycloalkyl)-($C_{1-6}$ alkyl)-(6-membered heterocycloalkyl).

In embodiments of Formula IB, n is 4, and each L forms the following linker: ($C_{1-6}$ alkoxy)-(5-12 membered heterocycloalkyl)-($C_{1-6}$ alkyl)-(5-12 membered heterocycloalkyl).

In embodiments of Formula IB, n is 4, and each L forms the following linker: ($C_{1-6}$ alkoxy)-(11-membered heterocycloalkyl)-($C_{1-6}$ alkyl)-(6-membered heterocycloalkyl).

In embodiments of Formula IB, 11-membered heterocycloalkyl is spirocyclic 11-membered heterocycloalkyl.

In embodiments of Formula IB, n is 6, and each L forms the following linker: ($C_{1-6}$ alkoxy)-(5-12 membered heterocycloalkyl)-(O)-(5-12 membered heterocycloalkyl)-($C_{1-6}$ alkyl)-(5-12 membered heterocycloalkyl), wherein 5-12 membered heterocycloalkyl is optionally substituted with $C_{1-6}$ alkyl.

In embodiments of Formula IB, n is 6, and each L forms the following linker: ($C_{1-6}$ alkoxy)-(5-membered heterocycloalkyl)-(O)-(6-membered heterocycloalkyl)-($C_{1-6}$ alkyl)-(6-membered heterocycloalkyl), wherein 5-membered heterocycloalkyl is optionally substituted with $C_{1-6}$ alkyl.

In embodiments of Formula IB, n is 4, and each L forms the following linker: ($C_{1-6}$ alkoxy)-(5-12 membered heterocycloalkyl)-($C_{1-6}$ alkyl)-(5-12 membered heterocycloalkyl).

In embodiments of Formula IB, n is 4, and each L forms the following linker: ($C_{1-6}$ alkoxy)-(6-membered heterocycloalkyl)-($C_{1-6}$ alkyl)-(9-membered heterocycloalkyl).

In embodiments of Formula IB, 9-membered heterocycloalkyl is spirocyclic 9-membered heterocycloalkyl.

In embodiments of Formula IB, n is 4, and each L forms the following linker: ($C_{1-6}$ alkoxy)-(5-12 membered heterocycloalkyl)-(O)-(5-12 membered heterocycloalkyl), wherein 5-12 membered heterocycloalkyl is optionally substituted with $C_{1-6}$ alkyl.

In embodiments of Formula IB, n is 4, and each L forms the following linker: ($C_{1-6}$ alkoxy)-(5-membered heterocycloalkyl)-(O)-(6-membered heterocycloalkyl), wherein 5-membered heterocycloalkyl is optionally substituted with $C_{1-6}$ alkyl.

In embodiments of Formula IB, each L forms the linker:

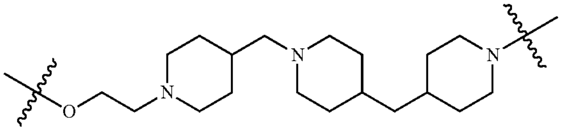

,

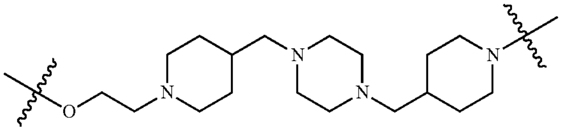

,

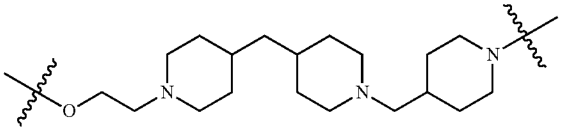

,

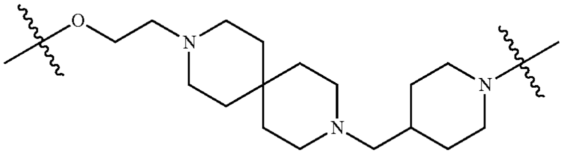

,

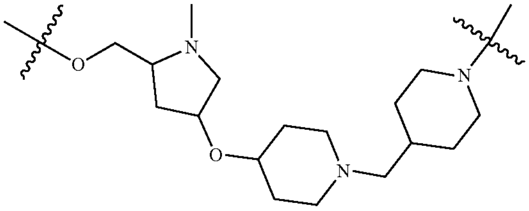

,

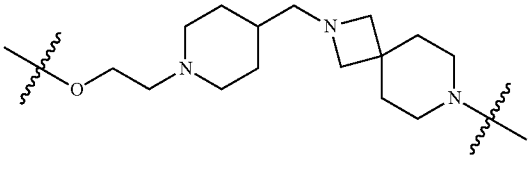

, or

-continued

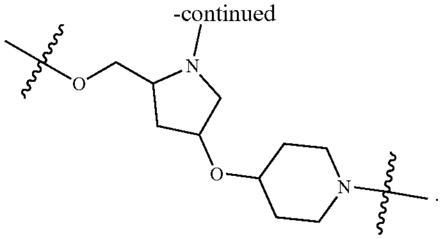

In embodiments, the compounds of Formula I have a structure of Formula IB-i:

(IB-i)

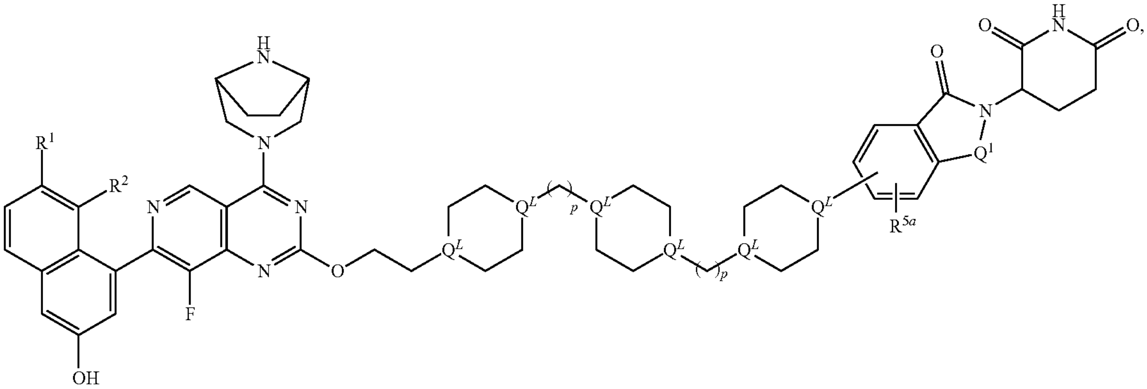

or a pharmaceutically acceptable salt thereof, wherein, $Q^1$ is selected from $C(R^{14})_2$, C(O), and $NR^{14}$;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl, $R^{5a}$ and $R^{14}$ are each independently selected from H, halo, $C_{1-6}$ alkyl, $C_{1-6}$ alkoxy, and $C_{1-6}$ haloalkyl;

each $Q^L$ is independently $CR^L$ or N;

each $R^L$ is independently H, halo, or CN; and each p is independently 1, 2, 3, 4, 5, or 6.

In embodiments of Formula IB-i, each $Q^L$ is independently $CR^L$ or N;

each $R^L$ is independently H or halo;

$R^1$ and $R^2$ are each independently selected from H, halo, $C_{1-6}$ alkyl, and $C_{2-6}$ alkynyl;

$R^3$ is selected from H, halo, and CN;

$R^{5a}$ and $R^{14}$ are each independently selected from H, $C_{1-6}$ alkyl, and $C_{1-6}$ alkoxy; and each p is 1, 2, 3, or 4.

In embodiments of Formula IB-i, each $Q^L$ is independently CH or N;

$R^1$ and $R^2$ are each independently selected from H, halo, $C_{1-3}$ alkyl, and C≡CH;

$R^3$ is halo;

$R^{5a}$ and $R^{14}$ are each independently selected from H, $C_{1-3}$ alkyl, and $C_{1-3}$ alkoxy; and each p is 1, 2, or 3.

In embodiments, the compounds of Formula I have a structure of Formula IC:

(IC)

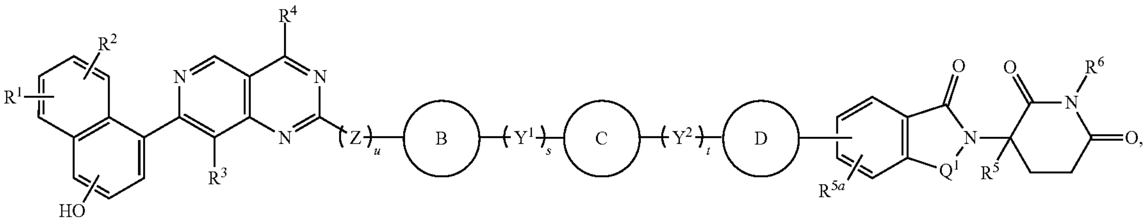

or a pharmaceutically acceptable salt thereof, wherein:

$Q^1$ is selected from $C(R^{14})_2$, C(O), and $NR^{14}$;

Ring B and Ring C are each independently selected from 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl;

Ring D is selected from a bond, $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl, provided that when Ring D is a bond, then $Y^2$ is also a bond and t is 0;

$Y^1$ and $Y^2$ are each independently selected from a bond, O, C(O), N(H), N($C_{1-6}$ alkyl), $C_{1-6}$ alkyl, $C_{1-6}$ haloalkyl, and $C_{1-6}$ alkoxy;

Z is selected from N(H), N($C_{1-6}$ alkyl), $C_{1-6}$ alkyl, $C_{1-6}$ haloalkyl, and $C_{1-6}$ alkoxy;

$R^1$ is halo or $C_{2-6}$ alkynyl;

$R^2$ is selected from H, halo, $C_{1-6}$ alkyl, and $C_{2-6}$ alkynyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with $R^{4a}$;

$R^{4a}$ is selected from H, $C_{1-6}$ alkyl, $C_{1-6}$ alkoxy, and $C_{1-6}$ haloalkyl;

$R^{5a}$, $R^5$, $R^6$, and $R^{14}$ are each independently selected from H, halo, $C_{1-6}$ alkyl, $C_{1-6}$ alkoxy, and $C_{1-6}$ haloalkyl;

s and t are each independently 0, 1, 2, or 3; and u is 1 or 2.

In embodiments of Formula IC, Ring B and Ring C are each independently selected from 3-12 membered heterocycloalkyl and 5-10 membered heteroaryl, wherein 3-12 membered heterocycloalkyl is optionally substituted with halo, CN, and $C_{1-6}$ alkyl.

In embodiments of Formula IC, Ring B and Ring C are each independently 3-12 membered heterocycloalkyl optionally substituted with halo, CN, and $C_{1-6}$ alkyl.

In embodiments of Formula IC, at least one of $Y^1$ and $Y^2$ is a bond and at least one of s and t is 0.

In embodiments of Formula IC, Ring D is selected from a bond, 3-12 membered heterocycloalkyl, and 5-10 membered heteroaryl, wherein 3-12 membered heterocycloalkyl is optionally substituted with halo, CN, and $C_{1-6}$ alkyl.

In embodiments of Formula IC, Ring D is selected from a bond, 3-6 membered heterocycloalkyl, and 5- or 6-membered heteroaryl, wherein 3-6 membered heterocycloalkyl is optionally substituted with halo, CN, and $C_{1-6}$ alkyl.

In embodiments, the compounds of Formula IC have a structure of Formula IC-i:

(IC-i)

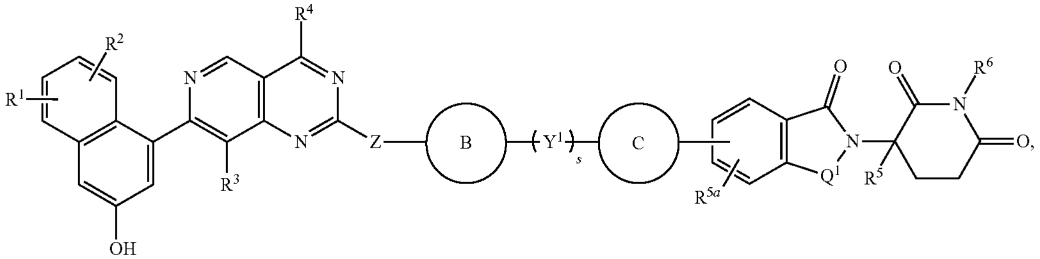

or a pharmaceutically acceptable salt thereof, wherein:

Ring B and Ring C are each independently selected from 5- or 6-membered heterocycloalkyl, 9-11 membered spirocyclic heterocycloalkyl, and 8-membered bridged heterocycloalkyl, wherein 5- or 6-membered heterocycloalkyl, 9-11 membered spirocyclic heterocycloalkyl, and 8-membered bridged heterocycloalkyl are optionally substituted with halo, CN, and $C_{1-6}$ alkyl;

$Y^1$ is selected from a bond, O, C(O), N(H), N($C_{1-6}$ alkyl), $C_{1-6}$ alkyl, $C_{1-6}$ haloalkyl, and $C_{1-6}$ alkoxy;

Z is selected from $C_{1-6}$ alkyl, $C_{1-6}$ haloalkyl, and $C_{1-6}$ alkoxy;

$R^1$ is halo or $C_{2-6}$ alkynyl;

$R^2$ is selected from H, halo, $C_{1-6}$ alkyl, and $C_{2-6}$ alkynyl; and s is 0, 1, 2, or 3.

In embodiments, the compounds of Formula IC-i have a structure of Formula IC-ia:

(IC-ia)

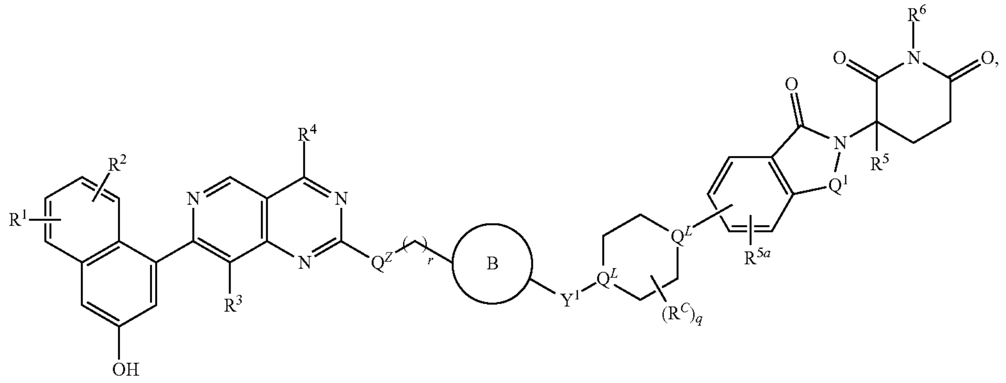

or a pharmaceutically acceptable salt thereof wherein:

Ring B is selected from 5- or 6-membered heterocycloalkyl, 9- or 11-membered spirocyclic heterocycloalkyl, and 8-membered fused heterocycloalkyl, wherein 5- or 6-membered heterocycloalkyl, 9- or 11-membered spirocyclic heterocycloalkyl, and 8-membered fused heterocycloalkyl are optionally substituted with halo, ON, and $C_{1-6}$ alkyl;

$Q^Z$ is O, NH, or N($C_{1-6}$ alkyl);

each $Q^L$ is independently $CR^L$ or N;

each $R^L$ is independently selected from H, halo, ON, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC-i has a structure of Formula IC-ib:

(IC-ib)

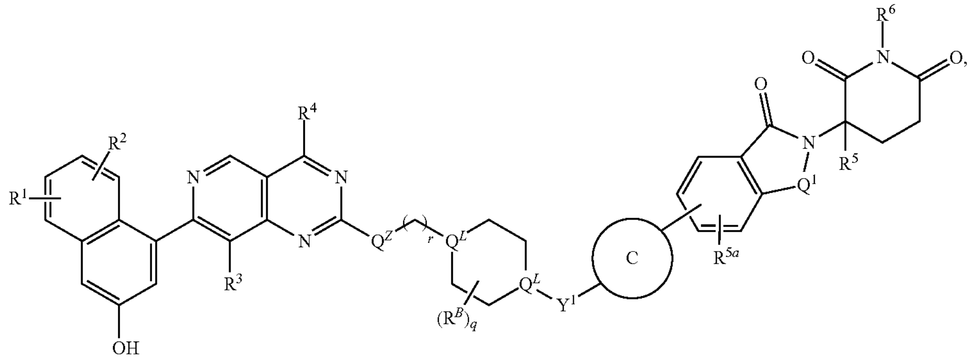

or a pharmaceutically acceptable salt thereof wherein:

Ring B is selected from 5- or 6-membered heterocycloalkyl, 9- or 11-membered spirocyclic heterocycloalkyl, and 8-membered fused heterocycloalkyl, wherein 5- or 6-membered heterocycloalkyl, 9- or 11-membered spirocyclic heterocycloalkyl, and 8-membered fused heterocycloalkyl are optionally substituted with halo, CN, and $C_{1-6}$ alkyl;

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

$R^B$ is halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC-ia has a structure of Formula IC-iai:

(IC-iai)

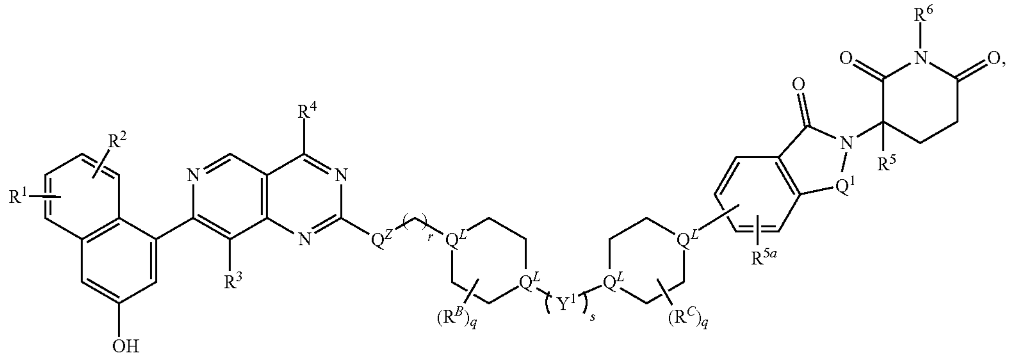

or a pharmaceutically acceptable salt thereof wherein:

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

$R^B$ and $R^C$ are each independently halo or $C_{1-6}$ alkyl;

$Y^1$ is $C_{1-6}$ alkyl or $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6;

sis 0, 1, 2, or 3; and each q is independently 0, 1, or 2.

In embodiments of Formula IC-iai, Ring B is 9 or 11-membered spirocyclic heterocycloalkyl.

In embodiments, the compound of Formula IC-ia has a structure of Formula IC-iaii:

(IC-iaii)

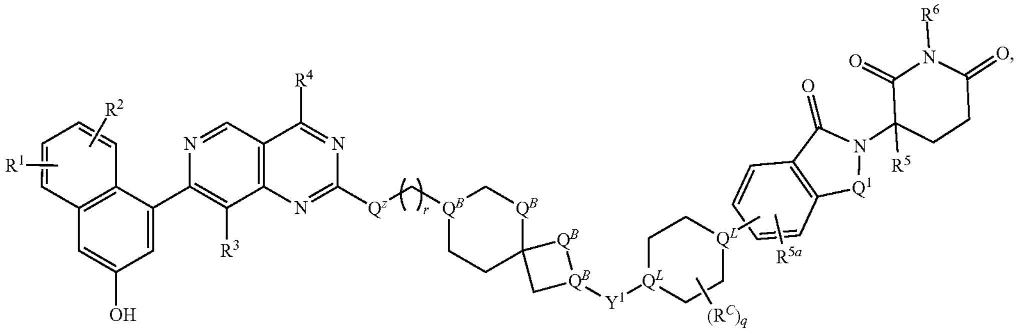

or a pharmaceutically acceptable salt thereof wherein:

each $Q^B$ is independently selected from CH, $CH_2$, N, NH, and N($C_{1-6}$ alkyl), provided that at least one $Q^B$ is N, NH, or N($C_{1-6}$ alkyl);

$Q^Z$ is O, NH, or N($C_{1-6}$ alkyl);

each $Q^L$ is independently $CR^L$ or N, provided that at least one $Q^L$ is N;

each $R^L$ is independently selected from H, halo, CN, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC-ia has a structure of Formula IC-iaiii:

(IC-iaiii)

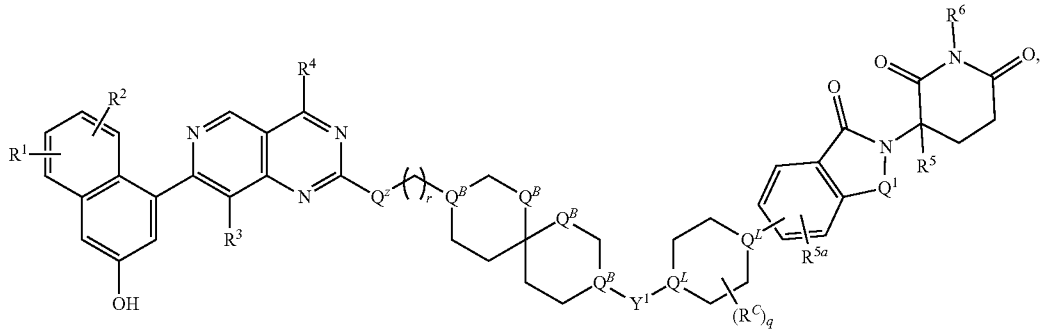

or a pharmaceutically acceptable salt thereof wherein:

each $Q^B$ is independently selected from CH, $CH_2$, N, NH, and N($C_{1-6}$ alkyl), provided that at least one $Q^B$ is N, NH, or N($C_{1-6}$ alkyl);

$Q^Z$ is O, NH, or N($C_{1-6}$ alkyl);

each $Q^L$ is independently $CR^L$ or N, provided that at least one $Q^L$ is N;

each $R^L$ is independently selected from H, halo, CN, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC-ia has a structure of Formula IC-iaiv:

(IC-iaiv)

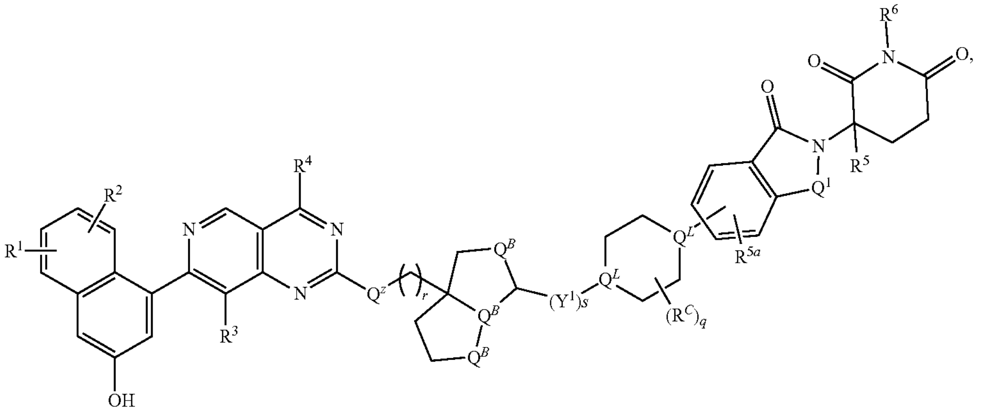

or a pharmaceutically acceptable salt thereof wherein:

each $Q^B$ is independently selected from $CH_2$, N, NH, and N($C_{1-6}$ alkyl), provided that at least one $Q^B$ is N, NH, or N($C_{1-6}$ alkyl);

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from O, C(O), N(H), N($C_{1-6}$ alkyl), $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6;

s is 0, 1, 2, or 3; and q is 0, 1, or 2.

In embodiments, the compound of Formula IC-ia has a structure of Formula IC-iav:

(IC-iav)

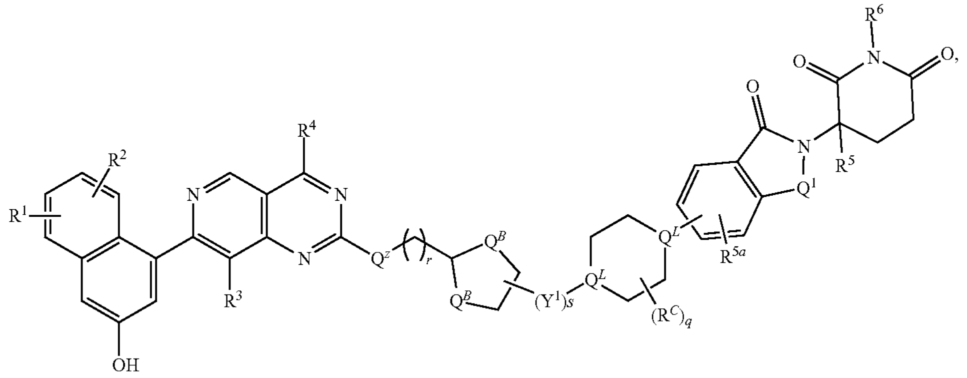

or a pharmaceutically acceptable salt thereof wherein:

each $Q^B$ is independently selected from $CH_2$, NH, and $N(C_{1-6}$ alkyl), provided that at least one $Q^B$ is NH or $N(C_{1-6}$ alkyl);

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from O, C(O), N(H), $N(C_{1-6}$ alkyl), $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6;

s is 0, 1, 2, or 3; and q is 0, 1, or 2.

In embodiments, the compound of Formula IC-ib has a structure of Formula IC-ibi:

(IC-ibi)

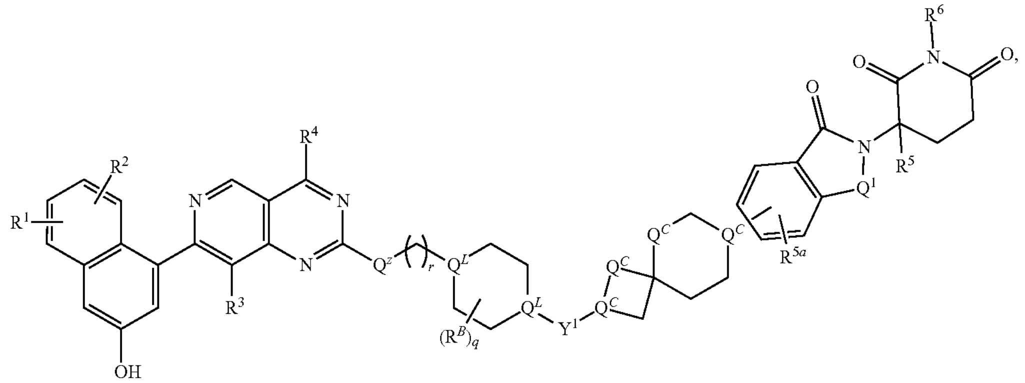

or a pharmaceutically acceptable salt thereof wherein:

each $Q^C$ is independently selected from CH, $CH_2$, N, NH, and $N(C_{1-6}$ alkyl), provided that at least one $Q^C$ is N, NH, or $N(C_{1-6}$ alkyl);

$Q^Z$ is O, NH, or $N(C_{1-6}$ alkyl);

each $Q^L$ is independently $CR^L$ or N, provided that at least one $Q^L$ is N;

each $R^L$ is independently selected from H, halo, CN, and $C_{1-6}$ alkyl;

each $R^B$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC-ib has a structure of Formula IC-ibii:

(IC-ibii)

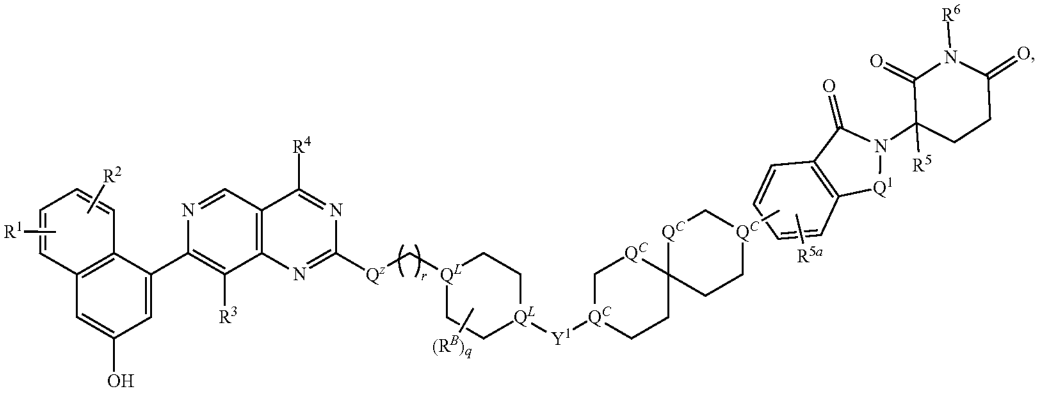

or a pharmaceutically acceptable salt thereof wherein:

each $Q^C$ is independently selected from CH, $CH_2$, N, NH, and N($C_{1-6}$ alkyl), provided that at least one $Q^C$ is N, NH, or N($C_{1-6}$ alkyl);

$Q^Z$ is O, NH, or N($C_{1-6}$ alkyl);

each $Q^L$ is independently $CR^L$ or N, provided that at least one $Q^L$ is N;

each $R^L$ is independently selected from H, halo, CN, and $C_{1-6}$ alkyl;

each $R^B$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula IC has a structure of Formula IC-ii:

(IC-ii)

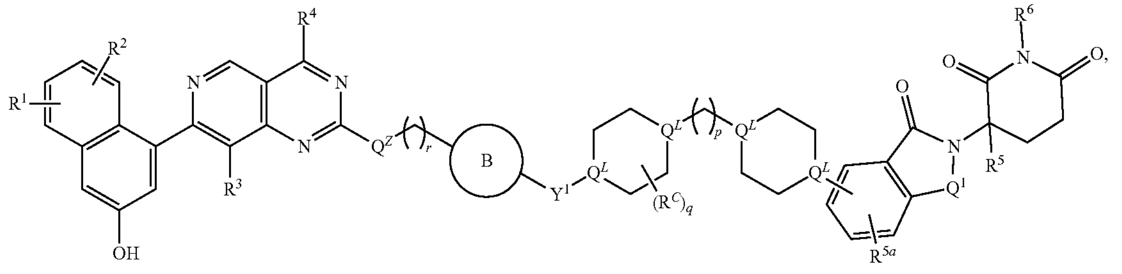

or a pharmaceutically acceptable salt thereof wherein:

Ring B is 5- or 6-membered heterocycloalkyl or 8-membered fused heterocycloalkyl, wherein 5- or 6-membered heterocycloalkyl and 8-membered fused heterocycloalkyl are optionally substituted with halo, CN, and $C_{1-6}$ alkyl;

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and q is 0, 1, or 2.

In embodiments of Formula IC-ii, Ring B is 8-membered fused heterocycloalkyl.

In embodiments, the compound of Formula IC-iia has a structure of Formula IC-iia:

(IC-iia)

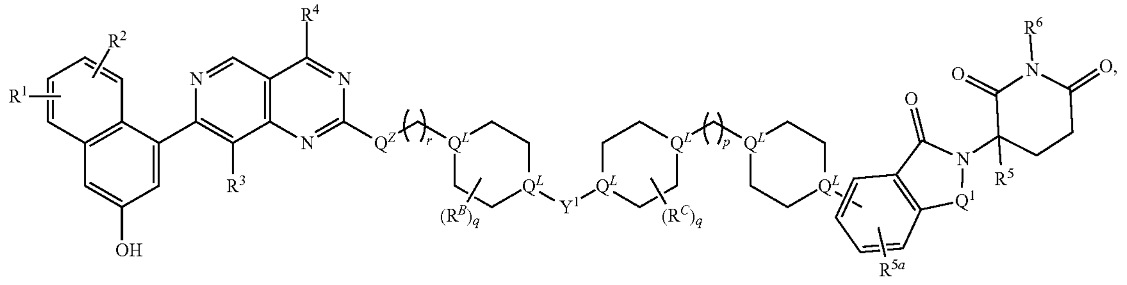

or a pharmaceutically acceptable salt thereof wherein:

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

$R^B$ and $R^C$ are each independently halo or $C_{1-6}$ alkyl;

$Y^1$ is $C_{1-6}$ alkyl or $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and each q is independently 0, 1, or 2.

In embodiments, the compound of Formula IC-ii, has a structure of Formula IC-iib:

(IC-iib)

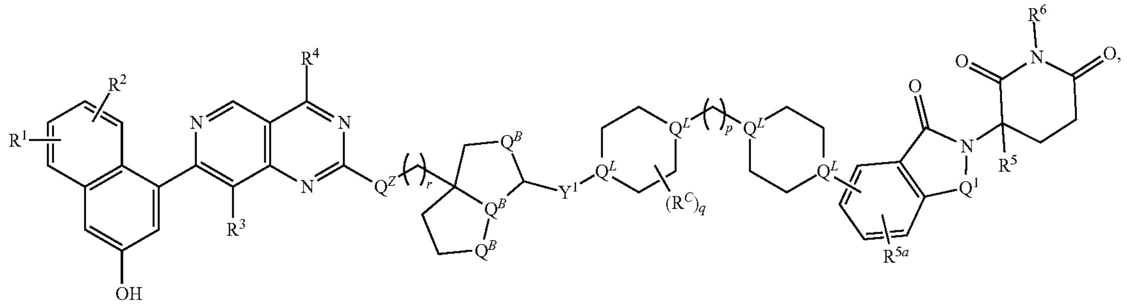

or a pharmaceutically acceptable salt thereof wherein:

each $Q^B$ is independently selected from $OH_2$, N, NH, and $N(C_{1-6}$ alkyl), provided that at least one $Q^B$ is N, NH, or $N(C_{1-6}$ alkyl);

$Q^Z$ is O, NH, or $N(C_{1-6}$ alkyl);

each $Q^L$ is independently $CR^L$ or N;

each $R^L$ is independently selected from H, halo, ON, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and q is 0, 1, or 2.

In embodiments, the compound of Formula IC-ii has a structure of Formula IC-iic:

(IC-iic)

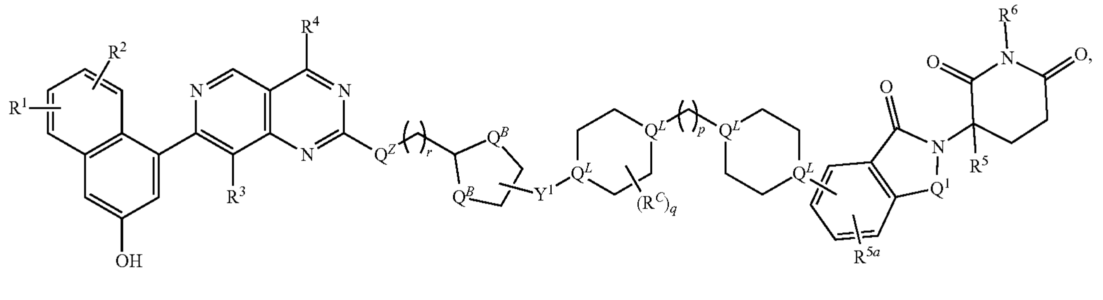

or a pharmaceutically acceptable salt thereof wherein:

each $Q^B$ is independently selected from $CH_2$, NH, and $N(C_{1-6}$ alkyl), provided that at least one $Q^B$ is NH or $N(C_{1-6}$ alkyl);

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from 0, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and q is 0, 1, or 2.

In embodiments, the compounds of Formula II have a structure of Formula IIA:

(IIA)

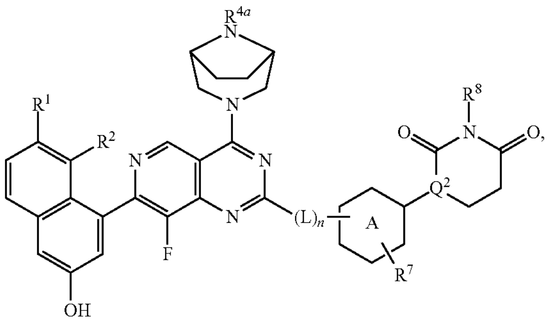

or a pharmaceutically acceptable salt thereof, wherein:

$Q^2$ is $CR^{14}$ or N;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl, $R^{4a}$ is selected from H, $C_{1-6}$ alkyl, $C_{1-6}$ alkoxy, and $C_{1-6}$ haloalkyl;

$R^8$ and $R^{14}$ are each independently selected from H, halo, $C_{1-6}$ alkyl, $C_{1-6}$ alkoxy, and $C_{1-6}$ haloalkyl;

$R^7$ is selected from H, =O, halo, $C_{1-6}$ alkyl, $C_{1-6}$ alkoxy, and $C_{1-6}$ haloalkyl;

Ring A is selected from phenyl, 6-membered heteroaryl, $C_6$ cycloalkyl, and 6-membered heterocycloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), $N(C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IIA, $Q^2$ is N;

$R^1$ and $R^2$ are each independently selected from H, halo, $C_{1-6}$ alkyl, and C≡CH;

$R^{4a}$ is H or $C_{1-6}$ alkyl;

$R^7$ is selected from H, =O, halo, $C_{1-6}$ alkyl, and $C_{1-6}$ alkoxy;

$R^8$ is selected from H, $C_{1-6}$ alkyl, and $C_{1-6}$ alkoxy;

Ring A is selected from phenyl, 6-membered heteroaryl, and 6-membered heterocycloalkyl;

each L is independently selected from $C_{1-6}$ alkyl, $C_{1-6}$ alkoxy, O, C(O), N(H), $N(C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IIA, $Q^2$ is N;

$R^1$ and $R^2$ are each independently selected from H, halo, $C_{1-6}$ alkyl, and C≡CH;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^7$ is selected from H, =O, halo, $C_{1-6}$ alkyl, and $C_{1-6}$ alkoxy;

$R^8$ is selected from H, $C_{1-6}$ alkyl, and $C_{1-6}$ alkoxy;

Ring A is phenyl or 6-membered heterocycloalkyl;

B is a bond or $C_{1-6}$ alkyl;

each L is independently selected from $C_{1-6}$ alkyl, $C_{1-6}$ alkoxy, O, C(O), N(H), $N(C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments, the compounds of Formula II have a structure of Formula IIB:

(IIB)

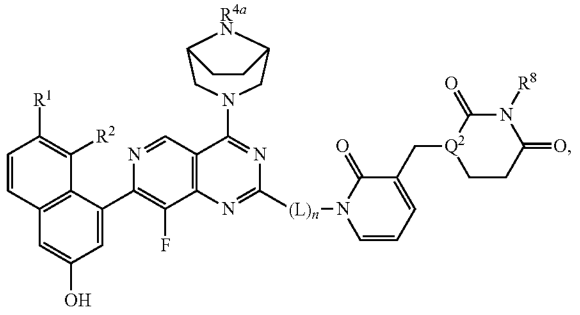

or a pharmaceutically acceptable salt thereof, wherein:

$Q^2$ is $CR^{14}$ or N;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl, $R^{4a}$ is selected from H, $C_{1-6}$ alkyl, $C_{1-6}$ alkoxy, and $C_{1-6}$ haloalkyl;

$R^8$ and $R^{14}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IIB, $Q^2$ is N;

$R^1$ and $R^2$ are each independently selected from H, halo, $C_{1-6}$ alkyl, and C≡CH;

$R^{4a}$ is H or $C_{1-6}$ alkyl;

$R^7$ is selected from H, =O, halo, $C_{1-6}$ alkyl, and $C_{1-6}$ alkoxy;

$R^8$ is selected from H, $C_{1-6}$ alkyl, and $C_{1-6}$ alkoxy;

Ring A is selected from phenyl, 6-membered heteroaryl, and 6-membered heterocycloalkyl;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IIB, $Q^2$ is N;

$R^1$ and $R^2$ are each independently selected from H, halo, $C_{1-6}$ alkyl, and C≡CH;

$R^4$ is $C_{6-8}$ cycloalkyl or 6-8 membered heterocycloalkyl, wherein $C_{6-8}$ cycloalkyl and 6-8 membered heterocycloalkyl are optionally substituted with $R^{4a}$;

$R^{4a}$ is H or $C_{1-6}$ alkyl;

$R^8$ is selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments, the compounds of Formula III have a structure of Formula IIIA:

(IIIA)

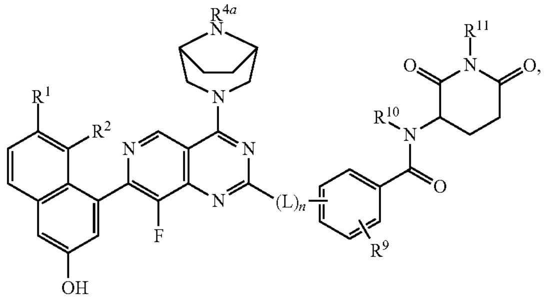

or a pharmaceutically acceptable salt thereof, wherein:

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl, $R^{4a}$ is selected from H, $C_{1-6}$ alkyl, $C_{1-6}$ alkoxy, and $C_{1-6}$ haloalkyl;

$R^9$ is selected from H, halo, $C_{1-6}$ alkyl, and $C_{1-6}$ alkoxy;

$R^{10}$ and $R^{11}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IIIA, $R^1$ and $R^2$ are each independently selected from H, halo, $C_{1-6}$ alkyl, and C≡CH;

$R^{4a}$ is H or $C_{1-6}$ alkyl;

$R^9$ is selected from H, halo, $C_{1-6}$ alkyl, and $C_{1-6}$ alkoxy;

$R^{10}$ and $R^{11}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IIIA, $R^1$ and $R^2$ are each independently selected from H, halo, $C_{1-6}$ alkyl, and C≡CH;

$R^{4a}$ is H or $C_{1-6}$ alkyl;

$R^9$ is selected from H, halo, $C_{1-6}$ alkyl, and $C_{1-6}$ alkoxy;

$R^{10}$ and $R^{11}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments, the compounds of Formula IV have a structure of Formula IVA:

(IVA)

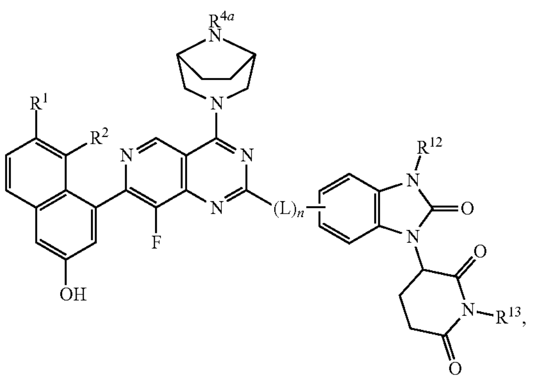

or a pharmaceutically acceptable salt thereof, wherein:

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl, $R^{4a}$ is selected from H, $C_{1-6}$ alkyl, $C_{1-6}$ alkoxy, and $C_{1-6}$ haloalkyl;

$R^{12}$ and $R^{13}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, 8, 9, or 10.

In embodiments of Formula IVA, $R^1$ and $R^2$ are each independently selected from H, halo, $C_{1-6}$ alkyl, and $C\equiv CH$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{3-11}$ cycloalkyl, 3-12 membered heterocycloalkyl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula IVA, $R^1$ and $R^2$ are each independently selected from H, halo, $C_{1-6}$ alkyl, and $C\equiv CH$;

$R^{4a}$ is H or $C_{1-6}$ alkyl;

$R^{12}$ and $R^{13}$ are each independently selected from H, $C_{1-6}$ alkyl, and $C_{1-6}$ alkoxy;

each L is independently selected from $C_{1-6}$ alkyl, $C_{1-6}$ alkoxy, O, C(O), N(H), N($C_{1-6}$ alkyl), $C_{4-7}$ cycloalkyl, 6-12 membered heterocycloalkyl, and 6-7 membered heteroaryl, wherein 6-12 membered heterocycloalkyl is optionally substituted with halo, CN, and $C_{1-6}$ alkyl; and n is 1, 2, 3, 4, 5, or 6.

In embodiments, the compounds of Formula IV have a structure of Formula IVB-a:

(IVB-a)

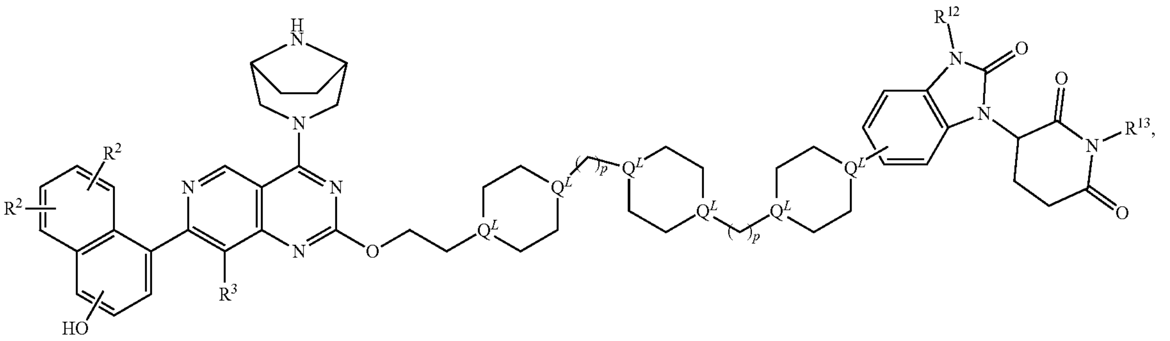

or a pharmaceutically acceptable salt thereof, wherein:

each $Q^L$ is independently $CR^L$ or N;

each $R^L$ is independently H, halo, or ON, and each p is 1, 2, 3, 4, 5, or 6.

In embodiments of Formula IVB-a, each $Q^L$ is independently $CR^L$ or N;

each $R^L$ is independently H or halo;

$R^1$ and $R^2$ are each independently selected from H, halo, $C_{1-6}$ alkyl, and $C_{2-6}$ alkynyl;

$R^3$ is selected from H, halo, and ON;

$R^{12}$ and $R^{13}$ are each independently selected from H, $C_{1-6}$ alkyl, and $C_{1-6}$ alkoxy; and each p is 1, 2, 3, or 4.

In embodiments of Formula IVB-a, each $Q^L$ is independently CH or N;

$R^1$ and $R^2$ are each independently selected from H, halo, $C_{1-3}$ alkyl, and $C\equiv CH$;

$R^3$ is halo;

$R^{12}$ and $R^{13}$ are each independently selected from H, $C_{1-3}$ alkyl, and $C_{1-3}$ alkoxy; and each p is 1, 2, or 3.

In embodiments, the compounds of Formula IV have a structure of Formula IVB:

(IVB)

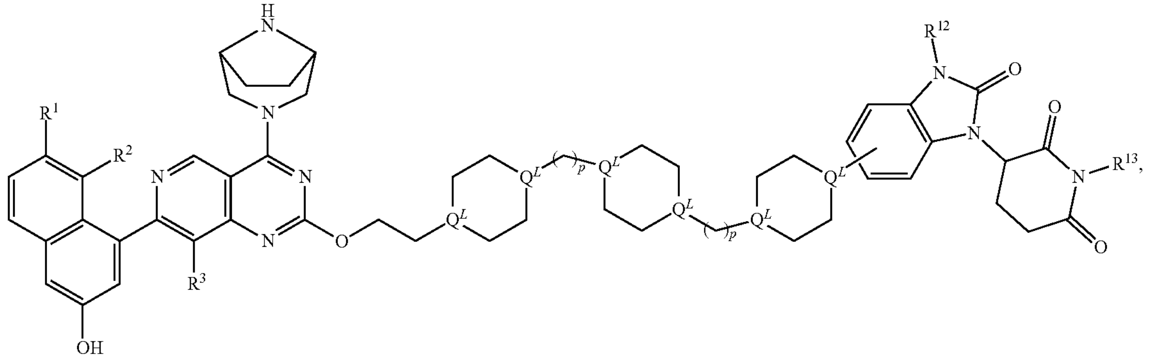

or a pharmaceutically acceptable salt thereof, wherein:

$R^1$ and $R^2$ are each independently selected from H, halo, $C_{1-6}$ alkyl, and $C_{2-6}$ alkynyl;

$R^3$ is selected from H, halo, and CN;

each $Q^L$ is independently $CR^L$ or N;

each $R^L$ is independently H, halo, or CN, and each p is 1, 2, 3, 4, 5, or 6; and $R^{12}$ and $R^{13}$ are each independently selected from H, $C_{1-6}$ alkyl, and $C_{1-6}$ alkoxy.

In embodiments of Formula IVB, each $Q^L$ is independently $CR^L$ or N;

each $R^L$ is independently H or halo;

$R^1$ and $R^2$ are each independently selected from H, halo, $C_{1-6}$ alkyl, and $C_{2-6}$ alkynyl;

$R^3$ is selected from H, halo, and CN;

$R^{12}$ and $R^{13}$ are each independently selected from H, $C_{1-6}$ alkyl, and $C_{1-6}$ alkoxy; and each p is 1, 2, 3, or 4.

In embodiments of Formula IVB, each $Q^L$ is independently CH or N;

$R^1$ and $R^2$ are each independently selected from H, halo, $C_{1-3}$ alkyl, and C≡CH;

$R^3$ is halo;

$R^{12}$ and $R^{13}$ are each independently selected from H, $C_{1-3}$ alkyl, and $C_{1-3}$ alkoxy; and each p is 1, 2, or 3.

In embodiments, the compounds of Formula V have the structure of Formula VA:

(VA)

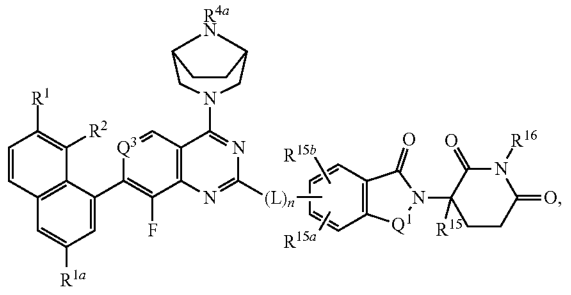

or a pharmaceutically acceptable salt thereof, wherein:

$Q^1$ is selected from $C(R^{14})_2$, C(O), and $NR^{14}$;

$Q^3$ is from $CR^{14}$ or N;

$R^{1a}$ is selected from OH, H, and halo;

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^{4a}$ is independently selected from H, OH, $C_{1-6}$ alkyl, $C_{1-6}$ alkoxy, and $C_{1-6}$ haloalkyl;

$R^{14}$, $R^{15a}$, $R^{15b}$, $R^{15}$, and $R^{16}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, 8, 9, or 10.

In embodiments of Formula VA, $Q^1$ is $C(R^{14})_2$ or C(O);

$Q^3$ is $CR^{14}$ or N;

$R^1$ and $R^2$ are each independently selected from H, halo, $C_{1-6}$ alkyl, $C_{3-6}$ cycloalkyl, and C≡CH;

$R^1$ is H or OH;

$R^{4a}$ is H or $C_{1-6}$ alkyl;

$R^{14}$, $R^{15a}$, $R^{15b}$, $R^{15}$, and $R^{16}$ are each independently selected from H, halo, $C_{1-6}$ alkyl and $C_{1-6}$ alkoxy;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, or 8.

In embodiments of Formula VA:

$Q^1$ is $C(R^{14})_2$ or C(O);

$Q^3$ is CH or N;

$R^1$ and $R^2$ are each independently selected from H, halo, $C_{1-3}$ alkyl, $C_{3-5}$ cycloalkyl and C≡CH;

$R^{1a}$ is H or OH;

$R^3$ is H or halo;

$R^{4a}$ is H or $C_{1-6}$ alkyl;

$R^{14}$, $R^{15a}$, $R^{15b}$, $R^{15}$, and $R^{16}$ are each independently selected from H, halo, $C_{1-3}$ alkyl and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 5-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In embodiments, the compounds of Formula VI have a structure of Formula VIA:

(VIA)

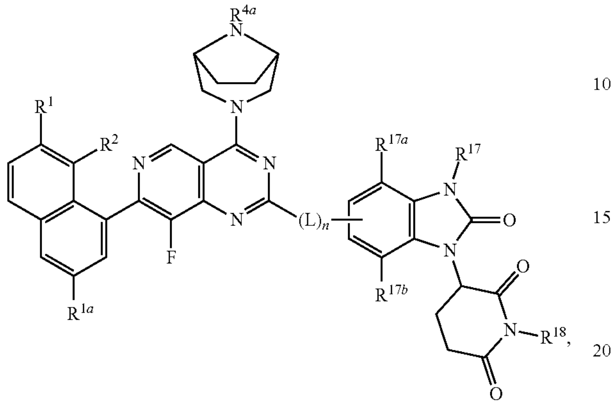

or a pharmaceutically acceptable salt thereof, wherein:

$R^1$ and $R^2$ are each independently selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^{4a}$ is independently selected from H, OH, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with 1 or 2 substituents independently selected from halo, CN, and $C_{1-6}$ alkyl; and n is 1, 2, 3, 4, 5, 6, 7, 8, 9, or 10.

In embodiments of Formula VIA:

$R^1$ and $R^2$ are each independently selected from H, halo, $C_{1-6}$ alkyl, $C_{3-6}$ cycloalkyl, and C≡CH;

$R^{4a}$ is H or $C_{1-6}$ alkyl;

$R^{17a}$, $R^{17b}$, $R^{17}$, and $R^{18}$ are each independently selected from H, halo, $C_{1-6}$ alkyl, and $C_{1-6}$ alkoxy;

each L is independently selected from $C_{1-6}$ alkyl, $C_{1-6}$ haloalkyl, $C_{1-6}$ alkoxy, $C_{1-6}$ haloalkoxy, O, C(O), N(H), N($C_{1-6}$ alkyl), $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl; and n is 1, 2, 3, 4, 5, 6, 7, or 8.

In embodiments of Formula VIA:

$R^1$ and $R^2$ are each independently selected from H, halo, $C_{1-3}$ alkyl, and C≡CH;

$R^{4a}$ is H or $C_{1-6}$ alkyl;

$R^{17a}$, $R^{17b}$, $R^{17}$, and $R^{18}$ are each independently selected from H, halo, $C_{1-3}$ alkyl and $C_{1-3}$ alkoxy;

each L is independently selected from $C_{1-6}$ alkyl, $C_{1-6}$ haloalkyl, $C_{1-6}$ alkoxy, O, C(O), N(H), N($C_{1-6}$ alkyl), $C_{4-7}$ cycloalkyl, 5-12 membered heterocycloalkyl, and 5-7 membered heteroaryl, wherein 5-12 membered heterocycloalkyl is optionally substituted with 1 or 2 substituents independently selected from halo, CN, and $C_{1-6}$ alkyl; and n is 1, 2, 3, 4, 5, or 6.

In embodiments, the compound of Formula VI has a structure of Formula VIAA:

(VIAA)

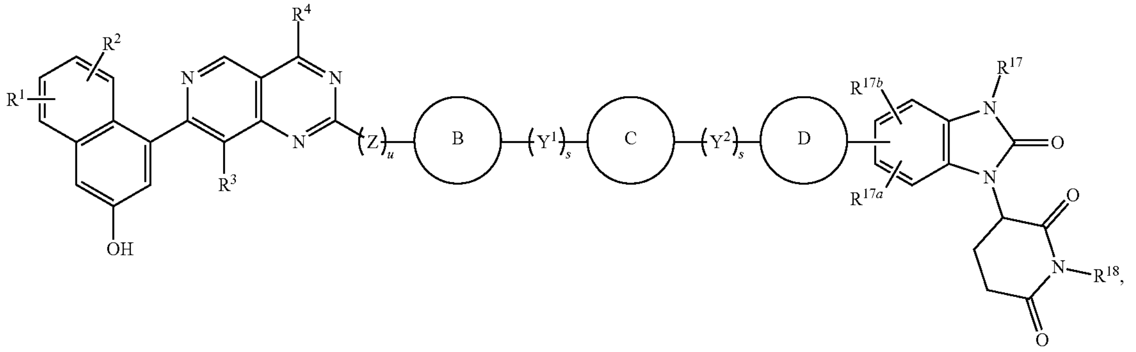

or a pharmaceutically acceptable salt thereof, wherein:

Ring B and Ring C are each independently selected from 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl;

Ring D is selected from a bond, $C_{3-11}$ cycloalkyl, 3-12 membered heterocycloalkyl, $C_{6-10}$ aryl, and 5-10 membered heteroaryl, wherein 3-12 membered heterocycloalkyl is optionally substituted with halo, CN, and $C_{1-6}$ alkyl, provided that when Ring D is a bond, then $Y^2$ is also a bond and t is 0;

$Y^1$ and $Y^2$ are each independently selected from a bond, O, C(O), N(H), N($C_{1-6}$ alkyl), $C_{1-6}$ alkyl, $C_{1-6}$ haloalkyl, and $C_{1-6}$ alkoxy;

Z is selected from N(H), N($C_{1-6}$ alkyl), $C_{1-6}$ alkyl, $C_{1-6}$ haloalkyl, and $C_{1-6}$ alkoxy;

$R^1$ is halo or $C_{2-6}$ alkynyl;

$R^2$ is selected from H, halo, $C_{1-6}$ alkyl, and $C_{2-6}$ alkynyl;

$R^3$ is selected from H, halo, CN, $C_{1-6}$ alkyl, $C_{1-6}$ alkoxy, and $C_{1-6}$ haloalkyl;

$R^4$ is selected from $C_{3-11}$ cycloalkyl, 3-10 membered heterocycloalkyl, $C_{6-10}$ aryl, and 3-10 membered heteroaryl, wherein $C_{3-11}$ cycloalkyl, 3-10 membered heterocycloalkyl, $C_{6-10}$ aryl, and 3-10 membered heteroaryl are optionally substituted with $R^{4a}$;

$R^{4a}$ is selected from H, $C_{1-6}$ alkyl, $C_{1-6}$ alkoxy, and $C_{1-6}$ haloalkyl;

$R^{17a}$, $R^{17b}$, $R^{17}$, and $R^{18}$ are each independently selected from H, halo, $C_{1-6}$ alkyl, $C_{1-6}$ alkoxy, and $C_{1-6}$ haloalkyl;

s and t are each independently 0, 1, 2, or 3; and u is 1 or 2.

In embodiments of Formula VIAA, Ring D is selected from a bond, 3-12 membered heterocycloalkyl, and 5-10 membered heteroaryl, wherein 3-12 membered heterocycloalkyl is optionally substituted with halo, CN, and $C_{1-6}$ alkyl.

In embodiments of Formula VIAA, Ring D is selected from a bond, 3-8 membered heterocycloalkyl, and 5- or 6-membered heteroaryl, wherein 3-8 membered heterocycloalkyl is optionally substituted with halo, CN, and $C_{1-6}$ alkyl.

In embodiments of Formula VIAA, Ring B is 8-membered fused heterocycloalkyl.

In embodiments, the compound of Formula VIAA has a structure of Formula VIAA-i:

(VIAA-i)

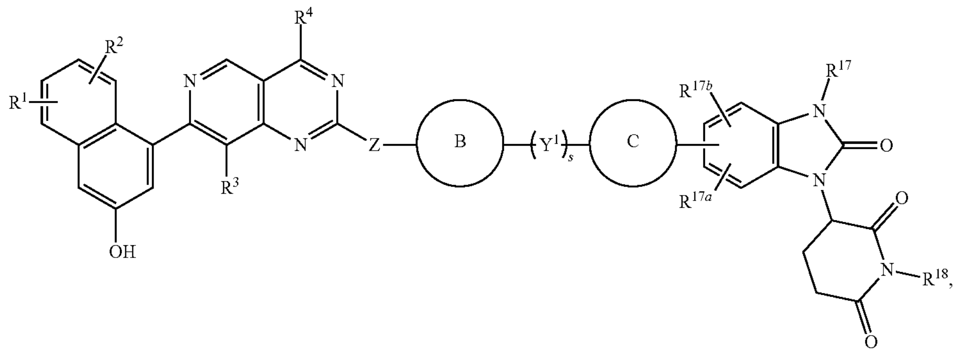

or a pharmaceutically acceptable salt thereof, wherein:

Ring B and Ring C are each independently selected from 5- or 6-membered heterocycloalkyl, 9-11 membered spirocyclic heterocycloalkyl, and 8-membered bridged heterocycloalkyl, wherein 5- or 6-membered heterocycloalkyl, 9-11 membered spirocyclic heterocycloalkyl, and 8-membered bridged heterocycloalkyl are optionally substituted with halo, CN, and $C_{1-6}$ alkyl;

$Y^1$ is selected from a bond, O, C(O), N(H), N($C_{1-6}$ alkyl), $C_{1-6}$ alkyl, $C_{1-6}$ haloalkyl, and $C_{1-6}$ alkoxy;

Z is selected from $C_{1-6}$ alkyl, $C_{1-6}$ haloalkyl, and $C_{1-6}$ alkoxy;

$R^1$ is halo or $C_{2-6}$ alkynyl;

$R^2$ is selected from H, halo, $C_{1-6}$ alkyl, and $C_{2-6}$ alkynyl; and s is 0, 1, 2, or 3.

In embodiments, the compound of Formula VIAA-i has a structure of Formula VIAA-ia:

(VIAA-ia)

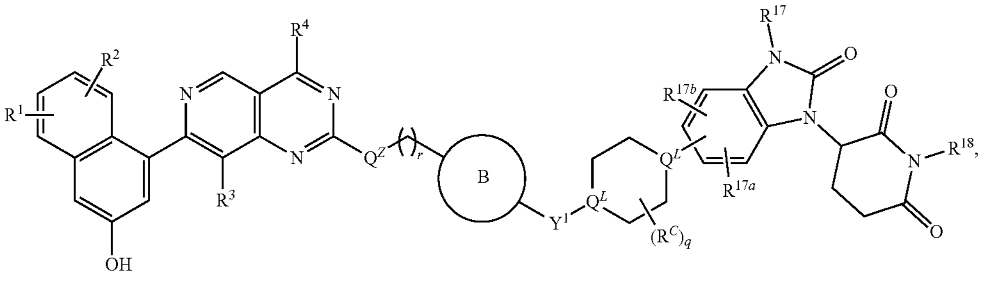

or a pharmaceutically acceptable salt thereof wherein:

Ring B is selected from 5- or 6-membered heterocycloalkyl, 9- or 11-membered spirocyclic heterocycloalkyl, and 8-membered fused heterocycloalkyl, wherein 5- or 6-membered heterocycloalkyl, 9- or 11-membered spirocyclic heterocycloalkyl, and 8-membered fused heterocycloalkyl are optionally substituted with halo, ON, and $C_{1-6}$ alkyl;

$Q^Z$ is O, NH, or N($C_{1-6}$ alkyl);

each $Q^L$ is independently $CR^L$ or N;

each $R^L$ is independently selected from H, halo, ON, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments, the compound of Formula VIAA-la has a structure of Formula VIAA-Iai:

(VIAA-iai)

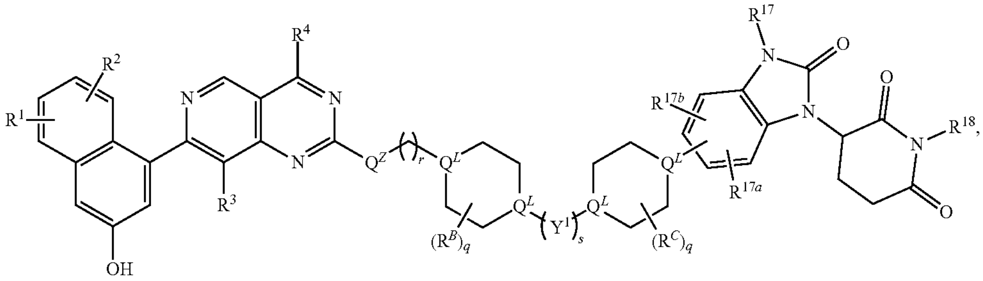

or a pharmaceutically acceptable salt thereof wherein:

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

$R^B$ and $R^C$ are each independently halo or $C_{1-6}$ alkyl;

$Y^1$ is $C_{1-6}$ alkyl or $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6;

s is 0, 1, 2, or 3; and each q is independently 0, 1, or 2.

In embodiments, the compound of Formula VIAA-ia has a structure of Formula VIAA-iaii:

(VIAA-iaii)

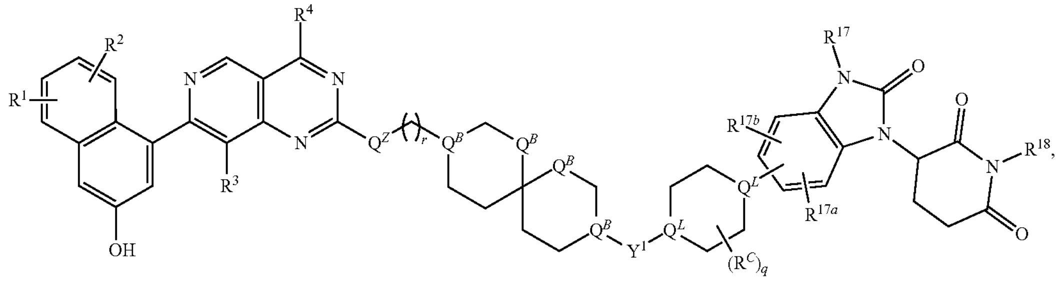

or a pharmaceutically acceptable salt thereof wherein:

each $Q^B$ is independently selected from CH, $CH_2$, N, NH, and N($C_{1-6}$ alkyl), provided that at least one $Q^B$ is N, NH, or N($C_{1-6}$ alkyl);

$Q^Z$ is O, NH, or N($C_{1-6}$ alkyl);

each $Q^L$ is independently $CR^L$ or N, provided that at least one $Q^L$ is N;

each $R^L$ is independently selected from H, halo, CN, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6; and q is 0, 1, or 2.

In embodiments of Formula VIAA-iaii, at least two $Q^B$ are $CH_2$.

In embodiments, the compound of Formula VIAA-ia has a structure of Formula VIAA-iaiii:

(VIAA-iaiii)

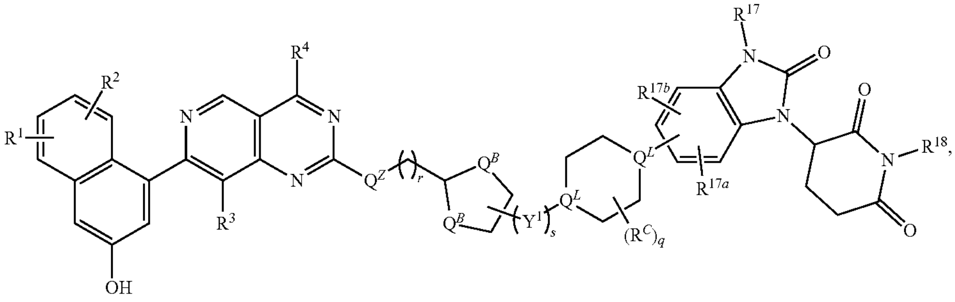

or a pharmaceutically acceptable salt thereof wherein:

each $Q^B$ is independently selected from $CH_2$, NH, and N($C_{1-6}$ alkyl), provided that at least one $Q^B$ is NH or N($C_{1-6}$ alkyl);

$Q^Z$ is O, NH, or N($C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from O, C(O), N(H), N($C_{1-6}$ alkyl), $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

r is 1, 2, 3, 4, 5, or 6;

s is 0, 1, 2, or 3; and q is 0, 1, or 2.

In embodiments, the compound of Formula VIAA-ii has a structure of Formula VIAA-iia:

(VIAA-iia)

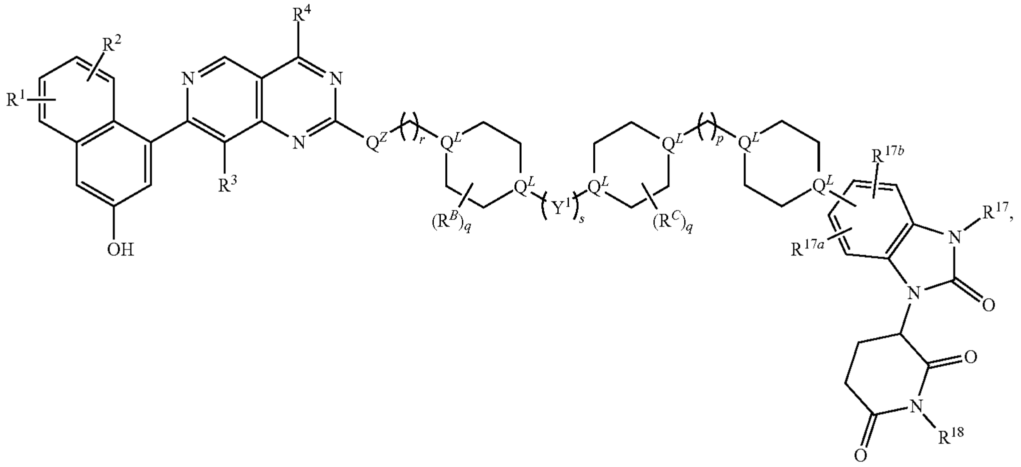

or a pharmaceutically acceptable salt thereof wherein:

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

$R^B$ and $R^C$ are each independently halo or $C_{1-6}$ alkyl;

$Y^1$ is $C_{1-6}$ alkyl or $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and each q is independently 0, 1, or 2.

In embodiments, the compound of Formula VIAA-ii has a structure of Formula VIAA-iib:

(VIAA-iib)

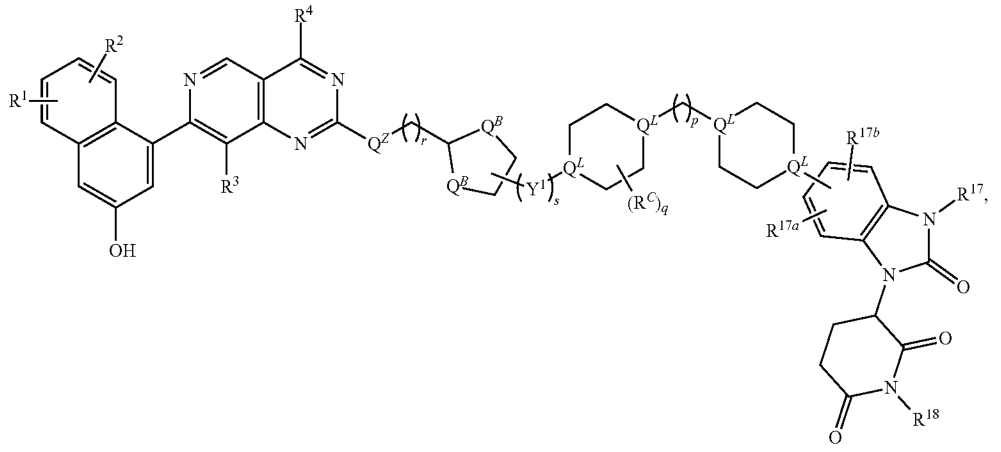

or a pharmaceutically acceptable salt thereof wherein:

each $Q^B$ is independently selected from $CH_2$, NH, and $N(C_{1-6}$ alkyl), provided that at least one $Q^B$ is NH or $N(C_{1-6}$ alkyl);

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from O, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and q is 0, 1, or 2.

In embodiments, the compound of Formula VIAA-ii has a structure of Formula VIAA-iic:

(VIAA-iic)

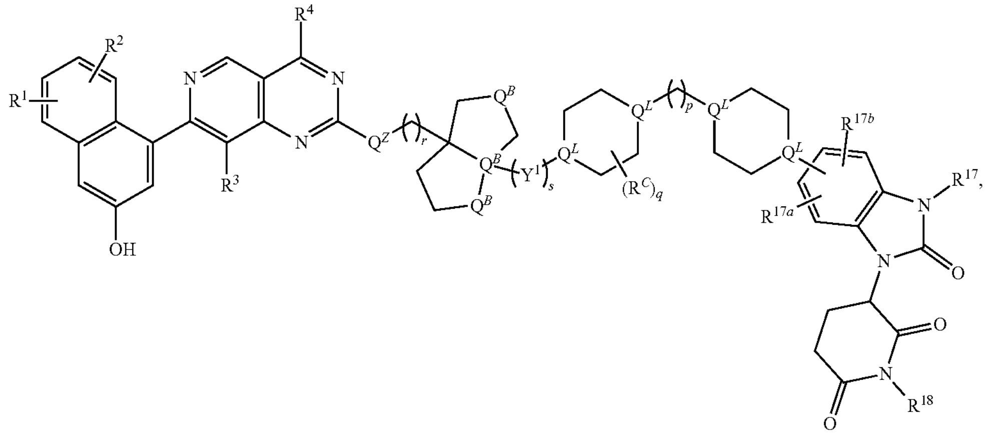

or a pharmaceutically acceptable salt thereof wherein:

each $Q^B$ is independently selected from $CH_2$, N, NH, and $N(C_{1-6}$ alkyl), provided that at least one $Q^B$ is N, NH, or $N(C_{1-6}$ alkyl);

$Q^Z$ is O, NH, or $N(C_{1-6}$ alkyl);

each $Q^L$ is independently $CR^L$ or N;

each $R^L$ is independently selected from H, halo, CN, and $C_{1-6}$ alkyl;

each $R^C$ is independently halo or $C_{1-6}$ alkyl;

$Y^1$ is selected from 0, $C_{1-6}$ alkyl, and $C_{1-6}$ haloalkyl;

$R^1$ is halo or $C_{2-6}$ alkynyl;

$R^2$ is selected from H, halo, $C_{1-6}$ alkyl, and $C_{2-6}$ alkynyl;

p and r are each independently 1, 2, 3, 4, 5, or 6; and q is 0, 1, or 2.

In embodiments of Formula VIAA-iic, at least two $Q^B$ are $CH_2$.

Various Embodiments of Formulae I-VIA, VIAA, VII, AI, AIV, and the Various Subgeneric Formulae Thereof, or Pharmaceutically Acceptable Salts Thereof In embodiments, $Q^1$ is $CH_2$ or C(O). In embodiments, $Q^2$ is N. In embodiments, $Q^3$ is CH or N. In embodiments, $R^{1a}$ is selected from H and OH. In embodiments, $R^{1b}$ and $R^{2b}$, together with the phenyl to which they attach, form naphthyl substituted with $R^1$ and $R^2$. In embodiments, $R^1$ is selected from H, halo, and $C_{1-6}$ alkyl. In embodiments, $R^1$ is H. In embodiments, $R^1$ is halo.

In embodiments, $R^1$ is $C_{1-6}$ alkyl. In embodiments, $R^{2a}$ is selected from H and halo. In embodiments, $R^2$ is selected from H, $C_{1-6}$ alkyl, and C≡CH. In embodiments, $R^2$ is $C_{3-6}$ cycloalkyl.

In embodiments, $R^2$ is H. In embodiments, $R^2$ is $C_{1-6}$ alkyl. In embodiments, $R^2$ is C≡CH.

In embodiments, $R^3$ is halo.

In embodiments $R^4$ is bridged 8-membered heterocycloalkyl optionally substituted with $R^{4a}$.

In embodiments of Formulae I-VI, $R^4$ is:

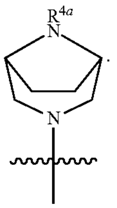

In embodiments, $R^{4a}$ is H or $C_{1-6}$ alkyl. In embodiments, $R^{5a}$ is H, halo, or $C_{1-6}$ alkoxy. In embodiments, $R^5$ is H or $C_{1-6}$ alkyl. In embodiments, $R^6$ is H or $C_{1-6}$ alkyl.

In embodiments, $R^7$ is selected from H, =O, halo, and $C_{1-6}$ alkoxy. In embodiments, wherein $R^7$ is =O. In embodiments, $R^7$ is halo. In embodiments, $R^7$ is $C_{1-6}$ alkoxy. In embodiments, $R^8$ is H or $C_{1-6}$ alkyl. In embodiments, $R^8$ is H. In embodiments, $R^9$ is selected from H, halo, and $C_{1-6}$ alkoxy. In embodiments, $R^9$ is halo.

In embodiments, $R^9$ is $C_{1-6}$ alkoxy. In embodiments, $R^{10}$ is H. In embodiments, $R^{11}$ is H.

In embodiments, $R^{12}$ is $C_{1-6}$ alkyl. In embodiments, $R^{13}$ is H. In embodiments, $R^{14}$ is H or $C_{1-6}$ alkyl. In embodiments, $R^{14}$ is H. In embodiments, $R^{14}$ is $C_{1-6}$ alkyl.

In embodiments, $R^{15a}$ is H, halo, or $C_{1-6}$ alkoxy. In embodiments, $R^{15b}$ is H, halo, or $C_{1-6}$ alkoxy. In embodiments, $R^{15}$ is H or $C_{1-6}$ alkyl. In embodiments, $R^{16}$ is H or $C_{1-6}$ alkyl. In embodiments, $R^{17a}$ and $R^{17b}$ are each independently H or halo. In embodiments, $R^{17}$ is $C_{1-6}$ alkyl. In embodiments, $R^{18}$ is H.

In embodiments, Ring A is phenyl. In embodiments, Ring A is 6-membered heterocycloalkyl. In embodiments, Ring A is dihydropyridinyl. In embodiments, B is a bond. In embodiments, B is $C_{1-6}$ alkyl.

In embodiments, each L is independently selected from $C_{1-6}$ alkyl, $C_{1-6}$ alkoxy, C(O), 5-12 membered heterocycloalkyl, wherein 5-12 membered heterocycloalkyl is optionally substituted with halo. In embodiments, 5-12 membered heterocycloalkyl is fused 8 membered heterocycloalkyl.

In embodiments, each L is independently selected from $C_{1-6}$ alkyl, $C_{1-6}$ alkoxy, and 6-12 membered heterocycloalkyl, wherein 6-12 membered heterocycloalkyl is optionally substituted with halo.

In embodiments, each L is independently selected from $C_{1-6}$ alkyl, $C_{1-6}$ alkoxy, 6-8 membered heterocycloalkyl, and 5-6 membered heteroaryl, wherein 6-8 membered heterocycloalkyl is optionally substituted with halo.

In embodiments, L forms the following linker: ($C_{1-6}$ alkoxy)-(6-12 membered heterocycloalkyl)-($C_{1-6}$ alkyl)-(6-12 membered heterocycloalkyl).

In embodiments, n is 4, and each L forms the following linker: ($C_{1-6}$ alkoxy)-(6-12 membered heterocycloalkyl)-($C_{1-6}$ alkyl)-(6-12 membered heterocycloalkyl).

In embodiments, n is 4, and each L forms the following linker: ($C_{1-6}$ alkoxy)-(6-membered heterocycloalkyl)-($C_{1-6}$ alkyl)-(7-membered heterocycloalkyl).

In embodiments, n is 4, and each L forms the following linker: ($C_{1-6}$ alkoxy)-(6-membered heterocycloalkyl)-($C_{1-6}$ alkyl)-(9-membered heterocycloalkyl).

In embodiments, n is 4, and each L forms the following linker: ($C_{1-6}$ alkoxy)-(6-membered heterocycloalkyl)-($C_{1-6}$ alkyl)-(11-membered heterocycloalkyl).

In embodiments, each L forms the linker:

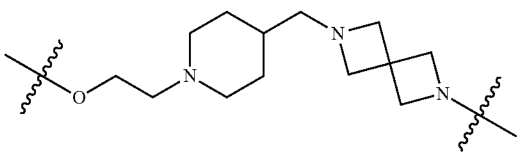

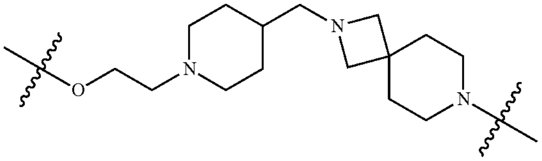

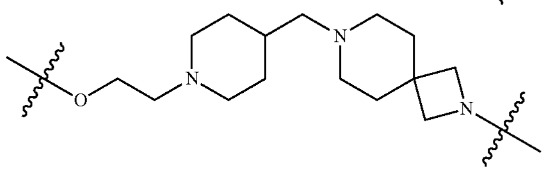

or

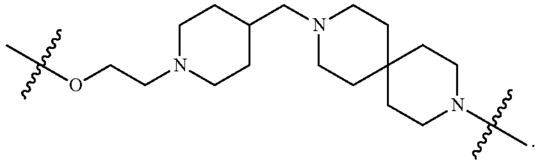

In embodiments, n is 6, and each L forms the following linker: ($C_{1-6}$ alkoxy)-(6-12 membered heterocycloalkyl)-($C_{1-6}$ alkyl)-(6-12 membered heterocycloalkyl)-($C_{1-6}$ alkyl)-(6-membered heterocycloalkyl).

In embodiments, n is 6, and each L forms the following linker: ($C_{1-6}$ alkoxy)-(6-membered heterocycloalkyl)-($C_{1-6}$ alkyl)-(6-membered heterocycloalkyl)-($C_{1-6}$ alkyl)-(6-membered heterocycloalkyl).

In embodiments, n is 4, and each L forms the following linker: ($C_{1-6}$ alkoxy)-(5-12 membered heterocycloalkyl)-($C_{1-6}$ alkyl)-(5-12 membered heterocycloalkyl).

In embodiments, n is 4, and each L forms the following linker: ($C_{1-6}$ alkoxy)-(11-membered heterocycloalkyl)-($C_{1-6}$ alkyl)-(6-membered heterocycloalkyl).

In embodiments, 11-membered heterocycloalkyl is spirocyclic 11-membered heterocycloalkyl.

In embodiments, n is 6, and each L forms the following linker: ($C_{1-6}$ alkoxy)-(5-12 membered heterocycloalkyl)-(O)-(5-12 membered heterocycloalkyl)-($C_{1-6}$ alkyl)-(5-12 membered heterocycloalkyl), wherein 5-12 membered heterocycloalkyl is optionally substituted with $C_{1-6}$ alkyl.

In embodiments, n is 6, and each L forms the following linker: ($C_{1-6}$ alkoxy)-(5-membered heterocycloalkyl)-(O)-(6-membered heterocycloalkyl)-($C_{1-6}$ alkyl)-(6-membered heterocycloalkyl), wherein 5 membered heterocycloalkyl is optionally substituted with $C_{1-6}$ alkyl.

In embodiments, n is 4, and each L forms the following linker: ($C_{1-6}$ alkoxy)-(5-12 membered heterocycloalkyl)-($C_{1-6}$ alkyl)-(5-12 membered heterocycloalkyl).

In embodiments, n is 4, and each L forms the following linker: ($C_{1-6}$ alkoxy)-(6-membered heterocycloalkyl)-($C_{1-6}$ alkyl)-(9-membered heterocycloalkyl).

In embodiments, 9-membered heterocycloalkyl is spirocyclic 9-membered heterocycloalkyl.

In embodiments, n is 4, and each L forms the following linker: ($C_{1-6}$ alkoxy)-(5-12 membered heterocycloalkyl)-(O)-(5-12 membered heterocycloalkyl), wherein 5-12 membered heterocycloalkyl is optionally substituted with $C_{1-6}$ alkyl.

In embodiments, n is 4, and each L forms the following linker: ($C_{1-6}$ alkoxy)-(5-membered heterocycloalkyl)-(O)-(6-membered heterocycloalkyl), wherein 5 membered heterocycloalkyl is optionally substituted with $C_{1-6}$ alkyl.

In embodiments, heterocycloalkyl contains 1, 2, or 3 heteroatoms independently selected from N, O, and S. In embodiments, heterocycloalkyl contains 1 or 2 heteroatoms independently selected from N, O, and S. In embodiments, heterocycloalkyl contains 1 or 2 heteroatoms independently selected from N and O. In embodiments, heterocycloalkyl contains 1 or 2 nitrogen heteroatoms.

In embodiments, each L forms the linker:

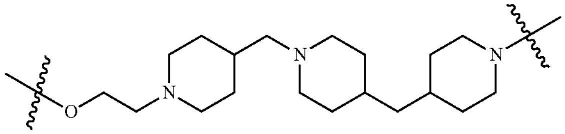

,

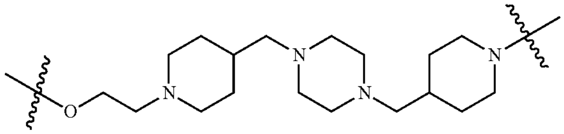

,

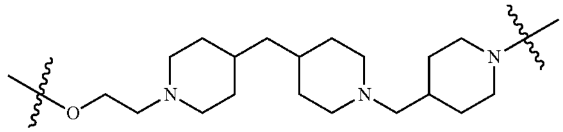

,

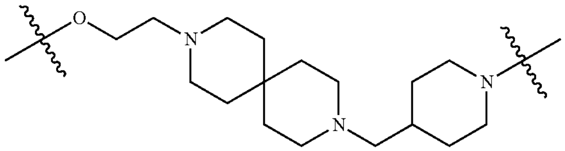

,

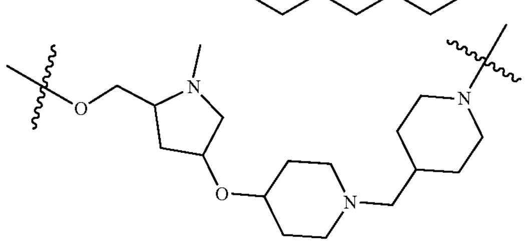

,

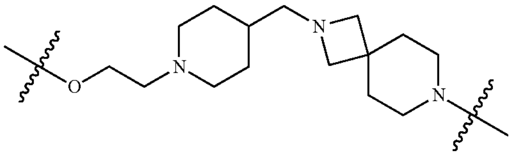

, or

-continued
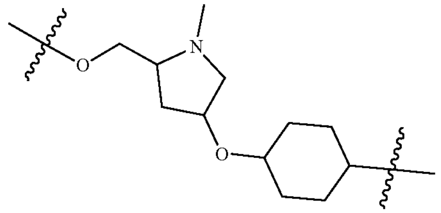
.
In embodiments, (L), is selected from:
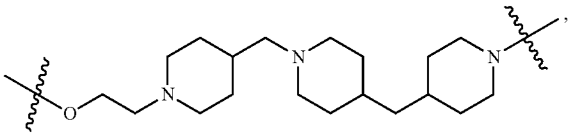
,
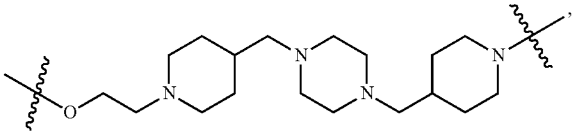
,
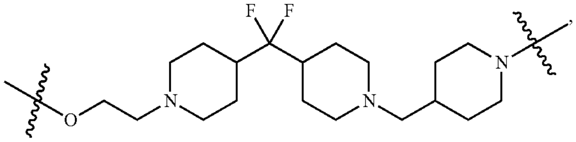
,
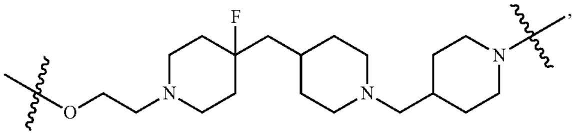
,
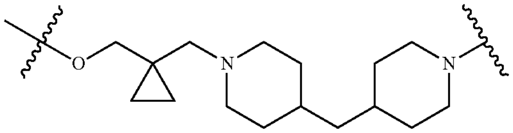
,
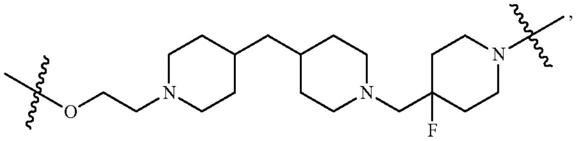
,
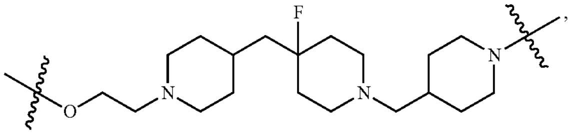
,
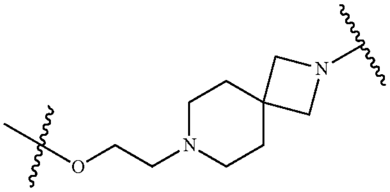
,
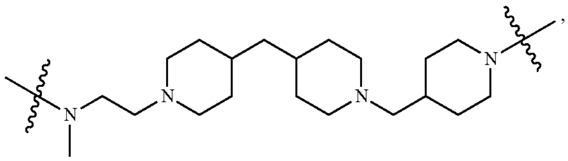
,
-continued
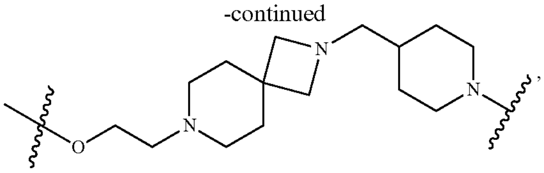
,
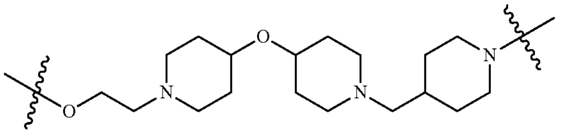
,
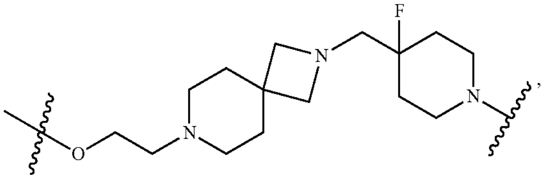
,
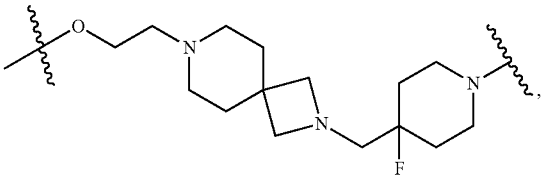
,
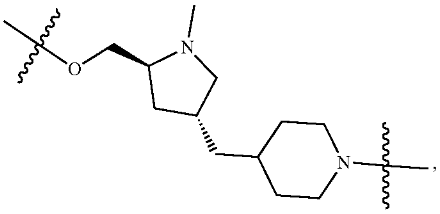
,
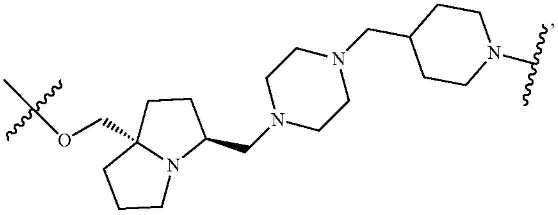
,
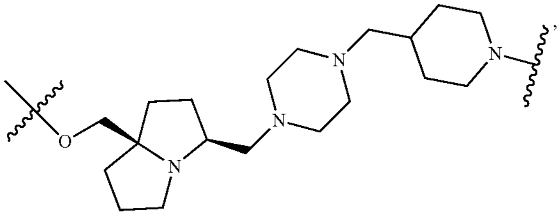
,
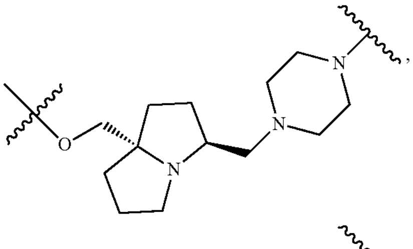
,
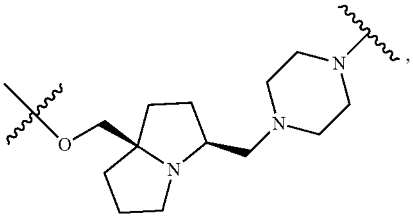
, -continued
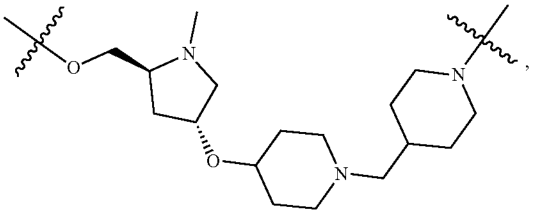
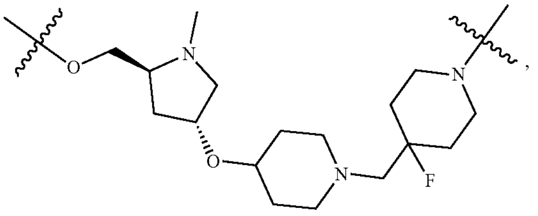
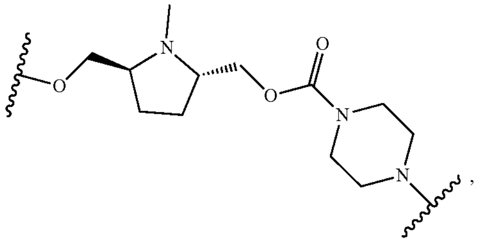
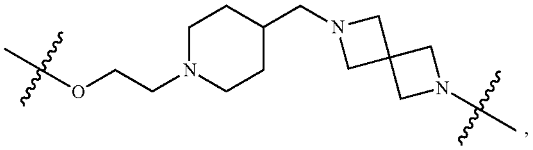
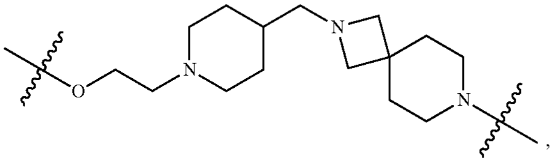
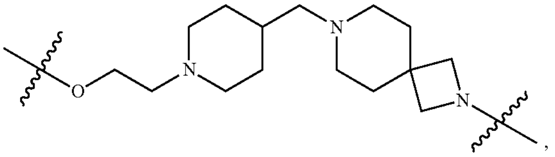
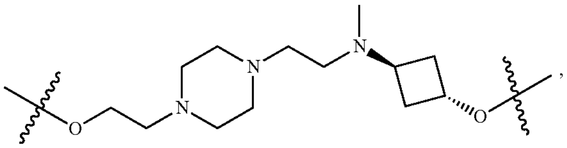
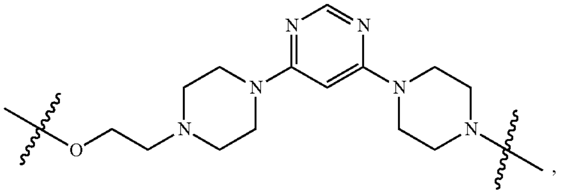
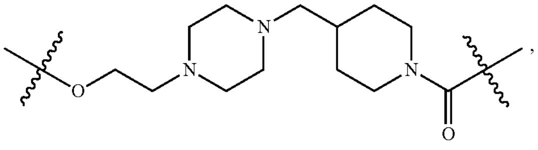
-continued
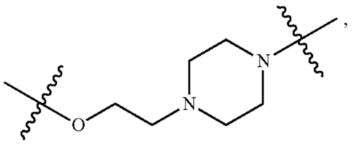
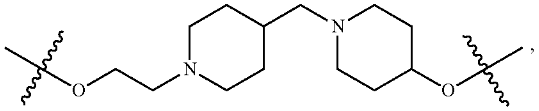
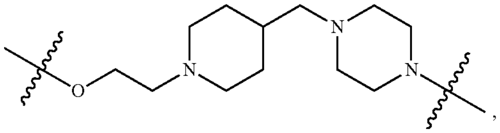
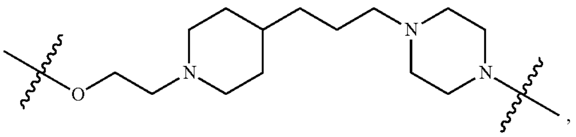
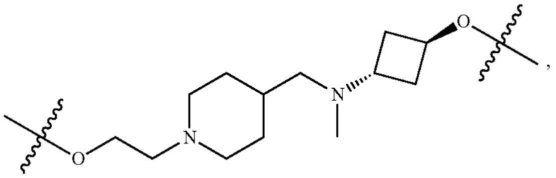
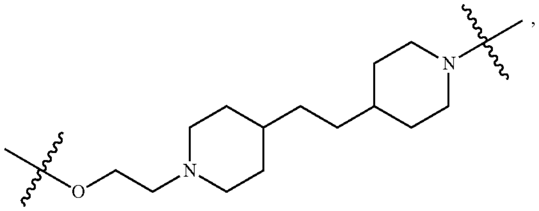
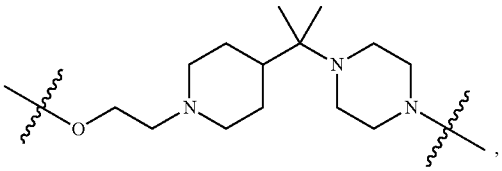
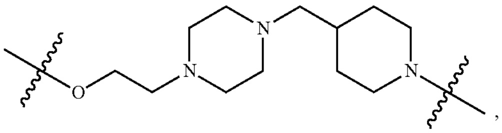
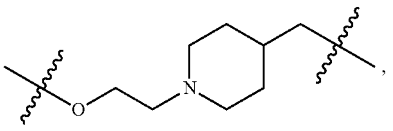
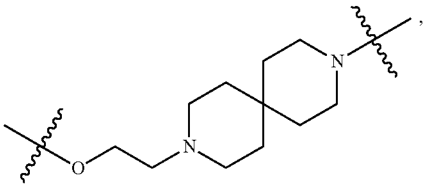
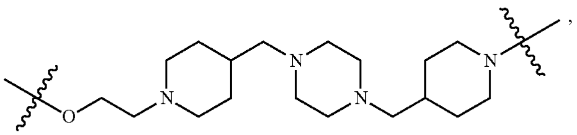

-continued

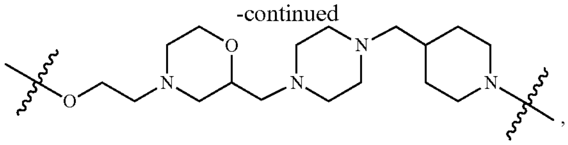,

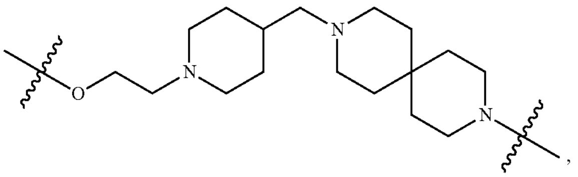,

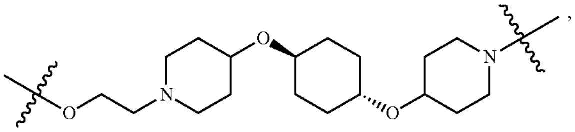,

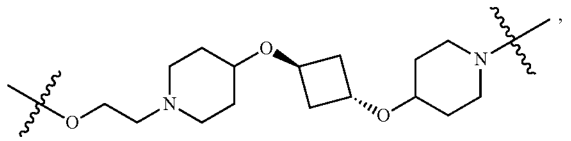,

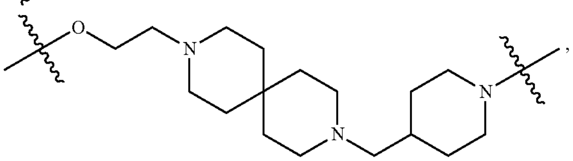,

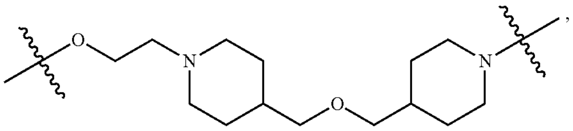,

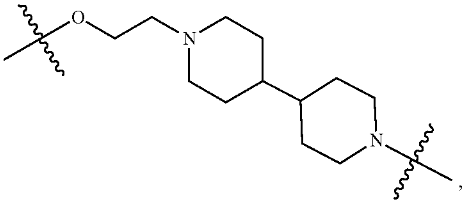,

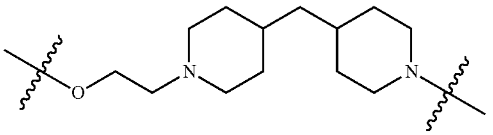,

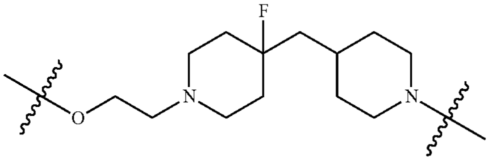,

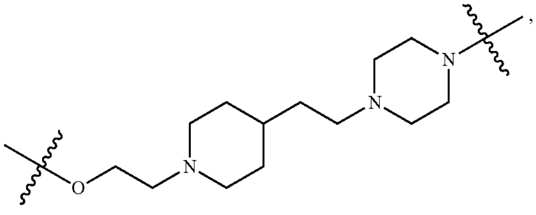,

-continued

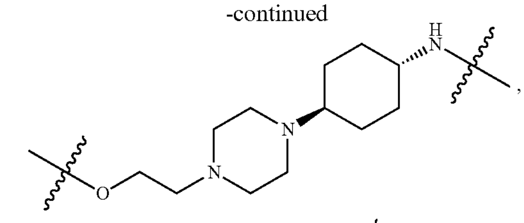,

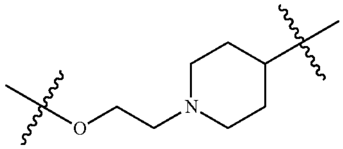,

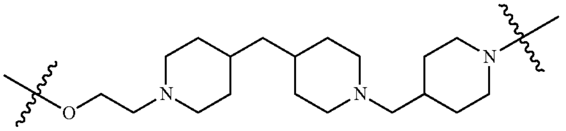,

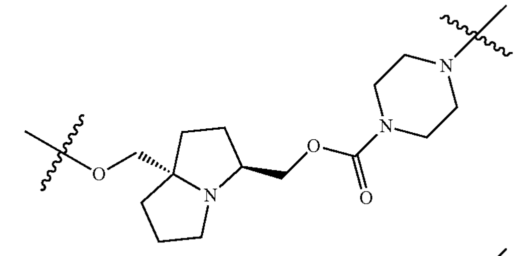,

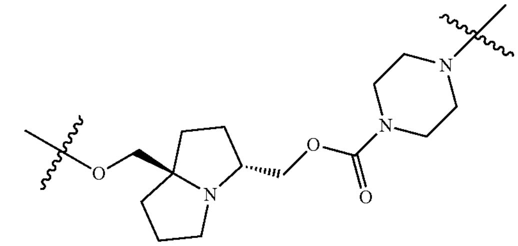,

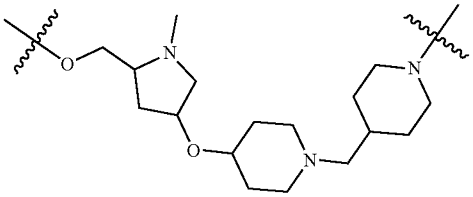, and

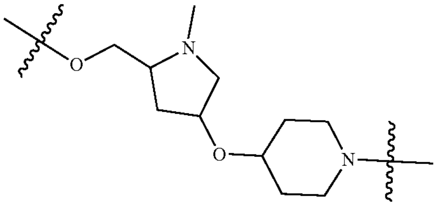.

In choosing compounds of the present invention, one of ordinary skill in the art will recognize that the various substituents are to be chosen in conformity with well-known principles of chemical structure connectivity and stability.

In embodiments, the compound of Formula I is selected from a compound in Table 1, or a pharmaceutically acceptable salt thereof.

??TABLE 1
| Compound | Structure |
|---|---|
| 1 | 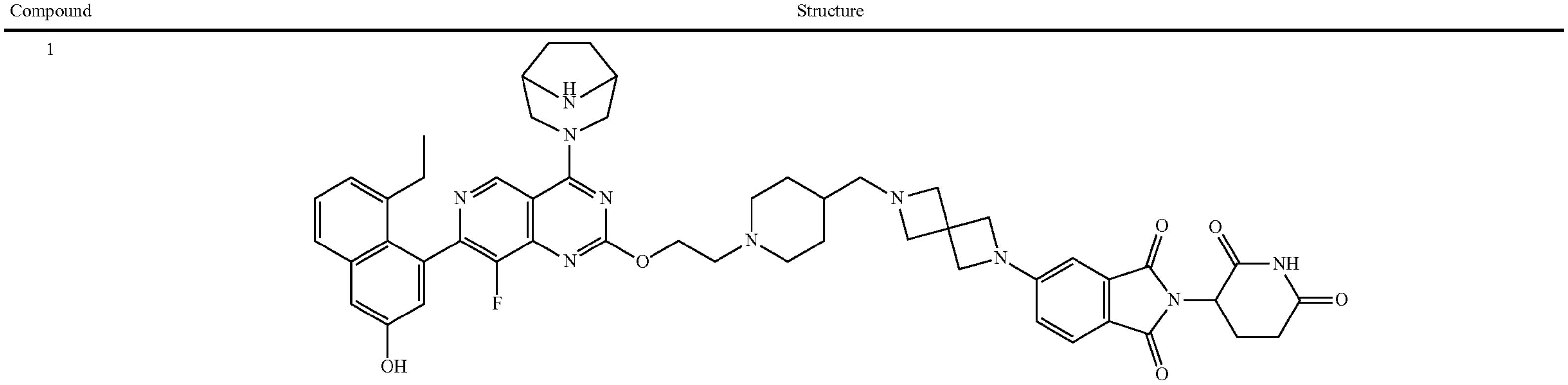 |
| 2 | 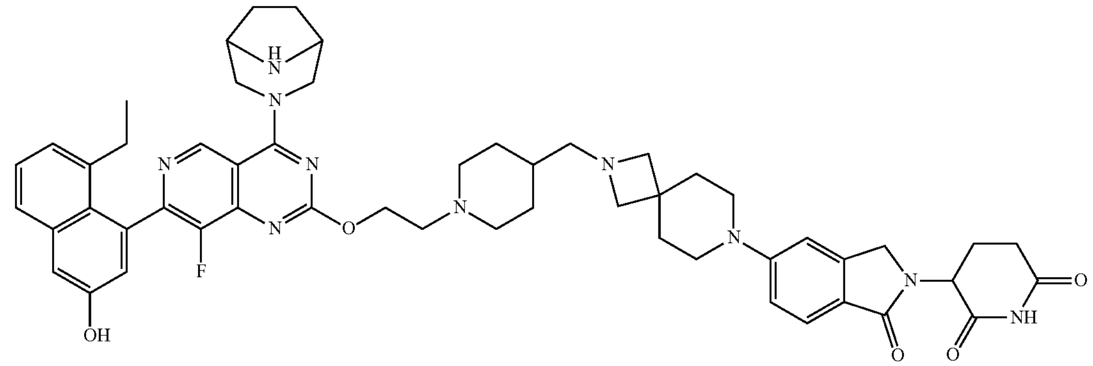 [SMILES: CCc1cccc2cc(O)cc(-c3ncc4c(N5CC6CCC(C5)N6)nc(OCCN5CCC(CN6CC7(CCN(c8ccc9c(c8)CN(C8CCC(=O)NC8=O)C9=O)CC7)C6)CC5)nc4c3F)c12] |

??TABLE 1-continued
| Compound | Structure |
| --- | --- |
| 3 | 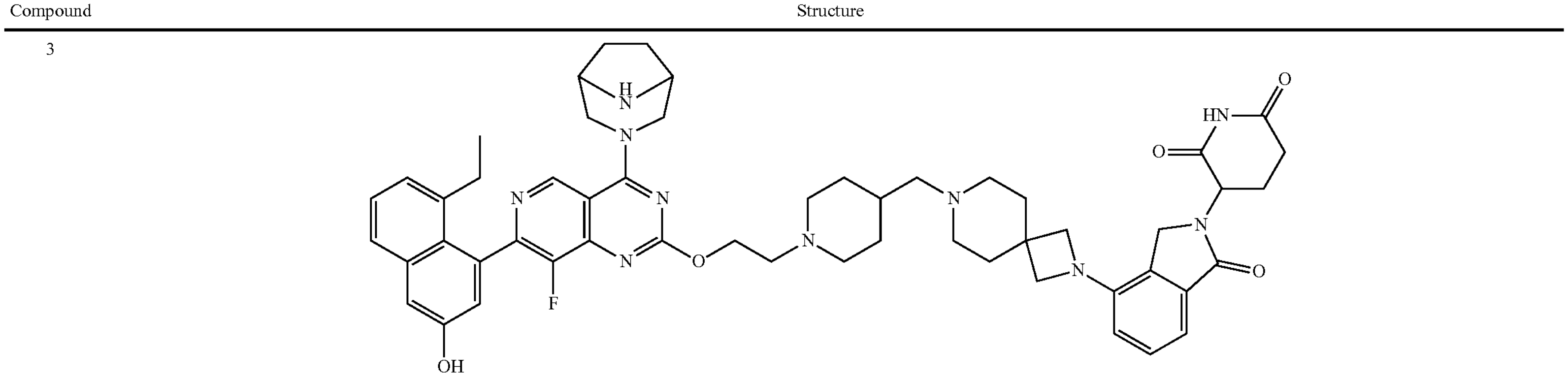 |
| 4 | 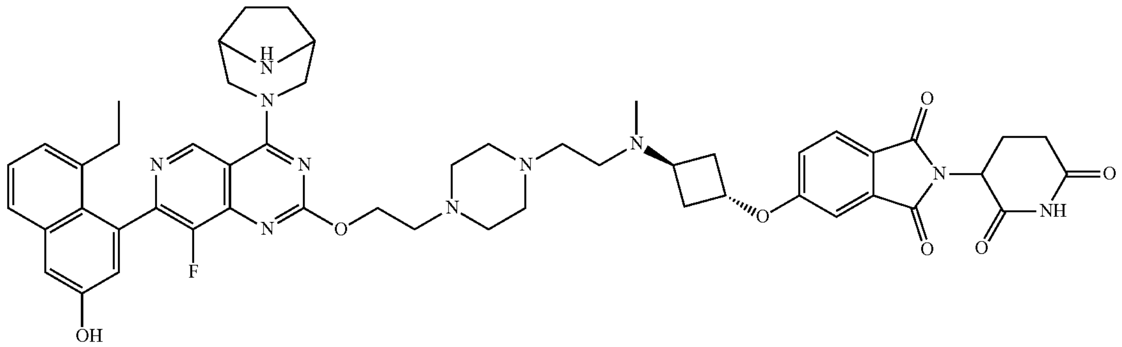 [SMILES: CCc1cccc2cc(O)cc(-c3ncc4c(N5CC6CCC(C5)N6)nc(OCCN5CCN(CCN(C)[C@H]6C[C@H](Oc7ccc8c(c7)C(=O)N(C7CCC(=O)NC7=O)C8=O)C6)CC5)nc4c3F)c12] |
| 5 | 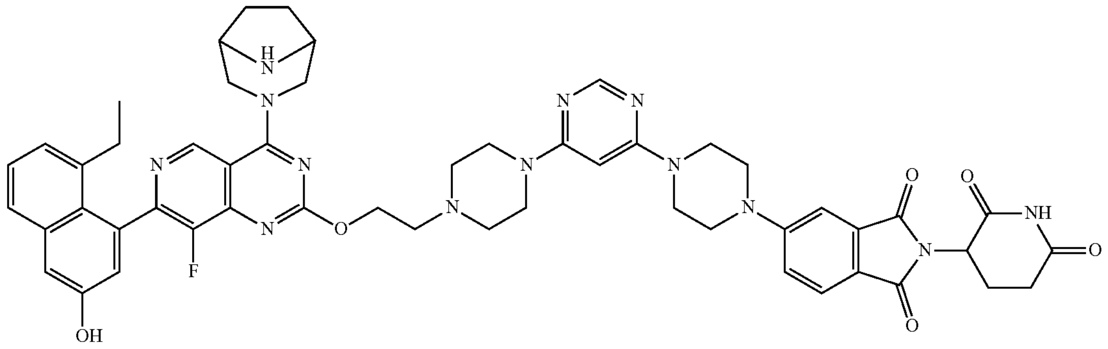 [SMILES: CCc1cccc2cc(O)cc(-c3ncc4c(N5CC6CCC(C5)N6)nc(OCCN5CCN(c6cc(N7CCN(c8ccc9c(c8)C(=O)N(C8CCC(=O)NC8=O)C9=O)CC7)ncn6)CC5)nc4c3F)c12] |

??TABLE 1-continued
| Compound | Structure |
|---|---|
| 6 | 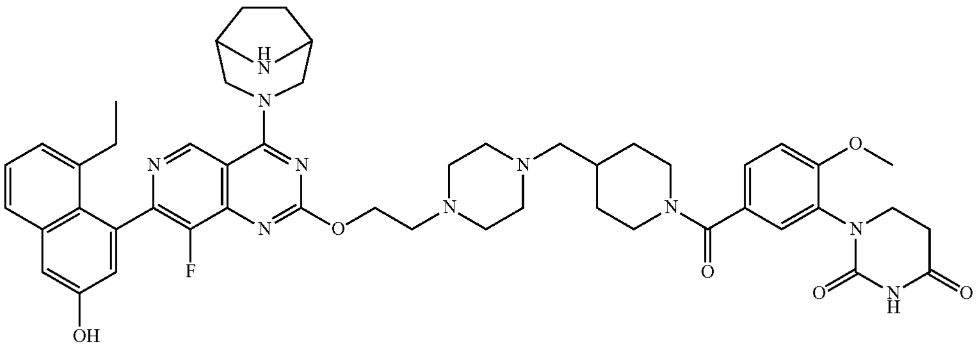 [SMILES: CCc1cccc2cc(O)cc(-c3ncc4c(N5CC6CCC(C5)N6)nc(OCCN5CCN(CC6CCN(C(=O)c7ccc(OC)c(N8CCC(=O)NC8=O)c7)CC6)CC5)nc4c3F)c12] |
| 7 | 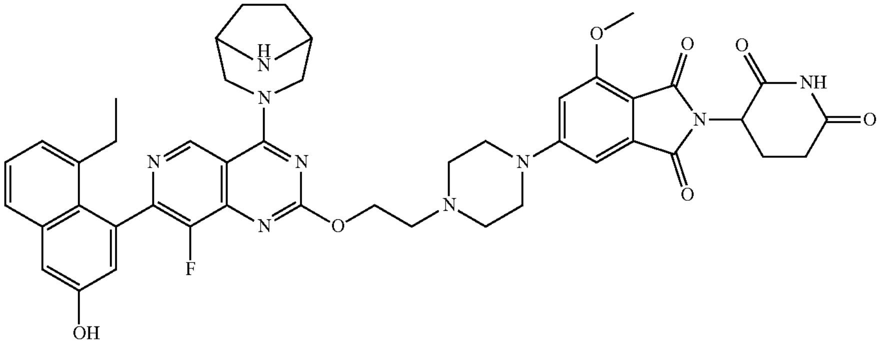 [SMILES: CCc1cccc2cc(O)cc(-c3ncc4c(N5CC6CCC(C5)N6)nc(OCCN5CCN(c6cc(OC)c7c(c6)C(=O)N(C6CCC(=O)NC6=O)C7=O)CC5)nc4c3F)c12] |
| 8 | 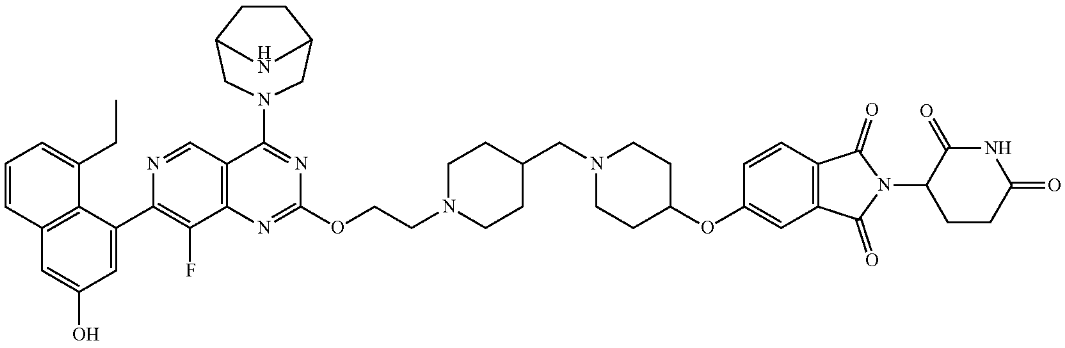 [SMILES: CCc1cccc2cc(O)cc(-c3ncc4c(N5CC6CCC(C5)N6)nc(OCCN5CCC(CN6CCC(Oc7ccc8c(c7)C(=O)N(C7CCC(=O)NC7=O)C8=O)CC6)CC5)nc4c3F)c12] |

??TABLE 1-continued
| Compound | Structure |
| --- | --- |
| 9 | 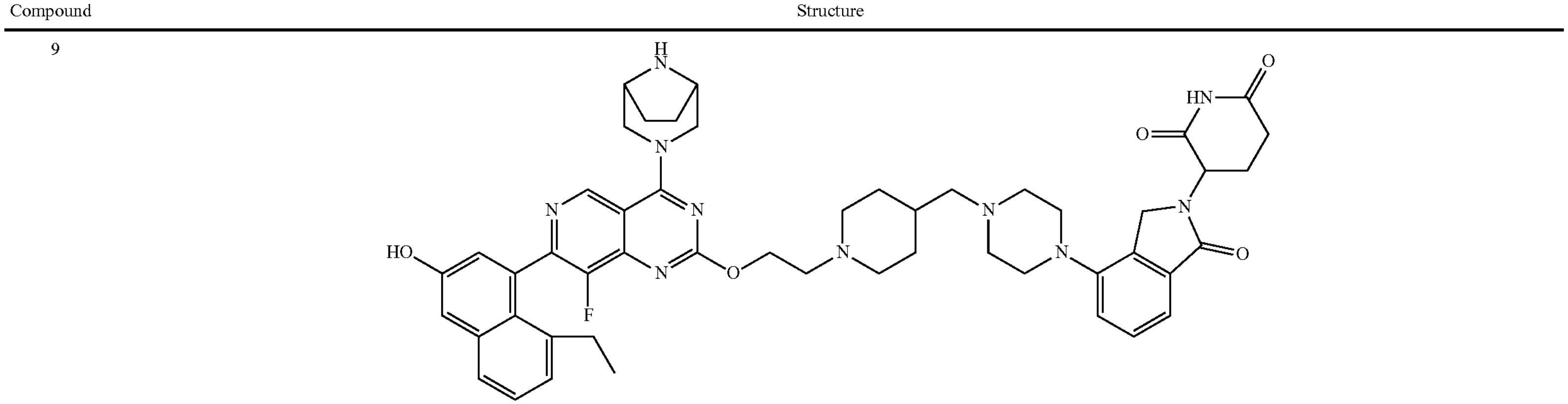 |
| 10 | 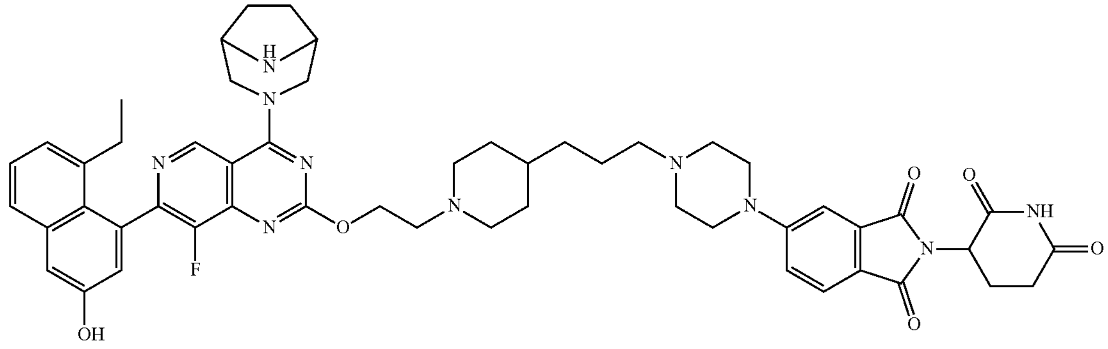 [SMILES: CCc1cccc2cc(O)cc(-c3ncc4c(N5CC6CCC(C5)N6)nc(OCCN5CCC(CCCN6CCN(c7ccc8c(c7)C(=O)N(C7CCC(=O)NC7=O)C8=O)CC6)CC5)nc4c3F)c12] |
| 11 | 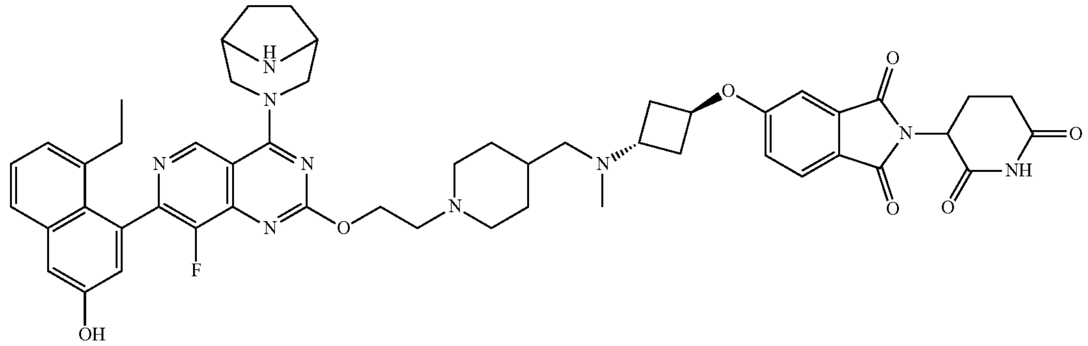 [SMILES: CCc1cccc2cc(O)cc(-c3ncc4c(N5CC6CCC(C5)N6)nc(OCCN5CCC(CN(C)[C@H]6C[C@H](Oc7ccc8c(c7)C(=O)N(C7CCC(=O)NC7=O)C8=O)C6)CC5)nc4c3F)c12] |

??TABLE 1-continued
| Compound | Structure |
| --- | --- |
| 12 | 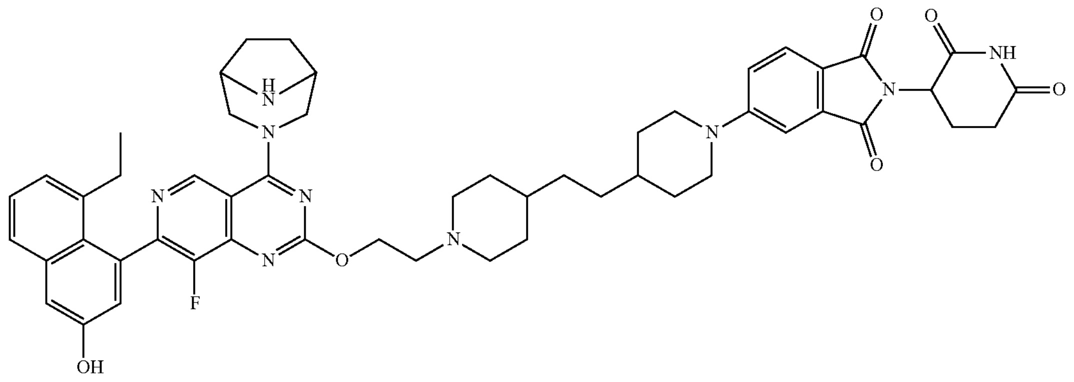 [SMILES: CCc1cccc2cc(O)cc(-c3ncc4c(N5CC6CCC(C5)N6)nc(OCCN5CCC(CCC6CCN(c7ccc8c(c7)C(=O)N(C7CCC(=O)NC7=O)C8=O)CC6)CC5)nc4c3F)c12] |
| 13 | 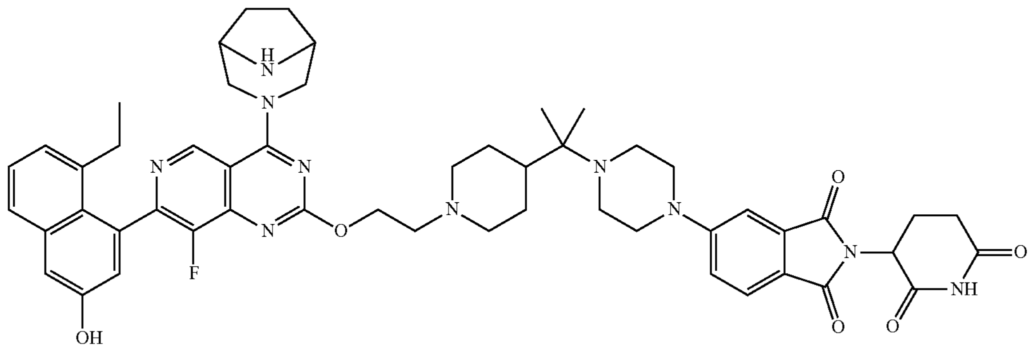 [SMILES: CCc1cccc2cc(O)cc(-c3ncc4c(N5CC6CCC(C5)N6)nc(OCCN5CCC(C(C)(C)N6CCN(c7ccc8c(c7)C(=O)N(C7CCC(=O)NC7=O)C8=O)CC6)CC5)nc4c3F)c12] |

??TABLE 1-continued
| Compound | Structure |
|---|---|
| 14 | 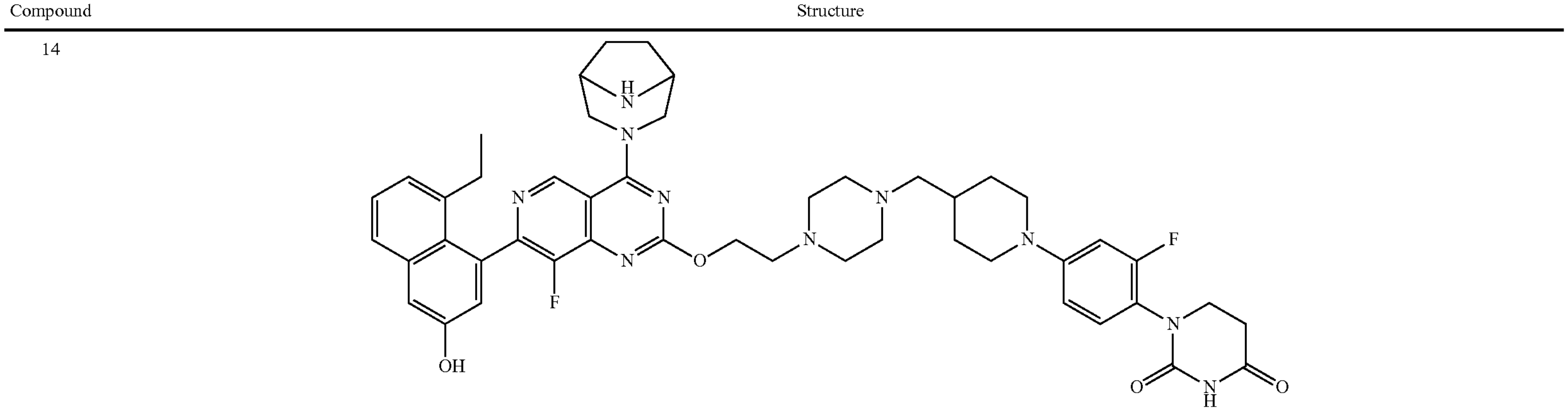 |
| 15 | 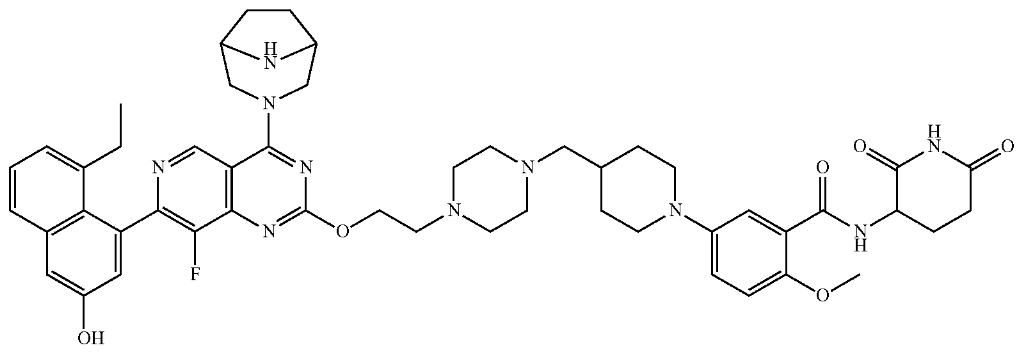 [SMILES: CCc1cccc2cc(O)cc(-c3ncc4c(N5CC6CCC(C5)N6)nc(OCCN5CCN(CC6CCN(c7ccc(OC)c(C(=O)NC8CCC(=O)NC8=O)c7)CC6)CC5)nc4c3F)c12] |

??TABLE 1-continued
| Compound | Structure |
|---|---|
| 16 | 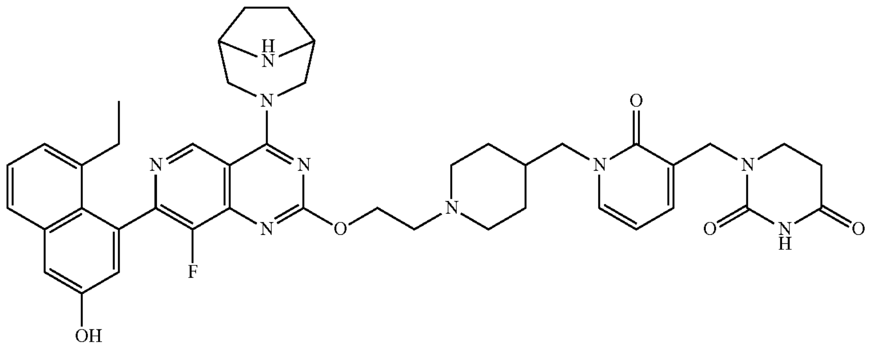 [SMILES: CCc1cccc2cc(O)cc(-c3ncc4c(N5CC6CCC(C5)N6)nc(OCCN5CCC(Cn6cccc(CN7CCC(=O)NC7=O)c6=O)CC5)nc4c3F)c12] |
| 17 | 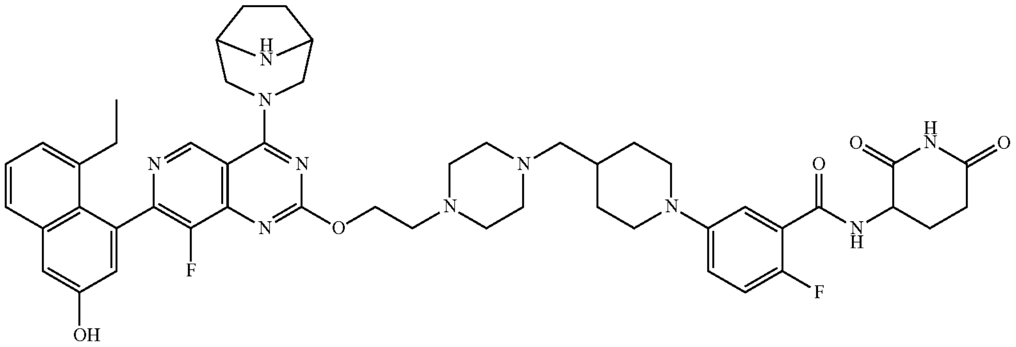 [SMILES: CCc1cccc2cc(O)cc(-c3ncc4c(N5CC6CCC(C5)N6)nc(OCCN5CCN(CC6CCN(c7ccc(F)c(C(=O)NC8CCC(=O)NC8=O)c7)CC6)CC5)nc4c3F)c12] |

??TABLE 1-continued
| Compound | Structure |
|---|---|
| 18 | 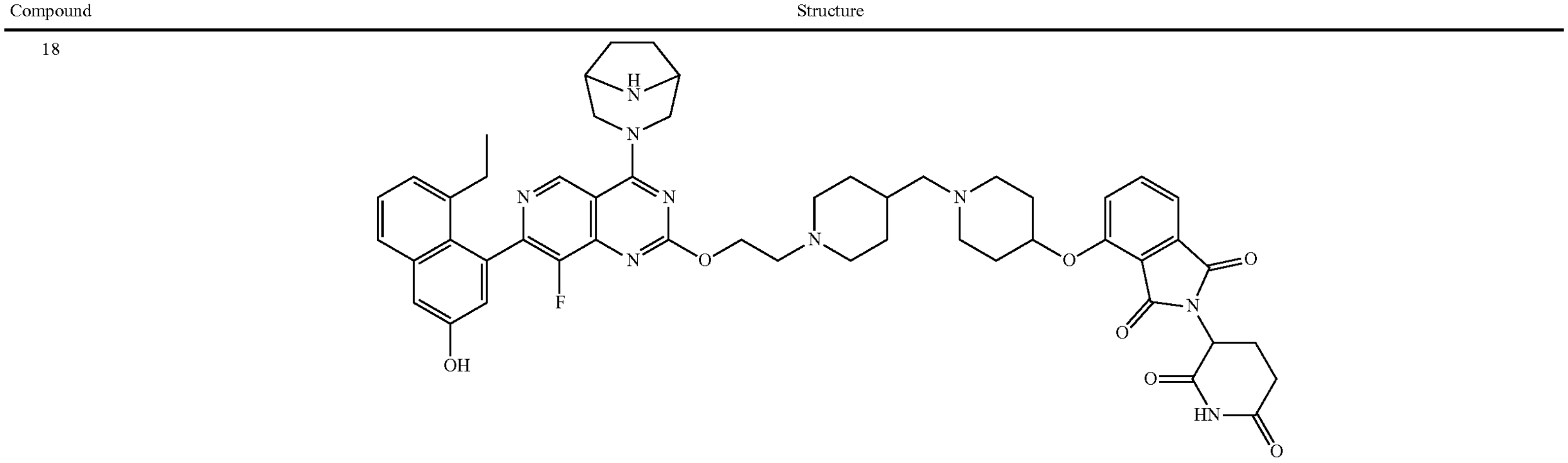 |
| 19 | 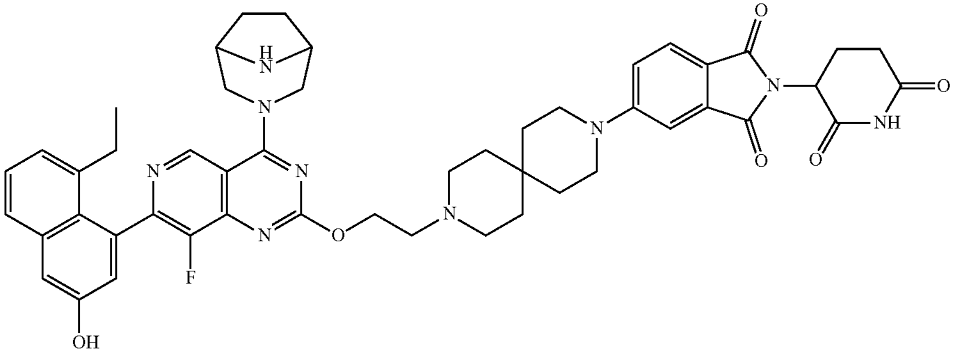 [SMILES: CCc1cccc2cc(O)cc(-c3ncc4c(N5CC6CCC(C5)N6)nc(OCCN5CCC6(CC5)CCN(c5ccc7c(c5)C(=O)N(C5CCC(=O)NC5=O)C7=O)CC6)nc4c3F)c12] |

??TABLE 1-continued
| Compound | Structure |
| --- | --- |
| 20 | 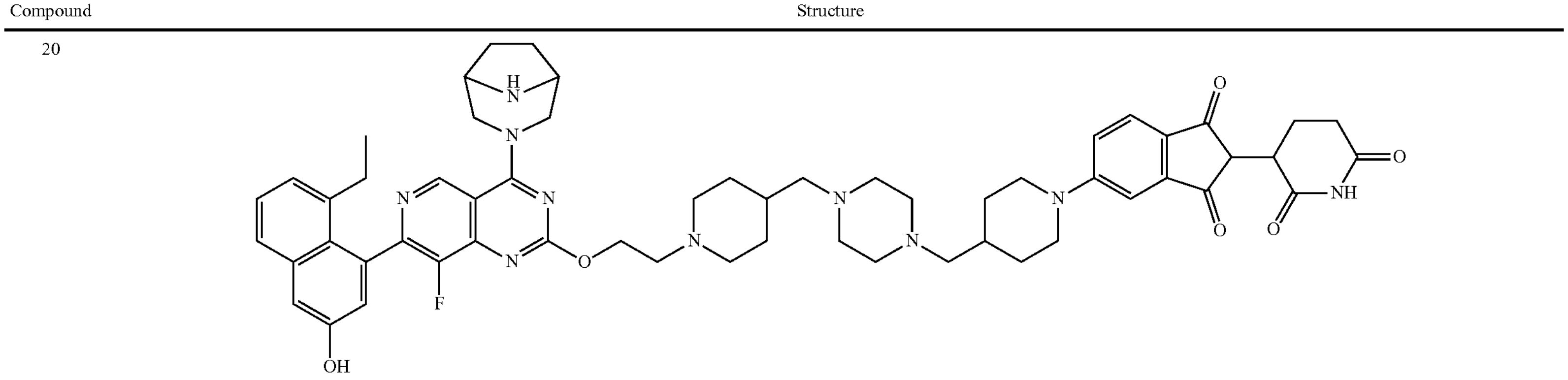 |
| 21 | 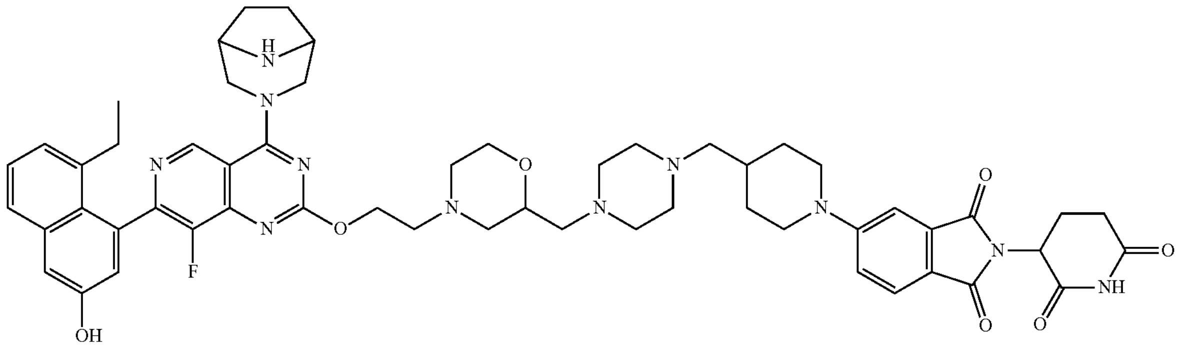 [SMILES: CCc1cccc2cc(O)cc(-c3ncc4c(N5CC6CCC(C5)N6)nc(OCCN5CCOC(CN6CCN(CC7CCN(c8ccc9c(c8)C(=O)N(C8CCC(=O)NC8=O)C9=O)CC7)CC6)C5)nc4c3F)c12] |

??TABLE 1-continued
| Compound | Structure |
|---|---|
| 22 | 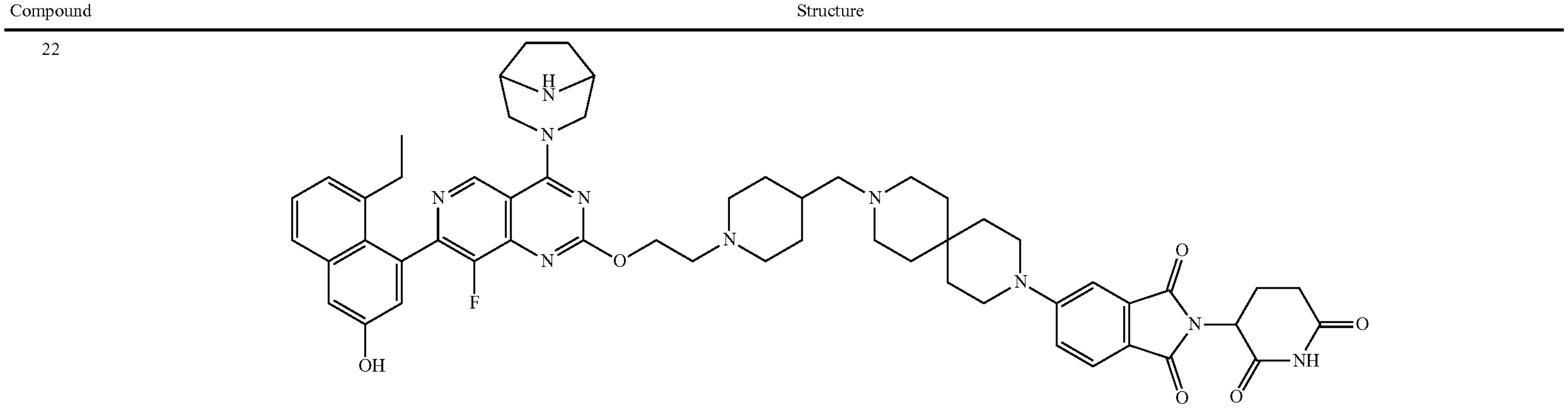 |
| 23 | 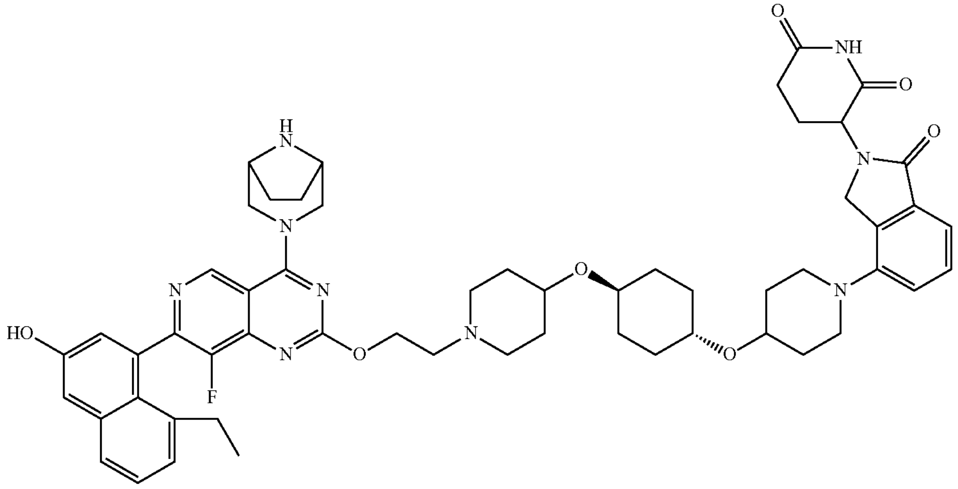 [SMILES: CCc1cccc2cc(O)cc(-c3ncc4c(N5CC6CCC(C5)N6)nc(OCCN5CCC(O[C@H]6CC[C@H](OC7CCN(c8cccc9c8CN(C8CCC(=O)NC8=O)C9=O)CC7)CC6)CC5)nc4c3F)c12] |

??TABLE 1-continued
| Compound | Structure |
|---|---|
| 24 | 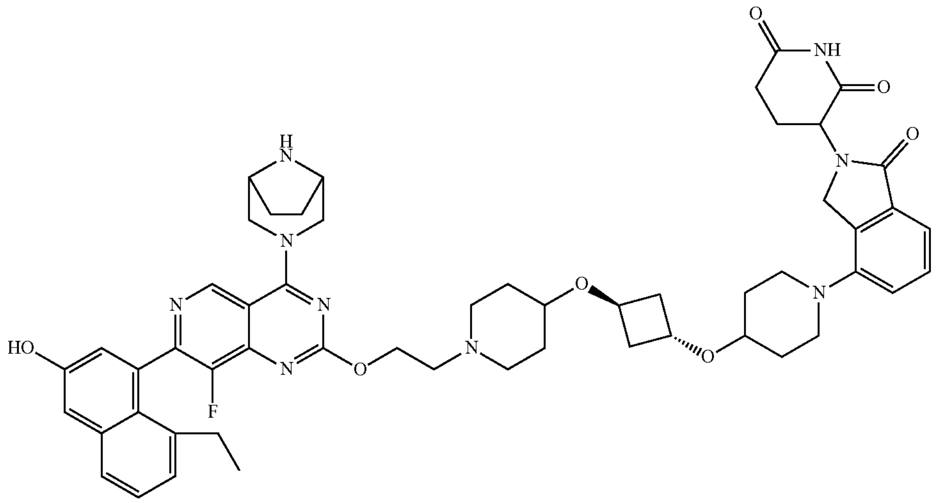 [SMILES: CCc1cccc2cc(O)cc(-c3ncc4c(N5CC6CCC(C5)N6)nc(OCCN5CCC(O[C@H]6C[C@H](OC7CCN(c8cccc9c8CN(C8CCC(=O)NC8=O)C9=O)CC7)C6)CC5)nc4c3F)c12] |
| 25 | 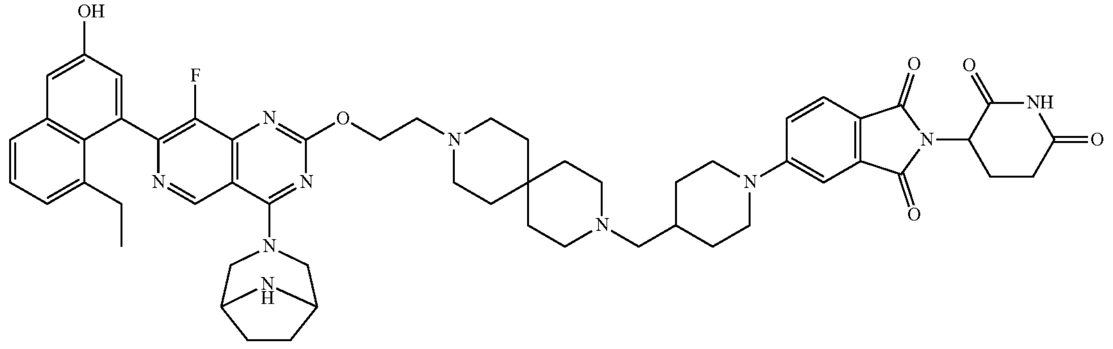 [SMILES: CCc1cccc2cc(O)cc(-c3ncc4c(N5CC6CCC(C5)N6)nc(OCCN5CCC6(CC5)CCN(CC5CCN(c7ccc8c(c7)C(=O)N(C7CCC(=O)NC7=O)C8=O)CC5)CC6)nc4c3F)c12] |

??TABLE 1-continued
| Compound | Structure |
|---|---|
| 26 | 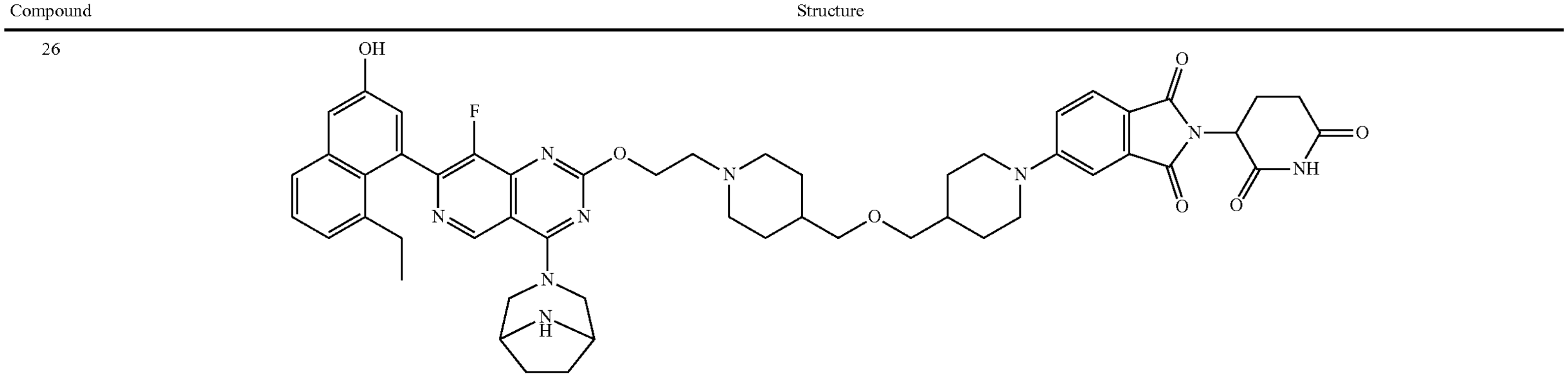 |
| 27 | 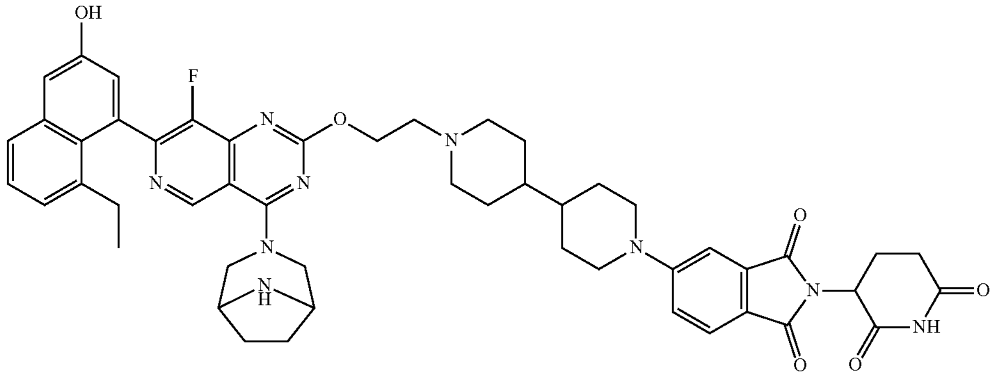 [SMILES: CCc1cccc2cc(O)cc(-c3ncc4c(N5CC6CCC(C5)N6)nc(OCCN5CCC(C6CCN(c7ccc8c(c7)C(=O)N(C7CCC(=O)NC7=O)C8=O)CC6)CC5)nc4c3F)c12] |

??TABLE 1-continued
| Compound | Structure |
| --- | --- |
| 28 | 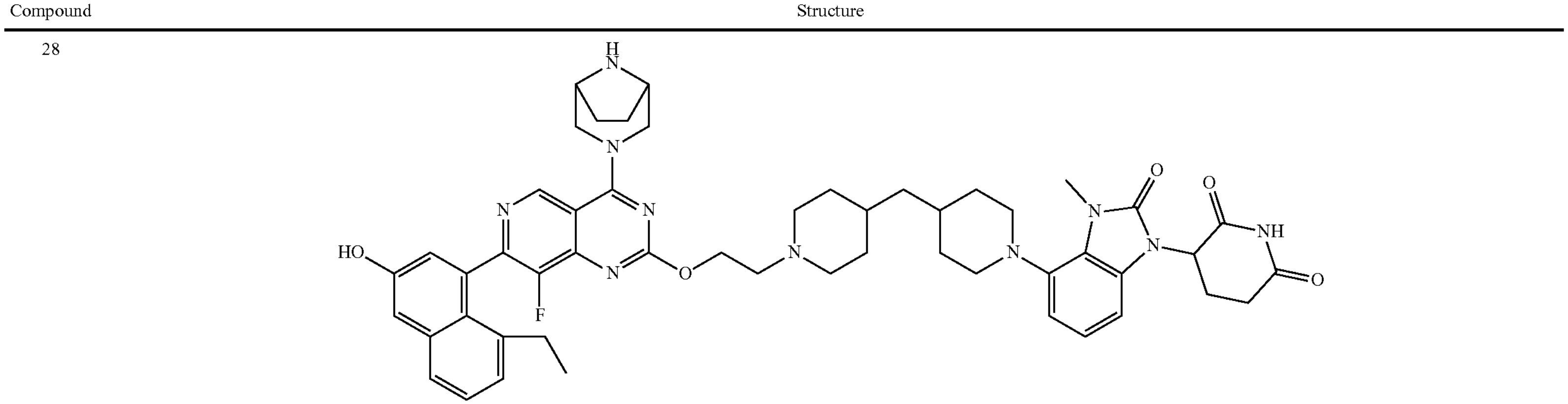 |
| 29 | 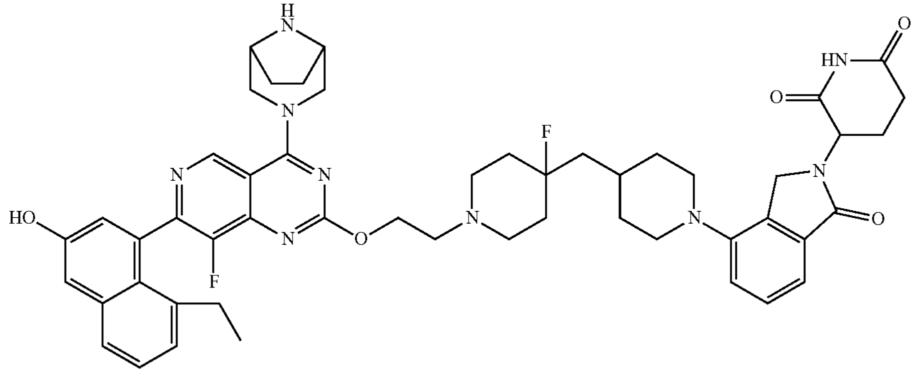 [SMILES: CCc1cccc2cc(O)cc(-c3ncc4c(N5CC6CCC(C5)N6)nc(OCCN5CCC(F)(CC6CCN(c7cccc8c7CN(C7CCC(=O)NC7=O)C8=O)CC6)CC5)nc4c3F)c12] |

??TABLE 1-continued
| Compound | Structure |
|---|---|
| 30 | 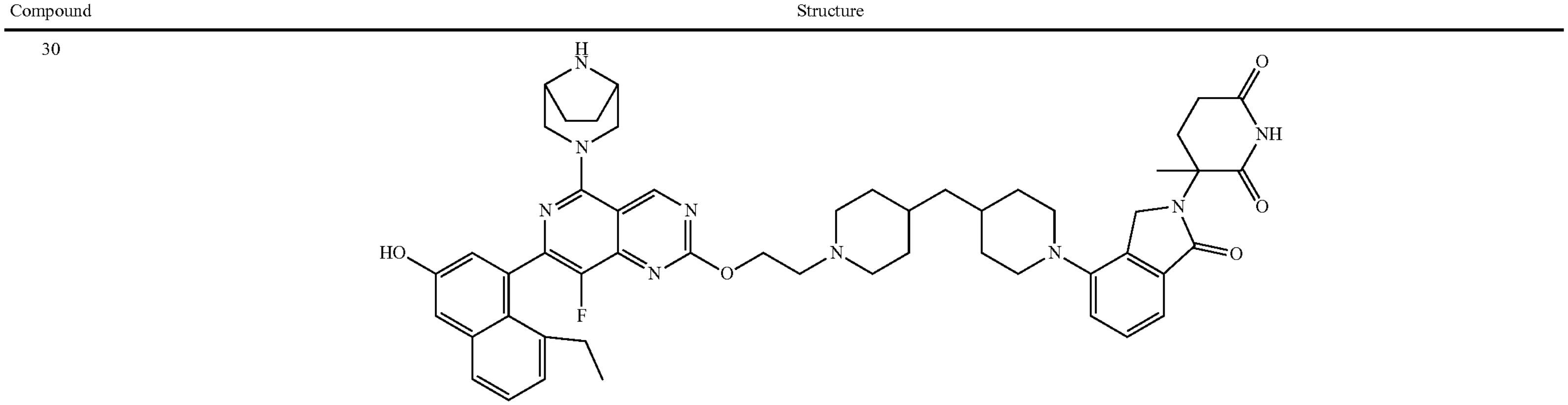 |
| 31 | 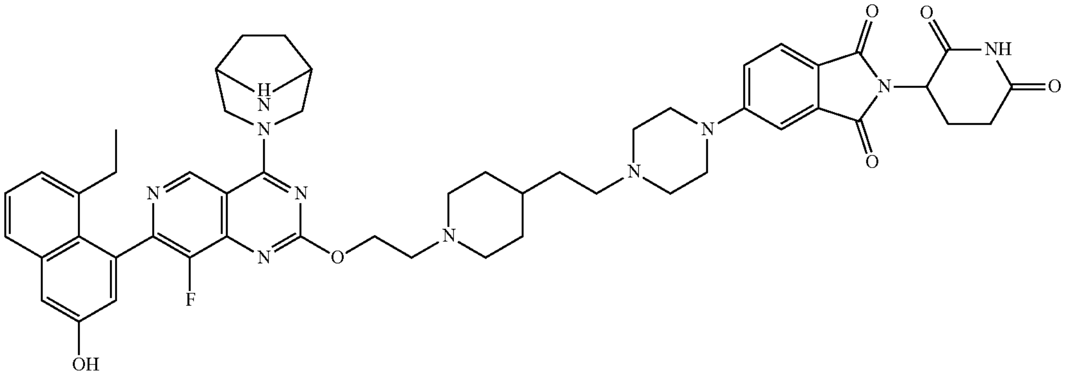 [SMILES: CCc1cccc2cc(O)cc(-c3ncc4c(N5CC6CCC(C5)N6)nc(OCCN5CCC(CCN6CCN(c7ccc8c(c7)C(=O)N(C7CCC(=O)NC7=O)C8=O)CC6)CC5)nc4c3F)c12] |

??TABLE 1-continued
| Compound | Structure |
|---|---|
| 32 | 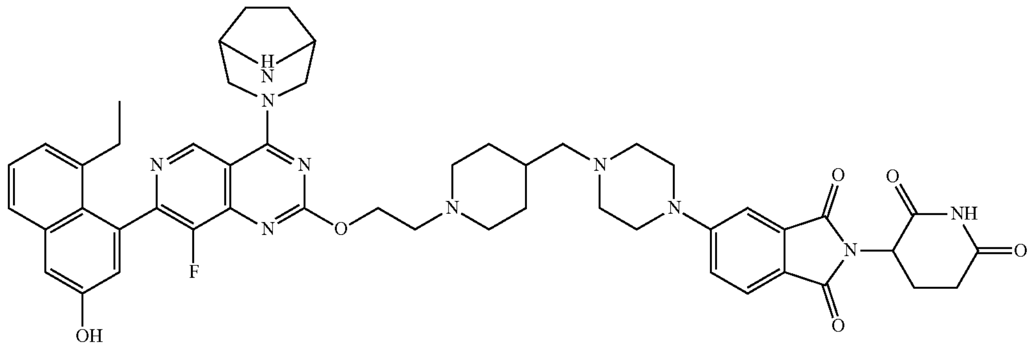 [SMILES: CCc1cccc2cc(O)cc(-c3ncc4c(N5CC6CCC(C5)N6)nc(OCCN5CCC(CN6CCN(c7ccc8c(c7)C(=O)N(C7CCC(=O)NC7=O)C8=O)CC6)CC5)nc4c3F)c12] |
| 33 | 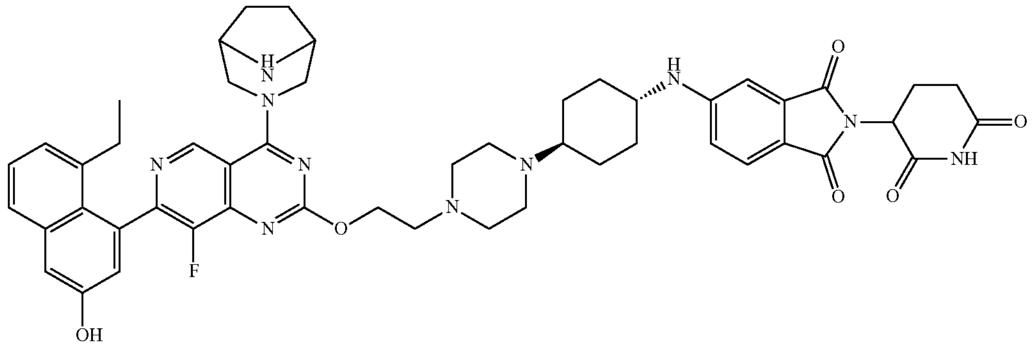 [SMILES: CCc1cccc2cc(O)cc(-c3ncc4c(N5CC6CCC(C5)N6)nc(OCCN5CCN([C@H]6CC[C@H](Nc7ccc8c(c7)C(=O)N(C7CCC(=O)NC7=O)C8=O)CC6)CC5)nc4c3F)c12] |
| 34 | 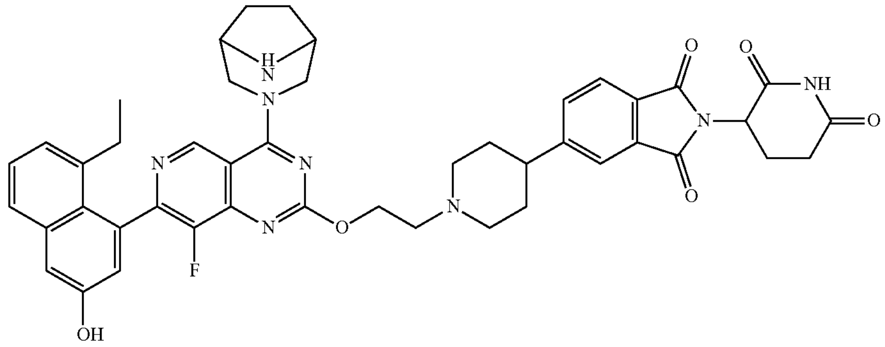 [SMILES: CCc1cccc2cc(O)cc(-c3ncc4c(N5CC6CCC(C5)N6)nc(OCCN5CCC(c6ccc7c(c6)C(=O)N(C6CCC(=O)NC6=O)C7=O)CC5)nc4c3F)c12] |

??TABLE 1-continued
| Compound | Structure |
|---|---|
| 35 | 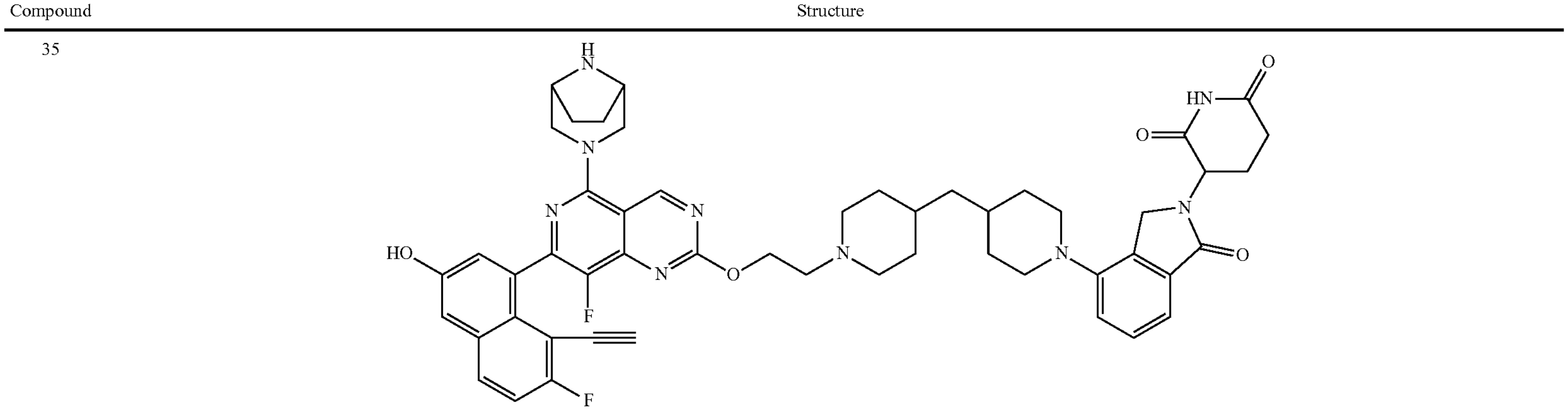 |
| 36 | 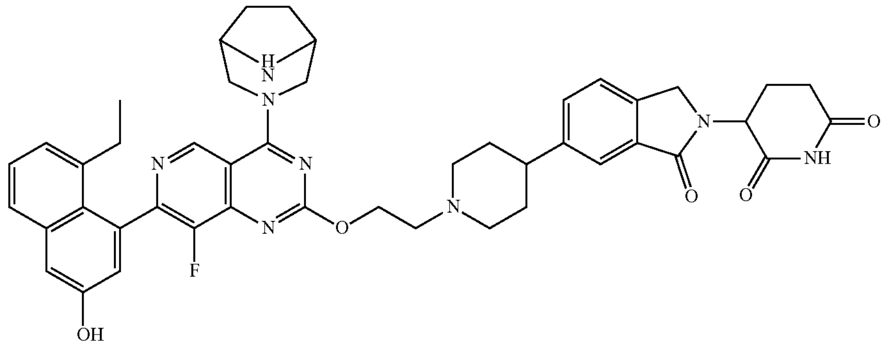 [SMILES: CCc1cccc2cc(O)cc(-c3ncc4c(N5CC6CCC(C5)N6)nc(OCCN5CCC(c6ccc7c(c6)C(=O)N(C6CCC(=O)NC6=O)C7)CC5)nc4c3F)c12] |

??TABLE 1-continued
| Compound | Structure |
| --- | --- |
| 37 | 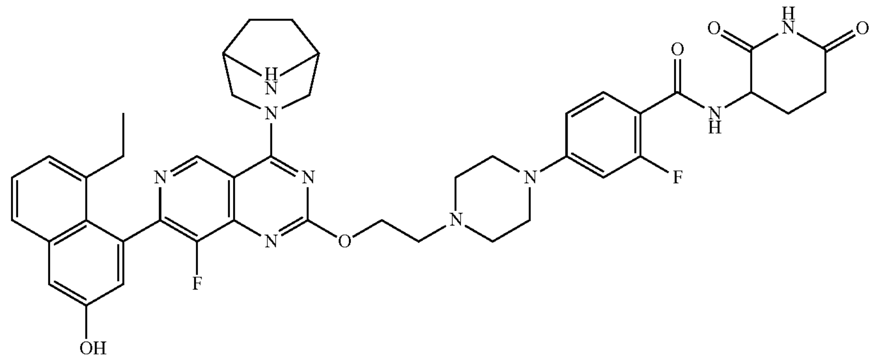 [SMILES: CCc1cccc2cc(O)cc(-c3ncc4c(N5CC6CCC(C5)N6)nc(OCCN5CCN(c6ccc(C(=O)NC7CCC(=O)NC7=O)c(F)c6)CC5)nc4c3F)c12] |
| 38 | 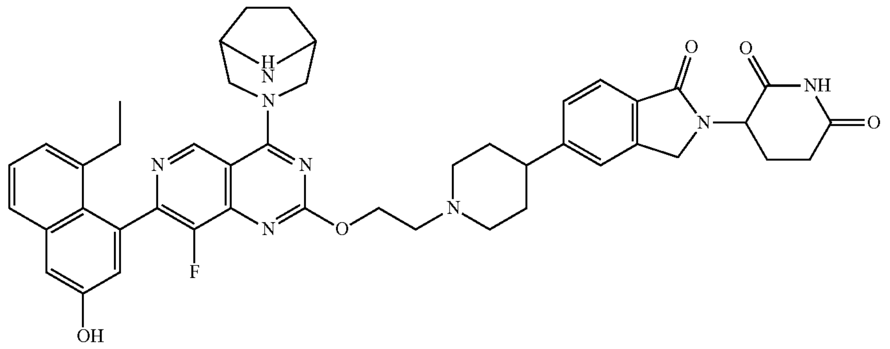 [SMILES: CCc1cccc2cc(O)cc(-c3ncc4c(N5CC6CCC(C5)N6)nc(OCCN5CCC(c6ccc7c(c6)CN(C6CCC(=O)NC6=O)C7=O)CC5)nc4c3F)c12] |
| 39 | 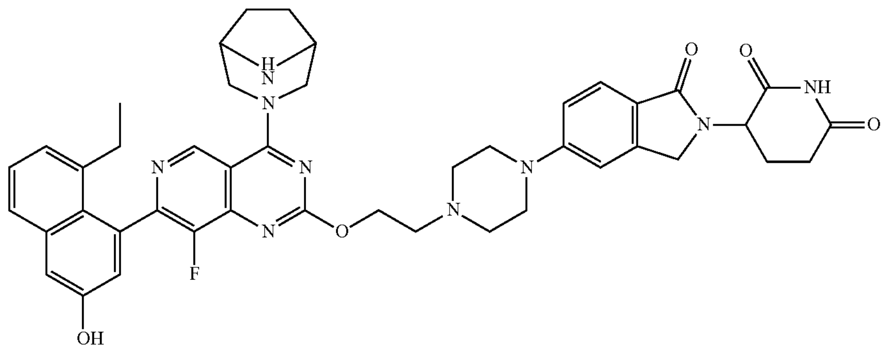 [SMILES: CCc1cccc2cc(O)cc(-c3ncc4c(N5CC6CCC(C5)N6)nc(OCCN5CCN(c6ccc7c(c6)CN(C6CCC(=O)NC6=O)C7=O)CC5)nc4c3F)c12] |

??TABLE 1-continued
| Compound | Structure |
| --- | --- |
| 40 | 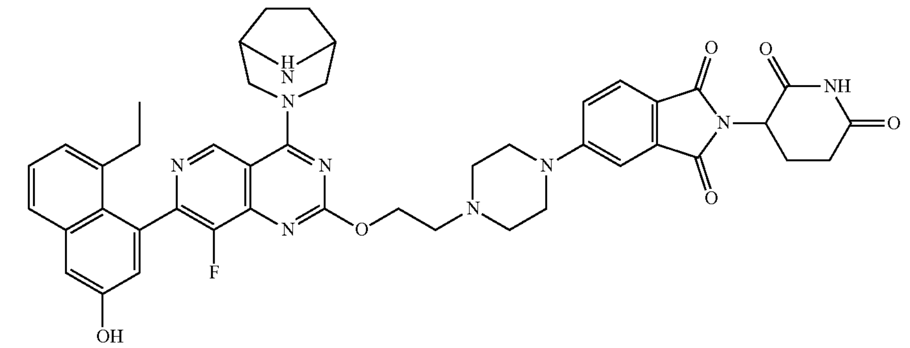 [SMILES: CCc1cccc2cc(O)cc(-c3ncc4c(N5CC6CCC(C5)N6)nc(OCCN5CCN(c6ccc7c(c6)C(=O)N(C6CCC(=O)NC6=O)C7=O)CC5)nc4c3F)c12] |
| 41 | 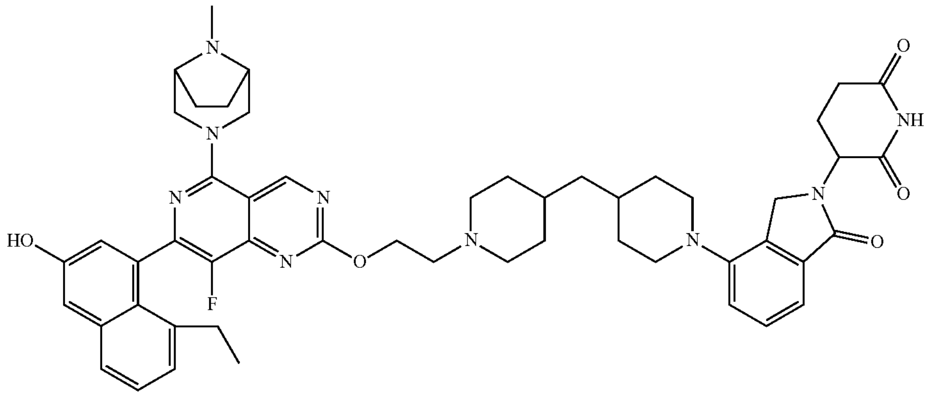 [SMILES: CCc1cccc2cc(O)cc(-c3nc(N4CC5CCC(C4)N5C)c4cnc(OCCN5CCC(CC6CCN(c7cccc8c7CN(C7CCC(=O)NC7=O)C8=O)CC6)CC5)nc4c3F)c12] |

??TABLE 1-continued
| Compound | Structure |
| --- | --- |
| 42 | 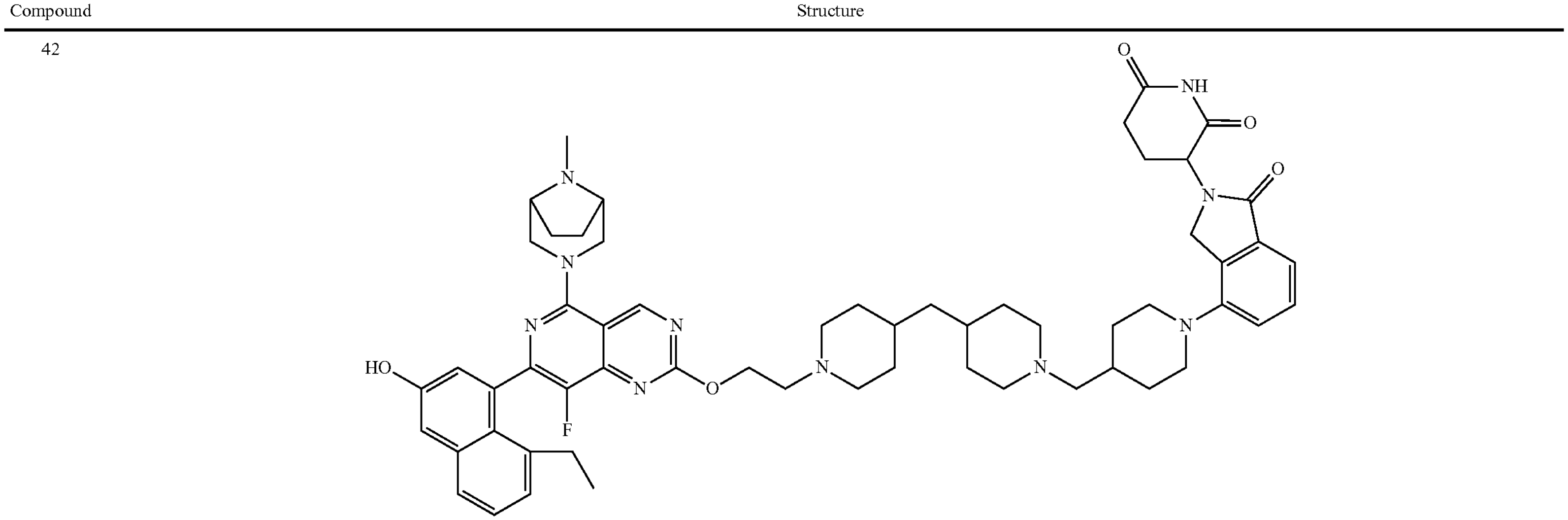 |
| 43 | 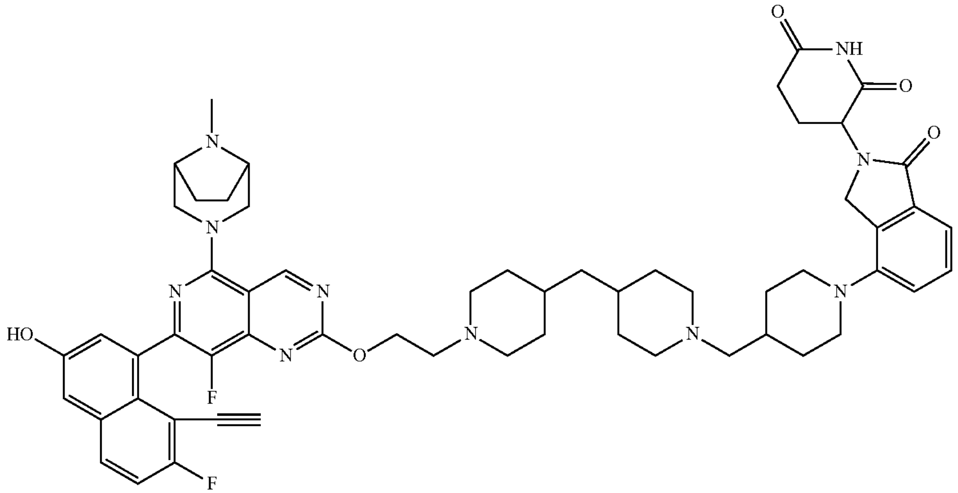 [SMILES: C#Cc1c(F)ccc2cc(O)cc(-c3nc(N4CC5CCC(C4)N5C)c4cnc(OCCN5CCC(CC6CCN(CC7CCN(c8cccc9c8CN(C8CCC(=O)NC8=O)C9=O)CC7)CC6)CC5)nc4c3F)c12] |

??TABLE 1-continued
| Compound | Structure |
|---|---|
| 44 | 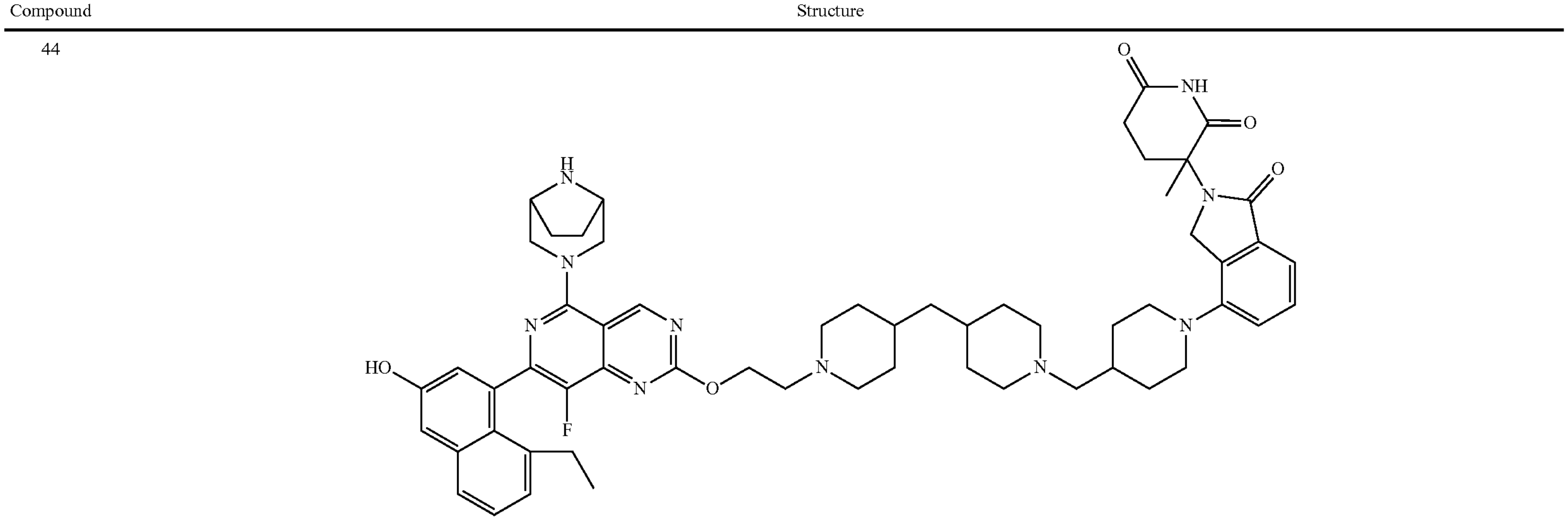 |
| 45 | 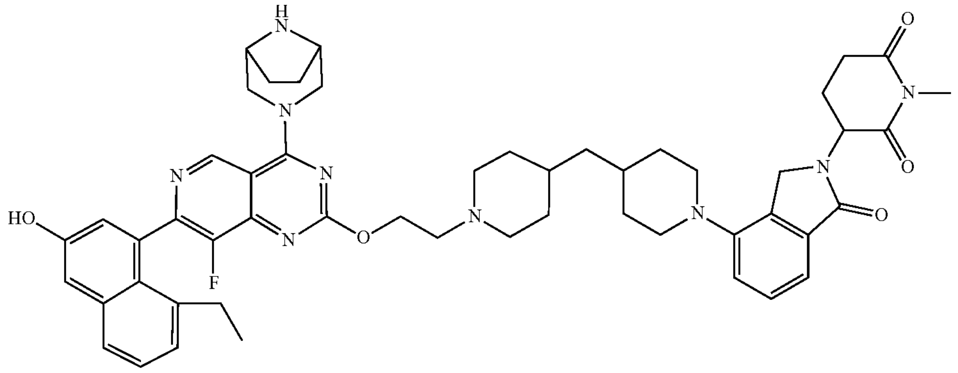 [SMILES: CCc1cccc2cc(O)cc(-c3ncc4c(N5CC6CCC(C5)N6)nc(OCCN5CCC(CC6CCN(c7cccc8c7CN(C7CCC(=O)N(C)C7=O)C8=O)CC6)CC5)nc4c3F)c12] |

??TABLE 1-continued
| Compound | Structure |
|---|---|
| 46 | 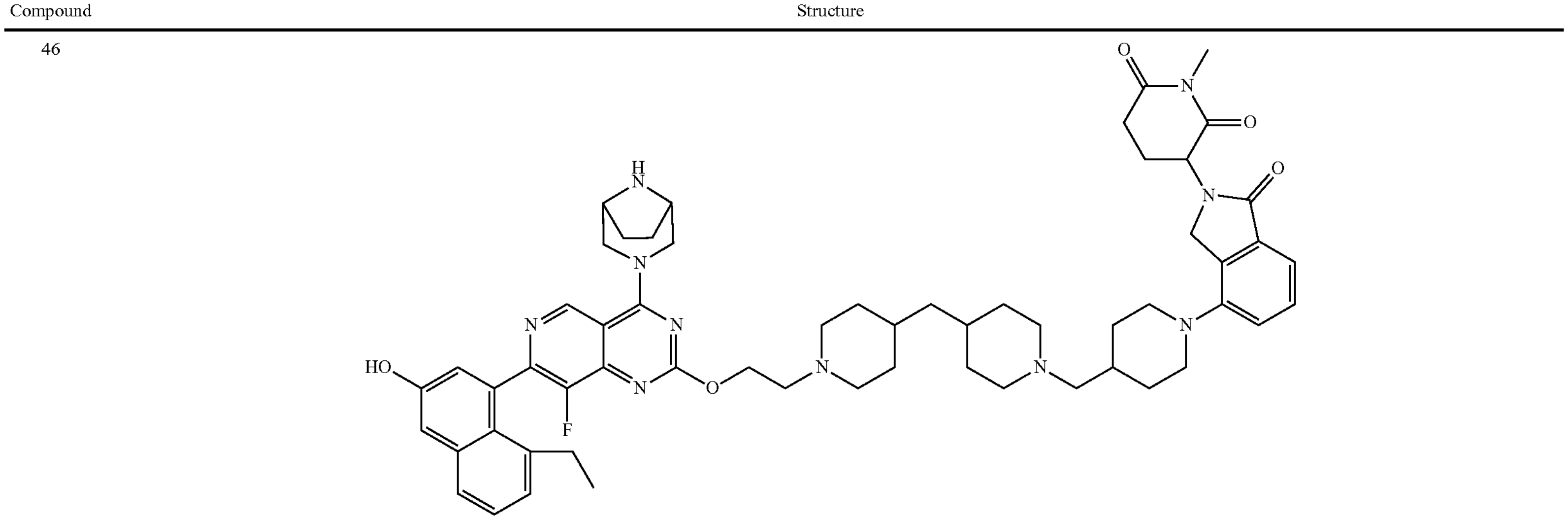 |
| 47 | 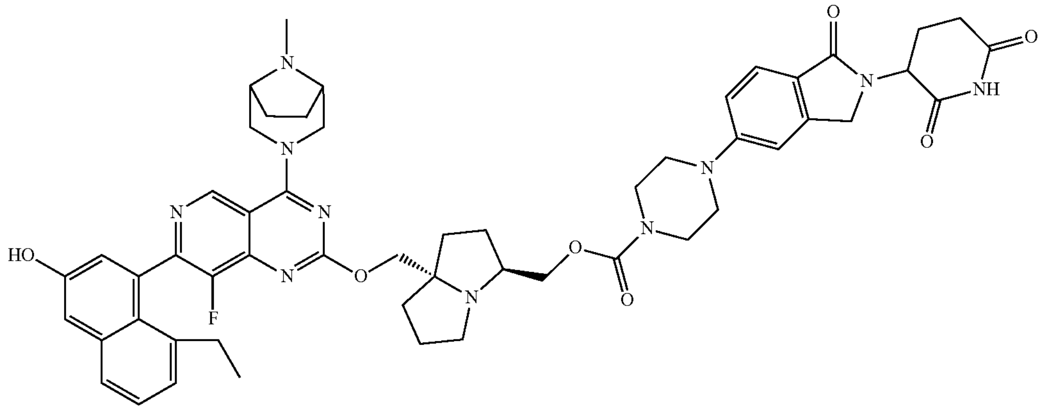 [SMILES: CCc1cccc2cc(O)cc(-c3ncc4c(N5CC6CCC(C5)N6C)nc(OC[C@@]56CCCN5[C@H](COC(=O)N5CCN(c7ccc8c(c7)CN(C7CCC(=O)NC7=O)C8=O)CC5)CC6)nc4c3F)c12] |

??TABLE 1-continued
| Compound | Structure |
| --- | --- |
| 48 | 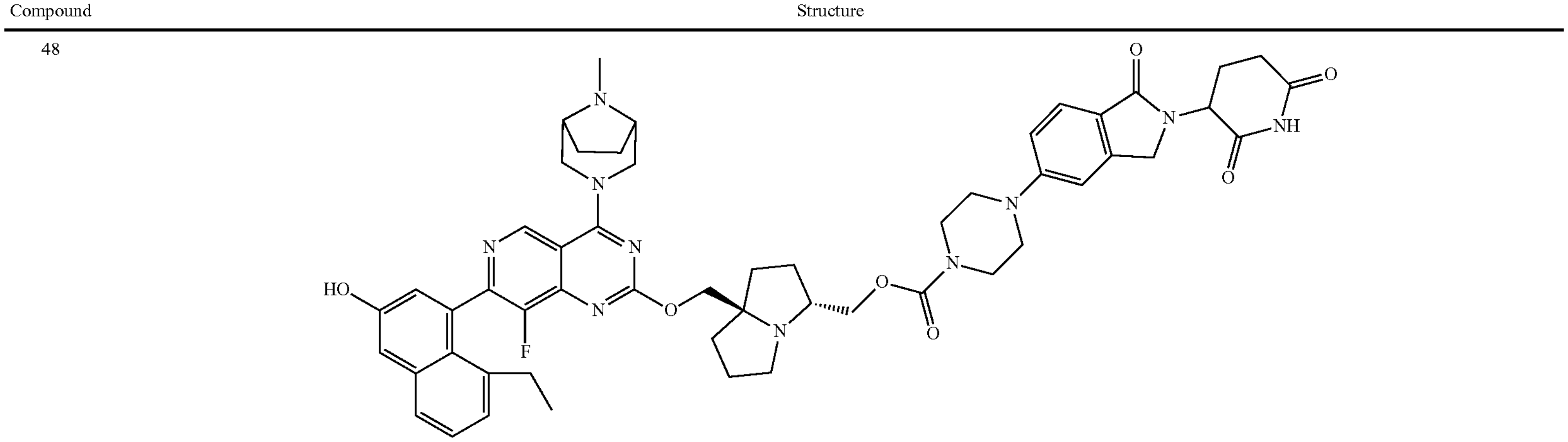 |
| 49 | 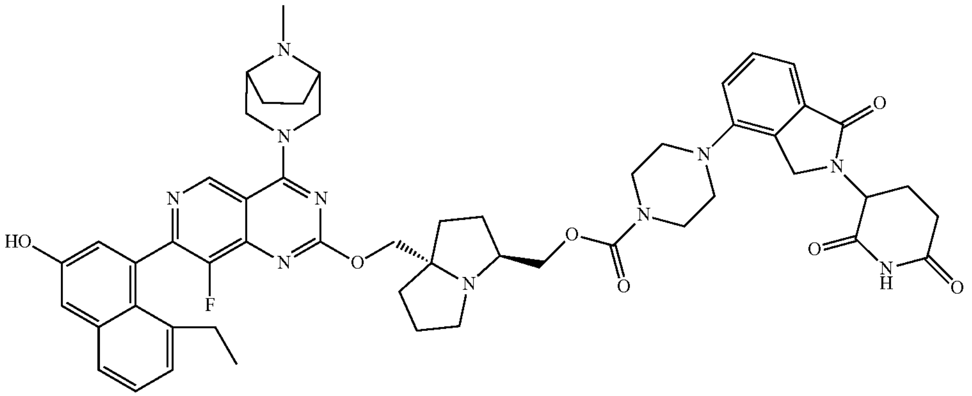 [SMILES: CCc1cccc2cc(O)cc(-c3ncc4c(N5CC6CCC(C5)N6C)nc(OC[C@@]56CCCN5[C@H](COC(=O)N5CCN(c7cccc8c7CN(C7CCC(=O)NC7=O)C8=O)CC5)CC6)nc4c3F)c12] |

??TABLE 1-continued
| Compound | Structure |
| --- | --- |
| 50 | 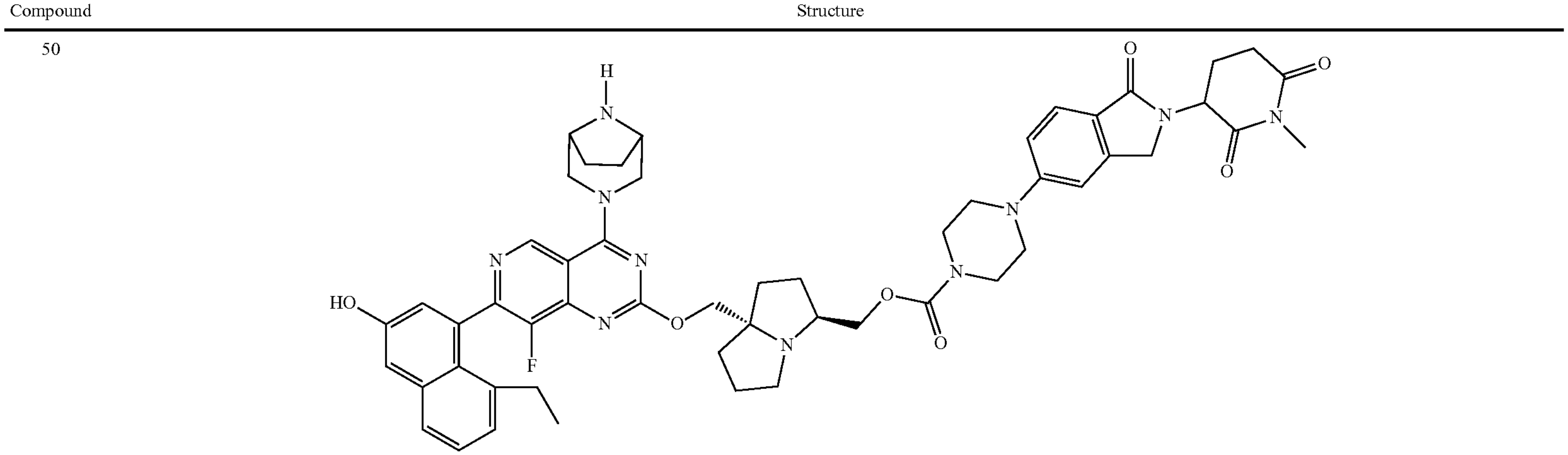 |
| 51 | 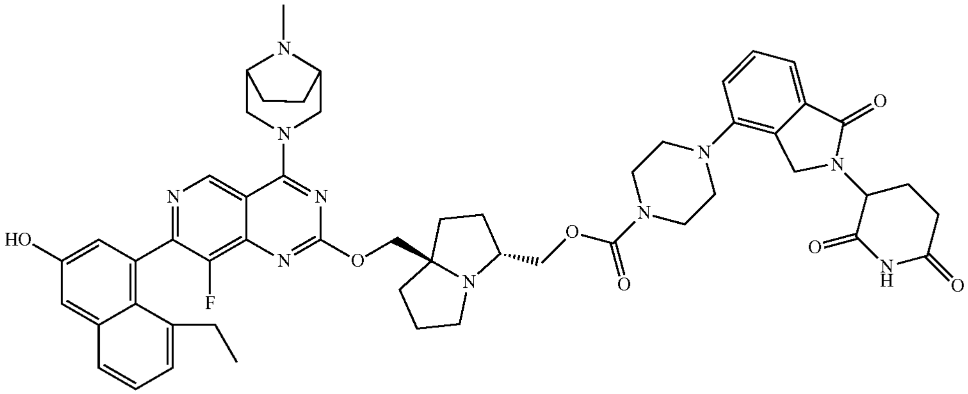 [SMILES: CCc1cccc2cc(O)cc(-c3ncc4c(N5CC6CCC(C5)N6C)nc(OC[C@]56CCCN5[C@@H](COC(=O)N5CCN(c7cccc8c7CN(C7CCC(=O)NC7=O)C8=O)CC5)CC6)nc4c3F)c12] |

??TABLE 1-continued
| Compound | Structure |
| --- | --- |
| 52 | 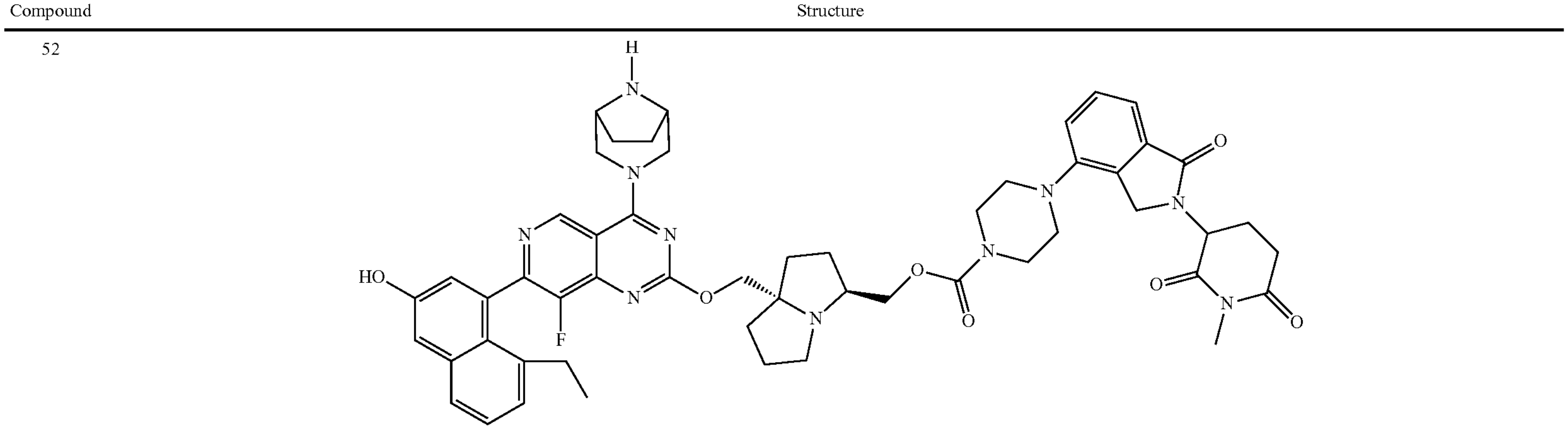 |
| 53 | 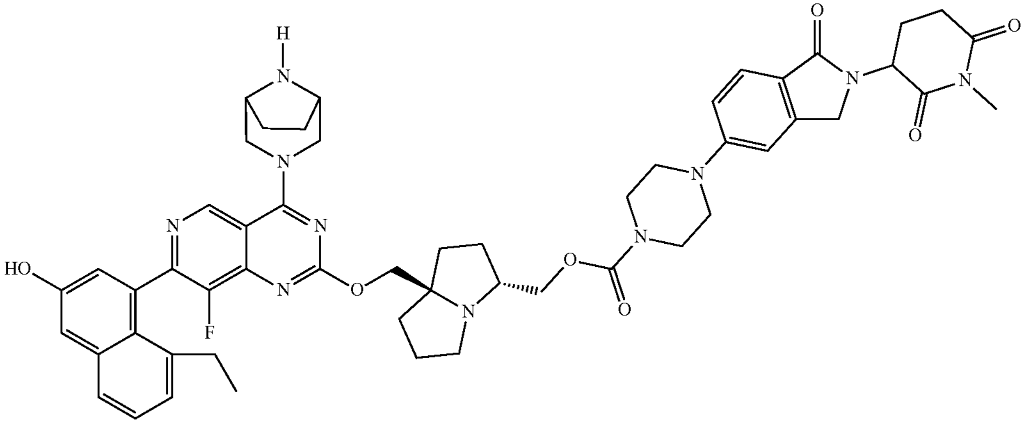 [SMILES: CCc1cccc2cc(O)cc(-c3ncc4c(N5CC6CCC(C5)N6)nc(OC[C@]56CCCN5[C@@H](COC(=O)N5CCN(c7ccc8c(c7)CN(C7CCC(=O)N(C)C7=O)C8=O)CC5)CC6)nc4c3F)c12] |

??TABLE 1-continued
| Compound | Structure |
| --- | --- |
| 54 | 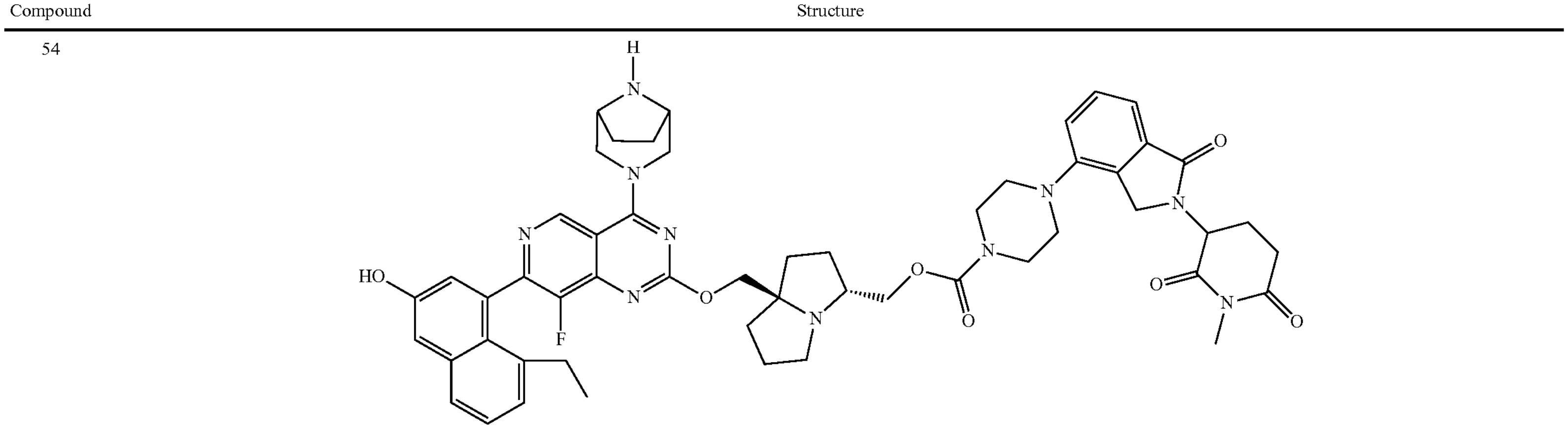 |
| 55 | 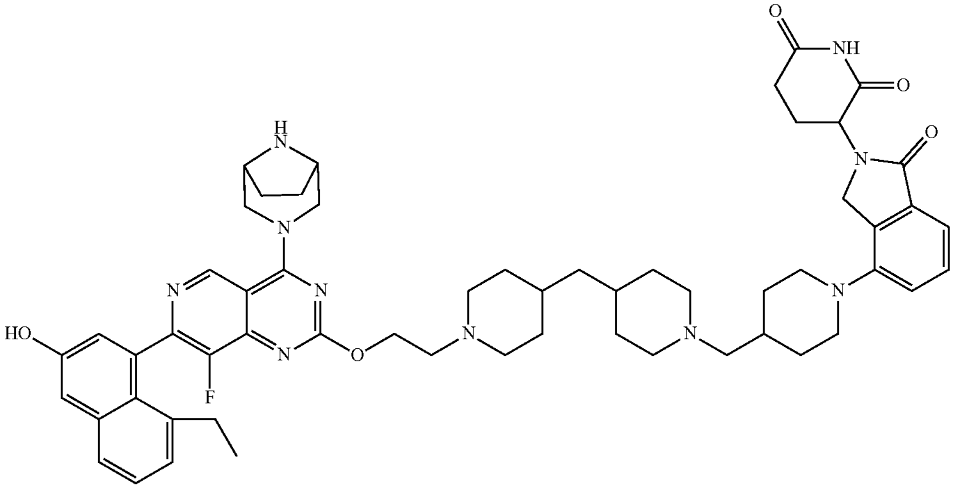 [SMILES: CCc1cccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12] |

??TABLE 1-continued
| Compound | Structure |
|---|---|
| 56 | 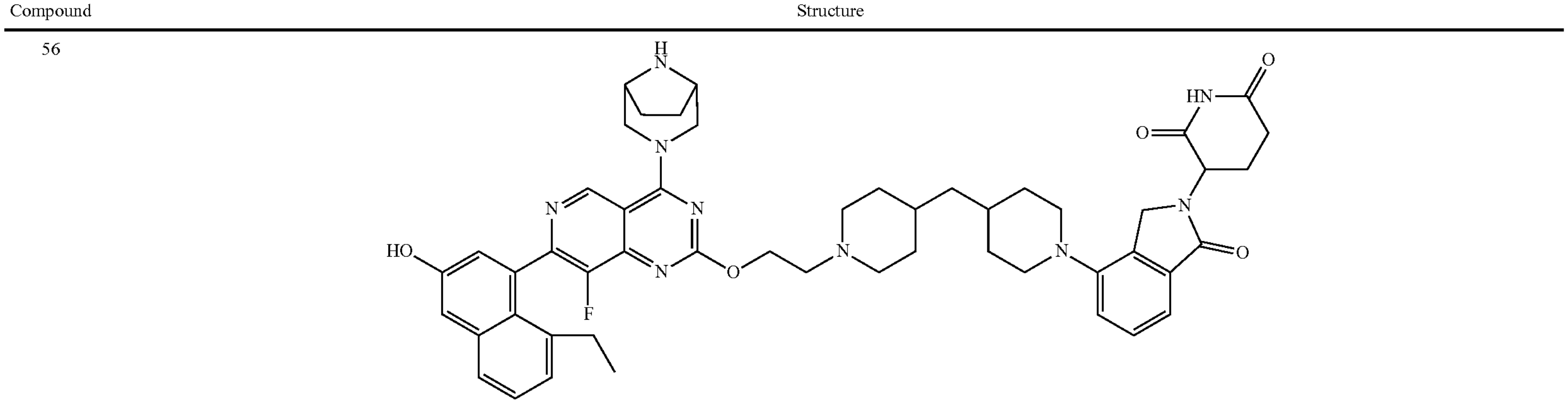 |
| 57 | 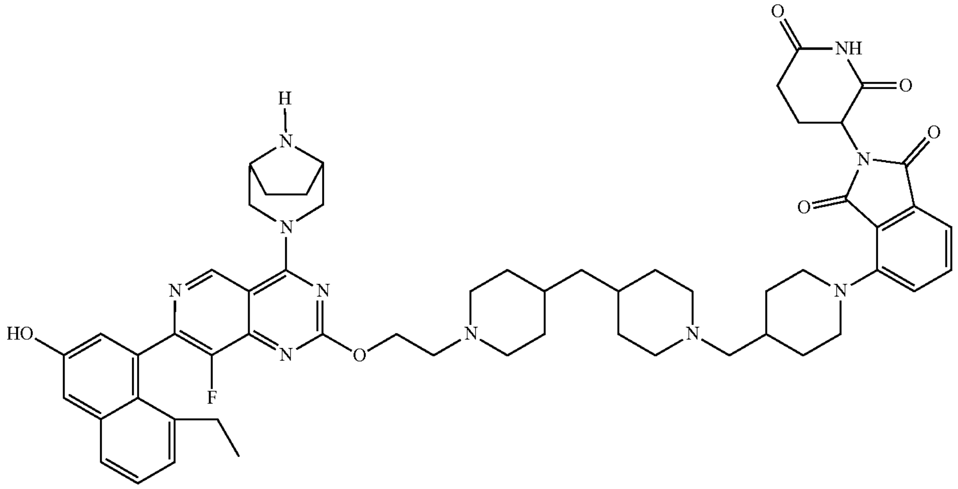 [SMILES: CCc1cccc2cc(O)cc(-c3ncc4c(N5CC6CCC(C5)N6)nc(OCCN5CCC(CC6CCN(CC7CCN(c8cccc9c8C(=O)N(C8CCC(=O)NC8=O)C9=O)CC7)CC6)CC5)nc4c3F)c12] |

??TABLE 1-continued
| Compound | Structure |
| --- | --- |
| 58 | 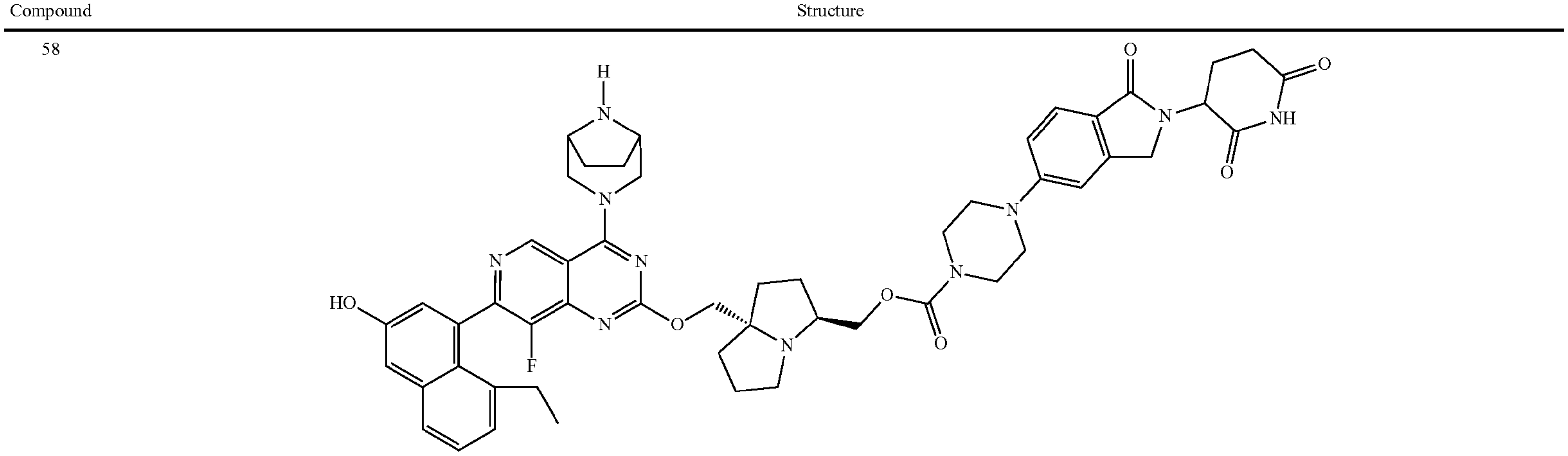 |
| 59 | 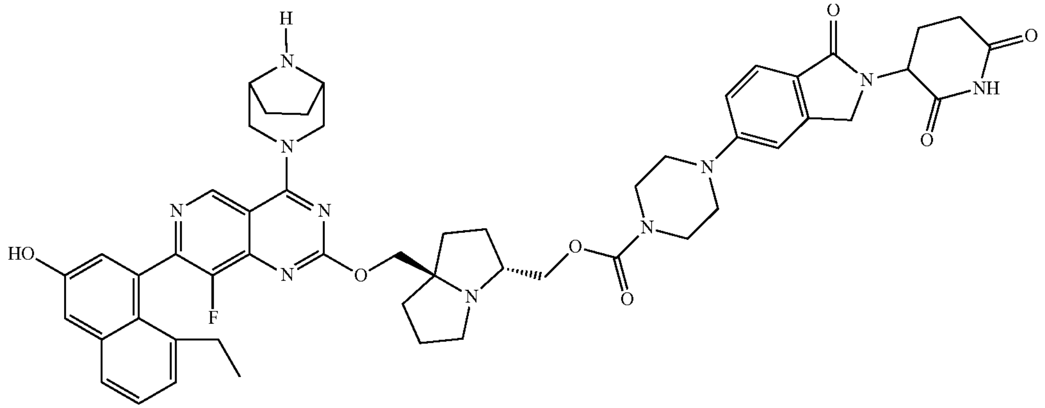 [SMILES: CCc1cccc2cc(O)cc(-c3ncc4c(N5CC6CCC(C5)N6)nc(OC[C@]56CCCN5[C@@H](COC(=O)N5CCN(c7ccc8c(c7)CN(C7CCC(=O)NC7=O)C8=O)CC5)CC6)nc4c3F)c12] |

??TABLE 1-continued
| Compound | Structure |
| --- | --- |
| 60 | 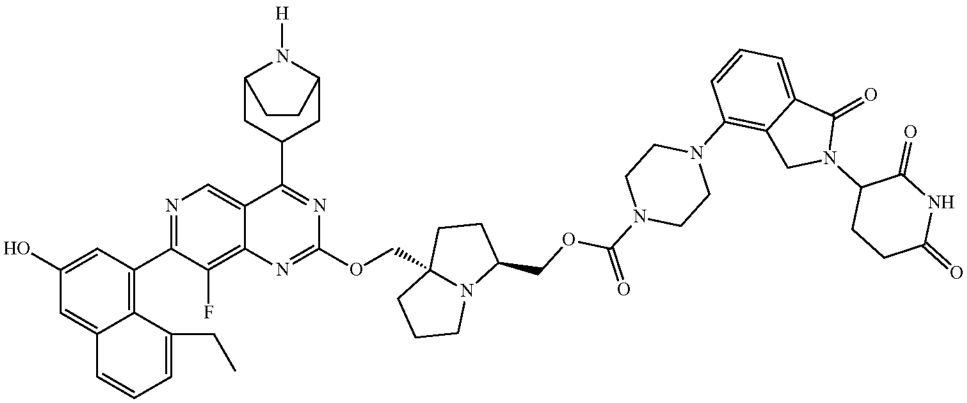 |
| 61 | 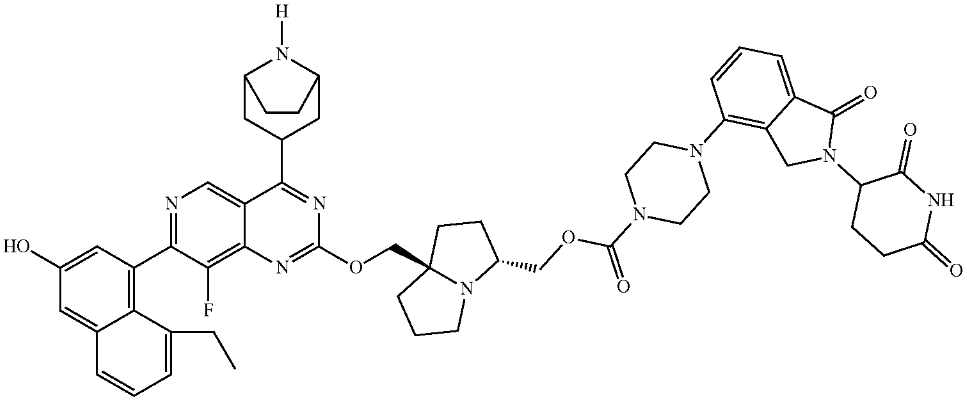 [SMILES: CCc1cccc2cc(O)cc(-c3ncc4c(C5CC6CCC(C5)N6)nc(OC[C@]56CCCN5[C@@H](COC(=O)N5CCN(c7cccc8c7CN(C7CCC(=O)NC7=O)C8=O)CC5)CC6)nc4c3F)c12] |

??TABLE 1-continued
| Compound | Structure |
|---|---|
| 62 | 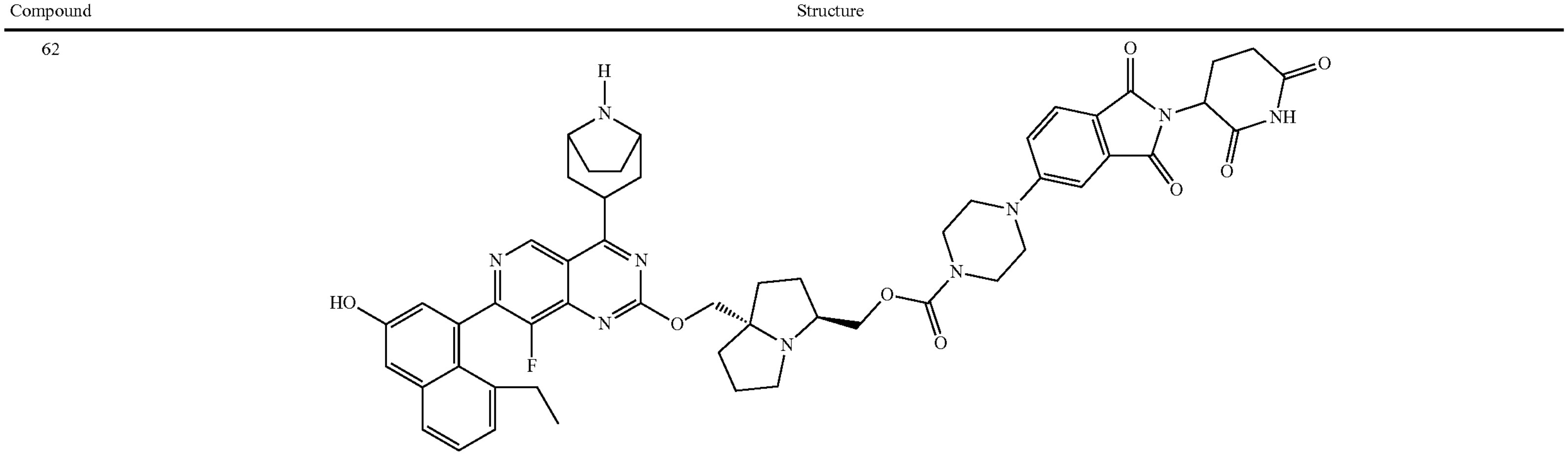 |
| 63 | 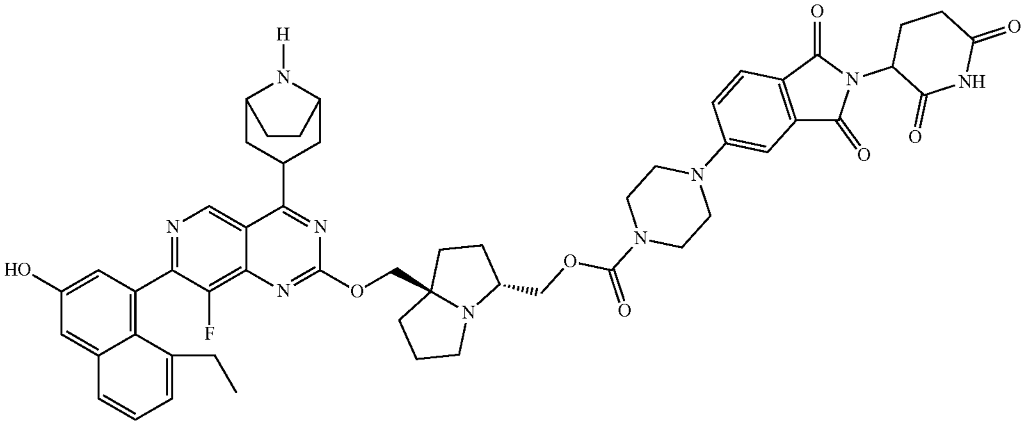 [SMILES: CCc1cccc2cc(O)cc(-c3ncc4c(C5CC6CCC(C5)N6)nc(OC[C@]56CCCN5[C@@H](COC(=O)N5CCN(c7ccc8c(c7)C(=O)N(C7CCC(=O)NC7=O)C8=O)CC5)CC6)nc4c3F)c12] |

??TABLE 1-continued
| Compound | Structure |
|---|---|
| 64 | 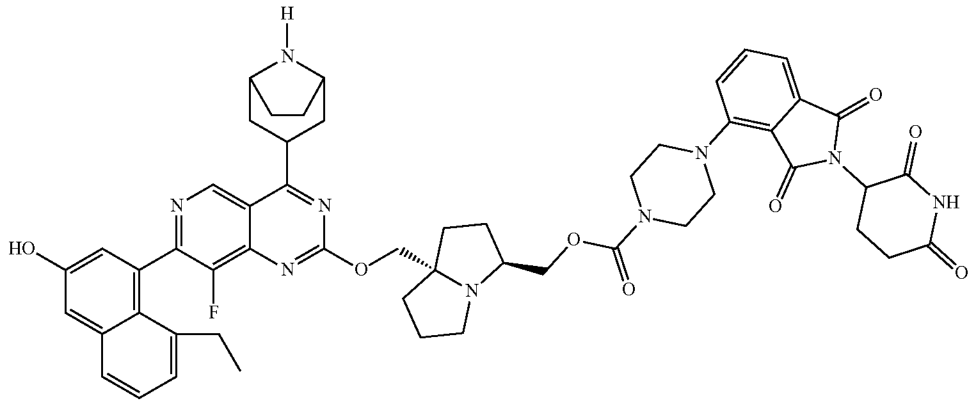 |
| 65 | 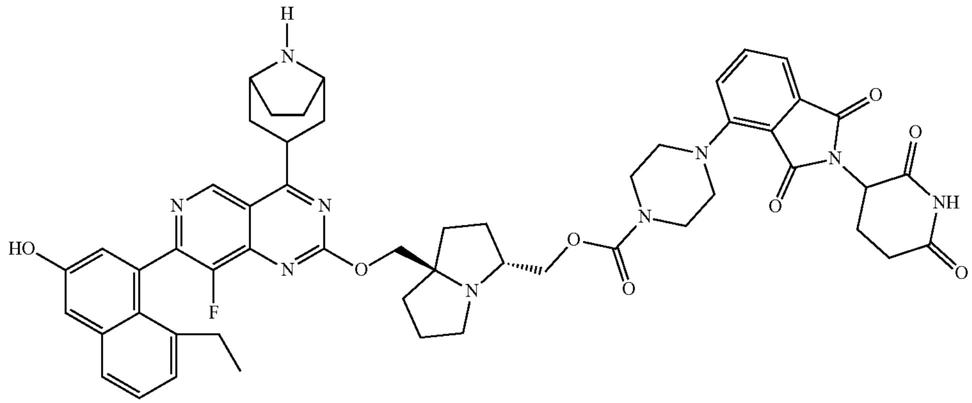 [SMILES: CCc1cccc2cc(O)cc(-c3ncc4c(C5CC6CCC(C5)N6)nc(OC[C@]56CCCN5[C@@H](COC(=O)N5CCN(c7cccc8c7C(=O)N(C7CCC(=O)NC7=O)C8=O)CC5)CC6)nc4c3F)c12] |

??TABLE 1-continued
| Compound | Structure |
|---|---|
| 66 | 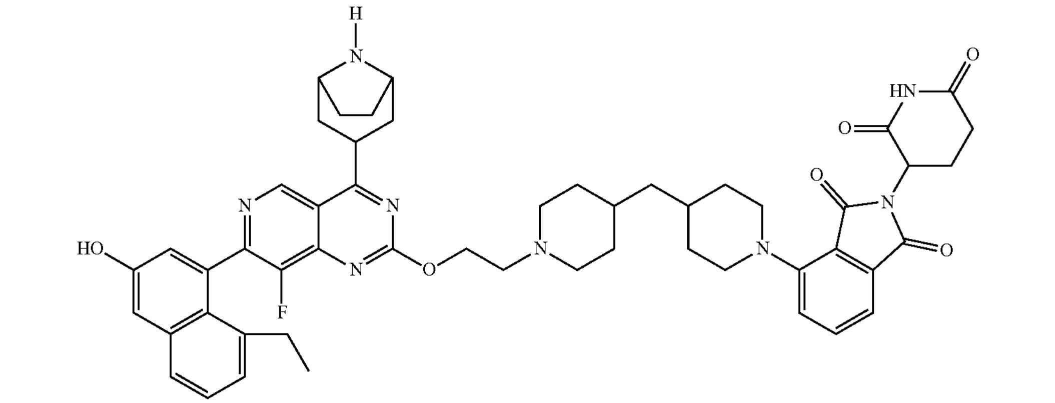 [SMILES: CCc1cccc2cc(O)cc(-c3ncc4c(C5CC6CCC(C5)N6)nc(OCCN5CCC(CC6CCN(c7cccc8c7C(=O)N(C7CCC(=O)NC7=O)C8=O)CC6)CC5)nc4c3F)c12] |
| 67 | 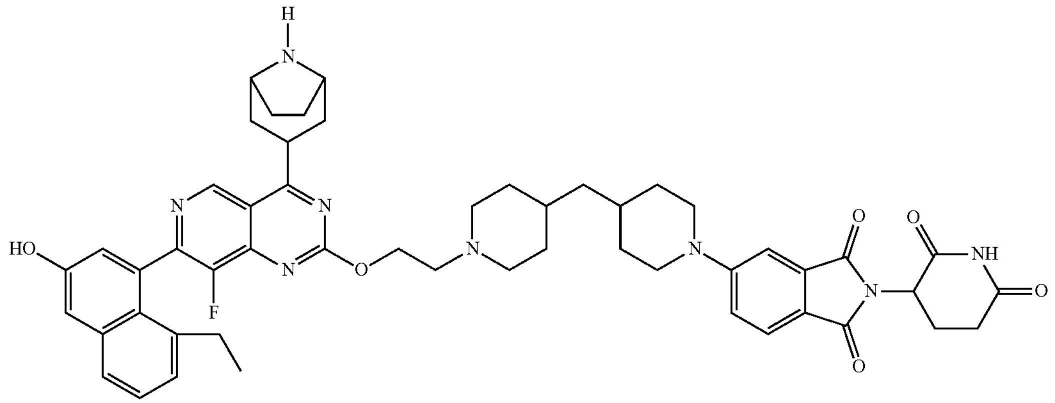 [SMILES: CCc1cccc2cc(O)cc(-c3ncc4c(C5CC6CCC(C5)N6)nc(OCCN5CCC(CC6CCN(c7ccc8c(c7)C(=O)N(C7CCC(=O)NC7=O)C8=O)CC6)CC5)nc4c3F)c12] |

??TABLE 1-continued
| Compound | Structure |
| --- | --- |
| 68 | 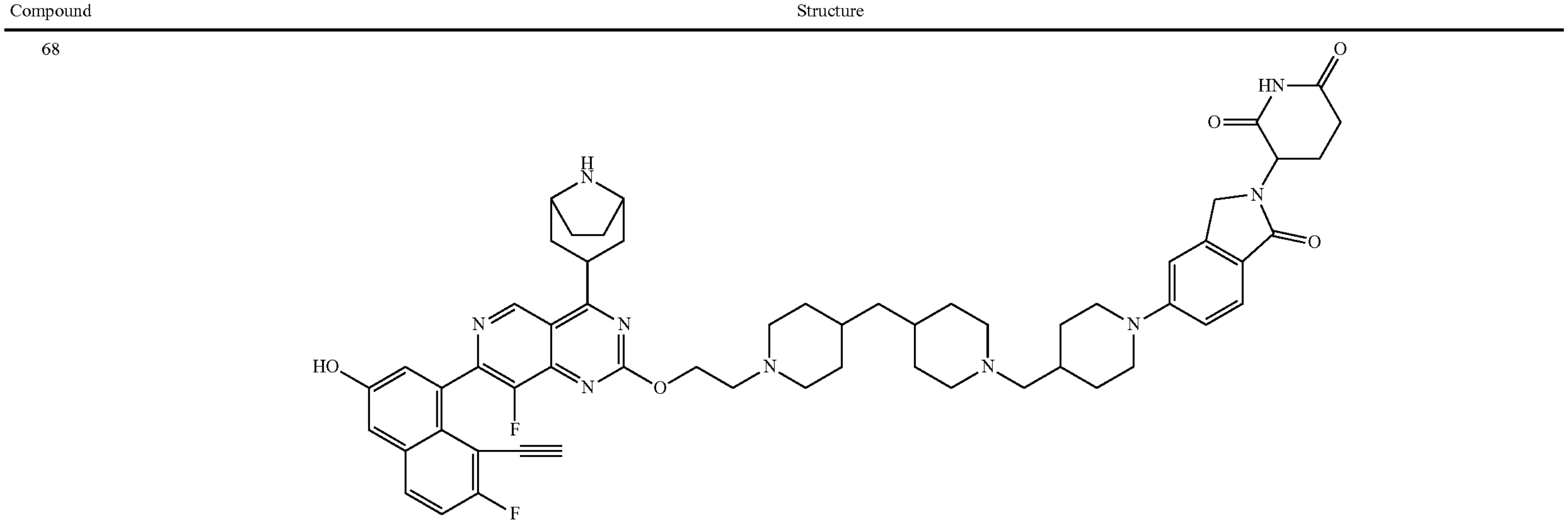 |
| 69 | 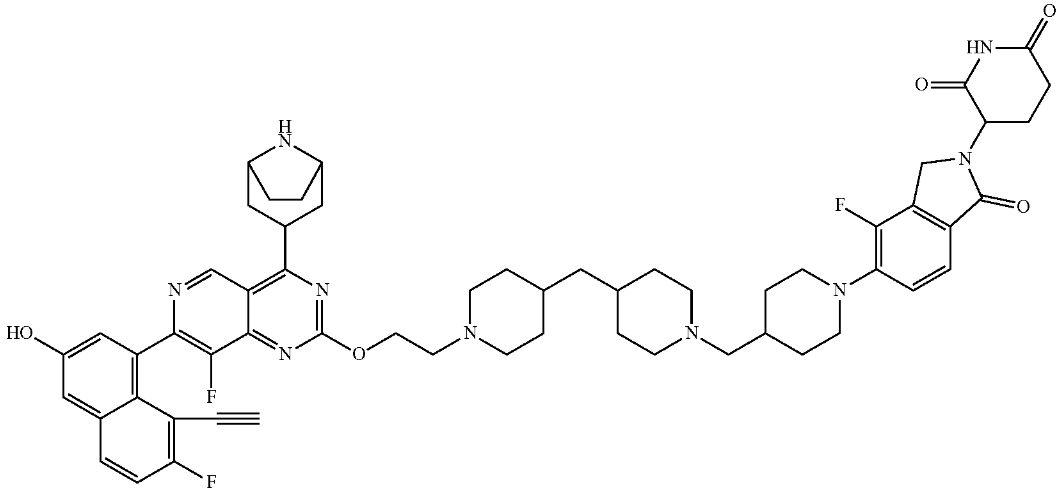 [SMILES: C#Cc1c(F)ccc2cc(O)cc(-c3ncc4c(C5CC6CCC(C5)N6)nc(OCCN5CCC(CC6CCN(CC7CCN(c8ccc9c(c8F)CN(C8CCC(=O)NC8=O)C9=O)CC7)CC6)CC5)nc4c3F)c12] |

??TABLE 1-continued
| Compound | Structure |
| --- | --- |
| 70 | 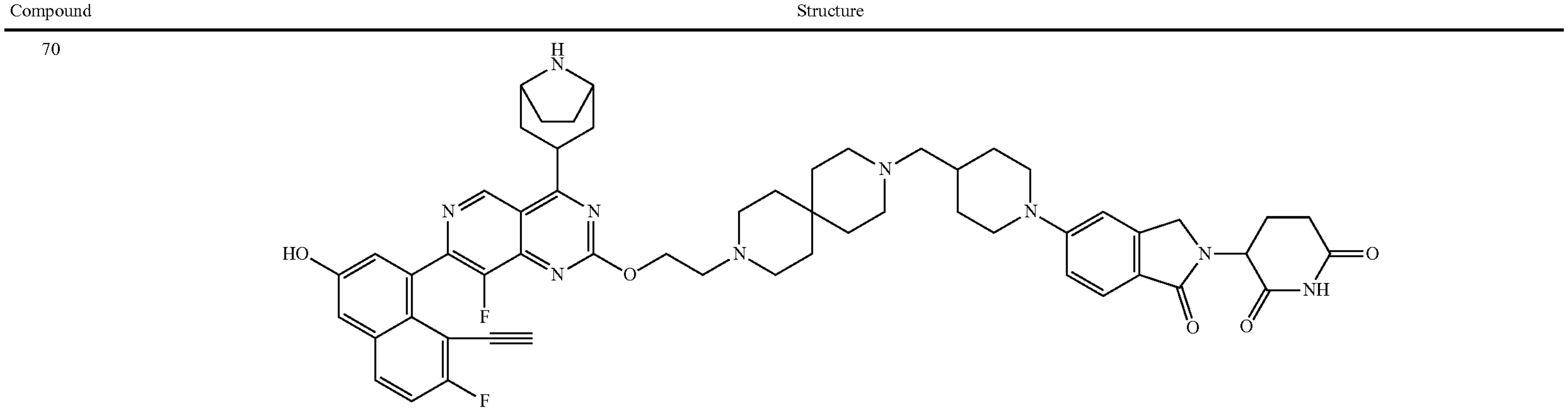 |
| 71 | 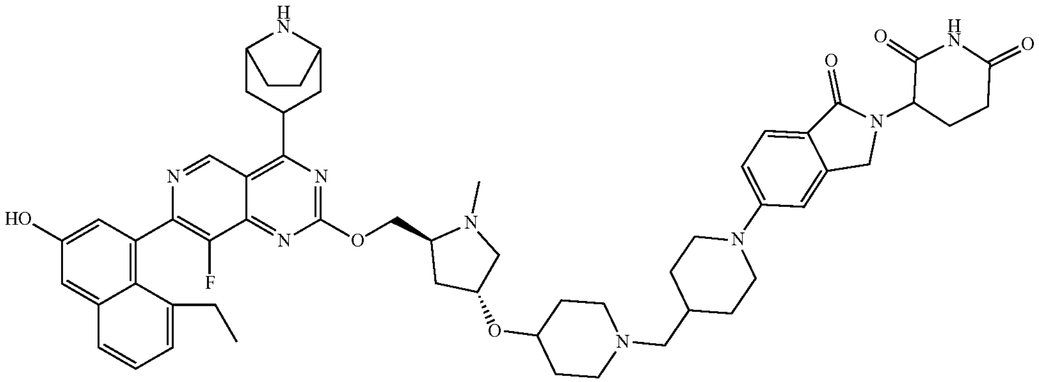 [SMILES: CCc1cccc2cc(O)cc(-c3ncc4c(C5CC6CCC(C5)N6)nc(OC[C@@H]5C[C@@H](OC6CCN(CC7CCN(c8ccc9c(c8)CN(C8CCC(=O)NC8=O)C9=O)CC7)CC6)CN5C)nc4c3F)c12] |

??TABLE 1-continued
| Compound | Structure |
| --- | --- |
| 72 | 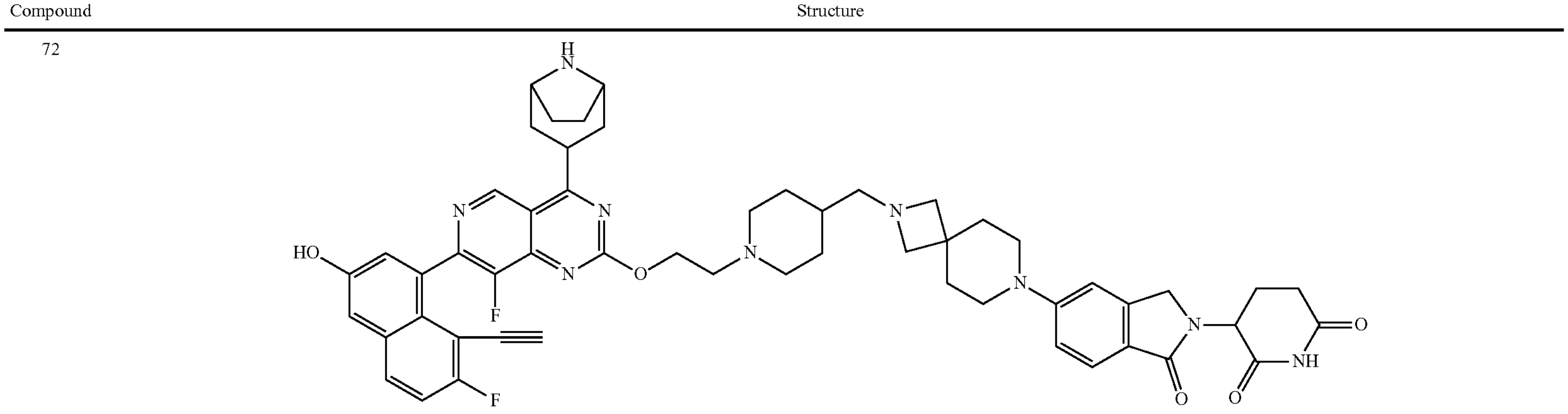 |
| 73 | 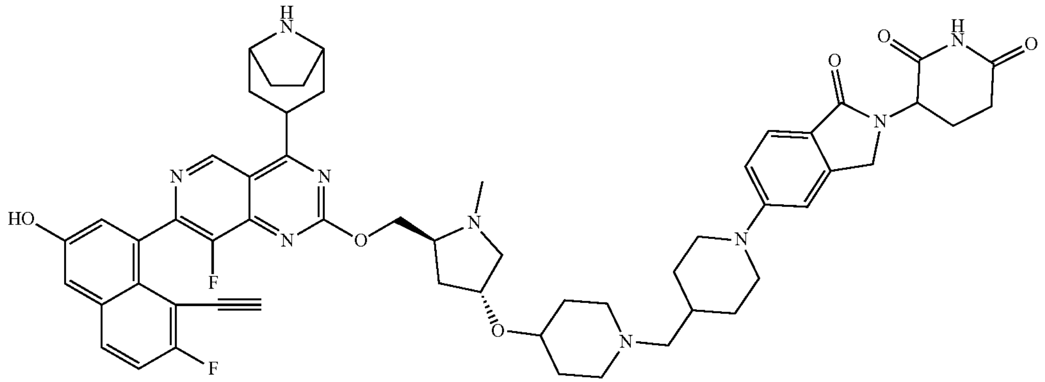 [SMILES: C#Cc1c(F)ccc2cc(O)cc(-c3ncc4c(C5CC6CCC(C5)N6)nc(OC[C@@H]5C[C@@H](OC6CCN(CC7CCN(c8ccc9c(c8)CN(C8CCC(=O)NC8=O)C9=O)CC7)CC6)CN5C)nc4c3F)c12] |

??TABLE 1-continued
| Compound | Structure |
|---|---|
| 74 | 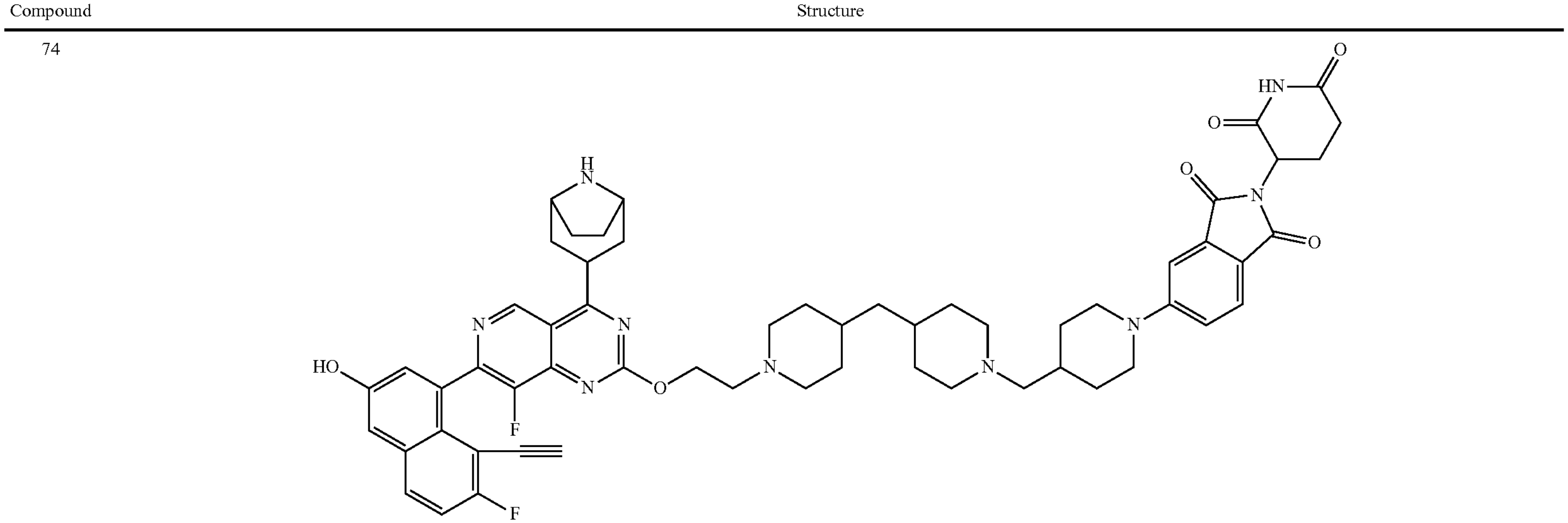 |
| 75 | 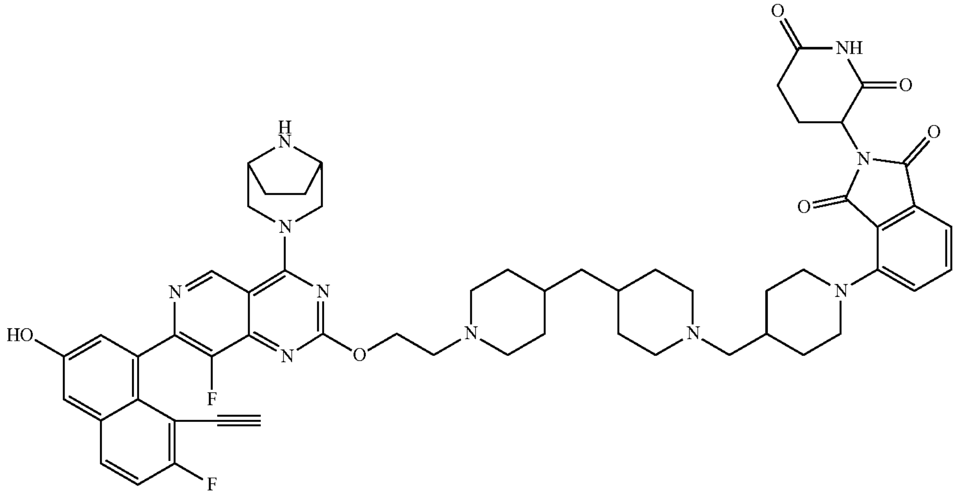 [SMILES: C#Cc1c(F)ccc2cc(O)cc(-c3ncc4c(N5CC6CCC(C5)N6)nc(OCCN5CCC(CC6CCN(CC7CCN(c8cccc9c8C(=O)N(C8CCC(=O)NC8=O)C9=O)CC7)CC6)CC5)nc4c3F)c12] |

??TABLE 1-continued
| Compound | Structure |
|---|---|
| 76 | 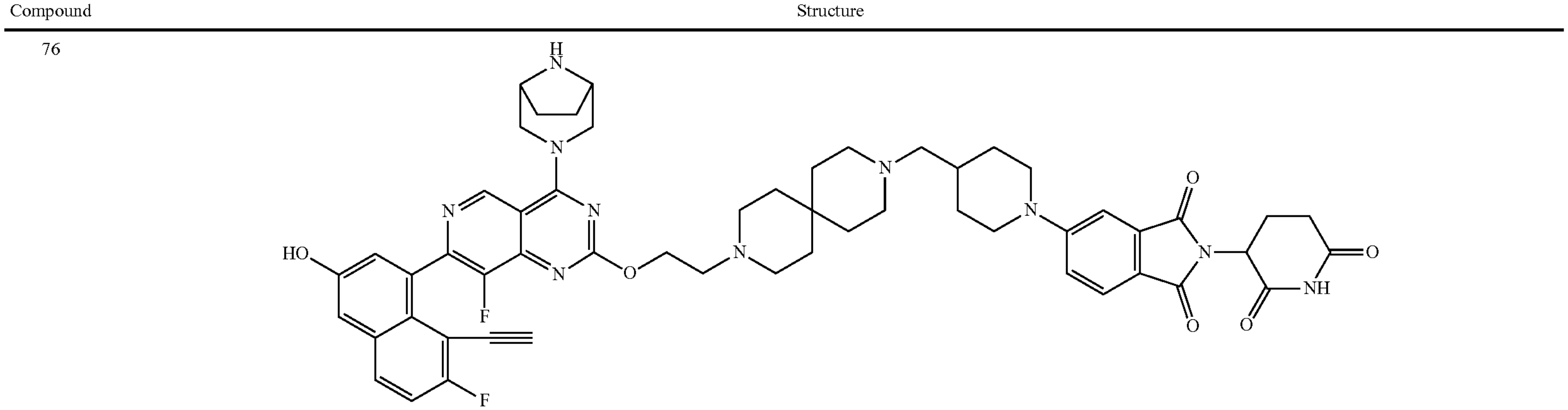 |
| 77 | 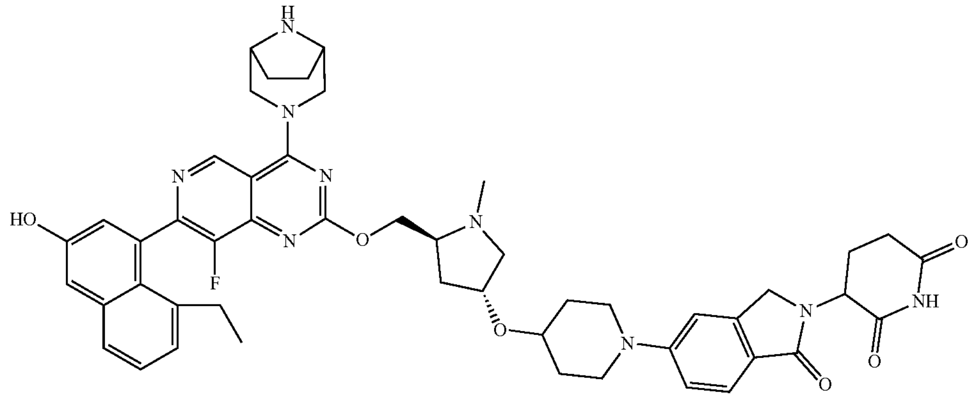 [SMILES: CCc1cccc2cc(O)cc(-c3ncc4c(N5CC6CCC(C5)N6)nc(OC[C@@H]5C[C@@H](OC6CCN(c7ccc8c(c7)CN(C7CCC(=O)NC7=O)C8=O)CC6)CN5C)nc4c3F)c12] |

??TABLE 1-continued
| Compound | Structure |
|---|---|
| 78 | 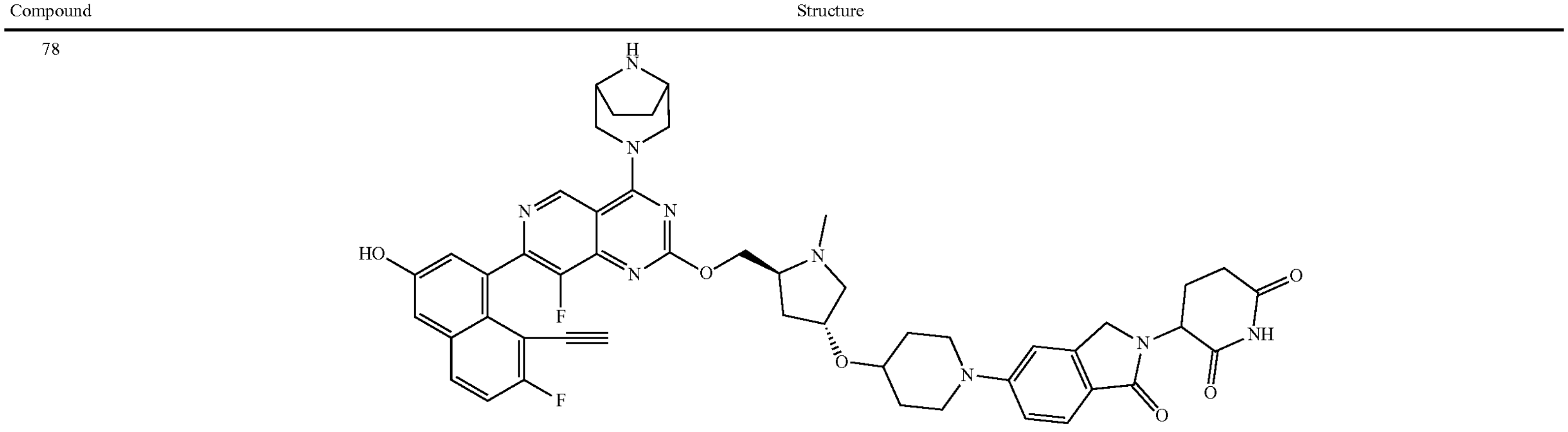 |
| 79 | 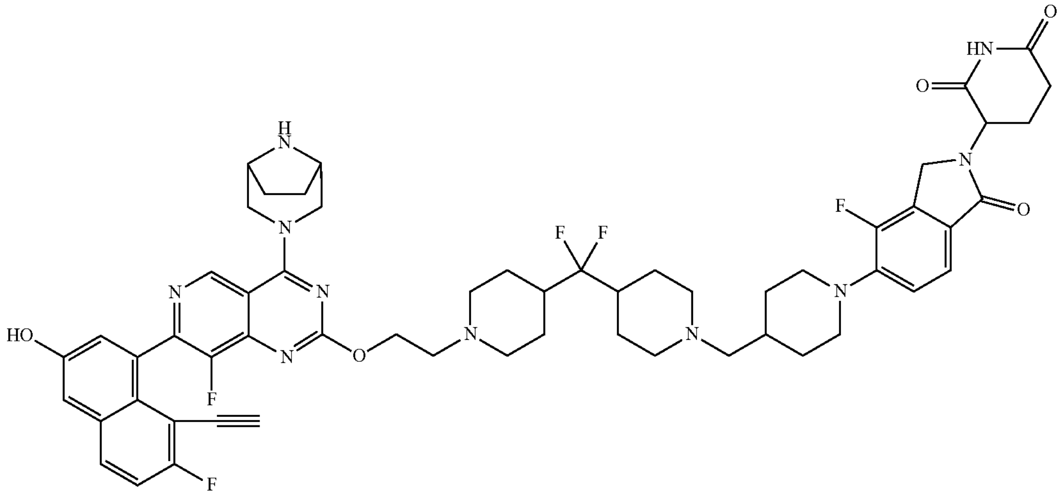 [SMILES: C#Cc1c(F)ccc2cc(O)cc(-c3ncc4c(N5CC6CCC(C5)N6)nc(OCCN5CCC(C(F)(F)C6CCN(CC7CCN(c8ccc9c(c8F)CN(C8CCC(=O)NC8=O)C9=O)CC7)CC6)CC5)nc4c3F)c12] |

??TABLE 1-continued
| Compound | Structure |
| --- | --- |
| 80 | 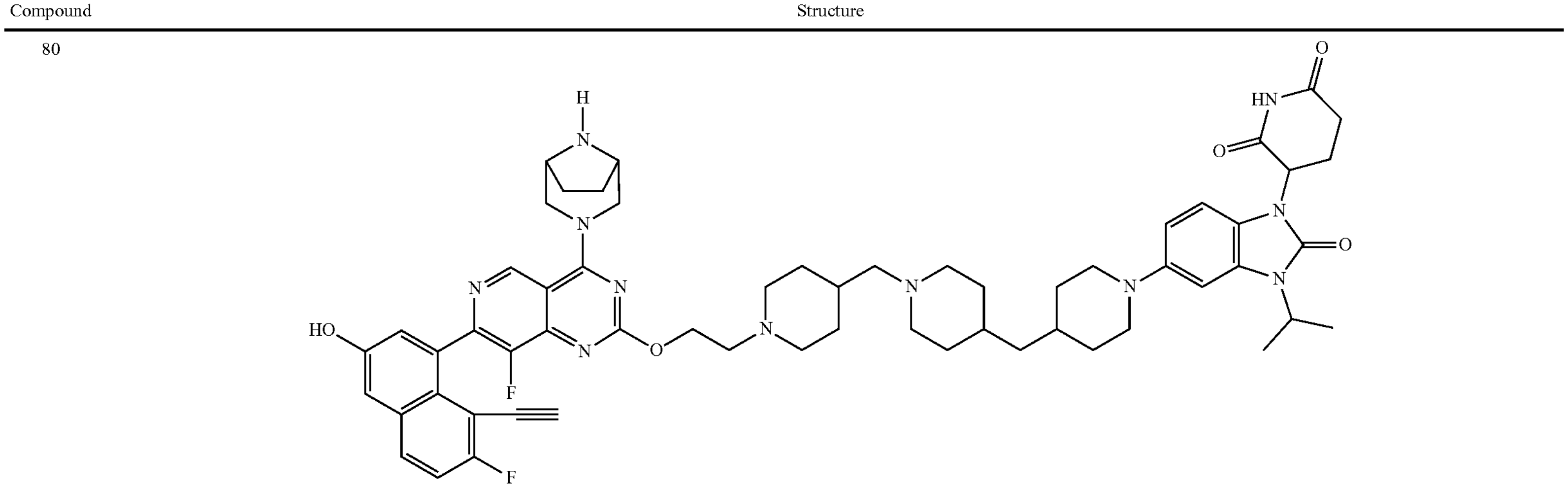 |
| 81 | 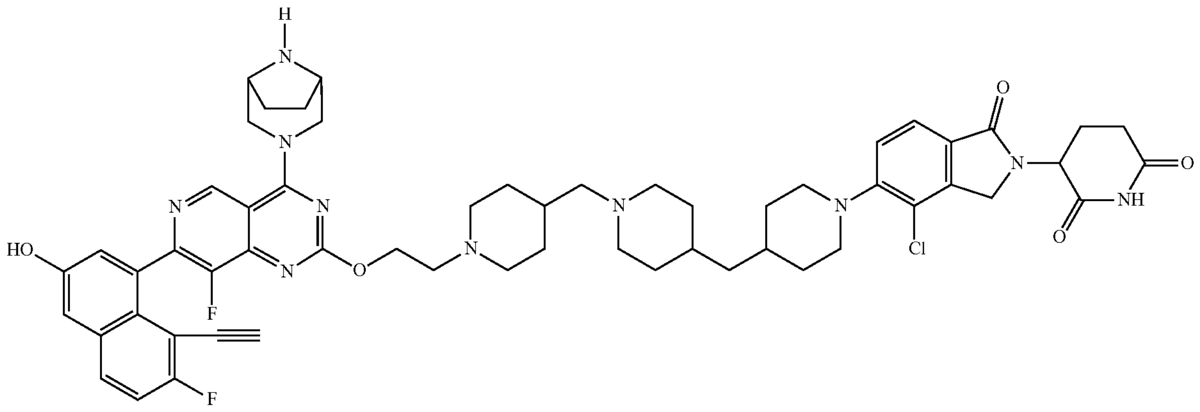 [SMILES: C#Cc1c(F)ccc2cc(O)cc(-c3ncc4c(N5CC6CCC(C5)N6)nc(OCCN5CCC(CN6CCC(CC7CCN(c8ccc9c(c8Cl)CN(C8CCC(=O)NC8=O)C9=O)CC7)CC6)CC5)nc4c3F)c12] |

??TABLE 1-continued
| Compound | Structure |
|---|---|
| 82 | 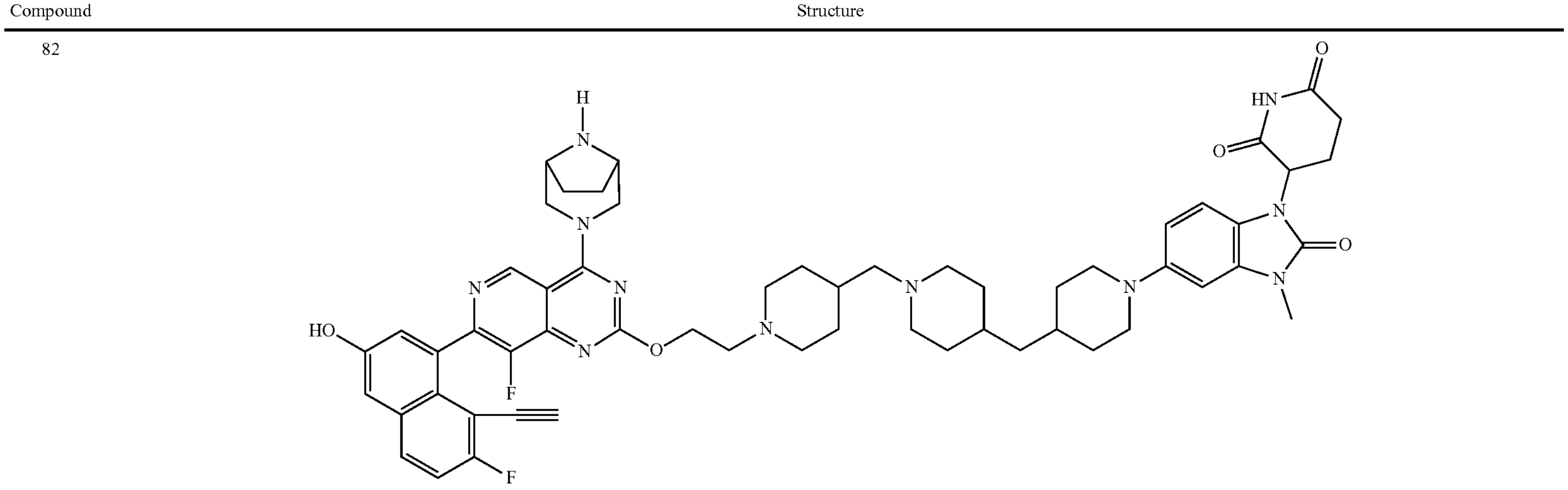 |
| 83 | 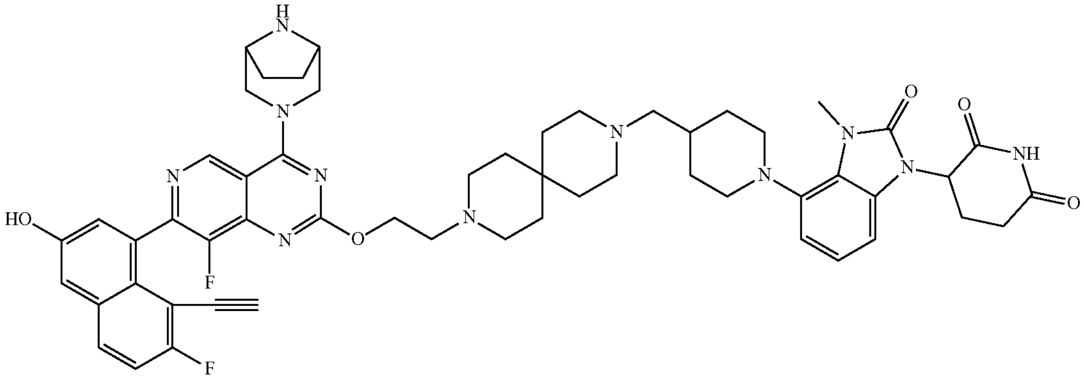 [SMILES: C#Cc1c(F)ccc2cc(O)cc(-c3ncc4c(N5CC6CCC(C5)N6)nc(OCCN5CCC6(CC5)CCN(CC5CCN(c7cccc8c7n(C)c(=O)n8C7CCC(=O)NC7=O)CC5)CC6)nc4c3F)c12] |

??TABLE 1-continued
| Compound | Structure |
|---|---|
| 84 | 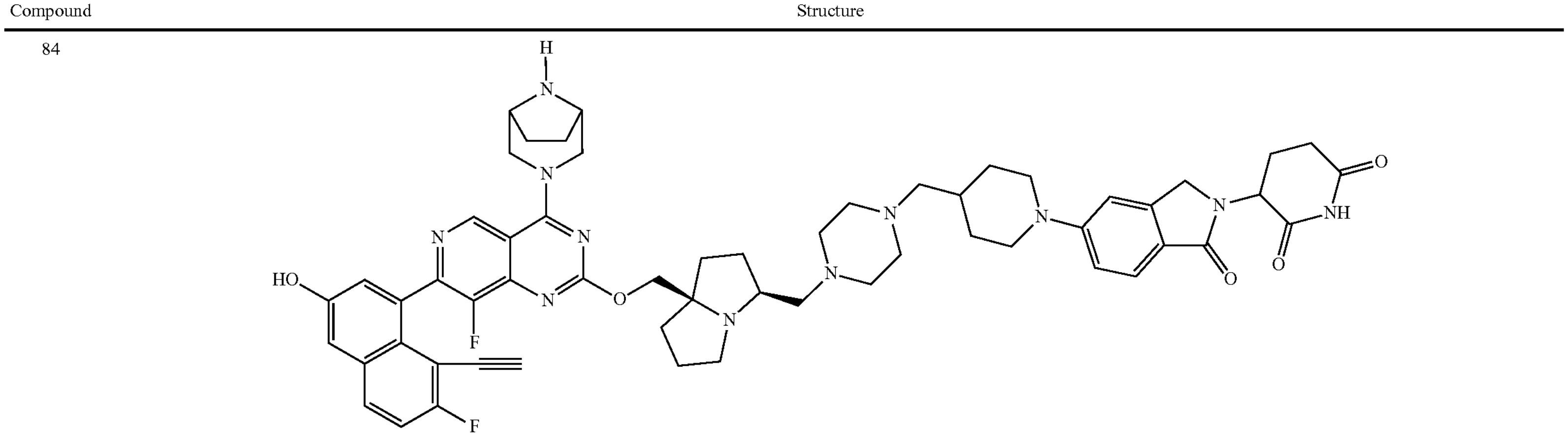 |
| 85 | 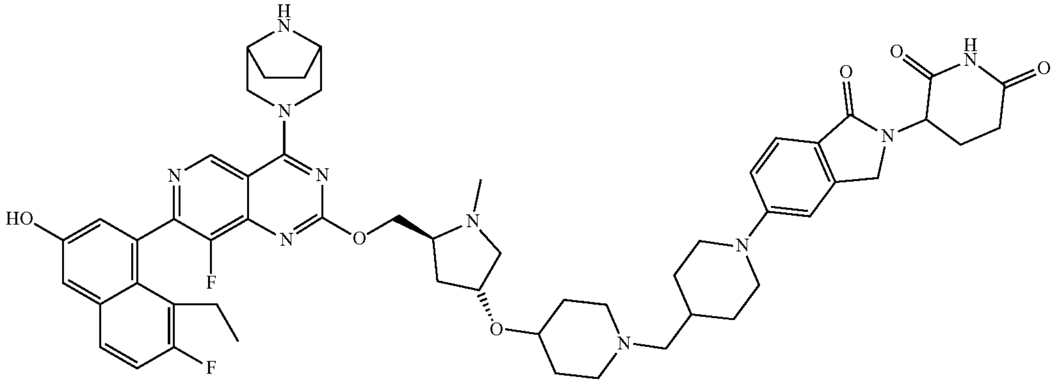 |

??TABLE 1-continued
| Compound | Structure |
|---|---|
| 86 | 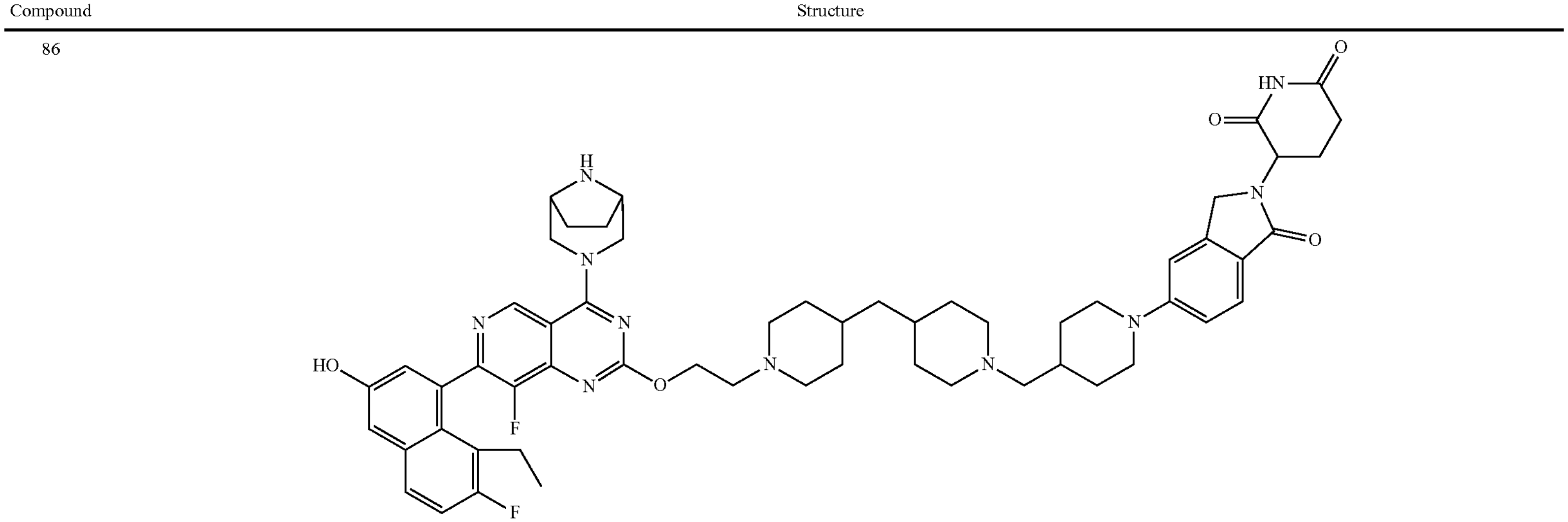 |
| 87 | 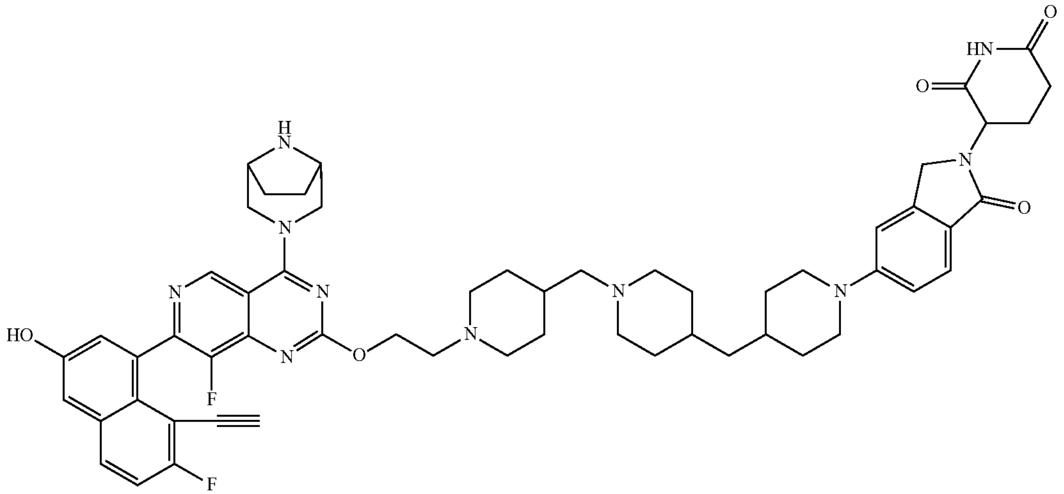 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)CN(C8CCC(=O)NC8=O)C9=O)CC7)CC6)CC5)nc4c3F)c12] |

??TABLE 1-continued
| Compound | Structure |
| --- | --- |
| 88 | 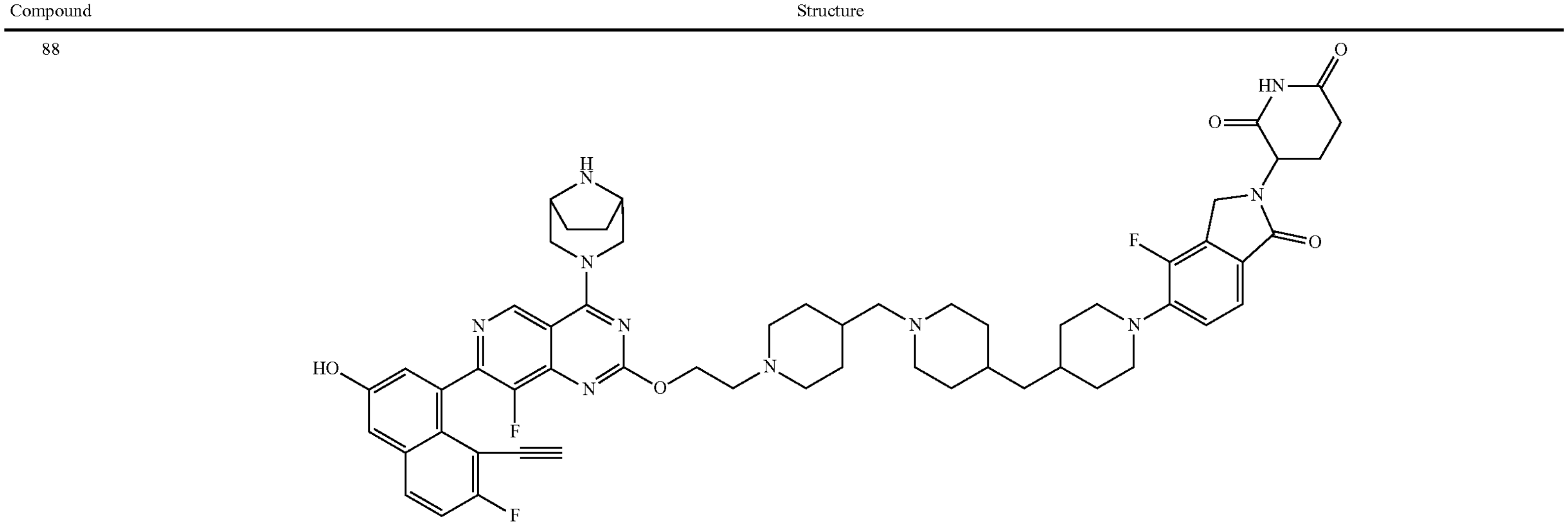 |
| 89 | 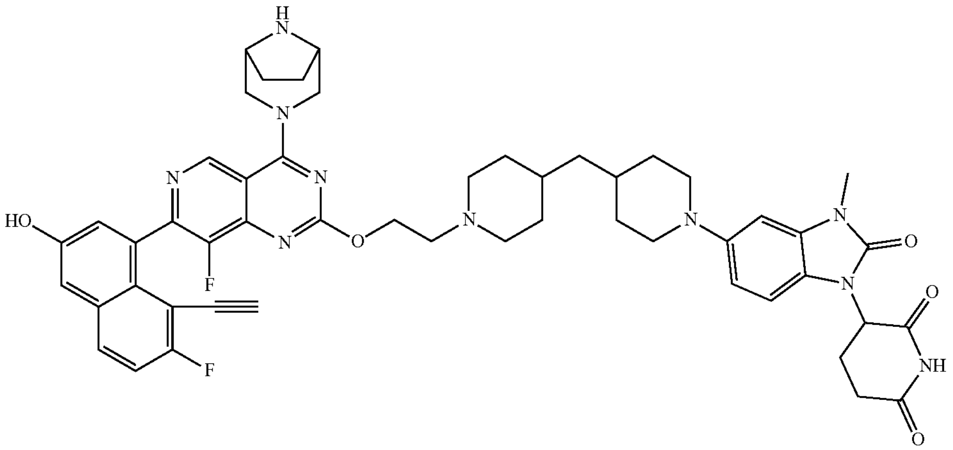 [SMILES: C#Cc1c(F)ccc2cc(O)cc(-c3ncc4c(N5CC6CCC(C5)N6)nc(OCCN5CCC(CC6CCN(c7ccc8c(c7)n(C)c(=O)n8C7CCC(=O)NC7=O)CC6)CC5)nc4c3F)c12] |

??TABLE 1-continued
| Compound | Structure |
| --- | --- |
| 90 | 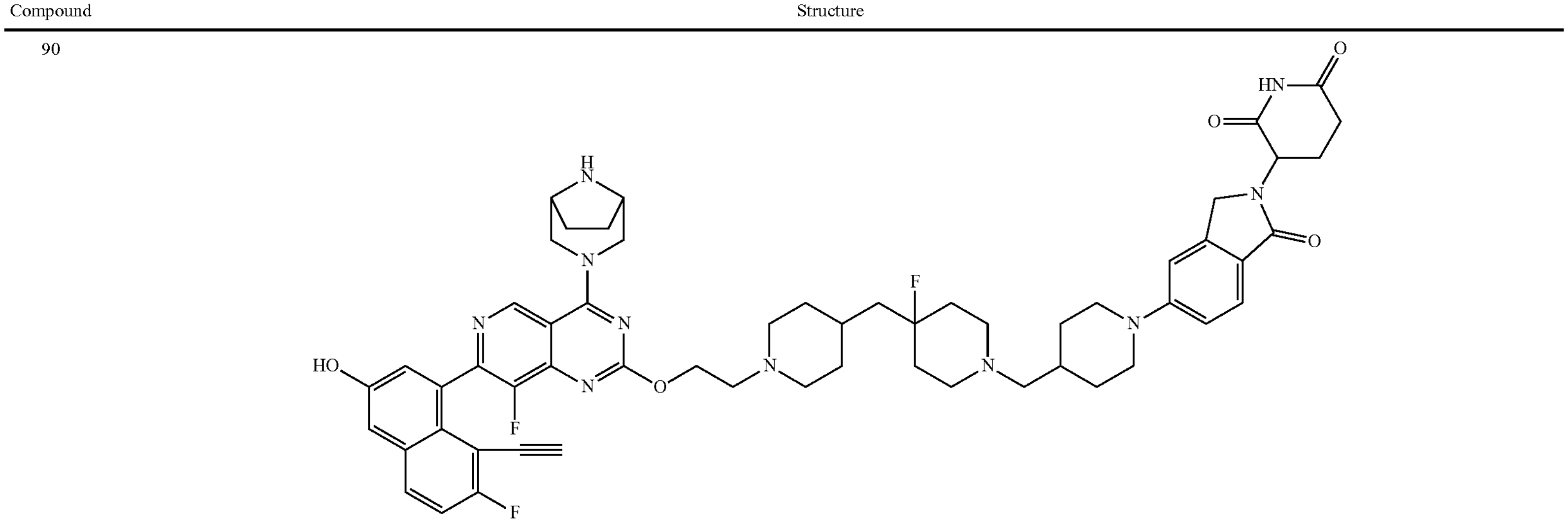 |
| 91 | 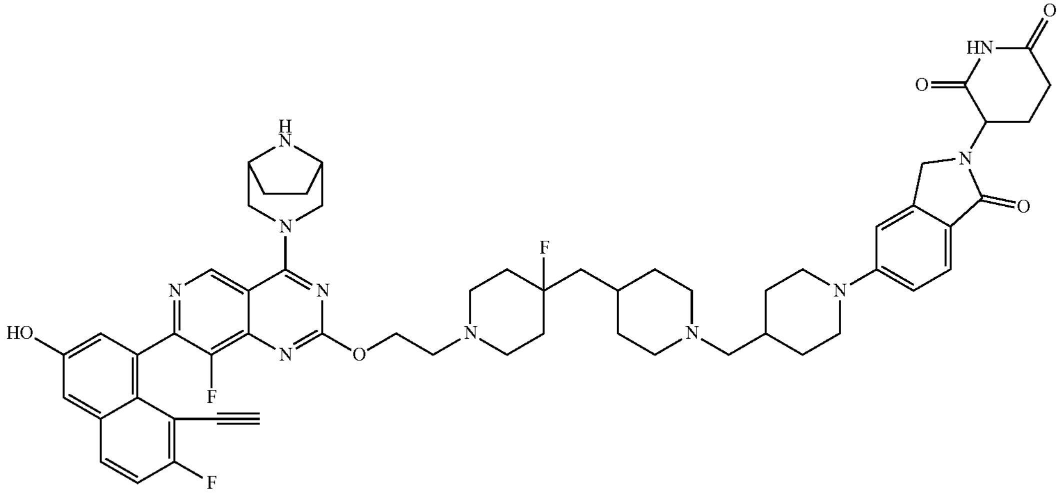 [SMILES: C#Cc1c(F)ccc2cc(O)cc(-c3ncc4c(N5CC6CCC(C5)N6)nc(OCCN5CCC(F)(CC6CCN(CC7CCN(c8ccc9c(c8)CN(C8CCC(=O)NC8=O)C9=O)CC7)CC6)CC5)nc4c3F)c12] |

??TABLE 1-continued
| Compound | Structure |
| --- | --- |
| 92 | 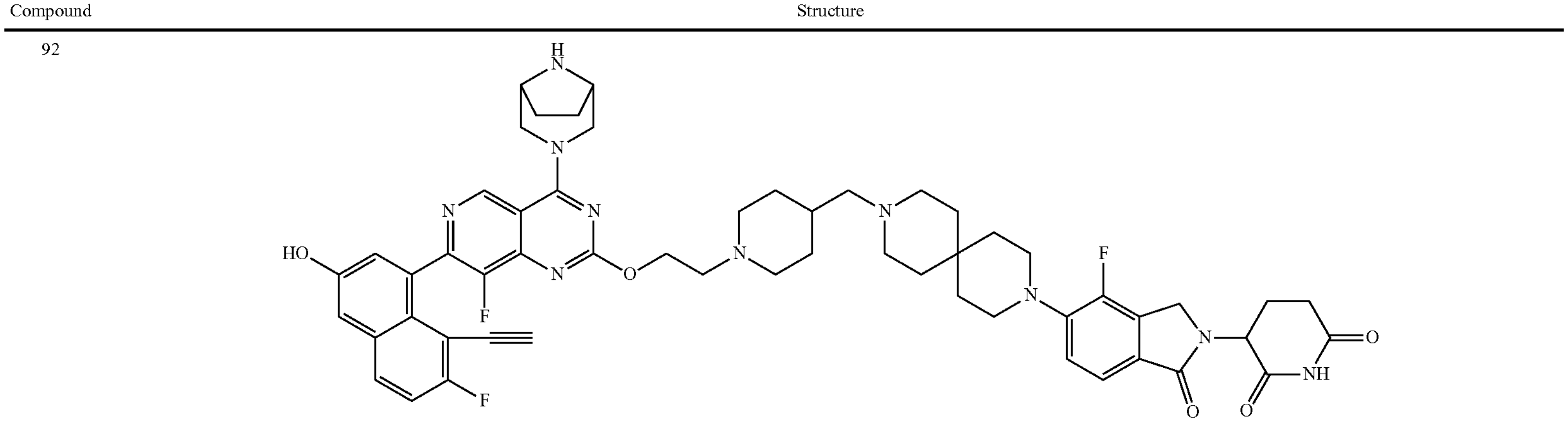 |
| 93 | 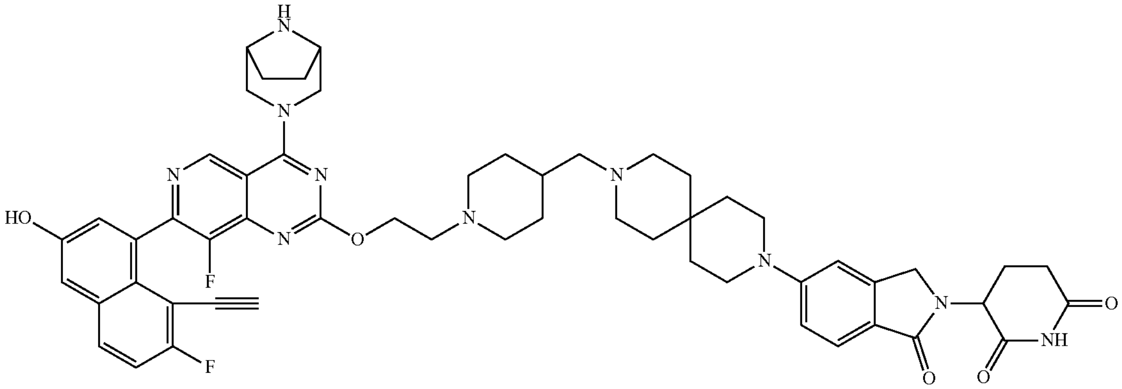 [SMILES: C#Cc1c(F)ccc2cc(O)cc(-c3ncc4c(N5CC6CCC(C5)N6)nc(OCCN5CCC(CN6CCC7(CC6)CCN(c6ccc8c(c6)CN(C6CCC(=O)NC6=O)C8=O)CC7)CC5)nc4c3F)c12] |

??TABLE 1-continued
| Compound | Structure |
|---|---|
| 94 | 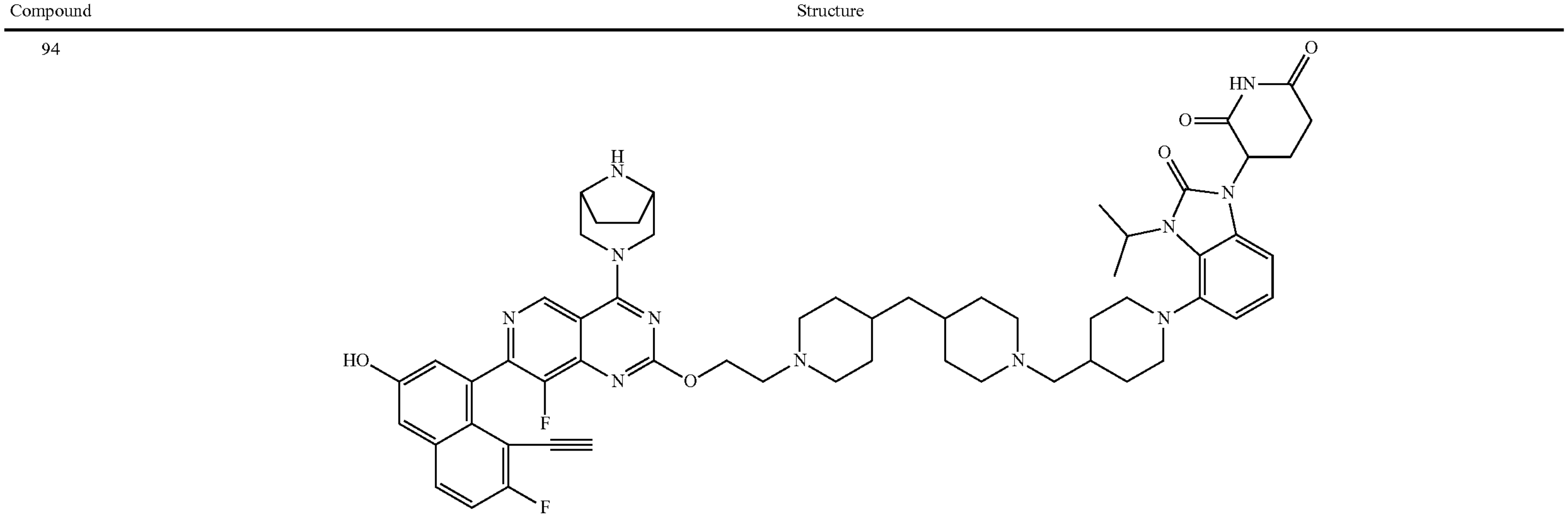 |
| 95 | 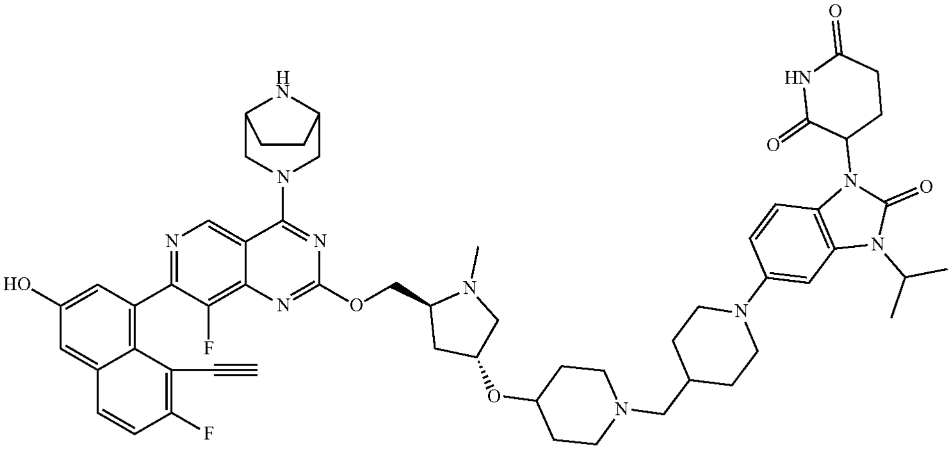 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8)n(C(C)C)c(=O)n9C8CCC(=O)NC8=O)CC7)CC6)CN5C)nc4c3F)c12] |

??TABLE 1-continued
| Compound | Structure |
| --- | --- |
| 96 | 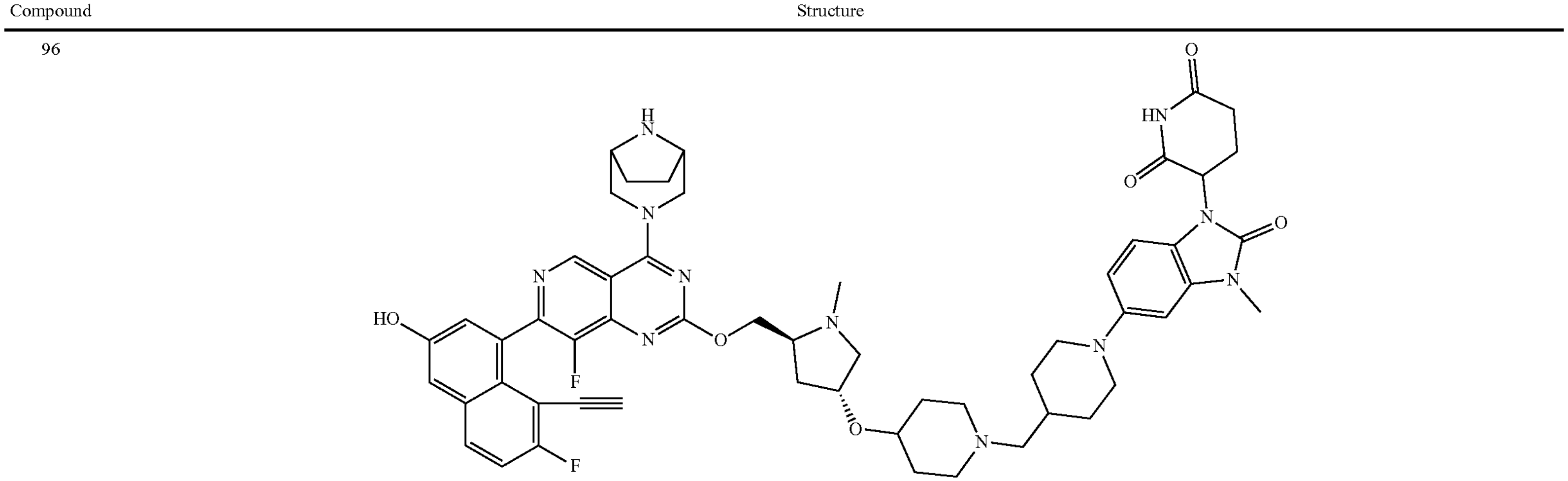 |
| 97 | 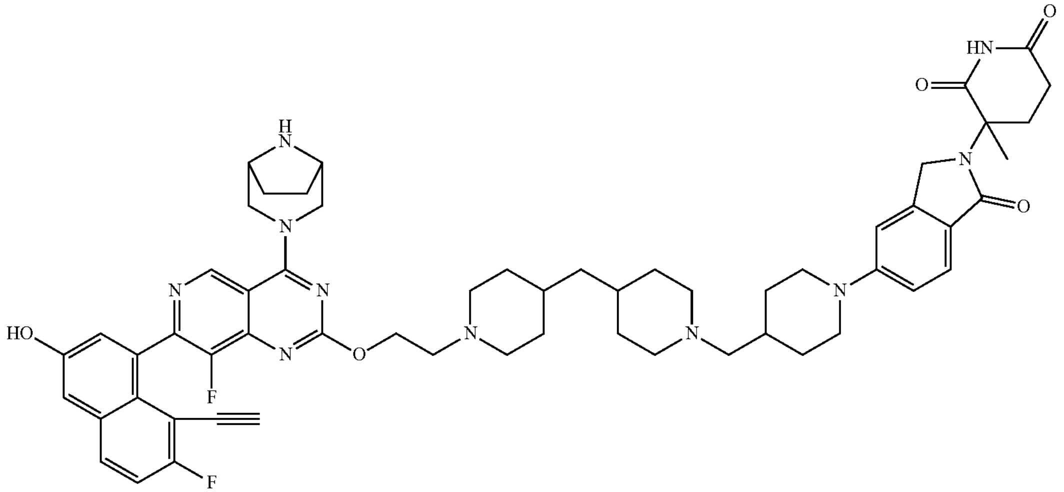 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)CN(C8(C)CCC(=O)NC8=O)C9=O)CC7)CC6)CC5)nc4c3F)c12] |

??TABLE 1-continued
| Compound | Structure |
| --- | --- |
| 98 | 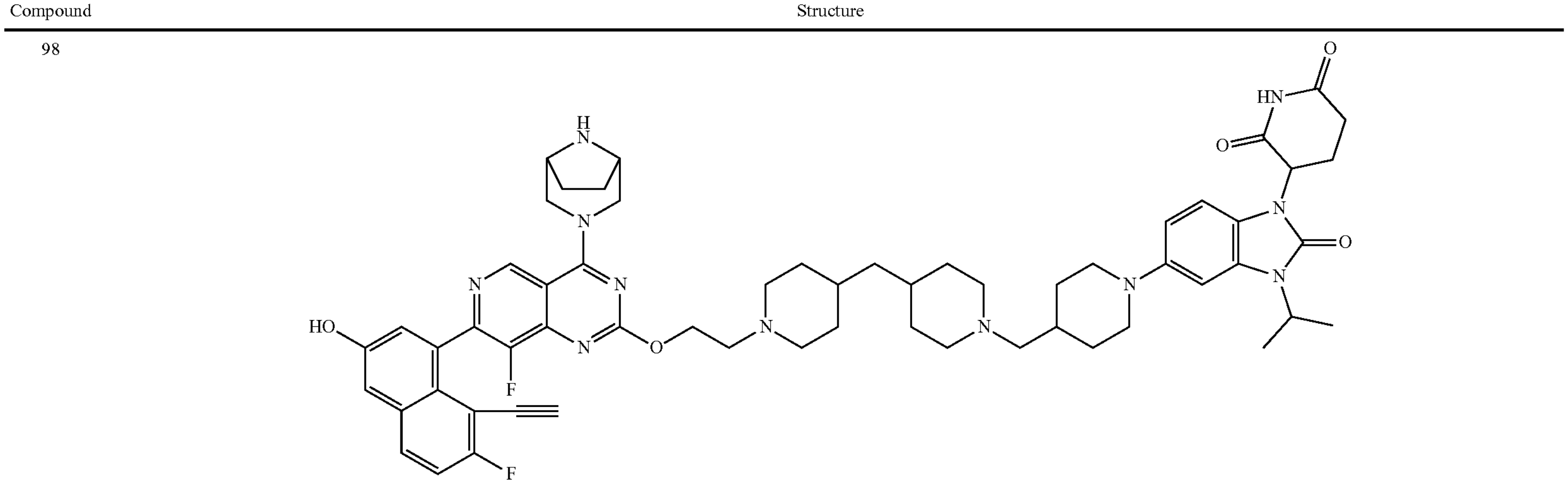 |
| 99 | 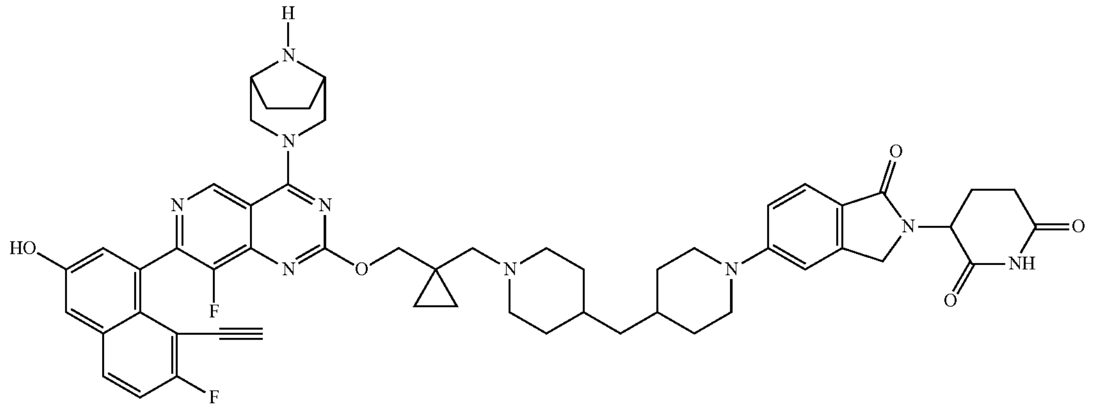 [SMILES: C#Cc1c(F)ccc2cc(O)cc(-c3ncc4c(N5CC6CCC(C5)N6)nc(OCC5(CN6CCC(CC7CCN(c8ccc9c(c8)CN(C8CCC(=O)NC8=O)C9=O)CC7)CC6)CC5)nc4c3F)c12] |

??TABLE 1-continued
| Compound | Structure |
| --- | --- |
| 100 | 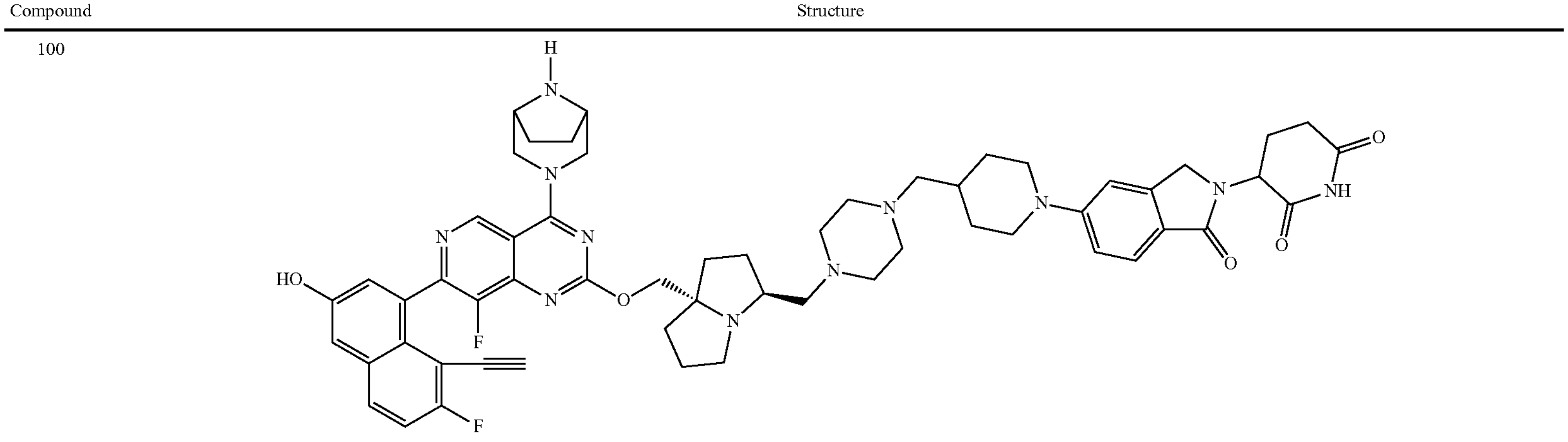 |
| 101 | 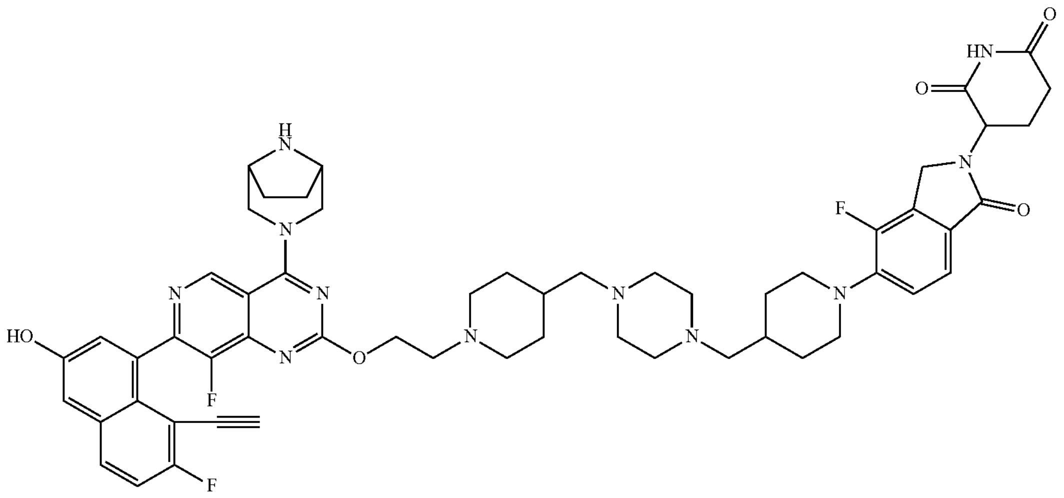 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)CC6)CC5)nc4c3F)c12] |

??TABLE 1-continued
| Compound | Structure |
| --- | --- |
| 102 | 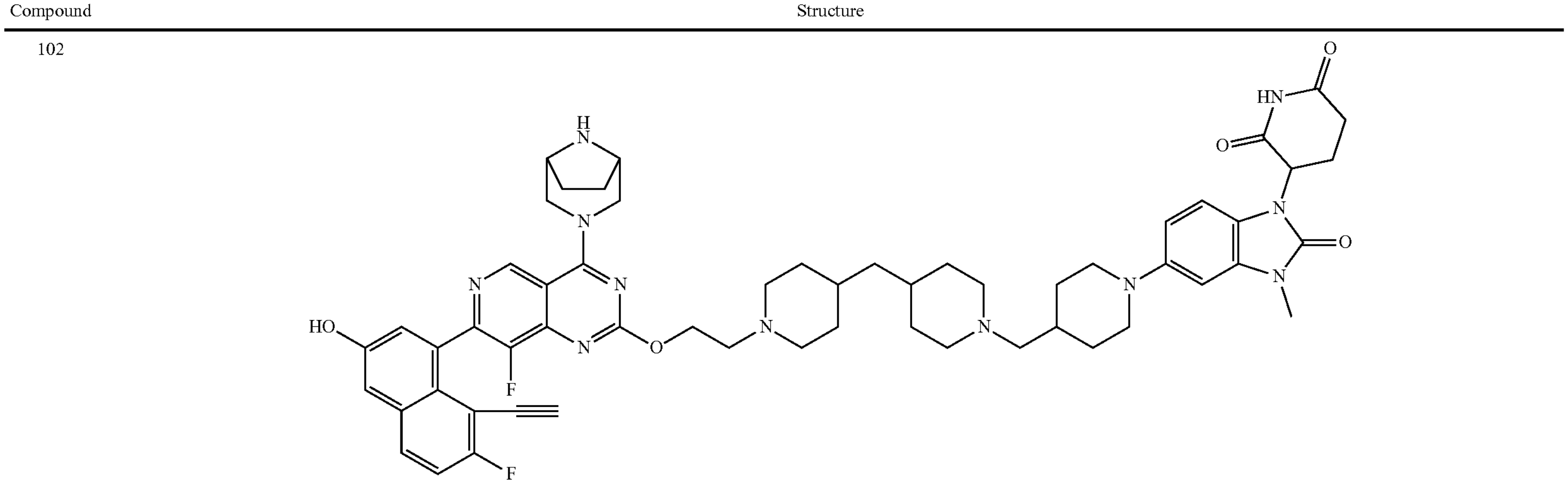 |
| 103 | 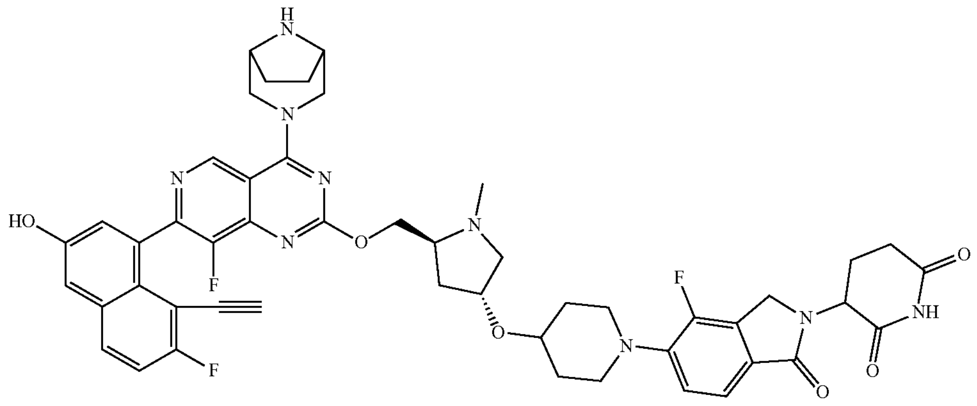 [SMILES: C#Cc1c(F)ccc2cc(O)cc(-c3ncc4c(N5CC6CCC(C5)N6)nc(OC[C@@H]5C[C@@H](OC6CCN(c7ccc8c(c7F)CN(C7CCC(=O)NC7=O)C8=O)CC6)CN5C)nc4c3F)c12] |

??TABLE 1-continued
| Compound | Structure |
| --- | --- |
| 104 | 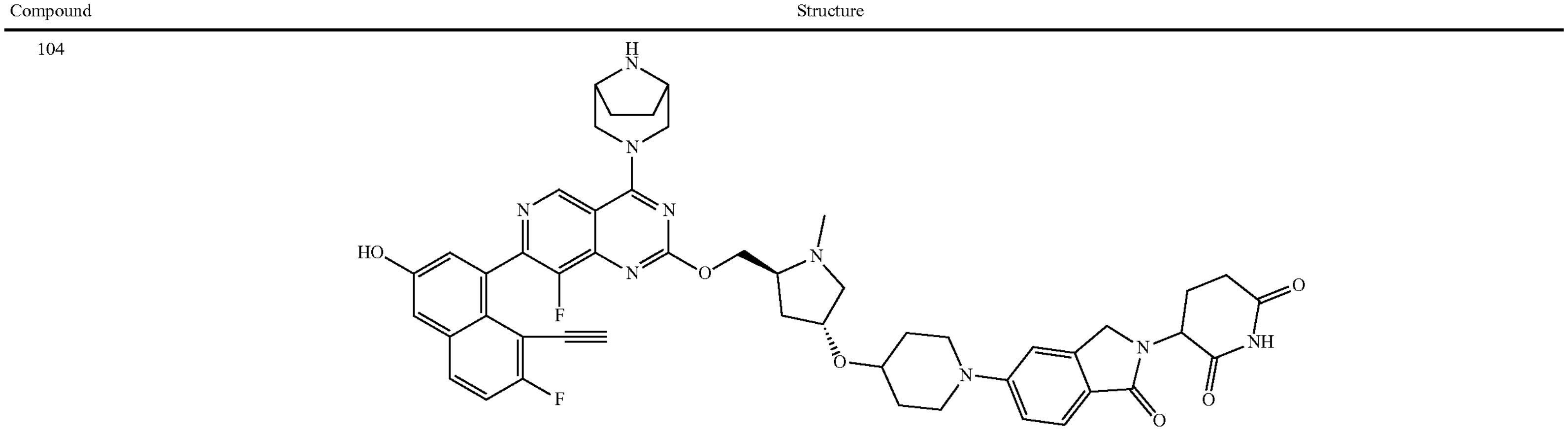 |
| 105 | 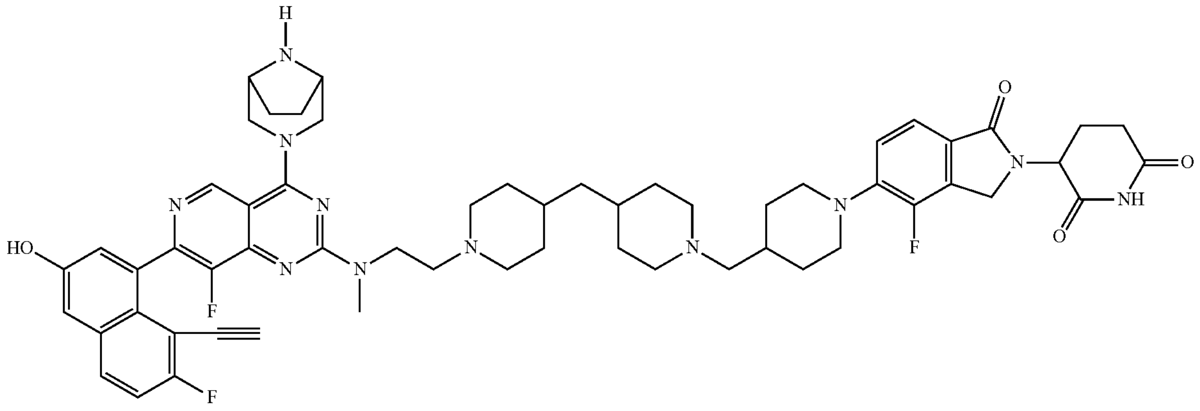 |

??TABLE 1-continued
| Compound | Structure |
| --- | --- |
| 106 | 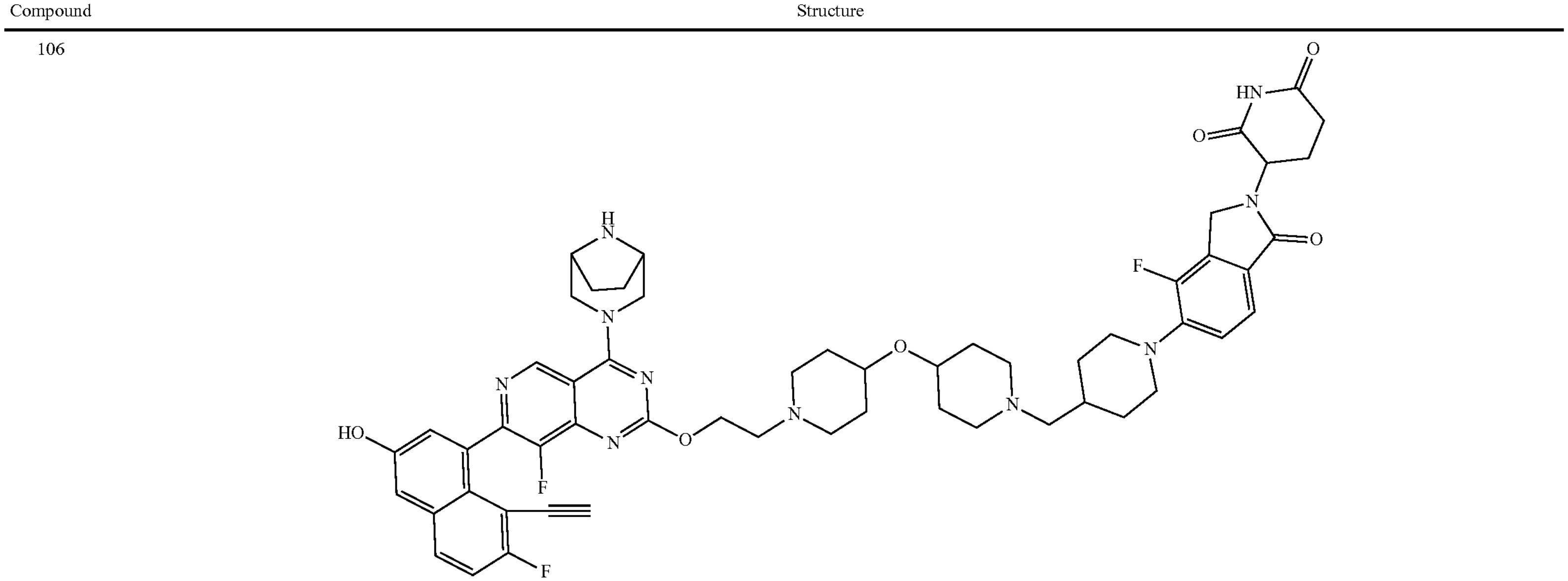 |
| 107 | 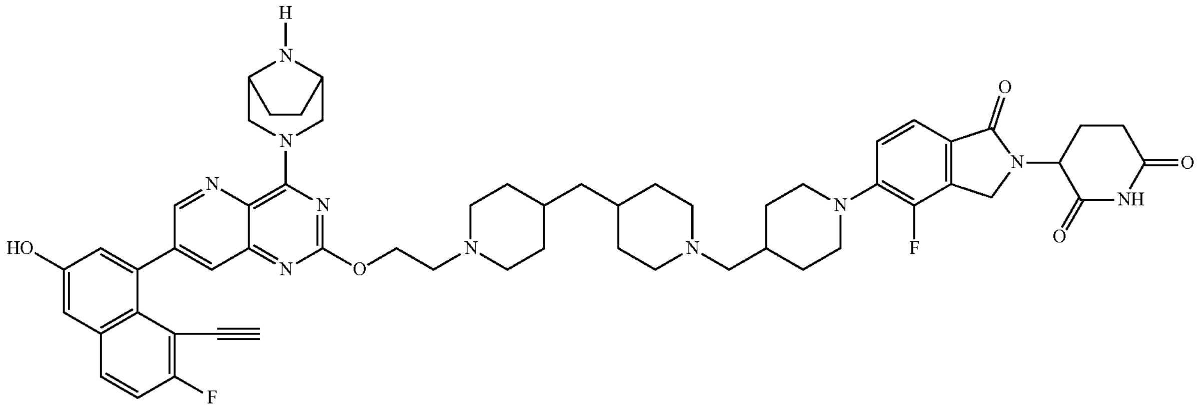 [SMILES: C#Cc1c(F)ccc2cc(O)cc(-c3cnc4c(N5CC6CCC(C5)N6)nc(OCCN5CCC(CC6CCN(CC7CCN(c8ccc9c(c8F)CN(C8CCC(=O)NC8=O)C9=O)CC7)CC6)CC5)nc4c3)c12] |

??TABLE 1-continued
| Compound | Structure |
|---|---|
| 108 | 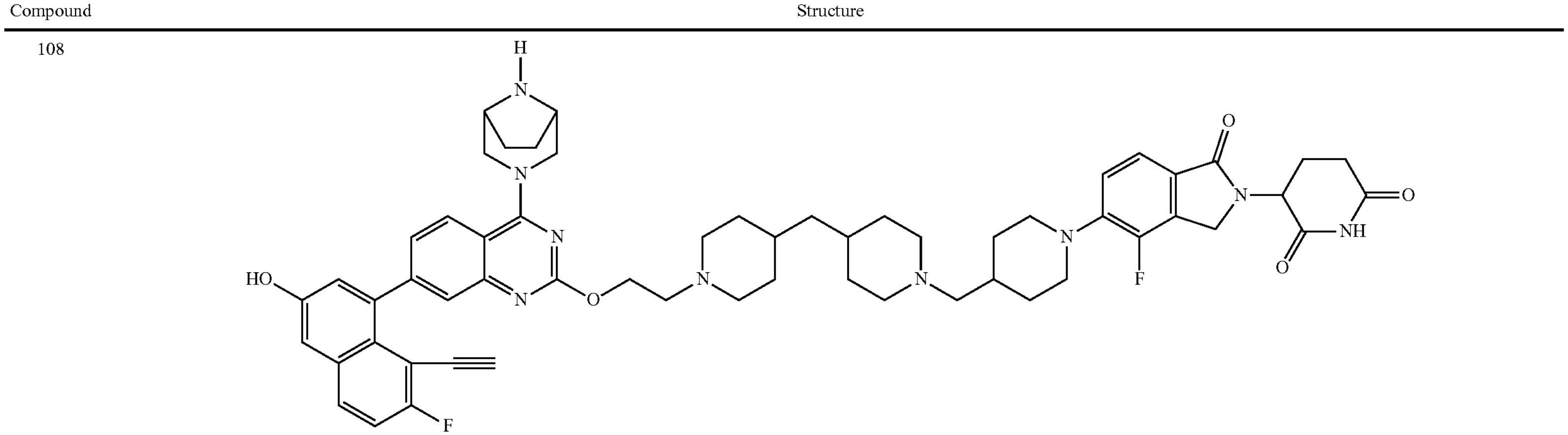 |
| 109 | 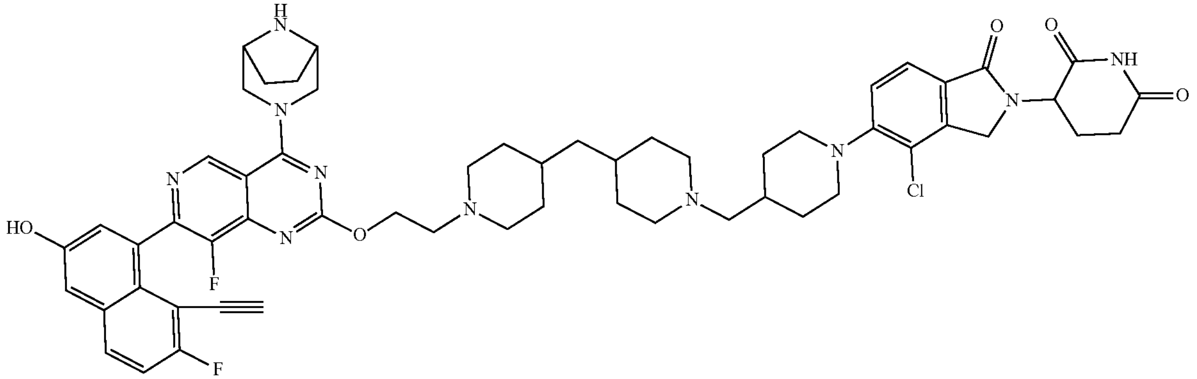 [SMILES: C#Cc1c(F)ccc2cc(O)cc(-c3ncc4c(N5CC6CCC(C5)N6)nc(OCCN5CCC(CC6CCN(CC7CCN(c8ccc9c(c8Cl)CN(C8CCC(=O)NC8=O)C9=O)CC7)CC6)CC5)nc4c3F)c12] |

??TABLE 1-continued
| Compound | Structure |
| --- | --- |
| 110 | 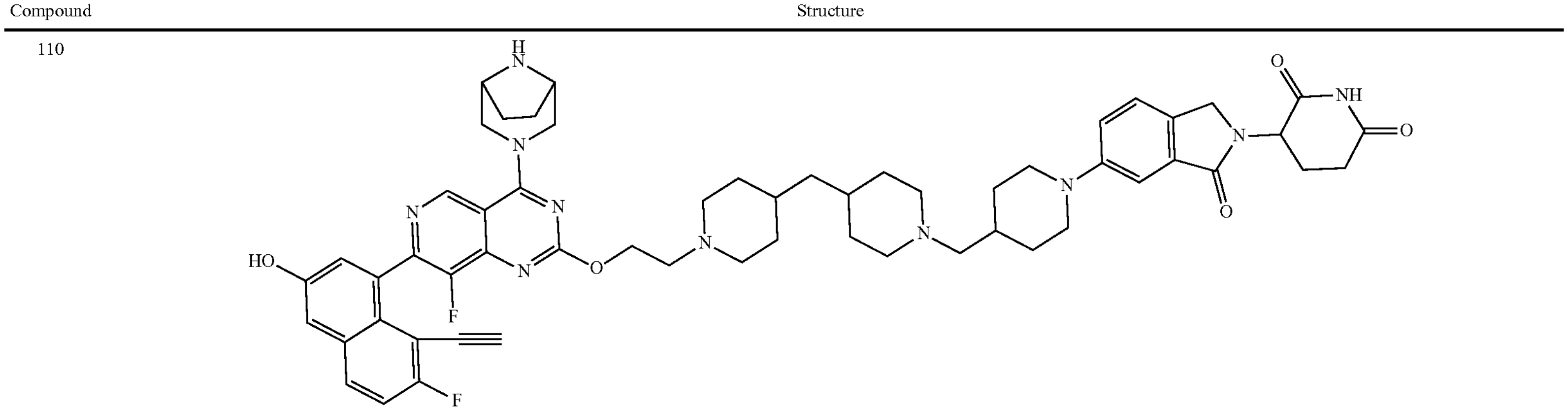 |
| 111 | 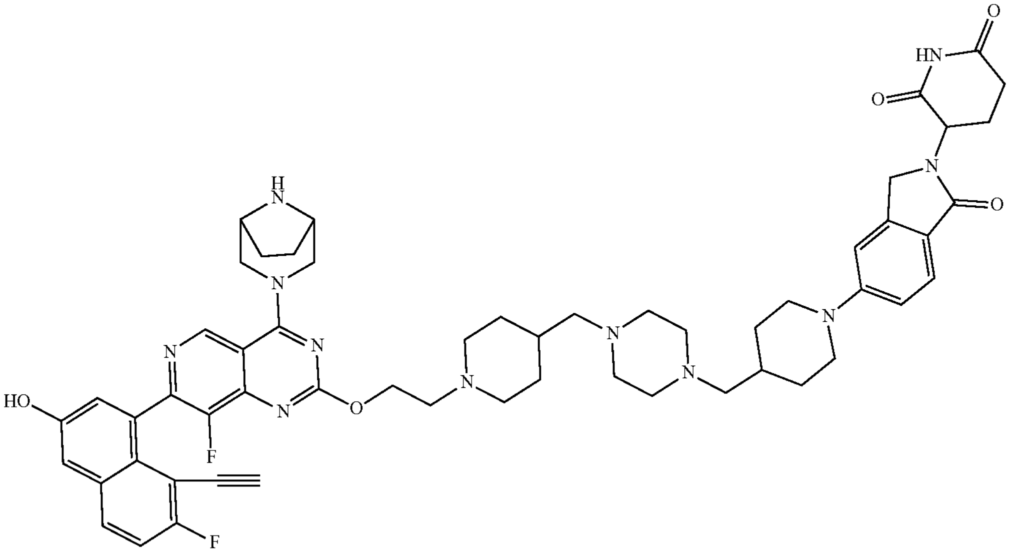 [SMILES: C#Cc1c(F)ccc2cc(O)cc(-c3ncc4c(N5CC6CCC(C5)N6)nc(OCCN5CCC(CN6CCN(CC7CCN(c8ccc9c(c8)CN(C8CCC(=O)NC8=O)C9=O)CC7)CC6)CC5)nc4c3F)c12] |

??TABLE 1-continued
| Compound | Structure |
|---|---|
| 112 | 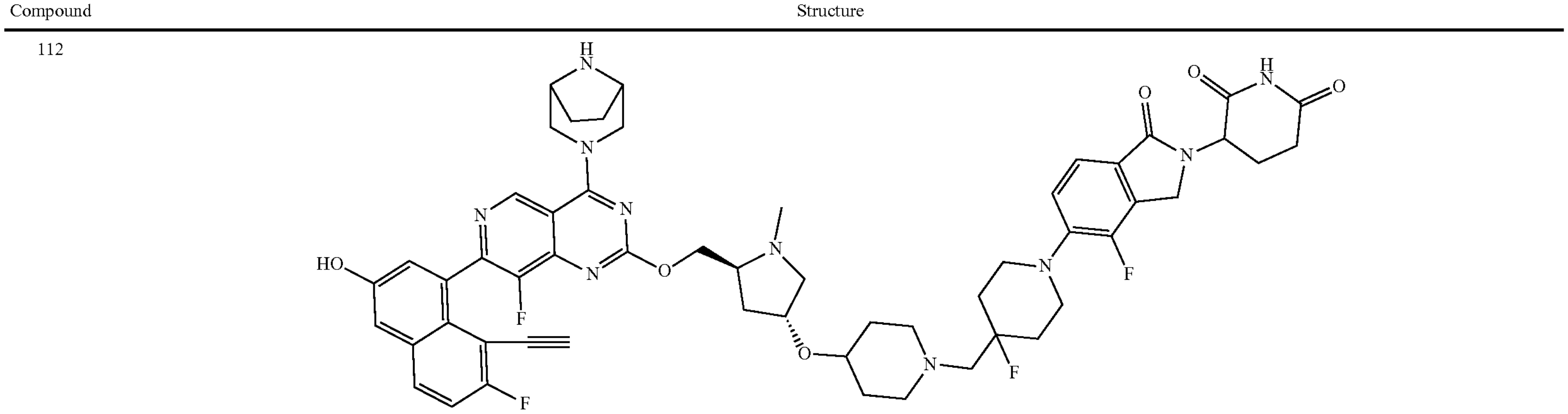 |
| 113 | 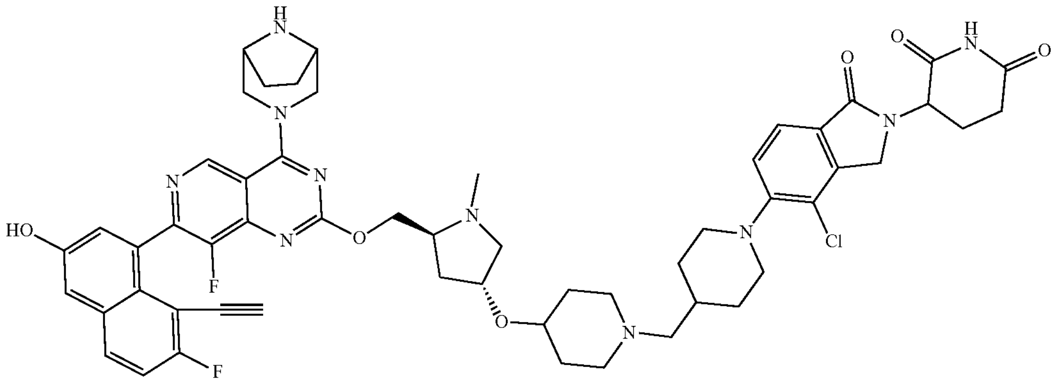 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8Cl)CN(C8CCC(=O)NC8=O)C9=O)CC7)CC6)CN5C)nc4c3F)c12] |

??TABLE 1-continued
| Compound | Structure |
|---|---|
| 114 | 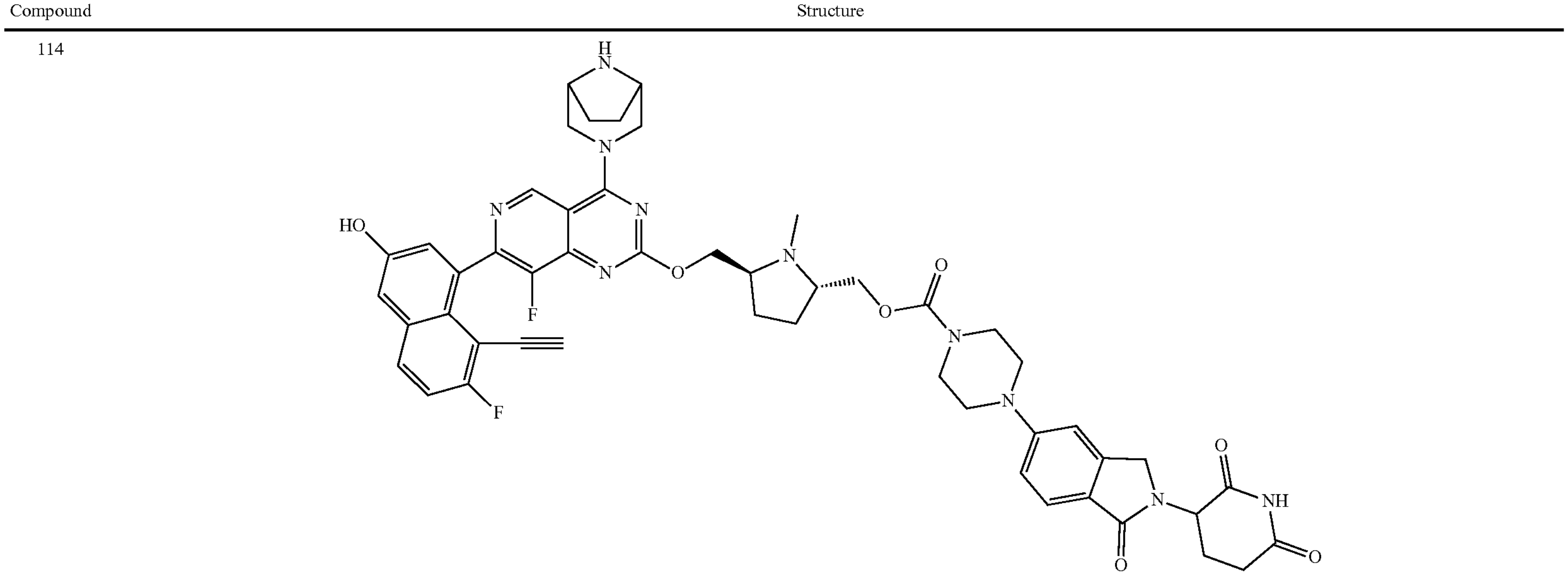 |
| 115 | 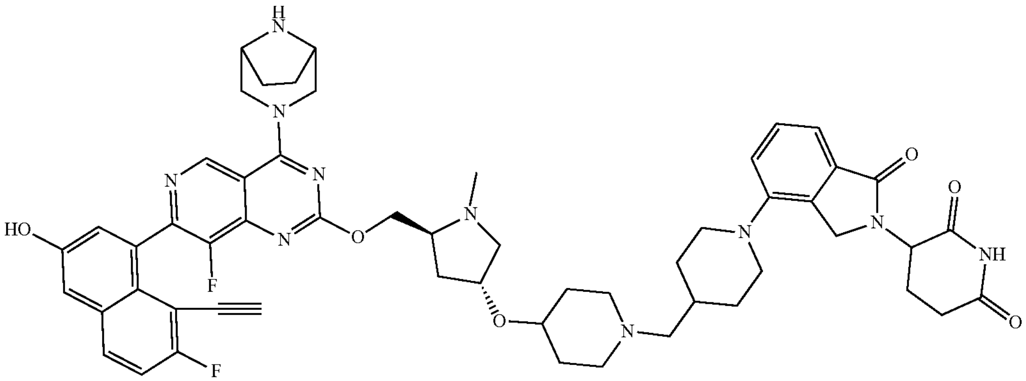 [SMILES: C#Cc1c(F)ccc2cc(O)cc(-c3ncc4c(N5CC6CCC(C5)N6)nc(OC[C@@H]5C[C@@H](OC6CCN(CC7CCN(c8cccc9c8CN(C8CCC(=O)NC8=O)C9=O)CC7)CC6)CN5C)nc4c3F)c12] |

??TABLE 1-continued
| Compound | Structure |
| --- | --- |
| 116 | 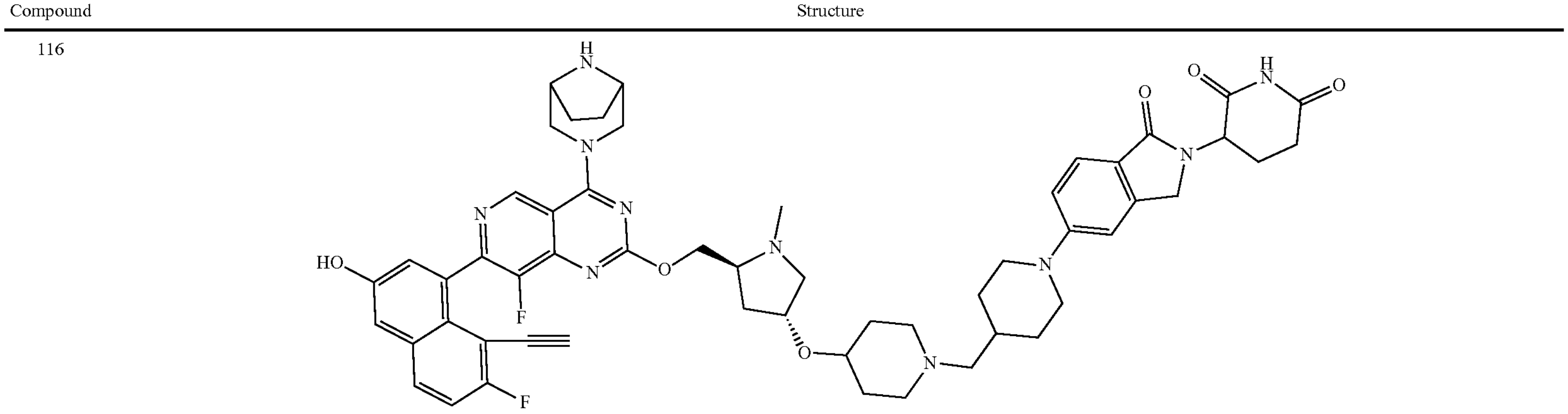 |
| 117 | 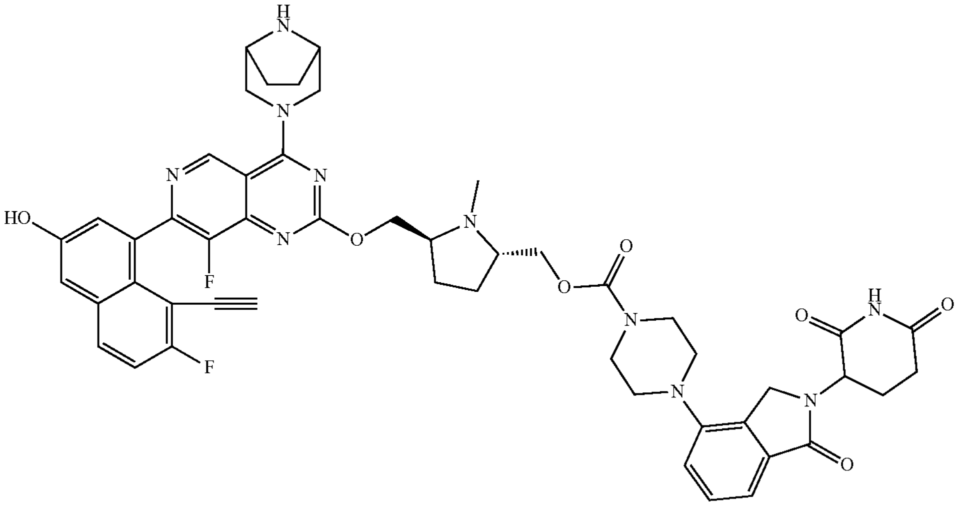 [SMILES: C#Cc1c(F)ccc2cc(O)cc(-c3ncc4c(N5CC6CCC(C5)N6)nc(OC[C@@H]5CC[C@@H](COC(=O)N6CCN(c7cccc8c7CN(C7CCC(=O)NC7=O)C8=O)CC6)N5C)nc4c3F)c12] |

??TABLE 1-continued
| Compound | Structure |
| --- | --- |
| 118 | 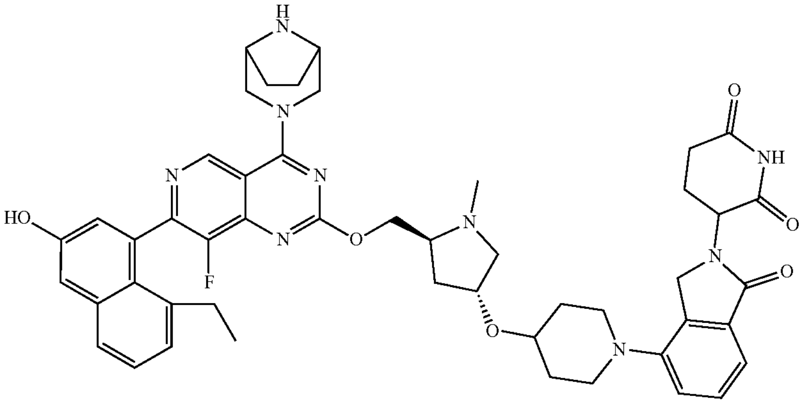 [SMILES: CCc1cccc2cc(O)cc(-c3ncc4c(N5CC6CCC(C5)N6)nc(OC[C@@H]5C[C@@H](OC6CCN(c7cccc8c7CN(C7CCC(=O)NC7=O)C8=O)CC6)CN5C)nc4c3F)c12] |
| 119 | 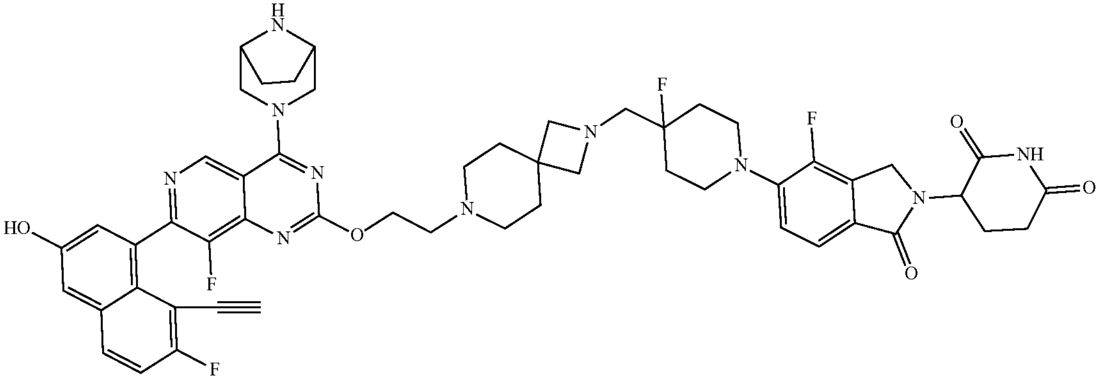 [SMILES: C#Cc1c(F)ccc2cc(O)cc(-c3ncc4c(N5CC6CCC(C5)N6)nc(OCCN5CCC6(CC5)CN(CC5(F)CCN(c7ccc8c(c7F)CN(C7CCC(=O)NC7=O)C8=O)CC5)C6)nc4c3F)c12] |

??TABLE 1-continued
| Compound | Structure |
| --- | --- |
| 120 | 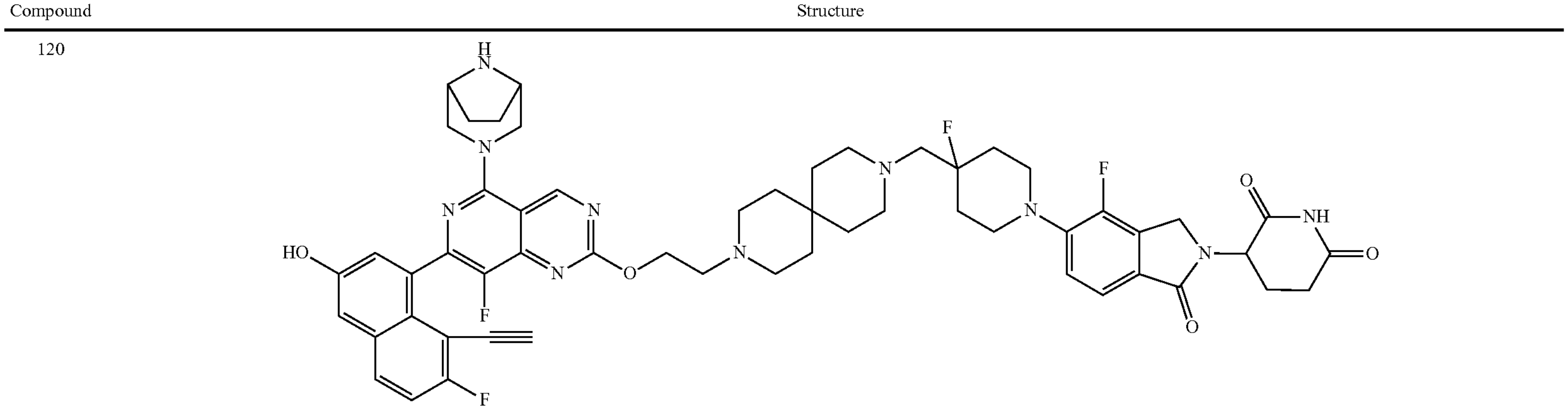 |
| 121 | 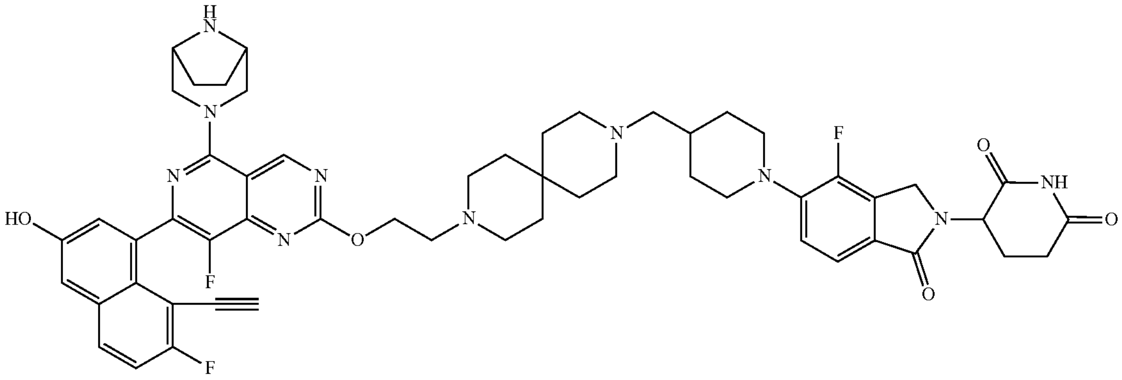 [SMILES: C#Cc1c(F)ccc2cc(O)cc(-c3nc(N4CC5CCC(C4)N5)c4cnc(OCCN5CCC6(CC5)CCN(CC5CCN(c7ccc8c(c7F)CN(C7CCC(=O)NC7=O)C8=O)CC5)CC6)nc4c3F)c12] |

??TABLE 1-continued
| Compound | Structure |
|---|---|
| 122 | 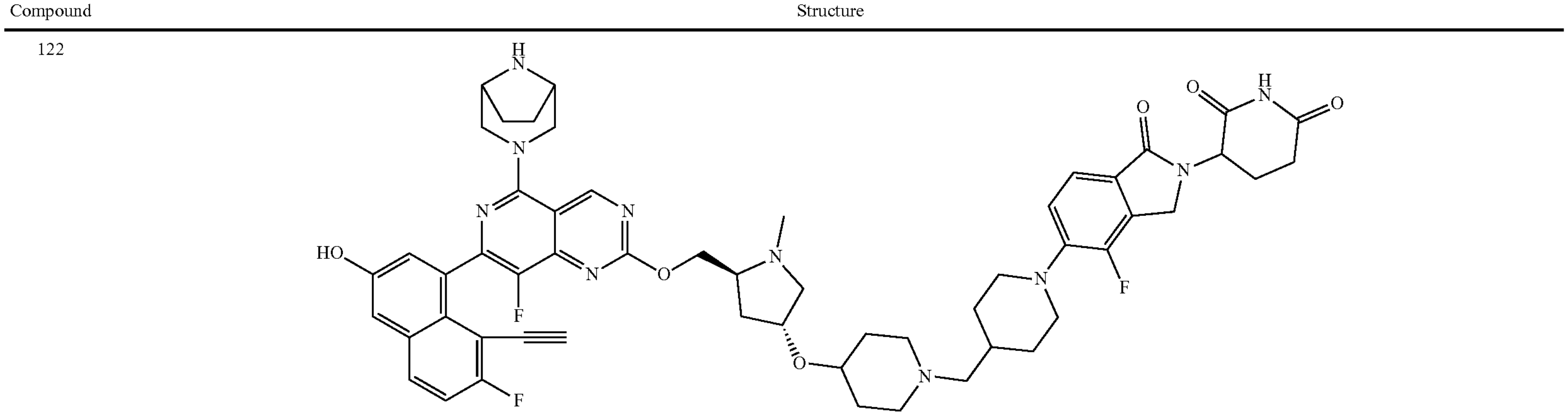 |
| 123 | 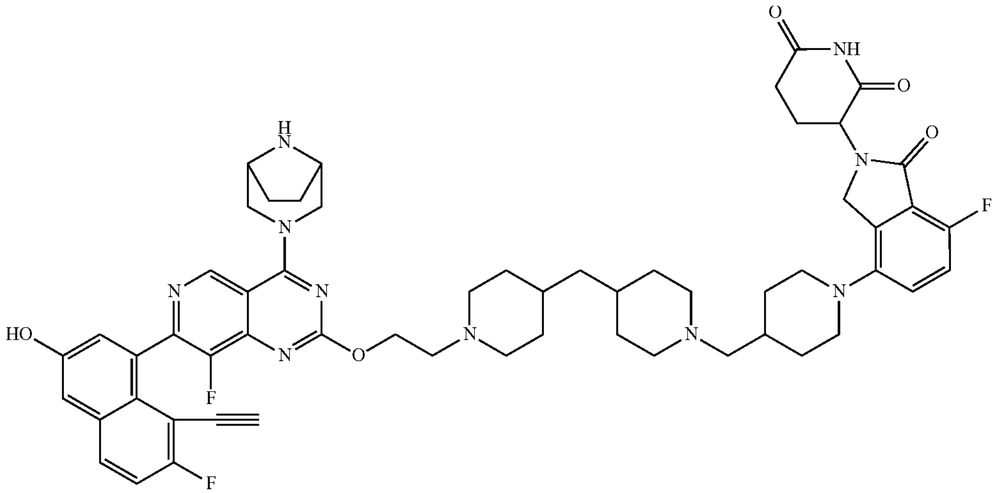 [SMILES: C#Cc1c(F)ccc2cc(O)cc(-c3ncc4c(N5CC6CCC(C5)N6)nc(OCCN5CCC(CC6CCN(CC7CCN(c8ccc(F)c9c8CN(C8CCC(=O)NC8=O)C9=O)CC7)CC6)CC5)nc4c3F)c12] |

??TABLE 1-continued
| Compound | Structure |
| --- | --- |
| 124 | 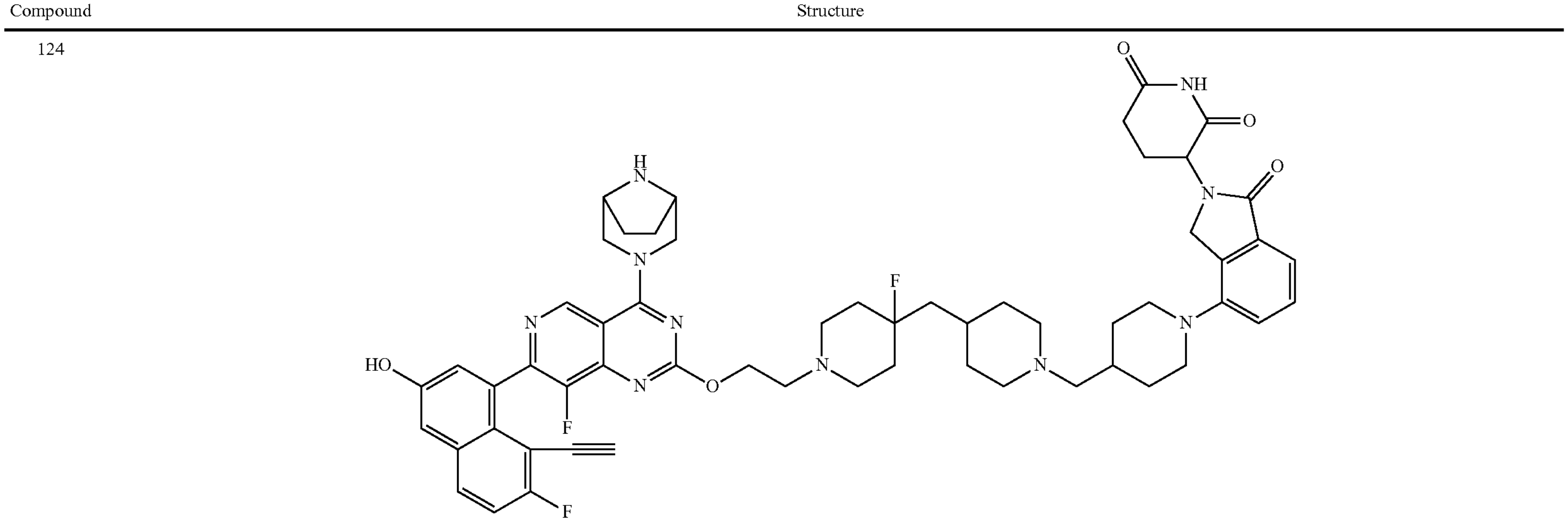 |
| 125 | 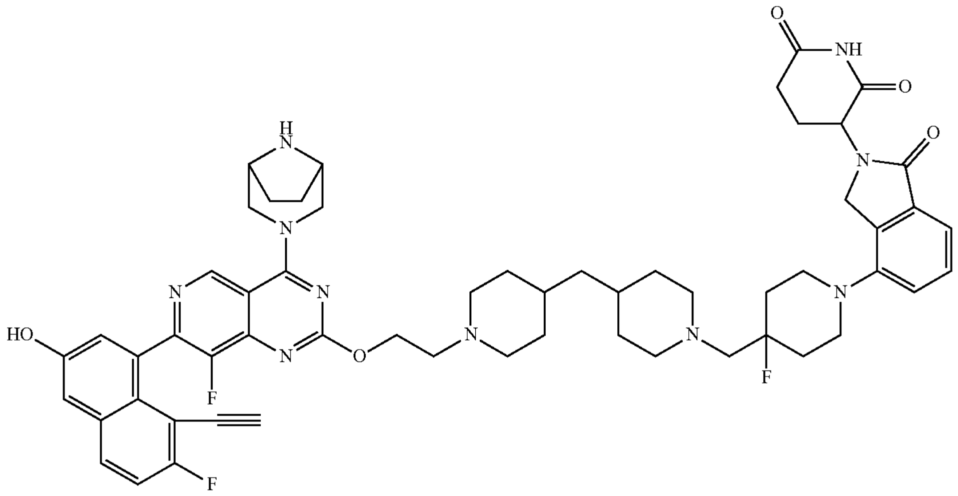 [SMILES: C#Cc1c(F)ccc2cc(O)cc(-c3ncc4c(N5CC6CCC(C5)N6)nc(OCCN5CCC(CC6CCN(CC7(F)CCN(c8cccc9c8CN(C8CCC(=O)NC8=O)C9=O)CC7)CC6)CC5)nc4c3F)c12] |

??TABLE 1-continued
| Compound | Structure |
|---|---|
| 126 | 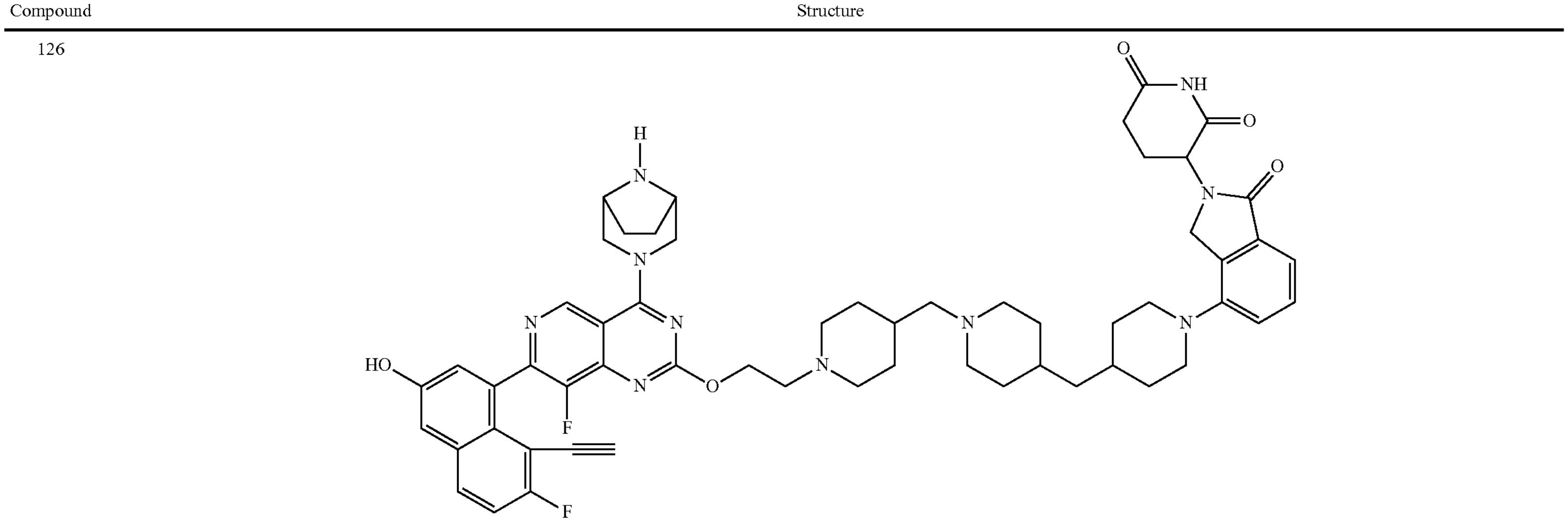 |
| 127 | 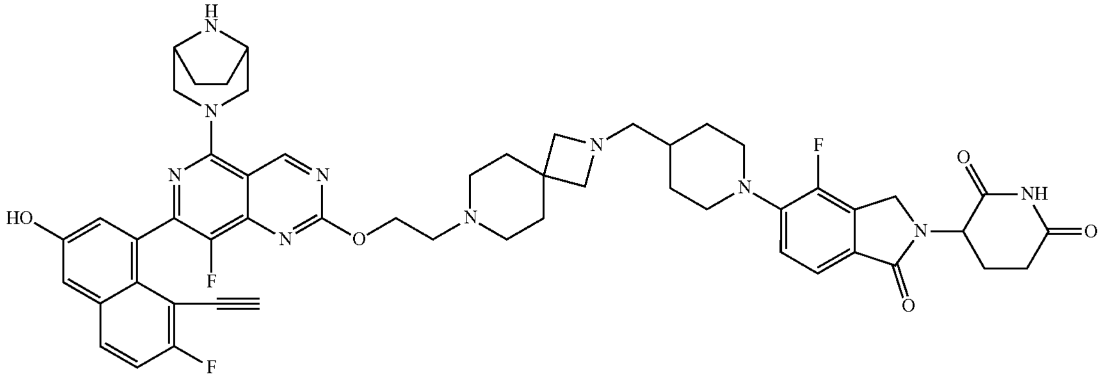 [SMILES: C#Cc1c(F)ccc2cc(O)cc(-c3nc(N4CC5CCC(C4)N5)c4cnc(OCCN5CCC6(CC5)CN(CC5CCN(c7ccc8c(c7F)CN(C7CCC(=O)NC7=O)C8=O)CC5)C6)nc4c3F)c12] |

??TABLE 1-continued
| Compound | Structure |
| --- | --- |
| 128 | 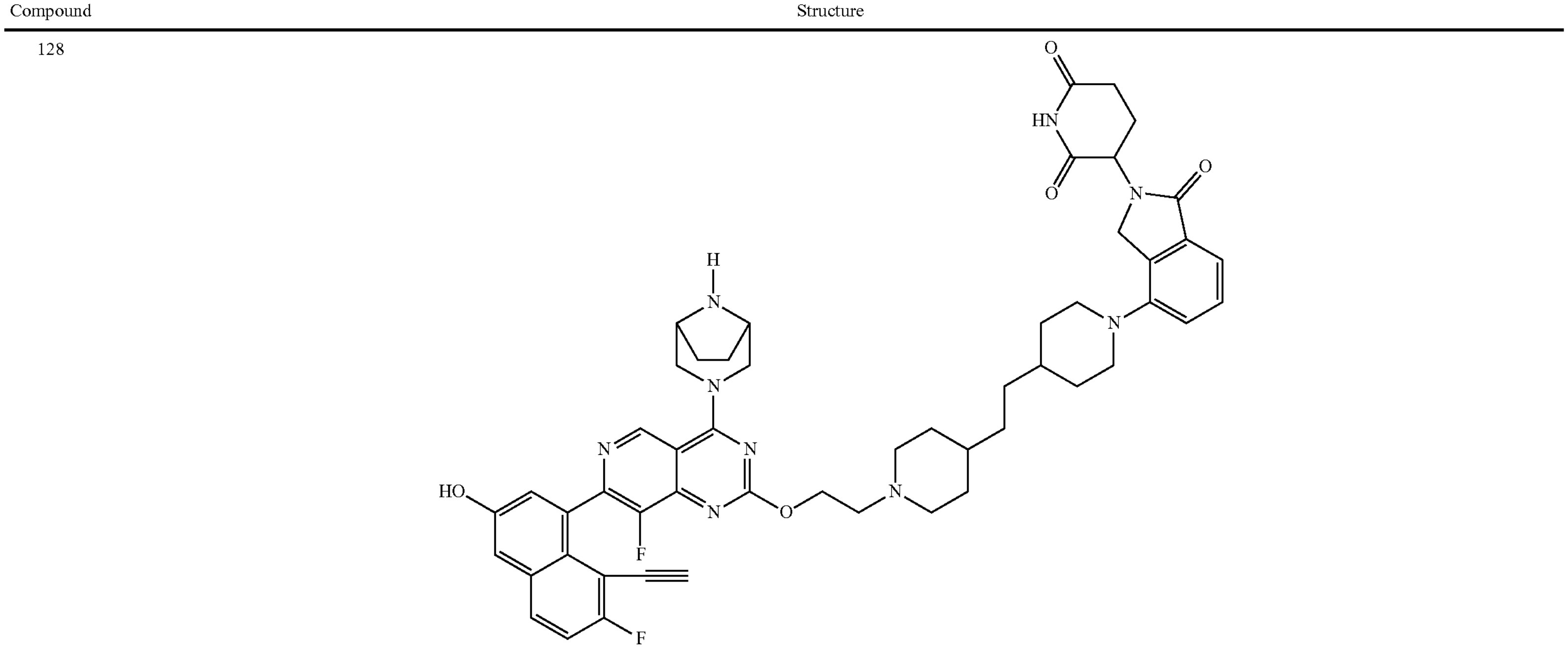 |
| 129 | 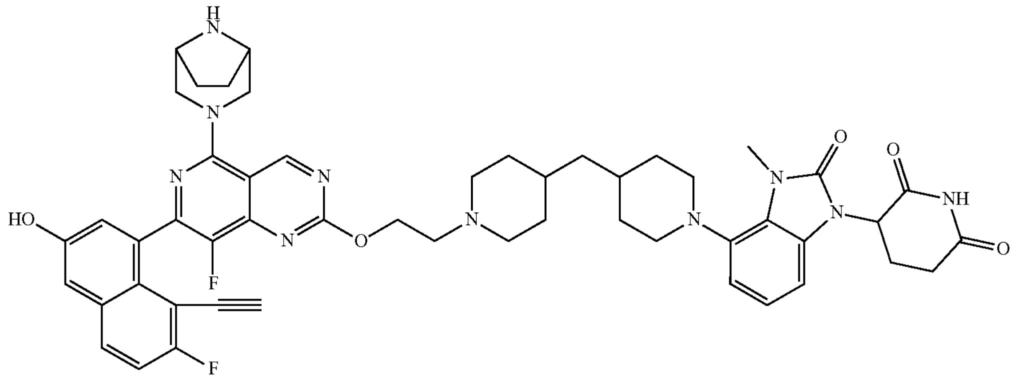 [SMILES: C#Cc1c(F)ccc2cc(O)cc(-c3nc(N4CC5CCC(C4)N5)c4cnc(OCCN5CCC(CC6CCN(c7cccc8c7n(C)c(=O)n8C7CCC(=O)NC7=O)CC6)CC5)nc4c3F)c12] |

??TABLE 1-continued
| Compound | Structure |
| --- | --- |
| 130 | 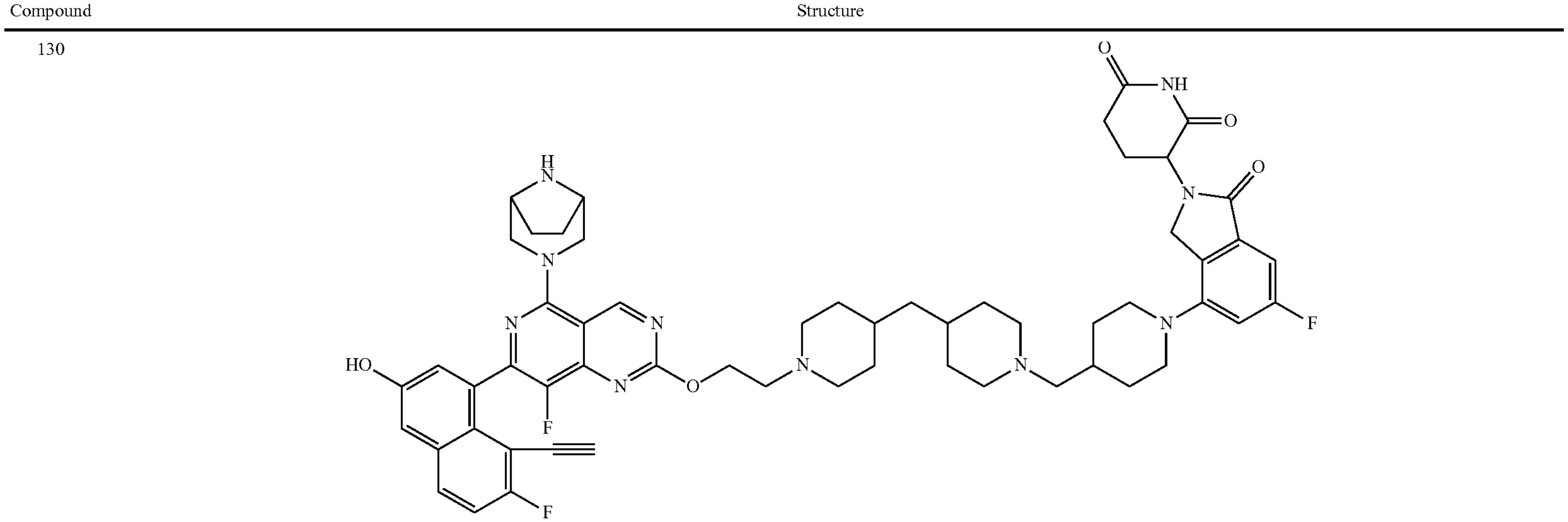 |
| 131 | 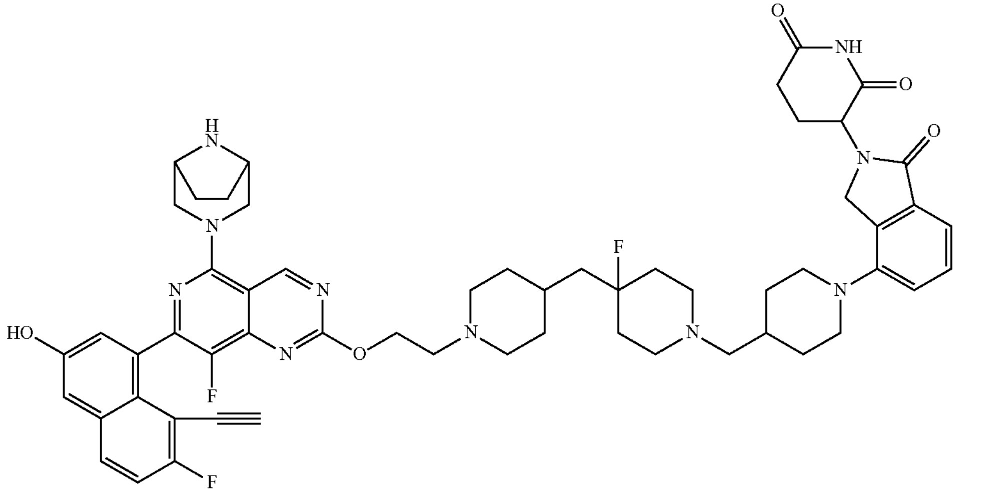 [SMILES: C#Cc1c(F)ccc2cc(O)cc(-c3nc(N4CC5CCC(C4)N5)c4cnc(OCCN5CCC(CC6(F)CCN(CC7CCN(c8cccc9c8CN(C8CCC(=O)NC8=O)C9=O)CC7)CC6)CC5)nc4c3F)c12] |

??TABLE 1-continued
| Compound | Structure |
|---|---|
| 132 | 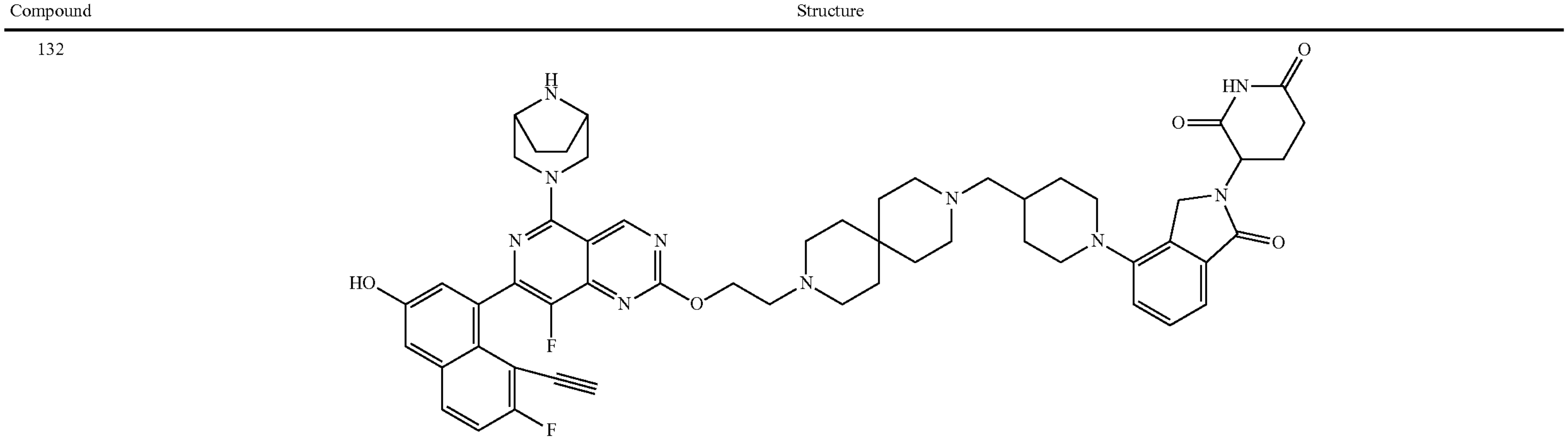 |
| 133 | 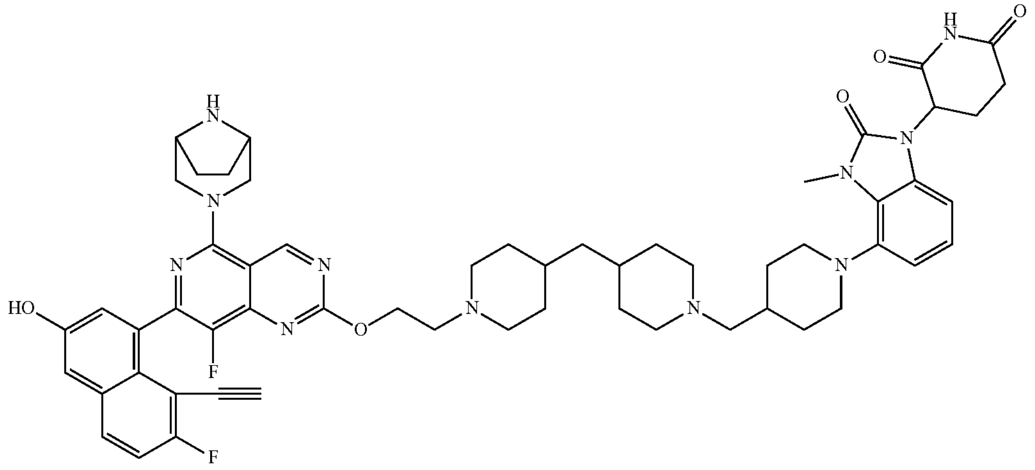 [SMILES: C#Cc1c(F)ccc2cc(O)cc(-c3nc(N4CC5CCC(C4)N5)c4cnc(OCCN5CCC(CC6CCN(CC7CCN(c8cccc9c8n(C)c(=O)n9C8CCC(=O)NC8=O)CC7)CC6)CC5)nc4c3F)c12] |

??TABLE 1-continued
| Compound | Structure |
| --- | --- |
| 134 | 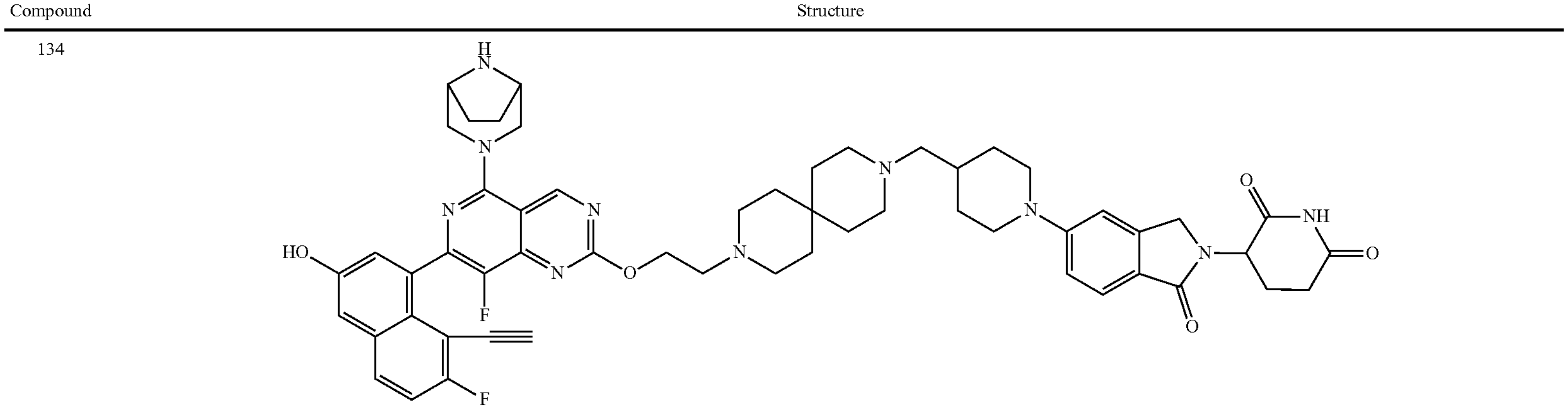 |
| 135 | 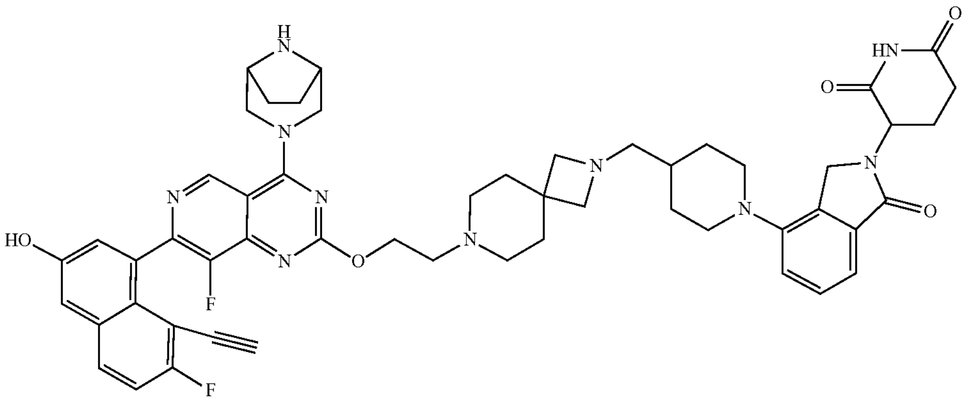 [SMILES: C#Cc1c(F)ccc2cc(O)cc(-c3ncc4c(N5CC6CCC(C5)N6)nc(OCCN5CCC6(CC5)CN(CC5CCN(c7cccc8c7CN(C7CCC(=O)NC7=O)C8=O)CC5)C6)nc4c3F)c12] |

??TABLE 1-continued
| Compound | Structure |
| --- | --- |
| 136 | 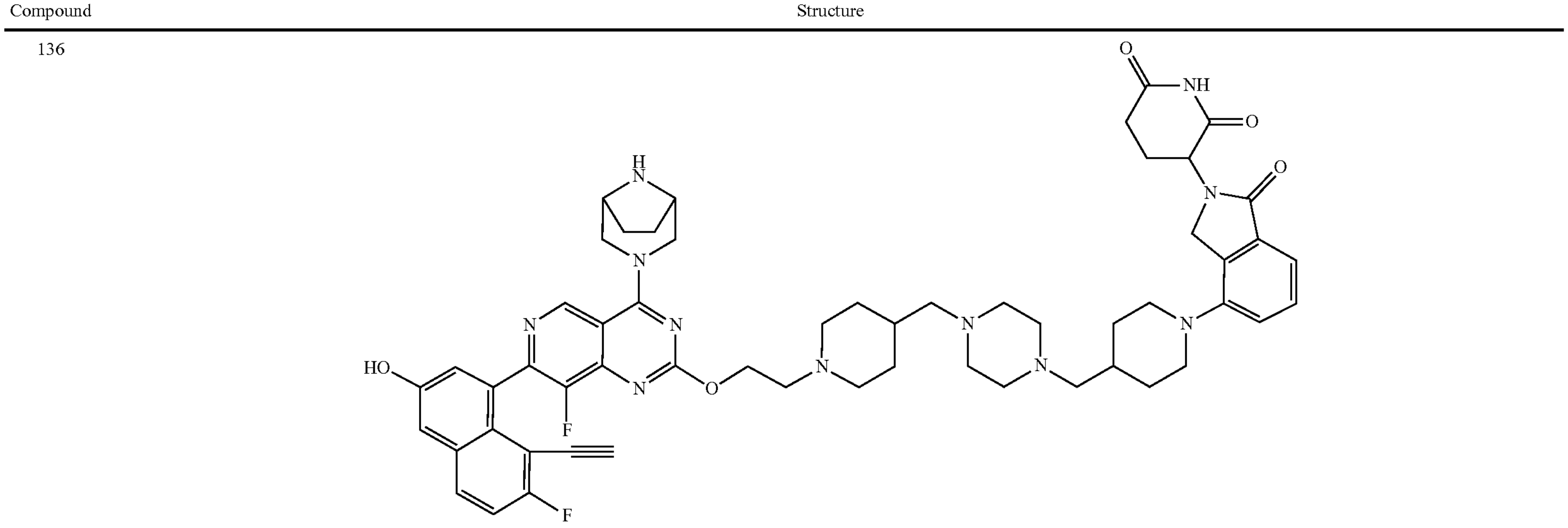 |
| 137 | 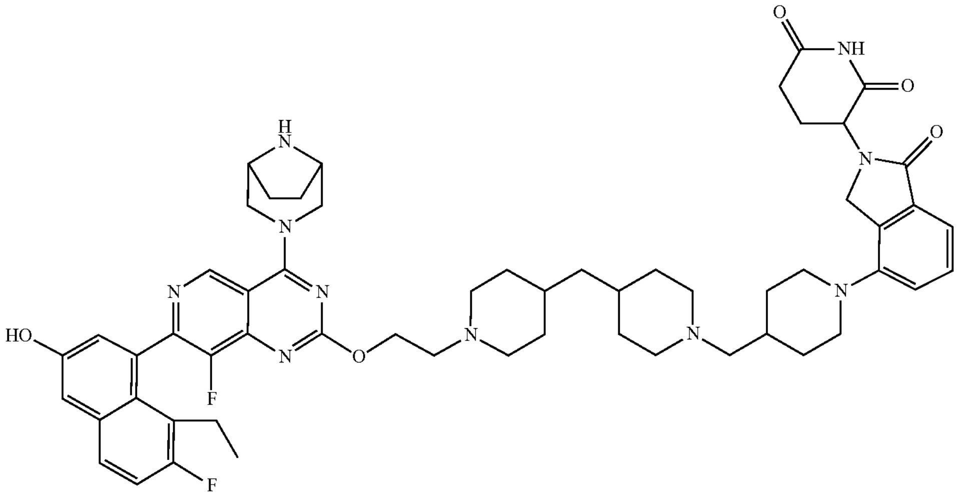 [SMILES: CCc1c(F)ccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12] |

??TABLE 1-continued
| Compound | Structure |
| --- | --- |
| 138 | 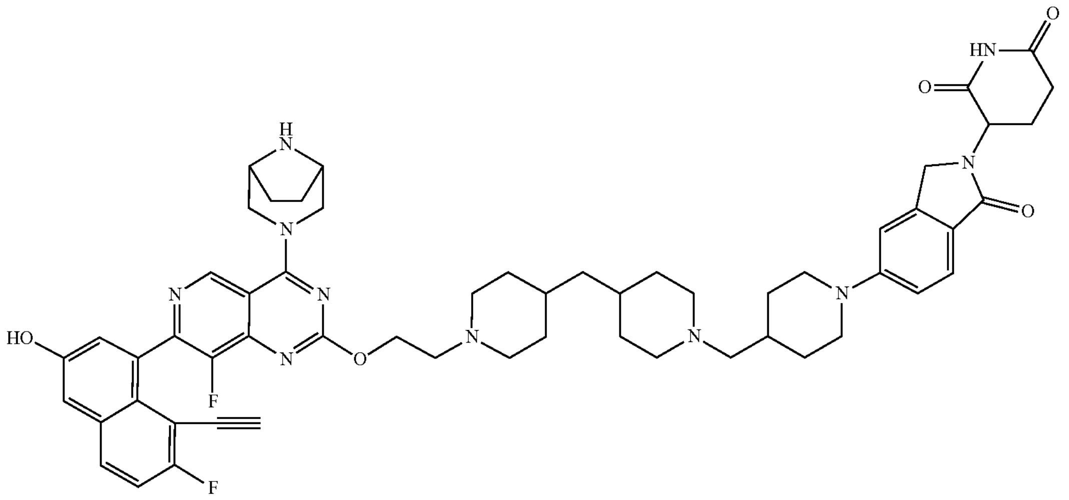 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)CN(C8CCC(=O)NC8=O)C9=O)CC7)CC6)CC5)nc4c3F)c12] |
| 139 | 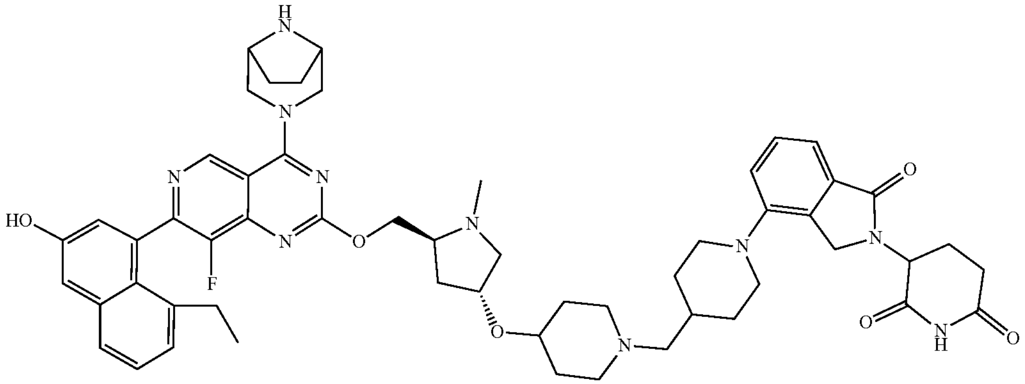 [SMILES: CCc1cccc2cc(O)cc(-c3ncc4c(N5CC6CCC(C5)N6)nc(OC[C@@H]5C[C@@H](OC6CCN(CC7CCN(c8cccc9c8CN(C8CCC(=O)NC8=O)C9=O)CC7)CC6)CN5C)nc4c3F)c12] |

??TABLE 1-continued
| Compound | Structure |
| --- | --- |
| 140 | 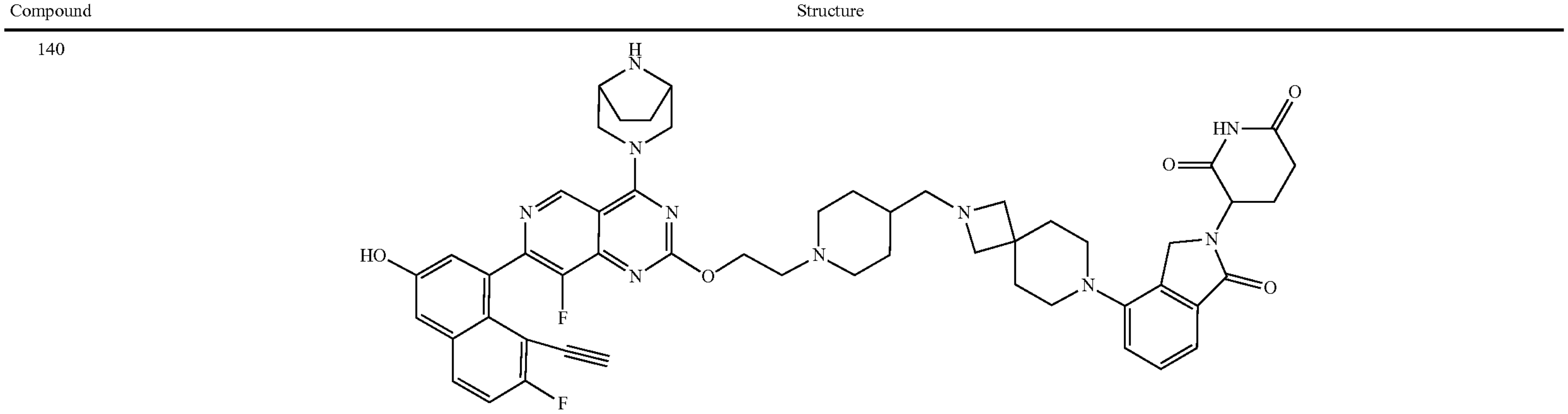 |
| 141 | 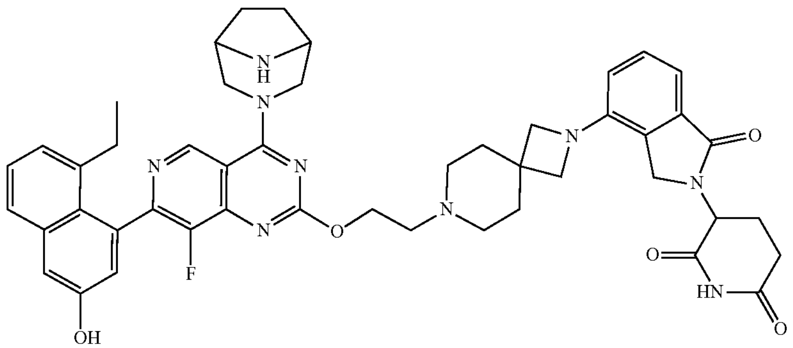 [SMILES: CCc1cccc2cc(O)cc(-c3ncc4c(N5CC6CCC(C5)N6)nc(OCCN5CCC6(CC5)CN(c5cccc7c5CN(C5CCC(=O)NC5=O)C7=O)C6)nc4c3F)c12] |

??TABLE 1-continued
| Compound | Structure |
|---|---|
| 142 | 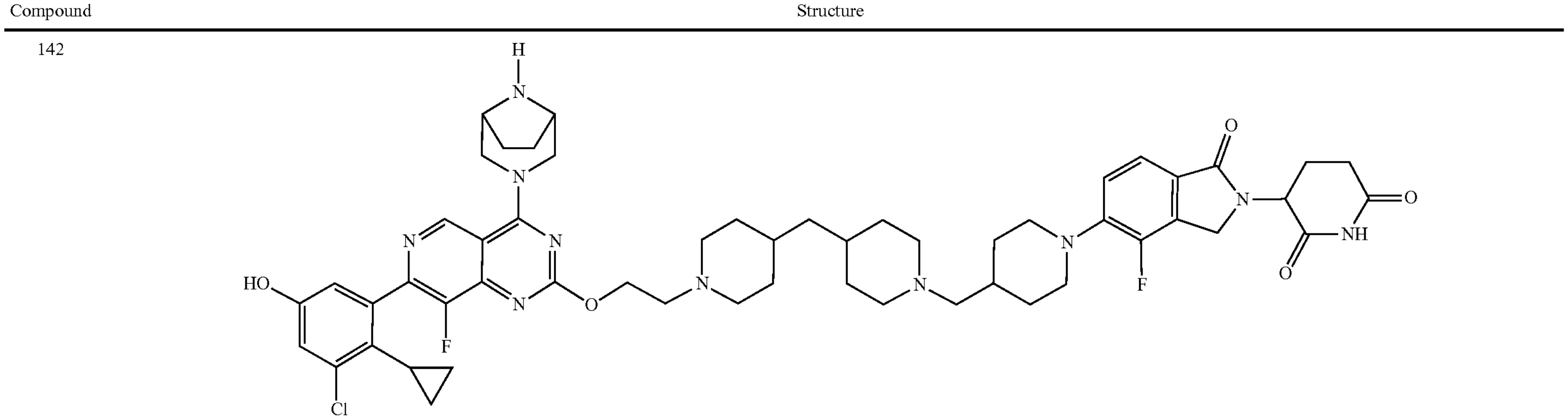 |
| 143 | 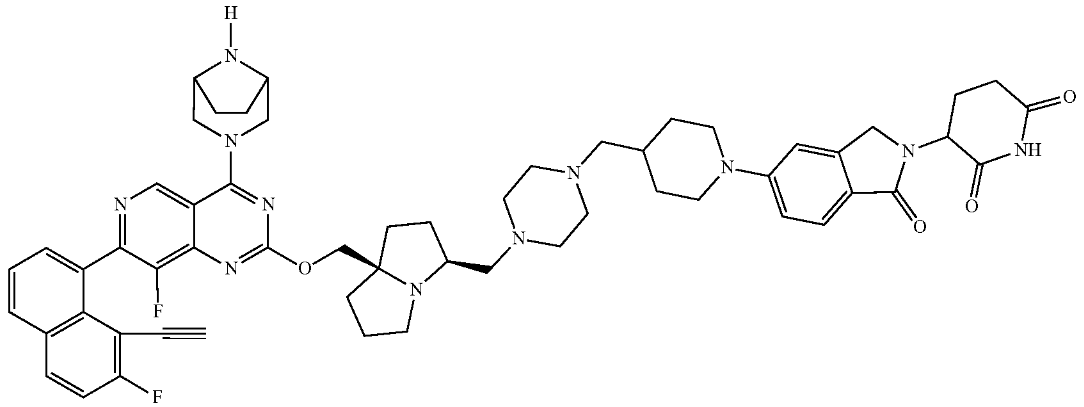 [SMILES: C#Cc1c(F)ccc2cccc(-c3ncc4c(N5CC6CCC(C5)N6)nc(OC[C@]56CCCN5[C@H](CN5CCN(CC7CCN(c8ccc9c(c8)CN(C8CCC(=O)NC8=O)C9=O)CC7)CC5)CC6)nc4c3F)c12] |

??TABLE 1-continued
| Compound | Structure |
|---|---|
| 144 | 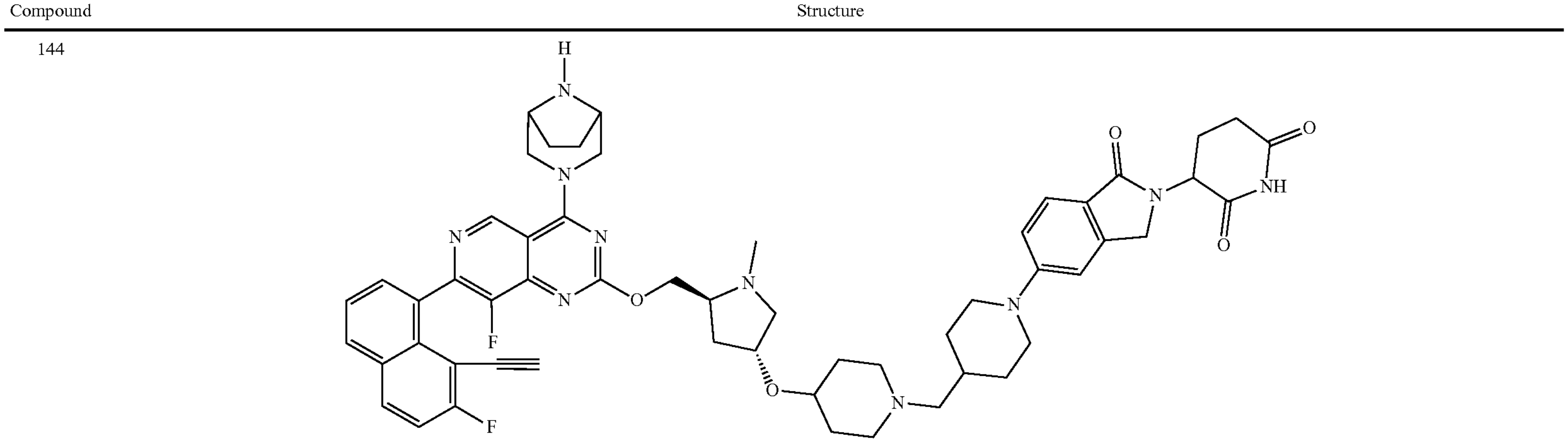 |
| 145 | 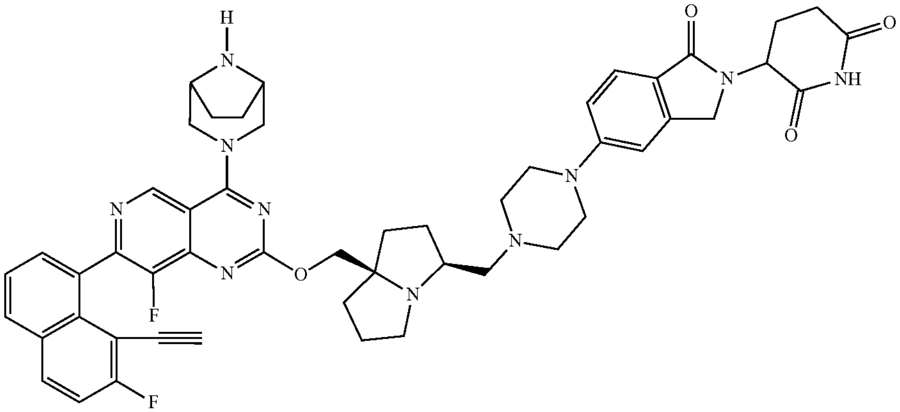 [SMILES: C#Cc1c(F)ccc2cccc(-c3ncc4c(N5CC6CCC(C5)N6)nc(OC[C@]56CCCN5[C@H](CN5CCN(c7ccc8c(c7)CN(C7CCC(=O)NC7=O)C8=O)CC5)CC6)nc4c3F)c12] |

??TABLE 1-continued
| Compound | Structure |
|---|---|
| 146 | 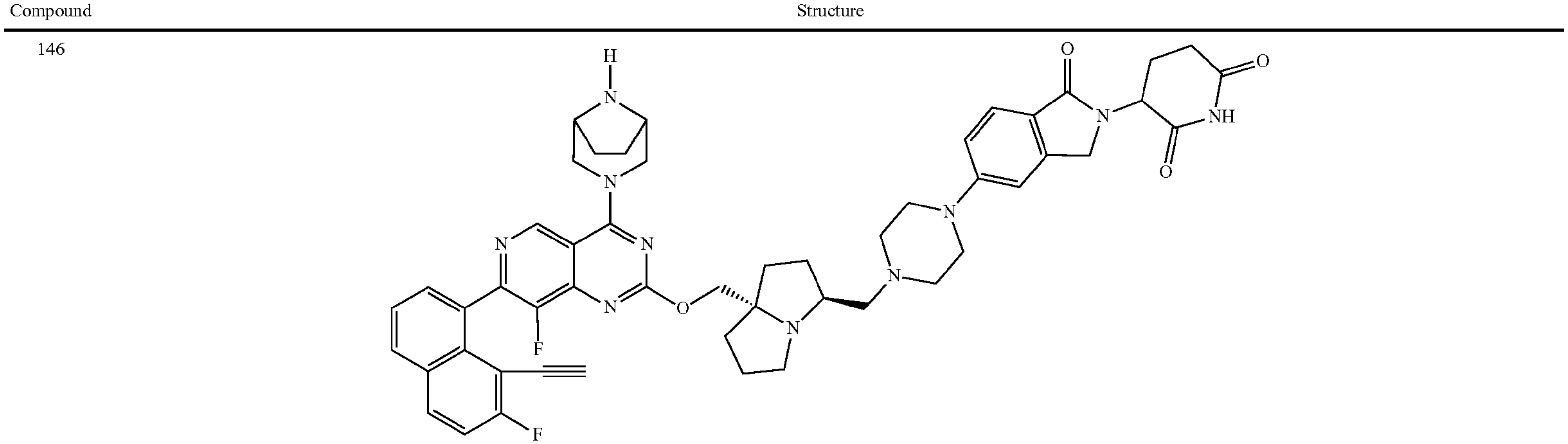 |
| 147 | 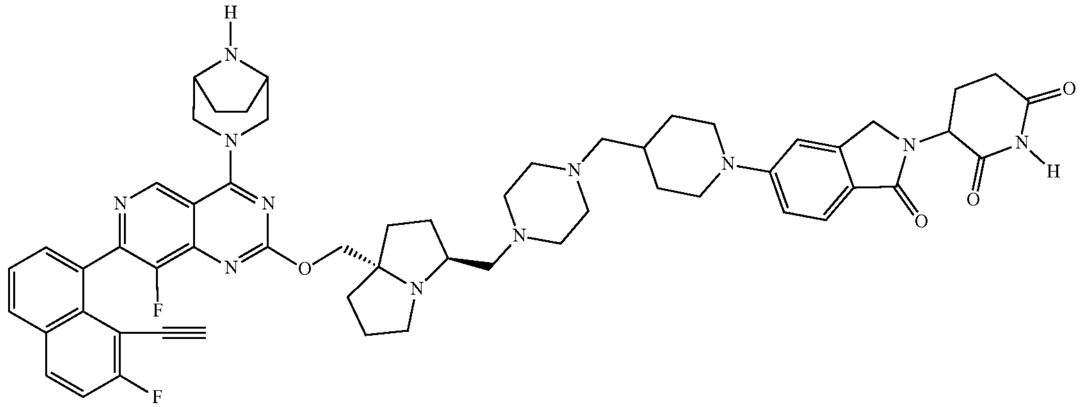 [SMILES: C#Cc1c(F)ccc2cccc(-c3ncc4c(N5CC6CCC(C5)N6)nc(OC[C@@]56CCCN5[C@H](CN5CCN(CC7CCN(c8ccc9c(c8)CN(C8CCC(=O)NC8=O)C9=O)CC7)CC5)CC6)nc4c3F)c12] |

??TABLE 1-continued
| Compound | Structure |
|---|---|
| 148 | 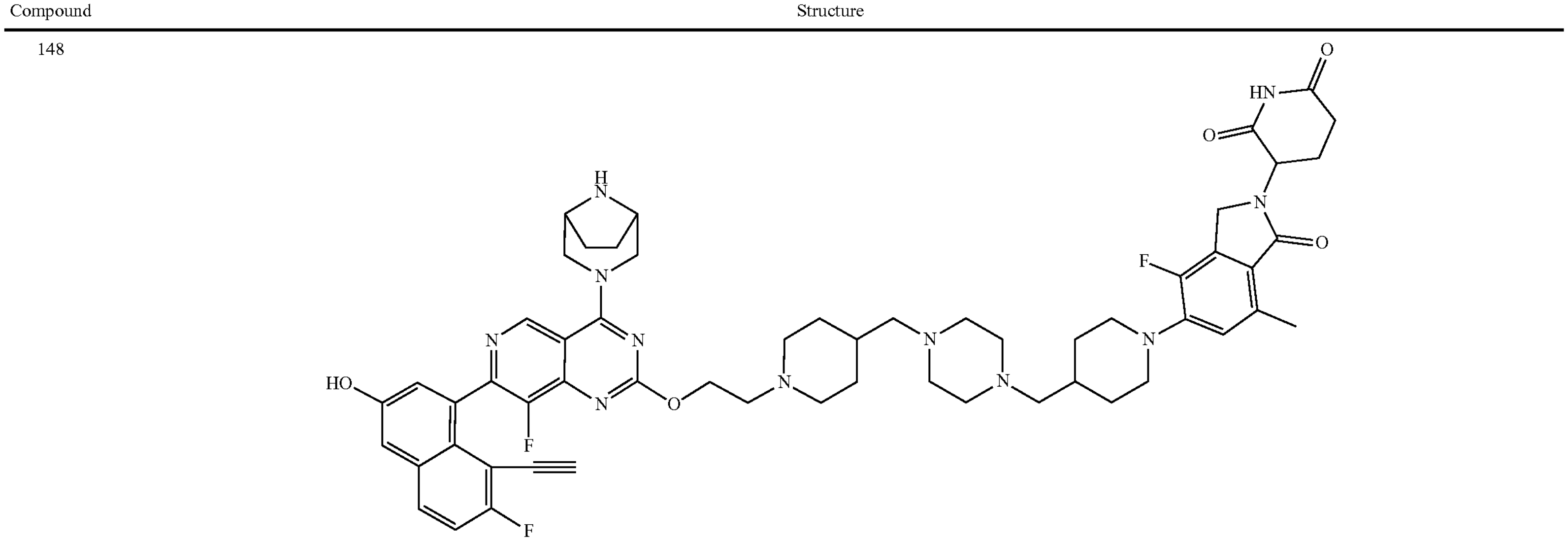 |
| 149 | 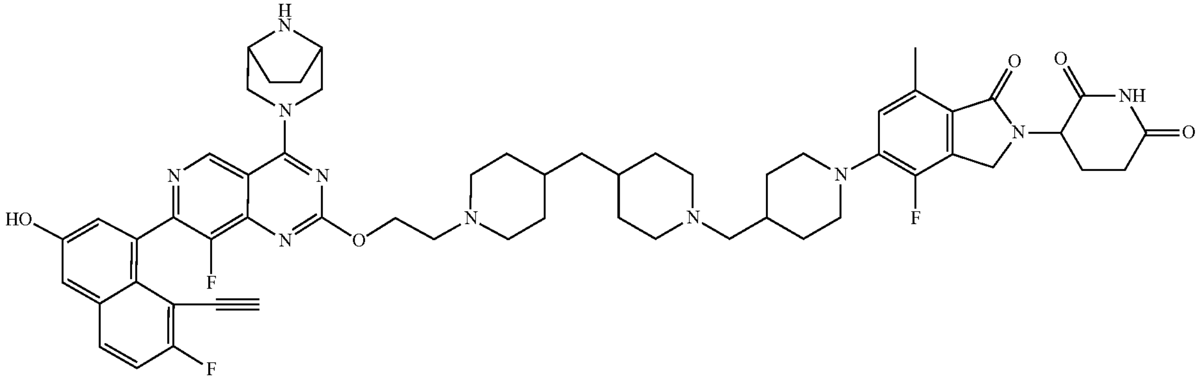 [SMILES: C#Cc1c(F)ccc2cc(O)cc(-c3ncc4c(N5CC6CCC(C5)N6)nc(OCCN5CCC(CC6CCN(CC7CCN(c8cc(C)c9c(c8F)CN(C8CCC(=O)NC8=O)C9=O)CC7)CC6)CC5)nc4c3F)c12] |

??TABLE 1-continued
| Compound | Structure |
| --- | --- |
| 150 | 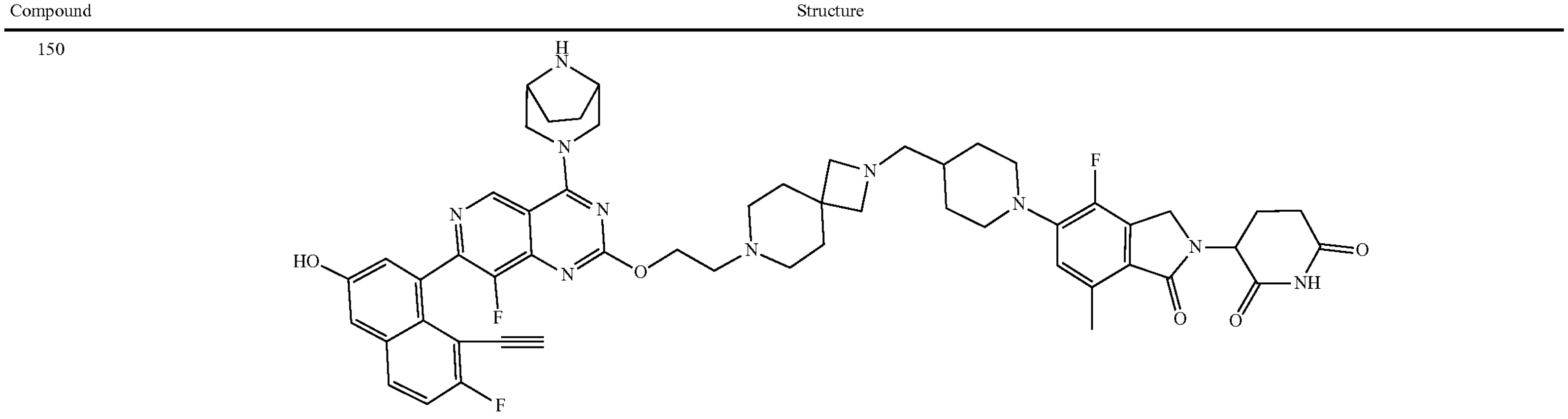 |
| 151 | 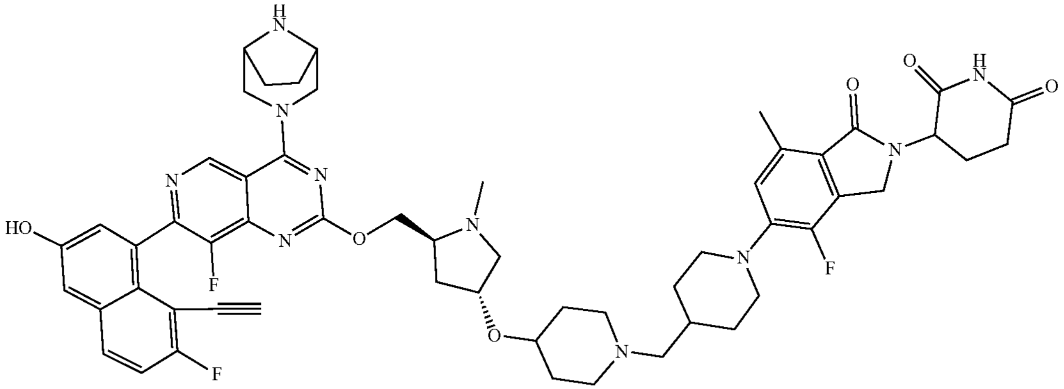 [SMILES: C#Cc1c(F)ccc2cc(O)cc(-c3ncc4c(N5CC6CCC(C5)N6)nc(OC[C@@H]5C[C@@H](OC6CCN(CC7CCN(c8cc(C)c9c(c8F)CN(C8CCC(=O)NC8=O)C9=O)CC7)CC6)CN5C)nc4c3F)c12] |

??TABLE 1-continued
| Compound | Structure |
|---|---|
| 152 | 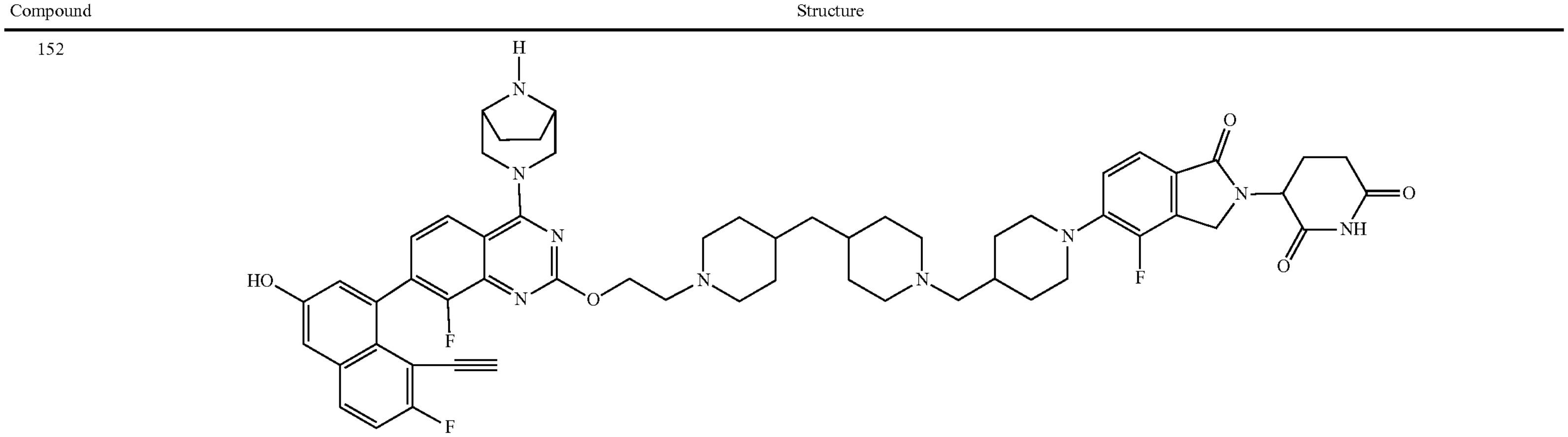 |
| 153 | 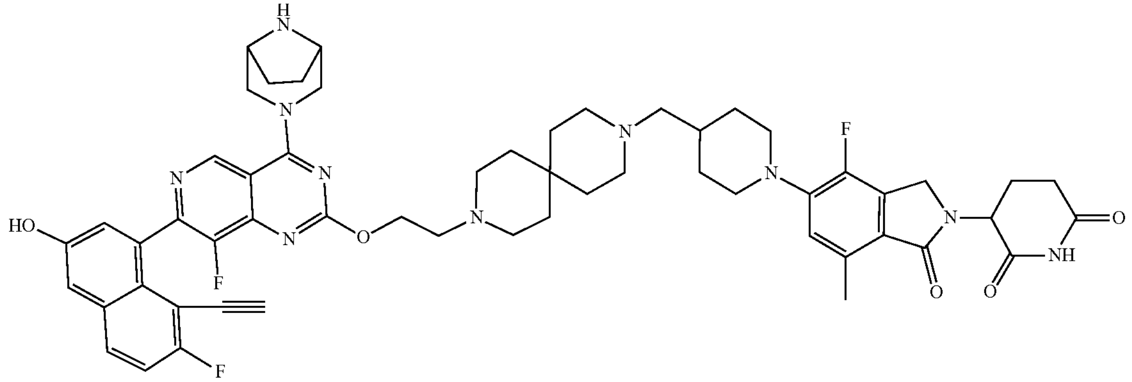 [SMILES: C#Cc1c(F)ccc2cc(O)cc(-c3ncc4c(N5CC6CCC(C5)N6)nc(OCCN5CCC6(CC5)CCN(CC5CCN(c7cc(C)c8c(c7F)CN(C7CCC(=O)NC7=O)C8=O)CC5)CC6)nc4c3F)c12] |

??TABLE 1-continued
| Compound | Structure |
| --- | --- |
| 154 | 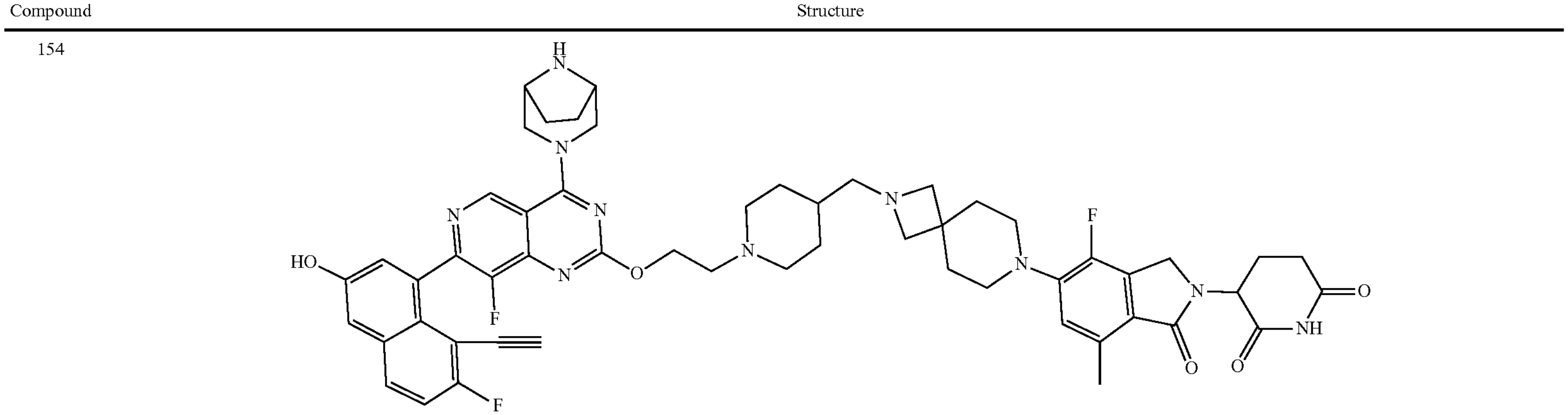 |
| 155 | 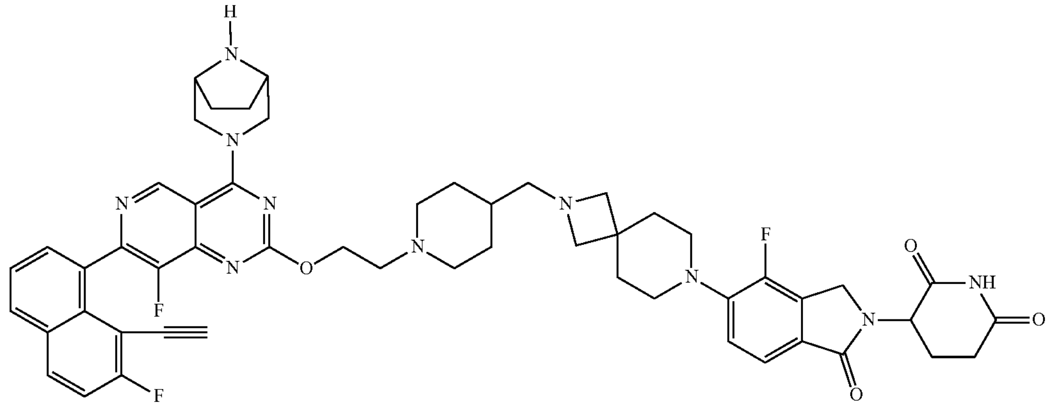 [SMILES: C#Cc1c(F)ccc2cccc(-c3ncc4c(N5CC6CCC(C5)N6)nc(OCCN5CCC(CN6CC7(CCN(c8ccc9c(c8F)CN(C8CCC(=O)NC8=O)C9=O)CC7)C6)CC5)nc4c3F)c12] |

??TABLE 1-continued
| Compound | Structure |
|---|---|
| 156 | 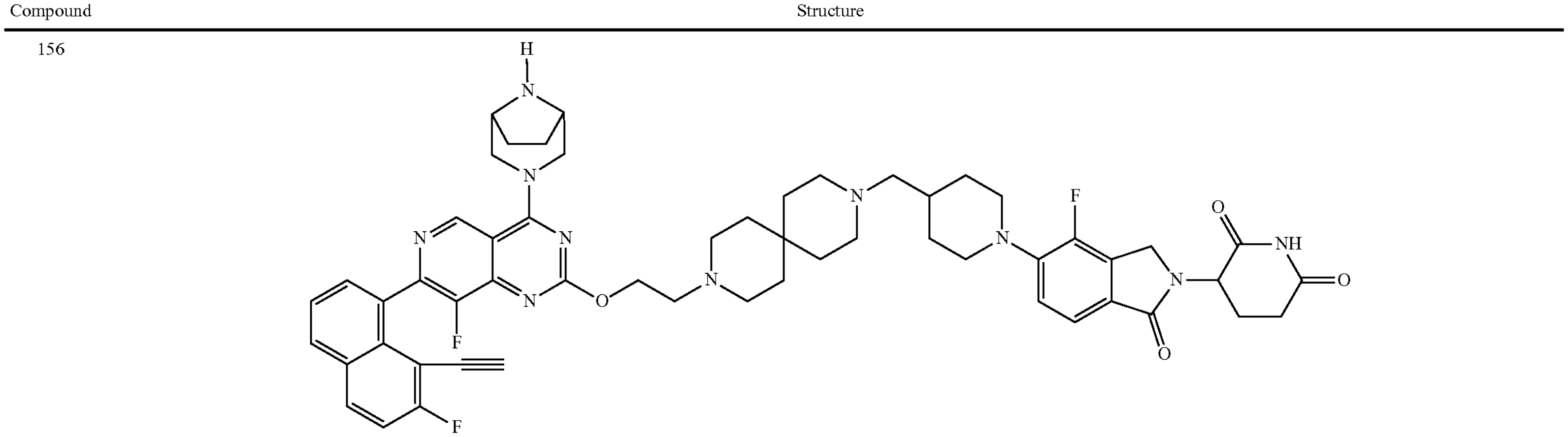 |
| 157 | 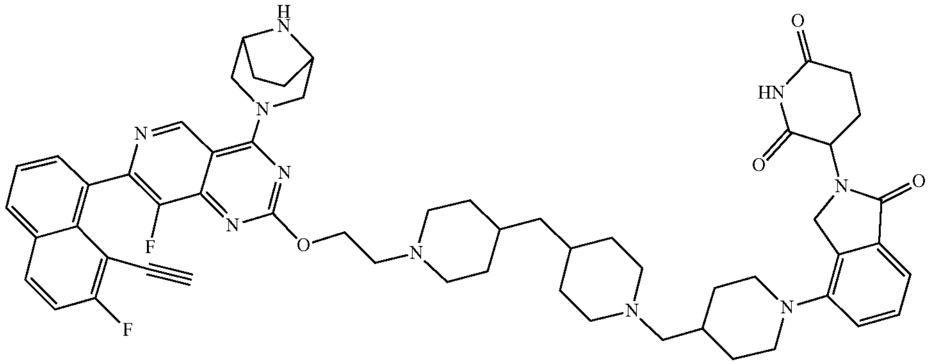 [SMILES: C#Cc1c(F)ccc2cccc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12] |

??TABLE 1-continued
| Compound | Structure |
| --- | --- |
| 158 | 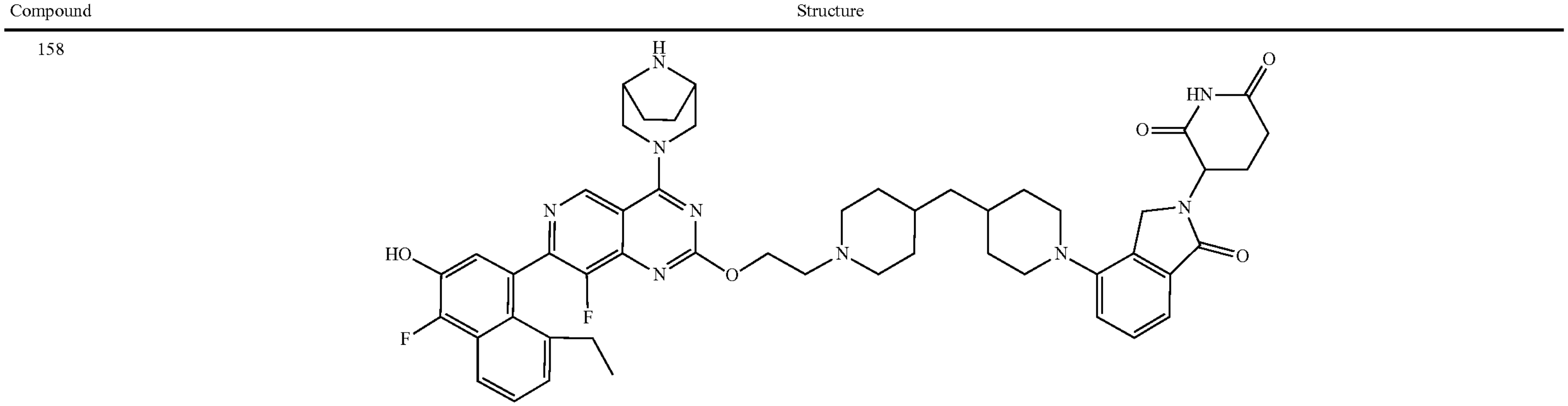 |
| 159 | 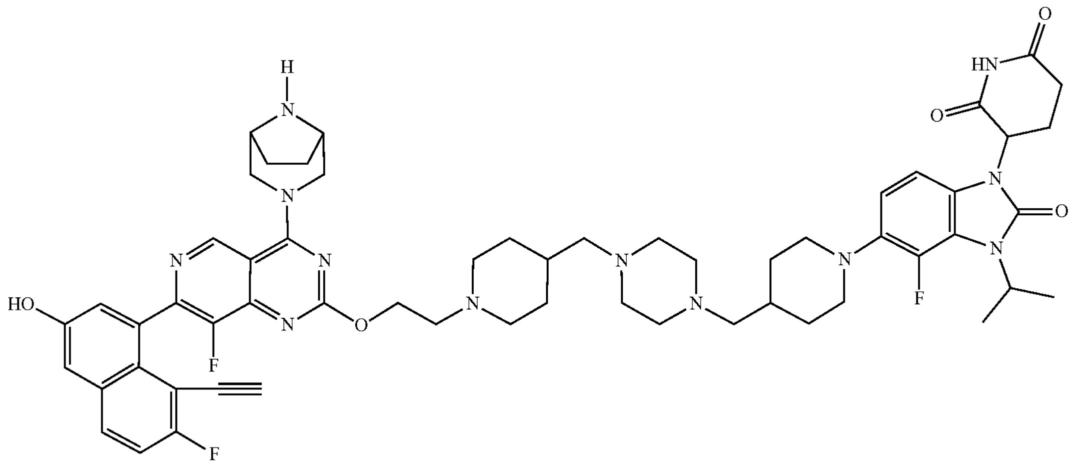 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)n(C(C)C)c(=O)n9C8CCC(=O)NC8=O)CC7)CC6)CC5)nc4c3F)c12] |

??TABLE 1-continued
| Compound | Structure |
| --- | --- |
| 160 | 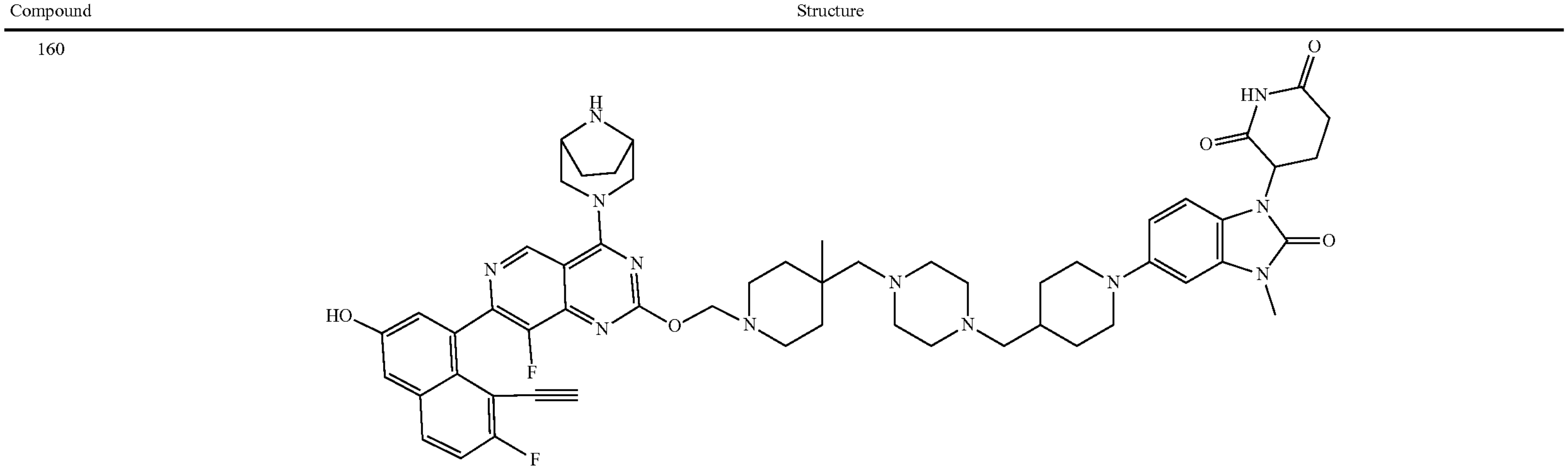 |
| 161 | 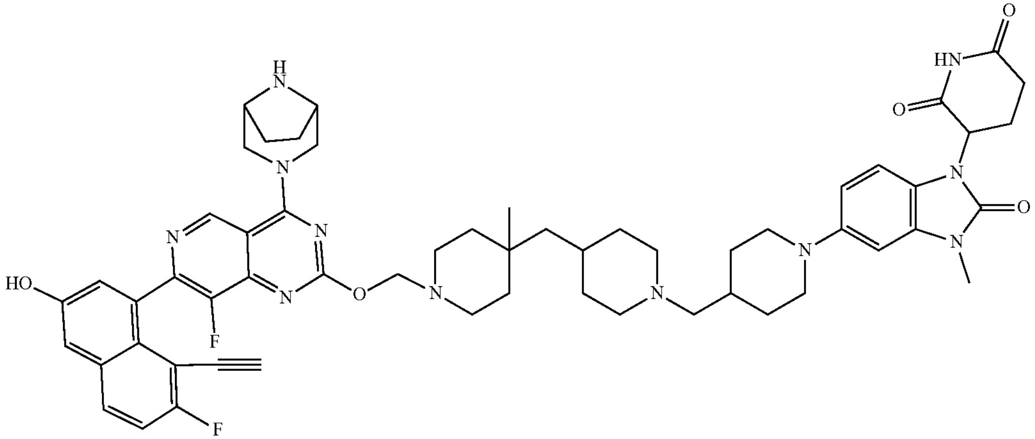 [SMILES: C#Cc1c(F)ccc2cc(O)cc(-c3ncc4c(N5CC6CCC(C5)N6)nc(OCN5CCC(C)(CC6CCN(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
|---|---|
| 162 | 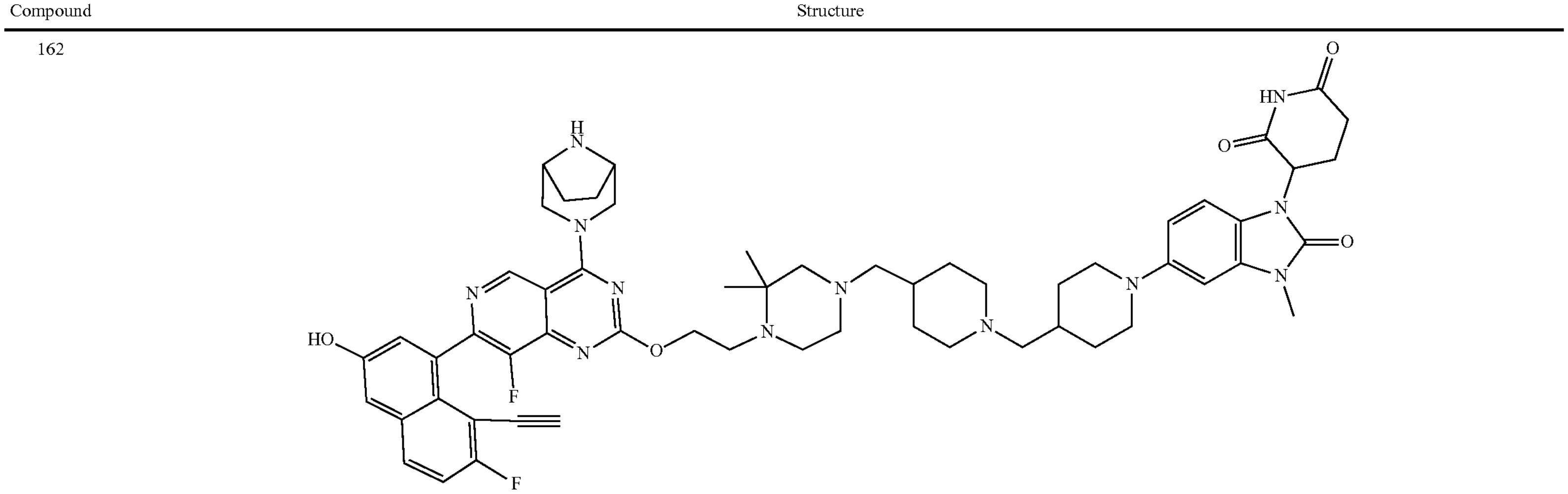 |
| 163 | 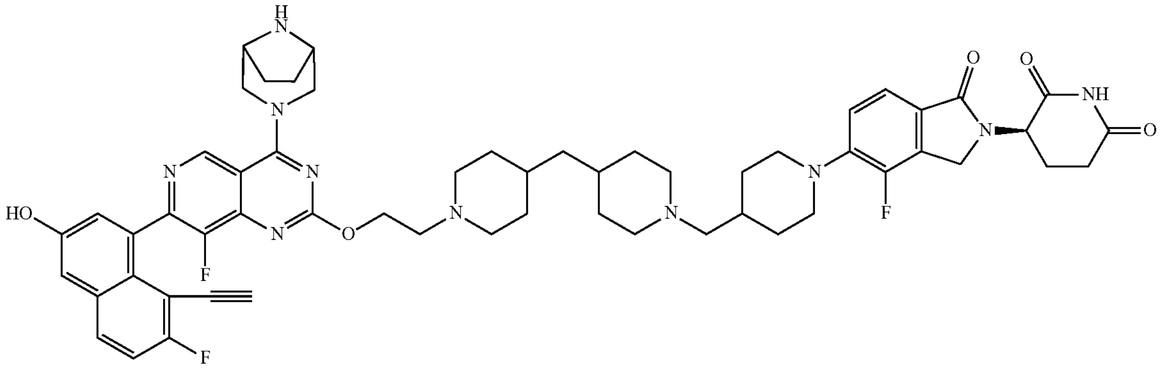 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)CN([C@@H]8CCC(=O)NC8=O)C9=O)CC7)CC6)CC5)nc4c3F)c12] |

??TABLE 1-continued
| Compound | Structure |
|---|---|
| 164 | 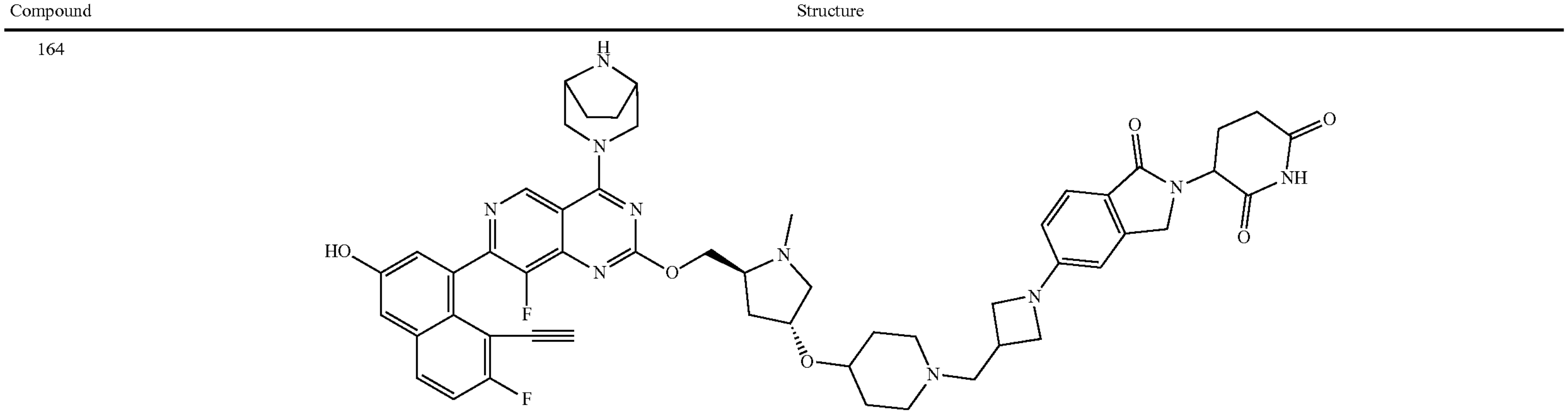 |
| 165 | 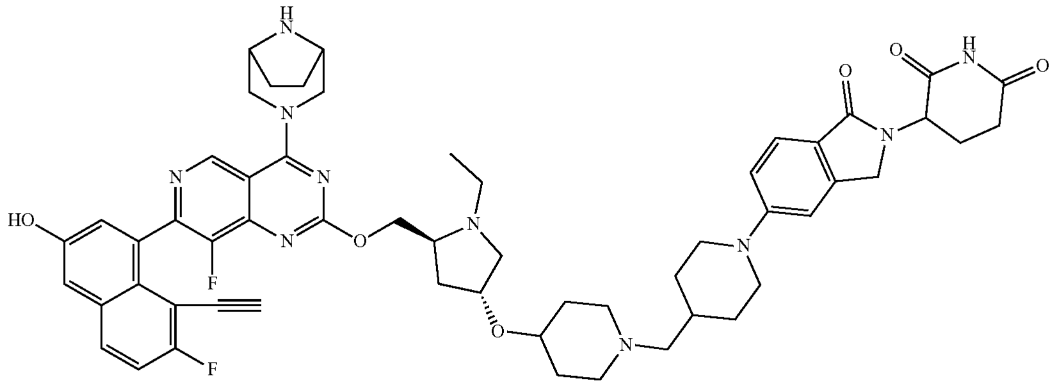 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8)CN(C8CCC(=O)NC8=O)C9=O)CC7)CC6)CN5CC)nc4c3F)c12] |

??TABLE 1-continued
| Compound | Structure |
| --- | --- |
| 166 | 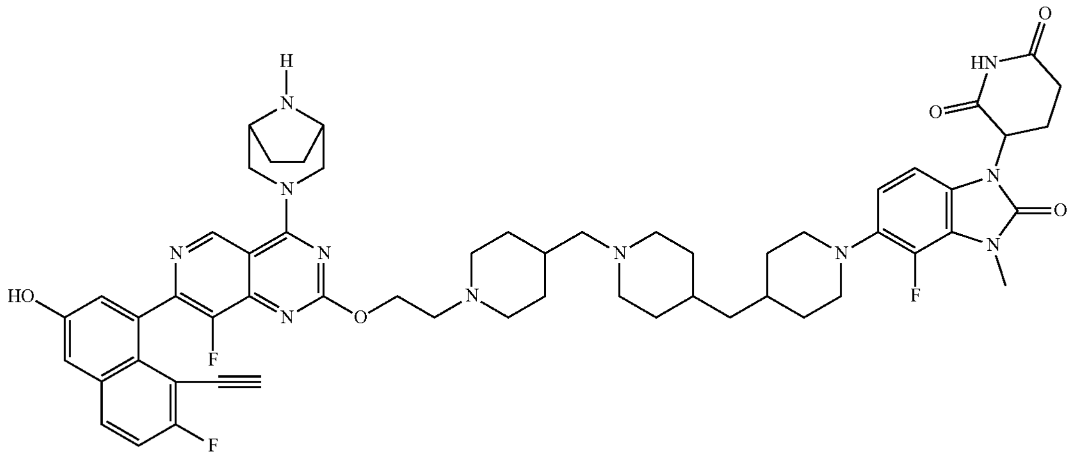 [SMILES: C#Cc1c(F)ccc2cc(O)cc(-c3ncc4c(N5CC6CCC(C5)N6)nc(OCCN5CCC(CN6CCC(CC7CCN(c8ccc9c(c8F)n(C)c(=O)n9C8CCC(=O)NC8=O)CC7)CC6)CC5)nc4c3F)c12] |
| 167 | 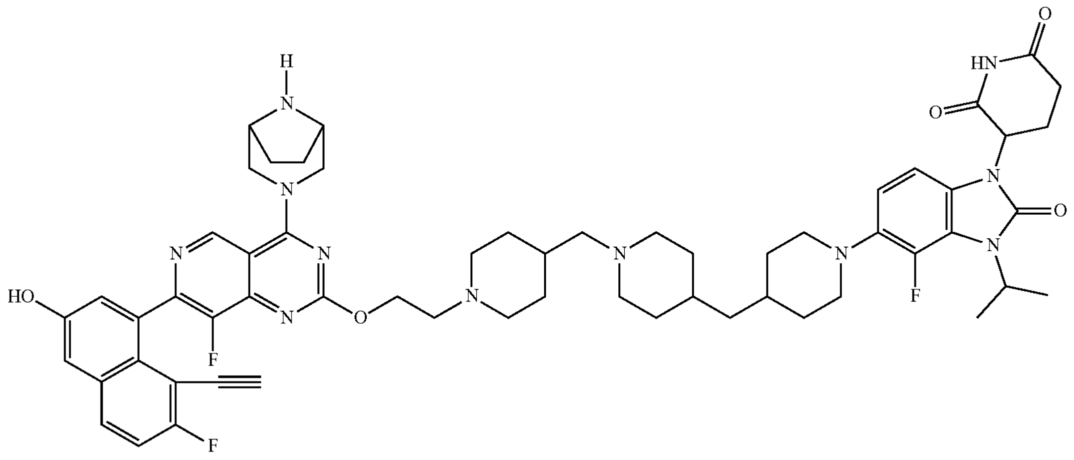 |

??TABLE 1-continued
| Compound | Structure |
| --- | --- |
| 168 | 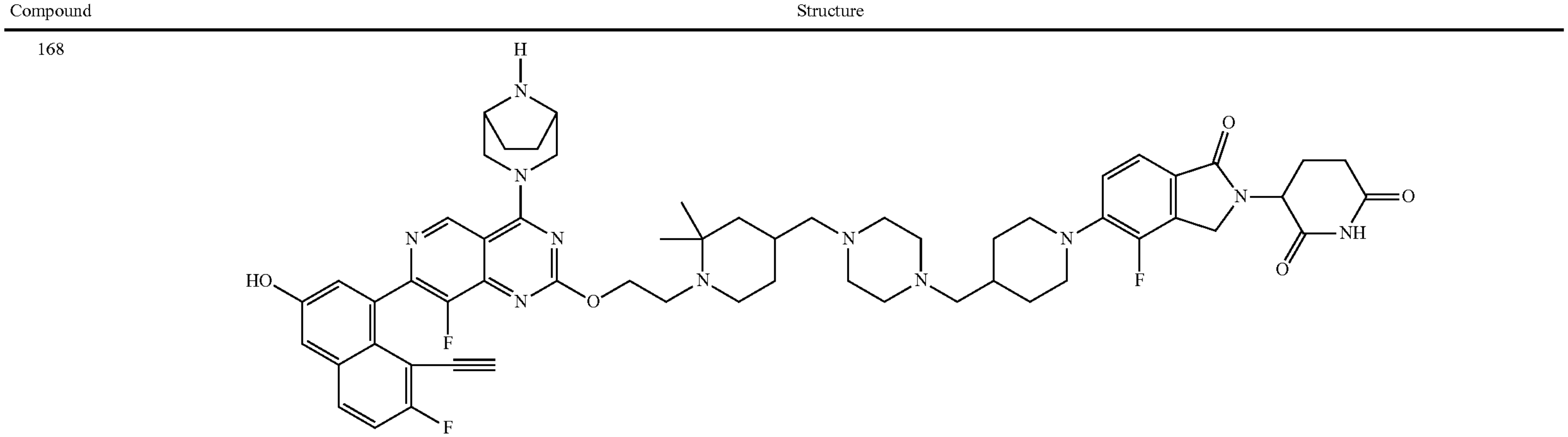 |
| 169 | 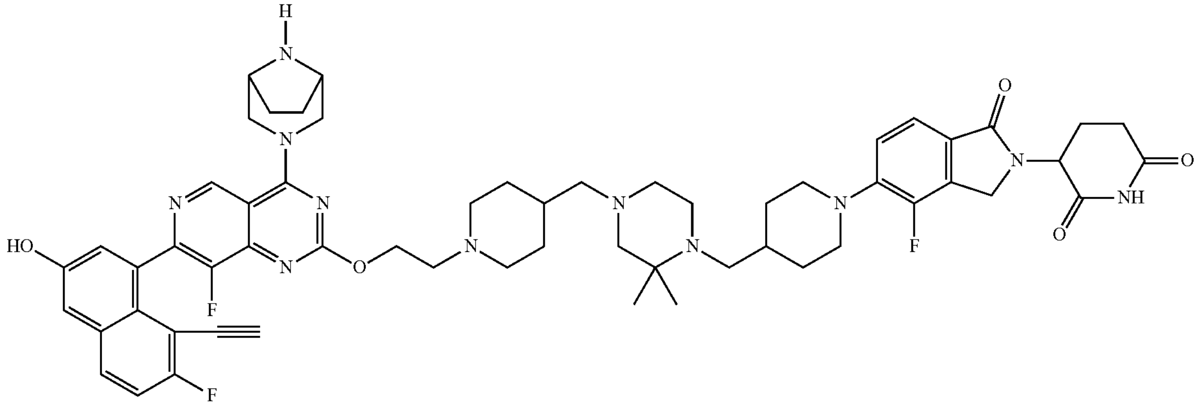 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)C(C)(C)C6)CC5)nc4c3F)c12] |

??TABLE 1-continued
| Compound | Structure |
| --- | --- |
| 170 | 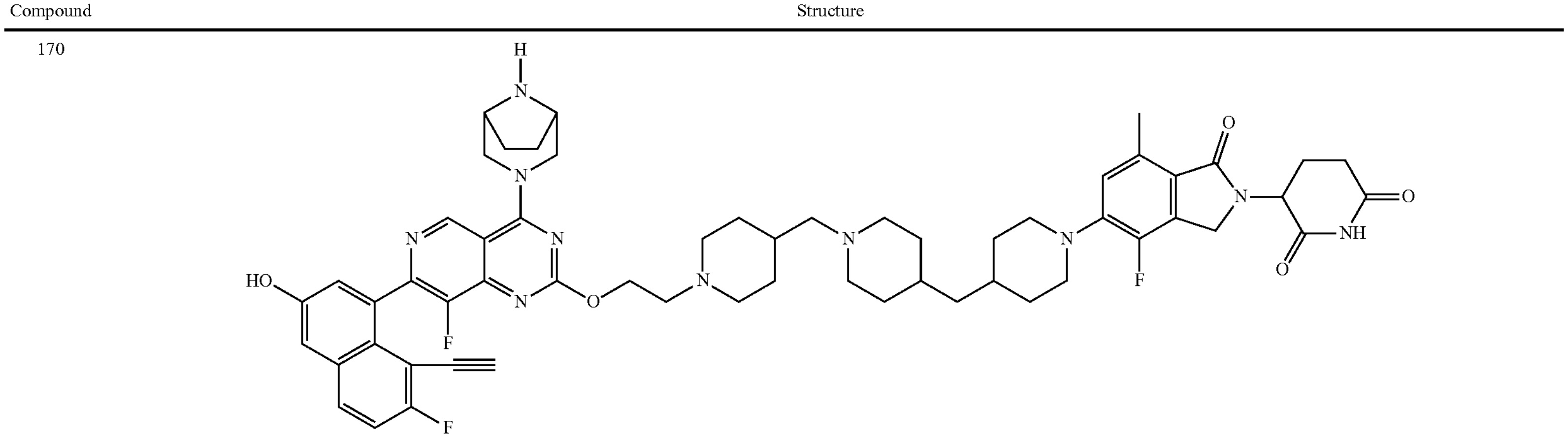 |
| 171 | 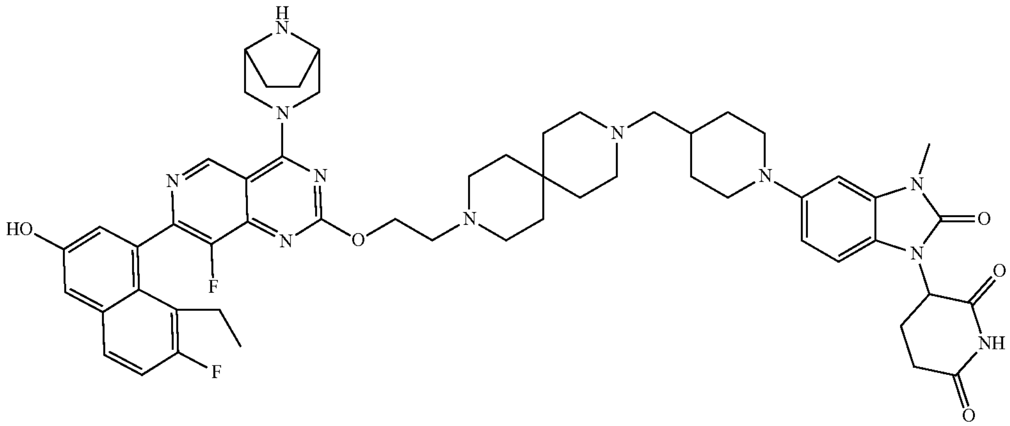 [SMILES: CCc1c(F)ccc2cc(O)cc(-c3ncc4c(N5CC6CCC(C5)N6)nc(OCCN5CCC6(CC5)CCN(CC5CCN(c7ccc8c(c7)n(C)c(=O)n8C7CCC(=O)NC7=O)CC5)CC6)nc4c3F)c12] |

??TABLE 1-continued
| Compound | Structure |
| --- | --- |
| 172 | 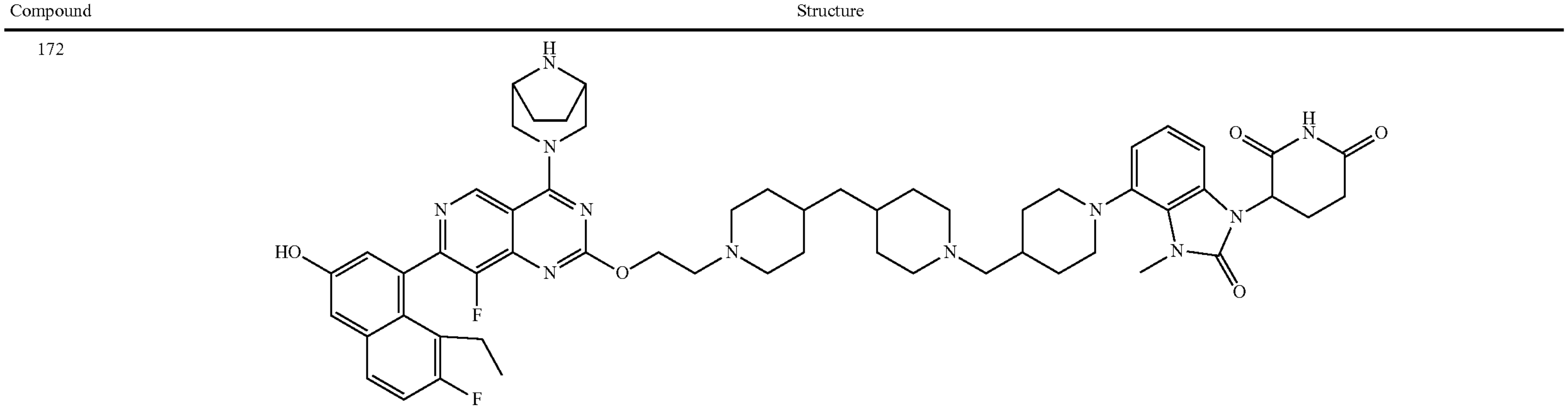 |
| 173 | 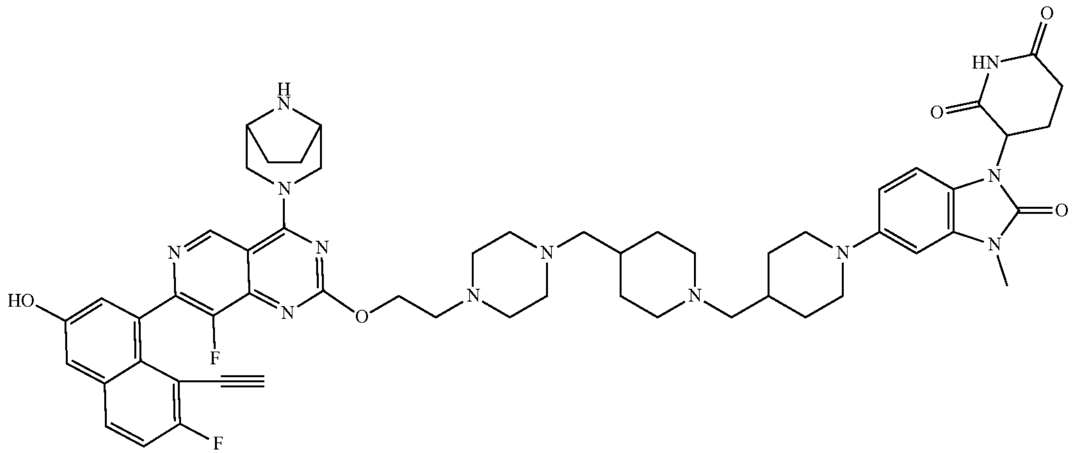 [SMILES: C#Cc1c(F)ccc2cc(O)cc(-c3ncc4c(N5CC6CCC(C5)N6)nc(OCCN5CCN(CC6CCN(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
|---|---|
| 174 | 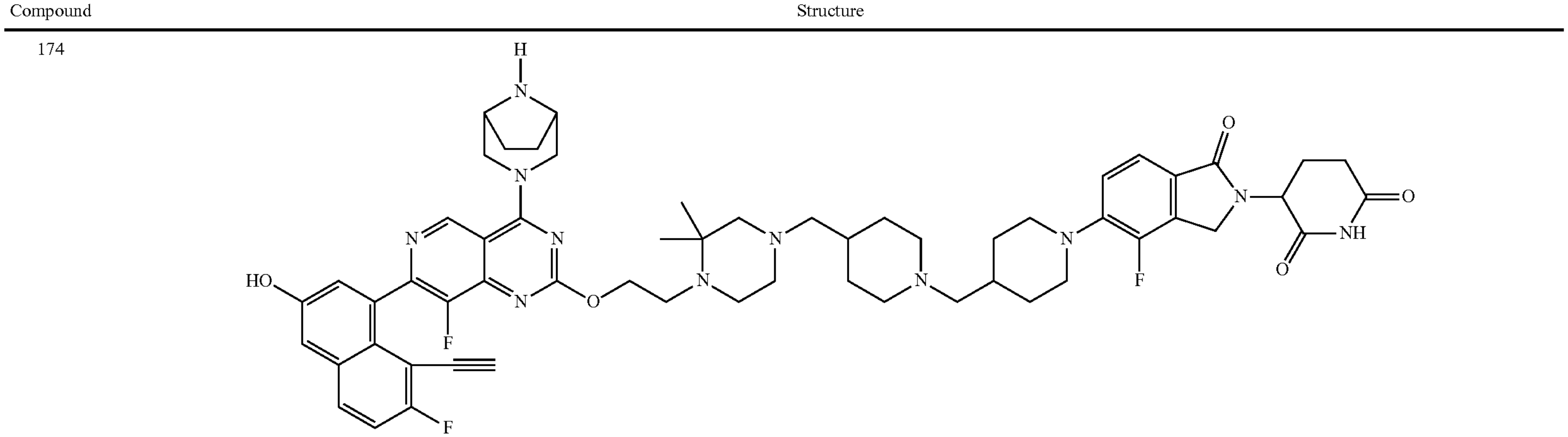 |
| 175 | 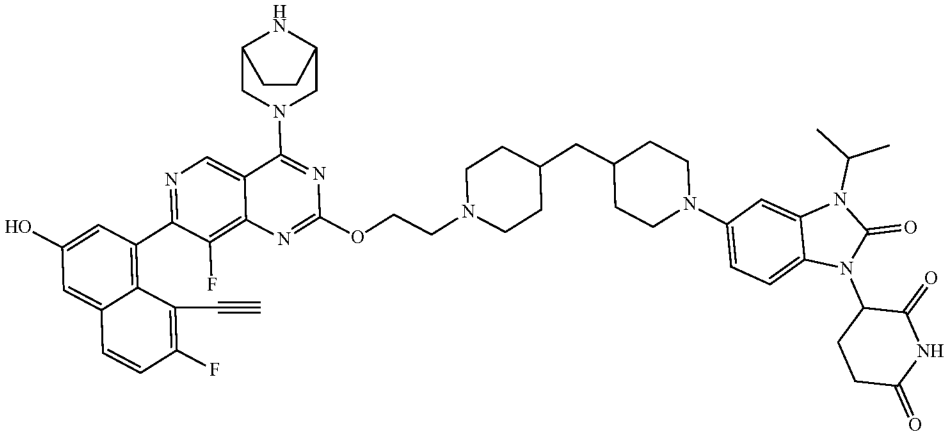 [SMILES: C#Cc1c(F)ccc2cc(O)cc(-c3ncc4c(N5CC6CCC(C5)N6)nc(OCCN5CCC(CC6CCN(c7ccc8c(c7)n(C(C)C)c(=O)n8C7CCC(=O)NC7=O)CC6)CC5)nc4c3F)c12] |

??TABLE 1-continued
| Compound | Structure |
| --- | --- |
| 176 | 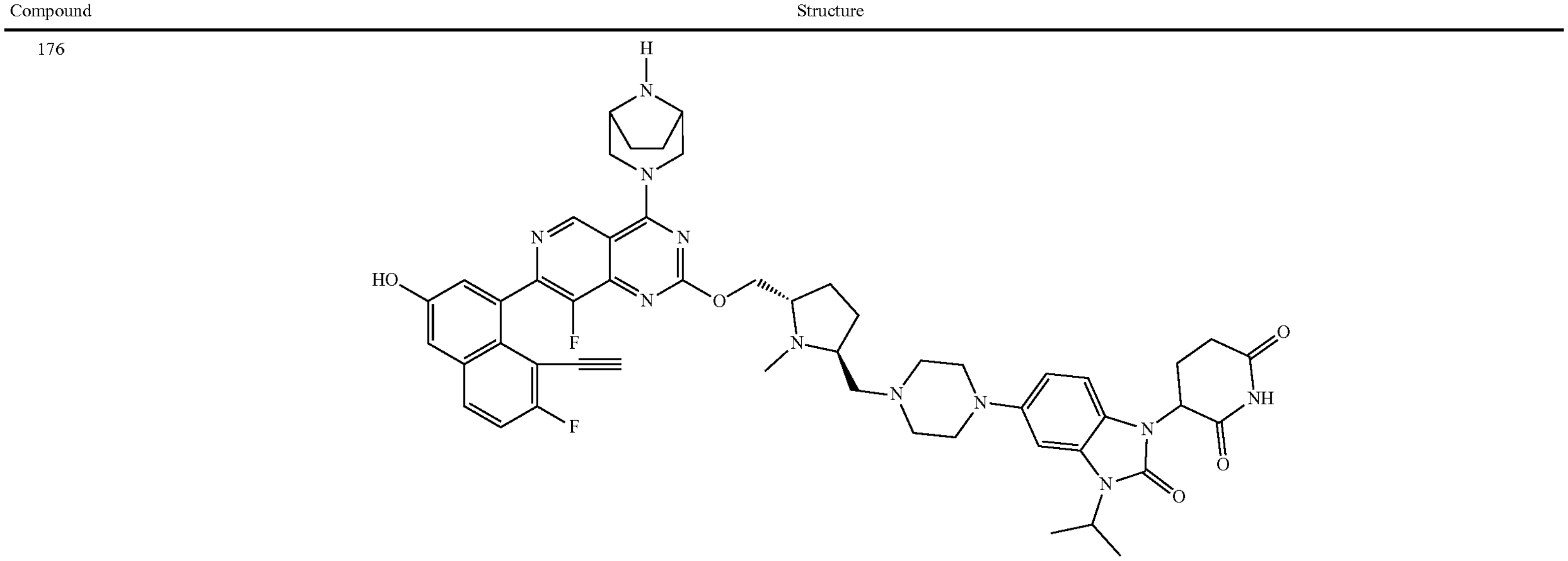 |
| 177 | 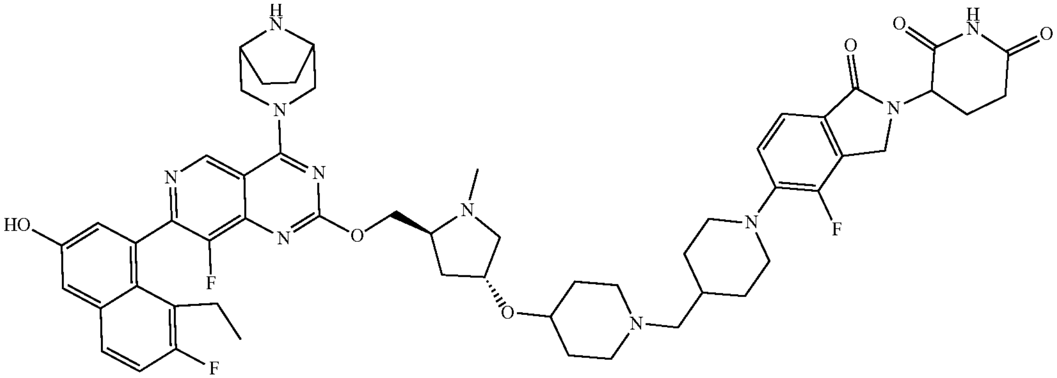 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8F)CN(C8CCC(=O)NC8=O)C9=O)CC7)CC6)CN5C)nc4c3F)c12] |

??TABLE 1-continued
| Compound | Structure |
| --- | --- |
| 178 | 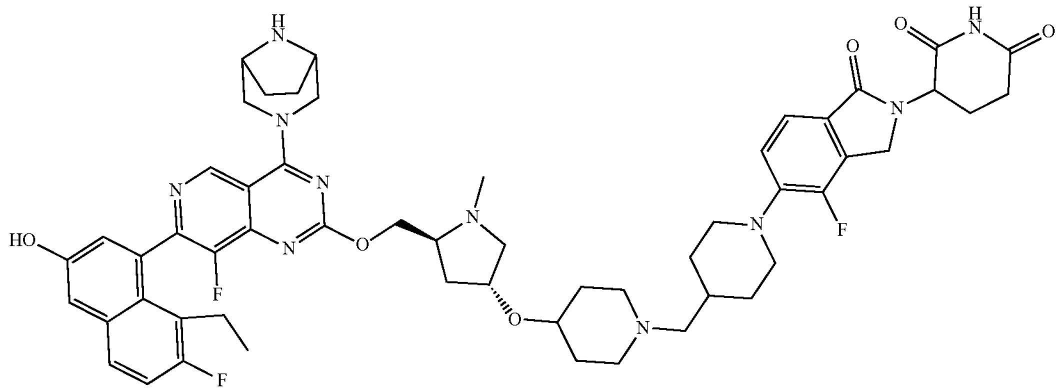 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8F)CN(C8CCC(=O)NC8=O)C9=O)CC7)CC6)CN5C)nc4c3F)c12] |
| 179 | 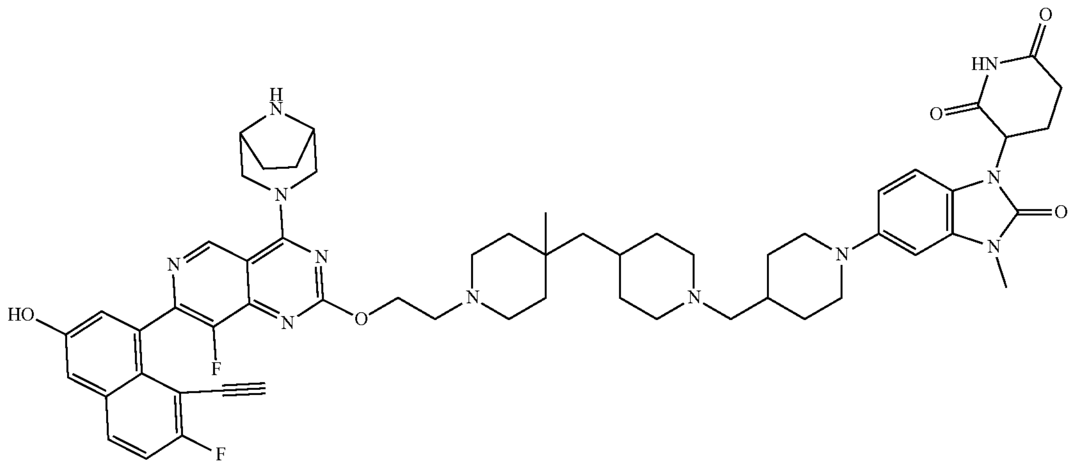 [SMILES: C#Cc1c(F)ccc2cc(O)cc(-c3ncc4c(N5CC6CCC(C5)N6)nc(OCCN5CCC(C)(CC6CCN(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
| --- | --- |
| 180 | 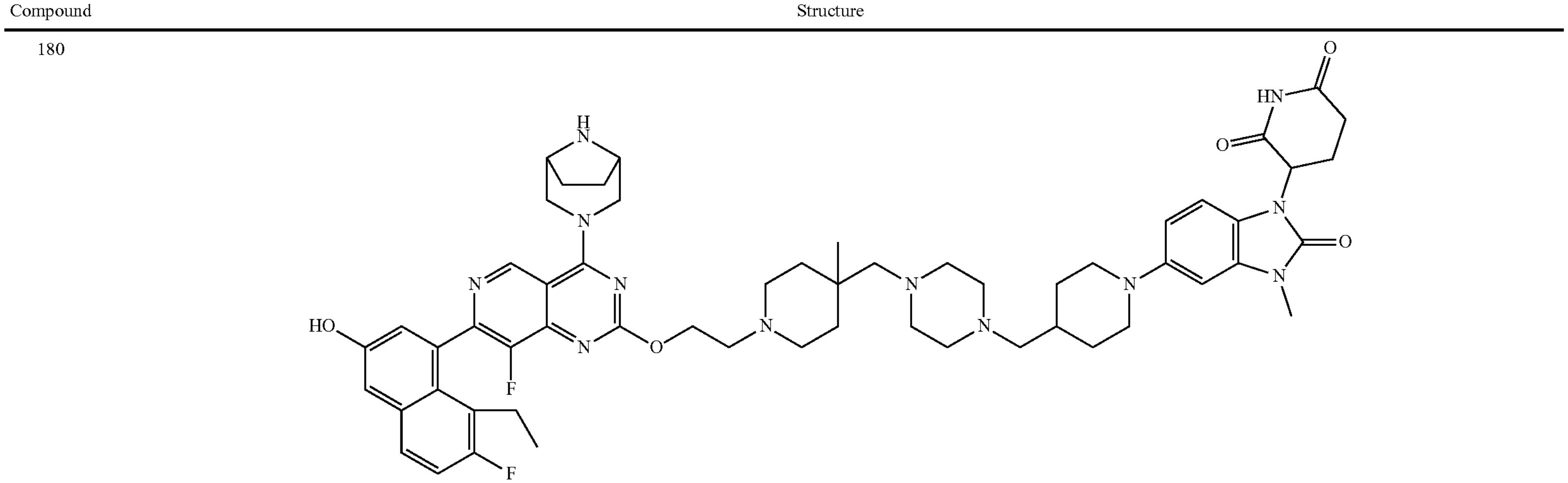 |
| 181 | 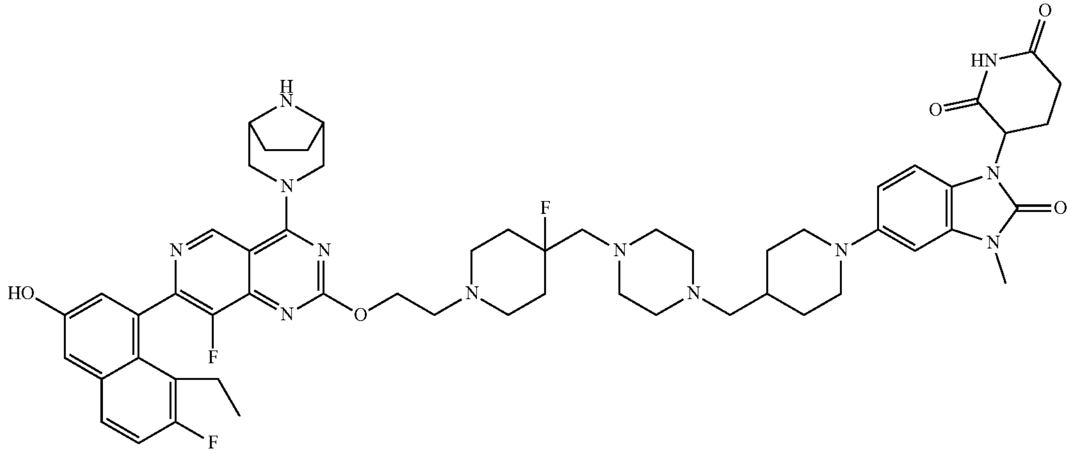 |

??TABLE 1-continued
| Compound | Structure |
| --- | --- |
| 182 | 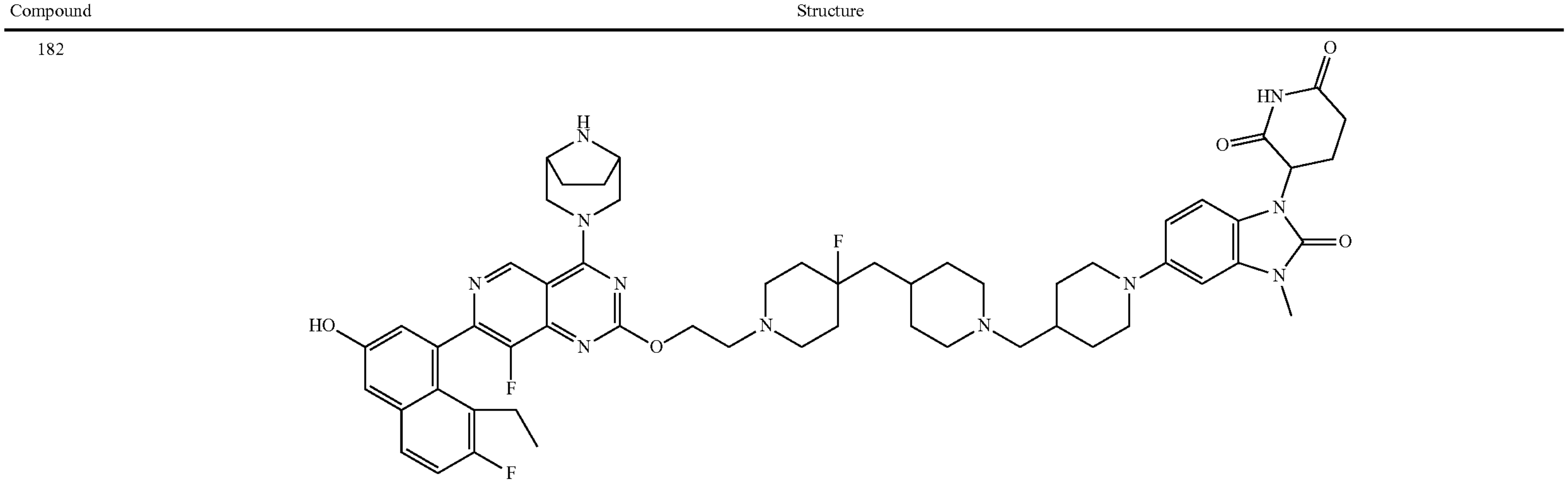 |
| 183 | 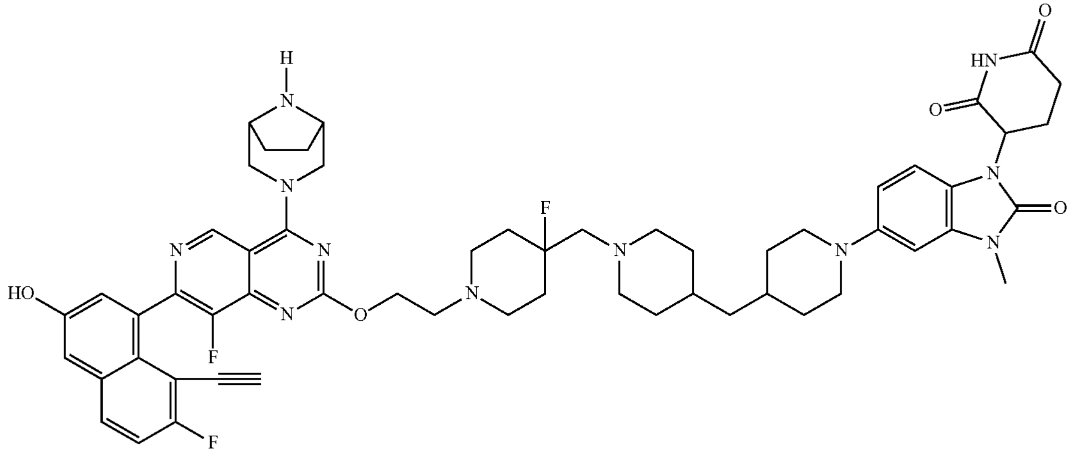 [SMILES: C#Cc1c(F)ccc2cc(O)cc(-c3ncc4c(N5CC6CCC(C5)N6)nc(OCCN5CCC(F)(CN6CCC(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
| --- | --- |
| 184 | 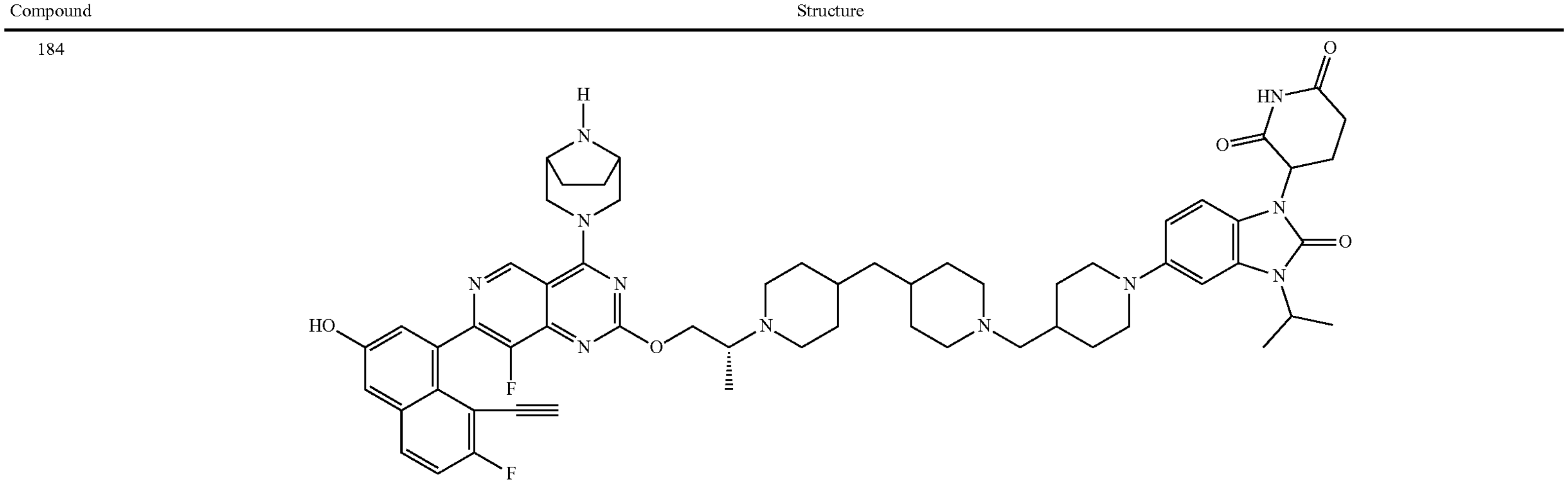 |
| 185 | 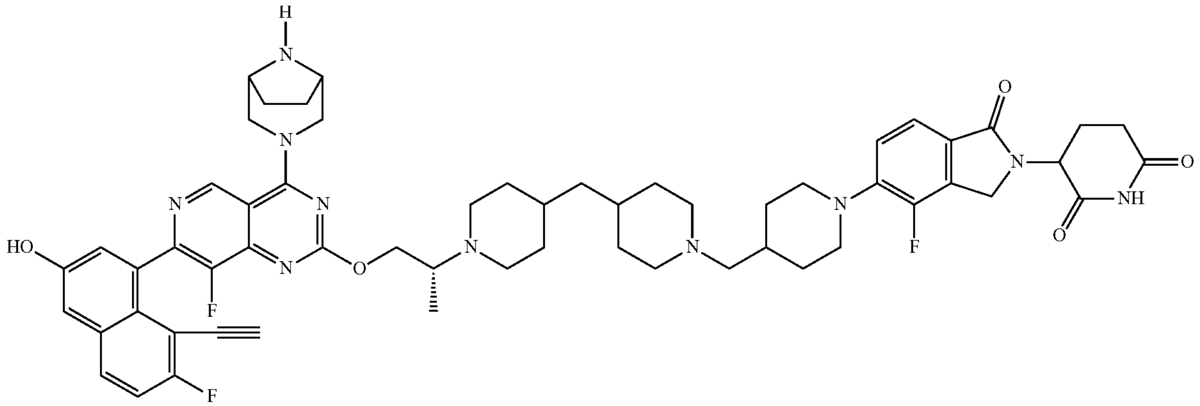 [SMILES: C#Cc1c(F)ccc2cc(O)cc(-c3ncc4c(N5CC6CCC(C5)N6)nc(OC[C@@H](C)N5CCC(CC6CCN(CC7CCN(c8ccc9c(c8F)CN(C8CCC(=O)NC8=O)C9=O)CC7)CC6)CC5)nc4c3F)c12] |

??TABLE 1-continued
| Compound | Structure |
|---|---|
| 186 | 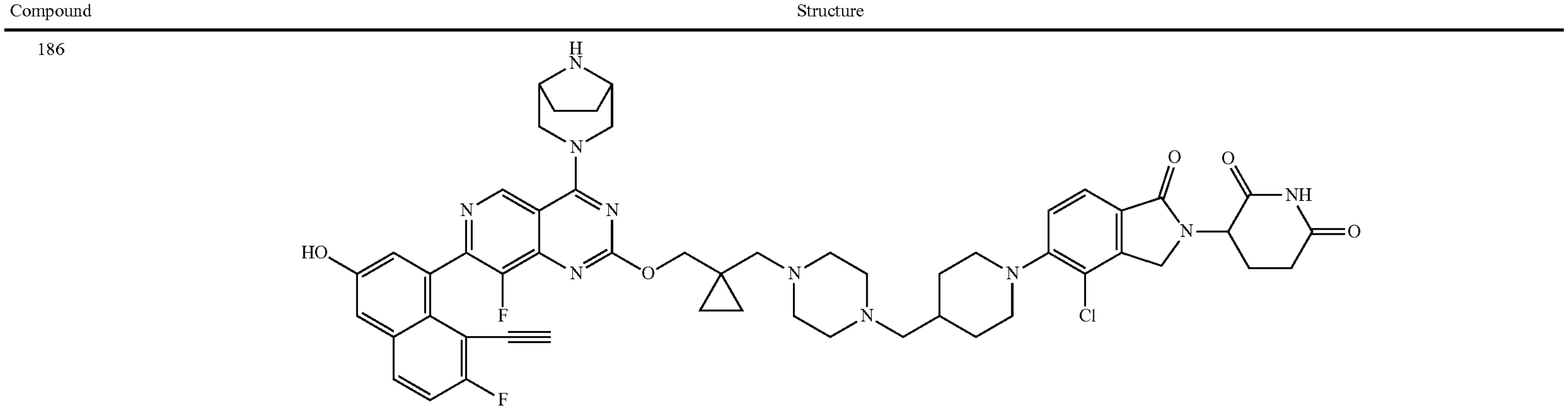 |
| 187 | 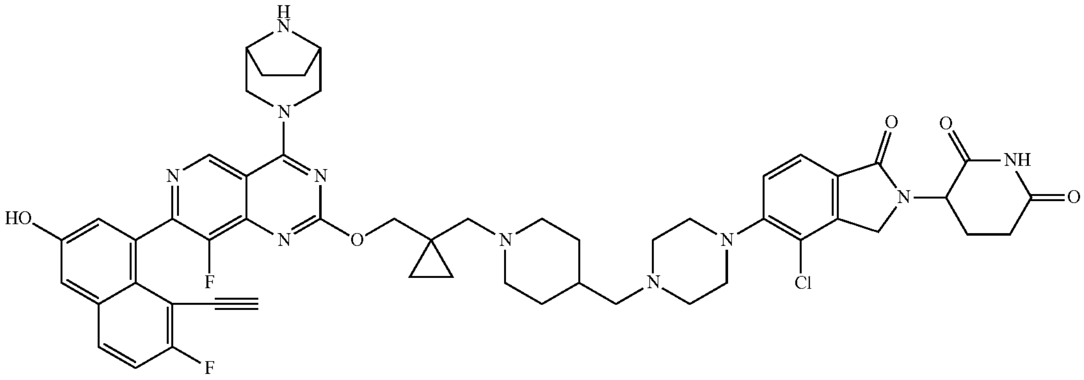 [SMILES: C#Cc1c(F)ccc2cc(O)cc(-c3ncc4c(N5CC6CCC(C5)N6)nc(OCC5(CN6CCC(CN7CCN(c8ccc9c(c8Cl)CN(C8CCC(=O)NC8=O)C9=O)CC7)CC6)CC5)nc4c3F)c12] |

??TABLE 1-continued
| Compound | Structure |
| --- | --- |
| 188 | 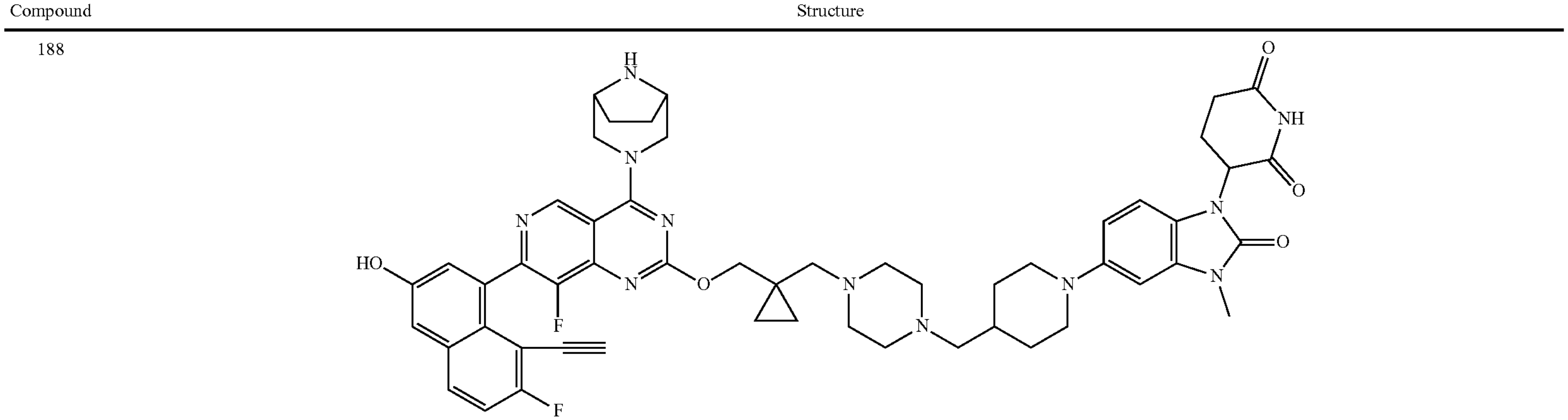 |
| 189 | 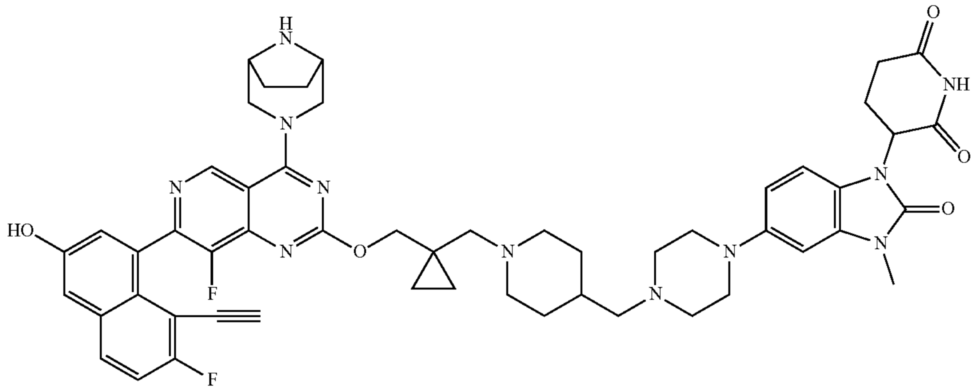 |

??TABLE 1-continued
| Compound | Structure |
|---|---|
| 190 | 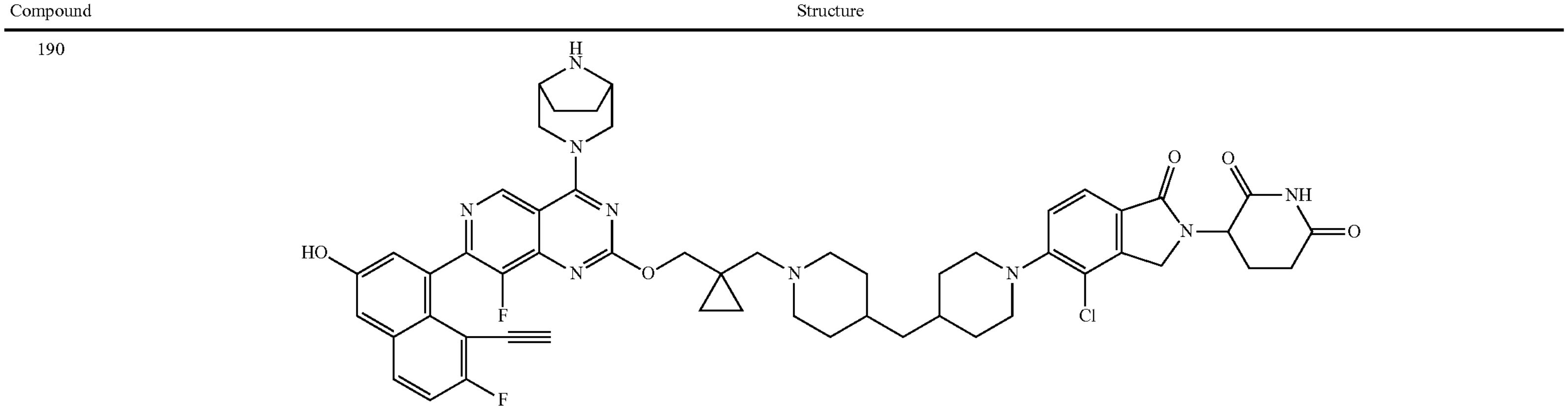 |
| 191 | 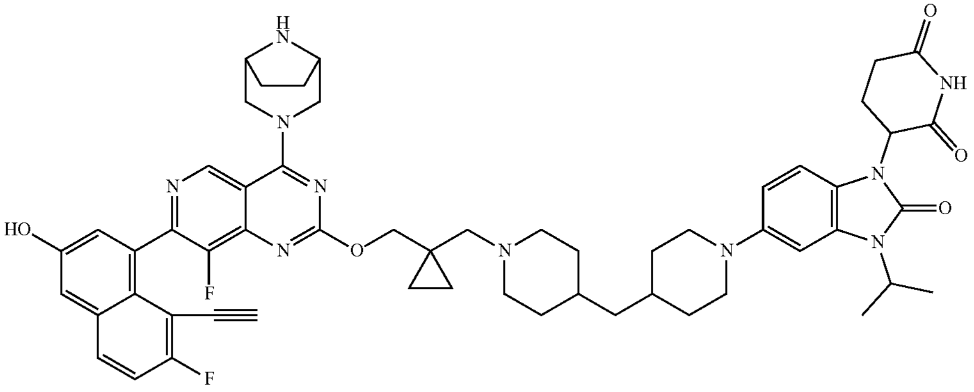 [SMILES: C#Cc1c(F)ccc2cc(O)cc(-c3ncc4c(N5CC6CCC(C5)N6)nc(OCC5(CN6CCC(CC7CCN(c8ccc9c(c8)n(C(C)C)c(=O)n9C8CCC(=O)NC8=O)CC7)CC6)CC5)nc4c3F)c12] |

??TABLE 1-continued
| Compound | Structure |
| --- | --- |
| 192 | 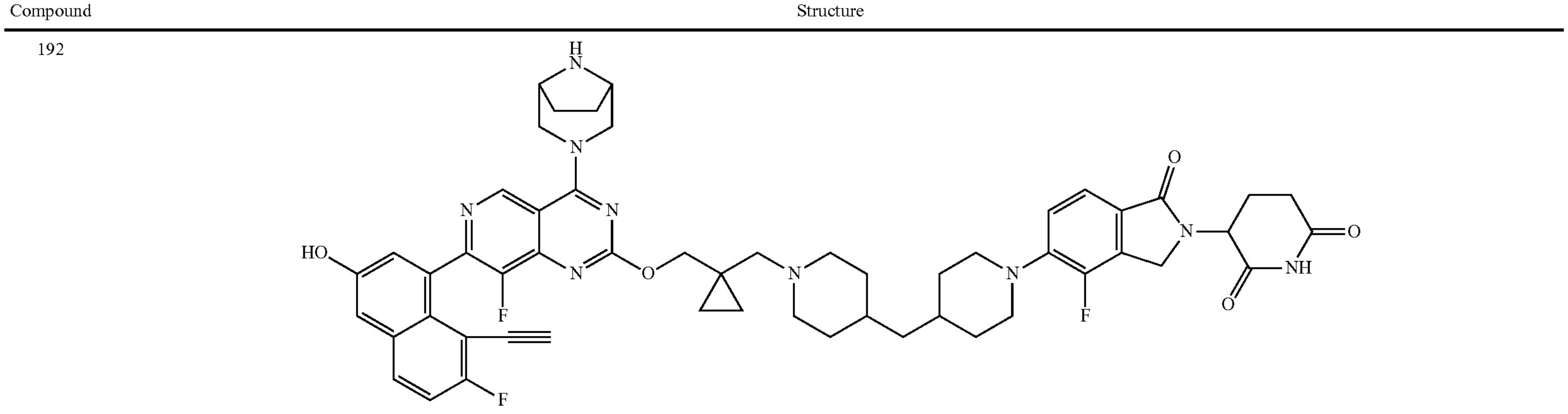 |
| 193 | 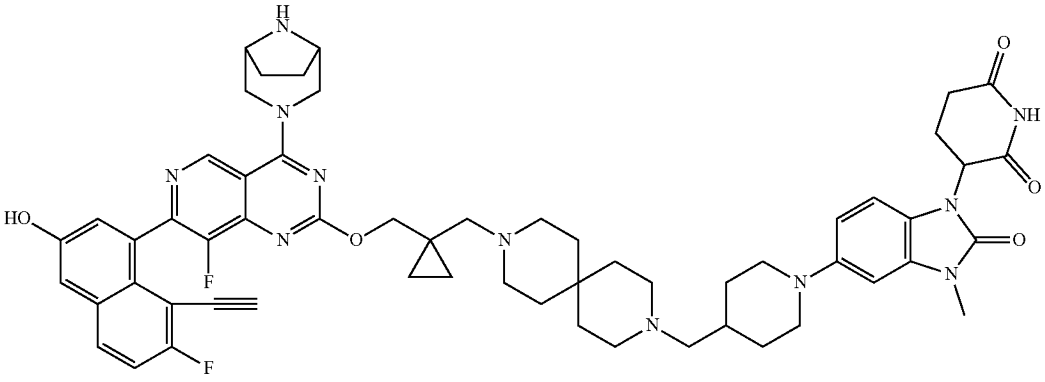 [SMILES: C#Cc1c(F)ccc2cc(O)cc(-c3ncc4c(N5CC6CCC(C5)N6)nc(OCC5(CN6CCC7(CCN(CC8CCN(c9ccc%10c(c9)n(C)c(=O)n%10C9CCC(=O)NC9=O)CC8)CC7)CC6)CC5)nc4c3F)c12] |

??TABLE 1-continued
| Compound | Structure |
| --- | --- |
| 194 | 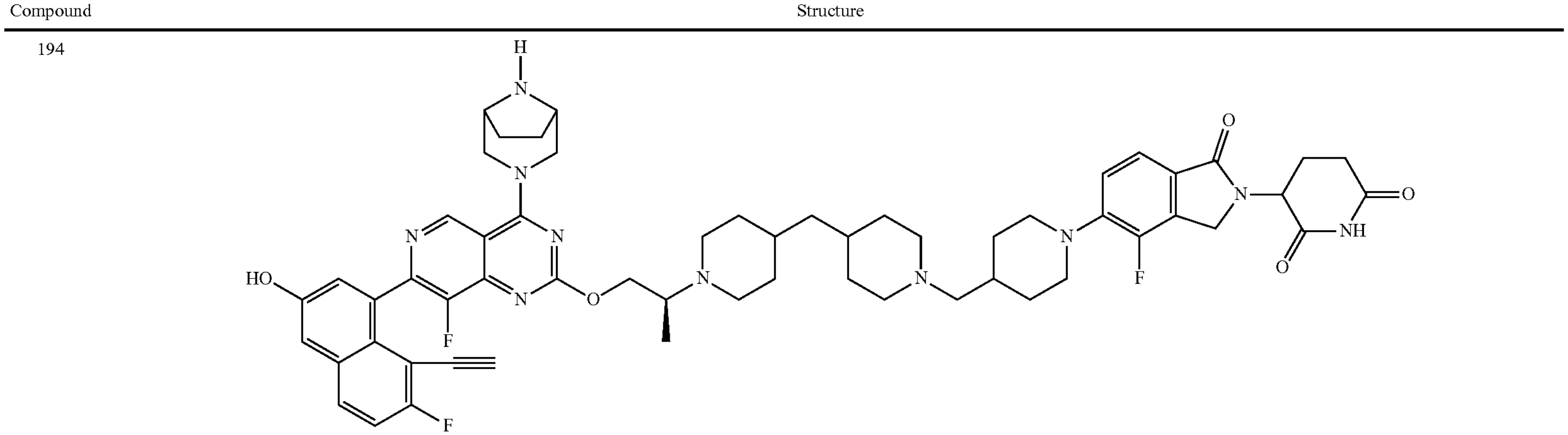 |
| 195 | 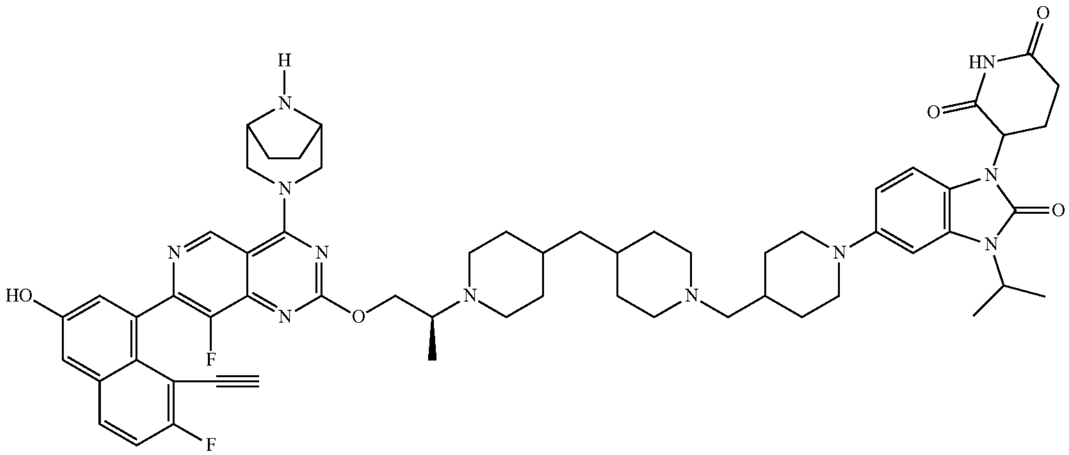 [SMILES: C#Cc1c(F)ccc2cc(O)cc(-c3ncc4c(N5CC6CCC(C5)N6)nc(OC[C@H](C)N5CCC(CC6CCN(CC7CCN(c8ccc9c(c8)n(C(C)C)c(=O)n9C8CCC(=O)NC8=O)CC7)CC6)CC5)nc4c3F)c12] |

??TABLE 1-continued
| Compound | Structure |
|---|---|
| 196 | 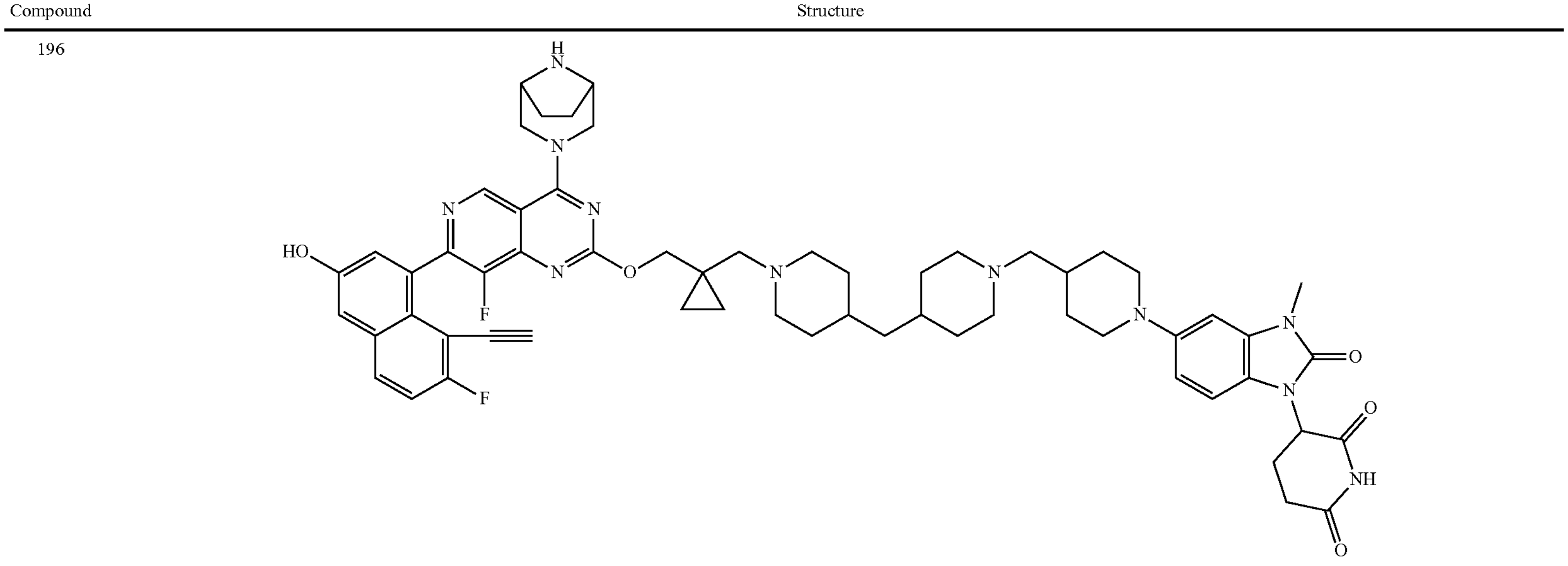 |
| 197 | 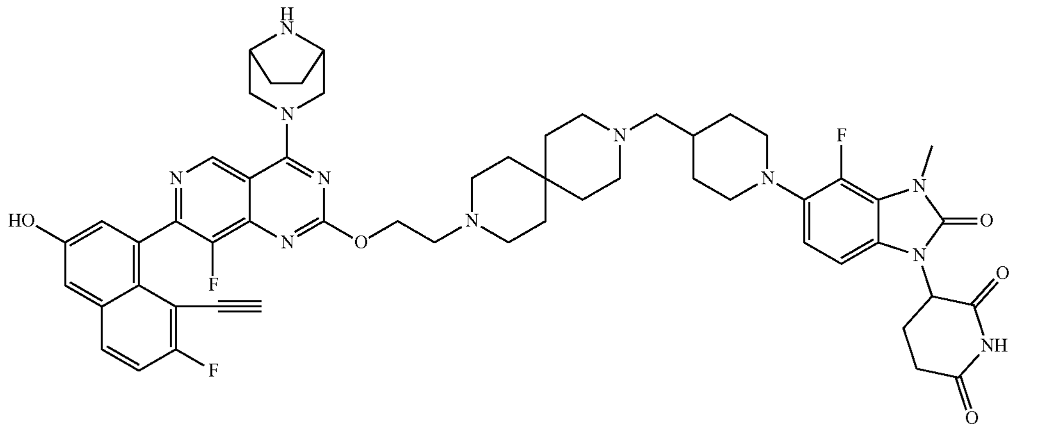 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7F)n(C)c(=O)n8C7CCC(=O)NC7=O)CC5)CC6)nc4c3F)c12] |

??TABLE 1-continued
| Compound | Structure |
| --- | --- |
| 198 | 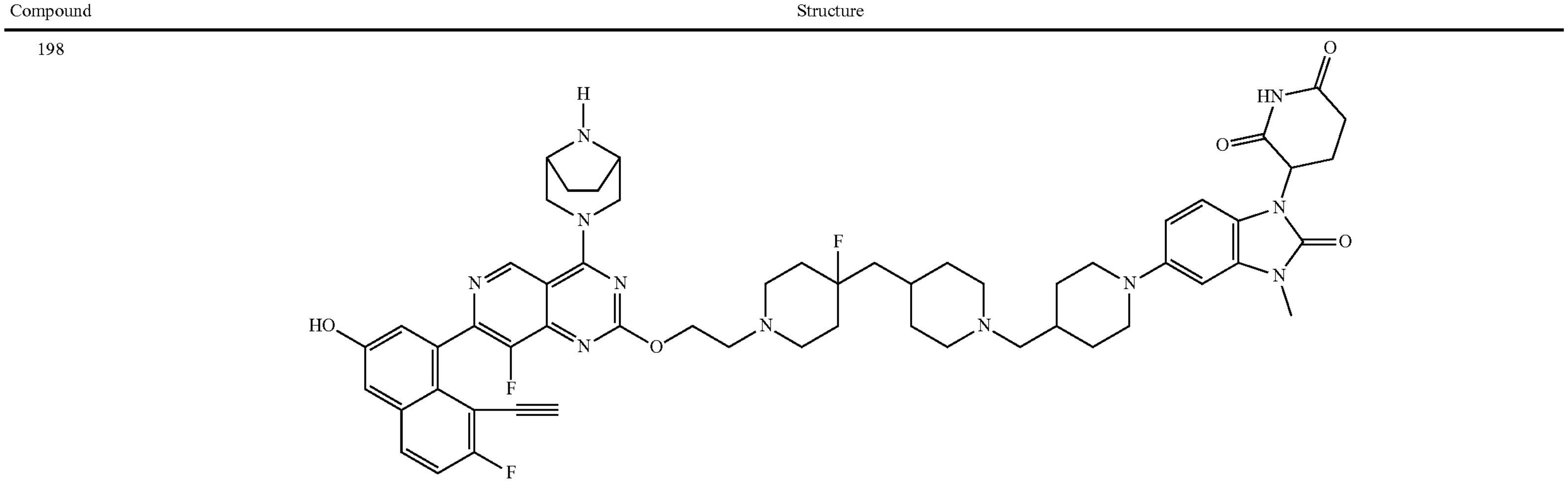 |
| 199 | 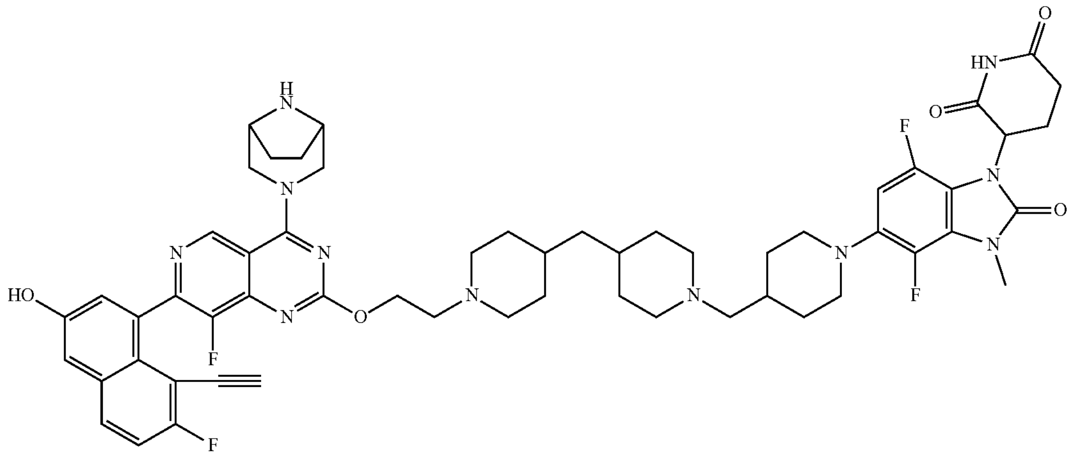 |

??TABLE 1-continued
| Compound | Structure |
| --- | --- |
| 200 | 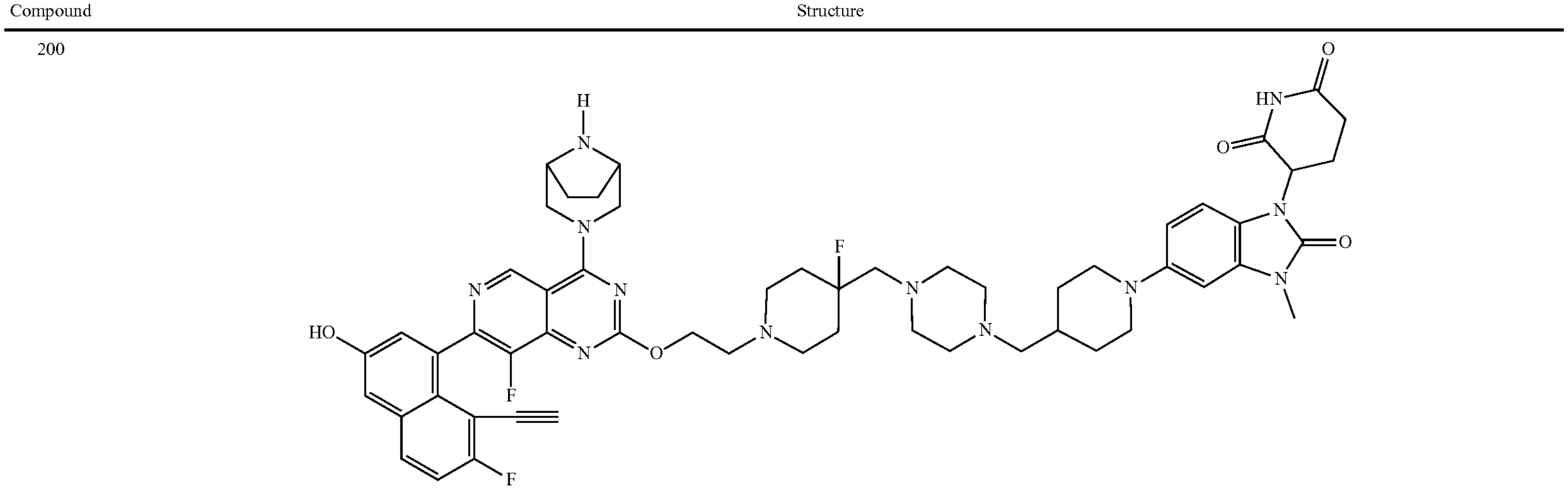 |
| 201 | 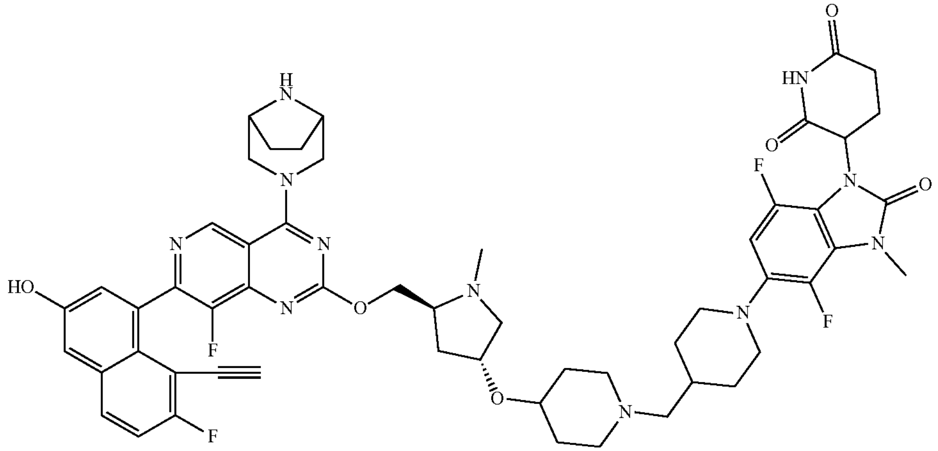 |

??TABLE 1-continued
| Compound | Structure |
|---|---|
| 202 | 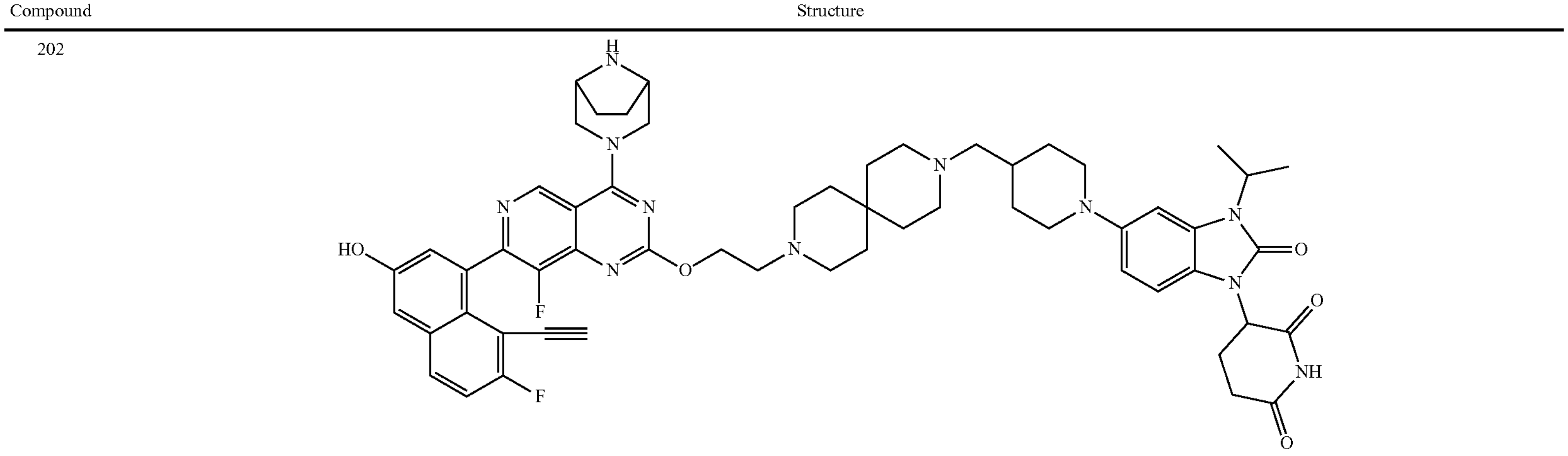 |
| 203 | 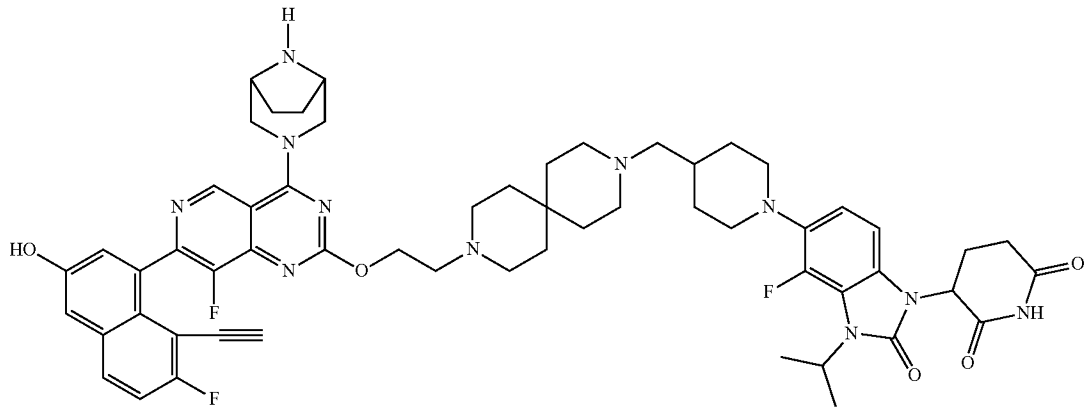 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7F)n(C(C)C)c(=O)n8C7CCC(=O)NC7=O)CC5)CC6)nc4c3F)c12] |

??TABLE 1-continued
| Compound | Structure |
| --- | --- |
| 204 | 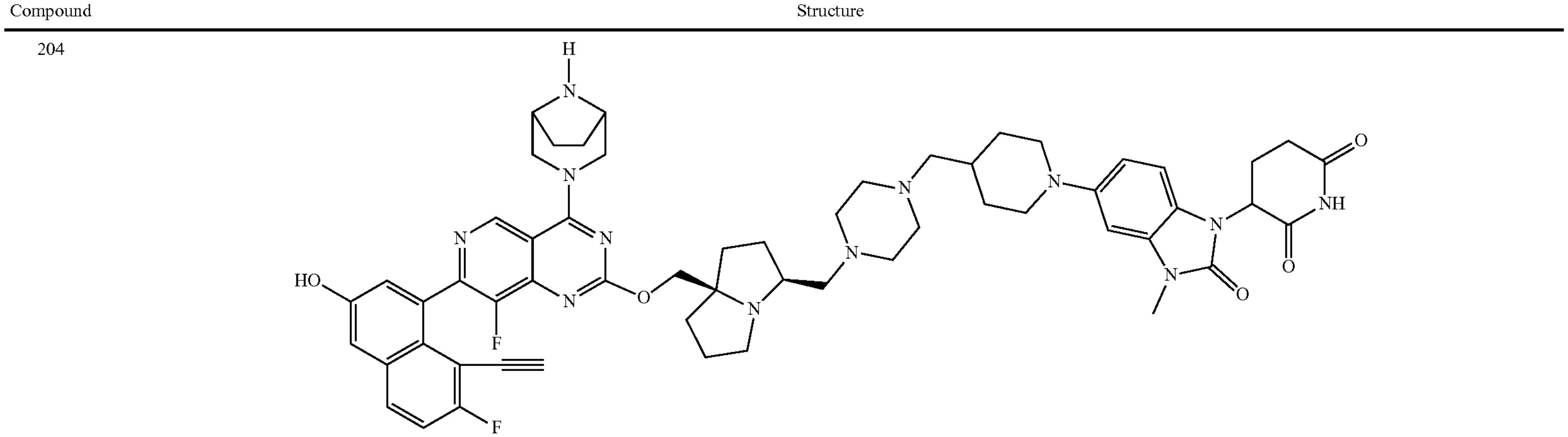 |
| 205 | 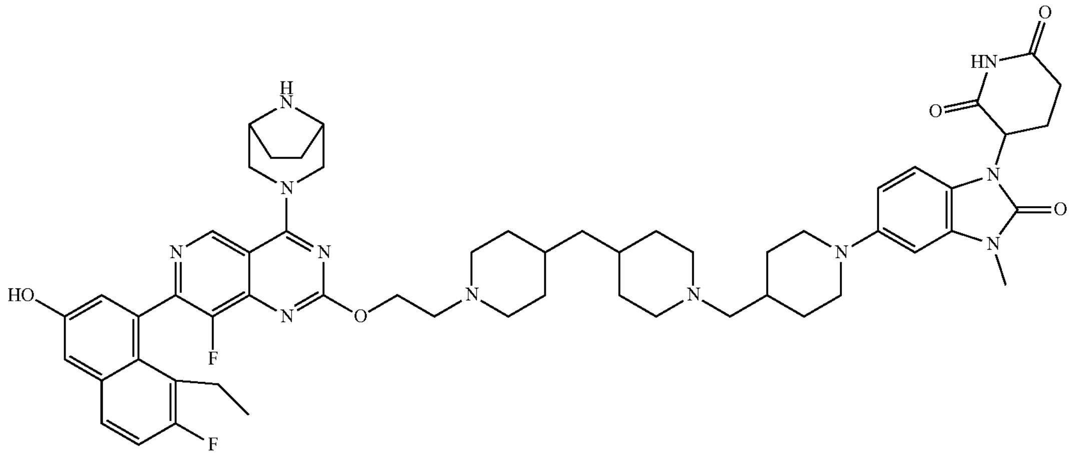 [SMILES: CCc1c(F)ccc2cc(O)cc(-c3ncc4c(N5CC6CCC(C5)N6)nc(OCCN5CCC(CC6CCN(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
|---|---|
| 206 | 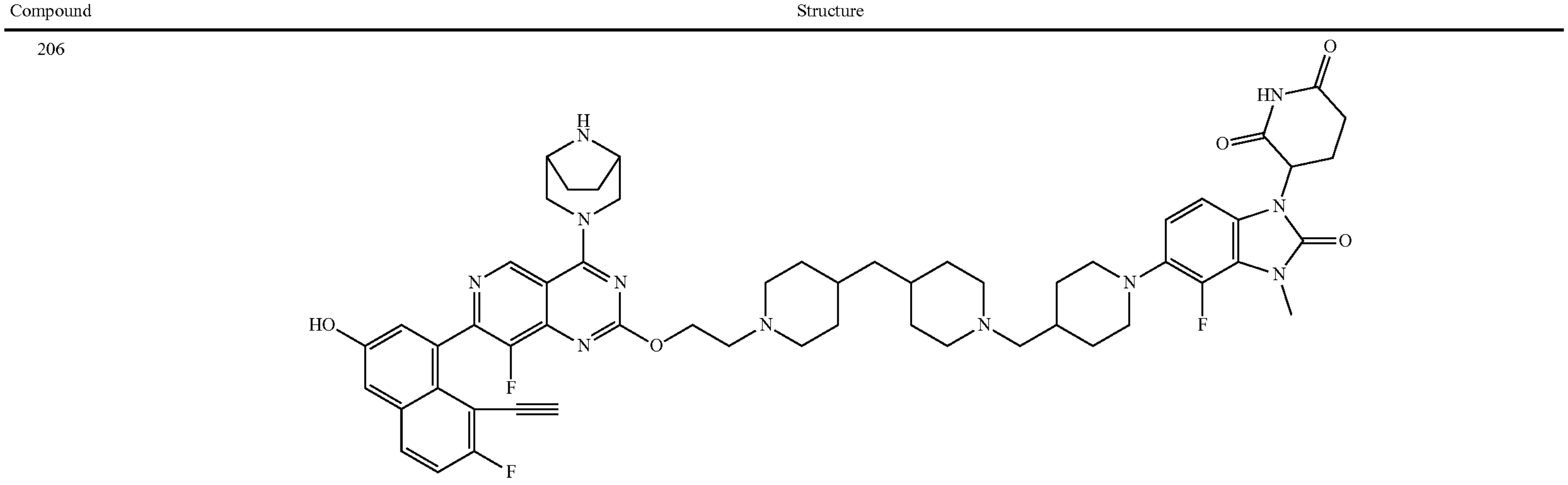 |
| 207 | 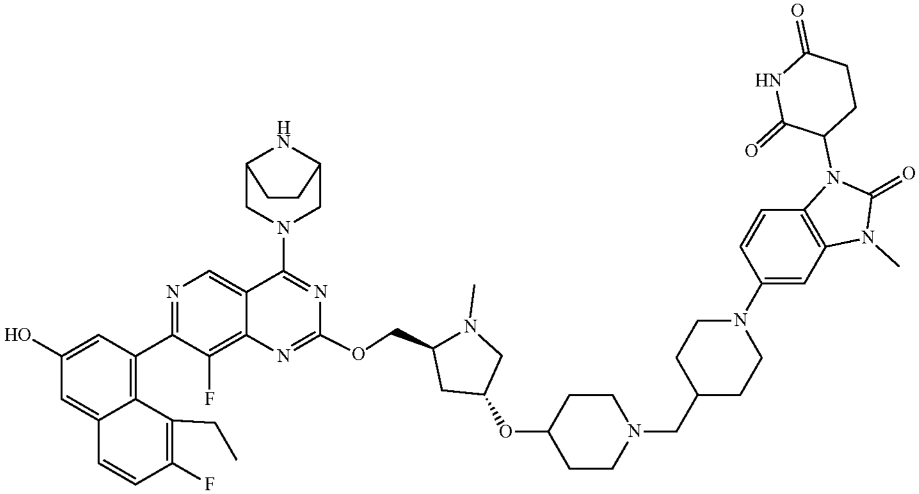 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8)n(C)c(=O)n9C8CCC(=O)NC8=O)CC7)CC6)CN5C)nc4c3F)c12] |

??TABLE 1-continued
| Compound | Structure |
|---|---|
| 208 | 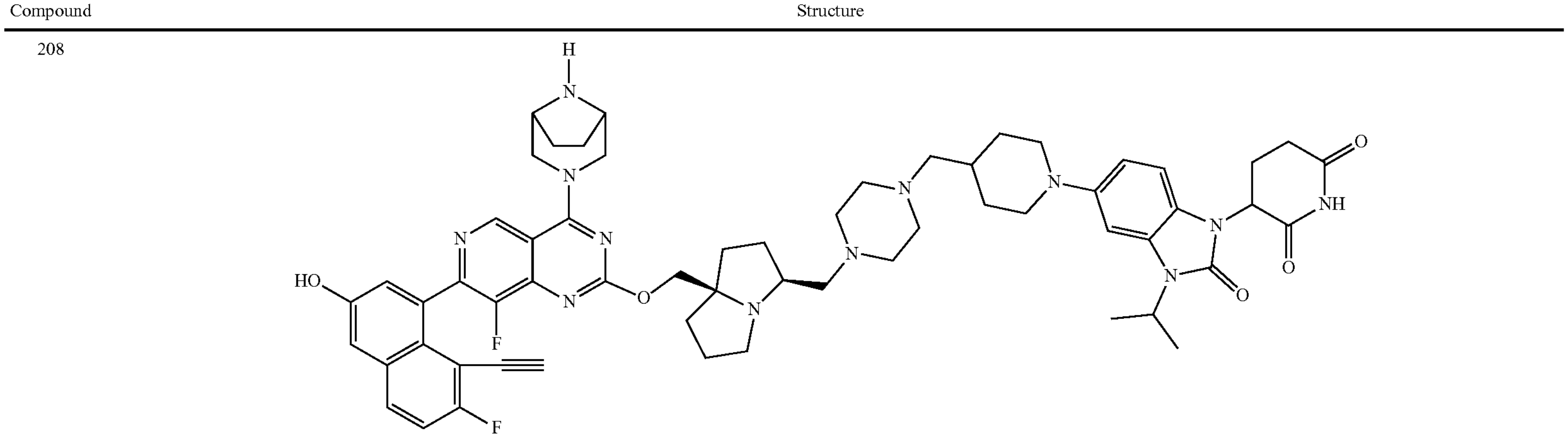 |
| 209 | 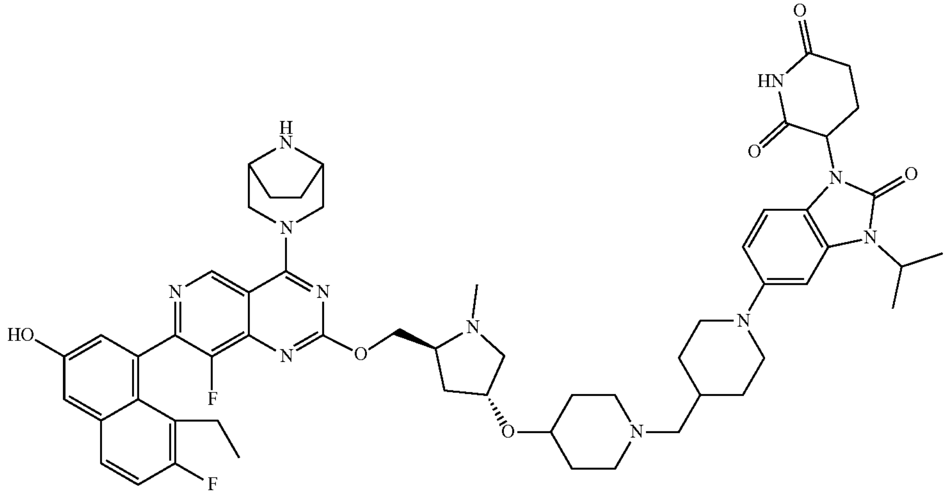 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8)n(C(C)C)c(=O)n9C8CCC(=O)NC8=O)CC7)CC6)CN5C)nc4c3F)c12] |

??TABLE 1-continued
| Compound | Structure |
|---|---|
| 210 | 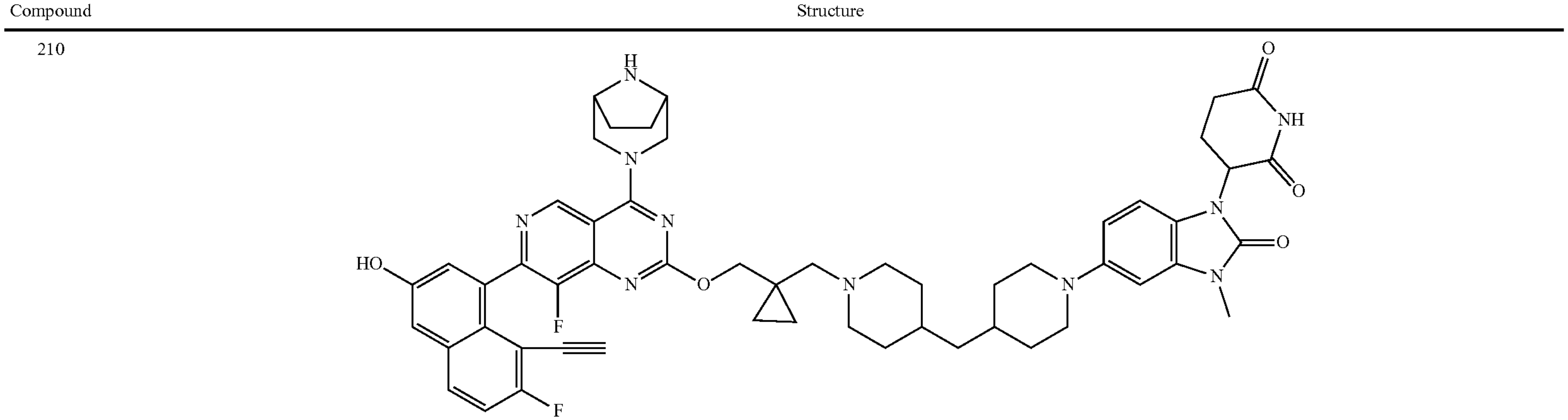 |
| 211 | 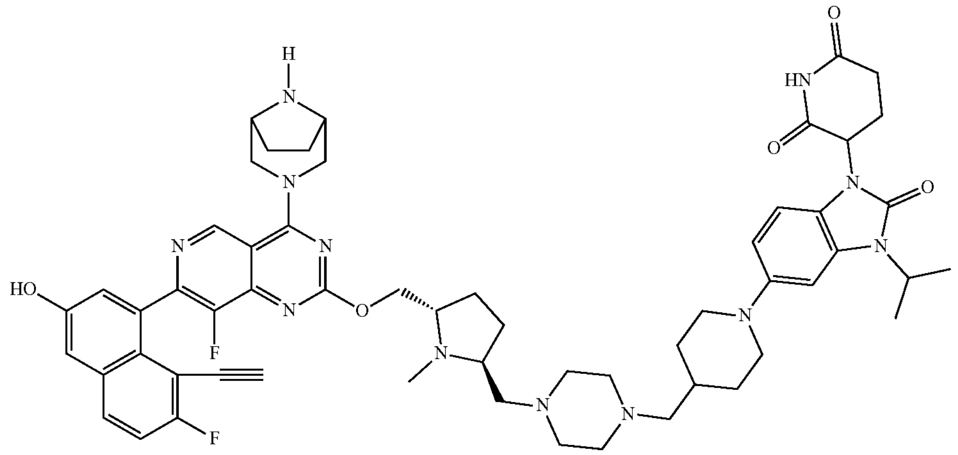 [SMILES: C#Cc1c(F)ccc2cc(O)cc(-c3ncc4c(N5CC6CCC(C5)N6)nc(OC[C@@H]5CC[C@@H](CN6CCN(CC7CCN(c8ccc9c(c8)n(C(C)C)c(=O)n9C8CCC(=O)NC8=O)CC7)CC6)N5C)nc4c3F)c12] |

??TABLE 1-continued
| Compound | Structure |
| --- | --- |
| 212 | 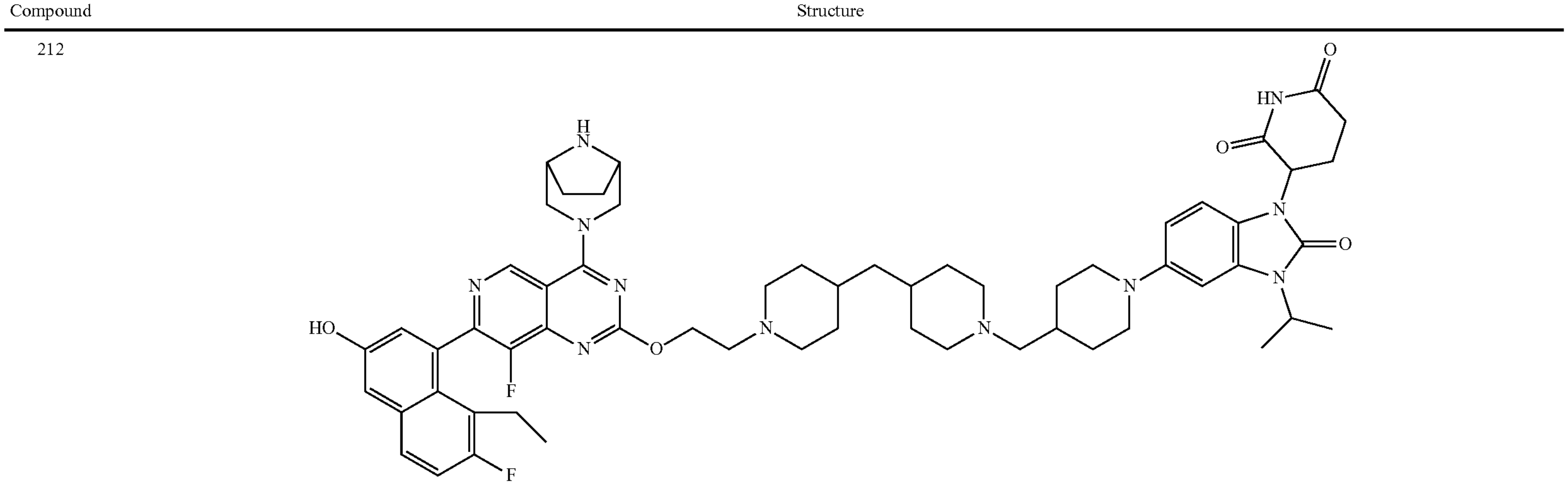 |
| 213 | 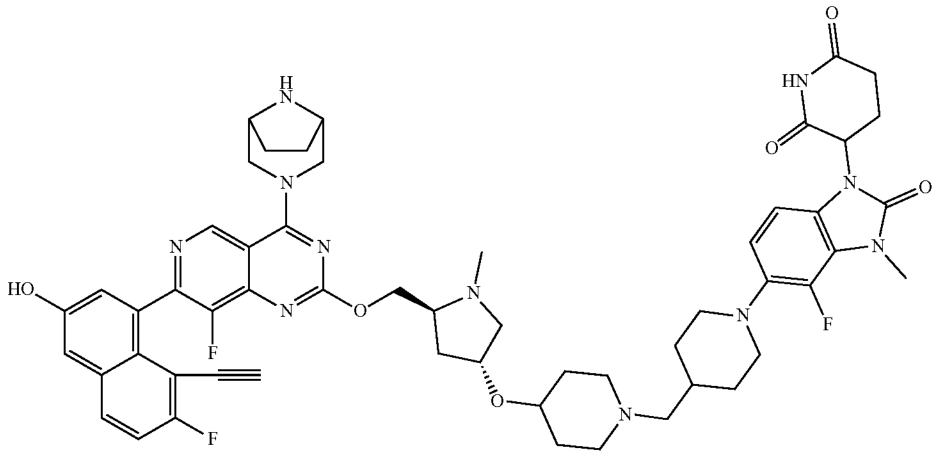 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8F)n(C)c(=O)n9C8CCC(=O)NC8=O)CC7)CC6)CN5C)nc4c3F)c12] |

??TABLE 1-continued
| Compound | Structure |
|---|---|
| 214 | 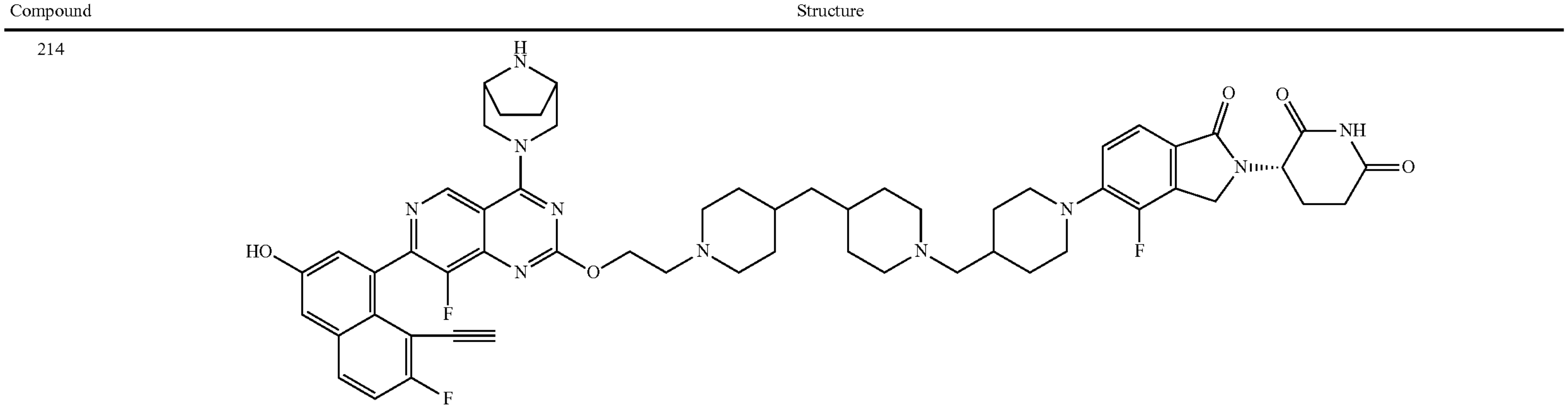 |
| 215 | 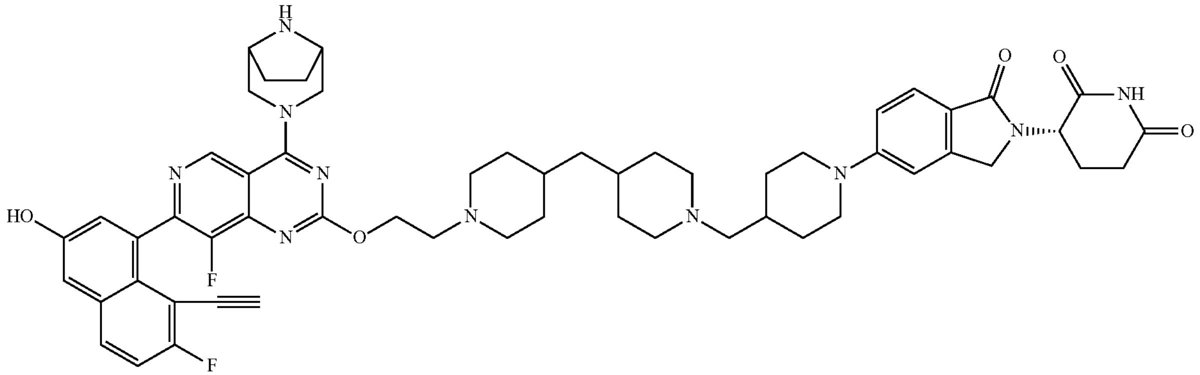 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)CN([C@H]8CCC(=O)NC8=O)C9=O)CC7)CC6)CC5)nc4c3F)c12] |

??TABLE 1-continued
| Compound | Structure |
| --- | --- |
| 216 | 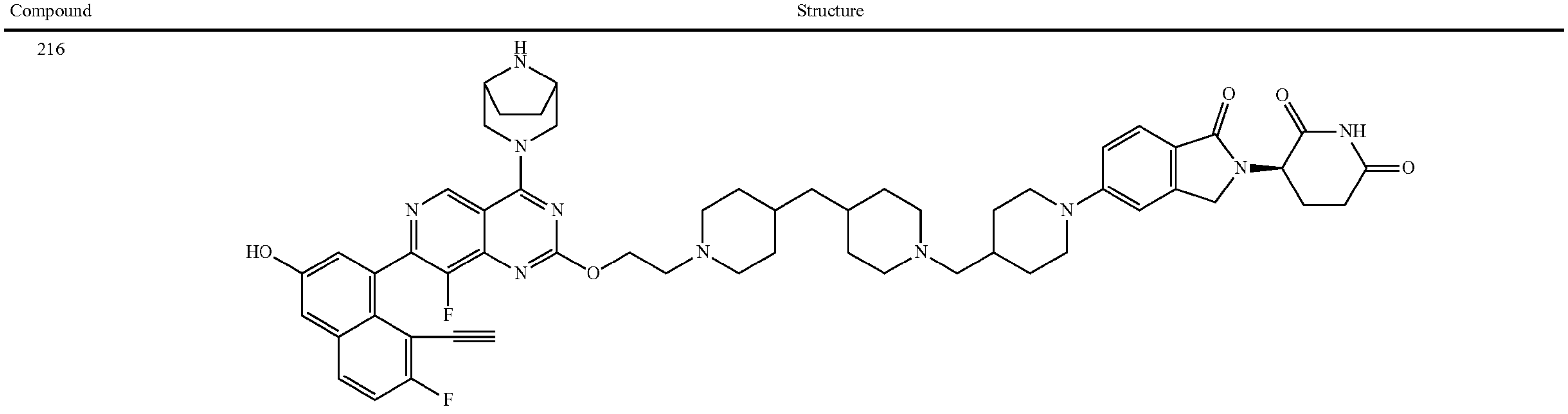 |
| 217 | 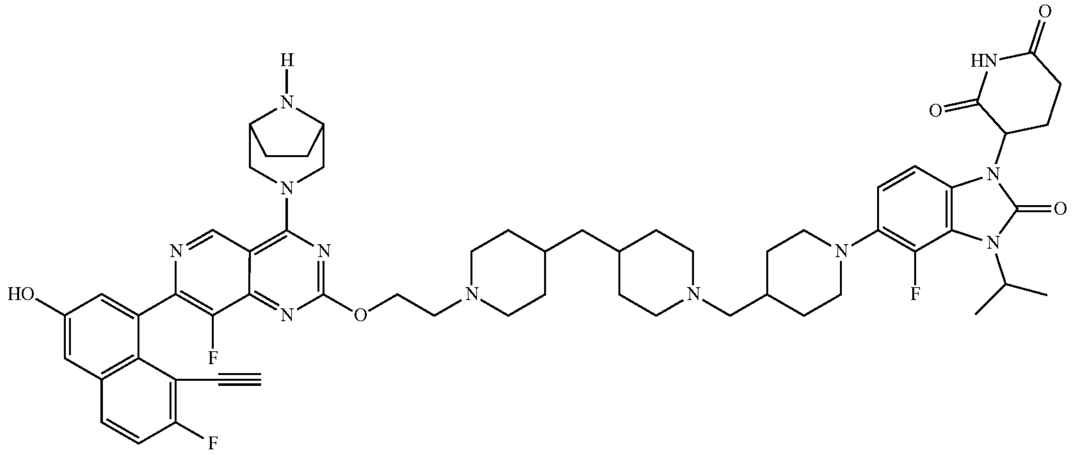 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)n(C(C)C)c(=O)n9C8CCC(=O)NC8=O)CC7)CC6)CC5)nc4c3F)c12] |

??TABLE 1-continued
| Compound | Structure |
|---|---|
| 218 | 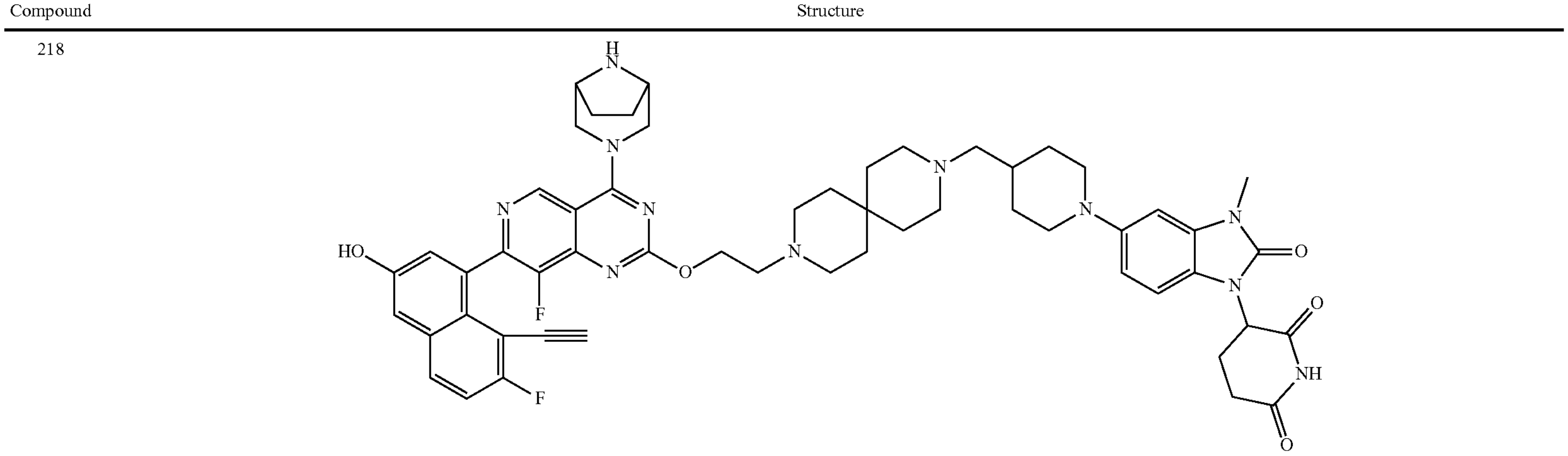 |
| 219 | 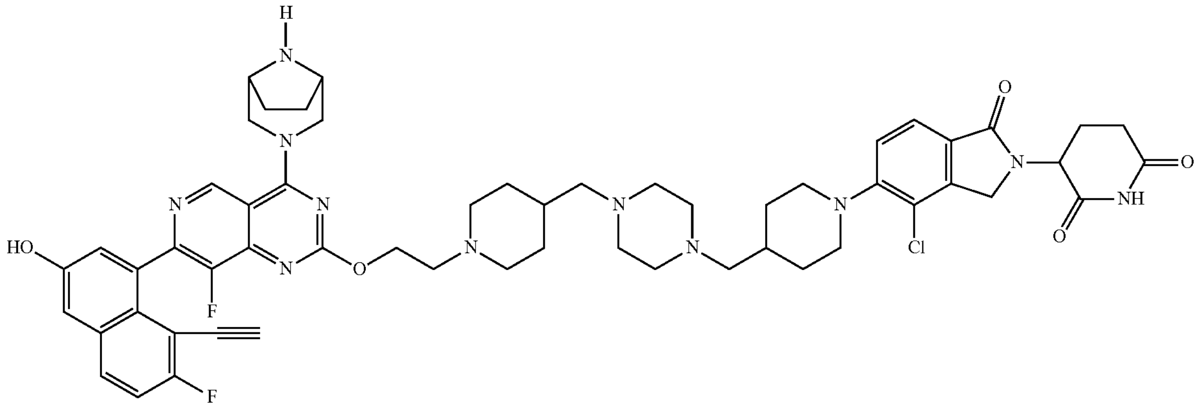 [SMILES: C#Cc1c(F)ccc2cc(O)cc(-c3ncc4c(N5CC6CCC(C5)N6)nc(OCCN5CCC(CN6CCN(CC7CCN(c8ccc9c(c8Cl)CN(C8CCC(=O)NC8=O)C9=O)CC7)CC6)CC5)nc4c3F)c12] |

??TABLE 1-continued
| Compound | Structure |
|---|---|
| 220 | 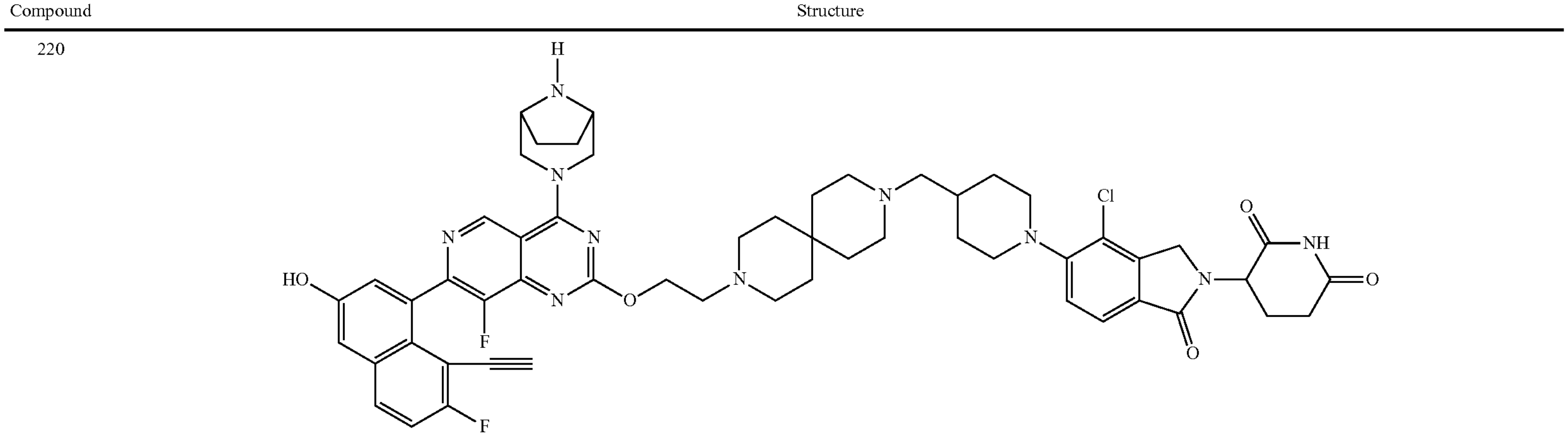 |
| 221 | 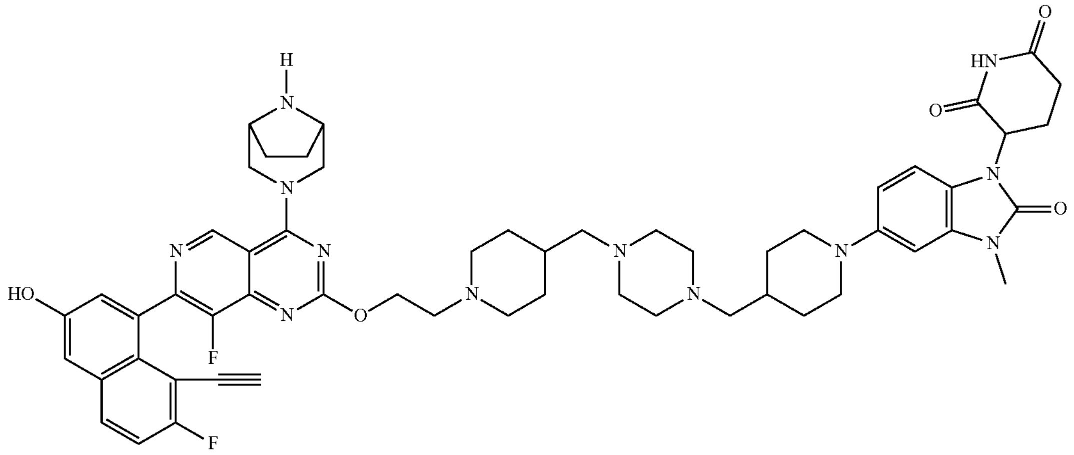 [SMILES: C#Cc1c(F)ccc2cc(O)cc(-c3ncc4c(N5CC6CCC(C5)N6)nc(OCCN5CCC(CN6CCN(CC7CCN(c8ccc9c(c8)n(C)c(=O)n9C8CCC(=O)NC8=O)CC7)CC6)CC5)nc4c3F)c12] |

??TABLE 1-continued
| Compound | Structure |
|---|---|
| 222 | 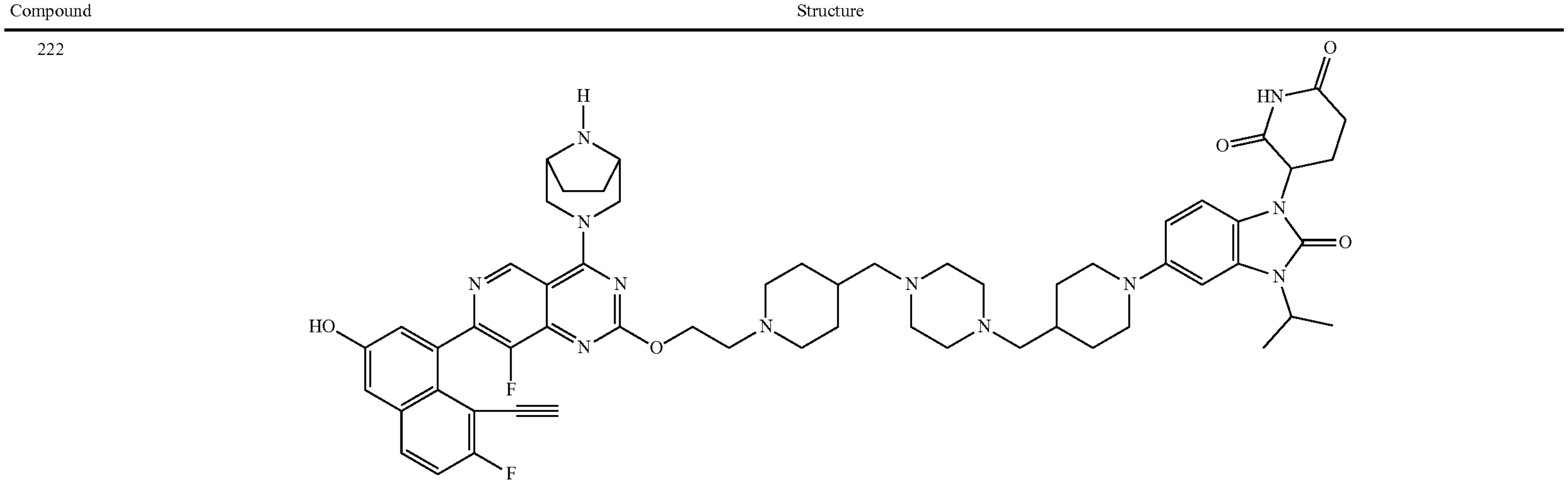 |
| 223 | 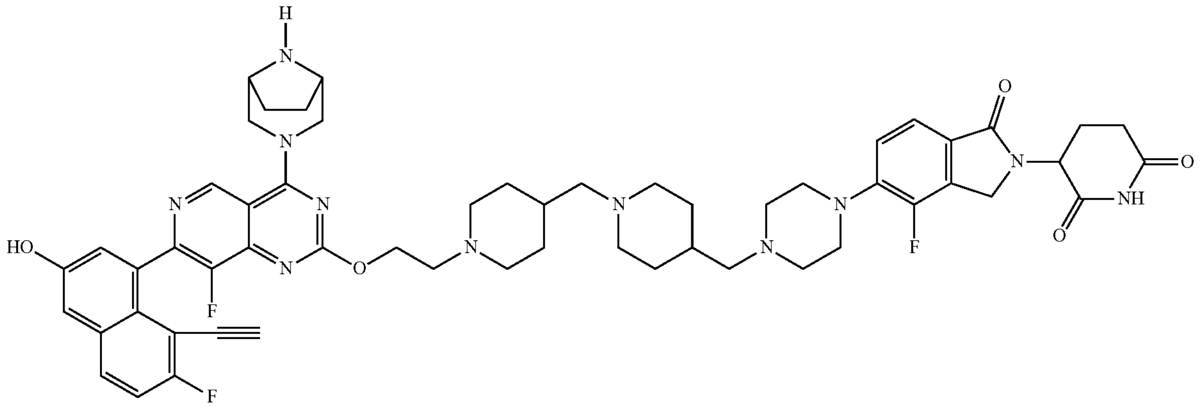 |

??TABLE 1-continued
| Compound | Structure |
| --- | --- |
| 224 | 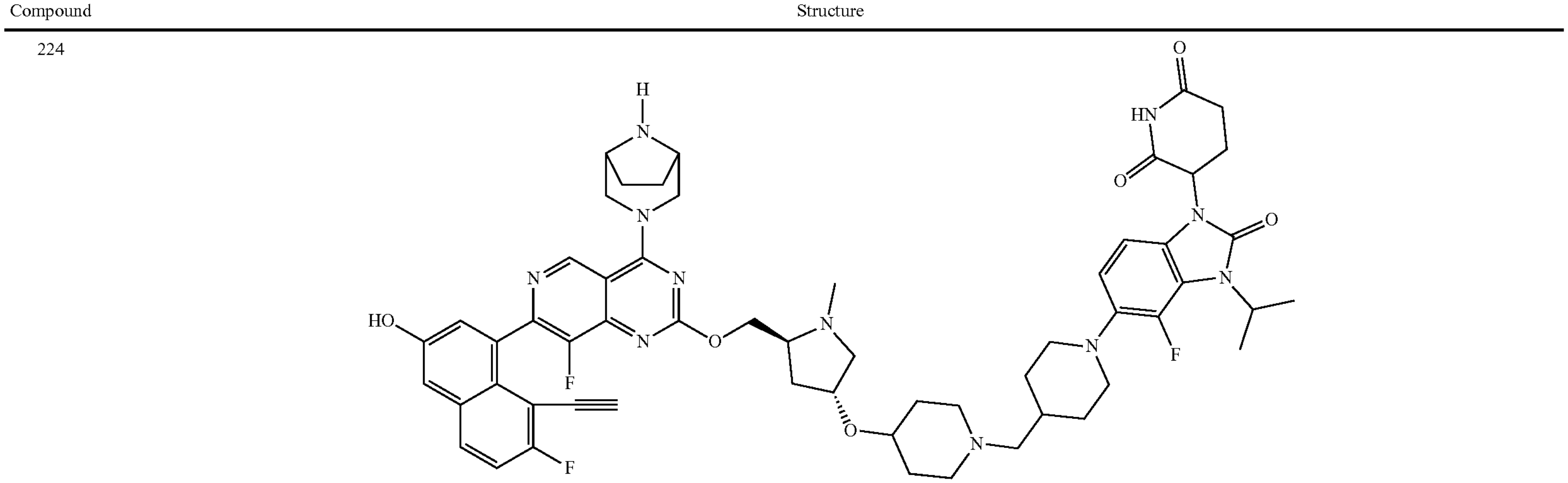 |
| 225 | 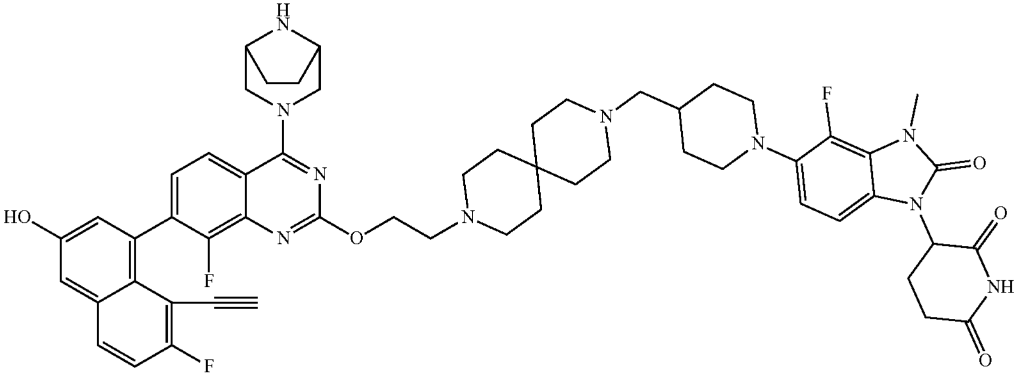 [SMILES: C#Cc1c(F)ccc2cc(O)cc(-c3ccc4c(N5CC6CCC(C5)N6)nc(OCCN5CCC6(CC5)CCN(CC5CCN(c7ccc8c(c7F)n(C)c(=O)n8C7CCC(=O)NC7=O)CC5)CC6)nc4c3F)c12] |

??TABLE 1-continued
| Compound | Structure |
| --- | --- |
| 226 | 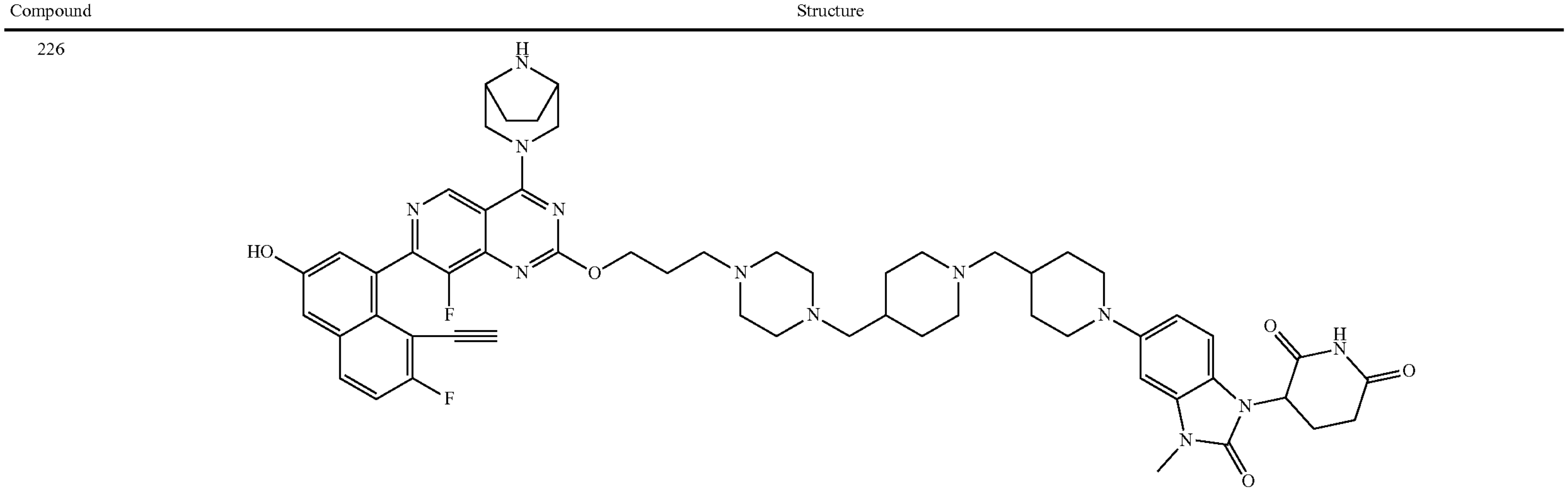 |
| 227 | 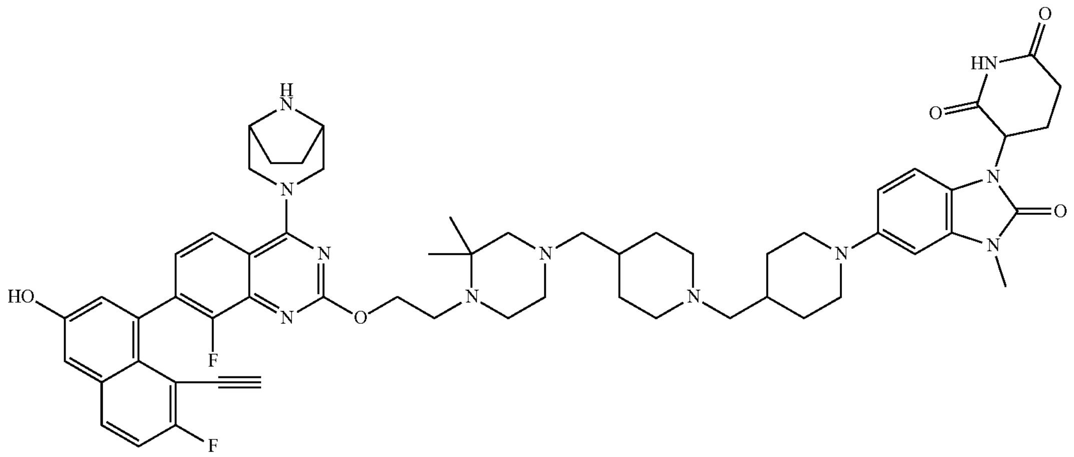 |

??TABLE 1-continued
| Compound | Structure |
| --- | --- |
| 228 | 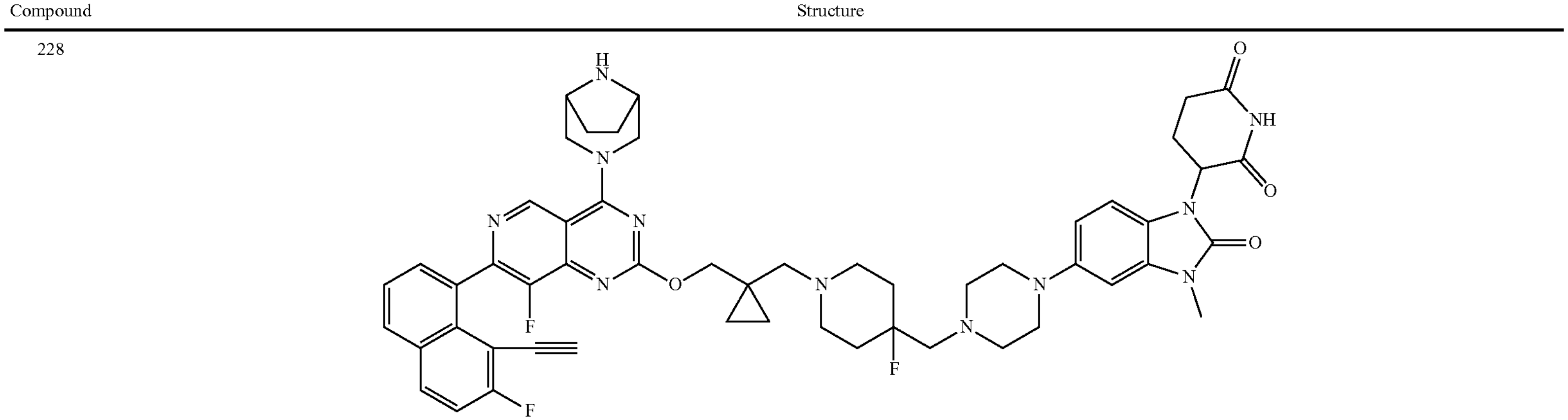 |
| 229 | 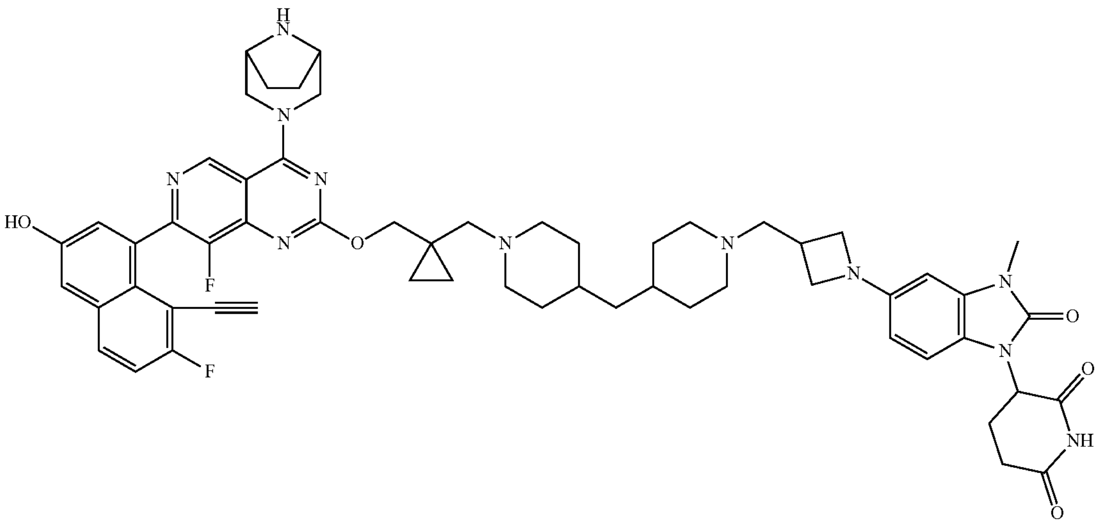 [SMILES: C#Cc1c(F)ccc2cc(O)cc(-c3ncc4c(N5CC6CCC(C5)N6)nc(OCC5(CN6CCC(CC7CCN(CC8CN(c9ccc%10c(c9)n(C)c(=O)n%10C9CCC(=O)NC9=O)C8)CC7)CC6)CC5)nc4c3F)c12] |

??TABLE 1-continued
| Compound | Structure |
| --- | --- |
| 230 | 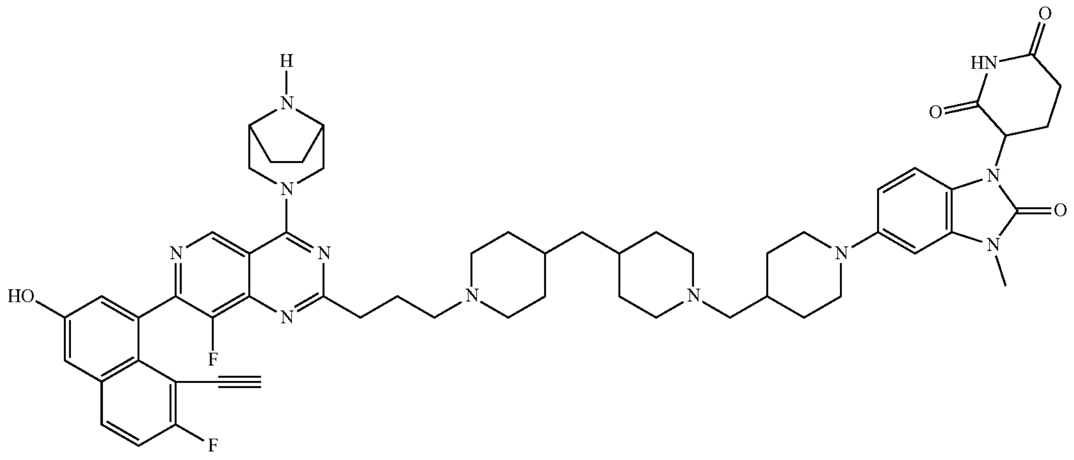 [SMILES: C#Cc1c(F)ccc2cc(O)cc(-c3ncc4c(N5CC6CCC(C5)N6)nc(CCCN5CCC(CC6CCN(CC7CCN(c8ccc9c(c8)n(C)c(=O)n9C8CCC(=O)NC8=O)CC7)CC6)CC5)nc4c3F)c12] |
| 231 | 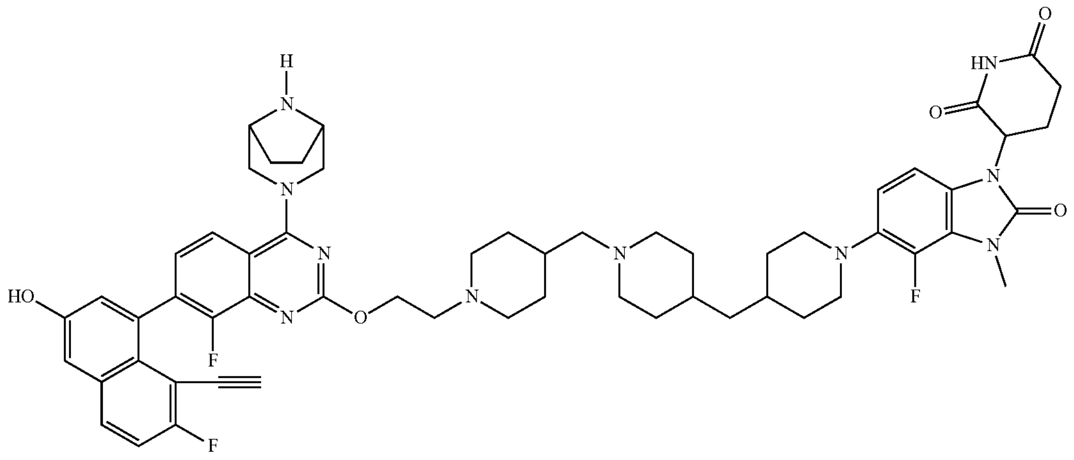 |

??TABLE 1-continued
| Compound | Structure |
| --- | --- |
| 232 | 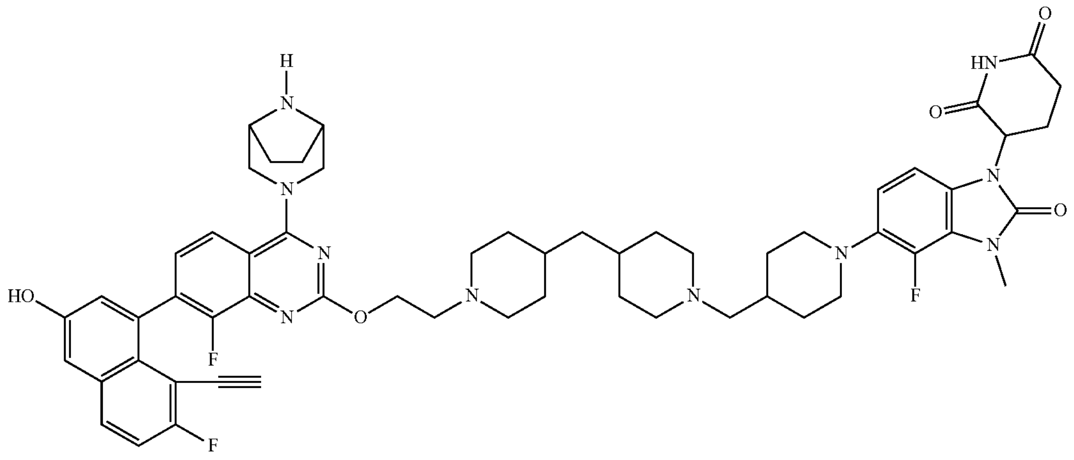 |
| 233 | 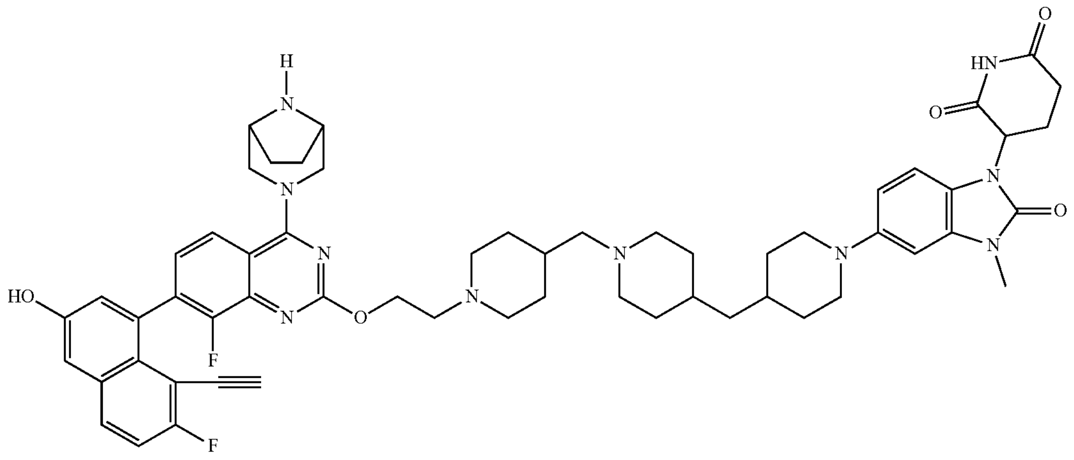 |

??TABLE 1-continued
| Compound | Structure |
| --- | --- |
| 234 | 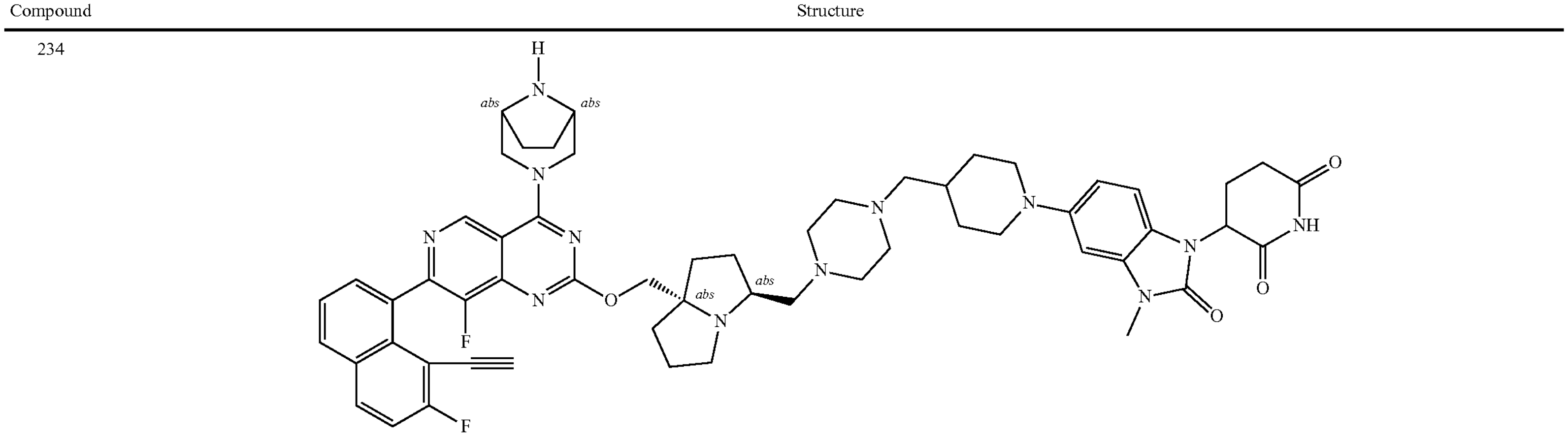 |
| 235 | 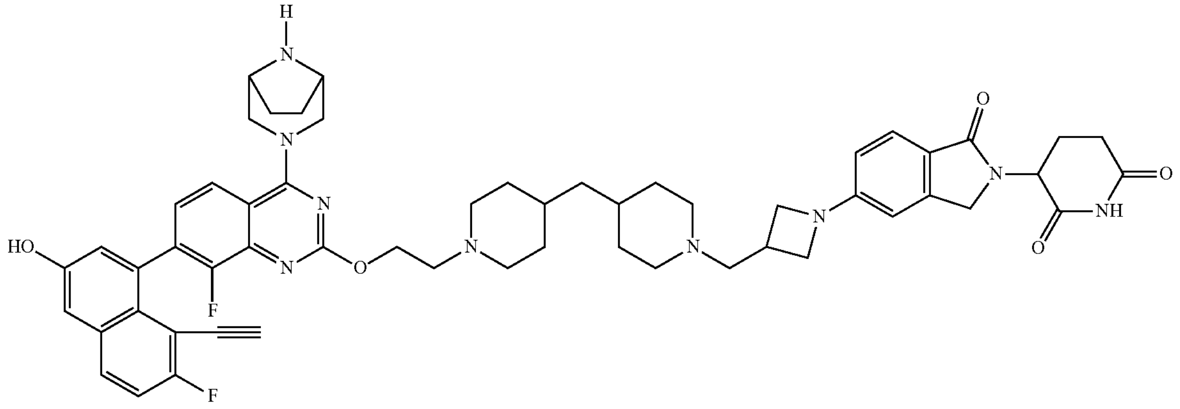 [SMILES: C#Cc1c(F)ccc2cc(O)cc(-c3ccc4c(N5CC6CCC(C5)N6)nc(OCCN5CCC(CC6CCN(CC7CN(c8ccc9c(c8)CN(C8CCC(=O)NC8=O)C9=O)C7)CC6)CC5)nc4c3F)c12] |

??TABLE 1-continued
| Compound | Structure |
| --- | --- |
| 236 | 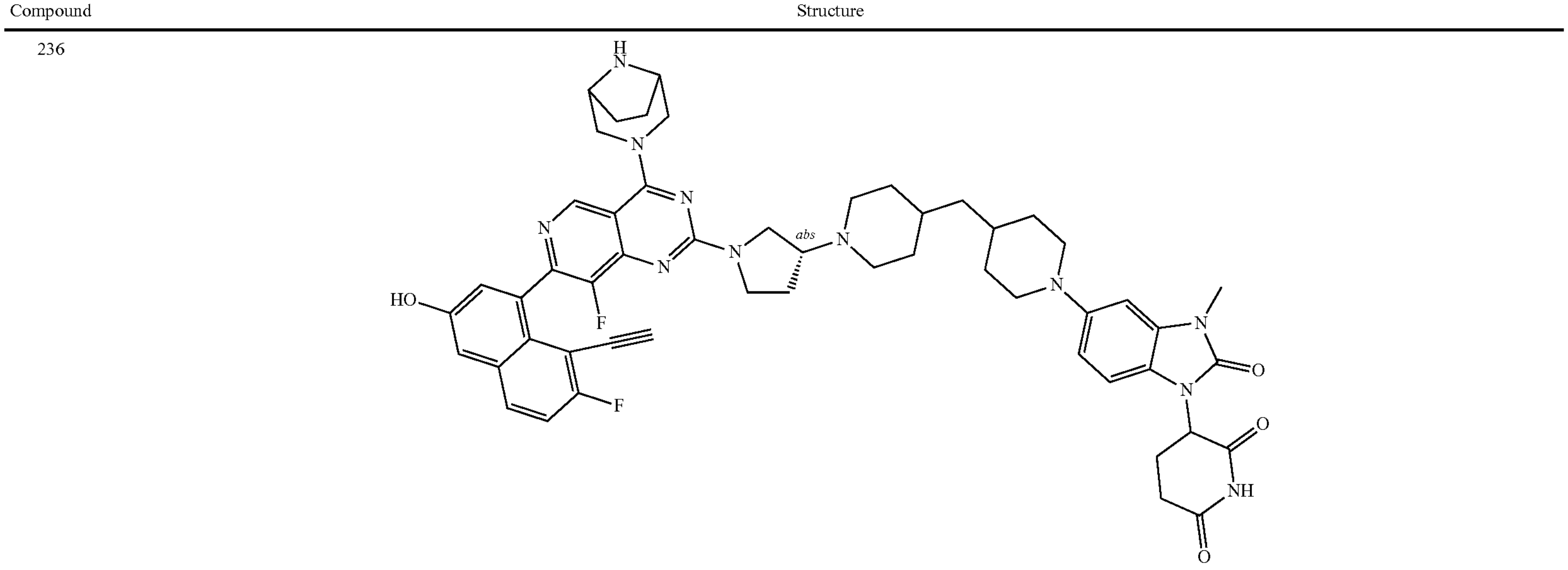 |
| 237 | 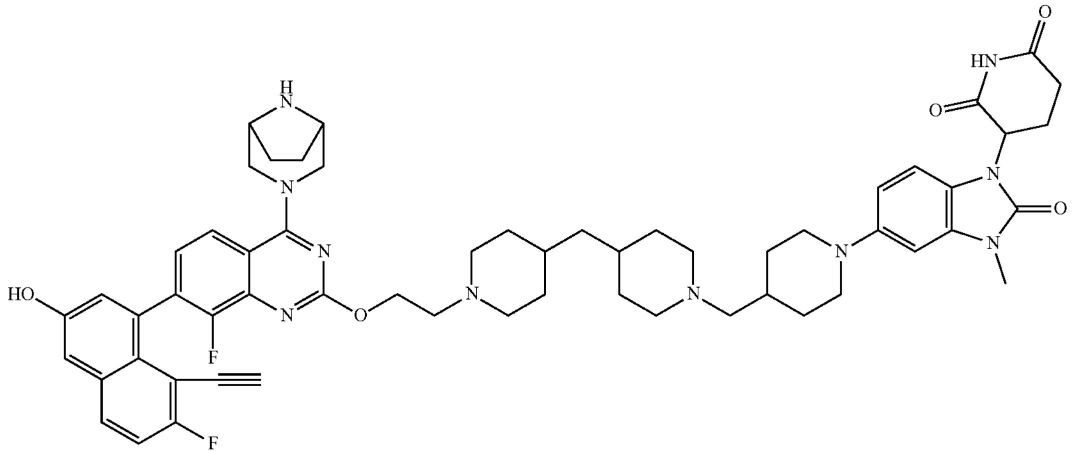 |

??TABLE 1-continued
| Compound | Structure |
| --- | --- |
| 238 | 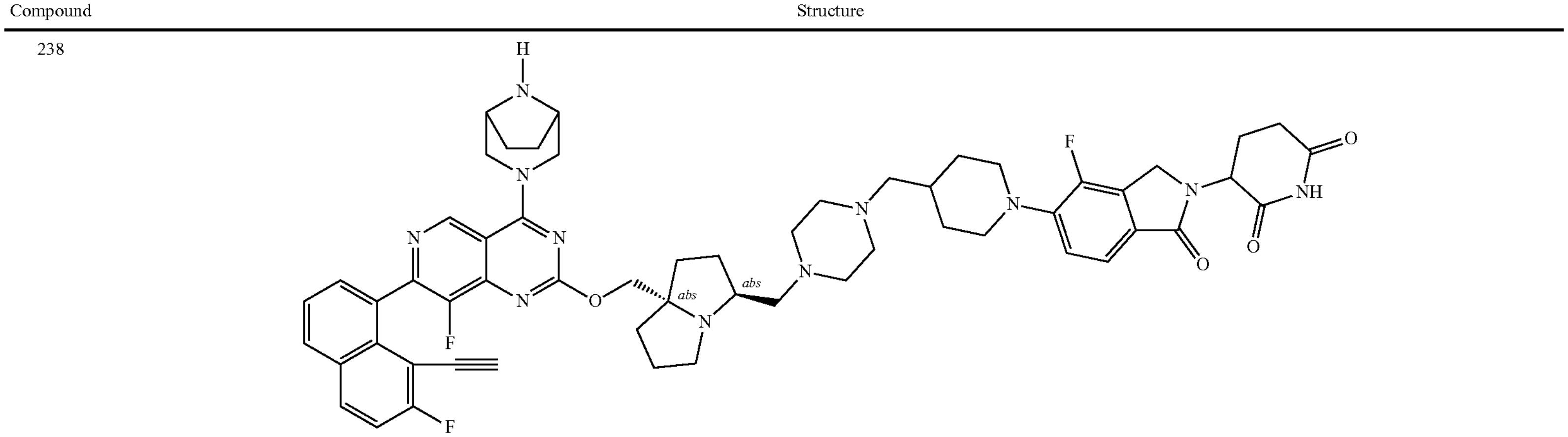 |
| 239 | 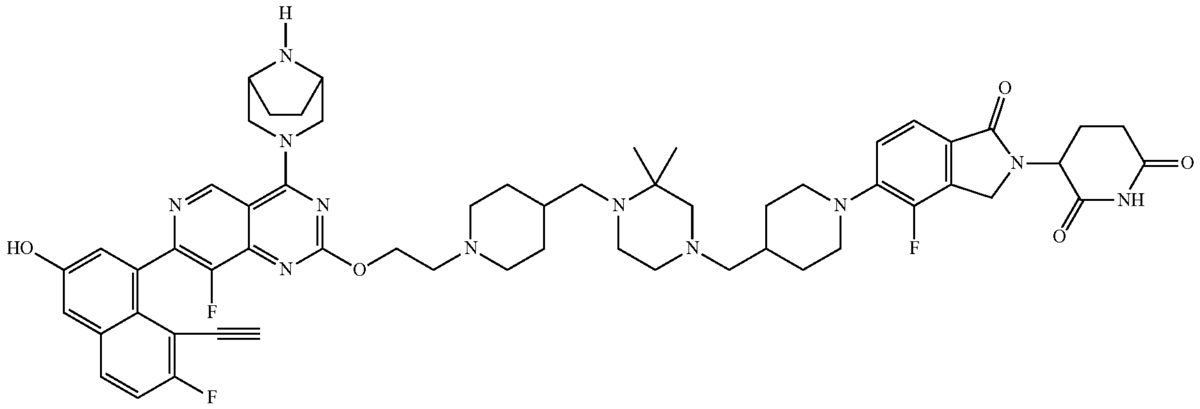 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)CC6(C)C)CC5)nc4c3F)c12] |

Also provided herein are pharmaceutical compositions comprising any of the compounds described herein or pharmaceutically acceptable salts thereof and a pharmaceutically acceptable carrier.

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound disclosed herein is a prodrug within the scope of the present disclosure.

Methods of Treatment

This application pertains to methods of treating or ameliorating a disease state or condition that is modulated through or causally related to the target protein, i.e., KRas.

Provided herein are methods of treating a disease or disorder comprising administering to a subject any of the compounds disclosed herein or pharmaceutically acceptable salts thereof, or a pharmaceutical composition disclosed herein.

In embodiments, the disease or disorder is cancer.

In embodiments, the cancer is bladder cancer, bowel cancer, breast cancer, cervical cancer, colon cancer, colorectal cancer, endometrial cancer, esophageal cancer, head cancer, kidney cancer, liver cancer, lung cancer, neck cancer, ovary cancer, pancreatic cancer, prostate cancer, stomach cancer, uterine cancer, ovarian cancer, testicular cancer, thyroid cancer, pineal cell tumor, carcinoma, cytoma, ependymoma, ganglioglioma, ganglioneuroma, gliobastoma, glioma, leukemia, lymphoma, medulloblastoma, melanoma, meningioma, myeloma, nephroblastoma, neuroblastoma, neurofibroma, oligodendroglioma peripheral neuroepithelioma, sarcoma, or schwannoma.

In embodiments, the carcinoma is teratocarcinoma. In embodiments, the cytoma is astrocytoma.

In embodiments, the carcinoma is squamous-cell carcinoma, basal cell carcinoma, adenocarcinoma, hepatocellular carcinoma, and renal cell carcinoma. In embodiments, the leukemia is precursor B-lymphoblastic leukemia, T-cell acute lymphoblastic Leukemia, adult T-cell leukemia, Philadelphia chromosome positive acute lymphoblastic leukemia, Philadelphia chromosome positive chronic myeloid leukemia, or acute lymphoblastic leukemia.

In embodiments, the lymphoma is Burkitt lymphoma, non-Hodgkin's lymphoma, precursor T-lymphoblastic lymphoma, peripheral T-cell lymphoma, precursor lymphoblastic lymphoma, diffuse large B-cell lymphoma, or B-cell lymphoma.

In embodiments, the lymphoma is Hodgkin's lymphoma (HL).

In embodiments, the nephroblastoma is Wilms' tumor. In embodiments, the sarcoma is selected from carcinosarcoma, Ewing's sarcoma, hemangiosarcoma, Kaposi's sarcoma, liposarcoma, myosarcoma, synovial sarcoma, and meningeal sarcoma.

Provided herein is a method for regulating KRas protein activity comprising administering to a subject any of the compounds disclosed herein or pharmaceutically acceptable salts thereof, or a pharmaceutical composition disclosed herein.

Also provided herein are methods for regulating cereblon protein activity comprising administering to a subject any of the compounds disclosed herein or pharmaceutically acceptable salts thereof, or a pharmaceutical composition disclosed herein.

Further provided herein are methods of degrading a target protein comprising contacting a cell with any of the compounds disclosed herein or pharmaceutically acceptable salts thereof, or a pharmaceutical composition disclosed herein.

Administration/Dosages/Formulations

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

To prolong the effect of a drug, it is often desirable to slow the absorption of the drug from subcutaneous or intramuscular injection. This may be accomplished using a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories that can be prepared by mixing the compounds of this disclosure with suitable non-irritating excipients or carriers such as cocoa butter, polyethylene glycol, or a suppository wax that are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants, or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams, and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present disclosure may be administered intratympanically, wherein a long, narrow, bore needle is passed through the ear canal and through the eardrum to administer medications into the middle ear space where they are absorbed by the inner ear.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means enough of the compound to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a subject in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular subject will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

Provided herein are kits comprising a compound capable of degrading KRas selected from one or more compounds disclosed herein, or pharmaceutically acceptable salts thereof, and instructions for use in treating a disorder associated with KRas.

The disclosure provides kits comprising a compound capable of degrading KRas selected from a compound disclosed herein, or a pharmaceutically acceptable salt thereof.

Provided herein are kits comprising a compound disclosed herein, or a pharmaceutically acceptable salt thereof, for the treatment of any of the indications disclosed herein.

Those skilled in the art will recognize, or be able to ascertain using no more than routine experimentation, numerous equivalents to the specific procedures, embodiments, claims, and examples described herein. Such equivalents were within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

The following examples further illustrate aspects of the present disclosure. However, they are in no way a limitation of the teachings of the present disclosure as set forth.

| Abbreviations | |
|---|---|
| AcOH or HOAc | Acetic acid |
| CBz | Benzyl chloroformate |
| Boc | tert-butoxycarbonyl |
| $CDCl_3$ | Chloroform-d |
| $CS_2CO_3$ | Cesium carbonate |
| DIEA | Diisopropylethylamine |
| $D_{max}$ | Maximal degradation (%) |
| DMF | N,N-Dimethylformamide |
| DMSO | Dimethyl sulfoxide |
| DMSO-$d_6$ | Deuterated dimethyl sulfoxide ($C_2D_6SO$) |
| DTT | Dithiothreitol |
| ESI | Electrospray ionization |
| EtOH | Ethanol |
| eq | Equivalent(s) |
| g | Gram(s) |
| h | Hour(s) |
| Hz | Hertz |
| HCl | Hydrochloric acid |
| HPLC | High performance liquid chromatography |
| $DC_{50}$ | Half maximal degradation concentration |
| $K_2CO_3$ | Potassium carbonate |
| $K_3PO_4$ | Potassium phosphate |
| min | Minute(s) |
| m/z | Mass/charge |
| MS | Mass spectrometry |
| MHz | Megahertz |
| MeOH | Methanol |
| MOM | Methoxymethyl |
| μL | Microliter(s) |
| μm | Micrometer(s) |
| mg | Milligram(s) |
| mm | Millimeter(s) |
| mL | Milliliter(s) |
| mmol | Millimole(s) |
| $NH_4Cl$ | Ammonium chloride |
| nM | Nanomolar |
| NMR | Nuclear magnetic resonance |
| Pd(dppf)$Cl_2$ | [1,1-Bis(diphenylphosphino)ferrocene] dichloropalladium(II), complex with dichloromethane |
| PMB | para-methoxybenzyl |
| psi | Pound(s) per square inch |
| TEA | Triethylamine |
| TFA | Trifluoroacetic acid |
| Tf | Trifluoromethanesulfonate |
| TIPS | Triisopropylsilyl ether |
| TBDPS | tert-butyldiphenylsilyl |
| THF | Tetrahydrofuran |
| TLC | Thin-layer chromatography |

Synthetic Procedures

Example 1: Synthesis of 3-[4-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl] oxyethyl]-4-piperidyl]methyl]-1-piperidyl]methyl]-1-piperidyl]-1-oxo-isoindolin-2-yl] piperidine-2,6-dione (Compound 43)

Step 1: Preparation of 2-chloro-3-fluoro-5-iodo-pyridin-4-amine

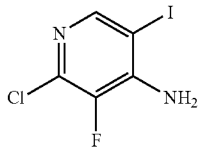

To a solution of 2-chloro-3-fluoro-pyridin-4-amine (2.00 g, 13.7 mmol, 1 eq) and NIS (3.68 g, 16.4 mmol, 1.2 eq) in $CH_3CN$ (15 mL) was added p-TsOH (118 mg, 0.682 mmol, 0.05 eq), and the reaction mixture was stirred at 70° C. for 16 hours. The reaction mixture was diluted with EtOAc (40 mL), and the resulting mixture was washed with saturated aqueous $Na_2CO_3$ (2×30 mL), saturated aqueous $Na_2SO_3$ (40 mL), brine (30 mL), dried over anhydrous $Na_2SO_4$, filtered, and concentrated under reduced pressure to give the title compound (3.63 g, 13.3 mmol, 98% yield) as a yellow solid. LC/MS (ESI) m/z: 272.8 $[M+H]^+$. $^1$H-NMR (400 MHz, DMSO-$d_6$) δ 8.09 (s, 1H), 6.67 (br s, 2H).

Step 2: Preparation of ethyl 4-amino-6-chloro-5-fluoro-pyridine-3-carboxylate

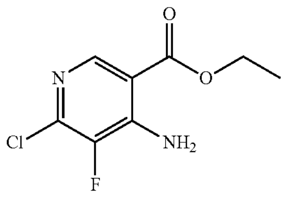

To a solution of 2-chloro-3-fluoro-5-iodo-pyridin-4-amine (3.63 g, 13.3 mmol, 1 eq) in EtOH (70 mL) were added triethylamine (4.85 g, 48.0 mmol, 6.68 mL, 3.6 eq) and $Pd(PPh_3)_2Cl_2$ (935 mg, 1.33 mmol, 0.1 eq), and the reaction mixture was stirred at 80° C. under CO (15 psi) (degassed under vacuum and purged with CO several times) for 16 hours. The reaction mixture was concentrated under reduced pressure to remove ~70% of EtOH and then filtered. The filter cake was washed with TBME (2×30 mL) and then dried under reduced pressure to give the title compound (3.40 g, crude) as a yellow solid. LC/MS (ESI) m/z: 219.0 $[M+H]^+$.

Step 3: Preparation of ethyl 6-chloro-5-fluoro-4-[(2,2,2-trichloroacetyl)carbamoylamino]pyridine-3-carboxylate

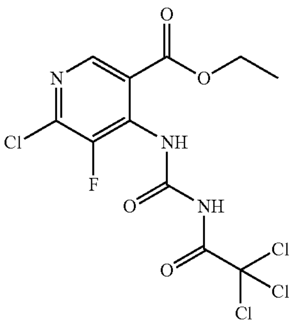 [SMILES: CCOC(=O)c1cnc(Cl)c(F)c1NC(=O)NC(=O)C(Cl)(Cl)Cl]

To a solution of ethyl 4-amino-6-chloro-5-fluoro-pyridine-3-carboxylate (3.40 g, 15.6 mmol, 1 eq) in THF (10 mL) was added 2,2,2-trichloroacetyl isocyanate (3.22 g, 17.1 mmol, 2.03 mL, 1.1 eq), and the reaction mixture was stirred at 20° C. under $N_2$ for 1 hour. The reaction mixture was concentrated under reduced pressure to give the title compound (6.10 g, crude) as a brown solid. LC/MS (ESI) m/z: 408.1 $[M+H]^+$.

Step 4: Preparation of 7-chloro-8-fluoro-pyrido[4,3-d]pyrimidine-2,4-diol

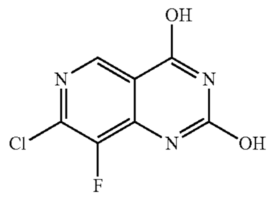 [SMILES: Oc1nc(O)c2cnc(Cl)c(F)c2n1]

To a solution of ethyl 6-chloro-5-fluoro-4-[(2,2,2-trichloroacetyl)carbamoylamino]pyridine-3-carboxylate (6.10 g, 15.0 mmol, 1 eq) in $CH_3OH$ (55 mL) was added ammonia (7 M, 10.7 mL, 5 eq), and the reaction mixture was stirred at 20° C. for 1 hour. The reaction mixture was filtered, and the filter cake was washed with TBME (3×20 mL), then dried under reduced pressure to give the title compound (3.03 g, 14.06 mmol, 94% yield) as a white solid. LC/MS (ESI) m/z: 216.1 $[M+H]^+$.

Step 5: Preparation of 2,4,7-trichloro-8-fluoro-pyrido[4,3-d]pyrimidine

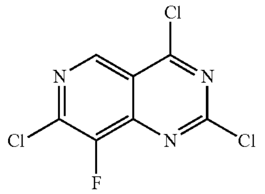 [SMILES: Fc1c(Cl)ncc2c(Cl)nc(Cl)nc12]

To a solution of 7-chloro-8-fluoro-pyrido[4,3-d]pyrimidine-2,4-diol (2.50 g, 11.6 mmol, 1 eq) in toluene (30 mL) were added DIEA (4.50 g, 34.8 mmol, 6.06 mL, 3 eq) and $POCl_3$ (8.89 g, 58.0 mmol, 5.39 mL, 5 eq), and the reaction mixture was stirred at 100° C. under $N_2$ for 1 hour. The reaction mixture was concentrated under reduced pressure to give the title compound (2.9 g, crude) as a yellow oil. LC/MS (ESI) m/z: 253.7 $[M+H]^+$.

Step 6: Preparation of tert-butyl 3-(2,7-dichloro-8-fluoro-pyrido[4,3-d]pyrimidin-4-yl)-3,8-diazabicyclo[3.2.1]octane-8-carboxylate

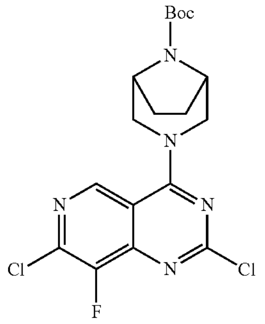 [SMILES: CC(C)(C)OC(=O)N1C2CCC1CN(c1nc(Cl)nc3c(F)c(Cl)ncc13)C2]

To a solution of 2,4,7-trichloro-8-fluoro-pyrido[4,3-d] pyrimidine (2.90 g, 11.5 mmol, 1 eq) in $CH_2Cl_2$ (50 mL) were added DIEA (7.42 g, 57.4 mmol, 5 eq) and tert-butyl (1S,5R)-3,8-diazabicyclo[3.2.1]octane-8-carboxylate (2.44 g, 11.5 mmol, 1 eq) at −40° C., and the reaction mixture was stirred at −40° C. under $N_2$ for 0.5 hour. The reaction mixture was poured into water (50 mL) and extracted with $CH_2Cl_2$ (3×50 mL). The combined organic layer was washed with brine (2×60 mL), dried over anhydrous $Na_2SO_4$, filtered, and concentrated under reduced pressure to give crude product. The crude product was purified by flash silica gel chromatography (eluent: 0-25% EtOAc/petroleum ether) to give the title compound (2.47 g, 5.77 mmol, 50% yield) as a yellow solid. LC/MS (ESI) m/z: 428.2 $[M+H]^+$. $^1$H-NMR (400 MHz, DMSO-$d_6$) δ 9.06 (s, 1H), 4.60-4.40 (m, 2H), 4.31-4.22 (m, 2H), 3.80-3.59 (m, 2H), 1.85-1.74 (m, 2H), 1.66-1.57 (m, 2H), 1.46 (s, 9H).

Step 7: Preparation of tert-butyl 3-[7-chloro-2-(2,2-dimethoxyethoxy)-8-fluoro-pyrido[4,3-d]pyrimidin-4-yl]-3,8-diazabicyclo[3.2.1]octane-8-carboxylate

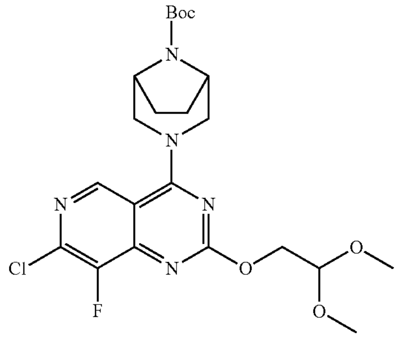 [SMILES: COC(COc1nc(N2CC3CCC(C2)N3C(=O)OC(C)(C)C)c2cnc(Cl)c(F)c2n1)OC]

To a solution of tert-butyl 3-(2,7-dichloro-8-fluoro-pyrido[4,3-d]pyrimidin-4-yl)-3,8-diazabicyclo[3.2.1]octane-8-carboxylate (500 mg, 1.17 mmol, 1 eq) and 2,2-dimethoxyethanol (186 mg, 1.75 mmol, 1.5 eq) in $CH_3CN$ (10 mL) were added $Cs_2CO_3$ (456 mg, 1.40 mmol, 1.2 eq) and DABCO (13 mg, 0.17 mmol, 0.1 eq), and the reaction mixture was stirred at 20° C. under $N_2$ for 16 hours. The reaction mixture was filtered, and the filtrate was concentrated under reduced pressure to give crude product. The crude product was purified by flash silica gel chromatography (eluent: 0-15% THF/petroleum ether) to give the title compound. LC/MS (ESI) m/z: 498.3 $[M+H]^+$. $^1$H-NMR (400 MHz, $CDCl_3$) δ 8.74 (s, 1H), 4.81 (t, J=5.6 Hz, 1H), 4.54-4.45 (m, 4H), 4.43-4.27 (m, 2H), 3.74-3.55 (m, 2H), 3.48 (s, 6H), 2.02-1.90 (m, 2H), 1.75-1.65 (m, 2H), 1.52 (s, 9H).

Step 8: Preparation of 5-[2-(4-fluorophenyl)acetyl]-2,2-dimethyl-1,3-dioxane-4,6-dione

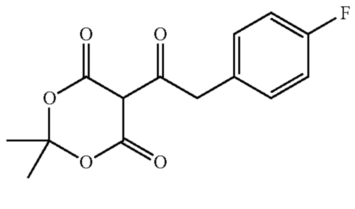 [SMILES: CC1(C)OC(=O)C(C(=O)Cc2ccc(F)cc2)C(=O)O1]

To a solution of 2-(4-fluorophenyl)acetic acid (50 g, 324.38 mmol, 1.0 eq), 2,2-dimethyl-1,3-dioxane-4,6-dione (51.4 g, 356.82 mmol, 1.1 eq), and DMAP (3.4 g, 27.57 mmol, 0.085 eq) in $CH_3CN$ (150 mL) was added DIEA (121 mL, 697.43 mmol, 2.2 eq) followed by 2,2-dimethylpropanoyl chloride (44 mL, 356.82 mmol, 1.1 eq) slowly over 3 hours while maintaining the temperature below 45° C. The reaction mixture was stirred at 45° C. for 3 hours. The reaction was cooled to 0° C. HCl (500 mL, 1 M, 1.54 eq) was then added, and the mixture was stirred at 0° C. for 30 minutes. The mixture was filtered, and the filter cake was washed with water ($CH_3CN$:Water=1:4, 500 mL). The filter cake was dissolved with $CH_2Cl_2$ (500 mL), dried over anhydrous sodium sulfate, filtered, and concentrated in vacuum to give the title compound (84.5 g, 301.52 mmol, 93% yield) as a white solid.

Step 9: Preparation of tert-butyl 4-(4-fluorophenyl)-3-oxo-butanoate

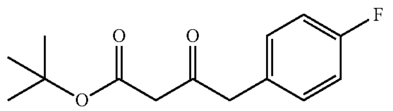 [SMILES: CC(C)(C)OC(=O)CC(=O)Cc1ccc(F)cc1]

A solution of 5-[2-(4-fluorophenyl)acetyl]-2,2-dimethyl-1,3-dioxane-4,6-dione (168 g, 601.25 mmol, 1.0 eq) in t-BuOH (500 mL) was stirred at 90° C. for 2.5 hours. The reaction mixture was concentrated in vacuum to give the title compound (151 g, 598.54 mmol, 100% yield) as a yellow oil. LC/MS (ESI) m/z: 197.1 $[M-56]^+$.

Step 10: Preparation of 4-(4-fluorophenyl)-3-oxo-butanoic acid

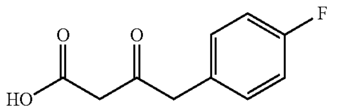 [SMILES: O=C(O)CC(=O)Cc1ccc(F)cc1]

To a solution of tert-butyl 4-(4-fluorophenyl)-3-oxo-butanoate (151 g, 598.54 mmol, 1.0 eq) in $CH_2Cl_2$ (300 mL) was added TFA (293 mL, 3.95 mol, 6.60 eq), and the reaction mixture was stirred at 20° C. for 1 hour. The mixture was concentrated in vacuum to give the title compound (115 g, 532.28 mmol, 89% yield) as a yellow solid. LC/MS (ESI) m/z: 197.1 $[M+H]^+$.

Step 11: Preparation of 7-fluoronaphthalene-1,3-diol

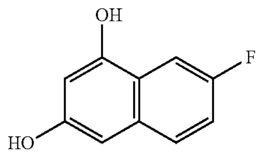 [SMILES: Oc1cc(O)c2cc(F)ccc2c1]

A solution of 4-(4-fluorophenyl)-3-oxo-butanoic acid (115 g, 586.21 mmol, 1.0 eq) in $CF_3SO_3H$ (1200 mL) was stirred at 20° C. for 16 hours. The reaction was cooled to 0°

C., and slowly poured onto ice-water (3.0 L). The resulting precipitate was filtered, and the filter cake was dissolved with ethyl acetate (200 mL×3). The combined organic phase was washed with saturated aqueous $NaHCO_3$ (40 mL×2) and brine (40 mL), dried over anhydrous sodium sulfate, filtered, and concentrated in vacuum to give the title compound (54.4 g, 267.18 mmol, 46% yield) as a red solid. LC/MS (ESI) m/z: 179.1 $[M+H]^+$. $^1H$ NMR (400 MHz, DMSO-$d_6$) b 10.19 (s, 1H), 9.49 (s, 1H), 7.67-7.53 (m, 2H), 7.25-7.20 (m, 1H), 6.64 (s, 1H), 6.56 (s, 1H).

Step 12: Preparation of 7-fluoro-8-(2-triisopropylsilylethynyl)naphthalene-1,3-diol

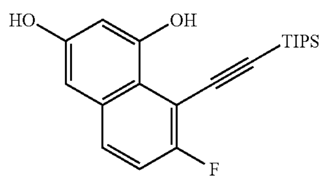

To a solution of 7-fluoronaphthalene-1,3-diol (43.5 g, 244.23 mmol, 1.0 eq), 2-bromoethynyl(triisopropyl)silane (67 g, 256.44 mmol, 1.05 eq), and KOAc (48 g, 488.45 mmol, 2.0 eq) in dioxane (300 mL) was added dichlororuthenium; 1-isopropyl-4-methyl-benzene (9.0 g, 14.65 mmol, 0.06 eq) under $N_2$, and the reaction mixture was stirred at 110° C. for 16 hours.

The mixture was filtered and concentrated in vacuum, and the resulting residue was purified by flash chromatography on $SiO_2$ (gradient: 0-20% ethyl acetate in petroleum ether) to afford the title compound (46.3 g, 124.11 mmol, 51% yield) as a black oil. LC/MS (ESI) m/z: 359.2 $[M+H]^+$. $^1H$ NMR (400 MHz, $CDCl_3$) δ 9.17 (s, 1H), 7.61-7.57 (m, 1H), 7.17 (t, J=8.8 Hz, 1H), 6.74 (d, J=2.4 Hz, 1H), 6.66 (d, J=2.0 Hz, 1H), 1.22-1.16 (m, 21H).

Step 13: Preparation of 7-fluoro-3-(methoxymethoxy)-8-(2-triisopropylsilylethynyl)naphthalen-1-ol

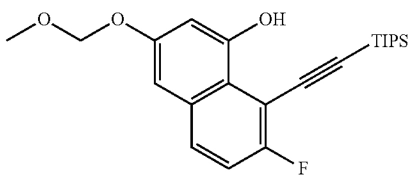

To a solution of 7-fluoro-8-(2-triisopropylsilylethynyl)naphthalene-1,3-diol (46.3 g, 129.14 mmol, 1.0 eq) in $CH_2Cl_2$ (450 mL) at 0° C. were added DIEA (67.5 mL, 387.43 mmol, 3.0 eq) and MOMCl (14.7 mL, 193.71 mmol, 1.5 eq), and the reaction mixture was stirred at 0° C. for 40 minutes. The reaction was quenched by addition of water (50 mL) at 0° C., then extracted with dichloromethane (50 mL×3). The combined organic extract was washed with brine (30 mL), dried over anhydrous sodium sulfate, filtered, and concentrated in vacuum. The resulting residue was purified by flash chromatography on $SiO_2$ (gradient: 0-15% dichloromethane in petroleum ether) to afford the title compound (26.8 g, 62.51 mmol, 48% yield) as a yellow oil. LC/MS (ESI) m/z: 403.1 $[M+H]^+$.

Step 14: Preparation of [7-fluoro-3-(methoxymethoxy)-8-(2-triisopropylsilylethynyl)-1-naphthyl]trifluoromethanesulfonate

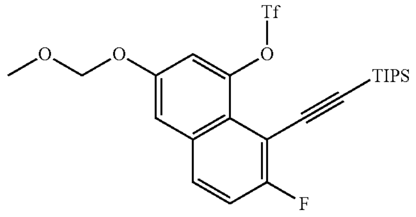

To a solution of 7-fluoro-3-(methoxymethoxy)-8-(2-triisopropylsilylethynyl)naphthalen-1-ol (21.8 g, 54.15 mmol, 1.0 eq) and DIEA (28.3 mL, 162.45 mmol, 3.0 eq) in $CH_2Cl_2$ (300 mL) at −40° C. was added $Tf_2O$ (13.4 mL, 81.23 mmol, 1.5 eq), and the reaction mixture was stirred at −40° C. for 40 minutes. The reaction was quenched by addition of water (150 mL) at −40° C., warmed to 25° C., and then extracted with dichloromethane (100 mL×3). The combined organic extract was washed with brine (50 mL), dried over anhydrous sodium sulfate, and concentrated in vacuum. The resulting residue was purified by flash chromatography on $SiO_2$ (gradient: 0-15% dichloromethane in petroleum ether) to the title compound (28 g, 51.95 mmol, 96% yield) as a yellow oil.

Step 15: Preparation of 2-[2-fluoro-6-(methoxymethoxy)-8-(4,4,5,5-tetramethyl-1,3,2-dioxaborolan-2-yl)-1-naphthyl]ethynyl-triisopropyl-silane

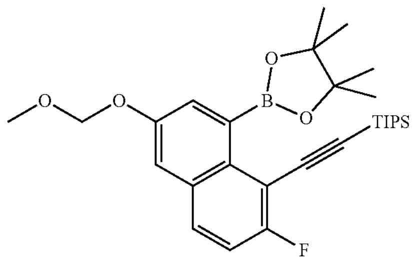

To a solution of [7-fluoro-3-(methoxymethoxy)-8-(2-triisopropylsilylethynyl)-1-naphthyl]trifluoromethanesulfonate (23.8 g, 44.52 mmol, 1.0 eq), 4,4,5,5-tetramethyl-2-(4,4,5,5-tetramethyl-1,3,2-dioxaborolan-2-yl)-1,3,2-dioxaborolane (22.6 g, 89.03 mmol, 2.0 eq), and KOAc (13.1 g, 133.55 mmol, 3.0 eq) in toluene (350 mL) was added Pd(dppf)$Cl_2$ (3.26 g, 4.45 mmol, 0.1 eq) under $N_2$, and the reaction mixture was stirred at 110° C. for 16 hours under $N_2$. The mixture was filtered through a pad of Celite® under vacuum and rinsed with ethyl acetate (80 mL×2). The filtrate was evaporated to dryness, and the resulting residue was purified by flash chromatography on $SiO_2$ (gradient: 0-3% ethyl acetate in petroleum ether) to afford the title compound (21.4 g, 27.97 mmol, 63% yield) as a yellow solid. LC/MS (ESI) m/z: 513.0 $[M+H]^+$.

Step 16: Preparation of tert-butyl 3-[2-(2,2-dimethoxyethoxy)-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

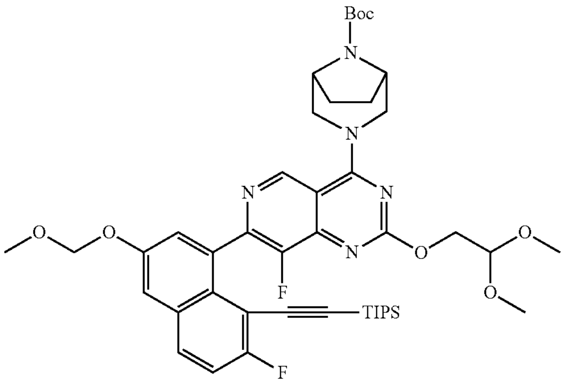

To a solution of tert-butyl 3-[7-chloro-2-(2,2-dimethoxyethoxy)-8-fluoro-pyrido[4,3-d]pyrimidin-4-yl]-3,8-diazabicyclo[3.2.1]octane-8-carboxylate (400 mg, 0.803 mmol, 1.0 eq) and 2-[2-fluoro-6-(methoxymethoxy)-8-(4,4,5,5-tetramethyl-1,3,2-dioxaborolan-2-yl)-1-naphthyl]ethynyl-triisopropyl-silane (494 mg, 0.964 mmol, 1.2 eq) in dioxane (10 mL) and $H_2O$ (2 mL) were added $K_3PO_4$ (512 mg, 2.41 mmol, 3.0 eq) and [2-(2-aminophenyl)phenyl]palladium (1+);bis(1-adamantyl)-butyl-phosphane;methanesulfonate (117 mg, 0.161 mmol, 0.2 eq) under $N_2$, and the reaction mixture was stirred at 85° C. for 15 hours under $N_2$. The mixture was dried over anhydrous sodium sulfate, filtered, and concentrated in vacuum. The resulting residue was purified by flash chromatography on $SiO_2$ (gradient: 0-27% ethyl acetate in petroleum ether) to afford the title compound (590 mg, 0.684 mmol, 85% yield) as a yellow solid. LC/MS (ESI) m/z: 848.4 $[M+H]^+$.

Step 17: Preparation of tert-butyl 3-[8-fluoro-7-[7-fluoro-3-hydroxy-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate

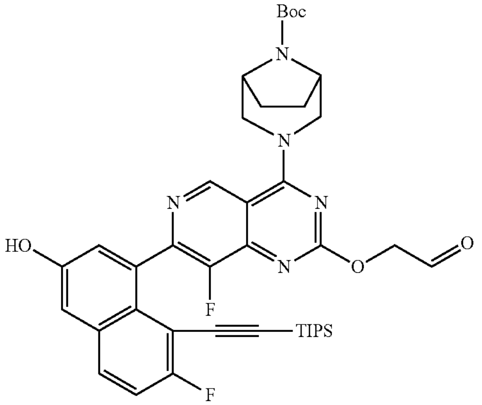

To a solution of tert-butyl 3-[2-(2,2-dimethoxyethoxy)-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (630 mg, 0.743 mmol, 1.0 eq) in acetone (1.6 mL) was added aqueous HCl (1.58 mL, 12 M, 25.51 eq), and the reaction mixture was stirred at 20° C. for 15 minutes. A solution of $NaHCO_3$ (867 μL, 22.29 mmol, 30.0 eq) in water (3 mL), $Boc_2O$ (341 μL, 1.49 mmol, 2.0 eq), and THF (3 mL) were added, and the reaction mixture was stirred at 20° C. for 1 hour. The mixture was diluted with water (20 mL) and extracted with ethyl acetate (40 mL×3). The combined organic extracts were washed with brine (20 mL), dried over anhydrous $Na_2SO_4$, filtered, and concentrated in vacuum. The resulting residue was purified by flash chromatography on $SiO_2$ (gradient: 0-50% ethyl acetate in petroleum ether) to afford the title compound (420 mg, 386.23 μmol, 52% yield) as a yellow solid. LC/MS (ESI) m/z: 758.4 $[M+H]^+$.

Step 18: Preparation of 2-bromo-6-[4-(dimethoxymethyl)-1-piperidyl]benzaldehyde

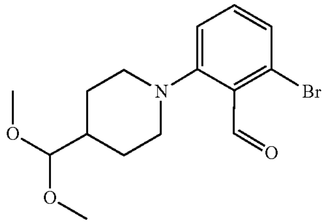 [SMILES: COC(OC)C1CCN(c2cccc(Br)c2C=O)CC1]

To a solution of 4-(dimethoxymethyl)piperidine (8.47 g, 53.20 mmol, 1.20 eq) and 2-bromo-6-fluoro-benzaldehyde (9.00 g, 44.33 mmol, 1 eq) in DMSO (90 mL) was added N,N-diisopropylethylamine (22.92 g, 177.33 mmol, 4.00 eq), and the reaction mixture was stirred at 100° C. for 12 hours. The residue was diluted with water (100 mL) and extracted with ethyl acetate (100 mL). The combined organic extracts were washed with brine (100 mL), dried over anhydrous sodium sulfate, filtered, and concentrated under reduced pressure. The residue was purified by flash silica gel chromatography (gradient: 0-7% ethyl acetate/petroleum ether) to give the title compound (11.10 g, 32.43 mmol, 73% yield) as a yellow solid. LC/MS (ESI) m/z: 344.1 $[M+H]^+$. $^1H$ NMR (400 MHz, $CDCl_3$) δ 10.22 (s, 1H), 7.31-7.28 (m, 2H), 7.14-7.04 (m, 1H), 4.19-4.13 (m, 1H), 3.42 (s, 6H), 3.36-3.28 (m, 2H), 2.86 (dd, J=2.0, 12.0 Hz, 2H), 1.93-1.84 (m, 2H), 1.78 (dd, J=4.0, 7.2, 15.2 Hz, 1H), 1.65-1.54 (m, 2H).

Step 19: Preparation of 3-[[2-bromo-6-[4-(dimethoxymethyl)-1-piperidyl]phenyl]methylamino]piperidine-2,6-dione

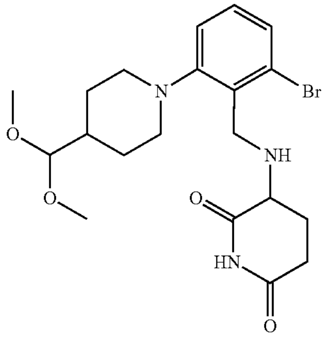 [SMILES: COC(OC)C1CCN(c2cccc(Br)c2CNC2CCC(=O)NC2=O)CC1]

To a solution of 3-aminopiperidine-2,6-dione (5.05 g, 30.68 mmol, 1.00 eq, hydrochloride) in methanol (100 mL) and dichloromethane (100 mL) was added sodium acetate (7.55 g, 92.04 mmol, 3.00 eq), and the resulting mixture was stirred at 25° C. for 1 hour. 2-Bromo-6-[4-(dimethoxymethyl)-1-piperidyl]benzaldehyde (10.50 g, 30.68 mmol, 1.00 eq) and 2-methylpyridine borane (6.56 g, 61.36 mmol, 2.00 eq) were then added, and the reaction mixture was stirred at 25° C. for 12 hours. The reaction mixture was filtered. and the filtrate was diluted with water (100 mL), then extracted with ethyl acetate (100 mL). The organic extract was washed with brine (100 mL), dried over anhydrous sodium sulfate, filtered, and concentrated under reduced pressure. The crude product was triturated with ethyl acetate/petroleum (3:1) to give the title compound (10.70 g, 23.55 mmol, 77% yield) as a purple solid. LC/MS (ESI) m/z: 456.1 $[M+H]^+$. $^1H$ NMR (400 MHz, $CDCl_3$) δ 10.78 (s, 1H), 7.36-7.29 (m, 1H), 7.21-7.11 (m, 2H), 4.12 (d, J=6.8 Hz, 1H), 3.99-3.82 (m, 2H), 3.30-3.27 (m, 6H), 3.23 (dd, J=4.8, 11.2 Hz, 1H), 3.09 (d, J=10.8 Hz, 1H), 3.01-2.81 (m, 1H), 2.77-2.65 (m, 1H), 2.60-2.53 (m, 2H), 2.48-2.41 (m, 1H), 2.35-2.22 (m, 1H), 1.80-1.61 (m, 4H), 1.51-1.30 (m, 2H).

Step 20: Preparation of 3-[4-[4-(dimethoxymethyl)-1-piperidyl]-1-oxo-isoindolin-2-yl]piperidine-2,6-dione

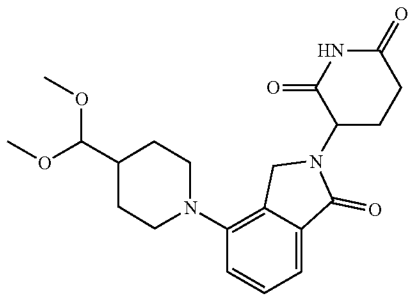 [SMILES: COC(OC)C1CCN(c2cccc3c2CN(C2CCC(=O)NC2=O)C3=O)CC1]

To a solution of 3-[[2-bromo-6-[4-(dimethoxymethyl)-1-piperidyl]phenyl]methylamino]piperidine-2,6-dione (10.70 g, 23.55 mmol, 1.00 eq) in DMF (150 mL) were added [1,1'-bis(diphenylphosphino)ferrocene]dichloropalladium (ii) (3.45 g, 4.71 mmol, 0.20 eq) and diisopropylethylamine (9.13 g, 70.65 mmol, 3.00 eq), and the reaction mixture was degassed and purged with carbon dioxide (3×), then stirred at 80° C. for 12 hours under carbon dioxide (50 Psi) atmosphere. The reaction mixture was filtered, and the filtrate was diluted with water (200 mL), then extracted with ethyl acetate (150 mL). The organic extract was washed with brine (150 mL), dried over anhydrous sodium sulfate, filtered, and concentrated under reduced pressure. The residue was purified by prep-HPLC (column: Phenomenex Luna C18 (250*80 mm*15 μm); mobile phase: [20-50% $CH_3CN$ in water (trifluoroacetic acid)]) to give the title compound (2.60 g, 6.48 mmol, 27% yield) as a white solid. LC/MS (ESI) m/z: 402.2 $[M+H]^+$.

Step 21: Preparation of 1-[2-(2,6-dioxo-3-piperidyl)-1-oxo-isoindolin-4-yl]piperidine-4-carbaldehyde

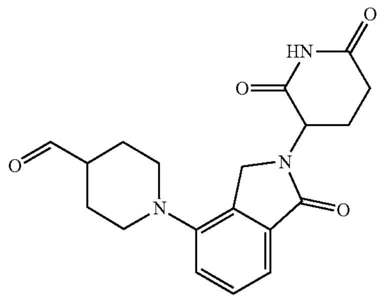 [SMILES: O=CC1CCN(c2cccc3c2CN(C2CCC(=O)NC2=O)C3=O)CC1]

To a solution of 3-[4-[4-(dimethoxymethyl)-1-piperidyl]-1-oxo-isoindolin-2-yl]piperidine-2,6-dione (70 mg, 0.17 mmol, 1.00 eq) in dichloromethane (2 mL) was added trifluoroacetic acid (60 mg, 0.52 mmol, 3.00 eq), and the reaction mixture was stirred at 25° C. for 1 hour. The mixture was concentrated under reduced pressure to give the title compound (80 mg, crude) as a colorless oil. LC/MS (ESI) m/z: 356.2 $[M+H]^+$.

Step 22: Preparation of tert-butyl 4-[[1-[[1-[2-(2,6-dioxo-3-piperidyl)-1-oxo-isoindolin-4-yl]-4-piperidyl]methyl]-4-piperidyl]methyl]piperidine-1-carboxylate

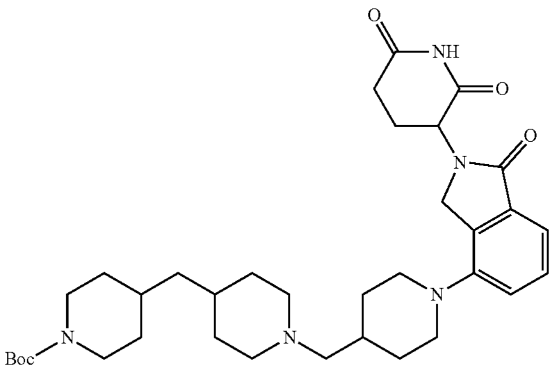 [SMILES: CC(C)(C)OC(=O)N1CCC(CC2CCN(CC3CCN(c4cccc5c4CN(C4CCC(=O)NC4=O)C5=O)CC3)CC2)CC1]

To a solution of 1-[2-(2,6-dioxo-3-piperidyl)-1-oxo-isoindolin-4-yl]piperidine-4-carbaldehyde (340 mg, 0.95 mmol, 1 eq) in dimethyl sulfoxide (3 mL) and dichloromethane (3 mL) were added N-methylmorpholine (484 mg, 4.78 mmol, 0.5 mL, 5 eq), tert-butyl 4-(4-piperidylmethyl) piperidine-1-carboxylate (324 mg, 1.15 mmol, 1.2 eq), and acetic acid (57 mg, 0.95 mmol, 0.1 mL, 1 eq), and the resulting mixture was stirred at 25° C. for 1 hour. Sodium triacetoxyborohydride (406 mg, 1.91 mmol, 2 eq) was then added, and the reaction mixture was stirred at 25° C. for 15 hours. The mixture was diluted with water (15 mL) and extracted with 5:1 dichloromethane/isopropanol (10×3 mL). The organic extract was washed with brine (10×3 mL), dried over anhydrous sodium sulfate, filtered, and concentrated in vacuum. The resulting residue was purified by flash silica gel chromatography (gradient: 0-100% ethyl acetate in petroleum ether gradient) to afford the title compound (312 mg, 0.50 mmol, 52% yield) as a yellow oil. LC/MS (ESI) m/z: 622.5 $[M+H]^+$. $^1H$ NMR (400 MHz, DMSO-$d_6$) δ 10.98 (s, 1H), 7.46-7.40 (m, 1H), 7.30 (d, J=7.2 Hz, 1H), 7.16 (d, J=7.6 Hz, 1H), 5.14-5.08 (m, 1H), 4.43 (d, J=17.2 Hz, 1H), 4.29 (d, J=17.2 Hz, 1H), 4.13 (s, 1H), 3.92 (s, 2H), 3.34 (d, J=0.8 Hz, 4H), 3.16 (s, 4H), 2.77 (d, J=10.8 Hz, 5H), 1.99-1.89 (m, 6H), 1.76-1.71 (m, 4H), 1.60 (d, J=12.4 Hz, 4H), 1.38 (s, 9H), 1.12 (s, 2H), 1.03 (d, J=6.0 Hz, 1H), 0.95-0.90 (m, 2H).

Step 23: Preparation 3-[1-oxo-4-[4-[[4-(4-piperidylmethyl)-1-piperidyl] methyl]-1-piperidyl]isoindolin-2-yl]piperidine-2,6-dione

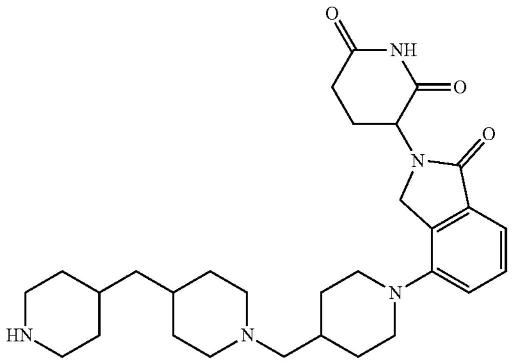 [SMILES: O=C1CCC(N2Cc3c(cccc3N3CCC(CN4CCC(CC5CCNCC5)CC4)CC3)C2=O)C(=O)N1]

To a solution of tert-butyl 4-[[1-[[1-[2-(2,6-dioxo-3-piperidyl)-1-oxo-isoindolin-4-yl]-4-piperidyl]methyl]-4-piperidyl]methyl]piperidine-1-carboxylate (412 mg, 0.66 mmol, 1 eq) in dichloromethane (3 mL) was added trifluoroacetic acid (1.54 g, 13.51 mmol, 1 mL, 20.38 eq), and the reaction mixture was stirred at 25° C. for 2 hours. The mixture was concentrated in vacuum, and the resulting residue was purified by prep-HPLC (column: Unisil 3-100 C18 Ultra 150*50 mm*3 μm; mobile phase: [1-18% $CH_3CN$ in water (formic acid)]) to afford the title compound (200 mg, 0.38 mmol, 58% yield) as a yellow solid. LC/MS (ESI) m/z: 522.4 $[M+H]^+$.

Step 24: Preparation of tert-butyl 3-[2-[2-[4-[[1-[[1-[2-(2,6-dioxo-3-piperidyl)-1-oxo-isoindolin-4-yl]-4-piperidyl]methyl]-4-piperidyl]methyl]-1-piperidyl] ethoxy]-8-fluoro-7-[7-fluoro-3-hydroxy-8-(2-triisopropylsilylethynyl)-1-naphthyl]pyrido [4,3-d]pyrimidin-4-yl]-3,8-diazabicyclo[3.2.1]octane-8-carboxylate

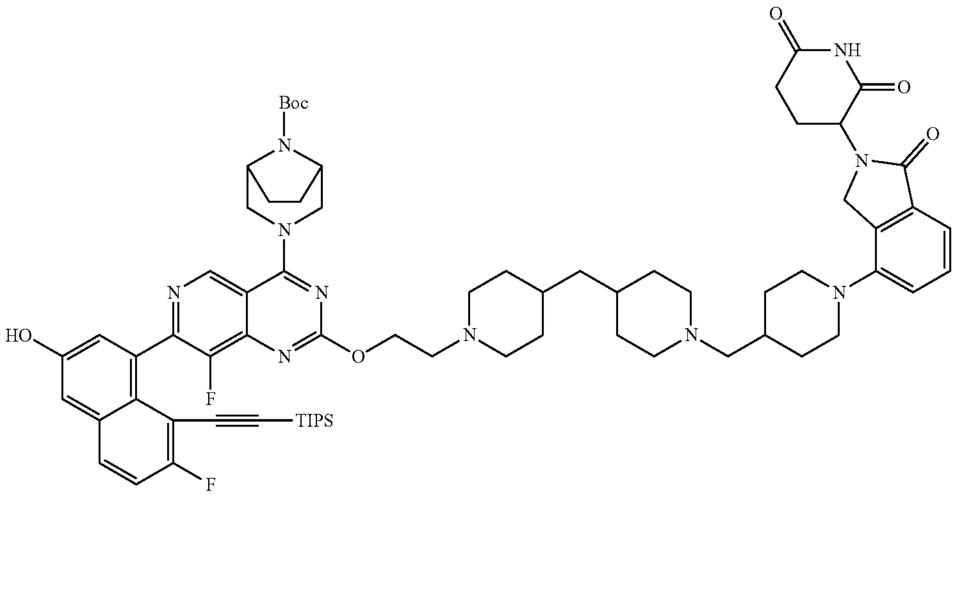

To a solution of 3-[1-oxo-4-[4-[[4-(4-piperidylmethyl)-1-piperidyl] methyl]-1-piperidyl]isoindolin-2-yl]piperidine-2,6-dione (90 mg, 0.17 mmol, 1 eq) in 1,2-dichloroethane (5 mL) and dimethyl sulfoxide (5 mL) was added 4-methylmorpholine (26 mg, 0.26 mmol, 28 μL, 1.5 eq), and the resulting mixture was stirred at 25° C. for 15 minutes. tert-Butyl 3-[8-fluoro-7-[7-fluoro-3-hydroxy-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (144 mg, 0.19 mmol, 1.1 eq) was then added, and the mixture was stirred for 0.5 h at 25° C. Sodium triacetoxyborohydride (110 mg, 0.52 mmol, 3 eq) was added, and the reaction mixture was stirred at 25° C. for 2 hours. The reaction was quenched with water (20 mL), and the resulting mixture was extracted with ethyl acetate (20 mL×3). The combined organic extract was washed with brine (20 mL), dried over anhydrous sodium sulfate, filtered, and concentrated. The resulting residue was purified by preparative TLC (dichloromethane/methanol=10/1) to afford the title compound (110 mg, 0.09 mmol, 50% yield) as a yellow solid. LC/MS (ESI) m/z: 1263.7 [M+H]$^+$.

Step 25: Preparation of tert-butyl 3-[2-[2-[4-[[1-[[1-[2-(2,6-dioxo-3-piperidyl)-1-oxo-isoindolin-4-yl]-4-piperidyl]methyl]-4-piperidyl]methyl]-1-piperidyl] ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate

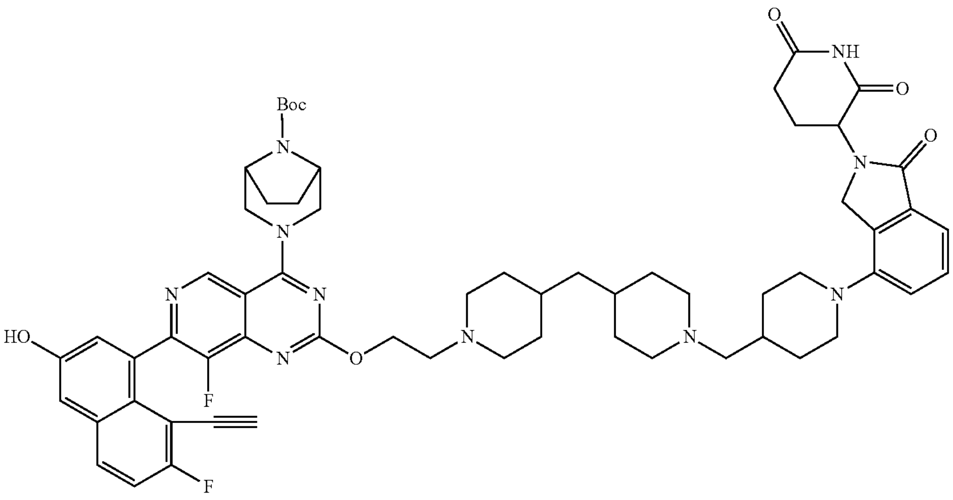 [SMILES: C#Cc1c(F)ccc2cc(O)cc(-c3ncc4c(N5CC6CCC(C5)N6C(=O)OC(C)(C)C)nc(OCCN5CCC(CC6CCN(CC7CCN(c8cccc9c8CN(C8CCC(=O)NC8=O)C9=O)CC7)CC6)CC5)nc4c3F)c12]

To a solution of tert-butyl 3-[2-[2-[4-[[1-[[1-[2-(2,6-dioxo-3-piperidyl)-1-oxo-isoindolin-4-yl]-4-piperidyl] methyl]-4-piperidyl]methyl]-1-piperidyl] ethoxy]-8-fluoro-7-[7-fluoro-3-hydroxy-8-(2-triisopropylsilylethynyl)-1-naphthyl]pyrido [4,3-d]pyrimidin-4-yl]-3,8-diazabicyclo [3.2.1]octane-8-carboxylate (100 mg, 0.08 mmol, 1 eq) in DMF (3 mL) at 20° C. was added cesium fluoride (240 mg, 1.58 mmol, 20 eq), and the reaction mixture was stirred at 20° C. for 2 hours. The reaction was quenched with water (20 mL), and the resulting mixture was extracted with ethyl acetate (20 mL×3). The combined organic extract was washed with brine (20 mL), dried over anhydrous sodium sulfate, filtered, and concentrated to afford the title compound (80 mg, 0.07 mmol, 91% yield) as a yellow oil. LC/MS (ESI) m/z: 1107.7 [M+H]$^+$.

Step 26: Preparation of 3-[4-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d] pyrimidin-2-yl] oxyethyl]-4-piperidyl]methyl]-1-piperidyl]methyl]-1-piperidyl]-1-oxo-isoindolin-2-yl] piperidine-2,6-dione (Compound 43)

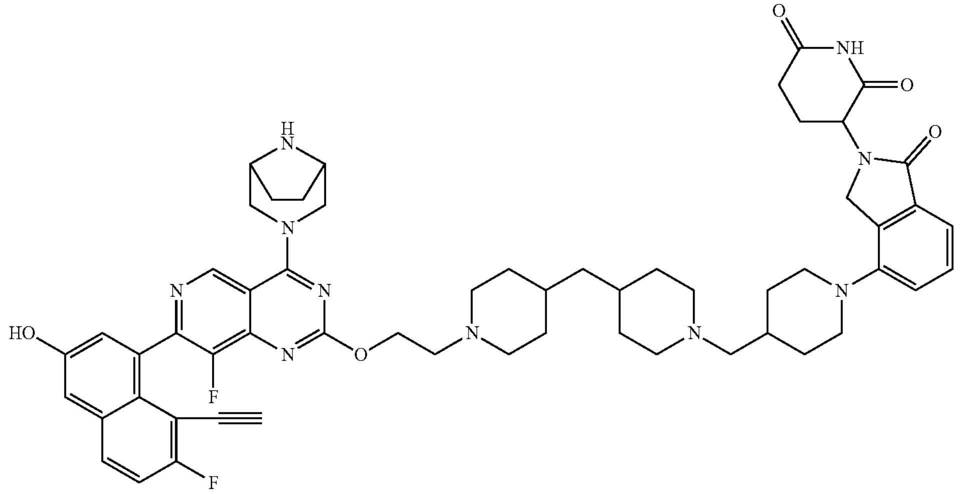 [SMILES: C#Cc1c(F)ccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12]

A solution of tert-butyl 3-[2-[2-[4-[[1-[[1-[2-(2,6-dioxo-3-piperidyl)-1-oxo-isoindolin-4-yl]-4-piperidyl]methyl]-4-piperidyl]methyl]-1-piperidyl] ethoxy]-7-(8-ethynyl-7-fluoro-3-hydroxy-1-naphthyl)-8-fluoro-pyrido[4,3-d] pyrimidin-4-yl]-3,8-diazabicyclo[3.2.1]octane-8-carboxylate (80 mg, 0.07 mmol, 1 eq) in formic acid (4 mL) was stirred at 25° C. for 2 hours. The reaction mixture was concentrated, and the resulting residue was purified by prep-HPLC {column: Phenomenex luna C18 150*40 mm*15 μm; mobile phase: [2-32% $CH_3CN$ in water (formic acid)]} to the title compound (62.7 mg, 0.05 mmol, 78% yield, formic acid salt) as a yellow solid.

Example 2: Synthesis of 3-[4-[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]-1-oxo-isoindolin-2-yl]piperidine-2,6-dione (Compound 35)

Step 1: Preparation of 2,6-dibenzyloxy pyridin-3-amine

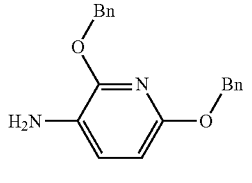 [SMILES: Nc1ccc(OCc2ccccc2)nc1OCc1ccccc1]

To a solution of phenylmethanol (16.59 g, 153.37 mmol, 16.0 mL, 2.5 eq) in tetrahydrofuran (200 mL) was added potassium tert-butoxide (17.21 g, 153.37 mmol, 2.5 eq) portion-wise, and the resulting mixture was stirred at 25° C. for 2 hours. 2,6-Dichloropyridin-3-amine (10 g, 61.35 mmol, 1 eq) was then added, and the reaction mixture was stirred at 75° C. for 24 hours. The mixture was cooled to 25° C., then diluted with ethyl acetate (600 mL). The organic layer was washed with water (100 mL×3), and the water layer wash extracted with ethyl acetate (100 mL×2). The combined organic extract was dried over anhydrous sodium sulfate, filtered, and concentrated under vacuum. The resulting residue was purified by silica gel column chromatography (petroleum ether/ethyl acetate=50/1 to 10:1) followed by prep-HPLC (column: Welch Ultimate XB-Diol 250*50*10 μm; mobile phase: [Heptane-EtOH (0.1% $NH_4OH$)]; B %: 1%-10%, 15 min) to get the title compound (3.1 g, 10.12 mmol, 16% yield) as a black orange oil. LC/MS (ESI) m/z: 307.4 $[M+H]^+$. $^1H$ NMR (400 MHz, $CDCl_3$) δ 7.51-7.30 (m, 10H), 6.99 (d, J=8.0 Hz, 1H), 6.28 (d, J=8.0 Hz, 1H), 5.39 (s, 2H), 5.28 (s, 2H), 3.27-2.56 (m, 2H).

Step 2: Preparation of 4-bromo-2-(2,6-dibenzyloxy-3-pyridyl)isoindolin-1-one

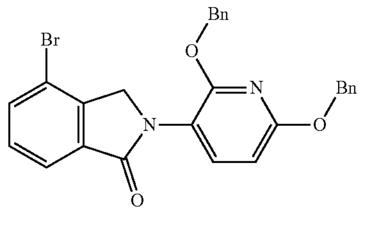 [SMILES: O=C1c2cccc(Br)c2CN1c1ccc(OCc2ccccc2)nc1OCc1ccccc1]

To a solution of 2,6-dibenzyloxypyridin-3-amine (1.2 g, 3.92 mmol, 1 eq) and methyl 3-bromo-2-(bromomethyl) benzoate (1.21 g, 3.92 mmol, 1 eq) in N,N-dimethylacetamide (12 mL) was added N,N-diisopropylethylamine (1.52 g, 11.75 mmol, 2.1 mL, 3 eq), and the reaction mixture was stirred at 120° C. for 12 hours. The mixture was cooled to 25° C., diluted with water (50 mL), and extracted with ethyl acetate (30 mL×3). The combined organic extract was washed with brine (30 mL×3), dried over anhydrous sodium sulfate, filtered, and concentrated under vacuum. The resulting residue was purified by silica gel column chromatography (petroleum ether/ethyl acetate=1/0 to 4:1) to afford the title compound (1.45 g, 2.89 mmol, 74% yield) as a yellow solid. LC/MS (ESI) m/z: 501.1 $[M+H]^+$. $^1H$ NMR (400 MHz, $CDCl_3$) δ 7.89 (d, J=7.6 Hz, 1H), 7.70 (dd, J=2.0, 7.6 Hz, 2H), 7.49-7.28 (m, 11H), 6.50 (d, J=8.4 Hz, 1H), 5.43 (s, 2H), 5.35 (s, 2H), 4.70 (s, 2H).

Step 3: Preparation of tert-butyl 4-[[1-[2-(2,6-dibenzyloxy-3-pyridyl)-1-oxo-isoindolin-4-yl]-4-piperidyl]methyl]piperidine-1-carboxylate

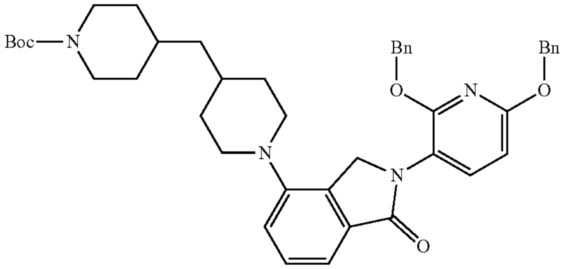 [SMILES: CC(C)(C)OC(=O)N1CCC(CC2CCN(c3cccc4c3CN(c3ccc(OCc5ccccc5)nc3OCc3ccccc3)C4=O)CC2)CC1]

To a mixture of 4-bromo-2-(2,6-dibenzyloxy-3-pyridyl) isoindolin-1-one (260 mg, 0.52 mmol, 1 eq), tert-butyl 4-(4-piperidylmethyl)piperidine-1-carboxylate (195 mg, 0.57 mmol, 1.1 eq, acetate), and cesium carbonate (507 mg, 1.56 mmol, 3 eq) in dioxane (5 mL) was added [2-(2-aminophenyl)phenyl]-chloro-palladium;dicyclohexyl-[3-(2,4,6-triisopropylphenyl)phenyl]phosphane (41 mg, 0.05 mmol, 0.1 eq), and the reaction mixture was degassed and purged with nitrogen (3×), then stirred at 100° C. for 12 hours. The reaction was cooled to 25° C., diluted with water (30 mL), and extracted with ethyl acetate (20 mL×2). The combined organic extract was dried over anhydrous sodium sulfate, filtered, and concentrated under vacuum. The resulting residue was purified by prep-TLC (petroleum ether/ethyl acetate=3/1) to get the title compound (320 mg, 0.46 mmol, 87% yield) as a light yellow gum. LC/MS (ESI) m/z: 703.2 $[M+H]^+$. $^1H$ NMR (400 MHz, DMSO-$d_6$) δ 7.81 (d, J=8.4 Hz, 1H), 7.52-7.25 (m, 13H), 7.14 (d, J=8.0 Hz, 1H), 6.55 (d, J=8.4 Hz, 1H), 5.38 (d, J=9.6 Hz, 4H), 4.73 (s, 2H), 3.92 (br d, J=11.2 Hz, 2H), 3.36 (br s, 2H), 2.69 (br t, J=10.8 Hz, 4H), 1.71 (br d, J=11.2 Hz, 2H), 1.62 (br d, J=12.8 Hz, 2H), 1.56-1.44 (m, 2H), 1.38 (s, 9H), 1.26-1.18 (m, 3H), 1.06-0.86 (m, 2H).

Step 4: Preparation of tert-butyl 4-[[1-[2-(2,6-dioxo-3-piperidyl)-1-oxo-isoindolin-4-yl]-4-piperidyl]methyl]piperidine-1-carboxylate

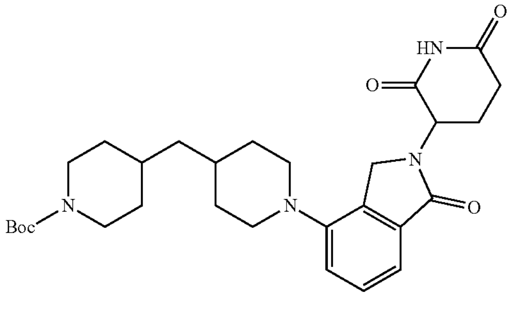 [SMILES: CC(C)(C)OC(=O)N1CCC(CC2CCN(c3cccc4c3CN(C3CCC(=O)NC3=O)C4=O)CC2)CC1]

To a solution of tert-butyl 4-[[1-[2-(2,6-dibenzyloxy-3-pyridyl)-1-oxo-isoindolin-4-yl]-4-piperidyl]methyl]piperidine-1-carboxylate (320 mg, 0.46 mmol, 1 eq) in ethyl acetate (10 mL) was added palladium on activated carbon catalyst (0.1 g, 10% purity) under nitrogen, and the resulting suspension was degassed and purged with hydrogen (3×), then stirred at 25° C. under hydrogen (15 Psi) for 16 h. The mixture was filtered through a pad of Celite®, and the filtrate was concentrated under vacuum. The resulting residue was purified by prep-TLC (dichloromethane/methanol=10/1) to afford the title compound (110 mg, 0.21 mmol, 46% yield) as a white solid. LC/MS (ESI) m/z: 547.3 $[M+Na]^+$. $^1H$ NMR (400 MHz, DMSO-$d_6$) δ 10.98 (s, 1H), 7.49-7.39 (m, 1H), 7.29 (d, J=7.2 Hz, 1H), 7.15 (d, J=8.0 Hz, 1H), 5.11 (dd, J=5.2, 13.2 Hz, 1H), 4.49-4.36 (m, 1H), 4.34-4.22 (m, 1H), 3.92 (br d, J=12.0 Hz, 2H), 3.42-3.34 (m, 2H), 3.31 (s, 1H), 2.99-2.83 (m, 1H), 2.80-2.55 (m, 5H), 2.05-1.90 (m, 1H), 1.75 (br d, J=11.6 Hz, 2H), 1.63 (br d, J=12.4 Hz, 2H), 1.58-1.47 (m, 2H), 1.39 (s, 9H), 1.25 (br d, J=12.0 Hz, 2H), 1.17 (br t, J=6.8 Hz, 2H), 1.04-0.87 (m, 2H).

Step 5: Preparation of 3-[1-oxo-4-[4-(4-piperidylmethyl)-1-piperidyl]isoindolin-2-yl]piperidine-2,6-dione

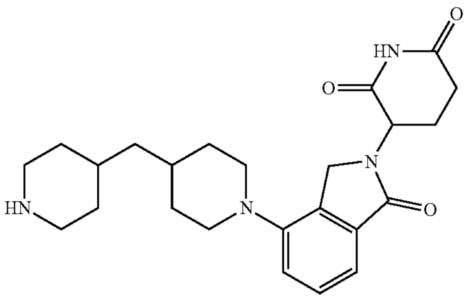 [SMILES: O=C1CCC(N2Cc3c(cccc3N3CCC(CC4CCNCC4)CC3)C2=O)C(=O)N1]

To a solution of tert-butyl 4-[[1-[2-(2,6-dioxo-3-piperidyl)-1-oxo-isoindolin-4-yl]-4-piperidyl]methyl]piperidine-1-carboxylate (220 mg, 0.42 mmol, 1 eq) in dichloromethane (5 mL) was added trifluoroacetic acid (1.54 g, 13.51 mmol, 1 mL, 32.21 eq), and the reaction mixture was stirred at 25° C. for 0.5 hour. The solution was concentrated under vacuum to get the title compound (220 mg, crude, trifluoroacetic acid salt) as a white solid. LC/MS (ESI) m/z: 425.1 $[M+H]^+$.

Step 6: Preparation of tert-butyl 3-[2-[2-[4-[[1-[2-(2,6-dioxo-3-piperidyl)-1-oxo-isoindolin-4-yl]-4-piperidyl]methyl]-1-piperidyl]ethoxy]-8-fluoro-7-[7-fluoro-3-hydroxy-8-(2-triisopropylsilylethynyl)-1-naphthyl]pyrido[4,3-d]pyrimidin-4-yl]-3,8-diazabicyclo[3.2.1]octane-8-carboxylate

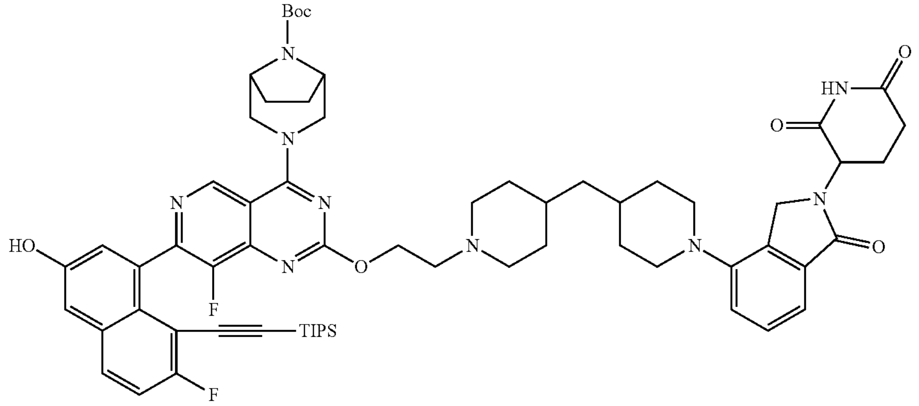

To a solution of 3-[1-oxo-4-[4-(4-piperidylmethyl)-1-piperidyl]isoindolin-2-yl]piperidine-2,6-dione (220 mg, 0.41 mmol, 1 eq, trifluoroacetic acid salt) in DMSO (3 mL) and 1,2-dichloroethane (3 mL) was added 4-methylmorpholine (124 mg, 1.23 mmol, 0.1 mL, 3 eq) followed by tert-butyl 3-[8-fluoro-7-[7-fluoro-3-hydroxy-8-(2-triisopropylsilyl-ethynyl)-1-naphthyl]-2-(2-oxoethoxy)pyrido[4,3-d]pyrimidin-4-yl]-3,8-diazabicyclo[3.2.1]octane-8-carboxylate (248 mg, 0.32 mmol, 0.8 eq) and acetic acid (25 mg, 0.41 mmol, 1 eq), and the resulting mixture was stirred at 25° C. for 0.5 hour. Sodium triacetoxyborohydride (260 mg, 1.23 mmol, 3 eq) was then added, and the reaction mixture was stirred at 25° C. for 12 hours. Water (20 mL) was added, and the mixture was extracted with ethyl acetate (20 mL×3). The combined organic extract was washed with brine (20 mL×2), dried over anhydrous sodium sulfate, filtered, and concentrated under vacuum. The resulting residue was purified by prep-TLC (dichloromethane/methanol=10/1) to afford the title compound (230 mg, 0.20 mmol, 48% yield) as a white solid. LC/MS (ESI) m/z: 1166.6 $[M+H]^+$.

Step 7: Preparation of tert-butyl 3-[2-[2-[4-[[1-[2-(2,6-dioxo-3-piperidyl)-1-oxo-isoindolin-4-yl]-4-piperidyl]methyl]-1-piperidyl]ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate

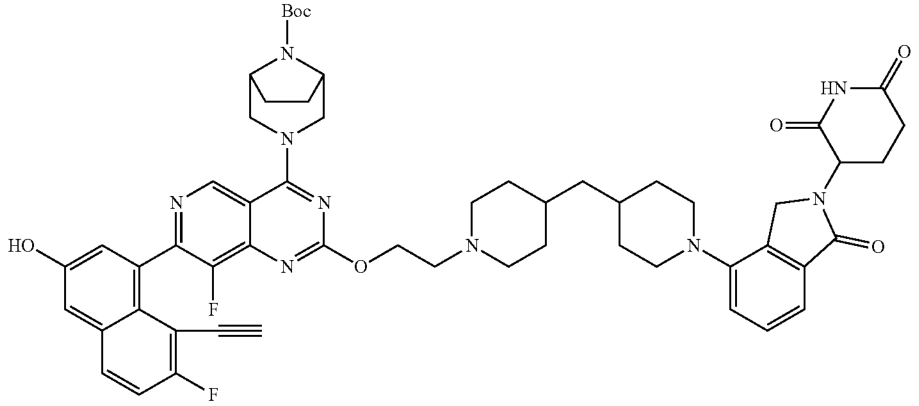 [SMILES: C#Cc1c(F)ccc2cc(O)cc(-c3ncc4c(N5CC6CCC(C5)N6C(=O)OC(C)(C)C)nc(OCCN5CCC(CC6CCN(c7cccc8c7CN(C7CCC(=O)NC7=O)C8=O)CC6)CC5)nc4c3F)c12]

To a solution of tert-butyl 3-[2-[2-[4-[[1-[2-(2,6-dioxo-3-piperidyl)-1-oxo-isoindolin-4-yl]-4-piperidyl]methyl]-1-piperidyl]ethoxy]-8-fluoro-7-[7-fluoro-3-hydroxy-8-(2-triisopropylsilylethynyl)-1-naphthyl]pyrido[4,3-d]pyrimidin-4-yl]-3,8-diazabicyclo[3.2.1]octane-8-carboxylate (230 mg, 0.20 mmol, 1 eq) in DMF (6 mL) was added cesium fluoride (449 mg, 2.96 mmol, 15 eq), and the reaction mixture was stirred at 25° C. for 1.5 hours. The mixture was diluted with ethyl acetate (200 mL), and the organic layer was washed with brine (20 mL×3), was dried over anhydrous sodium sulfate, filtered, and concentrated under vacuum. The resulting residue was purified by prep-TLC (dichloromethane/methanol=10/1) to the title compound (110 mg, 0.11 mmol, 55% yield) as a light yellow solid. LC/MS (ESI) m/z: 1010.1 $[M+H]^+$.

Step 8: Preparation of 3-[4-[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]-1-oxo-isoindolin-2-yl]piperidine-2,6-dione (Compound 35)

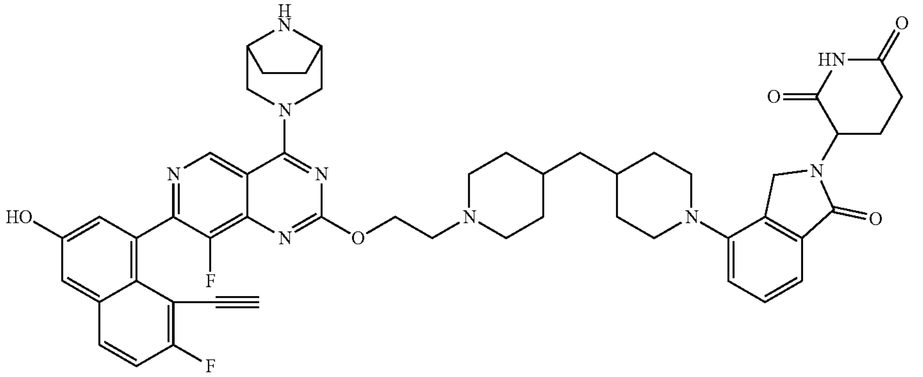 [SMILES: C#Cc1c(F)ccc2cc(O)cc(-c3ncc4c(N5CC6CCC(C5)N6)nc(OCCN5CCC(CC6CCN(c7cccc8c7CN(C7CCC(=O)NC7=O)C8=O)CC6)CC5)nc4c3F)c12]

To a solution of tert-butyl 3-[2-[2-[4-[[1-[2-(2,6-dioxo-3-piperidyl)-1-oxo-isoindolin-4-yl]-4-piperidyl]methyl]-1-piperidyl]ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate (110 mg, 0.11 mmol, 1 eq) in dichloromethane (5 mL) was added trifluoroacetic acid (1.54 g, 13.51 mmol, 1 mL, 124.03 eq), and the reaction mixture was stirred at 25° C. for 0.5 hour. The solution was concentrated, and the resulting residue was purified by prep-HPLC (column: Unisil 3-100 C18 Ultra 150*50 mm*3 μm; mobile phase: [9-39% $CH_3CN$ in water (formic acid)]) followed by prep-HPLC (column: Unisil 3-100 C18 Ultra 150*50 mm*3 μm; mobile phase: [8-38% CH3CN in water (formic acid)]) to afford the title compound (14.8 mg, 0.01 mmol, 13% yield, formic acid salt) as a yellow solid.

Example 3: Synthesis of 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione (Compound 55)

Step 1: Preparation of 8-(2-triisopropylsilylethynyl)naphthalene-1,3-diol

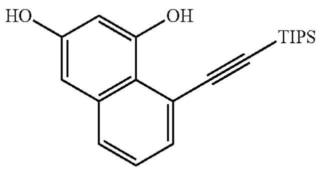

A solution of naphthalene-1,3-diol (50 g, 312.17 mmol, 1 eq), 2-bromoethynyl(triisopropyl) silane (97.87 g, 374.60 mmol, 1.2 eq), dichlororuthenium; 1-isopropyl-4-methylbenzene (19.12 g, 31.22 mmol, 0.1 eq) and potassium acetate (61.27 g, 624.34 mmol, 2 eq) in dioxane (600 mL) was stirred for 12 hours at 110° C. under nitrogen. The reaction mixture was concentrated, and the resulting residue was purified by silica gel column chromatography (petroleum ether/ethyl acetate=1/0 to 20/1) to afford the title compound (70 g, 205.56 mmol, 65% yield) as a yellow solid. LC/MS (ESI) m/z: 341.2 $[M+H]^+$. $^1H$ NMR (400 MHz, $CDCl_3$) δ 9.30 (s, 1H), 7.62 (d, J=8.4 Hz, 1H), 7.47 (d, J=6.4, 1H), 7.33-7.28 (m, 1H), 6.75 (d, J=2.4 Hz, 1H), 6.64 (d, J=2.8 Hz, 1H), 4.15 (s, 1H), 1.23-1.20 (m, 3H), 1.19-1.17 (m, 18H).

Step 2: Preparation of 3-(methoxymethoxy)-8-(2-triisopropylsilylethynyl) naphthalen-1-ol

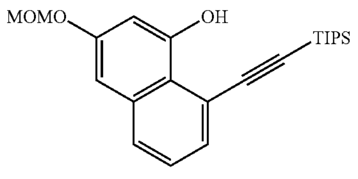

To a solution of 8-(2-triisopropylsilylethynyl)naphthalene-1,3-diol (270 g, 792.88 mmol, 1 eq) and N,N-diisopropylethylamine (307.42 g, 2.38 mol, 414 mL, 3 eq) in dichloromethane (2.5 L) at 0° C. was added chloro (methoxy)methane (96.44 g, 1.20 mol, 91 mL, 1.51 eq), and the reaction mixture was stirred for 25° C. for 3 hours. The reaction mixture was diluted with water (1000 mL) and extracted with dichloromethane (1000 mL×2). The combined organic extract was washed with brine (1000 mL), dried over anhydrous sodium sulfate, filtered, and concentrated. The resulting residue was purified by silica gel column chromatography (petroleum ether/ethyl acetate=1/0 to 10/1) to afford the title compound (185 g, 481.04 mmol, 61% yield) as a yellow oil. $^1$H NMR (400 MHz, $CDCl_3$) δ 9.26 (s, 1H), 7.68 (d, J=8.0 Hz, 1H), 7.50 (d, J=6.4, 1H), 7.34-7.29 (m, 1H), 7.00-6.96 (m, 1H), 6.77 (d, J=2.4 Hz, 1H), 5.27 (s, 2H), 3.51 (s, 3H), 1.27-1.22 (m, 3H), 1.20-1.17 (m, 18H).

Step 3: Preparation of [3-(methoxymethoxy)-8-(2-triisopropylsilylethynyl)-1-naphthyl]trifluoromethanesulfonate

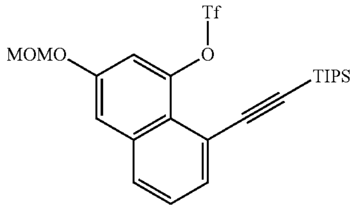

To a solution of 3-(methoxymethoxy)-8-(2-triisopropylsilylethynyl)naphthalen-1-ol (175 g, 455.04 mmol, 1 eq) and N,N-Diisopropylethylamine (176.43 g, 1.37 mol, 238 mL, 3 eq) in dichloromethane (2 L) at −40° C. was added trifluoromethylsulfonyl trifluoromethanesulfonate (192.58 g, 682.56 mmol, 113 mL, 1.5 eq) dropwise, and the reaction mixture was stirred for 1 hour at −40° C. under nitrogen. The reaction mixture was quenched with water (500 mL) and extracted with dichloromethane (300 mL×2). The combined organic extract was washed with brine (500 mL), dried over anhydrous sodium sulfate, filtered, and concentrated. The resulting residue was purified by silica gel column chromatography (petroleum ether/ethyl acetate=1/0 to 20/1) to afford the title compound (91 g, 144.69 mmol, 92% yield) as a yellow oil. $^1$H NMR (400 MHz, $CDCl_3$) δ 7.77-7.71 (m, 2H), 7.47-7.41 (m, 2H), 7.31 (d, J=2.4, 1H), 5.29 (s, 2H), 3.53 (s, 3H), 1.28-1.22 (m, 3H), 1.19-1.14 (m, 18H).

Step 4: Preparation of triisopropyl-[2-[6-(methoxymethoxy)-8-(4,4,5,5-tetramethyl-1,3,2-dioxaborolan-2-yl)-1-naphthyl]ethynyl]silane

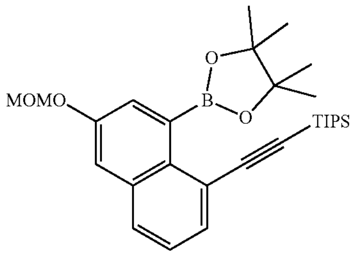

A mixture of [3-(methoxymethoxy)-8-(2-triisopropylsilylethynyl)-1-naphthyl]trifluoromethanesulfonate (192 g, 371.63 mmol, 1 eq), 4,4,5,5-tetramethyl-1,3,2-dioxaborolane (61.83 g, 483.12 mmol, 70 mL, 1.3 eq), triethylamine (112.82 g, 1.11 mol, 155 mL, 3 eq), and cyclopentyl(diphenyl)phosphane;dichloromethane;dichloropalladium;iron (30.35 g, 37.16 mmol, 0.1 eq) in acetonitrile (2 L) was stirred for 12 hours at 80° C. under nitrogen. The reaction mixture was concentrated, and the resulting residue was purified by silica gel column chromatography (petroleum ether/ethyl acetate=1/0 to 20/1) to afford the title compound (165 g, 333.64 mmol, 89% yield) as a yellow solid. LC/MS (ESI) m/z: 495.4 [M+H]$^+$. $^1$H NMR (400 MHz, $CDCl_3$) δ 7.73-7.65 (m, 2H), 7.47 (d, J=2.4 Hz, 1H), 7.40-7.33 (m, 2H), 5.29 (s, 2H), 3.51 (s, 3H), 1.44 (s, 12H), 1.20-1.18 (m, 3H), 1.17-1.15 (m, 18H).

Step 5: Preparation of 2-[8-ethynyl-3-(methoxymethoxy)-1-naphthyl]-4,4,5,5-tetramethyl-1,3,2-dioxaborolane

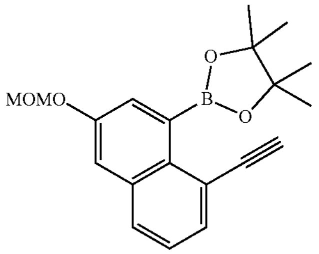

A solution of triisopropyl-[2-[6-(methoxymethoxy)-8-(4,4,5,5-tetramethyl-1,3,2-dioxaborolan-2-yl)-1-naphthyl]ethynyl]silane (81 g, 163.79 mmol, 1 eq) and cesium fluoride (497.59 g, 3.28 mol, 20 eq) in DMF (1.6 L) was stirred for 5 hours at 20° C. The reaction mixture was diluted with water (2000 mL) and extracted with ethyl acetate (2000 mL×2). The combined organic extract was washed with brine (2000 mL), dried over anhydrous sodium sulfate, filtered, and concentrated. The resulting residue was purified by silica gel column chromatography (petroleum ether/ethyl acetate=10/0 to 1/1) to afford the title compound (17 g, 57.79 mmol, 94% yield) as a yellow oil. LC/MS (ESI) m/z: 339.0 [M+H]$^+$. $^1$H NMR (400 MHz, $CDCl_3$) δ 7.75 (d, J=8.4 Hz, 1H), 7.67 (d, J=10.0 Hz, 1H), 7.46-7.40 (m, 2H), 7.39-7.34 (m, 1H), 5.29 (s, 2H), 3.52 (s, 3H), 3.36 (s, 1H), 1.45 (s, 12H).

Step 6: Preparation of 2-[8-ethyl-3-(methoxymethoxy)-1-naphthyl]-4,4,5,5-tetramethyl-1,3,2-dioxaborolane

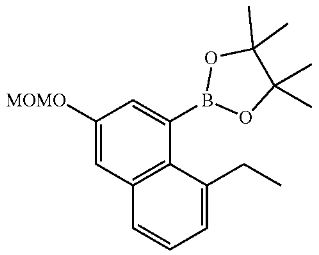

To 2-[8-ethynyl-3-(methoxymethoxy)-1-naphthyl]-4,4,5,5-tetramethyl-1,3,2-dioxaborolane (25 g, 73.92 mmol, 1 eq) in methanol (300 mL) and tetrahydrofuran (300 mL) was added palladium on activated carbon (5 g, 10% purity), and the reaction mixture was stirred for 5 hours at 20° C. under hydrogen atmosphere (15 psi). The reaction mixture was filtered through Celite® and the filtrate was concentrated to afford the title compound (14 g, 46.95 mmol, 81% yield) as a yellow oil. $^1H$ NMR (400 MHz, $CDCl_3$) δ 7.60 (d, J=7.6 Hz, 1H), 7.42 (d, J=2.8, 1H), 7.40-7.37 (m, 1H), 7.35 (t, J=4.0, 2.4 Hz, 3H), 7.27-7.24 (m, 1H), 5.29 (s, 2H), 3.52 (m, 3H), 1.45 (s, 12H), 1.36 (t, J=7.6, 7.2 Hz, 3H).

Step 7: Preparation of tert-butyl 3-[2-(2,2-dimethoxyethoxy)-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

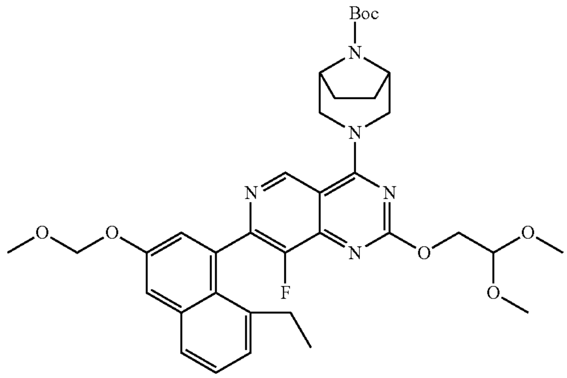

To a solution of tert-butyl 3-[7-chloro-2-(2,2-dimethoxyethoxy)-8-fluoro-pyrido[4,3-d]pyrimidin-4-yl]-3,8-diazabicyclo[3.2.1]octane-8-carboxylate (1.6 g, 3.21 mmol, 1 eq) and 2-[8-ethyl-3-(methoxymethoxy)-1-naphthyl]-4,4,5,5-tetramethyl-1,3,2-dioxaborolane (1.28 g, 3.73 mmol, 1.16 eq) in dioxane (15 mL) and $H_2O$ (3 mL) were added $Cs_2CO_3$ (2.62 g, 8.03 mmol, 2.5 eq) and [1,1'-bis(di-tert-butylphosphino)ferrocene]dichloropalladium(II) (418.8 mg, 0.643 mmol, 0.2 eq), and the reaction mixture was stirred at 110° C. for 16 hours under $N_2$. The mixture was diluted with EtOAc (150 mL), and the combined organic phase was washed with brine (30 mL), dried over anhydrous sodium sulfate, filtered, and concentrated in vacuo. The resulting the residue was purified by flash chromatography on silica gel (gradient: 10-30% EtOAc in petroleum ether) to afford the title compound (0.922 g, 1.28 mmol, 40% yield) as a brown solid.

LC/MS (ESI) m/z: 678.4 $[M+H]^+$.

Step 8: Preparation of tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate

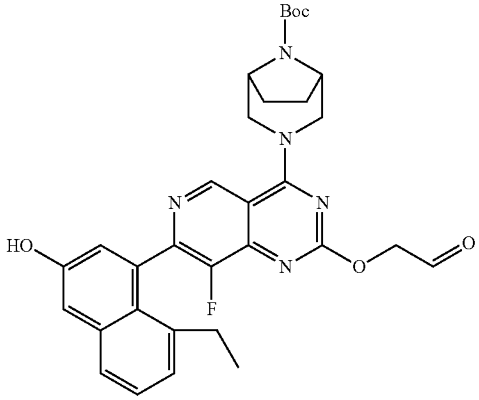 [SMILES: CCc1cccc2cc(O)cc(-c3ncc4c(N5CC6CCC(C5)N6C(=O)OC(C)(C)C)nc(OCC=O)nc4c3F)c12]

To a solution of tert-butyl 3-[2-(2,2-dimethoxyethoxy)-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (100 mg, 0.148 mmol, 1 eq) in acetone (0.37 mL) was added concentrated HCl (12 M, 0.37 mL, 30 eq) dropwise, and the reaction mixture was stirred at 20° C. for 5 minutes (9 batches were conducted in total). Saturated aqueous $NaHCO_3$ was then added until pH=8, and the resulting mixture was filtered, washing with water (10 mL) and petroleum ether (10 mL) to give 2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyacetaldehyde (640 mg crude) as a yellow solid. $Boc_2O$ (343.8 mg, 1.58 mmol, 1.2 eq) and a solution of $NaHCO_3$ (330.8 mg, 3.94 mmol, 3 eq) in $H_2O$ (2.5 mL) were then added, and the reaction mixture was stirred at 20° C. for 2 hours. The mixture was diluted with EtOAc (120 mL), and the organic phase was washed with brine (20 mL), dried over anhydrous sodium sulfate, filtered, and concentrated. The resulting residue was purified by flash chromatography on silica gel (gradient: 10-50% EtOAc in petroleum ether) to afford the title compound (430 mg, 46% yield) as a yellow solid. LC/MS (ESI) m/z: 588.4 $[M+H]^+$.

Step 9: Preparation of tert-butyl 3-[2-[2-[4-[[1-[[1-[2-(2,6-dioxo-3-piperidyl)-1-oxo-isoindolin-4-yl]-4-piperidyl]methyl]-4-piperidyl]methyl]-1-piperidyl]ethoxy]-7-(8-ethyl-3-hydroxy-1-naphthyl)-8-fluoro-pyrido[4,3-d]pyrimidin-4-yl]-3,8-diazabicyclo[3.2.1]octane-8-carboxylate

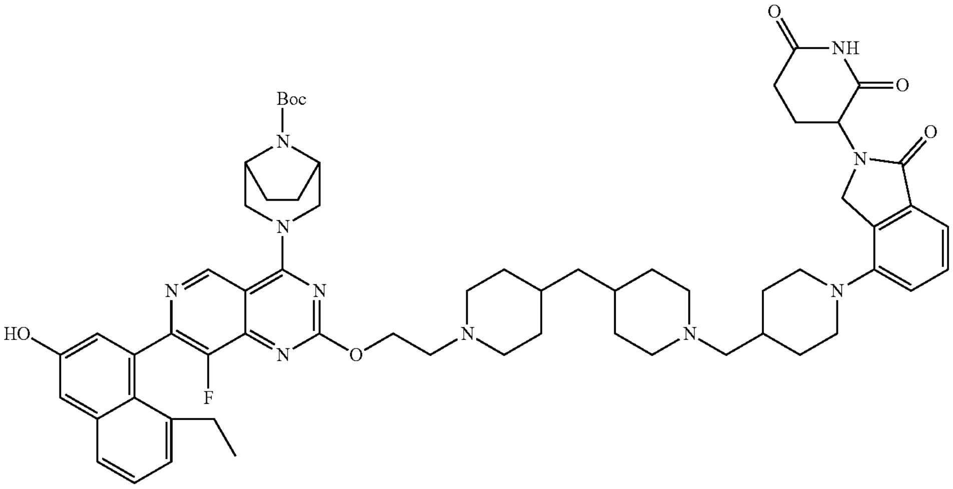 [SMILES: CCc1cccc2cc(O)cc(-c3ncc4c(N5CC6CCC(C5)N6C(=O)OC(C)(C)C)nc(OCCN5CCC(CC6CCN(CC7CCN(c8cccc9c8CN(C8CCC(=O)NC8=O)C9=O)CC7)CC6)CC5)nc4c3F)c12]

To a solution of tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate (150 mg, 0.255 mmol, 1 eq) and 3-[1-oxo-4-[4-[[4-(4-piperidylmethyl)-1-piperidyl]methyl]-1-piperidyl]isoindolin-2-yl]piperidine-2,6-dione (222 mg, 0.262 mmol, 75% purity, 1.03 eq, TFA) in isopropanol (3.5 mL) and dichloromethane (5 mL) were added NaOAc (42 mg, 0.51 mmol, 2 eq), AcOH (107 mg, 1.79 mmol, 102 µL, 7 eq), and 2-picoline borane complex (82 mg, 0.77 mmol, 3 eq), and the reaction mixture was stirred at 20° C. for 3 hours. The reaction mixture was concentrated under reduced pressure, and the crude product was purified by flash chromatography on $SiO_2$ (gradient: 0-20% methanol/dichloromethane) to give the title compound (255 mg, 0.233 mmol, 91% yield) as a white solid. LC/MS (ESI) m/z: 1093.4 $[M+H]^+$.

Step 10: Preparation of 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione (Compound 55)

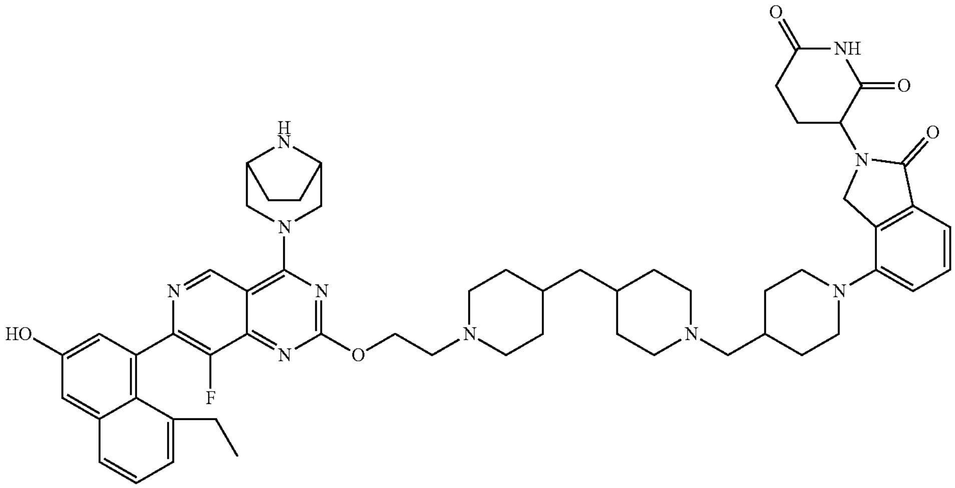 [SMILES: CCc1cccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12]

A solution of tert-butyl 3-[2-[2-[4-[[1-[[1-[2-(2,6-dioxo-3-piperidyl)-1-oxo-isoindolin-4-yl]-4-piperidyl]methyl]-4-piperidyl]methyl]-1-piperidyl]ethoxy]-7-(8-ethyl-3-hydroxy-1-naphthyl)-8-fluoro-pyrido[4,3-d]pyrimidin-4-yl]-3,8-diazabicyclo[3.2.1]octane-8-carboxylate (155 mg, 0.142 mmol, 1 eq) in HCOOH (5 mL) was stirred at 20° C. for 4 hours. The mixture was concentrated under reduced pressure, and the resulting crude product was purified by prep-HPLC (column: YMC Triart 30*150 mm*7 μm; mobile phase: [13-43% $CH_3CN$ in water (formic acid)]). Pure fractions were combined and dried by lyophilization to give the title compound (51.4 mg, 0.048 mmol, 34% yield, formic acid salt) as a white solid.

Example 4: Synthesis of 3-[4-[4-[[4-[[1-[2-[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl] oxyethyl]-4-piperidyl]methyl]-1-piperidyl]methyl]-1-piperidyl]-1-oxo-isoindolin-2-yl] piperidine-2,6-dione (Compound 42)

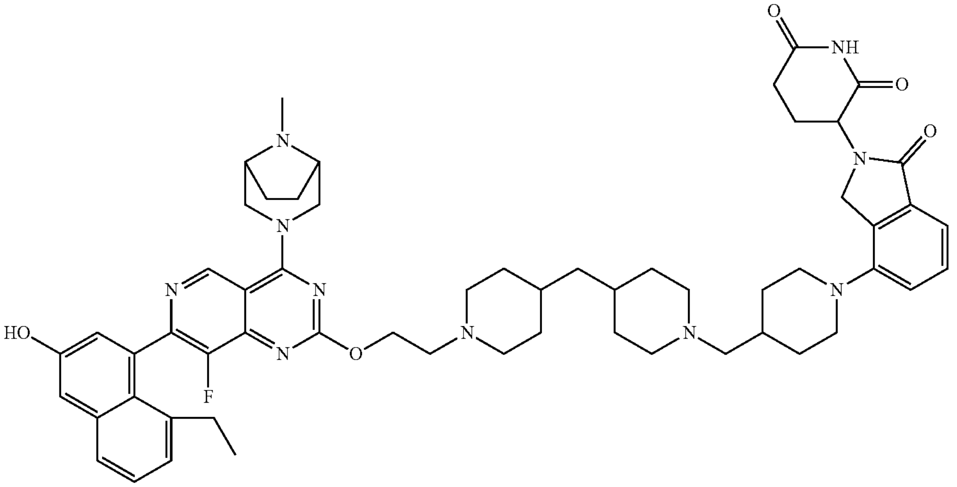 [SMILES: CCc1cccc2cc(O)cc(-c3ncc4c(N5CC6CCC(C5)N6C)nc(OCCN5CCC(CC6CCN(CC7CCN(c8cccc9c8CN(C8CCC(=O)NC8=O)C9=O)CC7)CC6)CC5)nc4c3F)c12]

To a solution of 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione (110 mg, 0.10 mmol, 1 eq, trifluoroacetate) in dichloromethane (2 mL) and methanol (2 mL) was added 4-methylmorpholine (15 mg, 0.15 mmol, 1.5 eq), and the mixture was stirred at 25° C. for 15 minutes. Formaldehyde (40 mg, 0.50 mmol, 37% purity, 5 eq) was then added, and the resulting mixture was stirred for 0.5 h at 25° C. Sodium triacetoxyborohydride (63 mg, 0.30 mmol, 3 eq) was then added, and the reaction mixture was stirred at 25° C. for 2 hours. The reaction mixture was concentrated, and the resulting residue was purified by prep-HPLC {column: Unisil 3-100 C18 Ultra 150*50 mm*3 μm; mobile phase: [1-31% $CH_3CN$ in water (formic acid)]} to afford the title compound (61.0 mg, 0.06 mmol, 56% yield) as a white solid.

Example 5: Synthesis of 3-[4-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxyethyl]-4-piperidyl]methyl]-1-piperidyl]-3-methyl-2-oxo-benzimidazol-1-yl]piperidine-2,6-dione (Compound 28)

Step 1: Preparation of 7-bromo-1-methylindoline-2,3-dione

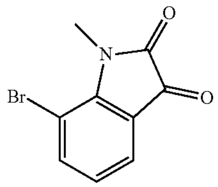

To a mixture of 7-bromoindoline-2,3-dione (12 g, 53.09 mmol, 1 eq), and potassium carbonate (11.01 g, 79.64 mmol, 1.5 eq), and water (1.2 mL) in DMF (60 mL) was added a solution of methyl iodide (8.44 g, 59.43 mmol, 3.7 mL, 1.12 eq) in DMF (24 mL) dropwise. And the reaction mixture was stirred at 25° C. for 2 hours. Water (120 mL) was then added, and the mixture was stirred at 0° C. for 1 hour. The resulting precipitate was collected by filtration, washed with water (50 mL×2), and dried in vacuo to afford the title compound (8 g, 33.33 mmol, 62% yield) as a red solid. LC/MS (ESI) m/z: 242.3 $[M+H]^+$. $^1H$ NMR (400 MHz, DMSO-$d_6$) δ 7.81 (br d, J=7.6 Hz, 1H) 7.55 (br d, J=7.2 Hz, 1H) 7.05 (t, J=8.0 Hz, 1H) 3.47 (s, 3H).

Step 2: Preparation of 3-bromo-2-(methylamino)benzoic acid

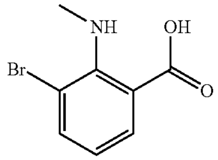

Aqueous hydrogen peroxide (38 g, 335.15 mmol, 32.20 mL, 30% purity, 10.06 eq) was added dropwise to a mixture of 7-bromo-1-methylindoline-2,3-dione (8 g, 33.33 mmol, 1 eq) and sodium hydroxide (2 M, 199.96 mL, 12 eq) below 15° C., and the reaction mixture was stirred at 25° C. for 5 hours. After the pH was adjusted to 4.0 with hydrochloric acid (1 M), the mixture was stirred at 10° C. for 1 hour, then extracted with ethyl acetate (80 mL×3). The combined organic extract was washed with water (60 mL), dried over anhydrous sodium sulfate, filtered, and concentrated under vacuum to afford the title compound (6.0 g, crude) as a brown oil. LC/MS (ESI) m/z: 252.2 $[M+Na]^+$.

Step 3: Preparation of 7-bromo-1-methyl-1H-benzo[d]imidazol-2(3H)-one

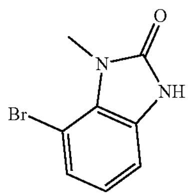

To a solution of 3-bromo-2-(methylamino)benzoic acid (6 g, 26.08 mmol, 1 eq, crude) and N,N-diisopropylethylamine (5.04 g, 39.01 mmol, 6.80 mL, 1.50 eq) in DMF (40 mL) was added diphenylphosphoryl azide (10.76 g, 39.10 mmol, 8.47 mL, 1.50 eq) dropwise at 75° C., and the reaction mixture was stirred at 75° C. for 3 hours. Water (30 mL) was added at 25° C., and the mixture was stirred at 0° C. for 0.5 hours. The resulting precipitate was collected by filtration, washed with water (30 mL) and diisopropylether (15 mL), then dried in vacuo at 50° C. to give the title compound (4 g, 17.62 mmol, 67% yield) as an off-white solid. LC/MS (ESI) m/z: 226.9 $[M+H]^+$. $^1H$ NMR (400 MHz, DMSO-$d_6$) δ 11.17 (br s, 1H) 7.14 (dd, J=8.0, 1.2 Hz, 1H) 6.96-6.99 (m, 1H) 6.88-6.93 (m, 1H) 3.55 (s, 3H).

Step 4: Preparation of 3-(4-bromo-3-methyl-2-oxo-2,3-dihydro-1H-benzo[d]imidazol-1-yl)-1-(4-methoxybenzyl)piperidine-2,6-dione

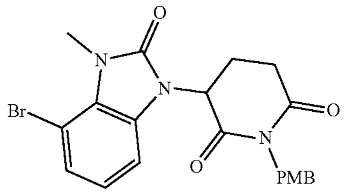

To a solution of 7-bromo-1-methyl-1H-benzo[d]imidazol-2(3H)-one (2.00 g, 8.81 mmol, 1 eq) in tetrahydrofuran (40 mL) was added potassium 2-methylpropan-2-olate (1 M, 10.67 mL, 1.21 eq), and the resulting mixture was stirred at 0° C. for 0.5 hours. 1-(4-Methoxybenzyl)-2,6-dioxopiperidin-3-yl trifluoromethanesulfonate (4.2 g, 11.01 mmol, 1.25 eq) in tetrahydrofuran (20 mL) was then added dropwise, and the reaction mixture was stirred at 0-25° C. for 0.5 hours. The reaction mixture was quenched by addition of 10% ammonium chloride solution (10 mL) at 0° C., and the resulting mixture was stirred at 0° C. for 1 hour, then extracted with ethyl acetate (50 mL×3). The combined organic extracts were washed with brine (50 mL), dried over anhydrous sodium sulfate, and concentrated under reduced pressure. The resulting residue was purified by silica gel column chromatography (petroleum ether/ethyl acetate=6/1 to 1/1) to afford the title compound (3.5 g, 7.64 mmol, 87% yield) as a white solid. LC/MS (ESI) m/z: 460.1 $[M+H]^+$. $^1H$ NMR (400 MHz, DMSO-$d_6$) δ 7.24 (dd, J=0.8, 8.0 Hz, 1H), 7.22-7.18 (m, 2H), 7.11-7.04 (br m, 1H), 6.97-6.92 (m, 1H), 6.88-6.82 (m, 2H), 5.57 (dd, J=5.6, 12.8 Hz, 1H), 4.79 (q, J=14.4 Hz, 2H), 3.72 (s, 3H), 3.64 (s, 3H), 3.12-2.97 (m, 1H), 2.89-2.64 (m, 2H), 2.13-2.01 (m, 1H).

Step 5: Preparation of tert-butyl 4-[[1-[1-[1-[(4-methoxyphenyl)methyl]-2,6-dioxo-3-piperidyl]-3-methyl-2-oxo-benzimidazol-4-yl]-4-piperidyl]methyl]piperidine-1-carboxylate

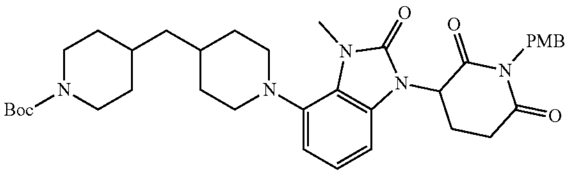

To a solution of 3-(4-bromo-3-methyl-2-oxo-2,3-dihydro-1H-benzo[d]imidazol-1-yl)-1-(4-methoxybenzyl)piperidine-2,6-dione (1 g, 2.18 mmol, 1 eq) and tert-butyl 4-(4-piperidylmethyl) piperidine-1-carboxylate (1.12 g, 3.27 mmol, 1.5 eq, acetic acid) in N,N-dimethylacetamide (20 mL) were added cesium carbonate (2.13 g, 6.54 mmol, 3 eq) and 1,3-bis[2,6-bis(1-propylbutyl)phenyl]-4,5-dichloro-2H-imidazol-1-ium-2-ide; 3-chloropyridine; dichloropalladium (212 mg, 0.22 mmol, 9.99e-2 eq), and the reaction mixture was stirred at 90° C. for 2 hours. The mixture was cooled to 25° C., and the residue was poured into water (50 mL) and stirred for 2 minutes. The aqueous phase was extracted with ethyl acetate (10 mL×3), and the combined organic extract was washed with brine (10 mL×2) and dried over anhydrous sodium sulfate. The residue was purified by prep-HPLC (column: Phenomenex luna C18 150*40 mm*15 μm; mobile phase: [68-98% $CH_3CN$ in water (formic acid)]) to afford the title compound (150 mg, 0.23 mmol, 10% yield) as a yellow solid. LC/MS (ESI) m/z: 660.4 $[M+H]^+$.

Step 6: Preparation of 3-[3-methyl-2-oxo-4-[4-(4-piperidylmethyl)-1-piperidyl]benzimidazol-1-yl]piperidine-2,6-dione

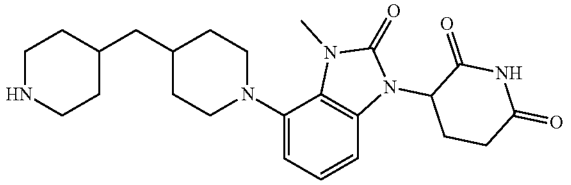 [SMILES: Cn1c(=O)n(C2CCC(=O)NC2=O)c2cccc(N3CCC(CC4CCNCC4)CC3)c21]

To a solution of tert-butyl 4-[[1-[1-[1-[(4-methoxyphenyl)methyl]-2,6-dioxo-3-piperidyl]-3-methyl-2-oxo-benzimidazol-4-yl]-4-piperidyl]methyl]piperidine-1-carboxylate (160 mg, 0.24 mmol, 1 eq) in toluene (1 mL) was added methanesulfonic acid (405 mg, 4.21 mmol, 0.3 mL, 17.38 eq), and the reaction mixture was stirred at 120° C. for 2 hours. The mixture was concentrated under reduced pressure at 45° C. to afford the title compound (110 mg, crude) as a white solid.

Step 7: Preparation of tert-butyl 3-[2-[2-[tert-butyl (dimethyl)silyl]oxyethoxy]-7-chloro-8-fluoro-pyrido [4,3-d]pyrimidin-4-yl]-3,8-diazabicyclo[3.2.1]octane-8-carboxylate

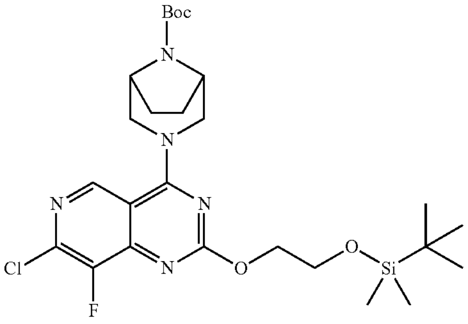 [SMILES: CC(C)(C)OC(=O)N1C2CCC1CN(c1nc(OCCO[Si](C)(C)C(C)(C)C)nc3c(F)c(Cl)ncc13)C2]

To a solution of tert-butyl 3-(2,7-dichloro-8-fluoro-pyrido [4,3-d]pyrimidin-4-yl)-3,8-diazabicyclo[3.2.1]octane-8-carboxylate (5 g, 11.67 mmol, 1 eq) and 1,4-diazabicyclo [2.2.2]octane (261.90 mg, 2.33 mmol, 256.77 μL, 0.2 eq) in acetonitrile (50 mL) at 25° C. were added 2-[tertbutyl (dimethyl)silyl]oxyethanol (2.47 g, 14.01 mmol, 1.2 eq) and cesium carbonate (11.41 g, 35.02 mmol, 3 eq), and the reaction mixture was stirred at 50° C. for 5 hours. The mixture was filtered, and the filtrate was concentrated. The resulting residue was purified by silica gel column chromatography (petroleum ether/ethyl acetate=10/1 to 3/1) to afford the title compound (4 g, 7.04 mmol, 60% yield) as a yellow solid. LC/MS (ESI) m/z: 568.3 $[M+H]^+$. $^1H$ NMR (400 MHz, $CDCl_3$) δ 8.73 (s, 1H), 4.56 (t, J=5.6 Hz, 2H), 4.48 (br d, J=12.8 Hz, 2H), 4.42-4.28 (m, 2H), 4.07-3.98 (m, 2H), 3.74-3.60 (m, 2H), 2.00-1.90 (m, 2H), 1.72 (br d, J=7.6 Hz, 2H), 1.52 (s, 9H), 0.92-0.86 (m, 9H), 0.09 (s, 6H).

Step 8: Preparation of tert-butyl 3-[2-[2-[tert-butyl (dimethyl)silyl]oxyethoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

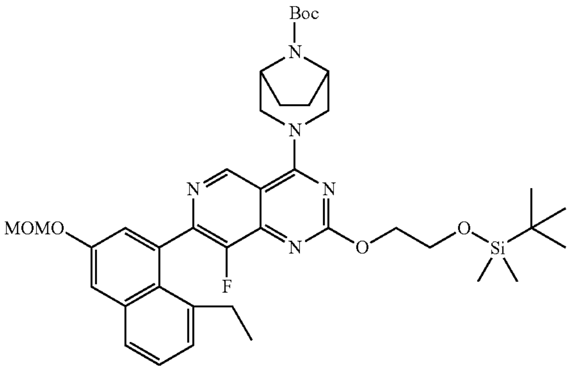

A mixture of tert-butyl tert-butyl 3-[2-[2-[tert-butyl(dimethyl)silyl]oxyethoxy]-7-chloro-8-fluoro-pyrido[4,3-d]pyrimidin-4-yl]-3,8-diazabicyclo[3.2.1]octane-8-carboxylate (4 g, 7.04 mmol, 1 eq), 2-[8-ethyl-3-(methoxymethoxy)-1-naphthyl]-4,4,5,5-tetramethyl-1,3,2-dioxaborolane (3.13 g, 9.15 mmol, 1.3 eq), potassium phosphate (4.48 g, 21.12 mmol, 3 eq), and [2-(2-aminophenyl)phenyl]palladium(1+); bis(1-adamantyl)-butyl-phosphane;methanesulfonate (513 mg, 704.03 μmol, 0.1 eq) in dioxane (50 mL) and water (6 mL) was stirred for 12 hours at 90° C. under nitrogen. The reaction mixture was concentrated, and the resulting residue was purified by silica gel column chromatography (petroleum ether/ethyl acetate=10/1 to 1/1) to afford the title compound (4.4 g, 5.88 mmol, 83% yield) as a yellow solid.

Step 9: Preparation of tert-butyl 3-[7-[8-ethyl-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate

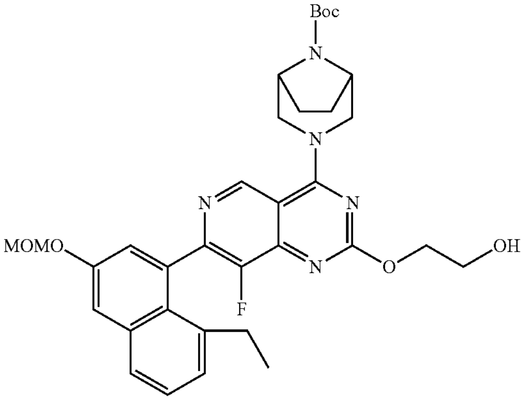

To a solution of tert-butyl 3-[2-[2-[tert-butyl(dimethyl) silyl]oxyethoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (4.4 g, 5.88 mmol, 1 eq) in DMF (40 mL) at 25° C. was added cesium fluoride (26.81 g, 176.48 mmol, 30 eq), and the reaction mixture was stirred for 12 hours at 25° C. The reaction mixture was diluted with water (50 mL) and extracted with ethyl acetate (50 mL×3). The combined organic extract was washed with brine (50 mL), dried over anhydrous sodium sulfate, filtered, and concentrated. The resulting residue was purified by silica gel column chromatography (petroleum ether/ethyl acetate=10/1 to 1/1) to afford the title compound (3.7 g, 5.84 mmol, 99% yield) as a yellow solid. $^1H$ NMR (400 MHz, $CDCl_3$) δ 9.04 (s, 1H), 7.71 (d, J=8.0 Hz, 1H), 7.54 (d, J=2.8 Hz, 1H), 7.42 (t, J=7.6 Hz, 1H), 7.24 (d, J=7.2 Hz, 1H), 7.19 (d, J=2.8 Hz, 1H), 5.31 (d, J=1.7 Hz, 2H), 4.70-4.59 (m, 3H), 4.53 (br d, J=12.4 Hz, 1H), 4.48-4.32 (m, 2H), 4.06-3.98 (m, 2H), 3.83-3.61 (m, 2H), 3.52 (s, 3H), 2.35 (br dd, J=7.6, 10.8 Hz, 2H), 2.04-1.97 (m, 2H), 1.86-1.64 (m, 2H), 1.53 (s, 9H), 0.95 (t, J=7.6 Hz, 3H).

Step 10: Preparation of tert-butyl (1R,5S)-3-(7-(8-ethyl-3-(methoxymethoxy)naphthalen-1-yl)-8-fluoro-2-(2-oxoethoxy)pyrido[4,3-d]pyrimidin-4-yl)-3,8-diazabicyclo[3.2.1]octane-8-carboxylate

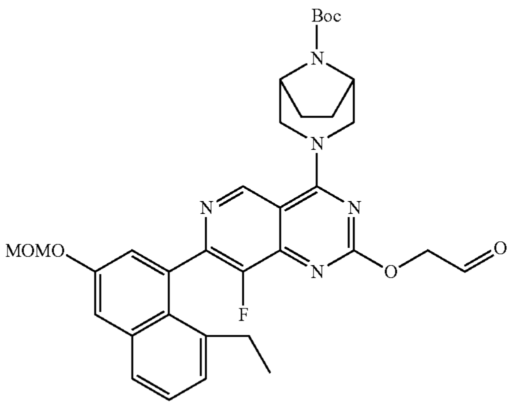

A solution of dimethyl sulfoxide (771 mg, 9.86 mmol, 0.8 mL, 2.5 eq) in dichloromethane (10 mL) was added dropwise to a solution of oxalyl chloride (751 mg, 5.92 mmol, 0.5 mL, 1.5 eq) in dichloromethane (10 mL) at −78° C. After 15 minutes, a solution of tert-butyl 3-[7-[8-ethyl-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate (2.5 g, 3.95 mmol, 1 eq) in dichloromethane (10 mL) was added dropwise. The reaction mixture was stirred at −78° C. for 30 minutes. Triethylamine (2.00 g, 19.73 mmol, 2.8 mL, 5 eq) was then added, and the reaction mixture was stirred at −78° C. the same temperature for 30 minutes, then allowed to warm to 25° C. over 1 hour. The reaction was quenched with saturated sodium sulfite solution (20 mL), and the resulting mixture was extracted with dichloromethane (20 mL×3). The combined organic phase was washed with saturated sodium bicarbonate solution (20 mL), dried over anhydrous sodium sulfate, filtered, and concentrated. The resulting residue was purified by silica gel column chromatography (petroleum ether/ethyl acetate=10/1 to 1/1) to afford the title compound (1.8 g, 2.85 mmol, 72% yield) as a yellow solid. LC/MS (ESI) m/z: 632.3 $[M+H]^+$.

Step 11: Preparation of tert-butyl 3-[2-[2-[4-[[1-[1-(2,6-dioxo-3-piperidyl)-3-methyl-2-oxo-benzimidazol-4-yl]-4-piperidyl]methyl]-1-piperidyl]ethoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

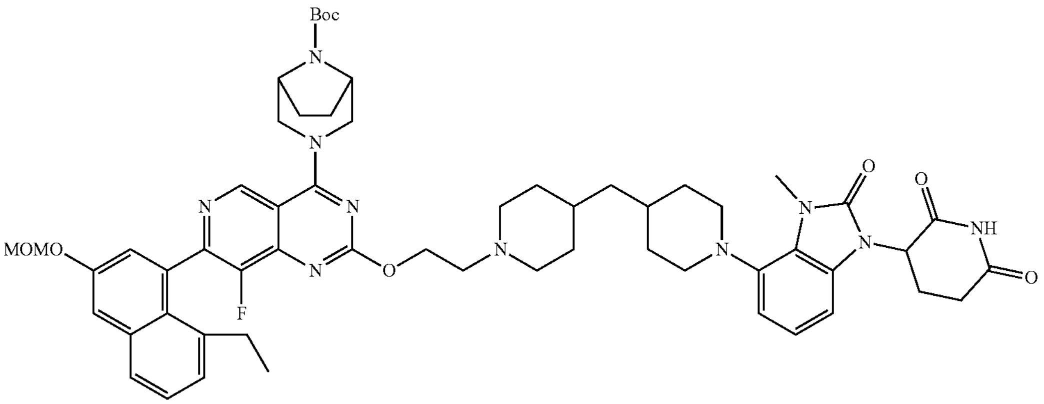

-

To a solution of 3-[3-methyl-2-oxo-4-[4-(4-piperidylmethyl)-1-piperidyl]benzimidazol-1-yl]piperidine-2,6-dione (102 mg, 0.18 mmol, 1 eq, trifluoroacetic acid) in dichloromethane (1 mL) and isopropyl alcohol (1 mL) were added diisopropylethylamine (119 mg, 0.92 mmol, 0.2 mL, 5 eq) and tert-butyl (1R,5S)-3-(7-(8-ethyl-3-(methoxymethoxy)naphthalen-1-yl)-8-fluoro-2-(2-oxoethoxy)pyrido[4,3-d]pyrimidin-4-yl)-3,8-diazabicyclo[3.2.1]octane-8-carboxylate (128 mg, 0.20 mmol, 1.1 eq), and the resulting mixture was stirred at 25° C. for 1 hour. Sodium triacetoxyborohydride (117 mg, 0.55 mmol, 3 eq) was then added, and the reaction mixture was stirred at 25° C. for 1 hour. The reaction mixture was diluted with water (50 mL) and extracted with dichloromethane (15 mL×3). The combined organic extract was washed with brine (50 mL), dried over anhydrous sodium sulfate, filtered, and concentrated in vacuum. The resulting residue was purified by prep-TLC (dichloromethane/methanol=10/1) to afford the title compound (86 mg, 0.08 mmol, 44% yield) as a white solid. LC/MS (ESI) m/z: 1055.7 $[M+H]^+$.

Step 12: Preparation of 3-[4-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-3-methyl-2-oxo-benzimidazol-1-yl]piperidine-2,6-dione (Compound 28)

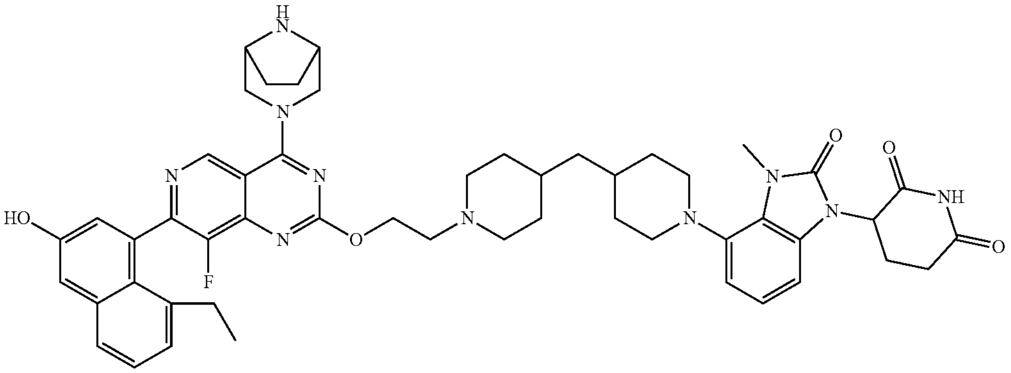 [SMILES: CCc1cccc2cc(O)cc(-c3ncc4c(N5CC6CCC(C5)N6)nc(OCCN5CCC(CC6CCN(c7cccc8c7n(C)c(=O)n8C7CCC(=O)NC7=O)CC6)CC5)nc4c3F)c12]

To a solution of tert-butyl 3-[2-[2-[4-[[1-[1-(2,6-dioxo-3-piperidyl)-3-methyl-2-oxo-benzimidazol-4-yl]-4-piperidyl]methyl]-1-piperidyl]ethoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (82 mg, 0.08 mmol, 1 eq) in dichloromethane (1 mL) was added trifluoroacetic acid (1.54 g, 13.51 mmol, 1 mL, 173.81 eq), and the reaction mixture was stirred at 25° C. for 0.5 hours. The solvent was concentrated under nitrogen flow, and the crude product was purified by reverse-phase HPLC (column: Phenomenex luna C18 150*25 mm*10 μm; mobile phase: [9-39% $CH_3CN$ in water (formic acid)]) to afford the title compound (26.2 mg, 0.03 mmol, 32% yield, bis-formic acid salt) as a white solid.

Example 6: Synthesis of 3-[4-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-1-oxo-isoindolin-2-yl]piperidine-2,6-dione (Compound 56)

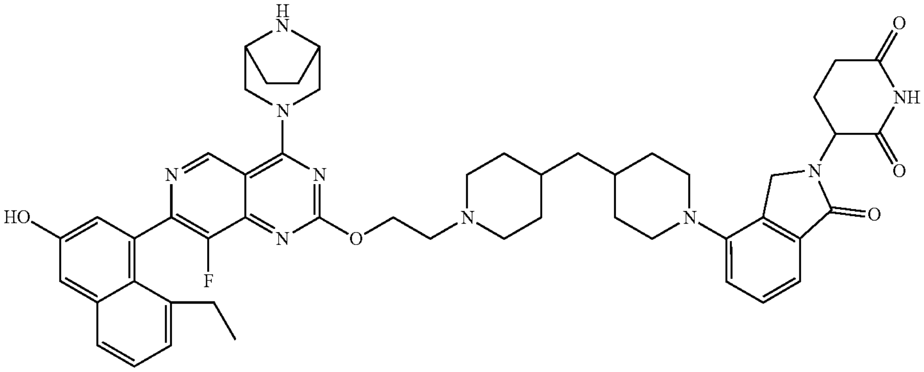 [SMILES: CCc1cccc2cc(O)cc(-c3ncc4c(N5CC6CCC(C5)N6)nc(OCCN5CCC(CC6CCN(c7cccc8c7CN(C7CCC(=O)NC7=O)C8=O)CC6)CC5)nc4c3F)c12]

The title compound was prepared in an analogous manner to 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione(bis-formic acid salt; as a white solid).

Example 7: Synthesis of 3-[4-[4-[[1-[2-[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl] oxyethyl]-4-piperidyl]methyl]-1-piperidyl]-1-oxo-isoindolin-2-yl]piperidine-2,6-dione (Compound 41)

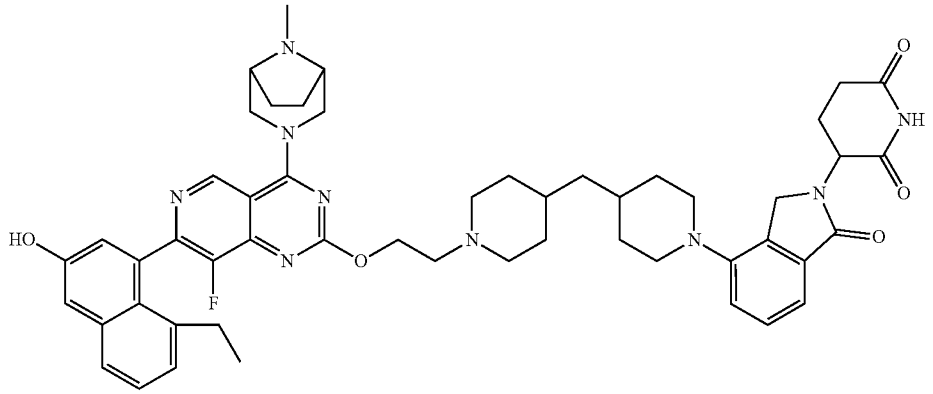 [SMILES: CCc1cccc2cc(O)cc(-c3ncc4c(N5CC6CCC(C5)N6C)nc(OCCN5CCC(CC6CCN(c7cccc8c7CN(C7CCC(=O)NC7=O)C8=O)CC6)CC5)nc4c3F)c12]

To a solution of formaldehyde (28 mg, 0.35 mmol, 37% purity, 5 eq) in dichloromethane (2 mL) and methanol (2 mL) was added 4-methylmorpholine (10 mg, 0.10 mmol, 1.5 eq), and the resulting mixture was stirred at 25° C. for 15 minutes. 3-[4-[4-[[1-[2-[4-(3,8-Diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-1-oxo-isoindolin-2-yl]piperidine-2,6-dione (70 mg, 0.07 mmol, 1 eq, trifluoroacetate) was then added, and the mixture was stirred for 0.5 hours at 25° C. Sodium triacetoxyborohydride (44 mg, 0.21 mmol, 3 eq) was then added, and the reaction mixture was stirred at 25° C. for 2 hours. The reaction mixture was concentrated, and the resulting residue was purified by prep-HPLC {column: Unisil 3-100 C18 Ultra 150*50 mm*3 μm; mobile phase: 9-39% $CH_3CN$ in [water (formic acid)]} to afford the title compound (65.1 mg, 0.06 mmol, 94% yield, formic acid salt) as a white solid.

Example 8: Synthesis of 5-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxyethyl]-4-piperidyl]methyl]-1-piperidyl]-2-(2,6-dioxo-3-piperidyl)isoindoline-1,3-dione (Compound 67)

Step 1: Preparation of tert-butyl 4-[[1-[2-(2,6-dioxo-3-piperidyl)-1,3-dioxo-isoindolin-5-yl]-4-piperidyl]methyl]piperidine-1-carboxylate

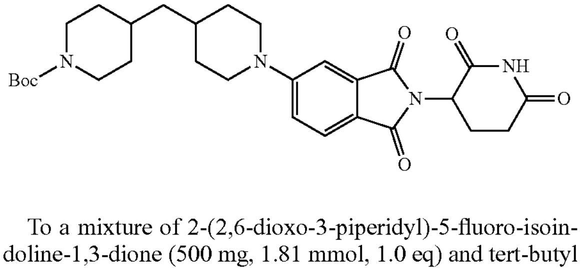

To a mixture of 2-(2,6-dioxo-3-piperidyl)-5-fluoro-isoindoline-1,3-dione (500 mg, 1.81 mmol, 1.0 eq) and tert-butyl 4-(4-piperidylmethyl)piperidine-1-carboxylate (613 mg, 2.17 mmol, 1.2 eq) in DMSO (10 mL) was added diisopropylethylamine (5.43 mmol, 946 μL, 3.0 eq) in one portion at 25° C., and the reaction mixture was stirred at 100° C. for 2 hours. The mixture was diluted with water (20 mL), and the aqueous phase was extracted with ethyl acetate (30 mL×4). The combined organic extract was washed with brine (30 mL), dried over anhydrous $Na_2SO_4$, and concentrated in vacuum. The crude product was purified flash chromatography on $SiO_2$ (gradient: 0-41% ethyl acetate in petroleum ether) to afford the title compound (310 mg, 0.541 mmol, 30% yield) as a yellow solid. LC/MS (ESI) m/z: 539.3 $[M+H]^+$.

Step 2: Preparation of 2-(2,6-dioxo-3-piperidyl)-5-[4-(4-piperidylmethyl)-1-piperidyl]isoindoline-1,3-dione

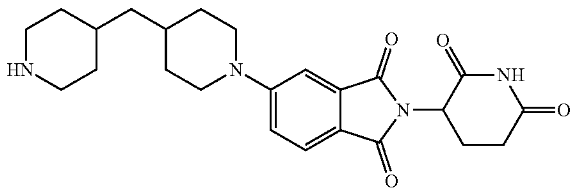 [SMILES: O=C1CCC(N2C(=O)c3ccc(N4CCC(CC5CCNCC5)CC4)cc3C2=O)C(=O)N1]

To a solution of tert-butyl 4-[[1-[2-(2,6-dioxo-3-piperidyl)-1,3-dioxo-isoindolin-5-yl]-4-piperidyl]methyl]piperidine-1-carboxylate (93 mg, 0.173 mmol, 1.0 eq) in dichloromethane (2 mL) was added HCl/dioxane (4 M, 432 μL, 10.0 eq), and the reaction mixture was stirred at 25° C. for 2 hours. The reaction mixture was concentrated in vacuum to afford the title compound (75 mg, 0.147 mmol, 85% yield) as a white solid. LC/MS (ESI) m/z: 439.0 $[M+H]^+$.

Step 3: Preparation of 5-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-2-(2,6-dioxo-3-piperidyl)isoindoline-1,3-dione (Compound 67)

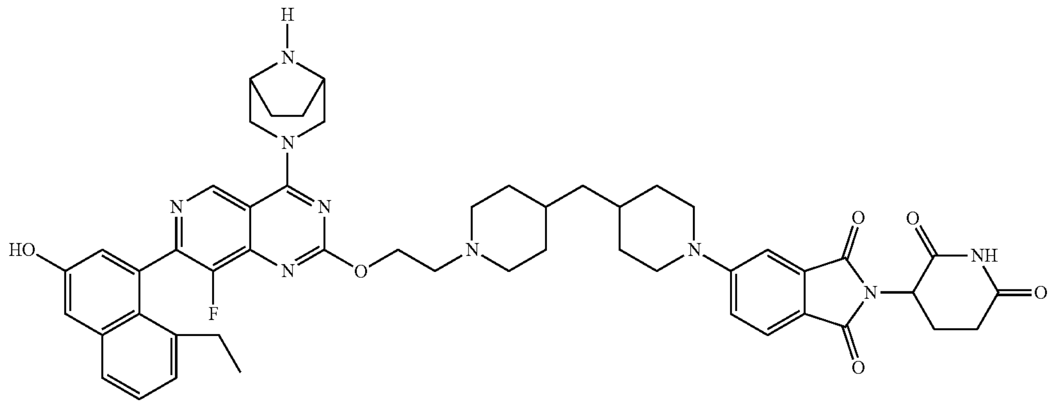 [SMILES: CCc1cccc2cc(O)cc(-c3ncc4c(N5CC6CCC(C5)N6)nc(OCCN5CCC(CC6CCN(c7ccc8c(c7)C(=O)N(C7CCC(=O)NC7=O)C8=O)CC6)CC5)nc4c3F)c12]

The title compound was prepared in an analogous manner to 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione starting from tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate and 2-(2,6-dioxo-3-piperidyl)-5-[4-(4-piperidylmethyl)-1-piperidyl]isoindoline-1,3-dione, and purified by prep-HPLC (column: Xtimate C18 100*30 mm*10 μm; mobile phase: [5-50% $CH_3CN$ in water (formic acid)]). Pure fractions were combined, then lyophilized to afford the title compound (32.1 mg, 0.035 mmol, 79% yield, formic acid salt) as a yellow solid.

Example 9: Synthesis of 4-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-2-(2,6-dioxo-3-piperidyl)isoindoline-1,3-dione (Compound 66)

Step 1: Preparation of tert-butyl 4-[[1-[2-(2,6-dioxo-3-piperidyl)-1,3-dioxo-isoindolin-4-yl]-4-piperidyl]methyl]piperidine-1-carboxylate

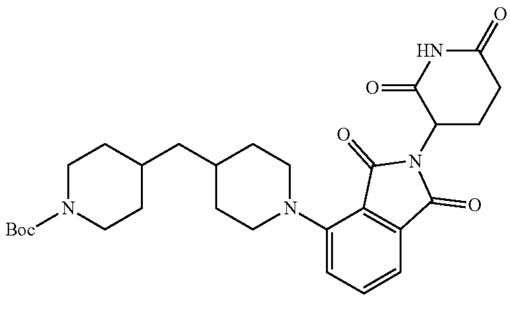 [SMILES: CC(C)(C)OC(=O)N1CCC(CC2CCN(c3cccc4c3C(=O)N(C3CCC(=O)NC3=O)C4=O)CC2)CC1]

To a solution of 2-(2,6-dioxo-3-piperidyl)-4-fluoro-isoindoline-1,3-dione (400 mg, 1.45 mmol, 1.0 eq) and tert-butyl 4-(4-piperidylmethyl) piperidine-1-carboxylate (450 mg, 1.59 mmol, 1.1 eq) in DMSO (10 mL) was added diisopropylethylamine (4.34 mmol, 757 μL, 3.0 eq), and the reaction mixture was stirred at 100° C. for 2 hours. The mixture was diluted with ethyl acetate (60 mL), then washed with water (20 mL×9), brine (20 mL), dried over anhydrous sodium sulfate, filtered, and concentrated. The resulting residue was purified by flash chromatography on $SiO_2$ (gradient: 0-29% ethyl acetate in petroleum ether) to afford the title compound (610 mg, 0.789 mmol, 55% yield) as a yellow solid. LC/MS (ESI) m/z: 483.3 $[M-C_4H_8+H]^+$.

Step 2: Preparation of 2-(2,6-dioxo-3-piperidyl)-4-[4-(4-piperidylmethyl)-1-piperidyl]isoindoline-1,3-dione

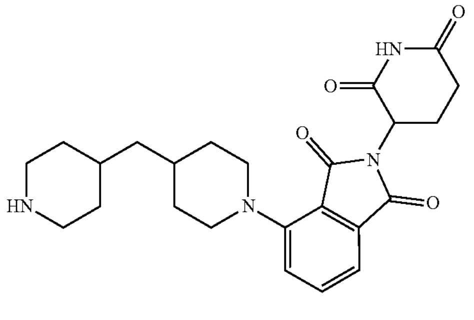 [SMILES: O=C1CCC(N2C(=O)c3cccc(N4CCC(CC5CCNCC5)CC4)c3C2=O)C(=O)N1]

To a solution of tert-butyl 4-[[1-[2-(2,6-dioxo-3-piperidyl)-1,3-dioxo-isoindolin-4-yl]-4-piperidyl]methyl]piperidine-1-carboxylate (200 mg, 0.371 mmol, 1.0 eq) in dichloromethane (2 mL) was added HCl/dioxane (4 M, 928 μL, 10.0 eq), and the reaction mixture was stirred at 25° C. for 2 hours. The reaction mixture was concentrated in vacuum to afford the title compound (139 mg, 285 mmol, 77% yield) as a yellow solid. LC/MS (ESI) m/z: 439.3 $[M+H]^+$.

Step 3: Preparation of 4-[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]-2-(2,6-dioxo-3-piperidyl)isoindoline-1,3-dione (Compound 66)

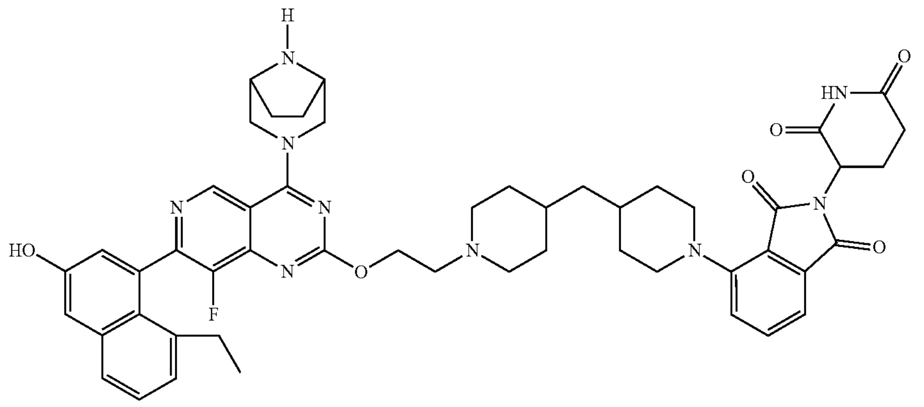 [SMILES: CCc1cccc2cc(O)cc(-c3ncc4c(N5CC6CCC(C5)N6)nc(OCCN5CCC(CC6CCN(c7cccc8c7C(=O)N(C7CCC(=O)NC7=O)C8=O)CC6)CC5)nc4c3F)c12]

The title compound was prepared in an analogous manner to 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione starting from tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate and 2-(2,6-dioxo-3-piperidyl)-4-[4-(4-piperidylmethyl)-1-piperidyl]isoindoline-1,3-dione, and purified by prep-HPLC (column: Xtimate C18 100*30 mm*10 μm; mobile phase: [10-50% $CH_3CN$ in water (formic acid)]). Pure fractions were combined, then lyophilized to afford the title compound (21.2 mg, 0.022 mmol, 57% yield, formic acid salt) as a yellow solid.

Example 10: Synthesis of 4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-2-(2,6-dioxo-3-piperidyl)isoindoline-1,3-dione (Compound 57)

Step 1: Preparation of 4-[4-(dimethoxymethyl)-1-piperidyl]-2-(2,6-dioxo-3-piperidyl)isoindoline-1,3-dione

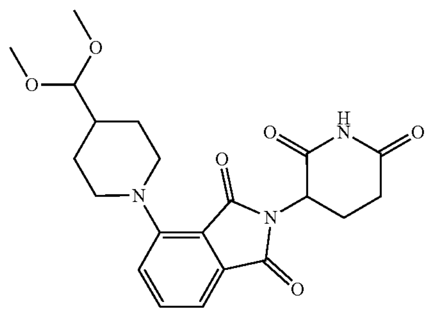 [SMILES: COC(OC)C1CCN(c2cccc3c2C(=O)N(C2CCC(=O)NC2=O)C3=O)CC1]

To a solution of 2-(2,6-dioxo-3-piperidyl)-4-fluoro-isoindoline-1,3-dione (800 mg, 2.90 mmol, 1.0 eq) in dimethyl sulfoxide (8 mL) was added 4-(dimethoxymethyl)piperidine (553 mg, 3.48 mmol, 1.2 eq), and the reaction mixture was stirred at 100° C. for 3 hours. The reaction mixture was diluted with water (10 mL), then extracted with ethyl acetate (20 mL×3). The combined organic extracts were washed with water (20 mL×3) and concentrated under reduced pressure. The crude product was purified by flash chromatography on $SiO_2$ (gradient: 0-4% methanol in dichloromethane) to afford the title compound (929 mg, 2.10 mmol, 72% yield) as a yellow solid. LC/MS (ESI) m/z: 416.2 $[M+H]^+$. $^1H$ NMR (400 MHz, $CDCl_3$) δ 7.97 (s, 1H), 7.64-7.60 (m, 1H), 7.46-7.43 (m, 1H), 5.00-4.95 (m, 1H), 3.79-3.75 (m, 2H), 3.40 (s, 6H). 2.93-2.72 (m, 4H), 2.16-2.11 (m, 1H), 1.94-1.91 (m, 2H), 1.87-1.82 (m, 1H), 1.70-1.57 (m, 4H).

Step 2: Preparation of 1-[2-(2,6-dioxo-3-piperidyl)-1,3-dioxo-isoindolin-4-yl]piperidine-4-carbaldehyde

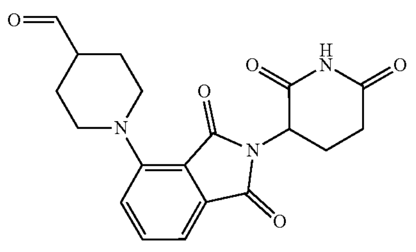 [SMILES: O=CC1CCN(c2cccc3c2C(=O)N(C2CCC(=O)NC2=O)C3=O)CC1]

To a solution of 4-[4-(dimethoxymethyl)-1-piperidyl]-2-(2,6-dioxo-3-piperidyl)isoindoline-1,3-dione (460 mg, 1.11 mmol, 1.0 eq) in tetrahydrofuran (9 mL) was added hydrochloric acid (1 M, 8.30 mL, 7.5 eq), and the reaction mixture was stirred at 20° C. for 1 hour. The reaction mixture was adjusted to pH=7 by addition of saturated sodium bicarbonate solution, then extracted with ethyl acetate (20 mL×3). The combined organic extracts were dried over anhydrous $Na_2SO_4$ and concentrated under reduced pressure to afford the title compound (398 mg, 0.98 mmol, 88% yield) as a yellow solid. LC/MS (ESI) m/z: 370.1 $[M+H]^+$. $^1H$ NMR (400 MHz, $CDCl_3$) δ 9.75 (s, 1H), 7.96 (s, 1H), 7.68-7.64 (m, 1H), 7.53-7.51 (m, 1H), 5.00-4.96 (m, 1H), 3.72-3.70 (m, 2H), 3.21 (s, 2H). 2.94-2.73 (m, 4H), 2.55-2.52 (m, 1H), 2.18-2.14 (m, 2H), 1.58 (s, 2H).

Step 3: Preparation of tert-butyl 4-[[1-[[1-[2-(2,6-dioxo-3-piperidyl)-1,3-dioxo-isoindolin-4-yl]-4-piperidyl]methyl]-4-piperidyl]methyl]piperidine-1-carboxylate

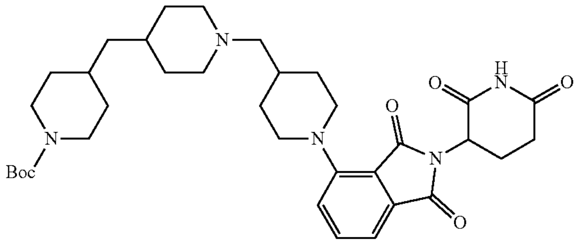 [SMILES: CC(C)(C)OC(=O)N1CCC(CC2CCN(CC3CCN(c4cccc5c4C(=O)N(C4CCC(=O)NC4=O)C5=O)CC3)CC2)CC1]

To a solution of 1-[2-(2,6-dioxo-3-piperidyl)-1,3-dioxo-isoindolin-4-yl]piperidine-4-carbaldehyde (398 mg, 1.08 mmol, 1 eq) and tert-butyl 4-(4-piperidylmethyl)piperidine-1-carboxylate (304 mg, 1.08 mmol, 1 eq) in isopropanol (3 mL) and dichloromethane (3 mL) were added acetic acid (259 mg, 4.31 mmol, 0.25 mL, 4 eq) and 2-methylpyridine borane (461 mg, 4.31 mmol, 4 eq) in one portion at 20° C., and the reaction mixture was stirred at 20° C. for 1 hour. The reaction mixture was adjusted to pH=6 by addition of triethylamine, then concentrated. The crude product was purified by flash chromatography (gradient: 0-100% ethyl acetate in petroleum ether) to afford the title compound (541 mg, 0.77 mmol, 71% yield) as a yellow solid. LC/MS (ESI) m/z: 636.4 $[M+H]^+$. $^1H$ NMR (400 MHz, $CDCl_3$) δ 7.59-7.55 (m, 1H), 7.37 (d, J=3.2 Hz, 1H), 7.17 (d, J=4.4 Hz, 1H), 4.98-4.94 (m, 1H), 4.10-4.08 (m, 2H), 3.76-3.71 (m, 2H), 3.15-3.09 (m, 2H), 2.95-2.65 (m, 7H), 2.47 (s, 2H), 2.23-2.16 (m, 1H), 2.14-2.09 (m, 1H), 2.05 (s, 2H), 1.98-1.88 (m, 3H), 1.72-1.49 (m, 8H), 1.46 (s, 9H), 1.43 (s, 1H), 1.20 (s, 2H), 1.11-1.01 (m, 2H).

Step 4: Preparation of 2-(2,6-dioxo-3-piperidyl)-4-[4-[[4-(4-piperidylmethyl)-1-piperidyl]methyl]-1-piperidyl]isoindoline-1,3-dione

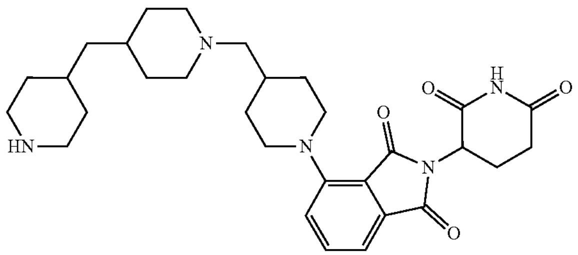 [SMILES: O=C1CCC(N2C(=O)c3cccc(N4CCC(CN5CCC(CC6CCNCC6)CC5)CC4)c3C2=O)C(=O)N1]

To a solution of tert-butyl 4-[[1-[[1-[2-(2,6-dioxo-3-piperidyl)-1,3-dioxo-isoindolin-4-yl]-4-piperidyl]methyl]-4-piperidyl]methyl]piperidine-1-carboxylate (130 mg, 0.20 mmol, 1 eq) in dichloromethane (2 mL) was added trifluoroacetic acid (466 mg, 4.09 mmol, 0.3 mL, 20 eq), and the reaction mixture was stirred at 20° C. for 1 hour. The mixture was concentrated to afford the title compound (328 mg, crude, TFA) as a yellow oil. LC/MS (ESI) m/z: 536.3 $[M+H]^+$.

Step 5: Preparation of 4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-2-(2,6-dioxo-3-piperidyl)isoindoline-1,3-dione (Compound 57)

The title compound was prepared in an analogous manner to 3-[4-[4-[[4-[[1-[2-[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-1-oxo-isoindolin-2-yl]piperidine-2,6-dione starting from tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate and 2-(2,6-dioxo-3-piperidyl)-4-[4-[[4-(4-piperidylmethyl)-1-piperidyl]methyl]-1-piperidyl]isoindoline-1,3-dione, and purified by prep-HPLC (column: Phenomenex C18 75*30 mm*3 μm; mobile phase: [3-43% $CH_3CN$ in water (formic acid)]) followed by prep-HPLC (column: Phenomenex C18 75*30 mm*3 μm; mobile phase: [3-33% $CH_3CN$ in water (formic acid)]). Pure fractions were combined and dried by lyophilization to afford the title compound (49.1 mg, 0.05 mmol, 48% yield, 27% yield, formic acid salt) as a yellow solid.

Example 11: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate (Compound 63)

Step 1: Preparation of 1-benzyl 2-methyl (2S)-pyrrolidine-1,2-dicarboxylate

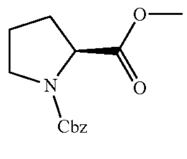 [SMILES: COC(=O)[C@@H]1CCCN1C(=O)OCc1ccccc1]

To a solution of methyl (2S)-pyrrolidine-2-carboxylate hydrochloride (40.0 g, 242 mmol, 1 eq) in $CH_2Cl_2$ (500 mL) were added TEA (56.2 g, 556 mmol, 2.3 eq) and CbzCl (53.6 g, 314 mmol, 1.3 eq), and the reaction mixture was stirred at 25° C. under $N_2$ for 16 hours. The reaction mixture was washed with water (100 mL), brine (100 mL), dried over anhydrous $Na_2SO_4$, filtered, and concentrated. The crude product was purified by flash silica gel chromatography (gradient: 0-10% THF in petroleum ether) to give the title compound (60.6 g, 230 mmol, 95% yield) as a colorless oil. LC/MS (ESI) m/z: 264.0 $[M+H]^+$.

Step 2: Preparation of 1-benzyl 2-methyl 2-but-3-enylpyrrolidine-1,2-dicarboxylate

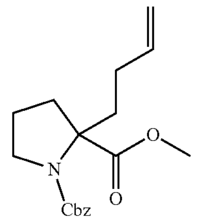 [SMILES: C=CCCC1(C(=O)OC)CCCN1C(=O)OCc1ccccc1]

To a stirred solution of 1-benzyl 2-methyl (2S)-pyrrolidine-1,2-dicarboxylate (27.5 g, 104 mmol, 1 eq) in THF (300 mL) at −78° C. was added LiHMDS (1 M, 125 mL, 1.2 eq), and the reaction mixture was stirred at −78° C. under $N_2$ for 0.5 hour. 4-Bromobut-1-ene (28.2 g, 209 mmol, 2 eq) was then added at −78° C., and the reaction mixture was stirred at 20° C. under $N_2$ for 16 hours. Two batches were conducted. The reaction mixture was quenched by addition of saturated $NH_4Cl$ solution (300 mL) and extracted with EtOAc (2×300 mL). The combined organic extract was washed with brine (300 mL), dried over anhydrous $Na_2SO_4$, filtered, and concentrated. The crude product was purified by flash silica gel chromatography (gradient: 0-8% THF in petroleum ether) to give the title compound (44.9 g, 141 mmol, 68% yield) as a yellow oil. LC/MS (ESI) m/z: 318.0 $[M+H]^+$.

Step 3: Preparation of 1-benzyl 2-methyl 2-[2-(oxiran-2-yl)ethyl]pyrrolidine-1,2-dicarboxylate

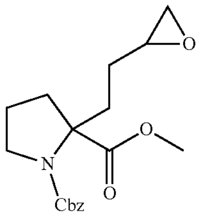 [SMILES: COC(=O)C1(CCC2CO2)CCCN1C(=O)OCc1ccccc1]

To a solution of 1-benzyl 2-methyl 2-but-3-enylpyrrolidine-1,2-dicarboxylate (44.9 g, 141 mmol, 1 eq) in $CH_2Cl_2$ (600 mL) was added m-CPBA (33.6 g, 156 mmol, 80% purity, 1.1 eq), and the reaction mixture was stirred at 20° C. for 16 hours. The reaction mixture was filtered, and the filtrate was washed with saturated aqueous $NaHSO_3$ (300 mL), $NaHCO_3$ (2×200 mL), and brine (200 mL), then dried over anhydrous $Na_2SO_4$, filtered, and concentrated. The crude product was purified by flash silica gel chromatography (gradient: 0-15% THF in petroleum ether) to give the title compound (37.5 g, 112 mmol, 80% yield) as a colorless oil. LC/MS (ESI) m/z: 334.2 $[M+H]^+$.

Step 4: Preparation of methyl 3-(hydroxymethyl)-1,2,3,5,6,7-hexahydropyrrolizine-8-carboxylate

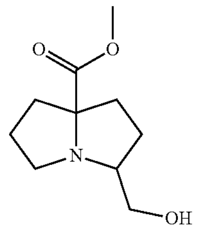

To a solution of 1-benzyl 2-methyl 2-[2-(oxiran-2-yl)ethyl]pyrrolidine-1,2-dicarboxylate (37.5 g, 112 mmol, 1 eq) in $CH_3OH$ (400 mL) was added Pd/C (3.0 g, 10% purity), and the reaction mixture was stirred at 25° C. under $H_2$ (15 psi) (degassed under vacuum and purged with $H_2$ several times) for 16 hours. The reaction mixture was filtered, and the filtrate was concentrated under reduced pressure to give the title compound (22.4 g, 112 mmol, 100% yield) as a yellow oil.

Step 5: Preparation of methyl (3S,7aR)-3-(((tert-butyldiphenylsilyl)oxy)methyl)tetrahydro-1H-pyrrolizine-7a(5H)-carboxylate and methyl (3R,7aR)-3-(((tert-butyldiphenylsilyl)oxy)methyl)tetrahydro-1H-pyrrolizine-7a(5H)-carboxylate

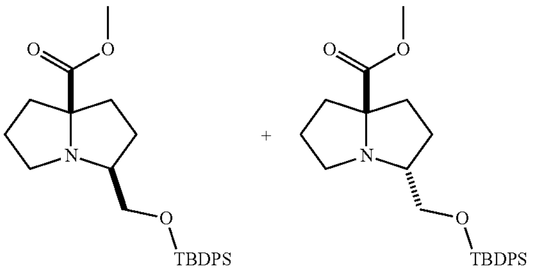

To a solution of methyl 3-(hydroxymethyl)-1,2,3,5,6,7-hexahydropyrrolizine-8-carboxylate (22.4 g, 112 mmol, 1 eq) and imidazole (9.95 g, 146 mmol, 1.3 eq) in $CH_2Cl_2$ (300 mL) was added TBDPSCl (37.1 g, 135 mmol, 1.2 eq), and the reaction mixture was stirred at 25° C. under $N_2$ for 16 hours. The reaction mixture was quenched by addition of water (100 mL) and extracted with $CH_2Cl_2$ (3×100 mL). The combined organic extract was washed with brine (2×100 mL), dried over anhydrous $Na_2SO_4$, filtered, and concentrated. The crude product was purified by flash silica gel chromatography (gradient: 0-10% THF in petroleum ether). Methyl (3S,7aR)-3-(((tert-butyldiphenylsilyl)oxy)methyl)tetrahydro-1H-pyrrolizine-7a(5H)-carboxylate (24.3 g, 39.7 mmol, 35% yield) was eluted first and isolated as a colorless oil (LC/MS (ESI) m/z: 438.2 $[M+H]^+$), then methyl (3R,7aR)-3-(((tert-butyldiphenylsilyl)oxy)methyl)tetrahydro-1H-pyrrolizine-7a(5H)-carboxylate (20.8 g, 43.0 mmol, 38% yield) was eluted and isolated as a colorless oil (LC/MS (ESI) m/z: 438.3 $[M+H]^+$).

Step 6: Preparation of methyl (3R,8R)-3-[[tert-butyl(diphenyl)silyl]oxymethyl]-1,2,3,5,6,7-hexahydropyrrolizine-8-carboxylate and methyl (3S,8S)-3-[[tert-butyl(diphenyl)silyl]oxymethyl]-1,2,3,5,6,7-hexahydropyrrolizine-8-carboxylate

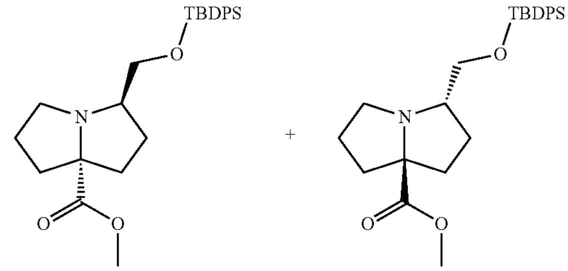

Methyl (3R,7aR)-3-(((tert-butyldiphenylsilyl)oxy)methyl)tetrahydro-1H-pyrrolizine-7a(5H)-carboxylate (20.8 g, 47.5 mmol, 1 eq) was separated by SFC (column: REGIS (s,s) WHELK-01 (250 mm*50 mm, 10 μm); mobile phase: [0.1% $NH_4OH$ EtOH]; B %: 25%, Flow Rate: 140 mL/min) to afford first eluted enantiomer methyl (3R,8R)-3-[[tert-butyl(diphenyl)silyl]oxymethyl]-1,2,3,5,6,7-hexahydropyrrolizine-8-carboxylate (9.78 g, 22.35 mmol, 47% yield) as a colorless oil (LC/MS (ESI) m/z: 438.2 $[M+H]^+$), and the later eluted enantiomer methyl (3S,8S)-3-[[tert-butyl(diphenyl)silyl]oxymethyl]-1,2,3,5,6,7-hexahydropyrrolizine-8-carboxylate (8.81 g, 20.1 mmol, 42.36% yield) as a colorless oil (LC/MS (ESI) m/z: 438.3 $[M+H]^+$).

Step 7: Preparation of [(3R,8R)-3-[[tert-butyl(diphenyl)silyl]oxymethyl]-1,2,3,5,6,7-hexahydropyrrolizin-8-yl]methanol

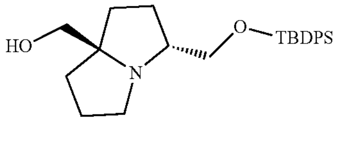

To a solution of methyl (3R,8R)-3-[[tert-butyl(diphenyl)silyl]oxymethyl]-1,2,3,5,6,7-hexahydropyrrolizine-8-carboxylate (2.69 g, 6.15 mmol, 1 eq) in THF (30 mL) at 0° C. was added $LiAlH_4$ (280 mg, 7.38 mmol, 1.2 eq), and the reaction mixture was stirred at 0° C. under $N_2$ for 1 hour. The reaction mixture was quenched by sequential addition of water (300 μL), 15% aq. NaOH (300 μL), and water (900 μL), then diluted with EtOAc (30 mL). The resulting suspension was dried over anhydrous $Na_2SO_4$, filtered, and concentrated. The crude product was purified by flash silica gel chromatography (gradient: 0-10% $CH_3OH$ in $CH_2Cl_2$) to give the title compound (2.07 g, 5.05 mmol, 82% yield) as a yellow oil. LC/MS (ESI) m/z: 410.1 $[M+H]^+$.

Step 8: Preparation of tert-butyl 3-[2-[[(3R,8R)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate

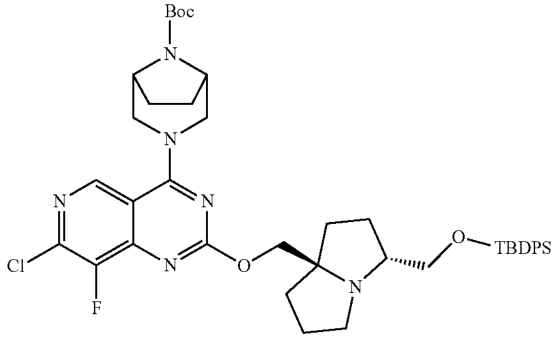

To a solution of [(3R,8R)-3-[[tert-butyl(diphenyl)silyl]oxymethyl]-1,2,3,5,6,7-hexahydropyrrolizin-8-yl]methanol (1.00 g, 2.44 mmol, 1 eq) and tert-butyl 3-(2,7-dichloro-8-fluoro-pyrido[4,3-d]pyrimidin-4-yl)-3,8-diazabicyclo[3.2.1]octane-8-carboxylate (1.05 g, 2.44 mmol, 1 eq) in dioxane (30 mL) were added $Cs_2CO_3$ (954 mg, 2.93 mmol, 1.2 eq) and DABCO (109 mg, 0.976 mmol, 0.4 eq), and the reaction mixture was stirred at 25° C. under $N_2$ for 40 hours. The reaction mixture was filtered, and the filtrate was concentrated. The crude product was purified by flash silica gel chromatography (gradient: 0-20% THF in petroleum ether) to give the title compound (1.16 g, 1.13 mmol, 46% yield) as a yellow solid. LC/MS (ESI) m/z: 801.2 $[M+H]^+$.

Step 9: Preparation of tert-butyl 3-[2-[[(3R,8R)-3-[[tert-butyl(diphenyl)silyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

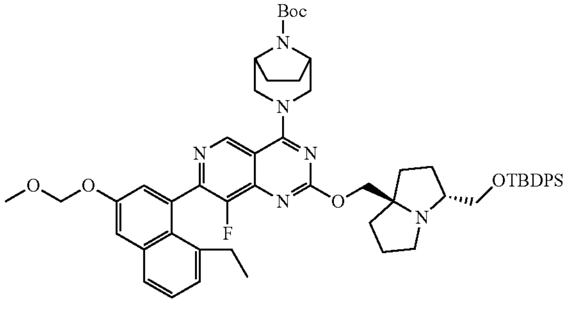

To a solution of tert-butyl 3-[2-[[(3R,8R)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (800 mg, 0.998 mmol, 1 eq) and 2-[8-ethyl-3-(methoxymethoxy)-1-naphthyl]-4,4,5,5-tetramethyl-1,3,2-dioxaborolane (376 mg, 1.10 mmol, 1.1 eq) in dioxane (20 mL) were added CataCXium© A Pd G3 (145 mg, 0.199 mmol, 0.2 eq) and $K_2CO_3$ (2.2 M, 2.04 mL, 4.5 eq), and the reaction mixture was stirred at 100° C. under $N_2$ (degassed under vacuum and purged with $N_2$ several times) for 12 hours. The reaction mixture was dried over anhydrous $Na_2SO_4$, filtered, and concentrated. The crude product was purified by flash silica gel chromatography (gradient: 0-30% THF in petroleum ether) to give the title compound (695 mg, 0.446 mmol, 63% purity) as a yellow solid. LC/MS (ESI) m/z: 981.3 [M+H]$^+$.

Step 10: Preparation of tert-butyl 3-[7-[8-ethyl-3-(methoxymethoxy)-1-naphthyl]-8-fluoro-2-[[(3R, 8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

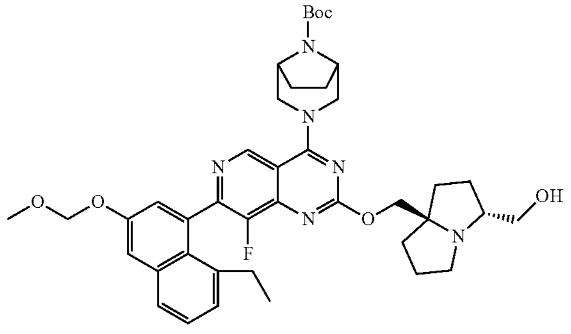 [SMILES: CCc1cccc2cc(OCOC)cc(-c3ncc4c(N5CC6CCC(C5)N6C(=O)OC(C)(C)C)nc(OC[C@]56CCCN5[C@@H](CO)CC6)nc4c3F)c12]

To a solution of tert-butyl 3-[2-[[(3R,8R)-3-[[tert-butyl(diphenyl)silyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (300 mg, 0.192 mmol, 63% purity, 1 eq) in THF (3 mL) was added TBAF (1 M, 458.59 µL, 1.5 eq), and the reaction mixture was stirred at 25° C. for 3 hours. The reaction mixture was quenched by addition of water (10 mL) and extracted with EtOAc (3×10 mL). The combined organic extract was washed with brine (3×10 mL), dried over anhydrous $Na_2SO_4$, filtered, and concentrated. The crude product was purified by prep-TLC (acidic silica gel, EtOAc) to give the title compound (201 mg, 0.271 mmol, 44% yield) as a yellow solid. LC/MS (ESI) m/z: 743.1 [M+H]$^+$.

Step 11: Preparation of tert-butyl 3-[2-[[(3R,8R)-3-[[4-[2-(2,6-dioxo-3-piperidyl)-1,3-dioxo-isoindolin-5-yl]piperazine-1-carbonyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

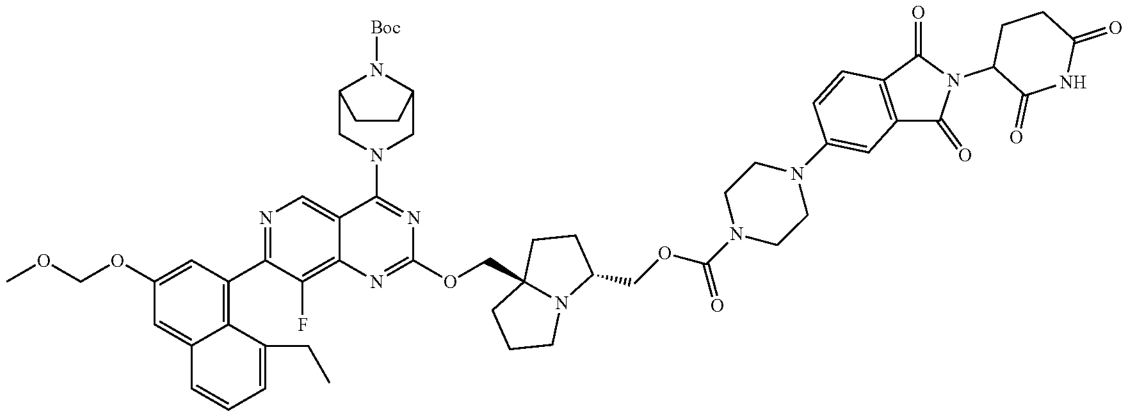 [SMILES: CCc1cccc2cc(OCOC)cc(-c3ncc4c(N5CC6CCC(C5)N6C(=O)OC(C)(C)C)nc(OC[C@]56CCCN5[C@@H](COC(=O)N5CCN(c7ccc8c(c7)C(=O)N(C7CCC(=O)NC7=O)C8=O)CC5)CC6)nc4c3F)c12]

To a solution of tert-butyl 3-[7-[8-ethyl-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (60 mg, 0.081 mmol, 1 eq) in THF (3 mL) were added triethylamine (65 mg, 0.65 mmol, 8 eq), DMAP (1 mg, 0.008 mmol, 0.1 eq), and (4-nitrophenyl) carbonochloridate (33 mg, 0.16 mmol, 2 eq), and the reaction mixture was stirred at 25° C. under $N_2$ for 16 hours. 2-(2,6-Dioxo-3-piperidyl)-5-piperazin-1-yl-isoindoline-1,3-dione (40.55 mg, 88.84 µmol, 1.1 eq, TFA) was then added, and the reaction mixture was stirred at 25° C. under $N_2$ for 1 hour. The reaction mixture was filtered, and the filtrate was concentrated under reduced pressure. The resulting crude product was purified by flash chromatography on $SiO_2$ (gradient: 0-5% methanol in dichloromethane) to give the title compound (77 mg, 0.069 mmol, 86% yield) as a yellow solid. LC/MS (ESI) m/z: 1111.3 [M+H]$^+$.

Step 12: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate (Compound 63)

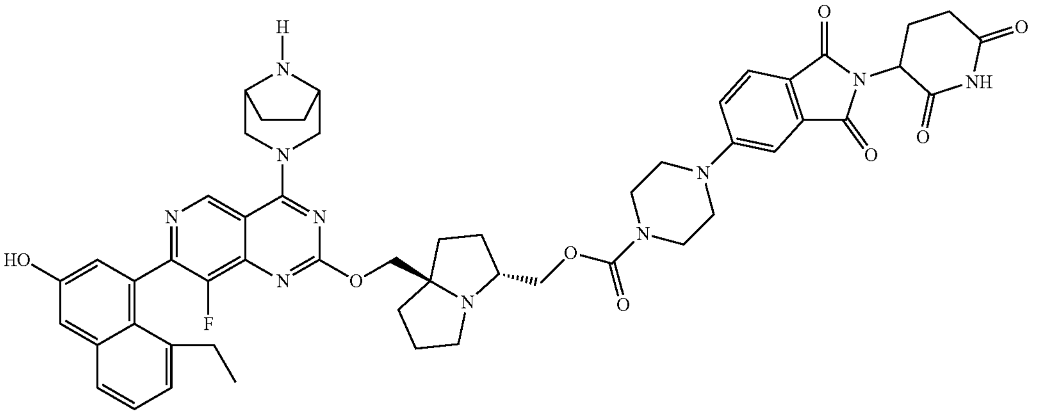 [SMILES: CCc1cccc2cc(O)cc(-c3ncc4c(N5CC6CCC(C5)N6)nc(OC[C@]56CCCN5[C@@H](COC(=O)N5CCN(c7ccc8c(c7)C(=O)N(C7CCC(=O)NC7=O)C8=O)CC5)CC6)nc4c3F)c12]

A solution of tert-butyl 3-[2-[[(3R,8R)-3-[[4-[2-(2,6-dioxo-3-piperidyl)-1,3-dioxo-isoindolin-5-yl]piperazine-1-carbonyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (77 mg, 0.069 mmol, 1 eq) in HCOOH (5 mL) was stirred at 25° C. for 3 hours. The reaction mixture was concentrated under reduced pressure, and the resulting crude product was purified by prep-HPLC (column: Phenomenex C18 75*30 mm*3 μm; mobile phase: [0-40% $CH_3CN$ in water (formic acid)]). Pure fractions were combined and dried by lyophilization to give the title compound (25.0 mg, 0.025 mmol, 36% yield, formic acid salt) as a yellow solid.

Example 12: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate (Compound 62)

Step 1: Preparation of [(3S,8S)-3-[[tert-butyl(diphenyl)silyl]oxymethyl]-1,2,3,5,6,7-hexahydropyrrolizin-8-yl]methanol

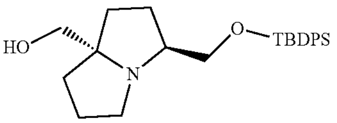

To a solution of methyl (3S,8S)-3-[[tert-butyl(diphenyl)silyl]oxymethyl]-1,2,3,5,6,7-hexahydropyrrolizine-8-carboxylate (1.57 g, 3.59 mmol, 1 eq) in THF (20 mL) at 0° C. was added $LiAlH_4$ (163 mg, 4.30 mmol, 1.2 eq), and the reaction mixture was stirred at 0° C. under $N_2$ for 1 hour. The reaction mixture was quenched by sequential addition of water (200 μL), 15% aq. NaOH (200 μL), and water (600 μL), then diluted with EtOAc (30 mL). The resulting suspension was dried over anhydrous $Na_2SO_4$, filtered and concentrated. The crude product was purified by flash silica gel chromatography (gradient: 0-10% $CH_3OH$ in $CH_2Cl_2$) to give the title compound (911 mg, 2.22 mmol, 62% yield) as a yellow oil. LC/MS (ESI) m/z: 410.3 $[M+H]^+$.

Step 2: Preparation of tert-butyl 3-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate

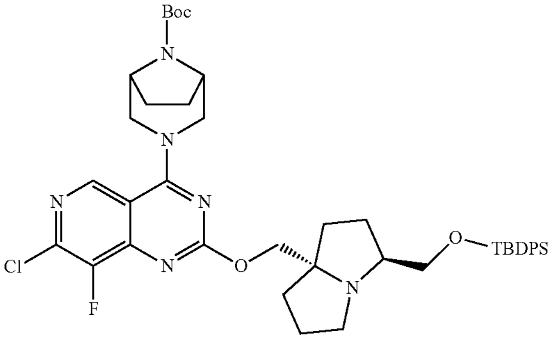

To a solution of [(3S,8S)-3-[[tert-butyl(diphenyl)silyl]oxymethyl]-1,2,3,5,6,7-hexahydropyrrolizin-8-yl]methanol (911 mg, 2.22 mmol, 1 eq) and tert-butyl 3-(2,7-dichloro-8-fluoro-pyrido[4,3-d]pyrimidin-4-yl)-3,8-diazabicyclo[3.2.1]octane-8-carboxylate (951 mg, 2.22 mmol, 1 eq) in dioxane (30 mL) were added $Cs_2CO_3$ (868 mg, 2.66 mmol, 1.2 eq) and DABCO (75 mg, 0.67 mmol, 0.3 eq), and the reaction mixture was stirred at 25° C. under $N_2$ for 16 hours. Additional DABCO (25 mg, 0.22 mmol, 0.1 eq) was added, and the reaction mixture was stirred at 25° C. under $N_2$ for 16 hours. The reaction mixture was filtered, and the filtrate was concentrated. The crude product was purified by prep-HPLC (35-65% $CH_3CN$ in water (0.225% formic acid)). Pure fractions were combined and dried by lyophilization to give the title compound (794 mg, 0.991 mmol, 45% yield) as a yellow solid. LC/MS (ESI) m/z: 801.2 $[M+H]^+$.

Step 3: Preparation of tert-butyl 3-[2-[[(3S,8S)-3-[[tert-butyl(diphenyl)silyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate

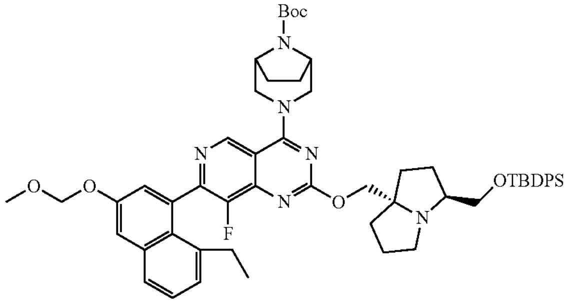

To a solution of tert-butyl 3-[2-[[(3S,8S)-3-[[tert-butyl (diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3,8-diazabicyclo[3.2.1]octane-8-carboxylate (100 mg, 0.125 mmol, 1 eq) and 2-[8-ethyl-3-(methoxymethoxy)-1-naphthyl]-4,4,5,5-tetramethyl-1,3,2-dioxaborolane (51 mg, 0.15 mmol, 1.2 eq) in dioxane (2.5 mL) were added $K_3PO_4$ (1.5 M, 125 μL, 1.5 eq) and CataCXium© A Pd G3 (18 mg, 0.025 mmol, 0.2 eq), and the reaction mixture was stirred at 100° C. under $N_2$ (degassed under vacuum and purged with $N_2$ several times) for 12 hours. The reaction mixture was quenched by addition of water (10 mL) and extracted with EtOAc (3×10 mL). The combined organic extract was washed with brine (2×10 mL), dried over anhydrous $Na_2SO_4$, filtered, and concentrated. The crude product was purified by flash silica gel chromatography (gradient: 0-20% THF in petroleum ether) to give the title compound (162 mg, 0.165 mmol, 66% yield) as a yellow solid. LC/MS (ESI) m/z: 981.3 $[M+H]^+$.

Step 4: Preparation of tert-butyl 3-[7-[8-ethyl-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

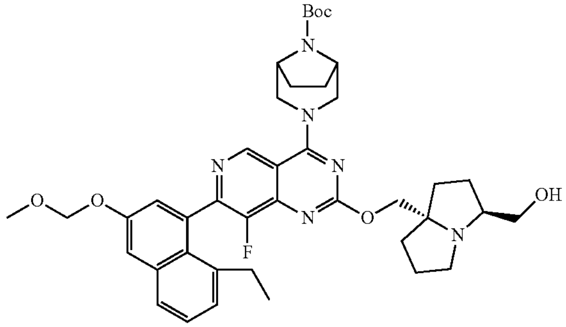 [SMILES: CCc1cccc2cc(OCOC)cc(-c3ncc4c(N5CC6CCC(C5)N6C(=O)OC(C)(C)C)nc(OC[C@@]56CCCN5[C@H](CO)CC6)nc4c3F)c12]

To a solution of tert-butyl 3-[2-[[(3S,8S)-3-[[tert-butyl (diphenyl)silyl]oxymethyl]-1,2,3,5,6,7-hexahydropyrrolizin-8-yl]methoxy]-7-[8-ethyl-3-(methoxymethoxy)-1-naphthyl]-8-fluoro-pyrido[4,3-d]pyrimidin-4-yl]-3,8-diazabicyclo[3.2.1]octane-8-carboxylate (162 mg, 0.165 mmol, 1 eq) in THF (2 mL) was added TBAF (1 M, 0.248 mL, 1.5 eq), and the reaction mixture was stirred at 25° C. for 3 hours. The reaction mixture was quenched by addition of water (10 mL) and extracted with EtOAc (3×10 mL). The combined organic extract was washed with brine (3×10 mL), dried over anhydrous $Na_2SO_4$, filtered, and concentrated. The crude product was purified by prep-TLC (acidic silica gel, EtOAc) to give the title compound (59 mg, 0.079 mmol, 48% yield) as a yellow solid. LC/MS (ESI) m/z: 743.1 $[M+H]^+$.

Step 5: Preparation of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate (Compound 62)

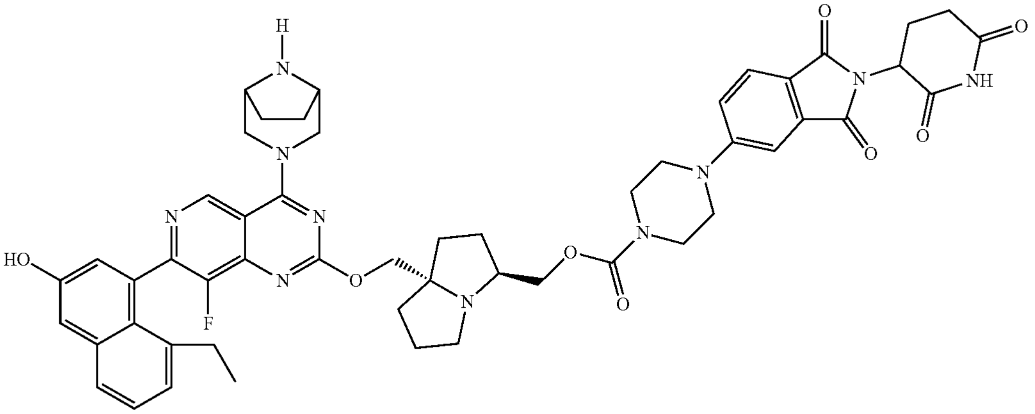 [SMILES: CCc1cccc2cc(O)cc(-c3ncc4c(N5CC6CCC(C5)N6)nc(OC[C@@]56CCCN5[C@H](COC(=O)N5CCN(c7ccc8c(c7)C(=O)N(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate, and purified by prep-HPLC (column: Phenomenex C18 75*30 mm*3 μm; mobile phase: [0-40% $CH_3CN$ in water (formic acid)]). Pure fractions were combined and dried by lyophilization to give the title compound (36.5 mg, 0.036 mmol, 56% yield, formic acid salt) as a yellow solid.

Example 13: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl 4-[2-(2,6-dioxo-3-piperidyl)-1-oxo-isoindolin-5-yl]piperazine-1-carboxylate (Compound 59)

Step 1: Preparation of 5-bromo-2-(2,6-dibenzyloxy-3-pyridyl)isoindolin-1-one

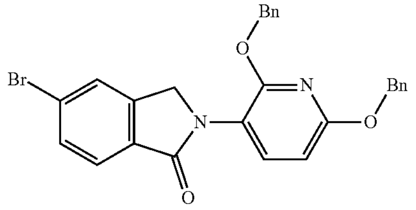 [SMILES: O=C1c2ccc(Br)cc2CN1c1ccc(OCc2ccccc2)nc1OCc1ccccc1]

To a mixture of 2,6-dibenzyloxypyridin-3-amine (2 g, 6.53 mmol, 1.0 eq) and methyl 4-bromo-2-(bromomethyl) benzoate (2.01 g, 6.53 mmol, 1.0 eq) in DMA (20 mL) was added diisopropylethylamine (3.41 mL, 19.58 mmol, 3.0 eq), and the reaction mixture was stirred at 125° C. for 15 hours. The mixture was cooled, then diluted with EtOAc (40 mL) and water (30 mL). The organic layer was separated, and the aqueous was extracted with EtOAc (30 mL×3).

The combined organic extracts were washed with water (30 mL×3), brine (30 mL×3), dried over $Na_2SO_4$, filtered, and concentrated under reduced pressure. The resulting residue was purified by flash chromatography on $SiO_2$ (gradient: 0-15% ethyl acetate in petroleum ether) to afford the title compound (1.3 g, 2.44 mmol, 37% yield) as a yellow solid. LC/MS (ESI) m/z: 502.9 $[M+H]^+$.

Step 2: Preparation of tert-butyl 4-[2-(2,6-dibenzyloxy-3-pyridyl)-1-oxo-isoindolin-5-yl]piperazine-1-carboxylate

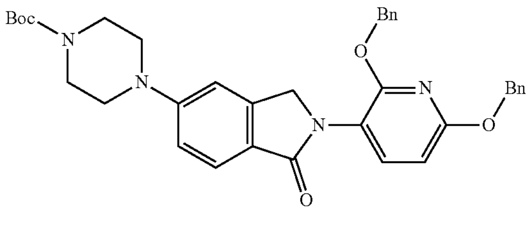 [SMILES: CC(C)(C)OC(=O)N1CCN(c2ccc3c(c2)CN(c2ccc(OCc4ccccc4)nc2OCc2ccccc2)C3=O)CC1]

To 5-bromo-2-(2,6-dibenzyloxy-3-pyridyl)isoindolin-1-one (1.3 g, 2.44 mmol, 94% purity, 1.0 eq) in dioxane (20 mL) were added tert-butyl piperazine-1-carboxylate (680.93 mg, 3.66 mmol, 1.5 eq), $Cs_2CO_3$ (2.38 g, 7.31 mmol, 3.0 eq), and [2-(2-aminophenyl)phenyl]-chloro-palladium;dicyclohexyl-[3-(2,4,6-triisopropylphenyl)phenyl]phosphane (191.77 mg, 243.73 μmol, 0.1 eq), and the reaction mixture was stirred at 110° C. for 15 hours under $N_2$ atmosphere. The reaction was cooled, diluted with water (20 mL), and extracted with EtOAc (20 mL×3). The combined organic extracts were dried over $Na_2SO_4$, filtered, and concentrated. The residue was purified by flash chromatography on $SiO_2$ (gradient: 0-50% ethyl acetate in petroleum ether) to afford the title compound (0.8 g, 1.13 mmol, 47% yield) as a yellow solid. LC/MS (ESI) m/z: 607.2 $[M+H]^+$.

Step 3: Preparation of tert-butyl 4-[2-(2,6-dioxo-3-piperidyl)-1-oxo-isoindolin-5-yl]piperazine-1-carboxylate

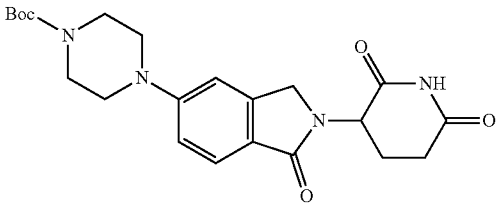 [SMILES: CC(C)(C)OC(=O)N1CCN(c2ccc3c(c2)CN(C2CCC(=O)NC2=O)C3=O)CC1]

To a solution of tert-butyl 4-[2-(2,6-dibenzyloxy-3-pyridyl)-1-oxo-isoindolin-5-yl]piperazine-1-carboxylate (800 mg, 1.13 mmol, 86% purity, 1.0 eq) in EtOAc (20 mL) was added Pd/C (0.1 g, 1.13 mmol, 10% purity, 1.0 eq) under Ar atmosphere, and the resulting suspension was degassed under vacuum and purged with $H_2$ several times. The reaction mixture was stirred under $H_2$ (15 psi) at 50° C. for 15 hours. The reaction mixture was filtered and concentrated under reduced pressure. The resulting residue was dissolved with EtOAc (20 mL). Pd/C (0.2 g, 1.13 mmol, 10% purity, 1.0 eq) was added under Ar, and the suspension was degassed under vacuum and purged with $H_2$ several times. The reaction mixture was stirred under $H_2$ (15 psi) at 50° C. for 15 hours. The mixture was filtered, and the cake was washed with 10:1 $CH_2Cl_2/CH_3OH$ (50 mL). The solvent was concentrated under reduced pressure to afford the title compound (380 mg, crude) as a purple solid. LC/MS (ESI) m/z: 429.0 $[M+H]^+$.

Step 4: Preparation of 3-(1-oxo-5-piperazin-1-yl-isoindolin-2-yl)piperidine-2,6-dione

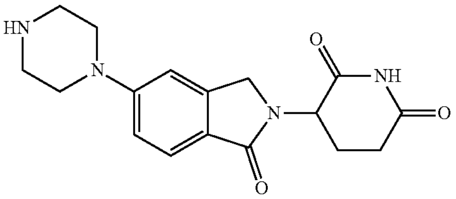 [SMILES: O=C1CCC(N2Cc3cc(N4CCNCC4)ccc3C2=O)C(=O)N1]

To tert-butyl 4-[2-(2,6-dioxo-3-piperidyl)-1-oxo-isoindolin-5-yl]piperazine-1-carboxylate (60 mg, 140.03 μmol, 1.0 eq) in $CH_2Cl_2$ (1 mL) was added TFA (1 mL, 13.51 mmol, 96.45 eq), and the reaction mixture was stirred at 25° C. for 1 hour. The mixture was concentrated under reduced pressure to afford the title compound (123.89 mg, crude, TFA salt) as a black brown oil. LC/MS (ESI) m/z: 329.1 $[M+H]^+$.

Step 5: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-5-yl]piperazine-1-carboxylate (Compound 59)

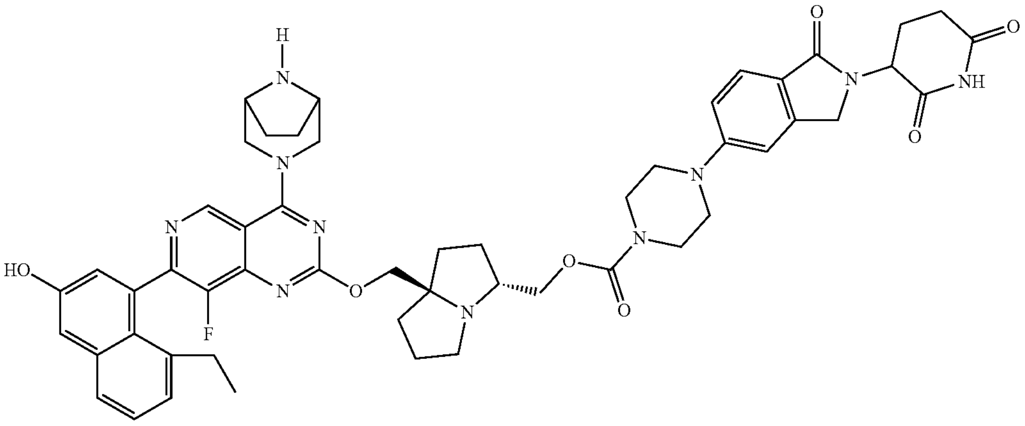 [SMILES: CCc1cccc2cc(O)cc(-c3ncc4c(N5CC6CCC(C5)N6)nc(OC[C@]56CCCN5[C@@H](COC(=O)N5CCN(c7ccc8c(c7)CN(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate and 3-(1-oxo-5-piperazin-1-yl-isoindolin-2-yl)piperidine-2,6-dione, and purified by prep-HPLC (column: Phenomenex C18 75*30 mm*3 μm; mobile phase: [2-42% $CH_3CN$ in water (formic acid)]). Pure fractions were combined and concentrated under reduced pressure, then lyophilized to afford the title compound (32.0 mg, 31.65 μmol, 20% yield, formic acid salt) as an off-white solid.

Example 14: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-5-yl]piperazine-1-carboxylate (Compound 58)

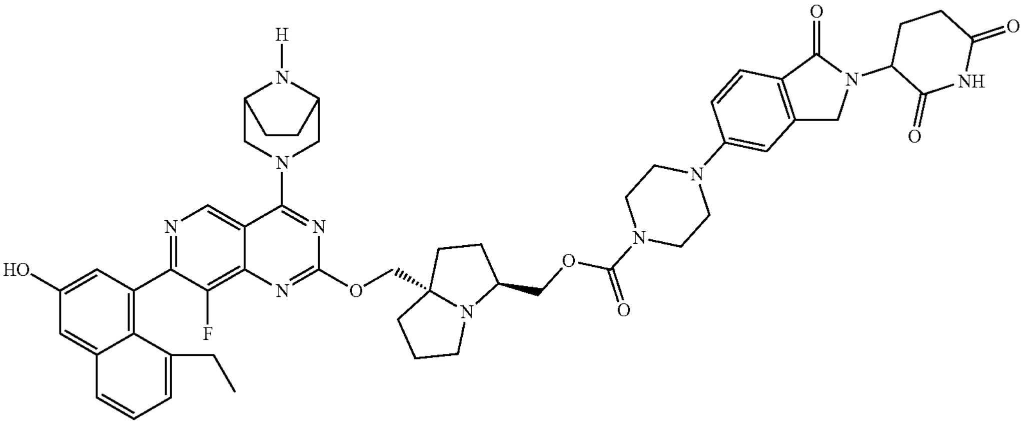 [SMILES: CCc1cccc2cc(O)cc(-c3ncc4c(N5CC6CCC(C5)N6)nc(OC[C@@]56CCCN5[C@H](COC(=O)N5CCN(c7ccc8c(c7)CN(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3S, 8S)-3-(hydroxymethyl)-1,2,3,5,6,7-hexahydropyrrolizin-8-yl]methoxy]pyrido[4,3-d]pyrimidin-4-yl]-3,8-diazabicyclo [3.2.1]octane-8-carboxylate and 3-(1-oxo-5-piperazin-1-yl-isoindolin-2-yl)piperidine-2,6-dione, and purified by pre-HPLC (column: Phenomenex C18 75*30 mm*3 μm; mobile phase: [2-42% $CH_3CN$ in water (formic acid)]). Pure fractions were combined and concentrated under reduced pressure, then lyophilized to afford the title compound (31.6 mg, 32.43 μmol, 24% yield, formic acid salt) as an off-white solid.

Example 15: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxymethyl]-1,2,3,5,6,7-hexahydropyrrolizin-3-yl] methyl 4-[2-(2,6-dioxo-3-piperidyl)-1,3-dioxo-isoindolin-4-yl]piperazine-1-carboxylate (Compound 65)

Step 1: Preparation of tert-butyl 4-[2-(2,6-dioxo-3-piperidyl)-1,3-dioxo-isoindolin-4-yl]piperazine-1-carboxylate

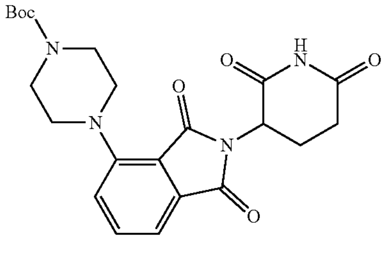 [SMILES: CC(C)(C)OC(=O)N1CCN(c2cccc3c2C(=O)N(C2CCC(=O)NC2=O)C3=O)CC1]

To a solution of 2-(2,6-dioxo-3-piperidyl)-4-fluoro-isoindoline-1,3-dione (500 mg, 1.81 mmol, 1.0 eq) and tert-butyl piperazine-1-carboxylate (405 mg, 2.17 mmol, 1.2 eq) in DMSO (8 mL) was added diisopropylethylamine (0.946 mL, 5.43 mmol, d=0.742 g/mL, 3.0 eq), and the reaction mixture was stirred at 100° C. for 3 hours. The mixture was diluted with $H_2O$ (20 mL), and the aqueous phase was extracted with dichloromethane (30 mL×3). The combined organic extract was washed with brine (20 mL), dried with anhydrous $Na_2SO_4$, filtered, and concentrated. The resulting residue was purified by flash chromatography on $SiO_2$ (gradient: 0~2% methanol in dichloromethane) to afford the title compound (600 mg, 1.10 mmol, 61% yield) as a yellow oil. LC/MS (ESI) m/z: 386.9 $[M-55]^+$. $^1H$ NMR (400 MHz, $CDCl_3$) δ 7.94 (s, 1H), 7.56 (dd, J=7.2, 8.4 Hz, 1H), 7.39 (d, J=7.0 Hz, 1H), 7.17 (d, J=8.4 Hz, 1H), 4.90 (dd, J=5.2, 12.4 Hz, 1H), 3.60 (t, J=4.8 Hz, 4H), 3.31-3.17 (m, 4H), 2.88-2.62 (m, 3H), 2.11-2.01 (m, 1H), 1.44-1.38 (m, 9H).

Step 2: Preparation of 2-(2,6-dioxo-3-piperidyl)-4-(piperazin-1-yl)isoindoline-1,3-dione

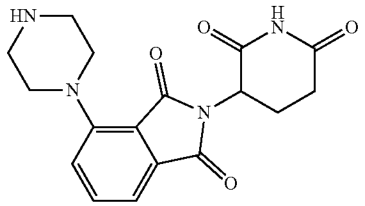 [SMILES: O=C1CCC(N2C(=O)c3cccc(N4CCNCC4)c3C2=O)C(=O)N1]

To a solution of tert-butyl 4-[2-(2,6-dioxo-3-piperidyl)-1,3-dioxo-isoindolin-4-yl]piperazine-1-carboxylate (600 mg, 1.10 mmol, 1.0 eq) in $CH_2Cl_2$ (8 mL) was added TFA (6.0 mL, 81.04 mmol, d=1.54 g/mL, 59.8 eq), and the reaction mixture was stirred at 20° C. for 0.5 hours. The mixture was concentrated in vacuum to afford the title compound (620 mg, crude, TFA) as a yellow solid. LC/MS (ESI) m/z: 343.1 $[M+H]^+$.

Step 3: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxymethyl]-1,2,3,5,6,7-hexahydropyrrolizin-3-yl] methyl 4-[2-(2,6-dioxo-3-piperidyl)-1,3-dioxo-isoindolin-4-yl]piperazine-1-carboxylate (Compound 65)

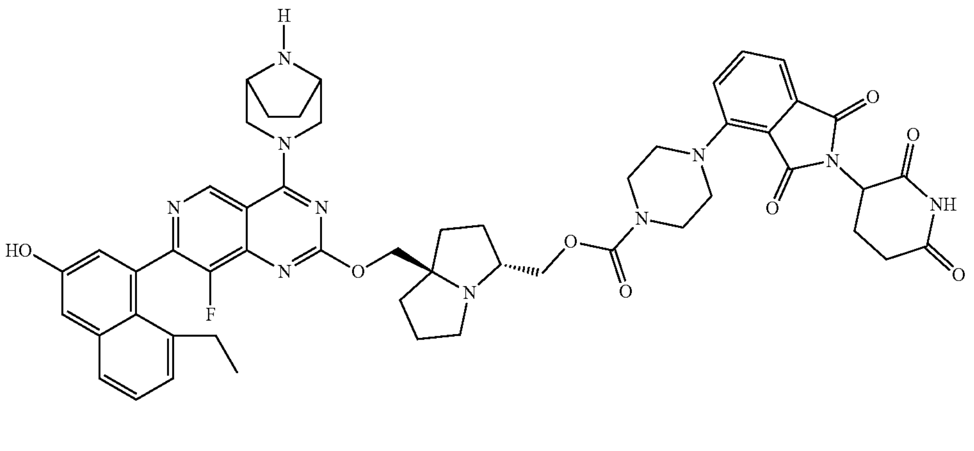 [SMILES: CCc1cccc2cc(O)cc(-c3ncc4c(N5CC6CCC(C5)N6)nc(OC[C@]56CCCN5[C@@H](COC(=O)N5CCN(c7cccc8c7C(=O)N(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3R, 8R)-3-(hydroxymethyl)-1,2,3,5,6,7-hexahydropyrrolizin-8-yl]methoxy]pyrido[4,3-d]pyrimidin-4-yl]-3,8-diazabicyclo [3.2.1]octane-8-carboxylate and 2-(2,6-dioxo-3-piperidyl)-4-(piperazin-1-yl)isoindoline-1,3-dione, and purified by prep-HPLC (Condition: [2-42% $CH_3CN$ in water (formic acid)]; Column: Phenomenex C18 75*30 mm*3 μm; Flow Rate: 25 mL/min). Pure fractions were combined and lyophilized to afford the title compound (36.3 mg, 0.037 mmol, 49% yield, formic acid salt) as a yellow solid.

Example 16: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxymethyl]-1,2,3,5,6,7-hexahydropyrrolizin-3-yl] methyl 4-[2-(2,6-dioxo-3-piperidyl)-1,3-dioxo-isoindolin-4-yl]piperazine-1-carboxylate (Compound 64)

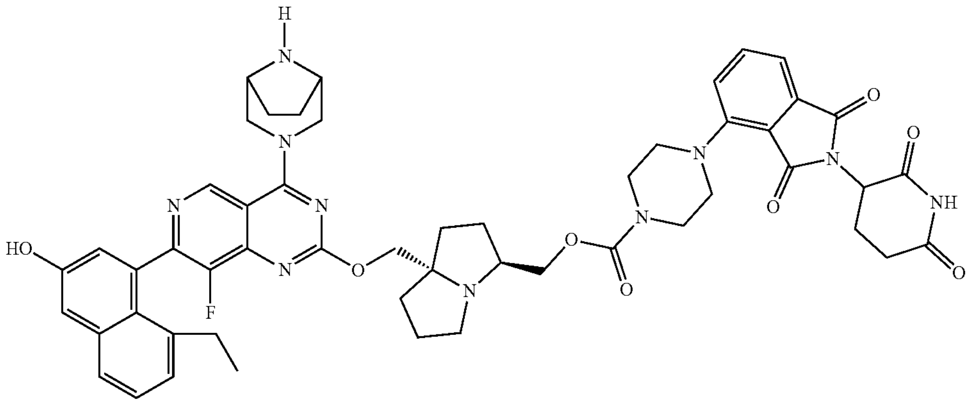 [SMILES: CCc1cccc2cc(O)cc(-c3ncc4c(N5CC6CCC(C5)N6)nc(OC[C@@]56CCCN5[C@H](COC(=O)N5CCN(c7cccc8c7C(=O)N(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3S, 8S)-3-(hydroxymethyl)-1,2,3,5,6,7-hexahydropyrrolizin-8-yl]methoxy]pyrido[4,3-d]pyrimidin-4-yl]-3,8-diazabicyclo [3.2.1]octane-8-carboxylate and 2-(2,6-dioxopiperidin-3-yl)-4-(piperazin-1-yl)isoindoline-1,3-dione, and purified by prep-HPLC (Condition: [2-42% $CH_3CN$ in water (formic acid)]; Column: Phenomenex C18 75*30 mm*3 μm; Flow Rate: 25 mL/min). Pure fractions were combined and lyophilized to afford the title compound (31.0 mg, 0.031 mmol, 47% yield, formic acid salt) as a yellow solid.

Example 17: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxymethyl]-1,2,3,5,6,7-hexahydropyrrolizin-3-yl] methyl 4-[2-(2,6-dioxo-3-piperidyl)-1-oxo-isoindolin-4-yl]piperazine-1-carboxylate (Compound 61)

Step 1: Preparation of tert-butyl 4-[2-(2,6-dibenzyloxy-3-pyridyl)-1-oxo-isoindolin-4-yl]piperazine-1-carboxylate

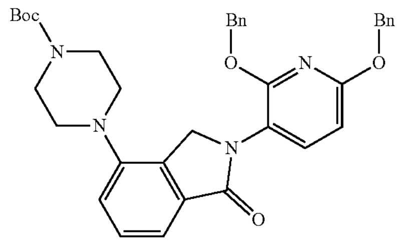 [SMILES: CC(C)(C)OC(=O)N1CCN(c2cccc3c2CN(c2ccc(OCc4ccccc4)nc2OCc2ccccc2)C3=O)CC1]

To a solution of 4-bromo-2-(2,6-dibenzyloxy-3-pyridyl) isoindolin-1-one (500 mg, 0.997 mmol, 1.0 eq) and tert-butyl piperazine-1-carboxylate (279 mg, 1.50 mmol, 1.5 eq) in dioxane (6 mL) were added $Cs_2CO_3$ (975 mg, 2.99 mmol, 3.0 eq) and [2-(2-aminophenyl)phenyl]-chloro-palladium; dicyclohexyl-[3-(2,4,6-triisopropylphenyl)phenyl]phosphane (78 mg, 0.100 mmol, 0.1 eq), and the reaction mixture was stirred at 110° C. for 12 hours. The mixture was filtered and concentrated, and the resulting residue was purified by flash chromatography on $SiO_2$ (gradient: 0-30% ethyl acetate in petroleum ether) to afford the title compound (410 mg, 0.642 mmol, 64% yield) as a yellow solid. LC/MS (ESI) m/z: 607.2 $[M+H]^+$.

Step 2: Preparation of tert-butyl 4-[2-(2,6-dioxo-3-piperidyl)-1-oxo-isoindolin-4-yl]piperazine-1-carboxylate

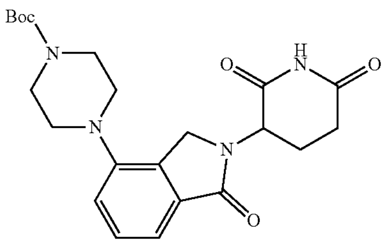 [SMILES: CC(C)(C)OC(=O)N1CCN(c2cccc3c2CN(C2CCC(=O)NC2=O)C3=O)CC1]

To a solution of tert-butyl 4-[2-(2,6-dibenzyloxy-3-pyridyl)-1-oxo-isoindolin-4-yl]piperazine-1-carboxylate (410 mg, 0.642 mmol, 1.0 eq) in EtOAc (10 mL) was added Pd/C (200 mg, 10% purity), and the reaction mixture was stirred at 50° C. for 12 hours under $H_2$(15 psi). The reaction was filtered and concentrated in vacuum to afford the title compound (300 mg, crude) as a light yellow oil. LC/MS (ESI) m/z: 429.1 $[M+H]^+$.

Step 3: Preparation of 3-(1-oxo-4-piperazin-1-yl-isoindolin-2-yl)piperidine-2,6-dione

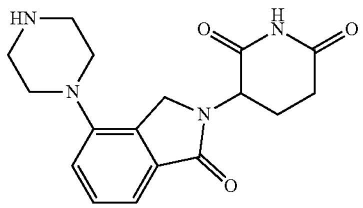 [SMILES: O=C1CCC(N2Cc3c(cccc3N3CCNCC3)C2=O)C(=O)N1]

To a solution of tert-butyl 4-[2-(2,6-dioxo-3-piperidyl)-1-oxo-isoindolin-4-yl]piperazine-1-carboxylate (300 mg, 0.700 mmol, 1.0 eq) in $CH_2Cl_2$ (4 mL) was added TFA (3.0 mL, 40.52 mmol, d=1.54 g/mL, 57.9 eq), and the reaction mixture was stirred at 20° C. for 0.5 hours. The reaction was concentrated in vacuum to afford the title compound (310 mg, crude, TFA) as a yellow solid. LC/MS (ESI) m/z: 329.0 $[M+H]^+$.

Step 4: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-4-yl]piperazine-1-carboxylate (Compound 61)

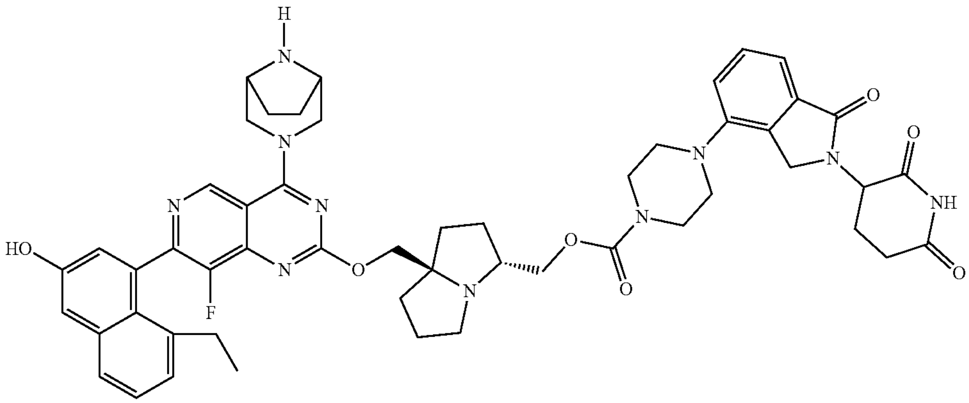

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate and 3-(1-oxo-4-piperazin-1-yl-isoindolin-2-yl)piperidine-2,6-dione, purified by prep-HPLC (5-40% $CH_3CN$ in water (formic acid); Gradient time: 25 min; Column: Phenomenex C18 75*30 mm*3 μm; Flow Rate: 25 mL/min). Pure fractions were combined and lyophilized to afford the title compound (28.3 mg, 29.14 μmol, 38% yield, formic acid salt) as a white solid.

Example 18: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-4-yl]piperazine-1-carboxylate (Compound 60)

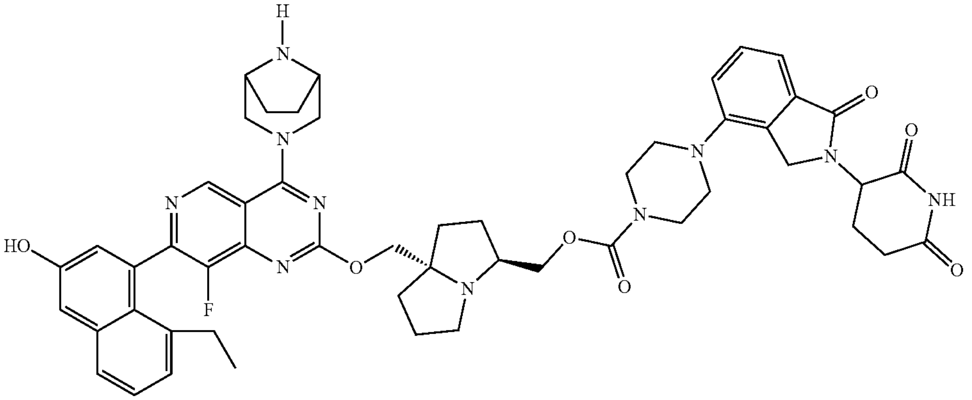 [SMILES: CCc1cccc2cc(O)cc(-c3ncc4c(N5CC6CCC(C5)N6)nc(OC[C@@]56CCCN5[C@H](COC(=O)N5CCN(c7cccc8c7CN(C7CCC(=O)NC7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(2,6-dioxo-3-piperidyl)-1,3-dioxo-isoindolin-5-yl]piperazine-1-carboxylate starting from tert-butyl 3-[7-[8-ethyl-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate and 3-(1-oxo-4-piperazin-1-yl-isoindolin-2-yl)piperidine-2,6-dione, and purified by prep-HPLC (5-40% $CH_3CN$ in water (formic acid); Gradient time: 25 min; Column: Phenomenex C18 75*30 mm*3 μm; Flow Rate: 25 mL/min). Pure fractions were combined and lyophilized to afford the title compound (22.9 mg, 0.024 mmol, 33% yield, formic acid salt) as a white solid.

Example 19: Synthesis of [(3R,8R)-8-[[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-5-yl]piperazine-1-carboxylate (Compound 48)

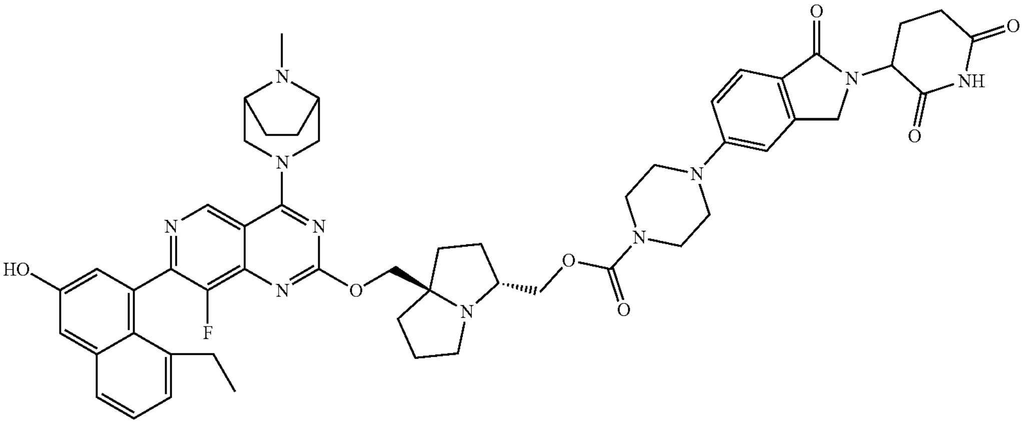 [SMILES: CCc1cccc2cc(O)cc(-c3ncc4c(N5CC6CCC(C5)N6C)nc(OC[C@]56CCCN5[C@@H](COC(=O)N5CCN(c7ccc8c(c7)CN(C7CCC(=O)NC7=O)C8=O)CC5)CC6)nc4c3F)c12]

To a solution of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-5-yl]piperazine-1-carboxylate (85.0 mg, 0.086 mmol, 1.0 eq, HCl) in $CH_2Cl_2$ (2 mL) and $CH_3OH$ (2 mL) were added formaldehyde (0.429 mmol, 32.0 μL, 37% purity, 5.0 eq) and 2-methylpyridine borane (14.0 mg, 0.129 mmol, 1.5 eq), and the reaction mixture was stirred at 25° C. for 1 hour. The mixture was concentrated, and the crude product was purified by prep-HPLC (column: Phenomenex C18 75*30 mm*3 μm; mobile phase: [5-35% $CH_3CN$ in water (formic acid)]). Pure fraction was lyophilized to afford the title compound (17.9 mg, 0.017 mmol, 20% yield, formic acid salt) as a yellow solid.

Example 20: Synthesis of [(3S,8S)-8-[[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-5-yl]piperazine-1-carboxylate (Compound 47)

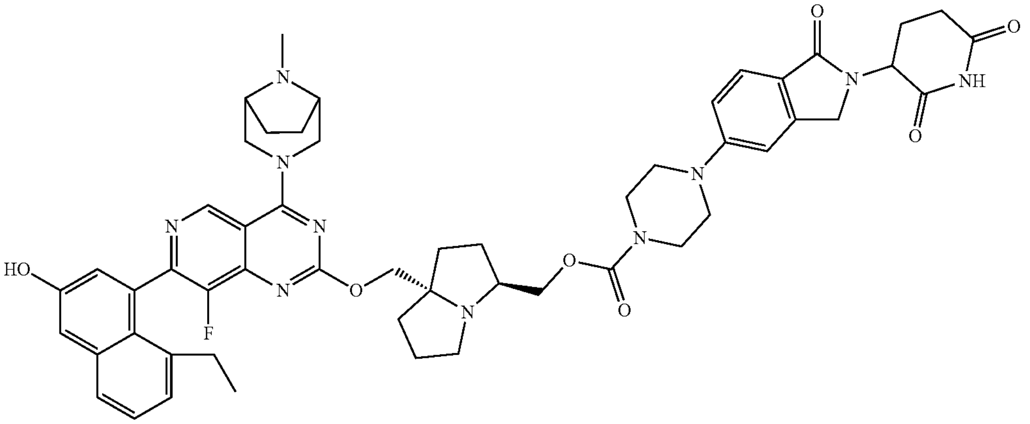 [SMILES: CCc1cccc2cc(O)cc(-c3ncc4c(N5CC6CCC(C5)N6C)nc(OC[C@@]56CCCN5[C@H](COC(=O)N5CCN(c7ccc8c(c7)CN(C7CCC(=O)NC7=O)C8=O)CC5)CC6)nc4c3F)c12]

The title compounds was prepared in an analogous manner to [(3R,8R)-8-[[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-5-yl]piperazine-1-carboxylate, and purified by prep-HPLC (column: Phenomenex C18 75*30 mm*3 μm; mobile phase: [5-35% $CH_3CN$ in water (formic acid)]). Pure fraction was lyophilized to afford the title compound (40.5 mg, 0.040 mmol, 29% yield, formic acid salt) as a yellow solid.

Example 21: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(1-methyl-2,6-dioxo-3-piperidyl)-1-oxo-isoindolin-5-yl]piperazine-1-carboxylate (Compound 53)

Step 1: Preparation of tert-butyl 4-[2-(1-methyl-2,6-dioxo-3-piperidyl)-1-oxo-isoindolin-5-yl]piperazine-1-carboxylate

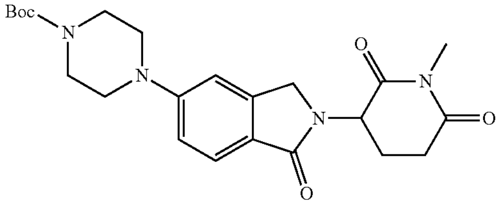 [SMILES: CN1C(=O)CCC(N2Cc3cc(N4CCN(C(=O)OC(C)(C)C)CC4)ccc3C2=O)C1=O]

To a solution of tert-butyl 4-[2-(2,6-dioxo-3-piperidyl)-1-oxo-isoindolin-5-yl]piperazine-1-carboxylate (430 mg, 1.00 mmol, 1.0 eq) in DMA (5 mL) were added $Cs_2CO_3$ (654.0 mg, 2.01 mmol, 2.0 eq) and $CH_3I$ (2.01 mmol, 125 μL, 2.0 eq), and the reaction mixture was stirred at 25° C. for 2 hours. The mixture was filtered, diluted with water (15 mL), and extracted with ethyl acetate (20 mL×3). The combined organic extract was washed with brine (15 mL×3), dried over $Na_2SO_4$, filtered, and concentrated under reduced pressure to afford the title compound (420 mg, crude) as a yellow solid. LC/MS (ESI) m/z: 443.1 $[M+H]^+$.

Step 2: Preparation of 1-methyl-3-(1-oxo-5-piperazin-1-yl-isoindolin-2-yl)piperidine-2,6-dione

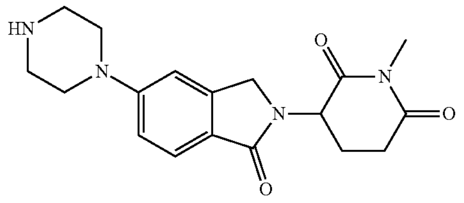 [SMILES: CN1C(=O)CCC(N2Cc3cc(N4CCNCC4)ccc3C2=O)C1=O]

To a solution of tert-butyl 4-[2-(1-methyl-2,6-dioxo-3-piperidyl)-1-oxo-isoindolin-5-yl]piperazine-1-carboxylate (420 mg, 949.14 μmol, 1 eq) in $CH_2Cl_2$ (5 mL) was added HCl/dioxane (5 mL, 4M), and the reaction mixture was stirred at 25° C. for 0.5 hour. Petroleum ether (30 mL) was then added, and the resulting mixture was stirred at 25° C. for 0.5 hour. The resulting precipitate was filtered to afford the title compound (350 mg, crude, HCl salt) as a yellow solid. LC/MS (ESI) m/z: 343.0 $[M+H]^+$.

Step 3: Preparation of tert-butyl 3-[7-[8-ethyl-3-(methoxymethoxy)-1-naphthyl]-8-fluoro-2-[[(3R,8R)-3-[[4-[2-(1-methyl-2,6-dioxo-3-piperidyl)-1-oxo-isoindolin-5-yl]piperazine-1-carbonyl]oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate

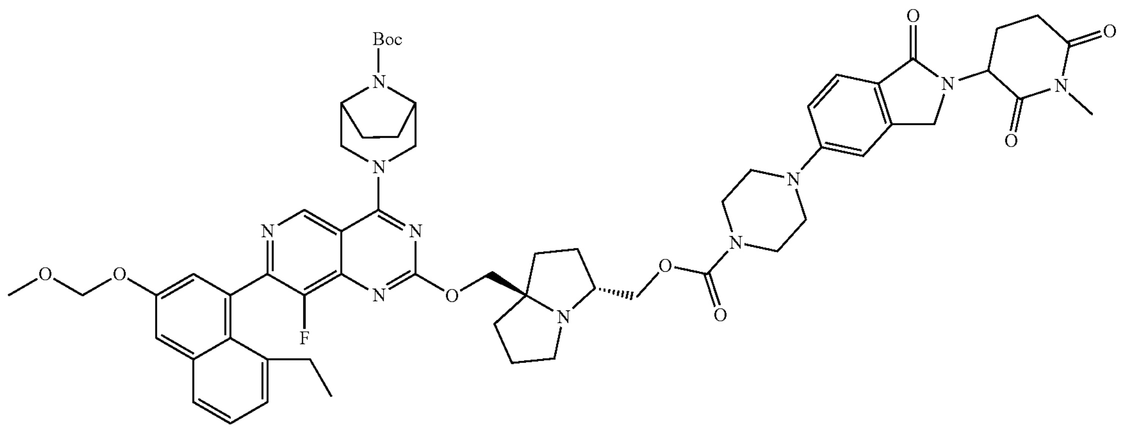 [SMILES: CCc1cccc2cc(OCOC)cc(-c3ncc4c(N5CC6CCC(C5)N6C(=O)OC(C)(C)C)nc(OC[C@]56CCCN5[C@@H](COC(=O)N5CCN(c7ccc8c(c7)CN(C7CCC(=O)N(C)C7=O)C8=O)CC5)CC6)nc4c3F)c12]

To a solution of tert-butyl 3-[7-[8-ethyl-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (80 mg, 0.1 mmol, 1.0 eq) in THF (3 mL) were added triethylamine (1.08 mmol, 150 μL, 10 eq), DMAP (1.0 mg, 0.001 mmol, 0.1 eq), and (4-nitrophenyl) carbonochloridate (37.0 mg, 0.183 mmol, 1.7 eq), and the reaction mixture was stirred at 40° C. for 15 hours. 1-Methyl-3-(1-oxo-5-piperazin-1-yl-isoindolin-2-yl)piperidine-2,6-dione (45.0 mg, 0.118 mmol, 1.1 eq, HCl) was then added, and the reaction mixture was stirred at 40° C. for 1 hour. The mixture was concentrated, and the resulting residue was purified by flash chromatography on $SiO_2$ (gradient: 0-5% methanol in dichloromethane) to afford the title compound (100 mg, 0.056 μmol, 53% yield) as a yellow solid. LC/MS (ESI) m/z: 1111.4 $[M+H]^+$.-

Step 4: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(1-methyl-2,6-dioxo-3-piperidyl)-1-oxo-isoindolin-5-yl]piperazine-1-carboxylate (Compound 53)

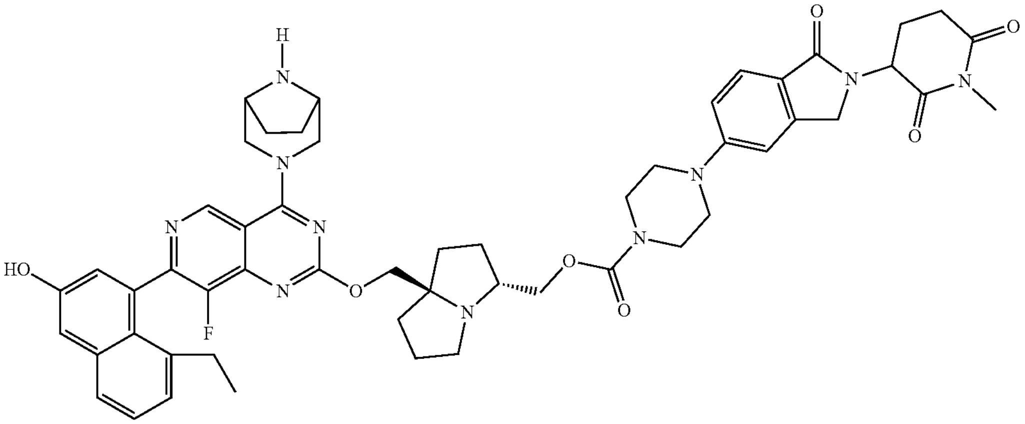 [SMILES: CCc1cccc2cc(O)cc(-c3ncc4c(N5CC6CCC(C5)N6)nc(OC[C@]56CCCN5[C@@H](COC(=O)N5CCN(c7ccc8c(c7)CN(C7CCC(=O)N(C)C7=O)C8=O)CC5)CC6)nc4c3F)c12]

A mixture of tert-butyl 3-[7-[8-ethyl-3-(methoxymethoxy)-1-naphthyl]-8-fluoro-2-[[(3R,8R)-3-[[4-[2-(1-methyl-2,6-dioxo-3-piperidyl)-1-oxo-isoindolin-5-yl]piperazine-1-carbonyl]oxymethyl]-1,2,3,5,6,7-hexahydropyrrolizin-8-yl]methoxy]pyrido[4,3-d]pyrimidin-4-yl]-3,8-diazabicyclo[3.2.1]octane-8-carboxylate (100 mg, 0.09 mmol, 1 eq) in $CH_2Cl_2$ (2 mL) and 4M HCl/dioxane (2 mL) was stirred at 25° C. for 0.5 hour. Petroleum ether (30 mL) was then added, and the resulting mixture was stirred at 25° C. for 0.5 hour. The resulting precipitate was collected and purified by prep-HPLC (column: Phenomenex C18 75*30 mm*3 μm; mobile phase: [5-40% $CH_3CN$ in water (formic acid)]). Pure fractions were lyophilized to afford the title compound (29.7 mg, 28.79 μmol, 32% yield, formic acid salt) as a white solid.

Example 22: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(1-methyl-2,6-dioxo-3-piperidyl)-1-oxo-isoindolin-5-yl]piperazine-1-carboxylate (Compound 50)

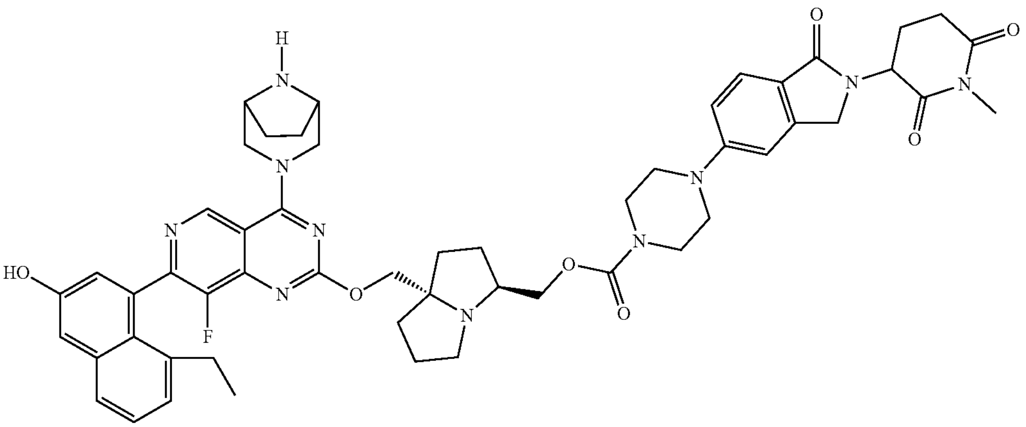 [SMILES: CCc1cccc2cc(O)cc(-c3ncc4c(N5CC6CCC(C5)N6)nc(OC[C@@]56CCCN5[C@H](COC(=O)N5CCN(c7ccc8c(c7)CN(C7CCC(=O)N(C)C7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(1-methyl-2,6-dioxo-3-piperidyl)-1-oxo-isoindolin-5-yl]piperazine-1-carboxylate (Compound 53) starting from tert-butyl 3-[7-[8-ethyl-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate, and purified by prep-HPLC (column: Phenomenex C18 75*30 mm*3 μm; mobile phase: [5-40% $CH_3CN$ in water (formic acid)]). Pure fractions were lyophilized to the title compound (30.2 mg, 0.029 mmol, 32% yield, formic acid salt) as a white solid.

Example 23: Synthesis of [(3R,8R)-8-[[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-4-yl]piperazine-1-carboxylate (Compound 51)

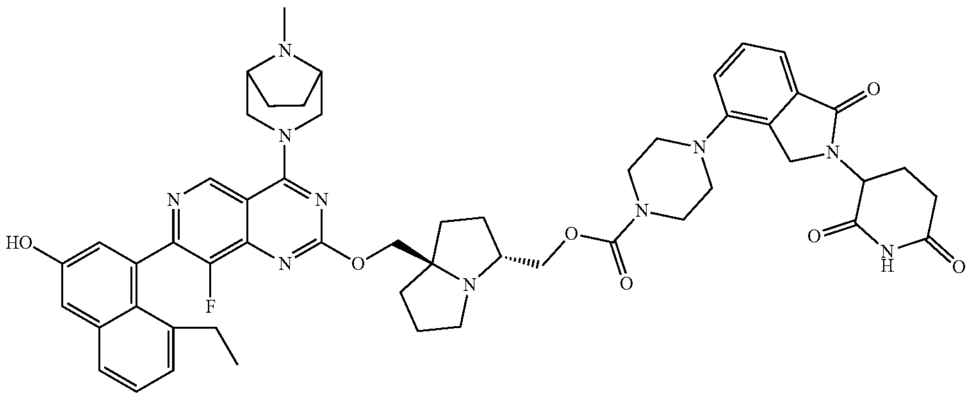 [SMILES: CCc1cccc2cc(O)cc(-c3ncc4c(N5CC6CCC(C5)N6C)nc(OC[C@]56CCCN5[C@@H](COC(=O)N5CCN(c7cccc8c7CN(C7CCC(=O)NC7=O)C8=O)CC5)CC6)nc4c3F)c12]

The title compounds was prepared in an analogous manner to [(3R,8R)-8-[[7-(8-ethyl-3-hydroxy-1-naphthyl)-8-fluoro-4-(8-methyl-3,8-diazabicyclo[3.2.1]octan-3-yl) pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-5-yl]piperazine-1-carboxylate starting from [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-4-yl]piperazine-1-carboxylate, and purified by prep-HPLC (column: Phenomenex C18 75*30 mm*3 μm; mobile phase: [5-35% $CH_3CN$ in water (formic acid)]) to give the title compound (22.2 mg, 0.021 mmol, 35% yield, formic acid salt) as a white solid.

Example 24: Synthesis of [(3S,8S)-8-[[7-(8-ethyl-3-hydroxy-1-naphthyl)-8-fluoro-4-(8-methyl-3,8-diazabicyclo[3.2.1]octan-3-yl)pyrido[4,3-d]pyrimidin-2-yl]oxymethyl]-1,2,3,5,6,7-hexahydropyrrolizin-3-yl] methyl 4-[2-(2,6-dioxo-3-piperidyl)-1-oxo-isoindolin-4-yl]piperazine-1-carboxylate (Compound 49)

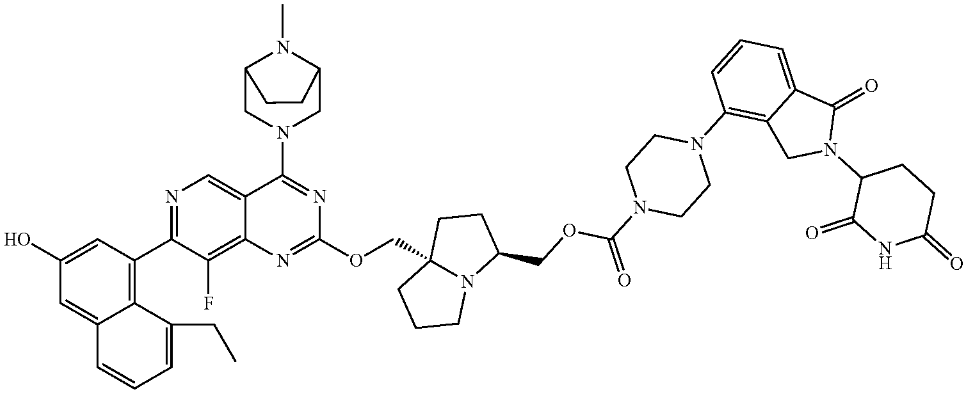 [SMILES: CCc1cccc2cc(O)cc(-c3ncc4c(N5CC6CCC(C5)N6C)nc(OC[C@@]56CCCN5[C@H](COC(=O)N5CCN(c7cccc8c7CN(C7CCC(=O)NC7=O)C8=O)CC5)CC6)nc4c3F)c12]

The title compounds was prepared in an analogous manner to [(3R,8R)-8-[[7-(8-ethyl-3-hydroxy-1-naphthyl)-8-fluoro-4-(8-methyl-3,8-diazabicyclo[3.2.1]octan-3-yl) pyrido[4,3-d]pyrimidin-2-yl]oxymethyl]-1,2,3,5,6,7-hexahydropyrrolizin-3-yl]methyl4-[2-(2,6-dioxo-3-piperidyl)-1-oxo-isoindolin-5-yl]piperazine-1-carboxylate starting from [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(2,6-dioxo-3-piperidyl)-1-oxo-isoindolin-4-yl]piperazine-1-carboxylate, purified by prep-HPLC (Column: Phenomenex C18 75*30 mm*3 μm; gradient: 5%-35% $CH_3CN$ in water ($NH_4HCO_3$); Gradient time: 25 min; Hold time: 4 min; Flow rate: 25 mL/min) to afford the title compound (58.3 mg, 0.059 mmol, 52% yield) as a yellow solid.

Example 25: Synthesis of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl] oxymethyl]-1,2,3,5,6,7-hexahydropyrrolizin-3-yl] methyl4-[2-(1-methyl-2,6-dioxo-3-piperidyl)-1-oxo-isoindolin-4-yl]piperazine-1-carboxylate (Compound 54)

Step 1: Preparation of tert-butyl 4-[2-(1-methyl-2,6-dioxo-3-piperidyl)-1-oxo-isoindolin-4-yl]piperazine-1-carboxylate

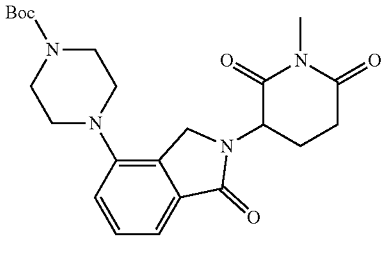 [SMILES: CN1C(=O)CCC(N2Cc3c(cccc3N3CCN(C(=O)OC(C)(C)C)CC3)C2=O)C1=O]

To a solution of tert-butyl 4-[2-(2,6-dioxo-3-piperidyl)-1-oxo-isoindolin-4-yl]piperazine-1-carboxylate (400 mg, 0.934 mmol, 1.0 eq) in DMF (8 mL) at 0° C. were added $Cs_2CO_3$ (608 mg, 1.87 mmol, 2.0 eq) and $CH_3I$ (0.116 mL, 1.87 mmol, d=2.28 g/mL, 2.0 eq), and the reaction mixture was stirred at 20° C. for 3 hours under $N_2$. The mixture was diluted with $H_2O$ (30 mL), and the aqueous phase was extracted with ethyl acetate (40 mL×3). The combined organic extract was washed with water (20 mL×3) and brine (20 mL×2), dried with anhydrous $Na_2SO_4$, filtered, and concentrated in vacuum to afford the title compound (490 mg, crude) as a yellow solid. LC/MS (ESI) m/z: 387.2 $[M-55]^+$.

Step 2: Preparation of 1-methyl-3-(1-oxo-4-piperazin-1-yl-isoindolin-2-yl)piperidine-2,6-dione

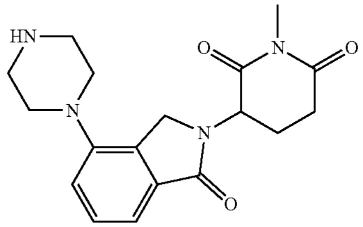 [SMILES: CN1C(=O)CCC(N2Cc3c(cccc3N3CCNCC3)C2=O)C1=O]

To a solution of tert-butyl 4-[2-(1-methyl-2,6-dioxo-3-piperidyl)-1-oxo-isoindolin-4-yl]piperazine-1-carboxylate (50 mg, 0.113 mmol, 1 eq) in $CH_2Cl_2$ (1 mL) was added 4M HCl/EtOAc (1 mL), and the reaction mixture was stirred at 20° C. for 20 min. The mixture was concentrated under reduced pressure to give the title compound (40 mg, 0.106 mmol, 93% yield, HCl salt) as a yellow solid. LC/MS (ESI) m/z: 343.0 $[M+H]^+$.

Step 3: Preparation of [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(1-methyl-2,6-dioxo-3-piperidyl)-1-oxo-isoindolin-4-yl]piperazine-1-carboxylate (Compound 54)

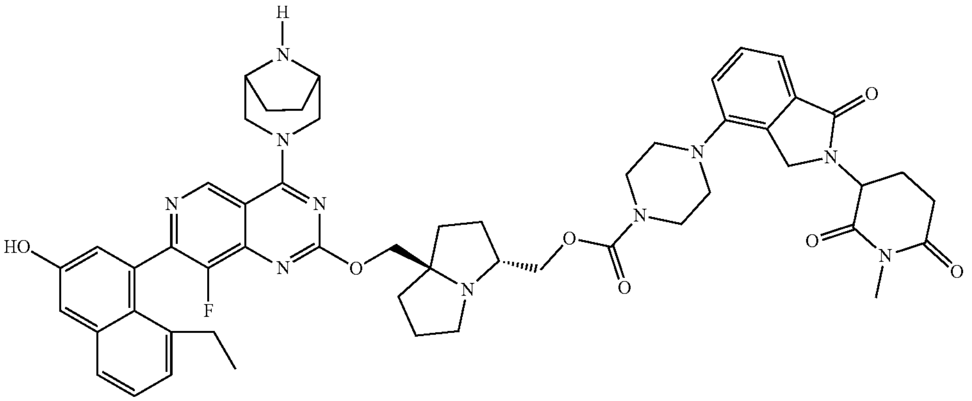 [SMILES: CCc1cccc2cc(O)cc(-c3ncc4c(N5CC6CCC(C5)N6)nc(OC[C@]56CCCN5[C@@H](COC(=O)N5CCN(c7cccc8c7CN(C7CCC(=O)N(C)C7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl4-[2-(1-methyl-2,6-dioxo-3-piperidyl)-1-oxo-isoindolin-5-yl]piperazine-1-carboxylate (Compound 53) starting from tert-butyl 3-[7-[8-ethyl-3-(methoxymethoxy)-1-naphthyl]-8-fluoro-2-[[(3R,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate and 1-methyl-3-(1-oxo-4-piperazin-1-yl-isoindolin-2-yl)piperidine-2,6-dione, and purified by prep-HPLC (column: Phenomenex C18 75*30 mm*3 μm; mobile phase: [5-40% $CH_3CN$ in water (formic acid)]). Pure fractions were combined and dried by lyophilization to give the title compound (30.8 mg, 0.030 mmol, 46% yield, formic acid salt) as a white solid.

Example 26: Synthesis of [(3S,8S)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl]methyl 4-[2-(1-methyl-2,6-dioxo-3-piperidyl)-1-oxo-isoindolin-4-yl]piperazine-1-carboxylate (Compound 52)

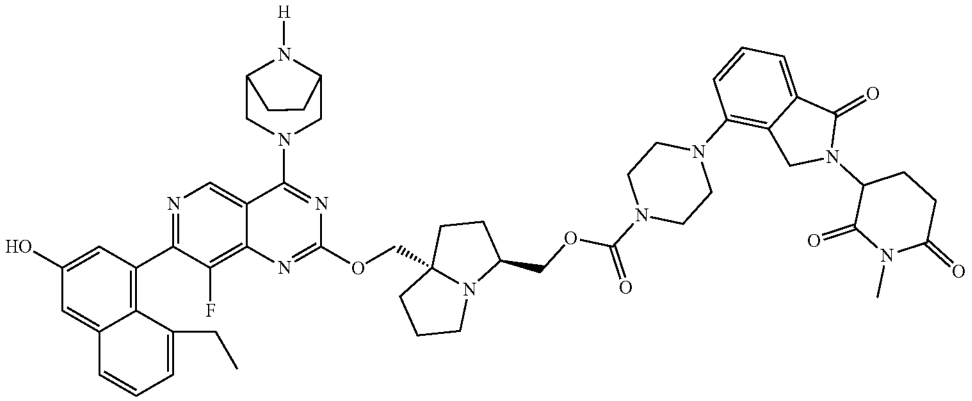 [SMILES: CCc1cccc2cc(O)cc(-c3ncc4c(N5CC6CCC(C5)N6)nc(OC[C@@]56CCCN5[C@H](COC(=O)N5CCN(c7cccc8c7CN(C7CCC(=O)N(C)C7=O)C8=O)CC5)CC6)nc4c3F)c12]

The title compound was prepared in an analogous manner to [(3R,8R)-8-[[4-(3,8-diazabicyclo[3.2.1]octan-3-yl)-7-(8-ethyl-3-hydroxy-1-naphthyl)-8-fluoro-pyrido[4,3-d]pyrimidin-2-yl]oxymethyl]-1,2,3,5,6,7-hexahydropyrrolizin-3-yl] methyl4-[2-(1-methyl-2,6-dioxo-3-piperidyl)-1-oxo-isoindolin-5-yl]piperazine-1-carboxylate (Compound 53) starting from tert-butyl 3-[7-[8-ethyl-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate and 1-methyl-3-(1-oxo-4-piperazin-1-yl-isoindolin-2-yl)piperidine-2,6-dione, and purified by prep-HPLC (gradient: 5-45% $CH_3CN$ in water (formic acid); Gradient time: 28 min; Hold time: 3 min; Flow rate: 25 mL/min). Pure fractions were combined and lyophilized under reduced pressure to afford the title compound (17.0 mg, 17.46 μmol, 28% yield, formic acid salt) as a white solid.

Example 27: Synthesis of 3-[6-(1-{2-[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]ethyl}piperidin-4-yl)-1-oxo-2,3-dihydro-1H-isoindol-2-yl]piperidine-2,6-dione (Compound 36)

Step 1: Preparation of tert-butyl 3-(2-(2-(4-(2-(2,6-dioxopiperidin-3-yl)-3-oxoisoindolin-5-yl)piperidin-1-yl)ethoxy)-7-(8-ethyl-3-hydroxynaphthalen-1-yl)-8-fluoropyrido[4,3-d]pyrimidin-4-yl)-3,8-diazabicyclo[3.2.1]octane-8-carboxylate

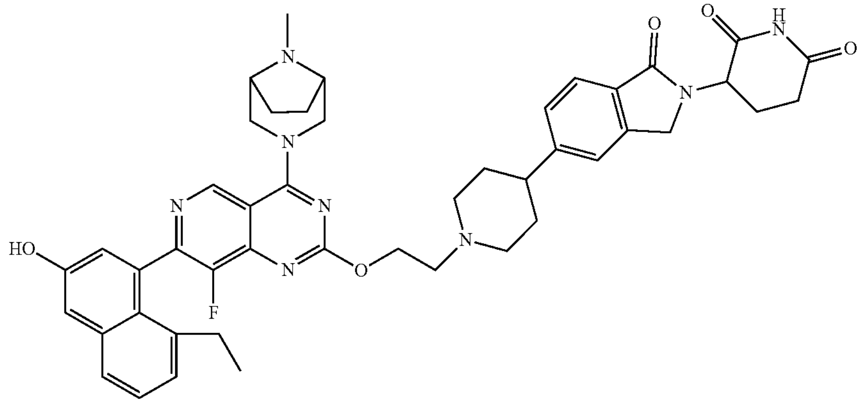 [SMILES: CCc1cccc2cc(O)cc(-c3ncc4c(N5CC6CCC(C5)N6C)nc(OCCN5CCC(c6ccc7c(c6)CN(C6CCC(=O)NC6=O)C7=O)CC5)nc4c3F)c12]

To a solution of tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate (51 μmol) in dichloromethane (1 mL) and isopropyl alcohol (0.1 mL) was added 3-(1-oxo-5-(piperidin-4-yl)isoindolin-2-yl) piperidine-2,6-dione (54 μmol), 2-methylpyridine borane complex (255 μmol) and acetic acid (204 μmol), the mixture was stirred at 20° C. for 1 h. The reaction mixture was filtered and concentrated. The residue was purified by preparative thin layer chromatography (dichloromethane: methanol=10:1) to afford product.

Step 2: Preparation of 3-[6-(1-{2-[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]ethyl}piperidin-4-yl)-1-oxo-2,3-dihydro-1H-isoindol-2-yl]piperidine-2,6-dione (Compound 36)

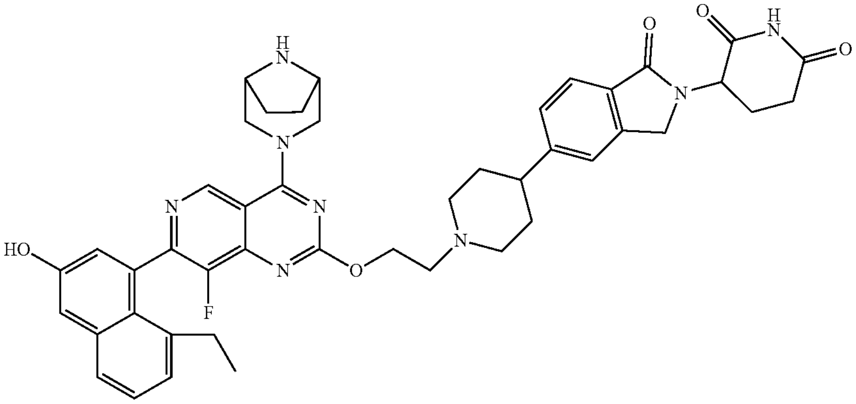 [SMILES: CCc1cccc2cc(O)cc(-c3ncc4c(N5CC6CCC(C5)N6)nc(OCCN5CCC(c6ccc7c(c6)CN(C6CCC(=O)NC6=O)C7=O)CC5)nc4c3F)c12]

To a solution of tert-butyl 3-[2-[2-[4-[2-(2,6-dioxo-3-piperidyl)-1-oxo-isoindolin-5-yl]-1-piperidyl]ethoxy]-7-(8-ethyl-3-hydroxy-1-naphthyl)-8-fluoro-pyrido[4,3-d]pyrimidin-4-yl]-3,8-diazabicyclo[3.2.1]octane-8-carboxylate (44 μmol) in hexafluoroisopropanol (1 mL) was added trifluoroacetic acid (0.2 mL) and stirred at 25° C. for 0.5 h. The reaction mixture was purified by preparative HPLC (Welch Xtimate C18 150×25 mm×5 μm; A: water with 0.225% v/v FA, B: acetonitrile; B %: 20-60; 25 min) and was then lyophilized to afford the title compound.

Compounds 1-8, 10-22, 25-27, 31-34, and 37-40 were prepared using a procedure analogous to the procedure used to prepare Compound 36.

Example 28: Synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-4-fluoro-1-oxo-isoindolin-2-yl]piperidine-2,6-dione (Compound 69)

Step 1: Preparation of methyl 2-bromo-3,4-difluorobenzoate

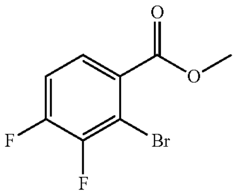

To a solution of 2-bromo-3,4-difluoro-benzoic acid (200 g, 843.8 mmol, 1 eq) in methanol (1.5 L) at 0° C. was added thionyl dichloride (200.8 g, 1.69 mol, 122.4 mL, 2 eq) dropwise, and the reaction mixture was stirred at 70° C. for 12 hours. The mixture was concentrated under vacuum, and the residue was diluted with water (600 mL) and extracted with EtOAc (3×200 mL). The combined organic extracts were washed with brine (2×200 mL), dried over anhydrous sodium sulfate, filtered, and concentrated under vacuum to give the title compound (208 g, 98%) as a yellow oil. $^1$H NMR (400 MHz, $CDCl_3$) δ 7.68 (ddd, J=2.0, 5.4, 8.8 Hz, 1H), 7.25-7.14 (m, 1H), 3.94 (s, 3H).

Step 2: Preparation of methyl 2-bromo-4-(4-(dimethoxymethyl)piperidin-1-yl)-3-fluorobenzoate

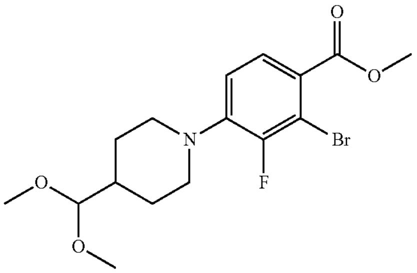

To a solution of methyl 2-bromo-3,4-difluoro-benzoate (208 g, 828.60 mmol, 1 eq) in dimethyl sulfoxide (1500 mL) were added diisopropylethylamine (321.3 g, 2.49 mol, 433.0 mL, 3 eq) and 4-(dimethoxymethyl)piperidine (138.5 g, 870.03 mmol, 1.05 eq), and the reaction mixture was stirred at 100° C. for 12 hours. The mixture was poured into water (1 L), and the aqueous mixture was extracted with EtOAc (3×300 mL). The combined organic extracts were washed with brine (3×500 mL), dried over anhydrous sodium sulfate, filtered, and concentrated under vacuum. The residue was purified by silica gel chromatography (gradient: 1-50% EtOAc in petroleum ether) to give the title compound (244 g, 75%) as a white solid. 10 LC/MS (ESI) m/z: 390.0, 392.0 $[M+H]^+$. $^1$H NMR (400 MHz, $CDCl_3$) δ 7.62 (dd, J=1.0, 8.6 Hz, 1H), 6.84 (t, J=8.4 Hz, 1H), 4.09 (d, J=7.0 Hz, 1H), 3.89 (s, 3H), 3.59 (br d, J=12.2 Hz, 2H), 3.38 (s, 6H), 2.74 (br t, J=11.6 Hz, 2H), 1.92-1.76 (m, 3H), 1.50 (br dd, J=3.4, 11.8 Hz, 2H).

Step 3: Preparation of methyl 4-(4-(dimethoxymethyl)piperidin-1-yl)-3-fluoro-2-vinylbenzoate

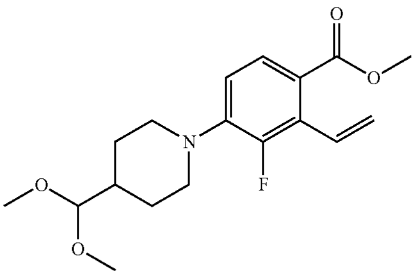

To a solution of methyl 2-bromo-4-(4-(dimethoxymethyl)piperidin-1-yl)-3-fluorobenzoate (170 g, 435.63 mmol, 1 eq) and potassium vinyltrifluoroborate (175.06 g, 1.31 mol, 3 eq) in dioxane (1.3 L) and water (250 mL) were added bis(diphenylphosphino)ferrocene]dichloropalladium(II) dichloromethane (17.8 g, 21.78 mmol, 0.05 eq) and sodium carbonate (115.4 g, 1.09 mol, 2.5 eq), and the reaction mixture was stirred at 110° C. for 12 hours. Water (1 L) was then added, and the aqueous mixture was extracted with EtOAc (3×600 mL). The combined organic extract was dried over anhydrous sodium sulfate, filtered, and concentrated under vacuum. The residue was purified by silica gel chromatography (1-25% EtOAc in petroleum ether) to afford the title compound (123 g, 83%) as a white solid. LC/MS (ESI) m/z: 338.1 $[M+H]^+$. $^1H$ NMR (400 MHz, $CDCl_3$) δ 7.64 (dd, J=1.2, 8.6 Hz, 1H), 7.04 (dd, J=11.8, 17.8 Hz, 1H), 6.83 (t, J=8.4 Hz, 1H), 5.74-5.46 (m, 2H), 4.11 (d, J=7.2 Hz, 1H), 3.85 (s, 3H), 3.64-3.52 (m, 2H), 3.38 (s, 6H), 2.71 (dt, J=1.8, 12.0 Hz, 2H), 1.86 (br dd, J=1.6, 13.0 Hz, 3H), 1.53 (br dd, J=3.6, 12.0 Hz, 2H).

Step 4: Preparation of methyl 4-(4-(dimethoxymethyl)piperidin-1-yl)-3-fluoro-2-formylbenzoate

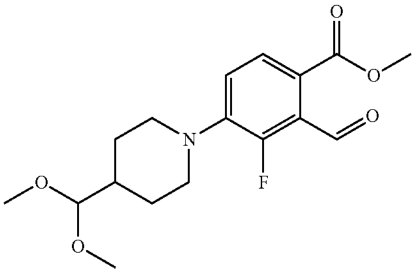

To a solution of methyl 4-(4-(dimethoxymethyl)piperidin-1-yl)-3-fluoro-2-vinylbenzoate (50 g, 148.20 mmol, 1 eq) in dioxane (450 mL) and water (150 mL) were added 2,6-lutidine (31.8 g, 296.40 mmol, 34.5 mL, 2 eq), potassium osmate(VI) dihydrate (1.1 g, 2.96 mmol, 0.02 eq), and sodium periodate (126.79 g, 592.79 mmol, 32.85 mL, 4 eq), and the reaction mixture was stirred at 20° C. for 1 hour. Water (300 mL) was then added, and the resulting mixture was filtered. The filtrate was extracted with EtOAc (2×200 mL), and the combined organic extract was dried over anhydrous sodium sulfate, filtered, and concentrated under vacuum. The residue was purified by silica gel chromatography (1-50% EtOAc in petroleum ether) to afford the title compound (36 g, 72% yield) as a yellow solid. $^1H$ NMR (400 MHz, $CDCl_3$) δ 10.42 (s, 1H), 7.65 (dd, J=0.8, 8.4 Hz, 1H), 7.01 (t, J=8.4 Hz, 1H), 4.09 (d, J=7.0 Hz, 1H), 3.90 (s, 3H), 3.63 (br d, J=12.2 Hz, 2H), 3.45-3.32 (m, 6H), 2.84-2.69 (m, 2H), 1.93-1.73 (m, 3H), 1.51 (br d, J=3.6 Hz, 2H).

Step 5: Preparation of 3-(5-(4-(dimethoxymethyl)piperidin-1-yl)-4-fluoro-1-oxoisoindolin-2-yl)piperidine-2,6-dione

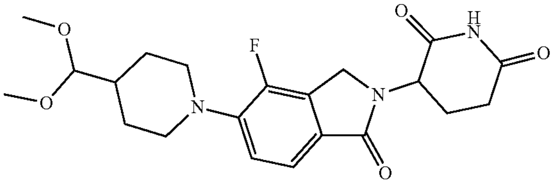 [SMILES: COC(OC)C1CCN(c2ccc3c(c2F)CN(C2CCC(=O)NC2=O)C3=O)CC1]

To a solution of 3-aminopiperidine-2,6-dione (20.4 g, 123.76 mmol, 1.2 eq, hydrochloride) in methanol (350 mL) was added sodium acetate (25.4 g, 309.41 mmol, 3 eq) followed by methyl 4-[4-(dimethoxymethyl)-1-piperidyl]-3-fluoro-2-formyl-benzoate (35 g, 103.14 mmol, 1 eq) and sodium cyanoborohydride (13.0 g, 206.27 mmol, 2 eq), and the reaction mixture was stirred at 40° C. for 12 hours. The mixture was filtered, and the cake was washed with methanol (2×20 mL). The cake was triturated twice with water (600 mL) at 20° C. for 30 minutes. The resulting material was collected and dried under vacuum to afford the title compound (37 g, 85%) as a purple solid. LC/MS (ESI) m/z: 420.1 $[M+H]^+$. $^1H$ NMR (400 MHz, DMSO-$d_6$) δ 10.97 (s, 1H), 7.46 (d, J=8.2 Hz, 1H), 7.23-7.05 (m, 1H), 5.15-4.99 (m, 1H), 4.52-4.42 (m, 1H), 4.36-4.26 (m, 1H), 4.12 (d, J=6.4 Hz, 1H), 3.49 (br d, J=4.8 Hz, 2H), 3.33 (s, 6H), 2.98-2.85 (m, 1H), 2.74 (br t, J=12.0 Hz, 2H), 2.61 (br s, 1H), 2.46-2.34 (m, 1H), 2.03-1.93 (m, 1H), 1.74 (br d, J=10.4 Hz, 3H), 1.40 (br d, J=10.2 Hz, 2H).

Step 6: Preparation of 1-(2-(2,6-dioxopiperidin-3-yl)-4-fluoro-1-oxoisoindolin-5-yl)piperidine-4-carbaldehyde

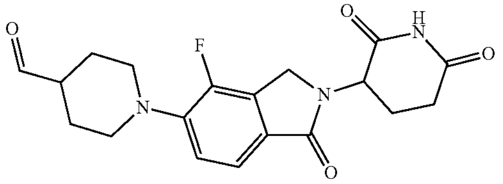 [SMILES: O=CC1CCN(c2ccc3c(c2F)CN(C2CCC(=O)NC2=O)C3=O)CC1]

To a solution of 3-(5-(4-(dimethoxymethyl)piperidin-1-yl)-4-fluoro-1-oxoisoindolin-2-yl)piperidine-2,6-dione (37 g, 88.21 mmol, 1 eq) in acetone (350 mL) and water (35 mL) was added p-toluenesulfonic acid (3.0 g, 17.64 mmol, 0.2 eq), and the reaction mixture was stirred at 70° C. for 12 hours. The mixture was filtered, and the cake was washed with acetone (3×30 mL). The resulting material was collected and dried under vacuum to afford the title compound (29 g, 88%) as a white. LC/MS (ESI) m/z: 374.1 $[M+H]^+$. $^1H$ NMR (400 MHz, DMSO-$d_6$) δ 10.97 (s, 1H), 9.65 (s, 1H), 7.47 (d, J=8.2 Hz, 1H), 7.17 (br t, J=7.8 Hz, 1H), 5.07

(br dd, J=5.0, 13.2 Hz, 1H), 4.56-4.43 (m, 1H), 4.38-4.22 (m, 1H), 3.50-3.37 (m, 2H), 3.00-2.82 (m, 3H), 2.64-2.52 (m, 2H), 2.43 (br d, J=4.2 Hz, 1H), 2.03-1.93 (m, 3H), 1.66 (br d, J=10.0 Hz, 2H).

Step 7: Preparation of tert-butyl 4-[[1-[[1-[2-(2,6-dioxo-3-piperidyl)-4-fluoro-1-oxo-isoindolin-5-yl]-4-piperidyl]methyl]-4-piperidyl]methyl]piperidine-1-carboxylate

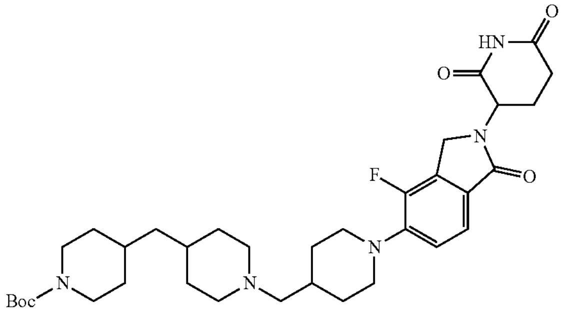 [SMILES: CC(C)(C)OC(=O)N1CCC(CC2CCN(CC3CCN(c4ccc5c(c4F)CN(C4CCC(=O)NC4=O)C5=O)CC3)CC2)CC1]

To a mixture of 1-(2-(2,6-dioxopiperidin-3-yl)-4-fluoro-1-oxoisoindolin-5-yl)piperidine-4-carbaldehyde (1.0 g, 2.68 mmol, 1 eq) and tert-butyl 4-(4-piperidylmethyl) piperidine-1-carboxylate (1.69 g, 3.21 mmol, 1.2 eq, acetate) in dichloromethane (10 mL) and dimethyl sulfoxide (10 mL) at 25° C. was added diisopropylethylamine (346 mg, 2.68 mmol, 0.4 mL, 1.0 eq), and the resulting mixture was stirred for 15 minutes under nitrogen. Sodium triacetoxyborohydride (1.70 g, 8.03 mmol, 3 eq) was then added, and the reaction mixture was stirred at 25° C. for 1 hour. The mixture was diluted with dichloromethane (50 mL), washed with brine (50 mL), dried over anhydrous sodium sulfate, filtered, and concentrated. The residue was purified by prep-TLC (dichloromethane/methanol=5/1) to the title compound (1.3 g, 2.03 mmol, 75% yield) as a white solid. LC/MS (ESI) m/z: 640.3 $[M+H]^+$.

Step 8: Preparation of 3-[4-fluoro-1-oxo-5-[4-[[4-(4-piperidylmethyl)-1-piperidyl]methyl]-1-piperidyl]isoindolin-2-yl]piperidine-2,6-dione

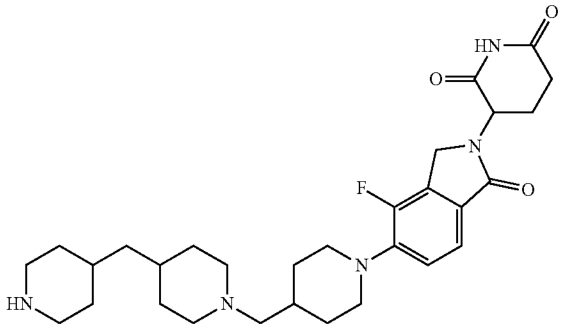 [SMILES: O=C1CCC(N2Cc3c(ccc(N4CCC(CN5CCC(CC6CCNCC6)CC5)CC4)c3F)C2=O)C(=O)N1]

To a solution of tert-butyl 4-[[1-[[1-[2-(2,6-dioxo-3-piperidyl)-4-fluoro-1-oxo-isoindolin-5-yl]-4-piperidyl]methyl]-4-piperidyl]methyl]piperidine-1-carboxylate (570 mg, 0.89 mmol, 1 eq) in dichloromethane (6 mL) was added trifluoroacetic acid (3.08 g, 27.01 mmol, 2 mL, 30.32 eq), and the reaction mixture was stirred at 25° C. for 0.5 hours. The mixture was concentrated under vacuum to afford the title compound (580 mg, crude, trifluoroacetate) as a brown gum. LC/MS (ESI) m/z: 540.5 $[M+H]^+$.

Step 9: Preparation of tert-butyl 3-[2-[2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]ethoxy]-8-fluoro-7-[7-fluoro-3-hydroxy-8-(2-triisopropylsilylethynyl)-1-naphthyl]pyrido[4,3-d]pyrimidin-4-yl]-3,8-diazabicyclo[3.2.1]octane-8-carboxylate

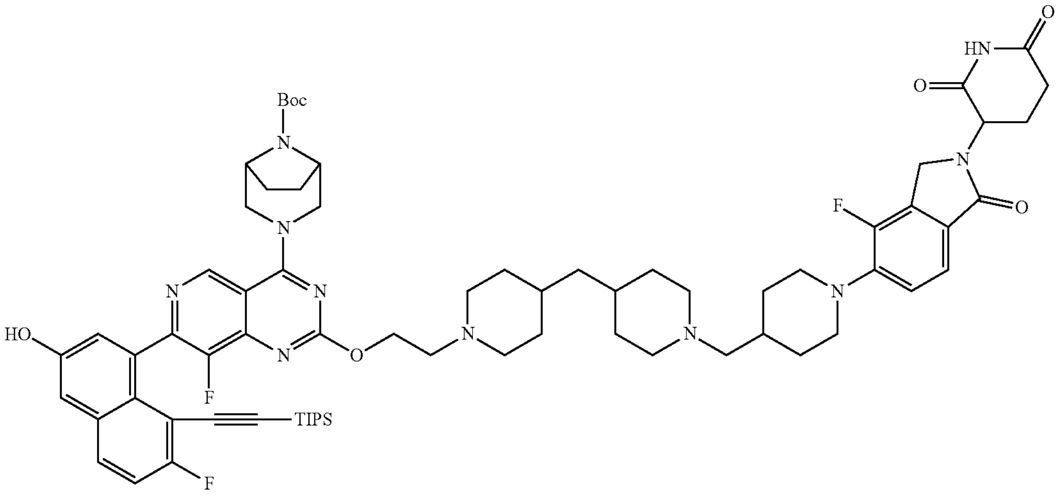

To a solution of 3-[4-fluoro-1-oxo-5-[4-[[4-(4-piperidylmethyl)-1-piperidyl]methyl]-1-piperidyl]isoindolin-2-yl]piperidine-2,6-dione (578 mg, 0.88 mmol, 1.49 eq, trifluoroacetate) in dichloromethane (5 mL) and isopropanol (5 mL) was added diisopropylethylamine (230 mg, 1.78 mmol, 0.3 mL, 3 eq) followed by tert-butyl 3-[8-fluoro-7-[7-fluoro-3-hydroxy-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (450 mg, 593.72 umol, 1 eq), and the resulting mixture was stirred at 25° C. for 10 minutes. Sodium triacetoxyborohydride (377 mg, 1.78 mmol, 3 eq) was then added, and the reaction mixture was stirred at 25° C. for 0.5 hours. The mixture was diluted with water (20 mL) and extracted with dichloromethane (2×30 mL). The combined organic extract was dried over anhydrous sodium sulfate, filtered, and concentrated under vacuum. The residue was purified by silica gel column chromatography ($CH_2Cl_2$/$CH_3OH$=20/1 to 6/1) to afford the title compound (470 mg, 0.36 mmol, 61% yield) as a light yellow solid. LC/MS (ESI) m/z: 1281.9 $[M+H]^+$.

Step 10: Preparation of tert-butyl 3-[2-[2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate

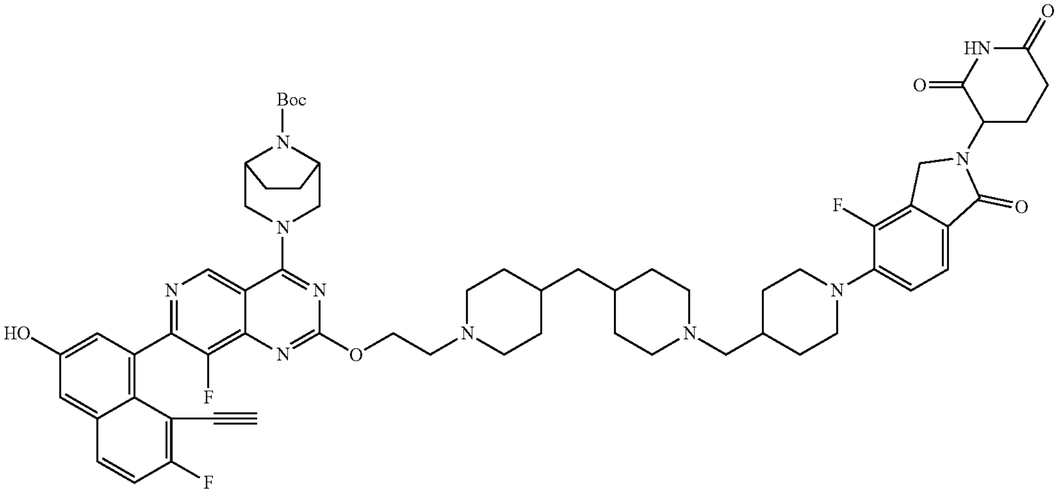 [SMILES: C#Cc1c(F)ccc2cc(O)cc(-c3ncc4c(N5CC6CCC(C5)N6C(=O)OC(C)(C)C)nc(OCCN5CCC(CC6CCN(CC7CCN(c8ccc9c(c8F)CN(C8CCC(=O)NC8=O)C9=O)CC7)CC6)CC5)nc4c3F)c12]

To a mixture of tert-butyl 3-[2-[2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]ethoxy]-8-fluoro-7-[7-fluoro-3-hydroxy-8-(2-triisopropylsilylethynyl)-1-naphthyl]pyrido[4,3-d]pyrimidin-4-yl]-3,8-diazabicyclo[3.2.1]octane-8-carboxylate (460 mg, 0.35 mmol, 1 eq) in DMF (5 mL) at 25° C. was added cesium fluoride (1.09 g, 7.18 mmol, 0.2 mL, 20 eq), and the reaction mixture was stirred at 25° C. for 2 hours. The mixture was diluted with dichloromethane (50 mL), washed with brine (50 mL), dried over anhydrous sodium sulfate, filtered, and concentrated. The residue was purified by silica gel chromatography ($CH_2Cl_2$/$CH_3OH$=5/1) to afford the title compound (168 mg, 0.14 mmol, 41% yield) as a white solid. LC/MS (ESI) m/z: 563.6 $[M/2+H]^+$.

Step 11: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]methyl]-1-piperidyl]-4-fluoro-1-oxo-isoindolin-2-yl]piperidine-2,6-dione (Compound 69)

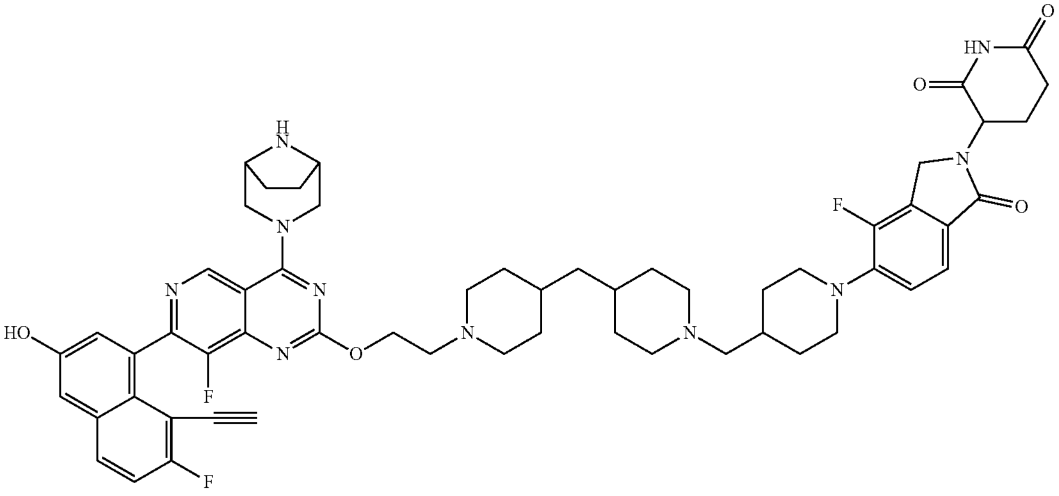 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)CN(C8CCC(=O)NC8=O)C9=O)CC7)CC6)CC5)nc4c3F)c12]

To a solution of tert-butyl 3-[2-[2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate (168 mg, 0.14 mmol, 1 eq) in dichloromethane (1.5 mL) was added hydrochloric acid/dioxane (4 M, 0.5 mL, 13.40 eq), and the reaction mixture was stirred at 25° C. for 15 minutes. The mixture was diluted with petroleum ether (6 mL) and the pH adjusted to 6. The mixture was concentrated in vacuum, and the residue was purified by prep-HPLC (column: Phenomenex Luna C18 150*25 mm*10 um; mobile phase: [6-36% $CH_3CN$ in water (formic acid)]) to afford the title compound (91.0 mg, 0.08 mmol, 56% yield, formic acid salt) as a yellow solid.

Example 29: Synthesis of 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl]piperidine-2,6-dione (Compound 193)

Step 1: Preparation of 2,6-bis(benzyloxy)-3-nitropyridine

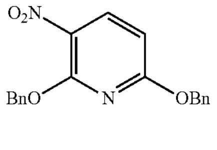 [SMILES: O=[N+]([O-])c1ccc(OCc2ccccc2)nc1OCc1ccccc1]

To a mixture of 2,6-dichloro-3-nitropyridine (25.0 g, 156 mmol) and phenylmethanol (40.6 mL, 390 mmol) in acetonitrile (500 mL) was added cesium carbonate (127.21 g, 390 mmol) in one portion under nitrogen atmosphere, and the mixture was stirred at 60° C. for 6 h. The mixture was cooled to 20° C. and filtered, and the filtrate was concentrated under reduced pressure. The residue was triturated with petroleum ether/methyl tert-butyl ether (1:1, 500 mL) to afford the title compound (49 g, 93%) as a yellow solid.

Step 2: Preparation of 2,6-bis(benzyloxy)pyridin-3-amine

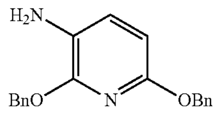

To a mixture of 2,6-bis(benzyloxy)-3-nitropyridine (95.0 g, 282 mmol) and ammonium chloride (226.6 g, 4.2 mol) in isopropanol (950 mL) and water (475 mL) was added iron (126.19 g, 2.26 mol) under nitrogen atmosphere, and the mixture was stirred at 90° C. for 16 h. The mixture was cooled to 20° C. and filtered. The filtrate was poured into ice-water (w/w=1/1, 1000 mL) and stirred for 5 minutes. The aqueous phase was extracted with ethyl acetate (2×1000 mL). The combined organic phase was washed with brine (3×1000 mL), dried over anhydrous sodium sulfate, filtered, and concentrated under reduced pressure. The residue was purified by prep-HPLC (1% to 20% hexane/ethanol over 15 min) to afford the title compound (61 g, 70%) as a brown oil. LC/MS (ESI) m/z: 307.2 $[M+H]^+$.

Step 3: Preparation of 2,6-dibenzyloxy-N-(4-bromo-2-nitro-phenyl)pyridin-3-amine

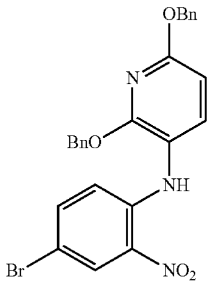 [SMILES: O=[N+]([O-])c1cc(Br)ccc1Nc1ccc(OCc2ccccc2)nc1OCc1ccccc1]

To a solution of 2,6-bis(benzyloxy)pyridin-3-amine (5.0 g, 16 mmol) and 4-bromo-1-fluoro-2-nitro-benzene (2.4 mL, 20 mmol) in tetrahydrofuran (50 mL) was added lithium bis(trimethylsilyl)amide in tetrahydrofuran (1 M, 24.5 mL), and the mixture was stirred at −78° C. for 1 h, then stirred at 25° C. for 11 h under nitrogen atmosphere. The reaction was slowly quenched with saturated ammonium chloride solution to adjust the pH to 8-9, then extracted with ethyl acetate (300 mL). The organic layer was washed with brine (3×20 mL), dried over anhydrous sodium sulfate, filtered, and concentrated under reduced pressure. The residue was purified by silica gel column chromatography (petroleum ether/ethyl acetate=1/0 to 100/1) to afford the title compound (9 g, crude) as a brown oil. LC/MS (ESI) m/z: 508.1 $[M+H]^+$.

Step 4: Preparation of 4-bromo-N1-(2,6-dibenzyloxy-3-pyridyl)benzene-1,2-diamine

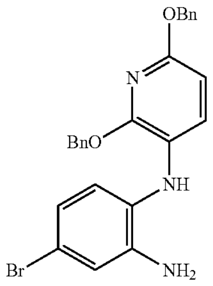 [SMILES: Nc1cc(Br)ccc1Nc1ccc(OCc2ccccc2)nc1OCc1ccccc1]

To a solution of 2,6-dibenzyloxy-N-(4-bromo-2-nitro-phenyl)pyridin-3-amine (8.0 g, 16 mmol) in ethanol (100 mL) and water (50 mL) were added iron (4.41 g, 79 mmol) and saturated aqueous ammonium chloride solution (8.45 g, 128 mmol), and the mixture was stirred at 80° C. for 4 h. The reaction mixture was filtered, and the filtrate was extracted with ethyl acetate (300 mL). The organic layer was washed with brine (3×30 mL), dried over anhydrous sodium sulfate, filtered, and concentrated under reduced pressure. The residue was purified by silica gel column chromatography (petroleum ether/ethyl acetate=1/0 then 10/1) to afford the title compound (2.8 g, 37%) as a brown solid.

Step 5: Preparation of 6-bromo-3-(2,6-dibenzyloxy-3-pyridyl)-1H-benzimidazol-2-one

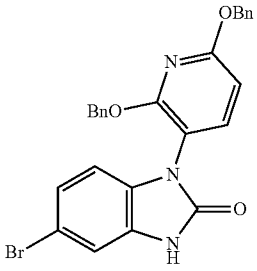 [SMILES: O=c1[nH]c2cc(Br)ccc2n1-c1ccc(OCc2ccccc2)nc1OCc1ccccc1]

To a solution of 4-bromo-N1-(2,6-dibenzyloxy-3-pyridyl)benzene-1,2-diamine (2.8 g, 6 mmol) in N,N-dimethyl formamide (30 mL) was added 4-dimethylaminopyridine (4.77 g, 29 mmol), and the mixture was stirred at 120° C. for 2 h. The reaction was poured into water and the resulting precipitate was filtered and dried to afford the title compound (2.8 g, 94%) as a yellow solid. LC/MS (ESI) m/z: 504.1 $[M+H]^+$.

Step 6: Preparation of 5-bromo-1-(2,6-dibenzyloxy-3-pyridyl)-3-methyl-benzimidazol-2-one

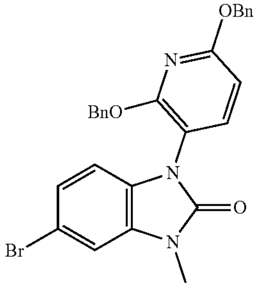 [SMILES: Cn1c(=O)n(-c2ccc(OCc3ccccc3)nc2OCc2ccccc2)c2ccc(Br)cc21]

To a solution of 6-bromo-3-(2,6-dibenzyloxy-3-pyridyl)-1H-benzimidazol-2-one (1.2 g, 2 mmol) in tetrahydrofuran (20 mL) was added sodium hydride (191 mg, 4.8 mmol, 60%) at 0° C., and the reaction mixture was stirred for 0.5 h. Iodomethane (0.2 mL, 4 mmol) was then added at 0° C., and the mixture was warmed to 25° C. and stirred for 15.5 h. The reaction mixture was diluted with saturated aqueous ammonium chloride solution (10 mL), and the resulting mixture was extracted with ethyl acetate (200 mL). The organic extract was washed with brine (3×20 mL), dried over anhydrous sodium sulfate, filtered, and concentrated under reduced pressure. The residue was purified by silica gel column chromatography (petroleum ether/ethyl acetate=1/0 to 5/1) to afford the title compound (1.1 g, crude) as a yellow oil. LC/MS (ESI) m/z: 516.4 $[M+H]^+$.

Step 7: Preparation of 1-(2,6-dibenzyloxy-3-pyridyl)-5-[4-(dimethoxymethyl)-1-piperidyl]-3-methyl-benzimidazol-2-one

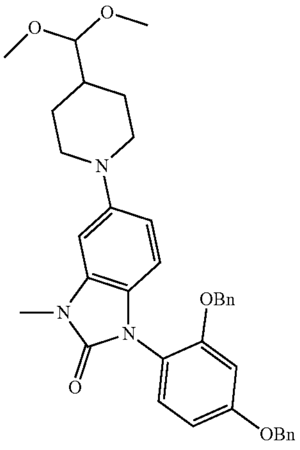 [SMILES: COC(OC)C1CCN(c2ccc3c(c2)n(C)c(=O)n3-c2ccc(OCc3ccccc3)cc2OCc2ccccc2)CC1]

To a solution of 5-bromo-1-(2,6-dibenzyloxy-3-pyridyl)-3-methyl-benzimidazol-2-one (1 g, 2 mmol) and 4-(dimethoxymethyl) piperidine (308 mg, 1.9 mmol) in 1,4-dioxane (15 mL) were added XPhos Pd G2 (152 mg, 0.2 mmol) and cesium carbonate (1.89 g, 5.8 mmol), and the mixture was stirred at 100° C. for 16 h. The reaction mixture was filtered, and the filtrate was concentrated under reduced pressure. The residue was purified by silica gel column chromatography (petroleum ether/ethyl acetate=1/1 then 1/2) to afford the title compound (760 mg, 66%) as a brown oil. LC/MS (ESI) m/z: 595.4 $[M+H]^+$.

Step 8: Preparation of 3-[5-[4-(dimethoxymethyl)-1-piperidyl]-3-methyl-2-oxo-benzimidazol-1-yl] piperidine-2,6-dione

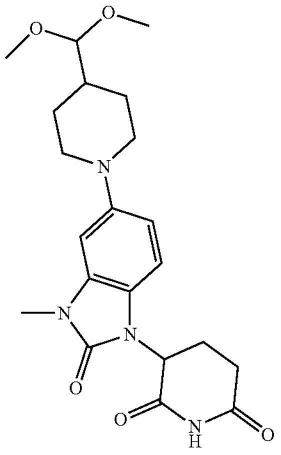 [SMILES: COC(OC)C1CCN(c2ccc3c(c2)n(C)c(=O)n3C2CCC(=O)NC2=O)CC1]

To a solution of 1-(2,6-dibenzyloxy-3-pyridyl)-5-[4-(dimethoxymethyl)-1-piperidyl]-3-methyl-benzimidazol-2-one (1.2 g, 2 mmol) in tetrahydrofuran (10 mL) was added 10% palladium on carbon (300 mg) under nitrogen atmosphere, and the suspension was degassed under vacuum and purged with hydrogen several times. The reaction mixture was stirred under hydrogen (50 psi) at 50° C. for 16 h. The mixture was filtered and concentrated under reduced pressure to afford the title compound (430 mg, 51%) as a brown oil. LC/MS (ESI) m/z: 417.3 $[M+H]^+$.

Step 9: Preparation of 1-[1-(2,6-dioxo-3-piperidyl)-3-methyl-2-oxo-benzimidazol-5-yl]piperidine-4-carbaldehyde

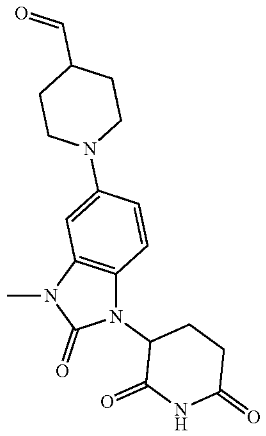 [SMILES: Cn1c(=O)n(C2CCC(=O)NC2=O)c2ccc(N3CCC(C=O)CC3)cc21]

To a solution of 3-[5-[4-(dimethoxymethyl)-1-piperidyl]-3-methyl-2-oxo-benzimidazol-1-yl]piperidine-2,6-dione (430 mg, 1 mmol) in dichloromethane (10 mL) was added trifluoroacetic acid (0.1 mL, 1 mmol), and the mixture was stirred at 25° C. for 4 h. The reaction mixture was concentrated under reduced pressure. The residue was triturated with ethyl acetate/methyl tert-butyl ether (1/10, 60 mL) to afford the title compound (380 mg, 99%) as a green oil. LC/MS (ESI) m/z: 389.3 $[M+H_3O]^+$.

Step 10: Preparation of tert-butyl 9-[[1-[1-(2,6-dioxo-3-piperidyl)-3-methyl-2-oxo-benzimidazol-5-yl]-4-piperidyl]methyl]-3,9-diazaspiro[5.5]undecane-3-carboxylate

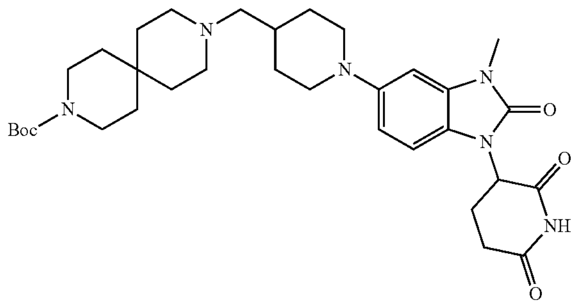 [SMILES: Cn1c(=O)n(C2CCC(=O)NC2=O)c2ccc(N3CCC(CN4CCC5(CC4)CCN(C(=O)OC(C)(C)C)CC5)CC3)cc21]

To a solution of 1-[1-(2,6-dioxo-3-piperidyl)-3-methyl-2-oxo-benzimidazol-5-yl]piperidine-4-carbaldehyde (250 mg, 0.7 mmol) and tert-butyl 3,9-diazaspiro[5.5]undecane-3-carboxylate (189 mg, 0.7 mmol) in dichloromethane (5 mL) and dimethyl sulfoxide (2 mL) were added acetic acid (41 mg, 0.7 mmol) and sodium triacetoxyborohydride (286 mg, 1.4 mmol), and the mixture was stirred at 25° C. for 2 h. The reaction mixture was diluted with water (15 mL) and extracted with dichloromethane (3×30 mL). The combined organic extracts were washed with brine (15 mL), dried over anhydrous sodium sulfate, filtered, and concentrated under reduced pressure to afford the title compound (280 mg, 68%) as a green oil. LC/MS (ESI) m/z: 609.4 $[M+H]^+$.

Step 11: Preparation of 3-[5-[4-(3,9-diazaspiro[5.5]undecan-3-ylmethyl)-1-piperidyl]-3-methyl-2-oxo-benzimidazol-1-yl]piperidine-2,6-dione

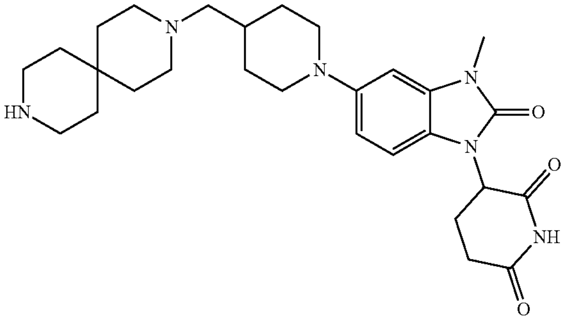 [SMILES: Cn1c(=O)n(C2CCC(=O)NC2=O)c2ccc(N3CCC(CN4CCC5(CCNCC5)CC4)CC3)cc21]

To a solution of tert-butyl 9-[[1-[1-(2,6-dioxo-3-piperidyl)-3-methyl-2-oxo-benzimidazol-5-yl]-4-piperidyl]methyl]-3,9-diazaspiro[5.5]undecane-3-carboxylate (410 mg, 0.7 mmol) in dichloromethane (10 mL) was added trifluoroacetic acid (3.0 mL, 40 mmol) at 25° C., and the reaction mixture was stirred for 1 h. The mixture was concentrated under reduced pressure, and the residue was triturated with ethyl acetate/methyl tert-butyl ether (1/10, 50 mL) to afford the title compound (490 mg, crude, di-trifluoroacetate salt) as a light yellow solid. LC/MS (ESI) m/z: 509.3 $[M+H]^+$.

Step 12: Preparation of 2,4,7-trichloro-8-fluoro-pyrido[4,3-d]pyrimidine

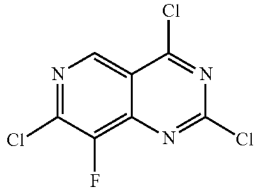 [SMILES: Fc1c(Cl)ncc2c(Cl)nc(Cl)nc12]

To a mixture of phosphorus oxychloride (240 mL, 2.6 mol) in N,N-diisopropylethylamine (100 mL) was added 7-chloro-8-fluoro-pyrido[4,3-d]pyrimidine-2,4-diol (24.0 g, 111 mmol) at 0° C., and the mixture was stirred for 2 h at 90° C. The reaction mixture was concentrated, and the residue was diluted with water (500 mL) and extracted with ethyl acetate (3×500 mL). The combined organic extract was washed with brine (500 mL), dried over anhydrous sodium sulfate, filtered, and concentrated in vacuo. The residue was purified by silica gel column chromatography (petroleum ether/ethyl acetate=20/1 then 3/1) to afford the title compound (14 g, 49%) as a yellow solid.

Step 13: Preparation of tert-butyl 3-(2,7-dichloro-8-fluoro-pyrido[4,3-d]pyrimidin-4-yl)-3,8-diazabicyclo[3.2.1]octane-8-carboxylate

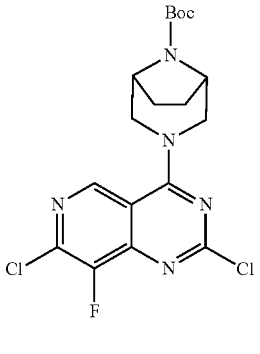 [SMILES: CC(C)(C)OC(=O)N1C2CCC1CN(c1nc(Cl)nc3c(F)c(Cl)ncc13)C2]

To a solution of 2,4,7-trichloro-8-fluoro-pyrido[4,3-d]pyrimidine (11 g, 43 mmol) and N,N-diisopropylethylamine (22.8 mL, 131 mmol) in N,N-dimethylformamide (100 mL) at −60° C. was added tert-butyl (1S,5R)-3,8-diazabicyclo[3.2.1] octane-8-carboxylate (8.32 g, 39 mmol), and the reaction mixture was stirred for −60° C. for 1 h. The mixture was filtered, and the filtrate was concentrated under reduced pressure to afford the title compound (14 g, 81%) as a yellow oil.

LC/MS (ESI) m/z: 428.1 $[M+H]^+$; $^1H$ NMR (400 MHz, $CDCl_3$) δ 8.85 (s, 1H), 4.65-4.35 (m, 4H), 3.90-3.55 (m, 2H), 2.05-1.90 (m, 2H), 1.72-1.60 (m, 2H), 1.53 (s, 9H).

Step 14: Preparation of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate

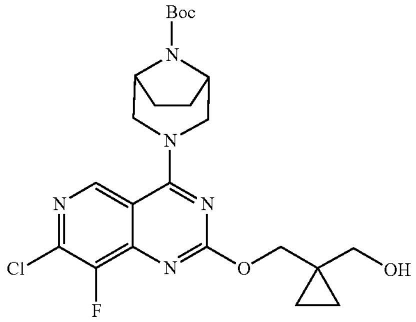 [SMILES: CC(C)(C)OC(=O)N1C2CCC1CN(c1nc(OCC3(CO)CC3)nc3c(F)c(Cl)ncc13)C2]

To a solution of [1-(hydroxymethyl)cyclopropyl]methanol (9.54 g, 93 mmol) in tetrahydrofuran (200 mL) was added lithium tert-butoxide (1 M, 70 mL), and the resulting mixture was stirred for 0.5 h. tert-Butyl 3-(2,7-dichloro-8-fluoro-pyrido[4,3-d]pyrimidin-4-yl)-3,8-diazabicyclo[3.2.1]octane-8-carboxylate (20 g, 47 mmol) in tetrahydrofuran (200 mL) was then added dropwise at 20° C., and the reaction mixture was stirred at 50° C. for 1.5 h. The mixture was concentrated under reduced pressure, and the residue was purified by silica gel chromatography (petroleum ether/dichloromethane=5/1 then petroleum ether/dichloromethane/ethyl acetate=5/1/5) to afford the title compound (9.54 g, 41%) as a white solid. LC/MS (ESI) m/z: 494.3 $[M+H]^+$; $^1H$ NMR (400 MHz, DMSO-$d_6$) δ 8.90 (s, 1H), 4.63 (s, 1H), 4.47 (d, J=12.4 Hz, 2H), 4.32-4.20 (m, 4H), 3.61 (d, J=12.4 Hz, 2H), 3.40-3.27 (m, 2H), 1.78 (d, J=4.0 Hz, 2H), 1.62 (d, J=7.6 Hz, 2H), 1.46 (s, 9H), 0.60-0.42 (m, 4H).

Step 15: Preparation of tert-butyl 3-[8-fluoro-7-[7-fluoro-3-(methoxymethoxy)-8-(2-triisopropyl silylethynyl)-1-naphthyl]-2-[[1-(hydroxymethyl)cyclopropyl]methoxy]pyrido[4,3-d]pyrimidin-4-yl]-3,8-diazabicyclo[3.2.1]octane-8-carboxylate

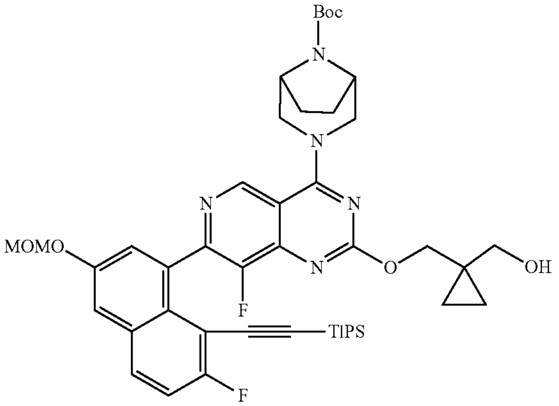

A mixture of tert-butyl 3-[7-chloro-8-fluoro-2-[[1-(hydroxymethyl)cyclopropyl]methoxy]pyrido[4,3-d]pyrimidin-4-yl]-3,8-diazabicyclo[3.2.1]octane-8-carboxylate (9.54 g, 19 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (10.9 g, 21 mmol), potassium phosphate (12.3 g, 58 mmol), and methanesulfonato(diadamantyl-n-butylphosphino)-2'-amino-1,1'-biphenyl-2-yl)palladium(II) (1.41 g, 2 mmol) in 1,4-dioxane (180 mL) and water (30 mL) was degassed and purged with nitrogen (3×), then stirred at 90° C. for 12 h under nitrogen atmosphere. The reaction mixture was filtered and concentrated under reduced pressure. The residue was purified by flash silica gel chromatography (0 to 50% ethyl acetate/petroleum ether) to afford the title compound (15.88 g, 97%) as a yellow solid. LC/MS (ESI) m/z: 844.7 $[M+H]^+$.

Step 16: Preparation of tert-butyl 3-[8-fluoro-7-[7-fluoro-3-(methoxymethoxy)-8-(2-triisopropylsilylethynyl)-1-naphthyl]-2-[(1-formylcyclopropyl)methoxy]pyrido[4,3-d]pyrimidin-4-yl]-3,8-diazabicyclo[3.2.1]octane-8-carboxylate

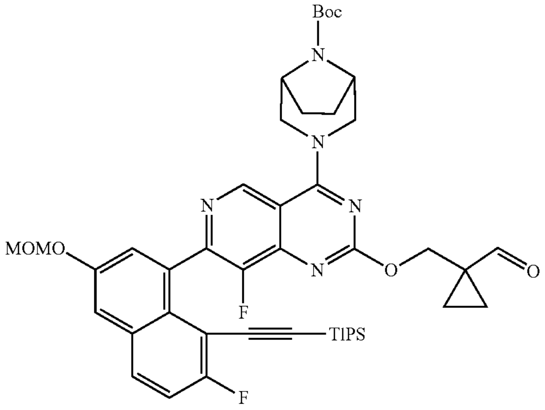

To a solution of tert-butyl 3-[8-fluoro-7-[7-fluoro-3-(methoxymethoxy)-8-(2-triisopropyl silylethynyl)-1-naphthyl]-2-[[1-(hydroxymethyl)cyclopropyl]methoxy]pyrido[4,3-d]pyrimidin-4-yl]-3,8-diazabicyclo[3.2.1]octane-8-carboxylate (5 g, 6 mmol) in dichloromethane (100 mL) was added Dess-Martin periodinane (7.0 mL, 12 mmol), and the mixture was stirred at 20° C. for 12 h. The mixture was poured into a mixture of saturated sodium thiosulfate solution (50 mL), sodium bicarbonate solution (50 mL), and water (50 mL). After stirring for 5 minutes, the aqueous phase was extracted with dichloromethane (2×50 mL). The combined organic extract was washed with brine (2×100 mL), dried over anhydrous sodium sulfate, filtered, and concentrated under reduced pressure. The residue was purified by silica gel chromatography (petroleum ether/ethyl acetate=10/1 then 2/1) to afford the title compound (3.51 g, 70%) as a yellow solid. LC/MS (ESI) m/z: 842.4 $[M+H]^+$.

Step 17: Preparation of tert-butyl 3-[2-[[1-[[9-[[1-[1-(2,6-dioxo-3-piperidyl)-3-methyl-2-oxo-benzimidazol-5-yl]-4-piperidyl]methyl]-3,9-diazaspiro[5.5]undecan-3-yl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

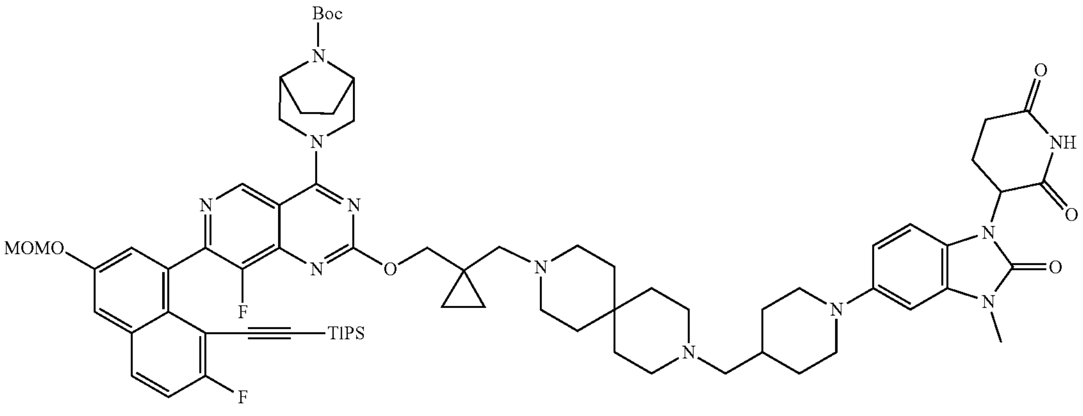

To a solution of 3-[5-[4-(3,9-diazaspiro[5.5]undecan-3-ylmethyl)-1-piperidyl]-3-methyl-2-oxo-benzimidazol-1-yl] piperidine-2,6-dione (648 mg, 0.9 mmol, 2 trifluoroacetate) in dichloromethane (7 mL) and dimethyl sulfoxide (7 mL) was added N,N-diisopropylethylamine (0.8 mL, 4 mmol), and the resulting mixture was stirred at 25° C. for 0.5 h. tert-Butyl 3-[8-fluoro-7-[7-fluoro-3-(methoxymethoxy)-8-(2-triisopropylsilylethynyl)-1-naphthyl]-2-[(1-formylcyclopropyl)methoxy]pyrido[4,3-d]pyrimidin-4-yl]-3,8-diazabicyclo[3.2.1]octane-8-carboxylate (741 mg, 0.9 mmol), acetic acid (0.5 mL, 9 mmol), and 2-methylpyridine borane (470 mg, 4 mmol) were then added, and the reaction mixture was stirred at 40° C. for 12 h. The reaction was diluted with water (30 mL) and extracted with ethyl acetate (3×20 mL). The combined organic extract was washed with brine (2×20 mL), dried over anhydrous sodium sulfate, filtered, and concentrated under reduced pressure. The residue was purified by silica gel column chromatography (dichloromethane/methanol=1:0 then 10:1) to afford the title compound (334 mg, 28%) as a yellow oil. LC/MS (ESI) m/z: 1335.7 $[M+H]^+$, $^1H$ NMR (400 MHz, DMSO-$d_6$) δ 11.05 (s, 1H), 9.16 (s, 1H), 8.10 (dd, J=6.0, 9.2 Hz, 1H), 7.74 (d, J=2.8 Hz, 1H), 7.56 (t, J=8.8 Hz, 1H), 7.33 (d, J=2.4 Hz, 1H), 6.93 (d, J=8.4 Hz, 1H), 6.82 (s, 1H), 6.63 (d, J=8.4 Hz, 1H), 5.75 (s, 2H), 5.36 (s, 4H), 4.38-4.16 (m, 6H), 3.81-3.69 (m, 1H), 3.66-3.51 (m, 3H), 3.50-3.39 (m, 5H), 3.17 (d, J=5.2 Hz, 5H), 3.01-2.87 (m, 3H), 2.74-2.56 (m, 6H), 2.44-2.32 (m, 5H), 1.93-1.85 (m, 5H), 1.70-1.60 (m, 4H), 1.46 (s, 9H), 1.40-1.28 (m, 4H), 0.81 (t, J=7.6 Hz, 18H), 0.64 (s, 2H), 0.52-0.41 (m, 5H).

Step 18: Preparation of tert-butyl 3-[2-[[1-[[9-[[1-[1-(2,6-dioxo-3-piperidyl)-3-methyl-2-oxo-benzimidazol-5-yl]-4-piperidyl]methyl]-3,9-diazaspiro[5.5]undecan-3-yl]methyl]cyclopropyl]methoxy]-7-[8-ethynyl-7-fluoro-3-(methoxymethoxy)-1-naphthyl]-8-fluoro-pyrido[4,3-d] pyrimidin-4-yl]-3,8-diazabicyclo[3.2.1]octane-8-carboxylate

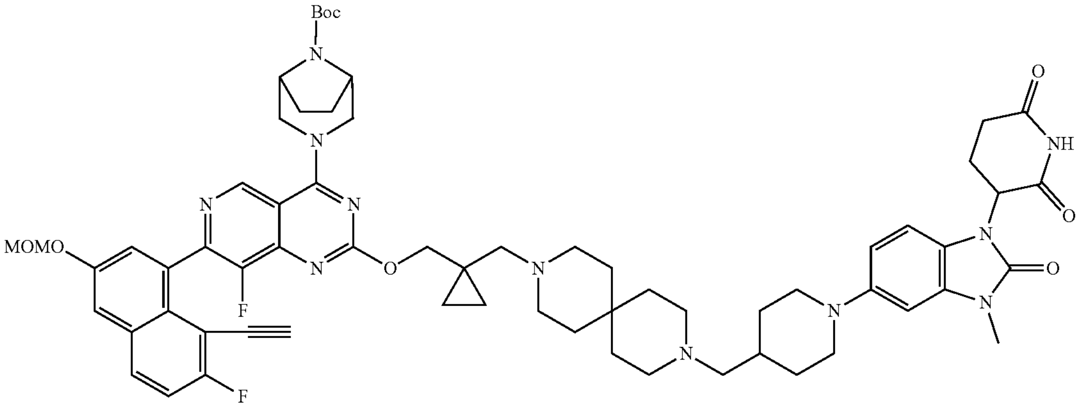

To a solution of tert-butyl 3-[2-[[1-[[9-[[1-[1-(2,6-dioxo-3-piperidyl)-3-methyl-2-oxo-benzimidazol-5-yl]-4-piperidyl]methyl]-3,9-diazaspiro[5.5]undecan-3-yl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo [3.2.1]octane-8-carboxylate (334 mg, 0.3 mmol) in N,N-dimethylformamide (5 mL) was added cesium fluoride (1.14 g, 7.5 mmol), and the reaction mixture was stirred at 25° C. for 1 h. The reaction was poured into ice-water (40 mL), and the aqueous phase was extracted with tetrahydrofuran/ethyl acetate (1/1, 2×20 mL). The combined organic extracts were washed with saturated sodium bicarbonate solution (2×20 mL), dried over anhydrous sodium sulfate, filtered, and concentrated under reduced pressure to afford the title compound (256 mg, 86%) as a yellow solid. LC/MS (ESI) m/z: 1178.8 $[M+H]^+$.

Step 19: Preparation of 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl]piperidine-2,6-dione

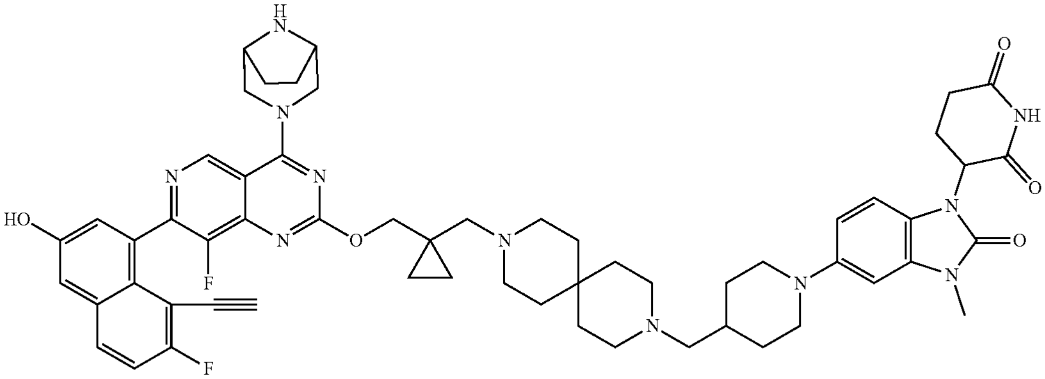 [SMILES: C#Cc1c(F)ccc2cc(O)cc(-c3ncc4c(N5CC6CCC(C5)N6)nc(OCC5(CN6CCC7(CCN(CC8CCN(c9ccc%10c(c9)n(C)c(=O)n%10C9CCC(=O)NC9=O)CC8)CC7)CC6)CC5)nc4c3F)c12]

To a solution of tert-butyl 3-[2-[[1-[[9-[[1-[1-(2,6-dioxo-3-piperidyl)-3-methyl-2-oxo-benzimidazol-5-yl]-4-piperidyl]methyl]-3,9-diazaspiro[5.5]undecan-3-yl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (256 mg, 0.2 mmol) in dichloromethane (3 mL) was added 4 M HCl in 1,4-dioxane (3 mL), and the reaction mixture was stirred at 25° C. for 15 min. The reaction mixture was suspended in petroleum ether (20 mL) and filtered, the filtered cake was dissolved with dimethyl sulfoxide (3 mL) and basified with N,N-diisopropylethylamine. The residue was purified by prep-HPLC (1% to 28% acetonitrile in water (formic acid) over 10 min) to afford the title compound (31.9 mg, 12%, di-formic acid salt) as a yellow solid. LC/MS (ESI) m/z: 1034.6 $[M+H]^+$; $^1H$ NMR (400 MHz, DMSO-$d_6$) δ 11.05 (s, 1H), 9.04 (s, 1H), 8.20 (s, 2H), 7.97 (dd, J=6.0, 9.2 Hz, 1H), 7.51-7.35 (m, 2H), 7.16 (d, J=2.4 Hz, 1H), 6.91 (d, J=8.8 Hz, 1H), 6.80 (d, J=2.0 Hz, 1H), 6.62 (dd, J=2.0, 8.8 Hz, 1H), 5.28 (dd, J=5.2, 12.8 Hz, 1H), 4.52 (d, J=11.6 Hz, 1H), 4.36-4.22 (m, 4H), 3.95-3.90 (m, 2H), 3.56 (d, J=12.4 Hz, 6H), 3.29 (s, 4H), 2.89 (s, 1H), 2.74-2.54 (m, 4H), 2.41-2.30 (m, 9H), 2.19 (d, J=6.8 Hz, 2H), 2.02-1.94 (m, 1H), 1.82-1.67 (m, 6H), 1.62 (s, 1H), 1.38 (s, 7H), 1.28-1.16 (m, 3H), 0.64 (s, 2H), 0.42 (s, 2H).

Example 30: Synthesis of 3-{5-[4-({4-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperazin-1-yl}methyl)piperidin-1-yl]-3-methyl-2-oxo-2,3-dihydro-1H-1,3-benzodiazol-1-yl}piperidine-2,6-dione (Compound 188)

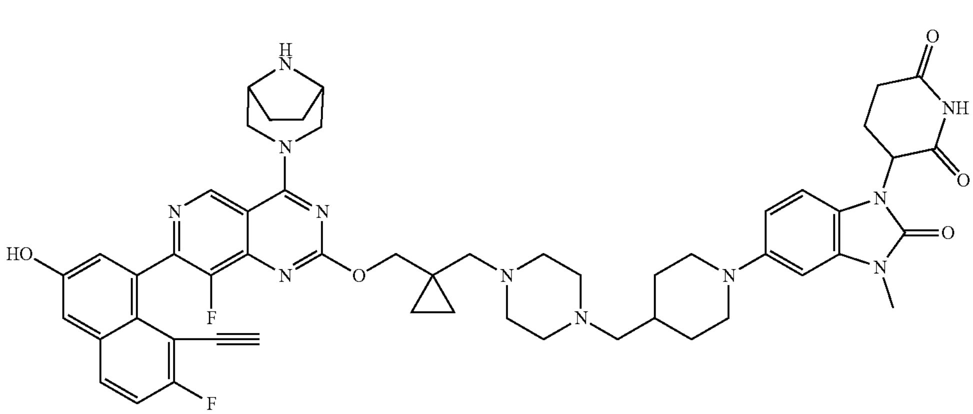 [SMILES: C#Cc1c(F)ccc2cc(O)cc(-c3ncc4c(N5CC6CCC(C5)N6)nc(OCC5(CN6CCN(CC7CCN(c8ccc9c(c8)n(C)c(=O)n9C8CCC(=O)NC8=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 966.7 $[M+H]^+$; $^1H$ NMR (400 MHz, DMSO-$d_6$) δ 11.04 (s, 1H), 9.04 (s, 1H), 8.21 (s, 2H), 7.97 (dd, J=6.0, 9.2 Hz, 1H), 7.46 (t, J=9.2 Hz, 1H), 7.39 (d, J=2.4 Hz, 1H), 7.18 (d, J=2.4 Hz, 1H), 6.91 (d, J=8.4 Hz, 1H), 6.80 (d, J=2.0 Hz, 1H), 6.61 (dd, J=2.0, 8.8 Hz, 1H), 5.27 (dd, J=5.2, 12.8 Hz, 1H), 4.53 (d, J=12.4 Hz, 1H), 4.37-4.27 (m, 3H), 3.93 (s, 1H), 3.69 (s, 5H), 3.61 (d, J=13.2 Hz, 4H), 3.55 (d, J=11.6 Hz, 4H), 3.29 (s, 3H), 2.91-2.83 (m, 1H), 2.70-2.64 (m, 1H), 2.62 (d, J=2.4 Hz, 1H), 2.61-2.55 (m, 2H), 2.36-2.26 (m, 5H), 2.12 (d, J=7.2 Hz, 2H), 2.02-1.94 (m, 1H), 1.81-1.68 (m, 6H), 1.65-1.53 (m, 1H), 1.27-1.15 (m, 2H), 0.64 (s, 2H), 0.41 (s, 2H).

Example 31: Synthesis of 3-{4-chloro-5-[4-({4-[(1-{[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]methyl}cyclopropyl)methyl]piperazin-1-yl}methyl)piperidin-1-yl]-1-oxo-2,3-dihydro-1H-isoindol-2-yl}piperidine-2,6-dione (Compound 186)

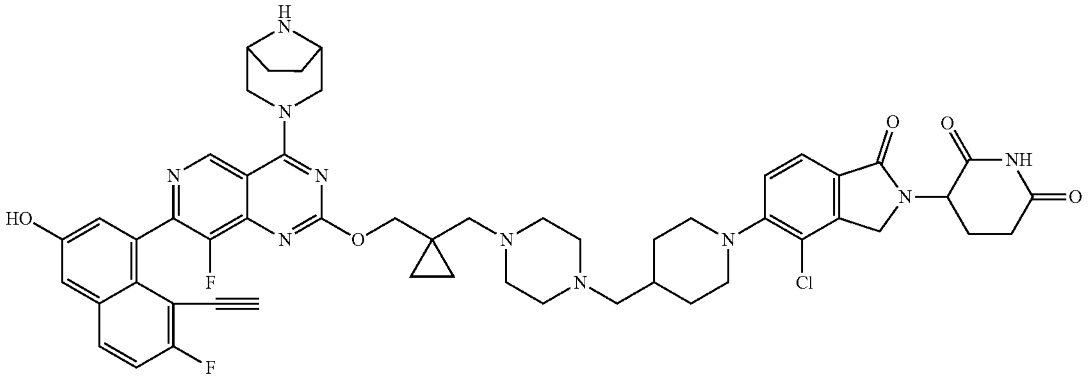 [SMILES: C#Cc1c(F)ccc2cc(O)cc(-c3ncc4c(N5CC6CCC(C5)N6)nc(OCC5(CN6CCN(CC7CCN(c8ccc9c(c8Cl)CN(C8CCC(=O)NC8=O)C9=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 985.6 $[M+H]^+$; $^1H$ NMR (400 MHz, DMSO-$d_6$) δ 10.98 (s, 1H), 9.03 (s, 1H), 8.21 (s, 1H), 7.97 (dd, J=6.0, 9.2 Hz, 1H), 7.63 (d, J=8.4 Hz, 1H), 7.46 (t, J=8.8 Hz, 1H), 7.39 (d, J=2.4 Hz, 1H), 7.29-7.21 (m, 1H), 7.17 (d, J=2.4 Hz, 1H), 5.09 (dd, J=5.2, 13.6 Hz, 1H), 4.56-4.47 (m, 1H), 4.45-4.36 (m, 1H), 4.34-4.20 (m, 4H), 3.94 (s, 1H), 3.71-3.54 (m, 6H), 3.39-3.34 (m, 2H), 2.94-2.85 (m, 1H), 2.75-2.65 (m, 2H), 2.62-2.56 (m, 1H), 2.47-2.22 (m, 10H), 2.18-2.11 (m, 2H), 2.04-1.93 (m, 1H), 1.84-1.75 (m, 2H), 1.74-1.56 (m, 5H), 1.36-1.18 (m, 2H), 0.69-0.58 (m, 2H), 0.47-0.35 (m, 2H).

Example 32: Synthesis of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-1-oxo-2,3-dihydro-1H-isoindol-2-yl}piperidine-2,6-dione (Compound 99)

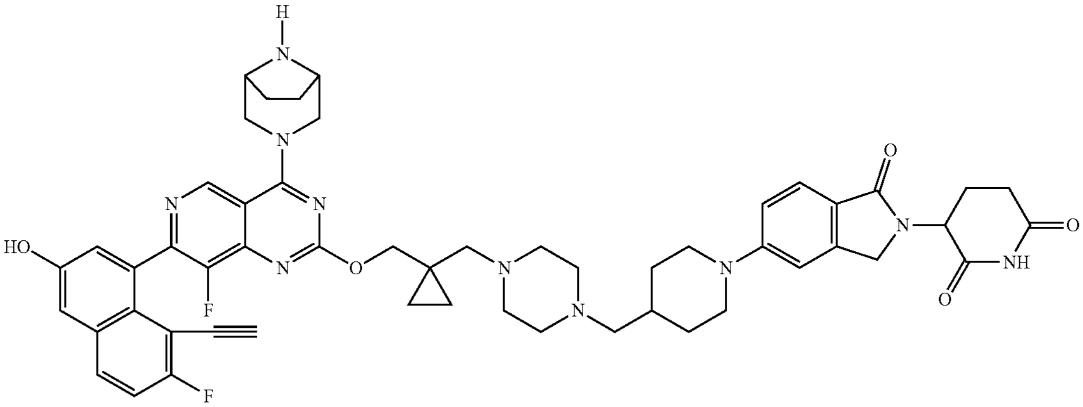 [SMILES: C#Cc1c(F)ccc2cc(O)cc(-c3ncc4c(N5CC6CCC(C5)N6)nc(OCC5(CN6CCN(CC7CCN(c8ccc9c(c8)CN(C8CCC(=O)NC8=O)C9=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 950.4 $[M+H]^+$; $^1H$ NMR (400 MHz, $CD_3OD-d_4$) δ 9.01 (s, 1H), 7.89-7.83 (m, 1H), 7.60 (d, J=8.4 Hz, 1H), 7.36-7.29 (m, 2H), 7.21 (d, J=2.4 Hz, 1H), 7.07-7.02 (m, 2H), 5.13-5.07 (m, 1H), 4.63 (br t, J=13.6 Hz, 3H), 4.51-4.47 (m, 1H), 4.40-4.32 (m, 3H), 3.88 (br d, J=11.6 Hz, 2H), 3.75-3.65 (m, 4H), 3.37 (s, 1H), 3.23-3.13 (m, 2H), 2.91-2.74 (m, 4H), 2.62-2.39 (m, 3H), 2.18-2.07 (m, 2H), 1.90-1.69 (m, 8H), 1.64-1.53 (m, 1H), 1.51-1.40 (m, 1H), 1.29-1.14 (m, 6H), 0.80-0.71 (m, 2H), 0.56 (br s, 2H).

Example 33: Synthesis of 3-{4-chloro-5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperazin-1-yl]-1-oxo-2,3-dihydro-1H-isoindol-2-yl}piperidine-2,6-dione (Compound 187)

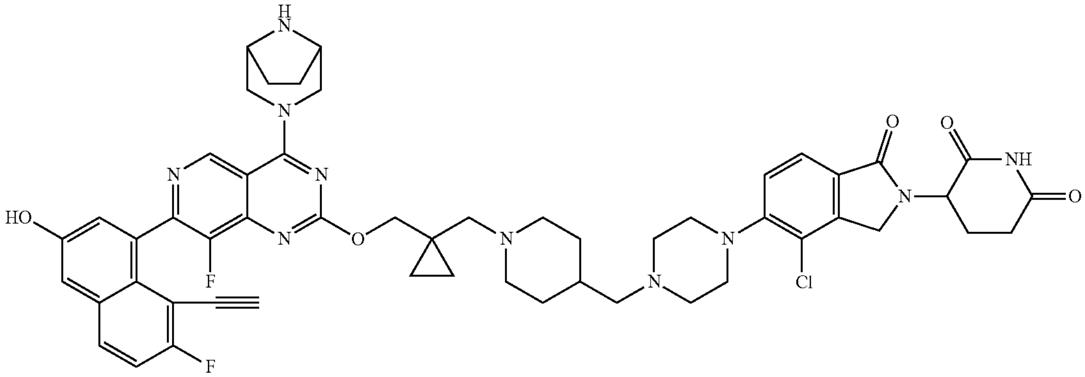

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid 15 salt). LC/MS (ESI) m/z: 985.6 $[M+H]^+$; $^1H$ NMR (400 MHz, DMSO-$d_6$) δ 10.97 (s, 1H), 9.04 (s, 1H), 8.19 (s, 2H), 7.97 (dd, J=6.0, 9.2 Hz, 1H), 7.65 (d, J=8.0 Hz, 1H), 7.46 (t, J=9.2 Hz, 1H), 7.39 (d, J=2.4 Hz, 1H), 7.26 (d, J=8.4 Hz, 1H), 7.17 (d, J=2.4 Hz, 1H), 5.09 (dd, J=5.2, 13.2 Hz, 1H), 4.52 (d, J=12.0 Hz, 1H), 4.41 (d, J=17.6 Hz, 1H), 4.35-4.26 (m, 4H), 3.93 (s, 1H), 3.70-3.65 (m, 4H), 3.62-3.57 (m, 2H), 3.07 (s, 4H), 3.00-2.85 (m, 4H), 2.63-2.56 (m, 1H), 2.48-2.41 (m, 2H), 2.36-2.29 (m, 2H), 2.16 (d, J=7.2 Hz, 2H), 2.03-1.95 (m, 1H), 1.89 (t, J=10.0 Hz, 2H), 1.77-1.63 (m, 6H), 1.56-1.43 (m, 1H), 1.08 (d, J=12.8 Hz, 2H), 0.65 (s, 2H), 0.42 (s, 2H).

Example 34: Synthesis of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperazin-1-yl]-3-methyl-2-oxo-2,3-dihydro-1H-1,3-benzodiazol-1-yl}piperidine-2,6-dione (Compound 189)

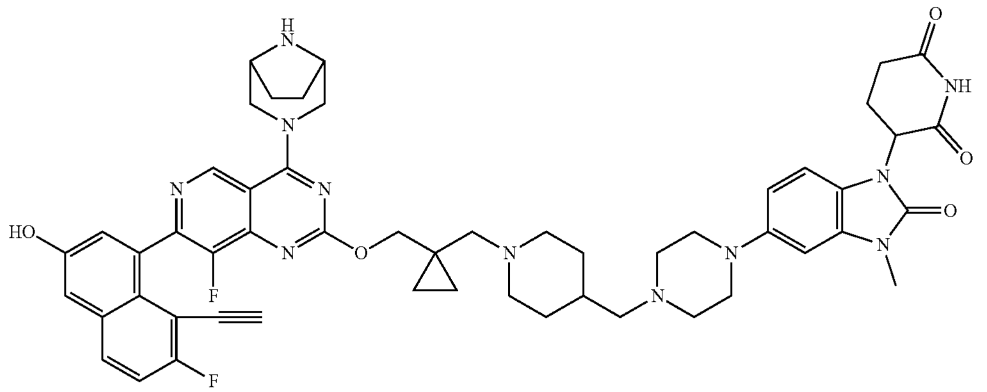 [SMILES: C#Cc1c(F)ccc2cc(O)cc(-c3ncc4c(N5CC6CCC(C5)N6)nc(OCC5(CN6CCC(CN7CCN(c8ccc9c(c8)n(C)c(=O)n9C8CCC(=O)NC8=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 966.6 $[M+H]^+$; $^1H$ NMR (400 MHz, DMSO-$d_6$) δ 11.06 (s, 1H), 9.03 (s, 1H), 8.20 (s, 1H), 7.97 (dd, J=6.0, 9.2 Hz, 1H), 7.46 (t, J=9.6 Hz, 1H), 7.39 (d, J=2.4 Hz, 1H), 7.17 (d, J=2.4 Hz, 1H), 6.96-6.90 (m, 1H), 6.83-6.79 (m, 1H), 6.60 (dd, J=1.6, 8.4 Hz, 1H), 5.28 (dd, J=5.2, 12.4 Hz, 1H), 4.51 (d, J=11.6 Hz, 1H), 4.35-4.23 (m, 3H), 3.93 (s, 1H), 3.70-3.58 (m, 5H), 3.29 (s, 3H), 3.08-3.01 (m, 4H), 2.99-2.92 (m, 2H), 2.90-2.84 (m, 1H), 2.72-2.57 (m, 2H), 2.47-2.43 (m, 4H), 2.34-2.29 (m, 2H), 2.13 (d, J=6.8 Hz, 2H), 2.01-1.94 (m, 1H), 1.92-1.84 (m, 2H), 1.74-1.62 (m, 6H), 1.52-1.44 (m, 1H), 1.12-1.00 (m, 2H), 0.64 (s, 2H), 0.41 (s, 2H).

Example 35: Synthesis of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-2-oxo-3-(propan-2-yl)-2,3-dihydro-1H-1,3-benzodiazol-1-yl}piperidine-2,6-dione (Compound 191)

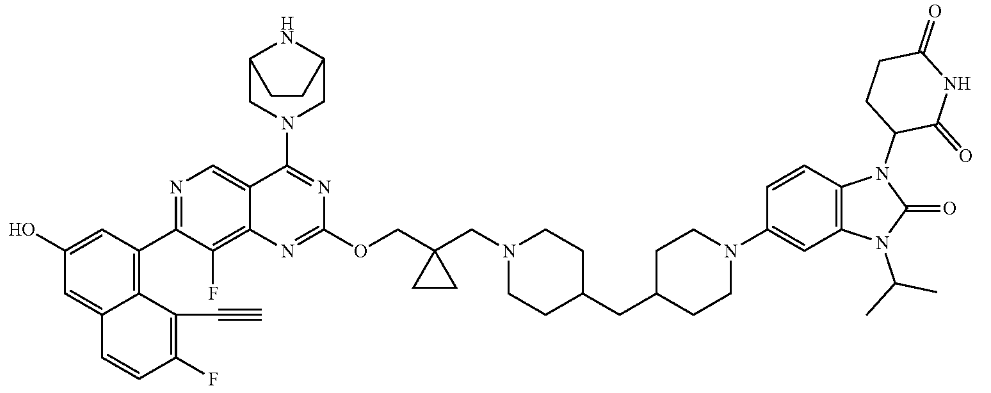 [SMILES: C#Cc1c(F)ccc2cc(O)cc(-c3ncc4c(N5CC6CCC(C5)N6)nc(OCC5(CN6CCC(CC7CCN(c8ccc9c(c8)n(C(C)C)c(=O)n9C8CCC(=O)NC8=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 993.7 $[M+H]^+$; $^1$H NMR (400 MHz, DMSO-$d_6$) δ 11.06 (s, 1H), 10.24 (s, 1H), 9.13 (s, 1H), 8.14 (s, 1H), 8.03-7.95 (m, 1H), 7.47 (t, J=8.8 Hz, 1H), 7.42-7.39 (m, 1H), 7.20-7.15 (m, 1H), 6.95-6.84 (m, 2H), 6.64-6.57 (m, 1H), 5.32-5.21 (m, 1H), 4.71-4.50 (m, 3H), 4.42-4.30 (m, 2H), 4.23-4.15 (m, 2H), 3.90 (s, 1H), 3.89-3.82 (m, 2H), 3.61-3.45 (m, 4H), 2.94-2.83 (m, 2H), 2.70-2.55 (m, 5H), 2.04-1.90 (m, 6H), 1.88-1.79 (m, 2H), 1.73-1.53 (m, 4H), 1.44 (d, J=6.8 Hz, 9H), 1.27-1.07 (m, 5H), 0.87-0.63 (m, 4H).

Example 36: Synthesis of 3-{4-chloro-5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-1-oxo-2,3-dihydro-1H-isoindol-2-yl}piperidine-2,6-dione (Compound 190)

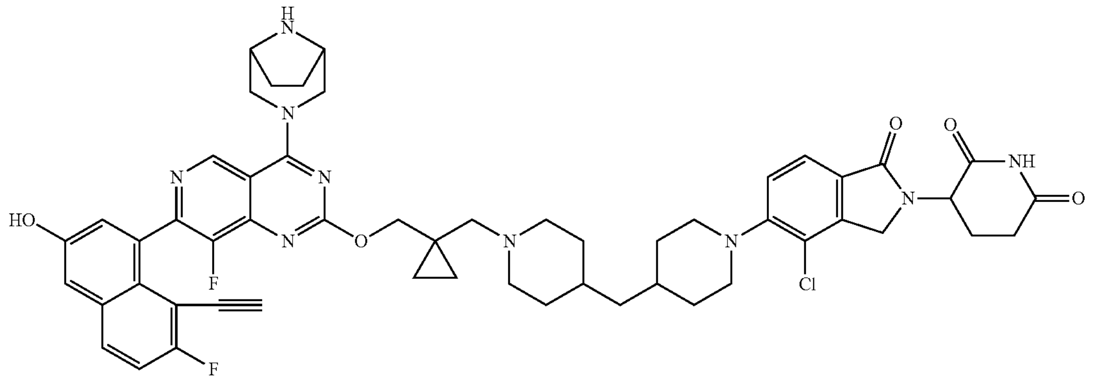

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid). LC/MS (ESI) m/z: 984.6 $[M+H]^+$; $^1H$ NMR (400 MHz, DMSO-$d_6$) δ 10.97 (s, 1H), 10.56-9.64 (m, 1H), 9.07 (s, 1H), 8.15 (s, 1H), 7.98 (dd, J=6.0, 9.2 Hz, 1H), 7.64 (d, J=8.0 Hz, 1H), 7.46 (t, J=9.2 Hz, 1H), 7.40 (d, J=2.4 Hz, 1H), 7.24 (d, J=8.4 Hz, 1H), 7.18 (d, J=2.4 Hz, 1H), 5.09 (dd, J=5.2, 13.2 Hz, 1H), 4.59 (d, J=12.4 Hz, 1H), 4.45-4.36 (m, 2H), 4.33-4.20 (m, 3H), 3.93 (s, 3H), 3.76 (dd, J=13.2, 17.6 Hz, 2H), 3.13-3.02 (m, 3H), 2.97-2.83 (m, 2H), 2.74-2.66 (m, 2H), 2.63-2.56 (m, 1H), 2.49-2.42 (m, 3H), 2.13-1.94 (m, 3H), 1.85 (s, 4H), 1.76-1.62 (m, 4H), 1.55-1.37 (m, 2H), 1.37-1.21 (m, 3H), 1.20-1.06 (m, 4H), 0.69 (s, 2H), 0.49 (s, 2H).

Example 37: Synthesis of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-4-fluoro-1-oxo-2,3-dihydro-1H-isoindol-2-yl}piperidine-2,6-dione (Compound 192)

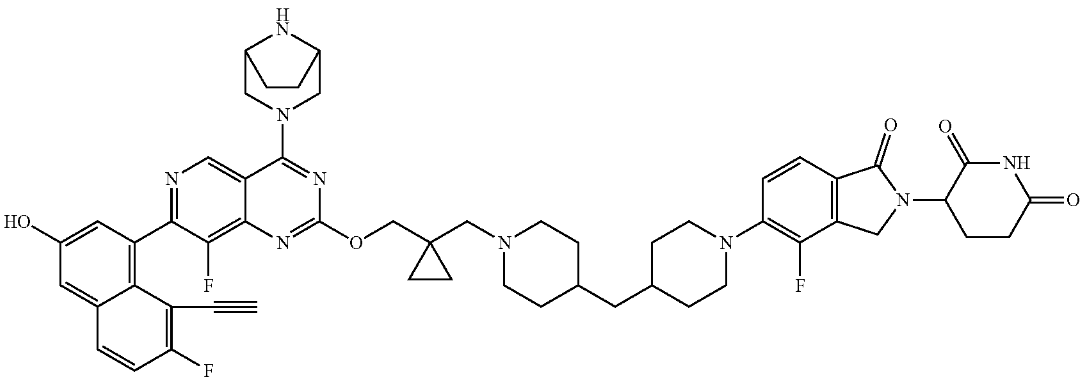 [SMILES: C#Cc1c(F)ccc2cc(O)cc(-c3ncc4c(N5CC6CCC(C5)N6)nc(OCC5(CN6CCC(CC7CCN(c8ccc9c(c8F)CN(C8CCC(=O)NC8=O)C9=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 968.7 $[M+H]^+$; $^1H$ NMR (400 MHz, DMSO-$d_6$) δ 10.97 (s, 1H), 9.04 (s, 1H), 8.19 (s, 2H), 7.97 (dd, J=6.0, 9.2 Hz, 1H), 7.49-7.42 (m, 2H), 7.39 (d, J=2.4 Hz, 1H), 7.19-7.10 (m, 2H), 5.07 (dd, J=5.2, 13.2 Hz, 1H), 4.54-4.44 (m, 2H), 4.34-4.26 (m, 4H), 3.95-3.91 (m, 1H), 3.66 (s, 3H), 3.59 (d, J=12.4 Hz, 2H), 3.45 (s, 3H), 3.00-2.88 (m, 4H), 2.77-2.70 (m, 2H), 2.32 (s, 2H), 2.00-1.93 (m, 1H), 1.91-1.83 (m, 2H), 1.76-1.67 (m, 6H), 1.60 (d, J=10.8 Hz, 2H), 1.51-1.44 (m, 1H), 1.36-1.18 (m, 4H), 1.16-1.04 (m, 4H), 0.67-0.59 (m, 2H), 0.41 (s, 2H).

Example 38: Synthesis of 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-4-fluoro-1-oxo-isoindolin-2-yl]piperidine-2,6-dione (Compound 194)

Step 1: Preparation of tert-butyl 4-[(2,6-dibenzyloxy-4-pyridyl)methyl]piperidine-1-carboxylate

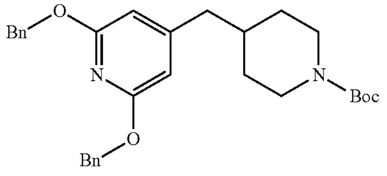 [SMILES: CC(C)(C)OC(=O)N1CCC(Cc2cc(OCc3ccccc3)nc(OCc3ccccc3)c2)CC1]

A mixture of tert-butyl 4-methylenepiperidine-1-carboxylate (12.5 g, 63 mmol) and 9-borabicyclo[3.3.1]nonane (0.5 M, 189 mL) was stirred at 85° C. for 2 h. The mixture was cooled to 25° C., and 2,6-dibenzyloxy-4-iodo-pyridine (34.0 g, 81 mmol), potassium carbonate (26.2 g, 189 mmol), and Pd(dppf)$Cl_2$ (5.16 g, 6 mmol) in water (250 mL) and THF (500 mL) were then added. The resulting mixture was stirred at 75° C. for 15 h under nitrogen atmosphere. The reaction was cooled to room temperature and extracted with ethyl acetate (3×200 mL). The combined organic extract was washed with brine (3×500 mL), dried over sodium sulfate, filtered, and concentrated under reduced pressure. The residue was suspended in ethyl acetate/petroleum ether (400 mL, V/V=1/1), filtered, and concentrated under reduced pressure. The residue was purified by flash column chromatography on silica gel (0-8% of THF in petroleum ether) to afford the title compound (61.7 g, 100%) as a black brown oil. LC/MS (ESI) m/z: 489.4 $[M+H]^+$.

Step 2: Preparation of tert-butyl 4-[(2,6-dioxo-4-piperidyl)methyl]piperidine-1-carboxylate

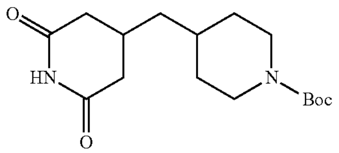 [SMILES: CC(C)(C)OC(=O)N1CCC(CC2CC(=O)NC(=O)C2)CC1]

To tert-butyl 4-[(2,6-dibenzyloxy-4-pyridyl)methyl]piperidine-1-carboxylate (57.7 g, 118 mmol) in ethyl acetate (2000 mL) was added 10% palladium on carbon (12.0 g, 11 mmol) under argon atmosphere, and the suspension was degassed under vacuum and purged with hydrogen several times. The mixture was stirred under hydrogen (30 psi) at 50° C. for 16 h. The mixture was filtered, washed with ethyl acetate, and the filtrate was concentrated under reduced pressure to afford the title compound (36.6 g, crude) as a white solid. LC/MS (ESI) m/z: 333.1 $[M+Na]^+$; $^1H$ NMR (400 MHz, $CDCl_3$) δ 8.24 (br s, 1H), 4.10 (m, 2H), 2.75-2.62 (m, 4H), 2.30-2.24 (m, 2H), 1.92-1.81 (m, 1H), 1.62 (br d, J=12.4 Hz, 3H), 1.45 (s, 9H), 1.33 (br t, J=6.4 Hz, 2H), 1.09 (br dd, J=4.0, 12.0 Hz, 2H).

Step 3: Preparation of tert-butyl 4-[[1-[(1S)-2-benzyloxy-1-methyl-ethyl]-2,6-dioxo-4-piperidyl]methyl]piperidine-1-carboxylate

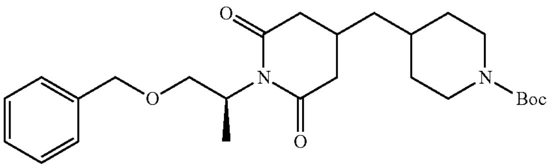 [SMILES: C[C@@H](COCc1ccccc1)N1C(=O)CC(CC2CCN(C(=O)OC(C)(C)C)CC2)CC1=O]

To a mixture of tert-butyl 4-[(2,6-dioxo-4-piperidyl)methyl]piperidine-1-carboxylate (13.6 g, 44 mmol), (2R)-1-benzyloxypropan-2-ol (9.47 g, 57 mmol), and $PPh_3$ (17.24 g, 66 mmol) in THF (200 mL) was added DIAD (12.74 mL, 66 mmol) at 0° C. under nitrogen atmosphere, and the mixture was stirred at 70° C. for 16 h. The reaction mixture was concentrated under reduced pressure. The residue was purified by flash column chromatography on silica gel (0-10% THF in petroleum ether over 40 min) to afford the title compound (18.5 g, 92%) as a colorless oil. LC/MS (ESI) m/z: 459.1 $[M+H]^+$.

Step 4: Preparation of tert-butyl 4-[[1-[(1S)-2-benzyloxy-1-methyl-ethyl]-4-piperidyl]methyl]piperidine-1-carboxylate

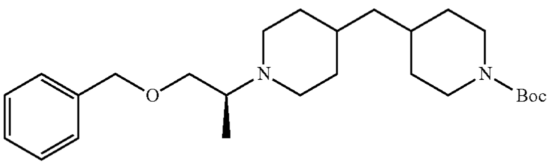 [SMILES: C[C@@H](COCc1ccccc1)N1CCC(CC2CCN(C(=O)OC(C)(C)C)CC2)CC1]

To tert-butyl 4-[[1-[(1S)-2-benzyloxy-1-methyl-ethyl]-2,6-dioxo-4-piperidyl]methyl]piperidine-1-carboxylate (8.0 g, 17 mmol) in THF (100 mL) at 0° C. was added $BH_3$—$Me_2S$ (10 M, 17.4 mL) dropwise, and the resulting suspension was stirred at 70° C. for 1 h. The reaction mixture was cooled to room temperature and quenched with water (25 mL) at 0° C. The resulting mixture was extracted with ethyl acetate (3×50 mL), and the combined organic extract was washed with brine (2×50 mL), dried over sodium sulfate, filtered, and concentrated under reduced pressure. The residue was dissolved DMF (60 mL), Oxone (21.4 g, 35 mmol) was added, and the resulting suspension was stirred at 25° C. for 3 h. The mixture was filtered and washed with ethyl acetate (100 mL). The filtrate was diluted with water (150 mL) and adjusted the pH to 8 by adding solid sodium bicarbonate. The mixture was extracted with ethyl acetate (3×100 mL), and the combined organic extract was washed with saturated sodium sulfite solution (2×50 mL), water (3×50 mL), and brine (100 mL), then dried over sodium sulfate, filtered, and concentrated under reduced pressure. The residue was purified by flash column chromatography on silica gel (0 to 4% methanol in dichloromethane) to afford the title compound (2.8 g, 37%) as a colorless oil. LC/MS (ESI) m/z: 431.4 $[M+H]^+$.

Step 5: Preparation of 1-[(1S)-2-benzyloxy-1-methyl-ethyl]-4-(4-piperidylmethyl)piperidine

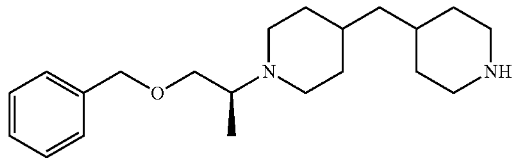 [SMILES: C[C@@H](COCc1ccccc1)N1CCC(CC2CCNCC2)CC1]

To a mixture of tert-butyl 4-[[1-[(1S)-2-benzyloxy-1-methyl-ethyl]-4-piperidyl]methyl]piperidine-1-carboxylate (2.8 g, 6 mmol) in dichloromethane (20 mL) was added 4 M HCl in 1,4-dioxane (16 mL), and the reaction mixture was stirred at 20° C. for 0.5 h. The mixture was concentrated under reduced pressure to afford the title compound (2.39 g, crude, HCl salt) as a colorless oil. LC/MS (ESI) m/z: 331.3 $[M+H]^+$.

Step 6: Preparation of 2-trimethylsilylethyl 4-[[1-[(1S)-2-benzyloxy-1-methyl-ethyl]-4-piperidyl]methyl]piperidine-1-carboxylate

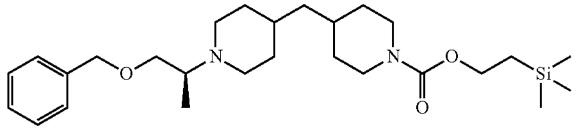 [SMILES: C[C@@H](COCc1ccccc1)N1CCC(CC2CCN(C(=O)OCC[Si](C)(C)C)CC2)CC1]

To a solution of 1-[(1S)-2-benzyloxy-1-methyl-ethyl]-4-(4-piperidylmethyl)piperidine (2.39 g, 6 mmol, HCl) in dichloromethane (30 mL) at 0° C. were added $Et_3N$ (9 mL, 65 mmol) and Teoc-OSu (1.69 g, 6 mmol), and the reaction mixture was allowed to warmed to 20° C. and stirred for 16 h. The mixture was diluted with water (30 mL) and extracted with dichloromethane (2×30 mL). The combined organic extract was washed with saturated sodium bicarbonate solution (10 mL) followed by brine (10 mL), dried over sodium sulfate, filtered, and concentrated under reduced pressure. The residue was purified by flash column chromatography on silica gel (0 to 3% methanol in dichloromethane) to afford the title compound (2.6 g, 84%) as a yellow oil. LC/MS (ESI) m/z: 475.3 $[M+H]^+$, $^1H$ NMR (400 MHz, $CDCl_3$) δ 7.40-7.28 (m, 5H), 4.53 (s, 2H), 4.21-4.06 (m, 4H), 3.58 (dd, J=5.6, 9.6 Hz, 1H), 3.38 (br d, J=2.4 Hz, 1H), 2.93-2.79 (m, 3H), 2.76-2.66 (m, 2H), 2.26 (br t, J=10.8 Hz, 2H), 1.64 (br d, J=12.4 Hz, 4H), 1.50 (br s, 1H), 1.27 (d, J=6.4 Hz, 3H), 1.17-1.12 (m, 2H), 1.10-0.98 (m, 7H), 0.07-0.02 (m, 9H).

Step 7: Preparation of 2-trimethylsilylethyl 4-[[1-[(1S)-2-hydroxy-1-methyl-ethyl]-4-piperidyl]methyl]piperidine-1-carboxylate

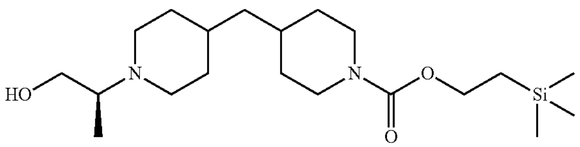 [SMILES: C[C@@H](CO)N1CCC(CC2CCN(C(=O)OCC[Si](C)(C)C)CC2)CC1]

To a solution of 2-trimethylsilylethyl 4-[[1-[(1S)-2-benzyloxy-1-methyl-ethyl]-4-piperidyl]methyl]piperidine-1-carboxylate (2.6 g, 5.5 mmol) in isopropanol (500 mL) was added 10% $Pd(OH)_2$ on carbon (1 g). The mixture was degassed under vacuum and purged with hydrogen several times, then stirred at 60° C. under hydrogen (50 psi) for 16 h. The reaction mixture was filtered, and the filtrate was concentrated under reduced pressure to afford the title compound (1.95 g, 93%) as a colorless oil. LC/MS (ESI) m/z: 385.2 $[M+H]^+$.

Step 8: Preparation of tert-butyl N-(2-chloro-3-fluoro-4-pyridyl)carbamate

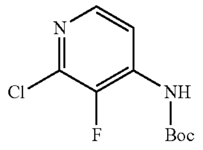

To a solution of 2-chloro-3-fluoro-pyridine-4-carboxylic acid (40.0 g, 228 mmol) in toluene (200 mL) and tert-butyl alcohol (262 mL, 2.73 mol) were added 4 A molecular sieves (68 g) and triethylamine (95.0 mL, 684 mmol), and the reaction mixture was stirred at 110° C. under nitrogen for 30 min. The reaction mixture was cooled to 20° C., diphenylphosporyl azide (DPPA) (74.0 mL, 342 mmol) was added, and the resulting mixture was stirred at 110° C. under nitrogen for 16 h. The reaction mixture was filtered, and the filtrate was poured into water (300 mL) and extracted with ethyl acetate (3×200 mL). The combined organic extract was washed with brine (50 mL), dried over anhydrous sodium sulfate, filtered, and concentrated under reduced pressure. The residue was purified by flash column chromatography on silica gel (0 to 8% ethyl acetate in petroleum ether over 15 min) to afford the title compound (108.8 g, 93%) as a yellow oil. LC/MS (ESI) m/z: 247.0 $[M+H]^+$.

Step 9: Preparation of 2-chloro-3-fluoro-pyridin-4-amine

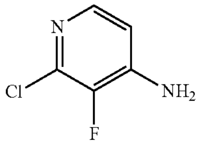

To a solution of tert-butyl N-(2-chloro-3-fluoro-4-pyridyl)carbamate (108.8 g, 422 mmol) in acetonitrile (120 mL) was added 4 M HCl in 1,4-dioxane (250 mL), and the mixture was stirred at 25° C. for 16 h. The reaction mixture was concentrated under reduced pressure, and the residue was diluted with water (100 mL) and saturated sodium bicarbonate solution to adjust the pH to 8-9. The mixture was then extracted with ethyl acetate (2×200 mL), and the combined organic extract was washed with brine (50 mL), dried over anhydrous sodium sulfate, filtered, and concentrated in vacuo to afford the title compound (58.6 g, 85%) as a white solid. LC/MS (ESI) m/z: 147.2 $[M+H]^+$.

Step 10: Preparation of 2-chloro-3-fluoro-5-iodo-pyridin-4-amine

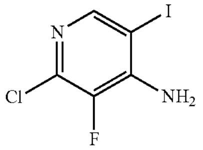

To a solution of 2-chloro-3-fluoro-pyridin-4-amine (58.6 g, 376 mmol) in acetonitrile (800 mL) was added NIS (108 g, 480 mmol) and TsOH (3.4 g, 20 mmol), and the mixture was stirred at 70° C. for 16 h under nitrogen atmosphere. The reaction mixture was diluted with saturated $Na_2S_2O_3$ solution (800 mL) and extracted with ethyl acetate (3×500 mL). The combined organic extract was washed with saturated sodium bicarbonate solution (3×500 mL) followed by brine (3×500 mL), dried over anhydrous sodium sulfate, filtered, and concentrated under reduced pressure to afford the title compound (110 g, 99%) as a yellow solid. LC/MS (ESI) m/z: 272.9 $[M+H]^+$.

Step 11: Preparation of ethyl 4-amino-6-chloro-5-fluoro-pyridine-3-carboxylate

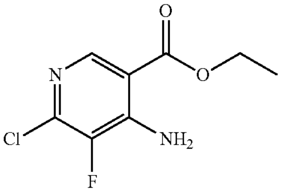

To a solution of 2-chloro-3-fluoro-5-iodo-pyridin-4-amine (108.8 g, 395 mmol) in ethanol (1000 mL) were added triethylamine (200 mL, 1.44 mol) and $Pd(PPh_3)_2Cl_2$ (14.0 g, 20 mmol). The resulting mixture was degassed under vacuum and purged with CO several times, then stirred at 80° C. under CO (15 psi) for 48 h. The reaction mixture was concentrated under reduced pressure and the suspension was filtered, washing with MTBE (2×300 mL). The filtrate was concentrated under reduced pressure to afford ethyl 4-amino-6-chloro-5-fluoro-pyridine-3-carboxylate (63.5 g, 60%) as a gray solid. LC/MS (ESI) m/z: 219.0 $[M+H]^+$.

Step 12: Preparation of 4-amino-6-chloro-5-fluoro-pyridine-3-carboxylic acid

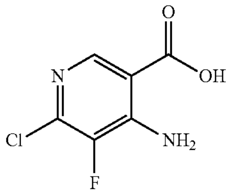 [SMILES: Nc1c(C(=O)O)cnc(Cl)c1F]

To a stirred solution of ethyl 4-amino-6-chloro-5-fluoro-pyridine-3-carboxylate (20.0 g, 91 mmol) in THF (180 mL) was added sodium hydroxide (14.6 g, 366 mmol) in water (90 mL), and the reaction mixture was stirred at 20° C. for 16 h. The reaction mixture was concentrated under reduced pressure, and the residue was diluted with 2 N aqueous HCl solution to adjust the pH to 2. The resultant suspension was filtered, and the filter cake was dissolved in ethyl acetate/THF (300 mL, v/v=2/1), dried over anhydrous sodium sulfate, filtered, and concentrated under reduced pressure to afford the title compound (17.1 g, crude) as a gray solid. LC/MS (ESI) m/z: 190.9 $[M+H]^+$.

Step 13: Preparation of 7-chloro-8-fluoro-2-thioxo-1H-pyrido[4,3-d]pyrimidin-4-one

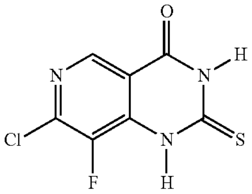 [SMILES: O=c1[nH]c(=S)[nH]c2c(F)c(Cl)ncc12]

A mixture of 4-amino-6-chloro-5-fluoro-pyridine-3-carboxylic acid (17.1 g, 90 mmol) in $POCl_3$ (167 mL, 1.8 mol) was stirred at 90° C. for 2 h. The mixture was concentrated under reduced pressure, and the resulting residue was dissolved in THF (150 mL). $NH_4SCN$ (13.7 mL, 179 mmol) in THF (150 mL) was then added, and the reaction mixture was stirred at 35° C. under nitrogen for 24 h. The reaction was diluted with water (400 mL) and extracted with ethyl acetate (3×200 mL). The combined organic extract was washed with brine (3×300 mL), dried over anhydrous sodium sulfate, filtered, and concentrated under reduced pressure. The residue was triturated with ethyl acetate/petroleum ether (50 mL, v/v=1/1) to afford the title compound (12.14 g, 58%) as a yellow solid. LC/MS (ESI) m/z: 231.8 $[M+H]^+$.

Step 14: Preparation of 7-chloro-8-fluoro-2-methylsulfanyl-3H-pyrido[4,3-d]pyrimidin-4-one

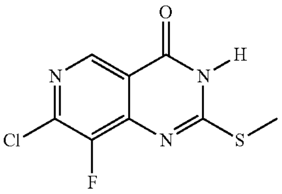

To a solution of 7-chloro-8-fluoro-2-thioxo-1H-pyrido[4,3-d]pyrimidin-4-one (12.14 g, 52 mmol) in DMF (120 mL) was added NaOMe (2.83 g, 52 mmol), and the reaction mixture was stirred at 20° C. under nitrogen for 10 min. $CH_3I$ (3.3 mL, 52 mmol) was then added slowly, and the mixture was stirred at 20° C. under nitrogen for 2 h. The reaction mixture was poured into ice water (200 mL) and filtered, washed the filter cake with ice water (3×80 mL) and dried to afford the title compound (11.3 g, 88%) as a yellow solid. LC/MS (ESI) m/z: 245.8 $[M+H]^+$.

Step 15: Preparation of 4,7-dichloro-8-fluoro-2-methylsulfanyl-pyrido[4,3-d]pyrimidine

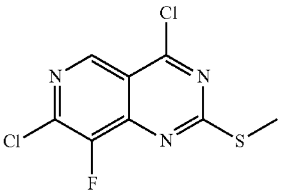

To 7-chloro-8-fluoro-2-methylsulfanyl-3H-pyrido[4,3-d]pyrimidin-4-one (5.0 g, 20 mmol) in toluene (50 mL) were added DIEA (7.1 mL, 41 mmol) and $POCl_3$ (7.6 mL, 81 mmol), and the reaction mixture was stirred at 90° C. under nitrogen for 2 h. The reaction mixture was concentrated under reduced pressure to afford the title compound (5.35 g, crude) as a brown solid. LC/MS (ESI) m/z: 263.8 $[M+H]^+$.

Step 16: Preparation of tert-butyl 3-(7-chloro-8-fluoro-2-methylsulfanyl-pyrido[4,3-d]pyrimidin-4-yl)-3,8-diazabicyclo[3.2.1]octane-8-carboxylate

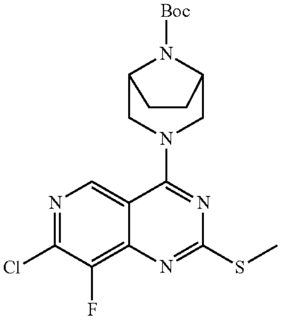 [SMILES: CSc1nc(N2CC3CCC(C2)N3C(=O)OC(C)(C)C)c2cnc(Cl)c(F)c2n1]

To 4,7-dichloro-8-fluoro-2-methylsulfanyl-pyrido[4,3-d]pyrimidine (5.35 g, 20 mmol) in DCM (50 mL) at −40° C. were added DIEA (17.6 mL, 101 mmol) and tert-butyl (1S,5R)-3,8-diazabicyclo[3.2.1]octane-8-carboxylate (4.30 g, 20 mmol) in DCM (50 mL), and the reaction mixture was stirred at −40° C. under nitrogen for 0.5 h. The reaction was poured into water (60 mL) and the mixture was extracted with DCM (2×60 mL). The combined organic extract was dried over anhydrous sodium sulfate, filtered, and concentrated under reduced pressure. The residue was purified by flash column chromatography on silica gel (0 to 25% ethyl acetate in petroleum ether) to afford the title compound (7.14 g, 80%) as a yellow solid. LC/MS (ESI) m/z: 440.0 [M+H]$^+$.

Step 17: Preparation of tert-butyl 3-[8-fluoro-7-[7-fluoro-3-(methoxymethoxy)-8-(2-triisopropylsilyl-ethynyl)-1-naphthyl]-2-methylthio-pyrido[4,3-d]pyrimidin-4-yl]-3,8-diazabicyclo[3.2.1]octane-8-carboxylate

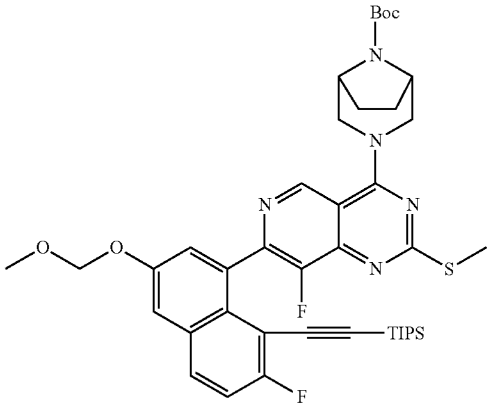

To a mixture of tert-butyl 3-(7-chloro-8-fluoro-2-methylsulfanyl-pyrido[4,3-d]pyrimidin-4-yl)-3,8-diazabicyclo[3.2.1]octane-8-carboxylate (1.6 g, 3.6 mmol) and 2-[2-fluoro-6-(methoxymethoxy)-8-(4,4,5,5-tetramethyl-1,3,2-dioxaborolan-2-yl)-1-naphthyl]ethynyl-triisopropyl-silane (2.2 g, 4.3 mmol) in 1,4-dioxane (60 mL) and water (12 mL) were added $K_3PO_4$ (2.3 g, 11 mmol) and (2'-amino-[1,1'-biphenyl]-2-yl)palladium(II) bis(1-adamantyl)-butyl-phosphaneylmethanesulfonate (521 mg, 0.7 mmol) under nitrogen atmosphere, and the reaction mixture was stirred at 90° C. for 15 h under nitrogen atmosphere. The reaction was cooled to room temperature and filtered, and the filtrate was dried over anhydrous sodium sulfate, filtered, and concentrated. The resulting residue was purified by flash column chromatography on silica gel (0 to 6% then up to 10% tetrahydrofuran in petroleum ether) to afford the title compound (2.80 g, 99%) as a yellow solid. LC/MS (ESI) m/z: 790.2 [M+H]$^+$.

Step 18: Preparation of tert-butyl 3-[8-fluoro-7-[7-fluoro-3-(methoxymethoxy)-8-(2-triisopropylsilyl-ethynyl)-1-naphthyl]-2-methylsulfonyl-pyrido[4,3-d]pyrimidin-4-yl]-3,8-diazabicyclo[3.2.1]octane-8-carboxylate

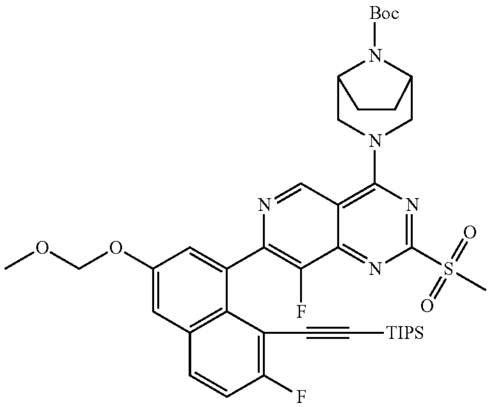

To a mixture of tert-butyl 3-[8-fluoro-7-[7-fluoro-3-(methoxymethoxy)-8-(2-triisopropylsilylethynyl)-1-naphthyl]-2-methylthio-pyrido[4,3-d]pyrimidin-4-yl]-3,8-diazabicyclo[3.2.1]octane-8-carboxylate (2.8 g, 3.5 mmol) and 4 A molecular sieves (3.0 g) in DMF (30 mL) at 40° C. was added oxone (6.6 g, 11 mmol), and the reaction mixture was stirred at 40° C. for 16 h. The mixture was diluted with ethyl acetate (100 mL) and filtered, and the filtrate was washed with saturated sodium bicarbonate solution (20 mL), water (2×30 mL), brine (30 mL), then dried over anhydrous sodium sulfate, filtered, and concentrated to afford the title compound (2.5 g, 70%) as a yellow solid. LC/MS (ESI) m/z: 822.1 [M+H]$^+$.

Step 19: Preparation of tert-butyl 3-[8-fluoro-7-[7-fluoro-3-(methoxymethoxy)-8-(2-triisopropylsilyl-ethynyl)-1-naphthyl]-2-[(2S)-2-[4-[[1-(2-trimethylsilylethoxycarbonyl)-4-piperidyl]methyl]-1-piperidyl]propoxy]pyrido[4,3-d]pyrimidin-4-yl]-3,8-diazabicyclo[3.2.1]octane-8-carboxylate

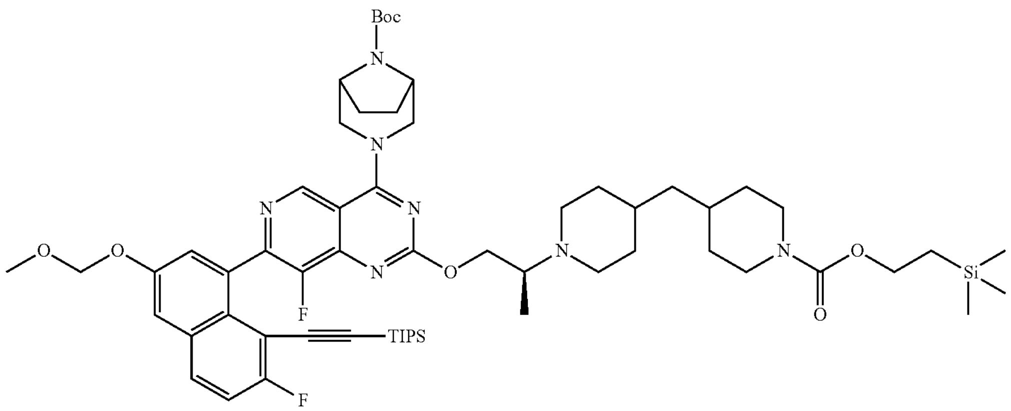

To a solution of tert-butyl 3-[8-fluoro-7-[7-fluoro-3-(methoxymethoxy)-8-(2-triisopropylsilylethynyl)-1-naphthyl]-2-methylsulfonyl-pyrido[4,3-d]pyrimidin-4-yl]-3,8-diazabicyclo[3.2.1]octane-8-carboxylate (2 g, 2 mmol) and 2-trimethylsilylethyl 4-[[1-[(1S)-2-hydroxy-1-methyl-ethyl]-4-piperidyl]methyl]piperidine-1-carboxylate (936 mg, 2.4 mmol) in 1,4-dioxane (30 mL) was added 4 A molecular sieves (4 g), and the mixture was stirred at 40° C. for 20 min under nitrogen atmosphere. t-BuONa (2 M, 3.0 mL) was then added at 0° C., and the mixture was stirred at 0° C. for 40 min. The reaction was quenched with saturated ammonium chloride solution (50 mL), filtered, and extracted with ethyl acetate (3×40 mL). The combined organic extracts were washed with brine (30 mL), dried over sodium sulfate, filtered, and concentrated under reduced pressure. The residue was purified by flash column chromatography on silica gel (0 to 3% methanol in dichloromethane) to afford the title compound (2.1 g, 77%) as a yellow solid. LC/MS (ESI) m/z: 1127.3 $[M+H]^+$.

Step 20: Preparation of tert-butyl 3-[7-[8-ethynyl-7-fluoro-3-(methoxymethoxy)-1-naphthyl]-8-fluoro-2-[(2S)-2-[4-(4-piperidylmethyl)-1-piperidyl]propoxy]pyrido[4,3-d]pyrimidin-4-yl]-3,8-diazabicyclo[3.2.1]octane-8-carboxylate

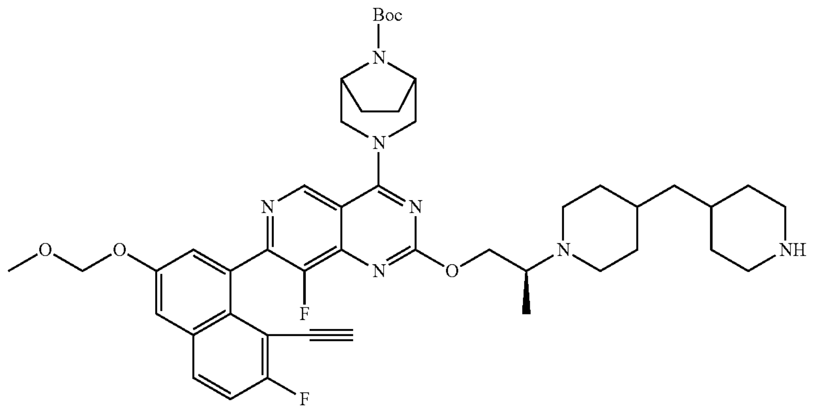 [SMILES: C#Cc1c(F)ccc2cc(OCOC)cc(-c3ncc4c(N5CC6CCC(C5)N6C(=O)OC(C)(C)C)nc(OC[C@H](C)N5CCC(CC6CCNCC6)CC5)nc4c3F)c12]

To a solution of tert-butyl 3-[8-fluoro-7-[7-fluoro-3-(methoxymethoxy)-8-(2-triisopropylsilylethynyl)-1-naphthyl]-2-[(2S)-2-[4-[[1-(2-trimethylsilylethoxycarbonyl)-4-piperidyl]methyl]-1-piperidyl]propoxy]pyrido[4,3-d]pyrimidin-4-yl]-3,8-diazabicyclo[3.2.1]octane-8-carboxylate (2.1 g, 2 mmol) in DMF (20 mL) was added cesium fluoride (2.8 g, 19 mmol), and the reaction mixture was stirred at 60° C. for 6 h. The mixture was filtered and washed with ethyl acetate (50 mL). The filtrate was diluted with water (50 mL) and extracted with ethyl acetate (2×40 mL). The combined organic extract was washed with water (3×30 mL) followed by brine (30 mL), dried over anhydrous sodium sulfate, filtered, and concentrated under reduced pressure to afford the title compound (1.5 g, 97%) as a yellow solid. LC/MS (ESI) m/z: 826.4 $[M+H]^+$.

Step 21: Preparation of tert-butyl 3-[2-[(2S)-2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

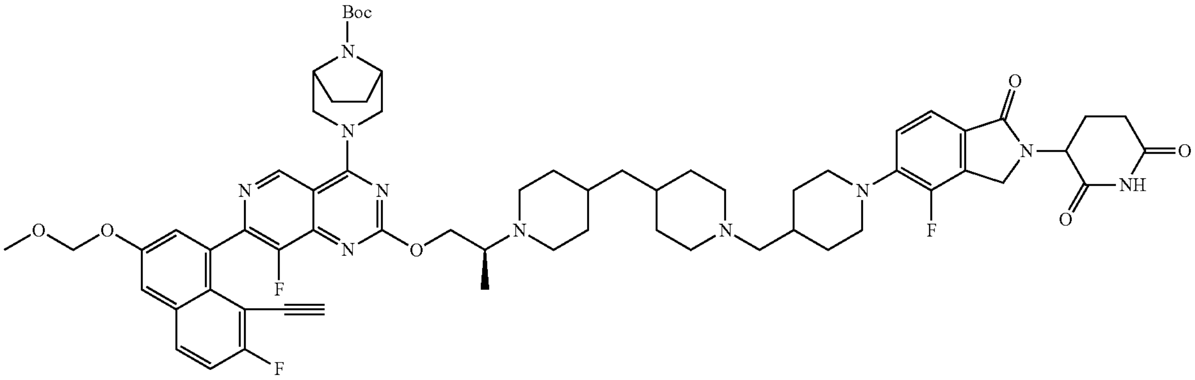 [SMILES: C#Cc1c(F)ccc2cc(OCOC)cc(-c3ncc4c(N5CC6CCC(C5)N6C(=O)OC(C)(C)C)nc(OC[C@H](C)N5CCC(CC6CCN(CC7CCN(c8ccc9c(c8F)CN(C8CCC(=O)NC8=O)C9=O)CC7)CC6)CC5)nc4c3F)c12]

To a solution of tert-butyl 3-[7-[8-ethynyl-7-fluoro-3-(methoxymethoxy)-1-naphthyl]-8-fluoro-2-[(2S)-2-[4-(4-piperidylmethyl)-1-piperidyl]propoxy]pyrido[4,3-d]pyrimidin-4-yl]-3,8-diazabicyclo[3.2.1]octane-8-carboxylate (500 mg, 0.6 mmol) and 1-[2-(2,6-dioxo-3-piperidyl)-4-fluoro-1-oxo-isoindolin-5-yl]piperidine-4-carbaldehyde (452 mg, 1.2 mmol) in dichloromethane (5 mL) and isopropanol (5 mL) were added acetic acid (0.14 mL, 2.4 mmol) and 2-methylpyridine borane (259 mg, 2.4 mmol), and the mixture was stirred at 20° C. for 16 h. The mixture was filtered and concentrated under reduced pressure. The residue was purified by flash column chromatography on silica gel (0 to 10% methanol in dichloromethane) to afford the title compound (300 mg, 42%) as a yellow solid. LC/MS (ESI) m/z: 1183.8 $[M+H]^+$.

Step 22: Preparation of 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-4-fluoro-1-oxo-isoindolin-2-yl]piperidine-2,6-dione

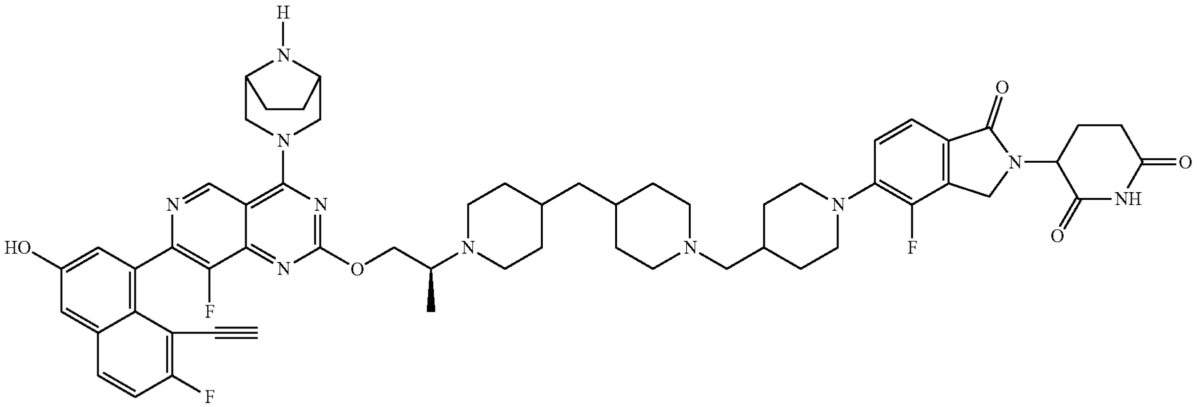 [SMILES: C#Cc1c(F)ccc2cc(O)cc(-c3ncc4c(N5CC6CCC(C5)N6)nc(OC[C@H](C)N5CCC(CC6CCN(CC7CCN(c8ccc9c(c8F)CN(C8CCC(=O)NC8=O)C9=O)CC7)CC6)CC5)nc4c3F)c12]

To tert-butyl 3-[2-[(2S)-2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (300 mg, 0.25 mmol) in dichloromethane (2 mL) was added 4 M HCl in 1,4-dioxane (1.90 mL), and the reaction mixture was stirred at 25° C. for 0.5 h. The mixture was diluted with petroleum ether (40 mL) and filtered, and the filter cake was dissolved in tetrahydrofuran (30 mL). Triethylamine was added to adjust the pH to 9, and the resulting mixture was filtered. The filtrate was concentrated under reduced pressure, and the resulting crude product was purified by prep-HPLC (28% to 68% acetonitrile in water (ammonium bicarbonate) over 32 min) to afford the title compound (106.0 mg, 40%) as a yellow solid. LC/MS (ESI) m/z: 1039.7 $[M+H]^+$, $^1H$ NMR (400 MHz, DMSO-$d_6$) δ 10.97 (br s, 1H), 10.15 (br dd, J=2.8, 5.2 Hz, 1H), 9.03 (s, 1H), 7.97 (dd, J=5.6, 9.2 Hz, 1H), 7.52-7.35 (m, 3H), 7.20-7.09 (m, 2H), 5.06 (dd, J=5.2, 1 Step 2: Hz, 1H), 4.53-4.42 (m, 3H), 4.30 (br d, J=16.8 Hz, 2H), 4.16 (br dd, J=6.0, 10.8 Hz, 1H), 3.91 (d, J=5.2 Hz, 1H), 3.62 (br d, J=12.4 Hz, 1H), 3.59-3.51 (m, 3H), 3.50-3.43 (m, 2H), 3.02-2.88 (m, 2H), 2.87-2.74 (m, 6H), 2.72 (br s, 1H), 2.59 (br d, J=16.8 Hz, 1H), 2.41 (br dd, J=4.8, 1 Step 2: Hz, 1H), 2.31-2.20 (m, 2H), 2.12 (br d, J=6.8 Hz, 2H), 1.98 (br dd, J=5.6, 11.2 Hz, 1H), 1.85-1.74 (m, 4H), 1.65 (br s, 5H), 1.56 (br d, J=10.4 Hz, 4H), 1.31-1.20 (m, 4H), 1.11-0.95 (m, 9H).

Example 39: Synthesis of 3-[5-(4-{[4-({1-[(2R)-1-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]propan-2-yl]piperidin-4-yl}methyl)piperidin-1-yl]methyl}piperidin-1-yl)-4-fluoro-1-oxo-2,3-dihydro-1H-isoindol-2-yl]piperidine-2,6-dione (Compound 185)

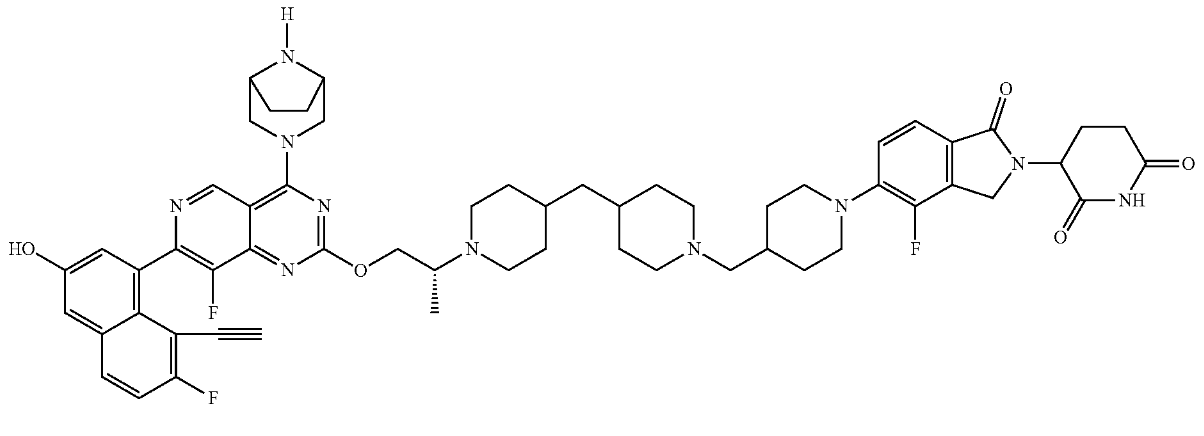 [SMILES: C#Cc1c(F)ccc2cc(O)cc(-c3ncc4c(N5CC6CCC(C5)N6)nc(OC[C@@H](C)N5CCC(CC6CCN(CC7CCN(c8ccc9c(c8F)CN(C8CCC(=O)NC8=O)C9=O)CC7)CC6)CC5)nc4c3F)c12]

The title compound was made in an analogous manner to 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-4-fluoro-1-oxo-isoindolin-2-yl]piperidine-2,6-dione. (off-white solid). LC/MS (ESI) m/z: 1039.5 $[M+H]^+$; $^1H$ NMR (400 MHz, DMSO-$d_6$) δ 10.97 (s, 1H), 10.49-9.89 (m, 1H), 9.03 (s, 1H), 7.97 (dd, J=6.0, 9.2 Hz, 1H), 7.50-7.43 (m, 2H), 7.39 (d, J=2.4 Hz, 1H), 7.21-7.09 (m, 2H), 5.06 (dd, J=5.2, 13.2 Hz, 1H), 4.56-4.42 (m, 3H), 4.30 (d, J=16.4 Hz, 2H), 4.16 (dd, J=5.6, 10.4 Hz, 1H), 3.91 (d, J=5.2 Hz, 1H), 3.62 (d, J=12.0 Hz, 1H), 3.58-3.51 (m, 3H), 3.47 (s, 2H), 3.01-2.71 (m, 9H), 2.62-2.56 (m, 1H), 2.44-2.34 (m, 1H), 2.25 (q, J=10.0 Hz, 2H), 2.12 (d, J=6.8 Hz, 2H), 2.01-1.91 (m, 1H), 1.84-1.74 (m, 4H), 1.69-1.62 (5H), 1.56 (d, J=9.2 Hz, 4H), 1.30-1.20 (m, 4H), 1.10-0.95 (m, 9H).

Example 40: Synthesis of 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-3-isopropyl-2-oxo-benzimidazol-1-yl]piperidine-2,6-dione (Compound 195)

Step 1: Preparation of 5-bromo-1-(2,6-dibenzyloxy-3-pyridyl)-3-isopropyl-benzimidazol-2-one

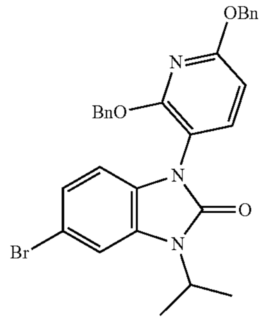 [SMILES: CC(C)n1c(=O)n(-c2ccc(OCc3ccccc3)nc2OCc2ccccc2)c2ccc(Br)cc21]

To a solution of 6-bromo-3-(2,6-dibenzyloxy-3-pyridyl)-1H-benzimidazol-2-one (1.3 g, 2.6 mmol) and 2-iodopropane (2.6 mL, 26 mmol) in N,N-dimethylformamide (15 mL) was added cesium carbonate (2.53 g, 7.8 mmol), and the reaction mixture was stirred at 60° C. for 16 h. The mixture was diluted with water (30 mL) and extracted with ethyl acetate (3×100 mL). The combined organic extracts were washed with brine (20 mL), dried over anhydrous sodium sulfate, filtered, and concentrated under reduced pressure. The residue was purified by silica gel column chromatography (petroleum ether/ethyl acetate=1/0 then 5/1) to afford the title compound (1 g, 71%) as a brown oil. LC/MS (ESI) m/z: 544.2 $[M+H]^+$.

Step 2: Preparation of 1-(2,6-dibenzyloxy-3-pyridyl)-5-[4-(dimethoxymethyl)-1-piperidyl]-3-isopropyl-benzimidazol-2-one

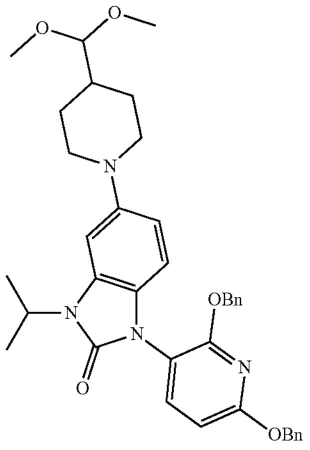 [SMILES: COC(OC)C1CCN(c2ccc3c(c2)n(C(C)C)c(=O)n3-c2ccc(OCc3ccccc3)nc2OCc2ccccc2)CC1]

To a solution of 4-(dimethoxymethyl)piperidine (468 mg, 2.9 mmol) and 5-bromo-1-(2,6-dibenzyloxy-3-pyridyl)-3-isopropyl-benzimidazol-2-one (1.6 g, 2.9 mmol) in 1,4-dioxane (20 mL) were added XPhos Pd G2 (231 mg, 0.3 mmol) and cesium carbonate (1.92 g, 6 mmol), and the mixture was stirred at 100° C. for 16 h. The reaction mixture was filtered, and the filtrate was concentrated under reduced pressure. The residue was purified by silica gel column chromatography (petroleum ether/ethyl acetate=3/1 then 1/1) to afford the title compound (1.6 g, 87%) as an orange oil. LC/MS (ESI) m/z: 623.4 $[M+H]^+$.

Step 3: Preparation of 3-[5-[4-(dimethoxymethyl)-1-piperidyl]-3-isopropyl-2-oxo-benzimidazol-1-yl]piperidine-2,6-dione

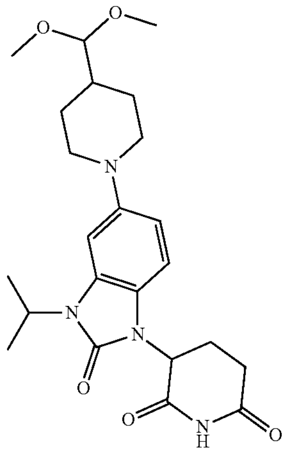 [SMILES: COC(OC)C1CCN(c2ccc3c(c2)n(C(C)C)c(=O)n3C2CCC(=O)NC2=O)CC1]

To a solution of 1-(2,6-dibenzyloxy-3-pyridyl)-5-[4-(dimethoxymethyl)-1-piperidyl]-3-isopropyl-benzimidazol-2-one (1.35 g, 2 mmol) in tetrahydrofuran (10 mL) was added 10% palladium on carbon (300 mg) under nitrogen atmosphere. The suspension was degassed under vacuum and purged with hydrogen (3×), and the mixture was stirred under hydrogen at 50° C. for 16 h. The reaction mixture was filtered and concentrated under reduced pressure to afford the title compound (800 mg, 83%) as a green solid. LC/MS (ESI) m/z: 445.3 $[M+H]^+$.

Step 4: Preparation of 1-[1-(2,6-dioxo-3-piperidyl)-3-isopropyl-2-oxo-benzimidazol-5-yl]piperidine-4-carbaldehyde

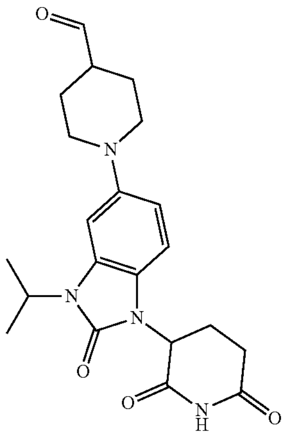 [SMILES: CC(C)n1c(=O)n(C2CCC(=O)NC2=O)c2ccc(N3CCC(C=O)CC3)cc21]

To a solution of 3-[5-[4-(dimethoxymethyl)-1-piperidyl]-3-isopropyl-2-oxo-benzimidazol-1-yl]piperidine-2,6-dione (800 mg, 1.8 mmol) in dichloromethane (10 mL) was added trifluoroacetic acid (0.13 mL, 1.8 mmol), and the mixture was stirred at 25° C. for 1 h. The reaction mixture was concentrated under reduced pressure. The residue was triturated with ethyl acetate/methyl tert-butyl ether (1/10, 100 mL) to afford the title compound (700 mg, 98%) as a green solid. LC/MS (ESI) m/z: 417.2 $[M+H_3O]^+$.

Step 5: Preparation of tert-butyl 3-[2-[(2S)-2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

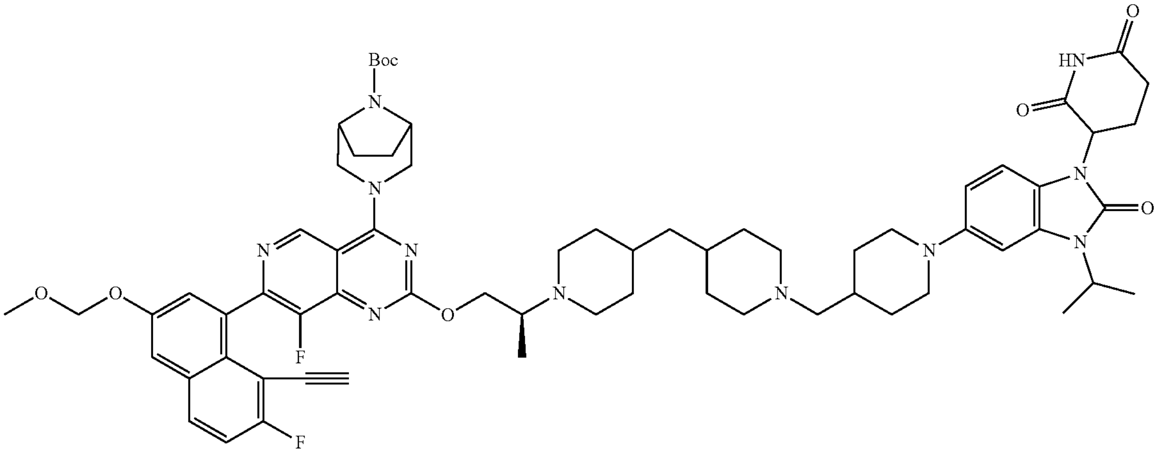 [SMILES: C#Cc1c(F)ccc2cc(OCOC)cc(-c3ncc4c(N5CC6CCC(C5)N6C(=O)OC(C)(C)C)nc(OC[C@H](C)N5CCC(CC6CCN(CC7CCN(c8ccc9c(c8)n(C(C)C)c(=O)n9C8CCC(=O)NC8=O)CC7)CC6)CC5)nc4c3F)c12]

To a solution of tert-butyl 3-[7-[8-ethynyl-7-fluoro-3-(methoxymethoxy)-1-naphthyl]-8-fluoro-2-[(2S)-2-[4-(4-piperidylmethyl)-1-piperidyl]propoxy]pyrido[4,3-d]pyrimidin-4-yl]-3,8-diazabicyclo[3.2.1]octane-8-carboxylate (700 mg, 0.8 mmol) and 1-[1-(2,6-dioxo-3-piperidyl)-3-isopropyl-2-oxo-benzimidazol-5-yl]piperidine-4-carbaldehyde (506 mg, 1.3 mmol) in dichloromethane (3 mL) were added acetic acid (195 μL, 3 mmol) and 2-methylpyridine borane (453 mg, 4 mmol), and the reaction mixture was stirred at 20° C. for 12 h. The mixture was concentrated under reduced pressure, and the residue was purified by flash column chromatography on silica gel (0 to 8% methanol in dichloromethane) to afford the title compound (0.4 g, 36%) as a yellow solid. LC/MS (ESI) m/z: 1208.6 $[M+H]^+$.

Step 6: Preparation of 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-3-isopropyl-2-oxo-benzimidazol-1-yl]piperidine-2,6-dione

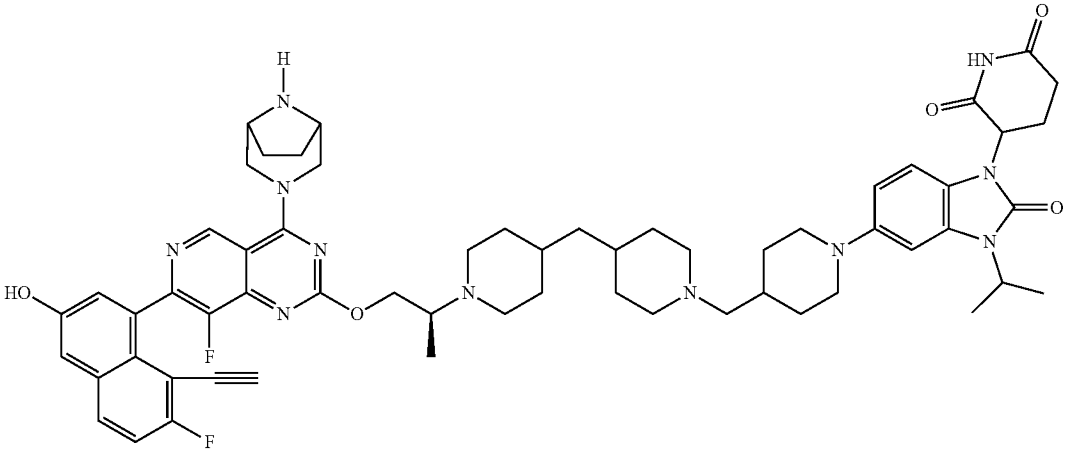 [SMILES: C#Cc1c(F)ccc2cc(O)cc(-c3ncc4c(N5CC6CCC(C5)N6)nc(OC[C@H](C)N5CCC(CC6CCN(CC7CCN(c8ccc9c(c8)n(C(C)C)c(=O)n9C8CCC(=O)NC8=O)CC7)CC6)CC5)nc4c3F)c12]

To a solution of tert-butyl 3-[2-[(2S)-2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl] propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (0.4 g, 0.3 mmol) in dichloromethane (3 mL) was added 4 M HCl in 1,4-dioxane (2.4 mL), and the reaction mixture was stirred at 20° C. for 0.25 h. The mixture was diluted with petroleum ether (40 mL) and filtered, and the filter cake was diluted with THF (30 mL). Triethylamine was added to adjust the pH to 9, and thee mixture was filtered, The filtrate was concentrated under reduced pressure, and the crude product was purified by prep-HPLC (58%-68% acetonitrile in water (ammonium bicarbonate) over 32 min) to afford the title compound (102.2 mg, 28%) as a yellow solid. LC/MS (ESI) m/z: 1064.5 $[M+H]^+$; $^1$H NMR (400 MHz, $CD_3OD$) δ 9.00 (s, 1H), 7.86 (dd, J=5.6, 9.2 Hz, 1H), 7.37-7.27 (m, 2H), 7.21 (d, J=2.4 Hz, 1H), 7.02-6.93 (m, 2H), 6.83-6.77 (m, 1H), 5.26 (dd, J=5.2, 12.6 Hz, 1H), 4.69-4.55 (m, 4H), 4.43-4.34 (m, 1H), 3.75-3.63 (m, 4H), 3.54 (br d, J=12.0 Hz, 2H), 3.36 (s, 1H), 3.13-3.06 (m, 1H), 3.02-2.87 (m, 5H), 2.80-2.65 (m, 4H), 2.49-2.38 (m, 2H), 2.27 (br d, J=6.4 Hz, 2H), 2.18-2.11 (m, 1H), 2.00-1.78 (m, 8H), 1.69 (br t, J=12.4 Hz, 5H), 1.58-1.51 (m, 6H), 1.44-1.34 (m, 4H), 1.28-1.15 (m, 9H).

Example 41: Synthesis of 3-[5-(4-{[4-({1-[(2R)-1-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]propan-2-yl] piperidin-4-yl}methyl)piperidin-1-yl] methyl}piperidin-1-yl)-2-oxo-3-(propan-2-yl)-2,3-dihydro-1H-1,3-benzodiazol-1-yl]piperidine-2,6-dione (Compound 184)

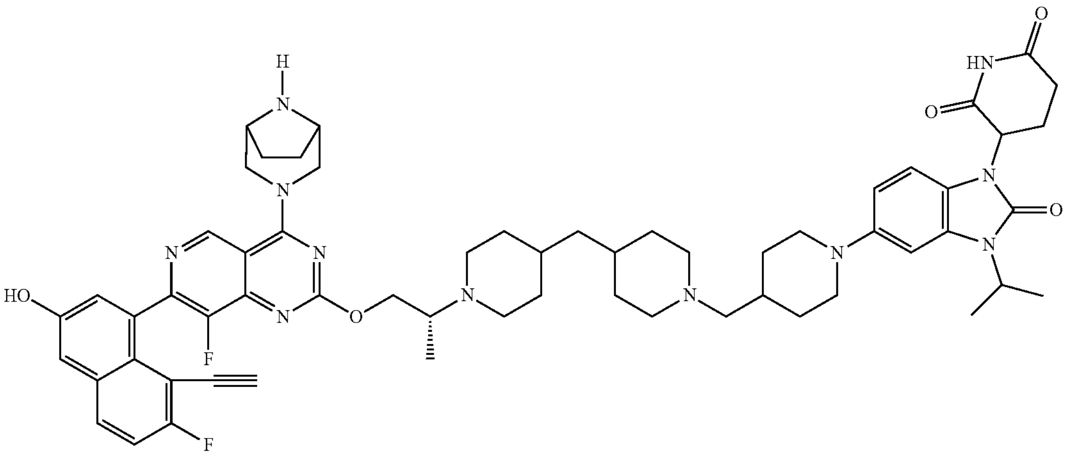 [SMILES: C#Cc1c(F)ccc2cc(O)cc(-c3ncc4c(N5CC6CCC(C5)N6)nc(OC[C@@H](C)N5CCC(CC6CCN(CC7CCN(c8ccc9c(c8)n(C(C)C)c(=O)n9C8CCC(=O)NC8=O)CC7)CC6)CC5)nc4c3F)c12]

The title compound was made in an analogous manner to 3-[5-[4-[[4-[[1-[(1S)-2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxy-1-methyl-ethyl]-4-piperidyl]methyl]-1-piperidyl]methyl]-1-piperidyl]-3-isopropyl-2-oxo-benzimidazol-1-yl]piperidine-2,6-dione. (off-white solid). LC/MS (ESI) m/z: 1064.6 $[M+H]^+$; $^1$H NMR (400 MHz, DMSO-$d_6$) δ 11.04 (s, 1H), 10.30-9.99 (m, 1H), 9.03 (s, 1H), 7.97 (dd, J=6.0, 9.2 Hz, 1H), 7.46 (t, J=9.2 Hz, 1H), 7.39 (d, J=2.4 Hz, 1H), 7.17 (s, 1H), 6.95-6.81 (m, 2H), 6.61 (dd, J=1.6, 8.8 Hz, 1H), 5.25 (dd, J=5.2, 12.8 Hz, 1H), 4.63-4.53 (m, 1H), 4.52-4.42 (m, 2H), 4.30 (d, J=12.4 Hz, 1H), 4.16 (dd, J=6.0, 10.8 Hz, 1H), 3.91 (d, J=5.2 Hz, 1H), 3.62 (d, J=11.8 Hz, 1H), 3.58-3.46 (m, 5H), 3.03-2.94 (m, 1H), 2.89-2.74 (m, 5H), 2.65-2.55 (m, 4H), 2.31-2.19 (m, 2H), 2.11 (d, J=6.8 Hz, 2H), 2.01-1.92 (m, 1H), 1.84-1.72 (m, 4H), 1.68-1.62 (m, 4H), 1.60-1.52 (m, 5H), 1.44 (d, J=6.8 Hz, 6H), 1.34-1.13 (m, 5H), 1.12-0.96 (m, 9H).

Example 42: Exemplary synthesis of 3-[5-[4-[[4-[[1-[[1-[[4-(3,8-diazabicyclo[3.2.1]octan-3-yl)-7-(8-ethynyl-7-fluoro-3-hydroxy-1-naphthyl)-8-fluoro-pyrido [4,3-d]pyrimidin-2-yl]oxymethyl] cyclopropyl]methyl]-4-piperidyl]methyl]-1-piperidyl] methyl]-1-piperidyl]-3-methyl-2-oxo-benzimidazol-1-yl]piperidine-2,6-dione (Compound 196)

Step 1: Preparation of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]piperidine-1-carboxylate

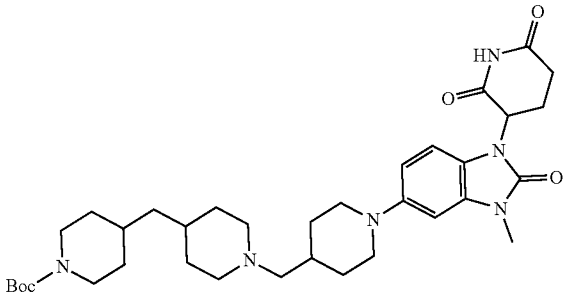 [SMILES: Cn1c(=O)n(C2CCC(=O)NC2=O)c2ccc(N3CCC(CN4CCC(CC5CCN(C(=O)OC(C)(C)C)CC5)CC4)CC3)cc21]

To a solution of tert-butyl 4-(4-piperidylmethyl)piperidine-1-carboxylate acetate (386 mg, 1 mmol) and 1-[1-(2,6-dioxo-3-piperidyl)-3-methyl-2-oxo-benzimidazol-5-yl]piperidine-4-carbaldehyde (380 mg, 1 mmol) in dichloromethane (5 mL) and dimethyl sulfoxide (2 mL) were added sodium triacetoxyborohydride (435 mg, 2 mmol) and N,N-diisopropylethylamine (0.4 mL, 2 mmol), and the reaction mixture was stirred at 25° C. for 2 h. The mixture was diluted with water (20 mL) and extracted with dichloromethane (3×40 mL). The combined organic extracts were washed with brine (20 mL), dried over anhydrous sodium sulfate, filtered, and concentrated under reduced pressure. The residue was triturated with ethyl acetate/ methyl tert-butyl ether (1/10, 60 mL) to afford the title compound (550 mg, 84%) as an off-white solid. LC/MS (ESI) m/z: 637.5 $[M+H]^+$.

Step 2: Preparation of 3-[3-methyl-2-oxo-5-[4-[[4-(4-piperidylmethyl)-1-piperidyl]methyl]-1-piperidyl]benzimidazol-1-yl]piperidine-2,6-dione

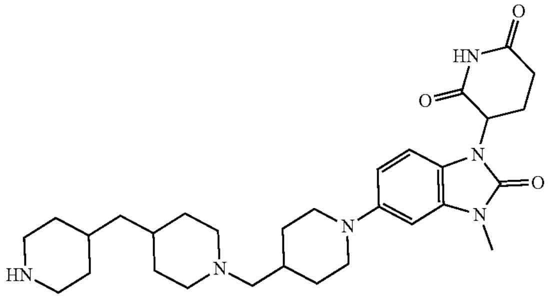 [SMILES: Cn1c(=O)n(C2CCC(=O)NC2=O)c2ccc(N3CCC(CN4CCC(CC5CCNCC5)CC4)CC3)cc21]

To a solution of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]piperidine-1-carboxylate (550 mg, 0.9 mmol) in dichloromethane (3 mL) was added trifluoroacetic acid (0.1 mL, 0.9 mmol), and the reaction mixture was stirred at 25° C. for 1 h. The mixture was concentrated under reduced pressure, and the residue was triturated with ethyl acetate/methyl tert-butyl ether (1/10, 60 mL) to afford the title compound (530 mg, 80%, di-trifluoroacetate) as a gray solid. LC/MS (ESI) m/z: 537.5 $[M+H]^+$.

Step 3: Preparation of tert-butyl 3-[2-[[1-[[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

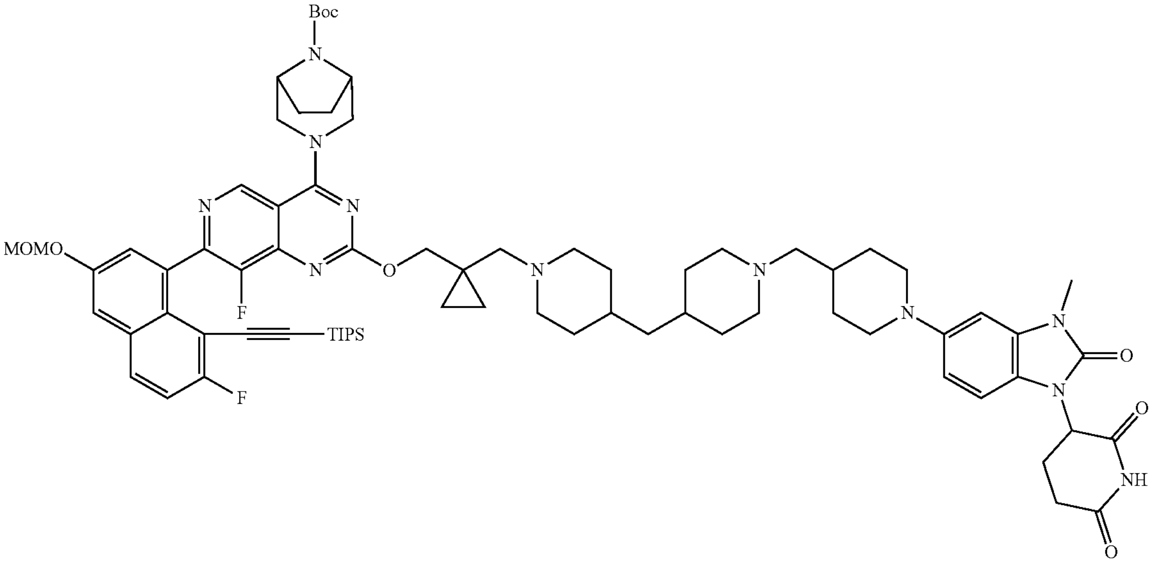

To a solution of 3-[3-methyl-2-oxo-5-[4-[[4-(4-piperidylmethyl)-1-piperidyl]methyl]-1-piperidyl]benzimidazol-1-yl]piperidine-2,6-dione (363 mg, 0.5 mmol, di-trifluoroacetate) in dichloromethane (4 mL) and dimethyl sulfoxide (4 mL) was added N,N-diisopropylethylamine (0.4 mL, 2 mmol), and the resulting mixture was stirred at 25° C. for 0.5 h. tert-Butyl 3-[8-fluoro-7-[7-fluoro-3-(methoxymethoxy)-8-(2-triisopropylsilylethynyl)-1-naphthyl]-2-[(1-formylcyclopropyl)methoxy]pyrido[4,3-d]pyrimidin-4-yl]-3,8-diazabicyclo [3.2.1]octane-8-carboxylate (400 mg, 0.5 mmol), 2-methylpyridine borane (254 mg, 2.4 mmol) and acetic acid (0.3 mL, 5 mmol) were then added, and the reaction mixture was stirred at 35° C. for 12 h. The mixture was diluted with water (30 mL) and extracted with ethyl acetate (3×20 mL). The combined organic extract was washed with brine (2×20 mL), dried over anhydrous sodium sulfate, filtered, and concentrated under reduced pressure. The residue was purified by preparative TLC (dichloromethane/methanol=10/1) to afford the title compound (340 mg, 52%) as a yellow solid. LC/MS (ESI) m/z: 1363.9 $[M+H]^+$, $^1H$ NMR (400 MHz, DMSO-$d_6$) δ 11.06 (s, 1H), 9.17 (s, 1H), 8.11 (dd, J=6.0, 9.2 Hz, 1H), 7.75 (d, J=2.4 Hz, 1H), 7.57 (t, J=8.8 Hz, 1H), 7.33 (d, J=2.4 Hz, 1H), 6.93 (d, J=8.4 Hz, 1H), 6.82 (s, 1H), 6.62 (d, J=8.4 Hz, 1H), 5.76 (s, 1H), 5.36 (s, 2H), 5.29 (dd, J=5.6, 12.8 Hz, 1H), 4.75 (d, J=12.4 Hz, 1H), 4.38-4.25 (m, 3H), 4.23-4.18 (m, 1H), 3.82-3.67 (m, 2H), 3.58 (d, J=10.8 Hz, 3H), 3.47-3.40 (m, 4H), 3.32-3.24 (m, 6H), 3.16 (d, J=5.2 Hz, 1H), 2.99-2.84 (m, 5H), 2.75-2.56 (m, 6H), 2.33 (d, J=2.0 Hz, 3H), 1.93-1.83 (m, 6H), 1.67-1.56 (m, 5H), 1.46 (s, 9H), 1.35-1.17 (m, 5H), 1.16-1.01 (m, 4H), 0.81 (t, J=8.0 Hz, 18H), 0.68-0.57 (m, 2H), 0.52-0.39 (m, 4H).

Step 4: Preparation of tert-butyl 3-[2-[[1-[[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

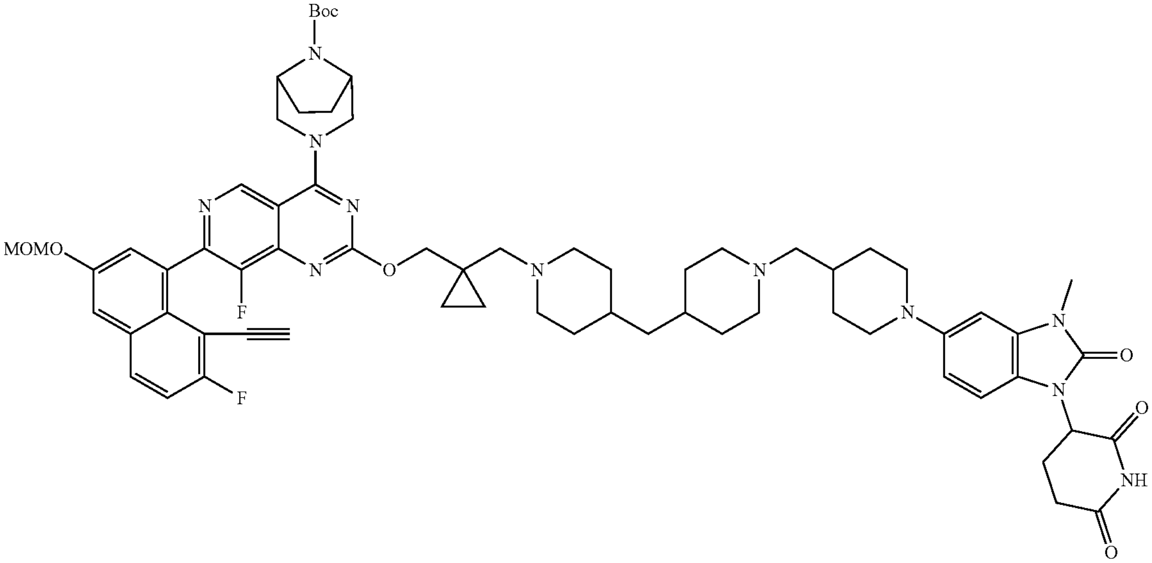

To a solution of tert-butyl 3-[2-[[1-[[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (340 mg, 0.25 mmol) in N,N-dimethylformamide (5 mL) was added cesium fluoride (0.3 mL, 7 mmol), and the reaction mixture was stirred at 25° C. for 1 h. The mixture was diluted with ice-water (40 mL) and extracted with tetrahydrofuran/ethyl acetate (1/1, 2×20 mL). The combined organic extracts were washed with saturated sodium bicarbonate solution (2×20 mL), dried over anhydrous sodium sulfate, filtered, and concentrated under reduced pressure to afford the title compound (273 mg, 90%) as a yellow solid. LC/MS (ESI) m/z: 1207.9 $[M+H]^+$.

Step 5: Preparation of 3-[5-[4-[[4-[[1-[[1-[[4-(3,8-diazabicyclo[3.2.1]octan-3-yl)-7-(8-ethynyl-7-fluoro-3-hydroxy-1-naphthyl)-8-fluoro-pyrido [4,3-d]pyrimidin-2-yl]oxymethyl]cyclopropyl]methyl]-4-piperidyl]methyl]-1-piperidyl] methyl]-1-piperidyl]-3-methyl-2-oxo-benzimidazol-1-yl]piperidine-2,6-dione

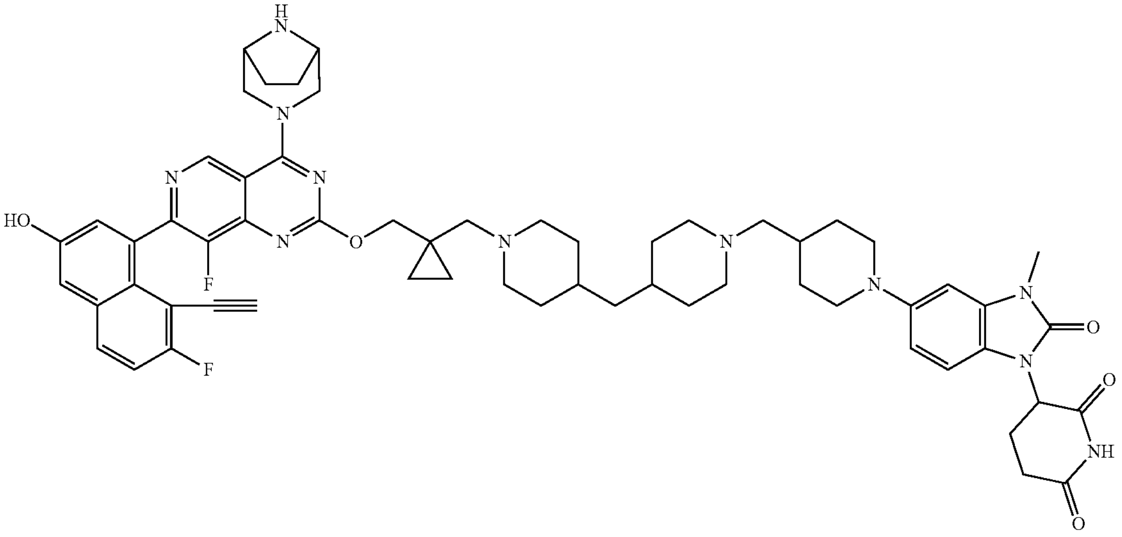 [SMILES: C#Cc1c(F)ccc2cc(O)cc(-c3ncc4c(N5CC6CCC(C5)N6)nc(OCC5(CN6CCC(CC7CCN(CC8CCN(c9ccc%10c(c9)n(C)c(=O)n%10C9CCC(=O)NC9=O)CC8)CC7)CC6)CC5)nc4c3F)c12]

To a solution of tert-butyl 3-[2-[[1-[[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]methyl] cyclopropyl]methoxy]-7-[8-ethynyl-7-fluoro-3-(methoxymethoxy)-1-naphthyl]-8-fluoro-pyrido[4,3-d] pyrimidin-4-yl]-3,8-diazabicyclo[3.2.1]octane-8-carboxylate (273 mg, 0.2 mmol) in dichloromethane (3 mL) was added 4 M HCl in 1,4-dioxane (3 mL), and the reaction mixture was stirred at 25° C. for 15 min. The mixture was suspended in petroleum ether (20 mL) and filtered. The filtered cake was diluted with dimethyl sulfoxide (3 mL) and basified with N,N-diisopropylethylamine. The mixture was purified by prep-HPLC (1% to 25% acetonitrile in water (formic acid) over 10 min) to afford the title compound (157.7 mg, 57%, tri-formic acid salt) as a yellow solid. LC/MS (ESI) m/z: 1062.7 $[M+H]^+$, $^1H$ NMR (400 MHz, DMSO-$d_6$) δ 11.05 (s, 1H), 9.05 (s, 1H), 8.21 (s, 3H), 7.98 (dd, J=6.0, 9.2 Hz, 1H), 7.46 (t, J=9.2 Hz, 1H), 7.39 (d, J=2.4 Hz, 1H), 7.18 (d, J=2.4 Hz, 1H), 6.92 (d, J=8.8 Hz, 1H), 6.81 (d, J=2.0 Hz, 1H), 6.62 (dd, J=2.0, 8.8 Hz, 1H), 5.28 (dd, J=5.2, 12.8 Hz, 1H), 4.54 (d, J=12.8 Hz, 2H), 4.43-4.15 (m, 4H), 3.93 (s, 1H), 3.76-3.50 (m, 6H), 3.30 (s, 3H), 3.01-2.79 (m, 5H), 2.73-2.56 (m, 4H), 2.41-2.27 (m, 2H), 2.20 (d, J=6.8 Hz, 2H), 2.04-1.84 (m, 5H), 1.83-1.71 (m, 6H), 1.69-1.51 (m, 5H), 1.39-1.18 (m, 4H), 1.16-0.97 (m, 6H), 0.65 (s, 2H), 0.42 (s, 2H).

Example 43: Synthesis of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-4-fluoro-3-methyl-2-oxo-2,3-dihydro-1H-1,3-benzodiazol-1-yl) piperidine-2,6-dione (Compound 197)

Step 1: Preparation of 3-bromo-2-fluoro-N-methyl-6-nitro-aniline

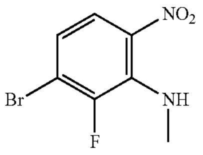

To a mixture of 1-bromo-2,3-difluoro-4-nitro-benzene (25 g, 0.1 mol) and methanamine hydrochloride (8.50 g, 126 mmol) in N,N-dimethylformamide (300 mL) was added potassium carbonate (43.5 g, 315 mmol), and the reaction mixture was stirred at 25° C. for 5 h. The mixture was diluted with water (400 mL) and extracted with ethyl acetate (1500 mL). The combined organic extracts were concentrated under reduced pressure, and the resulting residue was purified by silica gel column chromatography (petroleum ether/ethyl acetate=30/1 then 15/1) to afford the title compound (26 g, 99%) as a yellow solid.

Step 2: Preparation of 4-bromo-3-fluoro-nitrogen-methyl-benzene-1,2-diamine

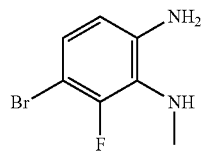

To a solution of 3-bromo-2-fluoro-N-methyl-6-nitro-aniline (26.0 g, 104 mmol) in ethanol (300 mL) and water (250 mL) was added iron powder (23.3 g, 418 mmol) and ammonium chloride (27.9 g, 522 mmol), and the reaction mixture was stirred at 80° C. for 3 h. The mixture was filtered and concentrated under reduced pressure. The residue was purified by silica gel column chromatography (petroleum ether/ethyl acetate=20/1 to 8/1) to afford the title compound (18 g, 78%) as a yellow solid.

Step 3: Preparation of 6-bromo-7-fluoro-1-methyl-1,3-dihydro-2H-benzo[d]imidazol-2-one

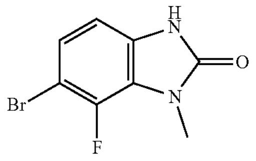

To a solution of 4-bromo-3-fluoro-nitrogen-methyl-benzene-1,2-diamine (18.0 g, 82.17 mmol) and triethylamine (10.8 g, 106.82 mmol, 14.9 mL) in tetrahydrofuran (200 mL) was added 1,1-carbonyldiimidazole (16.0 g, 98.61 mmol), and the reaction mixture was stirred at 70° C. for 10 h. The mixture was diluted with water (150 mL) and extracted with ethyl acetate (350 mL). The combined organic extracts were concentrated under reduced pressure, and the resulting residue was purified by column chromatography (petroleum ether/ethyl acetate=5/1 then 1/2) to afford the title compound (14 g, 69%) as a yellow solid. LC/MS (ESI) m/z: 245.0 $[M+H]^+$.

Step 4: Preparation of 5-bromo-4-fluoro-3-methyl-1-(2-trimethylsilylethoxymethyl)benzimidazol-2-one

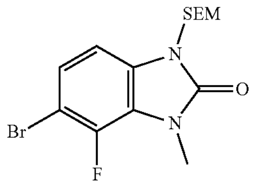 [SMILES: Cn1c(=O)n(COCC[Si](C)(C)C)c2ccc(Br)c(F)c21]

To a solution of 6-bromo-7-fluoro-1-methyl-1,3-dihydro-2H-benzo[d]imidazol-2-one (13 g, 53 mmol) in tetrahydrofuran (300 mL) was added sodium hydride (2.7 g, 69 mmol, 60%), and the resulting mixture was stirred at 0° C. for 1 h. 2-(Trimethylsilyl)ethoxymethyl chloride (1 M, 63.7 mL) was then added, and the reaction mixture was stirred at 0° C. for 2 h. The mixture was diluted with saturated ammonium chloride solution (800 mL) at 0° C., and then extracted with ethyl acetate (1500 mL). The organic extract was concentrated under reduced pressure, and the resulting residue was purified by silica gel column chromatography (petroleum ether/ethyl acetate=20/1 then 10/1) to afford the title compound (15 g, 75%) as a yellow solid. $^1H$ NMR (400 MHz, DMSO-$d_6$) δ 7.40 (dd, J=8.4, 6.4 Hz, 1H), 7.13 (d, J=8.4 Hz, 1H), 5.31 (s, 2H), 3.61 (t, J=8.0 Hz, 2H), 3.54 (d, J=1.6 Hz, 3H), 0.88-0.93 (m, 2H), 0.00 (s, 9H).

Step 5: Preparation of 5-[4-(dimethoxymethyl)-1-piperidyl]-4-fluoro-3-methyl-1-(2-trimethylsilylethoxymethyl) benzimidazol-2-one

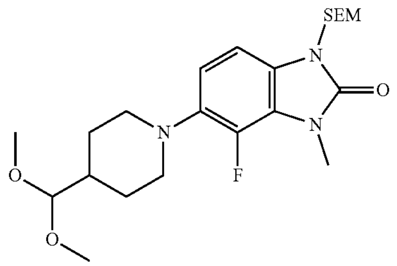 [SMILES: COC(OC)C1CCN(c2ccc3c(c2F)n(C)c(=O)n3COCC[Si](C)(C)C)CC1]

To a solution of 5-bromo-4-fluoro-3-methyl-1-(2-trimethylsilylethoxymethyl)benzimidazol-2-one (4.0 g, 11 mmol) and 4-(dimethoxymethyl)piperidine (2.0 g, 13 mmol) in 1,4-dioxane (50 mL) were added cesium carbonate (8.7 g, 27 mmol) and Pd-PEPPSI-IHeptCl (518 mg, 0.5 mmol), and the reaction mixture was stirred at 100° C. for 6 h. The mixture was filtered and concentrated under reduced pressure. The residue was purified by silica gel column chromatography (petroleum ether/ethyl acetate=8/1 then 6/1) to afford the title compound (4.4 g, 91%) as a yellow oil. LC/MS (ESI) m/z: 454.4 $[M+H]^+$.

Step 6: Preparation of 5-[4-(dimethoxymethyl)-1-piperidyl]-4-fluoro-3-methyl-1H-benzimidazol-2-one

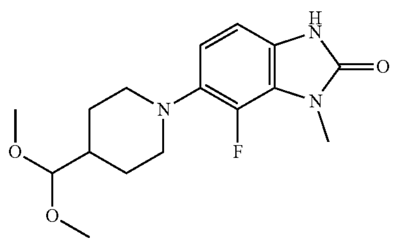 [SMILES: COC(OC)C1CCN(c2ccc3[nH]c(=O)n(C)c3c2F)CC1]

A solution of 5-[4-(dimethoxymethyl)-1-piperidyl]-4-fluoro-3-methyl-1-(2-trimethylsilylethoxymethyl) benzimidazol-2-one (4.4 g, 9.7 mmol) and tetrabutylammonium fluoride in THF (1 M, 48.5 mL) was stirred at 65° C. for 16 h. The mixture was filtered and concentrated under reduced pressure. The residue was purified by preparative TLC on silica gel (petroleum ether/ethyl acetate=1/1) to afford the title compound (1.4 g, 44%) as a yellow solid.

Step 7: Preparation of 1-(2,6-bis(benzyloxy)pyridin-3-yl)-5-(4-(dimethoxymethyl)piperidin-1-yl)-4-fluoro-3-methyl-1,3-dihydro-2H-benzo[d]imidazol-2-one

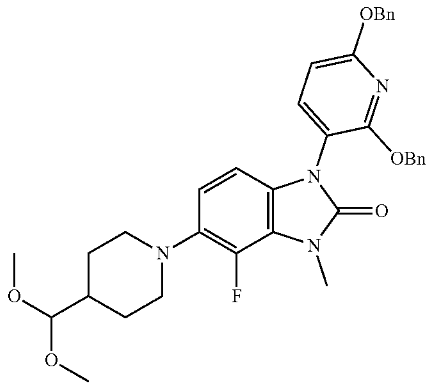 [SMILES: COC(OC)C1CCN(c2ccc3c(c2F)n(C)c(=O)n3-c2ccc(OCc3ccccc3)nc2OCc2ccccc2)CC1]

To a solution of 5-[4-(dimethoxymethyl)-1-piperidyl]-4-fluoro-3-methyl-1H-benzimidazol-2-one (2.6 g, 8 mmol) and 2,6-bis(benzyloxy)-3-iodopyridine (5.0 g, 12 mmol) in dimethyl sulfoxide (30 mL) were added cuprous oxide (230 mg, 1.6 mmol), N,N'-bis(2-furylmethyl)oxamide (798 mg, 3.2 mmol), and potassium phosphate (5.1 g, 24 mmol), and the reaction mixture was stirred at 120° C. for 10 h. The mixture was filtered and concentrated under reduced pressure. The residue was purified by prep-HPLC (65% to 95% acetonitrile in water (ammonium bicarbonate) over 20 min) to afford the title compound (1.8 g, 36%) as a yellow solid. LC/MS (ESI) m/z: 613.2 $[M+H]^+$.

Step 8: Preparation of 3-[5-[4-(dimethoxymethyl)-1-piperidyl]-4-fluoro-3-methyl-2-oxo-benzimidazol-1-yl]piperidine-2,6-dione

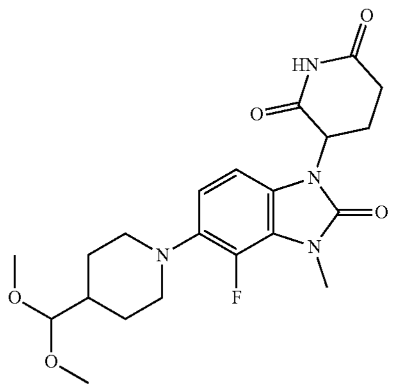 [SMILES: COC(OC)C1CCN(c2ccc3c(c2F)n(C)c(=O)n3C2CCC(=O)NC2=O)CC1]

To a solution of 1-(2,6-bis(benzyloxy)pyridin-3-yl)-5-(4-(dimethoxymethyl)piperidin-1-yl)-4-fluoro-3-methyl-1,3-dihydro-2H-benzo[d]imidazol-2-one (1.2 g, 2 mmol) in tetrahydrofuran (15 mL) was added 10% palladium on carbon (500 mg) under nitrogen atmosphere, and the mixture was degassed and purged with hydrogen (3×), then stirred under hydrogen (50 psi) at 50° C. for 16 h. The mixture was filtered and concentrated under reduced pressure. The residue was purified by preparative TLC on silica gel (petroleum ether/ethyl acetate=1/1) to afford the title compound (700 mg, 82%) as a yellow solid. LC/MS (ESI) m/z: 435.2 $[M+H]^+$.

Step 9: Preparation of 1-[1-(2,6-dioxo-3-piperidyl)-4-fluoro-3-methyl-2-oxo-benzimidazol-5-yl]piperidine-4-carbaldehyde

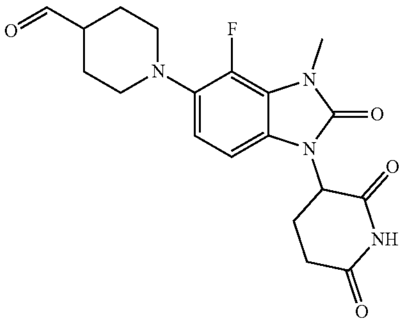 [SMILES: Cn1c(=O)n(C2CCC(=O)NC2=O)c2ccc(N3CCC(C=O)CC3)c(F)c21]

To a solution of 3-[5-[4-(dimethoxymethyl)-1-piperidyl]-4-fluoro-3-methyl-2-oxo-benzimidazol-1-yl]piperidine-2,6-dione (700 mg, 1.6 mmol) in dichloromethane (15 mL) was added trifluoroacetic acid (7.0 m, 94 mmol), and the reaction mixture was stirred at 25° C. for 1 h. The mixture was filtered and concentrated under reduced pressure. The crude product was triturated with methyl tert-butyl ether (80 mL) to afford the title compound (700 mg, crude) as a yellow solid. LC/MS (ESI) m/z: 407.1 $[M+H_3O]^+$.

Step 10: Preparation of tert-butyl 3-[2-[2-[tert-butyl(dimethyl)silyl]oxyethoxy]-7-chloro-8-fluoro-pyrido[4,3-d]pyrimidin-4-yl]-3,8-diazabicyclo[3.2.1]octane-8-carboxylate

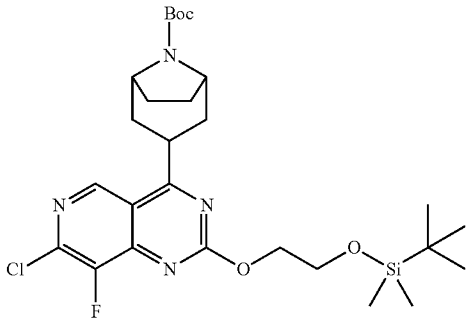 [SMILES: CC(C)(C)OC(=O)N1C2CCC1CC(c1nc(OCCO[Si](C)(C)C(C)(C)C)nc3c(F)c(Cl)ncc13)C2]

To a solution of tert-butyl 3-(2,7-dichloro-8-fluoro-pyrido[4,3-d]pyrimidin-4-yl)-3,8-diazabicyclo[3.2.1]octane-8-carboxylate (52.0 g, 121 mmol) and 1,4-diazabicyclo [2.2.2] octane (2.72 g, 25 mmol) in acetonitrile (1000 mL) were added 2-[tert-butyl(dimethyl)silyl]oxyethanol (25.69 g, 146 mmol) and cesium carbonate (118.68 g, 364 mmol) at 25° C., and the reaction mixture was stirred for 50° C. for 5 h. The mixture was filtered, and the filtrate was concentrated in vacuo. The residue was purified by silica gel column chromatography (petroleum ether/ethyl acetate=10/1 to 3/1) to afford the title compound (50 g, 72%) as a yellow solid. LC/MS (ESI) m/z: 568.3 $[M+H]^+$, $^1H$ NMR (400 MHz, $CDCl_3$) δ 8.73 (s, 1H), 4.56 (t, J=5.6 Hz, 2H), 4.48 (br d, J=12.8 Hz, 2H), 4.42-4.28 (m, 2H), 4.07-3.98 (m, 2H), 3.74-3.60 (m, 2H), 2.00-1.90 (m, 2H), 1.72 (br d, J=7.6 Hz, 2H), 1.52 (s, 9H), 0.92-0.86 (m, 9H), 0.09 (s, 6H).

Step 11: Preparation of tert-butyl 3-[7-chloro-8-fluoro-2-(2-hydroxyethoxy)pyrido[4,3-d]pyrimidin-4-yl]-3,8-diazabicyclo[3.2.1]octane-8-carboxylate

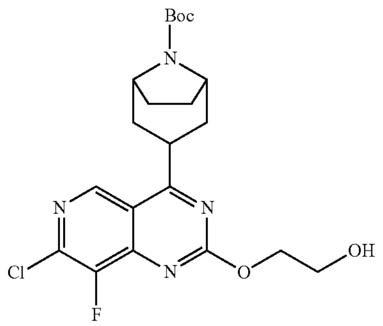 [SMILES: CC(C)(C)OC(=O)N1C2CCC1CC(c1nc(OCCO)nc3c(F)c(Cl)ncc13)C2]

To a solution of tert-butyl 3-[2-[2-[tert-butyl(dimethyl) silyl]oxyethoxy]-7-chloro-8-fluoro-pyrido[4,3-d]pyrimidin-4-yl]-3,8-diazabicyclo[3.2.1]octane-8-carboxylate (6.0 g, 10 mmol) in N, N-dimethylformamide (50 mL) at 25° C. was added cesium fluoride (8 mL, 0.2 mol), and the reaction mixture was stirred for 12 h at 25° C. The mixture was diluted with saturated ammonium chloride solution (50 mL) and extracted with ethyl acetate (3×50 mL). The combined organic extract was washed with brine (50 mL), dried over anhydrous sodium sulfate, filtered, and concentrated in vacuo. The residue was purified by column chromatography on silica gel (petroleum ether/ethyl acetate=10/1 then 1/1) to afford the title compound (3.5 g, 73%) as a yellow solid. LC/MS (ESI) m/z: 454.1 $[M+H]^+$.

Step 12: Preparation of tert-butyl 3-[8-fluoro-7-[7-fluoro-3-(methoxy methoxy)-8-(2-triisopropylsilylethynyl)-1-naphthyl]-2-(2-hydroxyethoxy)pyrido[4,3-d]pyrimidin-4-yl]-3,8-diazabicyclo[3.2.1]octane-8-carboxylate

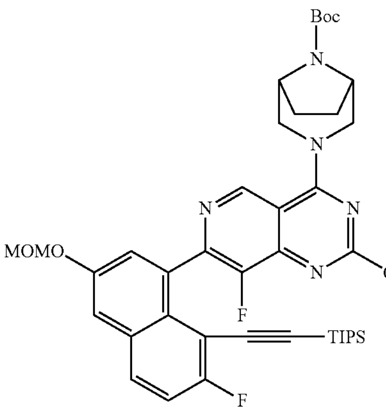

A mixture of tert-butyl 3-[7-chloro-8-fluoro-2-(2-hydroxyethoxy)pyrido[4,3-d]pyrimidin-4-yl]-3,8-diazabicyclo[3.2.1]octane-8-carboxylate (2.7 g, 6 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (3.05 g, 6 mmol), potassium phosphate (3.79 g, 18 mmol), and cataCXium A Pd G3 (433 mg, 0.6 mmol) in 1,4-dioxane (60 mL) and water (7 mL) was degassed and purged with nitrogen (3×), then stirred at 90° C. for 12 h under nitrogen atmosphere. The reaction mixture was quenched with water (100 mL) and extracted with ethyl acetate (3×100 mL). The combined organic extract was washed with brine (100 mL), dried over anhydrous sodium sulfate, filtered, and concentrated in vacuo. The residue was purified by column chromatography on silica gel (petroleum ether/ethyl acetate=10/1 then 1/1) to afford the title compound (4.5 g, 94%) as a yellow solid. LC/MS (ESI) m/z: 804.5 $[M+H]^+$.

Step 13: Preparation of tert-butyl-3-(8-fluoro-7-(7-fluoro-3-(methoxymethoxy)-8-((triisopropylsilyl) ethynyl)naphthalen-1-yl)-2-(2-oxoethoxy)pyrido[4,3-d]pyrimidin-4-yl)-3,8-diazabicyclo[3.2.1]octane-8-carboxylate

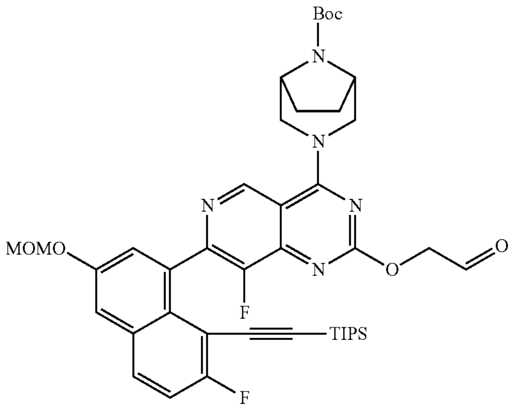

To dimethyl sulfoxide (1.0 mL) in dichloromethane (5 mL) at −78° C. was added oxalyl chloride (0.7 mL, 8 mmol) in dichloromethane (5 mL) dropwise, and the mixture was stirred at −78° C. for 30 min. A solution of tert-butyl 3-[8-fluoro-7-[7-fluoro-3-(methoxy methoxy)-8-(2-triisopropylsilylethynyl)-1-naphthyl]-2-(2-hydroxyethoxy)pyrido[4,3-d]pyrimidin-4-yl]-3,8-diazabicyclo[3.2.1]octane-8-carboxylate (4.3 g, 5 mmol) in dichloromethane (5 mL) was then added dropwise, and the reaction mixture was stirred at −78° C. for 30 min. Triethylamine (0.3 mL, 2 mmol) was then added, And the resulting mixture was stirred at −78° C. for 30 minutes, then warmed to 25° C. and stirred for 1 h. The reaction mixture was diluted with water (20 mL) and extracted with dichloromethane (3×20 mL). The combined organic extract was washed with brine (20 mL), dried over anhydrous sodium sulfate, filtered, and concentrated in vacuo. The residue was purified by column chromatography on silica gel (petroleum ether/ethyl acetate=10/1 then 1/1) to afford the title compound (4.0 g, 93%) as a yellow solid. LC/MS (ESI) m/z: 802.4 $[M+H]^+$; $^1H$ NMR (400 MHz, $CDCl_3$) δ 9.81 (s, 1H), 9.11 (s, 1H), 7.79 (dd, J=5.6, 9.2 Hz, 1H), 7.52 (d, J=2.4 Hz, 1H), 7.36-7.28 (m, 2H), 5.30 (d, J=Step 2: Hz, 2H), 5.07-4.96 (m, 1H), 4.92-4.84 (m, 1H), 4.84-4.66 (m, 1H), 4.54-4.31 (m, 3H), 4.24 (s, 1H), 3.94-3.72 (m, 1H), 3.51 (s, 3H), 2.03-1.92 (m, 2H), 1.78-1.65 (m, 2H), 1.54-1.51 (m, 9H), 0.87 (t, J=7.6 Hz, 18H), 0.64-0.50 (m, 3H).

Step 14: Preparation of tert-butyl 9-[[1-[1-(2,6-dioxo-3-piperidyl)-4-fluoro-3-methyl-2-oxo-benzimidazol-5-yl]-4-piperidyl]methyl]-3,9-diazaspiro[5.5]undecane-3-carboxylate

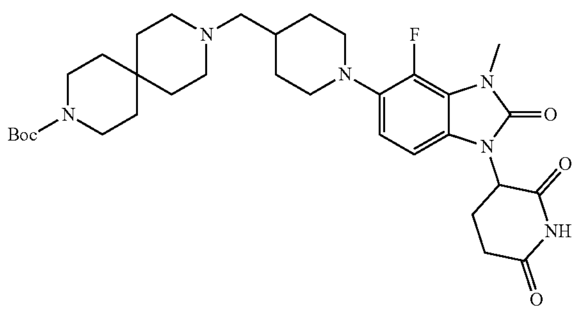 [SMILES: Cn1c(=O)n(C2CCC(=O)NC2=O)c2ccc(N3CCC(CN4CCC5(CC4)CCN(C(=O)OC(C)(C)C)CC5)CC3)c(F)c21]

To a mixture of 1-[1-(2,6-dioxo-3-piperidyl)-4-fluoro-3-methyl-2-oxo-benzimidazol-5-yl]piperidine-4-carbaldehyde (400 mg, 1 mmol) and tert-butyl 3,9-diazaspiro[5.5]undecane-3-carboxylate (314 mg, 1 mmol) in dichloromethane (2 mL) and dimethyl sulfoxide (2 mL) were added sodium triacetoxyborohydride (546 mg, 3 mmol) and acetic acid (0.1 mL, 1 mmol), and the reaction mixture was stirred at 25° C. for 2 h. The mixture was filtered and concentrated under reduced pressure. The residue was purified by prep-TLC (dichloromethane/methanol=10/1) to afford the title compound (450 mg, 69%) as a yellow solid. LC/MS (ESI) m/z: 627.4 $[M+H]^+$.

Step 15: Preparation of 3-[5-[4-(3,9-diazaspiro[5.5]undecan-3-ylmethyl)-1-piperidyl]-4-fluoro-3-methyl-2-oxo-benzimidazol-1-yl]piperidine-2,6-dione

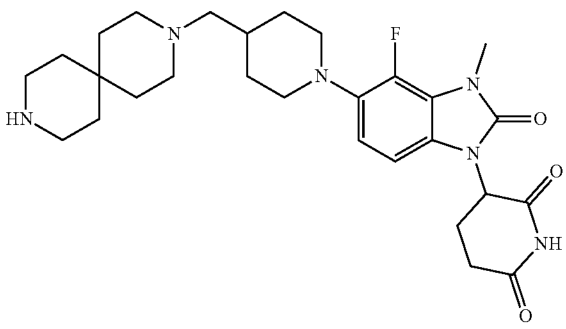 [SMILES: Cn1c(=O)n(C2CCC(=O)NC2=O)c2ccc(N3CCC(CN4CCC5(CCNCC5)CC4)CC3)c(F)c21]

To a solution of tert-butyl 9-[[1-[1-(2,6-dioxo-3-piperidyl)-4-fluoro-3-methyl-2-oxo-benzimidazol-5-yl]-4-piperidyl]methyl]-3,9-diazaspiro[5.5]undecane-3-carboxylate (400 mg, 0.6 mmol) in dichloromethane (30 mL) was added trifluoroacetic acid (8 mL), and the reaction mixture was stirred at 25° C. for 2 h. The mixture was concentrated under reduced pressure, and the residue was triturated with tert-butyl methyl ether (40 mL) to afford the title compound (400 mg, 97%, TFA salt) as a yellow solid. LC/MS (ESI) m/z: 527.3 $[M+H]^+$.

Step 16: Preparation of tert-butyl 3-[2-[2-[3-[[1-[1-(2,6-dioxo-3-piperidyl)-4-fluoro-3-methyl-2-oxo-benzimidazol-5-yl]-4-piperidyl]methyl]-3,9-diazaspiro[5.5] undecan-9-yl]ethoxy]-8-fluoro-7-[7-fluoro-3-(methoxymethoxy)-8-(2-triisopropylsilyl ethynyl)-1-naphthyl]pyrido[4,3-d]pyrimidin-4-yl]-3,8-diazabicyclo[3.2.1]octane-8-carboxylate

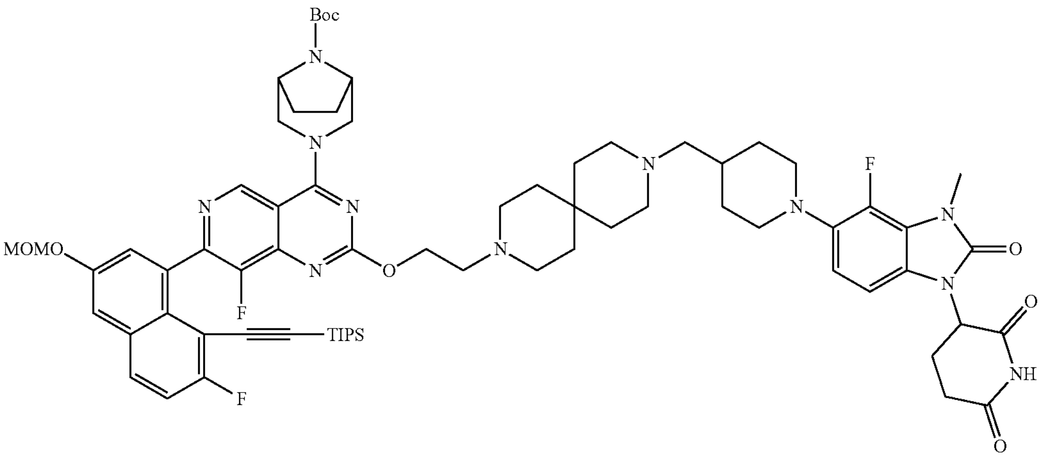

To a solution of 3-[5-[4-(3,9-diazaspiro[5.5]undecan-3-ylmethyl)-1-piperidyl]-4-fluoro-3-methyl-2-oxo-benzimidazol-1-yl]piperidine-2,6-dione trifluoroacetate (400 mg, 0.6 mmol) in dichloromethane (6 mL) and isopropanol (6 mL) were added N,N-diisopropylethylamine (0.1 mL, 0.8 mmol), acetic acid (56 mg, 0.94 mmol), tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (551 mg, 0.7 mmol), and sodium triacetoxyborohydride (331 mg, 1.6 mmol), and the reaction mixture was stirred at 25° C. for 2 h. The mixture was diluted with water (20 mL) and extracted with dichloromethane (200 mL). The organic extract was concentrated under reduced pressure, and the residue was purified by prep-TLC (dichloromethane/methanol=5/1) to afford the title compound (430 mg, 52%) as a yellow solid. LC/MS (ESI) m/z: 1312.9 $[M+H]^+$.

Step 17: Preparation of tert-butyl 3-[2-[2-[3-[[1-[1-(2,6-dioxo-3-piperidyl)-4-fluoro-3-methyl-2-oxo-benzimidazol-5-yl]-4-piperidyl]methyl]-3,9-diazaspiro[5.5] undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1] octane-8-carboxylate

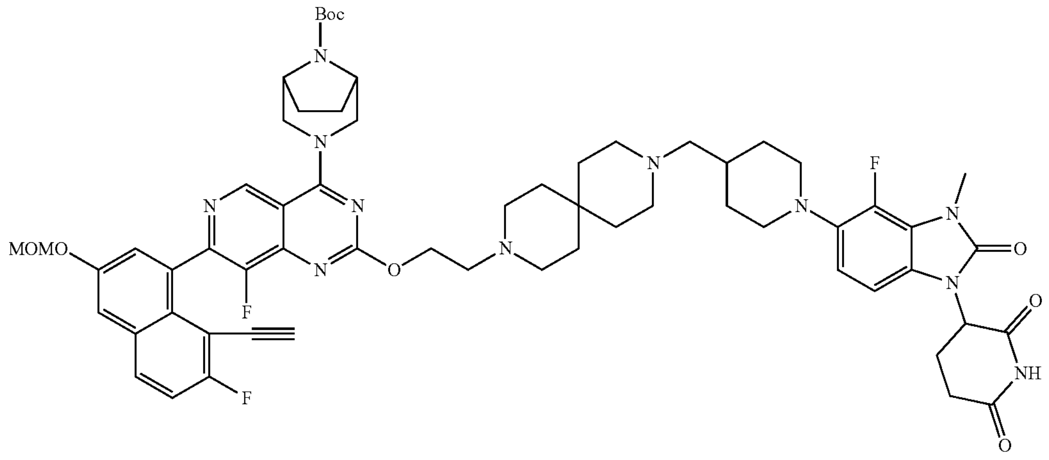

To a solution of tert-butyl 3-[2-[2-[3-[[1-[1-(2,6-dioxo-3-piperidyl)-4-fluoro-3-methyl-2-oxo-benzimidazol-5-yl]-4-piperidyl]methyl]-3,9-diazaspiro[5.5] undecan-9-yl] ethoxy]-8-fluoro-7-[7-fluoro-3-(methoxymethoxy)-8-(2-triisopropylsilyl ethynyl)-1-naphthyl]pyrido[4,3-d] pyrimidin-4-yl]-3,8-diazabicyclo[3.2.1]octane-8-carboxylate (400 mg, 0.3 mmol) in N,N-dimethylformamide (5 mL) was added cesium fluoride (1.4 g, 9 mmol), and the reaction mixture was stirred at 25° C. for 10 h. The mixture was filtered and concentrated under reduced pressure. The residue was purified by prep-HPLC (22% to 52% acetonitrile in water (trifluoroacetic acid) over 15 min) to afford the title compound (140 mg, 39%) as a yellow solid. LC/MS (ESI) m/z: 1156.6 $[M+H]^+$.

Step 18: Preparation of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-4-fluoro-3-methyl-2-oxo-2,3-dihydro-1H-1,3-benzodiazol-1-yl)piperidine-2,6-dione

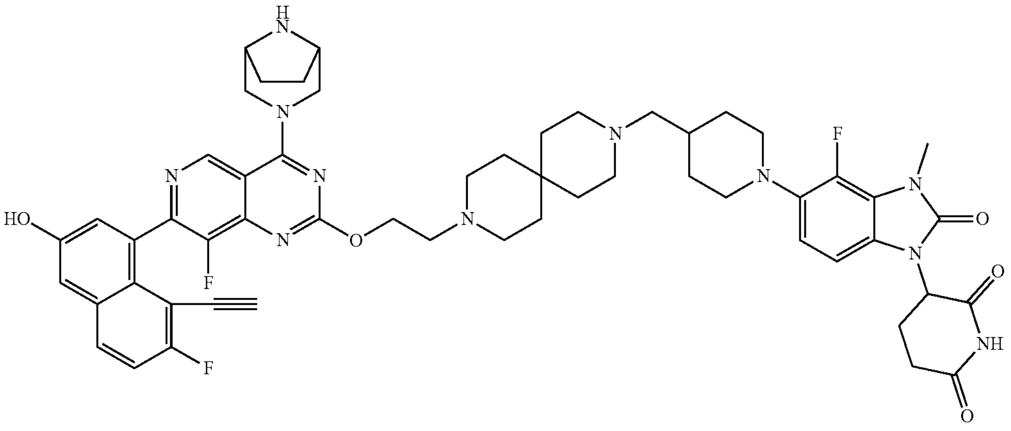 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7F)n(C)c(=O)n8C7CCC(=O)NC7=O)CC5)CC6)nc4c3F)c12]

To a solution of tert-butyl 3-[2-[2-[3-[[1-[1-(2,6-dioxo-3-piperidyl)-4-fluoro-3-methyl-2-oxo-benzimidazol-5-yl]-4-piperidyl]methyl]-3,9-diazaspiro[5.5] undecan-9-yl] ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (140 mg, 0.1 mmol) in dichloromethane (6 mL) was added 4 M HCl in 1,4-dioxane (1.7 mL), and the reaction mixture was stirred at 25° C. for 0.25 h. The mixture was filtered and concentrated under reduced pressure. The residue was purified by prep-HPLC (1% to 28% acetonitrile in water (formic acid) over 10 min) to afford the title compound (49.6 mg, 36%, di-formic acid salt) as a yellow solid. LC/MS (ESI) m/z: 1012.2 $[M+H]^+$, $^1H$ NMR (400 MHz, DMSO-$d_6$) δ 11.10 (s, 1H), 9.05 (s, 1H), 8.20 (s, 2H), 7.98 (dd, J=6.0, 9.2 Hz, 1H), 7.47 (t, J=9.2 Hz, 1H), 7.40 (d, J=2.4 Hz, 1H), 7.18 (d, J=2.4 Hz, 1H), 6.85 (d, J=8.8 Hz, 1H), 6.73 (t, J=8.4 Hz, 1H), 5.33 (dd, J=5.2, 12.8 Hz, 1H), 4.54-4.43 (m, 3H), 4.35 (br d, J=12.0 Hz, 1H), 3.93 (s, 1H), 3.69-3.60 (m, 6H), 3.47 (d, J=1.6 Hz, 4H), 3.21 (br d, J=11.6 Hz, 3H), 2.89 (br s, 1H), 2.75-2.69 (m, 2H), 2.66-2.59 (m, 3H), 2.46 (br s, 3H), 2.35 (br s, 4H), 2.22 (br d, J=7.2 Hz, 2H), 2.05-1.95 (m, 1H), 1.81-1.69 (m, 6H), 1.63 (br dd, J=5.2, 12.8 Hz, 1H), 1.42 (br s, 8H), 1.33-1.20 (m, 2H).

Example 44: Exemplary synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-3-methyl-2-oxo-benzimidazol-1-yl]piperidine-2,6-dione (Compound 198)

Step 1: Preparation of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-piperidine-1-carboxylate

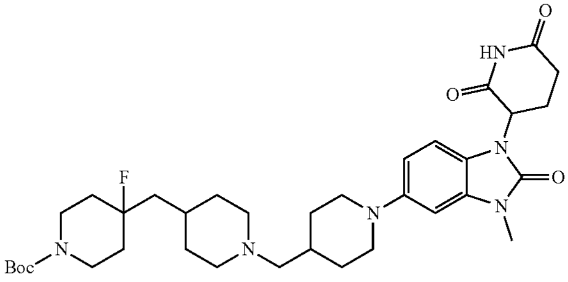 [SMILES: Cn1c(=O)n(C2CCC(=O)NC2=O)c2ccc(N3CCC(CN4CCC(CC5(F)CCN(C(=O)OC(C)(C)C)CC5)CC4)CC3)cc21]

To a solution of 1-[1-(2,6-dioxo-3-piperidyl)-3-methyl-2-oxo-benzimidazol-5-yl]piperidine-4-carbaldehyde (600 mg, 1.6 mmol) and tert-butyl 4-fluoro-4-(4-piperidylmethyl)piperidine-1-carboxylate (535 mg, 1.8 mmol) in dichloromethane (6.0 mL) were added acetic acid (0.3 mL, 5 mmol) and $NaBH(OAc)_3$ (858 mg, 4 mmol), and the reaction mixture was stirred at 25° C. for 12 h. The mixture was diluted with sodium bicarbonate solution (15 mL) and extracted with dichloromethane (3×15 mL). The combined organic extracts were washed with brine (15 mL), dried over sodium sulfate, filtered, and concentrated under reduced pressure. The residue was purified by flash column chromatography on silica gel (0 to 9% methanol in dichloromethane) to afford the title compound (810 mg, 68%) as a white solid. LC/MS (ESI) m/z: 655.2 $[M/+H]^+$.

Step 2: Preparation of 3-[5-[4-[[4-[(4-fluoro-4-piperidyl)methyl]-1-piperidyl]methyl]-1-piperidyl]-3-methyl-2-oxo-benzimidazol-1-yl]piperidine-2,6-dione

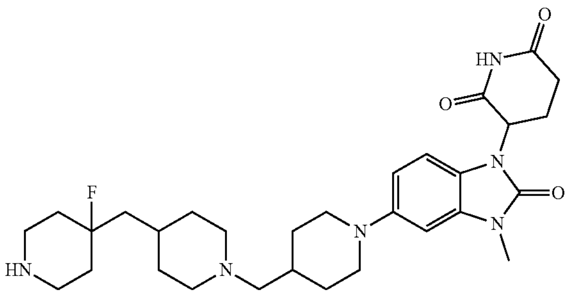 [SMILES: Cn1c(=O)n(C2CCC(=O)NC2=O)c2ccc(N3CCC(CN4CCC(CC5(F)CCNCC5)CC4)CC3)cc21]

To a solution of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-piperidine-1-carboxylate (810 mg, 1 mmol) in dichloromethane (8 mL) was added 4 M HCl in 1,4-dioxane (8.0 mL), and the reaction mixture was stirred at 25° C. for 30 min. The reaction mixture was evaporated from petroleum ether (2×15 mL) to afford the title compound (686 mg, crude, HCl salt) as a white solid. LC/MS (ESI) m/z: 555.3 $[M+H]^+$.

Step 3: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate To a mixture of 3-[5-[4-[[4-[(4-fluoro-4-piperidyl)methyl]-1-piperidyl]methyl]-1-piperidyl]-3-methyl-2-oxo-benzimidazol-1-yl]piperidine-2,6-dione (686 mg, 1.1 mmol) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (992 mg, 1 mmol) in dichloromethane (8.0 mL), isopropanol (8.0 mL), and DMSO (3.0 mL) were added sodium acetate (1.5 g, 18 mmol) and 2-methylpyridine borane (529 mg, 5 mmol), and the reaction mixture was stirred at 25° C. for 12 h. The mixture was filtered and concentrated. The residue was diluted with sodium bicarbonate solution (15 mL) and extracted with dichloromethane (3×20 mL). The combined organic extracts were washed with brine (15 mL), dried over sodium sulfate, filtered, and concentrated under reduced pressure. The residue was purified by flash column chromatography on silica gel (0 to 6% methanol in dichloromethane) followed by by prep-HPLC (6% to 46% acetonitrile in water (HCl) over 36 min) to afford the title compound (220 mg, 12%) as a white solid. LC/MS (ESI) m/z: 1341.0 $[M+H]^+$; $^1H$ NMR (400 MHz, $CDCl_3$) δ 9.08 (s, 1H), 8.40 (s, 1H), 8.15-7.95 (m, 1H), 7.80 (dd, J=5.6, 9.2 Hz, 1H), 7.52 (d, J=2.4 Hz, 1H), 7.35-7.29 (m, 2H), 6.69-6.62 (m, 3H), 5.36-5.25 (m, 2H), 5.18 (dd, J=5.6, 12.8 Hz, 1H), 4.80-4.58 (m, 3H), 4.49-4.32 (m, 2H), 4.21 (br d, J=12.4 Hz, 1H), 3.87-3.70 (m, 1H), 3.58-3.53 (m, 2H), 3.52 (s, 3H), 3.41 (s, 3H), 3.34-3.22 (m, 2H), 3.03-2.91 (m, 5H), 2.88-2.80 (m, 1H), 2.79-2.65 (m, 4H), 2.63-2.58 (m, 3H), 2.46-2.34 (m, 3H), 2.27-2.19 (m, 4H), 2.02-1.96 (m, 5H), 1.92-1.85 (m, 5H), 1.72 (br s, 3H), 1.64 (br s, 1H), 1.58 (br s, 1H), 1.53 (s, 9H), 0.87 (t, J=7.6 Hz, 18H), 0.56 (quin, J=7.2 Hz, 3H).

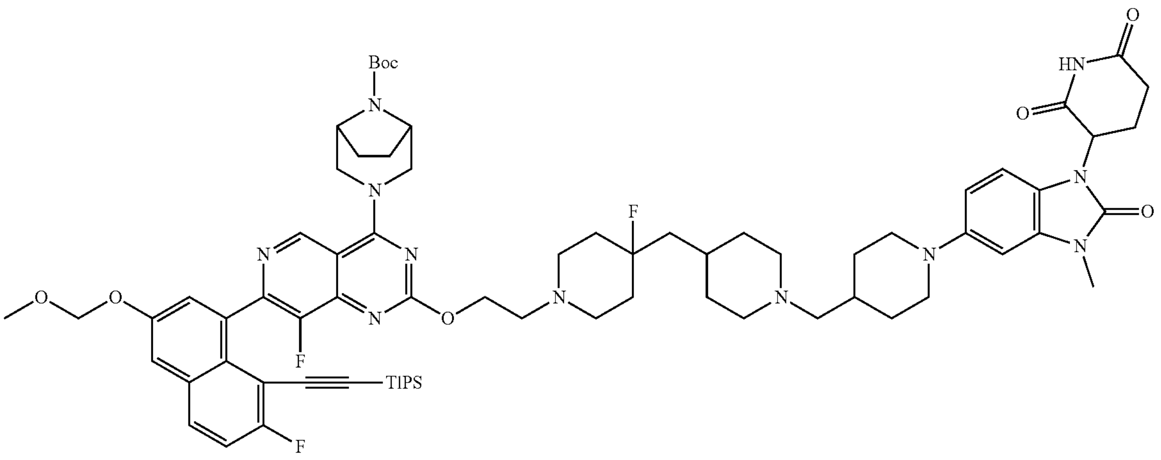

Step 4: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

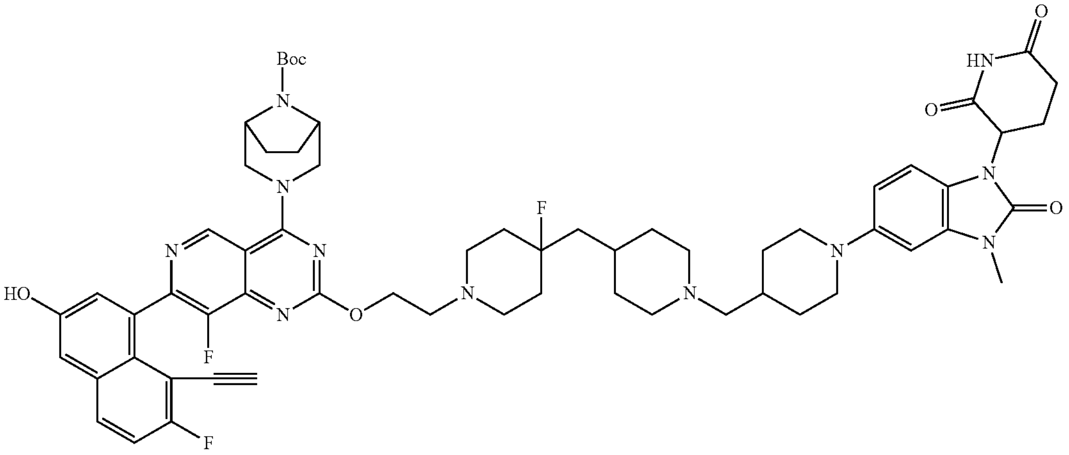

To a solution of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (340 mg, 0.2 mmol) in DMF (3.5 mL) was added cesium fluoride (578 mg, 3.8 mmol), and the reaction mixture was stirred at 25° C. for 1 h. The reaction mixture was filtered, and the filtrate was diluted with water (5.0 mL), then extracted with ethyl acetate (3×15 mL). The combined organic extracts were washed with water (6×5.0 mL) followed by brine (10 mL), dried over sodium sulfate, filtered, and concentrated under reduced pressure to afford the title compound (395 mg, crude) as a yellow foam. LC/MS (ESI) m/z: 1185.6 $[M+H]^+$.

Step 5: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-3-methyl-2-oxo-benzimidazol-1-yl]piperidine-2,6-dione

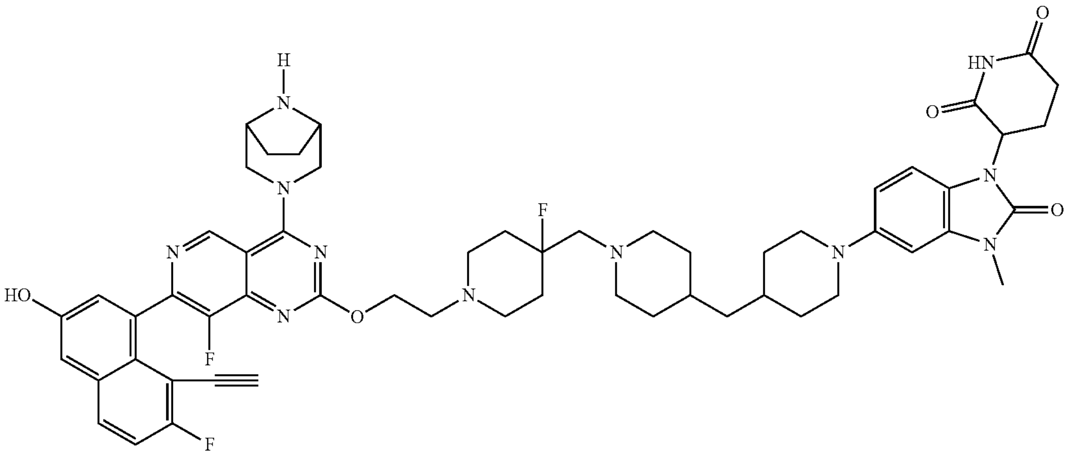 [SMILES: C#Cc1c(F)ccc2cc(O)cc(-c3ncc4c(N5CC6CCC(C5)N6)nc(OCCN5CCC(F)(CN6CCC(CC7CCN(c8ccc9c(c8)n(C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-4-fluoro-1-piperidyl] ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (309 mg, 0.2 mmol) in dichloromethane (4.0 mL) was added 4 M HCl in 1,4-dioxane (4.0 mL), and the reaction mixture was stirred at 25° C. for 30 min. The reaction mixture suspended in petroleum ether (30 mL) and filtered. The filter cake was dissolved in tetrahydrofuran (5 mL) and triethylamine was then added to adjust the pH to 8. The mixture was purified by prep-HPLC (20% to 60% acetonitrile in water (ammonium bicarbonate) over 32 min) to afford the title compound (112.2 mg, 32%) as a yellow solid. LC/MS (ESI) m/z: 1040.4 $[M+H]^+$; $^1H$ NMR (400 MHz, $CD_3OD$) δ 9.01 (s, 1H), 7.86 (dd, J=5.6, 8.8 Hz, 1H), 7.36-7.29 (m, 2H), 7.21 (d, J=2.4 Hz, 1H), 6.98 (d, J=8.4 Hz, 1H), 6.88 (d, J=2.0 Hz, 1H), 6.80 (dd, J=1.6, 9.2 Hz, 1H), 5.28 (dd, J=5.2, 12.8 Hz, 1H), 4.60 (br s, 4H), 3.77-3.63 (m, 4H), 3.59 (br d, J=12.0 Hz, 2H), 3.40 (s, 3H), 3.37 (s, 1H), 3.01-2.83 (m, 7H), 2.83-2.74 (m, 2H), 2.74-2.65 (m, 2H), 2.52-2.42 (m, 2H), 2.32-2.30 (m, 2H), 2.19-2.11 (m, 1H), 2.11-1.99 (m, 2H), 1.94-1.83 (m, 6H), 1.82-1.74 (m, 4H), 1.73-1.69 (m, 1H), 1.68-1.65 (m, 1H), 1.65-1.61 (m, 1H), 1.61-1.57 (m, 1H), 1.52 (br d, J=6.0 Hz, 1H), 1.28-1.28 (m, 1H), 1.48-1.26 (m, 4H).

Example 45: Exemplary Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-fluoropiperidin-4-yl)methyl]piperidin-4-yl}methyl)piperidin-1-yl]-3-methyl-2-oxo-2,3-dihydro-1H-1,3-benzodiazol-1-yl}piperidine-2,6-dione (Compound 183)

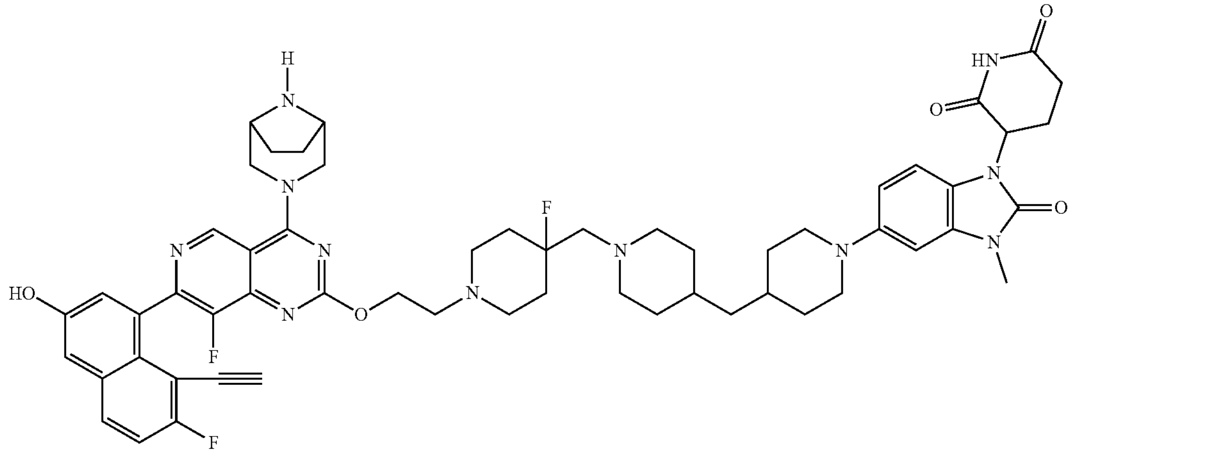

The title compound was made in an analogous manner to 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl] methyl]-1-piperidyl]methyl]-1-piperidyl]-3-methyl-2-oxo-benzimidazol-1-yl]piperidine-2,6-dione. (light yellow solid). LC/MS (ESI) m/z: 1040.5 $[M+H]^+$; $^1H$ NMR (400 MHz, $CD_3OD$) δ 9.01 (s, 1H), 7.88-7.84 (m, 1H), 7.35-7.30 (m, 2H), 7.21-7.20 (m, 1H), 6.99-6.96 (m, 1H), 6.87-6.86 (m, 1H), 6.81-6.78 (m, 1H), 5.30-5.25 (m, 1H), 4.69-4.57 (m, 4H), 3.73-3.67 (m, 4H), 3.58-3.54 (m, 2H), 3.40 (s, 3H), 3.37 (s, 1H), 2.95-2.87 (m, 7H), 2.81-2.75 (m, 2H), 2.70-2.65 (m, 2H), 2.52-2.44 (m, 4H), 2.18-2.09 (m, 3H), 1.90-1.79 (m, 9H), 1.70-1.61 (m, 3H), 1.55-1.46 (m, 1H), 1.39-1.34 (m, 3H), 1.25-1.19 (m, 4H).

Example 46: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4,7-difluoro-3-methyl-2-oxo-2,3-dihydro-1H-1,3-benzodiazol-1-yl}piperidine-2,6-dione (Compound 199)

Step 1: Preparation of 4-bromo-2,3,6-trifluoro-aniline

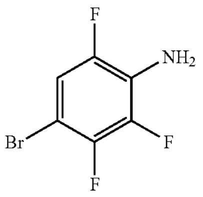 [SMILES: Nc1c(F)cc(Br)c(F)c1F]

To a solution of 2,3,6-trifluoroaniline (12.5 g, 85 mmol) in N,N-dimethylformamide (200 mL) was added 1-bromopyrrolidine-2,5-dione (18.15 g, 102 mmol), and the mixture was allowed to stir at 20° C. for 2 h. The reaction mixture was diluted with water (1000 mL) and extracted with ethyl acetate (3×150 mL). The combined organic extracts were washed with brine (3×300 mL), dried over anhydrous sodium sulfate, filtered, and concentrated under reduced pressure. The residue was purified by silica gel column chromatography (petroleum ether/ethyl acetate=1/0 to 20/1) to afford the title compound (37.3 g, 97%) as a dark red oil. $^1$H NMR (400 MHz, DMSO-$d_6$) δ 7.34-7.30 (m, 1H), 5.79-5.69 (m, 2H).

Step 2: Preparation of 1-bromo-2,3,5-trifluoro-4-nitro-benzene

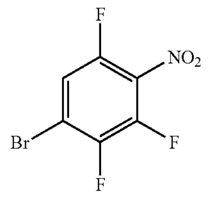 [SMILES: O=[N+]([O-])c1c(F)cc(Br)c(F)c1F]

To a suspension of sodium perborate tetrahydrate (85.1 mL, 442 mmol) in acetic acid (100 mL) was added a solution of 4-bromo-2,3,6-trifluoro-aniline (10 g, 44 mmol) in acetic acid (100 mL) dropwise, and the reaction mixture was stirred at 80° C. for 12 h. The mixture was diluted with water (1000 mL) and extracted with ethyl acetate (3×300 mL). The combined organic extracts were washed with brine (3×500 mL), dried over anhydrous sodium sulfate, filtered, and concentrated under reduced pressure. The residue was purified by silica gel column chromatography (petroleum ether/ethyl acetate=1/0) to afford the title compound (3.1 g, 27%) as a red solid. $^1$H NMR (400 MHz, DMSO-$d_6$) δ 8.20-8.15 (m, 1H).

Step 3: Preparation of 3-bromo-2,5-difluoro-N-methyl-6-nitroaniline

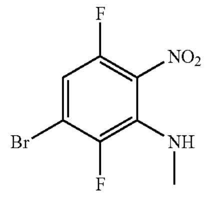

To a solution of 1-bromo-2,3,5-trifluoro-4-nitro-benzene (9.3 g, 36 mmol) in tetrahydrofuran (100 mL) were added methanamine hydrochloride (3.68 g, 54 mmol) and triethylamine (15.2 mL, 109 mmol) at 0° C., and the reaction mixture was stirred at 20° C. for 12 h. The mixture was diluted with water (60 mL) and extracted with ethyl acetate (3×30 mL). The combined organic extracts were washed with brine (3×50 mL), dried over anhydrous sodium sulfate, filtered, and concentrated under reduced pressure. The residue was purified by silica gel column chromatography (petroleum ether/ethyl acetate=1/0 to 50/1) to afford the title compound (9 g, 92%) as a dark red oil.

Step 4: Preparation of 5-bromo-3,6-difluoro-N1-methylbenzene-1,2-diamine

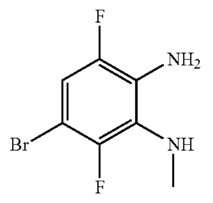

A mixture of 3-bromo-2,5-difluoro-N-methyl-6-nitroaniline (15 g, 56 mmol) and 3% platino-vanadium carbon (4 g) in tetrahydrofuran (300 mL) was loaded into a FLV1 flow chemistry reactor at 20° C., and the mixture was stirred for 10 minutes at 20° C. The backpressure regulator was set at 1.5 MPa, the flow rate of P1 was set at 0.5 mL/min, the flow rate of hydrogen was set at 30 mL/min, and the oven temperature was set at 60° C. The reaction mixture was stirred at 60° C. for 2.5 minutes, then filtered and concentrated under reduced pressure to afford the title compound (8 g, 60%) as a yellow oil.

Step 5: Preparation of 6-bromo-4,7-difluoro-1-methyl-1,3-dihydro-2H-benzo[d]imidazol-2-one

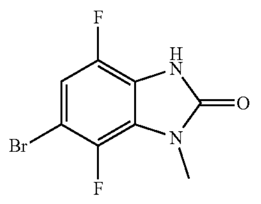

To a solution of 5-bromo-3,6-difluoro-N1-methylbenzene-1,2-diamine (8.0 g, 34 mmol) in tetrahydrofuran (100 mL) were added 1,1'-carbonyldiimidazole (6.02 g, 37 mmol) and triethylamine (7.1 mL, 51 mmol), and the reaction mixture was stirred at 70° C. for 10 h. The mixture was filtered and concentrated under reduced pressure. The residue was purified by prep-HPLC (20% to 50% acetonitrile in water (trifluoroacetic acid) over 30 min) to afford the title compound (6.5 g, 73%) as a yellow solid. LC/MS (ESI) m/z: 264.9 $[M+H]^+$.

Step 6: Preparation of 5-bromo-4,7-difluoro-3-methyl-1-(2-trimethylsilylethoxymethyl)benzimidazol-2-one

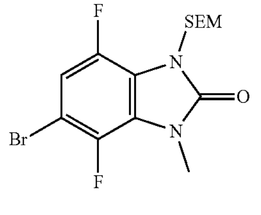 [SMILES: Cn1c(=O)n(COCC[Si](C)(C)C)c2c(F)cc(Br)c(F)c21]

To a solution of 5-bromo-4,7-difluoro-3-methyl-1H-benzimidazol-2-one (4.0 g, 15 mmol) in N,N-dimethylformamide (60 mL) was added sodium hydride (760 mg, 19 mmol, 60% in mineral oil), and the resulting mixture was stirred at 0° C. for 0.5 h under nitrogen atmosphere. 2-(Trimethyl silyl)ethoxymethyl chloride (4.0 mL, 23 mmol) was then added at 0° C., and the resulting mixture was stirred at 25° C. for 2 h. The reaction mixture was diluted with saturated ammonium chloride solution (60 mL) at 0° C. and extracted with ethyl acetate (200 mL). The combined organic extracts were concentrated under reduced pressure, and the residue was purified by silica gel column chromatography (petroleum ether/ethyl acetate=20/1 to 15/1) to afford the title compound (4.7 g, 74%) as white solid. $^1$H NMR (400 MHz, $CDCl_3$) δ 7.04 (br d, J=4.8, 1H), 5.36 (s, 2H), 3.66-3.60 (m, 5H), 0.95-0.91 (m, 2H), 0.02 (s, 9H).

Step 7: Preparation of 5-(4-(dimethoxymethyl)piperidin-1-yl)-4,7-difluoro-3-methyl-1-((2-(trimethylsilyl)ethoxy)methyl)-1,3-dihydro-2H-benzo[d]imidazol-2-one

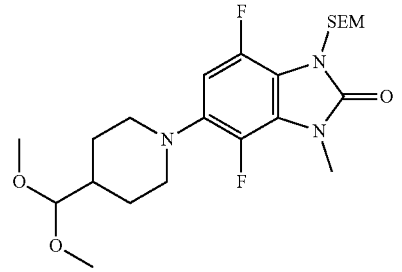 [SMILES: COC(OC)C1CCN(c2cc(F)c3c(c2F)n(C)c(=O)n3COCC[Si](C)(C)C)CC1]

To a mixture of 5-bromo-4,7-difluoro-3-methyl-1-(2-trimethylsilylethoxymethyl)benzimidazol-2-one (5.5 g, 14 mmol), 4-(dimethoxymethyl)piperidine (4.45 g, 28 mmol), and cesium carbonate (9.11 g, 28 mmol) in 1,4-dioxane (90 mL) was added Pd-PEPPSI-IPent (680 mg, 0.7 mmol) at 25° C. under nitrogen atmosphere, and the reaction mixture was heated to 100° C. and stirred for 6 h under nitrogen atmosphere. The mixture was cooled to 25° C., diluted with ethyl acetate (100 mL), then washed with brine (2×30 mL), dried over anhydrous sodium sulfate, filtered, and concentrated under reduced pressure. The residue was purified by silica gel chromatography (petroleum ether/ethyl acetate=10/1 then 4/1) to afford the title compound (5.7 g, 82%) as a white solid. LC/MS (ESI) m/z: 472.2 $[M+H]^+$.

Step 8: Preparation of 5-[4-(dimethoxymethyl)-1-piperidyl]-4,7-difluoro-3-methyl-1H-benzimidazol-2-one

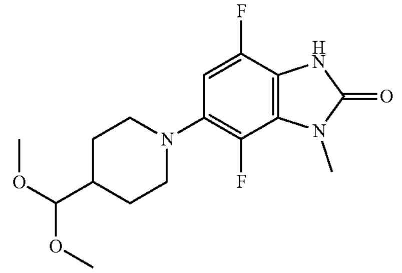 [SMILES: COC(OC)C1CCN(c2cc(F)c3[nH]c(=O)n(C)c3c2F)CC1]

A mixture of 5-(4-(dimethoxymethyl)piperidin-1-yl)-4,7-difluoro-3-methyl-1-((2-(trimethylsilyl)ethoxy)methyl)-1,3-dihydro-2H-benzo[d]imidazol-2-one (5.6 g, 12 mmol) in tetrabutylammonium fluoride (1 M in THF, 60 mL) was heated to 80° C. and stirred for 72 h under nitrogen atmosphere. The mixture was cooled to 25° C. and concentrated. The residue was poured into ice-water (w/w=1/1, 100 mL) and stirred for 15 min. The aqueous phase was extracted with ethyl acetate (3×100 mL). The combined organic extract was washed with brine (2×100 mL), dried over anhydrous sodium sulfate, filtered, and concentrated under reduced pressure. The residue was triturated with t-butyl methyl ether (50 mL) to afford the title compound (2.8 g, 69%) as a yellow solid. LC/MS (ESI) m/z: 342.1 $[M+H]^+$; $^1$H NMR (400 MHz, DMSO-$d_6$) δ 11.38 (s, 1H), 6.59 (br d, J=6.4 Hz, 1H), 4.12 (d, J=6.4 Hz, 1H), 3.40 (s, 3H), 3.28 (s, 6H), 3.26 (d, J=14.4 Hz, 2H), 2.57-2.51 (m, 2H), 1.73-1.70 (m, 3H), 1.38-1.37 (m, 2H).

Step 9: Preparation of 1-(2,6-dibenzyloxy-3-pyridyl)-5-[4-(dimethoxymethyl)-1-piperidyl]-4,7-difluoro-3-methyl-benzimidazol-2-one

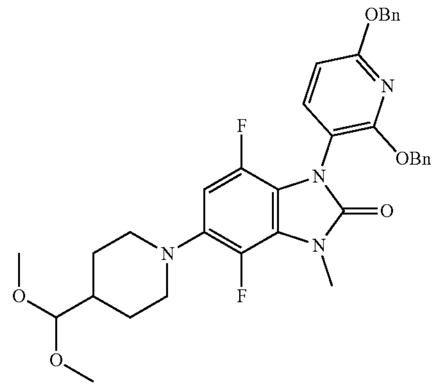 [SMILES: COC(OC)C1CCN(c2cc(F)c3c(c2F)n(C)c(=O)n3-c2ccc(OCc3ccccc3)nc2OCc2ccccc2)CC1]

To a solution of 5-[4-(dimethoxymethyl)-1-piperidyl]-4,7-difluoro-3-methyl-1H-benzimidazol-2-one (2.0 g, 6 mmol) and 2,6-dibenzyloxy-3-iodo-pyridine (7.33 g, 18 mmol) in dimethyl sulfoxide (50 mL) were added cuprous oxide (168 mg, 1.2 mmol), N,N'-bis(2-furylmethyl)oxamide (582 mg, 2.3 mmol), and potassium phosphate (3.73 g, 17.58 mmol) under nitrogen atmosphere, and the reaction mixture was heated to 120° C. and stirred for 24 h under nitrogen atmosphere. The mixture was cooled to 25° C. and poured into ice-water (w/w=1/1, 100 mL). The resulting mixture was extracted with ethyl acetate (3×100 mL), and the combined organic extract was washed with brine (2×100 mL), dried over anhydrous sodium sulfate, filtered, and concentrated under reduced pressure. The residue was purified by silica gel chromatography (petroleum ether/ethyl acetate=10/1 then 3/1) to afford the title compound (1.6 g, 43%) as a yellow solid. LC/MS (ESI) m/z: 631.3 $[M+H]^+$.

Step 10: Preparation of 3-[5-[4-(dimethoxymethyl)-1-piperidyl]-4,7-difluoro-3-methyl-2-oxo-benzimidazol-1-yl]piperidine-2,6-dione

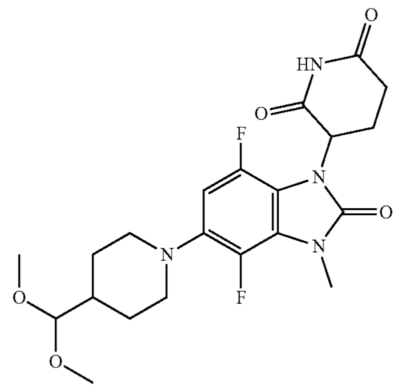 [SMILES: COC(OC)C1CCN(c2cc(F)c3c(c2F)n(C)c(=O)n3C2CCC(=O)NC2=O)CC1]

To a solution of 1-(2,6-dibenzyloxy-3-pyridyl)-5-[4-(dimethoxymethyl)-1-piperidyl]-4,7-difluoro-3-methyl-benzimidazol-2-one (1.4 g, 2 mmol) in tetrahydrofuran (15 mL) were added 10% palladium on carbon (0.3 g) and 20% palladium hydroxide on carbon (0.3 g) under nitrogen atmosphere. The suspension was degassed under vacuum and purged with hydrogen several times. The reaction mixture was then stirred under hydrogen (50 psi) at 50° C. for 16 h. The mixture was filtered and concentrated under reduced pressure. The resulting material was triturated with tert-butyl methyl ether (50 mL) to afford the title compound (740 mg, 73%) as a gray solid. LC/MS (ESI) m/z: 453.2 $[M+H]^+$.

Step 11: Preparation of 1-[1-(2,6-dioxo-3-piperidyl)-4,7-difluoro-3-methyl-2-oxo-benzimidazol-5-yl]piperidine-4-carbaldehyde

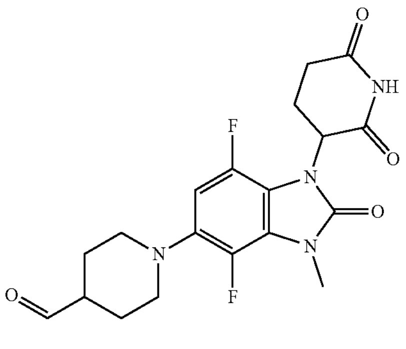 [SMILES: Cn1c(=O)n(C2CCC(=O)NC2=O)c2c(F)cc(N3CCC(C=O)CC3)c(F)c21]

To a solution of 3-[5-[4-(dimethoxymethyl)-1-piperidyl]-4,7-difluoro-3-methyl-2-oxo-benzimidazol-1-yl]piperidine-2,6-dione (740 mg, 1.6 mmol) in dichloromethane (3 mL) was added trifluoroacetic acid (3 mL), and the reaction mixture was stirred at 25° C. for 2 h. The mixture was concentrated under reduced pressure, and the residue was triturated with methyl tert-butyl ether (30 mL) to afford the title compound (525 mg, crude) as a yellow solid. LC/MS (ESI) m/z: 407.1 $[M+H]^+$.

Step 12: Preparation of tert-butyl 4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]piperidine-1-carboxylate

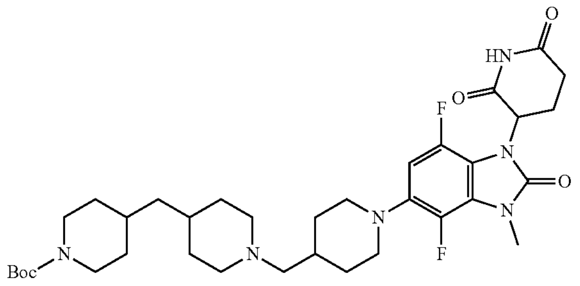 [SMILES: Cn1c(=O)n(C2CCC(=O)NC2=O)c2c(F)cc(N3CCC(CN4CCC(CC5CCN(C(=O)OC(C)(C)C)CC5)CC4)CC3)c(F)c21]

To a solution of 1-[1-(2,6-dioxo-3-piperidyl)-4,7-difluoro-3-methyl-2-oxo-benzimidazol-5-yl]piperidine-4-carbaldehyde (200 mg, 0.5 mmol) in dichloromethane (3 mL) and dimethyl sulfoxide (3 mL) were added N,N-diisopropylethylamine (0.3 mL, 1 mmol), tert-butyl 4-(4-piperidylmethyl)piperidine-1-carboxylate (167 mg, 0.6 mmol), and sodium triacetoxyborohydride (209 mg, 1 mmol), and the reaction mixture was stirred at 25° C. for 2 h. The mixture was poured into water (20 mL) and extracted with dichloromethane (2×10 mL). The combined organic extract was washed with brine (2×10 mL), dried over anhydrous sodium sulfate, filtered, and concentrated under reduced pressure to afford the title compound (290 mg, crude) as a yellow solid. LC/MS (ESI) m/z: 673.4 $[M+H]^+$.

Step 13: Preparation of 3-[4,7-difluoro-3-methyl-2-oxo-5-[4-[[4-(4-piperidylmethyl)-1-piperidyl]methyl]-1-piperidyl]benzimidazol-1-yl]piperidine-2,6-dione

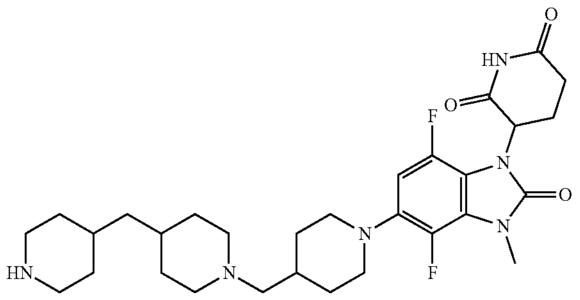

To a solution of tert-butyl 4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]piperidine-1-carboxylate (430 mg, 0.6 mmol) in dichloromethane (4 mL) was added trifluoroacetic acid (2.0 mL, 27 mmol), and the reaction mixture was stirred at 25° C. for 1 h. The mixture was concentrated under reduced pressure to afford the title compound (438 mg, crude, TFA salt) as a yellow gum. LC/MS (ESI) m/z: 573.5 $[M+H]^+$.

Step 14: Preparation of tert-butyl 3-[2-[2-[4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

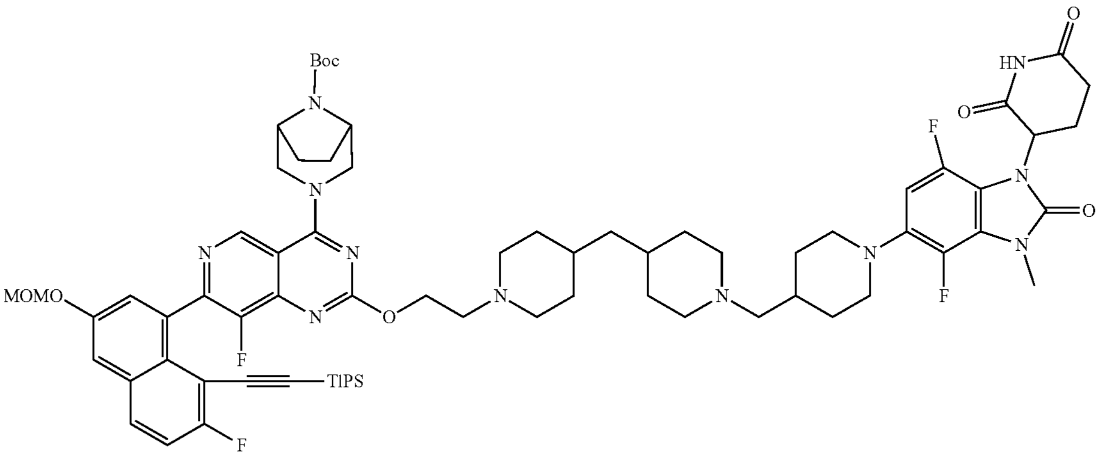

To a solution of 3-[4,7-difluoro-3-methyl-2-oxo-5-[4-[[4-(4-piperidylmethyl)-1-piperidyl]methyl]-1-piperidyl]benzimidazol-1-yl]piperidine-2,6-dione (438 mg, TFA salt) in dichloromethane (3 mL) and isopropanol (3 mL) were added N,N-diisopropylethylamine (0.3 mL, 2 mmol), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (614 mg, 0.8 mmol), and sodium triacetoxyborohydride (270 mg, 1.3 mmol), and the reaction mixture was stirred at 25° C. for 2 h. The mixture was poured into water (30 mL) and extracted with dichloromethane (2×15 mL). The combined organic extract was washed with brine (2×15 mL), dried over anhydrous sodium sulfate, filtered, and concentrated under reduced pressure. The residue was purified by flash silica gel chromatography (0 to 10% dichloromethane/methanol) to afford the title compound (410 mg, 47%) as a yellow solid. LC/MS (ESI) m/z: 1359.9 $[M+H]^+$.

Step 15: Preparation of tert-butyl 3-[2-[2-[4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

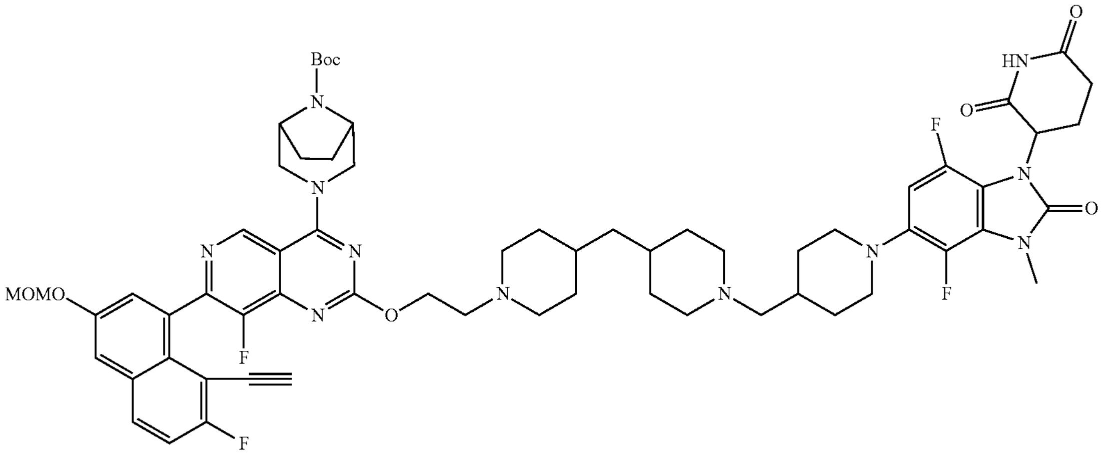

To a solution of tert-butyl 3-[2-[2-[4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (410 mg, 0.3 mmol) in N,N-dimethylformamide (10 mL) at 20° C. was added cesium fluoride (1.15 g, 7.5 mmol), and the reaction mixture was stirred for 2 h at 20° C. The mixture was diluted with water (20 mL) and extracted with ethyl acetate (3×20 mL). The combined organic extract was washed with saturated sodium bicarbonate solution (20 mL) followed by brine (20 mL), dried over anhydrous sodium sulfate, filtered, and concentrated in vacuo to afford the title compound (250 mg, 69%) as a yellow solid. LC/MS (ESI) m/z: 1202.8 [M+H]+.

Step 16: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4,7-difluoro-3-methyl-2-oxo-2,3-dihydro-1H-1,3-benzodiazol-1-yl}piperidine-2,6-dione

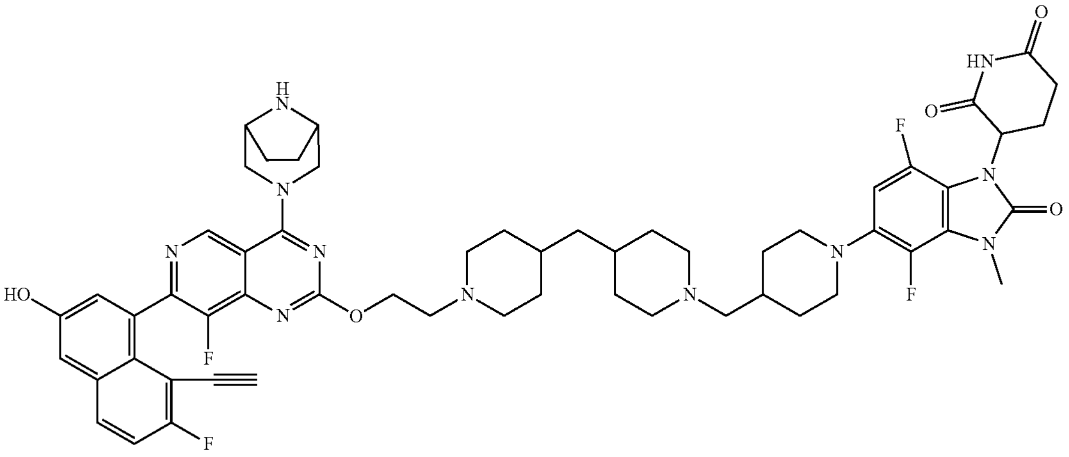 [SMILES: C#Cc1c(F)ccc2cc(O)cc(-c3ncc4c(N5CC6CCC(C5)N6)nc(OCCN5CCC(CC6CCN(CC7CCN(c8cc(F)c9c(c8F)n(C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-4,7-difluoro-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (250 mg, 0.2 mmol) in dichloromethane (5 mL) was added 4 M HCl in 1,4-dioxane (2.5 mL) at 20° C., and the reaction mixture was stirred for 0.5 h at 20° C. The mixture was suspended in tert-butyl methyl ether (5 mL) and filtered to afford a yellow solid. This crude product was purified by prep-HPLC (8% to 38% acetonitrile in water (formic acid) over 10 min) to afford the title compound (162.8 mg, 66%, di-formic acid salt) as a yellow solid. LC/MS (ESI) m/z: 1058.7 [M+H]+; $^1$H NMR (400 MHz, DMSO-$d_6$) δ 11.11 (br s, 1H), 9.06 (s, 1H), 8.20 (s, 3H), 7.97 (dd, J=6.0, 9.2 Hz, 1H), 7.46 (t, J=9.2 Hz, 1H), 7.40 (d, J=2.4 Hz, 1H), 7.18 (d, J=2.4 Hz, 1H), 6.64 (br dd, J=6.0, 12.4 Hz, 1H), 5.53-5.40 (m, 1H), 4.54 (br d, J=12.4 Hz, 1H), 4.47 (br t, J=5.6 Hz, 2H), 4.39 (br d, J=1 Step 2: Hz, 1H), 3.93 (s, 1H), 3.80 (br s, 3H), 3.72 (br t, J=1 Step 6: Hz, 4H), 3.49 (br s, 3H), 3.25-3.20 (m, 2H), 2.96 (br d, J=9.2 Hz, 3H), 2.88 (br d, J=10.8 Hz, 2H), 2.76-2.70 (m, 2H), 2.60 (br d, J=10.8 Hz, 2H), 2.25 (br d, J=6.4 Hz, 2H), 2.10-1.93 (m, 5H), 1.78 (br s, 6H), 1.67-1.55 (m, 5H), 1.36-1.23 (m, 4H), 1.16-1.03 (m, 6H).

Example 51: Synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]piperazin-1-yl]methyl]-1-piperidyl]-3-methyl-2-oxo-benzimidazol-1-yl]piperidine-2,6-dione (Compound 200)

Step 1: Preparation of tert-butyl 4-[[4-[[1-[1-(2,6-dioxo-3-piperidyl)-3-methyl-2-oxo-benzimidazol-5-yl]-4-piperidyl]methyl]piperazin-1-yl]methyl]-4-fluoro-piperidine-1-carboxylate

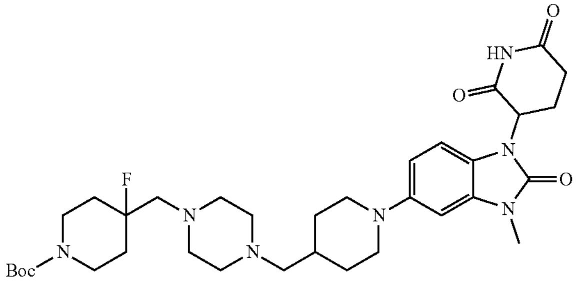 [SMILES: Cn1c(=O)n(C2CCC(=O)NC2=O)c2ccc(N3CCC(CN4CCN(CC5(F)CCN(C(=O)OC(C)(C)C)CC5)CC4)CC3)cc21]

To a solution of (3-[3-methyl-2-oxo-5-[4-(piperazin-1-ylmethyl)-1-piperidyl]benzimidazol-1-yl]piperidine-2,6-dione (400 mg, 0.9 mmol) and tert-butyl 4-fluoro-4-formyl-piperidine-1-carboxylate (419 mg, 1.8 mmol) in isopropanol (5 mL) and dichloromethane (5 mL) were added sodium acetate (744 mg, 9 mmol) and 2-picoline borane (291.4 mg, 2.7 mmol), and the reaction mixture was stirred at 20° C. for 15 h. The mixture was diluted with saturated sodium bicarbonate solution (30 mL) and extracted with dichloromethane (3×50 mL). The combined organic extract was washed with water (2×40 mL) and brine (30 mL), dried over anhydrous sodium sulfate, filtered, and concentrated under reduced pressure. The residue was purified by flash column chromatography on silica gel (0 to 5% methanol in dichloromethane) to afford the title compound (330 mg, 38%) as a white solid. LC/MS (ESI) m/z: 656.2 [M+H]+.

Step 2: Preparation of 3-[5-[4-[[4-[(4-fluoro-4-piperidyl)methyl]piperazin-1-yl]methyl]-1-piperidyl]-3-methyl-2-oxo-benzimidazol-1-yl]piperidine-2,6-dione

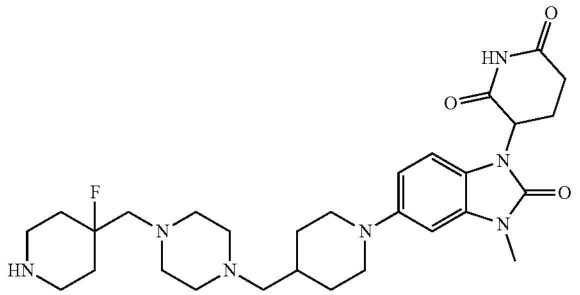 [SMILES: Cn1c(=O)n(C2CCC(=O)NC2=O)c2ccc(N3CCC(CN4CCN(CC5(F)CCNCC5)CC4)CC3)cc21]

To a solution of tert-butyl 4-[[4-[[1-[1-(2,6-dioxo-3-piperidyl)-3-methyl-2-oxo-benzimidazol-5-yl]-4-piperidyl] methyl]piperazin-1-yl]methyl]-4-fluoro-piperidine-1-carboxylate (330 mg, 0.3 mmol) in dichloromethane (3 mL) was added 4 M HCl in 1,4-dioxane (1.7 mL), and the reaction mixture was stirred at 20° C. for 15 min. The mixture was triturated with petroleum ether (50 mL) to afford the title compound (205 mg, crude, HCl salt) as a white solid. LC/MS (ESI) m/z: 556.3 $[M+H]^+$.

Step 3: Preparation of tert-butyl 3-[2-[2-[4-[[4-[[1-[1-(2,6-dioxo-3-piperidyl)-3-methyl-2-oxo-benzimidazol-5-yl]-4-piperidyl]methyl]piperazin-1-yl] methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d] pyrimidin-4-yl]-3,8-diazabicyclo[3.2.1]octane-8-carboxylate

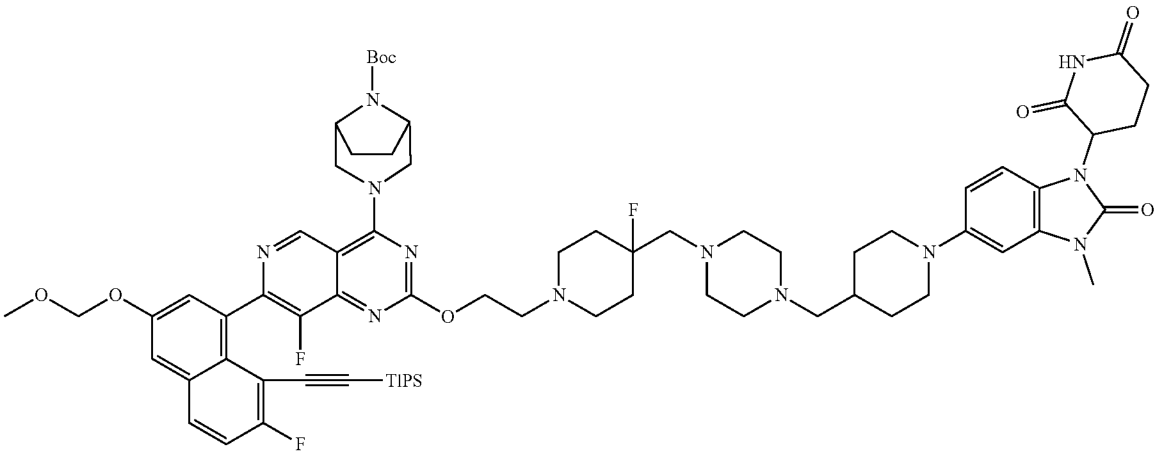

To a mixture of (3-[5-[4-[[4-[(4-fluoro-4-piperidyl) methyl]piperazin-1-yl]methyl]-1-piperidyl]-3-methyl-2-oxo-benzimidazol-1-yl]piperidine-2,6-dione (205 mg, 0.3 mmol, HCl) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (360 mg, 0.4 mmol) in dichloromethane (5 mL) and isopropanol (5 mL) were added sodium acetate (284 mg, 3.5 mmol) and 2-picoline borane (185 mg, 1.7 mmol), and the reaction mixture was stirred at 20° C. for 12 h. The mixture was concentrated under reduced pressure, and the residue was purified by flash column chromatography on silica gel (0 to 8% methanol in dichloromethane) to afford the title compound (400 mg, 79%) as a yellow solid. LC/MS (ESI) m/z: 671.6 $[M/2+H]^+$.

Step 4: Preparation of tert-butyl 3-[2-[2-[4-[[4-[[1-[1-(2,6-dioxo-3-piperidyl)-3-methyl-2-oxo-benzimidazol-5-yl]-4-piperidyl]methyl]piperazin-1-yl]methyl]-4-fluoro-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

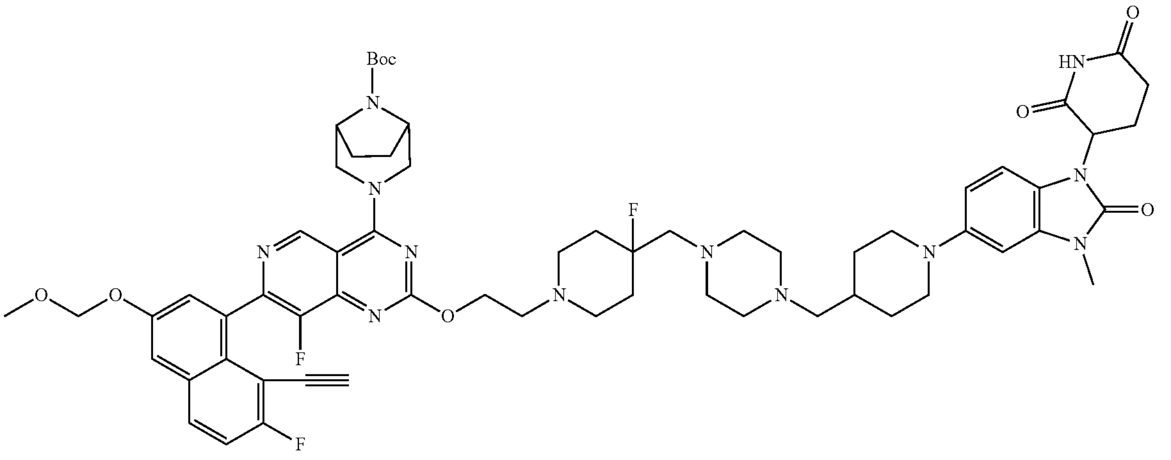 [SMILES: C#Cc1c(F)ccc2cc(OCOC)cc(-c3ncc4c(N5CC6CCC(C5)N6C(=O)OC(C)(C)C)nc(OCCN5CCC(F)(CN6CCN(CC7CCN(c8ccc9c(c8)n(C)c(=O)n9C8CCC(=O)NC8=O)CC7)CC6)CC5)nc4c3F)c12]

To a solution of tert-butyl 3-[2-[2-[4-[[4-[[1-[1-(2,6-dioxo-3-piperidyl)-3-methyl-2-oxo-benzimidazol-5-yl]-4-piperidyl]methyl]piperazin-1-yl]methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (400 mg, 0.3 mmol) in DMF (3 mL) was added cesium fluoride (624 mg, 4.1 mmol), and the reaction mixture was stirred at 20° C. for 1 h. The mixture was filtered, washing with ethyl acetate (30 mL). The filtrate was diluted with water (50 mL) and extracted with ethyl acetate (3×30 mL). The combined organic extract was washed with water (3×30 mL) followed by brine (30 mL), dried over anhydrous sodium sulfate, filtered, and concentrated under reduced pressure to afford the title compound (280 mg, crude) as a yellow solid. LC/MS (ESI) m/z: 593.6 $[M/2+H]^+$.

Step 5: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]piperazin-1-yl]methyl]-1-piperidyl]-3-methyl-2-oxo-benzimidazol-1-yl]piperidine-2,6-dione

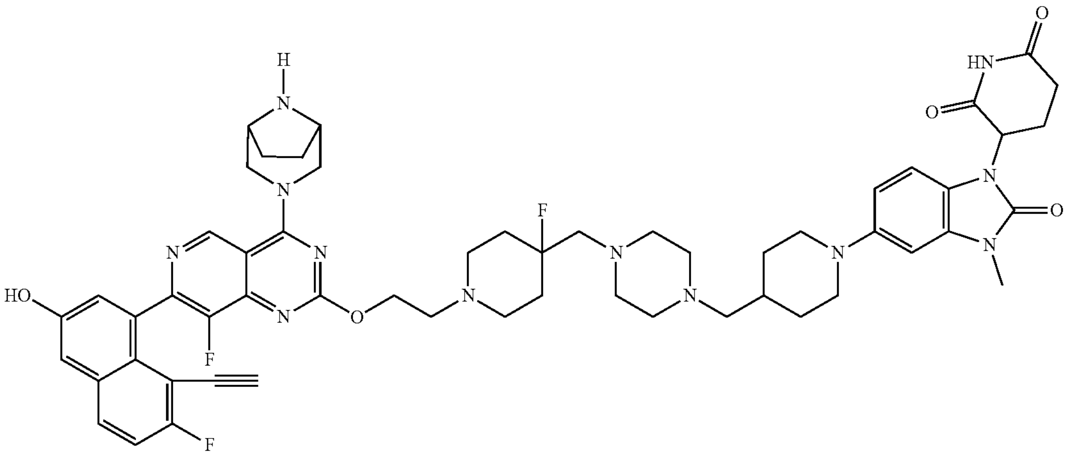 [SMILES: C#Cc1c(F)ccc2cc(O)cc(-c3ncc4c(N5CC6CCC(C5)N6)nc(OCCN5CCC(F)(CN6CCN(CC7CCN(c8ccc9c(c8)n(C)c(=O)n9C8CCC(=O)NC8=O)CC7)CC6)CC5)nc4c3F)c12]

To a solution of tert-butyl 3-[2-[2-[4-[[4-[[1-[1-(2,6-dioxo-3-piperidyl)-3-methyl-2-oxo-benzimidazol-5-yl]-4-piperidyl]methyl]piperazin-1-yl]methyl]-4-fluoro-1-piperidyl] ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (396 mg, 0.3 mmol) in dichloromethane (3 mL) was added 4 M HCl in 1,4-dioxane (2.5 mL), and the reaction mixture was stirred at 20° C. for 30 min. The mixture was suspended in petroleum ether (40 mL) and filtered. and the filter cake was dissolved in THF (30 mL). Triethylamine was added to adjust the pH to 9, and the resulting mixture was filtered and concentrated under reduced pressure. The residue was purified by prep-HPLC (16%-56% acetonitrile in water (ammonium bicarbonate) over 32 min) to afford the title compound (143.0 mg, 40%) as a white solid. LC/MS (ESI) m/z: 1041.8 $[M+H]^+$; $^1H$ NMR (400 MHz, DMSO-$d_6$) δ 11.05 (s, 1H), 10.22-10.08 (m, 1H), 9.03 (s, 1H), 7.97 (dd, J=5.6, 9.2 Hz, 1H), 7.46 (t, J=9.2 Hz, 1H), 7.39 (d, J=2.4 Hz, 1H), 7.17 (d, J=2.4 Hz, 1H), 6.91 (d, J=8.8 Hz, 1H), 6.80 (d, J=1.6 Hz, 1H), 6.61 (dd, J=2.0, 8.8 Hz, 1H), 5.28 (dd, J=5.2, 12.8 Hz, 1H), 4.52-4.40 (m, 3H), 4.32 (br d, J=11.6 Hz, 1H), 3.92 (s, 1H), 3.65-3.50 (m, 6H), 3.29 (s, 3H), 2.93-2.85 (m, 1H), 2.73-2.56 (m, 9H), 2.47-2.22 (m, 12H), 2.13 (br d, J=7.2 Hz, 2H), 2.01-1.94 (m, 1H), 1.80-1.54 (m, 11H), 1.27-1.15 (m, 2H).

Example 47: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl] piperidin-1-yl}-4,7-difluoro-3-methyl-2-oxo-2,3-dihydro-1H-1,3-benzodiazol-1-yl)piperidine-2,6-dione (Compound 201)

Step 1: Preparation of 1-(tert-butyl) 2-methyl (2S, 4R)-4-(pyridin-4-yloxy)pyrrolidine-1,2-dicarboxylate

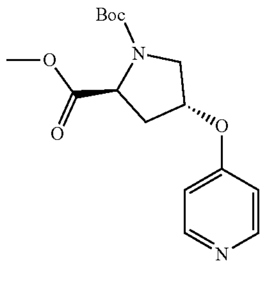 [SMILES: COC(=O)[C@@H]1C[C@@H](Oc2ccncc2)CN1C(=O)OC(C)(C)C]

To a mixture of 01-tert-butyl 02-methyl (2S,4S)-4-hydroxypyrrolidine-1,2-dicarboxylate (90 g, 367 mmol), pyridin-4-ol (41.87 g, 440 mmol) and triphenylphosphine (144.4 g, 550 mmol) in toluene (900 mL) at 0° C. was added diisopropyl azodicarboxylate (99.9 mL, 514 mmol) dropwise, and the mixture was purged with nitrogen and stirred at 100° C. for 3 h under nitrogen atmosphere. The reaction mixture was diluted with water (3000 mL) and extracted with ethyl acetate (1000 mL×3). The combined organic phase was washed with saturated brine (3000 mL), dried over anhydrous sodium sulfate, filtered, and concentrated under reduced pressure. The residue was purified by reversed-phase HPLC (10%-30% acetonitrile in water (formic acid) over 28 min) to afford the title compound (66 g, 56%) as a yellow solid. LC/MS (ESI) m/z: 323.0 $[M+H]^+$; $^1H$ NMR (400 MHz, $CDCl_3$) δ 8.46-8.44 (d, J=4.8 Hz, 2H), 6.78-6.77 (d, J=4.8 Hz, 2H), 3.87-3.77 (m, 4H), 2.59-2.55 (m, 1H), 2.33-2.26 (m, 1H), 1.70 (s, 3H), 1.46-1.43 (m, 9H).

Step 2: Preparation of 1-benzyl-4-(((3R,5S)-1-(tert-butoxycarbonyl)-5-(methoxycarbonyl)pyrrolidin-3-yl)oxy)pyridin-1-ium

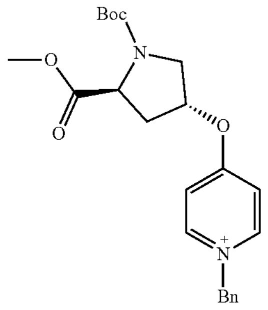

To a solution of 1-(tert-butyl) 2-methyl (2S,4R)-4-(pyridin-4-yloxy)pyrrolidine-1,2-dicarboxylate (10 g, 31 mmol) in acetonitrile (100 mL) was added benzyl bromide (4.42 mL, 37 mmol), and the mixture was degassed and purged with nitrogen, then stirred at 80° C. for 12 h under nitrogen atmosphere. The mixture was concentrated under reduced pressure to afford the title compound (15 g, crude) as a yellow oil. LC/MS (ESI) m/z: 413.49 $[M+H]^+$.

Step 3: Preparation of 1-(tert-butyl) 2-methyl (2S, 4R)-4-((1-benzyl-1,2,3,6-tetrahydropyridin-4-yl) oxy)pyrrolidine-1,2-dicarboxylate

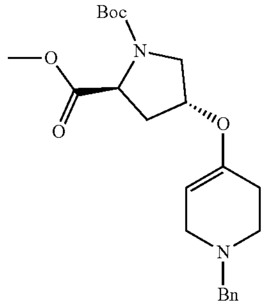 [SMILES: COC(=O)[C@@H]1C[C@@H](OC2=CCN(Cc3ccccc3)CC2)CN1C(=O)OC(C)(C)C]

To a solution of 1-benzyl-4-(((3R,5S)-1-(tert-butoxycarbonyl)-5-(methoxycarbonyl)pyrrolidin-3-yl)oxy)pyridin-1-ium (15 g, 30 mmol) in methanol (150 mL) at 0° C. was added sodium borohydride (3.48 g, 92 mmol), and the mixture was stirred at 25° C. for 2 h. The reaction mixture was diluted with saturated ammonium chloride solution (50 mL) and water (10 mL), then extracted with ethyl acetate (25 mL×2). The combined organic layers were washed with saturated sodium chloride (30 mL×2), dried over sodium sulfate, filtered, and concentrated under reduced pressure. The residue was purified by flash silica gel chromatography (petroleum ether/ethyl acetate=1:0 to 5:1) to afford the title compound (10.5 g, 83%) as a yellow oil. LC/MS (ESI) m/z: 416.23 $[M+H]^+$, $^1H$ NMR (400 MHz, DMSO-$d_6$) δ 7.35-

7.27 (m, 4H), 7.27-7.20 (m, 1H), 4.61 (d, J=3.6 Hz, 2H), 4.27-4.13 (m, 1H), 3.70-3.59 (m, 3H), 3.52 (s, 2H), 3.50-3.44 (m, 2H), 2.90 (s, 2H), 2.53-2.51 (m, 1H), 2.41-2.29 (m, 1H), 2.14-2.07 (m, 1H), 2.06 (d, J=6.8 Hz, 2H), 1.99 (s, 1H), 1.49-1.25 (m, 9H).

Step 4: Preparation of [(2S,4R)-4-[(1-benzyl-3,6-dihydro-2H-pyridin-4-yl)oxy]-1-methyl-pyrrolidin-2-yl]methanol

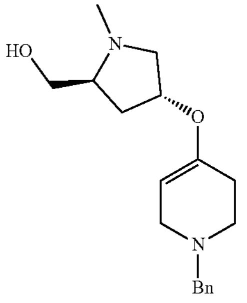 [SMILES: CN1C[C@H](OC2=CCN(Cc3ccccc3)CC2)C[C@H]1CO]

To a mixture of 1-(tert-butyl) 2-methyl (2S,4R)-4-((1-benzyl-1,2,3,6-tetrahydropyridin-4-yl)oxy)pyrrolidine-1,2-dicarboxylate (9.5 g, 23 mmol) in tetrahydrofuran (100 mL) was added lithium aluminum hydride (2.6 g, 68 mmol), and the mixture was stirred at 65° C. for 2 h under nitrogen atmosphere. The reaction mixture was quenched slowly with water (30 mL) followed by 1 M aqueous sodium hydroxide (30 mL). Sodium sulfate was then added, and the resulting mixture was filtered through a Celite pad. The filtrate was concentrated under reduced pressure, and the residue was purified by prep-HPLC (20%-55% ethanol in hexane over 13 min) to give the title compound (5.5 g, 80%) as a white oil. LC/MS (ESI) m/z: 302.42 $[M+H]^+$; $^1H$ NMR (400 MHz, DMSO-$d_6$) δ 7.36-7.27 (m, 4H), 7.27-7.19 (m, 1H), 4.51 (t, J=3.2 Hz, 1H), 4.43-4.33 (m, 2H), 3.51 (s, 2H), 3.46-3.41 (m, 4H), 3.27 (dd, J=5.6, 10.8 Hz, 2H), 2.88 (d, J=3.2 Hz, 2H), 2.25 (s, 3H), 2.03 (t, J=5.2 Hz, 2H), 1.85-1.75 (m, 2H).

Step 5: Preparation of [(2S,4R)-1-methyl-4-(4-piperidyloxy)pyrrolidin-2-yl]methanol

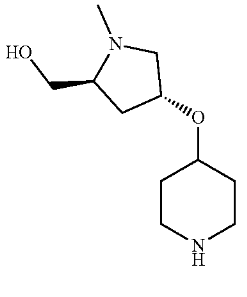

To a solution of [(2S,4R)-4-[(1-benzyl-3,6-dihydro-2H-pyridin-4-yl)oxy]-1-methyl-pyrrolidin-2-yl]methanol (2 g, 7 mmol) in tetrahydrofuran (20 mL) were added 10% palladium on carbon (500 mg, 0.7 mmol) and 20% palladium hydroxide (464.39 mg, 0.7 mmol). The suspension was degassed and purged with hydrogen several times, and the mixture was stirred under hydrogen (50 psi) at 50° C. for 12 h. The reaction mixture was filtered and concentrated under reduced pressure to give the title compound (1.2 g, 85%) as a yellow oil. LC/MS (ESI) m/z: 214.17 $[M+H]^+$.

Step 6: Preparation of 2-trimethylsilylethyl 4-[(3R,5S)-5-(hydroxymethyl)-1-methyl-pyrrolidin-3-yl]oxypiperidine-1-carboxylate

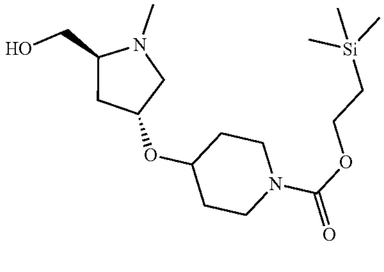 [SMILES: CN1C[C@H](OC2CCN(C(=O)OCC[Si](C)(C)C)CC2)C[C@H]1CO]

To a solution of [(2S,4R)-1-methyl-4-(4-piperidyloxy)pyrrolidin-2-yl]methanol (1.9 g, 9 mmol) in dioxane (40 mL) were added triethylamine (3.7 mL, 27 mmol) and (2,5-dioxopyrrolidin-1-yl) 2-trimethylsilylethyl carbonate (2.30 g, 8.9 mmol), and the mixture was stirred at 25° C. for 12 h. The reaction mixture was filtered and concentrated under reduced pressure. The residue was purified by prep-HPLC (25%-55% acetonitrile in water (formic acid) over 8 min) to give the title compound (1.02 g, 32%) as a colorless oil. LC/MS (ESI) m/z: 359.3 $[M+H]^+$; $^1H$ NMR (400 MHz, DMSO-$d_6$) δ 4.37 (s, 1H), 4.09-4.05 (m, 2H), 3.72-3.64 (m, 2H), 3.49-3.44 (m, 2H), 3.41-3.39 (m, 1H), 3.26-3.18 (m, 2H), 3.05-2.97 (m, 2H), 2.40-2.33 (m, 1H), 2.24 (s, 3H), 2.08 (dd, J=6.4, 9.2 Hz, 1H), 1.80-1.69 (m, 4H), 1.31-1.24 (m, 2H), 0.96-0.90 (m, 2H), 0.06-0.00 (m, 9H).

Step 7: Preparation of tert-butyl 3-[8-fluoro-7-[7-fluoro-3-(methoxymethoxy)-8-(2-triisopropylsilylethynyl)-1-naphthyl]-2-[[(2S,4R)-1-methyl-4-[[1-(2-trimethylsilylethoxycarbonyl)-4-piperidyl]oxy]pyrrolidin-2-yl]methoxy]pyrido[4,3-d]pyrimidin-4-yl]-3,8-diazabicyclo[3.2.1]octane-8-carboxylate

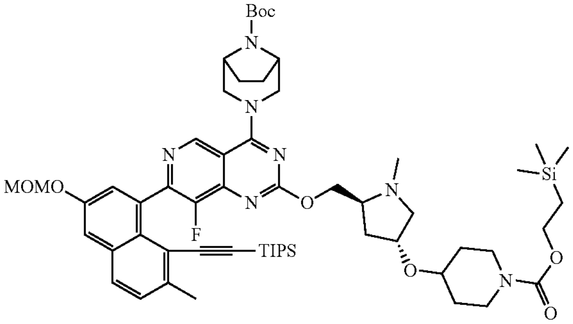

To a solution of tert-butyl 3-[8-fluoro-7-[7-fluoro-3-(methoxymethoxy)-8-(2-triisopropylsilylethynyl)-1-naphthyl]-2-methylsulfonyl-pyrido[4,3-d]pyrimidin-4-yl]-3,8-diazabicyclo[3.2.1]octane-8-carboxylate (4.3 g, 5 mmol) and 2-trimethylsilylethyl 4-[(3R,5S)-5-(hydroxymethyl)-1-methyl-pyrrolidin-3-yl]oxypiperidine-1-carboxylate (1.91 g, 5 mmol) in tetrahydrofuran (50 mL) at 0° C. was added lithium tert-butoxide (2.2 M, 9.5 mL), and the reaction mixture was stirred at 25° C. for 1 h. The mixture was diluted with water (20 mL) and extracted with ethyl acetate (2×20 mL). The combined organic extract was dried over anhydrous sodium sulfate, filtered, and concentrated under reduced pressure. The crude product was purified by prep-HPLC (55% to 85% acetonitrile in water (formic acid) over 20 min) to afford the title compound (2.6 g, 45%, formic acid salt) as a yellow gum. LC/MS (ESI) m/z: 1101.0 $[M+H]^+$, $^1H$ NMR (400 MHz, $CDCl_3$) δ 9.06 (s, 1H), 7.78 (dd, J=5.6, 9.0 Hz, 1H), 7.51 (d, J=2.5 Hz, 1H), 7.34-7.28 (m, 2H), 7.27 (s, 1H), 5.36-5.24 (m, 2H), 4.76 (s, 1H), 4.63-4.48 (m, 1H), 4.37 (dd, J=6.3, 10.8 Hz, 2H), 4.30-4.18 (m, 3H), 3.79 (s, 3H), 3.51 (s, 3H), 3.42-3.33 (m, 1H), 3.18-3.05 (m, 2H), 3.02-2.90 (m, 1H), 2.49 (d, J=2.0 Hz, 3H), 2.34 (J=3.9, 6.1, 9.7 Hz, 1H), 2.03-1.94 (m, 3H), 1.86-1.74 (m, 2H), 1.57-1.51 (m, 9H), 0.95-0.78 (m, 18H), 0.55 (quin, J=7.1 Hz, 3H), 0.10-0.02 (m, 9H).

Step 8: Preparation of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate

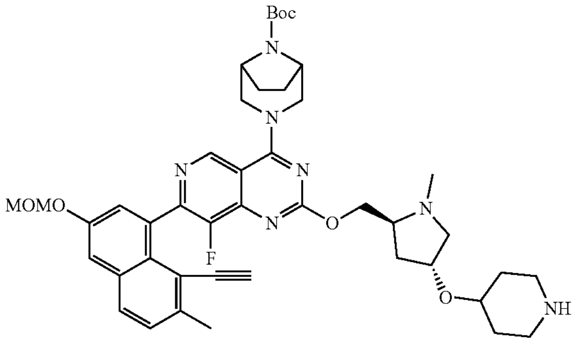

To a solution of tert-butyl 3-[8-fluoro-7-[7-fluoro-3-(methoxymethoxy)-8-(2-triisopropylsilylethynyl)-1-naphthyl]-2-[[(2S,4R)-1-methyl-4-[[1-(2-trimethylsilylethoxycarbonyl)-4-piperidyl]oxy]pyrrolidin-2-yl]methoxy]pyrido[4,3-d]pyrimidin-4-yl]-3,8-diazabicyclo[3.2.1]octane-8-carboxylate (2 g, 2 mmol) in N,N-dimethylformamide (20 mL) was added cesium fluoride (0.67 mL, 18 mmol), and the reaction mixture was stirred at 90° C. for 1 h. The mixture was diluted with water (30 mL) and extracted with ethyl acetate (3×30 mL). The combined organic extract was dried over anhydrous sodium sulfate, filtered, and concentrated under reduced pressure. The residue was purified by prep-HPLC (10%-40% acetonitrile in water (formic acid) over 11 min) to afford the title compound (1.3 g, 89%, formic acid salt) as a yellow solid. LC/MS (ESI) m/z: 800.5 $[M+H]^+$.

Step 9: Preparation of tert-butyl 3-[2-[[(2S,4R)-4-[[1-[[1-[1-(2,6-dioxo-3-piperidyl)-4,7-difluoro-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

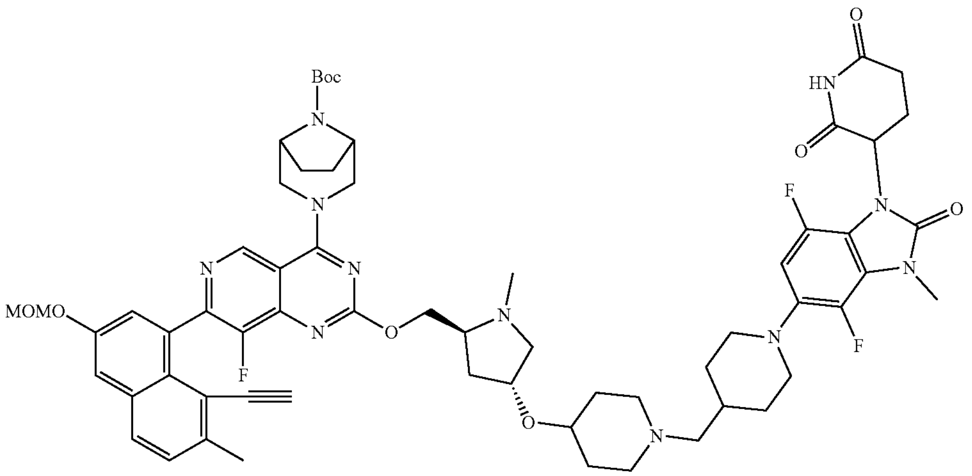

To a mixture of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate (200 mg, 0.2 mmol) and 1-[1-(2,6-dioxo-3-piperidyl)-4,7-difluoro-3-methyl-2-oxo-benzimidazol-5-yl]piperidine-4-carbaldehyde (100 mg, 0.2 mmol) in dichloromethane (2 mL) and isopropanol (1 mL) was added N,N-diisopropylethylamine (32 mg, 0.2 mmol), and the resulting mixture was stirred at 25° C. for 10 min. Sodium triacetoxyborohydride (158 mg, 0.7 mmol) was then added, and the reaction mixture was stirred at 25° C. for 0.5 h. The mixture was filtered and concentrated under reduced pressure to afford the title compound (250 mg, 84%) as a yellow solid. LC/MS (ESI) m/z: 596.2 $[M/2+H]^+$; $^1$H NMR (400 MHz, DMSO-$d_6$) δ 11.11 (s, 1H), 9.09 (s, 1H), 8.10 (dd, J=6.0, 9.2 Hz, 1H), 7.75 (d, J=2.8 Hz, 1H), 7.55 (t, J=9.2 Hz, 1H), 7.38 (d, J=2.0 Hz, 1H), 6.70-6.60 (m, 1H), 5.53-5.41 (m, 1H), 5.37 (s, 2H), 4.61-4.50 (m, 1H), 4.46-4.35 (m, 2H), 4.34-4.22 (m, 3H), 4.17-4.09 (m, 1H), 4.00-3.97 (m, 1H), 3.71-3.59 (m, 2H), 3.49 (s, 3H), 3.44 (s, 3H), 3.28-3.19 (m, 4H), 3.06-2.85 (m, 2H), 2.84-2.70 (m, 2H), 2.65-2.57 (m, 3H), 2.37 (s, 3H), 2.25-2.16 (m, 2H), 2.15-2.07 (m, 2H), 1.91 (s, 4H), 1.89-1.70 (m, 9H), 1.67-1.57 (m, 1H), 1.46 (s, 11H), 1.33-1.21 (m, 2H).

Step 4: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4,7-difluoro-3-methyl-2-oxo-2,3-dihydro-1H-1,3-benzodiazol-1-yl)piperidine-2,6-dione

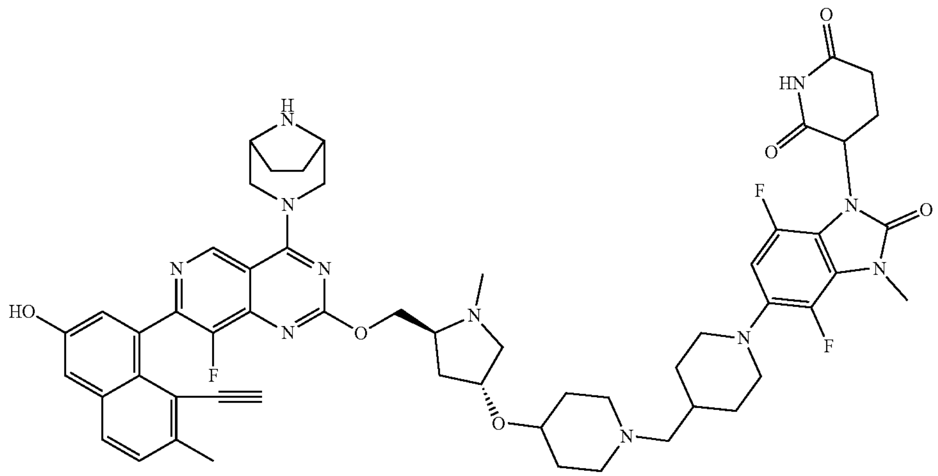 [SMILES: C#Cc1c(C)ccc2cc(O)cc(-c3ncc4c(N5CC6CCC(C5)N6)nc(OC[C@@H]5C[C@@H](OC6CCN(CC7CCN(c8cc(F)c9c(c8F)n(C)c(=O)n9C8CCC(=O)NC8=O)CC7)CC6)CN5C)nc4c3F)c12]

To a solution of tert-butyl 3-[2-[[(2S,4R)-4-[[1-[[1-[1-(2,6-dioxo-3-piperidyl)-4,7-difluoro-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (250 mg, 0.2 mmol) in dichloromethane (1 mL) was added 4 M HCl in 1,4-dioxane (1 mL), and the reaction mixture was stirred at 25° C. for 15 min. The mixture was filtered and concentrated under reduced pressure. The residue was purified by prep-HPLC (2% to 32% acetonitrile in water (formic acid) over 15 min) to afford the title compound (80.2 mg, 32%, di-formic acid salt) as a yellow solid. LC/MS (ESI) m/z: 1046.6 $[M+H]^+$; $^1$H NMR (400 MHz, DMSO-$d_6$) δ 11.11 (s, 1H), 9.05 (s, 1H), 8.19 (s, 2H), 7.97 (dd, J=6.0, 9.2 Hz, 1H), 7.46 (t, J=9.2 Hz, 1H), 7.39 (d, J=2.4 Hz, 1H), 7.18 (d, J=2.4 Hz, 1H), 6.70-6.59 (m, 1H), 5.52-5.39 (m, 1H), 4.56-4.49 (m, 1H), 4.41-4.33 (m, 2H), 4.26-4.21 (m, 1H), 4.14-4.09 (m, 1H), 3.94-3.92 (m, 1H), 3.78-3.70 (m, 3H), 3.70-3.61 (m, 2H), 3.49 (s, 3H), 3.33-3.20 (m, 4H), 3.04-2.90 (m, 1H), 2.84-2.75 (m, 1H), 2.73-2.55 (m, 5H), 2.35 (s, 3H), 2.22-1.97 (m, 7H), 1.93-1.84 (m, 2H), 1.83-1.70 (m, 8H), 1.63-1.51 (m, 1H), 1.46-1.32 (m, 2H), 1.30-1.18 (m, 2H).

Example 48: Synthesis of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-2-oxo-3-(propan-2-yl)-2,3-dihydro-1H-1,3-benzodiazol-1-yl)piperidine-2,6-dione (Compound 202)

Step 1: Preparation of tert-butyl 9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecane-3-carboxylate

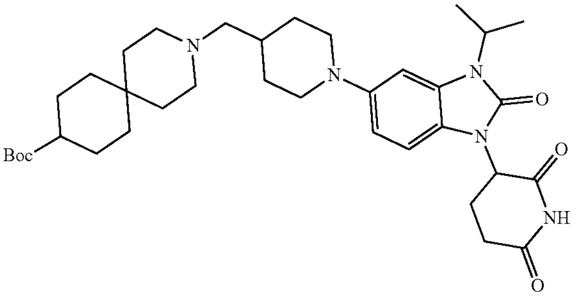 [SMILES: CC(C)n1c(=O)n(C2CCC(=O)NC2=O)c2ccc(N3CCC(CN4CCC5(CCC(C(=O)OC(C)(C)C)CC5)CC4)CC3)cc21]

To a solution of 1-(1-(2,6-dioxopiperidin-3-yl)-3-isopropyl-2-oxo-2,3-dihydro-1H-benzo[d]imidazol-5-yl)piperidine-4-carbaldehyde (800 mg, 2 mmol) and tert-butyl 3,9-diazaspiro[5.5]undecane-3-carboxylate (510 mg, 2 mmol) in dichloromethane (8 mL) and dimethyl sulfoxide (8 mL) was added acetic acid (0.2 mL, 4 mmol,) and the resulting mixture was stirred for 30 min. Sodium triacetoxyborohydride (851 mg, 4 mmol) was then added, and the reaction mixture was stirred at 25° C. for 2 h. The mixture was diluted with water (30 mL) and extracted with dichloromethane (2×30 mL). The combined organic extracts were washed with brine (2×30 mL), dried over anhydrous sodium sulfate, filtered, and concentrated under reduced pressure. The residue was purified by flash silica gel chromatography (0 to 100% ethyl acetate/petroleum ether then 0 to 15% dichloromethane/methanol) to afford the title compound (1 g, 78%) as a white solid. LC/MS (ESI) m/z: 637.4 $[M+H]^+$, $^1H$ NMR (400 MHz, $CDCl_3$) δ 8.91-8.18 (m, 1H), 6.81 (s, 1H), 6.67 (s, 2H), 5.20 (dd, J=5.2, 12.8 Hz, 1H), 4.67 (td, J=7.2, 1 Step 6: Hz, 1H), 3.56-3.47 (m, 3H), 3.43-3.34 (m, 4H), 2.95-2.88 (m, 1H), 2.86-2.74 (m, 3H), 2.73-2.64 (m, 4H), 2.63 (s, 2H), 2.61-2.56 (m, 1H), 2.25-2.17 (m, 1H), 2.04 (s, 2H), 1.95 (br d, J=12.4 Hz, 2H), 1.83 (br s, 1H), 1.73 (br s, 3H), 1.55 (d, J=7.2 Hz, 6H), 1.46 (s, 13H).

Step 2: Preparation of 3-(5-(4-((3,9-diazaspiro[5.5]undecan-3-yl)methyl)piperidin-1-yl)-3-isopropyl-2-oxo-2,3-dihydro-1H-benzo[d]imidazol-1-yl)piperidine-2,6-dione

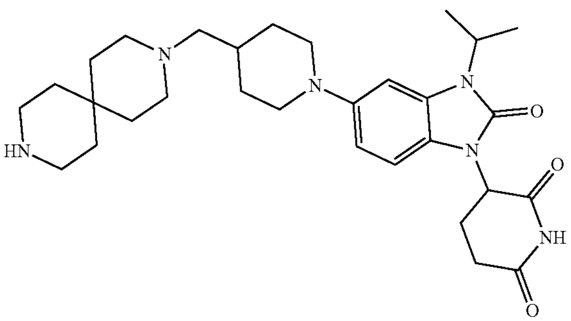 [SMILES: CC(C)n1c(=O)n(C2CCC(=O)NC2=O)c2ccc(N3CCC(CN4CCC5(CCNCC5)CC4)CC3)cc21]

To a solution of tert-butyl 9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecane-3-carboxylate (1 g, 1 mmol) in dichloromethane (10 mL) was added trifluoroacetic acid (5.0 mL, 67 mmol), and the reaction mixture was stirred at 25° C. for 1 h. The mixture was concentrated under reduced pressure to afford the title compound (1 g, 97%, TFA salt) as a pink oil. LC/MS (ESI) m/z: 537.5 $[M+H]^+$.

Step 3: Preparation of tert-butyl (1R,5S)-3-(2-(2-(9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecan-3-yl)ethoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate

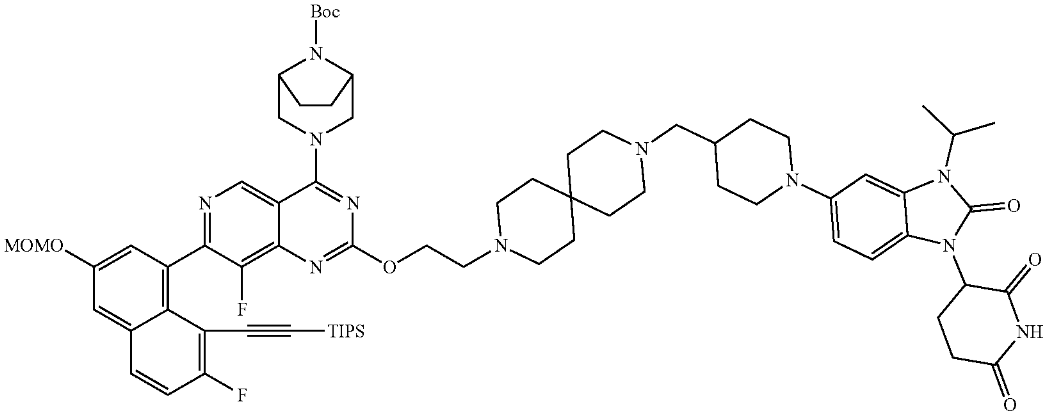

To a solution of 3-(5-(4-((3,9-diazaspiro[5.5]undecan-3-yl)methyl)piperidin-1-yl)-3-isopropyl-2-oxo-2,3-dihydro-1H-benzo[d]imidazol-1-yl)piperidine-2,6-dione trifluoroacetate (1.0 g, 1.5 mmol) in dichloromethane (10 mL) and isopropanol (10 mL) was added N,N-diisopropylethylamine (0.5 mL, 3 mmol), and the resulting mixture was stirred for 15 min. Acetic acid (0.2 mL, 3 mmol) and tert-butyl (1R,5S)-3-(8-fluoro-7-(7-fluoro-3-(methoxymethoxy)-8-((triisopropylsilyl)ethynyl)naphthalen-1-yl)-2-(2-oxoethoxy)pyrido [4,3-d]pyrimidin-4-yl)-3,8-diazabicyclo[3.2.1]octane-8-carboxylate (1.23 g, 1.5 mmol) were then added, and the mixture was stirred for 15 min. Sodium triacetoxyborohydride (651 mg, 3 mmol) was then added, and the reaction mixture was stirred at 25° C. for 2 h. The mixture was diluted with water (100 mL) and extracted with dichloromethane (2×100 mL). The combined organic extracts were washed with brine (2×100 mL), dried over anhydrous sodium sulfate, filtered, and concentrated under reduced pressure. The residue was purified by flash silica gel chromatography (0 to 100% ethyl acetate/petroleum ether then 0 to 15% dichloromethane/methanol) to afford the title compound (1.4 g, 68%) as a yellow solid. LC/MS (ESI) m/z: 1323.0 $[M+H]^+$.

Step 4: Preparation of tert-butyl (1R,5S)-3-(2-(2-(9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecan-3-yl)ethoxy)-7-(8-ethynyl-7-fluoro-3-(methoxy methoxy) naphthalen-1-yl)-8-fluoropyrido[4,3-d]pyrimidin-4-yl)-3,8-diazabicyclo[3.2.1] octane-8-carboxylate

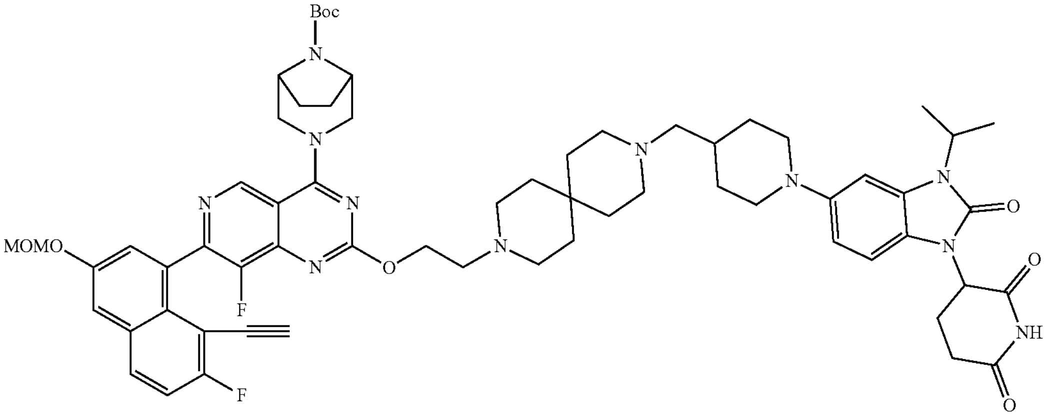

To a solution of tert-butyl (1R,5S)-3-(2-(2-(9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecan-3-yl)ethoxy)-8-fluoro-7-(7-fluoro-3-(methoxymethoxy)-8-((triisopropylsilyl)ethynyl) naphthalen-1-yl)pyrido[4,3-d]pyrimidin-4-yl)-3,8-diazabicyclo[3.2.1]octane-8-carboxylate (1.4 g, 1 mmol) in N,N-dimethylformamide (15 mL) was added cesium fluoride (3.22 g, 21 mmol), and the reaction mixture was stirred at 25° C. for 12 h. The residue was diluted with water (100 mL) and extracted with dichloromethane (2×100 mL). The combined organic extracts were washed with brine (2×100 mL), dried over anhydrous sodium sulfate, filtered, and concentrated under reduced pressure. The residue was purified by prep-HPLC (12% to 42% acetonitrile in water (formic acid) over 15 min) to afford the title compound (620 mg, 50%, formic acid salt) as a yellow solid. LC/MS (ESI) m/z: 1166.8 [M+H]$^+$.

Step 5: Preparation of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-2-oxo-3-(propan-2-yl)-2,3-dihydro-1H-1,3-benzodiazol-1-yl)piperidine-2,6-dione

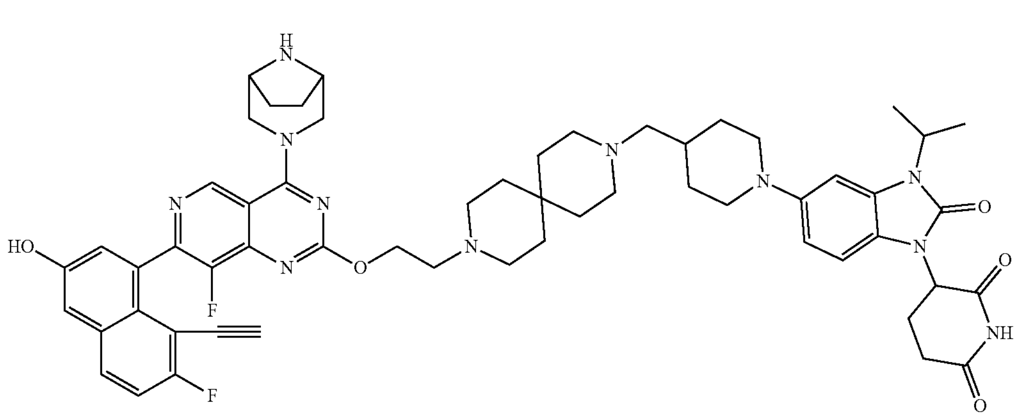 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7)n(C(C)C)c(=O)n8C7CCC(=O)NC7=O)CC5)CC6)nc4c3F)c12]

To a solution of tert-butyl (1R,5S)-3-(2-(2-(9-((1-(1-(2,6-dioxopiperidin-3-yl)-3-isopropyl-2-oxo-2,3-dihydro-1H-benzo[d]imidazol-5-yl)piperidin-4-yl)methyl)-3,9-diazaspiro[5.5]undecan-3-yl)ethoxy)-7-(8-ethynyl-7-fluoro-3-(methoxy methoxy)naphthalen-1-yl)-8-fluoropyrido[4,3-d]pyrimidin-4-yl)-3,8-diazabicyclo[3.2.1] octane-8-carboxylate (620 mg, 0.5 mmol) in dichloromethane (7 mL) was added 4 M HCl in 1,4-dioxane (6 mL), and the reaction mixture was stirred at 25° C. for 15 min. The mixture was suspended in petroleum ether (30 mL), filtered, and the filter cake was dissolved in dimethyl sulfoxide (5 mL) and N,N-diisopropylethylamine to adjust the pH to 7. The resulting solution was purified by prep-HPLC (1% to 28% acetonitrile in water (formic acid) over 15 min) to afford the title compound (235.6 mg, 38%, di-formic acid salt) as a yellow solid. LC/MS (ESI) m/z: 1023.6 $[M+H]^+$, $^1H$ NMR (400 MHz, DMSO-$d_6$) δ 11.06 (br s, 1H), 9.07 (s, 1H), 8.24 (s, 2H), 7.97 (dd, J=6.0, 9.2 Hz, 1H), 7.46 (t, J=9.2 Hz, 1H), 7.40 (d, J=2.4 Hz, 1H), 7.19 (d, J=2.4 Hz, 1H), 6.91 (d, J=8.8 Hz, 1H), 6.87 (d, J=1.6 Hz, 1H), 6.61 (dd, J=1.6, 8.8 Hz, 1H), 5.26 (br dd, J=5.6, 12.8 Hz, 1H), 4.65-4.52 (m, 2H), 4.48 (br t, J=5.6 Hz, 2H), 4.40 (br d, J=12.4 Hz, 1H), 3.94 (s, 1H), 3.83 (br s, 2H), 3.74 (br t, J=1 Step 6: Hz, 2H), 3.53 (br d, J=11.6 Hz, 2H), 2.96-2.82 (m, 1H), 2.77 (br t, J=5.2 Hz, 2H), 2.72-2.56 (m, 5H), 2.47 (br d, J=Step 2: Hz, 5H), 2.32 (br d, J=6.4 Hz, 2H), 2.03-1.93 (m, 1H), 1.85-1.74 (m, 6H), 1.72-1.57 (m, 2H), 1.44 (br d, J=6.8 Hz, 15H), 1.31-1.18 (m, 3H).

Example 49: Synthesis of 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-3-isopropyl-2-oxo-benzimidazol-1-yl]piperidine-2,6-dione (Compound 203)

Step 1: Preparation of 2,6-dibenzyloxy-N-(4-bromo-3-fluoro-2-nitro-phenyl)pyridin-3-amine

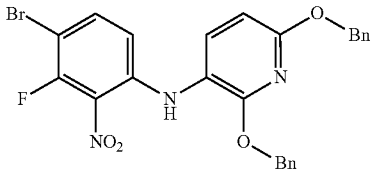

To a solution of 2,6-dibenzyloxypyridin-3-amine (4.9 g, 16 mmol) and 1-bromo-2,4-difluoro-3-nitro-benzene (3.81 g, 16 mmol) in DMSO (50 mL) was added DIEA (4.2 mL, 24 mmol), and the mixture was stirred at 110° C. for 18 h. The reaction mixture was diluted with water (50 mL) and extracted with ethyl acetate (3×70 mL). The combined organic extract was washed with water (6×20 mL) followed by brine (2×30 mL), dried over anhydrous sodium sulfate, filtered, and concentrated under reduced pressure. The residue was purified by flash column chromatography on silica gel (0 to 3% then up to 5% ethyl acetate in petroleum ether) to afford the title compound (5.09 g, 49%) as a dark brown solid. LC/MS (ESI) m/z: 524.2 $[M+H]^+$.

Step 2: Preparation of 4-bromo-N1-(2,6-dibenzyloxy-3-pyridyl)-3-fluoro-benzene-1,2-diamine

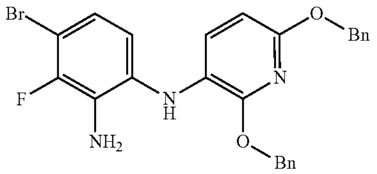 [SMILES: O=[N+]([O-])c1c(Nc2ccc(OCc3ccccc3)nc2OCc2ccccc2)ccc(Br)c1F]

To a solution of 2,6-dibenzyloxy-N-(4-bromo-3-fluoro-2-nitro-phenyl)pyridin-3-amine (5 g, 9 mmol) in isopropanol (80 mL), THF (10 mL), and water (10 mL) were added ammonium chloride (4.08 g, 76 mmol) and iron (2.66 g, 48 mmol), and the reaction mixture was stirred at 80° C. for 3 h. The mixture was filtered, washing with ethyl acetate (3×100 mL). The filtrate was washed with brine (50 mL), dried over anhydrous sodium sulfate, filtered, and concentrated under reduced pressure. The residue was purified by flash column chromatography on silica gel (0 to 3% then up to 5% ethyl acetate in petroleum ether) to afford the title compound (3.59 g, 64%) as a pink solid. LC/MS (ESI) m/z: 496.1 $[M+H]^+$.

Step 3: Preparation of 6-bromo-3-(2,6-dibenzyloxy-3-pyridyl)-7-fluoro-1H-benzimidazol-2-one

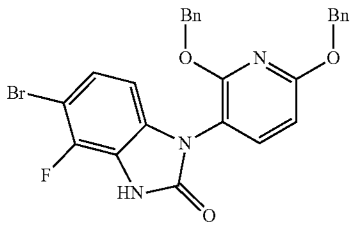 [SMILES: O=c1[nH]c2c(F)c(Br)ccc2n1-c1ccc(OCc2ccccc2)nc1OCc1ccccc1]

To a solution of 4-bromo-N1-(2,6-dibenzyloxy-3-pyridyl)-3-fluoro-benzene-1,2-diamine (3.6 g, 7.2 mmol) and triethylamine (3.01 mL, 22 mmol) in THF (60 mL) was added CDI (3.50 g, 22 mmol), and the reaction mixture was stirred at 70° C. for 16 h. The mixture was concentrated under reduced pressure, and the residue was diluted with water (50 mL) and extracted with chloromethane (3×50 mL). The combined organic extract was washed with water (3×20 mL) followed by brine (20 mL), dried over anhydrous sodium sulfate, filtered, and concentrated in vacuo. The residue was triturated with ethyl acetate/MTBE (1/1, 30 mL) to afford 2.7 g of product. The filtrate solution was concentrated under reduced pressure, and the resulting residue was purified by flash column chromatography on silica gel (0 to 30% THF in petroleum ether over 16 min) to afford 0.78 g of product. In total, 3.48 g (93%) of the title compound was obtained as a pink solid. LC/MS (ESI) m/z: 522.0 $[M+H]^+$.

Step 4: Preparation of 5-bromo-1-(2,6-dibenzyloxy-3-pyridyl)-4-fluoro-3-isopropyl-benzimidazol-2-one

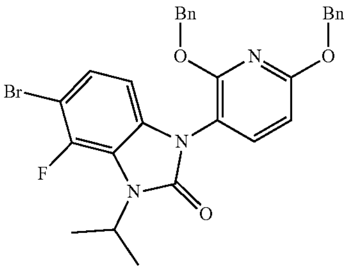 [SMILES: CC(C)n1c(=O)n(-c2ccc(OCc3ccccc3)nc2OCc2ccccc2)c2ccc(Br)c(F)c21]

To a solution of 6-bromo-3-(2,6-dibenzyloxy-3-pyridyl)-7-fluoro-1H-benzimidazol-2-one (3.1 g, 6 mmol) in DMF (30 mL) were added cesium carbonate (4.85 g, 15 mmol) and 2-iodopropane (1.8 mL, 18 mmol), and the reaction mixture was stirred at 20° C. for 16 h. The mixture was diluted with water (100 mL) and extracted with ethyl acetate (3×70 mL). The combined organic extract was washed with water (7×30 mL) followed by brine (30 mL), dried over anhydrous sodium sulfate, filtered, and concentrated under reduced pressure. The residue was purified by flash column chromatography on silica gel (0 to 15% ethyl acetate in petroleum ether over 8 min) to afford the title compound (3.01 g, 87%) as a yellow oily solid. LC/MS (ESI) m/z: 564.1 $[M+H]^+$.

Step 5: Preparation of 1-(2,6-dibenzyloxy-3-pyridyl)-5-[4-(1,3-dioxolan-2-yl)-1-piperidyl]-4-fluoro-3-isopropyl-benzimidazol-2-one

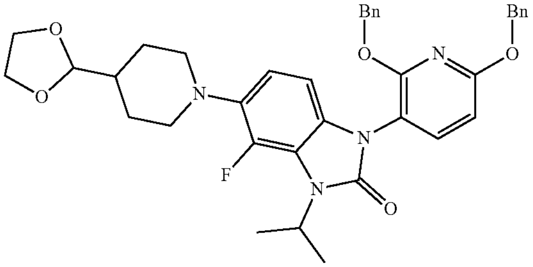 [SMILES: CC(C)n1c(=O)n(-c2ccc(OCc3ccccc3)nc2OCc2ccccc2)c2ccc(N3CCC(C4OCCO4)CC3)c(F)c21]

To a solution of 5-bromo-1-(2,6-dibenzyloxy-3-pyridyl)-4-fluoro-3-isopropyl-benzimidazol-2-one (1.0 g, 1.8 mmol) and 4-(1,3-dioxolan-2-yl)piperidine (559 mg, 3.6 mmol) in 1,4-dioxane (12 mL) were added t-BuONa (513 mg, 5.3 mmol) and BrettPhos Pd G3 (242 mg, 0.3 mmol) under nitrogen atmosphere, and the resulting mixture was degassed and purged with nitrogen (3×), then stirred at 90° C. for 12 h under nitrogen atmosphere. The mixture was suspended in dichloromethane (50 mL) and filtered, and the filtrate was concentrated under reduced pressure. The residue was purified by flash column chromatography on silica gel (0 to 15% then up to 17% ethyl acetate in petroleum ether) to afford the title compound (460 mg, 30%) as a yellow solid. LC/MS (ESI) m/z: 639.5 $[M+H]^+$.

Step 6: Preparation of 3-[5-[4-(1,3-dioxolan-2-yl)-1-piperidyl]-4-fluoro-3-isopropyl-2-oxo-benzimidazol-1-yl]piperidine-2,6-dione

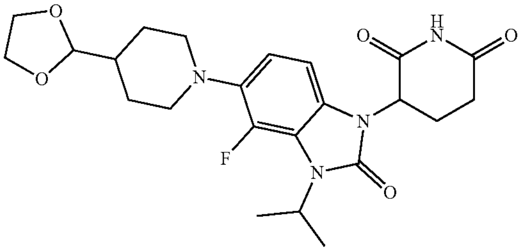 [SMILES: CC(C)n1c(=O)n(C2CCC(=O)NC2=O)c2ccc(N3CCC(C4OCCO4)CC3)c(F)c21]

To a solution of 1-(2,6-dibenzyloxy-3-pyridyl)-5-[4-(1,3-dioxolan-2-yl)-1-piperidyl]-4-fluoro-3-isopropyl-benzimidazol-2-one (460 mg, 0.7 mmol) in THF (30 mL) was added 10% $Pd(OH)_2$ on carbon (0.19 g) under argon, and the resulting mixture was degassed and purged with hydrogen (3×), then stirred at 50° C. for 16 h under hydrogen (50 psi). The mixture was filtered, washing with THF (100 mL), and the filtrate was concentrated under reduced pressure to afford the title compound (364 mg, 85%) as a white solid. LC/MS (ESI) m/z: 461.2 $[M+H]^+$.

Step 7: Preparation of 1-[1-(2,6-dioxo-3-piperidyl)-4-fluoro-3-isopropyl-2-oxo-benzimidazol-5-yl]piperidine-4-carbaldehyde

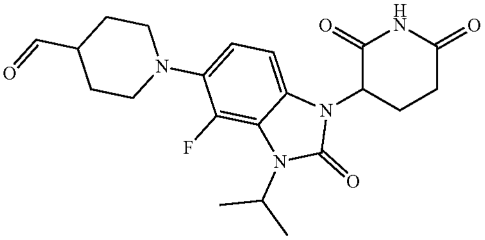 [SMILES: CC(C)n1c(=O)n(C2CCC(=O)NC2=O)c2ccc(N3CCC(C=O)CC3)c(F)c21]

To a solution of 3-[5-[4-(1,3-dioxolan-2-yl)-1-piperidyl]-4-fluoro-3-isopropyl-2-oxo-benzimidazol-1-yl]piperidine-2,6-dione (330 mg, 0.7 mmol) in acetone (4.0 mL) was added 3 M aqueous HCl solution (3.8 mL), and the mixture was stirred at 60° C. for 5 h. Then another 3 M aqueous HCl solution (2.5 mL) was added and stirred at 60° C. for 3 h. The mixture was concentrated under reduced pressure, then saturated sodium bicarbonate solution was added to adjust the pH to 8, and the mixture was extracted with methanol/dichloromethane (1:10, 3×50 mL). The combined organic phase was washed with brine (30 mL), dried over anhydrous sodium sulfate, filtered, and concentrated in vacuo to afford the title compound (272 mg, 80%) as a yellow solid. LC/MS (ESI) m/z: 417.1 $[M+H]^+$.

Step 8: Preparation of tert-butyl 9-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecane-3-carboxylate

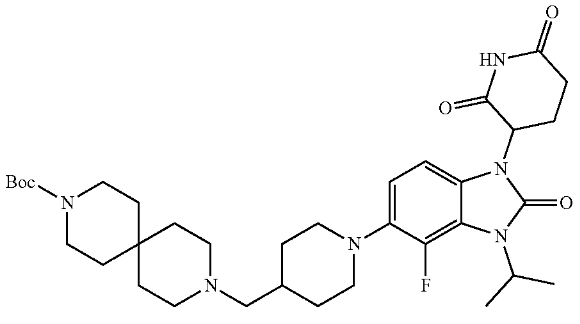 [SMILES: CC(C)n1c(=O)n(C2CCC(=O)NC2=O)c2ccc(N3CCC(CN4CCC5(CC4)CCN(C(=O)OC(C)(C)C)CC5)CC3)c(F)c21]

To a solution of 1-[1-(2,6-dioxo-3-piperidyl)-4-fluoro-3-isopropyl-2-oxo-benzimidazol-5-yl]piperidine-4-carbaldehyde (400 mg, 1 mmol) and tert-butyl 3,9-diazaspiro[5.5]undecane-3-carboxylate (318 mg, 1 mmol) in dichloromethane (5.0 mL) and isopropanol (5.0 mL) were added acetic acid (0.3 mL, 5 mmol) and 2-methylpyridine borane (411 mg, 3.8 mmol), and the reaction mixture was stirred at 25° C. for 12 h. Triethylamine was then added to adjust the pH to 8, and the resulting mixture was concentrated. The residue was purified by flash column chromatography on silica gel (0 to 6% methanol in dichloromethane) to afford the title compound (464 mg, 70%) as a white foam. LC/MS (ESI) m/z: 655.7 $[M+H]^+$.

Step 9: Preparation of 3-[5-[4-(3,9-diazaspiro[5.5]undecan-3-ylmethyl)-1-piperidyl]-4-fluoro-3-isopropyl-2-oxo-benzimidazol-1-yl]piperidine-2,6-dione

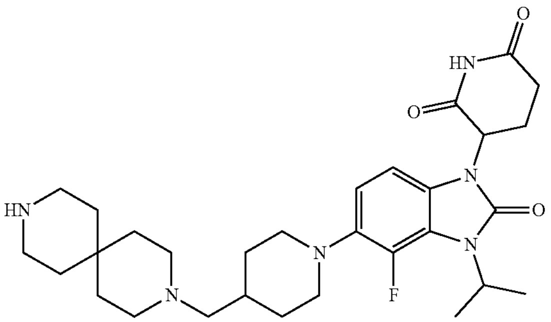 [SMILES: CC(C)n1c(=O)n(C2CCC(=O)NC2=O)c2ccc(N3CCC(CN4CCC5(CCNCC5)CC4)CC3)c(F)c21]

To a solution of tert-butyl 9-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecane-3-carboxylate (464 mg, 0.7 mmol) in dichloromethane (5.0 mL) was added 4 M HCl in 1,4-dioxane (5.0 mL), and the reaction mixture was stirred at 25° C. for 20 min. The reaction mixture was evaporated from petroleum ether (15 mL×2) to afford the title compound (470 mg, crude, 3 HCl salt) as a white solid. LC/MS (ESI) m/z: 555.5 $[M+H]^+$.

Step 10: Preparation of tert-butyl 3-[2-[2-[3-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

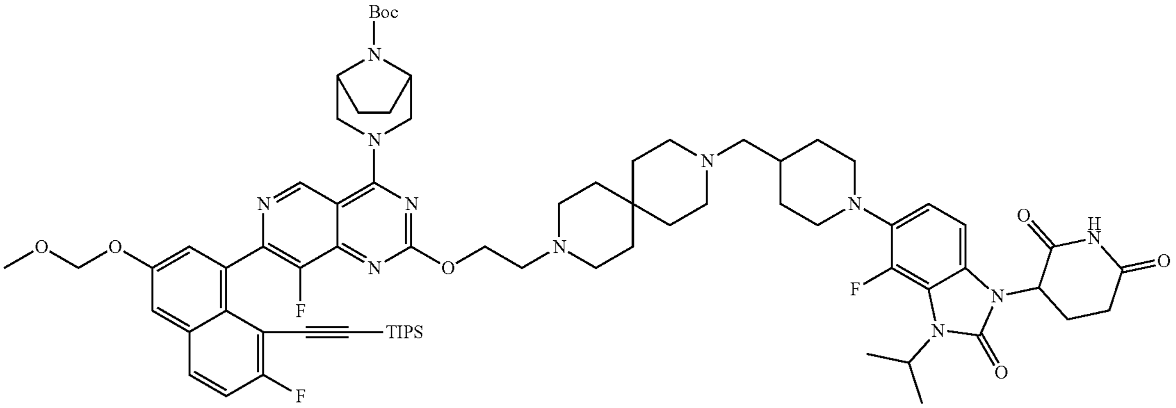

To 3-[5-[4-(3,9-diazaspiro[5.5]undecan-3-ylmethyl)-1-piperidyl]-4-fluoro-3-isopropyl-2-oxo-benzimidazol-1-yl]piperidine-2,6-dione (440 mg, 0.4 mmol, 3 HCl) in dichloromethane (5.0 mL) and DMSO (2.5 mL) were added sodium acetate (341 mg, 4 mmol), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (556 mg, 0.4 mmol), and $NaBH(OAc)_3$ (367 mg, 1.7 mmol), and the reaction mixture was stirred at 25° C. for 2 h. The mixture was diluted with saturated sodium bicarbonate solution (5.0 mL) and extracted with dichloromethane (3×30 mL). The combined organic extracts were washed with water (4×10 mL) followed by brine (15 mL), dried over sodium sulfate, filtered, and concentrated under reduced pressure. The residue was purified by flash column chromatography on silica gel (0 to 6% methanol in dichloromethane over 15 min) to afford the title compound (588 mg, 52%) as a yellow foam. LC/MS (ESI) m/z: 1341.9 $[M+H]^+$.

Step 11: Preparation of tert-butyl 3-[2-[2-[3-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

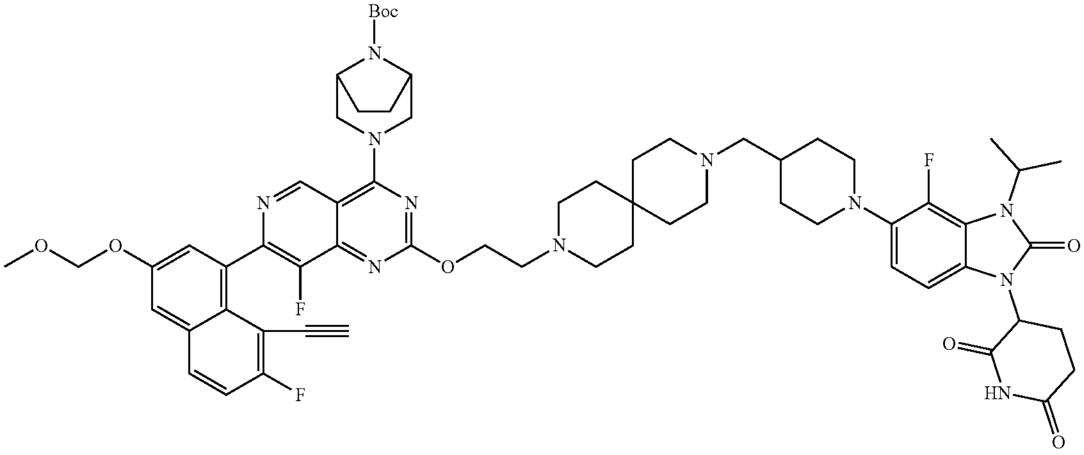 [SMILES: C#Cc1c(F)ccc2cc(OCOC)cc(-c3ncc4c(N5CC6CCC(C5)N6C(=O)OC(C)(C)C)nc(OCCN5CCC6(CC5)CCN(CC5CCN(c7ccc8c(c7F)n(C(C)C)c(=O)n8C7CCC(=O)NC7=O)CC5)CC6)nc4c3F)c12]

To a solution of tert-butyl 3-[2-[2-[3-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (588 mg, 0.4 mmol) in DMF (6.0 mL) was added cesium fluoride (333 mg, 2 mmol), and the reaction mixture was stirred at 25° C. for 12 h. The mixture was diluted with ethyl acetate (20 mL), then washed with water (3×10 mL). The aqueous phase was extracted with ethyl acetate (3×15 mL). The combined organic layers were washed with water (5.0 mL×6) followed by brine (2×15 mL), dried over sodium sulfate, filtered, and concentrated under reduced pressure to afford the title compound (488 mg, 54%) as a yellow foam. LC/MS (ESI) m/z: 1184.7 $[M+H]^+$.

Step 12: Preparation of 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-3-isopropyl-2-oxo-benzimidazol-1-yl]piperidine-2,6-dione

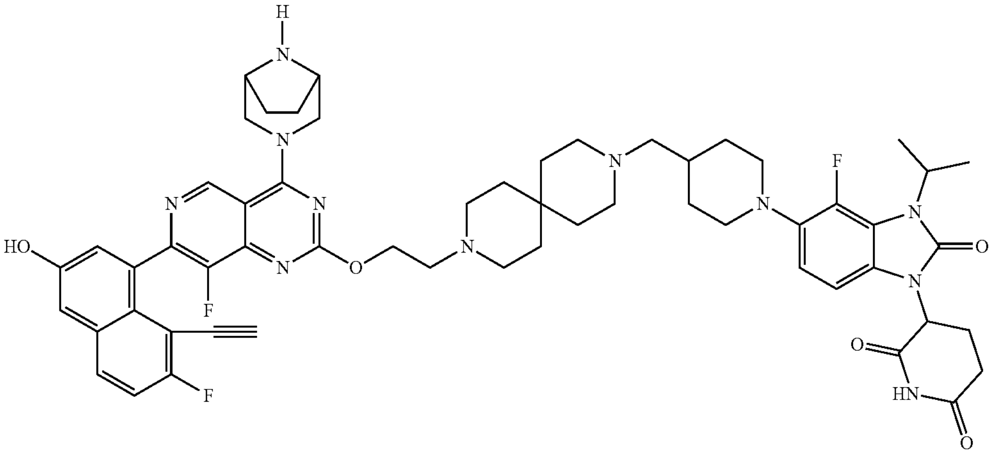 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7F)n(C(C)C)c(=O)n8C7CCC(=O)NC7=O)CC5)CC6)nc4c3F)c12]

To a solution of tert-butyl 3-[2-[2-[3-[[1-[1-(2,6-dioxo-3-piperidyl)-4-fluoro-3-isopropyl-2-oxo-benzimidazol-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (488 mg, 0.2 mmol) in dichloromethane (4.0 mL) was added 4 M HCl in 1,4-dioxane (4.0 mL), and the reaction mixture was stirred at 25° C. for 15 min. The mixture was diluted with tetrahydrofuran (30 mL) and triethylamine to adjust the pH to 8. The resulting mixture was filtered and concentrated under reduced pressure. The residue was purified by prep-HPLC (30% to 70% acetonitrile in water (ammonium bicarbonate) over 32 min) to afford the title compound (138.6 mg, 32%) as a yellow solid. LC/MS (ESI) m/z: 1040.5 $[M+H]^+$, $^1H$ NMR (400 MHz, $CD_3OD$) δ 9.01 (s, 1H), 7.86 (dd, J=5.6, 9.2 Hz, 1H), 7.36-7.28 (m, 2H), 7.21 (d, J=2.4 Hz, 1H), 6.90-6.80 (m, 2H), 5.28 (dd, J=5.2, 12.4 Hz, 1H), 4.73-4.54 (m, 5H), 3.75-3.62 (m, 4H), 3.37 (s, 1H), 2.95-2.84 (m, 3H), 2.84-2.71 (m, 3H), 2.71-2.65 (m, 2H), 2.62 (br s, 4H), 2.46 (br s, 4H), 2.32 (br d, J=6.4 Hz, 2H), 2.18-2.11 (m, 1H), 1.87 (br d, J=12.8 Hz, 4H), 1.83-1.77 (m, 2H), 1.75-1.66 (m, 1H), 1.57 (br s, 8H), 1.51 (br d, J=6.8 Hz, 6H), 1.48 (br s, 1H), 1.46-1.38 (m, 2H).

Example 50: Synthesis of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-3-methyl-2-oxo-benzimidazol-1-yl]piperidine-2,6-dione (Compound 204)

Step 7: Preparation of cis-[3-[[tert-butyl(diphenyl)silyl]oxymethyl]-1,2,3,5,6,7-hexahydropyrrolizin-8-yl]methanol

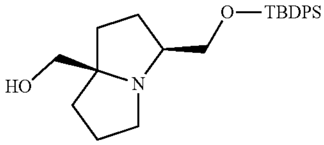

To a stirred solution of methyl 3-[[tert-butyl(diphenyl)silyl]oxymethyl]-1,2,3,5,6,7-hexahydropyrrolizine-8-carboxylate (1.0 g, 2 mmol) in tetrahydrofuran (15 mL) was added lithium aluminium hydride (104 mg, 2.7 mmol), and the reaction mixture was stirred at 0° C. for 30 min. The reaction mixture was diluted with water (0.1 mL), aqueous sodium hydroxide solution (0.1 mL, 15 wt %), and water (0.3 mL) sequentially at 0° C. The mixture was dried over anhydrous sodium sulfate, filtered, and concentrated under reduced pressure. The residue was purified by flash column chromatography on silica gel (0 to 50% ethyl acetate in petroleum ether over 10 min) to afford the title compound (477 mg, 48%) as a white oil. LC/MS (ESI) m/z: 410.3 $[M+H]^+$.

Step 8: Preparation of [(3R,8S)-3-[[tert-butyl(diphenyl)silyl]oxymethyl]-1,2,3,5,6,7-hexahydropyrrolizin-8-yl]methanol & [(3S,8R)-3-[[tert-butyl(diphenyl)silyl]oxymethyl]-1,2,3,5,6,7-hexahydropyrrolizin-8-yl]methanol

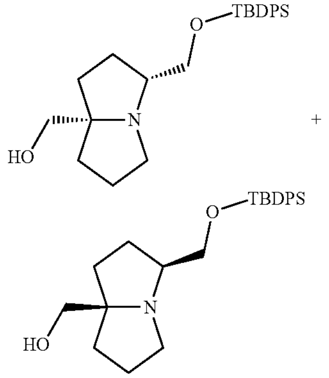

cis-[3-[[tert-butyl(diphenyl)silyl]oxymethyl]-1,2,3,5,6,7-hexahydropyrrolizin-8-yl]methanol (500 mg) was purified by SFC (column: DAICEL CHIRALCEL OX (250 mm*30 mm, 10 um); [0.1% $NH_3H_2O$-IPA], 35%) to afford the first eluted enantiomer [(3R,8S)-3-[[tert-butyl(diphenyl)silyl]oxymethyl]-1,2,3,5,6,7-hexahydropyrrolizin-8-yl]methanol (240 mg, 46%) as colorless oil, and then the later eluted enantiomer [(3S,8R)-3-[[tert-butyl(diphenyl)silyl]oxymethyl]-1,2,3,5,6,7-hexahydropyrrolizin-8-yl]methanol (265 mg, 49%) as colorless oil. LC/MS (ESI) m/z: 410.3 $[M+H]^+$.

Step 9: Preparation of tert-butyl 3-[2-[[(3S,8R)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

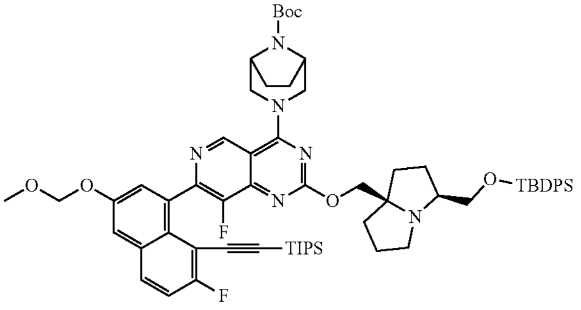

To a mixture of tert-butyl 3-[8-fluoro-7-[7-fluoro-3-(methoxymethoxy)-8-(2-triisopropylsilylethynyl)-1-naphthyl]-2-methylsulfonyl-pyrido[4,3-d]pyrimidin-4-yl]-3,8-diazabicyclo[3.2.1]octane-8-carboxylate (500 mg, 0.6 mmol), 4 A molecular sieves (500 mg), and [(3S,8R)-3-[[tert-butyl(diphenyl)silyl]oxymethyl]-1,2,3,5,6,7-hexahydropyrrolizin-8-yl]methanol (249 mg, 0.6 mmol) in tetrahydrofuran (6 mL) at 0° C. was added t-BuONa (146 mg, 1.5 mmol) under nitrogen atmosphere, and the reaction mixture was stirred at 0° C. for 30 min. The mixture was diluted with 0.2 M aqueous HCl solution (8 mL) and extracted with dichloromethane (3×40 mL). The combined organic phase was washed with brine (20 mL), dried over anhydrous sodium sulfate, filtered, and concentrated under reduced pressure. The residue was purified by flash column chromatography on silica gel (0 to 20% ethyl acetate in petroleum ether over 18 min) to afford the title compound (294 mg, 39%) as a yellow oil. LC/MS (ESI) m/z: 1151.5 $[M+H]^+$.

Step 10: Preparation of tert-butyl 3-[7-[8-ethynyl-7-fluoro-3-(methoxymethoxy)-1-naphthyl]-8-fluoro-2-[[(3S,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate

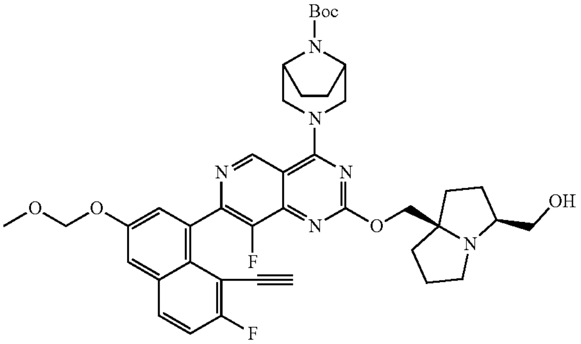 [SMILES: C#Cc1c(F)ccc2cc(OCOC)cc(-c3ncc4c(N5CC6CCC(C5)N6C(=O)OC(C)(C)C)nc(OC[C@]56CCCN5[C@H](CO)CC6)nc4c3F)c12]

To a solution of tert-butyl 3-[2-[[(3S,8R)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (294 mg, 0.3 mmol) in DMF (4 mL) was added cesium fluoride (310 mg, 2 mmol), and the reaction mixture was stirred at 30° C. for 12 h. The mixture was diluted with water (20 mL) and extracted with ethyl acetate (3×30 mL). The combined organic extract was washed with brine (20 mL), dried over anhydrous sodium sulfate, filtered, and concentrated under reduced pressure. The residue was purified by flash column chromatography on silica gel (0 to 2% then up to 7% methanol in dichloromethane) to afford the title compound (167 mg, 78%) as a yellow solid. LC/MS (ESI) m/z: 757.3 $[M+H]^+$.

Step 11: Preparation of tert-butyl 3-[7-[8-ethynyl-7-fluoro-3-(methoxymethoxy)-1-naphthyl]-8-fluoro-2-[[(3S,8R)-3-formyl-1,2,3,5,6,7-hexahydropyrrolizin-8-yl]methoxy]pyrido[4,3-d]pyrimidin-4-yl]-3,8-diazabicyclo[3.2.1]octane-8-carboxylate

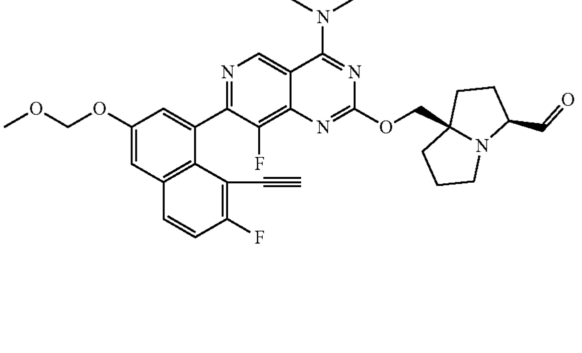

To a mixture of DMSO (413 μL) and dichloromethane (2 mL) at −67° C. was added a solution of oxalyl dichloride (290 μL, 3.3 mmol) in dichloromethane (3 mL) dropwise under nitrogen atmosphere, and the mixture was stirred for 15 min. tert-Butyl 3-[7-[8-ethynyl-7-fluoro-3-(methoxymethoxy)-1-naphthyl]-8-fluoro-2-[[(3S,8R)-3-(hydroxymethyl)-1,2,3,5,6,7-hexahydropyrrolizin-8-yl]methoxy]pyrido[4,3-d]pyrimidin-4-yl]-3,8-diazabicyclo[3.2.1]octane-8-carboxylate (500 mg, 0.7 mmol) in dichloromethane (4 mL) was then added dropwise, and the resulting mixture was stirred at −67° C. for 30 min. Triethylamine (2.3 mL) was then, and the reaction mixture was stirred at −67° C. for 20 min under nitrogen atmosphere. The mixture was diluted with saturated sodium bicarbonate solution (10 mL) and extracted with dichloromethane (3×50 mL). The combined organic extract was washed with brine (2×100 mL), dried over anhydrous sodium sulfate, filtered, and concentrated under reduced pressure to afford the title compound (498 mg, crude) in dichloromethane (3 mL) as a yellow solution. LC/MS (ESI) m/z: 773.2 $[M+H_3O]^+$.

Step 12: Preparation of tert-butyl 3-[2-[[(3S,8R)-3-[[4-[[1-[1-(2,6-dioxo-3-piperidyl)-3-methyl-2-oxo-benzimidazol-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

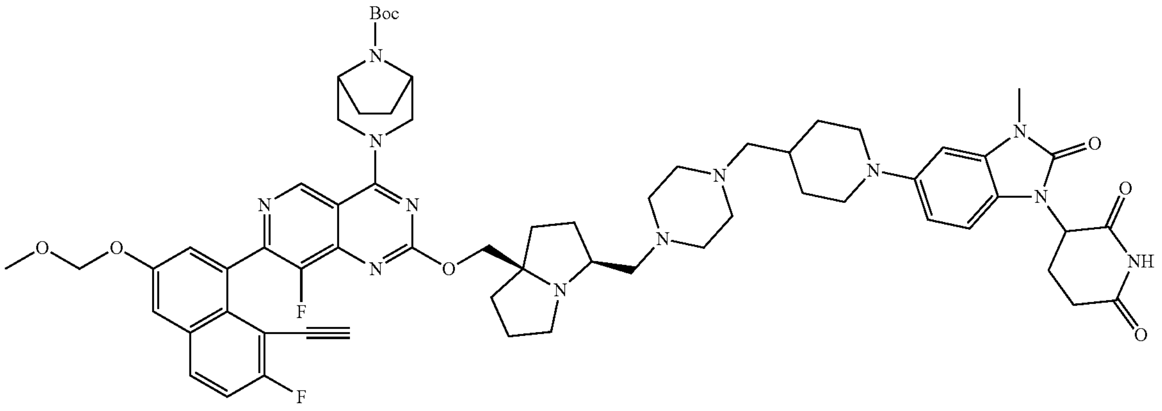 [SMILES: C#Cc1c(F)ccc2cc(OCOC)cc(-c3ncc4c(N5CC6CCC(C5)N6C(=O)OC(C)(C)C)nc(OC[C@]56CCCN5[C@H](CN5CCN(CC7CCN(c8ccc9c(c8)n(C)c(=O)n9C8CCC(=O)NC8=O)CC7)CC5)CC6)nc4c3F)c12]

To a mixture of 3-[3-methyl-2-oxo-5-[4-(piperazin-1-ylmethyl)-1-piperidyl]benzimidazol-1-yl]piperidine-2,6-dione (275 mg, 0.6 mmol) and tert-butyl 3-[7-[8-ethynyl-7-fluoro-3-(methoxymethoxy)-1-naphthyl]-8-fluoro-2-[[(3S,8R)-3-formyl-1,2,3,5,6,7-hexahydropyrrolizin-8-yl]methoxy]pyrido[4,3-d]pyrimidin-4-yl]-3,8-diazabicyclo[3.2.1]octane-8-carboxylate (376 mg, 0.5 mmol) in dichloromethane (15 mL) was added $NaBH(OAc)_3$ (264 mg, 1.3 mmol), and the reaction mixture was stirred at 25° C. for 12 h. The mixture was diluted with sodium bicarbonate (10 mL) and extracted with dichloromethane (3×40 mL). The combined organic extract was washed with brine (2×10 mL), dried over anhydrous sodium sulfate, filtered, and concentrated under reduced pressure. The residue was purified by flash column chromatography on silica gel (0 to 7% methanol in dichloromethane) to afford the title compound (255 mg, 43%) as a yellow solid. LC/MS (ESI) m/z: 1179.5 $[M+H]^+$.

Step 13: Preparation of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-3-methyl-2-oxo-benzimidazol-1-yl]piperidine-2,6-dione

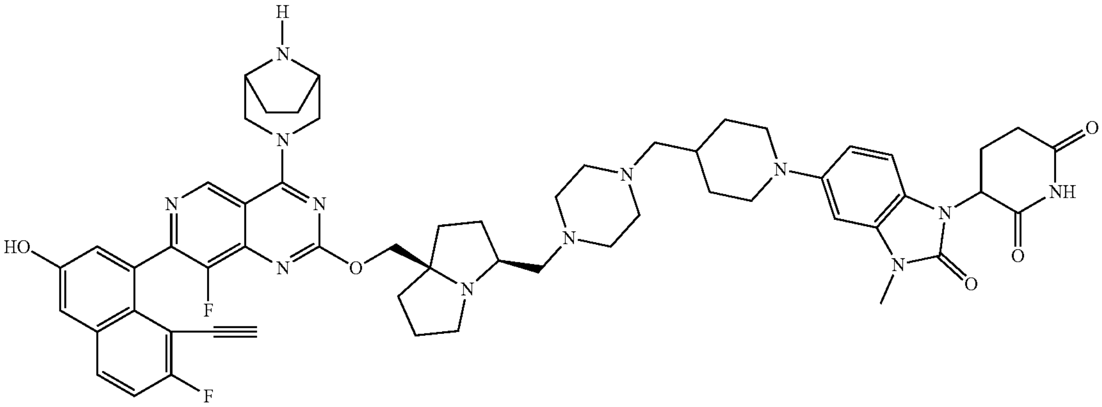 [SMILES: C#Cc1c(F)ccc2cc(O)cc(-c3ncc4c(N5CC6CCC(C5)N6)nc(OC[C@]56CCCN5[C@H](CN5CCN(CC7CCN(c8ccc9c(c8)n(C)c(=O)n9C8CCC(=O)NC8=O)CC7)CC5)CC6)nc4c3F)c12]

To a solution of tert-butyl 3-[2-[[(3S,8R)-3-[[4-[[1-[1-(2,6-dioxo-3-piperidyl)-3-methyl-2-oxo-benzimidazol-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (255 mg, 0.2 mmol) in dichloromethane (2.0 mL) was added 4 M HCl in 1,4-dioxane (2.0 mL), and the mixture was stirred at 25° C. for 10 min. The reaction mixture was suspended in petroleum ether (6 mL) and filtered. The sticky filter cake was diluted with THF (50 mL) and triethylamine to adjust the pH to 8. The mixture was filtered and concentrated under reduced pressure. The residue was purified by preparative HPLC (18% to 58% acetonitrile in water (ammonium bicarbonate) over 32 min) to afford the title compound (114.0 mg, 50%) as a yellow solid. LC/MS (ESI) m/z: 1035.7 [M+H]; $^1$H NMR (400 MHz, $CD_3OD$) δ 9.01 (d, J=2.4 Hz, 1H), 7.85 (ddd, J=3.2, 5.6, 9.2 Hz, 1H), 7.37-7.26 (m, 2H), 7.21 (d, J=2.4 Hz, 1H), 6.98 (d, J=8.4 Hz, 1H), 6.87 (s, 1H), 6.80 (br d, J=8.4 Hz, 1H), 5.28 (dd, J=5.6, 12.4 Hz, 1H), 4.69-4.55 (m, 2H), 4.32-4.20 (m, 2H), 3.75-3.64 (m, 4H), 3.57 (br d, J=11.6 Hz, 2H), 3.43-3.35 (m, 4H), 3.14-2.97 (m, 2H), 2.95-2.74 (m, 4H), 2.73-2.31 (m, 12H), 2.27-2.06 (m, 5H), 1.99-1.65 (m, 13H), 1.44-1.27 (m, 2H).

Example 51: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione (Compound 205)

Step 1: Preparation of 2-[8-ethynyl-7-fluoro-3-(methoxymethoxy)-1-naphthyl]-4,4,5,5-tetramethyl-1,3,2-dioxaborolane

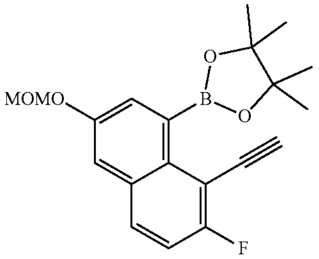

To a solution of 2-[2-fluoro-6-(methoxymethoxy)-8-(4,4,5,5-tetramethyl-1,3,2-dioxaborolan-2-yl)-1-naphthyl]ethynyl-triisopropyl-silane (5.0 g, 10 mmol) in N,N-dimethylformamide (50 mL) was added cesium fluoride (29.64 g, 195 mmol), and the reaction mixture was stirred at 25° C. for 12 h. The mixture was diluted with water (60 mL) and extracted with ethyl acetate (3×50 mL). The combined organic layer was washed with brine (2×40 mL), dried over anhydrous sodium sulfate, filtered, and concentrated under reduced pressure. The residue was purified by silica gel column chromatography (petroleum ether/ethyl acetate=20/1 then 4:1) to afford the title compound (3.3 g, 95%) as a light yellow solid. LC/MS (ESI) m/z: 356.8 $[M+H]^+$, $^1H$ NMR (400 MHz, DMSO-$d_6$) δ 7.97 (dd, J=6.0, 9.2 Hz, 1H), 7.58 (d, J=2.4 Hz, 1H), 7.48 (t, J=9.2 Hz, 1H), 7.34 (d, J=2.4 Hz, 1H), 5.32 (s, 2H), 5.01 (s, 1H), 3.42 (s, 3H), 1.37 (s, 12H).

Step 2: Preparation of 2-[8-ethyl-7-fluoro-3-(methoxymethoxy)-1-naphthyl]-4,4,5,5-tetramethyl-1,3,2-dioxaborolane

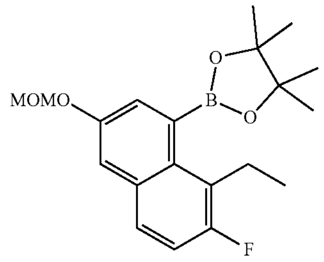

A mixture of 2-[8-ethynyl-7-fluoro-3-(methoxymethoxy)-1-naphthyl]-4,4,5,5-tetramethyl-1,3,2-dioxaborolane (3.3 g, 9 mmol) and platinum/aluminium oxide (0.3 g) in tetrahydrofuran (30 mL) and ethyl acetate (30 mL) was added into a FLV1 flow chemistry reactor at 20° C., and the mixture was stirred for 10 min at 20° C. The backpressure regulator was set to 0.5 MPa, the flow rate of P1 was at 0.5 mL/min, the hydrogen flow rate was 20 mL/min, and the reaction mixture was stirred at 40° C. for 20 min. The reaction solution was concentrated under reduced pressure. The residue was purified by silica gel column chromatography (petroleum ether/ethyl acetate=20/1 to 4:1) to afford the title compound (1.5 g, 45%) as a light yellow gum. $^1H$ NMR (400 MHz, $CDCl_3$) δ 7.66-7.51 (m, 1H), 7.47-7.33 (m, 2H), 7.25-7.13 (m, 1H), 5.41-5.26 (m, 2H), 3.64-3.51 (m, 3H), 3.25-3.06 (m, 2H), 1.58-1.44 (m, 12H), 1.32-1.25 (m, 3H).

Step 3: Preparation of tert-butyl 3-[7-[8-ethyl-7-fluoro-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate

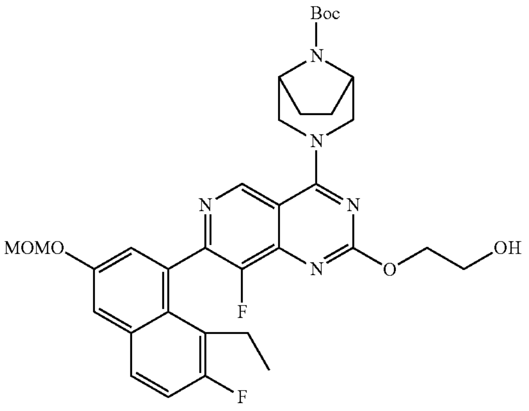

A mixture of 2-[8-ethyl-7-fluoro-3-(methoxymethoxy)-1-naphthyl]-4,4,5,5-tetramethyl-1,3,2-dioxaborolane (524 mg, 1.45 mmol), tert-butyl 3-[7-chloro-8-fluoro-2-(2-hydroxyethoxy)pyrido[4,3-d]pyrimidin-4-yl]-3,8-diazabicyclo [3.2.1]octane-8-carboxylate (600 mg, 1.3 mmol), potassium phosphate (842 mg, 4 mmol), and CataCXium A Pd G3 (97 mg, 0.1 mmol) in 1,4-dioxane (10 mL) and water (1 mL) was purged and degassed with nitrogen (3×), and the mixture was stirred at 90° C. for 16 h. The mixture was cooled to 25° C., diluted with water (30 mL) and extracted with ethyl acetate (3×20 mL). The combined organic extract was washed with brine (2×20 mL), dried over anhydrous sodium sulfate, filtered, and concentrated under reduced pressure. The residue was purified by silica gel column chromatography (petroleum ether/ethyl acetate=20/1 then 4:1) to afford the title compound (520 mg, 60%) as a light yellow solid. LC/MS (ESI) m/z: 652.2 $[M+H]^+$, $^1H$ NMR (400 MHz, DMSO-$d_6$) δ 9.15 (s, 1H), 7.89 (dd, J=6.0, 9.2 Hz, 1H), 7.67 (d, J=2.8 Hz, 1H), 7.43 (t, J=9.2 Hz, 1H), 7.22 (d, J=2.4 Hz, 1H), 5.34 (s, 2H), 4.91 (t, J=5.6 Hz, 1H), 4.63-4.47 (m, 2H), 4.40 (br t, J=4.8 Hz, 2H), 4.29 (br d, J=12.4 Hz, 2H), 3.77-3.70 (m, 3H), 3.62 (br d, J=12.8 Hz, 1H), 3.44-3.39 (m, 3H), 2.45-2.31 (m, 1H), 2.16 (ddd, J=2.8, 7.2, 14.4 Hz, 1H), 1.83 (br s, 2H), 1.69 (br d, J=8.4 Hz, 2H), 1.46 (s, 9H), 0.73 (t, J=7.6 Hz, 3H).

Step 4: Preparation of tert-butyl 3-[7-[8-ethyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate

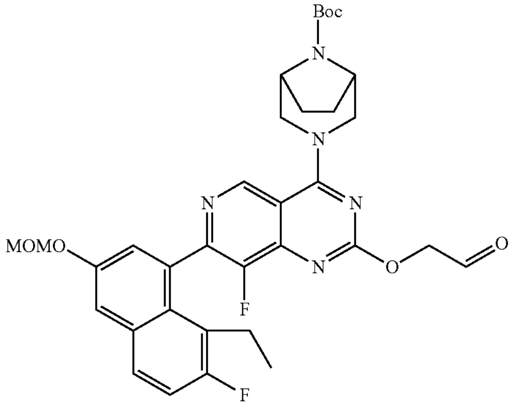

To a solution of dimethyl sulfoxide (156 mg, 2 mmol) in dichloromethane (3 mL) was added oxalyl dichloride (0.1 mL, 1 mmol) in dichloromethane (3 mL) dropwise at −65° C., and the mixture was stirred at −65° C. for 30 min. tert-Butyl 3-[7-[8-ethyl-7-fluoro-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate (520 mg, 0.8 mmol) in dichloromethane (3 mL) was then added dropwise, and the mixture was stirred at −65° C. for 0.5 h. Triethylamine (0.5 mL, 4 mmol) was then added, and the reaction mixture was stirred at −65° C. for 30 min, then warmed to 25° C. and stirred for 1 h. The reaction mixture was diluted with water (20 mL) and extracted with dichloromethane (3×20 mL). The combined organic phase was washed with brine (20 mL), dried over anhydrous sodium sulfate, filtered, and concentrated in vacuo to afford the title compound (500 mg, crude) as a yellow solid. LC/MS (ESI) m/z: 650.2 $[M+H]^+$.

Step 5: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

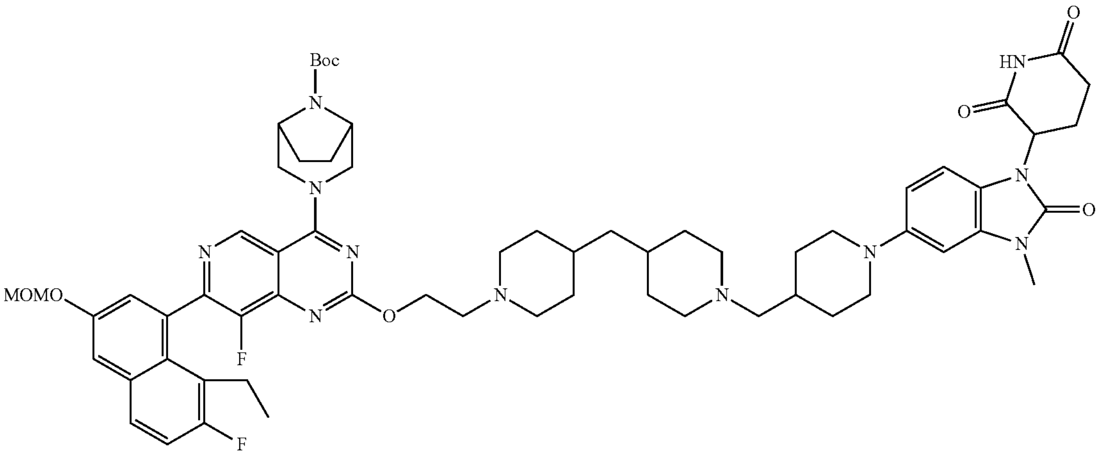

To a solution of 3-[3-methyl-2-oxo-5-[4-[[4-(4-piperidylmethyl)-1-piperidyl]methyl]-1-piperidyl]benzimidazol-1-yl]piperidine-2,6-dione trifluoroacetate (450 mg, 0.7 mmol) in dichloromethane (5 mL) and isopropanol (5 mL) were added N,N-diisopropylethylamine (0.2 mL, 1 mmol) and tert-butyl 3-[7-[8-ethyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate (899 mg, 1.4 mmol), and the resulting mixture was stirred at 25° C. for 0.5 h. Sodium triacetoxyborohydride (439.69 mg, 2 mmol) was then added, and the reaction mixture was stirred at 25° C. for 0.5 h. The mixture was diluted with water (30 mL) and extracted with dichloromethane (2×30 mL). The combined organic extract was dried over anhydrous sodium sulfate, filtered, and concentrated under reduced pressure. The residue was purified by flash silica gel chromatography (0 to 100% ethyl acetate/petroleum ether) to afford the title compound (590 mg, 73%) as a white solid. LC/MS (ESI) m/z: 1170.9 $[M+H]^+$.

Step 6: Preparation of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione

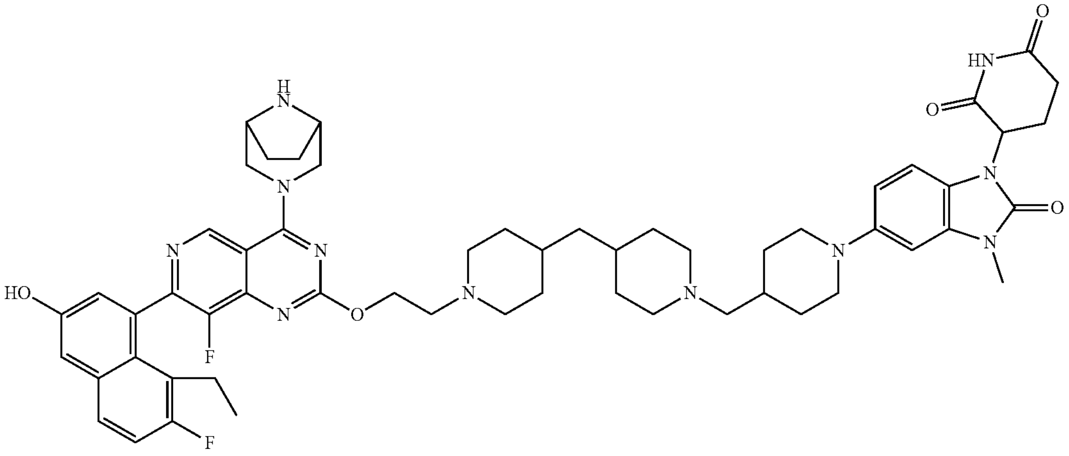 [SMILES: CCc1c(F)ccc2cc(O)cc(-c3ncc4c(N5CC6CCC(C5)N6)nc(OCCN5CCC(CC6CCN(CC7CCN(c8ccc9c(c8)n(C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (460 mg, 0.4 mmol) in dichloromethane (5 mL) was added 4 M HCl in 1,4-dioxane (5 mL), and the mixture was stirred at 25° C. for 0.5 h. The reaction mixture was suspended in petroleum ether (30 mL) and filtered under nitrogen atmosphere. The filtered cake was diluted with dimethyl sulfoxide (4 mL) and N,N-diisopropylethylamine to adjust the pH to 7. The resulting solution was purified by prep-HPLC (0% to 30% acetonitrile in water (formic acid) over 12 min) to afford the title compound (181.7 mg, 42%, formic acid salt) as a white solid. LC/MS (ESI) m/z: 1026.7 $[M+H]^+$; $^1H$ NMR (400 MHz, DMSO-$d_6$) δ 11.08 (br s, 1H), 9.13 (s, 1H), 8.26 (s, 3H), 7.77 (dd, J=6.0, 9.2 Hz, 1H), 7.41-7.30 (m, 2H), 7.03 (d, J=2.4 Hz, 1H), 6.93 (d, J=8.8 Hz, 1H), 6.82 (d, J=2.0 Hz, 1H), 6.62 (dd, J=2.0, 8.8 Hz, 1H), 5.29 (dd, J=5.2, 12.8 Hz, 1H), 4.63-4.39 (m, 4H), 3.92-3.66 (m, 4H), 3.57 (br d, J=11.6 Hz, 2H), 3.03-2.84 (m, 5H), 2.80-2.57 (m, 6H), 2.42-2.26 (m, 3H), 2.21-1.93 (m, 6H), 1.84-1.72 (m, 6H), 1.70-1.55 (m, 5H), 1.40-1.02 (m, 10H), 0.73 (t, J=7.6 Hz, 3H).

Example 52: Synthesis of 3-{4-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione (Compound 172)

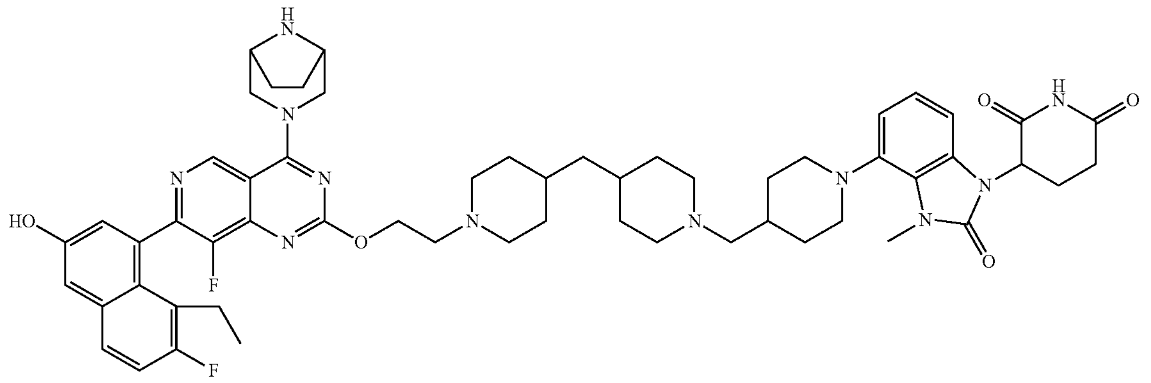 [SMILES: CCc1c(F)ccc2cc(O)cc(-c3ncc4c(N5CC6CCC(C5)N6)nc(OCCN5CCC(CC6CCN(CC7CCN(c8cccc9c8n(C)c(=O)n9C8CCC(=O)NC8=O)CC7)CC6)CC5)nc4c3F)c12]

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione. (white solid, formic acid salt). LC/MS (ESI) m/z: 1026.7 $[M+H]^+$; $^1H$ NMR (DMSO-$d_6$) b (br s, 1H), 9.13 (s, 1H), 8.26 (s, 3H), 7.77 (dd, J=6.0, 9.2 Hz, 1H), 7.41-7.30 (m, 2H), 7.03 (d, J=2.4 Hz, 1H), 6.93 (d, J=8.8 Hz, 1H), 6.82 (d, J=2.0 Hz, 1H), 6.62 (dd, J=2.0, 8.8 Hz, 1H), 5.29 (dd, J=5.2, 12.8 Hz, 1H), 4.63-4.39 (m, 4H), 3.92-3.66 (m, 4H), 3.57 (br d, J=11.6 Hz, 2H), 3.03-2.84 (m, 5H), 2.80-2.57 (m, 6H), 2.42-2.26 (m, 3H), 2.21-1.93 (m, 6H), 1.84-1.72 (m, 6H), 1.70-1.55 (m, 5H), 1.40-1.02 (m, 10H), 0.73 (t, J=7.6 Hz, 3H).

Example 53: Synthesis of 3-{4-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione (Compound 137)

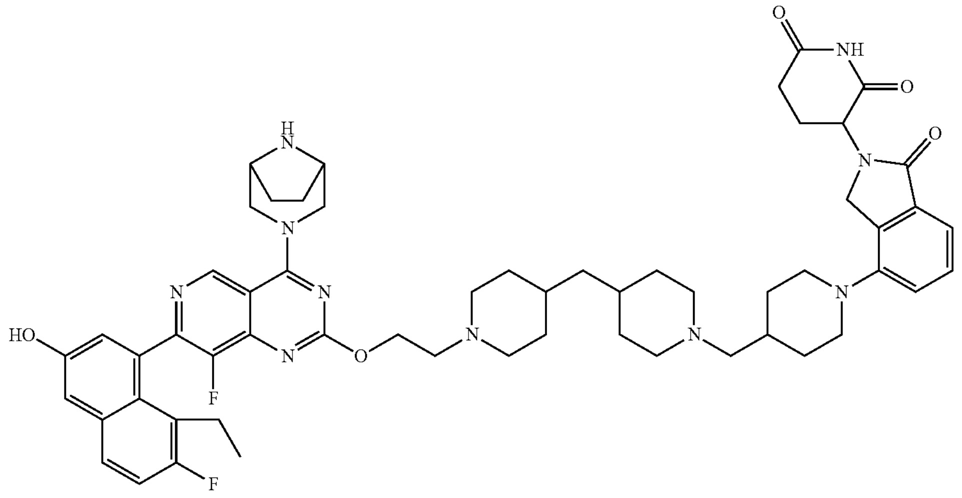 [SMILES: CCc1c(F)ccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12]

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione. (white solid, formic acid salt). LC/MS (ESI) m/z: 1011.8 $[M+H]^+$; $^1H$ NMR (400 MHz, DMSO-$d_6$) δ 10.98 (s, 1H), 9.13 (s, 1H), 8.17 (s, 2H), 7.80-7.72 (m, 1H), 7.42 (t, J=7.6 Hz, 1H), 7.37-7.32 (m, 2H), 7.29 (d, J=7.6 Hz, 1H), 7.15 (d, J=8.0 Hz, 1H), 7.02 (d, J=2.4 Hz, 1H), 5.15-5.08 (m, 1H), 4.62-4.47 (m, 5H), 4.45-4.39 (m, 1H), 4.31-4.25 (m, 1H), 3.96-3.88 (m, 2H), 2.86-2.72 (m, 3H), 3.42-3.31 (m, 2H), 3.05-2.89 (m, 5H), 2.82-2.76 (m, 2H), 2.74-2.65 (m, 2H), 2.63-2.55 (m, 1H), 2.39-2.30 (m, 3H), 2.19-2.07 (m, 5H), 2.04-1.95 (m, 1H), 1.88-1.72 (m, 7H), 1.66-1.58 (m, 4H), 1.42-1.17 (m, 6H), 1.15-1.05 (m, 4H), 0.72 (t, J=7.2 Hz, 3H).

Example 54: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione (Compound 86)

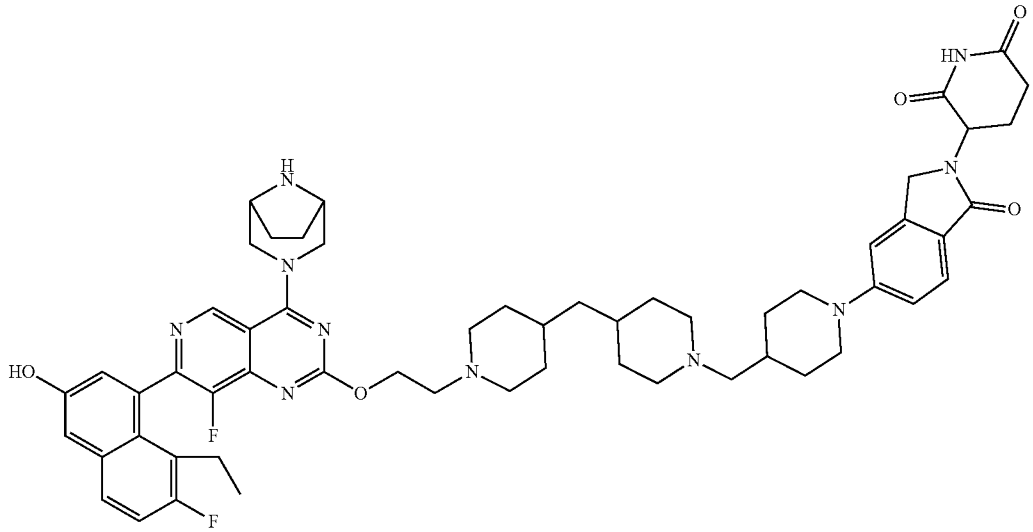 [SMILES: CCc1c(F)ccc2cc(O)cc(-c3ncc4c(N5CC6CCC(C5)N6)nc(OCCN5CCC(CC6CCN(CC7CCN(c8ccc9c(c8)CN(C8CCC(=O)NC8=O)C9=O)CC7)CC6)CC5)nc4c3F)c12]

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl) methyl]piperidin-1-yl}methyl)piperidin-1-yl]-3-methyl-2-oxo-2,3-dihydro-1H-1,3-benzodiazol-1-yl}piperidine-2,6-dione. (white solid, formic acid salt). LC/MS (ESI) m/z: 1011.7 $[M+H]^+$; $^1H$ NMR (400 MHz, DMSO-$d_6$) δ 10.94 (s, 1H), 9.14-9.06 (m, 1H), 8.19 (s, 3H), 7.76 (dd, J=6.0, 9.2 Hz, 1H), 7.49 (d, J=9.2 Hz, 1H), 7.39-7.30 (m, 2H), 7.09-6.99 (m, 3H), 5.03 (dd, J=5.2, 13.2 Hz, 1H), 4.51-4.40 (m, 4H), 4.33-4.28 (m, 1H), 4.16 (s, 1H), 3.85 (br d, J=12.8 Hz, 4H), 2.96-2.88 (m, 3H), 2.87-2.75 (m, 5H), 2.73-2.66 (m, 2H), 2.61-2.55 (m, 1H), 2.41-2.31 (m, 2H), 2.20-2.08 (m, 3H), 2.06-1.84 (m, 6H), 1.80-1.64 (m, 7H), 1.58 (br d, J=11.6 Hz, 4H), 1.39-1.21 (m, 3H), 1.20-0.99 (m, 8H), 0.72 (t, J=7.2 Hz, 3H).

Example 55: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}-4-methylpiperidin-4-yl)methyl]piperazin-1-yl}methyl)piperidin-1-yl]-3-methyl-2-oxo-2,3-dihydro-1H-1,3-benzodiazol-1-yl}piperidine-2,6-dione (Compound 180)

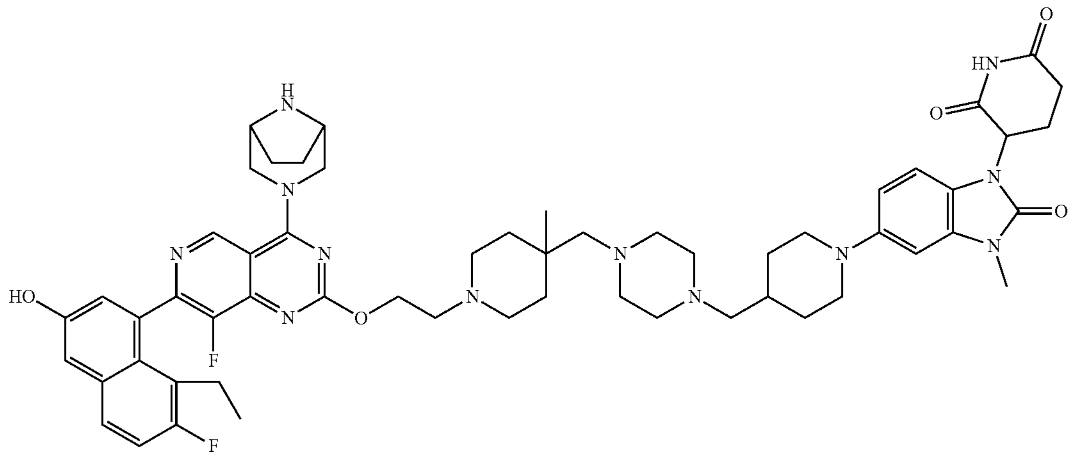

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl) methyl]piperidin-1-yl}methyl)piperidin-1-yl]-3-methyl-2-oxo-2,3-dihydro-1H-1,3-benzodiazol-1-yl}piperidine-2,6-dione. (yellow solid, formic acid salt.) LC/MS (ESI) m/z: 1041.3 $[M+H]^+$; $^1H$ NMR (400 MHz, DMSO-$d_6$) δ 11.07 (brs, 1H), 9.12 (s, 1H), 8.22 (s, 2H), 7.77 (dd, J=6.0, 9.2 Hz, 1H), 7.39-7.31 (m, 2H), 7.02 (d, J=2.4 Hz, 1H), 6.92 (d, J=8.4 Hz, 1H), 6.81 (d, J=2.0 Hz, 1H), 6.62 (dd, J=2.0, 8.8 Hz, 1H), 5.29 (dd, J=5.2, 12.8 Hz, 1H), 4.55-4.39 (m, 4H), 3.77-3.66 (m, 3H), 3.56 (br d, J=11.6 Hz, 2H), 3.30 (s, 3H), 3.00-2.67 (m, 2H), 2.55 (s, 4H), 2.47 (br d, J=4.0 Hz, 7H), 2.41-2.27 (m, 8H), 2.20-2.03 (m, 6H), 2.01-1.94 (m, 1H), 1.79-1.68 (m, 6H), 1.63-1.54 (m, 1H), 1.51-1.42 (m, 2H), 1.22 (br d, J=8.0 Hz, 4H), 0.85 (s, 3H), 0.73 (t, J=7.2 Hz, 3H).

Example 56: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}-4-fluoropiperidin-4-yl)methyl]piperazin-1-yl}methyl)piperidin-1-yl]-3-methyl-2-oxo-2,3-dihydro-1H-1,3-benzodiazol-1-yl}piperidine-2,6-dione (Compound 181)

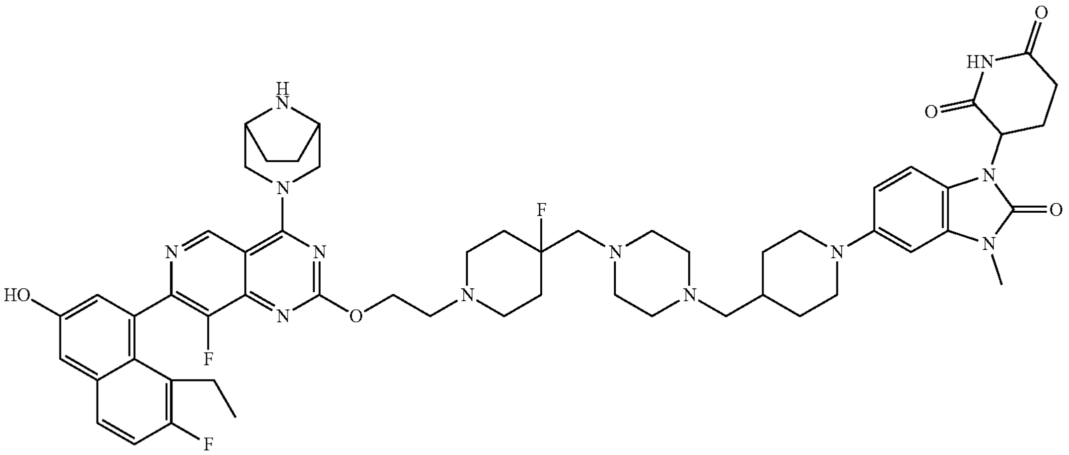 [SMILES: CCc1c(F)ccc2cc(O)cc(-c3ncc4c(N5CC6CCC(C5)N6)nc(OCCN5CCC(F)(CN6CCN(CC7CCN(c8ccc9c(c8)n(C)c(=O)n9C8CCC(=O)NC8=O)CC7)CC6)CC5)nc4c3F)c12]

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl) methyl]piperidin-1-yl}methyl)piperidin-1-yl]-3-methyl-2-oxo-2,3-dihydro-1H-1,3-benzodiazol-1-yl}piperidine-2,6-dione. (pink solid). LC/MS (ESI) m/z: 1045.8 $[M+H]^+$, $^1H$ NMR (400 MHz, DMSO-$d_6$) δ 11.06 (s, 1H), 9.10 (s, 1H), 8.22-8.17 (m, 2H), 7.76 (dd, J=6.0, 9.2 Hz, 1H), 7.38-7.31 (m, 2H), 7.02 (d, J=2.4 Hz, 1H), 6.91 (d, J=8.8 Hz, 1H), 6.80 (d, J=2.0 Hz, 1H), 6.61 (dd, J=2.0, 8.8 Hz, 1H), 5.28 (dd, J=5.2, 12.8 Hz, 1H), 4.51-4.41 (m, 4H), 3.70-3.60 (m, 5H), 3.56 (d, J=12.0 Hz, 3H), 3.29 (s, 3H), 2.92-2.83 (m, 1H), 2.76-2.65 (m, 5H), 2.64-2.55 (m, 4H), 2.46 (s, 3H), 2.40 (s, 2H), 2.36-2.28 (m, 6H), 2.13 (d, J=7.2 Hz, 3H), 2.02-1.94 (m, 1H), 1.82-1.71 (m, 5H), 1.68 (s, 4H), 1.62-1.51 (m, 2H), 1.22 (d, J=10.0 Hz, 2H), 0.72 (t, J=7.6 Hz, 3H).

Example 57: Exemplary Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}-4-fluoropiperidin-4-yl)methyl]piperidin-1-yl}methyl) piperidin-1-yl]-3-methyl-2-oxo-2,3-dihydro-1H-1,3-benzodiazol-1-yl}piperidine-2,6-dione (Compound 182)

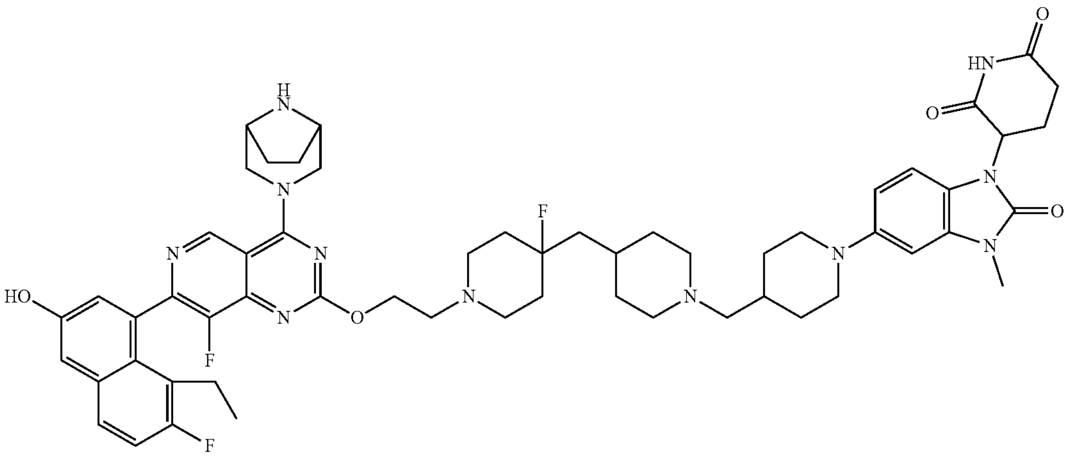 [SMILES: CCc1c(F)ccc2cc(O)cc(-c3ncc4c(N5CC6CCC(C5)N6)nc(OCCN5CCC(F)(CC6CCN(CC7CCN(c8ccc9c(c8)n(C)c(=O)n9C8CCC(=O)NC8=O)CC7)CC6)CC5)nc4c3F)c12]

The title compound was made in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione. (white solid, formic acid salt.) LC/MS (ESI) m/z: 1045.8 $[M+H]^+$; $^1H$ NMR (400 MHz, DMSO-$d_6$) δ 11.08 (brs, 1H), 9.12 (s, 1H), 8.27 (s, 2H), 7.77 (dd, J=6.0, 9.2 Hz, 1H), 7.44-7.30 (m, 2H), 7.03 (d, J=2.4 Hz, 1H), 6.92 (br d, J=8.8 Hz, 1H), 6.81 (d, J=1.6 Hz, 1H), 6.62 (br d, J=8.8 Hz, 1H), 5.29 (br dd, J=5.2, 12.8 Hz, 1H), 4.59-4.46 (m, 3H), 3.85-3.66 (m, 3H), 3.57 (br d, J=11.6 Hz, 2H), 3.30 (s, 3H), 2.99-2.82 (m, 3H), 2.81-2.69 (m, 4H), 2.66-2.56 (m, 3H), 2.41-2.26 (m, 4H), 2.19-2.10 (m, 1H), 2.08-1.98 (m, 2H), 1.82-1.62 (m, 10H), 1.57-1.43 (m, 3H), 1.24 (q, J=10.8 Hz, 3H), 0.73 (br t, J=7.2 Hz, 2H).

Example 58: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-3-methyl-2-oxo-2,3-dihydro-1H-1,3-benzodiazol-1-yl}piperidine-2,6-dione (Compound 206)

Step 1: Preparation of tert-butyl 4-[[1-[[1-[1-(2,6-dioxo-3-piperidyl)-4-fluoro-3-methyl-2-oxo-benzimidazol-5-yl]-4-piperidyl]methyl]-4-piperidyl]methyl]piperidine-1-carboxylate

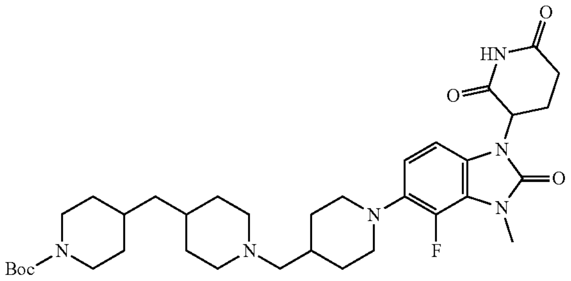 [SMILES: Cn1c(=O)n(C2CCC(=O)NC2=O)c2ccc(N3CCC(CN4CCC(CC5CCN(C(=O)OC(C)(C)C)CC5)CC4)CC3)c(F)c21]

To a solution of tert-butyl 4-(piperidin-4-ylmethyl)piperidine-1-carboxylate acetate (344 mg, 1 mmol) in dichloromethane (4 mL) and dimethyl sulfoxide (3 mL) were added N,N-diisopropylethylamine (0.15 mL, 0.9 mmol), acetic acid (70 mg, 1 mmol), 1-[1-(2,6-dioxo-3-piperidyl)-4-fluoro-3-methyl-2-oxo-benzimidazol-5-yl]piperidine-4-carbaldehyde (300 mg, 0.8 mmol), and sodium triacetoxyborohydride (409 mg, 1.9 mmol), and the reaction mixture was stirred at 25° C. for 2 h. The mixture was filtered and concentrated under reduced pressure, and the residue was purified by prep-TLC (dichloromethane/methanol=10/1) to afford the title compound (400 mg, 79%) as a yellow solid. LC/MS (ESI) m/z: 655.6 $[M+H]^+$.

Step 2: Preparation of 3-[4-fluoro-3-methyl-2-oxo-5-[4-[[4-(4-piperidylmethyl)-1-piperidyl]methyl]-1-piperidyl]benzimidazol-1-yl]piperidine-2,6-dione

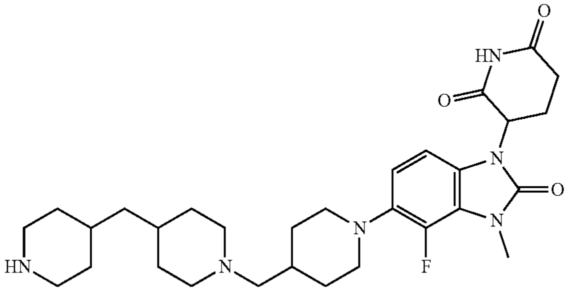 [SMILES: Cn1c(=O)n(C2CCC(=O)NC2=O)c2ccc(N3CCC(CN4CCC(CC5CCNCC5)CC4)CC3)c(F)c21]

To a solution of tert-butyl 4-[[1-[[1-[1-(2,6-dioxo-3-piperidyl)-4-fluoro-3-methyl-2-oxo-benzimidazol-5-yl]-4-piperidyl]methyl]-4-piperidyl]methyl]piperidine-1-carboxylate (400 mg, 0.6 mmol) in dichloromethane (6 mL) was added trifluoroacetic acid (2.0 mL, 27 mmol), and the reaction mixture was stirred at 25° C. for 1 h. The mixture was concentrated under reduced pressure, and the residue was purified by prep-HPLC (0% to 25% acetonitrile in water (trifluoroacetic acid) over 15 min) to afford the title compound (320 mg, 78%, TFA salt) as a yellow solid.

Step 3: Preparation of tert-butyl 3-[2-[2-[4-[[1-[[1-[1-(2,6-dioxo-3-piperidyl)-4-fluoro-3-methyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

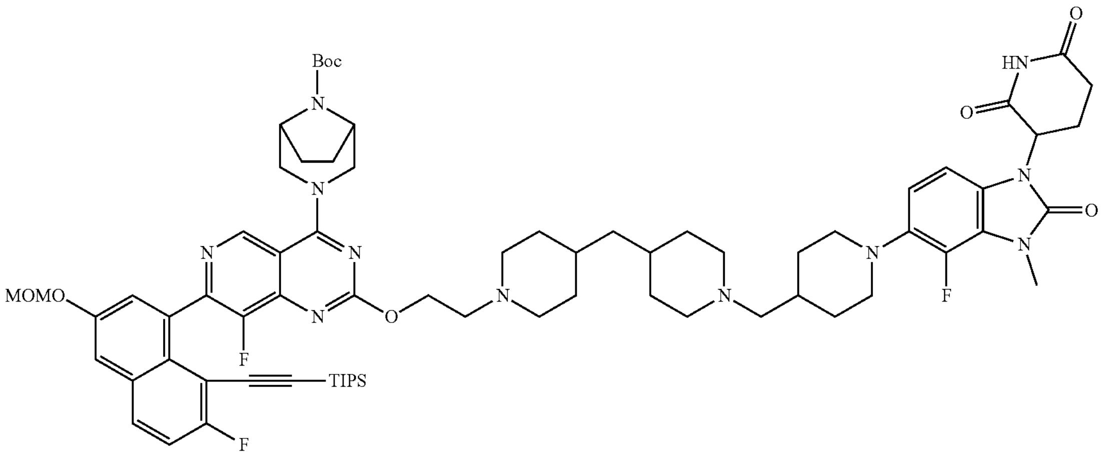

To a solution of 3-[4-fluoro-3-methyl-2-oxo-5-[4-[[4-(4-piperidylmethyl)-1-piperidyl]methyl]-1-piperidyl]benzimidazol-1-yl]piperidine-2,6-dione trifluoroacetate (230 mg, 0.3 mmol) in dichloromethane (3 mL) and isopropanol (3 mL) were added N,N-diisopropylethylamine (0.7 mL, 0.4 mmol), sodium triacetoxyborohydride (219 mg, 1 mmol), and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (303 mg, 0.4 mmol), and the reaction mixture was stirred at 25° C. for 1 h. The mixture was filtered and concentrated under reduced pressure, and the residue was purified by prep-TLC (dichloromethane/methanol=7/1) to afford the title compound (300 mg, 65%) as a yellow oil. LC/MS (ESI) m/z: 1342.1 $[M+H]^+$.

Step 4: Preparation of tert-butyl 3-[2-[2-[4-[[1-[[1-[1-(2,6-dioxo-3-piperidyl)-4-fluoro-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

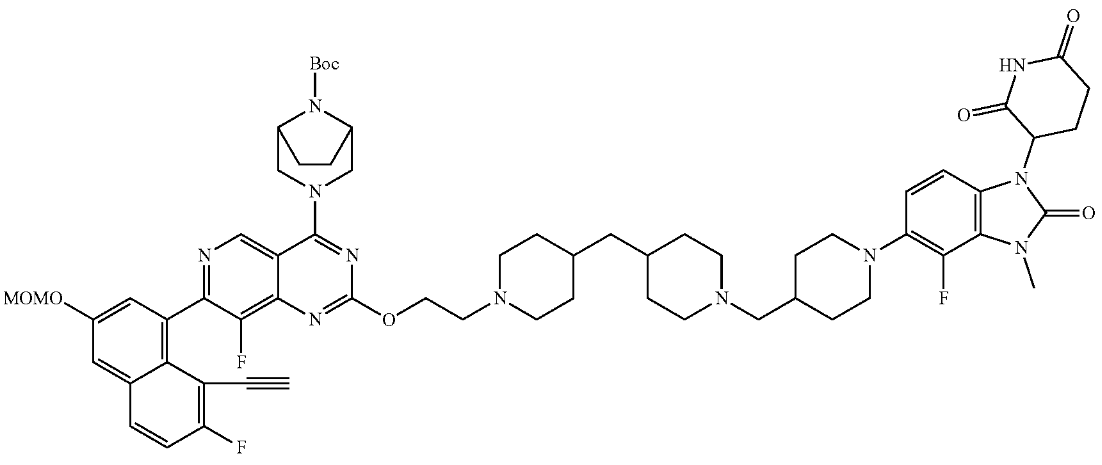

To a solution of tert-butyl 3-[2-[2-[4-[[1-[[1-[1-(2,6-dioxo-3-piperidyl)-4-fluoro-3-methyl-2-oxo-benzimidazol-5-yl]-4-piperidyl]methyl]-4-piperidyl] methyl]-1-piperidyl] ethoxy]-8-fluoro-7-[7-fluoro-3-(methoxymethoxy)-8-(2-triisopropylsilylethynyl)-1-naphthyl]pyrido[4,3-d] pyrimidin-4-yl]-3,8-diazabicyclo[3.2.1]octane-8-carboxylate (270 mg, 0.2 mmol) in N,N-dimethylformamide (15 mL) was added cesium fluoride (918 mg, 6 mmol), and the reaction mixture was stirred at 25° C. for 10 h. The mixture was filtered and concentrated under reduced pressure, and the residue was purified by prep-HPLC (23% to 43% acetonitrile in water (formic acid) over 10 min) to afford the title compound (230 mg, 96%, formic acid salt) as a yellow solid. LC/MS (ESI) m/z: 1184.9 $[M+H]^+$.

Step 5: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-3-methyl-2-oxo-2,3-dihydro-1H-1,3-benzodiazol-1-yl}piperidine-2,6-dione

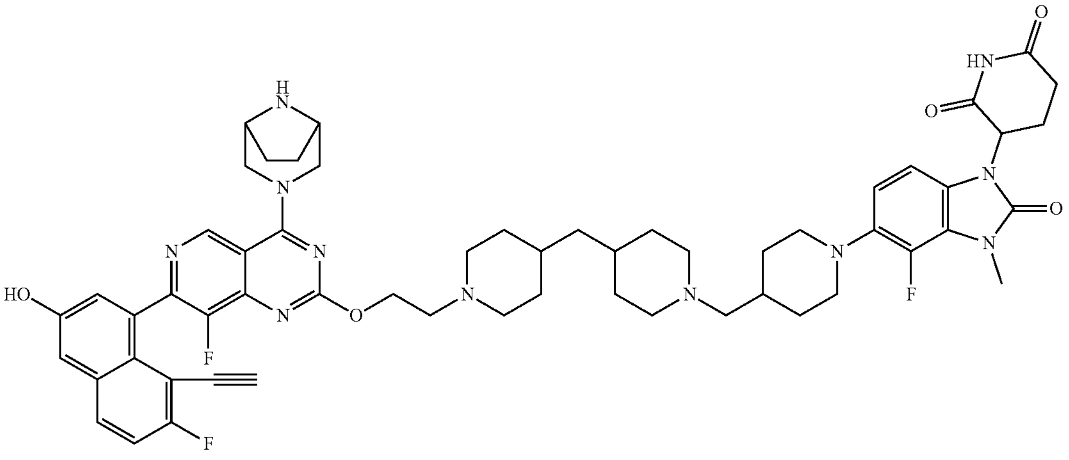 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)n(C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-4-fluoro-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (170 mg, 0.1 mmol) in dichloromethane (6 mL) was added 4 M HCl in 1,4-dioxane (1.9 mL), and the reaction mixture was stirred at 25° C. for 0.25 h. The mixture was filtered and concentrated under reduced pressure, and the residue was purified by prep-HPLC (1% to 30% acetonitrile in water (formic acid) over 10 min) to afford the title compound (62.8 mg, 39%, formic acid salt) as a yellow solid. LC/MS (ESI) m/z: 1040.2 $[M+H]^+$, $^1H$ NMR (400 MHz, DMSO-$d_6$) δ 11.11 (s, 1H), 9.06 (s, 1H), 8.21 (s, 2H), 7.98 (dd, J=9.2, 6.0 Hz, 1H), 7.47 (t, J=9.2 Hz, 1H), 7.40 (d, J=2.4 Hz, 1H), 7.18 (d, J=2.4 Hz, 1H), 6.88-6.80 (m, 1H), 6.73 (t, J=8.0 Hz, 1H), 5.33 (br dd, J=12.8, 5.6 Hz, 1H), 4.54-4.43 (m, 3H), 4.36 (br d, J=11.6 Hz, 1H), 3.94 (s, 1H), 3.73-3.60 (m, 4H), 3.47 (d, J=1.2 Hz, 3H), 3.21 (br d, J=11.2 Hz, 2H), 2.97-2.81 (m, 5H), 2.74-2.57 (m, 6H), 2.43 (br dd, J=3.6, 2.0 Hz, 1H), 2.20 (br d, J=7.2 Hz, 2H), 2.06-1.96 (m, 3H), 1.90 (br t, J=10.4 Hz, 2H), 1.81-1.70 (m, 6H), 1.59 (br d, J=11.2 Hz, 5H), 1.35-1.22 (m, 4H), 1.10 (br d, J=6.8 Hz, 6H).

Example 59: Synthesis of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione (Compound 207)

Step 1: Preparation of tert-butyl 3-[7-[8-ethyl-7-fluoro-3-(methoxy methoxy)-1-naphthyl]-8-fluoro-2-methylsulfanyl-pyrido[4,3-d]pyrimidin-4-yl]-3,8-diazabicyclo[3.2.1]octane-8-carboxylate

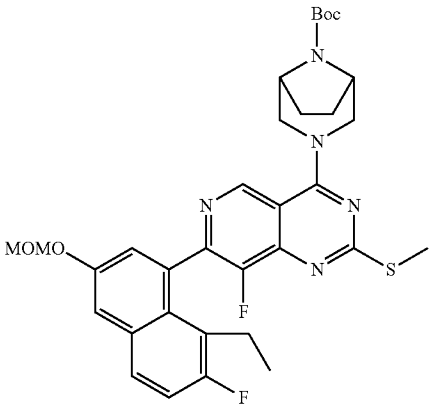

To a mixture of tert-butyl 3-(7-chloro-8-fluoro-2-methylsulfanyl-pyrido[4,3-d]pyrimidin-4-yl)-3,8-diazabicyclo [3.2.1]octane-8-carboxylate (500 mg, 1.1 mmol) and 2-[8-ethyl-7-fluoro-3-(methoxymethoxy)-1-naphthyl]-4,4,5,5-tetramethyl-1,3,2-dioxaborolane (450 mg, 1.3 mmol) in dioxane (10 mL) and water (1 mL) were added potassium phosphate (724 mg, 3.4 mmol) and methanesulfonato(di-adamantyl-n-butylphosphino)-2'-amino-1,1'-biphenyl-2-yl) palladium(II) (83 mg, 0.1 mmol), and the mixture was degassed and purged with nitrogen several times. The reaction mixture was stirred at 90° C. for 12 hours under nitrogen atmosphere. The mixture was filtered through a pad of celite, the filtrate solution was diluted with water (10 mL) and extracted with ethyl acetate (10 mL×3). The combined organic phase was washed with brine (10 mL×2), dried over anhydrous sodium sulfate, filtered, and concentrated under reduced pressure. The residue was purified by silica gel column chromatography (petroleum ether/ethyl acetate=1/0 to 1/1) to afford the title compound (627 mg, 89%) as a yellow gum. LC/MS (ESI) m/z: 638.3 [M+1]$^+$.

Step 2: Preparation of tert-butyl 3-[7-[8-ethyl-7-fluoro-3-(methoxymethoxy)-1-naphthyl]-8-fluoro-2-methylsulfonyl-pyrido[4,3-d]pyrimidin-4-yl]-3,8-diazabicyclo[3.2.1]octane-8-carboxylate

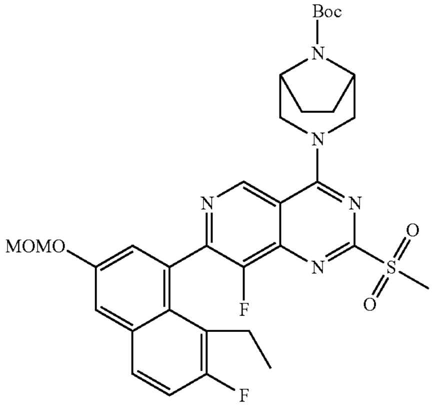

To a mixture of tert-butyl 3-[7-[8-ethyl-7-fluoro-3-(methoxymethoxy)-1-naphthyl]-8-fluoro-2-methylsulfanylpyrido[4,3-d]pyrimidin-4-yl]-3,8-diazabicyclo[3.2.1]octane-8-carboxylate (627 mg, 0.98 mmol) in N,N-dimethylformamide (6 mL) was added molecular sieves (4 A, 627 mg), and the mixture was stirred for 4 h, followed by the addition of Oxone (1.81 g, 3 mmol). The reaction mixture was stirred at 25° C. for 12 hours. The mixture was filtered, the filtrate solution was diluted with water (30 mL) and extracted with ethyl acetate (30 mL×2). The combined organic layers were washed with brine (30 mL×2), dried over anhydrous sodium sulfate, filtered, and concentrated under reduced pressure. The residue was purified by silica gel column chromatography (petroleum ether/ethyl acetate=1/0 to 1/1) to afford the title compound (365 mg, 58%) as a yellow gum. LC/MS (ESI) m/z: 670.2 [M+1]$^+$.

Step 3: Preparation of tert-butyl 3-[7-[8-ethyl-7-fluoro-3-(methoxy methoxy)-1-naphthyl]-8-fluoro-2-[[(2S,4R)-1-methyl-4-[[1-(2-trimethylsilyl ethoxy-carbonyl)-4-piperidyl]oxy]pyrrolidin-2-yl]methoxy] pyrido[4,3-d]pyrimidin-4-yl]-3,8-diazabicyclo[3.2.1] octane-8-carboxylate

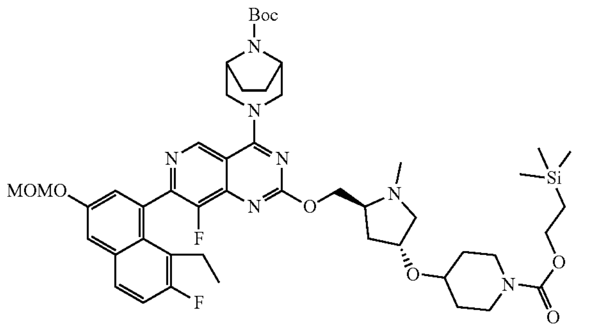

To a mixture of 2-trimethylsilylethyl 4-[(3R,5S)-5-(hydroxymethyl)-1-methyl-pyrrolidin-3-yl]oxypiperidine-1-carboxylate (221 mg, 0.6 mmol) and 4 A molecular sieves (6 mL) at 0° C. was added lithium tert-butoxide (1 M, 1.63 mL) followed by tert-butyl 3-[7-[8-ethyl-7-fluoro-3-(methoxymethoxy)-1-naphthyl]-8-fluoro-2-methylsulfonyl-pyrido[4,3-d]pyrimidin-4-yl]-3,8-diazabicyclo[3.2.1]octane-8-carboxylate (365 mg, 0.5 mmol), and the reaction mixture was stirred at 0° C. for 1 h. The mixture was diluted with ethyl acetate (20 mL) and washed with saturated ammonium chloride (3×20 mL). The organic extract was dried over anhydrous sodium sulfate, filtered, and concentrated under reduced pressure. The crude product was purified by prep-HPLC (45%-75% acetonitrile in water (formic acid) over 10 min) to afford the title compound (157 mg, 30%) as a brown gum. LC/MS (ESI) m/z: 948.8 [M+H]$^+$; $^1$H NMR (400 MHz, DMSO-$d_6$) δ 9.11 (s, 1H), 7.86 (dd, J=6.0, 9.2 Hz, 1H), 7.64 (d, J=2.8 Hz, 1H), 7.40 (t, J=9.6 Hz, 1H), 7.17 (d, J=2.4 Hz, 1H), 5.30 (s, 2H), 4.60-4.35 (m, 3H), 4.29-4.18 (m, 3H), 4.00-3.95 (m, 1H), 3.69-3.54 (m, 4H), 3.50-3.42 (m, 1H), 3.40-3.36 (m, 3H), 3.26-3.14 (m, 2H), 3.03-2.93 (m, 2H), 2.81-2.72 (m, 1H), 2.36-2.27 (m, 4H), 2.18-2.09 (m, 2H), 1.83-1.69 (m, 5H), 1.67-1.60 (m, 2H), 1.42 (s, 9H), 1.31-1.20 (m, 3H), 0.88 (d, J=8.0 Hz, 2H), 0.69 (t, J=7.2 Hz, 3H), −0.03 (s, 9H).

Step 4: Preparation of tert-butyl 3-[7-[8-ethyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate

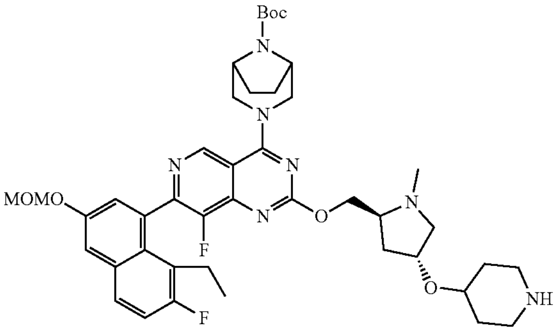

To a solution of tert-butyl 3-[7-[8-ethyl-7-fluoro-3-(methoxy methoxy)-1-naphthyl]-8-fluoro-2-[[(2S,4R)-1-methyl-4-[[1-(2-trimethylsilyl ethoxycarbonyl)-4-piperidyl]oxy]pyrrolidin-2-yl]methoxy]pyrido[4,3-d]pyrimidin-4-yl]-3,8-diazabicyclo[3.2.1]octane-8-carboxylate (157 mg, 0.2 mmol) in N,N-dimethylformamide (2 mL) at 25° C. was added cesium fluoride (251 mg, 2 mmol), and the reaction mixture was stirred at 90° C. for 1 h. The mixture was diluted with water (10 mL) and extracted with ethyl acetate (2×10 mL) followed by dichloromethane (2×10 mL). The combined organic extracts were dried over anhydrous sodium sulfate, filtered, and concentrated under reduced pressure to afford the title compound (128 mg, crude) as a yellow gum. LC/MS (ESI) m/z: 804.3 $[M+H]^+$.

Step 5: Preparation of tert-butyl 3-[2-[[(2S,4R)-4-[[1-[[1-[1-(2,6-dioxo-3-piperidyl)-3-methyl-2-oxo-benzimidazol-5-yl]-4-piperidyl]methyl]-4-piperidyl]oxy]-1-methyl-pyrrolidin-2-yl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

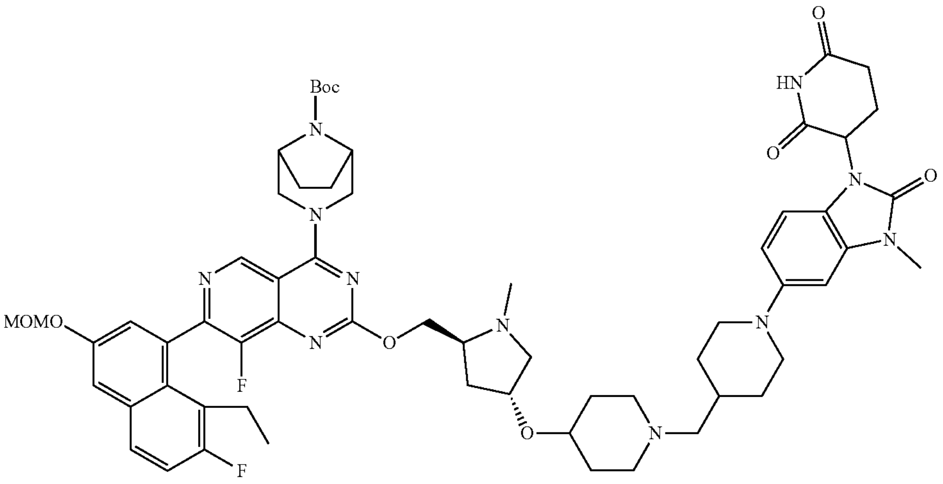

To a solution of tert-butyl 3-[7-[8-ethyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate formate (160 mg, 0.2 mmol) in dichloromethane (3 mL) and isopropanol (3 mL) were added N,N-diisopropylethylamine (29 mg, 0.2 mmol), acetic acid (17 mg, 0.3 mmol), 1-[1-(2,6-dioxo-3-piperidyl)-3-methyl-2-oxo-benzimidazol-5-yl]piperidine-4-carbaldehyde (77 mg, 0.2 mmol), and sodium triacetoxyborohydride (120 mg, 0.6 mmol), and the reaction mixture was stirred at 25° C. for 2 h. The mixture was filtered and concentrated under reduced pressure. The residue was purified by prep-TLC (dichloromethane/methanol=4/1) to afford the title compound (150 mg, 68%) as a yellow solid. LC/MS (ESI) m/z: 1158.9 $[M+H]^+$.

Step 6: Preparation of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione

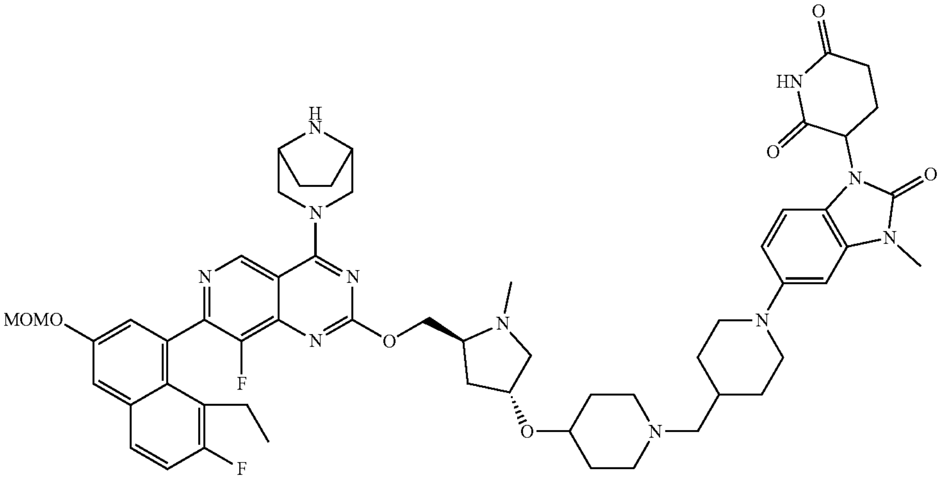

To a solution of tert-butyl 3-[2-[[(2S,4R)-4-[[1-[[1-[1-(2,6-dioxo-3-piperidyl)-3-methyl-2-oxo-benzimidazol-5-yl]-4-piperidyl]methyl]-4-piperidyl]oxy]-1-methyl-pyrrolidin-2-yl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (145 mg, 0.1 mmol) in dichloromethane (3 mL) was added 4 M hydrochloric acid in 1,4-dioxane (2 mL), and the reaction mixture was stirred at 25° C. for 0.25 h. The mixture was filtered and concentrated under reduced pressure. The residue was purified by prep-HPLC (1% to 25% acetonitrile in water (formic acid) over 10 min) to afford the title compound (64.2 mg, 46%, formic acid salt) as a white solid. LC/MS (ESI) m/z: 1014.2 $[M+H]^+$; $^1H$ NMR (400 MHz, DMSO-$d_6$) δ 11.06 (s, 1H), 9.11 (s, 1H), 8.19 (s, 2H), 7.77 (dd, J=6.0, 9.2 Hz, 1H), 7.40-7.31 (m, 2H), 7.02 (d, J=2.4 Hz, 1H), 6.92 (d, J=8.8 Hz, 1H), 6.81 (d, J=2.0 Hz, 1H), 6.62 (dd, J=2.0, 8.4 Hz, 1H), 5.29 (dd, J=5.2, 1 Step 2: Hz, 1H), 4.51-4.35 (m, 3H), 4.27 (dt, J=6.0, 11.6 Hz, 1H), 4.16-4.08 (m, 1H), 3.70-3.54 (m, 9H), 3.50-3.37 (m, 5H), 3.25 (m, 2H), 2.94-2.86 (m, 1H), 2.82-2.75 (m, 1H), 2.73-2.65 (m, 3H), 2.64-2.57 (m, 3H), 2.55 (s, 1H), 2.35 (s, 3H), 2.21-2.11 (m, 4H), 2.05-1.95 (m, 3H), 1.91-1.87 (m, 1H), 1.79 (br t, J=12.4 Hz, 4H), 1.68 (br d, J=6.8 Hz, 3H), 1.46-1.37 (m, 2H), 1.28-1.18 (m, 2H), 0.73 (t, J=7.2 Hz, 3H).

Example 60: Synthesis of 3-[4-(4-{[(3R,5S)-5-{[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]methyl}-1-methylpyrrolidin-3-yl]oxy}piperidin-1-yl)-1-oxo-2,3-dihydro-1H-isoindol-2-yl]piperidine-2,6-dione (Compound 118)

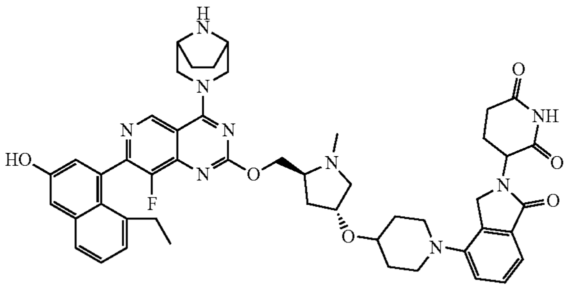 [SMILES: CCc1cccc2cc(O)cc(-c3ncc4c(N5CC6CCC(C5)N6)nc(OC[C@@H]5C[C@@H](OC6CCN(c7cccc8c7CN(C7CCC(=O)NC7=O)C8=O)CC6)CN5C)nc4c3F)c12]

The title compound was made in an analogous manner to 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione. (yellow solid, formic acid salt). LC/MS (ESI) m/z: 884.6 $[M+H]^+$; $^1H$ NMR (400 MHz, DMSO-$d_6$) δ 10.97 (s, 1H), 9.09 (s, 1H), 8.18 (s, 1H), 7.66 (d, J=8.4 Hz, 1H), 7.45-7.33 (m, 2H), 7.32-7.26 (m, 2H), 7.14 (dd, J=7.6, 14.4 Hz, 2H), 6.97 (d, J=2.4 Hz, 1H), 5.10 (dd, J=5.2, 13.2 Hz, 1H), 4.48-4.36 (m, 4H), 4.33-4.23 (m, 2H), 4.22-4.13 (m, 1H), 3.66 (d, J=1.2 Hz, 1H), 3.61-3.57 (m, 3H), 3.54-3.47 (m, 5H), 2.95-2.77 (m, 5H), 2.68-2.59 (m, 1H), 2.36 (s, 3H), 2.29-2.17 (m, 3H), 2.01-1.89 (m, 5H), 1.69-1.54 (m, 6H), 0.81 (t, J=7.6 Hz, 3H).

Example 61: Synthesis of 3-(4-{4-[(4-{[(3R,5S)-5-{[(4-{3,8-diazabicyclo[3.2.1]octan-3-yl}-7-(8-ethyl-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-1-oxo-2,3-dihydro-1H-isoindol-2-yl)piperidine-2,6-dione (Compound 139)

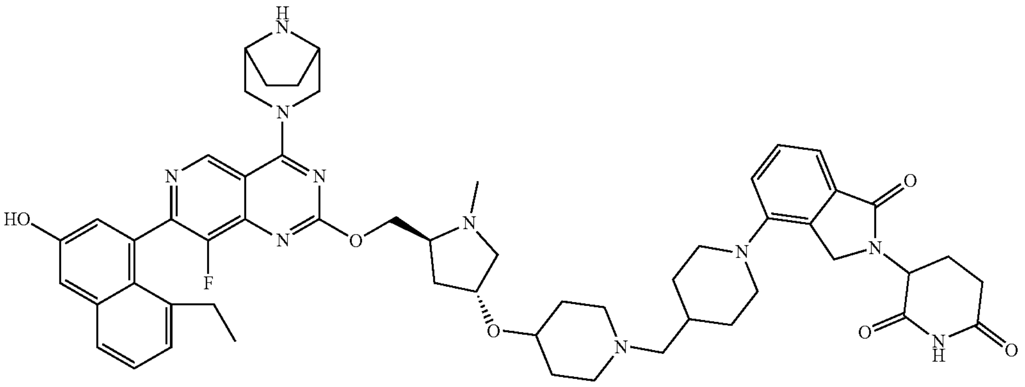 [SMILES: CCc1cccc2cc(O)cc(-c3ncc4c(N5CC6CCC(C5)N6)nc(OC[C@@H]5C[C@@H](OC6CCN(CC7CCN(c8cccc9c8CN(C8CCC(=O)NC8=O)C9=O)CC7)CC6)CN5C)nc4c3F)c12]

The title compound was made in an analogous manner to 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione. (white solid). LC/MS (ESI) m/z: 981.2 $[M+H]^+$; $^1H$ NMR (400 MHz, DMSO-$d_6$) δ 11.00-10.96 (m, 1H), 9.10 (s, 1H), 8.15 (s, 2H), 7.67 (d, J=8.0 Hz, 1H), 7.47-7.34 (m, 2H), 7.31-7.26 (m, 2H), 7.13 (t, J=7.6 Hz, 2H), 6.96 (d, J=2.4 Hz, 1H), 5.11 (dd, J=5.2, 13.2 Hz, 1H), 4.52-4.43 (m, 2H), 4.41-4.35 (m, 2H), 4.31-4.24 (m, 2H), 4.14-4.09 (m, 1H), 3.70 (d, J=11.6 Hz, 4H), 3.65-3.62 (m, 1H), 3.36 (s, 2H), 3.24 (d, J=5.6 Hz, 2H), 2.94-2.88 (m, 1H), 2.81-2.77 (m, 1H), 2.73-2.67 (m, 4H), 2.61-2.56 (m, 2H), 2.35 (s, 3H), 2.30-2.23 (m, 2H), 2.22-2.19 (m, 1H), 2.16 (d, J=7.6 Hz, 2H), 2.04-1.96 (m, 3H), 1.92-1.85 (m, 2H), 1.83-1.76 (m, 4H), 1.74-1.67 (m, 4H), 1.66-1.58 (m, 1H), 1.43-1.34 (m, 2H), 1.29-1.19 (m, 2H), 0.81 (t, J=7.2 Hz, 3H).

Example 62: Synthesis of 3-(4-chloro-5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-1-oxo-2,3-dihydro-1H-isoindol-2-yl)piperidine-2,6-dione (Compound 177)

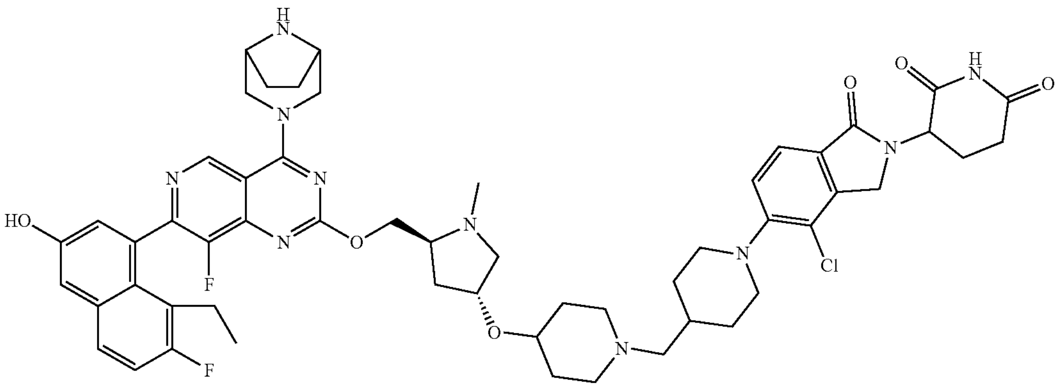

The title compound was made in an analogous manner to 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl) piperidine-2,6-dione. (white solid, formic acid salt). LC/MS (ESI) m/z: 1033.7 $[M+H]^+$; $^1$H NMR (400 MHz, DMSO-$d_6$) δ 10.99 (s, 1H), 9.12 (s, 1H), 8.18 (s, 2H), 7.76 (dd, J=6.0, 9.2 Hz, 1H), 7.64 (d, J=8.0 Hz, 1H), 7.42-7.30 (m, 2H), 7.25 (d, J=8.4 Hz, 1H), 7.02 (d, J=2.4 Hz, 1H), 5.09 (dd, J=5.2, 13.2 Hz, 1H), 4.53 (br t, J=15.2 Hz, 3H), 4.45-4.35 (m, 3H), 4.32-4.27 (m, 2H), 4.22 (s, 1H), 4.16-4.09 (m, 2H), 3.87 (br d, J=10.8 Hz, 2H), 3.80 (br d, J=13.2 Hz, 1H), 3.73 (br d, J=13.6 Hz, 1H), 3.42-3.31 (m, 3H), 3.26 (br dd, J=6.0, 9.2 Hz, 1H), 2.96-2.86 (m, 1H), 2.82 (br t, J=5.2 Hz, 1H), 2.78-2.66 (m, 4H), 2.59 (br d, J=16.8 Hz, 1H), 2.44 (br dd, J=4.8, 13.6 Hz, 1H), 2.36 (s, 4H), 2.28-2.18 (m, 3H), 2.16-2.05 (m, 3H), 1.98 (br dd, J=5.2, 10.4 Hz, 1H), 1.89 (br d, J=5.2 Hz, 1H), 1.85-1.76 (m, 7H), 1.72-1.59 (m, 1H), 1.51-1.37 (m, 2H), 1.29 (q, J=10.4 Hz, 2H), 0.72 (t, J=7.2 Hz, 3H).

Example 63: Synthesis of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl) piperidine-2,6-dione (Compound 178)

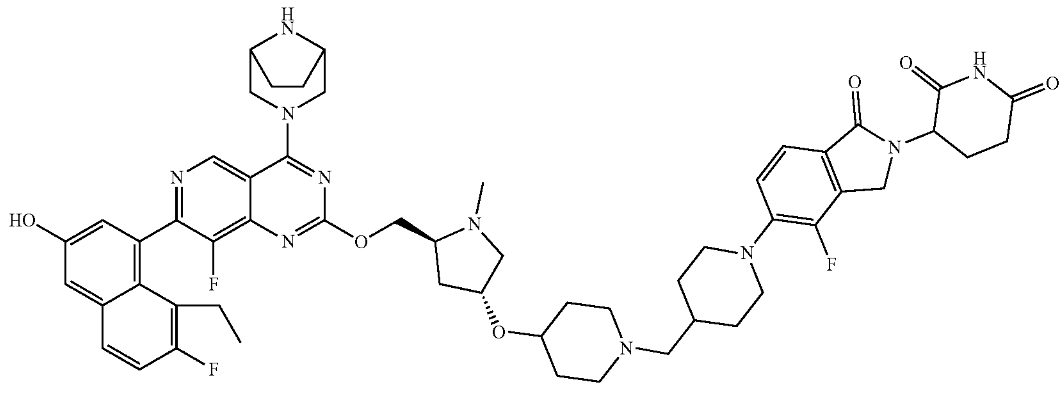 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8F)CN(C8CCC(=O)NC8=O)C9=O)CC7)CC6)CN5C)nc4c3F)c12]

The title compound was made in an analogous manner to 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl) piperidine-2,6-dione. (white solid, formic acid salt). LC/MS (ESI) m/z: 1017.7 $[M+H]^+$, $^1$H NMR (400 MHz, DMSO-$d_6$) δ 10.98 (br s, 1H), 9.11 (s, 1H), 8.21 (s, 1H), 7.76 (dd, J=6.0, 9.2 Hz, 1H), 7.46 (d, J=8.0 Hz, 1H), 7.39-7.29 (m, 2H), 7.14 (t, J=8.0 Hz, 1H), 7.02 (d, J=2.4 Hz, 1H), 5.07 (br dd, J=5.2, 13.3 Hz, 1H), 4.47 (br d, J=16.8 Hz, 3H), 4.41-4.37 (m, 1H), 4.34-4.23 (m, 4H), 4.14-4.10 (m, 1H), 3.80-3.65 (m, 5H), 3.47 (br s, 2H), 3.35-3.19 (m, 2H), 2.98-2.84 (m, 1H), 2.83-2.64 (m, 5H), 2.63-2.55 (m, 1H), 2.48-2.38 (m, 1H), 2.35 (s, 3H), 2.22-2.16 (m, 3H), 2.15-2.10 (m, 1H), 2.05 (br t, J=9.6 Hz, 2H), 2.00-1.94 (m, 1H), 1.92-1.84 (m, 2H), 1.83-1.63 (m, 8H), 1.49-1.34 (m, 2H), 1.32-1.15 (m, 2H), 0.72 (t, J=7.6 Hz, 3H)

Example 64: Synthesis of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-1-oxo-2,3-dihydro-1H-isoindol-2-yl)piperidine-2,6-dione (Compound 85)

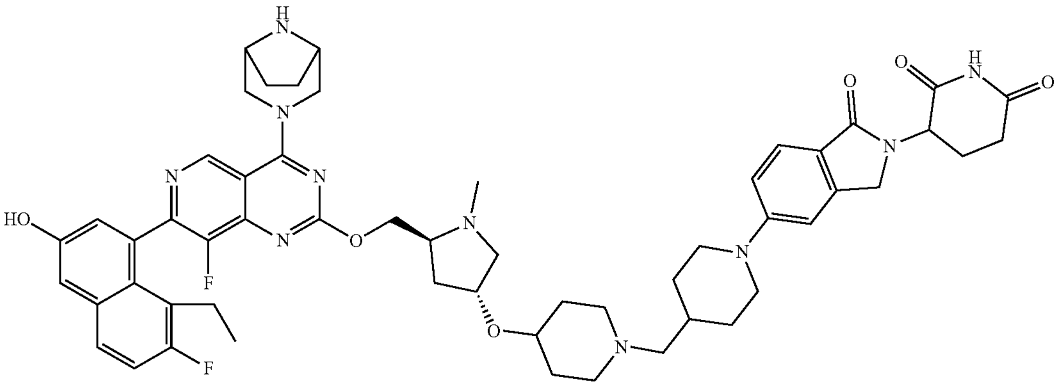 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8)CN(C8CCC(=O)NC8=O)C9=O)CC7)CC6)CN5C)nc4c3F)c12]

The title compound was made in an analogous manner to 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl) piperidine-2,6-dione. (white solid, formic acid salt). LC/MS (ESI) m/z: 1000.8 $[M+H]^+$; $^1H$ NMR (400 MHz, DMSO-$d_6$) δ 10.94 (s, 1H), 9.13 (s, 1H), 8.17 (s, 2H), 7.82-7.70 (m, 1H), 7.50 (d, J=8.8 Hz, 1H), 7.41-7.30 (m, 2H), 7.09-6.96 (m, 3H), 5.04 (dd, J=5.2, 13.2 Hz, 1H), 4.62-4.47 (m, 2H), 4.44-4.36 (m, 1H), 4.34-4.25 (m, 2H), 4.23-4.09 (m, 2H), 3.95-3.67 (m, 7H), 3.39-3.23 (m, 2H), 2.96-2.70 (m, 6H), 2.59 (d, J=16.4 Hz, 1H), 2.43-2.29 (m, 6H), 2.28-2.04 (m, 7H), 1.96-1.88 (m, 2H), 1.85-1.72 (m, 9H), 1.53-1.34 (m, 2H), 1.21-1.09 (m, 2H), 0.77-0.67 (m, 3H)

Example 65: Synthesis of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-3-isopropyl-2-oxo-benzimidazol-1-yl]piperidine-2,6-dione (Compound 208)

Step 1: Preparation of tert-butyl 3-[2-[[(3S,8R)-3-[[4-[[1-[1-(2,6-dioxo-3-piperidyl)-3-isopropyl-2-oxo-benzimidazol-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

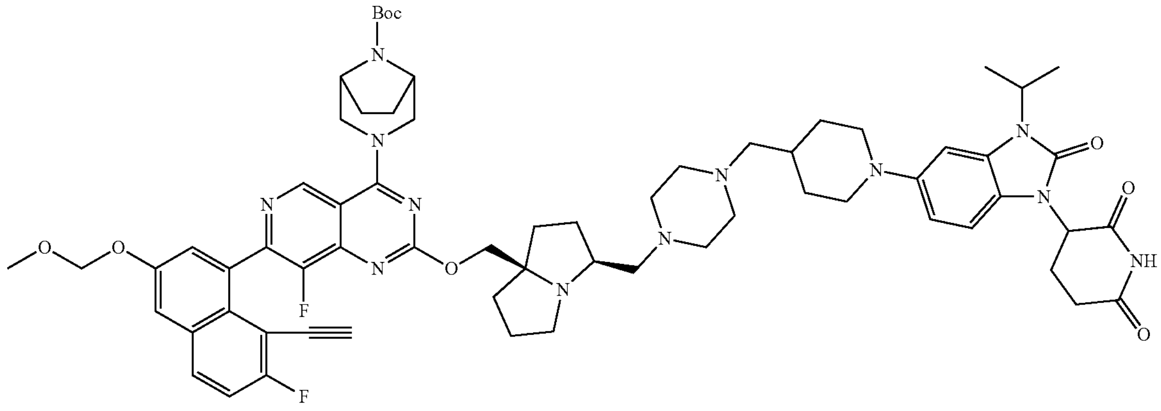

To a solution of 3-[3-isopropyl-2-oxo-5-[4-(piperazin-1-ylmethyl)-1-piperidyl]benzimidazol-1-yl]piperidine-2,6-dione (257.6 mg, 0.6 mmol) and tert-butyl 3-[7-[8-ethynyl-7-fluoro-3-(methoxymethoxy)-1-naphthyl]-8-fluoro-2-[[(3S,8R)-3-formyl-1,2,3,5,6,7-hexahydropyrrolizin-8-yl]methoxy]pyrido[4,3-d]pyrimidin-4-yl]-3,8-diazabicyclo[3.2.1]octane-8-carboxylate (415 mg, 0.6 mmol) in dichloromethane (15 mL) and DMSO (2.0 mL) was added $NaBH(OAc)_3$ (291 mg, 1.4 mmol), and the reaction mixture was stirred at 25° C. for 12 h. The mixture was quenched with sodium bicarbonate (10 mL) and stirred at 25° C. for 30 min. The mixture was concentrated under reduced pressure, and the residue was extracted with ethyl acetate (3×40 mL). The combined organic extract was washed with water (7×10 mL) followed by brine (2×10 mL), dried over anhydrous sodium sulfate, filtered, and concentrated under reduced pressure. The residue was purified by flash column chromatography on silica gel (0 to 7% methanol in dichloromethane over 20 min) to afford the title compound (379.8 mg, 57%) as a yellow solid. LC/MS (ESI) m/z: 1207.9 $[M+H]^+$.

Step 2: Preparation of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-3-isopropyl-2-oxo-benzimidazol-1-yl]piperidine-2,6-dione

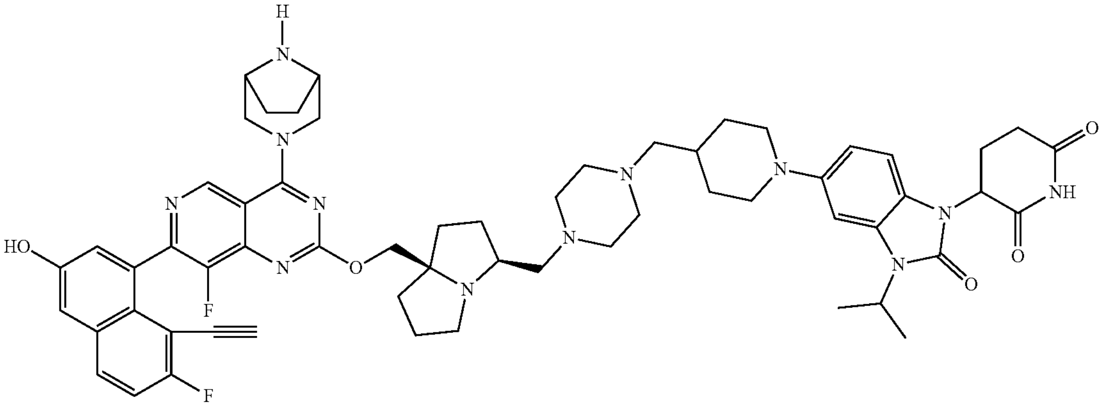 [SMILES: C#Cc1c(F)ccc2cc(O)cc(-c3ncc4c(N5CC6CCC(C5)N6)nc(OC[C@]56CCCN5[C@H](CN5CCN(CC7CCN(c8ccc9c(c8)n(C(C)C)c(=O)n9C8CCC(=O)NC8=O)CC7)CC5)CC6)nc4c3F)c12]

To a solution of tert-butyl 3-[2-[[(3S,8R)-3-[[4-[[1-[1-(2,6-dioxo-3-piperidyl)-3-isopropyl-2-oxo-benzimidazol-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (370 mg, 0.3 mmol) in dichloromethane (2.5 mL) was added 4 M HCl in 1,4-dioxane (2.5 mL), and the reaction mixture was stirred at 25° C. for 10 min. The reaction mixture was diluted with petroleum ether (3×20 mL), removing the supernatant each time. The remaining material was then diluted with THF (50 mL) and the pH adjusted to 8 by addition of triethylamine. The mixture was filtered, and the filtrate was concentrated under reduced pressure. The resulting residue was purified by preparative HPLC (24% to 64% acetonitrile in water (ammonium bicarbonate) over 32 min) to afford the title compound (124.7 mg, 38%) as a yellow solid. LC/MS (ESI) m/z: 1063.6 $[M+H]^+$, $^1H$ NMR (400 MHz, $CD_3OD$) δ 9.00 (d, J=2.4 Hz, 1H), 7.84 (m, J=2.4, 6.0, 9.0 Hz, 1H), 7.35-7.27 (m, 2H), 7.21 (d, J=2.4 Hz, 1H), 7.02-6.89 (m, 2H), 6.78 (br d, J=8.4 Hz, 1H), 5.26 (dd, J=5.2, 12.8 Hz, 1H), 4.68-4.55 (m, 3H), 4.33-4.18 (m, 2H), 3.75-3.60 (m, 4H), 3.52 (br d, J=11.6 Hz, 2H), 3.36 (s, 1H), 3.13-2.96 (m, 2H), 2.94-2.73 (m, 4H), 2.72-2.63 (m, 3H), 2.62-2.34 (m, 9H), 2.27-2.06 (m, 5H), 1.96-1.62 (m, 13H), 1.54 (dd, J=1.2, 6.8 Hz, 6H), 1.44-1.29 (m, 2H).

Example 66: Synthesis of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-2-oxo-3-(propan-2-yl)-2,3-dihydro-1H-1,3-benzodiazol-1-yl)piperidine-2,6-dione (Compound 209)

Step 1: Preparation of tert-butyl 3-[2-[[(2S,4R)-4-[[1-[[1-[1-(2,6-dioxo-3-piperidyl)-3-isopropyl-2-oxo-benzimidazol-5-yl]-4-piperidyl]methyl]-4-piperidyl]oxy]-1-methyl-pyrrolidin-2-yl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

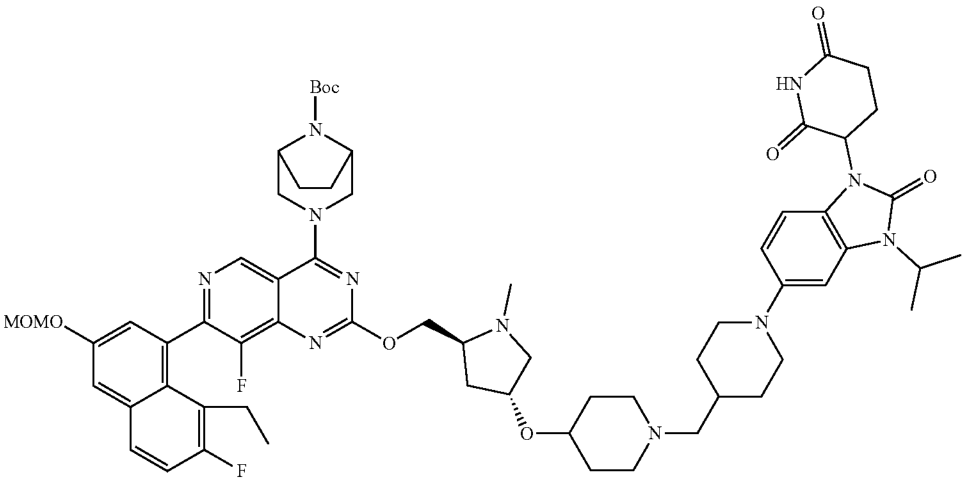

To a solution of tert-butyl 3-[7-[8-ethyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate formate (160 mg, 0.2 mmol) in dichloromethane (3 mL) and isopropanol (3 mL) were added N,N-diisopropylethylamine (29.2 mg, 0.2 mmol), acetic acid (17 mg, 0.3 mmol), 1-[1-(2,6-dioxo-3-piperidyl)-3-isopropyl-2-oxo-benzimidazol-5-yl]piperidine-4-carbaldehyde (90 mg, 0.2 mmol), and sodium triacetoxyborohydride (120 mg, 0.6 mmol), and the mixture was stirred at 25° C. for 2 h. The reaction mixture was filtered and concentrated under reduced pressure. The residue was purified by prep-TLC (dichloromethane/methanol=4/1) to afford the title compound (140 mg, 62%) as a yellow solid. LC/MS (ESI) m/z: 1187.0 [M+H]$^+$.

Step 2: Preparation of 3-(5-{4-[(4-{[(3R,5S)-5-{[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-2-oxo-3-(propan-2-yl)-2,3-dihydro-1H-1,3-benzodiazol-1-yl)piperidine-2,6-dione

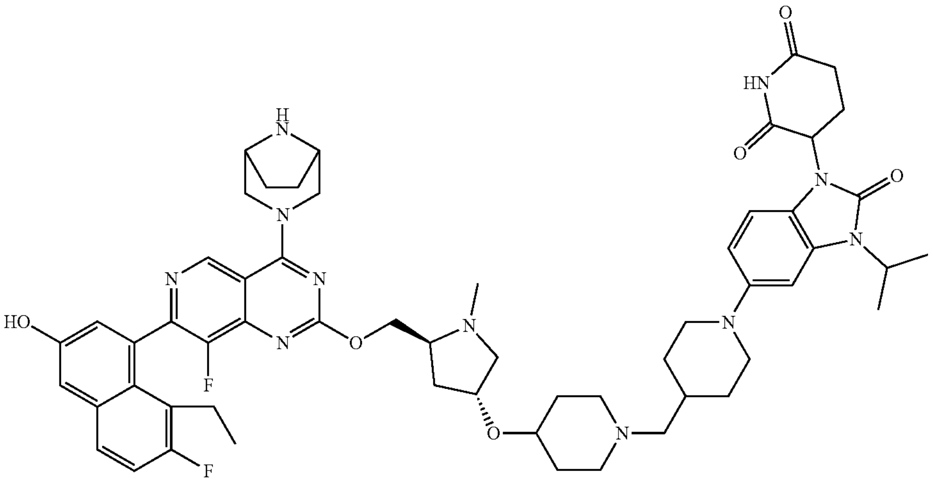 [SMILES: CCc1c(F)ccc2cc(O)cc(-c3ncc4c(N5CC6CCC(C5)N6)nc(OC[C@@H]5C[C@@H](OC6CCN(CC7CCN(c8ccc9c(c8)n(C(C)C)c(=O)n9C8CCC(=O)NC8=O)CC7)CC6)CN5C)nc4c3F)c12]

To a solution of tert-butyl 3-[2-[[(2S,4R)-4-[[1-[[1-[1-(2,6-dioxo-3-piperidyl)-3-isopropyl-2-oxo-benzimidazol-5-yl]-4-piperidyl]methyl]-4-piperidyl]oxy]-1-methyl-pyrrolidin-2-yl]methoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (135 mg, 0.1 mmol) in dichloromethane (3 mL) was added 4 M HCl in 1,4-dioxane (0.4 mL), and the mixture was stirred at 25° C. for 2 h. The reaction mixture was filtered and concentrated under reduced pressure. The residue was purified by prep-HPLC (1% to 25% acetonitrile in water (formic acid) over 10 min) to afford the title compound (51.1 mg, 30%) as a white solid. LC/MS (ESI) m/z: 1042.2 $[M+H]^+$, $^1H$ NMR (400 MHz, DMSO-$d_6$) δ 11.05 (s, 1H), 9.11 (s, 1H), 8.21 (s, 1H), 7.77 (dd, J=6.0, 9.2 Hz, 1H), 7.39-7.30 (m, 2H), 7.03 (d, J=2.4 Hz, 1H), 6.95-6.84 (m, 2H), 6.66-6.57 (m, 1H), 5.26 (br dd, J=5.6, 12.8 Hz, 1H), 4.58-4.58 (m, 1H), 4.58 (td, J=6.8, 14.0 Hz, 1H), 4.49-4.35 (m, 3H), 4.27 (td, J=5.6, 11.8 Hz, 1H), 4.12-4.11 (m, 1H), 4.16-4.09 (m, 1H), 3.70-3.58 (m, 5H), 3.54 (br d, J=12.0 Hz, 3H), 3.32-3.23 (m, 3H), 2.87 (br dd, J=4.8, 16.8 Hz, 1H), 2.79 (br t, J=5.2 Hz, 1H), 2.74-2.65 (m, 3H), 2.64-2.57 (m, 3H), 2.55 (s, 1H), 2.35 (s, 3H), 2.20-2.12 (m, 4H), 2.00-1.99 (m, 1H), 1.99 (br d, J=8.0 Hz, 3H), 1.88 (dt, J=4.8, 8.0 Hz, 2H), 1.79 (br t, J=12.0 Hz, 4H), 1.72-1.63 (m, 4H), 1.63-1.52 (m, 1H), 1.45 (d, J=6.8 Hz, 8H), 1.23 (br d, J=10.4 Hz, 2H), 0.73 (t, J=7.2 Hz, 3H).

Example 67: Synthesis of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-3-methyl-2-oxo-2,3-dihydro-1H-1,3-benzodiazol-1-yl}piperidine-2,6-dione (Compound 210)

Step 1: Preparation of tert-butyl 3-[2-[[1-[[4-[[1-[1-(2,6-dioxo-3-piperidyl)-3-methyl-2-oxo-benzimidazol-5-yl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

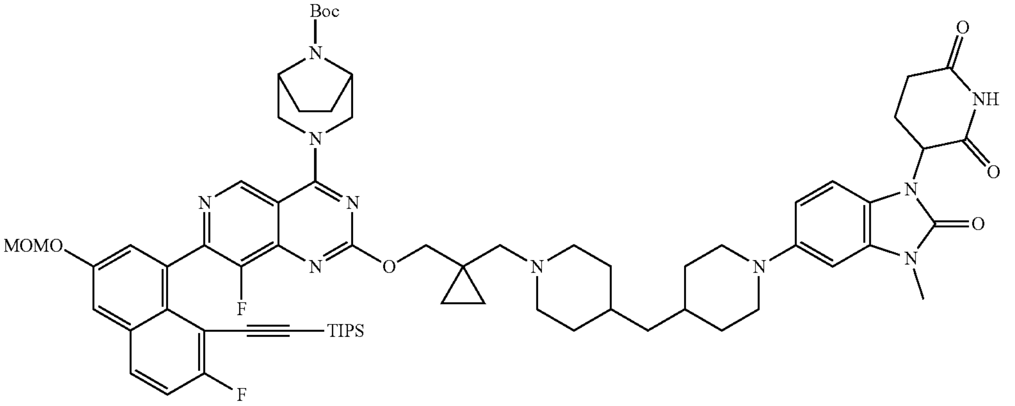

To a mixture of 3-[3-methyl-2-oxo-5-[4-(4-piperidylmethyl)-1-piperidyl]benzimidazol-1-yl]piperidine-2,6-dione trifluoroacetate (400 mg, 0.7 mmol) and tert-butyl 3-[8-fluoro-7-[7-fluoro-3-(methoxymethoxy)-8-(2-triisopropylsilylethynyl)-1-naphthyl]-2-[(1-formylcyclopropyl)methoxy]pyrido[4,3-d]pyrimidin-4-yl]-3,8-diazabicyclo[3.2.1]octane-8-carboxylate (669 mg, 0.8 mmol) in dichloromethane (10 mL) and isopropanol (10 mL) were added N,N-diisopropylethylamine (0.4 mL, 2.2 mmol) and 2-methylpyridine borane (232 mg, 2.17 mmol) under nitrogen atmosphere, and the mixture was stirred at 20° C. for 16 h. The reaction mixture was concentrated under reduced pressure, and the residue was purified by prep-HPLC (30% to 60% acetonitrile in water (formic acid) over 15 min) to afford the title compound (180 mg, 20%) as a white solid. LC/MS (ESI) m/z: 1266.0 $[M+H]^+$.

Step 2: Preparation of tert-butyl 3-[2-[[1-[[4-[[1-[1-(2,6-dioxo-3-piperidyl)-3-methyl-2-oxo-benzimidazol-5-yl]-4-piperidyl]methyl]-1-piperidyl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

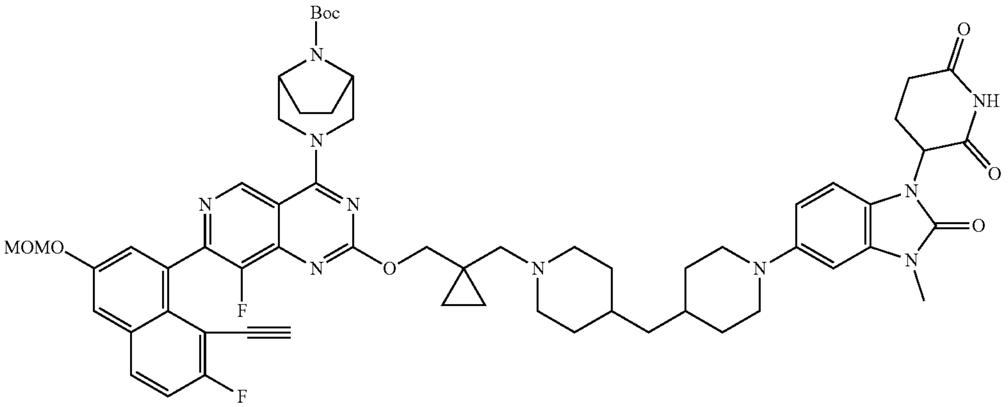

To tert-butyl 3-[2-[[1-[[4-[[1-[1-(2,6-dioxo-3-piperidyl)-3-methyl-2-oxo-benzimidazol-5-yl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (180 mg, 0.1 mmol) in N,N-dimethylformamide (5 mL) was added cesium fluoride (432 mg, 2.8 mmol), and the reaction mixture was stirred at 20° C. for 1 h. The mixture was filtered and concentrated under reduced pressure, and the residue was purified by prep-HPLC (25% to 55% acetonitrile in water (formic acid) over 7 min) to afford the title compound (132 mg, 84%) as a white solid. LC/MS (ESI) m/z: 1110.0 $[M+H]^+$.

Step 3: Preparation of 3-{5-[4-({1-[(1-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}cyclopropyl)methyl]piperidin-4-yl}methyl)piperidin-1-yl]-3-methyl-2-oxo-2,3-dihydro-1H-1,3-benzodiazol-1-yl}piperidine-2,6-dione

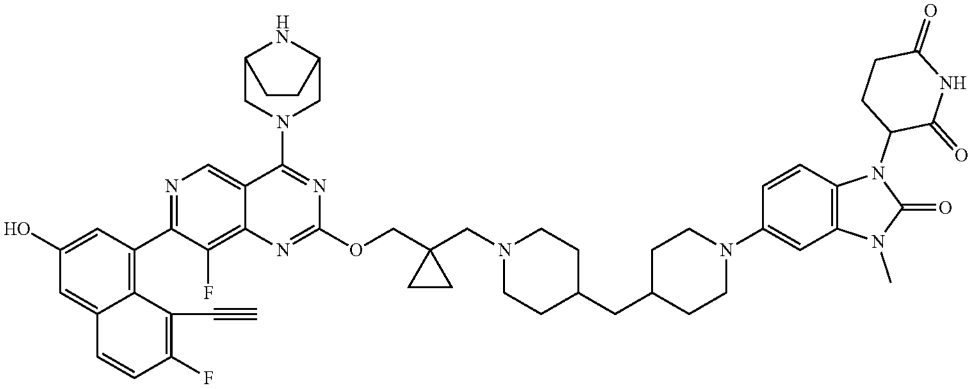

To a solution of tert-butyl 3-[2-[[1-[[4-[[1-[1-(2,6-dioxo-3-piperidyl)-3-methyl-2-oxo-benzimidazol-5-yl]-4-piperidyl]methyl]-1-piperidyl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (132 mg, 0.1 mmol) in dichloromethane (2 mL) was added 4 M HCl in 1,4-dioxane (2 mL), and the reaction mixture was stirred at 20° C. for 15 min. The mixture was suspended in petroleum ether (10 mL) and filtered. The filter cake was purified by prep-HPLC (0% to 30% acetonitrile in water (formic acid) over 12 min) to afford the title compound (56.8 mg, 43%, di-formic acid salt) as a yellow solid. LC/MS (ESI) m/z: 965.5 $[M+H]^+$, $^1H$ NMR (400 MHz, DMSO-$d_6$) δ 11.06 (s, 1H), 9.04 (s, 1H), 8.20 (s, 2H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 6.91 (d, J=8.8 Hz, 1H), 6.80 (d, J=2.0 Hz, 1H), 6.61 (dd, J=1.6, 8.8 Hz, 1H), 5.28 (dd, J=5.2, 12.8 Hz, 1H), 4.57-4.48 (m, 1H), 4.35-4.25 (m, 3H), 3.93 (s, 1H), 3.67 (s, 4H), 3.63-3.49 (m, 5H), 3.01-2.81 (m, 4H), 2.66-2.53 (m, 4H), 2.33 (s, 2H), 2.02-1.94 (m, 1H), 1.88 (t, J=11.2 Hz, 2H), 1.75-1.66 (m, 6H), 1.59 (d, J=11.2 Hz, 2H), 1.42 (s, 1H), 1.33 (d, J=Step 2: Hz, 1H), 1.26-1.18 (m, 2H), 1.15-0.98 (m, 5H), 0.64 (s, 2H), 0.41 (s, 2H).

Example 68: Synthesis of 3-(5-{4-[(4-{[(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl}piperazin-1-yl)methyl]piperidin-1-yl}-2-oxo-3-(propan-2-yl)-2,3-dihydro-1H-1,3-benzodiazol-1-yl)piperidine-2,6-dione (Compound 211)

Step 1: Preparation of (2R)-1-benzyloxyhex-5-en-2-ol

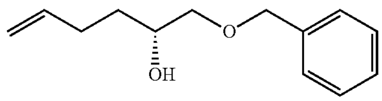

To a mixture of (2R)-2-(benzyloxymethyl)oxirane (38.4 mL, 253 mmol) in THF (500 mL) was added CuI (4.81 g, 25 mmol), and the resulting mixture was cooled to 0° C. Allyl(chloro)magnesium (2.0 M, 500 mL) was then added dropwise, and the reaction mixture was stirred at 0° C. for 1 h. The reaction was diluted with aqueous saturated ammonium chloride (500 mL) at 0° C. and extracted with ethyl acetate (500 mL×3). The combined organic layers were dried over sodium sulfate, filtered, and concentrated under reduced pressure to afford the title compound (46.36 g, crude) as a colorless oil. LC/MS (ESI) m/z: 207.1 $[M+H]^+$.

Step 2: Preparation of 2-[(1S)-1-(benzyloxymethyl)pent-4-enyl]isoindoline-1,3-dione

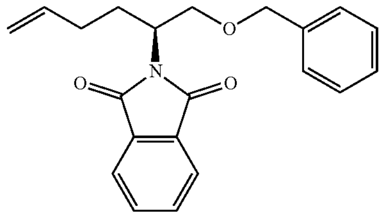 [SMILES: C=CCC[C@@H](COCc1ccccc1)N1C(=O)c2ccccc2C1=O]

To a mixture of (2R)-1-benzyloxyhex-5-en-2-ol (29.36 g, 142 mmol), isoindoline-1,3-dione (25.0 g, 170 mmol), and $PPh_3$ (44.0 g, 168 mmol) in THF (300 mL) at 0° C. was added DIAD (33.0 mL, 170 mmol), and the reaction mixture was stirred at 20° C. for 15 h. The mixture was concentrated under reduced pressure, and the resulting residue was purified by silica gel chromatography (0-10% ethyl acetate in petroleum ether) to afford the title compound (36.47 g, 63%) as a colorless oil. LC/MS (ESI) m/z: 336.1 [M+H]$^+$.

Step 3: Preparation of (2S)-1-benzyloxyhex-5-en-2-amine

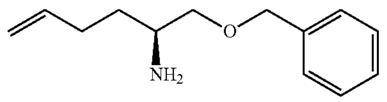

To 2-[(1S)-1-(benzyloxymethyl)pent-4-enyl]isoindoline-1,3-dione (54.66 g, 163 mmol) in ethanol (550 mL) was added hydrazine monohydrate (16.28 mL, 335 mmol), and the reaction mixture was stirred at 80° C. for 15 h. The mixture was filtered, and the filtrate was concentrated under reduced pressure. The residue was diluted with saturated ammonium bicarbonate solution (250 mL) and extracted with dichloromethane (500 mL). The organic layer was washed with saturated ammonium bicarbonate solution (250 mL×2), brine (250 mL×2), dried over anhydrous sodium sulfate, filtered, and concentrated under reduced pressure to afford (2S)-1-benzyloxyhex-5-en-2-amine (31.54 g, crude) as a colorless oil. LC/MS (ESI) m/z: 206.0 [M+H]$^+$.

Step 4: Preparation of N-[(1S)-1-(benzyloxymethyl) pent-4-enyl]benzamide

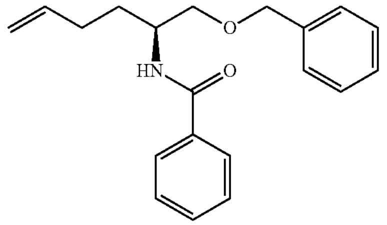 [SMILES: C=CCC[C@@H](COCc1ccccc1)NC(=O)c1ccccc1]

To (2S)-1-benzyloxyhex-5-en-2-amine (31.54 g, 154 mmol) in dichloromethane (300 mL) was added triethylamine (64.0 mL, 461 mmol), and the resulting mixture was cooled to 0° C. Benzoyl chloride (17.85 mL, 154 mmol) was then added dropwise, and the reaction mixture was stirred at 20° C. for 15 h. The mixture was washed with water (300 mL×2), then brine (300 mL×2), dried over sodium sulfate, filtered, and concentrated under reduced pressure. The residue was purified by silica gel chromatography (0-25% ethyl acetate in petroleum ether) to afford the title compound (44.11 g, 76%) as a white solid. LC/MS (ESI) m/z: 310.0 [M+H]$^+$.

Step 5: Preparation of [(2S,5S)-5-(benzyloxymethyl)pyrrolidin-2-yl]methyl benzoate

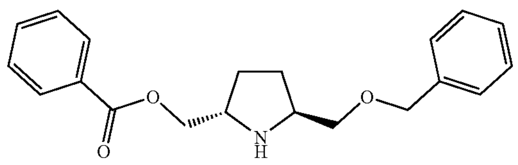 [SMILES: O=C(OC[C@@H]1CC[C@@H](COCc2ccccc2)N1)c1ccccc1]

To N-[(1S)-1-(benzyloxymethyl)pent-4-enyl]benzamide (44.11 g, 117 mmol) in acetonitrile (1500 mL) and water (500 mL) was added iodine (89.45 g, 352 mmol), and the reaction mixture was stirred at 20° C. for 15 h. The mixture was diluted with saturated aqueous $Na_2SO_3$ solution (500 mL), then extracted with ethyl acetate (1 L×3). The combined organic extract was washed with brine (1 L×2), dried over sodium sulfate, filtered, and concentrated under reduced pressure. The residue was triturated with ethyl acetate to afford the title compound (36.33 g, 90%) as a white solid. LC/MS (ESI) m/z: 326.0 [M+H]$^+$; $^1$H NMR (400 MHz, DMSO-$d_6$) δ 9.43-9.32 (m, 1H), 8.07 (br d, J=7.2 Hz, 2H), 7.76-7.64 (m, 1H), 7.62-7.50 (m, 2H), 7.45-7.24 (m, 5H), 4.57 (s, 2H), 4.54-4.38 (m, 2H), 4.04-3.94 (m, 1H), 3.91-3.83 (m, 1H), 3.74-3.63 (m, 2H), 2.23-2.09 (m, 2H), 1.86-1.67 (m, 2H).

Step 6: Preparation of [(2S,5S)-5-(benzyloxymethyl)-1-methyl-pyrrolidin-2-yl]methyl benzoate

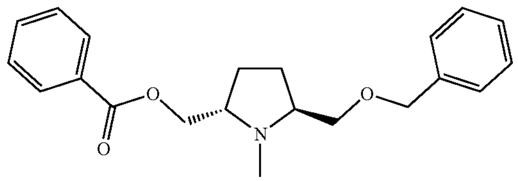 [SMILES: CN1[C@H](COCc2ccccc2)CC[C@H]1COC(=O)c1ccccc1]

To a mixture of [(2S,5S)-5-(benzyloxymethyl)pyrrolidin-2-yl]methyl benzoate (29.5 g, 86 mmol) and 37% formaldehyde (19.2 mL, 258 mmol) in i-PrOH (300 mL) and dichloromethane (300 mL) were added acetic acid (19.7 mL, 344 mmol) and 2-methylpyridine borane (46.0 g, 431 mmol), and the reaction mixture was stirred at 20° C. for 15 h. The mixture was concentrated under reduced pressure, and the resulting residue was purified by silica gel chromatography (0-10% methanol in DCM) to afford the title compound (47.64 g, crude) as a colorless oil. LC/MS (ESI) m/z: 340.0 [M+H]$^+$ Step 7: Preparation of [(2S,5S)-5-(hydroxymethyl)-1-methyl-pyrrolidin-2-yl]methyl benzoate

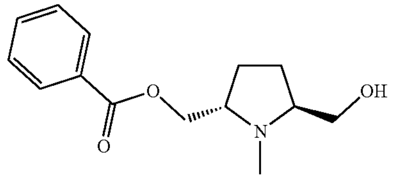 [SMILES: CN1[C@H](CO)CC[C@H]1COC(=O)c1ccccc1]

To a solution of [(2S,5S)-5-(benzyloxymethyl)-1-methyl-pyrrolidin-2-yl]methyl benzoate (30 g, 57 mmol) in $CH_2Cl_2$ (300 mL) under nitrogen at −78° C. was added $BBr_3$ (25.5 mL, 265 mmol), and the reaction mixture was stirred at −78° C. for 2 h under nitrogen. The mixture was diluted with water (200 mL) and concentrated under reduced pressure to remove $CH_2Cl_2$. The residue was extracted with MTBE (500 mL×3), and the pH of the aqueous layer was adjusted to 8 by addition of saturated sodium bicarbonate solution. The resulting aqueous mixture was then extracted with $CH_2Cl_2$/$CH_3OH$ (500 mL×3, V/V=10:1), and the combined organic extract was washed with brine (500 mL×2), dried over sodium sulfate, filtered, and concentrated under reduced pressure. The residue was purified by silica gel chromatography (0-4% then up to 10% $CH_3OH$ in $CH_2Cl_2$) to afford the title compound (9.25 g, 60%) as a yellow oil. LC/MS (ESI) m/z: 249.9 $[M+H]^+$.

Step 8: Preparation of [(2S,5S)-5-[[tert-butyl(diphenyl)silyl]oxymethyl]-1-methyl-pyrrolidin-2-yl]methyl benzoate

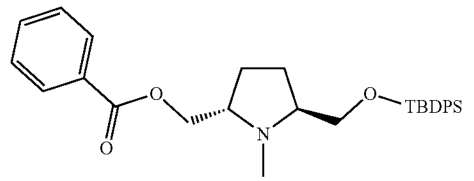

To [(2S,5S)-5-(hydroxymethyl)-1-methyl-pyrrolidin-2-yl]methyl benzoate (9.25 g, 34 mmol) in $CH_2Cl_2$ (150 mL) were added imidazole (2.79 g, 41 mmol) and TBDPSCI (9.68 mL, 38 mmol), and the reaction mixture was stirred at 20° C. for 15 h. The mixture was filtered, and the filtrate was washed with water (100 mL×3) followed by brine (100 mL×3), dried over sodium sulfate, filtered, and concentrated under reduced pressure. The residue was purified by silica gel chromatography (0-20% then up to 50% ethyl acetate in petroleum ether) to afford the title compound (16.5 g, 97%) as a colorless oil. LC/MS (ESI) m/z: 488.0 $[M+H]^+$.

Step 9: Preparation of [(2S,5S)-5-[[tert-butyl(diphenyl)silyl]oxymethyl]-1-methyl-pyrrolidin-2-yl]methanol

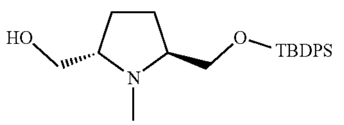

To [(2S,5S)-5-[[tert-butyl(diphenyl)silyl]oxymethyl]-1-methyl-pyrrolidin-2-yl]methyl benzoate (16.5 g, 33 mmol) in THF (100 mL) was added lithium hydroxide hydrate (6.96 g, 166 mmol) in water (60 mL), and the reaction mixture was stirred at 25° C. for 72 h. The mixture was extracted with EtOAc (100 mL×3), and the combined organic extract was washed with brine (100 mL×2), dried over $Na_2SO_4$, filtered, and concentrated under reduced pressure. The residue was purified by silica gel chromatography (0-4% then up to 10% $CH_3OH$ in $CH_2Cl_2$) to afford the title compound (11.8 g, 89%) as a yellow oil. LC/MS (ESI) m/z: 384.0 $[M+H]^+$, $^1H$ NMR (400 MHz, $CDCl_3$) δ 7.71-7.63 (m, 4H), 7.50-7.36 (m, 6H), 3.76-3.62 (m, 3H), 3.45 (dd, J=1.6, 10.8 Hz, 1H), 3.27 (br d, J=4.0 Hz, 1H), 3.00 (td, J=2.8, 5.6 Hz, 1H), 2.45 (s, 3H), 2.11-2.00 (m, 1H), 1.96-1.85 (m, 1H), 1.84-1.74 (m, 2H), 1.07 (s, 9H).

Step 10: Preparation of tert-butyl 3-[2-[[(2S,5S)-5-[[tert-butyl(diphenyl)silyl]oxymethyl]-1-methyl-pyrrolidin-2-yl]methoxy]-7-chloro-8-fluoro-pyrido[4,3-d]pyrimidin-4-yl]-3,8-diazabicyclo[3.2.1]octane-8-carboxylate

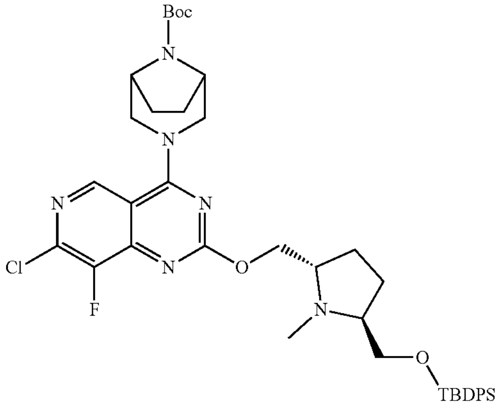

To a solution of tert-butyl 3-(2,7-dichloro-8-fluoro-pyrido[4,3-d]pyrimidin-4-yl)-3,8-diazabicyclo[3.2.1]octane-8-carboxylate (1.0 g, 2 mmol) and [(2S,5S)-5-[[tert-butyl(diphenyl)silyl]oxymethyl]-1-methyl-pyrrolidin-2-yl]methanol (895 mg, 2 mmol) in dioxane (20 mL) was added 4 A molecular sieves (1 g), and the resulting mixture was stirred at 40° C. for 20 minutes under nitrogen. The mixture was then cooled to 0° C. Sodium tert-butoxide (561 mg, 5.8 mmol) was then added, and the reaction mixture was stirred at 0° C. for 40 min. The mixture was diluted with saturated aqueous $NH_4Cl$ solution (30 mL) and extracted with ethyl acetate (30 mL×3). The combined organic extracts were washed with brine (30 mL), dried over $Na_2SO_4$, filtered, and concentrated under reduced pressure. The residue was purified by silica gel column chromatography (0-21% tetrahydrofuran in petroleum ether) to afford the title compound (1.25 g, 69%) as a yellow oil. LC/MS (ESI) m/z: 775.2 $[M+H]^+$.

Step 11: Preparation of tert-butyl 3-[2-[[(2S,5S)-5-[[tert-butyl(diphenyl)silyl]oxymethyl]-1-methyl-pyrrolidin-2-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

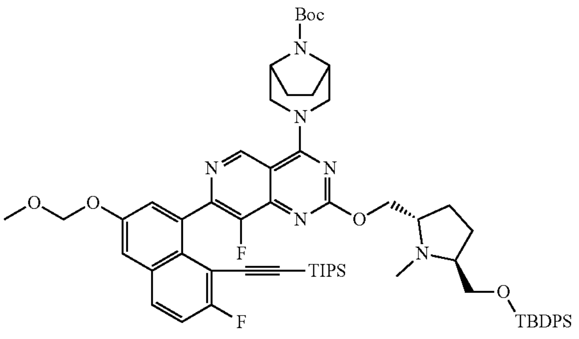

To a stirred solution of tert-butyl 3-[2-[[(2S,5S)-5-[[tert-butyl(diphenyl)silyl]oxymethyl]-1-methyl-pyrrolidin-2-yl]methoxy]-7-chloro-8-fluoro-pyrido[4,3-d]pyrimidin-4-yl]-3,8-diazabicyclo[3.2.1]octane-8-carboxylate (1.39 g, 2 mmol) and 2-[2-fluoro-6-(methoxymethoxy)-8-(4,4,5,5-tetramethyl-1,3,2-dioxaborolan-2-yl)-1-naphthyl]ethynyl-triisopropyl-silane (1.01 g, 2 mmol) in 1,4-dioxane (20 mL) and water (2 mL) were added $K_3PO_4$ (1.14 g, 5 mmol) and CataCXium A Pd G3 (130 mg, 0.2 mmol), and the reaction mixture was stirred at 85° C. under nitrogen for 16 h. The crude reaction mixture was dried over anhydrous sodium sulfate, filtered, and concentrated under reduced pressure. The residue was purified by flash column chromatography on silica gel (0 to 20% ethyl acetate in petroleum ether over 25 min) to afford the title compound (1.57 g, 78%) as a yellow solid. LC/MS (ESI) m/z: 1125.9 $[M+H]^+$.

Step 12: Preparation of tert-butyl 3-[7-[8-ethynyl-7-fluoro-3-(methoxymethoxy)-1-naphthyl]-8-fluoro-2-[[(2S,5S)-5-(hydroxymethyl)-1-methyl-pyrrolidin-2-yl]methoxy]pyrido[4,3-d]pyrimidin-4-yl]-3,8-diazabicyclo[3.2.1]octane-8-carboxylate

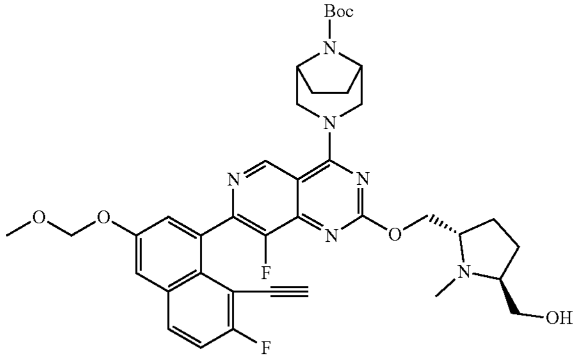 [SMILES: C#Cc1c(F)ccc2cc(OCOC)cc(-c3ncc4c(N5CC6CCC(C5)N6C(=O)OC(C)(C)C)nc(OC[C@@H]5CC[C@@H](CO)N5C)nc4c3F)c12]

To a solution of tert-butyl 3-[2-[[(2S,5S)-5-[[tert-butyl(diphenyl)silyl]oxymethyl]-1-methyl-pyrrolidin-2-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (1.57 g, 1.4 mmol) in DMF (15 mL) was added cesium fluoride (2.12 g, 14 mmol), and the mixture was stirred at 40° C. for 16 h. The reaction mixture was filtered and washed with ethyl acetate (30 mL). The filtrate was diluted with water (50 mL) and extracted with ethyl acetate (3x30 mL). The combined organic extract was washed with water (3x30 mL) followed by brine (30 mL), dried over anhydrous sodium sulfate, filtered, and concentrated under reduced pressure. The residue was purified by flash column chromatography on silica gel (0 to 15% methanol in dichloromethane) to afford the title compound (0.825 g, 81%) as a yellow solid. LC/MS (ESI) m/z: 731.3 $[M+H]^+$.

Step 13: Preparation of tert-butyl 3-[7-[8-ethynyl-7-fluoro-3-(methoxymethoxy)-1-naphthyl]-8-fluoro-2-[[(2S,5S)-5-formyl-1-methyl-pyrrolidin-2-yl]methoxy]pyrido[4,3-d]pyrimidin-4-yl]-3,8-diazabicyclo[3.2.1]octane-8-carboxylate

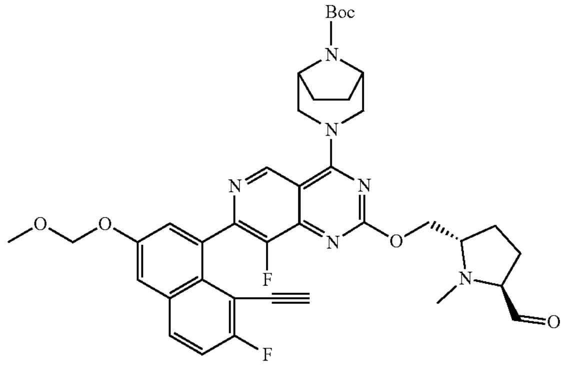 [SMILES: C#Cc1c(F)ccc2cc(OCOC)cc(-c3ncc4c(N5CC6CCC(C5)N6C(=O)OC(C)(C)C)nc(OC[C@@H]5CC[C@@H](C=O)N5C)nc4c3F)c12]

To DMSO (352 mg, 4.5 mmol) in dichloromethane (5 mL) at −67° C. was added oxalyl dichloride (429 mg, 3.4 mmol) in dichloromethane (1 mL) dropwise under nitrogen atmosphere, and the resulting mixture was stirred for 15 min. tert-Butyl 3-[7-[8-ethynyl-7-fluoro-3-(methoxymethoxy)-1-naphthyl]-8-fluoro-2-[[(2S,5S)-5-(hydroxymethyl)-1-methyl-pyrrolidin-2-yl]methoxy]pyrido[4,3-d]pyrimidin-4-yl]-3,8-diazabicyclo[3.2.1]octane-8-carboxylate (412 mg, 0.6 mmol) in dichloromethane (1.5 mL) was then added dropwise, and the mixture was stirred at −67° C. for 30 min. Triethylamine (2.4 mL, 17 mmol) was then added dropwise, and the reaction mixture was stirred at −67° C. for 15 min under nitrogen atmosphere. The reaction mixture was diluted with water (30 mL) and extracted with dichloromethane (3x30 mL). The combined organic extracts were washed with brine (30 mL), dried over sodium sulfate, filtered, and concentrated under reduced pressure to afford the title compound (410 mg, crude) as a yellow oil. LC/MS (ESI) m/z: 747.3 $[M+H_3O]^+$.

Step 14: Preparation of tert-butyl 3-[2-[[(2S,5S)-5-[[4-[[1-[1-(2,6-dioxo-3-piperidyl)-3-isopropyl-2-oxo-benzimidazol-5-yl]-4-piperidyl]methyl]piperazin-1-yl]methyl]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

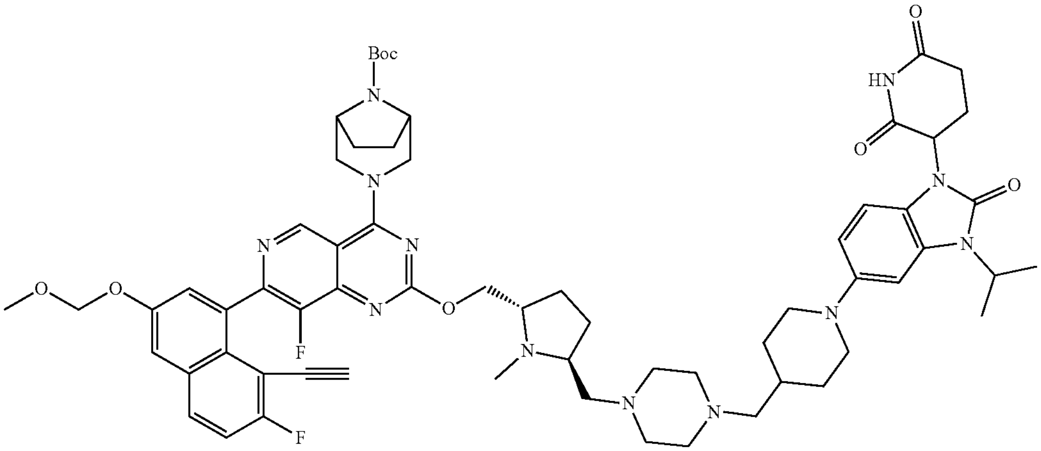 [SMILES: C#Cc1c(F)ccc2cc(OCOC)cc(-c3ncc4c(N5CC6CCC(C5)N6C(=O)OC(C)(C)C)nc(OC[C@@H]5CC[C@@H](CN6CCN(CC7CCN(c8ccc9c(c8)n(C(C)C)c(=O)n9C8CCC(=O)NC8=O)CC7)CC6)N5C)nc4c3F)c12]

To a mixture of tert-butyl 3-[7-[8-ethynyl-7-fluoro-3-(methoxymethoxy)-1-naphthyl]-8-fluoro-2-[[(2S,5S)-5-formyl-1-methyl-pyrrolidin-2-yl]methoxy]pyrido[4,3-d]pyrimidin-4-yl]-3,8-diazabicyclo[3.2.1]octane-8-carboxylate (410 mg, 0.6 mmol) and 3-[3-isopropyl-2-oxo-5-[4-(piperazin-1-ylmethyl)-1-piperidyl]benzimidazol-1-yl]piperidine-2,6-dione (298 mg, 0.6 mmol, HCl salt) in dichloromethane (15 mL) was added $NaBH(OAc)_3$ (298 mg, 1.4 mmol), and the reaction mixture was stirred at 25° C. for 16 h. The mixture was diluted with water (50 mL) and extracted with ethyl acetate (3×50 mL). The combined organic extracts were washed with water (3×50 mL), dried over sodium sulfate, filtered, and concentrated under reduced pressure. The residue was purified by flash column chromatography on silica gel (0 to 10% methyl alcohol in dichloromethane) to afford the title compound (370 mg, 55.67%) as a yellow solid. LC/MS (ESI) m/z: 1181.9 $[M+H]^+$.

Step 15: Preparation of 3-(5-{4-[(4-{[(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl}piperazin-1-yl)methyl]piperidin-1-yl}-2-oxo-3-(propan-2-yl)-2,3-dihydro-1H-1,3-benzodiazol-1-yl)piperidine-2,6-dione

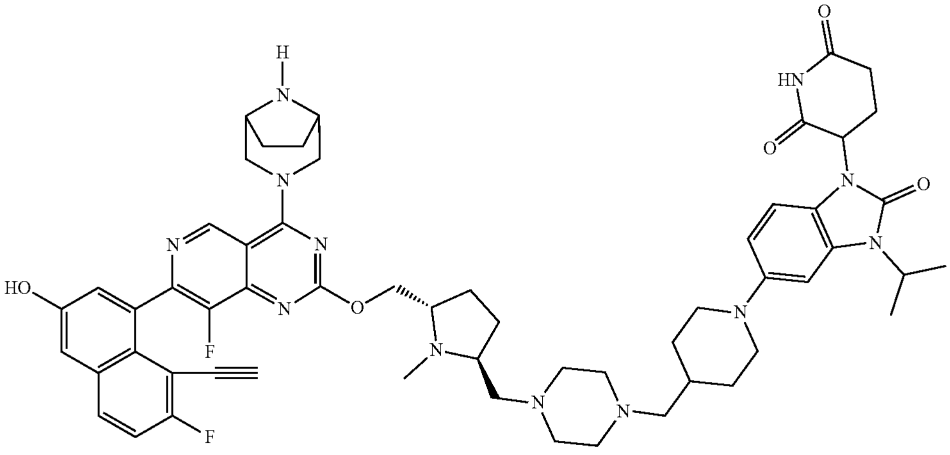 [SMILES: C#Cc1c(F)ccc2cc(O)cc(-c3ncc4c(N5CC6CCC(C5)N6)nc(OC[C@@H]5CC[C@@H](CN6CCN(CC7CCN(c8ccc9c(c8)n(C(C)C)c(=O)n9C8CCC(=O)NC8=O)CC7)CC6)N5C)nc4c3F)c12]

To a solution of tert-butyl 3-[2-[[(2S,5S)-5-[[4-[[1-[1-(2,6-dioxo-3-piperidyl)-3-isopropyl-2-oxo-benzimidazol-5-yl]-4-piperidyl]methyl]piperazin-1-yl]methyl]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (370 mg, 0.3 mmol) in dichloromethane (3 mL) was added 4 M HCl in 1,4-dioxane (3 mL), and the mixture was stirred at 25° C. for 10 min. The reaction mixture was suspended in petroleum ether (10 mL), filtered, and washed with petroleum ether (2×10 mL). The filter cake was dissolved with THF (10 mL) and triethylamine to adjust the pH to 8. The mixture was filtered, and the filtrate was concentrated under reduced pressure. The residue was purified by prep-HPLC (18%-58% acetonitrile in water (ammonium bicarbonate) over 32 min) to afford the title compound (123.2 mg, 39%) as an off-white solid. LC/MS (ESI) m/z: 1037.7 $[M+H]^+$; $^1$H NMR ($CD_3OD$) δ 9.01 (s, 1H), 7.86 (dd, J=5.6, 9.2 Hz, 1H), 7.37-7.29 (m, 2H), 7.21 (d, J=2.4 Hz, 1H), 7.00-6.94 (m, 2H), 6.80 (dd, J=1.6, 9.2 Hz, 1H), 5.27 (dd, J=5.2, 12.8 Hz, 1H), 4.68-4.55 (m, 5H), 4.54-4.46 (m, 1H), 3.76-3.64 (m, 4H), 3.53 (br d, J=11.6 Hz, 2H), 3.49-3.39 (m, 2H), 3.38 (s, 1H), 3.22-3.21 (m, 1H), 3.26-2.86 (m, 6H), 2.56-2.39 (m, 7H), 2.34-2.21 (m, 3H), 2.20-2.04 (m, 4H), 1.94-1.76 (m, 8H), 1.75-1.66 (m, 2H), 1.54 (d, J=6.8 Hz, 6H), 1.45-1.31 (m, 2H).

Example 69: Synthesis of 3-[5-(4-{[(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl}piperazin-1-yl)-2-oxo-3-(propan-2-yl)-2,3-dihydro-1H-1,3-benzodiazol-1-yl]piperidine-2,6-dione (Compound 176)

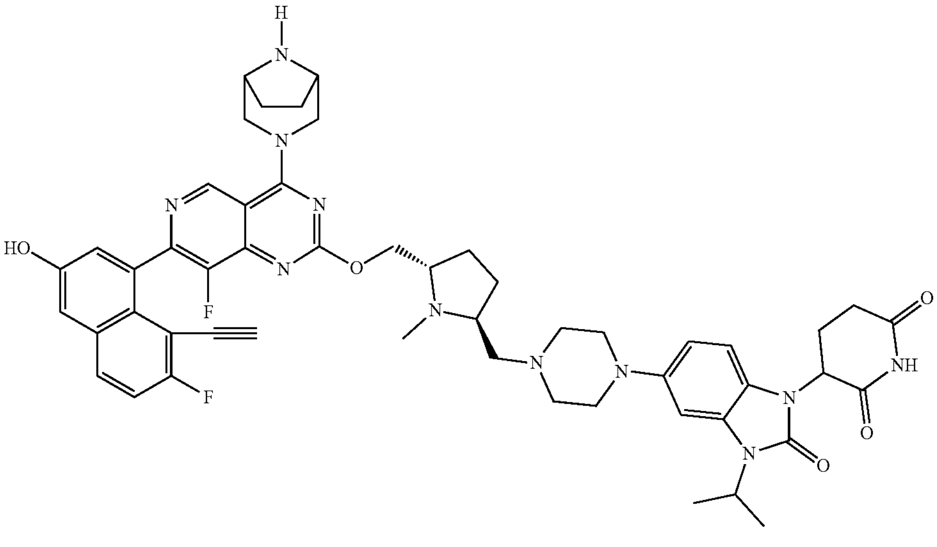 [SMILES: C#Cc1c(F)ccc2cc(O)cc(-c3ncc4c(N5CC6CCC(C5)N6)nc(OC[C@@H]5CC[C@@H](CN6CCN(c7ccc8c(c7)n(C(C)C)c(=O)n8C7CCC(=O)NC7=O)CC6)N5C)nc4c3F)c12]

The title compound was made in an analogous manner to 3-(5-{4-[(4-{[(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl}piperazin-1-yl)methyl]piperidin-1-yl}-2-oxo-3-(propan-2-yl)-2,3-dihydro-1H-1,3-benzodiazol-1-yl)piperidine-2,6-dione. (white solid). LC/MS (ESI) m/z: 940.4 $[M+H]^+$, $^1$H NMR ($CD_3OD$) δ 9.02 (s, 1H), 7.86 (dd, J=5.6, 9.2 Hz, 1H), 7.36-7.28 (m, 2H), 7.21 (d, J=2.4 Hz, 1H), 6.98 (d, J=8.4 Hz, 1H), 6.93 (d, J=2.0 Hz, 1H), 6.76 (br d, J=8.8 Hz, 1H), 5.26 (dd, J=5.6, 12.4 Hz, 1H), 4.68-4.56 (m, 5H), 4.54-4.48 (m, 1H), 3.75-3.65 (m, 4H), 3.49-3.41 (m, 1H), 3.38 (s, 1H), 3.14 (br t, J=4.0 Hz, 4H), 2.94-2.86 (m, 1H), 2.82-2.74 (m, 2H), 2.71-2.64 (m, 8H), 2.36 (dd, J=7.6, 12.4 Hz, 1H), 2.17-2.08 (m, 3H), 1.90-1.74 (m, 6H), 1.57-1.51 (m, 6H)

Example 70: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-2-oxo-3-(propan-2-yl)-2,3-dihydro-1H-1,3-benzodiazol-1-yl}piperidine-2,6-dione (Compound 212)

Step 1: Preparation of tert-butyl 4-[[1-[[1-[1-(2,6-dioxo-3-piperidyl)-3-isopropyl-2-oxo-benzimidazol-5-yl]-4-piperidyl]methyl]-4-piperidyl]methyl]piperidine-1-carboxylate

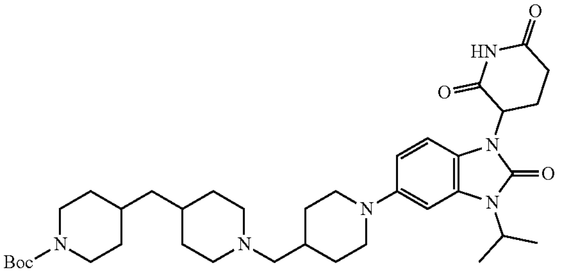 [SMILES: CC(C)n1c(=O)n(C2CCC(=O)NC2=O)c2ccc(N3CCC(CN4CCC(CC5CCN(C(=O)OC(C)(C)C)CC5)CC4)CC3)cc21]

To a solution of tert-butyl 4-(4-piperidylmethyl)piperidine-1-carboxylate acetate (662 mg, 1.9 mmol) and 1-[1-(2,6-dioxo-3-piperidyl)-3-isopropyl-2-oxo-benzimidazol-5-yl]piperidine-4-carbaldehyde (700 mg, 1.8 mmol) in dimethyl sulfoxide (2 mL) and dichloromethane (5 mL) were added sodium triacetoxyborohydride (745 mg, 3.5 mmol) and N,N-diisopropylethylamine (0.6 mL, 3 mmol), and the mixture was stirred at 25° C. for 2 h. The reaction mixture was diluted with water (20 mL) and extracted with dichloromethane (3×40 mL). The combined organic layers were washed with brine (20 mL), dried over anhydrous sodium sulfate, filtered, and concentrated under reduced pressure. The residue was triturated with ethyl acetate/methyl tert-butyl ether (1/10, 60 mL) to afford the title compound (1 g, 86%) as green solid. LC/MS (ESI) m/z: 665.4 $[M+H]^+$.

Step 2: Preparation of 3-[3-isopropyl-2-oxo-5-[4-[[4-(4-piperidylmethyl)-1-piperidyl]methyl]-1-piperidyl]benzimidazol-1-yl]piperidine-2,6-dione

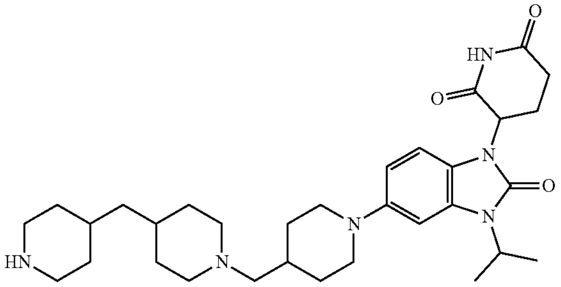 [SMILES: CC(C)n1c(=O)n(C2CCC(=O)NC2=O)c2ccc(N3CCC(CN4CCC(CC5CCNCC5)CC4)CC3)cc21]

To a solution of tert-butyl 4-[[1-[[1-[1-(2,6-dioxo-3-piperidyl)-3-isopropyl-2-oxo-benzimidazol-5-yl]-4-piperidyl]methyl]-4-piperidyl]methyl]piperidine-1-carboxylate (1.0 g, 1.5 mmol) in dichloromethane (12 mL) was added trifluoroacetic acid (3.0 mL, 40 mmol), and the mixture was stirred at 25° C. for 1 h. The reaction mixture was concentrated under reduced pressure, and the residue was triturated with ethyl acetate/methyl tert-butyl ether (1/10, 60 mL) to afford the title compound (1.1 g, 92%, 2 TFA salt) as a dark green solid. LC/MS (ESI) m/z: 565.5 $[M+H]^+$.

Step 3: Preparation of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

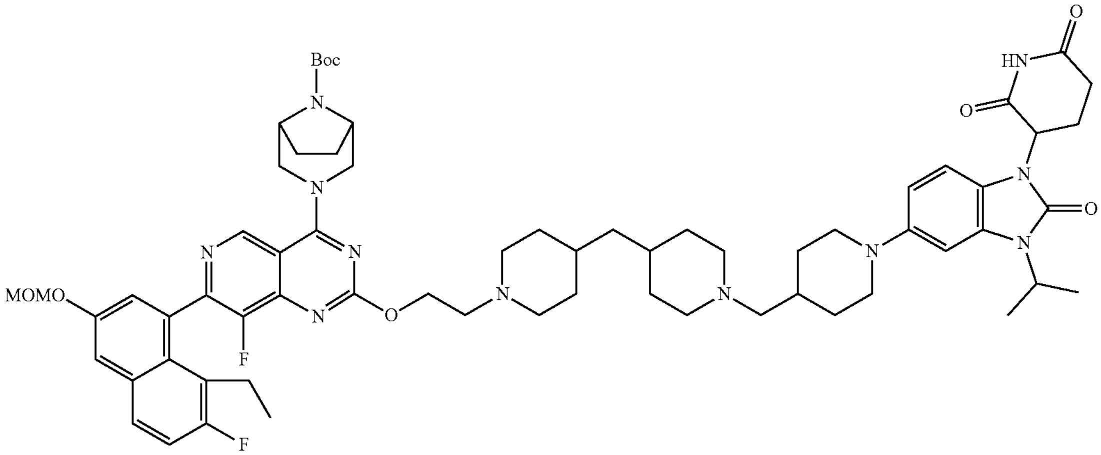

To a solution of 3-[3-isopropyl-2-oxo-5-[4-[[4-(4-piperidylmethyl)-1-piperidyl]methyl]-1-piperidyl]benzimidazol-1-yl]piperidine-2,6-dione di-trifluoroacetate (200 mg, 0.25 mmol) and tert-butyl 3-[7-[8-ethyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate (213 mg, 0.3 mmol) in isopropanol (5 mL) and dichloromethane (5 mL) were added sodium triacetoxyborohydride (107 mg, 0.5 mmol) and N,N-diisopropylethylamine (0.13 mL, 0.8 mmol), and the mixture was stirred at 25° C. for 2 h. The reaction mixture was diluted with water (15 mL) and extracted with dichloromethane (3×30 mL). The combined organic layers were washed with brine (15 mL), dried over anhydrous sodium sulfate, filtered, and concentrated under reduced pressure. The residue was purified by prep-HPLC (25%-55% acetonitrile in water (trifluoroacetic acid) over 15 min) to afford the title compound (150 mg, 50%) as a white solid. LC/MS (ESI) m/z: 1198.8 $[M+H]^+$.

Step 4: Preparation of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-2-oxo-3-(propan-2-yl)-2,3-dihydro-1H-1,3-benzodiazol-1-yl}piperidine-2,6-dione

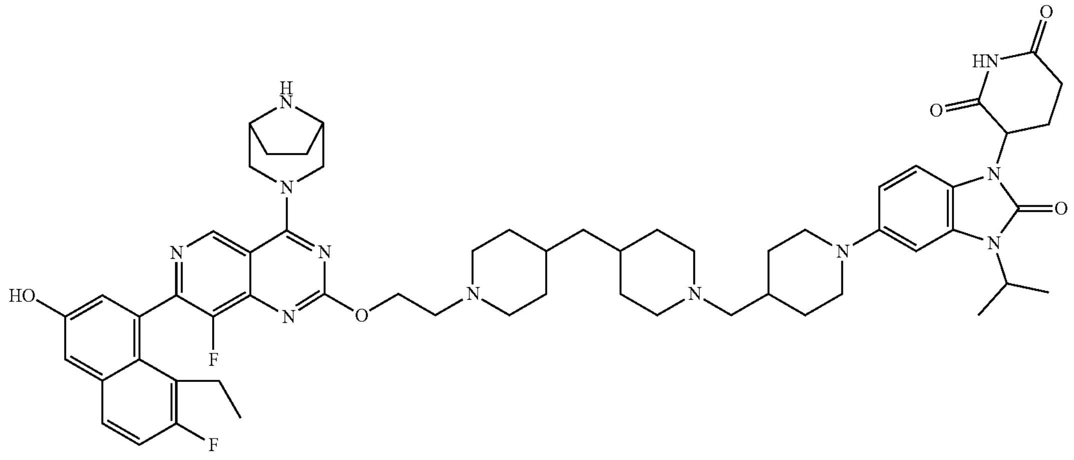 [SMILES: CCc1c(F)ccc2cc(O)cc(-c3ncc4c(N5CC6CCC(C5)N6)nc(OCCN5CCC(CC6CCN(CC7CCN(c8ccc9c(c8)n(C(C)C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-7-[8-ethyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (150 mg, 0.1 mmol) in dichloromethane (5 mL) was added 4 M HCl in 1,4-dioxane (0.3 mL), and the mixture was stirred at 25° C. for 15 min. The reaction mixture was triturated with ethyl acetate/methyl tert-butyl ether (1/10, 100 mL) to obtain a yellow solid. This crude material was purified by prep-HPLC (1% to 30% acetonitrile in water (formic acid) over 10 min) to afford the title compound (56.4 mg, 37%, tri-formic acid salt) as a white solid. LC/MS (ESI) m/z: 1054.8 $[M+H]^+$, $^1$HNMR (400 MHz, DMSO-$d_6$) δ 11.06 (s, 1H), 9.13-9.08 (m, 1H), 8.19 (s, 3H), 7.81-7.74 (m, 1H), 7.39-7.32 (m, 2H), 7.02 (d, J=2.4 Hz, 1H), 6.94-6.86 (m, 2H), 6.62 (br d, J=8.0 Hz, 1H), 5.32-5.22 (m, 1H), 4.62-4.54 (m, 1H), 4.51-4.41 (m, 4H), 3.65 (br s, 4H), 3.54 (br d, J=10.4 Hz, 4H), 2.98-2.90 (m, 3H), 2.89-2.83 (m, 3H), 2.72-2.66 (m, 3H), 2.64-2.56 (m, 3H), 2.41-2.32 (m, 2H), 2.18 (br d, J=6.8 Hz, 2H), 2.03-1.95 (m, 3H), 1.93-1.86 (m, 2H), 1.77 (br d, J=12.4 Hz, 2H), 1.70-1.65 (m, 3H), 1.62-1.55 (m, 5H), 1.44 (br d, J=6.8 Hz, 6H), 1.33-1.21 (m, 4H), 1.14-1.04 (m, 6H), 0.73 (br t, J=7.6 Hz, 3H).

Example 71: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]methyl}-1-methylpyrrolidin-3-yl]oxy}piperidin-1-yl)methyl]piperidin-1-yl}-4-fluoro-3-methyl-2-oxo-2,3-dihydro-1H-1,3-benzodiazol-1-yl)piperidine-2,6-dione (Compound 213)

Step 1: Preparation of tert-butyl 3-[2-[[(2S,4R)-4-[[1-[[1-[1-(2,6-dioxo-3-piperidyl)-4-fluoro-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

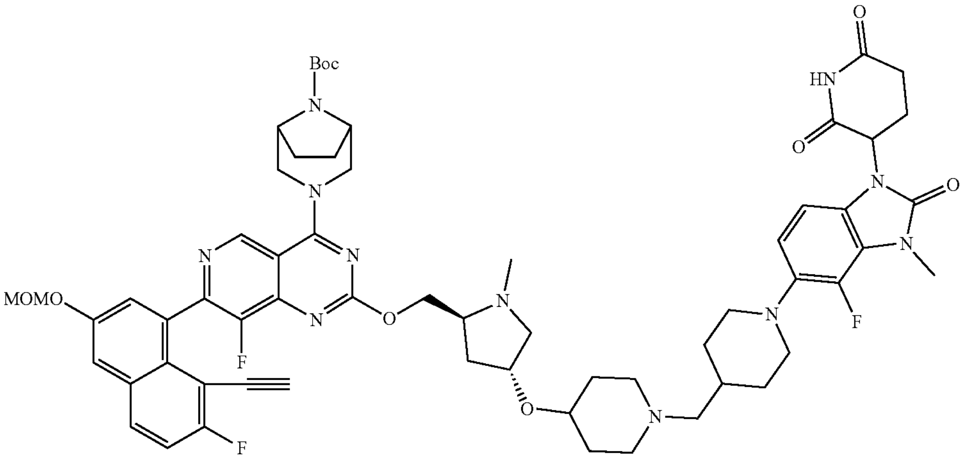

To a solution of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate formate (100 mg, 0.1 mmol) in dichloromethane (2 mL) and isopropanol (2 mL) were added N,N-diisopropylethylamine (22.9 mg, 0.2 mmol), 1-[1-(2,6-dioxo-3-piperidyl)-4-fluoro-3-methyl-2-oxo-benzimidazol-5-yl]piperidine-4-carbaldehyde (51 mg, 0.1 mmol), and sodium triacetoxyborohydride (63 mg, 0.3 mmol), and the mixture was stirred at 25° C. for 1 h. The reaction mixture was filtered and concentrated under reduced pressure. The residue was purified by prep-TLC (dichloromethane/methanol=4/1) to afford the title compound (90 mg, 64%) as a yellow solid. LC/MS (ESI) m/z: 1172.9 $[M+H]^+$.

Step 2: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-3-methyl-2-oxo-2,3-dihydro-1H-1,3-benzodiazol-1-yl)piperidine-2,6-dione

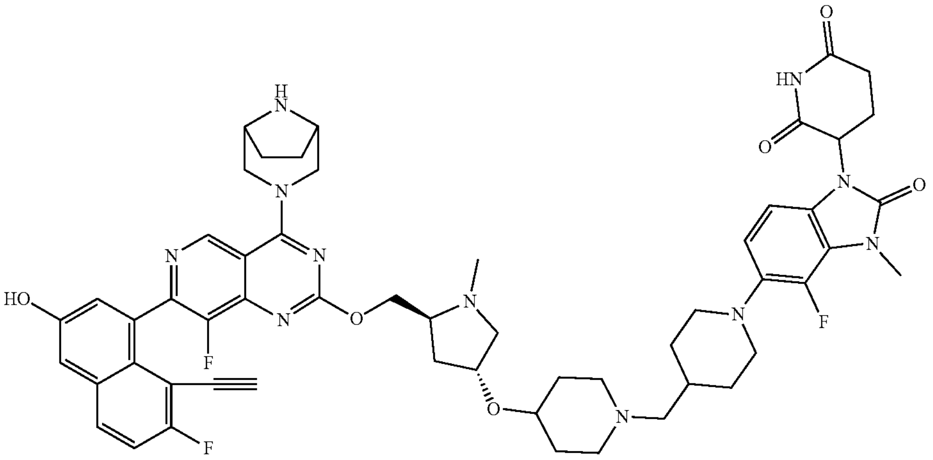 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8F)n(C)c(=O)n9C8CCC(=O)NC8=O)CC7)CC6)CN5C)nc4c3F)c12]

To a solution of tert-butyl 3-[2-[[(2S,4R)-4-[[1-[[1-[1-(2,6-dioxo-3-piperidyl)-4-fluoro-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (80 mg, 0.07 mmol) in dichloromethane (6 mL) was added 4 M HCl in 1,4-dioxane (3 mL), and the mixture was stirred at 25° C. for 0.2 h. The reaction mixture was filtered and concentrated under reduced pressure. The residue was purified by prep-HPLC (1% to 30% acetonitrile in water (formic acid) over 10 min) to afford the title compound (49.8 mg, 66%, formic acid salt) as a yellow solid. LC/MS (ESI) m/z: 1028.2 $[M+H]^+$; $^1H$ NMR (400 MHz, DMSO-$d_6$) δ 11.11 (s, 1H), 9.07 (s, 1H), 8.17 (s, 2H), 8.04-7.93 (m, 1H), 7.52-7.37 (m, 2H), 7.19 (br d, J=2.0 Hz, 1H), 6.64-6.91 (m, 2H), 5.33 (br dd, J=12.8, 4.8 Hz, 1H), 4.61-4.51 (m, 1H), 4.44-4.35 (m, 2H), 4.30-4.25 (m, 1H), 4.25-4.22 (m, 1H), 4.13-4.12 (m, 1H), 4.17-4.09 (m, 1H), 3.95 (br s, 1H), 3.83 (br s, 2H), 3.76-3.69 (m, 2H), 3.35-3.21 (m, 8H), 2.93-2.85 (m, 1H), 2.83-2.78 (m, 1H), 2.71 (br dd, J=4.4, 2.8 Hz, 2H), 2.63 (br s, 3H), 2.55 (s, 8H), 2.37 (s, 3H), 2.25-2.17 (m, 3H), 2.11-1.98 (m, 3H), 1.91-1.87 (m, 2H), 1.65-1.57 (m, 1H), 1.49-1.36 (m, 2H), 1.29-1.24 (m, 1H), 1.21 (br d, J=6.4 Hz, 3H).

Example 72: Synthesis of (3S)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-1-oxo-2,3-dihydro-1H-isoindol-2-yl}piperidine-2,6-dione (Compound 214)

Step 1: Preparation of methyl (S)-5-amino-4-(5-(4-(dimethoxymethyl)piperidin-1-yl)-4-fluoro-1-oxoisoindolin-2-yl)-5-oxopentanoate

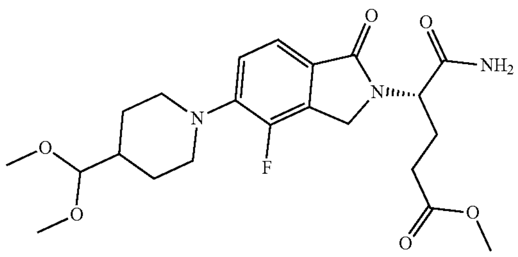

To a mixture of methyl 4-[4-(dimethoxymethyl)-1-piperidyl]-3-fluoro-2-formyl-benzoate (600 mg, 1.8 mmol) and methyl (4S)-4,5-diamino-5-oxo-pentanoate hydrochloride (417 mg, 2 mmol) in methanol (10 mL) was added sodium acetate (725 mg, 8.8 mmol), and the mixture was stirred at 20° C. for 0.5 h. Sodium cyanoborohydride (222 mg, 3.5 mmol) was then added, and the reaction mixture was stirred at 35° C. for 11 h. The reaction was concentrated under reduced pressure, and the resulting residue was diluted with ethyl acetate (100 mL) and washed with brine (60 mL×2). The combined organic extract was dried over anhydrous sodium sulfate, filtered, and concentrated under reduced pressure. The residue was purified by silica gel chromatography (petroleum ether/ethyl acetate=3:1 to 1:100) to afford the title compound (500 mg, 59%) as a light yellow solid. LC/MS (ESI) m/z: 452.3 [M+H]$^+$, $^1$H NMR (400 MHz, $CDCl_3$) δ 7.51 (d, J=8.4 Hz, 1H), 7.02 (t, J=7.8 Hz, 1H), 6.40 (br s, 1H), 5.48 (br s, 1H), 4.97-4.78 (m, 1H), 4.59-4.36 (m, 2H), 4.11 (d, J=7.2 Hz, 1H), 3.69-3.56 (m, 5H), 3.39 (s, 6H), 2.75 (br t, J=11.8 Hz, 2H), 2.52-2.29 (m, 3H), 2.19 (dt, J=5.4, 9.8 Hz, 1H), 1.92-1.80 (m, 3H), 1.61-1.44 (m, 2H).

Step 2: Preparation of (S)-3-(5-(4-(dimethoxymethyl)piperidin-1-yl)-4-fluoro-1-oxoisoindolin-2-yl) piperidine-2,6-dione

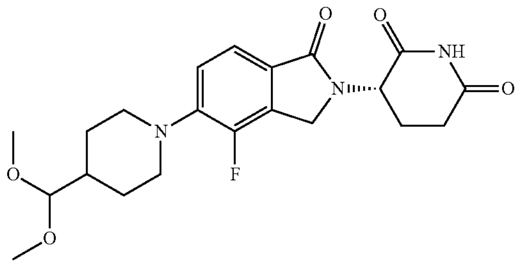 [SMILES: COC(OC)C1CCN(c2ccc3c(c2F)CN([C@H]2CCC(=O)NC2=O)C3=O)CC1]

To a solution of methyl methyl (S)-5-amino-4-(5-(4-(dimethoxymethyl)piperidin-1-yl)-4-fluoro-1-oxoisoindolin-2-yl)-5-oxopentanoate (500 mg, 1 mmol) in tetrahydrofuran (10 mL) at −20° C. was added lithium tert-butoxide solution (1 M, 2.2 mL), and the reaction mixture was stirred at −20° C. for 4 h. 2 M aqueous sulfuric acid solution was added to adjust the pH to 5 while keepojping the temperature at −20° C. Saturated sodium bicarbonate solution was added to adjust the pH to 8, and the resulting mixture was diluted with brine (50 mL) and extracted with ethyl acetate (2×50 mL). The combined organic extracts were washed with brine (3×50 mL), dried over anhydrous sodium sulfate, filtered, and concentrated under reduced pressure. The residue was triturated with ethyl acetate (20 mL) to afford the title compound (290 mg, 62%) as a white solid. LC/MS (ESI) m/z: 420.1 [M+H]$^+$.

Step 3: Preparation of (S)-1-(2-(2,6-dioxopiperidin-3-yl)-4-fluoro-1-oxoisoindolin-5-yl)piperidine-4-carbaldehyde

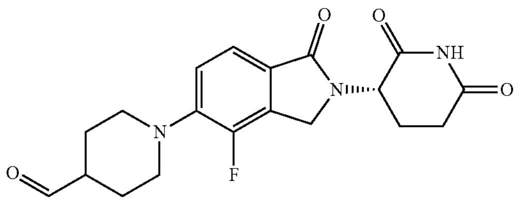 [SMILES: O=CC1CCN(c2ccc3c(c2F)CN([C@H]2CCC(=O)NC2=O)C3=O)CC1]

To a mixture of (S)-3-(5-(4-(dimethoxymethyl)piperidin-1-yl)-4-fluoro-1-oxoisoindolin-2-yl)piperidine-2,6-dione (290 mg, 0.7 mmol) in acetone (8 mL) and water (0.8 mL) was added p-toluenesulfonic acid monohydrate (23 mg, 0.1 mmol), and the reaction mixture was stirred at 70° C. for 2 h. The mixture was cooled to 25° C. and filtered, washing with acetone (2×50 mL). The filtrate solution was concentrated under reduced pressure to afford the title compound (130 mg, 50%) as an off-white solid. $^1$H NMR (400 MHz, DMSO-$d_6$) δ 10.97 (s, 1H), 9.65 (s, 1H), 7.47 (d, J=8.0 Hz, 1H), 7.26-7.12 (m, 1H), 5.08 (dd, J=5.2, 1 Step 6: Hz, 1H), 4.55-4.42 (m, 1H), 4.38-4.26 (m, 1H), 3.48-3.37 (m, 3H), 2.98-2.85 (m, 3H), 2.64-2.55 (m, 1H), 2.48-2.34 (m, 1H), 2.05-1.93 (m, 3H), 1.74-1.57 (m, 2H).

Step 4: Preparation of tert-butyl (S)-4-((1-((1-(2-(2,6-dioxopiperidin-3-yl)-4-fluoro-1-oxoisoindolin-5-yl)piperidin-4-yl)methyl)piperidin-4-yl)methyl)piperidine-1-carboxylate

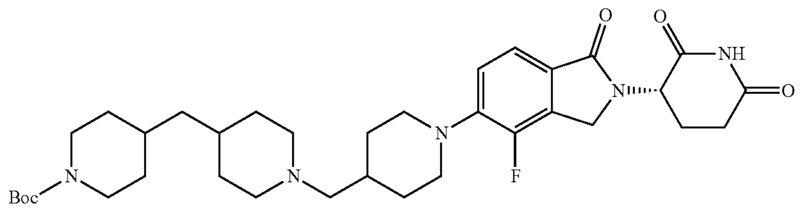 [SMILES: CC(C)(C)OC(=O)N1CCC(CC2CCN(CC3CCN(c4ccc5c(c4F)CN([C@H]4CCC(=O)NC4=O)C5=O)CC3)CC2)CC1]

To a solution of (S)-1-(2-(2,6-dioxopiperidin-3-yl)-4-fluoro-1-oxoisoindolin-5-yl)piperidine-4-carbaldehyde (130 mg, 0.3 mmol) in dichloromethane (3 mL) and dimethyl sulfoxide (0.8 mL) was added tert-butyl 4-(4-piperidylmethyl)piperidine-1-carboxylate (98 mg, 0.3 mmol), and the resulting mixture was stirred at 0° C. for 10 min. Sodium triacetoxyborohydride (221 mg, 1 mmol) was then added, and the reaction mixture was stirred at 0° C. for 0.5 h. The mixture was diluted with water (50 mL) and extracted with ethyl acetate (2×50 mL). The combined organic layers were washed with brine (2×50 mL), dried over anhydrous sodium sulfate, filtered, and concentrated under reduced pressure. The residue was purified by prep-TLC (dichloromethane: methanol=10:1) to afford the title compound (160 mg, 71%) as a white solid. LC/MS (ESI) m/z: 640.5 [M+H]$^+$.

Step 5: Preparation of (S)-3-(4-fluoro-1-oxo-5-(4-((4-(piperidin-4-ylmethyl)piperidin-1-yl)methyl)piperidin-1-yl)isoindolin-2-yl)piperidine-2,6-dione

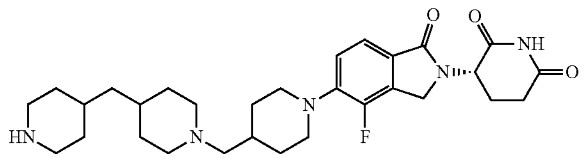 [SMILES: O=C1CC[C@H](N2Cc3c(ccc(N4CCC(CN5CCC(CC6CCNCC6)CC5)CC4)c3F)C2=O)C(=O)N1]

To tert-butyl (S)-4-((1-((1-(2-(2,6-dioxopiperidin-3-yl)-4-fluoro-1-oxoisoindolin-5-yl)piperidin-4-yl)methyl)piperidin-4-yl)methyl)piperidine-1-carboxylate (160 mg, 0.3 mmol) in dichloromethane (2 mL) at 25° C. was added trifluoroacetic acid (1.0 mL, 13 mmol), and the reaction mixture was stirred for 15 min. The reaction mixture was filtered and concentrated under reduced pressure. The residue was purified by prep-HPLC (1% to 30% acetonitrile in water (formic acid) over 10 min) to afford the title compound (100 mg, 74%) as a white solid. LC/MS (ESI) m/z: 540.3 $[M+H]^+$, $^1H$ NMR (400 MHz, DMSO-$d_6$) δ 10.97 (s, 1H), 7.55-7.42 (m, 1H), 7.26-7.05 (m, 1H), 5.08 (dd, J=5.2, 1 Step 6: Hz, 1H), 4.58-4.39 (m, 1H), 4.38-4.26 (m, 1H), 3.60-3.48 (m, 4H), 3.31-3.18 (m, 3H), 3.06-2.97 (m, 2H), 2.94-2.75 (m, 7H), 2.64-2.54 (m, 1H), 2.42-2.37 (m, 1H), 2.07-1.92 (m, 2H), 1.89-1.73 (m, 6H), 1.68-1.53 (m, 2H), 1.46-1.31 (m, 4H), 1.29-1.09 (m, 4H).

Step 6: Preparation of tert-butyl 3-[7-[8-ethynyl-7-fluoro-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate

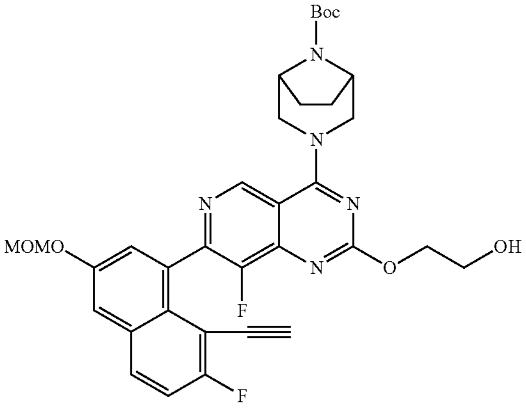

To a solution of tert-butyl 3-[8-fluoro-7-[7-fluoro-3-(methoxymethoxy)-8-(2-triisopropylsilylethynyl)-1-naphthyl]-2-(2-hydroxyethoxy)pyrido[4,3-d]pyrimidin-4-yl]-3,8-diazabicyclo[3.2.1]octane-8-carboxylate (2 g, 2 mmol) in N,N-dimethylformamide (20 mL) was added cesium fluoride (11.5 g, 76 mmol). The mixture was stirred at 25° C. for 0.5 hour. The reaction mixture was diluted with water (100 mL) and extracted with dichloromethane (80 mL×2). The combined organic phase was washed with brine (80 mL×2), dried with anhydrous sodium sulfate, filtered, and concentrated under reduced pressure. The residue was purified by column chromatography (dichloromethane:methanol=10:1) to afford tert-butyl 3-[7-[8-ethynyl-7-fluoro-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate (1.5 g, 93%) as a yellow solid.

Step 7: Preparation of tert-butyl 3-[7-[8-ethynyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate

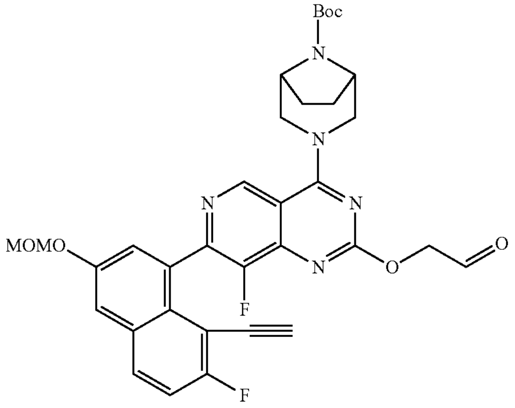

To a solution of tert-butyl 3-[7-[8-ethynyl-7-fluoro-3-(methoxymethoxy)-1-naphthyl]-8-fluoro-2-(2-hydroxyethoxy)pyrido[4,3-d]pyrimidin-4-yl]-3,8-diazabicyclo[3.2.1]octane-8-carboxylate (200 mg, 0.30 mmol) in dichloromethane (2 mL) were added Dess-Martin reagent (196 mg, 0.46 mmol) and sodium bicarbonate (51 mg, 0.61 mmol). The mixture was stirred at 25° C. for 1 hour. The reaction mixture was diluted with saturated aqueous sodium bicarbonate:saturated aqueous sodium thiosulfate:water (1:1:1, 45 mL) and extracted with dichloromethane (15 mL×2). The combined organic phase was washed with brine (30 mL), dried with anhydrous sodium sulfate, filtered, and concentrated under reduced pressure. The residue was purified by prep-TLC (petroleum ether:ethyl acetate=0:1) to afford tert-butyl 3-[7-[8-ethynyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate (118 mg, 59%) as a yellow solid. LC/MS (ESI) m/z: 646.3 $[M+1]^+$.

Step 8: Preparation of tert-butyl 3-[2-[2-[4-[[1-[[1-[2-[(3S)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

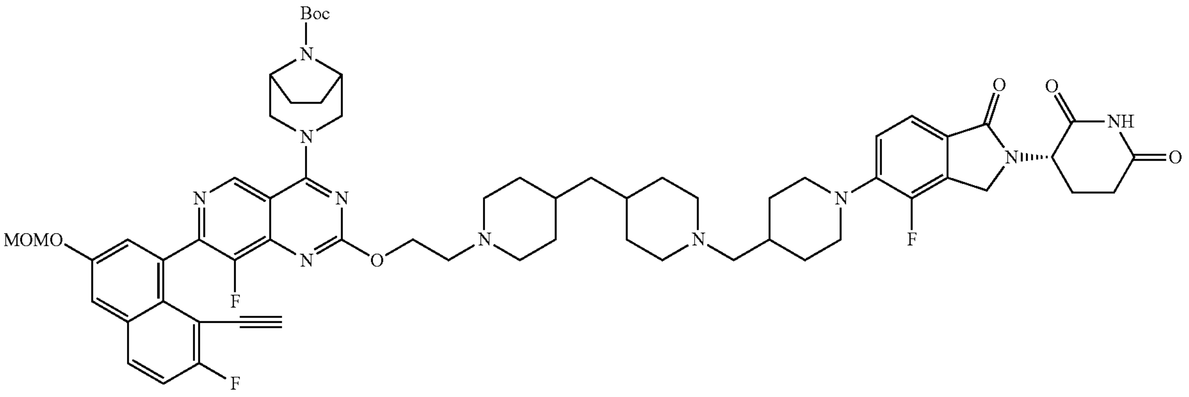

To a solution of (S)-3-(4-fluoro-1-oxo-5-(4-((4-(piperidin-4-ylmethyl)piperidin-1-yl)methyl)piperidin-1-yl)isoindolin-2-yl)piperidine-2,6-dione (100 mg, 0.2 mmol) and N-methylmorpholine (18 mg, 0.18 mmol) in dichloromethane (2 mL) and dimethyl sulfoxide (0.2 mL) was added tert-butyl 3-[7-[8-ethynyl-7-fluoro-3-(methoxymethoxy)-1-naphthyl]-8-fluoro-2-(2-oxoethoxy)pyrido[4,3-d]pyrimidin-4-yl]-3,8-diazabicyclo[3.2.1]octane-8-carboxylate (119 mg, 0.2 mmol), and the resulting mixture was stirred at 0° C. for 10 min. Sodium triacetoxyborohydride (117 mg, 0.6 mmol) was then added, and the reaction mixture was stirred at 0° C. for 0.5 h. The mixture was diluted with water (50 mL) and extracted with ethyl acetate (2×50 mL). The combined organic layers were washed with brine (2×50 mL), dried over sodium sulfate anhydrous, filtered, and concentrated under reduced pressure. The residue was purified by prep-TLC (dichloromethane/methanol=10:1) to afford the title compound (100 mg, 46%) as a white solid. LC/MS (ESI) m/z: 585.6 $[M/2+H]^+$.

Step 9: Preparation of (3S)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-1-oxo-2,3-dihydro-1H-isoindol-2-yl}piperidine-2,6-dione

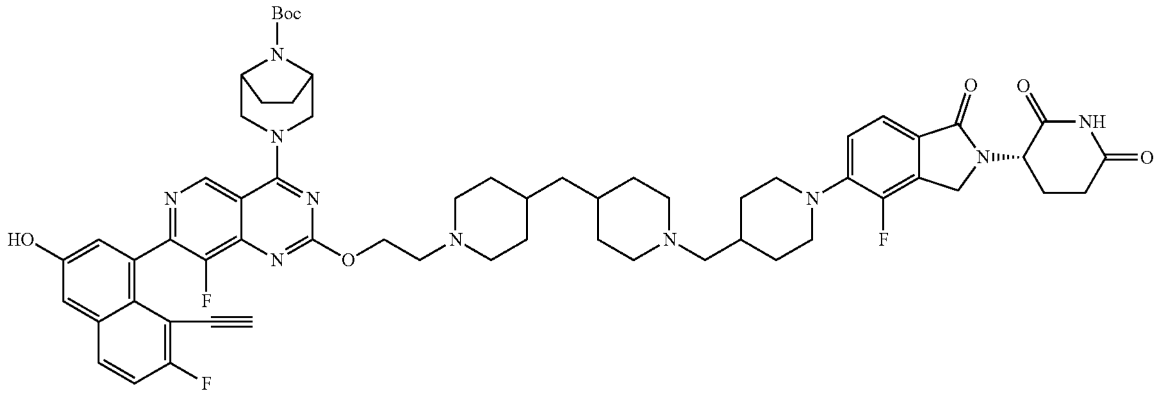 [SMILES: C#Cc1c(F)ccc2cc(O)cc(-c3ncc4c(N5CC6CCC(C5)N6C(=O)OC(C)(C)C)nc(OCCN5CCC(CC6CCN(CC7CCN(c8ccc9c(c8F)CN([C@H]8CCC(=O)NC8=O)C9=O)CC7)CC6)CC5)nc4c3F)c12]

To tert-butyl 3-[2-[2-[4-[[1-[[1-[2-[(3S)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (100 mg, 0.08 mmol) in dichloromethane (2 mL) at 25° C. was added 4 M HCl in 1,4-dioxane (0.5 mL), and the reaction mixture was stirred for 15 min. The mixture was filtered and concentrated under reduced pressure. The residue was purified by prep-HPLC (1% to 30% acetonitrile in water (formic acid) over 10 min) to afford the title compound (61.3 mg, 63%, di-formic acid salt) as a yellow solid. LC/MS (ESI) m/z: 1007.8 $[M+H]^+$, $^1H$ NMR (400 MHz, DMSO-$d_6$) δ 10.99 (s, 1H), 9.07 (s, 1H), 8.15 (s, 2H), 7.98 (dd, J=6.0, 9.2 Hz, 1H), 7.50-7.43 (m, 2H), 7.40 (d, J=2.4 Hz, 1H), 7.20-7.13 (m, 2H), 5.08 (dd, J=5.2, 13.6 Hz, 1H), 4.61-4.35 (m, 6H), 4.34-4.27 (m, 1H), 3.94 (s, 1H), 3.87-3.82 (m, 2H), 3.76-3.69 (m, 2H), 3.49-3.46 (m, 2H), 2.99-2.87 (m, 5H), 2.80-2.72 (m, 4H), 2.60-2.54 (m, 1H), 2.44-2.37 (m, 1H), 2.32-2.25 (m, 2H), 2.10-1.93 (m, 5H), 1.83-1.76 (m, 6H), 1.75-1.67 (m, 1H), 1.65-1.56 (m, 4H), 1.35-1.23 (m, 4H), 1.18-1.04 (m, 6H).

Example 73: Synthesis of (3R)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-1-oxo-2,3-dihydro-1H-isoindol-2-yl}piperidine-2,6-dione (Compound 163)

Step 1: Preparation of tert-butyl 3-[2-[2-[4-[[1-[[1-[2-[(3R)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate and tert-butyl 3-[2-[2-[4-[[1-[[1-[2-[(3S)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

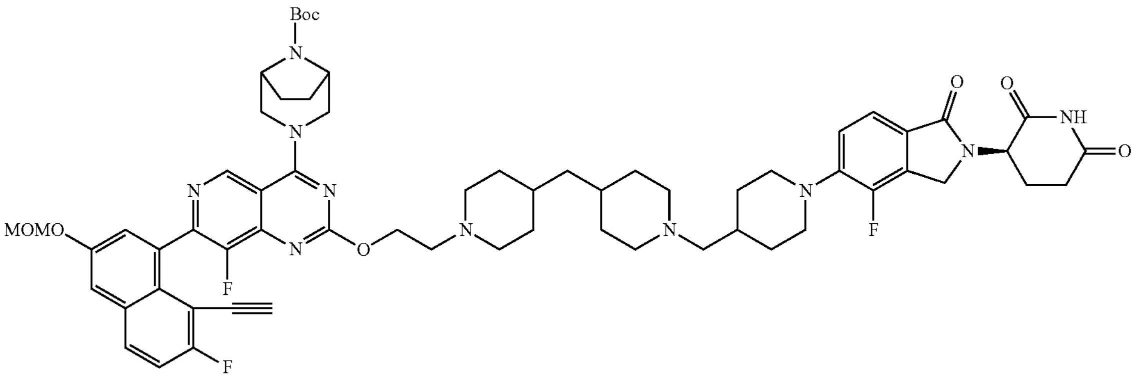

+

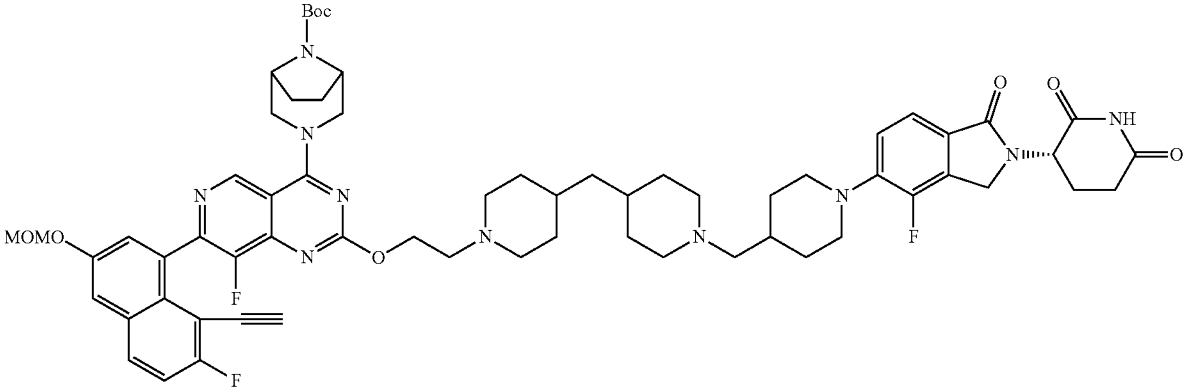

Tert-butyl 3-[2-[2-[4-[[1-[[1-[2-(2,6-dioxo-3-piperidyl)-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (2 g) was purified by chiral SFC (40% to 40% acetonitrile/isopropanol (0.1% $NH_4OH$) in $CO_2$), then further purified by prep-HPLC (30% to 60% acetonitrile in water (formic acid) over 10 min). tert-Butyl 3-[2-[2-[4-[[1-[[1-[2-[(3R)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (900 mg, 45%) was obtained as a pale yellow solid. $^1H$ NMR (400 MHz, DMSO-$d_6$) δ 10.97 (s, 1H), 9.09 (s, 1H), 8.23-8.17 (m, 1H), 8.14-8.06 (m, 1H), 7.79-7.71 (m, 1H), 7.55 (t, J=8.8 Hz, 1H), 7.50-7.43 (m, 1H), 7.40-7.31 (m, 1H), 7.19-7.09 (m, 1H), 5.37 (s, 2H), 5.07 (dd, J=4.8, 12.8 Hz, 1H), 4.61-4.36 (m, 6H), 4.35-4.26 (m, 3H), 3.98 (s, 1H), 3.69-3.60 (m, 2H), 3.49-3.39 (m, 5H), 3.01-2.88 (m, 3H), 2.87-2.81 (m, 2H), 2.79-2.67 (m, 4H), 2.63-2.54 (m, 1H), 2.43-2.37 (m, 1H), 2.26-2.15 (m, 2H), 2.06-1.73 (m, 11H), 1.63-1.55 (m, 4H), 1.46 (s, 9H), 1.36-1.23 (m, 4H), 1.15-0.99 (m, 6H). tert-Butyl 3-[2-[2-[4-[[1-[[1-[2-[(3S)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (900 mg, 45%) was obtained as a pale yellow solid. $^1H$ NMR (400 MHz, DMSO-$d_6$) δ 10.97 (s, 1H), 9.09 (s, 1H), 8.18 (s, 1H), 8.14-8.06 (m, 1H), 7.78-7.73 (m, 1H), 7.55 (t, J=8.8 Hz, 1H), 7.50-7.43 (m, 1H), 7.40-7.31 (m, 1H), 7.19-7.09 (m, 1H), 5.38 (s, 2H), 5.07 (dd, J=4.8, 12.8 Hz, 1H), 4.61-4.36 (m, 6H), 4.33-4.26 (m, 3H), 3.98 (s, 1H), 3.69-3.60 (m, 2H), 3.49-3.39 (m, 5H), 2.99-2.69 (m, 9H), 2.59 (d, J=16.0 Hz, 1H), 2.42-2.33 (m, 1H), 2.24-2.17 (m, 2H), 2.06-1.72 (m, 11H), 1.64-1.55 (m, 4H), 1.46 (s, 9H), 1.34-1.20 (m, 4H), 1.17-1.02 (m, 6H).

Step 2: Preparation of (3R)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-1-oxo-2,3-dihydro-1H-isoindol-2-yl}piperidine-2,6-dione

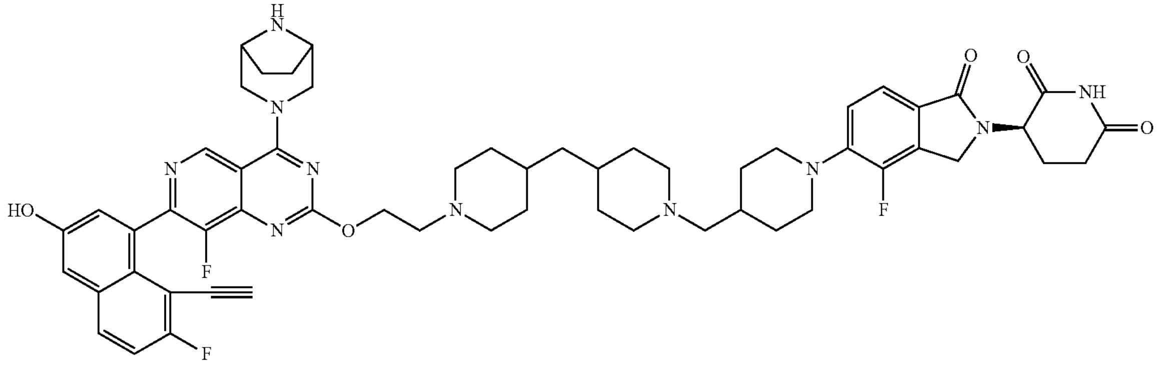 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)CN([C@@H]8CCC(=O)NC8=O)C9=O)CC7)CC6)CC5)nc4c3F)c12]

To tert-butyl 3-[2-[2-[4-[[1-[[1-[2-[(3R)-2,6-dioxo-3-piperidyl]-4-fluoro-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (900 mg, 0.8 mmol) in dichloromethane (10 mL) was added 4 M HCl in 1,4-dioxane (2 mL) at 25° C., and the mixture was stirred for 15 min. The reaction mixture was filtered and concentrated under reduced pressure. The residue was purified by prep-HPLC (0% to 20% acetonitrile in water (formic acid) over 30 min) to afford the title compound (352.9 mg, 42%, formic acid salt) as a yellow solid. LC/MS (ESI) m/z: 1025.8 $[M+H]^+$, $^1H$ NMR (400 MHz, DMSO-$d_6$) δ 10.98 (s, 1H), 9.05 (s, 1H), 8.25-8.23 (m, 1H), 8.23-8.23 (m, 1H), 7.97 (dd, J=6.0, 9.2 Hz, 1H), 7.50-7.42 (m, 2H), 7.41-7.37 (m, 1H), 7.23-7.08 (m, 2H), 5.07 (dd, J=5.2, 1 Step 2: Hz, 1H), 4.55-4.50 (m, 2H), 4.47-4.44 (m, 2H), 4.37-4.35 (m, 1H), 4.33-4.28 (m, 2H), 3.92 (s, 1H), 3.75-3.71 (m, 2H), 3.70-3.61 (m, 2H), 3.50-3.43 (m, 2H), 2.99-2.81 (m, 5H), 2.80-2.67 (m, 4H), 2.63-2.55 (m, 1H), 2.47-2.35 (m, 1H), 2.20 (d, J=6.8 Hz, 2H), 2.07-1.86 (m, 5H), 1.83-1.72 (m, 6H), 1.71-1.64 (m, 1H), 1.58 (d, J=12.0 Hz, 4H), 1.36-1.19 (m, 4H), 1.17-1.01 (m, 6H).

Example 74: Synthesis of (3S)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione (Compound 215)

Step 1: Preparation of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

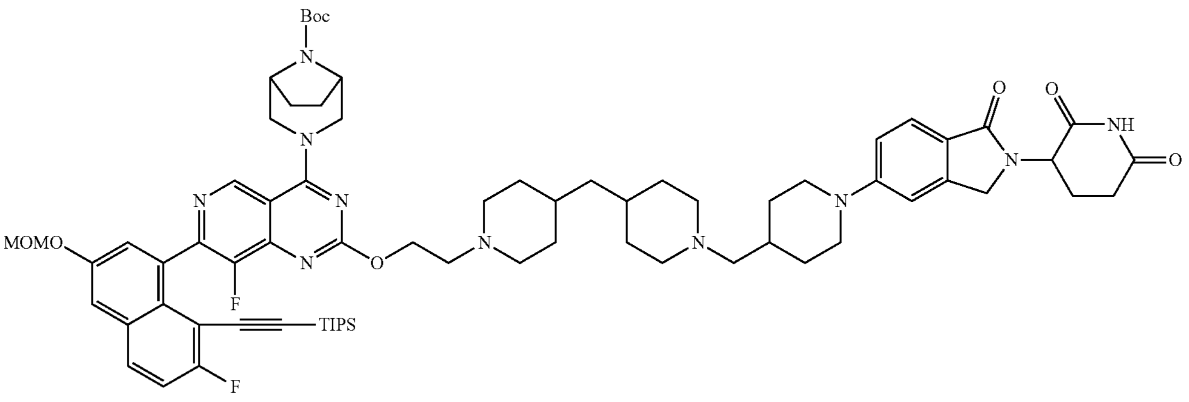

To a mixture of tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (2.6 g, 3 mmol), 3-[1-oxo-5-[4-[[4-(4-piperidylmethyl)-1-piperidyl] methyl]-1-piperidyl]isoindolin-2-yl]piperidine-2,6-dione trifluoroacetate (2.3 g, 4 mmol) and N,N-diisopropylethylamine (1.6 mL, 9.7 mmol) in dimethyl sulfoxide (6 mL) and dichloromethane (10 mL) was added sodium triacetoxyborohydride (1.37 g, 6.5 mmol), and the mixture was stirred at 25° C. for 1 h. The reaction mixture was concentrated under reduced pressure, and the residue was purified by prep-HPLC (45% to 75% acetonitrile in water (formic acid) over 15 min) to afford the title compound (1.7 g, 40%) as a white solid. LC/MS (ESI) m/z: 1308.9 $[M+H]^+$.

Step 2: Preparation of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

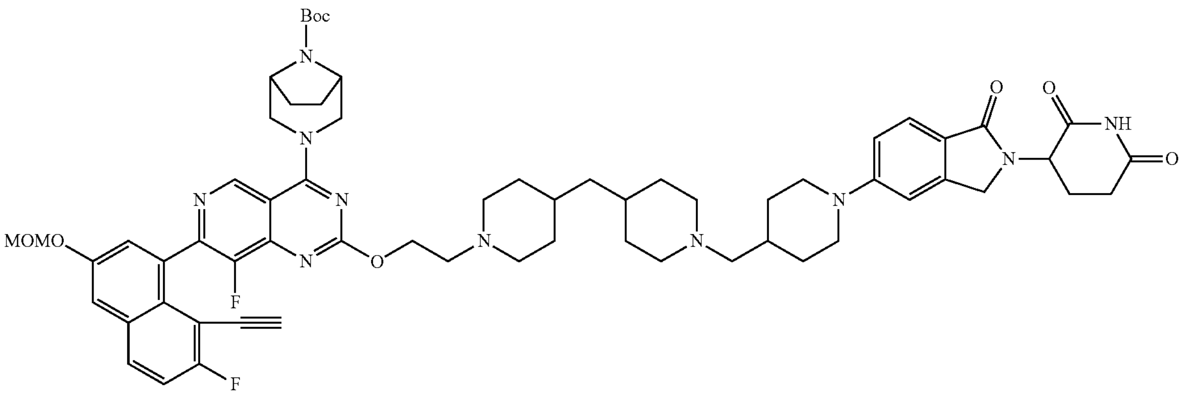

To a solution of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (1.7 g, 1.3 mmol) in N,N-dimethylformamide (20 mL) was added cesium fluoride (5.92 g, 39 mmol), and the mixture was stirred at 25° C. for 2 h. Trifluoroacetic acid was added to the reaction mixture to adjust the pH to 2-3, the mixture was filtered, and concentrated. The residue was purified by reversed-phase HPLC (30% to 60% acetonitrile in water (formic acid) over 12 min) to afford the title compound (1.3 g, 86%) as a yellow solid. LC/MS (ESI) m/z: 576.7 [M/2+H]$^+$.

Step 3: Preparation of tert-butyl 3-[2-[2-[4-[[1-[[1-[2-[(3R)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate and tert-butyl 3-[2-[2-[4-[[1-[[1-[2-[(3S)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate tert-Butyl 3-[2-[2-[4-[[1-[[1-[2-(2,6-dioxo-3-piperidyl)-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (400 mg) was purified by chiral SFC (75% to 75% acetonitrile/isopropanol (0.1% $NH_3H_2O$) in $CO_2$). The crude product was further purified by prep-HPLC (23% to 53% acetonitrile in water (formic acid) over 10 min, then 15% to 45% acetonitrile in water (formic acid) over 10 min) to afford tert-butyl 3-[2-[2-[4-[[1-[[1-[2-[(3R)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (150 mg, 37%) as a pale yellow solid and tert-butyl 3-[2-[2-[4-[[1-[[1-[2-[(3S)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (200 mg, 50%) as a pale yellow solid. LC/MS (ESI) m/z: 1151.8 [M+H]$^+$.

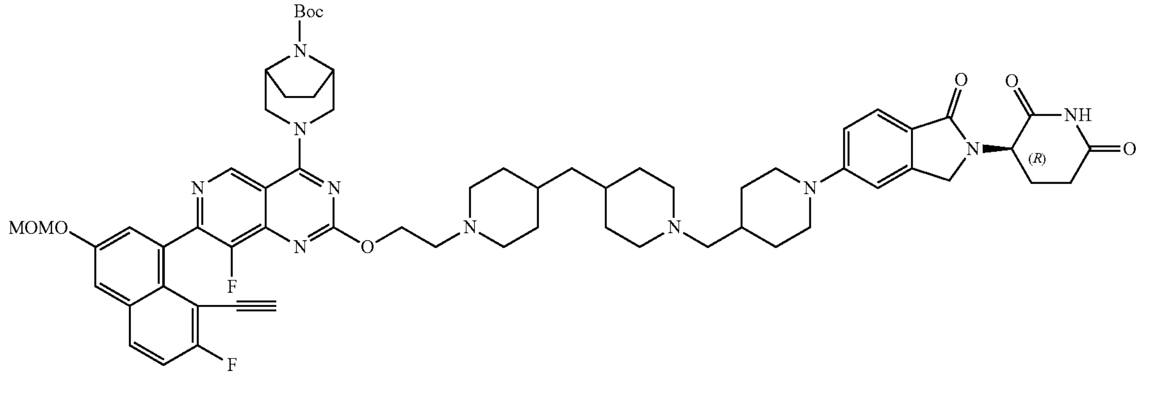

+

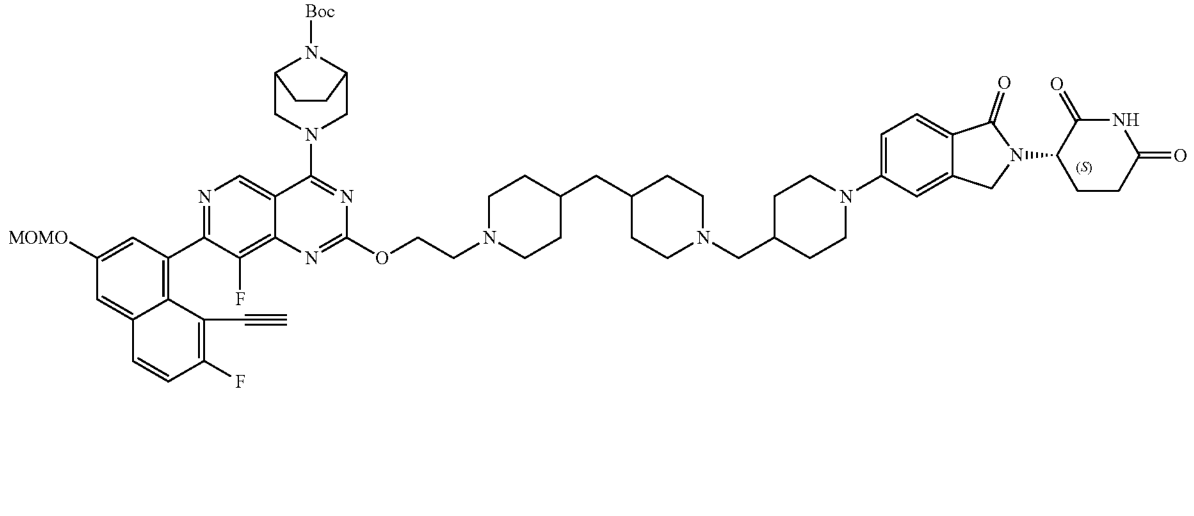

Step 4: Preparation of (3S)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione

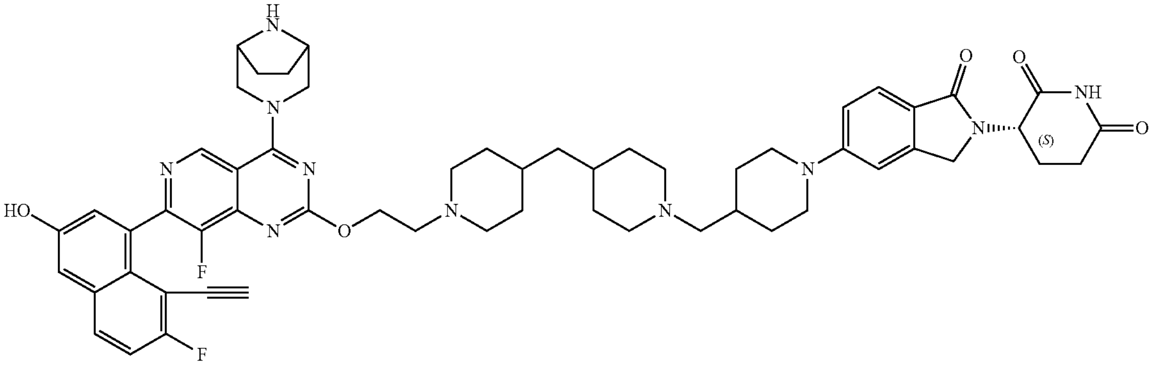

To a mixture of tert-butyl 3-[2-[2-[4-[[1-[[1-[2-[(3S)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (200 mg, 0.2 mmol) in dichloromethane (2 mL) at 25° C. was added 4 M HCl in 1,4-dioxane (0.6 mL), and the mixture was stirred for 15 min. The reaction mixture was filtered and concentrated under reduced pressure. The residue was purified by prep-HPLC (1% to 30% acetonitrile in water (formic acid) over 10 min) to afford the title compound (55.2 mg, 28%, di-formic acid salt) as a yellow solid. LC/MS (ESI) m/z: 1007.8 $[M+H]^+$; $^1$H NMR (400 MHz, DMSO-$d_6$) δ 10.94 (s, 1H), 9.06 (s, 1H), 8.24-8.18 (m, 2H), 7.98 (dd, J=6.0, 9.2 Hz, 1H), 7.54-7.45 (m, 2H), 7.40 (d, J=2.4 Hz, 1H), 7.21-7.17 (m, 1H), 7.07-7.00 (m, 2H), 5.04 (dd, J=6.0, 9.2 Hz, 1H), 4.59-4.37 (m, 4H), 4.34-4.27 (m, 1H), 4.22-4.14 (m, 1H), 3.93 (d, J=0.8 Hz, 1H), 3.89-3.77 (m, 4H), 3.76-3.65 (m, 2H), 3.02-2.68 (m, 9H), 2.62-2.54 (m, 1H), 2.43-2.31 (m, 1H), 2.28-2.14 (m, 2H), 2.13-1.89 (m, 5H), 1.87-1.68 (m, 7H), 1.59 (d, J=10.8 Hz, 4H), 1.38-1.25 (m, 2H), 1.24-1.02 (m, 8H).

Example 75: Synthesis of (3R)-3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione (Compound 216)

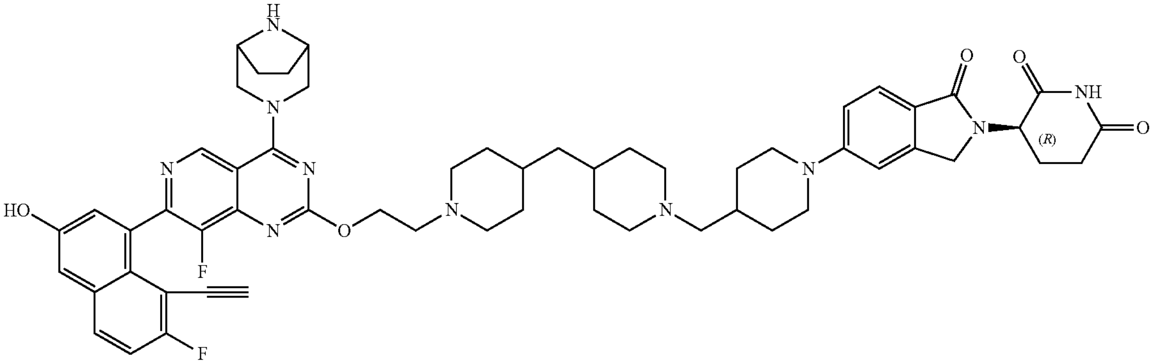

To a mixture of tert-butyl 3-[2-[2-[4-[[1-[[1-[2-[(3R)-2,6-dioxo-3-piperidyl]-1-oxo-isoindolin-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (150 mg, 0.1 mmol) in dichloromethane (2 mL) at 25° C. was added 4 M HCl in 1,4-dioxane (0.5 mL), and the mixture was stirred for 15 min. The reaction mixture was filtered and concentrated under reduced pressure. The residue was purified by prep-HPLC (1% to 30% acetonitrile in water (formic acid) over 10 min) to afford the title compound (37.8 mg, 27%, formic acid salt) as a yellow solid. LC/MS (ESI) m/z: 1107.7 $[M+H]^+$, $^1H$ NMR (400 MHz, DMSO-$d_6$) δ 10.93 (s, 1H), 9.05 (s, 1H), 8.24-8.18 (m, 1H), 7.97 (dd, J=6.0, 9.2 Hz, 1H), 7.53-7.43 (m, 2H), 7.39 (d, J=2.4 Hz, 1H), 7.18 (d, J=2.4 Hz, 1H), 7.06-6.99 (m, 2H), 5.04 (dd, J=5.2, 1 Step 2: Hz, 1H), 4.54-4.42 (m, 3H), 4.39-4.34 (m, 1H), 4.33-4.28 (m, 1H), 4.22-4.16 (m, 1H), 3.93 (d, J=0.8 Hz, 1H), 3.85 (d, J=12.4 Hz, 2H), 3.72-3.61 (m, 4H), 2.98-2.88 (m, 3H), 2.87-2.75 (m, 4H), 2.73-2.66 (m, 2H), 2.62-2.56 (m, 1H), 2.41-2.31 (m, 1H), 2.15 (d, J=6.0 Hz, 2H), 2.08-1.84 (m, 5H), 1.81-1.66 (m, 7H), 1.58 (d, J=10.8 Hz, 4H), 1.35-1.25 (m, 2H), 1.22-1.02 (m, 8H).

Example 76: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-2-oxo-3-(propan-2-yl)-2,3-dihydro-1H-1,3-benzodiazol-1-yl}piperidine-2,6-dione (Compound 217)

Step 1: Preparation of tert-butyl 4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]piperidine-1-carboxylate

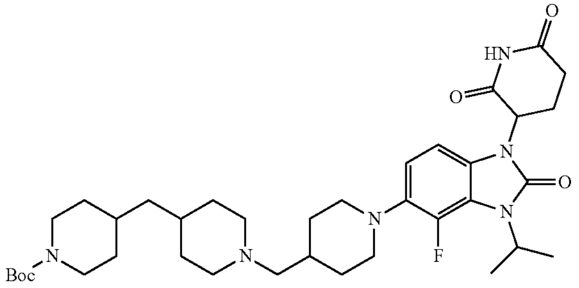 [SMILES: CC(C)n1c(=O)n(C2CCC(=O)NC2=O)c2ccc(N3CCC(CN4CCC(CC5CCN(C(=O)OC(C)(C)C)CC5)CC4)CC3)c(F)c21]

To a solution of 1-[1-(2,6-dioxo-3-piperidyl)-4-fluoro-3-isopropyl-2-oxo-benzimidazol-5-yl]piperidine-4-carbaldehyde (297 mg, 0.35 mmol, HCl salt) and tert-butyl 4-(4-piperidylmethyl)piperidine-1-carboxylate (262 mg, 0.9 mmol) in dichloromethane (4.0 mL) and isopropanol (4.0 mL) were added acetic acid (0.41 mL, 7 mmol) and 2-methylpyridine borane (305 mg, 2.9 mmol), and the reaction mixture was stirred at 25° C. for 12 h. The mixture was neutralized with triethylamine to adjust the pH to 7, then the mixture was concentrated under reduced pressure. The residue was purified by flash column chromatography on silica gel (0 to 7% methanol in dichloromethane) to afford to afford the title compound (305 mg, 59%) as a white foam. LC/MS (ESI) m/z: 683.5 $[M+H]^+$.

Step 2: Preparation of 3-[4-fluoro-3-isopropyl-2-oxo-5-[4-[[4-(4-piperidylmethyl)-1-piperidyl]methyl]-1-piperidyl]benzimidazol-1-yl]piperidine-2,6-dione

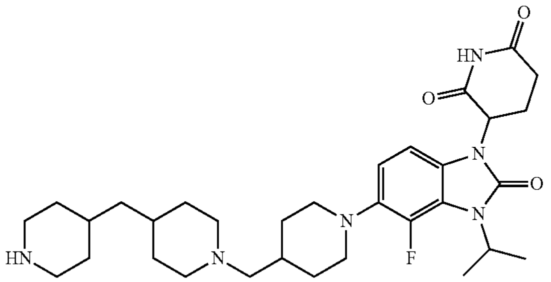 [SMILES: CC(C)n1c(=O)n(C2CCC(=O)NC2=O)c2ccc(N3CCC(CN4CCC(CC5CCNCC5)CC4)CC3)c(F)c21]

To a solution of tert-butyl 4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]piperidine-1-carboxylate (305 mg, 0.4 mmol) in dichloromethane (4.0 mL) was added 4 M HCl in 1,4-dioxane (4.0 mL), and the reaction mixture was stirred at 25° C. for 20 min. The mixture was concentrated under reduced pressure to afford the title compound (260 mg, crude, HCl salt) as a white solid. LC/MS (ESI) m/z: 583.4 $[M+H]^+$.

Step 3: Preparation of tert-butyl 3-[2-[2-[4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

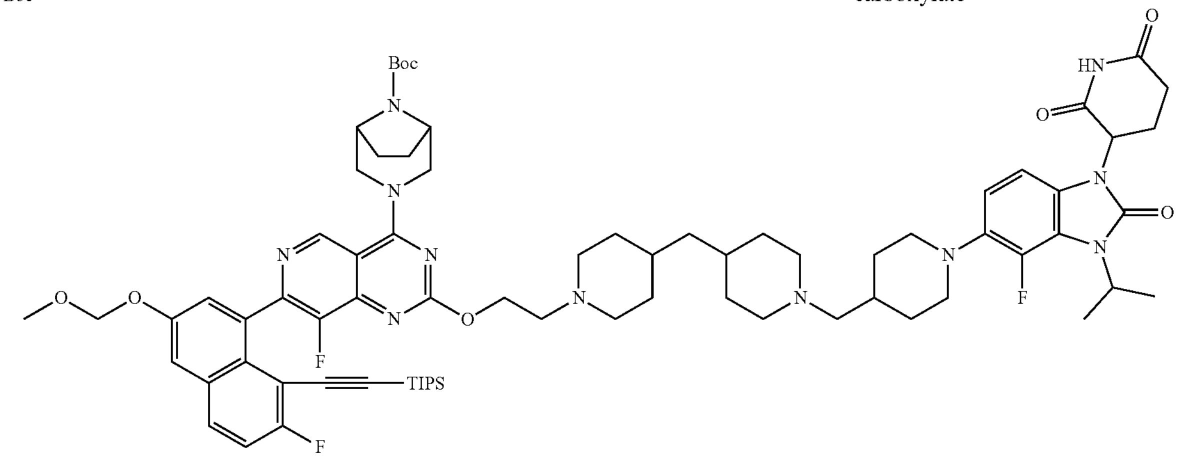

To a mixture of 3-[4-fluoro-3-isopropyl-2-oxo-5-[4-[[4-(4-piperidylmethyl)-1-piperidyl]methyl]-1-piperidyl]benzimidazol-1-yl]piperidine-2,6-dione (260 mg, 0.4 mmol) and tert-butyl 3-[8-fluoro-7-[7-fluoro-3-(methoxymethoxy)-8-(2-triisopropylsilylethynyl)-1-naphthyl]-2-(2-oxoethoxy) pyrido[4,3-d]pyrimidin-4-yl]-3,8-diazabicyclo[3.2.1]octane-8-carboxylate (501 mg, 0.6 mmol) in dichloromethane (5.0 mL) and isopropanol (5.0 mL) were added sodium acetate (366 mg, 4 mmol) and 2-methylpyridine borane (191 mg, 1.8 mmol), and the reaction mixture was stirred at 25° C. for 12 h. The mixture was filtered and concentrated under reduced pressure, then neutralized with triethylamine to adjust the pH to 7. The resulting mixture was concentrated under reduced pressure, and the residue was purified by flash column chromatography on silica gel (0 to 8% methanol in dichloromethane) to afford to afford the title compound (400 mg, 51%) as a yellow foam. LC/MS (ESI) m/z: 1369.5 [M+H]+.

Step 4: Preparation of tert-butyl 3-[2-[2-[4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

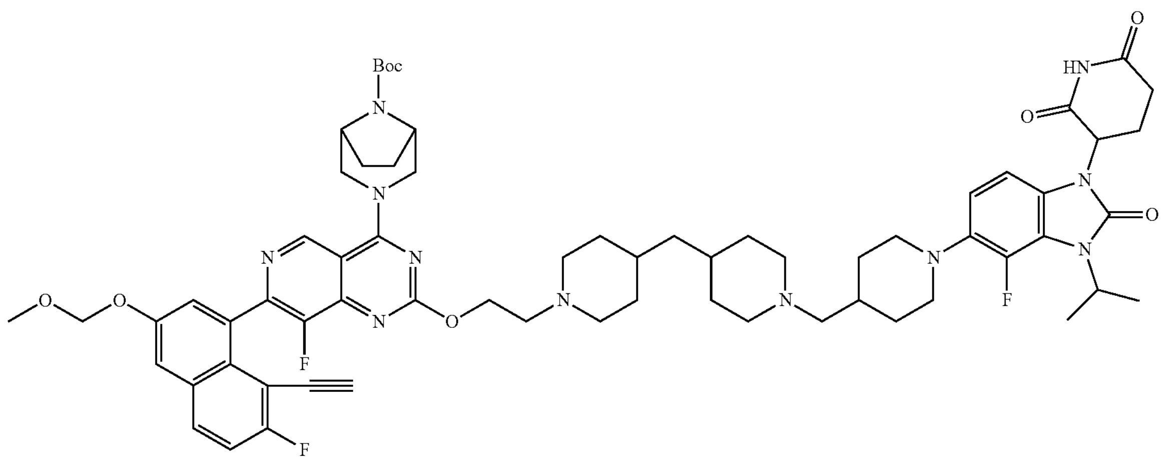 [SMILES: C#Cc1c(F)ccc2cc(OCOC)cc(-c3ncc4c(N5CC6CCC(C5)N6C(=O)OC(C)(C)C)nc(OCCN5CCC(CC6CCN(CC7CCN(c8ccc9c(c8F)n(C(C)C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]-1-piperidyl] ethoxy]-8-fluoro-7-[7-fluoro-3-(methoxymethoxy)-8-(2-triisopropylsilylethynyl)-1-naphthyl]pyrido[4,3-d] pyrimidin-4-yl]-3,8-diazabicyclo[3.2.1]octane-8-carboxylate (400 mg, 0.2 mmol) in DMF (4.0 mL) was added cesium fluoride (222 mg, 1.5 mmol), and the mixture was stirred at 25° C. for 12 h. The reaction mixture was diluted with water (30 mL) and extracted with ethyl acetate (3x30 mL). The combined organic extracts were washed with water (8x10 mL) followed by brine (2x30 mL), dried over sodium sulfate, filtered, and concentrated under reduced pressure. The residue was purified by prep-HPLC (2% to 42% acetonitrile in water (formic acid) over 36 min) to afford the title compound (132 mg, 37%) as a yellow solid. LC/MS (ESI) m/z: 1212.6 [M+H]+; $^1$H NMR (400 MHz, $CD_3OD$) δ 11.10 (s, 1H), 9.09 (s, 1H), 8.19-8.07 (m, 2H), 7.75 (d, J=2.0 Hz, 1H), 7.55 (t, J=9.2 Hz, 1H), 7.37 (d, J=2.4 Hz, 1H), 7.22 (s, 1H), 5.37 (s, 2H), 5.36-5.32 (m, 1H), 4.72 (td, J=6.8, 1 Step 5: Hz, 1H), 4.55 (br d, J=12.8 Hz, 1H), 4.49-4.38 (m, 3H), 4.30 (br s, 2H), 3.65 (br t, J=11.6 Hz, 3H), 3.44 (s, 8H), 3.06 (br d, J=17.2 Hz, 5H), 2.93 (br d, J=8.8 Hz, 2H), 2.83 (br d, J=10.4 Hz, 3H), 2.73 (br d, J=4.0 Hz, 1H), 2.68-2.66 (m, 2H), 2.60 (br d, J=16.0 Hz, 1H), 2.35-2.31 (m, 1H), 2.18 (br d, J=6.4 Hz, 2H), 1.90-1.81 (m, 4H), 1.74 (br d, J=10.8 Hz, 4H), 1.58 (br d, J=11.2 Hz, 4H), 1.47 (s, 9H), 1.41 (br d, J=7.2 Hz, 6H), 1.09 (br d, J=6.4 Hz, 6H).

Step 5: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-2-oxo-3-(propan-2-yl)-2,3-dihydro-1H-1,3-benzodiazol-1-yl}piperidine-2,6-dione

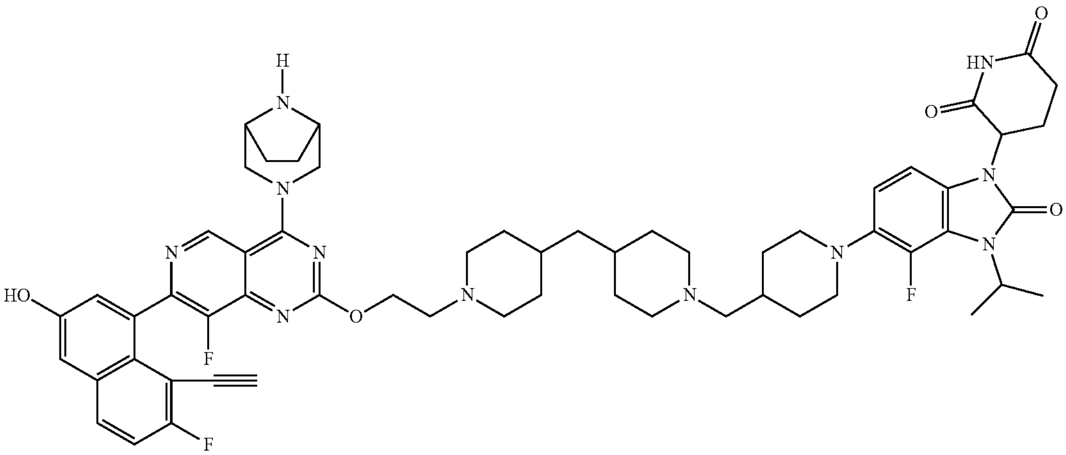 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)n(C(C)C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-4-fluoro-3-isopropyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (132 mg, 0.1 mmol) in dichloromethane (2.0 mL) was added 4 M HCl in 1,4-dioxane (2 mL), and the mixture was stirred at 25° C. for 20 min. The reaction mixture was suspended in petroleum ether (15 mL), filtered, and the filter cake was dissolved in tetrahydrofuran (5 mL) and triethylamine to adjust the pH to 8. The mixture was filtered, and the filtrate was concentrated under reduced pressure. The residue was purified by prep-HPLC (32% to 72% acetonitrile in water (ammonium bicarbonate) over 36 min) to afford the title compound (42.1 mg, 35%) as a yellow solid. LC/MS (ESI) m/z: 1068.7 $[M+H]^+$, $^1$H NMR (400 MHz, $CD_3OD$) δ 9.01 (s, 1H), 7.86 (dd, J=6.0, 9.2 Hz, 1H), 7.40-7.27 (m, 2H), 7.21 (d, J=2.4 Hz, 1H), 6.94-6.77 (m, 2H), 5.29 (dd, J=5.6, 12.8 Hz, 1H), 4.70-4.49 (m, 6H), 3.77-3.63 (m, 4H), 3.37 (s, 1H), 3.14-3.06 (m, 2H), 3.02-2.95 (m, 2H), 2.93-2.83 (m, 3H), 2.82-2.78 (m, 1H), 2.77-2.73 (m, 1H), 2.71 (br s, 1H), 2.69-2.65 (m, 1H), 2.33 (br dd, J=1.6, 4.4 Hz, 2H), 2.22-2.12 (m, 3H), 2.09-1.97 (m, 2H), 1.91-1.84 (m, 4H), 1.80 (br d, J=9.6 Hz, 2H), 1.75-1.65 (m, 5H), 1.51 (br d, J=7.2 Hz, 6H), 1.48-1.39 (m, 4H), 1.32-1.13 (m, 7H).

Example 77: Synthesis of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione (Compound 218)

Step 1: Preparation of tert-butyl 3-[2-[2-[3-[[1-[1-(2,6-dioxo-3-piperidyl)-3-methyl-2-oxo-benzimidazol-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

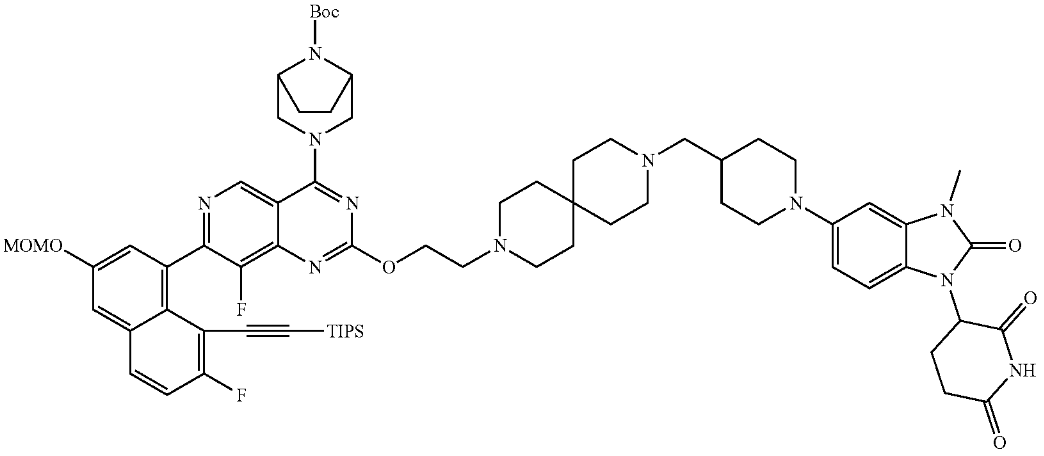

To a solution of tert-butyl tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (240 mg, 0.3 mmol) and 3-[5-[4-(3,9-diazaspiro[5.5]undecan-3-ylmethyl)-1-piperidyl]-3-methyl-2-oxo-benzimidazol-1-yl]piperidine-2,6-dione di-trifluoroacetate (200 mg, 0.3 mmol) in dichloromethane (5 mL) and isopropanol (5 mL) were added N,N-diisopropylethylamine (0.1 mL, 0.8 mmol) and sodium triacetoxyborohydride (115 mg, 0.5 mmol), and the mixture was stirred at 25° C. for 2 h. The reaction mixture was diluted with water (15 mL) and extracted with dichloromethane (3x30 mL). The combined organic layers were washed with brine (15 mL), dried over anhydrous sodium sulfate, filtered, and concentrated under reduced pressure to afford the title compound (300 mg, 85%) as a yellow solid. LC/MS (ESI) m/z: 1294.9 $[M+H]^+$.

Step 2: Preparation of tert-butyl 3-[2-[2-[3-[[1-[1-(2,6-dioxo-3-piperidyl)-3-methyl-2-oxo-benzimidazol-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

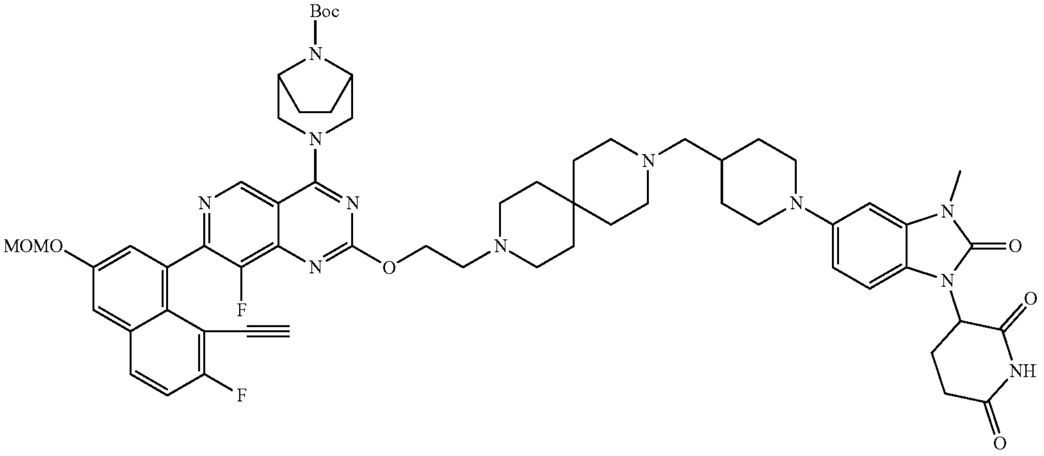

To a solution of tert-butyl 3-[2-[2-[3-[[1-[1-(2,6-dioxo-3-piperidyl)-3-methyl-2-oxo-benzimidazol-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (375 mg, 0.3 mmol) in N,N-dimethylformamide (5 mL) was added cesium fluoride (1.32 g, 8.7 mmol), and the mixture was stirred at 25° C. for 2 h. The reaction mixture was quenched with water (0.5 mL), filtered, and the filtrate solution was purified by prep-HPLC (20% to 50% acetonitrile in water (trifluoroacetic acid) over 9 min) to afford the title compound (145 mg, 44%) as an off-white solid. LC/MS (ESI) m/z: 1138.7 $[M+H]^+$.

Step 3: Preparation of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione

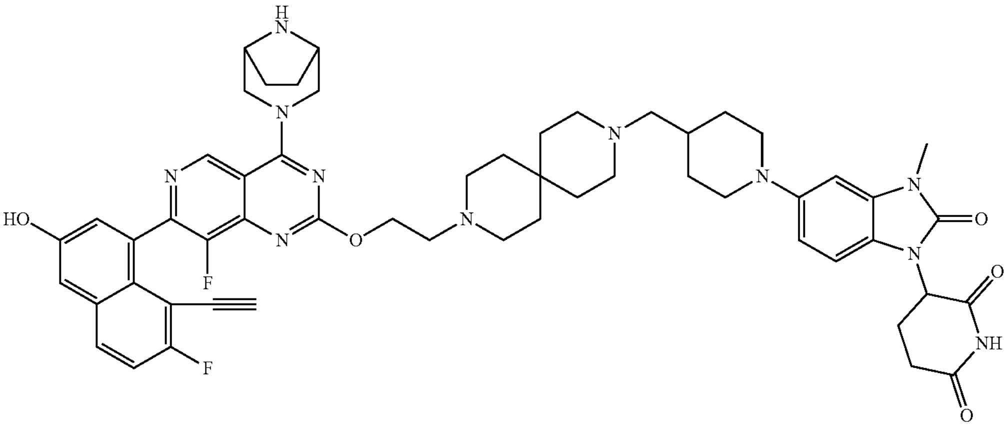 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7)n(C)c(=O)n8C7CCC(=O)NC7=O)CC5)CC6)nc4c3F)c12]

To a solution of tert-butyl 3-[2-[2-[3-[[1-[1-(2,6-dioxo-3-piperidyl)-3-methyl-2-oxo-benzimidazol-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (145 mg, 0.1 mmol) in dichloromethane (3 mL) was added 4 M HCl in 1,4-dioxane (0.03 mL), and the mixture was stirred at 25° C. for 15 min. The reaction mixture was triturated with ethyl acetate/methyl tertiary butyl ether (1/10, 100 mL) and then purified by prep-HPLC (1% to 25% acetonitrile in water (formic acid) over 10 min) to afford the title compound (39.4 mg, 28%, di-formic acid salt) as a yellow solid. LC/MS (ESI) m/z: 994.8 $[M+H]^+$, $^1H$ NMR (400 MHz, DMSO-$d_6$) δ 11.08-11.02 (m, 1H), 9.09-8.98 (m, 1H), 8.20 (s, 2H), 7.97 (dd, J=9.2, 6.0 Hz, 1H), 7.50-7.43 (m, 1H), 7.39 (d, J=2.4 Hz, 1H), 7.21-7.14 (m, 1H), 6.91 (br d, J=8.8 Hz, 1H), 6.80 (s, 1H), 6.64-6.58 (m, 1H), 5.28 (br dd, J=12.8, 5.2 Hz, 1H), 4.50 (br d, J=2.0 Hz, 1H), 4.45 (br t, J=5.2 Hz, 2H), 4.36-4.30 (m, 1H), 3.93-3.91 (m, 1H), 3.67 (br s, 2H), 3.56 (br d, J=12.0 Hz, 5H), 3.29 (s, 6H), 2.70 (br d, J=6.4 Hz, 3H), 2.65-2.57 (m, 4H), 2.33 (br s, 6H), 2.19 (br d, J=6.0 Hz, 2H), 2.01-1.95 (m, 1H), 1.79-1.74 (m, 2H), 1.69 (br s, 4H), 1.41 (br s, 8H), 1.29-1.27 (m, 1H), 1.26-1.19 (m, 2H).

Example 78: Synthesis of 3-(4-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione (Compound 83)

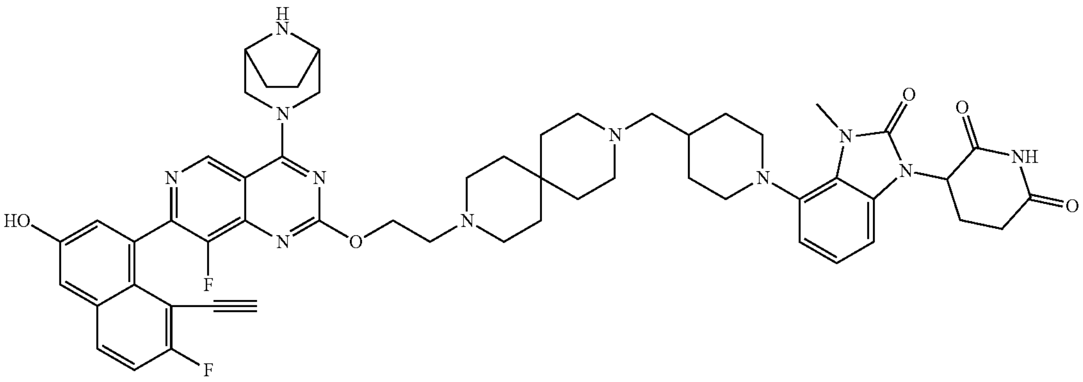 [SMILES: C#Cc1c(F)ccc2cc(O)cc(-c3ncc4c(N5CC6CCC(C5)N6)nc(OCCN5CCC6(CC5)CCN(CC5CCN(c7cccc8c7n(C)c(=O)n8C7CCC(=O)NC7=O)CC5)CC6)nc4c3F)c12]

The title compound was prepared in an analogous manner to 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione. (white solid, formic acid salt). LC/MS (ESI) m/z: 994.8 $[M+H]^+$, $^1H$ NMR (400 MHz, DMSO-$d_6$) δ 11.09 (s, 1H), 9.05 (s, 1H), 8.21 (s, 2H), 7.98 (dd, J=6.0, 9.2 Hz, 1H), 7.47 (t, J=9.2 Hz, 1H), 7.40 (d, J=2.4 Hz, 1H), 7.18 (d, J=2.4 Hz, 1H), 7.01-6.93 (m, 1H), 6.92-6.83 (m, 2H), 5.35 (br dd, J=5.6, 12.4 Hz, 1H), 4.54-4.43 (m, 3H), 4.35 (br d, J=11.6 Hz, 1H), 3.94 (s, 1H), 3.70-3.57 (m, 9H), 3.10 (br d, J=8.4 Hz, 2H), 2.93-2.83 (m, 1H), 2.76-2.61 (m, 6H), 2.46 (br s, 4H), 2.35 (br s, 4H), 2.26-2.19 (m, 2H), 2.03-1.96 (m, 1H), 1.84-1.76 (m, 2H), 1.71 (br s, 4H), 1.66-1.58 (m, 1H), 1.42 (br s, 8H), 1.35-1.25 (m, 2H).

Example 79: Synthesis of 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione (Compound 219)

Step 1: Preparation of tert-butyl-4-[[4-[[1-[4-chloro-2-(2,6-dioxo-3-piperidyl)-1-oxo-isoindolin-5-yl]-4-piperidyl]methyl]piperazin-1-yl]methyl]piperidine-1-carboxylate

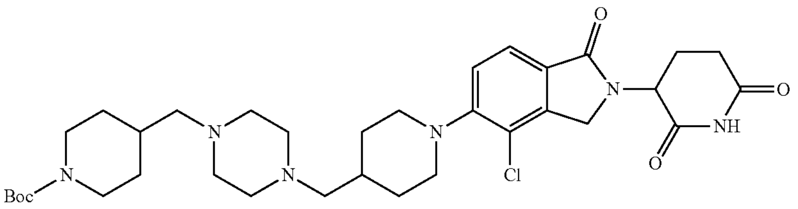 [SMILES: CC(C)(C)OC(=O)N1CCC(CN2CCN(CC3CCN(c4ccc5c(c4Cl)CN(C4CCC(=O)NC4=O)C5=O)CC3)CC2)CC1]

To a solution of 1-[4-chloro-2-(2,6-dioxo-3-piperidyl)-1-oxo-isoindolin-5-yl]piperidine-4-carbaldehyde (243 mg, 0.6 mmol) and tert-butyl 4-(piperazin-1-ylmethyl)piperidine-1-carboxylate (247 mg, 0.9 mmol) in dichloromethane (5 mL), isopropanol (5 mL) and THF (5 mL) was added acetic acid (0.2 mL, 4 mmol), and the resulting mixture was stirred at 40° C. for 12 h. 2-Methylpyridine borane (333 mg, 3 mmol) was then added, and the reaction mixture was stirred at 40° C. for 1 h. The mixture was concentrated under reduced pressure, and the residue was purified by flash column chromatography on silica gel (0 to 5% methanol in dichloromethane) to afford the title compound (191 mg, 47%) as a yellow solid. LC/MS (ESI) m/z: 657.3 $[M+H]^+$.

Step 2: Preparation of 3-[4-chloro-1-oxo-5-[4-[[4-(4-piperidylmethyl)piperazin-1-yl]methyl]-1-piperidyl]isoindolin-2-yl]piperidine-2,6-dione

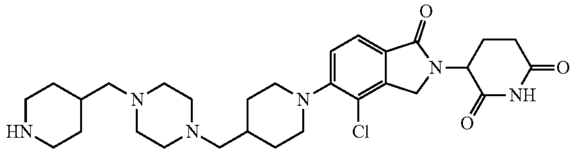 [SMILES: O=C1CCC(N2Cc3c(ccc(N4CCC(CN5CCN(CC6CCNCC6)CC5)CC4)c3Cl)C2=O)C(=O)N1]

To a solution of tert-butyl-4-[[4-[[1-[4-chloro-2-(2,6-dioxo-3-piperidyl)-1-oxo-isoindolin-5-yl]-4-piperidyl]methyl]piperazin-1-yl]methyl]piperidine-1-carboxylate (191 mg, 0.3 mmol) in dichloromethane (3 mL) was added 4 M HCl in 1,4-dioxane (3 mL), and the mixture was stirred at 20° C. for 30 min. The mixture was triturated with petroleum ether (20 mL) to afford the title compound (190 mg, crude, 3 HCl salt) as a white solid.

Step 3: Preparation of tert-butyl-3-[2-[2-[4-[[4-[[1-[4-chloro-2-(2,6-dioxo-3-piperidyl)-1-oxo-isoindolin-5-yl]-4-piperidyl]methyl]piperazin-1-yl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

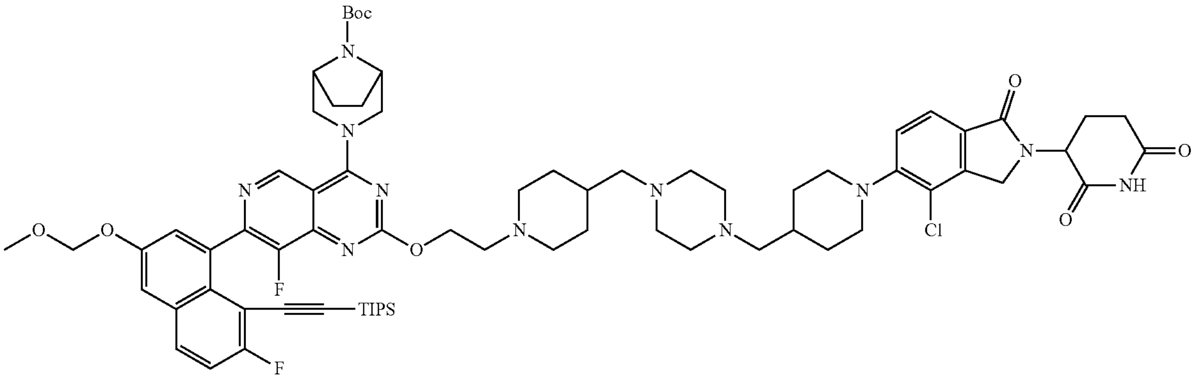

To a solution of 3-[4-chloro-1-oxo-5-[4-[[4-(4-piperidylmethyl)piperazin-1-yl]methyl]-1-piperidyl]isoindolin-2-yl]piperidine-2,6-dione (190 mg, 0.3 mmol, 3 HCl) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (457 mg, 0.6 mmol) in dichloromethane (10 mL), isopropanol (10 mL) and DMSO (4 mL) were added sodium acetate (187 mg, 2 mmol) and 2-methylpyridine borane (152 mg, 1.4 mmol), and the mixture was stirred at 15° C. for 16 h. The reaction mixture was concentrated under reduced pressure, and the residue was diluted with saturated sodium bicarbonate solution to adjust the pH to 8 and extracted with ethyl acetate (3×50 mL). The combined organic extract was washed with water (4×10 mL) followed by brine (10 mL), dried over anhydrous sodium sulfate, filtered, and concentrated in vacuo. The residue was purified by flash column chromatography on silica gel (0 to 8% then up to 10% methanol in dichloromethane) to afford the title compound (275 mg, 61%) as a yellow solid. LC/MS (ESI) m/z: 1342.7 $[M+H]^+$.

Step 4: Preparation of tert-butyl 3-[2-[2-[4-[[4-[[1-[4-chloro-2-(2,6-dioxo-3-piperidyl)-1-oxo-isoindolin-5-yl]-4-piperidyl]methyl]piperazin-1-yl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

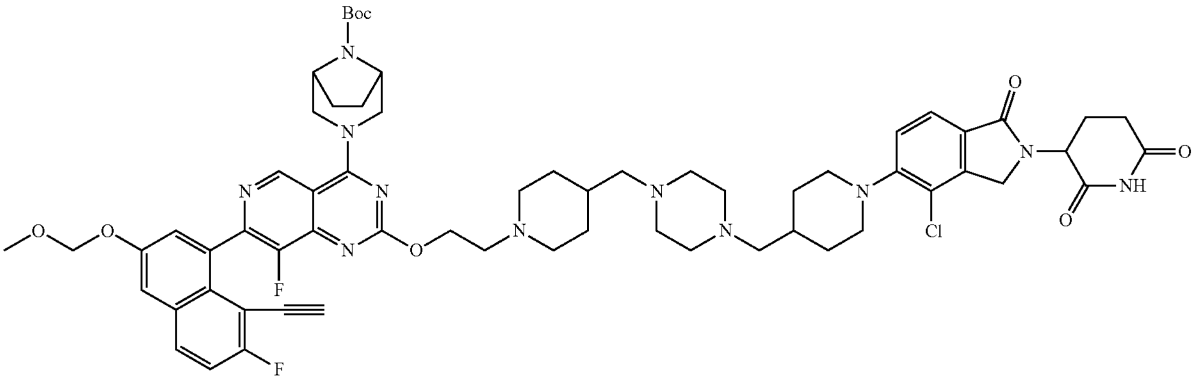 [SMILES: C#Cc1c(F)ccc2cc(OCOC)cc(-c3ncc4c(N5CC6CCC(C5)N6C(=O)OC(C)(C)C)nc(OCCN5CCC(CN6CCN(CC7CCN(c8ccc9c(c8Cl)CN(C8CCC(=O)NC8=O)C9=O)CC7)CC6)CC5)nc4c3F)c12]

To a solution of tert-butyl-3-[2-[2-[4-[[4-[[1-[4-chloro-2-(2,6-dioxo-3-piperidyl)-1-oxo-isoindolin-5-yl]-4-piperidyl] methyl]piperazin-1-yl]methyl]-1-piperidyl]ethoxy]-8-fluoro-7-[7-fluoro-3-(methoxymethoxy)-8-(2-triisopropylsilylethynyl)-1-naphthyl]pyrido[4,3-d] pyrimidin-4-yl]-3,8-diazabicyclo[3.2.1]octane-8-carboxylate (275 mg, 0.2 mmol) in THF (5 mL) was added TBAF (1 M, 0.3 mL), and the reaction mixture was stirred at 20° C. for 2 h. The mixture was diluted with ethyl acetate (100 mL), then washed with water (6×10 mL) followed by brine (2×10 mL), dried over anhydrous sodium sulfate, filtered, and concentrated in vacuo to afford the title compound (305 mg, crude) as a yellow solid. LC/MS (ESI) m/z: 1186.5 $[M+H]^+$.

Step 5: Preparation of 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl] piperazin-1-yl]methyl]-1-piperidyl]-1-oxo-isoindolin-2-yl]piperidine-2,6-dione

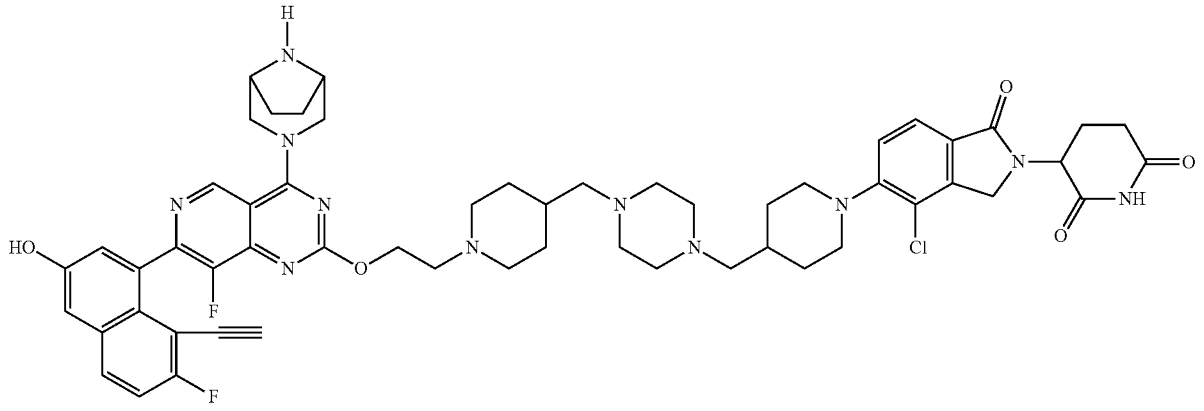 [SMILES: C#Cc1c(F)ccc2cc(O)cc(-c3ncc4c(N5CC6CCC(C5)N6)nc(OCCN5CCC(CN6CCN(CC7CCN(c8ccc9c(c8Cl)CN(C8CCC(=O)NC8=O)C9=O)CC7)CC6)CC5)nc4c3F)c12]

To a solution of tert-butyl 3-[2-[2-[4-[[4-[[1-[4-chloro-2-(2,6-dioxo-3-piperidyl)-1-oxo-isoindolin-5-yl]-4-piperidyl] methyl]piperazin-1-yl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1] octane-8-carboxylate (242 mg, 0.2 mmol) in dichloromethane (3 mL) was added 4 M HCl in 1,4-dioxane (3 mL), and the mixture was stirred at 20° C. for 20 min. The mixture was suspended in petroleum ether (30 mL), filtered, and the filter cake was diluted with THF (50 mL) and triethylamine (3 mL). The resulting mixture was filtered, and the filtrate was concentrated in vacuo. The residue was purified by prep-HPLC (20% to 60% acetonitrile in water (ammonium bicarbonate) over 36 min) to afford the title compound (88.9 mg, 42%) as a yellow solid. LC/MS (ESI) m/z: 1042.5 $[M+H]^+$; $^1H$ NMR (400 MHz, $CD_3OD$) δ 9.00 (s, 1H), 7.86 (dd, J=9.2, 5.6, Hz 1H), 7.67 (d, J=8.0 Hz, 1H), 7.36-7.28 (m, 2H), 7.26 (d, J=8.0 Hz, 1H), 7.21 (d, J=2.4 Hz, 1H), 5.17-5.08 (m, 1H), 4.71-4.54 (m, 5H), 4.52-4.37 (m, 2H), 3.77-3.61 (m, 4H), 3.54-3.43 (m, 2H), 3.37 (s, 1H), 3.15-3.03 (m, 2H), 2.97-2.83 (m, 3H), 2.82-2.70 (m, 3H), 2.63-2.36 (m, 8H), 2.29 (d, J=6.8 Hz, 2H), 2.25-2.11 (m, 5H), 1.97-1.70 (m, 9H), 1.67-1.53 (m, 1H), 1.51-1.36 (m, 2H), 1.34-1.19 (m, 2H).

Example 80: Synthesis of 3-(4-chloro-5-{4-[(9-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}-3,9-diazaspiro[5.5]undecan-3-yl)methyl]piperidin-1-yl}-1-oxo-2,3-dihydro-1H-isoindol-2-yl)piperidine-2,6-dione (Compound 220)

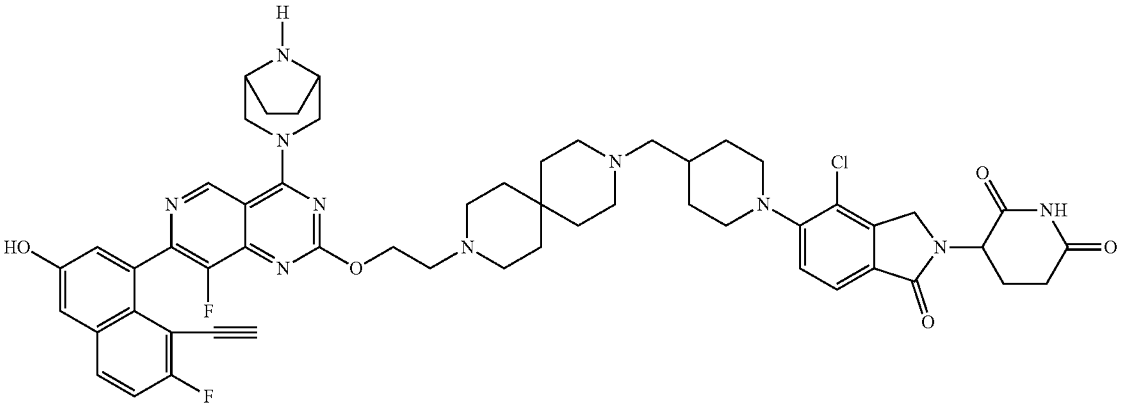 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7Cl)CN(C7CCC(=O)NC7=O)C8=O)CC5)CC6)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (yellow solid). LC/MS (ESI) m/z: 1013.4 $[M+H]^+$; $^1H$ NMR (400 MHz, $CD_3OD$) δ 9.01 (s, 1H), 7.86 (dd, J=5.6, 9.2 Hz, 1H), 7.76-7.64 (m, 1H), 7.39-7.24 (m, 3H), 7.21 (d, J=2.4 Hz, 1H), 5.19-5.06 (m, 1H), 4.68-4.56 (m, 5H), 4.52-4.36 (m, 3H), 3.75-3.64 (m, 4H), 3.48 (br d, J=2.0 Hz, 2H), 2.94-2.85 (m, 3H), 2.83-2.73 (m, 3H), 2.65 (br s, 4H), 2.59-2.50 (m, 4H), 2.40 (br d, J=5.2 Hz, 2H), 2.21-2.12 (m, 1H), 1.92-1.77 (m, 7H), 1.59 (br s, 7H), 1.53-1.38 (m, 3H).

Example 81: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-2,2-dimethylpiperidin-4-yl)methyl]piperazin-1-yl}methyl)piperidin-1-yl]-4-fluoro-1-oxo-2,3-dihydro-1H-isoindol-2-yl}piperidine-2,6-dione (Compound 168)

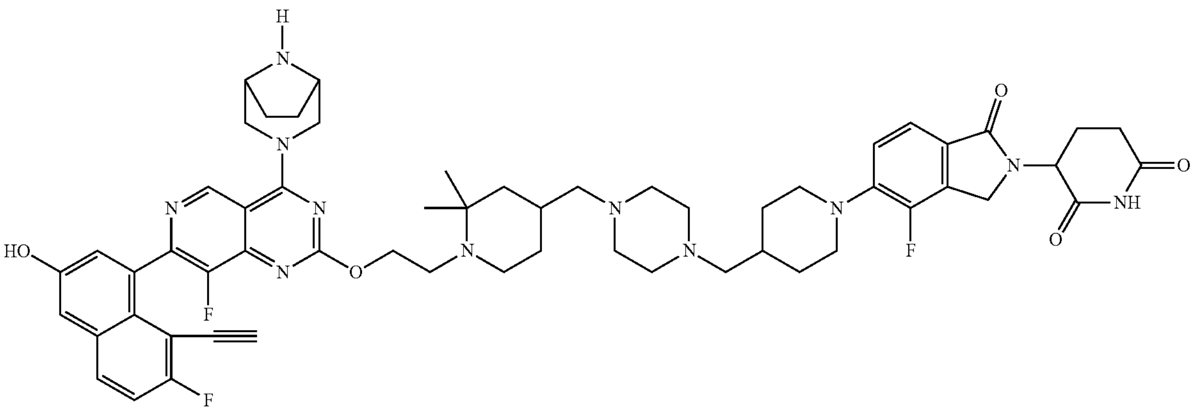

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. z, 1H), 7.87 (dd, J=8.8, 5.6 Hz, 1H), 7.52 (d, J=8.4 Hz, 1H), 7.37-7.29 (m, 2H), 7.24-7.13 (m, 2H), 5.11 (dd, J=13.2, 5.2 Hz, 1H), 4.71-4.42 (m, 7H), 3.79-3.64 (m, 4H), 3.63-3.55 (m, 2H), 3.45-3.34 (m, 2H), 2.95-2.73 (m, 5H), 2.61-2.39 (m, 9H), 2.33-2.25 (m, 2H), 2.20-2.11 (m, 3H), 1.94-1.70 (m, 10H), 1.65-1.57 (m, 1H), 1.48-1.32 (m, 2H), 1.29-1.03 (m, 8H).

Example 82: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-2,2-dimethylpiperazin-1-yl}methyl)piperidin-1-yl]-4-fluoro-1-oxo-2,3-dihydro-1H-isoindol-2-yl}piperidine-2,6-dione (Compound 169)

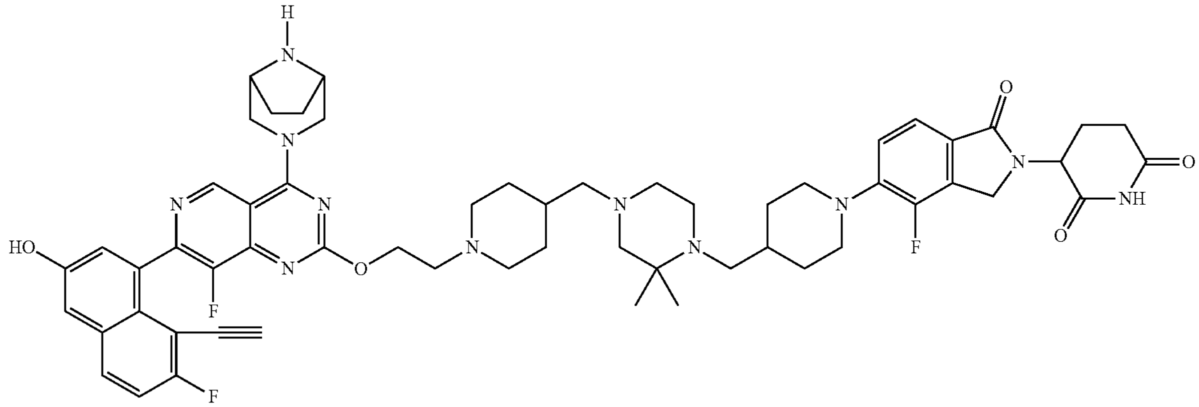 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)C(C)(C)C6)CC5)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (yellow solid). LC/MS (ESI) m/z: 1054.5 $[M+H]^+$, $^1H$ NMR (400 MHz, $CD_3OD$) δ 9.03 (s, 1H), 7.89-7.86 (m, 1H), 7.54 (d, J=8.0 Hz, 1H), 7.38-7.31 (m, 2H), 7.25-7.15 (m, 2H), 5.15-5.10 (m, 1H), 4.72-4.56 (m, 5H), 4.54-4.43 (m, 2H), 3.78-3.65 (m, 4H), 3.63-3.57 (m, 2H), 3.38 (s, 1H), 3.18-3.08 (m, 2H), 2.96-2.75 (m, 6H), 2.69-2.59 (m, 2H), 2.55-2.42 (m, 2H), 2.33-2.10 (m, 8H), 1.96-1.78 (m, 8H), 1.65-1.54 (m, 2H), 1.40-1.21 (m, 5H), 1.06 (s, 6H).

Example 83: Synthesis of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-4-fluoro-7-methyl-1-oxo-2,3-dihydro-1H-isoindol-2-yl)piperidine-2,6-dione (Compound 153)

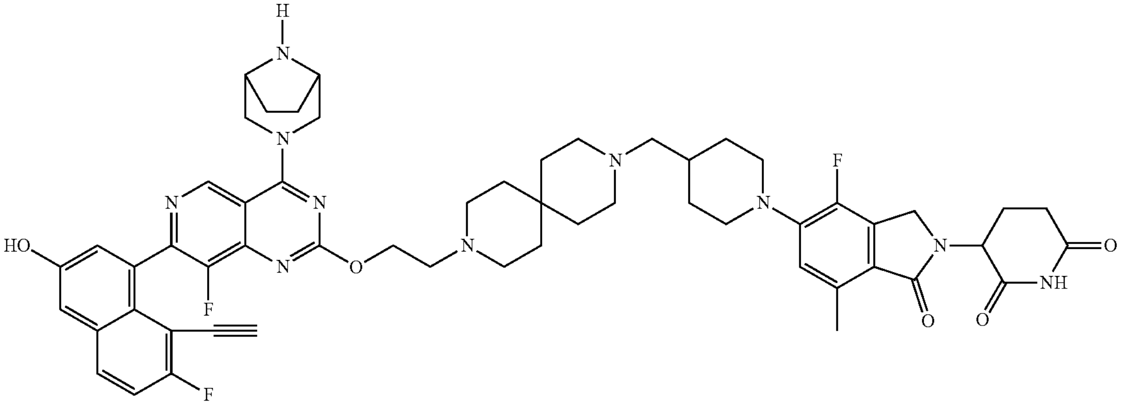 [SMILES: C#Cc1c(F)ccc2cc(O)cc(-c3ncc4c(N5CC6CCC(C5)N6)nc(OCCN5CCC6(CC5)CCN(CC5CCN(c7cc(C)c8c(c7F)CN(C7CCC(=O)NC7=O)C8=O)CC5)CC6)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (yellow solid, formic acid salt). LC/MS (ESI) m/z: 1011.2 $[M+H]^+$; $^1H$ NMR (400 MHz, DMSO) δ 10.97 (s, 1H), 9.06 (s, 1H), 8.18 (s, 2H), 7.98 (dd, J=6.0, 9.2 Hz, 1H), 7.46 (t, J=9.2 Hz, 1H), 7.40 (d, J=2.4 Hz, 1H), 7.18 (d, J=2.4 Hz, 1H), 6.88 (d, J=7.6 Hz, 1H), 5.02 (dd, J=5.2, 13.2 Hz, 1H), 4.58-4.44 (m, 3H), 4.39 (d, J=16.8 Hz, 2H), 4.22 (d, J=16.8 Hz, 1H), 3.94 (s, 1H), 3.81 (s, 2H), 3.72 (t, J=14.0 Hz, 2H), 3.47 (d, J=6.4 Hz, 2H), 2.95-2.84 (m, 1H), 2.79-2.69 (m, 4H), 2.61-2.54 (m, 2H), 2.53 (s, 3H), 2.49-2.38 (m, 8H), 2.35-2.19 (m, 3H), 1.99-1.91 (m, 1H), 1.83-1.60 (m, 8H), 1.44 (s, 8H), 1.30-1.20 (m, 2H).

Example 84: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperazin-1-yl}methyl)piperidin-1-yl]-4-fluoro-7-methyl-1-oxo-2,3-dihydro-1H-isoindol-2-yl}piperidine-2,6-dione (Compound 148)

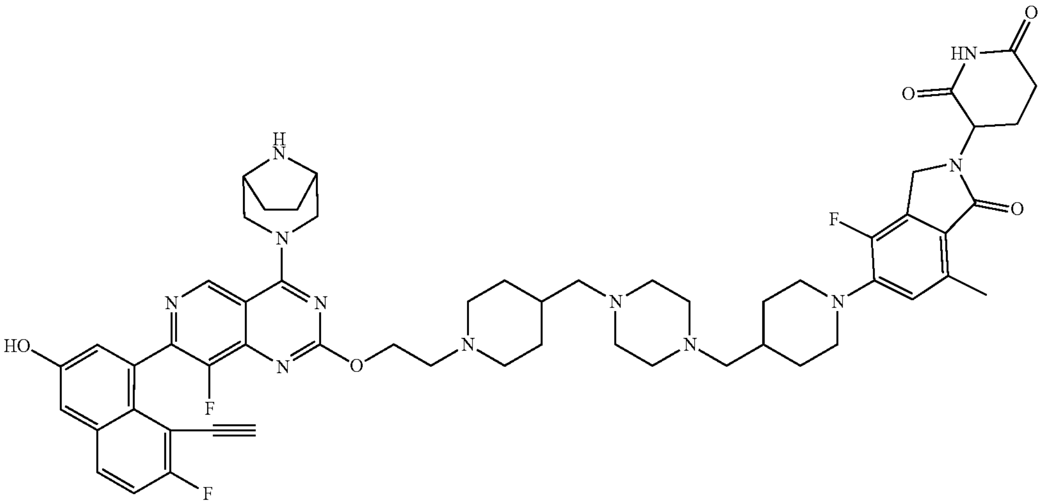 [SMILES: C#Cc1c(F)ccc2cc(O)cc(-c3ncc4c(N5CC6CCC(C5)N6)nc(OCCN5CCC(CN6CCN(CC7CCN(c8cc(C)c9c(c8F)CN(C8CCC(=O)NC8=O)C9=O)CC7)CC6)CC5)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (yellow solid, formic acid salt). LC/MS (ESI) m/z: 1040.2 $[M+H]^+$; $^1H$ NMR (400 MHz, DMSO) δ 11.00-10.90 (m, 1H), 9.06 (s, 1H), 8.18 (s, 2H), 8.01-7.94 (m, 1H), 7.46 (t, J=8.8 Hz, 1H), 7.39 (d, J=2.4 Hz, 1H), 7.18 (d, J=2.1 Hz, 1H), 6.87 (d, J=7.2 Hz, 1H), 5.02 (dd, J=5.2, 13.2 Hz, 1H), 4.53 (d, J=12.8 Hz, 1H), 4.46 (s, 2H), 4.42-4.33 (m, 2H), 4.23 (d, J=17.2 Hz, 1H), 3.93 (s, 1H), 3.76 (s, 2H), 3.73-3.64 (m, 2H), 3.47 (dd, J=2.4, 9.2 Hz, 2H), 2.99-2.88 (m, 3H), 2.79-2.65 (m, 5H), 2.63-2.55 (m, 2H), 2.53 (s, 3H), 2.43-2.24 (m, 9H), 2.16 (d, J=7.2 Hz, 2H), 2.09 (d, J=7.2 Hz, 2H), 2.06-2.00 (m, 2H), 1.97-1.92 (m, 1H), 1.81-1.72 (m, 6H), 1.65 (d, J=12.0 Hz, 3H), 1.53-1.41 (m, 1H), 1.30-1.18 (m, 2H), 1.15-1.01 (m, 2H).

Example 85: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-4-fluoro-7-methyl-1-oxo-2,3-dihydro-1H-isoindol-2-yl}piperidine-2,6-dione (Compound 170)

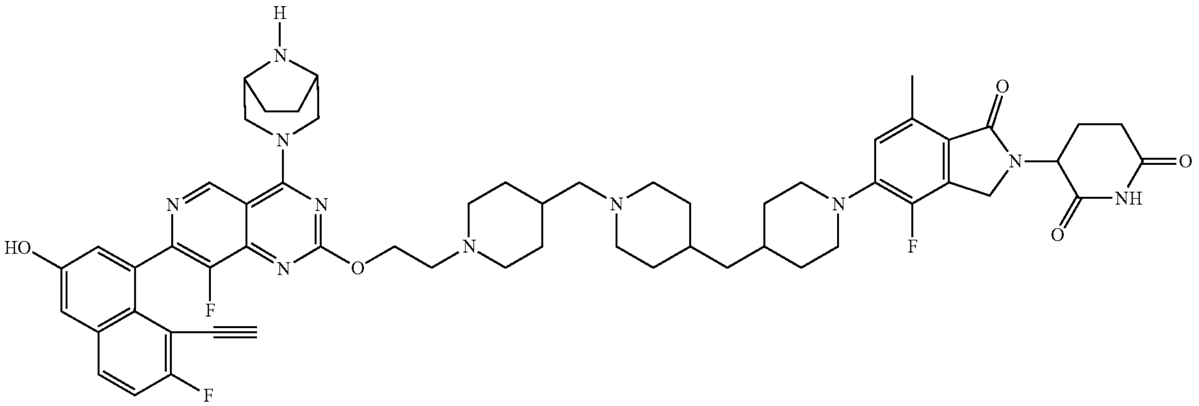 [SMILES: C#Cc1c(F)ccc2cc(O)cc(-c3ncc4c(N5CC6CCC(C5)N6)nc(OCCN5CCC(CN6CCC(CC7CCN(c8cc(C)c9c(c8F)CN(C8CCC(=O)NC8=O)C9=O)CC7)CC6)CC5)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. LC/MS (ESI) m/z: 1039.5 $[M+H]^+$, $^1H$ NMR (400 MHz, $CD_3OD$) δ 9.01 (s, 1H), 7.86 (dd, J=5.6, 9.2 Hz, 1H), 7.38-7.29 (m, 2H), 7.21 (d, J=2.4 Hz, 1H), 6.87 (br d, J=7.2 Hz, 1H), 5.06 (dd, J=5.2, 13.2 Hz, 1H), 4.67-4.56 (m, 5H), 4.51-4.30 (m, 3H), 3.76-3.63 (m, 4H), 3.56 (br d, J=9.2 Hz, 2H), 3.15-3.08 (m, 2H), 3.01 (br d, J=10.0 Hz, 2H), 2.92-2.85 (m, 3H), 2.81-2.73 (m, 3H), 2.58 (s, 3H), 2.48 (br dd, J=4.8, 13.2 Hz, 1H), 2.32 (br d, J=6.4 Hz, 2H), 2.28-2.00 (m, 6H), 1.88-1.70 (m, 10H), 1.42-1.22 (m, 9H).

Example 86: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperazin-1-yl}methyl)piperidin-1-yl]-3-methyl-2-oxo-2,3-dihydro-1H-1,3-benzodiazol-1-yl}piperidine-2,6-dione (Compound 221)

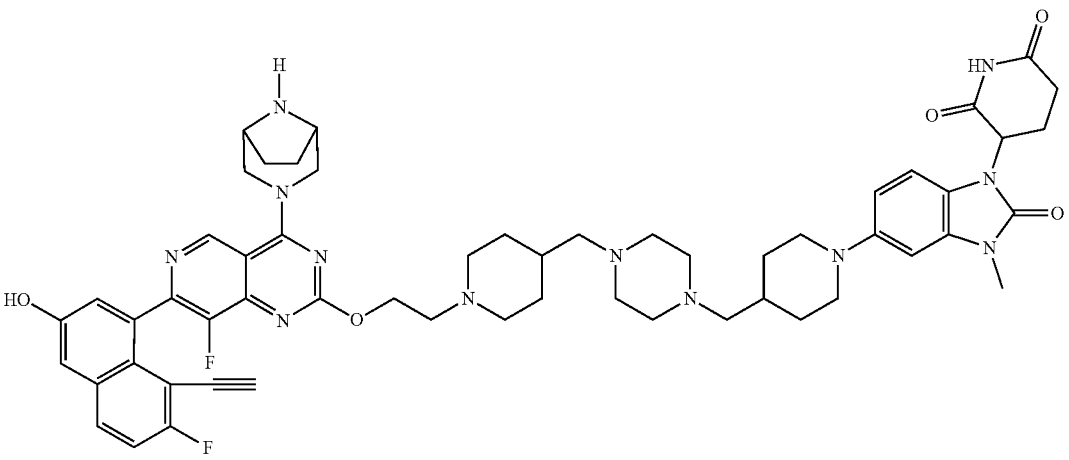 [SMILES: C#Cc1c(F)ccc2cc(O)cc(-c3ncc4c(N5CC6CCC(C5)N6)nc(OCCN5CCC(CN6CCN(CC7CCN(c8ccc9c(c8)n(C)c(=O)n9C8CCC(=O)NC8=O)CC7)CC6)CC5)nc4c3F)c12]

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. LC/MS (ESI) m/z: 1023.5 $[M+H]^+$; $^1H$ NMR (400 MHz, $CD_3OD$) δ 9.01 (s, 1H), 7.87-7.84 (m, 1H), 7.35-7.30 (m, 2H), 7.21-7.20 (m, 1H), 6.98-6.96 (m, 1H), 6.87-6.86 (m, 1H), 6.81-6.78 (m, 1H), 5.30-5.25 (m, 1H), 4.64-4.56 (m, 5H), 3.73-3.66 (m, 4H), 3.60-3.56 (m, 2H), 3.40 (s, 3H), 3.37 (s, 1H), Step 10: −3.07 (m, 2H), 2.92-2.66 (m, 7H), 2.49 (s, 6H), 2.28-2.16 (m, 8H), 1.91-1.60 (m, 10H), 1.43-1.22 (m, 4H).

Example 87: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperazin-1-yl}methyl)piperidin-1-yl]-2-oxo-3-(propan-2-yl)-2,3-dihydro-1H-1,3-benzodiazol-1-yl}piperidine-2,6-dione (Compound 222)

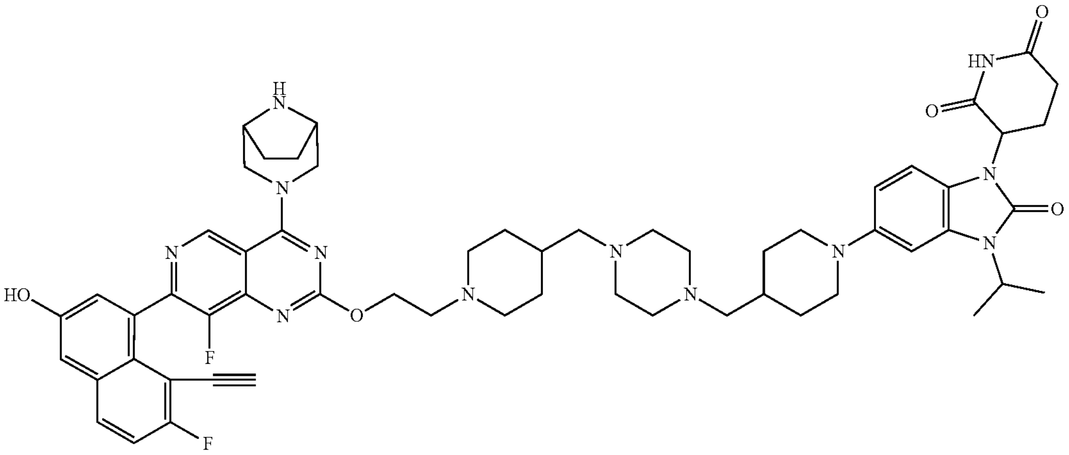

The title compound was prepared in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (yellow solid). LC/MS (ESI) m/z: 1051.5 $[M+H]^+$; $^1H$ NMR (400 MHz, $CD_3OD$) δ 9.01 (s, 1H), 7.86 (dd, J=5.6, 9.2 Hz, 1H), 7.40-7.28 (m, 2H), 7.21 (d, J=2.4 Hz, 1H), 7.06-6.88 (m, 2H), 6.80 (dd, J=1.6, 8.4 Hz, 1H), 5.26 (dd, J=5.2, 12.8 Hz, 1H), 4.69-4.51 (m, 6H), 3.77-3.60 (m, 4H), 3.58-3.50 (m, 2H), 3.37 (s, 1H), 3.15-3.05 (m, 3H), 2.93-2.67 (m, 7H), 2.57-2.42 (m, 6H), 2.31-2.09 (m, 7H), 1.96-1.75 (m, 8H), 1.73-1.53 (m, 8H), 1.43-1.37 (m, 2H), 1.29-1.26 (m, 2H).

Example 88: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperazin-1-yl]-4-fluoro-1-oxo-2,3-dihydro-1H-isoindol-2-yl}piperidine-2,6-dione (Compound 223)

Step 1: Preparation of tert-butyl 4-[[4-[2-(2,6-dioxo-3-piperidyl)-4-fluoro-1-oxo-isoindolin-5-yl]piperazin-1-yl]methyl]piperidine-1-carboxylate

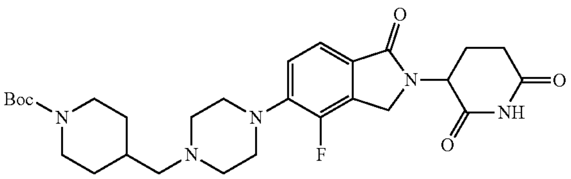 [SMILES: CC(C)(C)OC(=O)N1CCC(CN2CCN(c3ccc4c(c3F)CN(C3CCC(=O)NC3=O)C4=O)CC2)CC1]

To a mixture of 3-(4,5-difluoro-1-oxo-isoindolin-2-yl)piperidine-2,6-dione (3.0 g, 11 mmol) and tert-butyl 4-(piperazin-1-ylmethyl)piperidine-1-carboxylate (6.07 g, 21 mmol) in DMSO (40 mL) was added DIEA (5.6 mL, 32 mmol), and the mixture was stirred at 140° C. for 15 h. The reaction mixture was cooled and poured into water (300 mL), filtered, and the filter cake was triturated with MTBE (50 mL) to afford the title compound (2.5 g, 40%) as a brown solid. LC/MS (ESI) m/z: 544.3 $[M+H]^+$.

Step 2: Preparation of 3-[4-fluoro-1-oxo-5-[4-(4-piperidylmethyl)piperazin-1-yl]isoindolin-2-yl]piperidine-2,6-dione

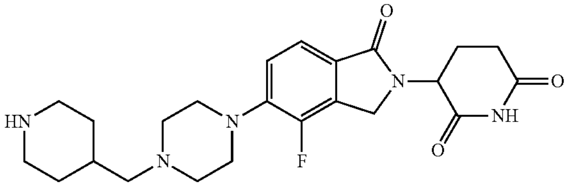 [SMILES: O=C1CCC(N2Cc3c(ccc(N4CCN(CC5CCNCC5)CC4)c3F)C2=O)C(=O)N1]

To tert-butyl 4-[[4-[2-(2,6-dioxo-3-piperidyl)-4-fluoro-1-oxo-isoindolin-5-yl]piperazin-1-yl]methyl]piperidine-1-carboxylate (0.66 g, 1 mmol) in dichloromethane (6 mL) was added 4 M HCl in 1,4-dioxane (6 mL), and the mixture was stirred at 25° C. for 0.5 h. The reaction mixture was concentrated under reduced pressure to afford the title compound (541 mg, crude, HCl salt) as an off-white solid. LC/MS (ESI) m/z: 444.0 $[M+H]^+$.

Step 3: Preparation of tert-butyl 4-[[4-[[4-[2-(2,6-dioxo-3-piperidyl)-4-fluoro-1-oxo-isoindolin-5-yl]piperazin-1-yl]methyl]-1-piperidyl]methyl]piperidine-1-carboxylate

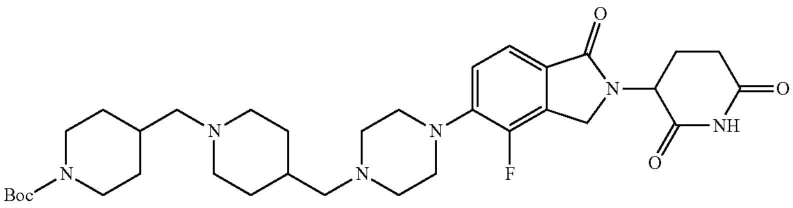 [SMILES: CC(C)(C)OC(=O)N1CCC(CN2CCC(CN3CCN(c4ccc5c(c4F)CN(C4CCC(=O)NC4=O)C5=O)CC3)CC2)CC1]

To a mixture of 3-[4-fluoro-1-oxo-5-[4-(4-piperidylmethyl)piperazin-1-yl]isoindolin-2-yl]piperidine-2,6-dione (541 mg, 1 mmol, HCl) and tert-butyl 4-formylpiperidine-1-carboxylate (481 mg, 2 mmol) in dichloromethane (15 mL) and isopropanol (10 mL) were added sodium acetate (462 mg, 5.6 mmol) and 2-methylpyridine borane (603 mg, 5.6 mmol), and the reaction mixture was stirred at 25° C. for 70 h. The mixture was diluted with saturated sodium bicarbonate solution (10 mL) and extracted with dichloromethane/methanol (3×30 mL, V:V=10:1). The combined organic extract was dried over sodium sulfate, filtered, and concentrated under reduced pressure. The residue was purified by flash column chromatography on silica gel (0-8% then up to 10% 2 M $NH_3$/methanol in dichloromethane) to afford the title compound (440 mg, 61%) as a yellow solid. LC/MS (ESI) m/z: 641.7 $[M+H]^+$.

Step 4: Preparation of 3-[4-fluoro-1-oxo-5-[4-[[1-(4-piperidylmethyl)-4-piperidyl]methyl]piperazin-1-yl]isoindolin-2-yl]piperidine-2,6-dione

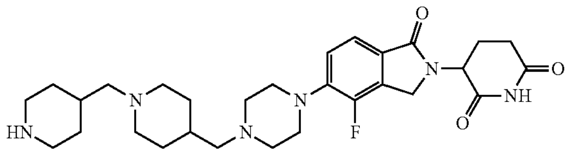 [SMILES: O=C1CCC(N2Cc3c(ccc(N4CCN(CC5CCN(CC6CCNCC6)CC5)CC4)c3F)C2=O)C(=O)N1]

To a mixture of tert-butyl 4-[[4-[[4-[2-(2,6-dioxo-3-piperidyl)-4-fluoro-1-oxo-isoindolin-5-yl]piperazin-1-yl]methyl]-1-piperidyl]methyl]piperidine-1-carboxylate (440 mg, 0.7 mmol) in dichloromethane (5 mL) was added 4 M HCl in 1,4-dioxane (5 mL), and the reaction mixture was stirred at 25° C. for 0.5 h. The mixture was concentrated under reduced pressure to afford the title compound (396 mg, crude, HCl salt) as an off-white solid. LC/MS (ESI) m/z: 541.4 $[M+H]^+$.

Step 5: Preparation of tert-butyl 3-[2-[2-[4-[[4-[[4-[2-(2,6-dioxo-3-piperidyl)-4-fluoro-1-oxo-isoindolin-5-yl]piperazin-1-yl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

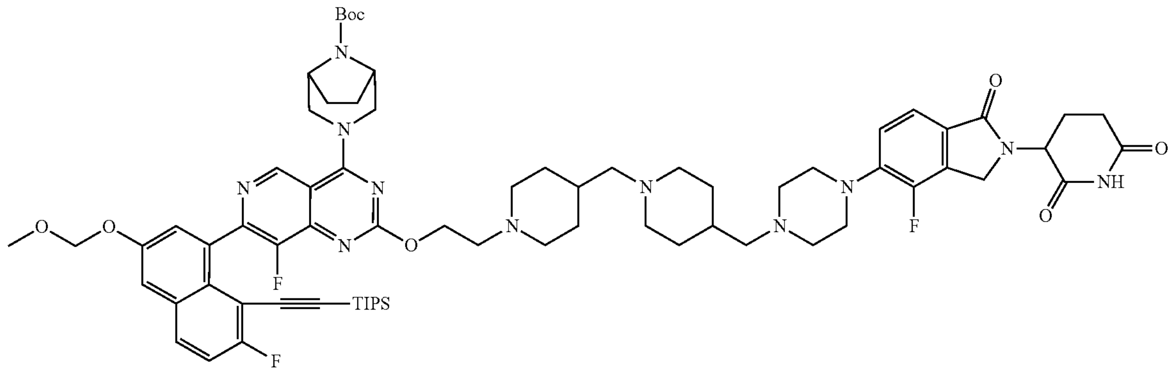

To a mixture of 3-[4-fluoro-1-oxo-5-[4-[[1-(4-piperidylmethyl)-4-piperidyl]methyl]piperazin-1-yl]isoindolin-2-yl]piperidine-2,6-dione (396 mg, 0.7 mmol, HCl) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (551 mg, 0.7 mmol) in dichloromethane (5 mL) and isopropanol (5 mL) were added sodium acetate (282 mg, 3.4 mmol) and 2-methylpyridine borane (367 mg, 3.4 mmol), and the reaction mixture was stirred at 30° C. for 15 h. The reaction was quenched with saturated sodium bicarbonate solution (10 mL) and extracted with dichloromethane/methanol (3x30 mL, V:V=10:1). The combined organic extract was dried over sodium sulfate, filtered, and concentrated under reduced pressure. The residue was purified by flash column chromatography on silica gel (0-10% 2 M $NH_3$/methanol in dichloromethane) to afford the title compound (717 mg, 71%) as a yellow solid. LC/MS (ESI) m/z: 1327.1 $[M+H]^+$.

Step 6: Preparation of tert-butyl 3-[2-[2-[4-[[4-[[4-[2-(2,6-dioxo-3-piperidyl)-4-fluoro-1-oxo-isoindolin-5-yl]piperazin-1-yl]methyl]-1-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

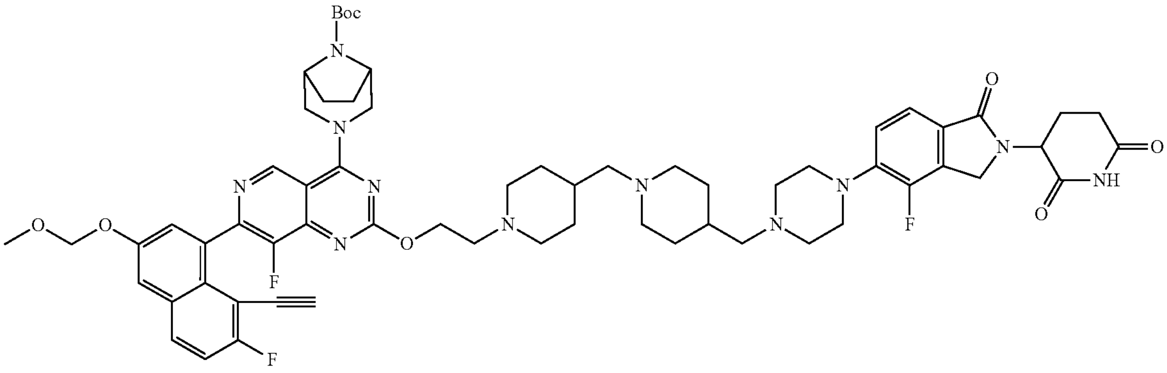 [SMILES: C#Cc1c(F)ccc2cc(OCOC)cc(-c3ncc4c(N5CC6CCC(C5)N6C(=O)OC(C)(C)C)nc(OCCN5CCC(CN6CCC(CN7CCN(c8ccc9c(c8F)CN(C8CCC(=O)NC8=O)C9=O)CC7)CC6)CC5)nc4c3F)c12]

To tert-butyl 3-[2-[2-[4-[[4-[[4-[2-(2,6-dioxo-3-piperidyl)-4-fluoro-1-oxo-isoindolin-5-yl]piperazin-1-yl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (717 mg, 0.5 mmol) in THF (10 mL) was added TBAF (1.0 M, 975 μL), and the reaction mixture was stirred at 25° C. for 1 h. The mixture was diluted with ethyl acetate (50 mL) and washed with water (3x20 mL) followed by brine (20 mL). The organic layer was dried over sodium sulfate, filtered, and concentrated under reduced pressure to afford the title compound (569 mg, crude) as a yellow solid. LC/MS (ESI) m/z: 1170.7 $[M+H]^+$.

Step 7: Preparation of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperazin-1-yl]-4-fluoro-1-oxo-2,3-dihydro-1H-isoindol-2-yl}piperidine-2,6-dione

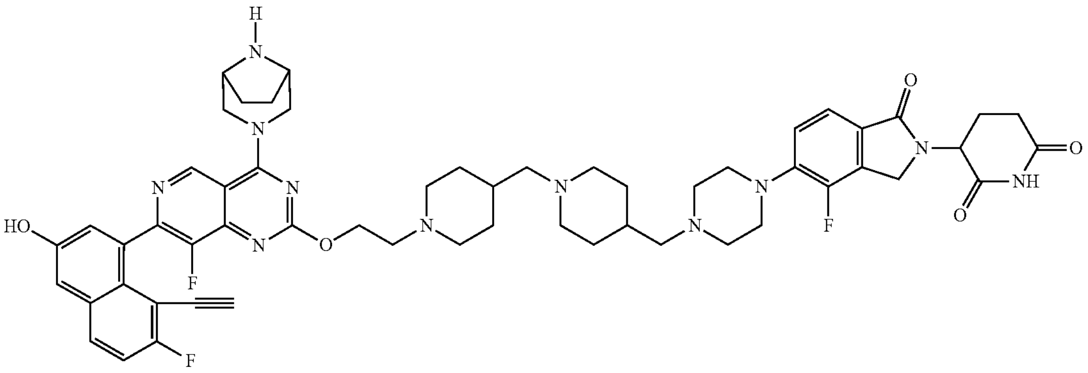 [SMILES: C#Cc1c(F)ccc2cc(O)cc(-c3ncc4c(N5CC6CCC(C5)N6)nc(OCCN5CCC(CN6CCC(CN7CCN(c8ccc9c(c8F)CN(C8CCC(=O)NC8=O)C9=O)CC7)CC6)CC5)nc4c3F)c12]

To tert-butyl 3-[2-[2-[4-[[4-[[4-[2-(2,6-dioxo-3-piperidyl)-4-fluoro-1-oxo-isoindolin-5-yl]piperazin-1-yl]methyl]-1-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (569 mg, 0.5 mmol) in dichloromethane (5 mL) was added 4 M HCl in 1,4-dioxane (5 mL), and the reaction mixture was stirred at 25° C. for 5 min. The mixture was suspended in petroleum ether (30 mL) and filtered. The filter cake was dissolved in THF (30 mL) and triethylamine to adjust the pH to 8. The resulting mixture was filtered and concentrated under reduced pressure. The residue was purified by prep-HPLC (16%-56% acetonitrile in water (ammonium bicarbonate) over 36 min) to afford the title compound (162.7 mg, 33%) as an off-white solid. LC/MS (ESI) m/z: 1026.3 $[M+H]^+$, $^1H$ NMR (400 MHz, $CD_3OD$) δ 9.01 (s, 1H), 7.86 (dd, J=5.6, 9.2 Hz, 1H), 7.54 (d, J=8.0 Hz, 1H), 7.40-7.27 (m, 2H), 7.24-7.11 (m, 2H), 5.11 (dd, J=5.2, 1 Step 2: Hz, 1H), 4.68-4.41 (m, 6H), 3.78-3.60 (m, 4H), 3.37 (s, 1H), 3.24 (br s, 4H), Step 10: (br dd, J=2.8, 4.8 Hz, 2H), 2.98-2.73 (m, 6H), 2.61 (br s, 4H), 2.55-2.43 (m, 1H), 2.32-2.12 (m, 7H), 2.05-1.96 (m, 2H), 1.93-1.73 (m, 8H), 1.68-1.56 (m, 2H), 1.28 (q, J=11.2 Hz, 4H).

Example 89: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-2-oxo-3-(propan-2-yl)-2,3-dihydro-1H-1,3-benzodiazol-1-yl)piperidine-2,6-dione (Compound 224)

Step 1: Preparation of tert-butyl 3-[2-[[(2S,4R)-4-[[1-[[1-[1-(2,6-dioxo-3-piperidyl)-4-fluoro-3-isopropyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

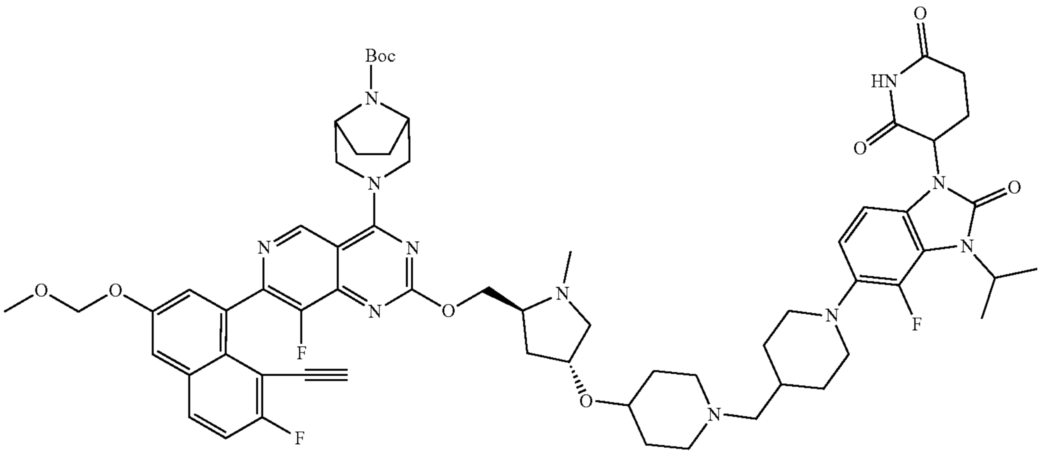 [SMILES: C#Cc1c(F)ccc2cc(OCOC)cc(-c3ncc4c(N5CC6CCC(C5)N6C(=O)OC(C)(C)C)nc(OC[C@@H]5C[C@@H](OC6CCN(CC7CCN(c8ccc9c(c8F)n(C(C)C)c(=O)n9C8CCC(=O)NC8=O)CC7)CC6)CN5C)nc4c3F)c12]

To a solution of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate (260 mg, 0.3 mmol) and 1-[1-(2,6-dioxo-3-piperidyl)-4-fluoro-3-isopropyl-2-oxo-benzimidazol-5-yl]piperidine-4-carbaldehyde (176 mg, 0.4 mmol) in dichloromethane (4.0 mL) and isopropanol (2.0 mL) were added acetic acid (93 μL, 1.6 mmol) and 2-methylpyridine borane (174 mg, 1.6 mmol), and the mixture was stirred at 25° C. for 1 h. The reaction mixture was concentrated under reduced pressure, and the residue was purified by flash column chromatography on silica gel (0 to 7% methanol in dichloromethane) to afford the title compound (200 mg, 48%) as a yellow solid. LC/MS (ESI) m/z: 1200.8 $[M+H]^+$.

Step 2: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-2-oxo-3-(propan-2-yl)-2,3-dihydro-1H-1,3-benzodiazol-1-yl)piperidine-2,6-dione

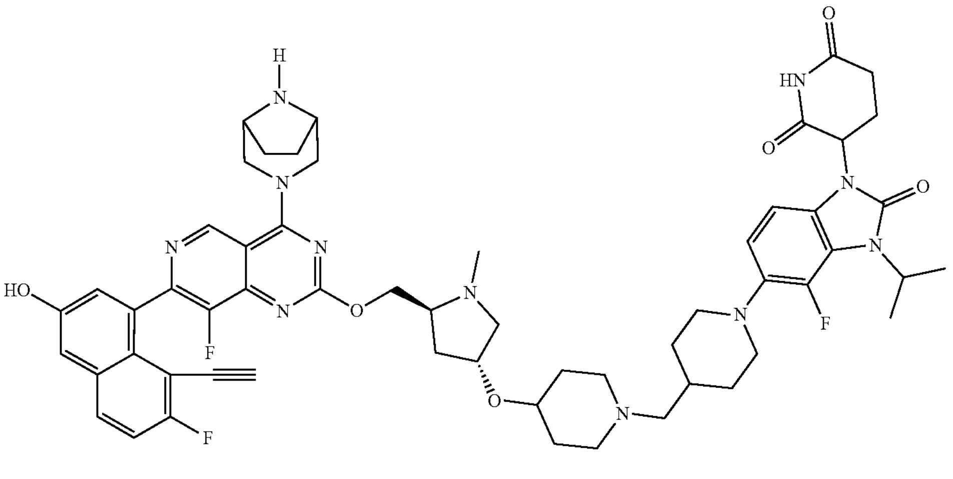 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8F)n(C(C)C)c(=O)n9C8CCC(=O)NC8=O)CC7)CC6)CN5C)nc4c3F)c12]

To a solution of tert-butyl 3-[2-[[(2S,4R)-4-[[1-[[1-[1-(2,6-dioxo-3-piperidyl)-4-fluoro-3-isopropyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (200 mg, 0.2 mmol) in dichloromethane (6.0 mL) was added 4 M HCl in 1,4-dioxane (1.7 mL), and the mixture was stirred at 25° C. for 30 min. The mixture was suspended in petroleum ether (50 mL) and filtered. The filter cake was diluted with tetrahydrofuran (40 mL) and triethylamine (5 mL), filtered, and concentrated under reduced pressure. The residue was purified by prep-HPLC (22% to 62% acetonitrile in water (ammonium bicarbonate) over 36 min) to afford the title compound (38.0 mg, 21%) as a white solid. LC/MS (ESI) m/z: 1005.4 $[M+H]^+$, $^1H$ NMR (400 MHz, $CD_3OD$) δ 9.01 (s, 1H), 7.87-7.83 (m, 1H), 7.39-7.26 (m, 2H), 7.21 (d, J=2.4 Hz, 1H), 6.91-6.79 (m, 2H), 5.30-5.26 (m, 1H), 4.67-4.55 (m, 4H), 4.53-4.39 (m, 3H), 4.26-4.20 (m, 1H), 3.77-3.62 (m, 4H), 3.50-3.34 (m, 3H), 3.04-2.99 (m, 1H), 2.93-2.85 (m, 1H), 2.83-2.64 (m, 6H), 2.52 (s, 3H), 2.40-2.36 (m, 1H), 2.28 (d, J=6.0 Hz, 2H), 2.22-2.11 (m, 3H), 2.08-1.98 (m, 2H), 1.96-1.75 (m, 8H), 1.73-1.57 (m, 3H), 1.51 (d, J=6.8 Hz, 8H).

Example 90: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione (Compound 80)

Step 1: Preparation of tert-butyl 4-[[1-[1-(2,6-dibenzyloxy-3-pyridyl)-3-isopropyl-2-oxo-benzimidazol-5-yl]-4-piperidyl]methyl]piperidine-1-carboxylate

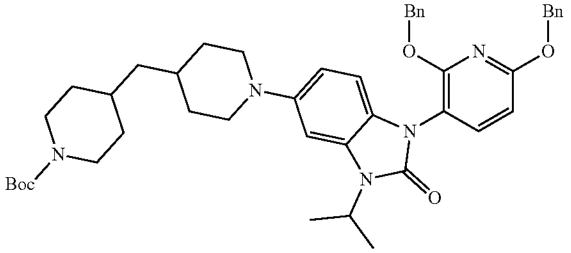 [SMILES: CC(C)n1c(=O)n(-c2ccc(OCc3ccccc3)nc2OCc2ccccc2)c2ccc(N3CCC(CC4CCN(C(=O)OC(C)(C)C)CC4)CC3)cc21]

To a solution of 5-bromo-1-(2,6-dibenzyloxy-3-pyridyl)-3-isopropyl-benzimidazol-2-one (711 mg, 1.3 mmol) and tert-butyl 4-(4-piperidylmethyl)piperidine-1-carboxylate (368.8 mg, 1.3 mmol) in 1,4-dioxane (10 mL) was added cesium carbonate (1.28 g, 3.9 mmol), and the resulting the mixture was degassed and purged with nitrogen for 10 min.

XPhos (124.5 mg, 261 μmol) and $Pd_2(dba)_3$ (119.6 mg, 130 μmol) were then added, and the reaction mixture was stirred at 100° C. for 16 h. The crude reaction mixture was dried over anhydrous sodium sulfate, filtered, and concentrated under reduced pressure. The residue was purified by flash column chromatography on silica gel (0 to 50% ethyl acetate in petroleum ether) to afford the title compound (800 mg, 77%) as a yellow solid. LC/MS (ESI) m/z: 746.7 $[M+H]^+$.

Step 2: Preparation of tert-butyl 4-[[1-[1-(2,6-dioxo-3-piperidyl)-3-isopropyl-2-oxo-benzimidazol-5-yl]-4-piperidyl]methyl]piperidine-1-carboxylate

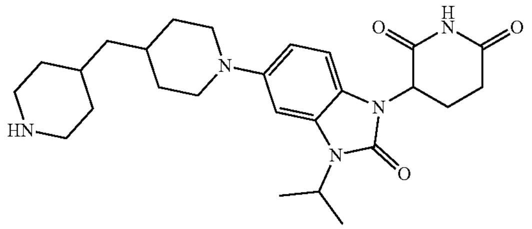 [SMILES: CC(C)n1c(=O)n(C2CCC(=O)NC2=O)c2ccc(N3CCC(CC4CCNCC4)CC3)cc21]

To a solution of tert-butyl 4-[[1-[1-(2,6-dibenzyloxy-3-pyridyl)-3-isopropyl-2-oxo-benzimidazol-5-yl]-4-piperidyl]methyl]piperidine-1-carboxylate (800 mg, 1 mmol) in THF (10 mL) was added 20% $Pd(OH)_2$ on carbon (286 mg, 0.4 mmol), and the suspension was degassed and purged with hydrogen several times. The reaction mixture was stirred under hydrogen (50 psi) at 50° C. for 16 h, then filtered and concentrated under reduced pressure to afford the title compound (578 mg, crude) as a white solid. LC/MS (ESI) m/z: 568.3 $[M+H]^+$.

Step 3: Preparation of 3-[3-isopropyl-2-oxo-5-[4-(4-piperidylmethyl)-1-piperidyl]benzimidazol-1-yl]piperidine-2,6-dione

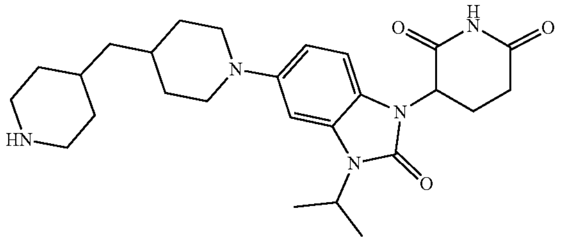 [SMILES: CC(C)n1c(=O)n(C2CCC(=O)NC2=O)c2ccc(N3CCC(CC4CCNCC4)CC3)cc21]

To a solution of tert-butyl 4-[[1-[1-(2,6-dioxo-3-piperidyl)-3-isopropyl-2-oxo-benzimidazol-5-yl]-4-piperidyl]methyl]piperidine-1-carboxylate (578 mg, 1 mmol) in dichloromethane (5 mL) was added 4 M HCl in 1,4-dioxane (5.1 mL), and the reaction mixture was stirred at 25° C. for 1 h. The mixture was concentrated and triturated with petroleum ether (3×10 mL) to afford the title compound (513 mg, crude, HCl salt) as a white solid. LC/MS (ESI) m/z: 468.3 $[M+H]^+$.

Step 4: Preparation of tert-butyl 4-[[4-[[1-[1-(2,6-dioxo-3-piperidyl)-3-isopropyl-2-oxo-benzimidazol-5-yl]-4-piperidyl]methyl]-1-piperidyl]methyl]piperidine-1-carboxylate

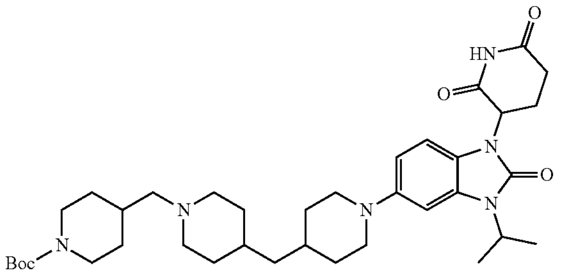 [SMILES: CC(C)n1c(=O)n(C2CCC(=O)NC2=O)c2ccc(N3CCC(CC4CCN(CC5CCN(C(=O)OC(C)(C)C)CC5)CC4)CC3)cc21]

To a solution of 3-[3-isopropyl-2-oxo-5-[4-(4-piperidylmethyl)-1-piperidyl]benzimidazol-1-yl]piperidine-2,6-dione (513 mg, 1 mmol, HCl) in dichloromethane (5 mL) and isopropanol (5 mL) were added sodium acetate (667.9 mg, 8 mmol), tert-butyl 4-formylpiperidine-1-carboxylate (651 mg, 3 mmol), and 2-methylpyridine borane (435 mg, 4 mmol), and the reaction mixture was stirred at 25° C. for 1 h. The mixture was diluted with triethylamine to adjust the pH to 8, then concentrated in vacuo. The residue was purified by flash column chromatography on silica gel (0 to 7% methanol in dichloromethane) to afford the title compound (642 mg, 83%) as a light yellow solid. LC/MS (ESI) m/z: 665.4 $[M+H]^+$.

Step 5: Preparation of 3-[3-isopropyl-2-oxo-5-[4-[[1-(4-piperidylmethyl)-4-piperidyl]methyl]-1-piperidyl]benzimidazol-1-yl]piperidine-2,6-dione

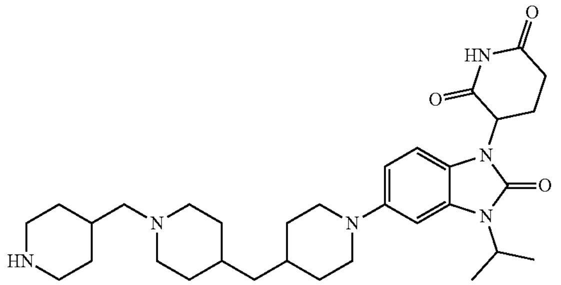 [SMILES: CC(C)n1c(=O)n(C2CCC(=O)NC2=O)c2ccc(N3CCC(CC4CCN(CC5CCNCC5)CC4)CC3)cc21]

To a solution of tert-butyl 4-[[4-[[1-[1-(2,6-dioxo-3-piperidyl)-3-isopropyl-2-oxo-benzimidazol-5-yl]-4-piperidyl]methyl]-1-piperidyl]methyl]piperidine-1-carboxylate (517 mg, 0.7 mmol) in dichloromethane (4 mL) was added 4 M HCl in 1,4-dioxane (3.38 mL), and the reaction mixture was stirred at 25° C. for 30 min. The mixture concentrated in vacuo, and the residue was triturated with petroleum ether (3×10 mL) to afford the title compound (406 mg, crude, HCl salt) as a purple solid. LC/MS (ESI) m/z: 565.3 $[M+H]^+$ Step 6: Preparation of tert-butyl 3-[2-[2-[4-[[4-[[1-[1-(2,6-dioxo-3-piperidyl)-3-isopropyl-2-oxo-benzimidazol-5-yl]-4-piperidyl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

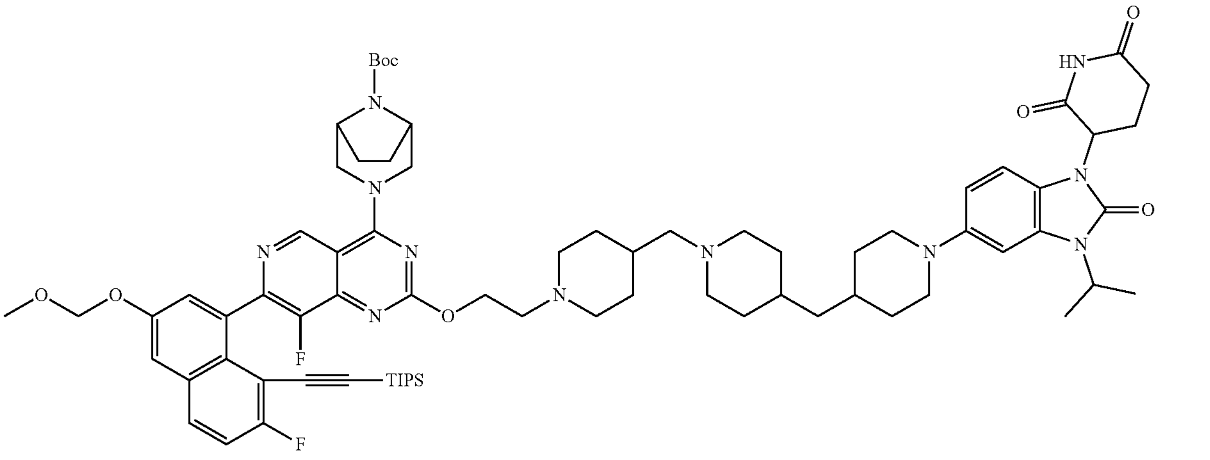

To a solution of 3-[3-isopropyl-2-oxo-5-[4-[[4-(4-piperidylmethyl)-1-piperidyl]methyl]-1-piperidyl]benzimidazol-1-yl]piperidine-2,6-dione (406 mg, 0.7 mmol, HCl) in dichloromethane (4 mL) and isopropanol (4 mL) were added sodium acetate (755.4 mg, 9 mmol), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (492.3 mg, 0.6 mmol), and 2-methylpyridine borane (262.7 mg, 2.5 mmol), and the reaction mixture was stirred at 25° C. for 1 h. The mixture was diluted with triethylamine to adjust the pH to 8, and then the suspension was concentrated in vacuo. The residue was purified by flash column chromatography on silica gel (0 to 7% methanol in dichloromethane) to afford the title compound (612 mg, 66%) as a white solid. LC/MS (ESI) m/z: 676.4 $[M/2+H]^+$.

Step 7: Preparation of tert-butyl (1R,5S)-3-(2-(2-(4-((4-((1-(1-(2,6-dioxopiperidin-3-yl)-3-isopropyl-2-oxo-2,3-dihydro-1H-benzo[d]imidazol-5-yl)piperidin-4-yl)methyl)piperidin-1-yl)methyl)piperidin-1-yl)ethoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

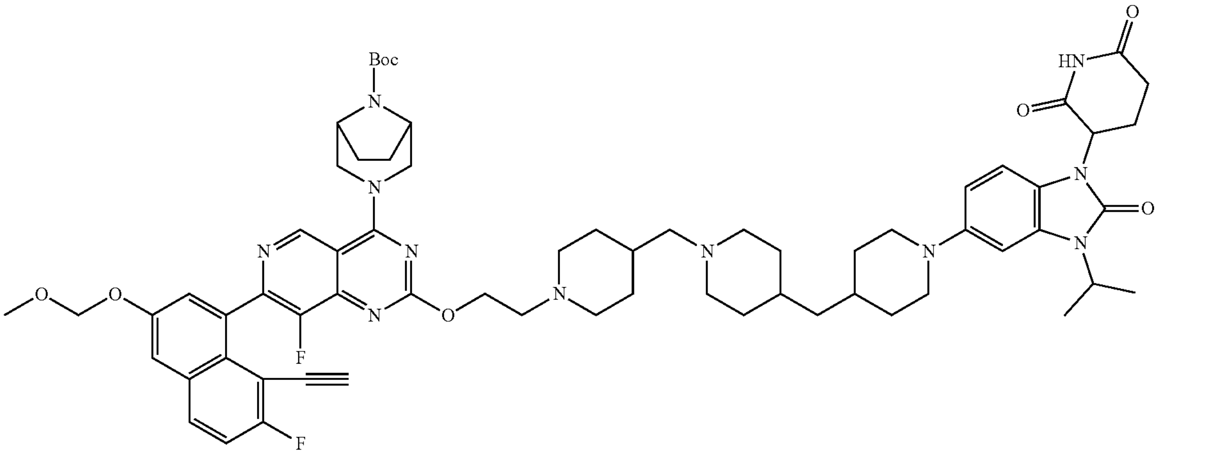 [SMILES: C#Cc1c(F)ccc2cc(OCOC)cc(-c3ncc4c(N5CC6CCC(C5)N6C(=O)OC(C)(C)C)nc(OCCN5CCC(CN6CCC(CC7CCN(c8ccc9c(c8)n(C(C)C)c(=O)n9C8CCC(=O)NC8=O)CC7)CC6)CC5)nc4c3F)c12]

To a solution of tert-butyl 3-[2-[2-[4-[[4-[[1-[1-(2,6-dioxo-3-piperidyl)-3-isopropyl-2-oxo-benzimidazol-5-yl]-4-piperidyl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (600 mg, 0.4 mmol) in DMF (10 mL) was added cesium fluoride (303.64 mg, 2 mmol), and the mixture was stirred at 25° C. for 16 h. The reaction mixture was filter, washing with ethyl acetate (30 mL), and the filtrate was diluted with water (50 mL) and extracted with ethyl acetate (3×30 mL). The combined organic extracts were washed with water (3×30 mL) followed brine (30 mL), dried over anhydrous sodium sulfate, filtered, and concentrated under reduced pressure to afford the title compound (550 mg, 92%) as a yellow solid. LC/MS (ESI) m/z: 598.0 [1/2 M+H]$^+$.

Step 8: Preparation of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione

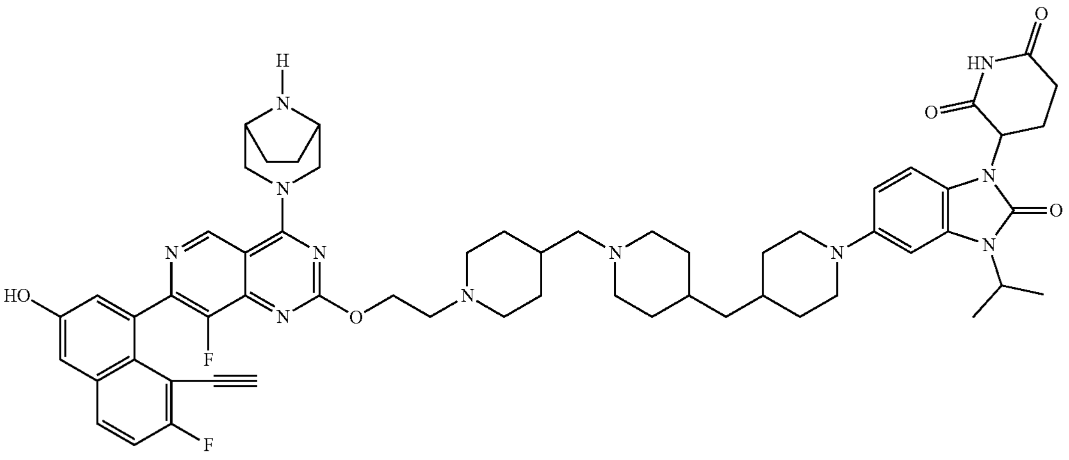 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)n(C(C)C)c(=O)n9C8CCC(=O)NC8=O)CC7)CC6)CC5)nc4c3F)c12]

To a solution of tert-butyl 3-[2-[2-[4-[[4-[[1-[1-(2,6-dioxo-3-piperidyl)-3-isopropyl-2-oxo-benzimidazol-5-yl]-4-piperidyl]methyl]-1-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (550 mg, 0.4 mmol) in dichloromethane (5 mL) was added 4 M HCl in 1,4-dioxane (5 mL), and the mixture was stirred at 25° C. for 10 min. The reaction mixture was concentrated under reduced pressure. The residue was purified by prep-HPLC (26%-66% acetonitrile in water (ammonium bicarbonate) over 36 min) to afford the title compound (189.4 mg, 47%) as an off-white solid. LC/MS (ESI) m/z: 1050.6 [M+H]$^+$; $^1$H NMR ($CD_3OD$, 400 MHz) δ 9.01 (s, 1H), 7.90-7.82 (m, 1H), 7.37-7.28 (m, 2H), 7.23-7.18 (m, 1H), 7.00-6.93 (m, 2H), 6.80 (dd, J=2.0, 8.4 Hz, 1H), 5.26 (dd, J=5.2, 12.8 Hz, 1H), 4.70-4.57 (m, 6H), 3.74-3.64 (m, 4H), 3.52 (br d, J=11.8 Hz, 2H), 3.37 (s, 1H), 3.12-3.06 (m, 2H), 2.96-2.91 (m, 2H), 2.86 (br t, J=5.6 Hz, 2H), 2.83-2.75 (m, 2H), 2.74-2.67 (m, 2H), 2.66-2.63 (m, 1H), 2.28-2.14 (m, 5H), 2.04-1.96 (m, 2H), 1.90-1.77 (m, 8H), 1.71 (br d, J=12.8 Hz, 2H), 1.56-1.50 (m, 7H), 1.42-1.30 (m, 4H), 1.30-1.19 (m, 6H).

Example 91: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-4-fluoro-2-oxo-3-(propan-2-yl)-2,3-dihydro-1H-1,3-benzodiazol-1-yl}piperidine-2,6-dione (Compound 167)

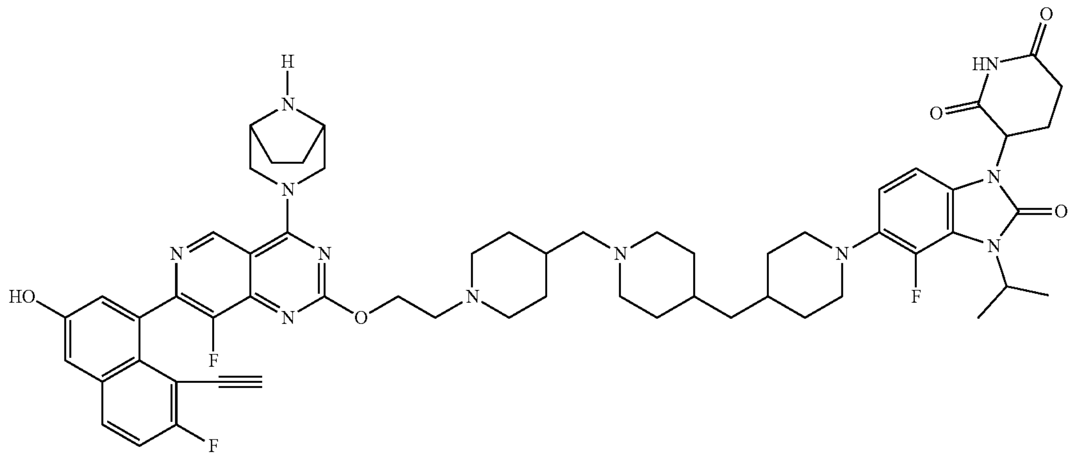 [SMILES: C#Cc1c(F)ccc2cc(O)cc(-c3ncc4c(N5CC6CCC(C5)N6)nc(OCCN5CCC(CN6CCC(CC7CCN(c8ccc9c(c8F)n(C(C)C)c(=O)n9C8CCC(=O)NC8=O)CC7)CC6)CC5)nc4c3F)c12]

The title compound was prepared in an analogous manner to 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione. (yellow solid.) LC/MS (ESI) m/z: 1068.6 $[M+H]^+$; $^1H$ NMR (400 MHz, $CD_3OD$) δ 9.01 (s, 1H), 7.86 (dd, J=5.6, 9.2 Hz, 1H), 7.36-7.29 (m, 2H), 7.21 (d, J=2.4 Hz, 1H), 6.89-6.80 (m, 2H), 5.28 (dd, J=5.2, 12.4 Hz, 1H), 4.67-4.55 (m, 5H), 3.74-3.64 (m, 4H), 3.37 (s, 1H), 3.14-3.08 (m, 2H), 2.99 (br d, J=11.2 Hz, 2H), 2.93-2.85 (m, 3H), 2.83-2.75 (m, 2H), 2.74-2.67 (m, 2H), 2.31 (br d, J=6.4 Hz, 2H), 2.26-2.19 (m, 2H), 2.18-2.10 (m, 2H), 2.09-2.00 (m, 2H), 1.90-1.84 (m, 2H), 1.83-1.77 (m, 6H), 1.73 (br d, J=13.2 Hz, 2H), 1.69-1.58 (m, 2H), 1.51 (br d, J=6.8 Hz, 6H), 1.41 (br d, J=11.6 Hz, 2H), 1.33-1.23 (m, 8H).

Example 92: Synthesis of 3-{4-chloro-5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-1-oxo-2,3-dihydro-1H-isoindol-2-yl}piperidine-2,6-dione (Compound 81)

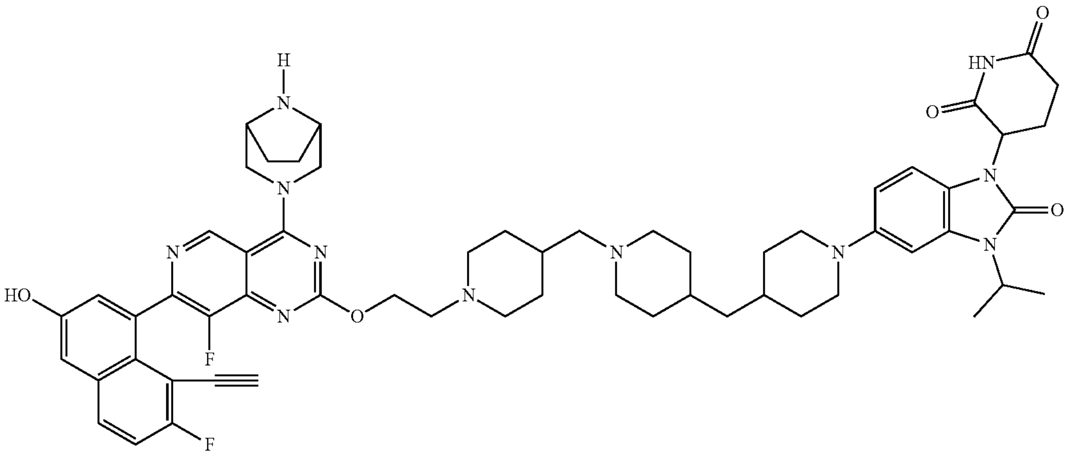 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)n(C(C)C)c(=O)n9C8CCC(=O)NC8=O)CC7)CC6)CC5)nc4c3F)c12]

The title compound was prepared in an analogous manner to 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione. (yellow solid). LC/MS (ESI) m/z: 1041.5 $[M+H]^+$; $^1H$ NMR (400 MHz, $CD_3OD$) δ 9.00 (s, 1H), 7.85 (dd, J=5.6, 9.2 Hz, 1H), 7.66 (d, J=8.4 Hz, 1H), 7.36-7.16 (m, 4H), 5.12 (dd, J=5.2, 13.2 Hz, 1H), 4.67-4.54 (m, 4H), 4.50-4.36 (m, 2H), 3.75-3.62 (m, 4H), 3.50-3.43 (m, 2H), 3.36 (s, 1H), 3.08 (dd, J=1.6, 4.0 Hz, 2H), 2.98-2.82 (m, 5H), 2.81-2.70 (m, 3H), 2.57-2.43 (m, 1H), 2.28-2.10 (m, 5H), 1.99 (s, 2H), 1.89-1.67 (m, 10H), 1.65-1.53 (m, 2H), 1.49-1.36 (m, 3H), 1.25 (d, J=6.8 Hz, 6H).

Example 93: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-3-methyl-2-oxo-2,3-dihydro-1H-1,3-benzodiazol-1-yl}piperidine-2,6-dione (Compound 82)

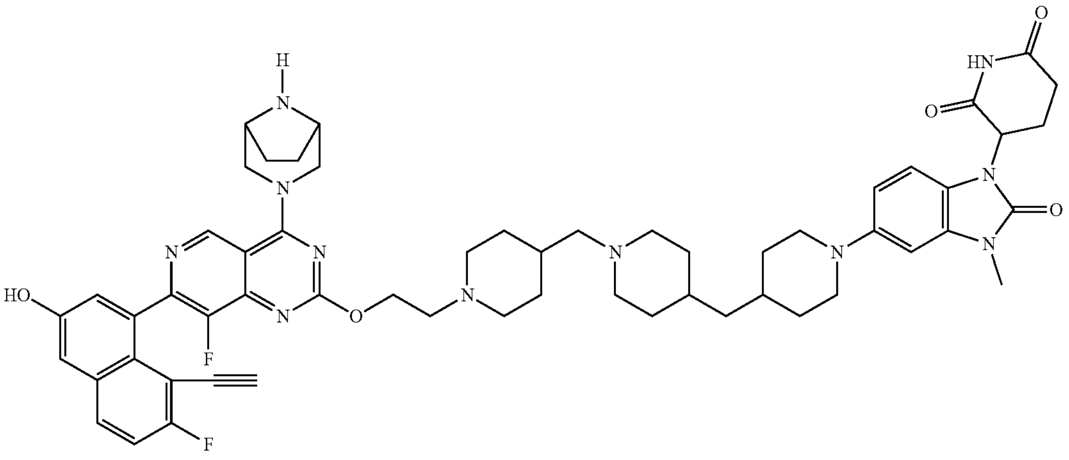 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)n(C)c(=O)n9C8CCC(=O)NC8=O)CC7)CC6)CC5)nc4c3F)c12]

The title compound was prepared in an analogous manner to 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione (light yellow solid). LC/MS (ESI) m/z: 1022.5 $[M+H]^+$, $^1H$ NMR (400 MHz, $CD_3OD$) δ 9.00 (s, 1H), 7.88-7.84 (m, 1H), 7.35-7.30 (m, 2H), 7.21-7.20 (m, 1H), 6.99-6.97 (m, 1H), 6.87-6.86 (m, 1H), 6.81-6.79 (m, 1H), 5.30-5.25 (m, 1H), 4.66-4.57 (m, 5H), 3.73-3.66 (m, 4H), 3.59-3.55 (m, 2H), 3.40 (s, 3H), 3.37 (s, 1H), 3.13-3.09 (m, 2H), 2.95-2.91 (m, 3H), 2.89-2.85 (m, 2H), 2.82-2.75 (m, 2H), 2.71-2.65 (m, 2H), 2.25-2.13 (m, 5H), 2.02-1.96 (m, 2H), 1.89-1.77 (m, 8H), 1.72-1.69 (m, 2H), 1.40-1.21 (m, 10H).

Example 94: Exemplary synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperazin-1-yl}methyl)piperidin-1-yl]-4-fluoro-2-oxo-3-(propan-2-yl)-2,3-dihydro-1H-1,3-benzodiazol-1-yl}piperidine-2,6-dione (Compound 159)

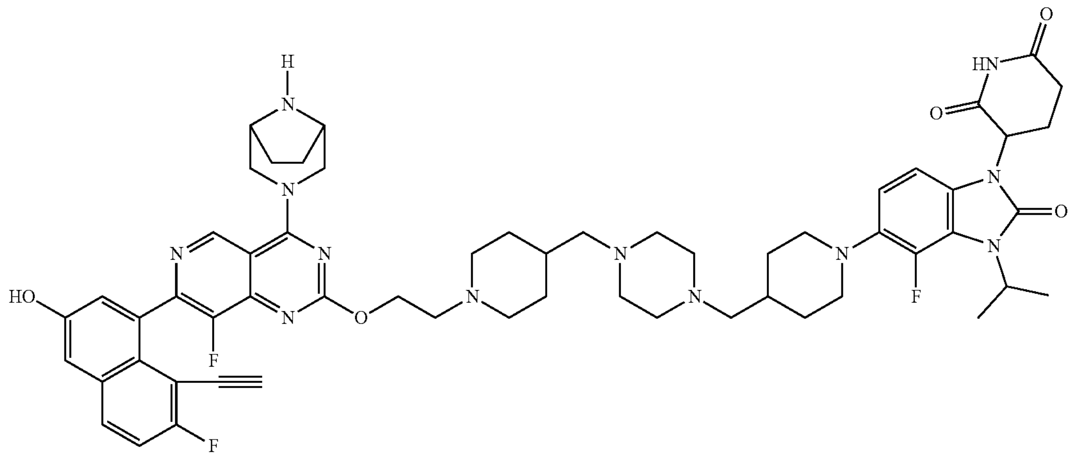 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)n(C(C)C)c(=O)n9C8CCC(=O)NC8=O)CC7)CC6)CC5)nc4c3F)c12]

The title compound was prepared in an analogous manner to 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-2-oxo-3-(propan-2-yl)-2,3-dihydro-1H-1,3-benzodiazol-1-yl}piperidine-2,6-dione. (yellow solid). LC/MS (ESI) m/z: 1069.5 $[M+H]^+$, $^1H$ NMR (400 MHz, $CD_3OD$) δ 9.01 (s, 1H), 7.86 (dd, J=9.2, 5.6 Hz, 1H), 7.40-7.26 (m, 2H), 7.21 (d, J=2.4 Hz, 1H), 6.92-6.76 (m, 2H), 5.28 (dd, J=12.4, 5.2 Hz, 1H), 4.69-4.53 (m, 5H), 3.77-3.64 (m, 4H), 3.37 (s, 1H), 3.15-3.05 (m, 2H), 2.95-2.65 (m, 8H), 2.60-2.36 (m, 8H), 2.31-2.09 (m, 8H), 1.95-1.74 (m, 9H), 1.60-1.40 (m, 9H), 1.35-1.19 (m, 2H).

Example 95: Synthesis of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-1-oxo-isoindolin-2-yl]piperidine-2,6-dione (Compound 84)

Step 1: Preparation of tert-butyl 3-[2-[[(3S,8R)-3-[[4-[[1-[2-(2,6-dioxo-3-piperidyl)-1-oxo-isoindolin-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

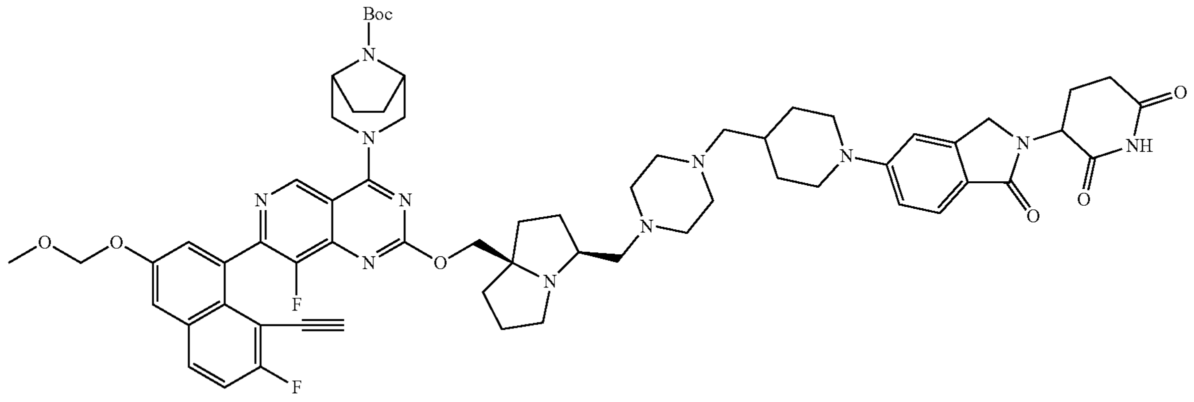 [SMILES: C#Cc1c(F)ccc2cc(OCOC)cc(-c3ncc4c(N5CC6CCC(C5)N6C(=O)OC(C)(C)C)nc(OC[C@]56CCCN5[C@H](CN5CCN(CC7CCN(c8ccc9c(c8)CN(C8CCC(=O)NC8=O)C9=O)CC7)CC5)CC6)nc4c3F)c12]

To a mixture of tert-butyl 3-[7-[8-ethynyl-7-fluoro-3-(methoxymethoxy)-1-naphthyl]-8-fluoro-2-[[(3S,8R)-3-formyl-1,2,3,5,6,7-hexahydropyrrolizin-8-yl]methoxy]pyrido[4,3-d]pyrimidin-4-yl]-3,8-diazabicyclo[3.2.1]octane-8-carboxylate (498 mg, 0.6 mmol) and 3-[1-oxo-5-[4-(piperazin-1-ylmethyl)-1-piperidyl]isoindolin-2-yl]piperidine-2,6-dione (372 mg, 0.6 mmol, HCl salt) in dichloromethane (10 mL) was added sodium triacetoxy-borohydride (420 mg, 2 mmol), and the reaction mixture was stirred at 25° C. for 10 h. The reaction was quenched with saturated sodium bicarbonate solution (10 mL) and concentrated under reduced pressure. The residue was extracted with ethyl acetate (100 mL×3), and the combined organic extract was washed with brine (100 mL×3), dried over anhydrous sodium sulfate, filtered, and concentrated. The residue was purified by flash column chromatography on silica gel (0 to 4% then up to 10% methanol in dichloromethane) to afford the title compound (287 mg, 37%) as a yellow solid. LC/MS (ESI) m/z: 583.0 $[M/2+H]^+$.

Step 2: Preparation of 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-1-oxo-isoindolin-2-yl]piperidine-2,6-dione

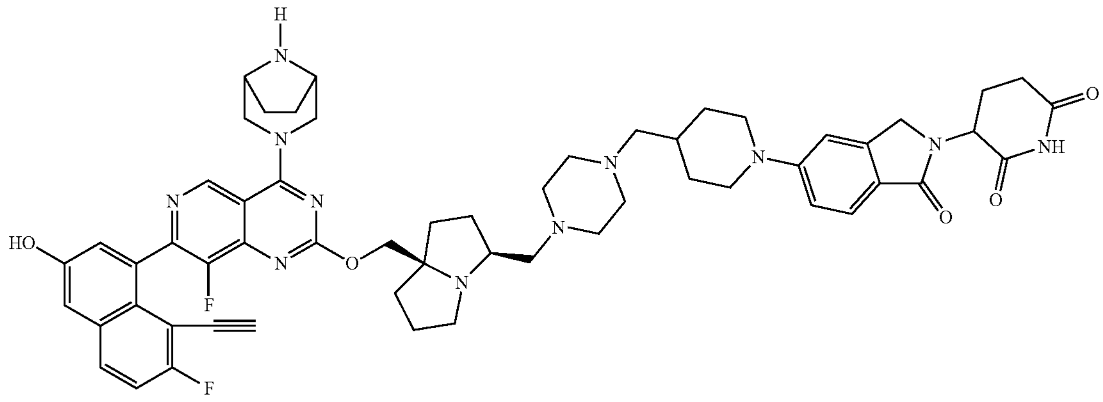 [SMILES: C#Cc1c(F)ccc2cc(O)cc(-c3ncc4c(N5CC6CCC(C5)N6)nc(OC[C@]56CCCN5[C@H](CN5CCN(CC7CCN(c8ccc9c(c8)CN(C8CCC(=O)NC8=O)C9=O)CC7)CC5)CC6)nc4c3F)c12]

To a solution of tert-butyl 3-[2-[[(3S,8R)-3-[[4-[[1-[2-(2,6-dioxo-3-piperidyl)-1-oxo-isoindolin-5-yl]-4-piperidyl]methyl]piperazin-1-yl]methyl]-1,2,3,5,6,7-hexahydropyrrolizin-8-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (287 mg, 0.2 mmol) in dichloromethane (5 mL) was added 4 M HCl in 1,4-dioxane (5.0 mL), and the mixture was stirred at 25° C. for 10 min. The reaction mixture was concentrated, and the residue was dissolved in THF (10 mL) and triethylamine to adjust the pH to 8. The resulting mixture was filtered, and the filtrate was concentrated under reduced pressure. The residue was purified by prep-HPLC (26% to 66% acetonitrile in water (ammonium bicarbonate) over 36 min) to afford the title compound (44.1 mg, 18%) as a white solid. LC/MS (ESI) m/z: 1020.5 $[M+H]^+$, $^1$H NMR (400 MHz, $CD_3OD$) δ 9.02 (d, J=4.4 Hz, 1H), 7.92-7.80 (m, 1H), 7.61 (d, J=8.0 Hz, 1H), 7.37-7.25 (m, 2H), 7.21 (d, J=2.4 Hz, 1H), 7.09-7.01 (m, 2H), 5.13-5.08 (m, 1H), 4.69-4.55 (m, 4H), 4.41-4.25 (m, 5H), 3.92-3.86 (m, 2H), 3.75-3.64 (m, 5H), 3.37 (d, J=2.0 Hz, 1H), 2.90-2.77 (m, 5H), 2.60-2.40 (m, 10H), 2.22 (d, J=6.0 Hz, 4H), 1.94-1.71 (m, 13H), 1.31-1.21 (m, 2H).

Compounds 143, 145, 146 and 147, 234, and 238 were prepared using a procedure analogous to the procedure used to prepare Compound 84.

Example 96: Synthesis of 3-(5-{4-[(4-{[(3S,7aS)-7a-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-hexahydro-1H-pyrrolizin-3-yl]methyl}piperazin-1-yl)methyl]piperidin-1-yl}-1-oxo-2,3-dihydro-1H-isoindol-2-yl)piperidine-2,6-dione (Compound 100)

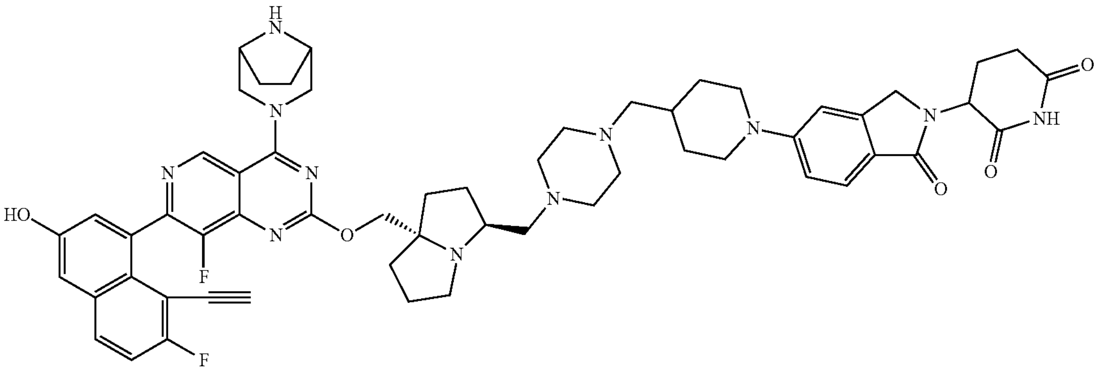 [SMILES: C#Cc1c(F)ccc2cc(O)cc(-c3ncc4c(N5CC6CCC(C5)N6)nc(OC[C@@]56CCCN5[C@H](CN5CCN(CC7CCN(c8ccc9c(c8)CN(C8CCC(=O)NC8=O)C9=O)CC7)CC5)CC6)nc4c3F)c12]

The title compound was made in an analogous manner to 3-[5-[4-[[4-[[(3S,8R)-8-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]-1,2,3,5,6,7-hexahydropyrrolizin-3-yl]methyl]piperazin-1-yl]methyl]-1-piperidyl]-1-oxo-isoindolin-2-yl]piperidine-2,6-dione. (yellow solid). LC/MS (ESI) m/z: 1020.5 $[M+H]^+$; $^1$H NMR (400 MHz, $CD_3OD-d_4$) δ 9.02 (s, 1H), 7.87-7.85 (m, 1H), 7.62 (dd, J=2.4, 8.8 Hz, 1H), 7.40-7.26 (m, 2H), 7.21 (t, J=2.0 Hz, 1H), 7.10-7.00 (m, 2H), 5.09 (d, J=4.8 Hz, 1H), 4.68-4.54 (m, 4H), 4.48-4.28 (m, 5H), 3.90 (d, J=12.4 Hz, 2H), 3.77-3.60 (m, 5H), 3.36 (s, 1H), 2.91-2.78 (m, 5H), 2.64-2.43 (m, 9H), 2.29-2.17 (m, 4H), 1.95-1.69 (m, 14H), 1.33-1.22 (m, 2H).

Example 97: Synthesis of 3-[5-[4-[[1-[[1-[2-[4-(3,8-diazabicyclo[3.2.1]octan-3-yl)-7-(8-ethynyl-7-fluoro-3-hydroxy-1-naphthyl)-8-fluoropyrido[4,3-d]pyrimidin-2-yl]oxyethyl]-4-piperidyl]methyl]-4-piperidyl]methyl]-1-piperidyl]-1-oxo-isoindolin-2-yl]piperidine-2,6-dione (Compound 87)

Step 1: Preparation of tert-butyl 4-[[1-(3-bromo-4-methoxycarbonyl-phenyl)-4-piperidyl]methyl]piperidine-1-carboxylate

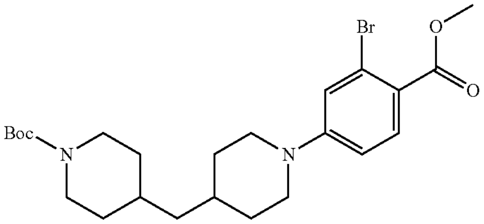 [SMILES: COC(=O)c1ccc(N2CCC(CC3CCN(C(=O)OC(C)(C)C)CC3)CC2)cc1Br]

To a solution of methyl 2-bromo-4-fluoro-benzoate (5.0 g, 21 mmol) and tert-butyl 4-(4-piperidylmethyl)piperidine-1-carboxylate di-acetate (8.64 g, 21 mmol) in dimethyl sulfoxide (50 mL) was added N,N-diisopropylethylamine (11.2 mL, 64 mmol), and the mixture was stirred at 120° C. for 12 h. The reaction mixture was diluted with water (200 mL) and extracted with ethyl acetate (2×100 mL). The combined organic layers were washed with brine (2×100 mL), dried over sodium sulfate anhydrous, filtered, and concentrated under reduced pressure. The residue was purified by column chromatography on silica gel (petroleum ether/ethyl acetate=1/0 to 7/3) to afford the title compound (7 g, 66%) as a yellow solid. LC/MS (ESI) m/z: 495.1 $[M+H]^+$; $^1$HNMR (400 MHz, DMSO-$d_6$) δ 7.75-7.69 (m, 1H), 7.15-7.09 (m, 1H), 6.97-6.90 (m, 1H), 3.96-3.82 (m, 4H), 3.79-3.72 (m, 3H), 2.86-2.75 (m, 2H), 2.74-2.56 (m, 2H), 1.75-1.50 (m, 6H), 1.42-1.36 (m, 9H), 1.05 (d, J=4.0 Hz, 4H), 1.01-0.87 (m, 2H).

Step 2: Preparation of tert-butyl 4-[[1-(4-methoxy-carbonyl-3-vinyl-phenyl)-4-piperidyl]methyl]piperidine-1-carboxylate

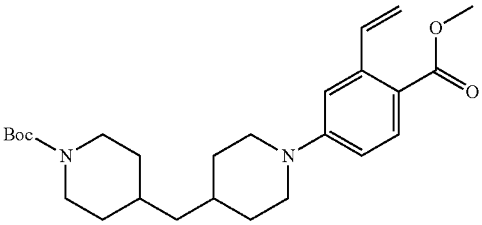 [SMILES: C=Cc1cc(N2CCC(CC3CCN(C(=O)OC(C)(C)C)CC3)CC2)ccc1C(=O)OC]

A mixture of tert-butyl 4-[[1-(3-bromo-4-methoxycarbonyl-phenyl)-4-piperidyl]methyl]piperidine-1-carboxylate (7.5 g, 15 mmol), potassium vinyltrifluoroborate (6.08 g, 45 mmol), sodium carbonate (4.01 g, 38 mmol), and [1,1'-bis(diphenylphosphino)ferrocene]dichloropalladium(II) (1.11 g, 1.5 mmol) in 1,4-dioxane (100 mL) and water (20 mL) was degassed and purged with nitrogen several times, then stirred at 90° C. for 12 h under nitrogen atmosphere. The reaction mixture was diluted with water (200 mL) and extracted with ethyl acetate (2×100 mL). The combined organic layers were washed with brine (2×100 mL), dried over anhydrous sodium sulfate, filtered, and concentrated under reduced pressure. The residue was purified by silica gel chromatography (petroleum ether/ethyl 10 acetate=1/0 to 10/1) to afford the title compound (5.4 g, 81%) as a gray solid. $^{1}$HNMR (400 MHz, DMSO-$d_6$) δ 7.73 (d, J=8.8 Hz, 1H), 7.53-7.42 (m, 1H), 7.03-6.97 (m, 1H), 6.94-6.84 (m, 1H), 5.75-5.64 (m, 1H), 5.32-5.23 (m, 1H), 3.91 (d, J=12.8 Hz, 4H), 3.77-3.70 (m, 3H), 2.85-2.56 (m, 4H), 1.77-1.48 (m, 6H), 1.44-1.34 (m, 9H), 1.18-1.08 (m, 4H), 1.01-0.86 (m, 2H).

Step 3: Preparation of tert-butyl 4-[[1-(3-formyl-4-methoxycarbonyl-phenyl)-4-piperidyl]methyl]piperidine-1-carboxylate

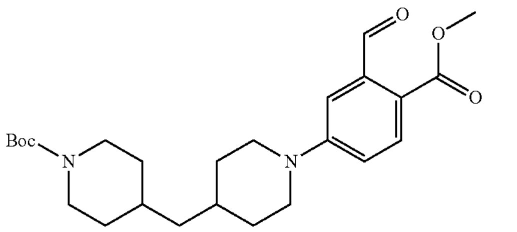 [SMILES: COC(=O)c1ccc(N2CCC(CC3CCN(C(=O)OC(C)(C)C)CC3)CC2)cc1C=O]

To a solution of tert-butyl 4-[[1-(4-methoxycarbonyl-3-vinyl-phenyl)-4-piperidyl]methyl]piperidine-1-carboxylate (5.4 g, 12 mmol) in 1,4-dioxane (75 mL) and water (25 mL) were added 2,6-dimethylpyridine (2.8 mL, 24 mmol), potassium osmate(VI) (90 mg, 0.2 mmol), and sodium periodate (4.1 mL, 73 mmol), and the mixture was stirred for 2 h at 20° C. The reaction mixture was diluted with water (200 mL) and extracted with ethyl acetate (3×100 mL). The combined organic extract was washed with brine (200 mL), dried over anhydrous sodium sulfate, filtered, and concentrated in vacuo. The residue was purified by silica gel chromatography (petroleum ether/ethyl acetate=1/0 then 85/15) to afford the title compound (1.8 g, 33%) as a yellow gum. LC/MS (ESI) m/z: 467.2 [M+Na]$^{+}$.

Step 4: Preparation of tert-butyl 4-[[1-[2-(2,6-dioxo-3-piperidyl)-1-oxo-isoindolin-5-yl]-4-piperidyl]methyl]piperidine-1-carboxylate

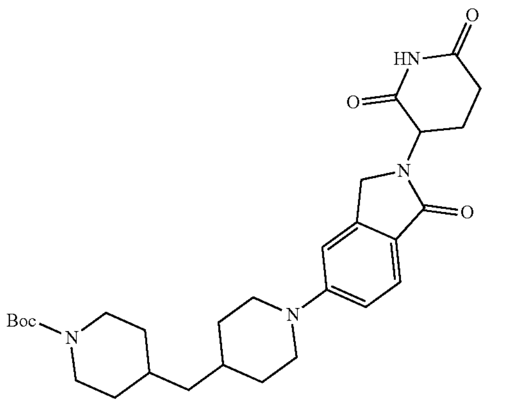 [SMILES: CC(C)(C)OC(=O)N1CCC(CC2CCN(c3ccc4c(c3)CN(C3CCC(=O)NC3=O)C4=O)CC2)CC1]

To a solution of tert-butyl 4-[[1-(3-formyl-4-methoxycarbonyl-phenyl)-4-piperidyl]methyl]piperidine-1-carboxylate (1.8 g, 4 mmol) and 3-aminopiperidine-2,6-dione (1 g, 6 mmol, hydrochloride) in methanol (20 mL) were added sodium acetate (498 mg, 6 mmol), sodium cyanoborohydride (509 mg, 8 mmol), and acetic acid (1.2 mL, 20 mmol), and the mixture was stirred at 40° C. for 12 h. The reaction mixture was concentrated under reduced pressure, and the residue was triturated with methyl tert-butyl ether to afford the title compound (1.5 g, 71%) as a gray solid. LC/MS (ESI) m/z: 557.3 [M+23]$^{+}$.

Step 5: Preparation of 3-[1-oxo-5-[4-(4-piperidylmethyl)-1-piperidyl]isoindolin-2-yl]piperidine-2,6-dione

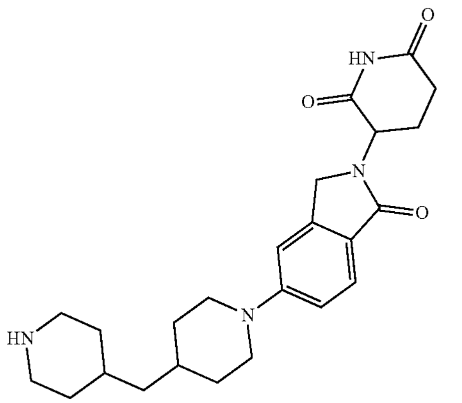 [SMILES: O=C1CCC(N2Cc3cc(N4CCC(CC5CCNCC5)CC4)ccc3C2=O)C(=O)N1]

To a solution of tert-butyl 4-[[1-[2-(2,6-dioxo-3-piperidyl)-1-oxo-isoindolin-5-yl]-4-piperidyl]methyl]piperidine-1-carboxylate (400 mg, 0.8 mmol) in dichloromethane (3 mL) was added trifluoroacetic acid (1.0 mL, 13 mmol), and the reaction mixture was stirred at 20° C. for 1 h. The mixture was concentrated under reduced pressure to afford the title compound (410 mg, crude, TFA salt) as a brown gum. LC/MS (ESI) m/z: 425.2 [M+H]$^{+}$.

Step 6: Preparation of tert-butyl 4-[[4-[[1-[2-(2,6-dioxo-3-piperidyl)-1-oxo-isoindolin-5-yl]-4-piperidyl]methyl]-1-piperidyl]methyl]piperidine-1-carboxylate

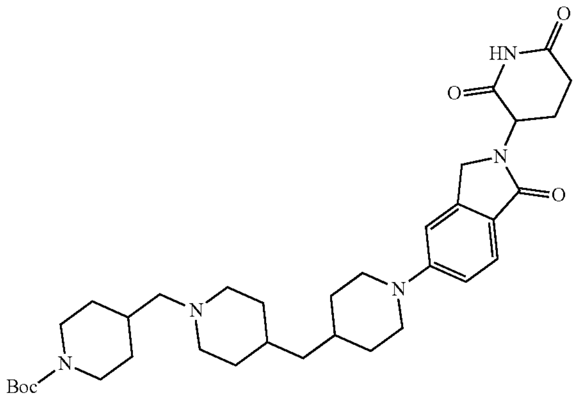 [SMILES: CC(C)(C)OC(=O)N1CCC(CN2CCC(CC3CCN(c4ccc5c(c4)CN(C4CCC(=O)NC4=O)C5=O)CC3)CC2)CC1]

To a solution of 3-[1-oxo-5-[4-(4-piperidylmethyl)-1-piperidyl]isoindolin-2-yl]piperidine-2,6-dione (410 mg, 0.8 mmol, trifluoroacetate) and tert-butyl 4-formylpiperidine-1-carboxylate (246 mg, 1.1 mmol) in dichloromethane (4 mL) and isopropanol (4 mL) was added N,N-diisopropylethylamine (0.66 mL, 3.8 mmol), and the resulting mixture was stirred for 0.5 h. Sodium triacetoxyborohydride (323 mg, 1.5 mmol) was then added, and the reaction mixture was stirred at 25° C. for 1.5 h. The mixture was poured into water (30 mL) and extracted with dichloromethane/isopropanol (1:1, 30 mL). The combined organic extract was washed with brine (2×20 mL), dried over anhydrous sodium sulfate, filtered, and concentrated under reduced pressure to afford the title compound (500 mg, crude) as a yellow solid.

Step 7: Preparation of 3-[1-oxo-5-[4-[[1-(4-piperidylmethyl)-4-piperidyl]methyl]-1-piperidyl]isoindolin-2-yl]piperidine-2,6-dione

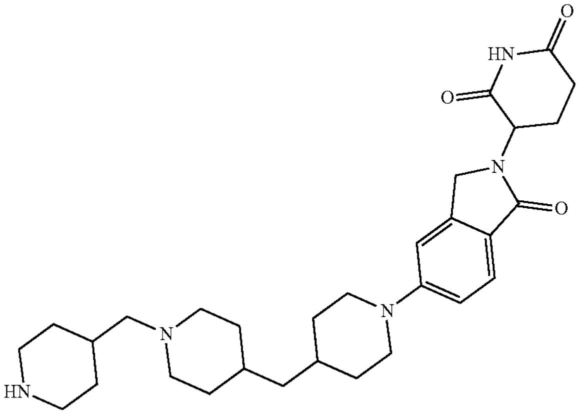 [SMILES: O=C1CCC(N2Cc3cc(N4CCC(CC5CCN(CC6CCNCC6)CC5)CC4)ccc3C2=O)C(=O)N1]

To a solution of tert-butyl 4-[[4-[[1-[2-(2,6-dioxo-3-piperidyl)-1-oxo-isoindolin-5-yl]-4-piperidyl]methyl]-1-piperidyl]methyl]piperidine-1-carboxylate (470 mg, 0.8 mmol) in dichloromethane (12 mL) was added trifluoroacetic acid (3.0 mL, 40 mmol), and the reaction mixture was stirred at 25° C. for 0.5 h. The mixture was concentrated under reduced pressure to afford the title compound (480 mg, crude, TFA salt) as a light yellow gum. LC/MS (ESI) m/z: 522.3 $[M+H]^+$.

Step 8: Preparation of tert-butyl 3-[2-[2-[4-[[4-[[1-[2-(2,6-dioxo-3-piperidyl)-1-oxo-isoindolin-5-yl]-4-piperidyl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate To a solution of 3-[1-oxo-5-[4-[[1-(4-piperidylmethyl)-4-piperidyl]methyl]-1-piperidyl]isoindolin-2-yl]piperidine-2,6-dione (480 mg, 0.8 mmol, trifluoroacetate) in dichloromethane (6 mL) and isopropanol (6 mL) were added N,N-diisopropylethylamine (0.3 mL, 1 mmol) and tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (666 mg, 0.8 mmol), and the resulting mixture was stirred at 25° C. for 0.5 h. Sodium triacetoxyborohydride (480 mg, 2 mmol) was then added, and the mixture was stirred at 25° C. for 1 h. The reaction mixture was diluted with water (20 mL) and extracted with dichloromethane (2×20 mL). The combined organic extract was dried over anhydrous sodium sulfate, filtered, and concentrated under reduced pressure. The residue was purified by prep-HPLC (22% to 52% acetonitrile in water (formic acid) over 11 min) to afford the title compound (360 mg, 36%) as a white solid. LC/MS (ESI) m/z: 1308.7 $[M+H]^+$, $^1H$ NMR (400 MHz, DMSO-$d_6$) δ 10.94 (s, 1H), 9.20 (s, 1H), 8.19-8.05 (m, 1H), 7.75 (d, J=2.4 Hz, 1H), 7.57 (t, J=8.8 Hz, 1H), 7.50 (d, J=8.8 Hz, 1H), 7.33 (d, J=2.4 Hz, 1H), 7.11-7.00 (m, 2H), 5.36 (s, 2H), 5.04 (dd, J=5.2, 1 Step 2: Hz, 1H), 4.73 (d, J=12.8 Hz, 1H), 4.52 (d, J=4.8 Hz, 2H), 4.38-4.15 (m, 5H), 3.87 (d, J=12.4 Hz, 2H), 3.76 (d, J=11.2 Hz, 1H), 3.43 (s, 3H), 3.40 (s, 3H), 3.24-3.04 (m, 3H), 2.97-2.70 (m, 7H), 2.67-2.54 (m, 2H), 2.42-2.23 (m, 2H), 2.03-1.67 (m, 12H), 1.65-1.53 (m, 3H), 1.46 (s, 9H), 1.39-1.23 (m, 4H), 1.21-1.06 (m, 4H), 0.81 (t, J=8.0 Hz, 18H), 0.49 (quin, J=7.6 Hz, 3H).

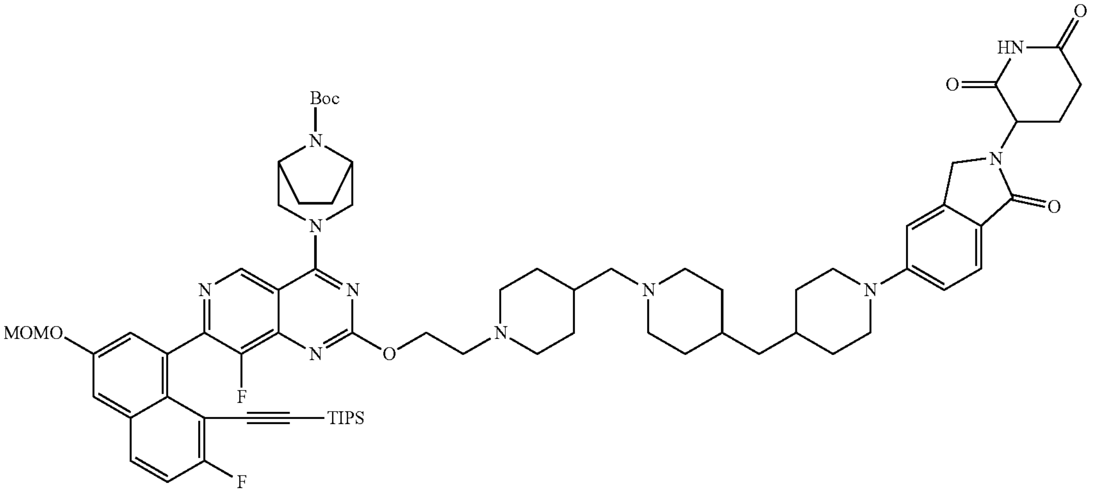

Step 8: Preparation of tert-butyl 3-[2-[2-[4-[[4-[[1-[2-(2,6-dioxo-3-piperidyl)-1-oxo-isoindolin-5-yl]-4-piperidyl]methyl]-1-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

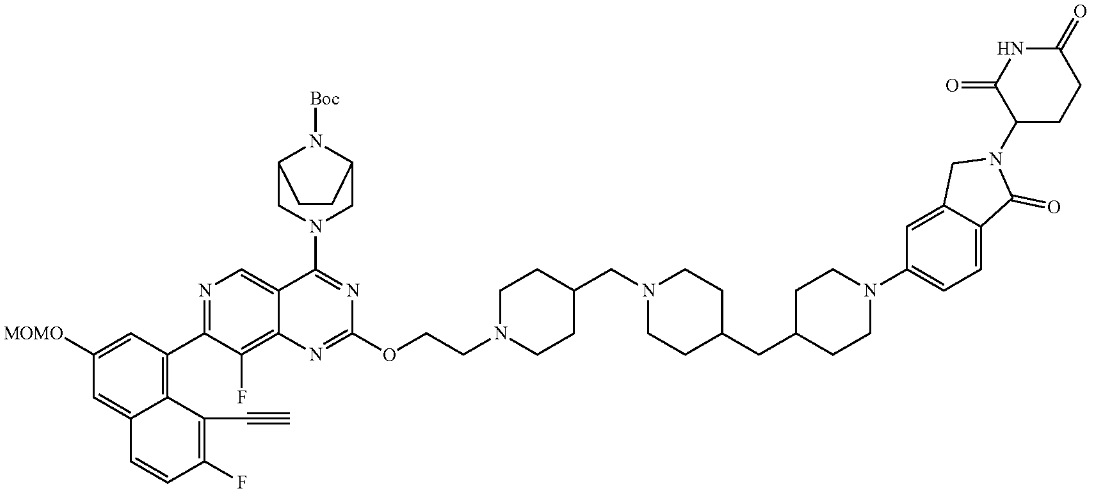

To a solution of tert-butyl 3-[2-[2-[4-[[4-[[1-[2-(2,6-dioxo-3-piperidyl)-1-oxo-isoindolin-5-yl]-4-piperidyl]methyl]-1-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (360 mg, 0.3 mmol) in N,N-dimethylformamide (6 mL) was added cesium fluoride (836 mg, 5.5 mmol), and the reaction mixture was stirred at 25° C. for 2 h. The mixture was diluted with dichloromethane (150 mL) and washed with water (2×20 mL). The organic layer was dried over anhydrous sodium sulfate, filtered, and concentrated under reduced pressure to afford the title compound (320 mg, crude) as a brown solid. LC/MS (ESI) m/z: 1151.5 [M+H]+.

Step 9: Preparation of 3-[5-[4-[[1-[[1-[2-[4-(3,8-diazabicyclo[3.2.1]octan-3-yl)-7-(8-ethynyl-7-fluoro-3-hydroxy-1-naphthyl)-8-fluoropyrido[4,3-d]pyrimidin-2-yl]oxyethyl]-4-piperidyl]methyl]-4-piperidyl]methyl]-1-piperidyl]-1-oxo-isoindolin-2-yl]piperidine-2,6-dione

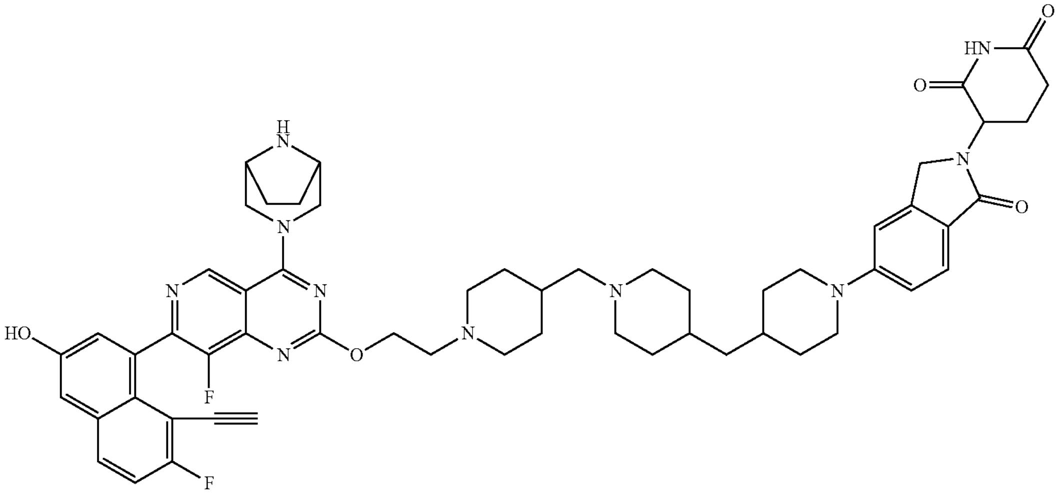 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)CN(C8CCC(=O)NC8=O)C9=O)CC7)CC6)CC5)nc4c3F)c12]

To a solution of tert-butyl 3-[2-[2-[4-[[4-[[1-[2-(2,6-dioxo-3-piperidyl)-1-oxo-isoindolin-5-yl]-4-piperidyl]methyl]-1-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (320 mg, 0.3 mmol) in dichloromethane (5 mL) was added 4 M HCl in 1,4-dioxane (5 mL), and the reaction mixture was stirred at 25° C. for 15 min. The mixture was triturated with petroleum ether (20 mL), then further purified by prep-HPLC (0% to 30% acetonitrile in water (formic acid) over 7 min) to afford the title compound (191.3 mg, 59%, tri-formic acid salt) as a yellow solid. LC/MS (ESI) m/z: 968.8 $[M+H]^+$; $^1$HNMR (400 MHz, DMSO-$d_6$) δ 10.94 (s, 1H), 9.06 (s, 1H), 8.21 (s, 3H), 7.97 (dd, J=6.0, 9.2 Hz, 1H), 7.54-7.42 (m, 2H), 7.39 (d, J=2.4 Hz, 1H), 7.18 (d, J=2.4 Hz, 1H), 7.07-6.94 (m, 2H), 5.04 (dd, J=5.2, 1 Step 2: Hz, 1H), 4.61-4.45 (m, 3H), 4.41-4.26 (m, 2H), 4.22-4.13 (m, 1H), 3.94 (s, 1H), 3.88-3.75 (m, 4H), 3.70 (t, J=14.0 Hz, 2H), 3.00-2.93 (m, 2H), 2.92-2.83 (m, 3H), 2.82-2.77 (m, 2H), 2.74 (d, J=5.6 Hz, 3H), 2.59 (d, J=2.4 Hz, 3H), 2.38-2.31 (m, 1H), 2.20 (d, J=6.8 Hz, 2H), 2.10-1.92 (m, 5H), 1.77 (s, 3H), 1.73-1.58 (m, 6H), 1.57-1.30 (m, 3H), 1.22-1.01 (m, 8H).

Example 98: Synthesis of 3-{4-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-1-oxo-2,3-dihydro-1H-isoindol-2-yl}piperidine-2,6-dione (Compound 126)

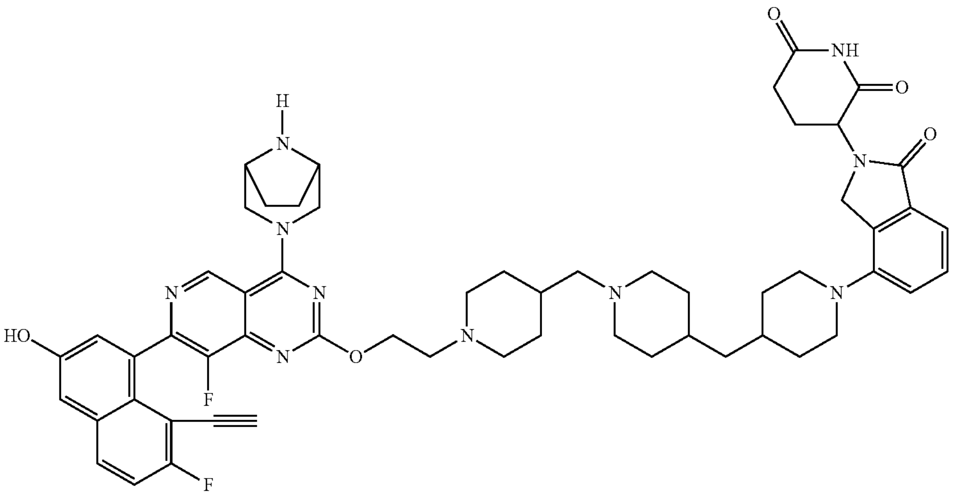 [SMILES: C#Cc1c(F)ccc2cc(O)cc(-c3ncc4c(N5CC6CCC(C5)N6)nc(OCCN5CCC(CN6CCC(CC7CCN(c8cccc9c8CN(C8CCC(=O)NC8=O)C9=O)CC7)CC6)CC5)nc4c3F)c12]

The title compound was made in an analogous manner to 3-[5-[4-[[1-[[1-[2-[4-(3,8-diazabicyclo[3.2.1]octan-3-yl)-7-(8-ethynyl-7-fluoro-3-hydroxy-1-naphthyl)-8-fluoropyrido[4,3-d]pyrimidin-2-yl]oxyethyl]-4-piperidyl]methyl]-4-piperidyl]methyl]-1-piperidyl]-1-oxo-isoindolin-2-yl]piperidine-2,6-dione. (light yellow solid). LC/MS (ESI) m/z: 1007.4 $[M+H]^+$; $^1$H NMR (400 MHz, $CD_3OD$-$d_4$) δ 9.00 (s, 1H), 7.88-7.84 (m, 1H), 7.45-7.42 (m, 2H), 7.35-7.30 (m, 2H), 7.24-7.21 (m, 2H), 5.16-5.12 (m, 1H), 4.66-4.56 (m, 5H), 4.48-4.47 (m, 2H), 3.73-3.66 (m, 4H), 3.40 (s, 1H), 3.38 (s, 2H), 3.13-3.10 (m, 2H), 3.01-2.99 (m, 2H), 2.92-2.86 (m, 3H), 2.80-2.73 (m, 3H), 2.58-2.50 (m, 1H), 2.34-2.31 (m, 2H), 2.24-2.07 (m, 5H), 1.87-1.72 (m, 10H), 1.48-1.22 (m, 10H).

Example 99: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-4-fluoro-1-oxo-2,3-dihydro-1H-isoindol-2-yl}piperidine-2,6-dione (Compound 88)

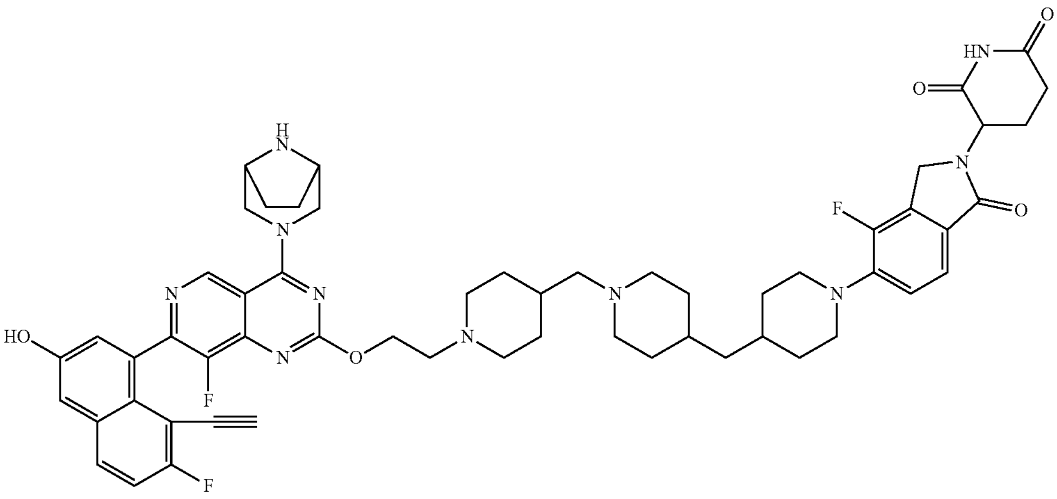 [SMILES: C#Cc1c(F)ccc2cc(O)cc(-c3ncc4c(N5CC6CCC(C5)N6)nc(OCCN5CCC(CN6CCC(CC7CCN(c8ccc9c(c8F)CN(C8CCC(=O)NC8=O)C9=O)CC7)CC6)CC5)nc4c3F)c12]

The title compound was made in an analogous manner to 3-[5-[4-[[1-[[1-[2-[4-(3,8-diazabicyclo[3.2.1]octan-3-yl)-7-(8-ethynyl-7-fluoro-3-hydroxy-1-naphthyl)-8-fluoropyrido[4,3-d]pyrimidin-2-yl]oxyethyl]-4-piperidyl]methyl]-4-piperidyl]methyl]-1-piperidyl]-1-oxo-isoindolin-2-yl]piperidine-2,6-dione. (yellow solid, formic acid salt). LC/MS (ESI) m/z: 1025.8 $[M+H]^+$; $^1H$ NMR (400 MHz, DMSO-$d_6$) δ 10.97 (s, 1H), 9.06 (s, 1H), 8.20 (s, 3H), 8.01-7.92 (m, 1H), 7.51-7.41 (m, 2H), 7.39 (d, J=2.4 Hz, 1H), 7.21-7.10 (m, 2H), 5.07 (dd, J=5.2, 13.2 Hz, 1H), 4.59-4.42 (m, 4H), 4.41-4.26 (m, 2H), 3.93 (s, 1H), 3.80-3.64 (m, 4H), 3.47 (d, J=1.2 Hz, 2H), 2.99-2.82 (m, 5H), 2.80-2.69 (m, 4H), 2.64-2.53 (m, 2H), 2.45-2.30 (m, 2H), 2.23-2.14 (m, 2H), 2.08-1.92 (m, 5H), 1.81-1.69 (m, 6H), 1.64 (t, J=11.6 Hz, 4H), 1.51 (d, J=1.6 Hz, 2H), 1.42-1.32 (m, 1H), 1.31-1.22 (m, 2H), 1.21-1.03 (m, 6H).

Example 100: Synthesis of 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione (Compound 89)

Step 1: Preparation of tert-butyl 4-[[1-[1-(2,6-dibenzyloxy-3-pyridyl)-3-methyl-2-oxo-benzimidazol-5-yl]-4-piperidyl]methyl]piperidine-1-carboxylate

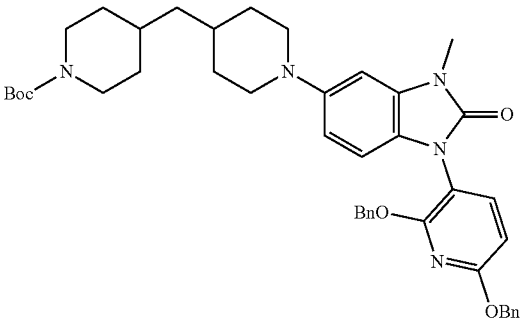 [SMILES: Cn1c(=O)n(-c2ccc(OCc3ccccc3)nc2OCc2ccccc2)c2ccc(N3CCC(CC4CCN(C(=O)OC(C)(C)C)CC4)CC3)cc21]

To a mixture of 5-bromo-1-(2,6-dibenzyloxy-3-pyridyl)-3-methyl-benzimidazol-2-one (1 g, 2 mmol), tert-butyl4-(4-piperidylmethyl)piperidine-1-carboxylate acetate (800 mg, 2 mmol), and cesium carbonate (1.89 g, 5.8 mmol) in 1,4-dioxane (30 mL) was added CPhos Pd G3 (156 mg, 0.2 mmol), and the mixture was stirred at 100° C. for 16 h under nitrogen atmosphere. The reaction mixture was filtered and concentrated under reduced pressure. The residue was purified by prep-HPLC (acetonitrile in water (formic acid) to afford the title compound (810 mg, 58%) as a brown solid. LC/MS (ESI) m/z: 718.5 $[M+H]^+$.

Step 2: Preparation of tert-butyl 4-[[1-[1-(2,6-dioxo-3-piperidyl)-3-methyl-2-oxo-benzimidazol-5-yl]-4-piperidyl]methyl]piperidine-1-carboxylate

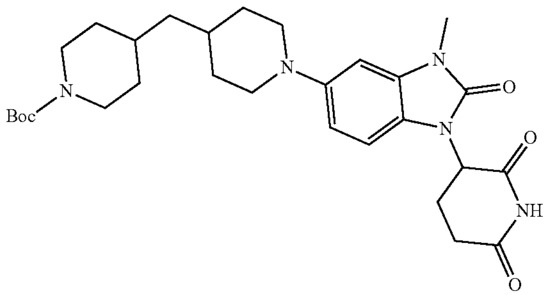 [SMILES: Cn1c(=O)n(C2CCC(=O)NC2=O)c2ccc(N3CCC(CC4CCN(C(=O)OC(C)(C)C)CC4)CC3)cc21]

To a solution of tert-butyl 4-[[1-[1-(2,6-dibenzyloxy-3-pyridyl)-3-methyl-2-oxo-benzimidazol-5-yl]-4-piperidyl]methyl]piperidine-1-carboxylate (810 mg, 1 mmol) in tetrahydrofuran (20 mL) was added 10% palladium on carbon (300 mg) under nitrogen atmosphere, and the resulting mixture was degassed under vacuum and purged with hydrogen several times. The mixture was stirred under hydrogen at 50° C. for 16 h. The reaction mixture was filtered and concentrated under reduced pressure to afford the title compound (570 mg, 94%) as a brown solid. LC/MS (ESI) m/z: 540.5 [M+H]$^+$.

Step 3: Preparation of 3-[3-methyl-2-oxo-5-[4-(4-piperidylmethyl)-1-piperidyl]benzimidazol-1-yl]piperidine-2,6-dione

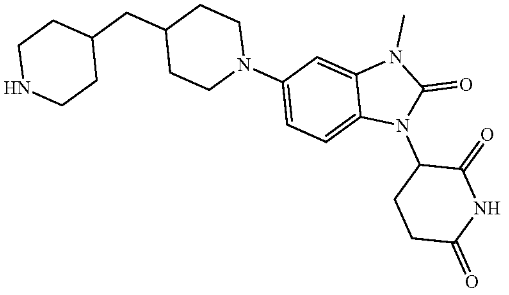 [SMILES: Cn1c(=O)n(C2CCC(=O)NC2=O)c2ccc(N3CCC(CC4CCNCC4)CC3)cc21]

To tert-butyl 4-[[1-[1-(2,6-dioxo-3-piperidyl)-3-methyl-2-oxo-benzimidazol-5-yl]-4-piperidyl]methyl]piperidine-1-carboxylate (570 mg, 1 mmol) in dichloromethane (3 mL) was added trifluoroacetic acid (1.0 mL, 13 mmol), and the mixture was stirred at 25° C. for 1 h. The reaction mixture was concentrated under reduced pressure. The residue was purified by prep-HPLC (1% to 20% acetonitrile in water (formic acid) over 11 min) to afford the title compound (520 mg, 93%, di-formic acid salt) as a yellow solid. LC/MS (ESI) m/z: 440.3 [M+H]$^+$.

Step 4: Preparation of tert-butyl 3-[2-[2-[4-[[1-[1-(2,6-dioxo-3-piperidyl)-3-methyl-2-oxo-benzimidazol-5-yl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

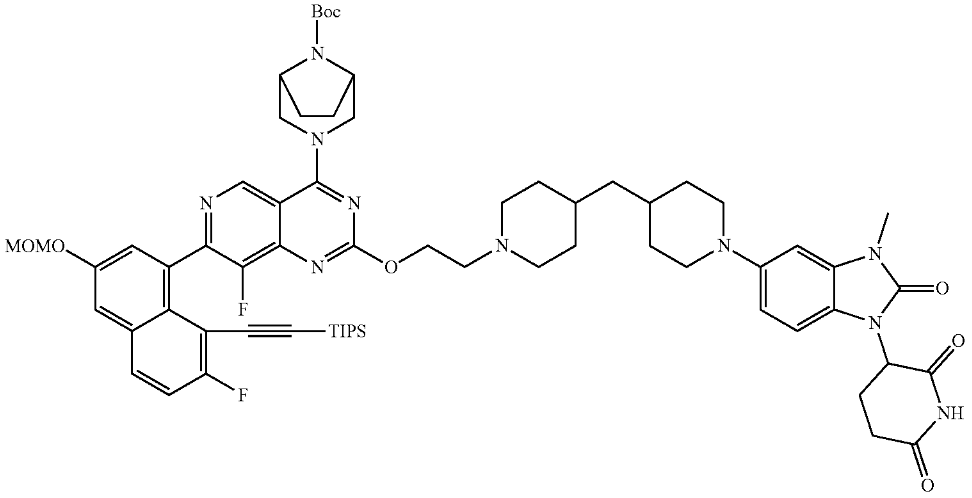

To a mixture of 3-[3-methyl-2-oxo-5-[4-(4-piperidylmethyl)-1-piperidyl]benzimidazol-1-yl]piperidine-2,6-dione (300 mg, 0.6 mmol, di-formic acid salt) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (498 mg, 0.6 mmol) in isopropanol (5 mL) and dichloromethane (5 mL) were added N,N-diisopropylethylamine (0.3 mL, 2 mmol) and sodium triacetoxyborohydride (239 mg, 1 mmol), and the mixture was stirred at 25° C. for 2 h. The reaction mixture was diluted with water (15 mL) and extracted with dichloromethane (3×30 mL). The combined organic extracts were washed with brine (15 mL), dried over anhydrous sodium sulfate, filtered, and concentrated under reduced pressure to afford the title compound (680 mg, crude) as a yellow solid. LC/MS (ESI) m/z: 1225.6 [M+H]$^+$.

Step 5: Preparation of tert-butyl 3-[2-[2-[4-[[1-[1-(2,6-dioxo-3-piperidyl)-3-methyl-2-oxo-benzimidazol-5-yl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

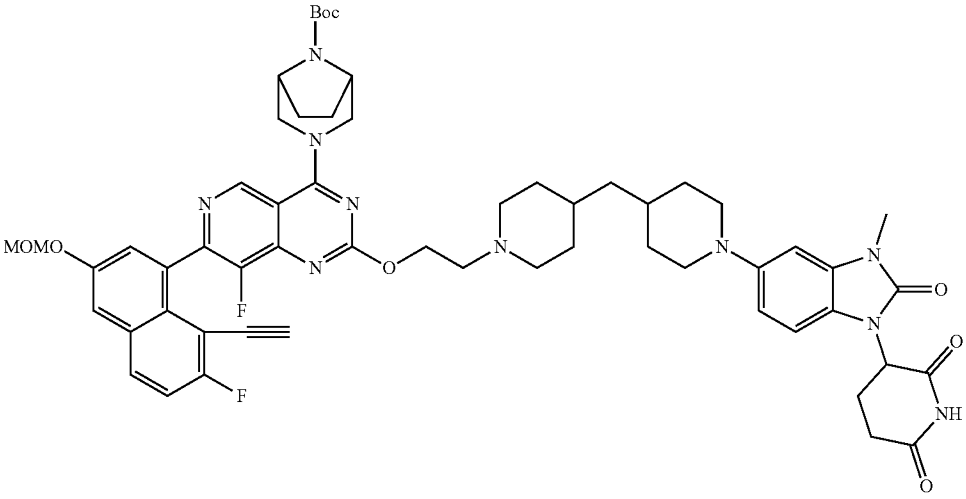

To a solution of tert-butyl 3-[2-[2-[4-[[1-[1-(2,6-dioxo-3-piperidyl)-3-methyl-2-oxo-benzimidazol-5-yl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (680 mg, 0.6 mmol) in N,N-dimethylformamide (5 mL) was added cesium fluoride (2.53 g, 17 mmol), and the mixture was stirred at 25° C. for 16 h.

The reaction was quenched with water (0.5 mL), and the crude solution was directly purified by prep-HPLC (25% to 55% acetonitrile in water (TFA) over 15 min) to afford the title compound (180 mg, 30%) as a yellow solid. LC/MS (ESI) m/z: 1069.5 [M+H]$^+$.

Step 6: Preparation of 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione

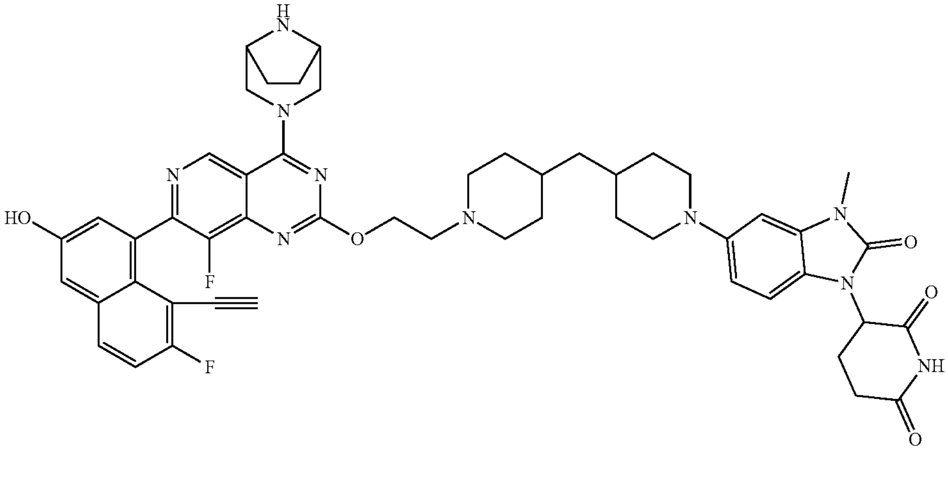 [SMILES: C#Cc1c(F)ccc2cc(O)cc(-c3ncc4c(N5CC6CCC(C5)N6)nc(OCCN5CCC(CC6CCN(c7ccc8c(c7)n(C)c(=O)n8C7CCC(=O)NC7=O)CC6)CC5)nc4c3F)c12]

To a solution of tert-butyl 3-[2-[2-[4-[[1-[1-(2,6-dioxo-3-piperidyl)-3-methyl-2-oxo-benzimidazol-5-yl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (180 mg, 0.2 mmol) in dichloromethane (4 mL) was added 4 M HCl in 1,4-dioxane (4 mL), and the reaction was stirred at 25° C. for 15 min. The mixture was triturated with petroleum ether (20 mL), then further purified by prep-HPLC (0% to 30% acetonitrile in water (formic acid) over 7 min) to afford the title compound (33.6 mg, 19%, di-formic acid salt) as a yellow solid. LC/MS (ESI) m/z: 925.3 $[M+H]^+$, $^1$HNMR (400 MHz, DMSO-$d_6$) δ 11.06 (br d, J=1.6 Hz, 1H), 9.05 (s, 1H), 8.20 (s, 2H), 7.97 (dd, J=6.0, 9.2 Hz, 1H), 7.46 (t, J=9.2 Hz, 1H), 7.39 (d, J=2.4 Hz, 1H), 7.18 (d, J=2.0 Hz, 1H), 6.91 (br d, J=8.8 Hz, 1H), 6.80 (s, 1H), 6.66-6.55 (m, 1H), 5.28 (br dd, J=5.2, 12.8 Hz, 1H), 4.54-4.43 (m, 3H), 4.36 (br d, J=11.2 Hz, 1H), 3.94 (s, 1H), 3.73-3.62 (m, 4H), 3.59-3.42 (m, 3H), 3.29 (s, 3H), 2.97-2.87 (m, 3H), 2.73-2.61 (m, 7H), 2.07-1.97 (m, 3H), 1.75-1.67 (m, 5H), 1.62 (br d, J=10.4 Hz, 2H), 1.51-1.31 (m, 3H), 1.29-1.20 (m, 2H), 1.19-1.06 (m, 4H).

Example 101: Synthesis of 3-(5-{2-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-2,7-diazaspiro[3.5]nonan-7-yl}-4-fluoro-7-methyl-1-oxo-2,3-dihydro-1H-isoindol-2-yl)piperidine-2,6-dione (Compound 154)

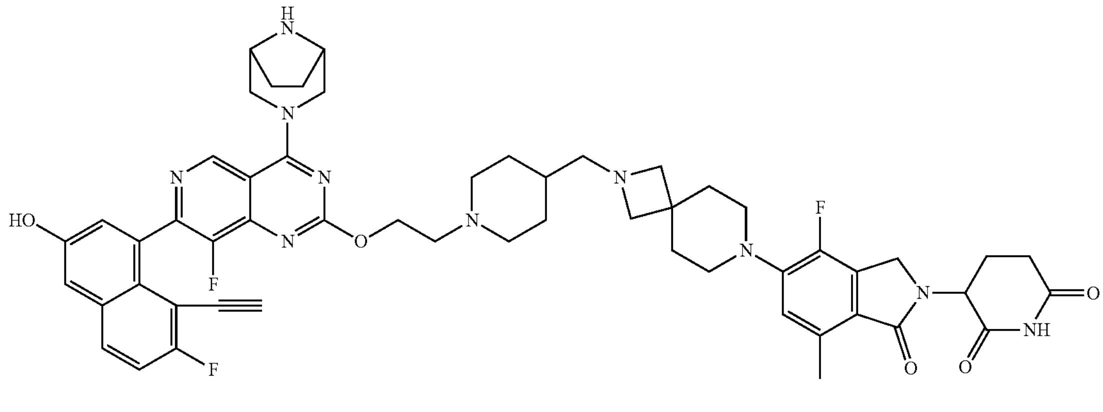 [SMILES: C#Cc1c(F)ccc2cc(O)cc(-c3ncc4c(N5CC6CCC(C5)N6)nc(OCCN5CCC(CN6CC7(CCN(c8cc(C)c9c(c8F)CN(C8CCC(=O)NC8=O)C9=O)CC7)C6)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione. (orange solid, formic acid salt). LC/MS (ESI) m/z: 983.2 $[M+H]^+$; $^1$H NMR (400 MHz, DMSO-$d_6$) δ 10.98 (s, 1H), 10.28 (brs, 1H), 9.13 (s, 1H), 8.14 (s, 1H), 7.99 (dd, J=6.0, 9.2 Hz, 1H), 7.48 (t, J=9.2 Hz, 1H), 7.41 (d, J=2.4 Hz, 1H), 7.18 (d, J=2.0 Hz, 1H), 6.89 (br d, J=7.2 Hz, 1H), 5.03 (br dd, J=5.0, 13.2 Hz, 1H), 4.74-4.57 (m, 3H), 4.53 (br d, J=13.6 Hz, 1H), 4.39 (br d, J=16.8 Hz, 1H), 4.26-4.14 (m, 3H), 3.95-3.83 (m, 6H), 3.16-2.97 (m, 8H), 2.94-2.85 (m, 1H), 2.61-2.52 (m, 7H), 2.45-2.37 (m, 3H), 1.95 (br d, J=9.6 Hz, 10H), 1.85-1.67 (m, 3H), 1.46-1.19 (m, 2H).

Example 102: Synthesis of 3-(4-{4-[2-(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)ethyl]piperidin-1-yl}-1-oxo-2,3-dihydro-1H-isoindol-2-yl)piperidine-2,6-dione (Compound 128)

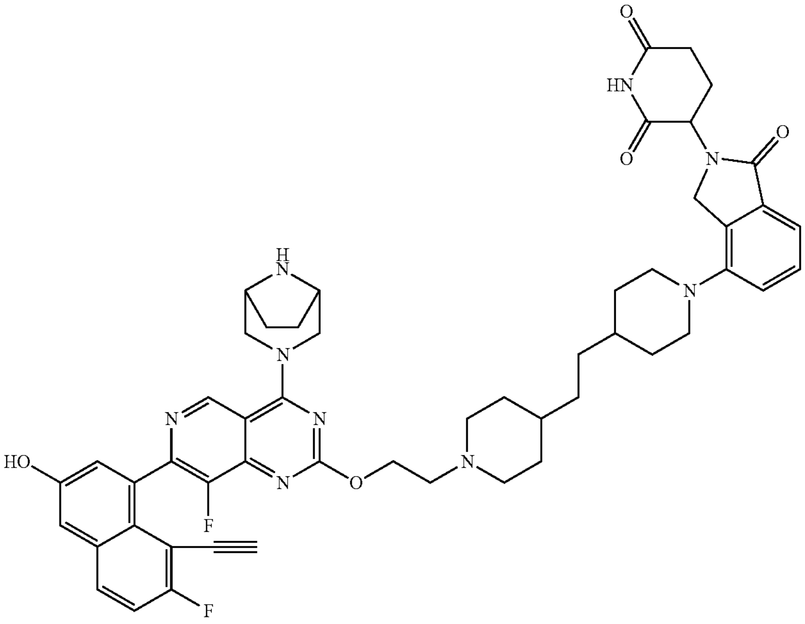 [SMILES: C#Cc1c(F)ccc2cc(O)cc(-c3ncc4c(N5CC6CCC(C5)N6)nc(OCCN5CCC(CCC6CCN(c7cccc8c7CN(C7CCC(=O)NC7=O)C8=O)CC6)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione. (yellow solid, formic acid salt). LC/MS (ESI) m/z: 924.6 $[M+H]^+$; $^1H$ NMR (400 MHz, DMSO-$d_6$) δ 10.97 (s, 1H), 9.04 (s, 1H), 8.17-8.15 (m, 1H), 7.97 (dd, J1=6.0 Hz, J2=9.2 Hz, 1H), 7.51-7.36 (m, 3H), 7.28 (d, J=7.2 Hz, 1H), 7.20-7.11 (m, 2H), 5.15-5.06 (m, 1H), 4.57-4.20 (m, 8H), 3.92 (s, 1H), 3.65-3.61 (m, 4H), 2.99-2.88 (m, 4H), 2.75-2.65 (m, 6H), 2.06-1.94 (m, 3H), 1.78-1.61 (m, 8H), 1.31-1.06 (m, 10H).

Example 110: Synthesis of 3-(4-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione (Compound 129)

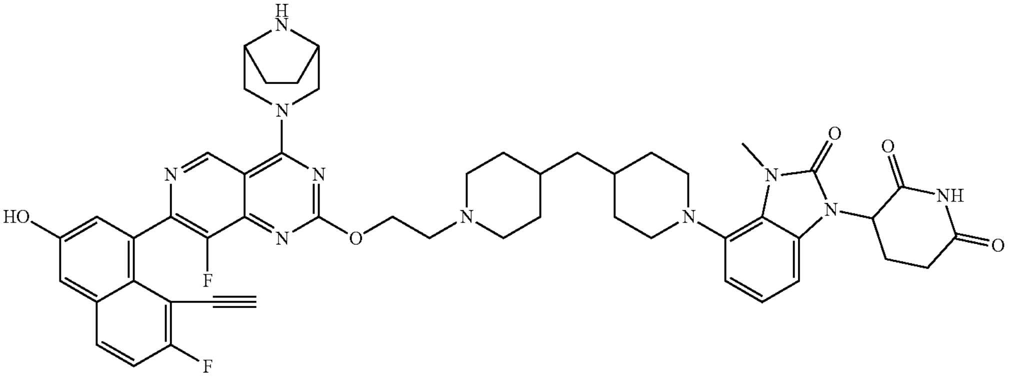 [SMILES: C#Cc1c(F)ccc2cc(O)cc(-c3ncc4c(N5CC6CCC(C5)N6)nc(OCCN5CCC(CC6CCN(c7cccc8c7n(C)c(=O)n8C7CCC(=O)NC7=O)CC6)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione. (yellow solid). LC/MS (ESI) m/z: 925.6 $[M+H]^+$; $^1H$ NMR (400 MHz, DMSO-$d_6$) δ 11.08 (s, 1H), 9.05 (s, 1H), 8.18 (s, 2H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 6.99-6.92 (m, 1H), 6.90-6.82 (m, 2H), 5.38-5.30 (m, 1H), 4.52-4.42 (m, 3H), 4.39-4.33 (m, 1H), 3.93 (s, 1H), 3.69 (s, 2H), 3.64 (s, 1H), 3.61 (s, 3H), 3.58 (s, 1H), 3.08 (d, J=9.6 Hz, 2H), 2.96 (d, J=10.4 Hz, 2H), 2.89-2.83 (m, 1H), 2.74-2.62 (m, 6H), 2.45 (s, 1H), 2.07-1.96 (m, 3H), 1.72 (s, 6H), 1.66-1.59 (m, 2H), 1.50-1.41 (m, 1H), 1.37-1.25 (m, 3H), 1.19-1.06 (m, 4H).

Example 103: Synthesis of 3-(4-{2-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-2,7-diazaspiro[3.5]nonan-7-yl}-1-oxo-2,3-dihydro-1H-isoindol-2-yl)piperidine-2,6-dione (Compound 140)

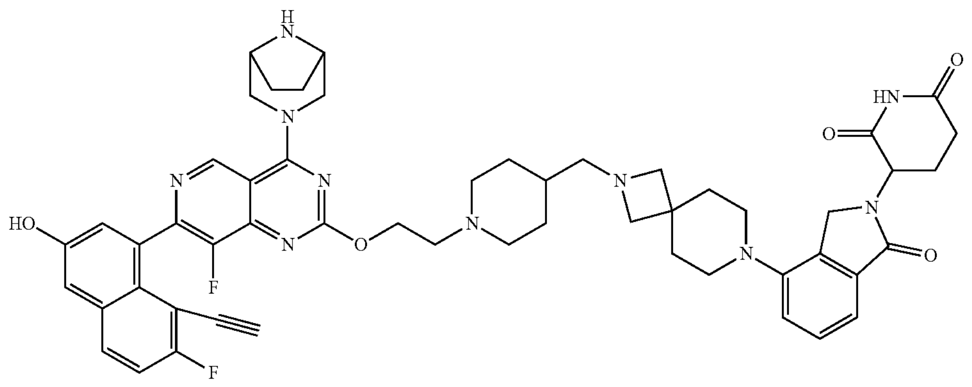 [SMILES: C#Cc1c(F)ccc2cc(O)cc(-c3ncc4c(N5CC6CCC(C5)N6)nc(OCCN5CCC(CN6CC7(CCN(c8cccc9c8CN(C8CCC(=O)NC8=O)C9=O)CC7)C6)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione. (yellow solid). LC/MS (ESI) m/z: 951.6 $[M+H]^+$; $^1H$ NMR (400 MHz, DMSO-$d_6$) δ 11.03-10.96 (m, 1H), 9.06 (s, 1H), 8.19 (s, 2H), 7.98 (dd, J=6.0, 9.2 Hz, 1H), 7.49-7.42 (m, 2H), 7.40 (d, J=2.4 Hz, 1H), 7.30 (d, J=7.6 Hz, 1H), 7.19-7.12 (m, 2H), 5.11 (dd, J=5.2, 13.2 Hz, 1H), 4.54 (d, J=12.4 Hz, 1H), 4.45 (d, J=6.0 Hz, 2H), 4.41-4.37 (m, 2H), 4.29-4.26 (m, 1H), 3.94 (s, 1H), 3.82 (s, 2H), 3.71 (s, 2H), 3.35 (s, 2H), 2.95 (d, J=6.0 Hz, 8H), 2.88 (d, J=5.4 Hz, 1H), 2.73-2.70 (m, 2H), 2.61 (s, 2H), 2.56 (s, 1H), 2.46-2.42 (m, 1H), 2.06-1.96 (m, 4H), 1.84 (s, 4H), 1.78 (s, 4H), 1.64 (d, J=10.8 Hz, 2H), 1.40 (dd, J=2.4, 7.6 Hz, 1H), 1.20-1.10 (m, 2H).

Example 104: Synthesis of 3-(5-{9-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-3,9-diazaspiro[5.5]undecan-3-yl}-4-fluoro-1-oxo-2,3-dihydro-1H-isoindol-2-yl)piperidine-2,6-dione (Compound 92)

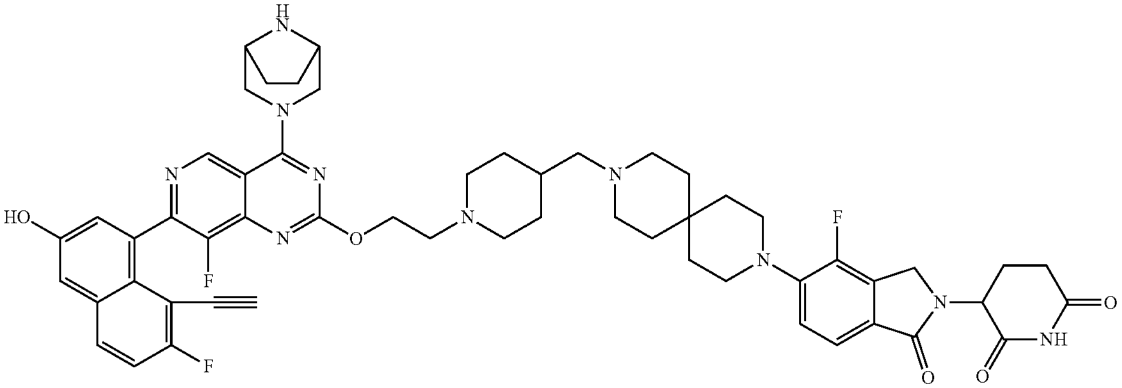 [SMILES: C#Cc1c(F)ccc2cc(O)cc(-c3ncc4c(N5CC6CCC(C5)N6)nc(OCCN5CCC(CN6CCC7(CC6)CCN(c6ccc8c(c6F)CN(C6CCC(=O)NC6=O)C8=O)CC7)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}-3-methyl-2-oxo-2,3-dihydro-1H-1,3-benzodiazol-1-yl)piperidine-2,6-dione. (yellow solid, formic acid salt.) LC/MS (ESI) m/z: 997.7 $[M+H]^+$, $^1H$ NMR (400 MHz, DMSO-$d_6$) δ 10.98 (s, 1H), 9.05 (s, 1H), 8.21 (s, 2H), 7.97 (dd, J=6.0, 9.2 Hz, 1H), 7.55-7.42 (m, 2H), 7.39 (d, J=2.4 Hz, 1H), 7.21-7.11 (m, 2H), 5.07 (dd, J=5.2, 13.2 Hz, 1H), 4.56-4.41 (m, 5H), 4.40-4.23 (m, 3H), 3.94 (s, 1H), 3.73-3.59 (m, 4H), 3.09 (b s, 4H), 2.99-2.86 (m, 3H), 2.71 (t, J=4.8 Hz, 2H), 2.58 (d, J=16.8 Hz, 1H), 2.46-2.31 (m, 5H), 2.19 (d, J=6.8 Hz, 2H), 2.11-1.89 (m, 3H), 1.74 (s, 4H), 1.65 (d, J=11.2 Hz, 2H), 1.60-1.39 (m, 9H), 1.20-0.99 (m, 2H).

Example 105: Synthesis of 3-(5-{9-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-3,9-diazaspiro[5.5]undecan-3-yl}-1-oxo-2,3-dihydro-1H-isoindol-2-yl)piperidine-2,6-dione (Compound 93)

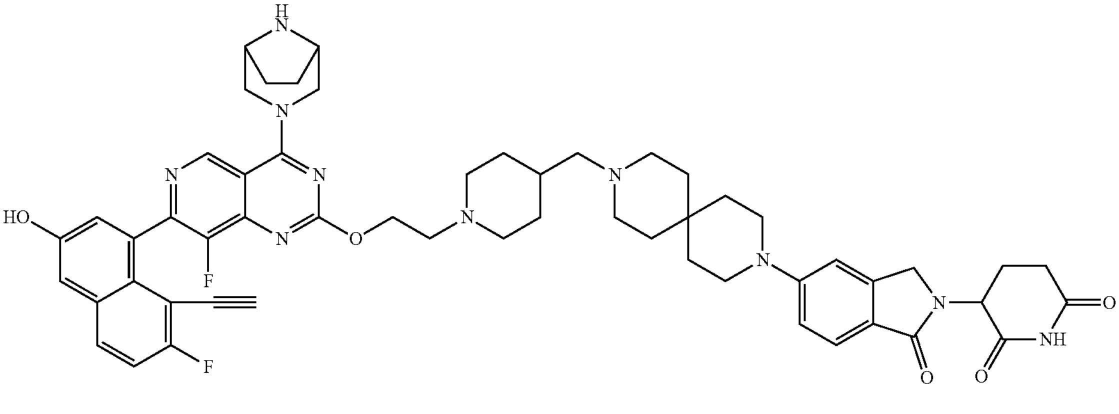 [SMILES: C#Cc1c(F)ccc2cc(O)cc(-c3ncc4c(N5CC6CCC(C5)N6)nc(OCCN5CCC(CN6CCC7(CC6)CCN(c6ccc8c(c6)CN(C6CCC(=O)NC6=O)C8=O)CC7)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl) methyl]piperidin-1-yl}-3-methyl-2-oxo-2,3-dihydro-1H-1, 3-benzodiazol-1-yl)piperidine-2,6-dione. (yellow solid, formic acid salt.) LC/MS (ESI) m/z: 979.7 $[M+H]^+$; $^1H$ NMR (400 MHz, DMSO-$d_6$) δ 10.94 (s, 1H), 9.04 (s, 1H), 8.20 (s, 2H), 7.96 (dd, J=6.0, 9.2 Hz, 1H), 7.58-7.42 (m, 2H), 7.38 (d, J=2.4 Hz, 1H), 7.17 (d, J=2.4 Hz, 1H), 7.07-6.95 (m, 2H), 5.03 (dd, J=5.2, 13.2 Hz, 1H), 4.50 (d, J=12.0 Hz, 1H), 4.44 (t, J=5.6 Hz, 2H), 4.39-4.31 (m, 2H), 4.28 (s, 1H), 4.17 (d, J=16.8 Hz, 2H), 3.93 (s, 1H), 3.70 (s, 2H), 3.67-3.60 (m, 2H), 3.28 (d, J=0.8 Hz, 4H), 2.98-2.82 (m, 3H), 2.70 (t, J=5.2 Hz, 2H), 2.62-2.53 (m, 1H), 2.43-2.26 (m, 5H), 2.21-2.12 (m, 2H), 2.08-1.88 (m, 3H), 1.73 (s, 4H), 1.68-1.59 (m, 2H), 1.48 (d, J=4.4 Hz, 9H), 1.17-0.94 (m, 2H).

Example 106: Synthesis of 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl] piperidin-1-yl}-2-oxo-3-(propan-2-yl)-2,3-dihydro-1H-1,3-benzodiazol-1-yl)piperidine-2,6-dione (Compound 175)

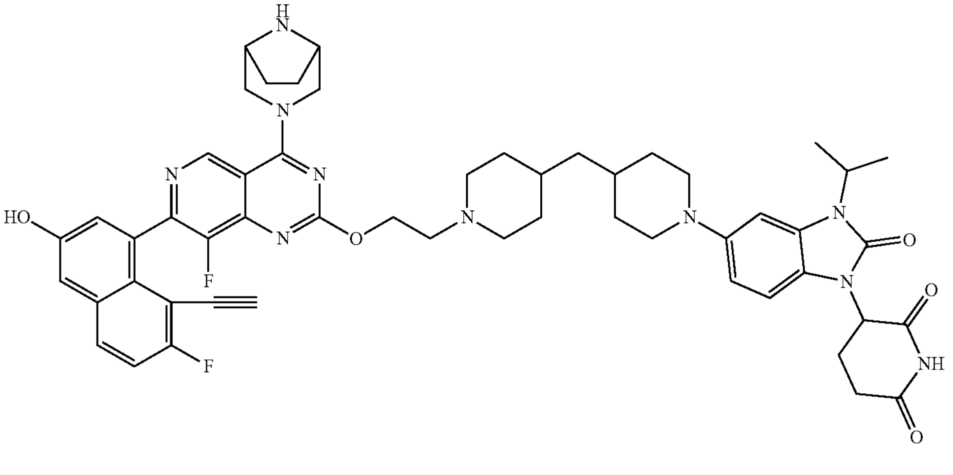 [SMILES: C#Cc1c(F)ccc2cc(O)cc(-c3ncc4c(N5CC6CCC(C5)N6)nc(OCCN5CCC(CC6CCN(c7ccc8c(c7)n(C(C)C)c(=O)n8C7CCC(=O)NC7=O)CC6)CC5)nc4c3F)c12]

The title compound was made in an analogous manner to 3-(5-{4-[(1-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}piperidin-4-yl) methyl]piperidin-1-yl}-3-methyl-2-oxo-2,3-dihydro-1H-1, 3-benzodiazol-1-yl)piperidine-2,6-dione. (yellow solid, formic acid salt). LC/MS (ESI) m/z: 953.6 $[M+H]^+$, $^1H$ NMR (400 MHz, DMSO-$d_6$) δ 11.05 (s, 1H), 9.08 (s, 1H), 8.15 (s, 2H), 7.98 (dd, J=6.0, 9.2 Hz, 1H), 7.47 (t, J=9.2 Hz, 1H), 7.40 (d, J=2.4 Hz, 1H), 7.18 (d, J=2.4 Hz, 1H), 6.94-6.84 (m, 2H), 6.64-6.57 (m, 1H), 5.26 (dd, J=5.6, 13.1 Hz, 1H), 4.61-4.54 (m, 2H), 4.53-4.46 (m, 2H), 4.42 (d, J=13.2 Hz, 1H), 3.94 (s, 1H), 3.90 (s, 2H), 3.75 (t, J=12.4 Hz, 3H), 3.52 (d, J=11.6 Hz, 4H), 3.01 (s, 3H), 2.90-2.83 (m, 1H), 2.78 (s, 2H), 2.68-2.60 (m, 2H), 2.58 (s, 1H), 2.54 (s, 1H), 2.12 (t, J=10.8 Hz, 2H), 2.01-1.92 (m, 1H), 1.82 (s, 4H), 1.71 (d, J=12.4 Hz, 2H), 1.67-1.61 (m, 2H), 1.44 (d, J=6.8 Hz, 6H), 1.29-1.20 (m, 2H), 1.19-1.08 (m, 4H).

Example 107: Synthesis of 3-[5-[4-[[4-[[1-[2-[4-(3, 8-diazabicyclo [3.2.1]octan-3-yl)-7-(8-ethynyl-7-fluoro-3-hydroxy-1-naphthyl)-8-fluoro-pyrido[4,3-d] pyrimidin-2-yl]oxyethyl]-4-fluoro-4-piperidyl] methyl]-1-piperidyl]methyl]-1-piperidyl]-1-oxo-isoindolin-2-yl]piperidine-2,6-dione (Compound 91)

Step 1: Preparation of tert-butyl 4-[[1-[[1-[2-(2,6-dioxo-3-piperidyl)-1-oxo-isoindolin-5-yl]-4-piperidyl]methyl]-4-piperidyl]methyl]-4-fluoro-piperidine-1-carboxylate

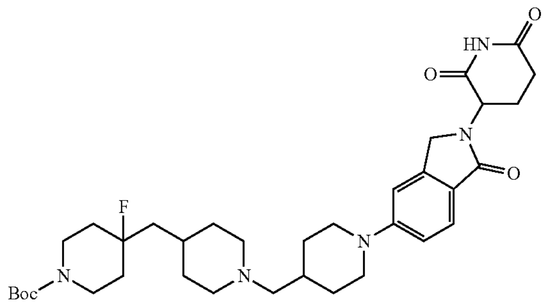 [SMILES: CC(C)(C)OC(=O)N1CCC(F)(CC2CCN(CC3CCN(c4ccc5c(c4)CN(C4CCC(=O)NC4=O)C5=O)CC3)CC2)CC1]

To a mixture of tert-butyl 4-fluoro-4-(4-piperidylmethyl) piperidine-1-carboxylate (700 mg, 2 mmol), diisopropylethylamine (0.8 mL, 5 mmol), and 1-[2-(2,6-dioxo-3-piperidyl)-1-oxo-isoindolin-5-yl]piperidine-4-carbaldehyde (911 mg, 2 mmol) in dimethyl sulfoxide (5 mL) and dichloromethane (5 mL) was added sodium triacetoxyborohydride (1.48 g, 7 mmol) under nitrogen atmosphere, and the mixture was stirred at 25° C. for 2 h. The reaction mixture was concentrated under reduced pressure, and the residue was purified by prep-HPLC (20% to 50% acetonitrile in water (formic acid) over 7 min) to afford the title compound (850 mg, 57%) as a white solid. LC/MS (ESI) m/z: 640.4 $[M+H]^+$.

Step 2: Preparation of 3-[5-[4-[[4-[(4-fluoro-4-piperidyl)methyl]-1-piperidyl]methyl]-1-piperidyl]-1-oxo-isoindolin-2-yl]piperidine-2,6-dione

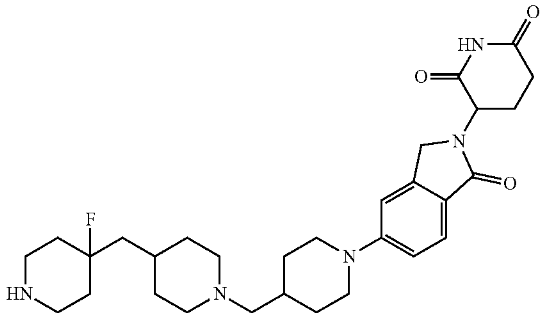 [SMILES: O=C1CCC(N2Cc3cc(N4CCC(CN5CCC(CC6(F)CCNCC6)CC5)CC4)ccc3C2=O)C(=O)N1]

To a mixture of tert-butyl 4-[[1-[[1-[2-(2,6-dioxo-3-piperidyl)-1-oxo-isoindolin-5-yl]-4-piperidyl]methyl]-4-piperidyl]methyl]-4-fluoro-piperidine-1-carboxylate (430 mg, 0.7 mmol) in dichloromethane (6 mL) was added trifluoroacetic acid (2.0 mL, 27 mmol) under nitrogen atmosphere, and the mixture was stirred at 20° C. for 1 h. The reaction mixture was concentrated under reduced pressure to afford the title compound (439 mg, crude, trifluoroacetate) as a yellow solid. LC/MS (ESI) m/z: 540.4 $[M+H]^+$.

Step 3: Preparation of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

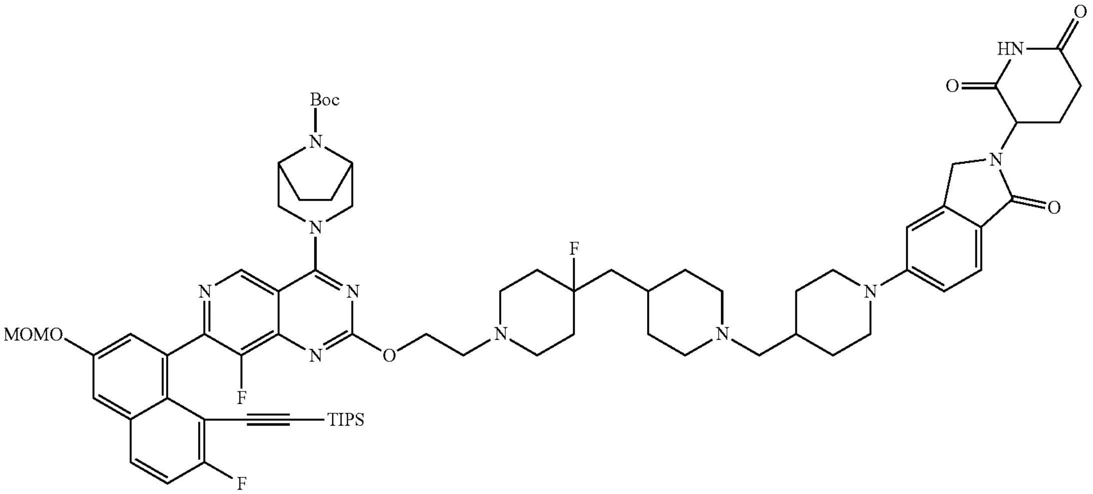

To a mixture of tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (592 mg, 0.7 mmol) and 3-[5-[4-[[4-[(4-fluoro-4-piperidyl)methyl]-1-piperidyl]methyl]-1-piperidyl]-1-oxo-isoindolin-2-yl]piperidine-2,6-dione (439 mg, 0.7 mmol, trifluoroacetate) in N,N-dimethylformamide (2 mL) were added sodium triacetoxyborohydride (427 mg, 2 mmol) and N,N-diisopropylethylamine (0.2 mL, 1 mmol) under nitrogen atmosphere, and the mixture was stirred at 20° C. for 16 h. The mixture was poured into ice-water (w/w=1/1, 10 mL) and extracted with ethyl acetate (10 mL×4). The combined organic extract was washed with brine (2×15 mL), dried over anhydrous sodium sulfate, filtered, and concentrated under reduced pressure. The residue was purified by prep-HPLC (30% to 60% acetonitrile in water (formic acid) over 9 min) to afford the title compound (530 mg, 59%) as a yellow solid. LC/MS (ESI) m/z: 1326.1 $[M+H]^+$.

Step 4: Preparation of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-4-fluoro-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

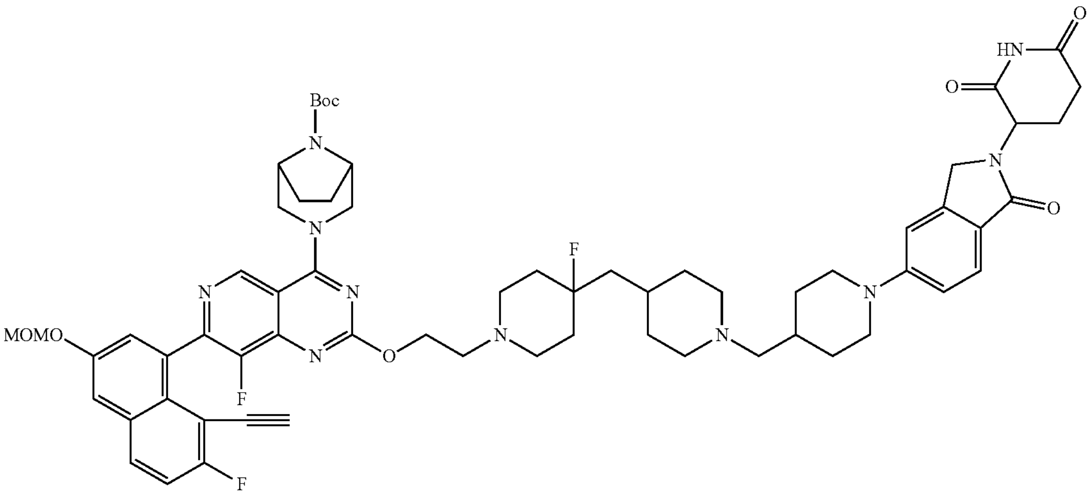

To tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-4-fluoro-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo [3.2.1]octane-8-carboxylate (460 mg, 0.4 mmol) in N,N-dimethylformamide (3 mL) was added cesium fluoride (1.05 g, 7 mmol) under nitrogen atmosphere, and the reaction mixture was stirred at 25° C. for 1 h. The mixture was concentrated under reduced pressure, and the residue was purified by prep-HPLC (22% to 52% acetonitrile in water (formic acid) over 7 min) to afford the title compound (280 mg, 69%) as a yellow solid. LC/MS (ESI) m/z: 1169.9 $[M+H]^+$.

Step 5: Preparation of 3-[5-[4-[[4-[[1-[2-[4-(3,8-diazabicyclo [3.2.1]octan-3-yl)-7-(8-ethynyl-7-fluoro-3-hydroxy-1-naphthyl)-8-fluoro-pyrido[4,3-d] pyrimidin-2-yl]oxyethyl]-4-fluoro-4-piperidyl] methyl]-1-piperidyl]methyl]-1-piperidyl]-1-oxo-isoindolin-2-yl]piperidine-2,6-dione

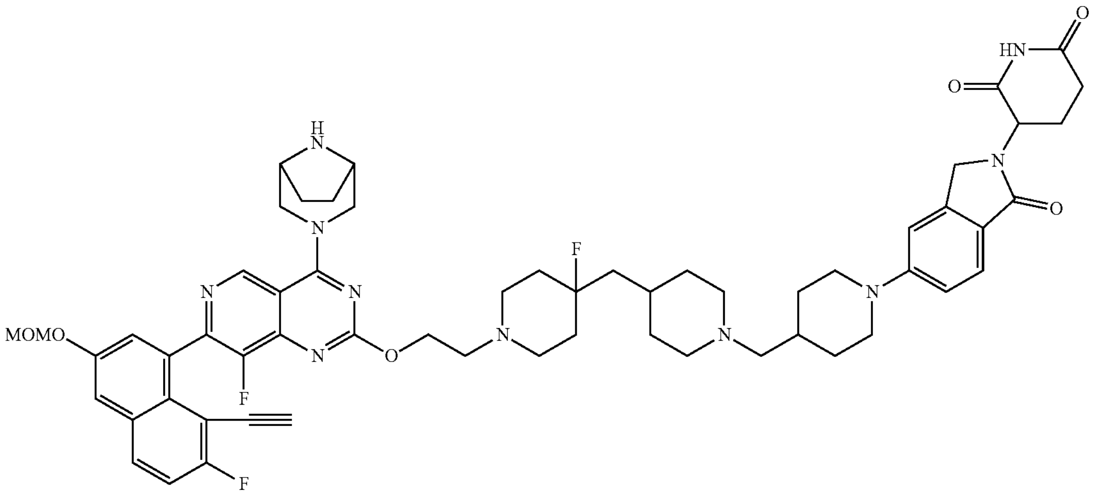

To a solution of tert-butyl 3-[2-[2-[4-[[1-[[1-[2-(2,6-dioxo-3-piperidyl)-1-oxo-isoindolin-5-yl]-4-piperidyl]methyl]-4-piperidyl]methyl]-4-fluoro-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (280 mg, 0.2 mmol) in dichloromethane (4 mL) was added 4 M HCl in 1,4-dioxane (4 mL), and the reaction mixture was stirred at 20° C. for 15 min. The mixture was suspended in petroleum ether (5 mL), filtered, and the filter cake was purified by prep-HPLC (0% to 30% acetonitrile in water (formic acid) over 7 min) to afford the title compound (102.6 mg, 38%, di-formic acid salt) as a yellow solid. LC/MS (ESI) m/z: 1025.5 $[M+H]^+$; $^1H$ NMR (400 MHz, DMSO-$d_6$) δ 10.94 (s, 1H), 9.05 (s, 1H), 8.18 (s, 2H), 7.98 (dd, J=6.0, 9.2 Hz, 1H), 7.51-7.43 (m, 2H), 7.39 (d, J=2.4 Hz, 1H), 7.17 (d, J=2.4 Hz, 1H), 7.05-6.99 (m, 2H), 5.04 (dd, J=5.2, 1 Step 2: Hz, 1H), 4.57-4.40 (m, 4H), 4.40-4.32 (m, 2H), 4.29 (s, 1H), 4.23-4.14 (m, 2H), 3.93 (d, J=0.8 Hz, 1H), 3.87 (s, 1H), 3.84 (s, 1H), 3.65 (d, J=14.4 Hz, 4H), 2.89 (s, 1H), 2.81 (d, J=11.2 Hz, 4H), 2.72 (d, J=5.6 Hz, 4H), 2.61-2.55 (m, 1H), 2.35-2.24 (m, 3H), 2.16 (d, J=6.0 Hz, 2H), 1.99-1.88 (m, 3H), 1.74 (s, 8H), 1.66 (d, J=12.0 Hz, 3H), 1.56-1.43 (m, 4H), 1.24-1.11 (m, 4H).

Example 108: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-fluoropiperidin-4-yl)methyl]piperidin-1-yl}methyl)piperidin-1-yl]-1-oxo-2,3-dihydro-1H-isoindol-2-yl}piperidine-2,6-dione (Compound 124)

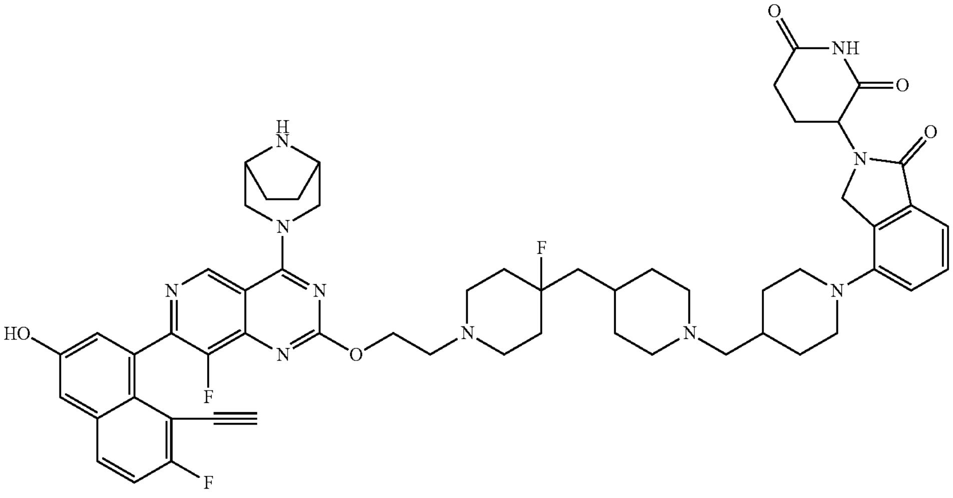 [SMILES: C#Cc1c(F)ccc2cc(O)cc(-c3ncc4c(N5CC6CCC(C5)N6)nc(OCCN5CCC(F)(CC6CCN(CC7CCN(c8cccc9c8CN(C8CCC(=O)NC8=O)C9=O)CC7)CC6)CC5)nc4c3F)c12]

The title compound was prepared in an analogous manner to 3-[5-[4-[[4-[[1-[2-[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-1-oxo-isoindolin-2-yl]piperidine-2,6-dione. (yellow solid, formic acid salt). LC/MS (ESI) m/z: 1025.3 $[M+H]^+$; $^1H$ NMR (400 MHz, DMSO-$d_6$) δ 11.00 (s, 1H), 9.11 (s, 1H), 8.16 (s, 1H), 7.99 (dd, J=6.0, 9.2 Hz, 1H), 7.57-7.38 (m, 3H), 7.32 (d, J=7.6 Hz, 1H), 7.24-7.11 (m, 2H), 5.12 (dd, J=5.2, 13.2 Hz, 1H), 4.65 (br d, J=12.8 Hz, 1H), 4.56-4.48 (m, 3H), 4.44 (br d, J=17.6 Hz, 1H), 4.29 (br d, J=17.2 Hz, 1H), 4.16 (br s, 2H), 3.95 (s, 1H), 3.83 (br d, J=13.6 Hz, 2H), 3.45-3.33 (m, 4H), 3.23 (br d, J=9.2 Hz, 2H), 2.97-2.89 (m, 1H), 2.81 (br d, J=6.0 Hz, 4H), 2.75 (br d, J=12.0 Hz, 3H), 2.60 (br d, J=16.0 Hz, 2H), 2.53 (br d, J=2.0 Hz, 1H), 2.49-2.34 (m, 4H), 2.05-1.92 (m, 5H), 1.82 (br t, J=11.6 Hz, 6H), 1.71 (br d, J=10.0 Hz, 2H), 1.62-1.48 (m, 3H), 1.45-1.26 (m, 4H).

Example 109: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-4-fluoropiperidin-1-yl}methyl)piperidin-1-yl]-1-oxo-2,3-dihydro-1H-isoindol-2-yl}piperidine-2,6-dione (Compound 90)

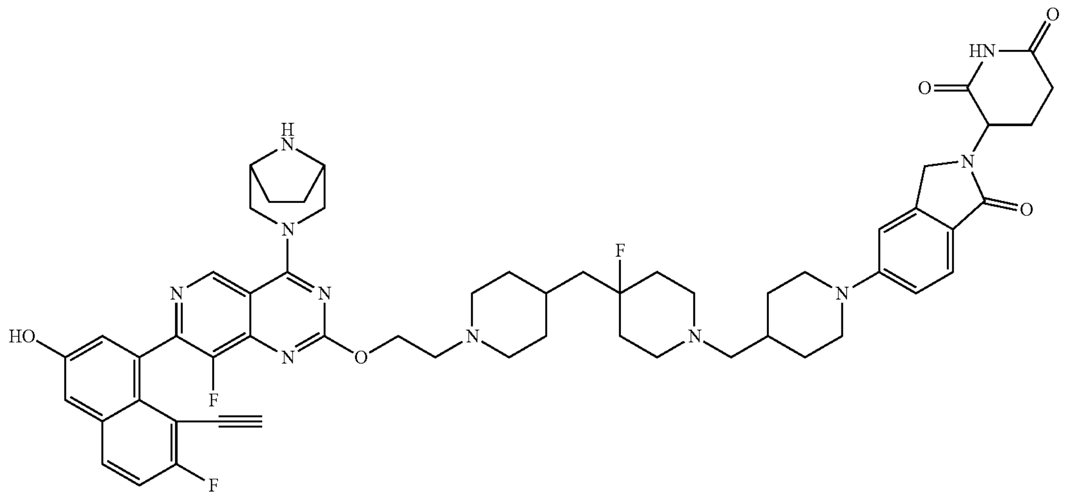 [SMILES: C#Cc1c(F)ccc2cc(O)cc(-c3ncc4c(N5CC6CCC(C5)N6)nc(OCCN5CCC(CC6(F)CCN(CC7CCN(c8ccc9c(c8)CN(C8CCC(=O)NC8=O)C9=O)CC7)CC6)CC5)nc4c3F)c12]

The title compound was prepared in an analogous manner to 3-[5-[4-[[4-[[1-[2-[4-(3,8-diazabicyclo [3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-1-oxo-isoindolin-2-yl]piperidine-2,6-dione. (yellow solid, formic acid salt). LC/MS (ESI) m/z: 1024.9 $[M+H]^+$; $^1H$ NMR (400 MHz, DMSO-$d_6$) δ 10.94 (s, 1H), 8.99 (s, 1H), 8.20 (s, 3H), 7.97 (dd, J=6.0, 8.8 Hz, 1H), 7.53-7.42 (m, 2H), 7.39 (s, 1H), 7.22-7.08 (m, 1H), 7.07-6.93 (m, 2H), 5.04 (dd, J=5.2, 13.2 Hz, 1H), 4.36-4.13 (m, 5H), 3.90-3.81 (m, 5H), 3.62 (s, 10H), 2.94-2.75 (m, 6H), 2.64-2.52 (m, 4H), 2.39-2.28 (m, 2H), 2.18-2.08 (m, 4H), 2.02-1.91 (m, 2H), 1.80-1.62 (m, 9H), 1.60-1.34 (m, 7H), 1.25-1.07 (m, 3H).

Example 110: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]methyl}-1-methylpyrrolidin-3-yl]oxy}piperidin-1-yl)methyl]piperidin-1-yl}-2-oxo-3-(propan-2-yl)-2,3-dihydro-1H-1,3-benzodiazol-1-yl)piperidine-2,6-dione (Compound 95)

Step 1: Preparation of tert-butyl 3-[2-[[(2S,4R)-4-[[1-[[1-[1-(2,6-dioxo-3-piperidyl)-3-isopropyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

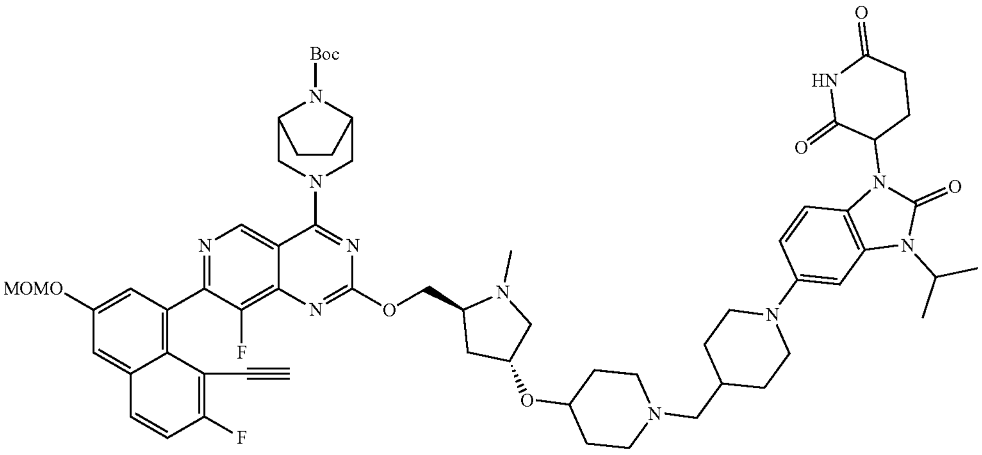

To a solution of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate (200 mg, 0.2 mmol, formate) and 1-[1-(2,6-dioxo-3-piperidyl)-3-isopropyl-2-oxo-benzimidazol-5-yl]piperidine-4-carbaldehyde (113 mg, 0.3 mmol) in dichloromethane (5 mL) and isopropanol (5 mL) were added N,N-diisopropylethylamine (0.1 mL, 0.7 mmol) and sodium triacetoxyborohydride (100 mg, 0.5 mmol), and the mixture was stirred at 25° C. for 2 h. The reaction mixture was diluted with water (15 mL) and extracted with dichloromethane (3×30 mL). The combined organic extracts were washed with brine (15 mL), dried over anhydrous sodium sulfate, filtered, and concentrated under reduced pressure. The residue was purified by prep-HPLC (22% to 52% acetonitrile in water (trifluoroacetic acid) over 15 min) to afford the title compound (270 mg, 97%, TFA salt) as an orange solid. LC/MS (ESI) m/z: 1182.9 $[M+H]^+$.

Step 2: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-2-oxo-3-(propan-2-yl)-2,3-dihydro-1H-1,3-benzodiazol-1-yl)piperidine-2,6-dione

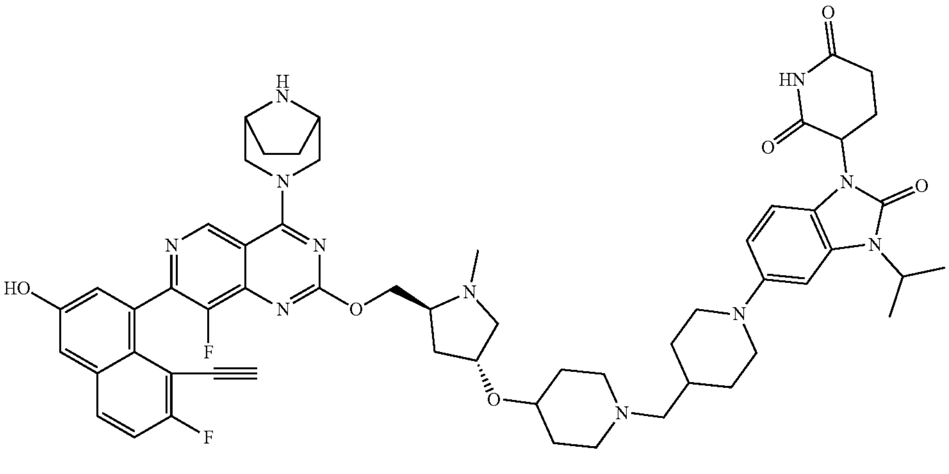 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8)n(C(C)C)c(=O)n9C8CCC(=O)NC8=O)CC7)CC6)CN5C)nc4c3F)c12]

To a solution of tert-butyl 3-[2-[[(2S,4R)-4-[[1-[[1-[1-(2,6-dioxo-3-piperidyl)-3-isopropyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (270 mg, 0.2 mmol) in dichloromethane (4 mL) was added 4 M HCl in 1,4-dioxane (2 mL), and the mixture was stirred at 25° C. for 0.5 h. The reaction mixture was triturated with ethyl acetate/methyl tert-butyl ether (1/10, 100 mL), then further purified by prep-HPLC (1% to 30% acetonitrile in water (formic acid) over 10 min) to afford the title compound (110.7 mg, 42%, di-formic acid salt) as a yellow solid. LC/MS (ESI) 10 m/z: 1038.7 $[M+H]^+$; $^1$HNMR (400 MHz, DMSO-$d_6$) δ 11.06 (s, 1H), 9.06 (s, 1H), 8.20 (s, 2H), 7.97 (dd, J=9.2, 6.0 Hz, 1H), 7.46 (t, J=9.2 Hz, 1H), 7.39 (d, J=2.4 Hz, 1H), 7.18 (d, J=2.4 Hz, 1H), 6.94-6.84 (m, 2H), 6.61 (dd, J=8.8, 1.6 Hz, 1H), 5.26 (br dd, J=12.8, 5.2 Hz, 1H), 4.64-4.47 (m, 3H), 4.37 (br dd, J=11.2, 4.8 Hz, 2H), 4.24 (dt, J=10.8, 5.2 Hz, 2H), 4.16-4.07 (m, 2H), 3.94 (d, J=2.0 Hz, 1H), 3.74 (br s, 3H), 3.69-3.62 (m, 2H), 3.53 (br d, J=11.2 Hz, 2H), 3.34-3.24 (m, 2H), 2.93-2.75 (m, 2H), 2.71-2.65 (m, 2H), 2.64-2.56 (m, 3H), 2.35 (s, 3H), 2.21-2.14 (m, 3H), 2.08-1.95 (m, 3H), 1.92-1.85 (m, 2H), 1.84-1.73 (m, 8H), 1.44 (d, J=6.8 Hz, 8H), 1.29-1.17 (m, 2H).

Example 111: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione (Compound 96)

Step 1: Preparation of tert-butyl 3-[2-[[(2S,4R)-4-[[1-[[1-[1-(2,6-dioxo-3-piperidyl)-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

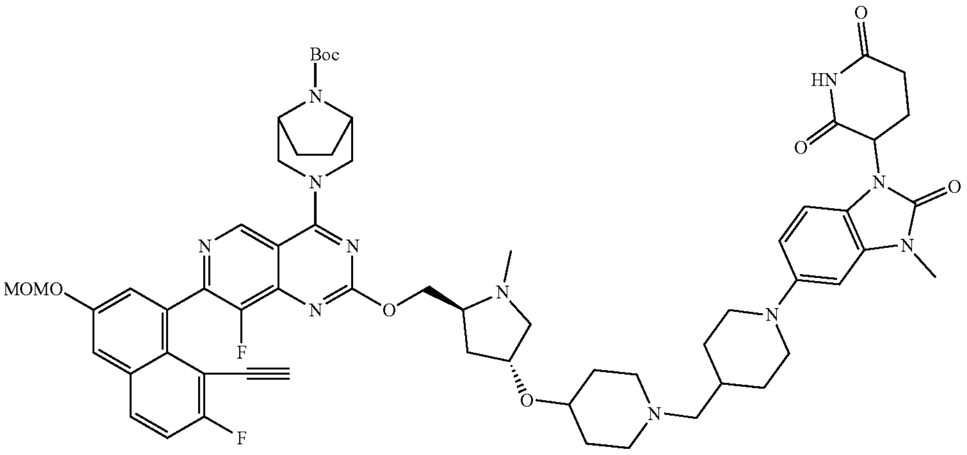

To a solution of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d] pyrimidin-4-yl]-3,8-diazabicyclo[3.2.1]octane-8-carboxylate (210 mg, 0.3 mmol, formate) in dichloromethane (3 mL) and isopropanol (3 mL) at 25° C. were added N,N-diisopropylethylamine (0.1 mL, 0.7 mmol), 1-[1-(2,6-dioxo-3-piperidyl)-3-methyl-2-oxo-benzimidazol-5-yl]piperidine-4-carbaldehyde (130 mg, 0.3 mmol, trifluoroacetate), and sodium triacetoxyborohydride (105 mg, 0.5 mmol), and the reaction mixture was stirred at at 25° C. for 2 h. The mixture was diluted with water (10 mL) and extracted with dichloromethane/isopropanol (2/1, 3×10 mL). The combined organic extracts were washed with brine (10 mL), dried over anhydrous sodium sulfate, filtered, and concentrated under reduced pressure. The residue was purified by preparative HPLC (22%-52% acetonitrile in water (TFA) over 9 min) to afford the title compound (150 mg, 44%, di-TFA salt) as a brown solid. LC/MS (ESI) m/z: 1154.6 $[M+H]^+$.

Step 2: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-3-methyl-2-oxo-2,3-dihydro-1H-1,3-benzodiazol-1-yl)piperidine-2,6-dione

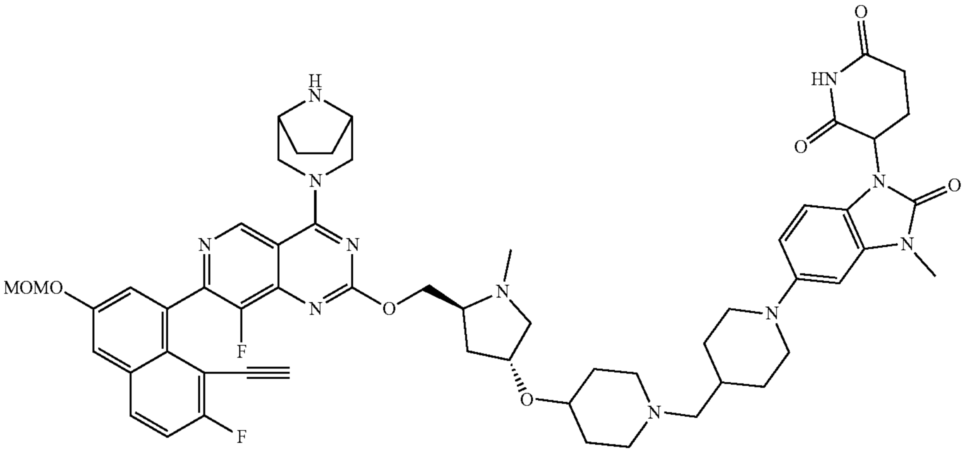

To a solution of tert-butyl 3-[2-[[(2S,4R)-4-[[1-[[1-[1-(2,6-dioxo-3-piperidyl)-3-methyl-2-oxo-benzimidazol-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (150 mg, 0.1 mmol, di-trifluoroacetate) in dichloromethane (5 mL) at 25° C. was added 4 M HCl in 1,4-dioxane (3 mL), and the reaction mixture was stirred for 15 min. The mixture was suspended in methyl tert-butyl ether (50 mL), filtered, and the filter cake was purified by preparative HPLC (1%-30% acetonitrile in water (formic acid) over 10 min) to afford the title compound (78.1 mg, 63%, tri-formic acid salt) as an orange solid. LC/MS (ESI) m/z: 1010.7 $[M+H]^+$, $^1H$ NMR (400 MHz, DMSO-$d_6$) δ 11.06 (s, 1H), 9.07 (s, 1H), 8.20 (s, 3H), 7.98 (dd, J=6.0, 9.2 Hz, 1H), 7.47 (t, J=9.2 Hz, 1H), 7.40 (d, J=2.4 Hz, 1H), 7.19 (d, J=2.4 Hz, 1H), 6.92 (d, J=8.8 Hz, 1H), 6.81 (d, J=2.0 Hz, 1H), 6.62 (dd, J=2.0, 8.8 Hz, 1H), 5.29 (dd, J=5.6, 12.8 Hz, 1H), 4.58-4.53 (m, 1H), 4.42-4.37 (m, 2H), 4.28-4.24 (m, 2H), 4.16-4.12 (m, 2H), 3.95-3.93 (m, 1H), 3.80-3.78 (m, 2H), 3.72-3.68 (m, 2H), 3.59-3.53 (m, 2H), 3.31-3.24 (m, 5H), 2.90-2.67 (m, 5H), 2.65-2.56 (m, 3H), 2.36 (s, 3H), 2.23-2.16 (m, 3H), 2.10-1.96 (m, 3H), 1.94-1.86 (m, 2H), 1.84-1.73 (m, 8H), 1.66-1.56 (m, 1H), 1.48-1.37 (m, 2H), 1.29-1.17 (m, 2H).

Example 112: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-2-oxo-3-(propan-2-yl)-2,3-dihydro-1H-1,3-benzodiazol-1-yl}piperidine-2,6-dione (Compound 98)

Step 1: Preparation of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylat

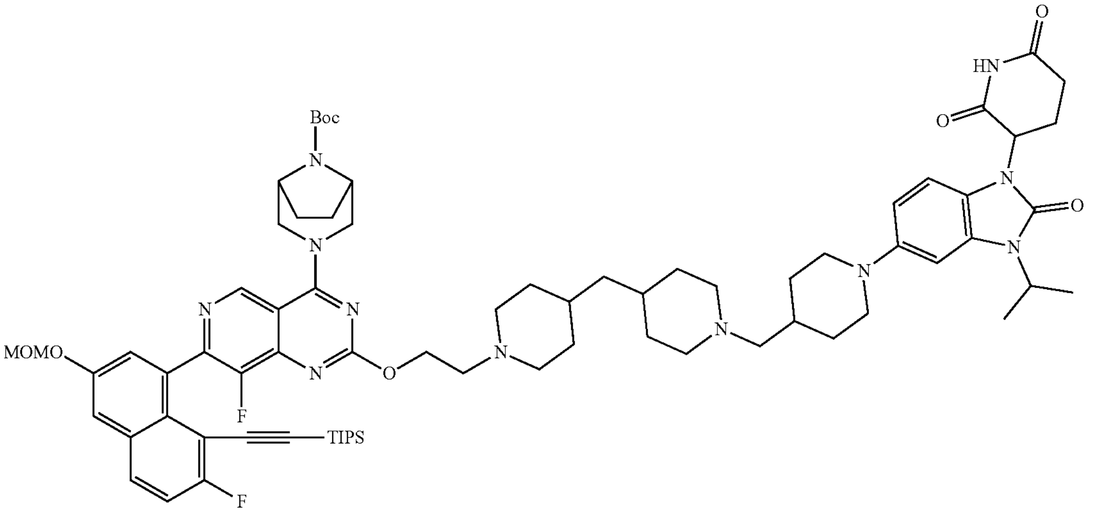

To a mixture of tert-butyl tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (334 mg, 0.4 mmol) and 3-[3-isopropyl-2-oxo-5-[4-[[4-(4-piperidylmethyl)-1-piperidyl]methyl]-1-piperidyl]benzimidazol-1-yl]piperidine-2,6-dione di-trifluoroacetate (300 mg, 0.4 mmol) in dichloromethane (5 mL) and isopropanol (5 mL) were added N,N-diisopropylethylamine (0.2 mL, 1 mmol) and sodium triacetoxyborohydride (160 mg, 0.8 mmol), and the mixture was stirred at 25° C. for 2 h. The reaction mixture was diluted with water (15 mL) and extracted with dichloromethane (3×30 mL). The combined organic layers were washed with brine (15 mL), dried over anhydrous sodium sulfate, filtered, and concentrated under reduced pressure to afford the title compound (480 mg, 94%) as a yellow solid. LC/MS (ESI) m/z: 1350.9 $[M+H]^+$.

Step 2: Preparation of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

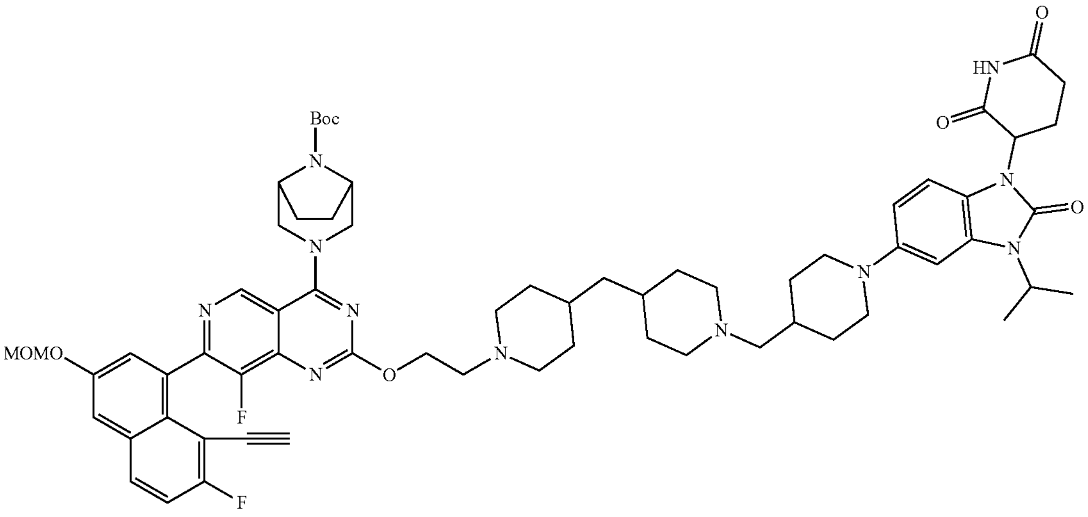

To a solution of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (560 mg, 0.4 mmol) in N,N-dimethylformamide (5 mL) was added cesium fluoride (1.89 g, 12 mmol), and the mixture was stirred at 25° C. for 2 h. The reaction mixture was quenched with water (0.5 mL), and the crude solution was directly purified by prep-HPLC (22% to 52% acetonitrile in water (trifluoroacetic acid) over 15 min) to afford the title compound (300 mg, 61%, TFA salt) as a colorless solid. LC/MS (ESI) m/z: 1195.8 $[M+H]^+$.

Step 3: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-2-oxo-3-(propan-2-yl)-2,3-dihydro-1H-1,3-benzodiazol-1-yl}piperidine-2,6-dione

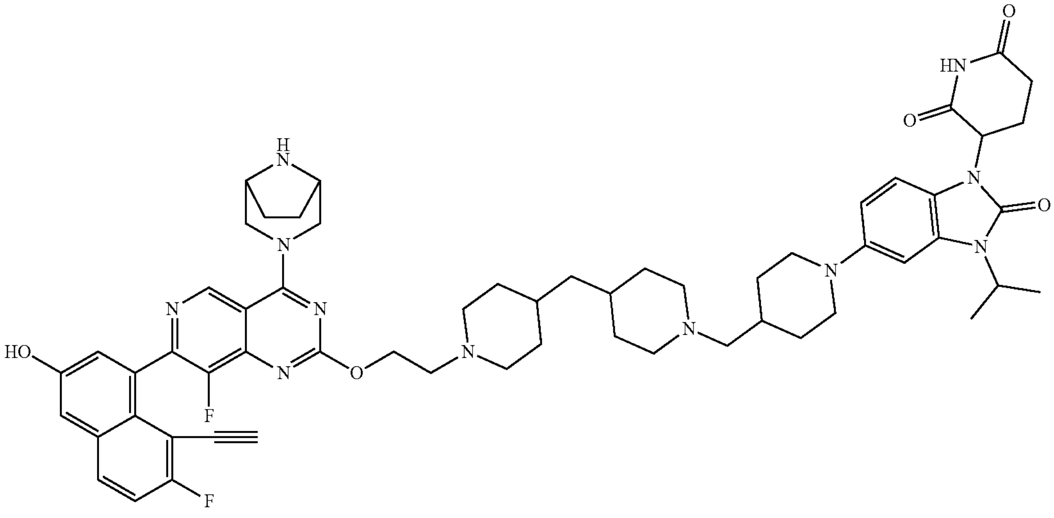 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)n(C(C)C)c(=O)n9C8CCC(=O)NC8=O)CC7)CC6)CC5)nc4c3F)c12]

To a solution of tert-butyl 3-[2-[2-[4-[[1-[[1-[1-(2,6-dioxo-3-piperidyl)-3-isopropyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (300 mg, 0.3 mmol) in dichloromethane (4 mL) was added 4 M HCl in 1,4-dioxane (2 mL), and the mixture was stirred at 25° C. for 1 h. The reaction mixture was triturated with ethyl acetate/methyl tert-butyl ether (1/10, 100 mL), then purified by prep-HPLC (1% to 30% acetonitrile in water (formic acid) over 10 min) to afford the title compound (117.4 mg, 40%, di-formic acid salt) as a yellow solid. LC/MS (ESI) m/z: 1050.7 $[M+H]^+$; $^1$HNMR (400 MHz, DMSO-$d_6$) δ 11.06 (s, 1H), 9.04 (s, 1H), 8.18 (s, 2H), 8.01-7.93 (m, 1H), 7.46 (t, J=9.2 Hz, 1H), 7.39 (d, J=2.4 Hz, 1H), 7.17 (d, J=2.4 Hz, 1H), 6.95-6.84 (m, 2H), 6.64-6.59 (m, 1H), 5.30-5.22 (m, 1H), 4.60-4.54 (m, 1H), 4.52-4.42 (m, 3H), 4.34 (br d, J=11.2 Hz, 1H), 3.93 (s, 1H), 3.67-3.58 (m, 5H), 3.51 (br s, 2H), 2.97-2.80 (m, 6H), 2.72-2.65 (m, 3H), 2.64-2.55 (m, 4H), 2.17 (br d, J=6.4 Hz, 2H), 2.03-1.94 (m, 3H), 1.92-1.83 (m, 2H), 1.76 (br d, J=12.8 Hz, 2H), 1.70 (br s, 3H), 1.63-1.55 (m, 5H), 1.44 (d, J=6.8 Hz, 6H), 1.32-1.18 (m, 4H), 1.13-1.03 (m, 6H).

Example 113: Synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-4-fluoro-1-oxo-isoindolin-2-yl]piperidine-2,6-dione (Compound 101)

Step 1: Preparation of tert-butyl 4-[[4-[[1-[2-(2,6-dioxo-3-piperidyl)-4-fluoro-1-oxo-isoindolin-5-yl]-4-piperidyl]methyl]piperazin-1-yl]methyl]piperidine-1-carboxylate

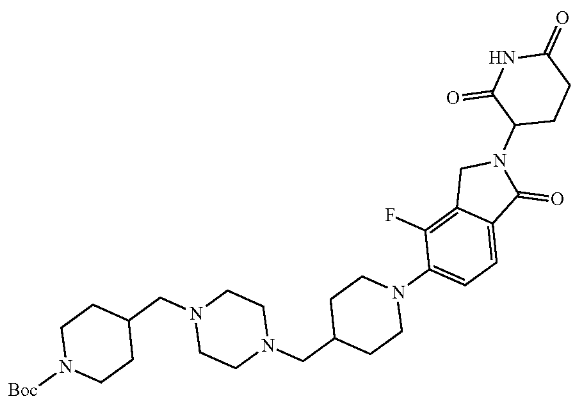 [SMILES: CC(C)(C)OC(=O)N1CCC(CN2CCN(CC3CCN(c4ccc5c(c4F)CN(C4CCC(=O)NC4=O)C5=O)CC3)CC2)CC1]

To a solution of 1-[2-(2,6-dioxo-3-piperidyl)-4-fluoro-1-oxo-isoindolin-5-yl]piperidine-4-carbaldehyde (500 mg, 1.3 mmol) in dichloromethane (5 mL) and dimethylsulfoxide (5 mL) were added tert-butyl 4-(piperazin-1-ylmethyl)piperidine-1-carboxylate (455 mg, 1.6 mmol) and sodium triacetoxyborohydride (568 mg, 2.7 mmol), and the resulting mixture was stirred at 25° C. for 12 h. The reaction mixture was diluted with water (30 mL) and extracted with dichloromethane (3×20 mL). The organic extract was dried over anhydrous sodium sulfate, filtered, and concentrated under reduced pressure. The residue was purified by preparative TLC (dichloromethane/methanol=7/1) to afford the title compound (500 mg, 58%) as a yellow solid. LC/MS (ESI) m/z: 641.4 $[M+H]^+$; $^1$H NMR (400 MHz, DMSO-$d_6$) δ 10.98 (s, 1H), 7.46 (d, J=8.0 Hz, 1H), 7.15 (t, J=7.8 Hz, 1H), 5.07 (dd, J=5.2, 1 Step 3: Hz, 1H), 4.54-4.40 (m, 1H), 4.30 (d, J=17.2 Hz, 1H), 3.90 (d, J=12.0 Hz, 2H), 3.47 (s, 2H), 3.17 (d, J=5.2 Hz, 1H), 2.99-2.84 (m, 1H), 2.82-2.70 (m, 3H), 2.69-2.60 (m, 2H), 2.46-2.40 (m, 3H), 2.33 (s, 5H), 2.16 (d, J=6.8 Hz, 2H), 2.09 (d, J=6.0 Hz, 2H), 2.00-1.94 (m, 1H), 1.79 (d, J=11.2 Hz, 2H), 1.64 (d, J=10.8 Hz, 4H), 1.41-1.36 (m, 1H), 1.38 (s, 8H), 1.25 (d, J=12.4 Hz, 3H), 0.91 (d, J=10.4 Hz, 2H).

Step 2: Preparation of 3-[4-fluoro-1-oxo-5-[4-[[4-(4-piperidylmethyl)piperazin-1-yl]methyl]-1-piperidyl]isoindolin-2-yl]piperidine-2,6-dione

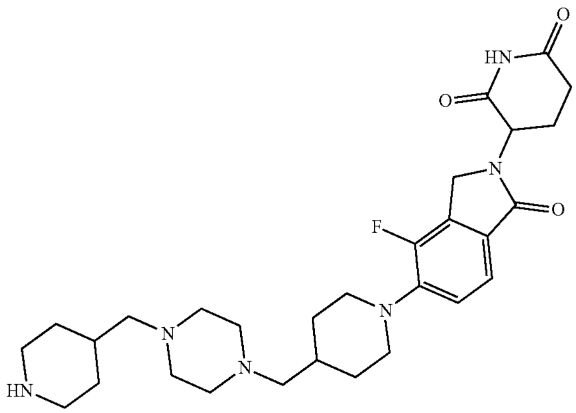 [SMILES: O=C1CCC(N2Cc3c(ccc(N4CCC(CN5CCN(CC6CCNCC6)CC5)CC4)c3F)C2=O)C(=O)N1]

To a solution of tert-butyl 4-[[4-[[1-[2-(2,6-dioxo-3-piperidyl)-4-fluoro-1-oxo-isoindolin-5-yl]-4-piperidyl]methyl]piperazin-1-yl]methyl]piperidine-1-carboxylate (350 mg, 0.5 mmol) in dichloromethane (5 mL) was added trifluoroacetic acid (1.0 mL, 13 mmol), and the mixture was stirred at 25° C. for 0.5 h. The mixture was concentrated under reduced pressure to afford the title compound (357 mg, crude, TFA salt) as a yellow gum. LC/MS (ESI) m/z: 541.3 $[M+H]^+$.

Step 3: Preparation of tert-butyl 3-[2-[2-[4-[[4-[[1-[2-(2,6-dioxo-3-piperidyl)-4-fluoro-1-oxo-isoindolin-5-yl]-4-piperidyl]methyl]piperazin-1-yl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

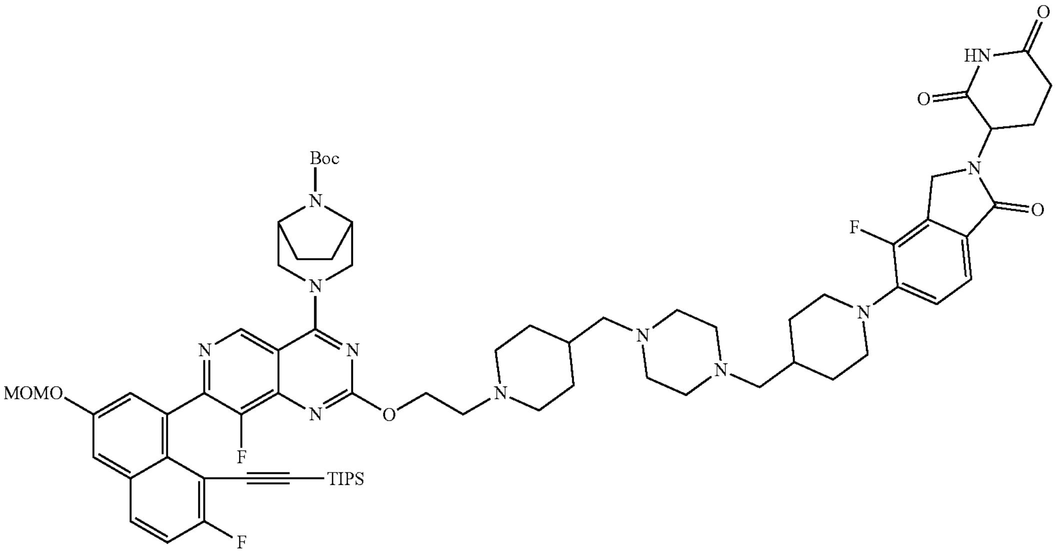

To a solution of 3-[4-fluoro-1-oxo-5-[4-[[4-(4-piperidylmethyl)piperazin-1-yl]methyl]-1-piperidyl]isoindolin-2-yl]piperidine-2,6-dione (510 mg, 0.8 mmol, TFA) in dichloromethane (5 mL) and isopropyl alcohol (5 mL) were added diisopropylethylamine (0.41 mL, 2 mmol), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (625 mg, 0.8 mmol), and sodium triacetoxyborohydride (330 mg, 1.6 mmol), and the reaction mixture was stirred at 25° C. for 12 h. The mixture was diluted with water (20 mL) and extracted with dichloromethane (3×20 mL). The organic extract was dried over anhydrous sodium sulfate, filtered, and concentrated under reduced pressure. The residue was purified by preparative TLC (dichloromethane/methanol=8/1) to afford the title compound (550 mg, 53%) as a yellow gum. LC/MS (ESI) m/z: 1326.7 [M+H]$^+$.

Step 4: Preparation of tert-butyl 3-[2-[2-[4-[[4-[[1-[2-(2,6-dioxo-3-piperidyl)-4-fluoro-1-oxo-isoindolin-5-yl]-4-piperidyl]methyl]piperazin-1-yl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

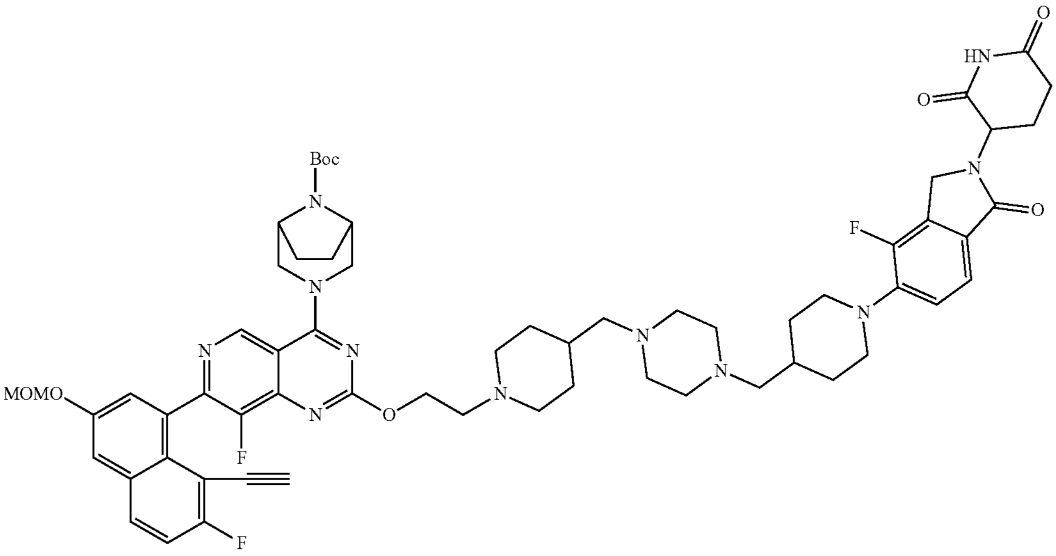

To a solution of tert-butyl 3-[2-[2-[4-[[4-[[1-[2-(2,6-dioxo-3-piperidyl)-4-fluoro-1-oxo-isoindolin-5-yl]-4-piperidyl]methyl]piperazin-1-yl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (550 mg, 0.4 mmol) in N,N-dimethylformamide (6 mL) was added cesium fluoride (1.26 g, 8 mmol), and the mixture was stirred at 25° C. for 12 h. The reaction mixture was diluted with water (20 mL) and extracted with water (3x30 mL). The organic extract was dried over anhydrous sodium sulfate, filtered, and concentrated under reduced pressure. The residue was purified by prep-HPLC (12% to 42% acetonitrile in water (formic acid) over 11 min) to afford the title compound (343 mg, 71%) as a yellow solid. LC/MS (ESI) m/z: 1170.6 $[M+H]^+$.

Step 5: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-4-fluoro-1-oxo-isoindolin-2-yl]piperidine-2,6-dione

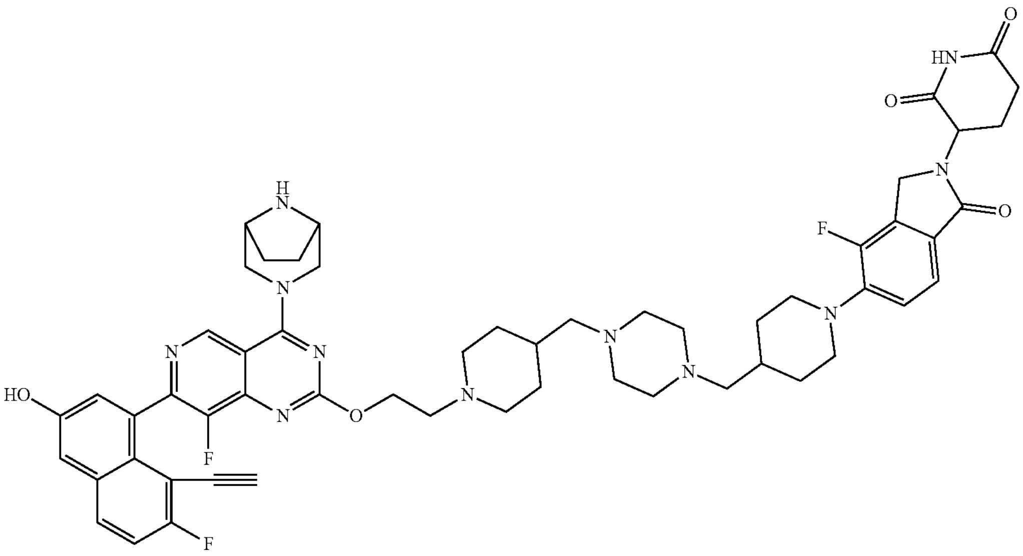 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)CC6)CC5)nc4c3F)c12]

To tert-butyl 3-[2-[2-[4-[[4-[[1-[2-(2,6-dioxo-3-piperidyl)-4-fluoro-1-oxo-isoindolin-5-yl]-4-piperidyl]methyl]piperazin-1-yl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (548 mg, 0.5 mmol) in dichloromethane (5 mL) was added 4 M HCl in 1,4-dioxane (5 mL), and the mixture was stirred at 20° C. for 15 min. The reaction mixture suspended in petroleum ether (10 mL) and filtered. The filtered cake was purified by prep-HPLC (10% to 40% acetonitrile in water (formic acid) over 10 min) to afford the title compound (332 mg, 65%, formic acid salt) as a yellow solid. LC/MS (ESI) m/z: 1026.7 $[M+H]^+$, $^1H$ NMR (400 MHz, DMSO-$d_6$) δ 10.98 (s, 1H), 10.32-10.19 (m, 1H), 9.13 (s, 1H), 8.14 (s, 1H), 7.99 (dd, J=6.0, 9.2 Hz, 1H), 7.51-7.44 (m, 2H), 7.41 (d, J=2.4 Hz, 1H), 7.20-7.13 (m, 2H), 5.07 (dd, J=4.8, 13.2 Hz, 1H), 4.70-4.58 (m, 3H), 4.55-4.44 (m, 2H), 4.30 (d, J=17.2 Hz, 1H), 4.17 (s, 2H), 3.94 (s, 1H), 3.88 (d, J=14.8 Hz, 2H), 3.52-3.45 (m, 4H), 3.21-3.13 (m, 3H), 2.96-2.85 (m, 2H), 2.81-2.75 (m, 2H), 2.61 (d, J=1.6 Hz, 3H), 2.57 (s, 3H), 2.54 (s, 2H), 2.43 (d, J=4.4 Hz, 1H), 2.41-2.36 (m, 2H), 2.32 (dd, J=2.0, 6.8 Hz, 2H), 1.95 (s, 6H), 1.86-1.71 (m, 6H), 1.37-1.20 (m, 5H).

Example 114: Synthesis of-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl] oxyethyl]-4-piperidyl]methyl]-1-piperidyl]methyl]-1-piperidyl]-3-methyl-2-oxo-benzimidazol-1-yl]piperidine-2,6-dione (Compound 102)

Step 1: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

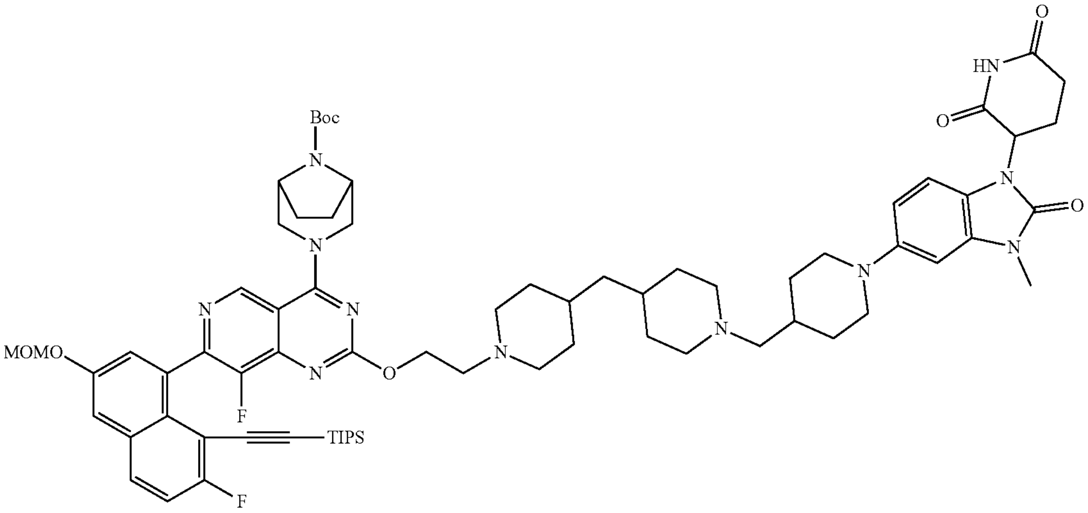

To a solution of tert-butyl 3-[8-fluoro-7-[7-fluoro-3-(methoxymethoxy)-8-(2-triisopropyl silylethynyl)-1-naphthyl]-2-(2-oxoethoxy)pyrido[4,3-d]pyrimidin-4-yl]-3,8-diazabicyclo [3.2.1]octane-8-carboxylate (346 mg, 0.4 mmol) and 3-[3-methyl-2-oxo-5-[4-[[4-(4-piperidylmethyl)-1-piperidyl]methyl]-1-piperidyl]benzimidazol-1-yl]piperidine-2,6-dione di-trifluoroacetate (300 mg, 0.4 mmol) in dichloromethane (4 mL) and isopropanol (4 mL) were added N,N-diisopropylethylamine (0.2 mL, 1 mmol) and sodium triacetoxyborohydride (166 mg, 0.8 mmol), and the mixture was stirred at 25° C. for 2 h. The reaction mixture was diluted with water (15 mL) and extracted with dichloromethane (3x30 mL). The combined organic extracts were washed with brine (15 mL), dried over anhydrous sodium sulfate, filtered, and concentrated under reduced pressure. The residue was triturated with ethyl acetate/methyl tert-butyl ether (1/10, 100 mL) to afford the title compound (400 mg, 77%) as a yellow solid. LC/MS (ESI) m/z: 662.3 $[M/2+H]^+$.

Step 2: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

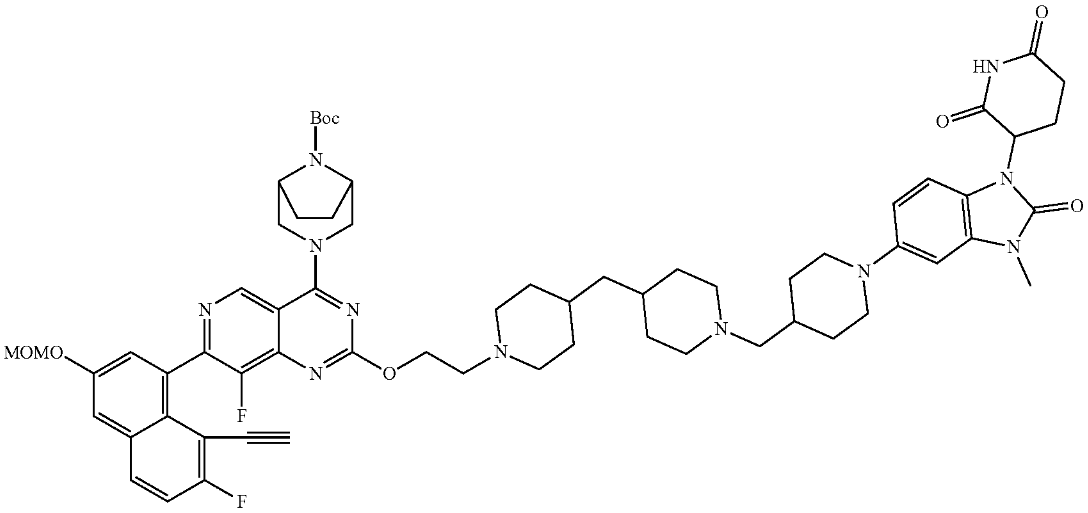

To a solution of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (400 mg, 0.3 mmol) in N,N-dimethylformamide (5 mL) was added cesium fluoride (1.38 g, 9 mmol), and the mixture was stirred at 25° C. for 4 h. The reaction mixture was quenched with water (0.5 mL), and the crude solution was directly purified by prep-HPLC (22% to 52% acetonitrile in water (trifluoroacetic acid) over 15 min) to afford the title compound (190 mg, 53%, TFA salt) as an off-white solid. LC/MS (ESI) m/z: 584.1 $[M/2+H]^+$.

Step 3: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl] oxyethyl]-4-piperidyl]methyl]-1-piperidyl]methyl]-1-piperidyl]-3-methyl-2-oxo-benzimidazol-1-yl]piperidine-2,6-dione

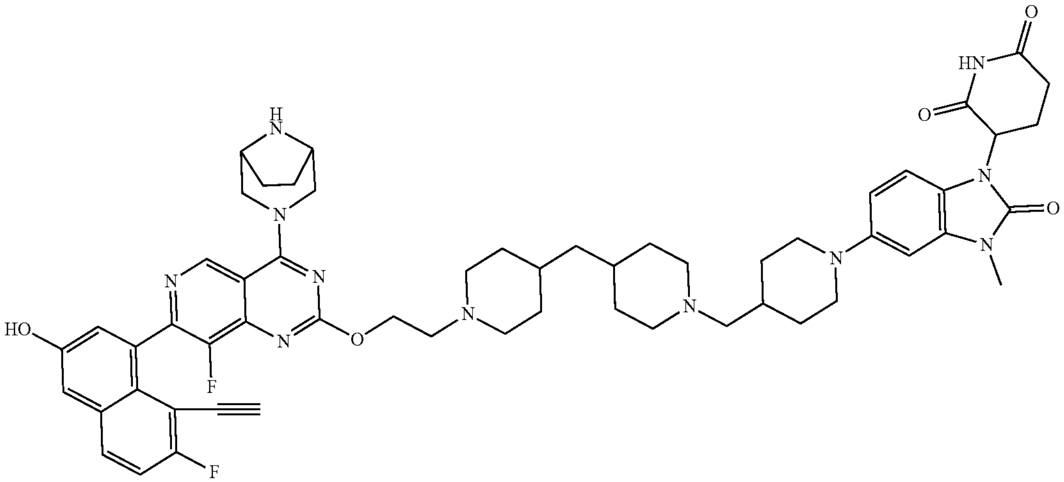 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)n(C)c(=O)n9C8CCC(=O)NC8=O)CC7)CC6)CC5)nc4c3F)c12]

To tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (190 mg, 0.16 mmol) in dichloromethane (5 mL) was added 4 M HCl in 1,4-dioxane (2 mL), and the mixture was stirred at 25° C. for 1 h. The reaction mixture was triturated with ethyl acetate/tert-butyl methyl ether (1/10, 60 mL, then purified by prep-HPLC (1% to 25% acetonitrile in water (formic acid) over 10 min) to afford the title compound (43.8 mg, 23%, di-formic acid salt) as a yellow solid. LC/MS (ESI) m/z: 1022.6 $[M+H]^+$, $^1$HNMR (400 MHz, DMSO-$d_6$) δ 11.06 (s, 1H), 9.05 (s, 1H), 8.18 (s, 2H), 7.97 (dd, J=9.2, 6.0 Hz, 1H), 7.46 (t, J=9.2 Hz, 1H), 7.39 (d, J=2.4 Hz, 1H), 7.17 (d, J=2.4 Hz, 1H), 6.92 (d, J=8.8 Hz, 1H), 6.81 (d, J=2.0 Hz, 1H), 6.62 (dd, J=8.8, 2.0 Hz, 1H), 5.21-5.33 (m, 1H), 4.54-4.48 (m, 1H), 4.47-4.42 (m, 2H), 4.36 (br d, J=11.6 Hz, 1H), 3.93 (s, 1H), 3.69 (br s, 2H), 3.60 (br d, J=15.2 Hz, 4H), 3.29 (s, 3H), 2.97-2.91 (m, 2H), 2.89-2.83 (m, 3H), 2.71 (br s, 2H), 2.66-2.55 (m, 4H), 2.22-2.18 (m, 2H), 2.04-1.86 (m, 6H), 1.80-1.71 (m, 6H), 1.59 (br d, J=11.2 Hz, 6H), 1.33-1.19 (m, 4H), 1.13-1.04 (m, 6H).

Example 115: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione (Compound 133)

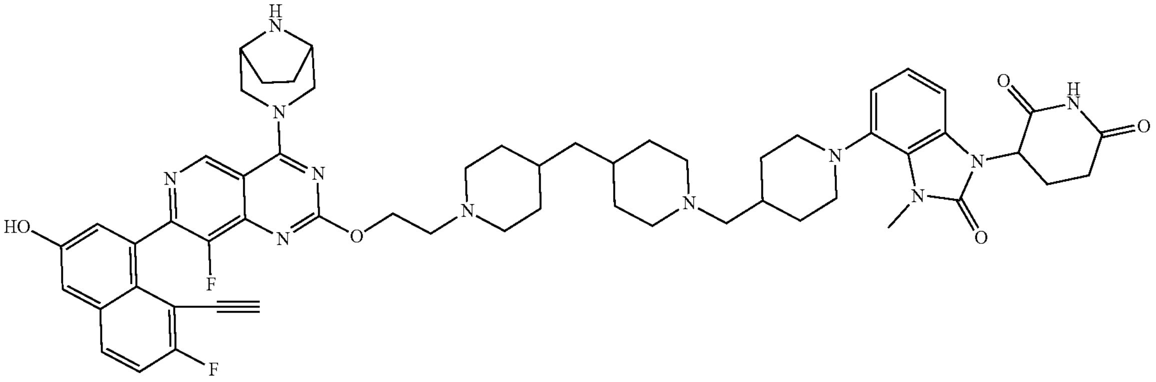 [SMILES: C#Cc1c(F)ccc2cc(O)cc(-c3ncc4c(N5CC6CCC(C5)N6)nc(OCCN5CCC(CC6CCN(CC7CCN(c8cccc9c8n(C)c(=O)n9C8CCC(=O)NC8=O)CC7)CC6)CC5)nc4c3F)c12]

The title compound was made in an analogous manner to 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl] oxyethyl]-4-piperidyl]methyl]-1-piperidyl]methyl]-1-piperidyl]-3-methyl-2-oxo-benzimidazol-1-yl]piperidine-2,6-dione. (yellow solid, formic acid salt). LC/MS (ESI) m/z: 1022.19 $[M+H]^+$; $^1$H NMR (400 MHz, DMSO-$d_6$) δ 11.08 (s, 1H), 9.05 (s, 1H), 8.18 (s, 3H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 7.02-6.92 (m, 1H), 6.91-6.82 (m, 2H), 5.36-5.31 (m, 1H), 4.51-4.48 (m, 1H), 4.45 (t, J=5.2 Hz, 2H), 4.36-4.33 (m, 1H), 3.92 (s, 1H), 3.65 (s, 2H), 3.61 (s, 3H), 3.10 (d, J=8.4 Hz, 4H), 2.97-2.81 (m, 7H), 2.73-2.63 (m, 6H), 2.20 (dd, J=1.2, 4.0 Hz, 2H), 2.04-1.96 (m, 3H), 1.93-1.85 (m, 2H), 1.81-1.76 (m, 2H), 1.71 (s, 3H), 1.60-1.57 (m, 5H), 1.29 (d, J=6.4 Hz, 4H), 1.15-1.04 (m, 6H).

Example 116: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-2-oxo-3-(propan-2-yl)-2,3-dihydro-1H-1,3-benzodiazol-1-yl}piperidine-2,6-dione (Compound 94)

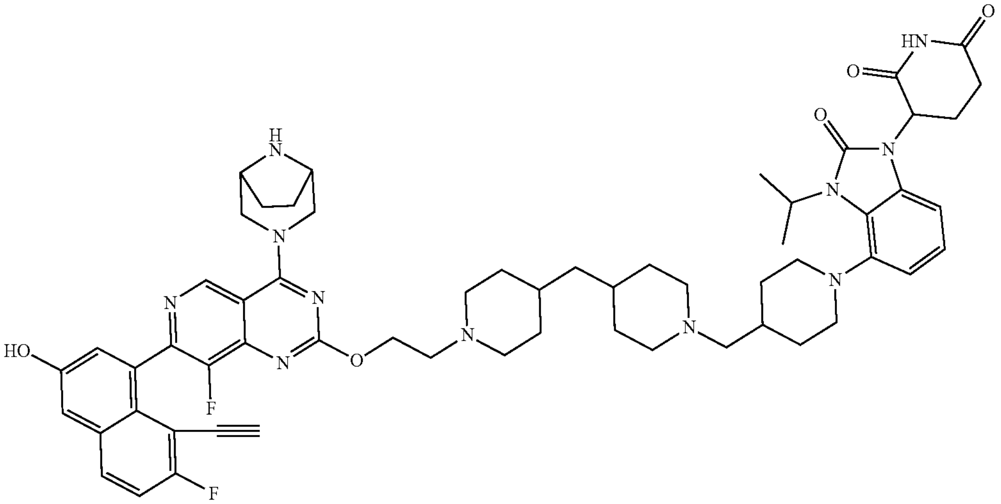 [SMILES: C#Cc1c(F)ccc2cc(O)cc(-c3ncc4c(N5CC6CCC(C5)N6)nc(OCCN5CCC(CC6CCN(CC7CCN(c8cccc9c8n(C(C)C)c(=O)n9C8CCC(=O)NC8=O)CC7)CC6)CC5)nc4c3F)c12]

The title compound was made in an analogous manner to 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl] oxyethyl]-4-piperidyl]methyl]-1-piperidyl]methyl]-1-piperidyl]-3-methyl-2-oxo-benzimidazol-1-yl]piperidine-2,6-dione. (yellow solid, formic acid salt). LC/MS (ESI) m/z: 1050.8 $[M+H]^+$; $^1H$ NMR (400 MHz, DMSO-$d_6$) δ 11.06 (s, 1H), 9.06 (s, 1H), 8.16 (s, 2H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 7.02-6.91 (m, 1H), 6.90-6.76 (m, 2H), 5.66-5.54 (m, 1H), 5.28 (br dd, J=5.2, 12.8 Hz, 1H), 4.54 (br d, J=12.4 Hz, 1H), 4.47 (br t, J=5.2 Hz, 2H), 4.39 (br d, J=12.8 Hz, 1H), 3.93 (s, 1H), 3.83 (br s, 2H), 3.71 (br s, 3H), 3.08 (br d, J=10.4 Hz, 2H), 3.00-2.82 (m, 6H), 2.76-2.70 (m, 2H), 2.69-2.56 (m, 4H), 2.30 (br d, J=6.0 Hz, 2H), 2.10-1.92 (m, 5H), 1.85-1.72 (m, 6H), 1.69-1.55 (m, 5H), 1.45 (dd, J=6.8, 10.8 Hz, 6H), 1.37-1.20 (m, 4H), 1.19-1.03 (m, 6H).

Example 117: Synthesis of 3-{4-chloro-5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-piperidine-2,6-dione (Compound 109)

Step 1: Preparation of tert-butyl 4-((1-((1-(4-chloro-2-(2,6-dioxopiperidin-3-yl)-1-oxoisoindolin-5-yl)piperidin-4-yl)methyl)piperidin-4-yl)methyl)piperidine-1-carboxylate

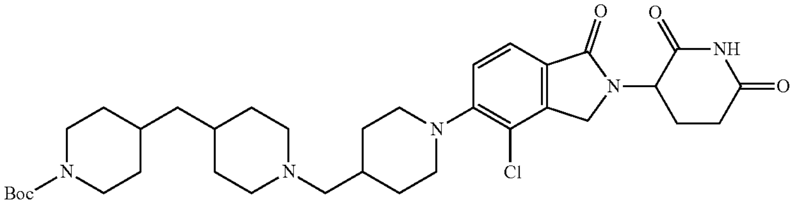 [SMILES: CC(C)(C)OC(=O)N1CCC(CC2CCN(CC3CCN(c4ccc5c(c4Cl)CN(C4CCC(=O)NC4=O)C5=O)CC3)CC2)CC1]

To a solution of 1-(4-chloro-2-(2,6-dioxopiperidin-3-yl)-1-oxoisoindolin-5-yl)piperidine-4-carbaldehyde (1 g, 3 mmol) in dichloromethane (10 mL) and dimethyl sulfoxide (10 mL) was added tert-butyl 4-(piperidin-4-ylmethyl)piperidine-1-carboxylate acetate (878 mg, 2.6 mmol), and the resulting mixture was stirred for 30 min. Sodium triacetoxyborohydride (1.09 g, 5 mmol) was then added at 0° C., and the reaction mixture was stirred at 25° C. for 1 h. The mixture was diluted with water (30 mL) and extracted with dichloromethane/isopropanol (5:1, 2×30 mL). The combined organic extracts were washed with brine (2×30 mL), dried over anhydrous sodium sulfate, filtered, and concentrated under reduced pressure to afford the title compound (1.61 g, 95%) as a white solid. LC/MS (ESI) m/z: 656.5 $[M+H]^+$, $^1H$ NMR (400 MHz, DMSO-$d_6$) δ 10.98 (s, 1H), 7.74-7.57 (m, 1H), 7.37-7.15 (m, 1H), 5.10 (br dd, J=4.8, 13.2 Hz, 1H), 4.47-4.36 (m, 1H), 4.31-4.21 (m, 1H), 4.09 (q, J=5.2 Hz, 1H), 3.99-3.82 (m, 2H), 3.59-3.46 (m, 2H), 3.44-3.37 (m, 2H), 3.17 (d, J=5.2 Hz, 3H), 3.06-2.98 (m, 1H), 2.96-2.87 (m, 2H), 2.80-2.65 (m, 4H), 2.59 (br d, J=18.8 Hz, 2H), 2.04-1.96 (m, 2H), 1.95-1.86 (m, 2H), 1.84-1.76 (m, 2H), 1.68-1.57 (m, 3H), 1.53-1.43 (m, 3H), 1.38 (s, 9H), 1.14 (br d, J=6.0 Hz, 2H), 1.01-0.85 (m, 2H).

Step 2: Preparation of 3-(4-chloro-1-oxo-5-(4-((4-(piperidin-4-ylmethyl) piperidin-1-yl)methyl)piperidin-1-yl)isoindolin-2-yl)piperidine-2,6-dione

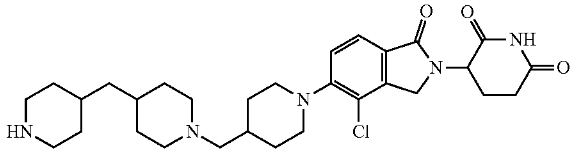 [SMILES: O=C1CCC(N2Cc3c(ccc(N4CCC(CN5CCC(CC6CCNCC6)CC5)CC4)c3Cl)C2=O)C(=O)N1]

To a solution of tert-butyl 4-((1-((1-(4-chloro-2-(2,6-dioxopiperidin-3-yl)-1-oxoisoindolin-5-yl)piperidin-4-yl)methyl)piperidin-4-yl)methyl)piperidine-1-carboxylate (1.61 g, 2 mmol) in dichloromethane (16 mL) was added trifluoroacetic acid (8 mL, 0.1 mol), and the reaction mixture was stirred at at 25° C. for 1 h. The mixture was concentrated under reduced pressure to afford the title compound (1.6 g, 97%, TFA salt) as a brown oil. LC/MS (ESI) m/z: 556.4 $[M+H]^+$.

Step 3: Preparation of tert-butyl (1R,5S)-3-(2-(2-(4-((1-((1-(4-chloro-2-(2,6-dioxopiperidin-3-yl)-1-oxoisoindolin-5-yl)piperidin-4-yl)methyl)piperidin-4-yl)methyl)piperidin-1-yl)ethoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate

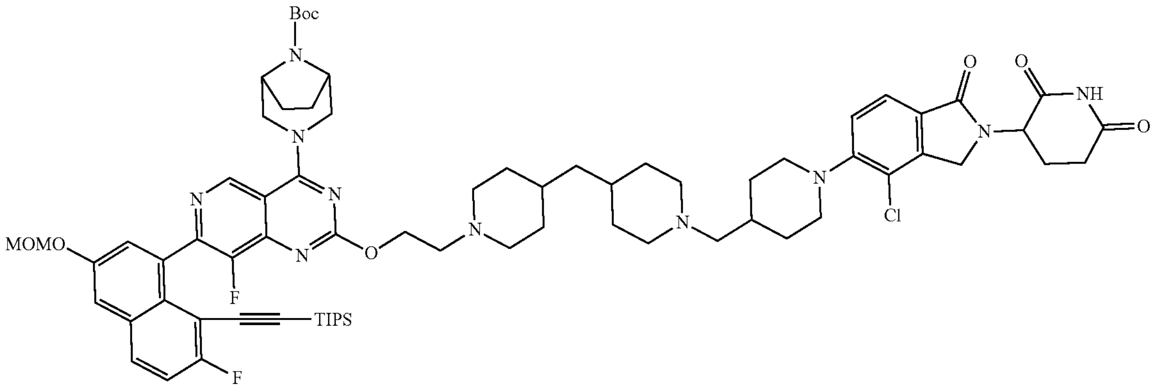

To a solution of 3-(4-chloro-1-oxo-5-(4-((4-(piperidin-4-ylmethyl) piperidin-1-yl)methyl)piperidin-1-yl)isoindolin-2-yl)piperidine-2,6-dione trifluoroacetate (1.6 g, 2 mmol) in dichloromethane (16 mL) and isopropanol (16 mL) were added N,N-diisopropylethylamine (0.8 mL, 5 mmol) and tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (2.11 g, 2.6 mmol), and the mixture stirred for 15 min. Sodium triacetoxyborohydride (1.01 g, 4.8 mmol) was then added at 0° C., and the reaction mixture was stirred at 25° C. for 12 h. The mixture was diluted with water (30 mL) and extracted with dichloromethane (2×30 mL). The combined organic extracts were washed with brine (2×30 mL), dried over anhydrous sodium sulfate, filtered, and concentrated under reduced pressure. The residue was purified by flash silica gel chromatography (0 to 100% ethyl acetate/petroleum ether then 0 to 9% dichloromethane/methanol) to afford the title compound (2.2 g, 68%) as a yellow solid. LC/MS (ESI) m/z: 1341.7 $[M+H]^+$.

Step 4: Preparation of tert-butyl (1R,5S)-3-(2-(2-(4-((1-((1-(4-chloro-2-(2,6-dioxopiperidin-3-yl)-1-oxoisoindolin-5-yl)piperidin-4-yl)methyl)piperidin-4-yl)methyl)piperidin-1-yl)ethoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

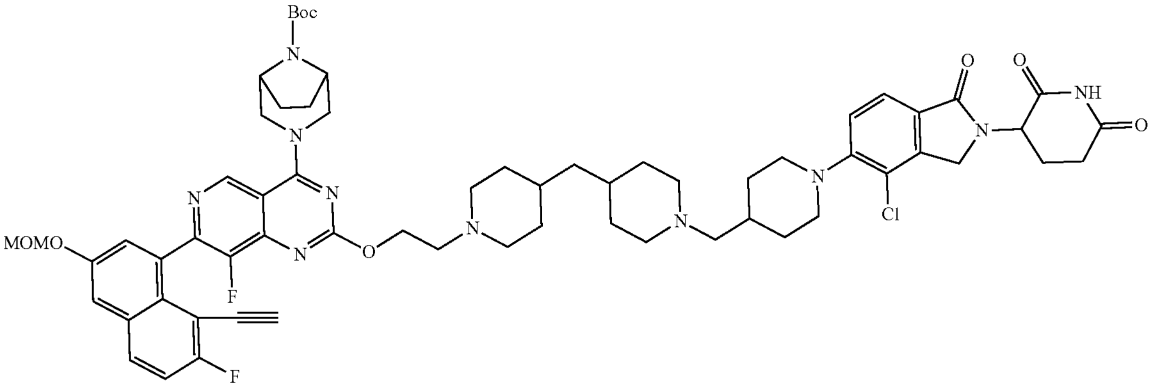

To a solution of tert-butyl (1R,5S)-3-(2-(2-(4-((1-((1-(4-chloro-2-(2,6-dioxopiperidin-3-yl)-1-oxoisoindolin-5-yl)piperidin-4-yl)methyl)piperidin-4-yl)methyl)piperidin-1-yl)ethoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate (2.2 g, 1.6 mmol) in N,N-dimethylformamide (22 mL) was added cesium fluoride (7.47 g, 49 mmol), and the mixture was stirred at 25° C. for 12 h. The reaction mixture was diluted with water (30 mL) and extracted with dichloromethane/isopropanol (5:1, 2×30 mL). The combined organic layers were dried over anhydrous sodium sulfate, filtered, and concentrated under reduced pressure. The residue was purified by prep-HPLC (30% to 60% acetonitrile in water (formic acid) over 10 min) to afford the title compound (1.8 g, 92%) as a yellow solid. LC/MS (ESI) m/z: 1185.6 [M+H]$^+$.

Step 5: Preparation of 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione

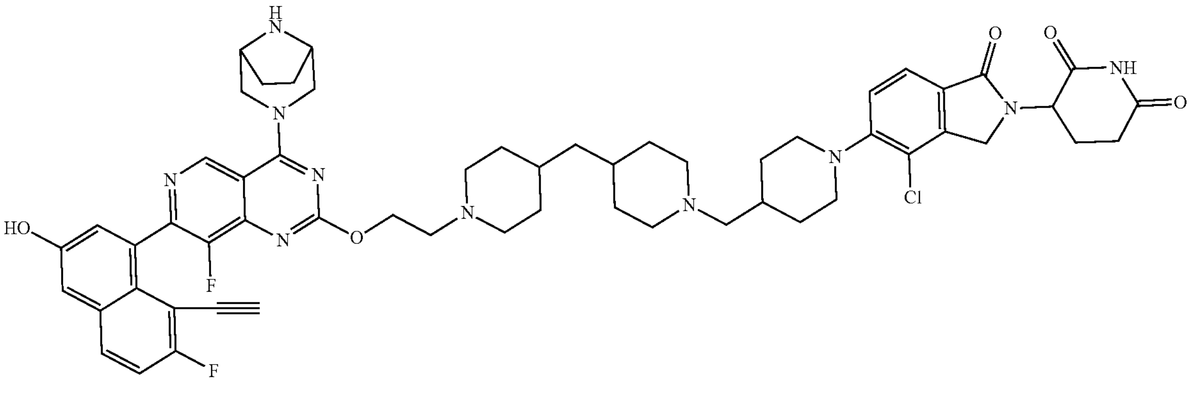 [SMILES: C#Cc1c(F)ccc2cc(O)cc(-c3ncc4c(N5CC6CCC(C5)N6)nc(OCCN5CCC(CC6CCN(CC7CCN(c8ccc9c(c8Cl)CN(C8CCC(=O)NC8=O)C9=O)CC7)CC6)CC5)nc4c3F)c12]

To tert-butyl (1R,5S)-3-(2-(2-(4-((1-((1-(4-chloro-2-(2,6-dioxopiperidin-3-yl)-1-oxoisoindolin-5-yl)piperidin-4-yl)methyl)piperidin-4-yl)methyl)piperidin-1-yl)ethoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (1.8 g, 1.5 mmol) in dichloromethane (18 mL) was added 4 M HCl in 1,4-dioxane (18 mL), and the reaction mixture was stirred at 25° C. for 15 min. The mixture was suspended in petroleum ether (50 mL) and filtered. The filter cake was dissolved in dimethyl sulfoxide and N,N-diisopropylethylamine to adjust the pH to 7. The mixture was purified by prep-HPLC (1% to 30% acetonitrile in water (formic acid) over 11 min) to afford the title compound (785.5 mg, 45%, di-formic acid salt) as a yellow solid. LC/MS (ESI) m/z: 1041.7 $[M+H]^+$, $^1H$ NMR (400 MHz, DMSO-$d_6$) δ 10.98 (s, 1H), 9.07 (s, 1H), 8.19 (s, 2H), 7.98 (dd, J=6.0, 9.2 Hz, 1H), 7.64 (d, J=8.0 Hz, 1H), 7.46 (t, J=9.2 Hz, 1H), 7.40 (d, J=2.4 Hz, 1H), 7.25 (d, J=8.4 Hz, 1H), 7.19 (d, J=2.4 Hz, 1H), 5.09 (dd, J=5.2, 1 Step 2: Hz, 1H), 4.63-4.53 (m, 1H), 4.53-4.46 (m, 2H), 4.45-4.38 (m, 2H), 4.25 (br d, J=17.6 Hz, 1H), 3.97-3.87 (m, 3H), 3.77 (br t, J=11.2 Hz, 2H), 3.38 (br s, 2H), 3.04-2.85 (m, 5H), 2.81-2.68 (m, 4H), 2.59 (br d, J=15.6 Hz, 1H), 2.44 (br dd, J=4.4, 1 Step 6: Hz, 1H), 2.36 (br d, J=6.0 Hz, 2H), 2.16-2.04 (m, 4H), 2.02-1.94 (m, 1H), 1.92-1.68 (m, 8H), 1.62 (br d, J=10.8 Hz, 4H), 1.40-1.25 (m, 4H), 1.24-1.06 (m, 6H).

Example 118: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-7-methyl-1-oxo-2,3-dihydro-1H-isoindol-2-yl}piperidine-2,6-dione (Compound 149)

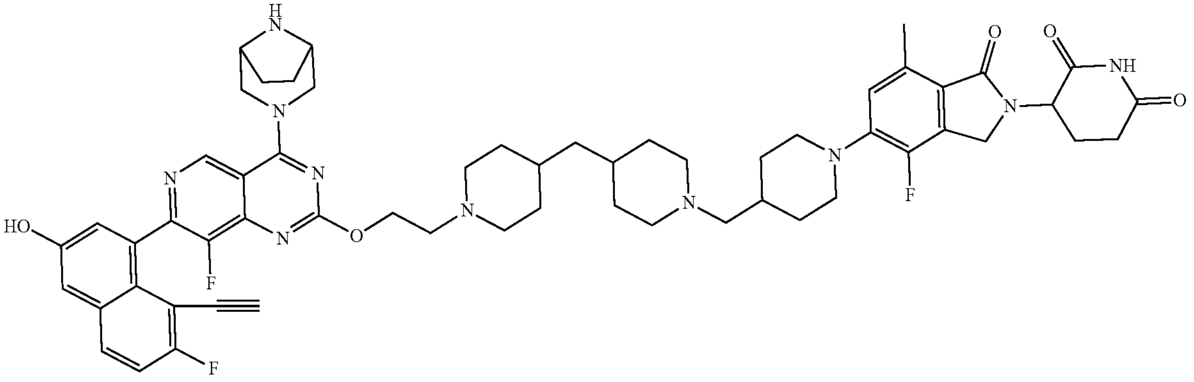 [SMILES: C#Cc1c(F)ccc2cc(O)cc(-c3ncc4c(N5CC6CCC(C5)N6)nc(OCCN5CCC(CC6CCN(CC7CCN(c8cc(C)c9c(c8F)CN(C8CCC(=O)NC8=O)C9=O)CC7)CC6)CC5)nc4c3F)c12]

The title compound was prepared in an analogous manner to 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione. (yellow solid). LC/MS (ESI) m/z: 1039.3 $[M+H]^+$, $^1H$ NMR (400 MHz, DMSO-$d_6$) δ 0.97 (s, 1H), 9.05 (s, 1H), 8.21 (s, 3H), 7.97 (dd, J=6.0, 9.2 Hz, 1H), 7.50-7.34 (m, 2H), 7.18 (d, J=2.4 Hz, 1H), 6.87 (d, J=7.2 Hz, 1H), 5.02 (dd, J=4.8, 13.2 Hz, 1H), 4.56-4.33 (m, 5H), 4.22 (d, J=16.8 Hz, 1H), 3.93 (s, 1H), 3.79-3.60 (m, 4H), 3.47 (dd, J=3.2, 4.4 Hz, 2H), 3.01-2.81 (m, 5H), 2.79-2.65 (m, 4H), 2.65-2.51 (m, 5H), 2.49-2.31 (m, 3H), 2.25-2.17 (m, 2H), 2.10-1.85 (m, 5H), 1.83-1.64 (m, 7H), 1.59 (d, J=11.2 Hz, 4H), 1.39-1.19 (m, 4H), 1.16-1.00 (m, 6H).

Example 119: Synthesis of 3-{6-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-1-oxo-2,3-dihydro-1H-isoindol-2-yl}piperidine-2,6-dione (Compound 110)

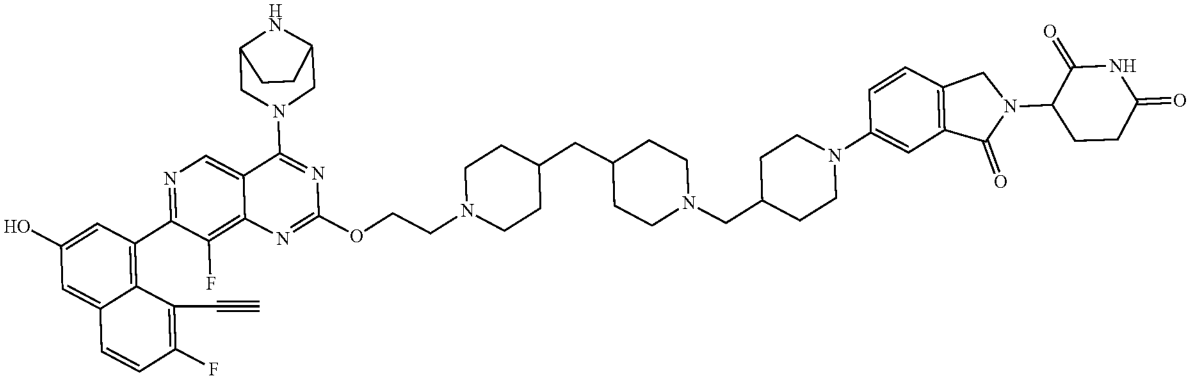 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)C(=O)N(C8CCC(=O)NC8=O)C9)CC7)CC6)CC5)nc4c3F)c12]

The title compound was prepared in an analogous manner to 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione. (yellow solid, formic acid salt.) LC/MS (ESI) m/z: 1007.3 $[M+H]^+$; $^1H$ NMR (400 MHz, DMSO-$d_6$) δ 10.99 (s, 1H), 9.08 (s, 1H), 8.21 (s, 3H), 7.99 (dd, J=6.0, 9.2 Hz, 1H), 7.47 (t, J=9.2 Hz, 1H), 7.44-7.37 (m, 2H), 7.25 (dd, J=2.0, 8.4 Hz, 1H), 7.19 (d, J=2.4 Hz, 1H), 7.15 (d, J=1.6 Hz, 1H), 5.10 (dd, J=5.2, 13.2 Hz, 1H), 4.57 (d, J=12.4 Hz, 1H), 4.52-4.48 (m, 2H), 4.42 (d, J=12.4 Hz, 1H), 4.37-4.30 (m, 1H), 4.24-4.17 (m, 1H), 3.95 (s, 1H), 3.90-3.88 (m, 2H), 3.81-3.69 (m, 4H), 3.05-2.87 (m, 5H), 2.82-2.68 (m, 4H), 2.63-2.57 (m, 2H), 2.43-2.29 (m, 4H), 2.13-2.07 (m, 4H), 2.01-1.94 (m, 1H), 1.87-1.71 (m, 7H), 1.63-1.57 (m, 4H), 1.41-1.29 (m, 2H), 1.27-1.04 (m, 8H).

Example 120: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)-4-fluoropiperidin-1-yl]-1-oxo-2,3-dihydro-1H-isoindol-2-yl}piperidine-2,6-dione (Compound 125)

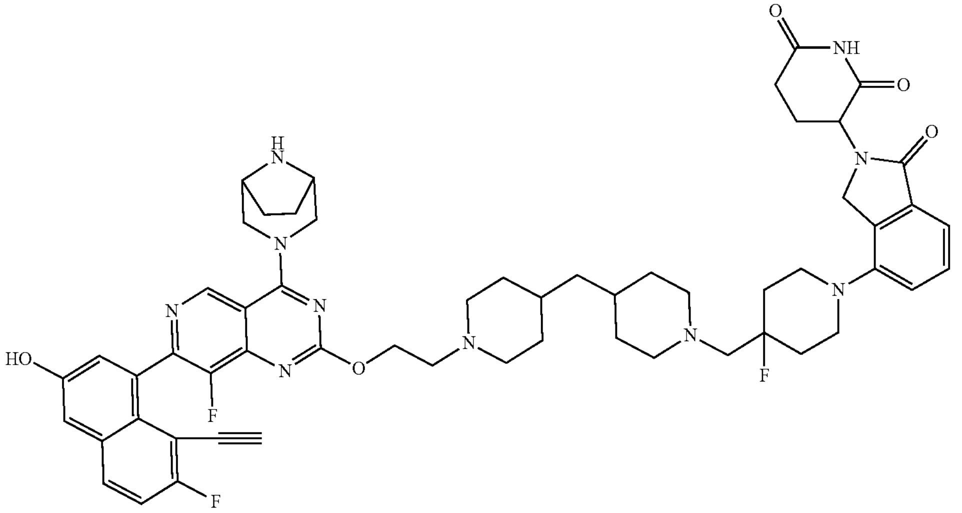 [SMILES: C#Cc1c(F)ccc2cc(O)cc(-c3ncc4c(N5CC6CCC(C5)N6)nc(OCCN5CCC(CC6CCN(CC7(F)CCN(c8cccc9c8CN(C8CCC(=O)NC8=O)C9=O)CC7)CC6)CC5)nc4c3F)c12]

The title compound was prepared in an analogous manner to 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione. (yellow solid, formic acid salt). LC/MS (ESI) m/z: 1026.3 $[M+H]^+$; $^1H$ NMR (400 MHz, DMSO-$d_6$) δ 10.98 (s, 1H), 9.06 (s, 1H), 8.17 (s, 2H), 7.98 (dd, J=6.0, 9.2 Hz, 1H), 7.52-7.37 (m, 3H), 7.31 (d, J=7.6 Hz, 1H), 7.22-7.13 (m, 2H), 5.12 (dd, J=5.2, 13.2 Hz, 1H), 4.56-4.36 (m, 5H), 4.29 (d, J=17.2 Hz, 1H), 3.93 (s, 1H), 3.78 (s, 3H), 3.71 (d, J=14.8 Hz, 5H), 3.44 (dd, J=3.2, 7.6 Hz, 3H), 3.25-3.20 (m, 2H), 3.02-2.91 (m, 5H), 2.87 (d, J=10.4 Hz, 2H), 2.72 (t, J=5.8 Hz, 2H), 2.59 (s, 1H), 2.05 (t, J=10.4 Hz, 4H), 2.00-1.88 (m, 3H), 1.88-1.82 (m, 1H), 1.77 (s, 4H), 1.57 (t, J=13.2 Hz, 3H), 1.35-1.22 (m, 2H), 1.15-1.03 (m, 5H).

Example 121: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-6-fluoro-1-oxo-2,3-dihydro-1H-isoindol-2-yl}piperidine-2,6-dione (Compound 130)

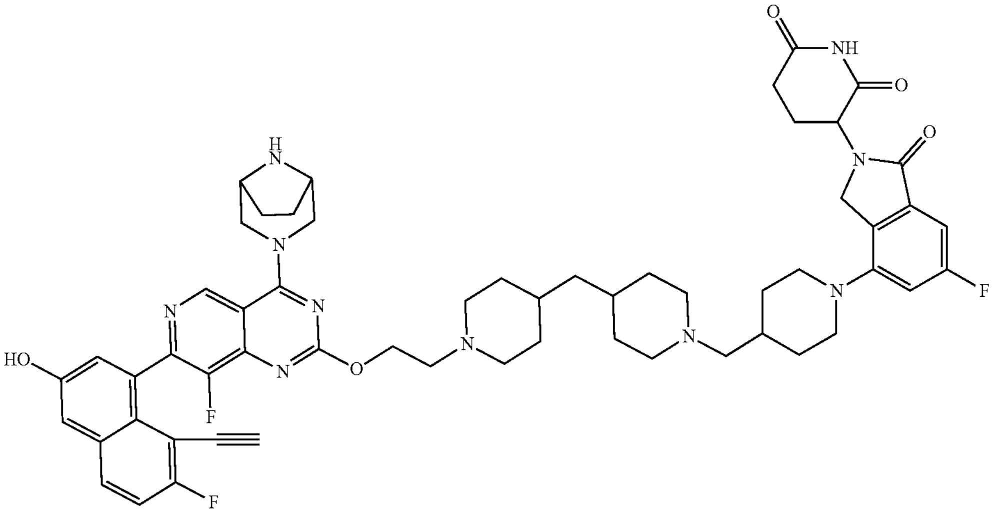 [SMILES: C#Cc1c(F)ccc2cc(O)cc(-c3ncc4c(N5CC6CCC(C5)N6)nc(OCCN5CCC(CC6CCN(CC7CCN(c8cc(F)cc9c8CN(C8CCC(=O)NC8=O)C9=O)CC7)CC6)CC5)nc4c3F)c12]

The title compound was prepared in an analogous manner to 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione. (yellow solid, formic acid salt). LC/MS (ESI) m/z: 1025.3 $[M+H]^+$, $^1H$ NMR (400 MHz, DMSO-$d_6$) δ 11.00 (s, 1H), 9.07 (s, 1H), 8.22 (s, 3H), 7.97 (dd, J=6.0, 9.2 Hz, 1H), 7.46 (t, J=9.2 Hz, 1H), 7.40 (d, J=2.4 Hz, 1H), 7.18 (d, J=2.4 Hz, 1H), 6.99 (dd, J=2.0, 7.2 Hz, 1H), 6.92 (dd, J=2.0, 12.0 Hz, 1H), 5.10 (dd, J=5.2, 13.2 Hz, 3H), 5.00-4.78 (m, 3H), 4.56 (d, J=12.8 Hz, 1H), 4.51-4.36 (m, 4H), 4.33-4.22 (m, 1H), 3.93 (s, 1H), 3.86 (s, 2H), 3.74 (t, J=12.4 Hz, 2H), 3.54-3.36 (m, 2H), 3.05-2.94 (m, 2H), 2.89 (d, J=11.2 Hz, 2H), 2.83-2.68 (m, 4H), 2.63-2.52 (m, 2H), 2.47-2.40 (m, 1H), 2.26 (d, J=6.4 Hz, 2H), 2.15-1.93 (m, 5H), 1.87-1.68 (m, 6H), 1.60 (d, J=11.6 Hz, 3H), 1.31 (d, J=4.0 Hz, 2H), 1.26-1.18 (m, 2H), 1.18-1.02 (m, 5H).

Example 122: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]-4-fluoropiperidin-1-yl}methyl)piperidin-1-yl]-1-oxo-2,3-dihydro-1H-isoindol-2-yl}piperidine-2,6-dione (Compound 131)

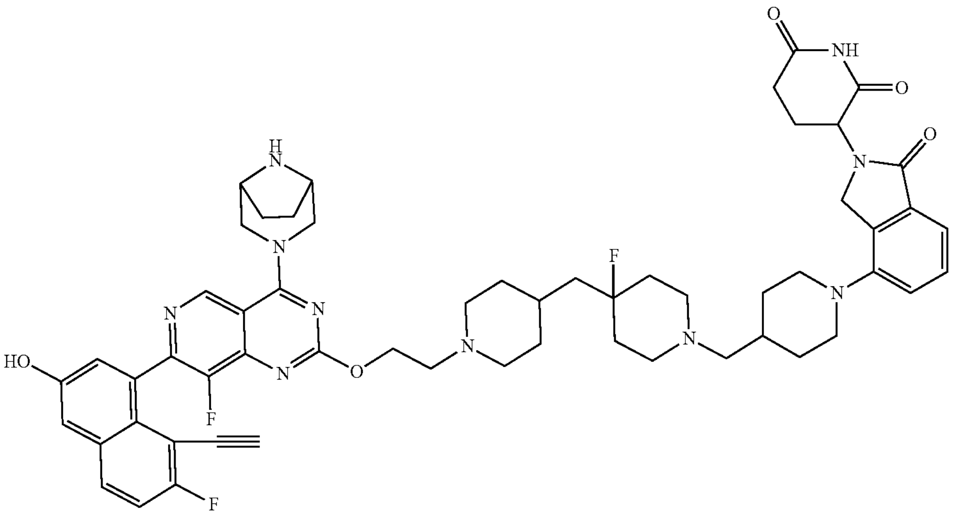 [SMILES: C#Cc1c(F)ccc2cc(O)cc(-c3ncc4c(N5CC6CCC(C5)N6)nc(OCCN5CCC(CC6(F)CCN(CC7CCN(c8cccc9c8CN(C8CCC(=O)NC8=O)C9=O)CC7)CC6)CC5)nc4c3F)c12]

The title compound was prepared in an analogous manner to 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl)piperidin-1-yl)-4-chloro-1-oxoisoindolin-2-yl)piperidine-2,6-dione. (white solid, formic acid salt). LC/MS (ESI) m/z: 1025.5 $[M+H]^+$; $^1H$ NMR (400 MHz, DMSO-$d_6$) δ 11.00 (s, 1H), 9.79-9.48 (m, 2H), 9.42-9.26 (m, 1H), 9.16 (s, 1H), 8.00 (dd, J=6.0, 9.2 Hz, 1H), 7.55-7.39 (m, 3H), 7.33 (d, J=7.6 Hz, 1H), 7.23-7.14 (m, 2H), 5.13 (dd, J=5.2, 13.2 Hz, 1H), 4.90-4.53 (m, 4H), 4.50-4.38 (m, 1H), 4.35-4.19 (m, 3H), 3.73-3.34 (m, 10H), 3.19-2.87 (m, 7H), 2.84-2.70 (m, 2H), 2.69-2.57 (m, 2H), 2.21-1.71 (m, 16H), 1.71-1.27 (m, 6H).

Example 123: Synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione (Compound 111)

Step 1: Preparation of tert-butyl 4-[[4-[[1-[2-(2,6-dioxo-3-piperidyl)-1-oxo-isoindolin-5-yl]-4-piperidyl]methyl]piperazin-1-yl]methyl]piperidine-1-carboxylate

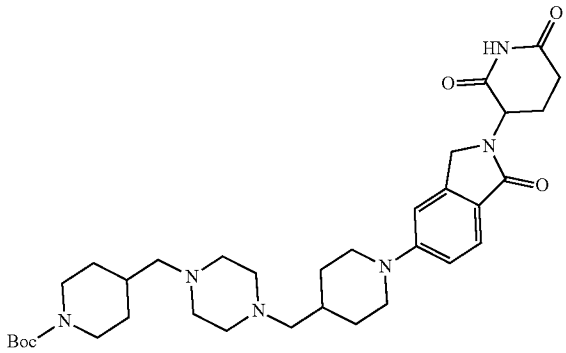 [SMILES: CC(C)(C)OC(=O)N1CCC(CN2CCN(CC3CCN(c4ccc5c(c4)CN(C4CCC(=O)NC4=O)C5=O)CC3)CC2)CC1]

To a solution of 1-[2-(2,6-dioxo-3-piperidyl)-1-oxo-isoindolin-5-yl]piperidine-4-carbaldehyde (500 mg, 1.4 mmol) in dichloromethane (5 mL) and isopropanol (5 mL) were added N,N-diisopropylethylamine (0.1 mL, 0.7 mmol), tert-butyl 4-(piperazin-1-ylmethyl)piperidine-1-carboxylate (398 mg, 1.4 mmol), and sodium triacetoxyborohydride (894 mg, 4 mmol), and the reaction mixture was stirred at 25° C. for 12 h. The mixture was diluted with water (20 mL) and extracted with dichloromethane (3×20 mL). The organic extract was dried over anhydrous sodium sulfate, filtered, and concentrated under reduced pressure. The residue was purified by preparative TLC (dichloromethane/methanol=8/1) to afford the title compound (242 mg, 27%) as a yellow solid. LC/MS (ESI) m/z: 623.5[M+H]$^+$; $^1$H NMR (400 MHz, $CDCl_3$) δ 8.23 (d, J=0.8 Hz, 1H), 7.72 (d, J=8.8 Hz, 1H), 6.98 (d, J=8.4 Hz, 1H), 6.87 (s, 1H), 5.21 (dd, J=5.2, 1 Step 2: Hz, 1H), 4.46-4.34 (m, 1H), 4.30-4.21 (m, 1H), 4.18-4.00 (m, 2H), 3.83 (d, J=12.8 Hz, 2H), 2.93-2.80 (m, 5H), 2.76-2.55 (m, 9H), 2.44-2.28 (m, 5H), 2.25-2.17 (m, 1H), 1.96-1.82 (m, 2H), 1.73 (d, J=12.0 Hz, 3H), 1.46 (s, 9H), 1.40-1.22 (m, 3H), 1.18-1.02 (m, 2H).

Step 2: Preparation of 3-[1-oxo-5-[4-[[4-(4-piperidylmethyl)piperazin-1-yl]methyl]-1-piperidyl]isoindolin-2-yl]piperidine-2,6-dione

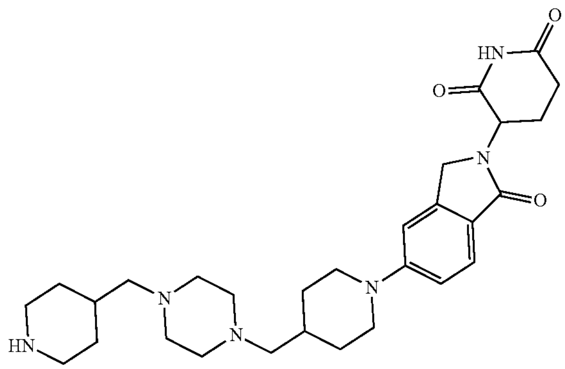 [SMILES: O=C1CCC(N2Cc3cc(N4CCC(CN5CCN(CC6CCNCC6)CC5)CC4)ccc3C2=O)C(=O)N1]

To a solution of tert-butyl 4-[[4-[[1-[2-(2,6-dioxo-3-piperidyl)-1-oxo-isoindolin-5-yl]-4-piperidyl]methyl]piperazin-1-yl]methyl]piperidine-1-carboxylate (242 mg, 0.4 mmol) in dichloromethane (4 mL) was added trifluoroacetic acid (1.0 mL, 13 mmol), and the mixture was stirred at 25° C. for 0.5 h. The reaction mixture was concentrated to afford 3-[1-oxo-5-[4-[[4-(4-piperidylmethyl)piperazin-1-yl]methyl]-1-piperidyl]isoindolin-2-yl]piperidine-2,6-dione (247 mg, crude, TFA salt) as a yellow gum. LC/MS (ESI) m/z: 523.4 [M+H]$^+$.

Step 3: Preparation of tert-butyl 3-[2-[2-[4-[[4-[[1-[2-(2,6-dioxo-3-piperidyl)-1-oxo-isoindolin-5-yl]-4-piperidyl]methyl]piperazin-1-yl]methyl]-1-piperidyl]ethoxy]-8-fluoro-7-[7-fluoro-3-hydroxy-8-(2-triisopropylsilylethynyl)-1-naphthyl]pyrido[4,3-d]pyrimidin-4-yl]-3,8-diazabicyclo[3.2.1]octane-8-carboxylate

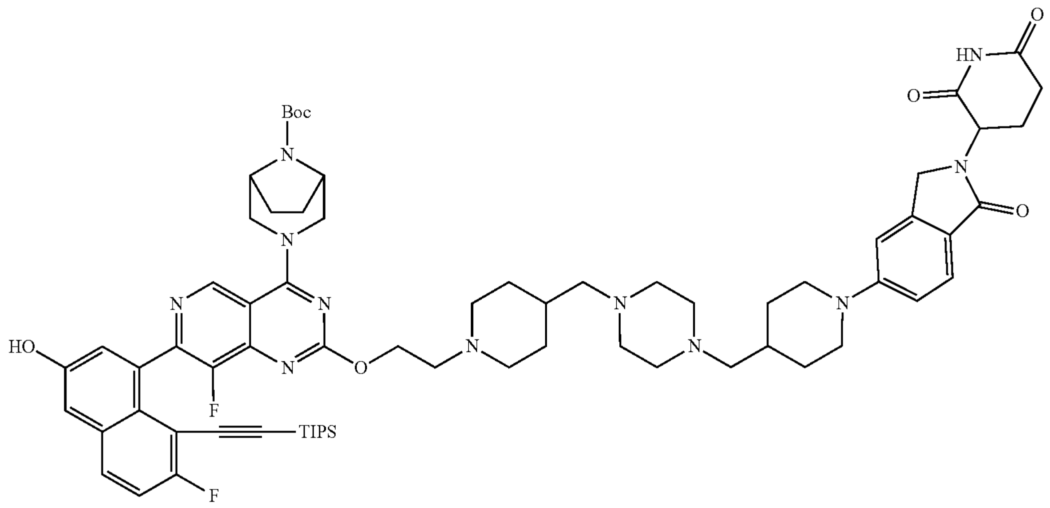

To a solution of 3-[1-oxo-5-[4-[[4-(4-piperidylmethyl) piperazin-1-yl]methyl]-1-piperidyl]isoindolin-2-yl]piperidine-2,6-dione trifluoroacetate (247 mg, 0.4 mmol) in dichloromethane (3 mL), isopropanol (3 mL) and N,N-diisopropylethylamine (0.2 mL, 1 mmol) were added tert-butyl 3-[8-fluoro-7-[7-fluoro-3-hydroxy-8-(2-triisopropylsilylethynyl)-1-naphthyl]-2-(2-oxoethoxy)pyrido[4,3-d] pyrimidin-4-yl]-3,8-diazabicyclo[3.2.1]octane-8-carboxylate (294 mg, 0.4 mmol) and sodium triacetoxyborohydride (164 mg, 0.8 mmol), and the mixture was stirred at 25° C. for 1 h. The reaction mixture was diluted with water (20 mL) and extracted with dichloromethane (3x20 mL). The organic extract was dried over anhydrous sodium sulfate, filtered, and concentrated under reduced pressure. The residue was purified by preparative TLC (dichloromethane/methanol=7/1) to afford the title compound (300 mg, 61%) as a yellow solid. LC/MS (ESI) m/z: 1264.9 $[M+H]^+$, $^1H$ NMR (400 MHz, DMSO-$d_6$) δ 10.93 (s, 1H), 10.26 (s, 1H), 9.16 (s, 1H), 7.97 (dd, J=6.0, 9.2 Hz, 1H), 7.52-7.43 (m, 2H), 7.40 (d, J=2.4 Hz, 1H), 7.17 (d, J=2.0 Hz, 1H), 7.07-6.98 (m, 2H), 5.03 (dd, J=5.2, 1 Step 2: Hz, 1H), 4.73 (d, J=12.4 Hz, 1H), 4.59-4.40 (m, 2H), 4.35-4.23 (m, 4H), 3.85 (d, J=12.0 Hz, 2H), 3.74 (d, J=12.0 Hz, 1H), 3.64-3.52 (m, 1H), 3.41-3.34 (m, 2H), 2.95-2.74 (m, 5H), 2.60 (s, 2H), 2.46-2.30 (m, 6H), 2.28-2.05 (m, 5H), 2.02-1.92 (m, 2H), 1.89-1.82 (m, 2H), 1.81-1.62 (m, 6H), 1.46 (s, 9H), 1.33-1.21 (m, 6H), 1.16 (d, J=8.8 Hz, 3H), 0.81 (t, J=8.0 Hz, 18H), 0.57-0.41 (m, 3H).

Step 4: Preparation of tert-butyl 3-[2-[2-[4-[[4-[[1-[2-(2,6-dioxo-3-piperidyl)-1-oxo-isoindolin-5-yl]-4-piperidyl]methyl]piperazin-1-yl]methyl]-1-piperidyl] ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate

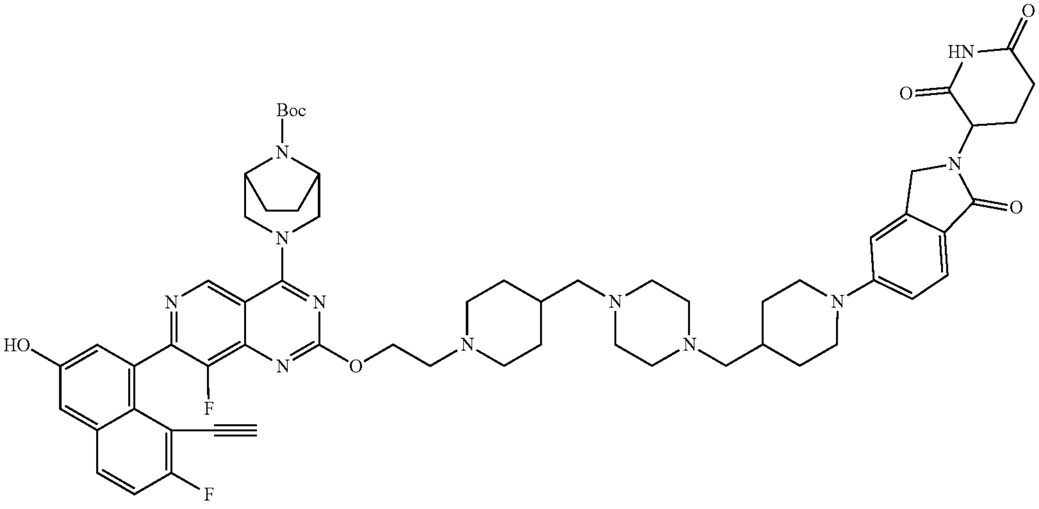 [SMILES: C#Cc1c(F)ccc2cc(O)cc(-c3ncc4c(N5CC6CCC(C5)N6C(=O)OC(C)(C)C)nc(OCCN5CCC(CN6CCN(CC7CCN(c8ccc9c(c8)CN(C8CCC(=O)NC8=O)C9=O)CC7)CC6)CC5)nc4c3F)c12]

To tert-butyl 3-[2-[2-[4-[[4-[[1-[2-(2,6-dioxo-3-piperidyl)-1-oxo-isoindolin-5-yl]-4-piperidyl]methyl]piperazin-1-yl]methyl]-1-piperidyl]ethoxy]-8-fluoro-7-[7-fluoro-3-hydroxy-8-(2-triisopropylsilylethynyl)-1-naphthyl]pyrido [4,3-d]pyrimidin-4-yl]-3,8-diazabicyclo[3.2.1]octane-8-carboxylate (300 mg, 0.2 mmol) in N,N-dimethylformamide (3 mL) was added cesium fluoride (1.08 g, 7 mmol), and the mixture was stirred at 25° C. for 1 h. The reaction mixture was diluted with water (20 mL) and extracted with dichloromethane (3x20 mL). The organic extract was dried over anhydrous sodium sulfate, filtered, and concentrated under reduced pressure. The residue was purified by preparative TLC (dichloromethane/methanol=7/1) to afford the title compound (274 mg, crude) as a yellow gum. LC/MS (ESI) m/z: 1108.6 $[M+H]^+$.

Step 5: Preparation of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione

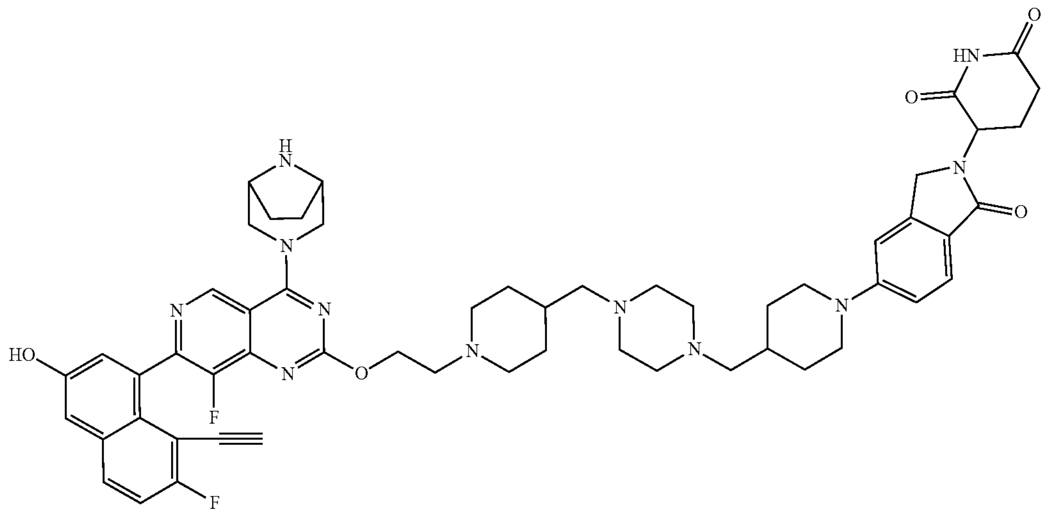 [SMILES: C#Cc1c(F)ccc2cc(O)cc(-c3ncc4c(N5CC6CCC(C5)N6)nc(OCCN5CCC(CN6CCN(CC7CCN(c8ccc9c(c8)CN(C8CCC(=O)NC8=O)C9=O)CC7)CC6)CC5)nc4c3F)c12]

To tert-butyl 3-[2-[2-[4-[[4-[[1-[2-(2,6-dioxo-3-piperidyl)-1-oxo-isoindolin-5-yl]-4-piperidyl]methyl]piperazin-1-yl]methyl]-1-piperidyl]ethoxy]-7-(8-ethynyl-7-fluoro-3-hydroxy-1-naphthyl)-8-fluoro-pyrido[4,3-d]pyrimidin-4-yl]-3,8-diazabicyclo[3.2.1]octane-8-carboxylate (274 mg, 0.25 mmol) in dichloromethane (6 mL) was added 4 M HCl in 1,4-dioxane (6 mL), and the reaction mixture was stirred at 25° C. for 15 min. The mixture was suspended in petroleum ether (10 mL) and filtered. The filtered cake was dissolved with dimethyl sulfoxide (3 mL) and N,N-diisopropylethylamine to adjust the pH to 8. The mixture was purified by prep-HPLC (1% to 30% acetonitrile in water (formic acid) over 10 min) to afford the title compound (107 mg, 43%, 3 formic acid salt) as a yellow solid. LC/MS (ESI) m/z: 1008.3 $[M+H]^+$; $^1H$ NMR (400 MHz, DMSO-$d_6$) δ 10.94 (s, 1H), 9.05 (s, 1H), 8.20 (s, 3H), 7.97 (dd, J=6.0, 9.2 Hz, 1H), 7.53-7.42 (m, 2H), 7.39 (d, J=2.4 Hz, 1H), 7.18 (d, J=2.0 Hz, 1H), 7.10-6.98 (m, 2H), 5.04 (dd, J=5.2, 1 Step 2: Hz, 1H), 4.57-4.42 (m, 3H), 4.41-4.26 (m, 2H), 4.20 (s, 1H), 3.93 (s, 1H), 3.85 (d, J=12.4 Hz, 2H), 3.78-3.72 (m, 2H), 3.68 (s, 2H), 3.01-2.87 (m, 3H), 2.85-2.75 (m, 2H), 2.74-2.66 (m, 2H), 2.63-2.52 (m, 3H), 2.42-2.22 (m, 8H), 2.18-1.91 (m, 6H), 1.75 (s, 6H), 1.64 (d, J=11.2 Hz, 2H), 1.47 (d, J=1.2 Hz, 1H), 1.26-0.98 (m, 5H).

Example 124: Synthesis of 3-{4-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperazin-1-yl}methyl)piperidin-1-yl]-1-oxo-2,3-dihydro-1H-isoindol-2-yl}piperidine-2,6-dione (Compound 136)

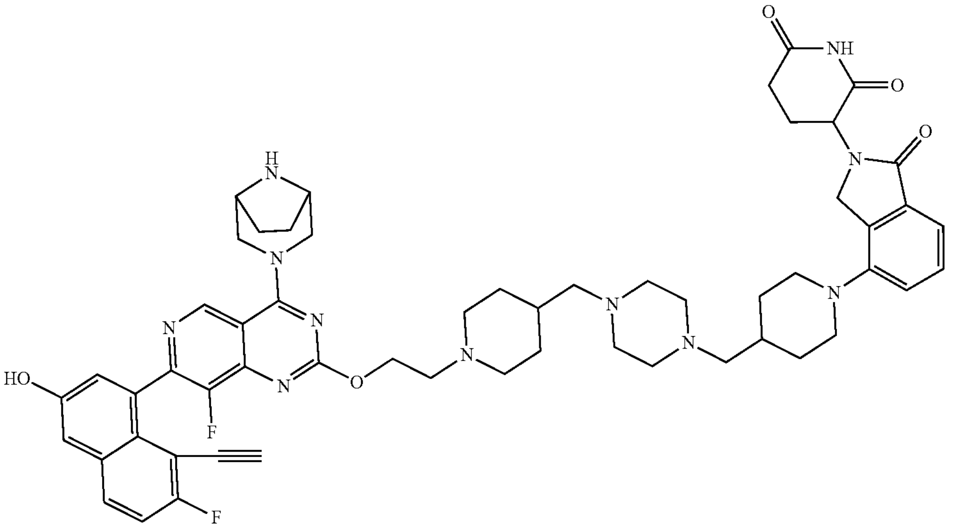 [SMILES: C#Cc1c(F)ccc2cc(O)cc(-c3ncc4c(N5CC6CCC(C5)N6)nc(OCCN5CCC(CN6CCN(CC7CCN(c8cccc9c8CN(C8CCC(=O)NC8=O)C9=O)CC7)CC6)CC5)nc4c3F)c12]

The title compound was prepared in an analogous manner to 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (orange solid, formic acid salt). LC/MS (ESI) m/z: 1008.8 $[M+H]^+$, $^1H$ NMR (400 MHz, DMSO-$d_6$) δ 10.98 (br s, 1H), 9.05 (s, 1H), 8.20 (s, 3H), 7.98 (dd, J=6.0, 9.2 Hz, 1H), 7.57-7.35 (m, 3H), 7.28 (d, J=7.6 Hz, 1H), 7.20-7.06 (m, 2H), 5.11 (br dd, J=5.2, 13.2 Hz, 1H), 4.56-4.41 (m, 3H), 4.40-4.20 (m, 3H), 3.93 (s, 1H), 3.72-3.59 (m, 2H), 3.36 (t, J=12.0 Hz, 2H), 3.01-2.83 (m, 3H), 2.77-2.65 (m, 4H), 2.58 (br d, J=17.6 Hz, 4H), 2.49-2.43 (m, 4H), 2.41-2.23 (m, 6H), 2.16 (br d, J=7.2 Hz, 2H), 2.12-1.93 (m, 5H), 1.83-1.71 (m, 5H), 1.64 (d, J=11.2 Hz, 3H), 1.38 (s, 1H), 1.34-1.16 (m, 2H), 1.15-0.98 (m, 2H).

Example 125: Synthesis of 3-(5-(4-((4-(((3R,5S)-5-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)-1-methylpyrrolidin-3-yl)oxy)piperidin-1-yl)methyl)piperidin-1-yl)-4-chloro-1-oxoisoindolin-2-yl)piperidine-2,6-dione (Compound 113)

Step 1: Preparation of tert-butyl (1R,5S)-3-(2-(((2S,4R)-4-((1-((1-(4-chloro-2-(2,6-dioxopiperidin-3-yl)-1-oxoisoindolin-5-yl)piperidin-4-yl)methyl)piperidin-4-yl)oxy)-1-methylpyrrolidin-2-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate

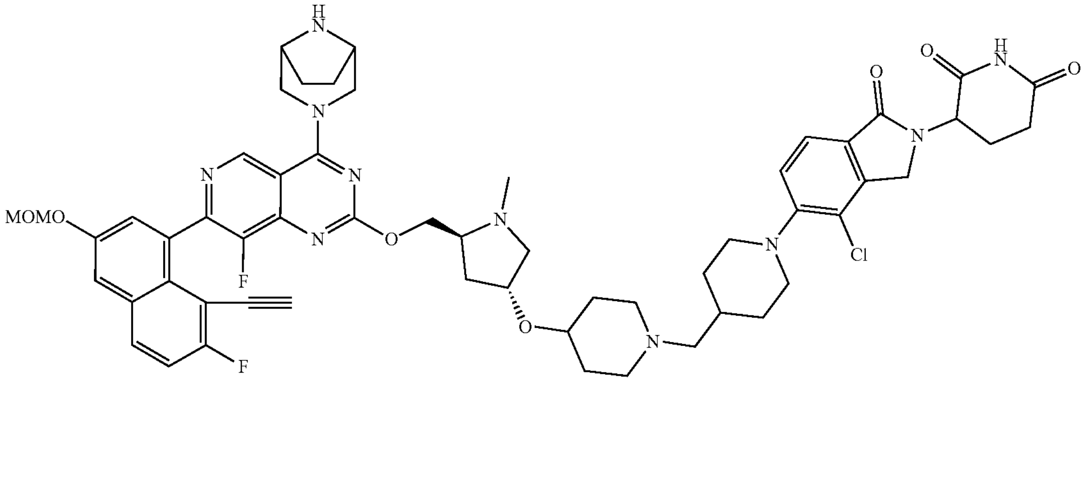

To a solution of 1-(4-chloro-2-(2,6-dioxopiperidin-3-yl)-1-oxoisoindolin-5-yl)piperidine-4-carbaldehyde (122 mg, 0.3 mmol) and tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate (250 mg, 0.3 mmol) in dichloromethane (2 mL) and dimethyl sulfoxide (2 mL) was added N-methylmorpholine (63 mg, 0.6 mmol), and the resulting mixture was stirred at 25° C. for 10 min. Acetic acid (38 mg, 0.6 mmol) was added then added, and the mixture was stirred for 20 min at 25° C. Sodium triacetoxyborohydride (132 mg, 0.6 mmol) was then added, and the reaction mixture was stirred at 25° C. for 12 h. The mixture was diluted with water (30 mL) and extracted with chloroform/isopropanol (5:1, 2×30 mL). The combined organic extracts were washed with brine (2×30 mL), dried over anhydrous sodium sulfate, filtered, and concentrated under reduced pressure. The residue was purified by prep-TLC (dichloromethane/methanol=10:1) to afford the title compound (240 mg, 65%) as a yellow solid. LC/MS (ESI) m/z: 1173.6 $[M+H]^+$.

Step 2: Preparation of 3-(5-(4-((4-(((3R,5S)-5-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)-1-methylpyrrolidin-3-yl)oxy)piperidin-1-yl)methyl)piperidin-1-yl)-4-chloro-1-oxoisoindolin-2-yl)piperidine-2,6-dione

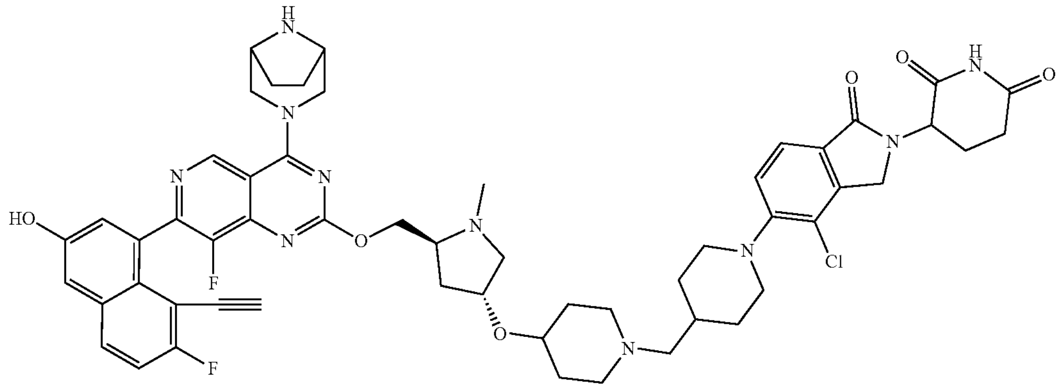 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8Cl)CN(C8CCC(=O)NC8=O)C9=O)CC7)CC6)CN5C)nc4c3F)c12]

To tert-butyl (1R,5S)-3-(2-(((2S,4R)-4-((1-((1-(4-chloro-2-(2,6-dioxopiperidin-3-yl)-1-oxoisoindolin-5-yl)piperidin-4-yl)methyl)piperidin-4-yl)oxy)-1-methylpyrrolidin-2-yl)methoxy)-7-(8-ethynyl-7-fluoro-3-(methoxymethoxy)naphthalen-1-yl)-8-fluoropyrido[4,3-d]pyrimidin-4-yl)-3,8-diazabicyclo[3.2.1]octane-8-carboxylate (240 mg, 0.2 mmol) in dichloromethane (2 mL) was added 4 M HCl in 1,4-dioxane (2 mL), and the mixture was stirred at 25° C. for 15 min. The mixture was evaporated from petroleum ether (2×100 mL), and the resulting residue was diluted with tetrahydrofuran (50 mL) and triethylamine to adjust the pH to 7. The resulting suspension was filtered, and the filtrate was concentrated under reduced pressure. The residue was purified by prep-HPLC (3% to 33% acetonitrile in water (formic acid) over 10 min) to afford the title compound (94.0 mg, 41%, di-formic acid salt) as a yellow solid. LC/MS (ESI) m/z: 1030.2 $[M+H]^+$, $^1H$ NMR (400 MHz, DMSO-$d_6$) δ 11.00 (s, 1H), 9.06 (s, 1H), 8.21 (s, 2H), 7.98 (dd, J=6.0, 9.2 Hz, 1H), 7.64 (d, J=8.0 Hz, 1H), 7.46 (t, J=9.2 Hz, 1H), 7.39 (d, J=2.4 Hz, 1H), 7.25 (d, J=8.4 Hz, 1H), 7.18 (d, J=2.4 Hz, 1H), 5.10 (dd, J=4.8, 1 Step 2: Hz, 1H), 4.53 (d, J=12.4 Hz, 1H), 4.44-4.33 (m, 3H), 4.29-4.20 (m, 2H), 4.16-4.09 (m, 1H), 3.95 (d, J=2.0 Hz, 1H), 3.77-3.61 (m, 4H), 3.37 (d, J=5.6 Hz, 2H), 3.33-3.20 (m, 2H), 2.98-2.85 (m, 1H), 2.83-2.76 (m, 1H), 2.75-2.65 (m, 4H), 2.58 (d, J=16.4 Hz, 1H), 2.37-2.32 (m, 4H), 2.23-2.14 (m, 3H), 2.07-1.96 (m, 3H), 1.93-1.85 (m, 2H), 1.80 (d, J=10.4 Hz, 4H), 1.77-1.71 (m, 4H), 1.70-1.58 (m, 2H), 1.41 (d, J=9.2 Hz, 2H), 1.33-1.22 (m, 2H).

Example 126: Synthesis of 3-(4-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]methyl}-1-methylpyrrolidin-3-yl]oxy}piperidin-1-yl)methyl]piperidin-1-yl}-1-oxo-2,3-dihydro-1H-isoindol-2-yl)piperidine-2,6-dione (Compound 115)

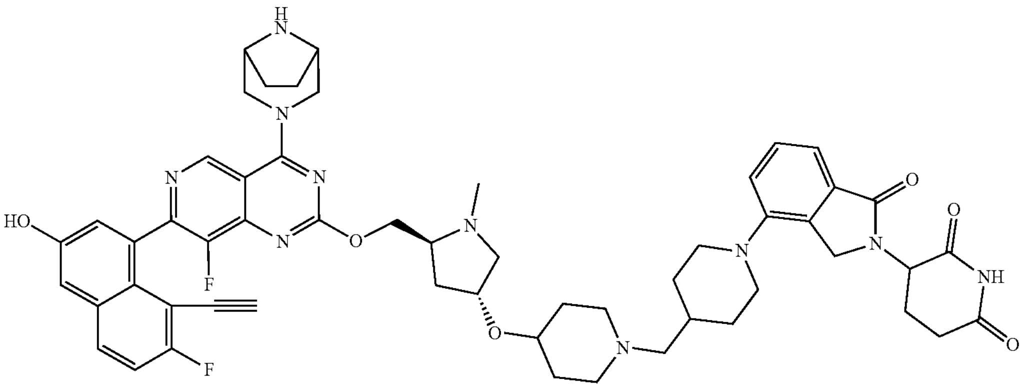 [SMILES: C#Cc1c(F)ccc2cc(O)cc(-c3ncc4c(N5CC6CCC(C5)N6)nc(OC[C@@H]5C[C@@H](OC6CCN(CC7CCN(c8cccc9c8CN(C8CCC(=O)NC8=O)C9=O)CC7)CC6)CN5C)nc4c3F)c12]

The title compound was prepared in an analogous manner to 3-(5-(4-((4-(((3R,5S)-5-(((4-((1R,5S)-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)methyl)-1-methylpyrrolidin-3-yl)oxy)piperidin-1-yl)methyl)piperidin-1-yl)-4-chloro-1-oxoisoindolin-2-yl)piperidine-2,6-dione. (yellow solid, formic acid salt). LC/MS (ESI) m/z: 995.3 $[M+H]^+$, $^1H$ NMR (400 MHz, DMSO-$d_6$) δ 10.97 (s, 1H), 9.06 (s, 1H), 8.17 (s, 2H), 7.98 (dd, J=6.0, 9.2 Hz, 1H), 7.50-7.37 (m, 3H), 7.32-7.26 (m, 1H), 7.21-7.11 (m, 2H), 5.11 (dd, J=5.2, 9.2 Hz, 1H), 4.61-4.51 (m, 1H), 4.46-4.36 (m, 3H), 4.33-4.24 (m, 2H), 4.16-4.10 (m, 1H), 3.95-3.92 (m, 1H), 3.83 (s, 2H), 3.77-3.69 (m, 2H), 3.40-3.25 (m, 4H), 2.99-2.86 (m, 1H), 2.85-2.78 (m, 1H), 2.75-2.66 (m, 4H), 2.62-2.54 (m, 2H), 2.36 (s, 3H), 2.23-2.16 (m, 3H), 2.11-1.99 (m, 3H), 1.94-1.73 (m, 11H), 1.69-1.60 (m, 1H), 1.48-1.36 (m, 2H), 1.34-1.19 (m, 2H).

Example 127: Synthesis of 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione (Compound 121)

Step 1: Preparation of tert-butyl 9-[[1-[2-(2,6-dioxo-3-piperidyl)-4-fluoro-1-oxo-isoindolin-5-yl]-4-piperidyl]methyl]-3,9-diazaspiro[5.5]undecane-3-carboxylate

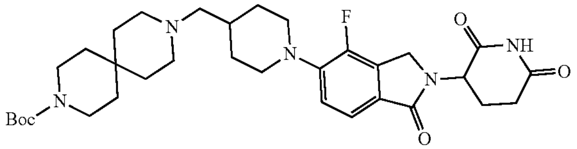 [SMILES: CC(C)(C)OC(=O)N1CCC2(CCN(CC3CCN(c4ccc5c(c4F)CN(C4CCC(=O)NC4=O)C5=O)CC3)CC2)CC1]

To a solution of tert-butyl 3,9-diazaspiro[5.5]undecane-3-carboxylate (337 mg, 1.3 mmol) in dichloromethane (5 mL) and isopropanol (5 mL) were added N,N-diisopropylethylamine (0.2 mL, 1 mmol) and 1-[2-(2,6-dioxo-3-piperidyl)-4-fluoro-1-oxo-isoindolin-5-yl]piperidine-4-carbaldehyde (450 mg, 1.2 mmol), and the mixture was stirred for 15 min at 25° C. Sodium triacetoxyborohydride (766 mg, 3.6 mmol) was then added, and the mixture was stirred for 0.5 h. The reaction mixture was diluted with water (20 mL) and extracted with dichloromethane (3×20 mL). The combined organic extract was washed with brine (20 mL), dried over anhydrous sodium sulfate, filtered, and concentrated in vacuo. The residue was purified by preparative TLC (dichloromethane/methanol=10:1) to afford the title compound (600 mg, 81%) as a yellow solid. LC/MS (ESI) m/z: 612.5 $[M+H]^+$.

Step 2: Preparation of 3-[5-[4-(3,9-diazaspiro[5.5]undecan-3-ylmethyl)-1-piperidyl]-4-fluoro-1-oxo-isoindolin-2-yl]piperidine-2,6-dione

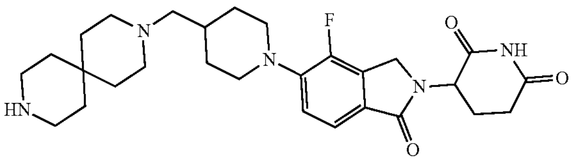 [SMILES: O=C1CCC(N2Cc3c(ccc(N4CCC(CN5CCC6(CCNCC6)CC5)CC4)c3F)C2=O)C(=O)N1]

To a solution of tert-butyl 9-[[1-[2-(2,6-dioxo-3-piperidyl)-4-fluoro-1-oxo-isoindolin-5-yl]-4-piperidyl]methyl]-3,9-diazaspiro[5.5]undecane-3-carboxylate (600 mg, 1 mmol) in dichloromethane (6 mL) was added trifluoroacetic acid (6.0 mL, 81 mmol) at 20° C., and the reaction mixture was stirred for 0.5 h at 20° C. The mixture was concentrated in vacuo to afford the title compound (610 mg, 99%, TFA salt) as yellow oil. LC/MS (ESI) m/z: 512.4 $[M+H]^+$.

Step 3: Preparation of tert-butyl 3-[2-[2-[3-[[1-[2-(2,6-dioxo-3-piperidyl)-4-fluoro-1-oxo-isoindolin-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

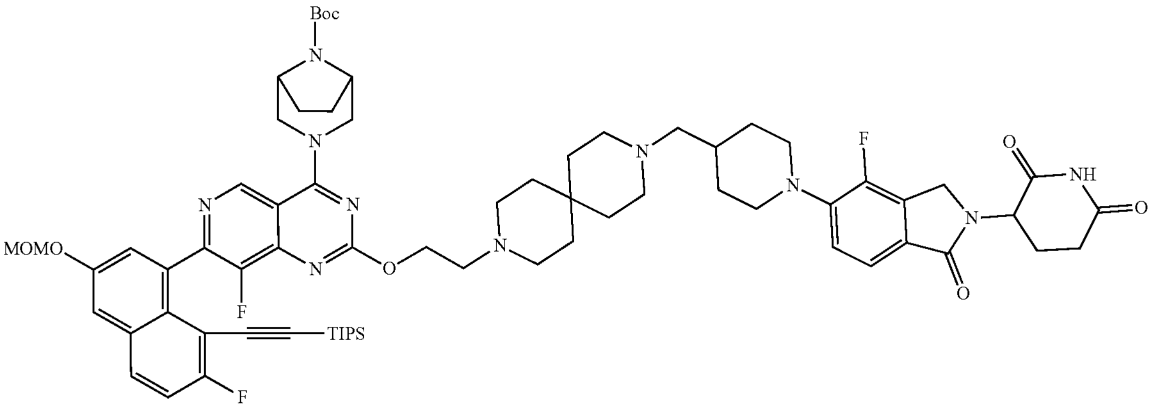

To 3-[5-[4-(3,9-diazaspiro[5.5]undecan-3-ylmethyl)-1-piperidyl]-4-fluoro-1-oxo-isoindolin-2-yl]piperidine-2,6-dione trifluoroacetic (610 mg, 0.97 mmol) in dichloromethane (8 mL) and isopropanol (8 mL) were added N,N-diisopropylethylamine (0.3 mL, 2 mmol) and tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (860 mg, 1 mmol), and the mixture was stirred for 0.5 h at 25° C. Sodium triacetoxyborohydride (620 mg, 2.9 mmol) was then added, and the mixture was stirred at 25° C. for 2 h. The reaction mixture was diluted with water (20 mL) and extracted with dichloromethane (20 mL×3). The combined organic extract was washed with brine (20 mL), dried over anhydrous sodium sulfate, filtered, and concentrated in vacuo. The residue was purified by preparative TLC (dichloromethane/methanol=10:1) to afford the title compound (1 g, 79%) as a yellow solid. LC/MS (ESI) m/z: 1298.8 $[M+H]^+$.

Step 4: Preparation of tert-butyl 3-[2-[2-[3-[[1-[2-(2,6-dioxo-3-piperidyl)-4-fluoro-1-oxo-isoindolin-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

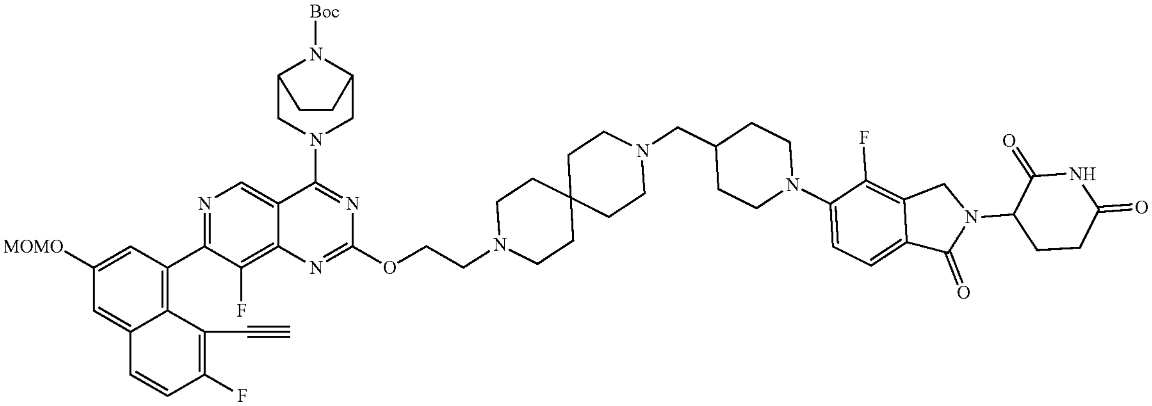

To tert-butyl 3-[2-[2-[3-[[1-[2-(2,6-dioxo-3-piperidyl)-4-fluoro-1-oxo-isoindolin-5-yl]-4-piperidyl]methyl]-3,9-diazaspiro[5.5]undecan-9-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (1 g, 0.8 mmol) in N,N-dimethylformamide (10 mL) at 25° C. was added cesium fluoride (3.51 g, 23 mmol), and the mixture was stirred for 2 h at 25° C. The reaction mixture was diluted with water (10 mL) and extracted with ethyl acetate (20 mL×3). The combined organic extract was washed with brine (20 mL), dried over anhydrous sodium sulfate, filtered, and concentrated in vacuo to afford the title compound (700 mg, 80%) as a yellow solid. LC/MS (ESI) m/z: 1141.7 $[M+H]^+$.

Step 5: Preparation of 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione

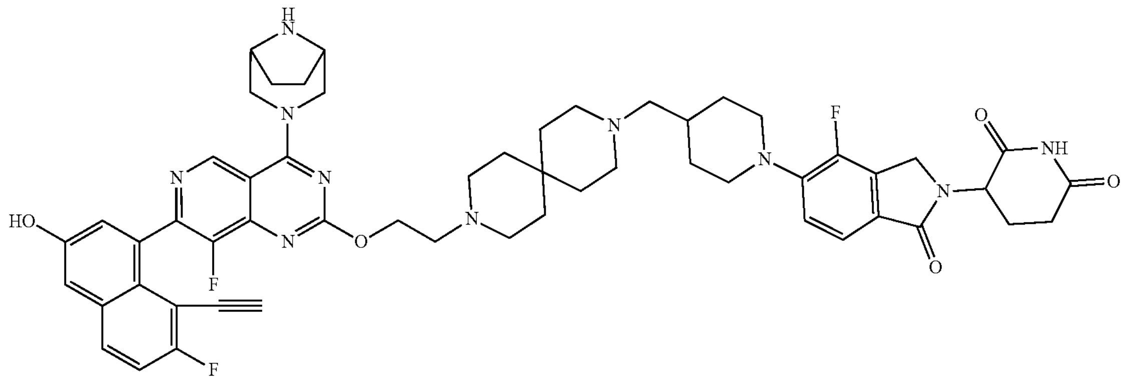 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7F)CN(C7CCC(=O)NC7=O)C8=O)CC5)CC6)nc4c3F)c12]

To tert-butyl 3-[2-[2-[3-[[1-[2-(2,6-dioxo-3-piperidyl)-4-fluoro-1-oxo-isoindolin-5-yl]-4-piperidyl]methyl]-3,9-diazaspiro[5.5]undecan-9-yl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (700 mg, 0.6 mmol) in dichloromethane (8 mL) was added 4 M HCl in 1,4-dioxane (4 mL) at 20° C., and the mixture was stirred for 0.5 h at 20° C. The reaction mixture was poured into methyl tert-butyl ether (10 mL) and filtered. The filter cake was purified by prep-HPLC (0%-30% acetonitrile in water (formic acid) over 11 min) to afford the title compound (214 mg, 33%, formic acid salt) as a yellow solid. LC/MS (ESI) m/z: 997.8 $[M+H]^+$; $^1H$ NMR (400 MHz, DMSO-$d_6$) δ 10.97 (s, 1H), 9.07 (s, 1H), 8.17 (s, 2H), 8.01-7.95 (m, 1H), 7.49-7.43 (m, 2H), 7.40 (d, J=2.4 Hz, 1H), 7.20-7.10 (m, 2H), 5.07 (dd, J=13.6, 5.2 Hz, 1H), 4.57-4.52 (m, 1H), 4.50-4.45 (m, 3H), 4.42-4.36 (m, 2H), 4.35-4.25 (m, 2H), 3.93 (s, 1H), 3.85-3.81 (m, 3H), 3.77-3.70 (m, 4H), 3.50-3.43 (m, 4H), 2.97-2.85 (m, 2H), 2.80-2.72 (m, 4H), 2.62-2.56 (m, 1H), 2.41-2.37 (m, 1H), 2.35-2.27 (m, 3H), 2.00-1.93 (m, 1H), 1.85-1.75 (m, 6H), 1.74-1.65 (m, 1H), 1.50-1.40 (m, 8H), 1.33-1.22 (m, 2H).

Example 128: Synthesis of 3-(5-{4-[(7-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-2,7-diazaspiro[3.5]nonan-2-yl)methyl]-4-fluoropiperidin-1-yl}-4-fluoro-1-oxo-2,3-dihydro-1H-isoindol-2-yl)piperidine-2,6-dione (Compound 119)

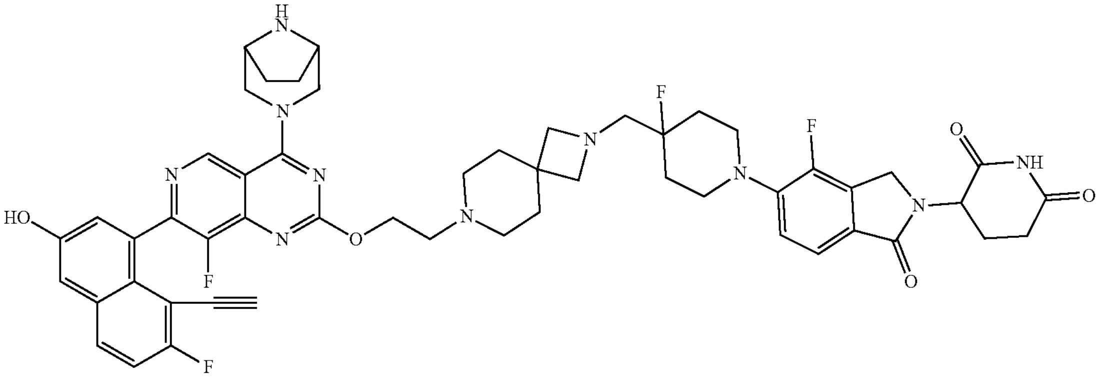 [SMILES: C#Cc1c(F)ccc2cc(O)cc(-c3ncc4c(N5CC6CCC(C5)N6)nc(OCCN5CCC6(CC5)CN(CC5(F)CCN(c7ccc8c(c7F)CN(C7CCC(=O)NC7=O)C8=O)CC5)C6)nc4c3F)c12]

The title compound was made in an analogous manner to 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione. (orange solid, formic acid salt). LC/MS (ESI) m/z: 987.2 $[M+H]^+$; $^1H$ NMR (400 MHz, DMSO-$d_6$) δ 10.98 (s, 1H), 9.08 (s, 1H), 8.14 (s, 2H), 7.98 (dd, J=5.6, 9.2 Hz, 1H), 7.56-7.43 (m, 2H), 7.40 (d, J=2.6 Hz, 1H), 7.27-7.13 (m, 2H), 5.07 (dd, J=4.6, 13.4 Hz, 1H), 4.60 (d, J=13.2 Hz, 1H), 4.54-4.40 (m, 4H), 4.31 (d, J=16.8 Hz, 1H), 3.99 (s, 2H), 3.93 (s, 1H), 3.79-3.70 (m, 2H), 3.53-3.40 (m, 3H), 3.04 (s, 4H), 3.00-2.82 (m, 3H), 2.72 (d, J=12.4 Hz, 3H), 2.65 (s, 1H), 2.62-2.53 (m, 3H), 2.47-2.34 (m, 4H), 1.98 (dd, J=6.0, 11.2 Hz, 1H), 1.91-1.81 (m, 6H), 1.80-1.71 (m, 2H), 1.68 (s, 3H).

Example 129: Synthesis of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]-4-fluoropiperidin-1-yl}-4-fluoro-1-oxo-2,3-dihydro-1H-isoindol-2-yl)piperidine-2,6-dione (Compound 120)

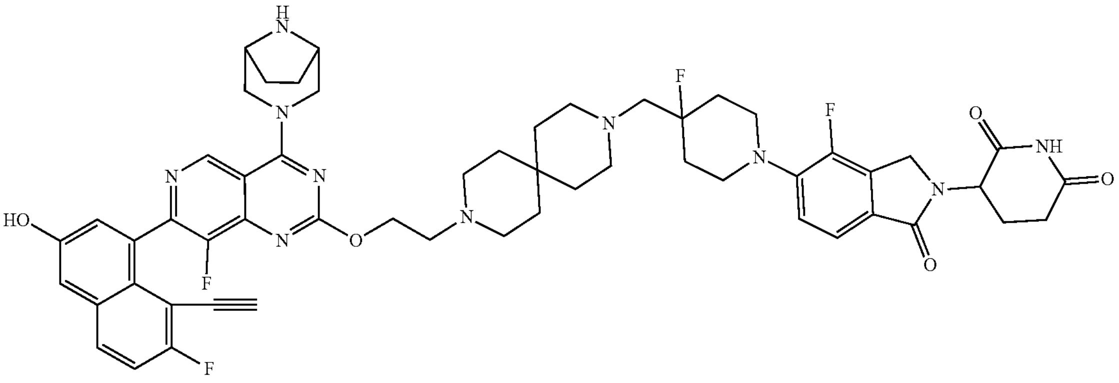 [SMILES: C#Cc1c(F)ccc2cc(O)cc(-c3ncc4c(N5CC6CCC(C5)N6)nc(OCCN5CCC6(CC5)CCN(CC5(F)CCN(c7ccc8c(c7F)CN(C7CCC(=O)NC7=O)C8=O)CC5)CC6)nc4c3F)c12]

The title compound was made in an analogous manner to 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione. (yellow solid). LC/MS (ESI) m/z: 1015.2 $[M+H]^+$; $^1H$ NMR (400 MHz, DMSO-$d_6$) δ 10.99 (s, 1H), 9.07 (s, 1H), 8.15 (s, 2H), 7.98 (dd, J=6.0, 9.0 Hz, 1H), 7.50-7.44 (m, 2H), 7.40 (d, J=2.4 Hz, 1H), 7.23-7.15 (m, 2H), 5.07 (dd, J=5.2, 13.2 Hz, 1H), 4.65-4.36 (m, 6H), 4.31 (d, J=16.8 Hz, 1H), 3.96-3.87 (m, 4H), 3.74 (t, J=12.8 Hz, 4H), 3.02 (dd, J=10.0, 11.2 Hz, 4H), 2.96-2.88 (m, 2H), 2.81 (s, 3H), 2.60 (s, 1H), 2.55 (s, 4H), 2.02-1.88 (m, 4H), 1.87-1.68 (m, 6H), 1.49-1.35 (m, 8H).

Example 130: Synthesis of 3-(4-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-1-oxo-2,3-dihydro-1H-isoindol-2-yl)piperidine-2,6-dione (Compound 132)

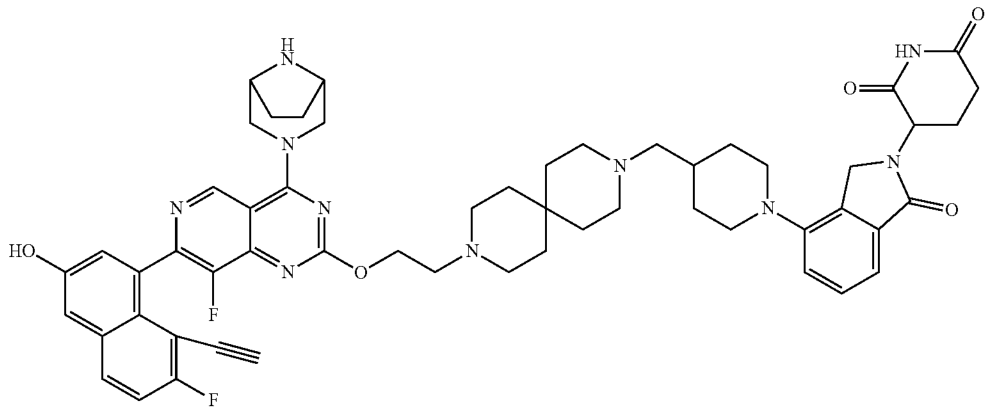 [SMILES: C#Cc1c(F)ccc2cc(O)cc(-c3ncc4c(N5CC6CCC(C5)N6)nc(OCCN5CCC6(CC5)CCN(CC5CCN(c7cccc8c7CN(C7CCC(=O)NC7=O)C8=O)CC5)CC6)nc4c3F)c12]

The title compound was made in an analogous manner to 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione. (yellow solid). LC/MS (ESI) m/z: 979.7 $[M+H]^+$; $^1H$ NMR (400 MHz, DMSO-$d_6$) δ 10.98 (s, 1H), 9.05 (s, 1H), 8.19 (s, 3H), 7.97 (dd, J=6.0, 9.2 Hz, 1H), 7.52-7.37 (m, 3H), 7.28 (d, J=7.2 Hz, 1H), 7.20-7.12 (m, 2H), 5.11 (dd, J=5.2, 13.2 Hz, 1H), 4.51 (d, J=12.4 Hz, 1H), 4.47-4.43 (m, 2H), 4.41-4.34 (m, 2H), 4.27 (d, J=17.2 Hz, 2H), 3.93 (s, 1H), 3.70 (s, 2H), 3.64 (s, 2H), 3.40-3.32 (m, 4H), 2.98-2.85 (m, 2H), 2.75-2.68 (m, 4H), 2.58 (d, J=17.2 Hz, 2H), 2.46-2.43 (m, 2H), 2.35 (s, 4H), 2.22 (d, J=7.2 Hz, 2H), 2.03-1.94 (m, 1H), 1.79 (d, J=12.4 Hz, 2H), 1.72 (s, 4H), 1.41 (s, 8H), 1.28-1.19 (m, 2H).

Example 131: Synthesis of 3-(4-{4-[(7-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-2,7-diazaspiro[3.5]nonan-2-yl)methyl]piperidin-1-yl}-1-oxo-2,3-dihydro-1H-isoindol-2-yl)piperidine-2,6-dione (Compound 135)

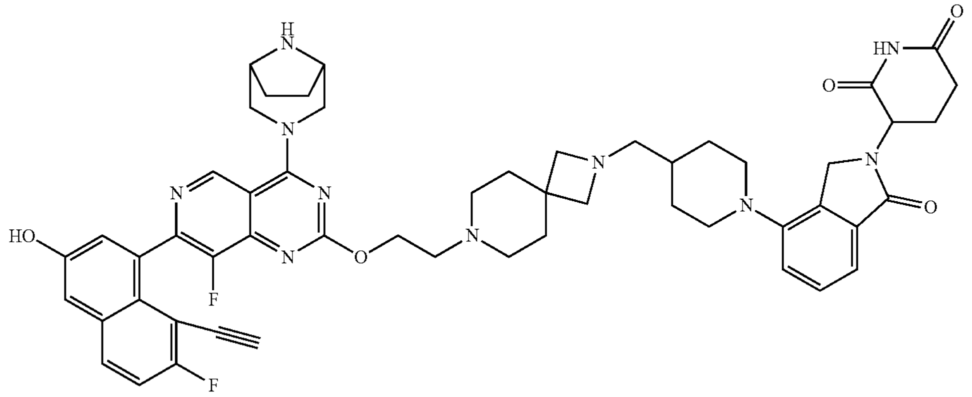 [SMILES: C#Cc1c(F)ccc2cc(O)cc(-c3ncc4c(N5CC6CCC(C5)N6)nc(OCCN5CCC6(CC5)CN(CC5CCN(c7cccc8c7CN(C7CCC(=O)NC7=O)C8=O)CC5)C6)nc4c3F)c12]

The title compound was made in an analogous manner to 3-[5-[4-[[9-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-3,9-diazaspiro[5.5]undecan-3-yl]methyl]-1-piperidyl]-4-fluoro-1-oxo-isoindolin-2-yl]piperidine-2,6-dione. (white solid). LC/MS (ESI) m/z: 951.7 $[M+H]^+$, $^1H$ NMR (400 MHz, DMSO-$d_6$) δ 10.97 (s, 1H), 9.11-9.02 (m, 1H), 8.19 (s, 2H), 8.01-7.92 (m, 1H), 7.49-7.37 (m, 3H), 7.31-7.27 (m, 1H), 7.19-7.11 (m, 2H), 5.15-5.06 (m, 1H), 4.51-4.24 (m, 7H), 3.90 (d, J=5.2 Hz, 1H), 3.63 (d, J=6.0 Hz, 4H), 3.34 (s, 4H), 3.02 (s, 3H), 2.95-2.89 (m, 1H), 2.73-2.55 (m, 7H), 2.43-2.35 (m, 5H), 2.02-1.95 (m, 1H), 1.75 (d, J=12.4 Hz, 2H), 1.71-1.63 (m, 7H), 1.49-1.41 (m, 1H), 1.30-1.21 (m, 2H).

Example 132: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione (Compound 122)

Step 1: Preparation of tert-butyl 3-[2-[[(2S,4R)-4-[[1-[[1-[2-(2,6-dioxo-3-piperidyl)-4-fluoro-1-oxo-isoindolin-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

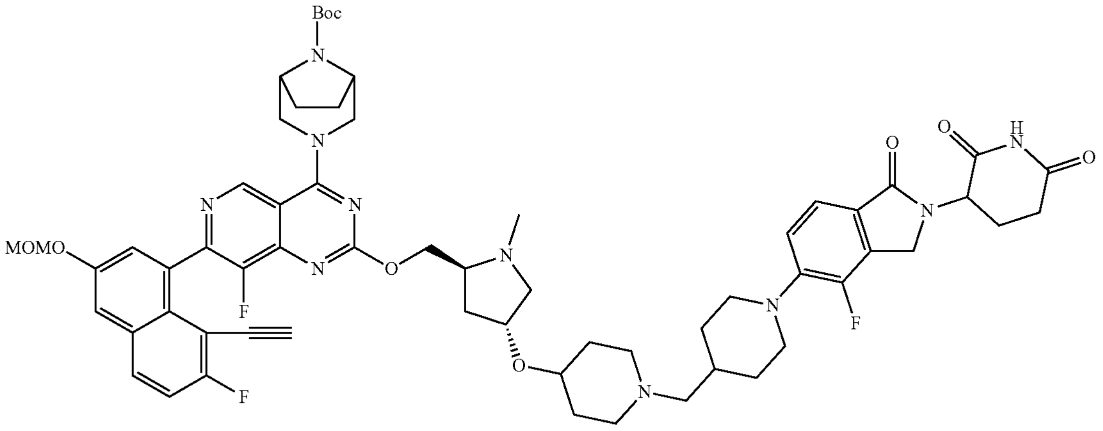

To a solution of tert-butyl 3-[7-[8-ethynyl-7-fluoro-3-(methoxymethoxy)-1-naphthyl]-8-fluoro-2-[[(2S,4R)-1-methyl-4-(4-piperidyloxy)pyrrolidin-2-yl]methoxy]pyrido[4,3-d]pyrimidin-4-yl]-3,8-diazabicyclo[3.2.1]octane-8-carboxylate (260 mg, 0.3 mmol) in dichloromethane (4 mL) and isopropyl alcohol (4 mL) were added diisopropylethylamine (0.03 mL, 0.2 mmol), 1-[2-(2,6-dioxo-3-piperidyl)-4-fluoro-1-oxo-isoindolin-5-yl]piperidine-4-carbaldehyde (121 mg, 0.3 mmol), and sodium triacetoxyborohydride (206 mg, 0.97 mmol), and the mixture was stirred at 25° C. for 12 h. The reaction mixture was diluted with water (20 mL) and extracted with dichloromethane/isopropanol (3×20 mL). The organic extract was dried over anhydrous sodium sulfate, filtered, and concentrated under reduced pressure. The residue was purified by preparative TLC (dichloromethane/methanol=8/1) to afford the title compound (128 mg, 34%) as a yellow solid. LC/MS (ESI) m/z: 1157.6 $[M+H]^+$.

Step 2: Preparation of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione

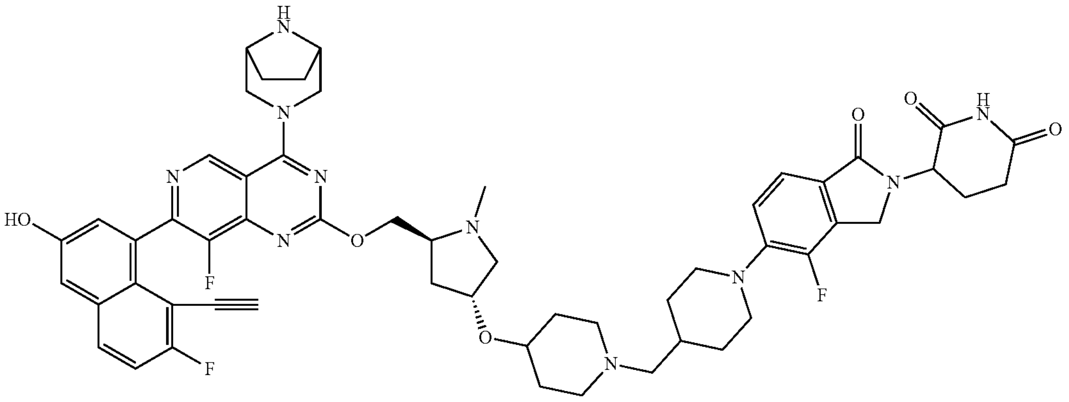 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8F)CN(C8CCC(=O)NC8=O)C9=O)CC7)CC6)CN5C)nc4c3F)c12]

-

To tert-butyl 3-[2-[[(2S,4R)-4-[[1-[[1-[2-(2,6-dioxo-3-piperidyl)-4-fluoro-1-oxo-isoindolin-5-yl]-4-piperidyl]methyl]-4-piperidyl]oxy]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (128 mg, 0.11 mmol) in dichloromethane (3 mL) was added 4 M HCl in 1,4-dioxane (3 mL), and the mixture was stirred at 25° C. for 15 min. The reaction mixture was triturated with methyl tert-butyl ether (30 mL), then purified by prep-HPLC (1% to 30% acetonitrile in water (formic acid) over 10 min) to afford the title compound (99 mg, 85%, di-formic acid salt) as a yellow solid. LC/MS (ESI) m/z: 1013.2 $[M+H]^+$, $^1H$ NMR (400 MHz, DMSO-$d_6$) δ 10.98 (s, 1H), 9.05 (s, 1H), 8.18 (s, 3H), 7.97 (dd, J=6.0, 9.3 Hz, 1H), 7.55-7.43 (m, 2H), 7.39 (d, J=2.5 Hz, 1H), 7.20-7.10 (m, 2H), 5.07 (dd, J=5.0, 1 Step 3: Hz, 1H), 4.58-4.47 (m, 2H), 4.45 (s, 1H), 4.41-4.30 (m, 3H), 4.29-4.18 (m, 2H), 4.15-4.07 (m, 2H), 3.94 (d, J=2.0 Hz, 1H), 3.31-3.23 (m, 4H), 2.98-2.84 (m, 2H), 2.77 (d, J=1 Step 8: Hz, 2H), 2.73-2.64 (m, 3H), 2.63-2.55 (m, 2H), 2.41 (dd, J=4.6, 13.0 Hz, 2H), 2.36-2.32 (m, 3H), 2.22-2.12 (m, 3H), 2.07-1.94 (m, 3H), 1.92-1.84 (m, 2H), 1.83-1.71 (m, 7H), 1.68-1.56 (m, 1H), 1.49-1.33 (m, 2H), 1.31-1.17 (m, 2H).

Example 133: Synthesis of 3-(5-{3-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]azetidin-1-yl}-1-oxo-2,3-dihydro-1H-isoindol-2-yl)piperidine-2,6-dione (Compound 164)

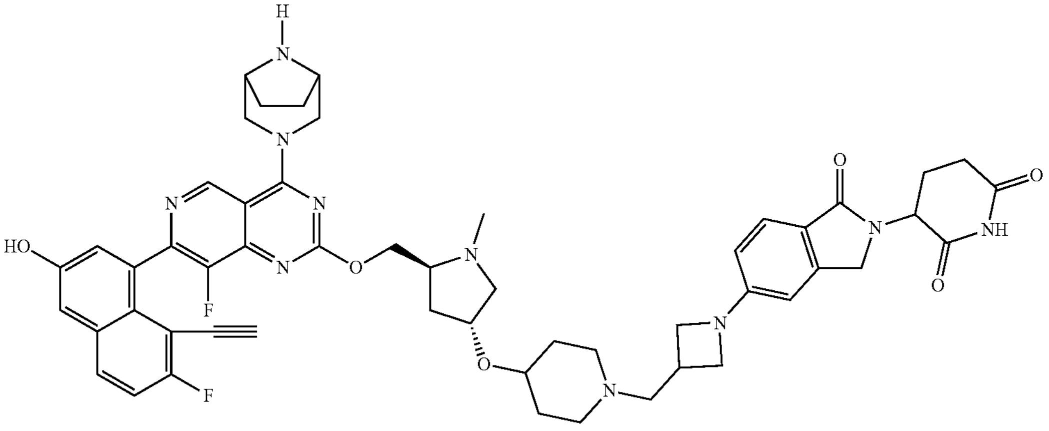 [SMILES: C#Cc1c(F)ccc2cc(O)cc(-c3ncc4c(N5CC6CCC(C5)N6)nc(OC[C@@H]5C[C@@H](OC6CCN(CC7CN(c8ccc9c(c8)CN(C8CCC(=O)NC8=O)C9=O)C7)CC6)CN5C)nc4c3F)c12]

The title compound was prepared in an analogous manner to 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione. (light 10 yellow solid). LC/MS (ESI) m/z: 967.6 $[M+H]^+$, $^1H$ NMR (400 MHz, DMSO-$d_6$) δ 9.01 (s, 1H), 7.87-7.84 (m, 1H), 7.59-7.56 (m, 1H), 7.35-7.29 (m, 2H), 7.21-7.20 (m, 1H), 6.50-6.48 (m, 2H), 5.09-5.05 (m, 1H), 4.65-4.56 (m, 2H), 4.49-4.47 (m, 2H), 4.36-4.34 (m, 2H), 4.25-4.23 (m, 1H), 4.12-4.08 (m, 2H), 3.73-3.61 (m, 6H), 3.48-3.43 (m, 1H), 3.39-3.35 (m, 2H), 3.05-2.99 (m, 2H), 2.92-2.84 (m, 1H), 2.79-2.74 (m, 3H), 2.70-2.67 (m, 2H), 2.52 (s, 3H), 2.46-2.37 (m, 2H), 2.27-2.21 (m, 2H), 2.15-2.00 (m, 3H), 1.92-1.79 (m, 6H), 1.62-1.57 (m, 2H).

Example 134: Synthesis of 3-[5-(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)-4-fluoro-1-oxo-2,3-dihydro-1H-isoindol-2-yl]piperidine-2,6-dione (Compound 103)

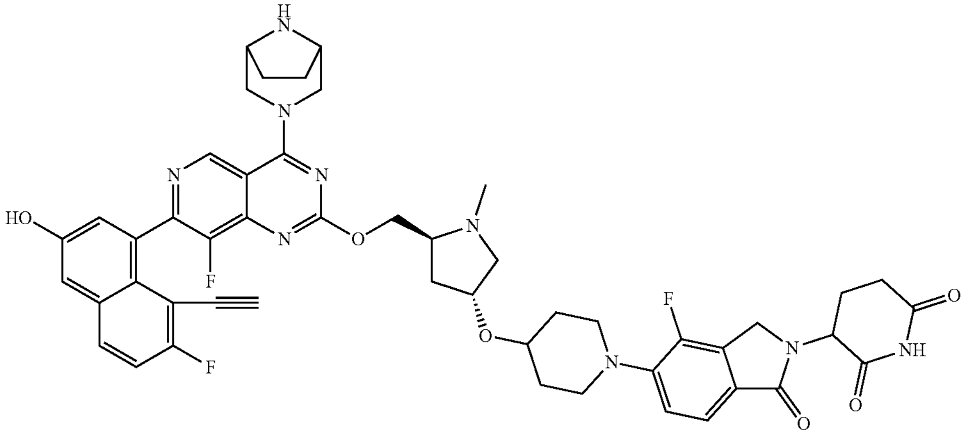 [SMILES: C#Cc1c(F)ccc2cc(O)cc(-c3ncc4c(N5CC6CCC(C5)N6)nc(OC[C@@H]5C[C@@H](OC6CCN(c7ccc8c(c7F)CN(C7CCC(=O)NC7=O)C8=O)CC6)CN5C)nc4c3F)c12]

The title compound was prepared in an analogous manner to 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione. (yellow solid, formic acid salt). LC/MS (ESI) m/z: 917.2 $[M+H]^+$; $^1H$ NMR (400 MHz, DMSO-$d_6$) b 10.98 (s, 1H), 9.06 (s, 1H), 8.12 (s, 1H), 8.01-7.93 (m, 1H), 7.50-7.42 (m, 2H), 7.39 (d, J=2.4 Hz, 1H), 7.19-7.12 (m, 2H), 7.24-7.17 (m, 1H), 7.07-6.97 (m, 2H), 5.05 (dd, J=5.2, 9.2 Hz, 1H), 4.56-4.51 (m, 1H), 4.50-4.45 (m, 1H), 4.42-4.35 (m, 2H), 4.33-4.28 (m, 1H), 4.25-4.15 (m, 2H), 3.96-3.93 (m, 1H), 3.79-3.64 (m, 5H), 3.56-3.48 (m, 2H), 3.41-3.26 (m, 4H), 2.96-2.87 (m, 3H), 2.85-2.76 (m, 1H), 2.62-2.55 (m, 1H), 2.44-2.38 (m, 1H), 2.37 (s, 3H), 2.25-2.19 (m, 1H), 1.99-1.86 (m, 5H), 1.77-1.74 (m, 3H), 1.63-1.53 (m, 2H).

Example 135: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-7-methyl-1-oxo-2,3-dihydro-1H-isoindol-2-yl)piperidine-2,6-dione (Compound 151)

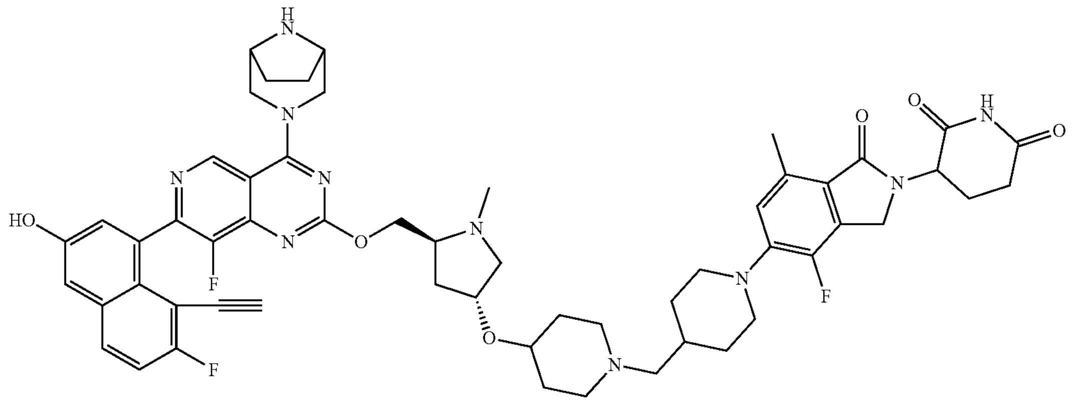 [SMILES: C#Cc1c(F)ccc2cc(O)cc(-c3ncc4c(N5CC6CCC(C5)N6)nc(OC[C@@H]5C[C@@H](OC6CCN(CC7CCN(c8cc(C)c9c(c8F)CN(C8CCC(=O)NC8=O)C9=O)CC7)CC6)CN5C)nc4c3F)c12]

The title compound was prepared in an analogous manner to 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione. 20 (yellow solid, formic acid salt). LC/MS (ESI) m/z: 1027.2 $[M+H]^+$; $^1H$ NMR (400 MHz, DMSO-$d_6$) δ 10.97 (s, 1H), 9.07 (s, 1H), 8.19 (s, 2H), 7.98 (dd, J=6.0, 9.2 Hz, 1H), 7.46 (t, J=9.2 Hz, 1H), 7.40 (d, J=2.4 Hz, 1H), 7.19 (d, J=2.4 Hz, 1H), 6.87 (d, J=7.6 Hz, 1H), 5.02 (dd, J=5.2, 13.2 Hz, 1H), 4.57 (br d, J=12.8 Hz, 1H), 4.45-4.33 (m, 3H), 4.30-4.19 (m, 2H), 4.13 (quin, J=5.6 Hz, 1H), 3.95 (d, J=2.8 Hz, 1H), 3.89 (br s, 2H), 3.81-3.69 (m, 2H), 3.47 (br d, J=8.8 Hz, 2H), 3.37-3.22 (m, 2H), 2.96-2.77 (m, 2H), 2.77-2.64 (m, 4H), 2.63-2.54 (m, 1H), 2.52 (s, 3H), 2.47-2.38 (m, 1H), 2.36 (s, 3H), 2.25-2.16 (m, 3H), 2.14-2.02 (m, 2H), 1.99-1.85 (m, 3H), 1.85-1.73 (m, 8H), 1.66 (br s, 2H), 1.50-1.36 (m, 2H), 1.30-1.18 (m, 2H).

Example 136: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]-4-fluoropiperidin-1-yl}-4-fluoro-1-oxo-2,3-dihydro-1H-isoindol-2-yl)piperidine-2,6-dione (Compound 112)

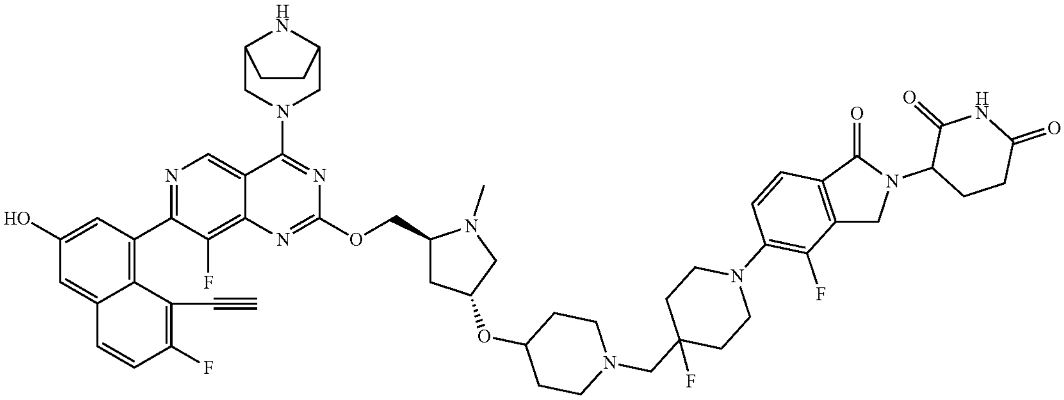 [SMILES: C#Cc1c(F)ccc2cc(O)cc(-c3ncc4c(N5CC6CCC(C5)N6)nc(OC[C@@H]5C[C@@H](OC6CCN(CC7(F)CCN(c8ccc9c(c8F)CN(C8CCC(=O)NC8=O)C9=O)CC7)CC6)CN5C)nc4c3F)c12]

The title compound was prepared in an analogous manner to 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione. (yellow solid, formic acid salt). LC/MS (ESI) m/z: 1031.2 $[M+H]^+$; $^1H$ NMR (400 MHz, DMSO-$d_6$) δ 10.99 (s, 1H), 9.04 (s, 1H), 8.20 (s, 2H), 7.97 (dd, J=6.0, 9.2 Hz, 1H), 7.50-7.43 (m, 2H), 7.39 (d, J=2.4 Hz, 1H), 7.24-7.15 (m, 2H), 5.07 (dd, J=4.8, 13.2 Hz, 1H), 4.52-4.45 (m, 2H), 4.41-4.29 (m, 3H), 4.24-4.20 (m, 1H), 4.14-4.09 (m, 1H), 3.94 (d, J=2.0 Hz, 1H), 3.59 (s, 5H), 3.05-2.97 (m, 3H), 2.94 (s, 2H), 2.81-2.73 (m, 4H), 2.60 (d, J=2.8 Hz, 2H), 2.37-2.31 (m, 5H), 2.24-2.13 (m, 4H), 2.02-1.93 (m, 3H), 1.92-1.85 (m, 3H), 1.78 (d, J=8.4 Hz, 4H), 1.72-1.65 (m, 4H), 1.45-1.34 (m, 2H).

Example 137: Synthesis of 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-ethylpyrrolidin-3-yl]oxy}piperidin-1-yl)methyl]piperidin-1-yl}-1-oxo-2,3-dihydro-1H-isoindol-2-yl)piperidine-2,6-dione (Compound 165)

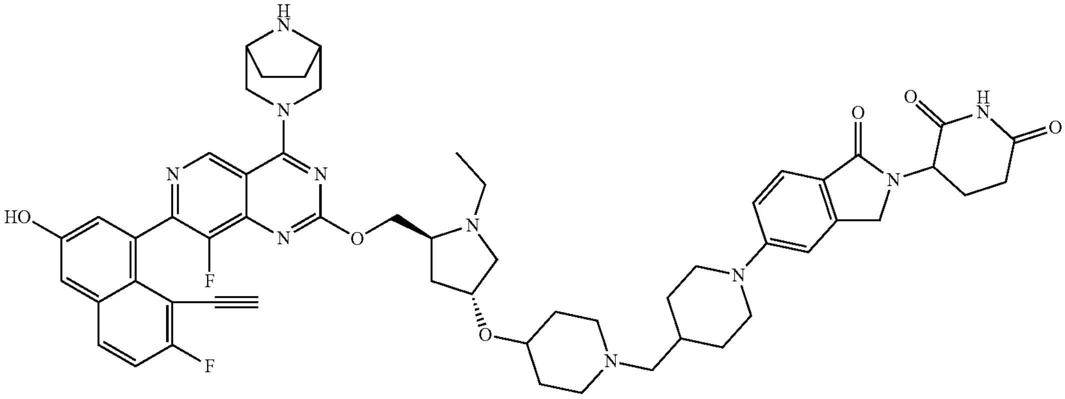 [SMILES: C#Cc1c(F)ccc2cc(O)cc(-c3ncc4c(N5CC6CCC(C5)N6)nc(OC[C@@H]5C[C@@H](OC6CCN(CC7CCN(c8ccc9c(c8)CN(C8CCC(=O)NC8=O)C9=O)CC7)CC6)CN5CC)nc4c3F)c12]

The title compound was prepared in an analogous manner to 3-(5-{4-[(4-{[(3R,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-3-yl]oxy}piperidin-1-yl)methyl]piperidin-1-yl}-4-fluoro-1-oxo-2,3-dihydro-1H-isoindol-2-yl)piperidine-2,6-dione. (yellow solid, formic acid salt). LC/MS (ESI) m/z: 1009.8 $[M+H]^+$; $^1H$ NMR (400 MHz, DMSO-$d_6$) δ 10.98-10.91 (m, 1H), 9.06 (s, 1H), 8.16 (s, 2H), 7.98 (dd, J=6.0, 9.2 Hz, 1H), 7.52-7.44 (m, 2H), 7.40 (d, J=2.4 Hz, 1H), 7.18 (s, 1H), 7.06-7.00 (m, 2H), 5.07-5.00 (m, 1H), 4.54 (br d, J=12.8 Hz, 1H), 4.42-4.34 (m, 2H), 4.31 (br d, J=17.2 Hz, 1H), 4.22-4.12 (m, 3H), 3.94 (s, 1H), 3.86 (br d, J=12.0 Hz, 2H), 3.79 (br s, 2H), 3.75-3.64 (m, 3H), 3.31-3.26 (m, 2H), 2.98 (br dd, J=4.0, 10.0 Hz, 1H), 2.92 (td, J=5.2, 8.0 Hz, 2H), 2.80 (br t, J=11.6 Hz, 2H), 2.72-2.66 (m, 2H), 2.60 (br s, 1H), 2.37 (br d, J=5.2 Hz, 1H), 2.21-2.12 (m, 3H), 2.03 (br dd, J=8.4, 12.0 Hz, 2H), 1.98-1.93 (m, 1H), 1.90-1.84 (m, 2H), 1.82-1.70 (m, 9H), 1.45-1.35 (m, 2H), 1.21-1.12 (m, 2H), 1.03-0.96 (m, 3H).

Example 138: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}-4-methylpiperidin-4-yl)methyl]piperidin-1-yl}methyl)piperidin-1-yl]-3-methyl-2-oxo-2,3-dihydro-1H-1,3-benzodiazol-1-yl}piperidine-2,6-dione (Compound 179)

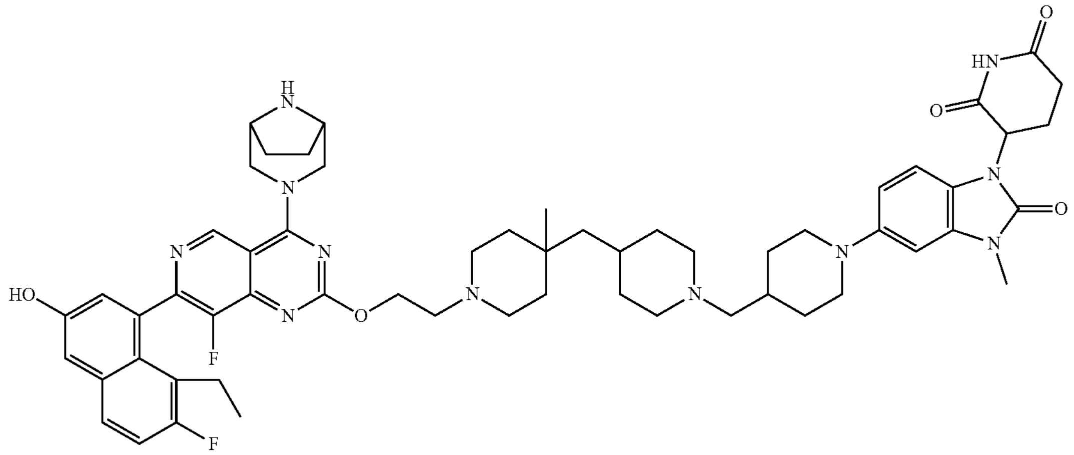 [SMILES: CCc1c(F)ccc2cc(O)cc(-c3ncc4c(N5CC6CCC(C5)N6)nc(OCCN5CCC(C)(CC6CCN(CC7CCN(c8ccc9c(c8)n(C)c(=O)n9C8CCC(=O)NC8=O)CC7)CC6)CC5)nc4c3F)c12]

The title compound was prepared in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione. (white solid, formic acid salt.) LC/MS (ESI) m/z: 1040.6 $[M+H]^+$, $^1H$ NMR (400 MHz, DMSO-$d_6$) δ 11.14-10.94 (m, 1H), 9.10 (s, 1H), 8.22 (s, 2H), 7.76 (dd, J=6.0, 9.2 Hz, 1H), 7.39-7.27 (m, 2H), 7.01 (d, J=2.4 Hz, 1H), 6.96-6.87 (m, 1H), 6.84-6.75 (m, 1H), 6.67-6.55 (m, 1H), 5.27 (br dd, J=5.6, 12.8 Hz, 1H), 4.54-4.39 (m, 4H), 3.55 (br d, J=12.0 Hz, 7H), 3.31-3.27 (m, 3H), 2.95-2.83 (m, 1H), 2.79 (br d, J=10.8 Hz, 2H), 2.72 (br t, J=5.6 Hz, 2H), 2.69-2.65 (m, 1H), 2.64-2.54 (m, 5H), 2.52 (br d, J=2.0 Hz, 2H), 2.42-2.31 (m, 3H), 2.21-2.09 (m, 3H), 2.03-1.88 (m, 3H), 1.76 (br d, J=12.8 Hz, 2H), 1.72-1.65 (m, 3H), 1.59 (br d, J=11.2 Hz, 3H), 1.41-1.16 (m, 8H), 1.13 (br d, J=4.4 Hz, 2H), 0.87 (s, 3H), 0.72 (t, J=7.6 Hz, 3H).

Example 139: Synthesis of 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-4-fluoro-3-methyl-2-oxo-2,3-dihydro-1H-1,3-benzodiazol-1-yl}piperidine-2,6-dione (Compound 166)

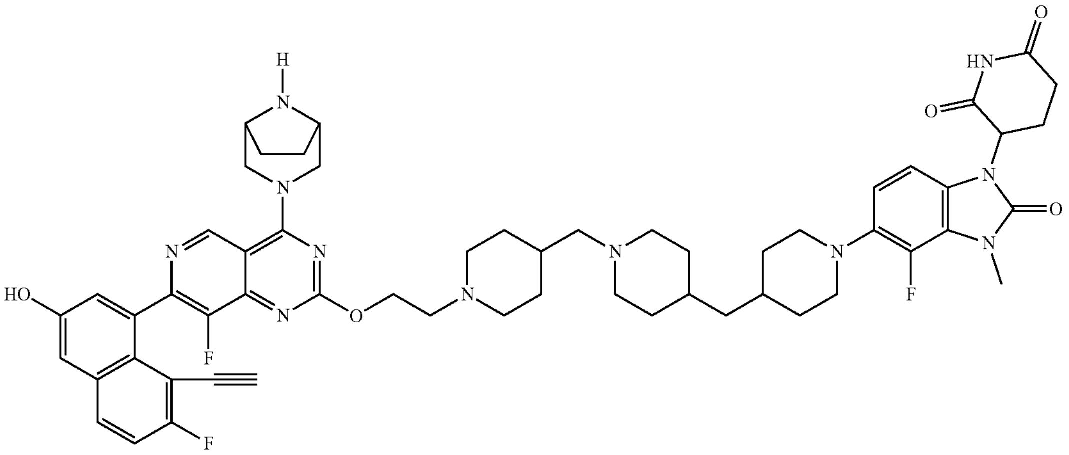 [SMILES: C#Cc1c(F)ccc2cc(O)cc(-c3ncc4c(N5CC6CCC(C5)N6)nc(OCCN5CCC(CN6CCC(CC7CCN(c8ccc9c(c8F)n(C)c(=O)n9C8CCC(=O)NC8=O)CC7)CC6)CC5)nc4c3F)c12]

The title compound was prepared in an analogous manner to 3-{5-[4-({1-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-4-yl}methyl)piperidin-1-yl]-2-oxo-3-(propan-2-yl)-2,3-dihydro-1H-1,3-benzodiazol-1-yl}piperidine-2,6-dione. (yellow solid, formic acid salt.) LC/MS (ESI) m/z: 1040.4 $[M+H]^+$; $^1H$ NMR (400 MHz, DMSO-$d_6$) δ 11.10 (s, 1H), 9.04 (s, 1H), 7.99-7.95 (m, 1H), 7.54-7.35 (m, 2H), 7.17 (d, J=2.4 Hz, 1H), 6.83 (d, J=8.4 Hz, 1H), 6.71 (t, J=8.0 Hz, 1H), 5.37-5.24 (m, 1H), 4.54-4.42 (m, 3H), 4.35 (d, J=12.0 Hz, 1H), 3.93 (s, 1H), 3.66 (s, 5H), 3.20 (d, J=10.8 Hz, 4H), 2.97-2.79 (m, 6H), 2.72-2.57 (m, 7H), 2.26 (s, 1H), 2.13 (br d, J=6.4 Hz, 2H), 2.06-1.96 (m, 3H), 1.88 (t, J=10.8 Hz, 2H), 1.71 (s, 5H), 1.62 (t, J=11.8 Hz, 4H), 1.52-1.39 (m, 2H), 1.36-1.21 (m, 3H), 1.19-1.02 (m, 6H).

Example 140: Synthesis of 3-(5-{4-[(9-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione (Compound 171)

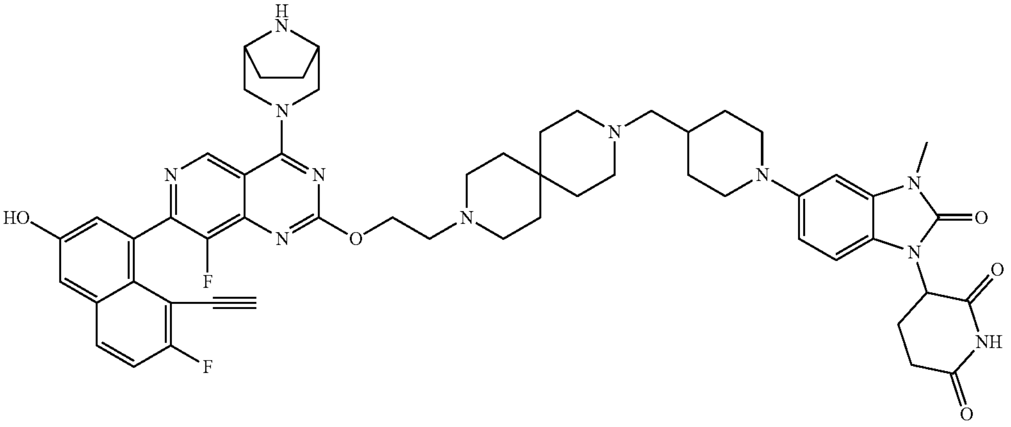 [SMILES: C#Cc1c(F)ccc2cc(O)cc(-c3ncc4c(N5CC6CCC(C5)N6)nc(OCCN5CCC6(CC5)CCN(CC5CCN(c7ccc8c(c7)n(C)c(=O)n8C7CCC(=O)NC7=O)CC5)CC6)nc4c3F)c12]

The title compound was prepared in an analogous manner to 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoro-pyrido[4,3-d]pyrimidin-2-yl)oxy]ethyl}-3,9-diazaspiro[5.5]undecan-3-yl)methyl]piperidin-1-yl}-3-methyl-2-oxo-2,3-dihydro-1H-1,3-benzodiazol-1-yl)piperidine-2,6-dione. (yellow solid, formic acid salt.) LC/MS (ESI) m/z: 998.7 $[M+H]^+$; $^1H$ NMR (400 MHz, DMSO-$d_6$) δ 11.06 (s, 1H), 9.11 (s, 1H), 8.20 (s, 3H), 7.76 (dd, J=6.0, 9.2 Hz, 1H), 7.40-7.30 (m, 2H), 7.01 (d, J=2.4 Hz, 1H), 6.92 (d, J=8.8 Hz, 1H), 6.81 (d, J=2.0 Hz, 1H), 6.62 (dd, J=2.0, 8.8 Hz, 1H), 5.28 (dd, J=5.2, 12.8 Hz, 1H), 4.54-4.39 (m, 5H), 3.83-3.62 (m, 5H), 3.56 (d, J=12.0 Hz, 2H), 3.29 (s, 3H), 2.94-2.83 (m, 1H), 2.78-2.66 (m, 3H), 2.64-2.56 (m, 3H), 2.47 (s, 3H), 2.43-2.31 (m, 5H), 2.24 (d, J=6.8 Hz, 2H), 2.18-2.09 (m, 1H), 2.02-1.94 (m, 1H), 1.82-1.58 (m, 7H), 1.42 (s, 8H), 1.30-1.15 (m, 3H), 0.72 (t, J=7.2 Hz, 3H).

Example 141: Synthesis of 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}-4-methylpiperidin-4-yl)methyl]piperazin-1-yl}methyl)piperidin-1-yl]-3-methyl-2-oxo-2,3-dihydro-1H-1,3-benzodiazol-1-yl}piperidine-2,6-dione (Compound 180)

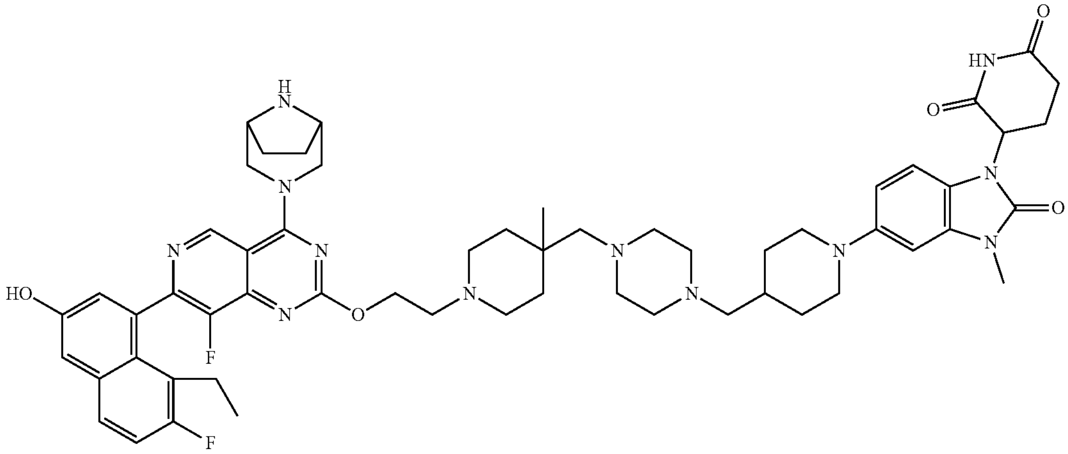

The title compound was prepared in an analogous manner to 3-{5-[4-({4-[(1-{2-[(4-{3,8-diazabicyclo[3.2.1]octan-3-yl}-7-(8-ethyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-3-methyl-2-oxo-2,3-dihydro-1H-1,3-benzodiazol-1-yl}piperidine-2,6-dione. (yellow solid, formic acid salt.) LC/MS (ESI) m/z: 1041.3 $[M+H]^+$, $^1H$ NMR (400 MHz, DMSO-$d_6$) δ 11.07 (brs, 1H), 9.12 (s, 1H), 8.22 (s, 2H), 7.77 (dd, J=6.0, 9.2 Hz, 1H), 7.39-7.31 (m, 2H), 7.02 (d, J=2.4 Hz, 1H), 6.92 (d, J=8.4 Hz, 1H), 6.81 (d, J=2.0 Hz, 1H), 6.62 (dd, J=2.0, 8.8 Hz, 1H), 5.29 (dd, J=5.2, 12.8 Hz, 1H), 4.55-4.39 (m, 4H), 3.77-3.66 (m, 3H), 3.56 (br d, J=11.6 Hz, 2H), 3.30 (s, 3H), 3.00-2.67 (m, 2H), 2.55 (s, 4H), 2.47 (br d, J=4.0 Hz, 7H), 2.41-2.27 (m, 8H), 2.20-2.03 (m, 6H), 2.01-1.94 (m, 1H), 1.79-1.68 (m, 6H), 1.63-1.54 (m, 1H), 1.51-1.42 (m, 2H), 1.22 (br d, J=8.0 Hz, 4H), 0.85 (s, 3H), 0.73 (t, J=7.2 Hz, 3H).

Example 142: Synthesis of 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,3-dimethylpiperazin-1-yl)methyl]piperidin-1-yl}methyl)piperidin-1-yl]-3-methyl-2-oxo-2,3-dihydro-1H-1,3-benzodiazol-1-yl}piperidine-2,6-dione (Compound 162)

Step 1: Preparation of tert-butyl 4-[(1-benzyloxycarbonyl-4-piperidyl)methyl]-2,2-dimethyl-piperazine-1-carboxylate

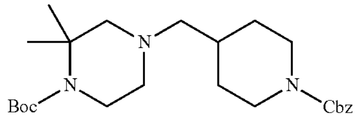 [SMILES: CC(C)(C)OC(=O)N1CCN(CC2CCN(C(=O)OCc3ccccc3)CC2)CC1(C)C]

To a solution of tert-butyl 2,2-dimethylpiperazine-1-carboxylate (10 g, 47 mmol) in dichloromethane (250 mL) were added benzyl 4-formylpiperidine-1-carboxylate (12.5 g, 50 mmol), acetic acid (1.3 mL, 23 mmol), and sodium triacetoxyborohydride (19.8 g, 93 mmol), and the reaction mixture was stirred at 25° C. for 16 h. The reaction was diluted with saturated aqueous sodium bicarbonate solution (50 mL) and extracted with dichloromethane (300 mL×3). The combined organic layers were washed with and brine (100 mL), dried over anhydrous sodium sulfate, filtered, and concentrated under reduced pressure. The residue was purified by prep-HPLC (acetonitrile in water (formic acid)) to afford the title compound (20 g, 96%) as a colorless oil. LC/MS (ESI) m/z: 446.3 $[M+H]^+$; $^1H$ NMR (400 MHz, $CDCl_3$) δ 7.39-7.29 (m, 5H), 5.13 (s, 2H), 4.25-4.14 (m, 2H), 3.49-3.32 (m, 2H), 2.78 (s, 2H), 2.36 (t, J=5.6 Hz, 2H), 2.12 (s, 3H), 1.77 (d, J=13.2 Hz, 2H), 1.70-1.60 (m, 2H), 1.46 (s, 9H), 1.37 (s, 6H), 1.18-1.02 (m, 2H).

Step 2: Preparation of tert-butyl 2,2-dimethyl-4-(4-piperidylmethyl)piperazine-1-carboxylate

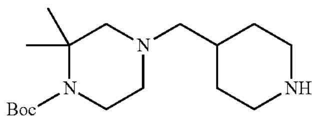 [SMILES: CC(C)(C)OC(=O)N1CCN(CC2CCNCC2)CC1(C)C]

To a solution of tert-butyl 4-[(1-benzyloxycarbonyl-4-piperidyl)methyl]-2,2-dimethyl-piperazine-1-carboxylate (23.4 g, 52 mmol) in tetrahydrofuran (300 mL) was added 10% palladium on carbon (4 g) under nitrogen, and the resulting mixture was degassed under vacuum and purged with hydrogen, then stirred under hydrogen (50 psi) at 40° C. for 20 h. The mixture was filtered, and the filtrate was concentrated under reduced pressure to afford the title compound (16 g, crude) as a brown oil. LC/MS (ESI) m/z: 312.2 $[M+H]^+$; $^1H$ NMR (400 MHz, $CDCl_3$) δ 3.45-3.37 (m, 2H), 3.09 (d, J=12.0 Hz, 2H), 2.60 (dt, J=2.4, 12.0 Hz, 2H), 2.40-2.31 (m, 2H), 2.13-2.08 (m, 4H), 2.03 (s, 1H), 1.76 (d, J=12.0 Hz, 2H), 1.58 (tdd, J=3.6, 7.2, 14.8 Hz, 1H), 1.46 (s, 9H), 1.37 (s, 6H), 1.17-1.05 (m, 2H).

Step 3: Preparation of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]-2,2-dimethyl-piperazine-1-carboxylate

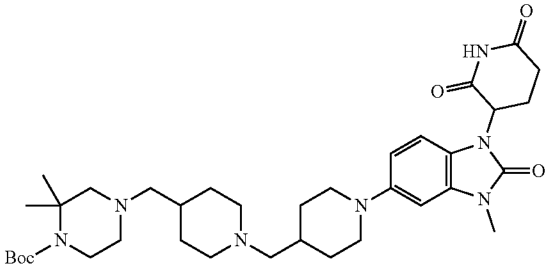 [SMILES: Cn1c(=O)n(C2CCC(=O)NC2=O)c2ccc(N3CCC(CN4CCC(CN5CCN(C(=O)OC(C)(C)C)C(C)(C)C5)CC4)CC3)cc21]

To a solution of tert-butyl 2,2-dimethyl-4-(4-piperidylmethyl)piperazine-1-carboxylate (360 mg, 1.2 mmol) in dichloromethane (15 mL) and dimethyl sulfoxide (5 mL) were added 1-[1-(2,6-dioxo-3-piperidyl)-3-methyl-2-oxo-benzimidazol-5-yl]piperidine-4-carbaldehyde trifluoroacetate (500 mg, 1 mmol), N,N-diisopropylethylamine (0.7 mL, 4 mmol), and sodium triacetoxyborohydride (438 mg, 2 mmol), and the reaction mixture was stirred at 25° C. for 1 h. The mixture was diluted with saturated aqueous sodium bicarbonate solution (20 mL) and extracted with dichloromethane (50 mL×2). The combined organic extracts were washed with brine (20 mL), dried over anhydrous sodium sulfate, filtered, and concentrated under reduced pressure. The residue was triturated with methyl tert-butyl ether (40 mL) to afford the title compound (680 mg, crude) as an off-white solid. LC/MS (ESI) m/z: 666.5 $[M+H]^+$.

Step 4: Preparation of 3-[5-[4-[[4-[(3,3-dimethylpiperazin-1-yl) methyl]-1-piperidyl]methyl]-1-piperidyl]-3-methyl-2-oxobenzimidazol-1-yl]piperidine-2,6-dione

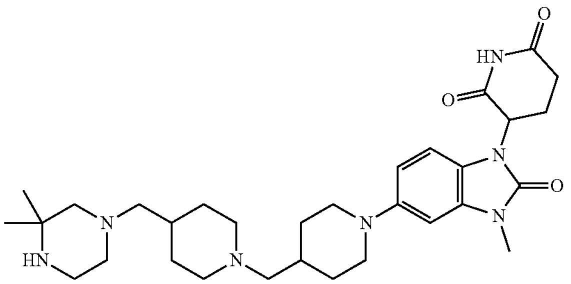 [SMILES: Cn1c(=O)n(C2CCC(=O)NC2=O)c2ccc(N3CCC(CN4CCC(CN5CCNC(C)(C)C5)CC4)CC3)cc21]

To a solution of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]-2,2-dimethyl-piperazine-1-carboxylate (680 mg, 1 mmol) in dichloromethane (15 mL) was added trifluoroacetic acid (5.0 mL, 67 mmol), and the mixture was stirred at 25° C. for 1 h. The reaction mixture was concentrated under reduced pressure, and the residue was purified by prep-HPLC (acetonitrile in water (formic acid)) to afford the title compound (420 mg, 58%, 3 formic acid salt) as a colorless oil. LC/MS (ESI) m/z: 566.4 $[M+H]^+$.

Step 5: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-2,2-dimethyl-piperazin-1-yl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

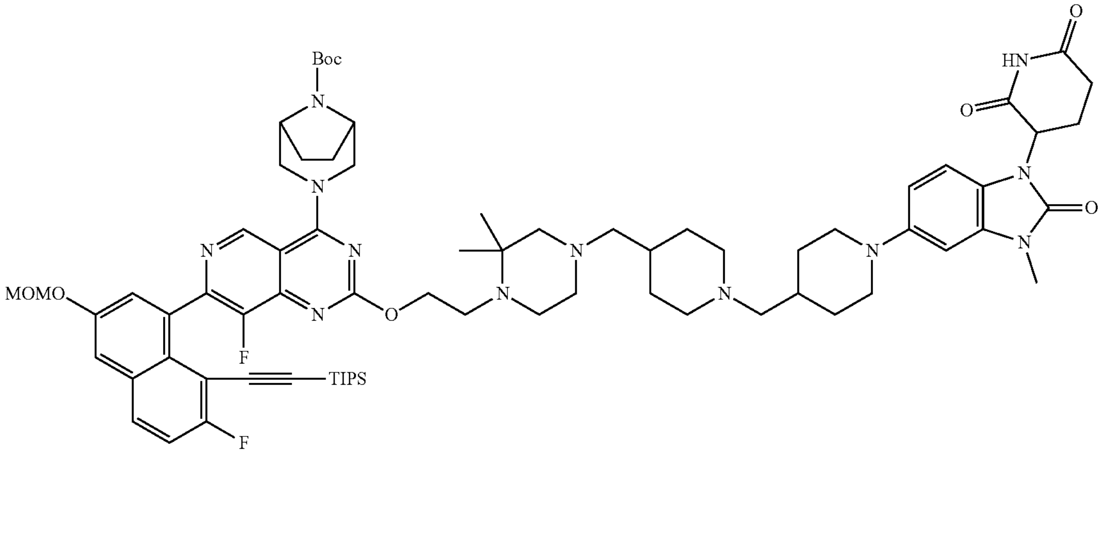

To a mixture of 3-[5-[4-[[4-[(3,3-dimethylpiperazin-1-yl)methyl]-1-piperidyl]methyl]-1-piperidyl]-3-methyl-2-oxobenzimidazol-1-yl]piperidine-2,6-dione (171 mg, 0.2 mmol, 3 formate) and tert-butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (234 mg, 0.3 mmol) in dimethyl sulfoxide (3 mL) and dichloromethane (3 mL) were added N,N-diisopropylethylamine (171 mg, 1.3 mmol) and titanium(IV) isopropylate (0.1 mL, 0.5 mol), and the mixture was allowed to stir at 45° C. for 3 h. Sodium triacetoxyborohydride (103 mg, 0.5 mmol) was then added, and the reaction mixture was stirred at 45° C. for 6 h. The mixture was diluted with ethyl acetate (50 mL) and washed with brine (20 mL×3), dried over anhydrous sodium sulfate, filtered, and concentrated under reduced pressure. The residue was purified by silica gel chromatography (dichloromethane/methanol=100/1 to 10/1) to afford the title compound (200 mg, 61%) as a yellow solid. LC/MS (ESI) m/z: 676.7 $[M/2+H]^+$.

Step 6: Preparation of 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,3-dimethylpiperazin-1-yl)methyl]piperidin-1-yl}methyl)piperidin-1-yl]-3-methyl-2-oxo-2,3-dihydro-1H-1,3-benzodiazol-1-yl}piperidine-2,6-dione

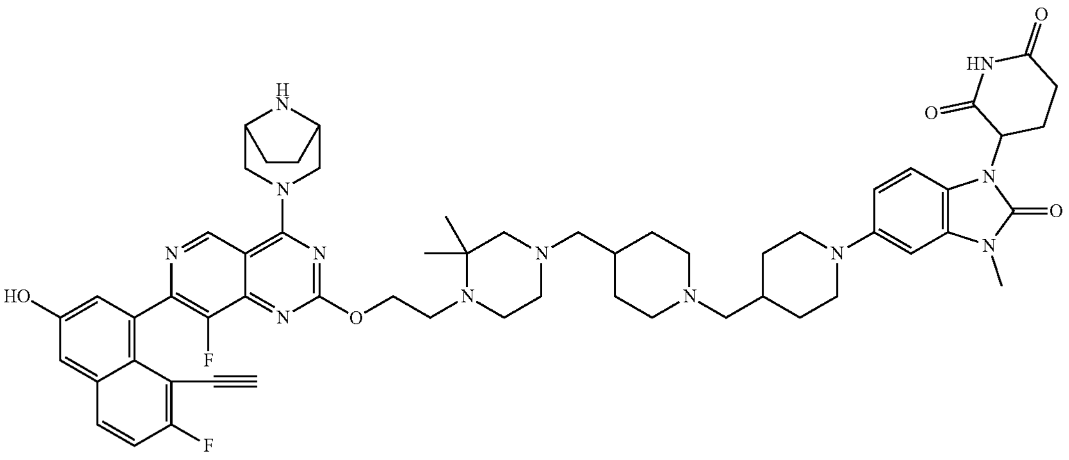 [SMILES: C#Cc1c(F)ccc2cc(O)cc(-c3ncc4c(N5CC6CCC(C5)N6)nc(OCCN5CCN(CC6CCN(CC7CCN(c8ccc9c(c8)n(C)c(=O)n9C8CCC(=O)NC8=O)CC7)CC6)CC5(C)C)nc4c3F)c12]

The title compound can be prepared in an analogous manner to step 17 and 18 of 3-(5-{4-[(9-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,9-diazaspiro[5.5]undecan-3-yl)methyl]piperidin-1-yl}-4-fluoro-3-methyl-2-oxo-2,3-dihydro-1H-1,3-benzodiazol-1-yl)piperidine-2,6-dione. (yellow solid, formic acid salt). LC/MS (ESI) m/z: 1051.6 $[M+H]^+$, $^1H$ NMR (400 MHz, DMSO-$d_6$) δ 11.05 (s, 1H), 9.04 (s, 1H), 8.23 (s, 2H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 6.91 (d, J=8.8 Hz, 1H), 6.80 (d, J=1.6 Hz, 1H), 6.65-6.57 (m, 1H), 5.28 (dd, J=5.2, 12.8 Hz, 1H), 4.52-4.46 (m, 1H), 4.38-4.29 (m, 3H), 3.91 (s, 1H), 3.65 (s, 8H), 3.56 (d, J=12.4 Hz, 5H), 3.29 (s, 3H), 2.89-2.79 (m, 3H), 2.67-2.56 (m, 6H), 2.18 (d, J=6.8 Hz, 2H), 2.03-1.94 (m, 4H), 1.89 (t, J=11.2 Hz, 2H), 1.77 (d, J=11.2 Hz, 2H), 1.72-1.57 (m, 7H), 1.44 (d, J=4.0 Hz, 1H), 1.28-1.17 (m, 2H), 1.15-1.03 (m, 2H), 0.98 (s, 6H).

Example 143: Synthesis of 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperazin-1-yl)methyl]piperidin-1-yl}methyl)piperidin-1-yl]-3-methyl-2-oxo-2,3-dihydro-1H-1,3-benzodiazol-1-yl}piperidine-2,6-dione (Compound 173)

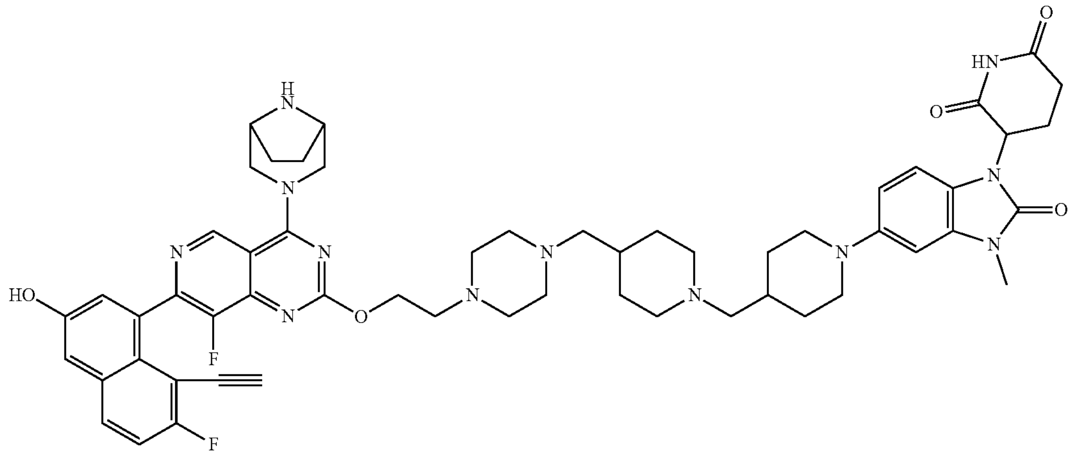 [SMILES: C#Cc1c(F)ccc2cc(O)cc(-c3ncc4c(N5CC6CCC(C5)N6)nc(OCCN5CCN(CC6CCN(CC7CCN(c8ccc9c(c8)n(C)c(=O)n9C8CCC(=O)NC8=O)CC7)CC6)CC5)nc4c3F)c12]

The title compound was prepared in an analogous manner to 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,3-dimethylpiperazin-1-yl)methyl]piperidin-1-yl}methyl)piperidin-1-yl]-3-methyl-2-oxo-2,3-dihydro-1H-1,3-benzodiazol-1-yl}piperidine-2,6-dione. (yellow solid, formic acid salt). LC/MS (ESI) m/z: 1023.6 $[M+H]^+$; $^1H$ NMR (400 MHz, DMSO-$d_6$) δ 11.05 (s, 1H), 9.05 (s, 1H), 8.21 (s, 2H), 7.97 (dd, J=6.0, 9.2 Hz, 1H), 7.46 (t, J=9.2 Hz, 1H), 7.39 (d, J=2.4 Hz, 1H), 7.18 (d, J=2.4 Hz, 1H), 6.92 (d, J=8.8 Hz, 1H), 6.80 (d, J=2.0 Hz, 1H), 6.62 (dd, J=2.0, 8.8 Hz, 1H), 5.28 (dd, J=5.2, 12.8 Hz, 1H), 4.52 (d, J=12.4 Hz, 1H), 4.45 (t, J=5.6 Hz, 2H), 4.41-4.34 (m, 1H), 3.92 (s, 1H), 3.77-3.60 (m, 4H), 3.56 (d, J=11.6 Hz, 2H), 3.30 (s, 3H), 2.95-2.80 (m, 3H), 2.72-2.67 (m, 2H), 2.66-2.54 (m, 4H), 2.49-2.47 (m, 4H), 2.33 (d, J=1.6 Hz, 4H), 2.22 (d, J=6.8 Hz, 2H), 2.10 (d, J=6.8 Hz, 2H), 2.00-1.88 (m, 3H), 1.65 (d, J=10.4 Hz, 3H), 1.85-1.57 (m, 6H), 1.47 (s, 1H), 1.31-1.18 (m, 2H), 1.15-1.05 (m, 2H).

Example 144: Synthesis of 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,3-dimethylpiperazin-1-yl)methyl]piperidin-1-yl}methyl)piperidin-1-yl]-4-fluoro-1-oxo-2,3-dihydro-1H-isoindol-2-yl}piperidine-2,6-dione (Compound 174)

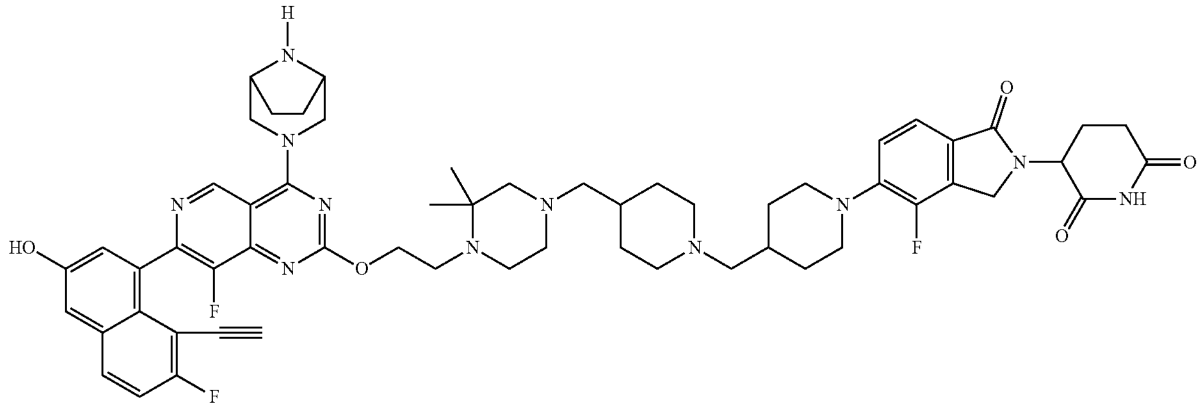 [SMILES: C#Cc1c(F)ccc2cc(O)cc(-c3ncc4c(N5CC6CCC(C5)N6)nc(OCCN5CCN(CC6CCN(CC7CCN(c8ccc9c(c8F)CN(C8CCC(=O)NC8=O)C9=O)CC7)CC6)CC5(C)C)nc4c3F)c12]

The title compound was prepared in an analogous manner to 3-{5-[4-({4-[(4-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-3,3-dimethylpiperazin-1-yl)methyl]piperidin-1-yl}methyl)piperidin-1-yl]-3-methyl-2-oxo-2,3-dihydro-1H-1,3-benzodiazol-1-yl}piperidine-2,6-dione. (off-white solid). LC/MS (ESI) m/z: 1054.7 $[M+H]^+$; $^1H$ NMR (400 MHz, DMSO-$d_6$) b 10.97 (s, 1H), 10.24-10.06 (m, 1H), 9.03 (s, 1H), 7.97 (dd, J=6.0, 9.2 Hz, 1H), 7.50-7.42 (m, 2H), 7.39 (d, J=2.4 Hz, 1H), 7.20-7.11 (m, 2H), 5.06 (dd, J=5.2, 13.2 Hz, 1H), 4.52-4.42 (m, 2H), 4.37-4.26 (m, 4H), 3.91 (s, 1H), 3.66-3.55 (m, 4H), 3.52-3.41 (m, 3H), 2.96-2.71 (m, 6H), 2.61 (br s, 3H), 2.56 (br d, J=1.6 Hz, 1H), 2.47-2.35 (m, 2H), 2.15 (br d, J=4.0 Hz, 2H), 2.09-1.93 (m, 5H), 1.92-1.71 (m, 5H), 1.71-1.60 (m, 7H), 1.48-1.38 (m, 1H), 1.30-1.19 (m, 2H), 1.16-1.03 (m, 2H), 0.97 (s, 6H).

Example 145: Synthesis of [(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl 4-[2-(2,6-dioxopiperidin-3-yl)-1-oxo-2,3-dihydro-1H-isoindol-5-yl]piperazine-1-carboxylate (Compound 114)

Step 1: Preparation of 5-bromo-2-(2,6-dibenzyloxy-3-pyridyl)isoindolin-1-one

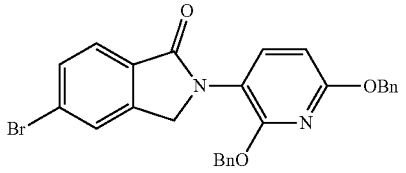 [SMILES: O=C1c2ccc(Br)cc2CN1c1ccc(OCc2ccccc2)nc1OCc1ccccc1]

To a solution of 2,6-dibenzyloxypyridin-3-amine (5.0 g, 16 mmol) and methyl 4-bromo-2-(bromomethyl)benzoate (5.03 g, 16 mmol) in N,N-dimethylacetamide (50 mL) was added diisopropylethylamine (8.5 mL, 49 mmol), and the mixture was stirred at 120° C. for 12 h. The reaction mixture was diluted with water (50 mL) and extracted with ethyl acetate (50 mL×2). The combined organic layers were washed with brine (20 mL), dried over sodium sulfate, filtered, and concentrated under reduced pressure. The residue was purified by prep-HPLC (60%-90% acetonitrile in water (trifluoroacetic acid) over 23 min) to afford the title compound (6.02 g, 74%) as a dark brown solid. LC/MS (ESI) m/z: 501.1 $[M+H]^+$; $^1H$ NMR (400 MHz, DMSO-$d_6$) δ 7.91 (s, 1H), 7.78 (d, J=8.4 Hz, 1H), 7.72-7.71 (m, 1H), 7.43-7.28 (m, 11H), 6.55 (d, J=8.4 Hz, 1H), 5.40 (s, 2H), 5.34 (s, 2H), 4.78 (s, 2H).

Step 2: Preparation of tert-butyl 4-[2-(2,6-dibenzyloxy-3-pyridyl)-1-oxo-isoindolin-5-yl]piperazine-1-carboxylate

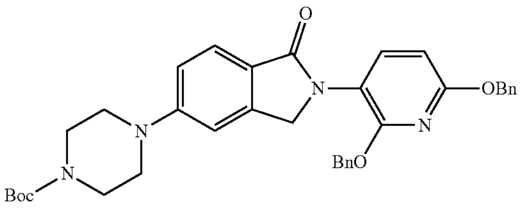 [SMILES: CC(C)(C)OC(=O)N1CCN(c2ccc3c(c2)CN(c2ccc(OCc4ccccc4)nc2OCc2ccccc2)C3=O)CC1]

To a solution of 5-bromo-2-(2,6-dibenzyloxy-3-pyridyl)isoindolin-1-one (900 mg, 1.8 mmol) and tert-butyl piperazine-1-carboxylate (334 mg, 1.8 mmol) in dioxane (10 mL) were added [2-(2-aminophenyl)phenyl]-chloro-palladium; dicyclohexyl-[3-(2,4,6-triisopropylphenyl)phenyl]phosphane (141 mg, 0.18 mmol) and cesium carbonate (1.17 g, 3.6 mmol), and the mixture was stirred at 100° C. for 12 h. The reaction mixture was filtered and concentrated under reduced pressure. The residue was purified by silica gel column chromatography (petroleum ether/ethyl acetate=10/1 to 1/1) to afford the title compound (623 mg, 57%) as a white solid. LC/MS (ESI) m/z: 607.4 $[M+H]^+$; $^1H$ NMR (400 MHz, DMSO-$d_6$) b 7.75 (d, J=8.4 Hz, 1H), 7.58 (d, J=8.4 Hz, 1H), 7.44-7.28 (m, 10H), 7.14-7.06 (m, 2H), 6.53 (d, J=8.4 Hz, 1H), 5.40 (s, 2H), 5.35 (s, 2H), 4.68 (s, 2H), 3.50-3.44 (m, 4H), 3.32-3.28 (m, 4H), 1.43 (s, 9H).

Step 3: Preparation of tert-butyl 4-[2-(2,6-dioxo-3-piperidyl)-1-oxo-isoindolin-5-yl]piperazine-1-carboxylate

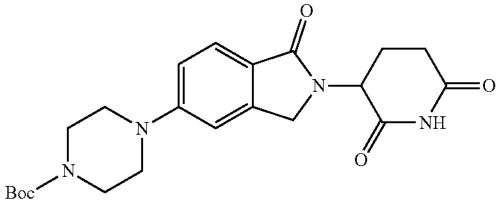 [SMILES: CC(C)(C)OC(=O)N1CCN(c2ccc3c(c2)CN(C2CCC(=O)NC2=O)C3=O)CC1]

To a solution of tert-butyl 4-[2-(2,6-dibenzyloxy-3-pyridyl)-1-oxo-isoindolin-5-yl]piperazine-1-carboxylate (673 mg, 1 mmol) in tetrahydrofuran (10 mL) was added 10% palladium on carbon (100 mg), and the resulting mixture was degassed in vacuum and purged with hydrogen several times, then stirred under hydrogen (50 Psi) at 50° C. for 12 h. The reaction mixture was filtered and concentrated under reduced pressure to afford the title compound (480 mg, crude) as a white solid. LC/MS (ESI) m/z: 429.4 $[M+H]^+$.

Step 4: Preparation of 3-(1-oxo-5-piperazin-1-yl-isoindolin-2-yl)piperidine-2,6-dione

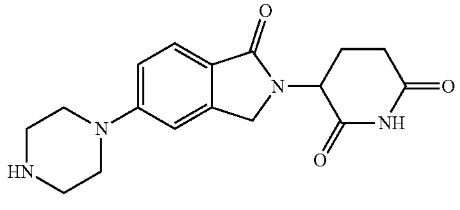 [SMILES: O=C1CCC(N2Cc3cc(N4CCNCC4)ccc3C2=O)C(=O)N1]

To a solution of tert-butyl 4-[2-(2,6-dioxo-3-piperidyl)-1-oxo-isoindolin-5-yl]piperazine-1-carboxylate (480 mg, 1.1 mmol) in dichloromethane (5 mL) was added trifluoroacetic acid (0.08 mL, 1 mmol), and the mixture was stirred at 25° C. for 1 h. The reaction mixture was filtered and concentrated under reduced pressure. The residue was purified by prep-HPLC (0%-16% acetonitrile in water (formic acid) over 10 min) to afford the title compound (366 mg, 96%, formic acid salt) as a white solid. LC/MS(ESI) m/z: 329.1 $[M+H]^+$; $^1H$ NMR (400 MHz, DMSO-$d_6$) δ 10.95 (s, 1H), 8.81-8.75 (m, 1H), 7.59 (d, J=8.4 Hz, 1H), 7.24-7.10 (m, 2H), 5.07 (dd, J=5.2, 13.2 Hz, 1H), 4.41-4.19 (m, 2H), 3.52-3.48 (m, 4H), 3.26 (s, 4H), 2.97-2.87 (m, 1H), 2.64-2.57 (m, 1H), 2.43-2.36 (m, 1H), 2.03-1.94 (m, 1H).

Step 5: Preparation of tert-butyl 3-[2-[[(2S,5S)-5-[[4-[2-(2,6-dioxo-3-piperidyl)-1-oxo-isoindolin-5-yl]piperazine-1-carbonyl]oxymethyl]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

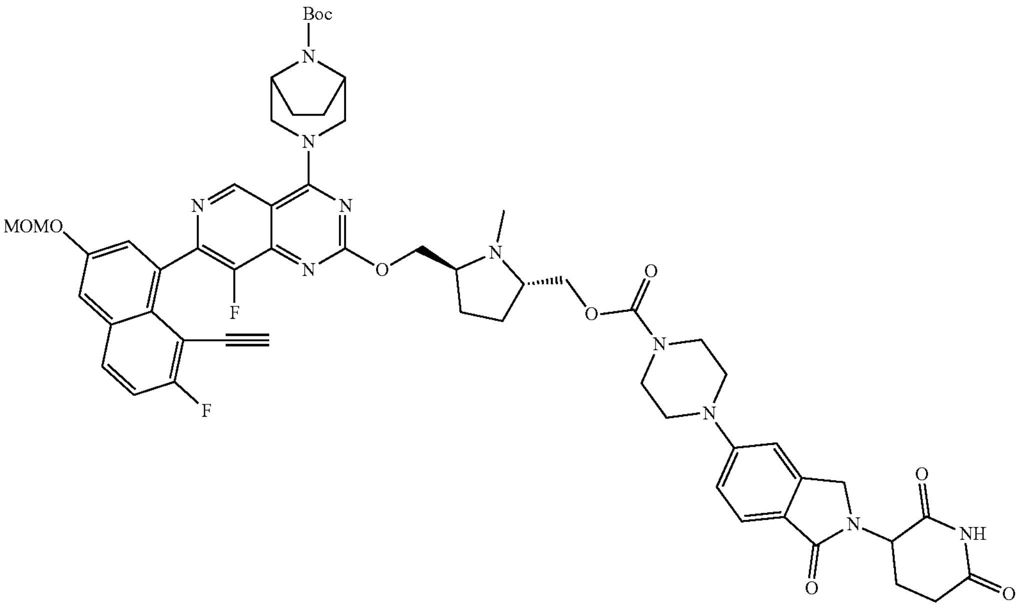

To a solution of tert-butyl 3-[7-[8-ethynyl-7-fluoro-3-(methoxymethoxy)-1-naphthyl]-8-fluoro-2-[[(2S,5S)-1-methyl-5-[(4-nitrophenoxy)carbonyloxymethyl]pyrrolidin-2-yl]methoxy]pyrido[4,3-d]pyrimidin-4-yl]-3,8-diazabicyclo[3.2.1]octane-8-carboxylate (490 mg, 0.5 mmol) in tetrahydrofuran (5 mL) at 0° C. were added dimethylaminopyridine (7 mg, 0.05 mmol), triethylamine (0.2 mL, 2 mmol), and 3-(1-oxo-5-piperazin-1-yl-isoindolin-2-yl)piperidine-2,6-dione formate (208 mg, 0.55 mmol), and the mixture was stirred at 25° C. for 2 h. The reaction mixture was filtered and concentrated under reduced pressure. The residue was purified by prep-HPLC (27%-57% acetonitrile in water (formic acid) over 10 min) to afford the title compound (220 mg, 37%) as a yellow solid. LC/MS (ESI) m/z: 1085.8 $[M+H]^+$.

Step 6: Preparation of [(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl 4-[2-(2,6-dioxopiperidin-3-yl)-1-oxo-2,3-dihydro-1H-isoindol-5-yl]piperazine-1-carboxylate

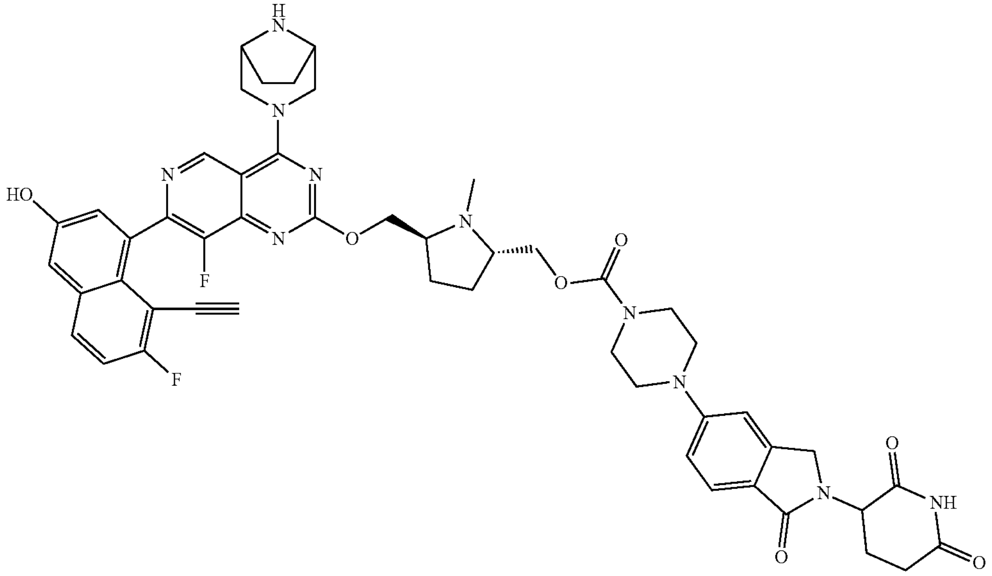 [SMILES: C#Cc1c(F)ccc2cc(O)cc(-c3ncc4c(N5CC6CCC(C5)N6)nc(OC[C@@H]5CC[C@@H](COC(=O)N6CCN(c7ccc8c(c7)CN(C7CCC(=O)NC7=O)C8=O)CC6)N5C)nc4c3F)c12]

To a solution of tert-butyl 3-[2-[[(2S,5S)-5-[[4-[2-(2,6-dioxo-3-piperidyl)-1-oxo-isoindolin-5-yl]piperazine-1-carbonyl]oxymethyl]-1-methyl-pyrrolidin-2-yl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1] octane-8-carboxylate (220 mg, 0.2 mmol) in dichloromethane (1 mL) was added 4 M hydrochloric acid in dioxane (0.05 mL), and the mixture was stirred at 25° C. for 10 min. The reaction mixture was concentrated under reduced pressure, and the residue was purified by prep-HPLC (4%-34% acetonitrile in water (formic acid) over 10 min) to afford the title compound (57.0 mg, 28%, formic acid salt) as a yellow solid. LC/MS (ESI) m/z: 941.2 $[M+H]^+$; $^1H$ NMR (400 MHz, DMSO-$d_6$) δ 10.97-10.89 (m, 1H), 9.02 (t, J=2.8 Hz, 1H), 8.16 (d, J=3.2 Hz, 1H), 7.96 (dd, J=6.0, 9.6 Hz, 1H), 7.52 (d, J=8.4 Hz, 1H), 7.45 (t, J=8.8 Hz, 1H), 7.38 (d, J=2.4 Hz, 1H), 7.16 (d, J=2.4 Hz, 1H), 7.08-7.00 (m, 2H), 5.06-5.00 (m, 1H), 4.49-4.39 (m, 2H), 4.31 (d, J=16.8 Hz, 2H), 4.24-4.16 (m, 2H), 4.04 (t, J=5.2 Hz, 2H), 3.92 (s, 1H), 3.66-3.58 (m, 6H), 3.51 (d, J=1.6 Hz, 6H), 3.19-3.14 (m, 4H), 2.95-2.83 (m, 2H), 2.60-2.56 (m, 2H), 2.35 (d, J=4.0 Hz, 1H), 2.02-1.90 (m, 3H), 1.67 (s, 5H), 1.63-1.58 (m, 1H).

Example 146: Synthesis of [(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl 4-[2-(2,6-dioxopiperidin-3-yl)-1-oxo-2,3-dihydro-1H-isoindol-4-yl]piperazine-1-carboxylate (Compound 117)

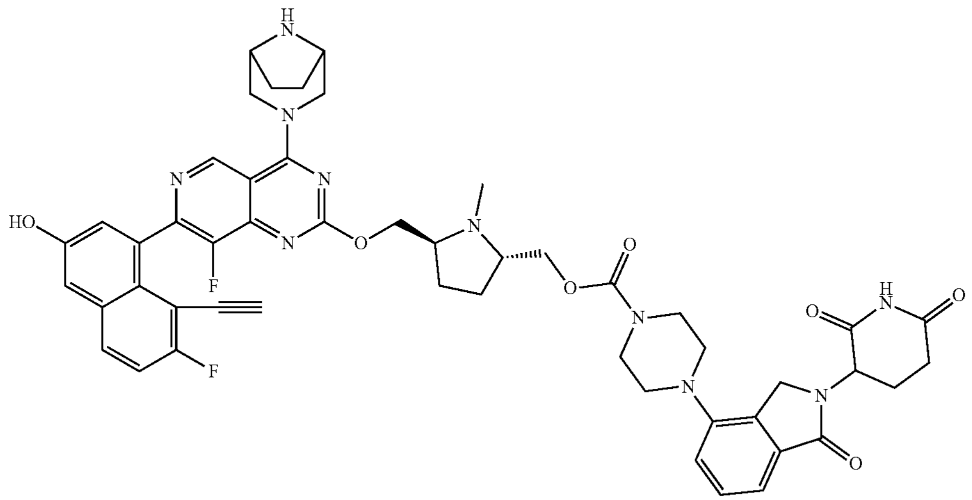 [SMILES: C#Cc1c(F)ccc2cc(O)cc(-c3ncc4c(N5CC6CCC(C5)N6)nc(OC[C@@H]5CC[C@@H](COC(=O)N6CCN(c7cccc8c7CN(C7CCC(=O)NC7=O)C8=O)CC6)N5C)nc4c3F)c12]

The title compound was made in an analogous manner to [(2S,5S)-5-{[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]methyl}-1-methylpyrrolidin-2-yl]methyl 4-[2-(2,6-dioxopiperidin-3-yl)-1-oxo-2,3-dihydro-1H-isoindol-5-yl]piperazine-1-carboxylate. (yellow solid). LC/MS (ESI) m/z: 941.6 $[M+H]^+$, $^1H$ NMR (400 MHz, DMSO-$d_6$) δ 10.98 (s, 1H), 9.08-8.97 (m, 1H), 8.17 (s, 1H), 7.97 (dd, J=5.6, 9.2 Hz, 1H), 7.50-7.40 (m, 2H), 7.39 (d, J=2.4 Hz, 1H), 7.34 (d, J=7.6 Hz, 1H), 7.20-7.14 (m, 2H), 5.12 (dd, J=5.2, 13.2 Hz, 1H), 4.52-4.40 (m, 3H), 4.37-4.27 (m, 2H), 4.26-4.19 (m, 1H), 4.11-4.03 (m, 2H), 3.92 (s, 1H), 3.64 (s, 4H), 3.53 (s, 2H), 3.24-3.22 (m, 2H), 3.16 (d, J=2.0 Hz, 2H), 3.06-3.00 (m, 4H), 2.92-2.87 (m, 1H), 2.64-2.54 (m, 2H), 2.51-2.51 (m, 3H), 2.45-2.40 (m, 1H), 2.04-1.95 (m, 3H), 1.70 (s, 6H).

Example 147: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)oxy]piperidin-1-yl}methyl)piperidin-1-yl]-4-fluoro-1-oxo-2,3-dihydro-1H-isoindol-2-yl}piperidine-2,6-dione (Compound 106)

Step 1: Preparation of tert-butyl 4-((1-((1-(2-(2,6-dioxopiperidin-3-yl)-4-fluoro-1-oxoisoindolin-5-yl)piperidin-4-yl)methyl)piperidin-4-yl)oxy)piperidine-1-carboxylate

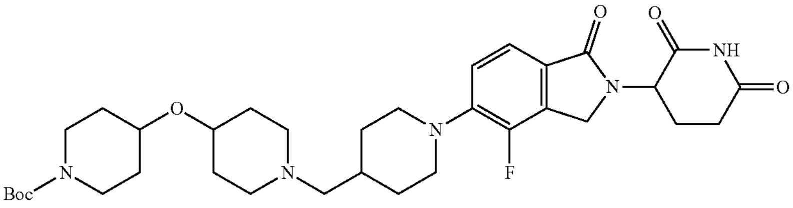

To a solution of 1-(2-(2,6-dioxopiperidin-3-yl)-4-fluoro-1-oxoisoindolin-5-yl)piperidine-4-carbaldehyde (400 mg, 1.1 mmol) and tert-butyl 4-(piperidin-4-yloxy) piperidine-1-carboxylate (305 mg, 1.1 mmol) in dichloromethane (4 mL) and dimethyl sulfoxide (4 mL) was added acetic acid (0.12 mL), and the mixture was stirred at 25° C. for 10 min. Sodium triacetoxyborohydride (454 mg, 2.1 mmol) was then added, and the mixture was stirred at 25° C. for 30 min. The reaction mixture was diluted with water (30 mL) and extracted with chloroform/isopropanol (5:1, 30 mL×2). The combined organic extracts were washed with brine (30 mL×2), dried over anhydrous sodium sulfate, filtered, and concentrated under reduced pressure. The residue was purified by flash silica gel chromatography (0-100% ethyl acetate/petroleum ether, then 0-15% dichloromethane/methanol) to afford the title compound (610 mg, 89%) as a white solid. LC/MS (ESI) m/z: 642.2 $[M+H]^+$.

Step 2: Preparation of 3-(4-fluoro-1-oxo-5-(4-((4-(piperidin-4-yloxy)piperidin-1-yl)methyl) piperidin-1-yl)isoindolin-2-yl)piperidine-2,6-dione

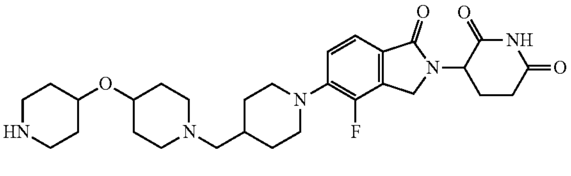 [SMILES: O=C1CCC(N2Cc3c(ccc(N4CCC(CN5CCC(OC6CCNCC6)CC5)CC4)c3F)C2=O)C(=O)N1]

To a solution of tert-butyl 4-((1-((1-(2-(2,6-dioxopiperidin-3-yl)-4-fluoro-1-oxoisoindolin-5-yl)piperidin-4-yl)methyl)piperidin-4-yl)oxy)piperidine-1-carboxylate (350 mg, 0.55 mmol) in dichloromethane (3 mL) was added trifluoroacetic acid (3.5 mL), and the mixture was stirred at 25° C. for 30 min. The reaction mixture was concentrated under reduced pressure to afford the title compound (350 mg, crude, TFA salt) as a brown oil.

Step 3: Preparation of tert-butyl (1R,5S)-3-(2-(2-(4-((1-((1-(2-(2,6-dioxopiperidin-3-yl)-4-fluoro-1-oxoisoindolin-5-yl)piperidin-4-yl)methyl)piperidin-4-yl)oxy)piperidin-1-yl)ethoxy)-8-fluoro-7-(7-fluoro-3-(methoxymethoxy)-8-((triisopropylsilyl)ethynyl)naphthalen-1-yl)pyrido[4,3-d]pyrimidin-4-yl)-3,8-diazabicyclo[3.2.1]octane-8-carboxylate

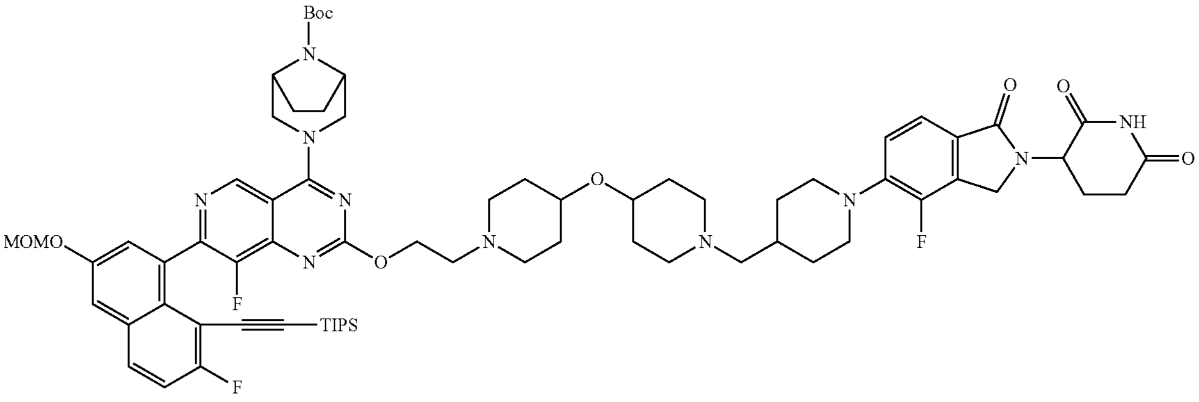

To a solution of 3-(4-fluoro-1-oxo-5-(4-((4-(piperidin-4-yloxy)piperidin-1-yl)methyl) piperidin-1-yl)isoindolin-2-yl) piperidine-2,6-dione trifluoroacetate (350 mg, 0.5 mmol) in dichloromethane (4 mL) and isopropanol (4 mL) was added N,N-diisopropylethylamine (0.28 mL, 1.6 mmol), and the mixture was stirred at 25° C. for 10 minutes. tert-Butyl-3-(8-fluoro-7-(7-fluoro-3-(methoxymethoxy)-8-((triisopropylsilyl)ethynyl)naphthalen-1-yl)-2-(2-oxoethoxy)pyrido[4,3-d]pyrimidin-4-yl)-3,8-diazabicyclo[3.2.1]octane-8-carboxylate (728 mg, 0.9 mmol) and acetic acid (0.06 mL, 1 mmol) were then added, and the resulting mixture was stirred for 20 minutes. Sodium triacetoxyborohydride (226 mg, 1 mmol) was then added, and the reaction mixture was stirred at 25° C. for 1 h. The mixture was diluted with water (30 mL) and extracted with chloroform/isopropanol (5:1, 30 mL×2). The combined organic layers were washed with brine (30 mL×2), dried over anhydrous sodium sulfate, filtered, and concentrated under reduced pressure. The residue was purified by flash silica gel chromatography (0-100% ethyl acetate/petroleum ether, then 0-15% dichloromethane/methanol) to afford the title compound (430 mg, 61%) as a brown oil. LC/MS (ESI) m/z: 1328.6 [M+H]+.

Step 4: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)oxy]piperidin-1-yl}methyl)piperidin-1-yl]-4-fluoro-1-oxo-2,3-dihydro-1H-isoindol-2-yl}piperidine-2,6-dione

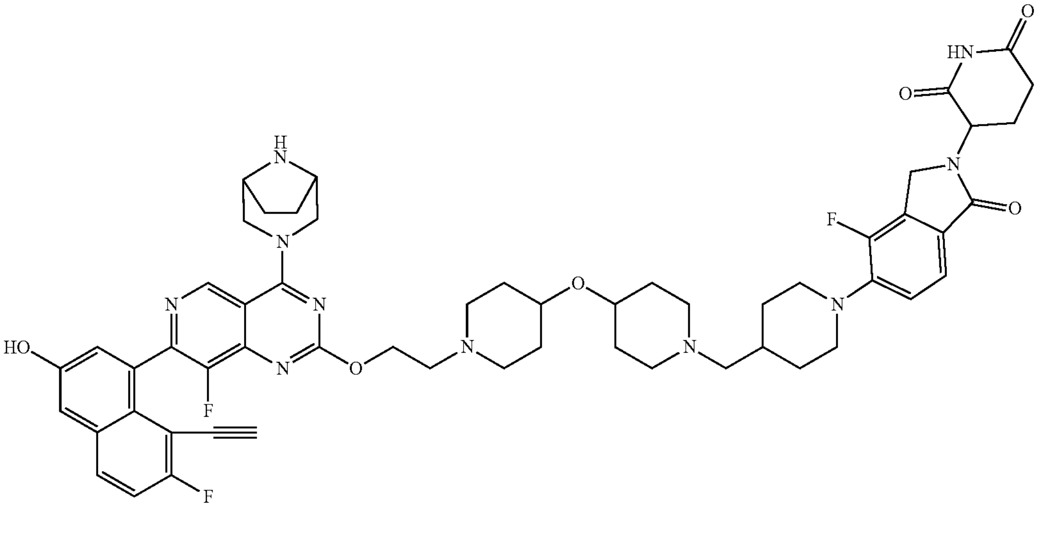 [SMILES: C#Cc1c(F)ccc2cc(O)cc(-c3ncc4c(N5CC6CCC(C5)N6)nc(OCCN5CCC(OC6CCN(CC7CCN(c8ccc9c(c8F)CN(C8CCC(=O)NC8=O)C9=O)CC7)CC6)CC5)nc4c3F)c12]

The title compound can be prepared in an analogous manner to step 4 and 5 of 3-(5-(4-((4-((1-(2-((4-(-3,8-diazabicyclo[3.2.1]octan-3-yl)-7-(8-ethynyl-7-fluoro-3-hydroxynaphthalen-1-yl)-8-fluoropyrido[4,3-d]pyrimidin-2-yl)oxy)ethyl)piperidin-4-yl)methyl)piperidin-1-yl)methyl) piperidin-1-yl)-4-chloro-1-oxoisoindolin-2-yl)piperidine-2,6-dione. (yellow solid, formic acid salt). LC/MS (ESI) m/z: 1028.3 $[M+H]^+$; $^1H$ NMR (400 MHz, DMSO-$d_6$) δ 10.99 (s, 1H), 9.05 (s, 1H), 8.21 (s, 2H), 7.98 (dd, J=5.8, 9.2 Hz, 1H), 7.51-7.42 (m, 2H), 7.39 (d, J=2.4 Hz, 1H), 7.20-7.10 (m, 2H), 5.07 (dd, J=5.2, 13.2 Hz, 1H), 4.55-4.43 (m, 4H), 4.39-4.27 (m, 3H), 3.94 (s, 1H), 3.76-3.71 (m, 2H), 3.69-3.62 (m, 2H), 3.52-3.44 (m, 2H), 3.39 (s, 2H), 3.16 (s, 2H), 2.97-2.85 (m, 1H), 2.83-2.64 (m, 8H), 2.62-2.54 (m, 1H), 2.44-2.31 (m, 1H), 2.17 (d, J=6.4 Hz, 3H), 2.08-1.94 (m, 3H), 1.75 (s, 9H), 1.69-1.59 (m, 1H), 1.47-1.32 (m, 4H), 1.31-1.17 (m, 2H).

Example 148: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-methylpiperidin-4-yl)methyl]piperazin-1-yl}methyl)piperidin-1-yl]-3-methyl-2-oxo-2,3-dihydro-1H-1,3-benzodiazol-1-yl}piperidine-2,6-dione (Compound 160)

Step 1: Preparation of tert-butyl 4-formyl-4-methyl-piperidine-1-carboxylate

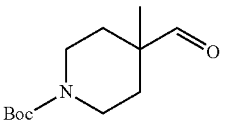

To a solution of tert-butyl 4-(hydroxymethyl)-4-methylpiperidine-1-carboxylate (5.0 g, 22 mmol) in dichloromethane (80 mL) were added Dess-Martin reagent (13.8 g, 33 mmol) and sodium bicarbonate (3.7 g, 44 mmol), and the mixture was stirred at 0° C. for 1 h. The reaction mixture was diluted with water/sodium bicarbonate/sodium sulfite (1:1:1, 180 mL), then extracted with dichloromethane (100 mL). The organic extract was washed with sodium bicarbonate (100 mL×3), dried over anhydrous sodium sulfate, filtered, and concentrated under reduced pressure. The residue was purified by silica gel column chromatography (petroleum ether/ethyl acetate=6/1 to 3/1) to afford the title compound (4 g, 80%) as a yellow oil.

Step 2: Preparation of benzyl 4-[(1-tert-butoxycarbonyl-4-methyl-4-piperidyl)methyl]piperazine-1-carboxylate

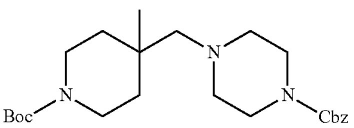 [SMILES: CC1(CN2CCN(C(=O)OCc3ccccc3)CC2)CCN(C(=O)OC(C)(C)C)CC1]

To a solution of tert-butyl 4-formyl-4-methyl-piperidine-1-carboxylate (3.1 g, 14 mmol) and benzyl piperazine-1-carboxylate (2.2 mL, 11 mmol) in dichloromethane (35 mL) were added chloro(triisopropoxy)titanium (5.7 mL, 17 mmol) and sodium triacetoxyborohydride (7.2 g, 34 mmol), and the mixture was stirred at 25° C. for 1 h. The reaction mixture was filtered, and the filtrate was concentrated under reduced pressure. The residue was purified by silica gel column chromatography (petroleum ether/ethyl acetate=10/1 to 4/1) to afford the title compound (3.4 g, 69%) as a yellow oil. LC/MS (ESI) m/z: 432.2 $[M+H]^+$.

Step 3: Preparation of tert-butyl 4-methyl-4-(piperazin-1-ylmethyl)piperidine-1-carboxylate

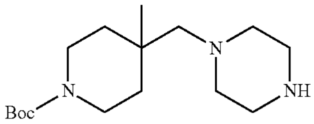 [SMILES: CC1(CN2CCNCC2)CCN(C(=O)OC(C)(C)C)CC1]

To a solution of benzyl 4-[(1-tert-butoxycarbonyl-4-methyl-4-piperidyl)methyl]piperazine-1-carboxylate (3.4 g, 8 mmol) in tetrahydrofuran (30 mL) were added 10% palladium on carbon (500 mg) and 20% palladium hydroxide on carbon (500 mg), and the suspension was degassed under vacuum and purged with hydrogen, then stirred at 50° C. for 16 h under hydrogen (50 psi). The reaction mixture was filtered and concentrated under reduced pressure to afford the title compound (2.3 g, crude) as a yellow oil. LC/MS (ESI) m/z: 298.3 $[M+H]^+$.

Step 4: Preparation of tert-butyl 4-[[4-[[1-[1-(2,6-dioxo-3-piperidyl)-3-methyl-2-oxo-benzimidazol-5-yl]-4-piperidyl]methyl]piperazin-1-yl]methyl]-4-methyl-piperidine-1-carboxylate

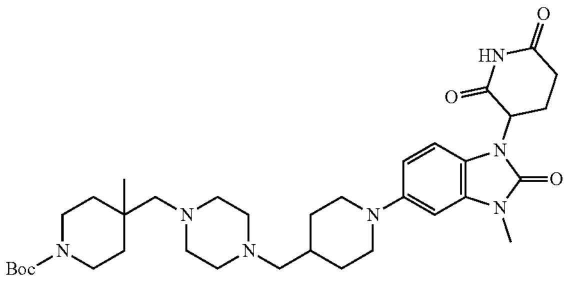 [SMILES: Cn1c(=O)n(C2CCC(=O)NC2=O)c2ccc(N3CCC(CN4CCN(CC5(C)CCN(C(=O)OC(C)(C)C)CC5)CC4)CC3)cc21]

To a solution of tert-butyl 4-methyl-4-(piperazin-1-ylmethyl)piperidine-1-carboxylate (2.2 g, 7.4 mmol) and 1-[1-(2,6-dioxo-3-piperidyl)-3-methyl-2-oxo-benzimidazol-5-yl] piperidine-4-carbaldehyde (2.7 g, 7.4 mmol) in dichloromethane (15 mL) and isopropanol (15 mL) were added sodium triacetoxyborohydride (4.7 g, 22 mmol) and acetic acid (0.4 mL, 7 mmol), and the mixture was stirred at 25° C. for 1 h. The reaction mixture was filtered and concentrated under reduced pressure. The residue was purified by silica gel column chromatography (petroleum ether/ethyl acetate=10/1 to 5/1) to afford the title compound (4.0 g, 82%) as a yellow solid. LC/MS (ESI) m/z: 652.4 $[M+H]^+$.

Step 5: Preparation of 3-[3-methyl-5-[4-[[4-[(4-methyl-4-piperidyl)methyl]piperazin-1-yl]methyl]-1-piperidyl]-2-oxo-benzimidazol-1-yl]piperidine-2,6-dione

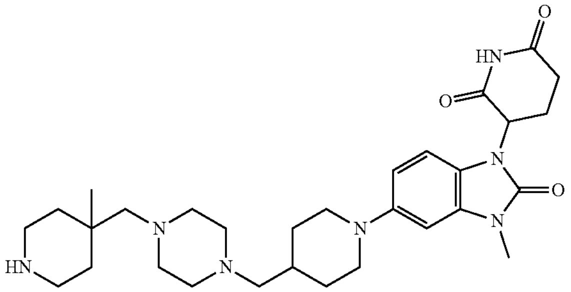 [SMILES: Cn1c(=O)n(C2CCC(=O)NC2=O)c2ccc(N3CCC(CN4CCN(CC5(C)CCNCC5)CC4)CC3)cc21]

To a solution of tert-butyl 4-[[4-[[1-[1-(2,6-dioxo-3-piperidyl)-3-methyl-2-oxo-benzimidazol-5-yl]-4-piperidyl]methyl]piperazin-1-yl]methyl]-4-methyl-piperidine-1-carboxylate (4 g, 6 mmol) in dichloromethane (30 mL) was added trifluoroacetic acid (10.0 mL, 135 mmol), and the mixture was stirred at 25° C. for 1 h. The reaction mixture was concentrated under reduced pressure, and the residue was purified by prep-HPLC (1%-30% acetonitrile in water (formic acid) over 9 min) to afford the title compound (2 g, 54%, formic acid salt) as a yellow solid.

Step 6: Preparation of tert-butyl 3-[2-[2-[4-[[4-[[1-[1-(2,6-dioxo-3-piperidyl)-3-methyl-2-oxo-benzimidazol-5-yl]-4-piperidyl]methyl]piperazin-1-yl]methyl]-4-methyl-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1] octane-8-carboxylate

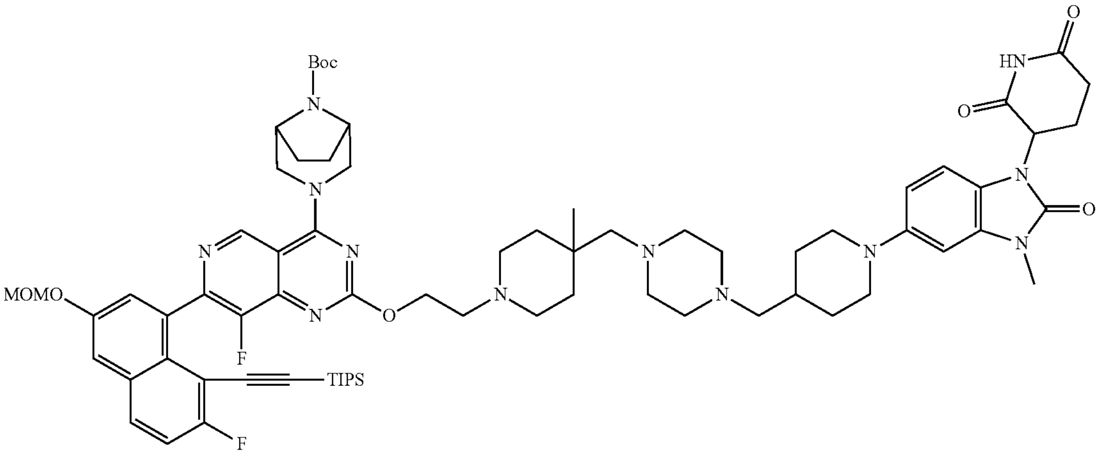

To a solution of 3-[3-methyl-5-[4-[[4-[(4-methyl-4-piperidyl)methyl]piperazin-1-yl]methyl]-1-piperidyl]-2-oxo-benzimidazol-1-yl]piperidine-2,6-dione formate (300 mg, 0.5 mmol) in dichloromethane (4 mL) and isopropanol (4 mL) were added N,N-diisopropylethylamine (0.1 mL, 0.6 mmol), acetic acid (45 mg, 0.75 mmol), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (483 mg, 0.6 mmol), and sodium triacetoxyborohydride (319 mg, 1.5 mmol), and the mixture was stirred at 25° C. for 1 h. The reaction mixture was filtered and concentrated under reduced pressure. The residue was purified by prep-TLC (dichloromethane/methanol=6/1) to afford the title compound (570 mg, 84%) as a yellow solid. LC/MS (ESI) m/z: 1337.6 [M+H]$^+$.

Step 7: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-methylpiperidin-4-yl)methyl]piperazin-1-yl}methyl)piperidin-1-yl]-3-methyl-2-oxo-2,3-dihydro-1H-1,3-benzodiazol-1-yl}piperidine-2,6-dione

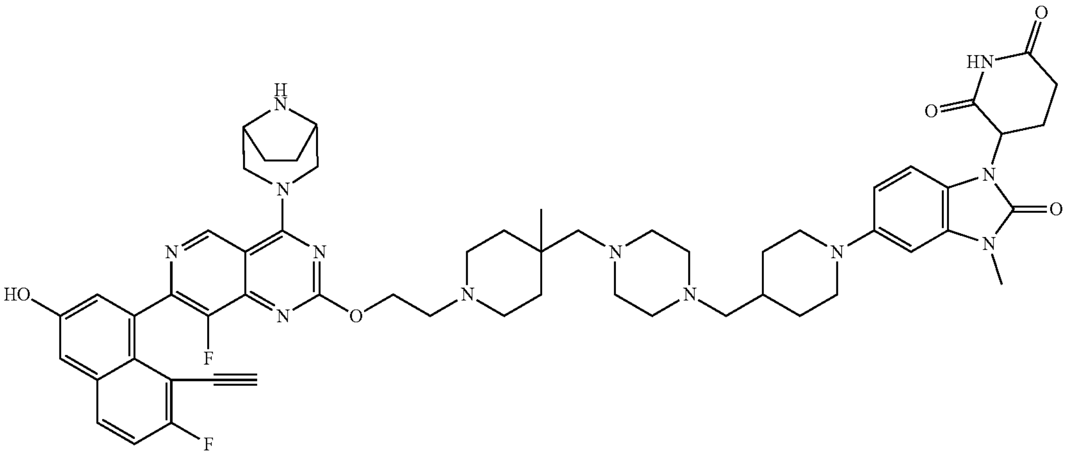 [SMILES: C#Cc1c(F)ccc2cc(O)cc(-c3ncc4c(N5CC6CCC(C5)N6)nc(OCCN5CCC(C)(CN6CCN(CC7CCN(c8ccc9c(c8)n(C)c(=O)n9C8CCC(=O)NC8=O)CC7)CC6)CC5)nc4c3F)c12]

The title compound can be prepared in an analogous manner to step 4 and 5 of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-3-methyl-2-oxo-benzimidazol-1-yl]piperidine-2,6-dione. (yellow solid, formic acid salt). LC/MS (ESI) m/z: 1037.2 [M+H]$^+$; $^1$H NMR (400 MHz, DMSO-$d_6$) δ 11.07 (brs, 1H), 9.06 (s, 1H), 8.21 (s, 2H), 8.05-7.92 (m, 1H), 7.47 (t, J=9.2 Hz, 1H), 7.40 (d, J=2.4 Hz, 1H), 7.18 (d, J=2.4 Hz, 1H), 6.92 (d, J=8.4 Hz, 1H), 6.83-6.77 (m, 1H), 6.62 (dd, J=2.0, 8.8 Hz, 1H), 5.29 (dd, J=5.6, 12.8 Hz, 1H), 4.53 (br d, J=12.4 Hz, 1H), 4.47 (br t, J=5.2 Hz, 2H), 4.38 (br d, J=12.4 Hz, 1H), 3.94 (s, 2H), 3.74 (br d, J=10.0 Hz, 4H), 3.67 (br d, J=14.4 Hz, 3H), 3.56 (br d, J=11.6 Hz, 2H), 3.30 (s, 4H), 2.95-2.84 (m, 1H), 2.76 (br s, 2H), 2.63-2.62 (m, 1H), 2.69-2.57 (m, 6H), 2.47 (br s, 3H), 2.40-2.31 (m, 6H), 2.14 (br d, J=6.8 Hz, 2H), 2.09 (s, 2H), 2.03-1.95 (m, 1H), 1.76 (br s, 6H), 1.65-1.55 (m, 1H), 1.47-1.47 (m, 1H), 1.47 (br d, J=9.2 Hz, 2H), 1.22 (br d, J=11.2 Hz, 4H), 0.85 (s, 3H).

Example 149: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-methylpiperidin-4-yl)methyl]piperidin-1-yl}methyl)piperidin-1-yl]-3-methyl-2-oxo-2,3-dihydro-1H-1,3-benzodiazol-1-yl}piperidine-2,6-dione (Compound 161)

Step 1: Preparation of tert-butyl 4-(bromomethyl)-4-methyl-piperidine-1-carboxylate

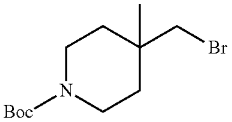 [SMILES: CC1(CBr)CCN(C(=O)OC(C)(C)C)CC1]

To a solution of tert-butyl 4-(hydroxymethyl)-4-methyl-piperidine-1-carboxylate (17 g, 74 mmol) in tetrahydrofuran (300 mL) was added triphenyl phosphine (23.33 g, 89 mmol), and the mixture was stirred at 20° C. for 0.5 h. Carbon tetrabromide (27.04 g, 82 mmol) in tetrahydrofuran (100 mL) was then added dropwise at 0° C., and the reaction mixture was stirred at 50° C. for 12 h under nitrogen. The reaction mixture was diluted with water (200 mL), then extracted with ethyl acetate (200 mL×3). The combined organic extract was washed with brine (200 mL), dried over anhydrous sodium sulfate, filtered, and concentrated in vacuo. The residue was purified by silica gel column chromatography (petroleum ether/ethyl acetate=1/0 to 10/1) to afford the title compound (20 g, 92%) as a yellow oil. $^1$H NMR (400 MHz, $CDCl_3$) b 3.63 (br d, J=13.6 Hz, 2H), 3.36-3.30 (m, 2H), 3.16 (ddd, J=4.0, 9.6, 13.6 Hz, 2H), 1.56-1.46 (m, 2H), 1.46 (s, 9H), 1.43-1.37 (m, 2H), 1.07 (s, 3H).

Step 2: Preparation of tert-butyl 4-methyl-4-(4-pyridylmethyl)piperidine-1-carboxylate

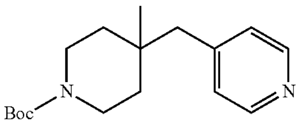 [SMILES: CC1(Cc2ccncc2)CCN(C(=O)OC(C)(C)C)CC1]

4-Bromopyridine (4.92 g, 31 mmol), tert-butyl 4-(bromomethyl)-4-methyl-piperidine-1-carboxylate (7.0 g, 24 mmol), bis[3,5-difluoro-2-[5-(trifluoro methyl)-2-pyridyl] phenyl]4-tertbutyl-2-(4-tert-butyl-2-pyridyl)pyridine iridium hexafluorophosphate (269 mg, 0.24 mmol), 4-tert-butyl-2-(4-tert-butyl-2-pyridyl)pyridine nickel(II) dichloride (48 mg, 0.12 mmol), bis(trimethylsilyl)silyl-trimethyl-silane (7.4 mL, 24 mmol), and sodium carbonate (5.08 g, 48 mmol) in 1,2-dimethoxyethane (50 mL) were combined in a sealed tube under nitrogen. The reaction was stirred and irradiated with a 34 W blue LED lamp (7 cm away) with cooling fan to keep the reaction temperature at 25° C. for 4 h. The reaction mixture was diluted with water (20 mL) and extracted with ethyl acetate (20 mL×3). The combined organic phase was washed with brine (20 mL), dried over anhydrous sodium sulfate, filtered, and concentrated in vacuo. The residue was purified by silica gel column chromatography (petroleum ether/ethyl acetate=100/1 to 3/1) to afford the title compound (2.9 g, 42%) as a yellow oil.

Step 3: Preparation of tert-butyl 4-methyl-4-(4-piperidylmethyl)piperidine-1-carboxylate

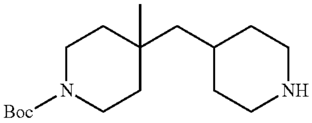 [SMILES: CC1(CC2CCNCC2)CCN(C(=O)OC(C)(C)C)CC1]

To a solution of tert-butyl 4-methyl-4-(4-pyridylmethyl) piperidine-1-carboxylate (2.6 g, 9 mmol) and acetic acid (1.1 mL, 19 mmol) in ethanol (30 mL) was added platinum(iv) oxide (407 mg, 1.8 mmol) under nitrogen. The suspension was degassed under vacuum and purged with hydrogen, then stirred under hydrogen (2 mpa) at 50° C. for 48 h. The mixture was filtered through celite, and the filtrate was concentrated in vacuo to afford the title compound (3 g, 80%, acetic acid salt) as a yellow oil. LC/MS (ESI) m/z: 297.2 $[M+H]^+$; $^1H$ NMR (400 MHz, DMSO-$d_6$) δ 8.48-6.22 (m, 3H), 3.49-3.39 (m, 2H), 3.18-3.08 (m, 2H), 3.03 (br d, J=12.4 Hz, 2H), 2.72-2.61 (m, 2H), 1.70-1.61 (m, 2H), 1.59-1.48 (m, 1H), 1.38 (s, 9H), 1.33-1.20 (m, 6H), 1.15 (d, J=4.8 Hz, 2H).

Step 4: Preparation of tert-butyl 4-[[1-[[1-[1-(2,6-dioxo-3-piperidyl)-3-methyl-2-oxo-benzimidazol-5-yl]-4-piperidyl]methyl]-4-piperidyl]methyl]-4-methyl-piperidine-1-carboxylate

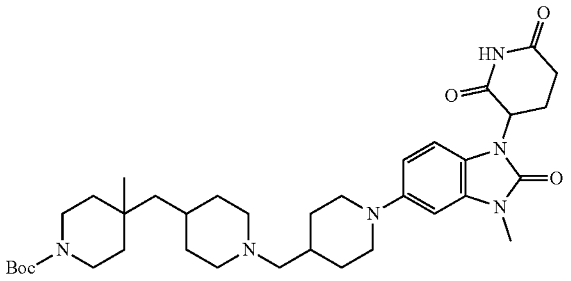 [SMILES: Cn1c(=O)n(C2CCC(=O)NC2=O)c2ccc(N3CCC(CN4CCC(CC5(C)CCN(C(=O)OC(C)(C)C)CC5)CC4)CC3)cc21]

To a solution of tert-butyl 4-methyl-4-(4-piperidylmethyl) piperidine-1-carboxylate diacetate (1.29 g, 3 mmol) in dichloromethane (10 mL) and dimethyl sulfoxide (10 mL) was added N,N-diisopropylethylamine (1.1 mL, 6 mmol), and the mixture was stirred at 25° C. for 10 min. 1-[1-(2,6-dioxo-3-piperidyl)-3-methyl-2-oxo-benzimidazol-5-yl]piperidine-4-carbaldehyde trifluoroacetate (1 g, 2 mmol) was then added, and the resulting mixture was stirred for 20 minutes. Sodium triacetoxyborohydride (1.31 g, 6 mmol) was then added, and the reaction mixture was stirred at 25° C. for 0.5 h. The mixture was diluted with water (20 mL) and extracted with dichloromethane (20 mL×3). The combined organic phase was washed with brine (20 mL), dried over anhydrous sodium sulfate, filtered, and concentrated in vacuo. The residue was purified by silica gel column chromatography (dichloromethane/methanol=100/1 to 10/1) to afford the title compound (1 g, 74%) as a yellow solid. LC/MS (ESI) m/z: 651.5 $[M+H]^+$; $^1H$ NMR (400 MHz, $CDCl_3$) δ 9.26-7.93 (m, 1H), 6.74-6.52 (m, 3H), 5.20 (dd, J=5.2, 12.8 Hz, 1H), 3.66-3.51 (m, 4H), 3.49 (s, 1H), 3.40 (s, 3H), 3.39-3.28 (m, 2H), 3.15 (ddd, J=3.6, 9.6, 13.2 Hz, 2H), 3.08-3.08 (m, 1H), 2.99-2.79 (m, 2H), 2.74-2.65 (m, 4H), 2.55-2.38 (m, 2H), 2.29-2.14 (m, 1H), 1.93 (br d, J=13.2 Hz, 2H), 1.88-1.62 (m, 5H), 1.51 (br dd, J=2.8, 12.8 Hz, 2H), 1.46 (s, 9H), 1.39-1.25 (m, 7H).

Step 5: Preparation of 3-[3-methyl-5-[4-[[4-[(4-methyl-4-piperidyl)methyl]-1-piperidyl]methyl]-1-piperidyl]-2-oxo-benzimidazol-1-yl]piperidine-2,6-dione

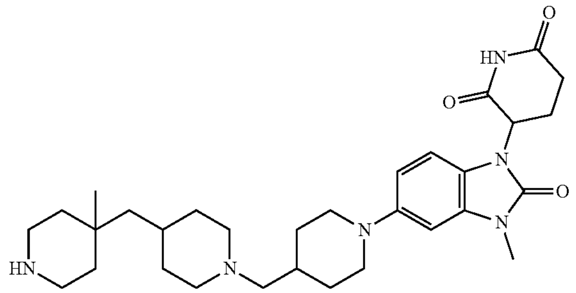 [SMILES: Cn1c(=O)n(C2CCC(=O)NC2=O)c2ccc(N3CCC(CN4CCC(CC5(C)CCNCC5)CC4)CC3)cc21]

To a solution of tert-butyl 4-[[1-[[1-[1-(2,6-dioxo-3-piperidyl)-3-methyl-2-oxo-benzimidazol-5-yl]-4-piperidyl] methyl]-4-piperidyl]methyl]-4-methyl-piperidine-1-carboxylate (1 g, 1 mmol) in dichloromethane (10 mL) was added trifluoroacetic acid (10 mL), and the mixture was stirred for 0.5 h at 25° C. The reaction mixture was concentrated in vacuo to afford the title compound (1 g, 97%, TFA salt) as a yellow solid. LC/MS (ESI) m/z: 551.3 $[M+H]^+$.

Step 6: Preparation of tert-butyl 3-[2-[2-[4-[[1-[[1-[1-(2,6-dioxo-3-piperidyl)-3-methyl-2-oxo-benzimidazol-5-yl]-4-piperidyl]methyl]-4-piperidyl]methyl]-4-methyl-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

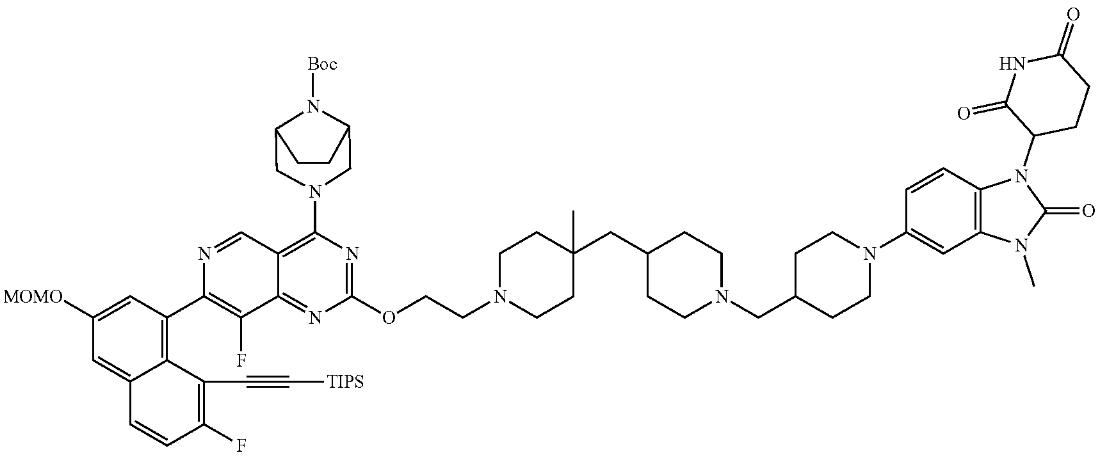

To a solution of 3-[3-methyl-5-[4-[[4-[(4-methyl-4-piperidyl)methyl]-1-piperidyl]methyl]-1-piperidyl]-2-oxo-benzimidazol-1-yl]piperidine-2,6-dione trifluoroacetate (350 mg, 0.5 mmol) in dichloromethane (5 mL) and isopropanol (5 mL) was added N,N-diisopropylethylamine (0.3 mL, 1 mmol), and the mixture was stirred at 25° C. for 10 min. Tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (422 mg, 0.5 mmol) was then added, and the resulting mixture was stirred for 20 minutes at 25° C. Sodium triacetoxyborohydride (335 mg, 1.6 mmol) was then added, and the reaction mixture was stirred at 25° C. for 0.5 h. The mixture was diluted with water (20 mL) and extracted with dichloromethane (20 mL×3). The combined organic phase was washed with brine (20 mL), dried over anhydrous sodium sulfate, filtered, and concentrated in vacuo. The residue was purified by preparative TLC (dichloromethane/methanol=10/1) to afford the title compound (300 mg, 43%) as a yellow solid. LC/MS (ESI) m/z: 1337.0 $[M+H]^+$.

Step 7: Preparation of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}-4-methylpiperidin-4-yl)methyl]piperidin-1-yl}methyl)piperidin-1-yl]-3-methyl-2-oxo-2,3-dihydro-1H-1,3-benzodiazol-1-yl}piperidine-2,6-dione

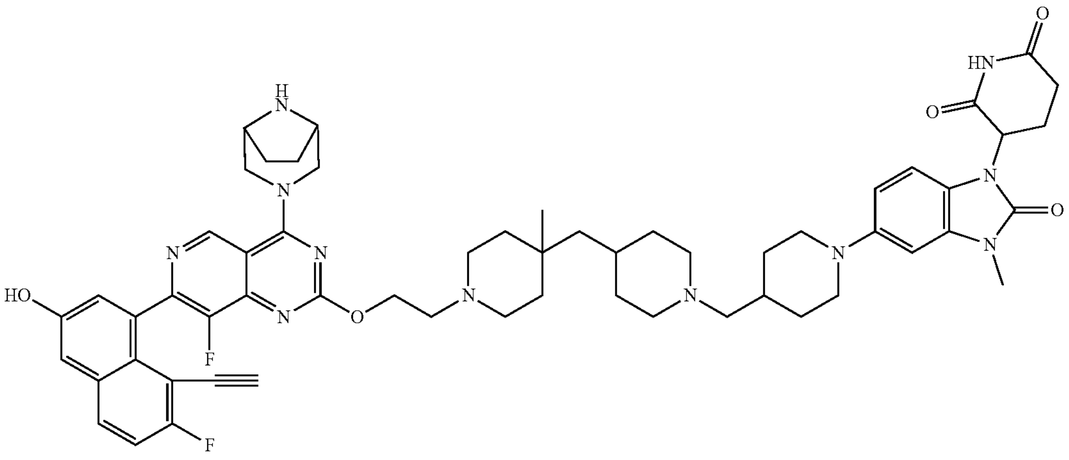 [SMILES: C#Cc1c(F)ccc2cc(O)cc(-c3ncc4c(N5CC6CCC(C5)N6)nc(OCCN5CCC(C)(CC6CCN(CC7CCN(c8ccc9c(c8)n(C)c(=O)n9C8CCC(=O)NC8=O)CC7)CC6)CC5)nc4c3F)c12]

The title compound was prepared in an analogous manner to step 4 and 5 of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-fluoro-4-piperidyl]methyl]-1-piperidyl]methyl]-1-piperidyl]-3-methyl-2-oxo-benzimidazol-1-yl]piperidine-2,6-dione. (yellow solid, formic acid salt). LC/MS (ESI) m/z: 1036.5 $[M+H]^+$; $^1H$ NMR (400 MHz, DMSO-$d_6$) δ 11.05 (brs, 1H), 9.05 (s, 1H), 8.21 (s, 2H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 6.91 (d, J=8.8 Hz, 1H), 6.80 (d, J=2.0 Hz, 1H), 6.61 (dd, J=2.0, 8.8 Hz, 1H), 5.27 (dd, J=5.6, 12.8 Hz, 1H), 4.51 (br d, J=13.2 Hz, 1H), 4.46 (br t, J=5.6 Hz, 2H), 4.35 (br d, J=10.8 Hz, 1H), 3.92 (s, 1H), 3.55-3.51 (m, 5H), 3.29 (s, 3H), 2.93-2.84 (m, 1H), 2.79 (br d, J=11.6 Hz, 2H), 2.73 (br t, J=5.2 Hz, 2H), 2.70-2.66 (m, 1H), 2.65-2.60 (m, 2H), 2.58 (br d, J=9.2 Hz, 3H), 2.52 (br s, 2H), 2.42-2.31 (m, 3H), 2.18 (br d, J=6.8 Hz, 2H), 2.02-1.88 (m, 3H), 1.80-1.69 (m, 6H), 1.60 (br d, J=12.4 Hz, 3H), 1.43-1.28 (m, 5H), 1.27-1.17 (m, 4H), 1.14 (br d, J=4.4 Hz, 2H).

Example 150: Synthesis of 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)difluoromethyl]piperidin-1-yl}methyl)piperidin-1-yl]-4-fluoro-1-oxo-2,3-dihydro-1H-isoindol-2-yl}piperidine-2,6-dione (Compound 79)

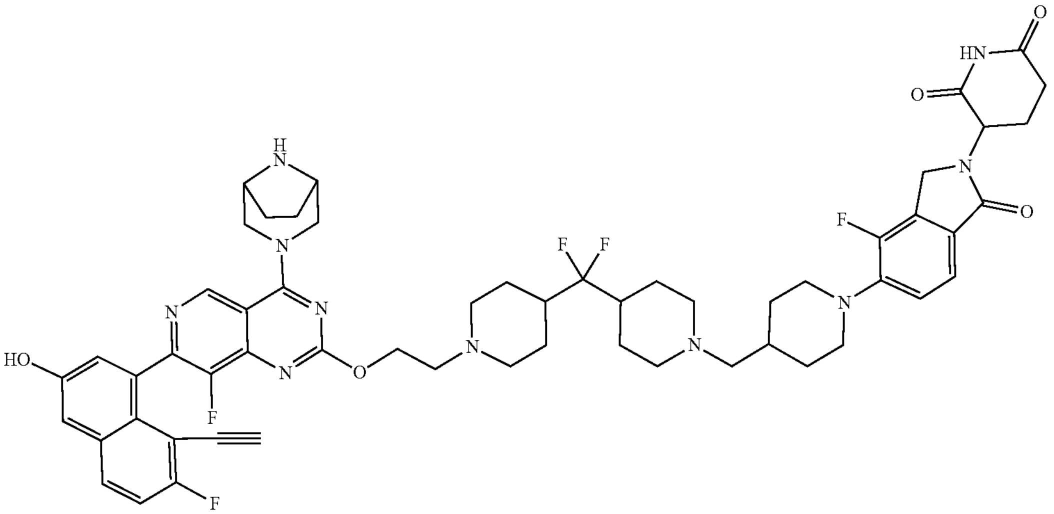 [SMILES: C#Cc1c(F)ccc2cc(O)cc(-c3ncc4c(N5CC6CCC(C5)N6)nc(OCCN5CCC(C(F)(F)C6CCN(CC7CCN(c8ccc9c(c8F)CN(C8CCC(=O)NC8=O)C9=O)CC7)CC6)CC5)nc4c3F)c12]

The title compound was prepared in an analogous manner to 3-{5-[4-({4-[(1-{2-[(4-{3,8-diazabicyclo[3.2.1]octan-3-yl}-7-(8-ethynyl-7-fluoro-3-hydroxynaphthalen-1-yl)-8-fluoropyrido[4,3-d]pyrimidin-2-yl)oxy]ethyl}piperidin-4-yl)methyl]piperidin-1-yl}methyl)piperidin-1-yl]-4-fluoro-1-oxo-2,3-dihydro-1H-isoindol-2-yl}piperidine-2,6-dione. (yellow solid, formic acid salt). LC/MS (ESI) m/z: 1061.6 $[M+H]^+$, $^1H$ NMR (400 MHz, DMSO-$d_6$) δ 10.99 (s, 1H), 9.06 (s, 1H), 8.21 (s, 2H), 7.98 (dd, J=6.0, 9.2 Hz, 1H), 7.52-7.43 (m, 2H), 7.40 (d, J=2.4 Hz, 1H), 7.20-7.13 (m, 2H), 5.07 (dd, J=5.2, 13.2 Hz, 1H), 4.56-4.44 (m, 4H), 4.38-4.29 (m, 2H), 3.93 (s, 1H), 3.72-3.62 (m, 4H), 3.54-3.40 (m, 3H), 3.02 (d, J=10.4 Hz, 2H), 2.95-2.85 (m, 3H), 2.82-2.67 (m, 4H), 2.64-2.56 (m, 1H), 2.46-2.37 (m, 1H), 2.17 (d, J=6.8 Hz, 2H), 2.07-1.94 (m, 3H), 1.92-1.59 (m, 16H), 1.43-1.37 (m, 4H), 1.32-1.22 (m, 2H).

Example 151: Synthesis of 3-[5-[4-[[4-[[1-[3-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]propyl]-4-piperidyl]methyl]-1-piperidyl]methyl]-1-piperidyl]-3-methyl-2-oxo-benzimidazol-1-yl]piperidine-2,6-dione (Compound 230)

Step 1: Preparation of tert-butyl 4-(4-pyridylmethyl)piperidine-1-carboxylate

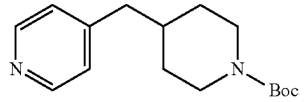 [SMILES: CC(C)(C)OC(=O)N1CCC(Cc2ccncc2)CC1]

To a solution of tert-butyl 4-methylenepiperidine-1-carboxylate (25 g, 126.73 mmol, 1.0 eq) in THF (40 mL) was added 9-BBN (0.5 M, 304.15 mL, 1.2 eq) dropwise under $N_2$ atmosphere at 25° C., and the reaction was stirred at 85° C. for 2 hours. The reaction was cooled to 25° C. and diluted with $H_2O$ (45 mL). 4-Bromopyridine (28 g, 177.42 mmol, 1.4 eq), $K_2CO_3$ (52 g, 380.18 mmol, 3.0 eq), and Pd(dppf)$Cl_2{\cdot}CH_2Cl_2$ (10 g, 12.67 mmol, 0.1 eq) were then added, and the reaction mixture was stirred at 75° C. for 16 hours under $N_2$ atmosphere. The reaction was quenched by addition of water (30 mL), and the organic layer was separated. The aqueous layer was extracted with ethyl acetate (70 mL×3), and the combined organic layers were washed with brine (30 mL), dried over $Na_2SO_4$, filtered, and concentrated in vacuum. The resulting residue was purified by flash chromatography on $SiO_2$ (gradient 0-50% ethyl acetate in petroleum ether) to afford the title compound (32.5 g, 87% yield) as a yellow solid. LC/MS (ESI) m/z: 277.1 $[M+H]^+$.

Step 2: Preparation of 4-(4-piperidylmethyl)pyridine

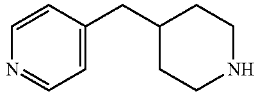 [SMILES: c1cc(CC2CCNCC2)ccn1]

To a solution of tert-butyl 4-(4-pyridylmethyl)piperidine-1-carboxylate (32.5 g, 94% purity 110.54 mmol, 1.0 eq) in $CH_2Cl_2$ (300 mL) was added HCl in dioxane (4 M, 300 mL), and the reaction mixture was stirred at 25° C. for 0.5 hour. The mixture was diluted with petroleum ether (200 mL), filtered, and the filtrate concentrated in vacuum to afford the title compound (23 g, crude, HCl salt) as a yellow oil. LC/MS (ESI) m/z: 177.1 $[M+H]^+$.

Step 3: Preparation of 2-trimethylsilylethyl 4-(4-pyridylmethyl) piperidine-1-carboxylate

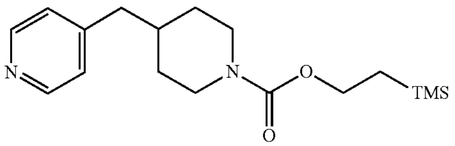 [SMILES: C[Si](C)(C)CCOC(=O)N1CCC(Cc2ccncc2)CC1]

To a solution of 4-(4-piperidylmethyl)pyridine (20.7 g, 97.31 mmol, 1.0 eq, HCl) in $CH_2Cl_2$ (400 mL) were added (2,5-dioxopyrrolidin-1-yl) 2-trimethylsilylethyl carbonate (30.28 g, 116.77 mmol) and $Et_3N$ (10 mL, 71.85 mmol), and the reaction mixture was stirred at 25° C. for 16 hours. The mixture was diluted with water (150 mL), the organic layer separated, and the aqueous layer was further extracted with $CH_2Cl_2$ (100 mL×3). The combined organic extracts were washed with brine (100 mL), dried over $Na_2SO_4$, filtered, and concentrated under reduced pressure. The resulting residue, which was purified by flash chromatography on $SiO_2$ (gradient 0-26% $CH_3OH$ in $CH_2Cl_2$) to afford the title compound (38 g, 99% yield) as a yellow solid. LC/MS (ESI) m/z: 321.2 $[M+H]^+$.

Step 4: Preparation of 2-trimethylsilylethyl 4-(4-piperidylmethyl)piperidine-1-carboxylate

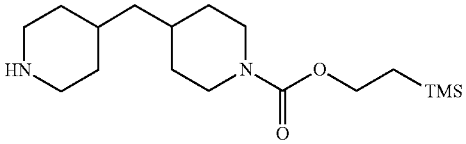 [SMILES: C[Si](C)(C)CCOC(=O)N1CCC(CC2CCNCC2)CC1]

To a solution of 2-trimethylsilylethyl 4-(4-pyridylmethyl) piperidine-1-carboxylate (10 g, 31.20 mmol, 1.0 eq) in EtOH (150 mL) were added HOAc (5.36 mL, 93.60 mmol, 3.0 eq) and $PtO_2$ (1.49 g, 6.55 mmol, 0.21 eq), and the resulting mixture was degassed and purged with Argon (3×), then with $H_2$ (3×). The reaction mixture was then stirred at 75° C. for 48 hours under $H_2$ (50 psi) atmosphere. The mixture was filtered, and the filtrate was concentrated. The resulting residue was diluted with $CH_3CN$ (100 mL) and water (50 mL), and the pH adjusted (pH 7-8) by addition of saturated $NaHCO_3$. The mixture was lyophilized, and the resulting residue was dissolved with $CH_2Cl_2$ (200 mL) and filtered. The filtrate was dried over anhydrous $Na_2SO_4$, filtered, and concentrated under reduced pressure to give the title compound (12.1 g, crude) as a brown solid. LC/MS (ESI) m/z: 327.3 $[M+H]^+$; $^1H$ NMR (400 MHz, $CDCl_3$) δ 4.17-4.01 (m, 4H), 3.26 (d, J=10.4 Hz, 1H), 2.84-2.61 (m, 4H), 2.60-2.40 (m, 1H), 1.95 (s, 1H), 1.74 (d, J=13.2 Hz, 1H), 1.62 (d, J=12.0 Hz, 3H), 1.54-1.47 (m, 1H), 1.43-1.35 (m, 1H), 1.35-1.12 (m, 3H), 1.1-1.04 (m, 2H), 1.04-0.93 (m, 3H), 0.03 (s, 9H).

Step 5: Preparation of tert-butyl 3-[2-but-3-enyl-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

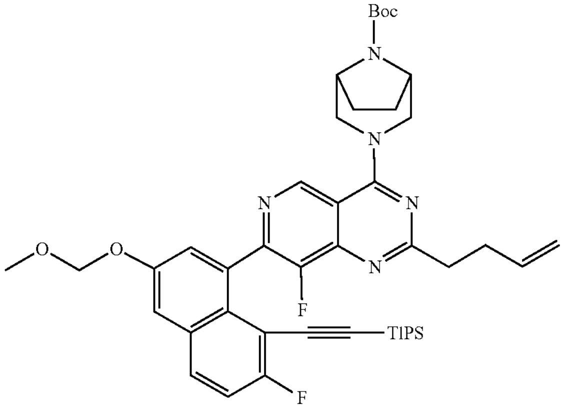

To a solution of tert-butyl 3-[8-fluoro-7-[7-fluoro-3-(methoxymethoxy)-8-(2-triisopropylsilylethynyl)-1-naphthyl]-2-methylsulfonyl-pyrido[4,3-d]pyrimidin-4-yl]-3,8-diazabicyclo[3.2.1]octane-8-carboxylate (1.0 g, 1.22 mmol, 1.0 eq) in THF (20 mL) at 0° C. under $N_2$ was added bromo(but-3-enyl)magnesium (0.5 M, 7.30 mL, 3.0 eq), and the reaction mixture was stirred at 0° C. under $N_2$ for 5 minutes. The reaction was quenched with saturated $NH_4Cl$ solution (50 mL), and the resulting mixture was extracted with ethyl acetate (40 mL×3). The combined organic extract was washed with brine (30 mL), dried over anhydrous sodium sulfate, filtered, and concentrated under reduced pressure. The crude product was purified by flash chromatography on $SiO_2$ (gradient 0-30% THF in petroleum ether) followed by prep-HPLC (column: Xtimate C18 150*40 mm*10 um; mobile phase: [64-98% $CH_3CN$ in water (TFA)]). The pure fractions were treated with saturated $NaHCO_3$ solution to adjust the pH (pH ~7-8), and the resulting mixture was lyophilized). $CH_2Cl_2$ (60 mL) was then added, the mixture was filtered, and the filter cake was washed with $CH_2Cl_2$ (40 mL). The filtrate was concentrated in vacuum to give the title compound (550 mg, 57% yield) as a light yellow solid. LC/MS (ESI) m/z: 798.4 $[M+H]^+$. $^1H$ NMR (400 MHz, $CDCl_3$) δ 9.13 (s, 1H), 7.79 (dd, J=5.6, 9.2 Hz, 1H), 7.52 (d, J=2.4 Hz, 1H), 7.34-7.28 (m, 2H), 5.99 (dd, J=6.4, 10.4, 17.2 Hz, 1H), 5.33-5.27 (m, 2H), 5.14 (dd, J=1.2, 17.2 Hz, 1H), 5.03 (d, J=10.0 Hz, 1H), 4.97-4.83 (m, 1H), 4.51-4.31 (m, 2H), 4.23 (d, J=12.4 Hz, 1H), 3.93-3.74 (m, 1H), 3.51 (s, 3H), 3.49-3.38 (m, 1H), 3.12-2.96 (m, 2H), 2.66 (q, J=7.2 Hz, 2H), 1.99 (s, 2H), 1.58 (s, 2H), 1.54 (s, 9H), 0.85 (t, J=7.6 Hz, 18H), 0.50 (m, 3H).

Step 6: Preparation of tert-butyl 3-[8-fluoro-7-[7-fluoro-3-(methoxymethoxy)-8-(2-triisopropylsilyl-ethynyl)-1-naphthyl]-2-(3-oxopropyl)pyrido[4,3-d]pyrimidin-4-yl]-3,8-diazabicyclo[3.2.1]octane-8-carboxylate

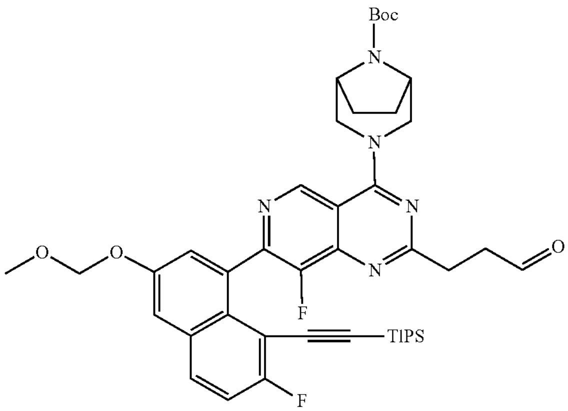

To a solution of tert-butyl 3-[2-but-3-enyl-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (550 mg, 0.69 mmol, 1.0 eq) in dioxane (15 mL) were added 2,6-lutidine (0.32 mL, 2.76 mmol, 4.0 eq) and $NaIO_4$ (589 mg, 2.76 mmol, 4.0 eq) in water (5 mL) followed by $K_2OsO_4·2H_2O$ (25 mg, 0.069 mmol, 0.1 eq), and the reaction mixture was stirred at 20° C. for 2 hours. The mixture was filtered, diluted with saturated aqueous $Na_2SO_3$ (30 mL), and then extracted with EtOAc (30 mL×2). The combined organic extract was washed with water (20 mL) and brine (20 mL), dried over anhydrous $Na_2SO_4$, filtered, and concentrated under reduced pressure to give the title compound (550 mg 100% yield) as a yellow solid. LC/MS (ESI) m/z: 800.4 $[M+H]^+$.

Step 7: Preparation tert-butyl 3-[8-fluoro-7-[7-fluoro-3-(methoxymethoxy)-8-(2-triisopropylsilyl-ethynyl)-1-naphthyl]-2-[3-[4-[[1-(2-trimethylsily-lethoxycarbonyl)-4-piperidyl]methyl]-1-piperidyl]propyl]pyrido[4,3-d]pyrimidin-4-yl]-3,8-diazabicyclo[3.2.1]octane-8-carboxylate

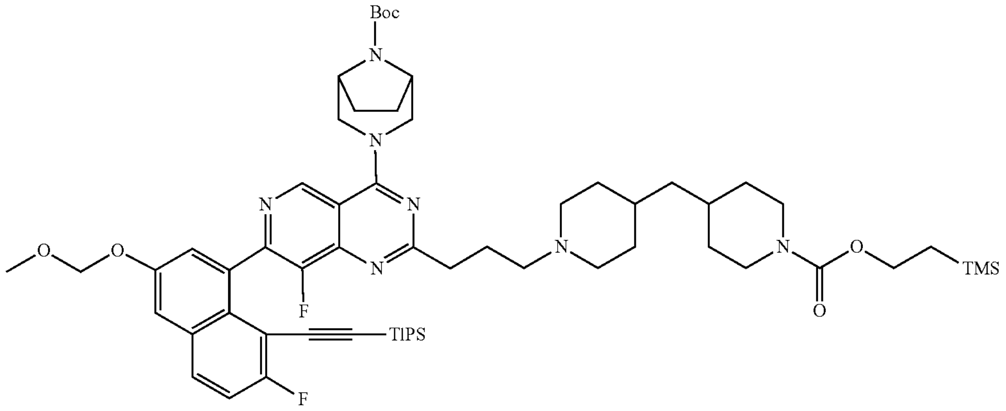

To a solution of tert-butyl 3-[8-fluoro-7-[7-fluoro-3-(methoxymethoxy)-8-(2-triisopropylsilylethynyl)-1-naphthyl]-2-(3-oxopropyl)pyrido[4,3-d]pyrimidin-4-yl]-3,8-diazabicyclo[3.2.1]octane-8-carboxylate (550 mg, 0.69 mmol, 1.0 eq) and 2-trimethylsilylethyl 4-(4-piperidylmethyl)piperidine-1-carboxylate (673 mg, 2.06 mmol, 3.0 eq) in $CH_2Cl_2$ (5 mL) and i-PrOH (5 mL) was added HOAc (0.16 mL, 2.75 mmol, 4.0 eq) followed by $NaBH(OAc)_3$ (583 mg, 2.75 mmol, 4.0 eq), and the reaction mixture was stirred at 20° C. for 16 hours. The reaction was quenched with saturated $NaHCO_3$ solution (50 mL), and the resulting mixture was extracted with $CH_2Cl_2$ (40 mL×3). The combined organic extract was washed with water (50 mL) and brine (50 mL), dried over anhydrous $Na_2SO_4$, filtered, and concentrated under reduced pressure. The crude product was purified by flash chromatography on $SiO_2$ (gradient 0-4% $CH_3OH$ in $CH_2Cl_2$) to afford the title compound (670 mg, 88% yield) as a yellow solid. LC/MS (ESI) m/z: 1110.7 $[M+H]^+$.

Step 8: Preparation of tert-butyl 3-[7-[8-ethynyl-7-fluoro-3-(methoxymethoxy)-1-naphthyl]-8-fluoro-2-[3-[4-(4-piperidylmethyl)-1-piperidyl]propyl]pyrido[4,3-d]pyrimidin-4-yl]-3,8-diazabicyclo[3.2.1]octane-8-carboxylate

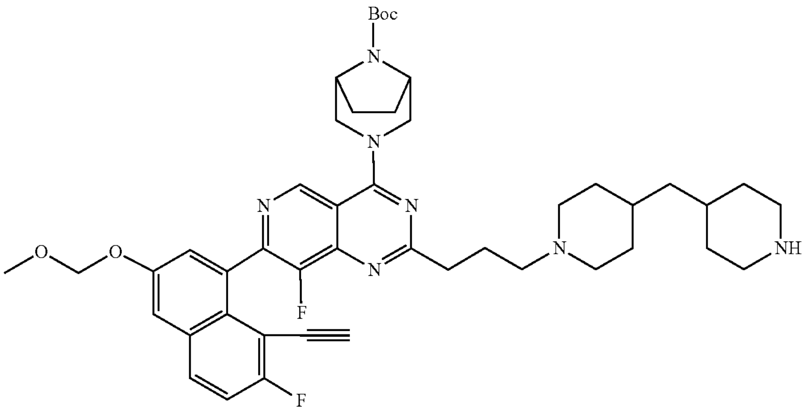 [SMILES: C#Cc1c(F)ccc2cc(OCOC)cc(-c3ncc4c(N5CC6CCC(C5)N6C(=O)OC(C)(C)C)nc(CCCN5CCC(CC6CCNCC6)CC5)nc4c3F)c12]

To a solution of tert-butyl 3-[8-fluoro-7-[7-fluoro-3-(methoxymethoxy)-8-(2-triisopropylsilylethynyl)-1-naphthyl]-2-[3-[4-[[1-(2-trimethylsilylethoxycarbonyl)-4-piperidyl]methyl]-1-piperidyl]propyl]pyrido[4,3-d]pyrimidin-4-yl]-3,8-diazabicyclo[3.2.1]octane-8-carboxylate (620 mg, 0.56 mmol, 1.0 eq) in DMF (10 mL) was added CsF (848 mg, 5.58 mmol, 10.0 eq), and the reaction mixture was stirred at 60° C. for 6 hours. The mixture was filtered, and the filter cake was washed with ethyl acetate (50 mL). The resulting mixture was diluted with water (50 mL) and extracted with ethyl acetate (40 mL×3). The combined extract was washed with water (30 mL×3) and brine (30 mL), dried over anhydrous $Na_2SO_4$, filtered, and concentrated under reduced pressure to give the title compound (450 mg, 100% yield) as a yellow solid. LC/MS (ESI) m/z: 810.5 $[M+H]^+$.

Step 9: Preparation of tert-butyl 3-[2-[3-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]propyl]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

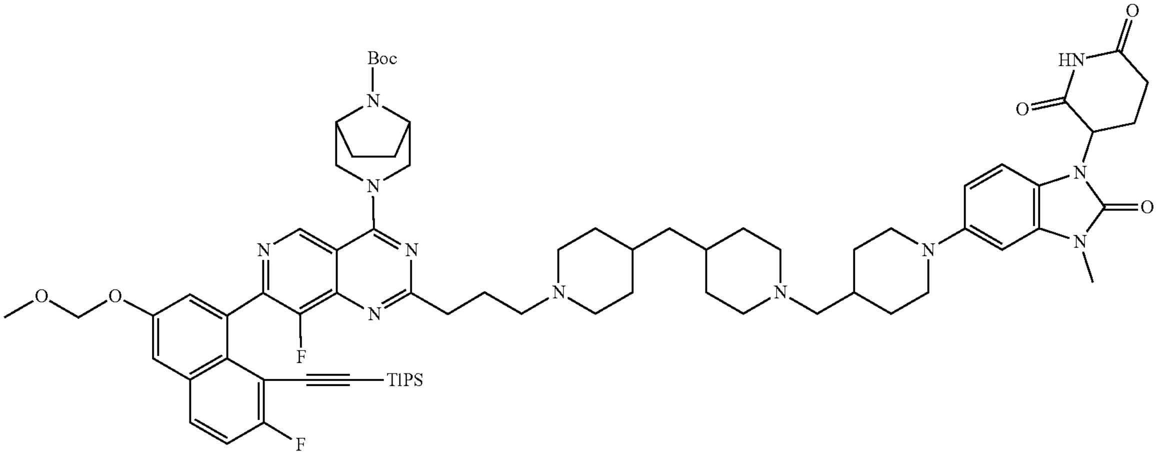

To a solution of tert-butyl 3-[7-[8-ethynyl-7-fluoro-3-(methoxymethoxy)-1-naphthyl]-8-fluoro-2-[3-[4-(4-piperidylmethyl)-1-piperidyl]propyl]pyrido[4,3-d]pyrimidin-4-yl]-3,8-diazabicyclo[3.2.1]octane-8-carboxylate (470 mg, 0.580 mmol, 1.0 eq) and 1-[1-(2,6-dioxo-3-piperidyl)-3-methyl-2-oxo-benzimidazol-5-yl]piperidine-4-carbaldehyde (300 mg, 0.812 mmol, 1.4 eq) in $CH_2Cl_2$ (3.0 mL) and i-PrOH (3.0 mL) were added HOAc (135 μL, 2.32 mmol, 4.0 eq) and $NaBH(OAc)_3$ (368 mg, 1.74 mmol, 3.0 eq), and the reaction mixture was stirred at 20° C. for 1 hour. The mixture was concentrated under reduced pressure, and the resulting residue was purified by flash chromatography on $SiO_2$ (gradient: 0-10% $CH_3OH$ in $CH_2Cl_2$) to afford the title compound (304 mg, 33% yield) as a yellow solid. LC/MS (ESI) m/z: 1164.7 $[M+H]^+$ Step 10: Preparation of 3-[5-[4-[[4-[[1-[3-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]propyl]-4-piperidyl]methyl]-1-piperidyl]methyl]-1-piperidyl]-3-methyl-2-oxo-benzimidazol-1-yl]piperidine-2,6-dione

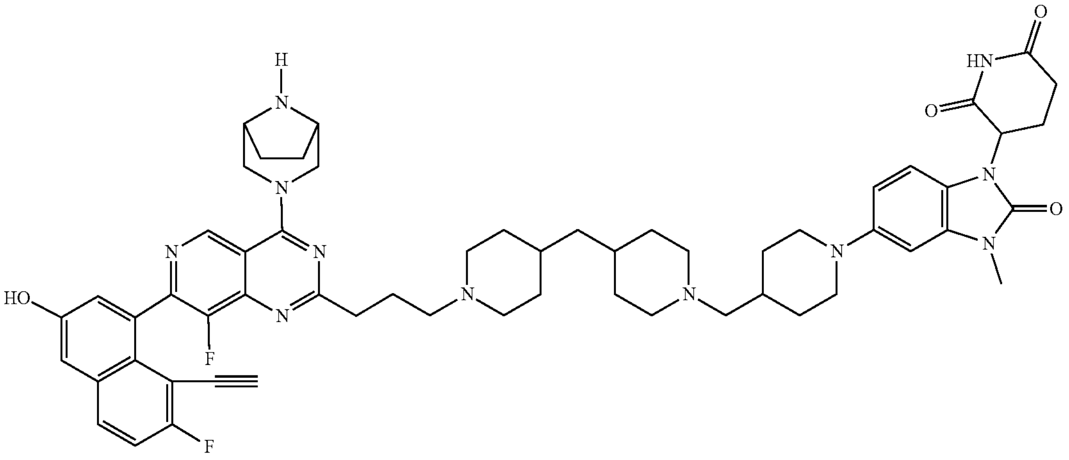 [SMILES: C#Cc1c(F)ccc2cc(O)cc(-c3ncc4c(N5CC6CCC(C5)N6)nc(CCCN5CCC(CC6CCN(CC7CCN(c8ccc9c(c8)n(C)c(=O)n9C8CCC(=O)NC8=O)CC7)CC6)CC5)nc4c3F)c12]

To a solution of tert-butyl 3-[2-[3-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]propyl]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (304 mg, 0.191 mmol, 1.0 eq) in $CH_2Cl_2$ (3.0 mL) was added HCl in dioxane (4 M, 1.9 mL, 30 eq), and the reaction mixture was stirred at 20° C. for 0.25 hour. The mixture was diluted with petroleum ether (40 mL) and filtered, and the filter cake was dissolved in THF (30 mL), then treated with $Et_3N$ to adjust the pH (pH-9). The resulting mixture was filtered, and the filtrate was concentrated under reduced pressure. The crude product was purified by pre-HPLC (FA condition: column: Xtimate C18 150*40 mm*10 um; mobile phase: [0-24% $CH_3CN$ in water (FA)]), then lyophilized to afford the title compound (105.3 mg, 36% yield, 2HCOOH) as a yellow solid. LC/MS (ESI) m/z: 1020.5 $[M+H]^+$. 1H NMR (400 MHz, $CD_3OD$) δ 9.16 (s, 1H), 8.46 (s, 2H), 7.90 (dd, J=5.6, 9.2 Hz, 1H), 7.43-7.30 (m, 2H), 7.24 (d, J=2.4 Hz, 1H), 6.99 (d, J=8.8 Hz, 1H), 6.90-6.75 (m, 2H), 5.29 (dd, J=5.4, 12.4 Hz, 1H), 4.80 (br d, J=12.8 Hz, 3H), 4.00 (br s, 2H), 3.91-3.80 (m, 2H), 3.66-3.48 (m, 6H), 3.40 (s, 3H), 3.36 (s, 1H), 3.21 (br s, 2H), 3.07

(br t, J=6.8 Hz, 2H), 3.00-2.72 (m, 11H), 2.39-2.24 (m, 2H), 2.19-2.11 (m, 1H), 2.03-1.86 (m, 10H), 1.73-1.60 (m, 2H), 1.56-1.40 (m, 6H), 1.29-1.16 (m, 2H).

Example 152: Synthesis of 3-[5-[3-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]methyl]azetidin-1-yl]-1-oxo-isoindolin-2-yl]piperidine-2,6-dione (Compound 235)

Step 1: Preparation of benzyl 3-(dimethoxymethyl)azetidine-1-carboxylate

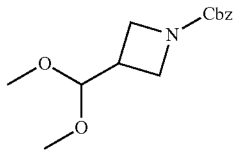 [SMILES: COC(OC)C1CN(C(=O)OCc2ccccc2)C1]

To a solution of benzyl 3-formylazetidine-1-carboxylate (8.9 g, 40.69 mmol, 1.0 eq) in MeOH (180 mL) were added $TsOH-H_2O$ (387 mg, 2.03 mmol, 0.05 eq) and trimethoxymethane (22.3 mL, 203.43 mmol, 5.0 eq), and the reaction mixture was stirred at 25° C. for 10 hours. The mixture was concentrated, and the residue was diluted with water (50 mL) and extracted with ethyl acetate (100 mL×3). The combined organic extract was washed with brine (100 mL×3), dried over anhydrous $Na_2SO_4$, filtered, and concentrated under reduced pressure. The residue was purified by flash chromatography on $SiO_2$ (gradient: 0-30% ethyl acetate in petroleum ether) to afford the title compound (7.3 g, 68% yield) as a colorless oil. LC/MS (ESI) m/z: 266.2 $[M+H]^+$. 1H NMR (400 MHz, $CDCl_3$) δ 7.40-7.31 (m, 5H), 5.10 (s, 2H), 4.53 (d, J=6.8 Hz, 1H), 4.09-4.00 (m, 2H), 3.87 (dd, J=5.6, 8.8 Hz, 2H), 3.35 (s, 6H), 2.91-2.78 (m, 1H).

Step 2: Preparation of 3-(dimethoxymethyl)azetidine

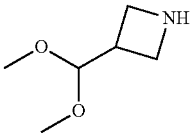

To a solution of benzyl 3-(dimethoxymethyl)azetidine-1-carboxylate (7.3 g, 27.52 mmol, 1.0 eq) in 2,2,2-trifluoroethanol (150 mL) was added Pd/C (730 mg, 0.686 mmol, 10% purity), and the reaction mixture was stirred at 45° C. for 16 hours under $H_2$ (15 psi). The mixture was filtered through celite pad under vacuum and rinsed with ethyl acetate (100 mL). The filtrate was concentrated under reduced pressure to afford the title compound (3.8 g) as a yellow oil. $^1$H NMR (400 MHz, $CDCl_3$) δ 4.60 (d, J=6.4 Hz, 1H), 3.84-3.78 (m, 2H), 3.74-3.67 (m, 2H), 3.36 (s, 6H), 3.09-2.98 (m, 1H).

Step 3: Preparation of 2-(2-benzyloxy-6-hydroxy-3-pyridyl)-5-[3-(dimethoxymethyl)azetidin-1-yl]isoindolin-1-one

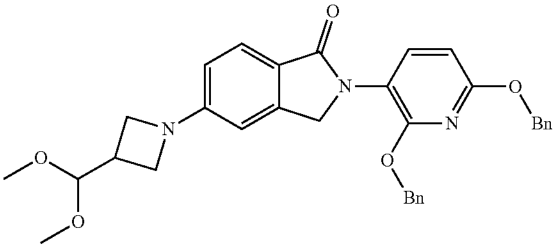 [SMILES: COC(OC)C1CN(c2ccc3c(c2)CN(c2ccc(OCc4ccccc4)nc2OCc2ccccc2)C3=O)C1]

To a solution of 5-bromo-2-(2,6-dibenzyloxy-3-pyridyl) isoindolin-1-one (3.4 g, 6.78 mmol, 1.0 eq) in dioxane (40 mL) were added 3-(dimethoxymethyl)azetidine (1.23 g, 8.82 mmol, 1.3 eq), $Cs_2CO_3$ (6.63 g, 20.34 mmol, 3.0 eq), and BrettPhos Pd $G_3$ (615 mg, 0.68 mmol, 0.1 eq), and the reaction mixture was stirred at 100° C. for 16 hours under $N_2$. The mixture was diluted with water (30 mL) and extracted with dichloromethane (50 mL×3). The combined organic extracts were washed with brine (15 mL), dried over $Na_2SO_4$, filtered, and concentrated under reduced pressure. The residue was purified by flash chromatography on $SiO_2$ (gradient: 0-3% methanol in dichloromethane) to afford the title compound (1.0 g, 32% yield) as a brown solid. LC/MS (ESI) m/z: 552.2 [M+H]$^+$.

Step 4: Preparation of 3-[5-[3-(dimethoxymethyl)azetidin-1-yl]-1-oxo-isoindolin-2-yl]piperidine-2,6-dione

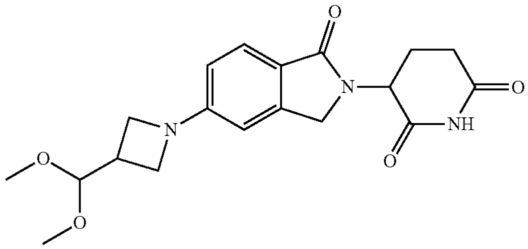 [SMILES: COC(OC)C1CN(c2ccc3c(c2)CN(C2CCC(=O)NC2=O)C3=O)C1]

To a solution of 2-(2-benzyloxy-6-hydroxy-3-pyridyl)-5-[3-(dimethoxymethyl)azetidin-1-yl]isoindolin-1-one (1.0 g, 2.17 mmol, 1.0 eq) in THF (30 mL) was added $Pd(OH)_2/C$ (609 mg, 0.87 mmol, 20% purity, 0.4 eq), and the suspension was degassed and purged with $H_2$ (3×). The reaction mixture was stirred under $H_2$ (50 Psi) at 50° C. for 16 hours. The mixture was filtered and concentrated under reduced pressure to afford the title compound (691 mg, crude) as an off-white solid. LC/MS (ESI) m/z: 374.1 [M+H]$^+$.

Step 5: Preparation of 1-[2-(2,6-dioxo-3-piperidyl)-1-oxo-isoindolin-5-yl]azetidine-3-carbaldehyde

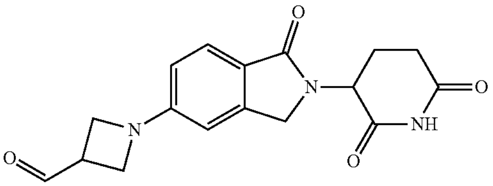 [SMILES: O=CC1CN(c2ccc3c(c2)CN(C2CCC(=O)NC2=O)C3=O)C1]

To a solution of 3-[5-[3-(dimethoxymethyl)azetidin-1-yl]-1-oxo-isoindolin-2-yl]piperidine-2,6-dione (335 mg, 0.90 mmol, 1.0 eq) in dichloromethane (2 mL) was added TFA (1 mL), and the reaction mixture was stirred at 40° C. for 2 hours. The mixture was concentrated under reduced pressure to afford the title compound (354 mg, crude, TFA salt) as a brown oil. LC.MS (ESI) m/z: 346.1 [M+$H_3O$]$^+$.

Step 6: Preparation of tert-butyl 4-[[1-[[1-[2-(2,6-dioxo-3-piperidyl)-1-oxo-isoindolin-5-yl]azetidin-3-yl]methyl]-4-piperidyl]methyl]piperidine-1-carboxylate

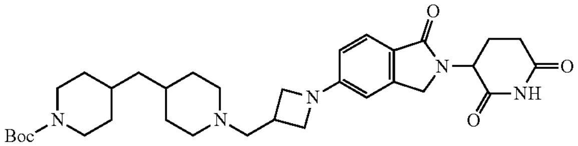 [SMILES: CC(C)(C)OC(=O)N1CCC(CC2CCN(CC3CN(c4ccc5c(c4)CN(C4CCC(=O)NC4=O)C5=O)C3)CC2)CC1]

To a solution of 1-[2-(2,6-dioxo-3-piperidyl)-1-oxo-isoindolin-5-yl]azetidine-3-carbaldehyde (390 mg, 0.88 mmol, 1.0 eq, TFA salt) in $CH_2Cl_2$ (5 mL) and i-PrOH (5 mL) were added NaOAc (725 mg, 8.84 mmol, 10.0 eq), tert-butyl 4-(4-piperidylmethyl)piperidine-1-carboxylate (324 mg, 1.15 mmol, 1.3 eq) and 2-picoline borane complex (473 mg, 4.42 mmol, 5.0 eq), and the reaction mixture was stirred at 20° C. for 16 hours. The mixture was filtered, and the filtrate was concentrated under reduced pressure. The residue was purified by flash chromatography on $SiO_2$ (gradient 0-9% methanol in dichloromethane) to afford the title compound (310 mg, 59% yield) as a light yellow solid. LC/MS (ESI) m/z: 594.6 $[M+H]^+$.

Step 7: Preparation of 3-[1-oxo-5-[3-[[4-(4-piperidylmethyl)-1-piperidyl]methyl]azetidin-1-yl]isoindolin-2-yl]piperidine-2,6-dione

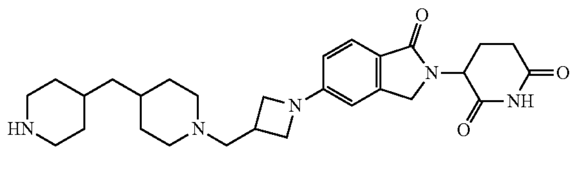 [SMILES: O=C1CCC(N2Cc3cc(N4CC(CN5CCC(CC6CCNCC6)CC5)C4)ccc3C2=O)C(=O)N1]

To a solution of tert-butyl 4-[[1-[[1-[2-(2,6-dioxo-3-piperidyl)-1-oxo-isoindolin-5-yl]azetidin-3-yl]methyl]-4-piperidyl]methyl]piperidine-1-carboxylate (300 mg, 0.51 mmol, 1.0 eq) in dichloromethane (2 mL) was added TFA (1 mL), and the reaction mixture was stirred at 20° C. for 30 minutes. The mixture was concentrated under reduced pressure to afford the title compound (302 mg, crude, TFA salt) as a light yellow oil. LC/MS (ESI) m/z: 494.3 $[M+H]^+$.

Step 8: Preparation of tert-butyl 3-[2-[2-[4-[[1-[[1-[2-(2,6-dioxo-3-piperidyl)-1-oxo-isoindolin-5-yl]azetidin-3-yl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

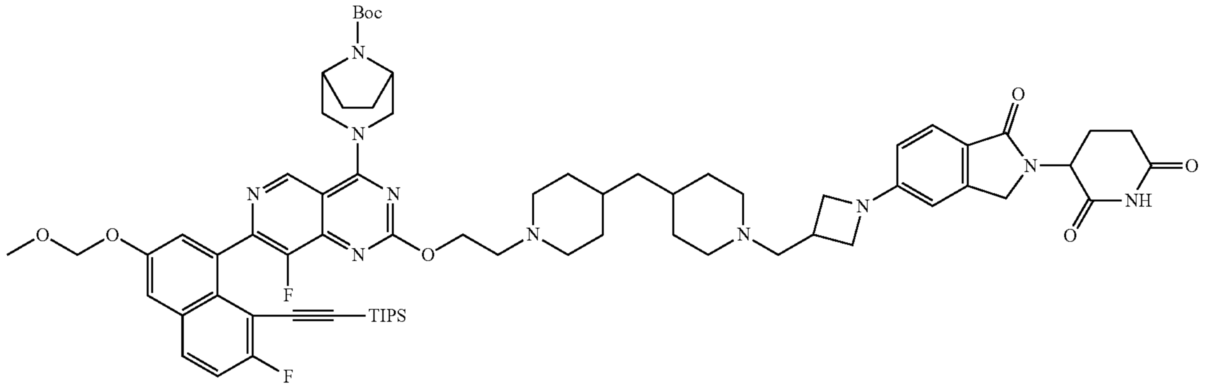

To a solution of 3-[1-oxo-5-[3-[[4-(4-piperidylmethyl)-1-piperidyl]methyl]azetidin-1-yl]isoindolin-2-yl]piperidine-2,6-dione (302 mg, 0.49 mmol, 1.2 eq, TFA salt) in $CH_2Cl_2$ (4 mL) and i-PrOH (4 mL) were added NaOAc (506 mg, 6.17 mmol, 15.0 eq), tert-butyl 3-[8-fluoro-7-[7-fluoro-3-(methoxymethoxy)-8-(2-triisopropylsilylethynyl)-1-naphthyl]-2-(2-oxoethoxy)pyrido[4,3-d]pyrimidin-4-yl]-3,8-diazabicyclo[3.2.1]octane-8-carboxylate (330 mg, 0.41 mmol, 1.0 eq), and 2-picoline borane complex (220 mg, 2.06 mmol, 5.0 eq), and the reaction mixture was stirred at 20° C. for 16 hours. The mixture was treated with triethylamine to pH ~6, then filtered. The filtrate was concentrated under reduced pressure, and the residue was purified flash chromatography on $SiO_2$ (gradient: 0-15% methanol in dichloromethane) to afford the title compound (475 mg, 90% yield) as a light yellow oil. LC/MS (ESI) m/z: 1280.0 $[M+H]^+$.

Step 9: Preparation of tert-butyl 3-[2-[2-[4-[[1-[[1-[2-(2,6-dioxo-3-piperidyl)-1-oxo-isoindolin-5-yl]azetidin-3-yl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

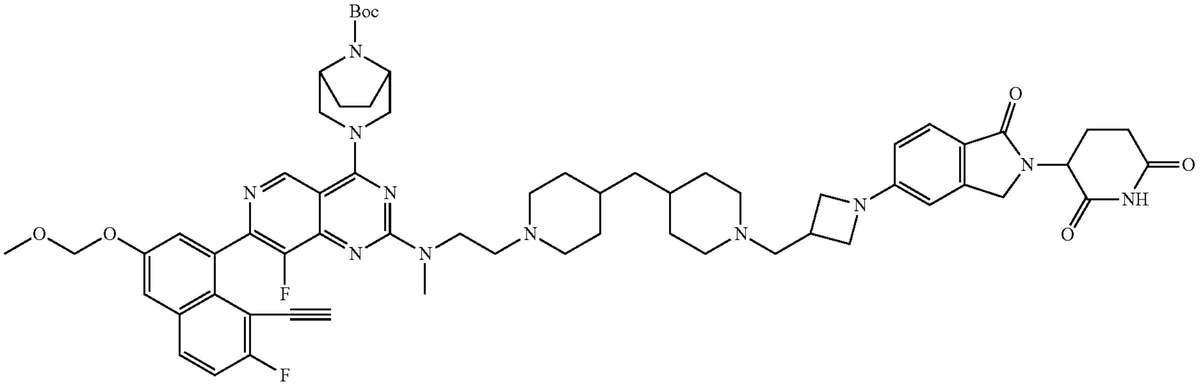 [SMILES: C#Cc1c(F)ccc2cc(OCOC)cc(-c3ncc4c(N5CC6CCC(C5)N6C(=O)OC(C)(C)C)nc(N(C)CCN5CCC(CC6CCN(CC7CN(c8ccc9c(c8)CN(C8CCC(=O)NC8=O)C9=O)C7)CC6)CC5)nc4c3F)c12]

To a solution of tert-butyl 3-[2-[2-[4-[[1-[[1-[2-(2,6-dioxo-3-piperidyl)-1-oxo-isoindolin-5-yl]azetidin-3-yl]methyl]-4-piperidyl]methyl]-1-piperidyl]ethoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (475 mg, 0.37 mmol, 1.0 eq) in DMF (5 mL) was added CsF (282 mg, 1.86 mmol, 5.0 eq), and the reaction mixture was stirred at 20° C. for 16 hours. The mixture was diluted with ethyl acetate (30 mL) and filtered. The filtrate was washed with water (8 mL×5), and the organic layer was dried over $Na_2SO_4$, filtered and concentrated under reduced pressure to afford the title compound (243 mg, crude) as a light yellow oil. LC/MS (ESI) m/z: 1123.8 $[M+H]^+$.

Step 10: Preparation of 3-[5-[3-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-1-piperidyl]methyl]azetidin-1-yl]-1-oxo-isoindolin-2-yl]piperidine-2,6-dione

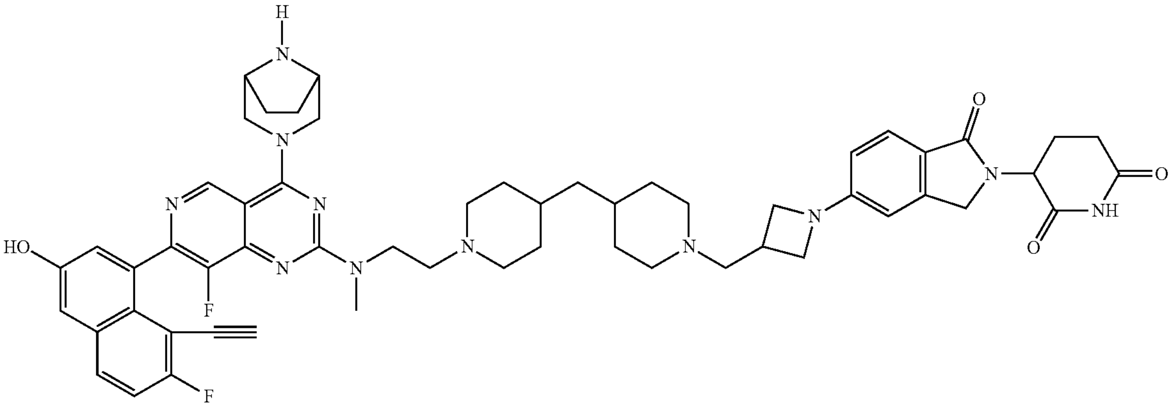 [SMILES: C#Cc1c(F)ccc2cc(O)cc(-c3ncc4c(N5CC6CCC(C5)N6)nc(N(C)CCN5CCC(CC6CCN(CC7CN(c8ccc9c(c8)CN(C8CCC(=O)NC8=O)C9=O)C7)CC6)CC5)nc4c3F)c12]

To a solution of tert-butyl 3-[2-[2-[4-[[1-[[1-[2-(2,6-dioxo-3-piperidyl)-1-oxo-isoindolin-5-yl]azetidin-3-yl]methyl]-4-piperidyl]methyl]-1-piperidyl]ethoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (243 mg, 0.22 mmol, 1.0 eq) in $CH_2Cl_2$ (3 mL) was added TFA (1 mL), and the reaction mixture was stirred at 20° C. for 1 hour. The mixture concentrated, and the residue was taken up in THF (20 mL) and adjusted to pH ~8 by adding solid $NaHCO_3$. The resulting mixture was dried over $Na_2SO_4$, filtered, and concentrated under reduced pressure. The residue was purified by prep-HPLC {column: Xtimate C18 150*40 mm*10 um; mobile phase: [20-60% $CH_3CN$ in water ($NH_4HCO_3$)]}. Pure fractions were combined and dried by lyophilization to afford the title compound (40.1 mg, 19% yield) as a light yellow solid. LC/MS (ESI) m/z: 979.4 $[M+H]^+$; $^1H$ NMR (400 MHz, $CD_3OD$) δ 9.01 (s, 1H), 7.88-7.84 (m, 1H), 7.59-7.56 (m, 1H), 7.35-7.30 (m, 2H), 7.21-7.20 (m, 1H), 6.51-6.49 (m, 2H), 5.11-5.06 (m, 1H), 4.64-4.57 (m, 4H), 4.37-4.35 (m, 2H), 4.14-4.10 (m, 2H), 3.74-3.61 (m, 6H), 3.38 (s, 1H), 3.13-3.02 (m, 3H), 2.93-2.85 (m, 5H), 2.79-2.66 (m, 3H), 2.47-2.40 (m, 1H), 2.21-2.03 (m, 5H), 1.89-1.79 (m, 4H), 1.72-1.70 (m, 4H), 1.47-1.39 (m, 2H), 1.29-1.17 (m, 6H).

Example 153: Synthesis of 3-[5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]-3,3-dimethyl-piperazin-1-yl]methyl]-1-piperidyl]-4-fluoro-1-oxo-isoindolin-2-yl]piperidine-2,6-dione (Compound 239)

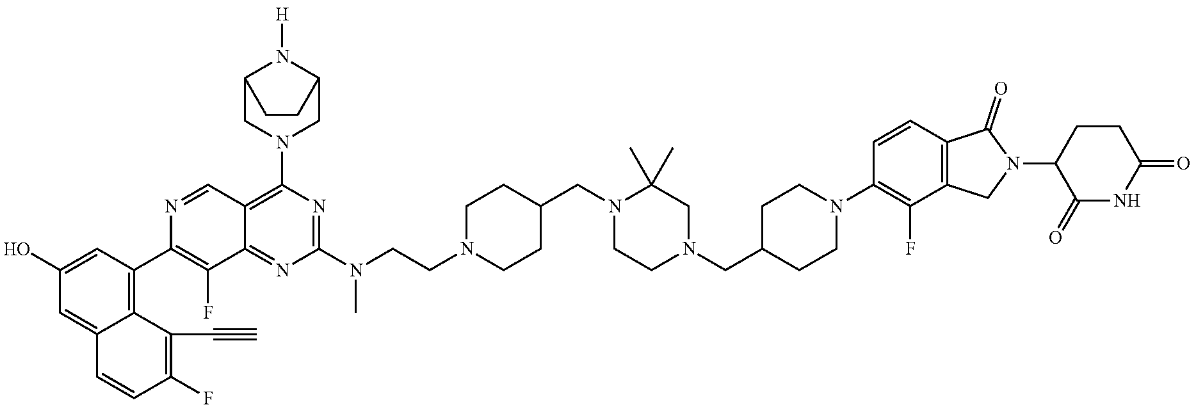 [SMILES: C#Cc1c(F)ccc2cc(O)cc(-c3ncc4c(N5CC6CCC(C5)N6)nc(N(C)CCN5CCC(CN6CCN(CC7CCN(c8ccc9c(c8F)CN(C8CCC(=O)NC8=O)C9=O)CC7)CC6(C)C)CC5)nc4c3F)c12]

The title compound was made in an analogous manner to 3-[4-chloro-5-[4-[[4-[[1-[2-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxyethyl]-4-piperidyl]methyl]piperazin-1-yl]methyl]-1-piperidyl]-1-oxo-isoindolin-2-yl]piperidine-2,6-dione. (white solid). LC/MS (ESI) m/z: 1054.5 $[M+1]^+$; $^1H$ NMR (400 MHz, $CD_3OD$) δ 9.02 (s, 1H), 7.87 (dd, J=5.6, 9.2 Hz, 1H), 7.53 (d, J=8.0 Hz, 1H), 7.40-7.30 (m, 2H), 7.23-7.15 (m, 2H), 5.12 (dd, J=5.2, 13.2 Hz, 1H), 4.70-4.56 (m, 5H), 4.53-4.40 (m, 2H), 3.77-3.64 (m, 4H), 3.63-3.53 (m, 2H), 3.39 (s, 1H), 3.17-3.09 (m, 2H), 2.95-2.85 (m, 3H), 2.82 (m, 3H), 2.62-2.55 (m, 2H), 2.53-2.43 (m, 2H), 2.27-2.09 (m, 8H), 1.96-1.78 (m, 8H), 1.74-1.63 (m, 1H), 1.50-1.35 (m, 3H), 1.31-1.16 (m, 3H), 1.04 (s, 6H).

Example 154: Synthesis of 3-[5-[4-[[4-[[1-[3-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxypropyl]-4-piperidyl]methyl]-1-piperidyl]methyl]-1-piperidyl]-3-methyl-2-oxo-benzimidazol-1-yl]piperidine-2,6-dione (Compound 226)

Step 1: Preparation of tert-butyl 4-[[1-(3-hydroxypropyl)-4-piperidyl]methyl]piperidine-1-carboxylate

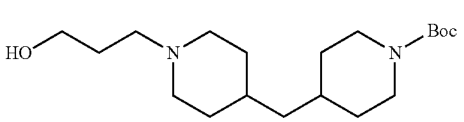 [SMILES: CC(C)(C)OC(=O)N1CCC(CC2CCN(CCCO)CC2)CC1]

To a mixture of tert-butyl 4-(4-piperidylmethyl)piperidine-1-carboxylate (3 g, 7.45 mmol, 1 eq, 2 acetic acid) and 3-bromopropan-1-ol (1.04 g, 7.45 mmol, 673 μL, 1 eq) in dimethylsulfoxide (30 mL) was added N, N-diisopropylethylamine (2.89 g, 22.36 mmol, 3.89 mL, 3 eq) and potassium iodide (619 mg, 3.73 mmol, 0.5 eq), and the reaction mixture was stirred at 100° C. for 12 h. mixture was concentrated, and the resulting residue was purified by prep-HPLC {column: Waters Xbridge 150*25 mm*5 um; mobile phase: [10-40% $CH_3CN$ in water (FA)]} to afford the title compound (1.1 g, 43% yield) as a yellow oil. $^1H$ NMR (400 MHz, $CDCl_3$) δ 4.10-4.00 (m, 2H), 3.79 (t, J=5.2 Hz, 2H), 3.13-3.07 (m, 2H), 2.67-2.60 (m, 4H), 2.04-1.95 (m, 2H), 1.77-1.73 (m, 2H), 1.72-1.65 (m, 2H), 1.63-1.55 (m, 2H), 1.45 (s, 9H), 1.40-1.35 (m, 1H), 1.32-1.22 (m, 3H), 1.15 (t, J=6.8 Hz, 2H), 1.10-1.00 (m, 2H).

Step 2: Preparation of 3-[4-(4-piperidylmethyl)-1-piperidyl]propan-1-ol

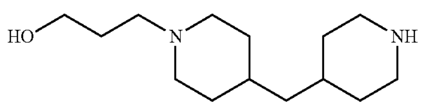 [SMILES: OCCCN1CCC(CC2CCNCC2)CC1]

To a solution of tert-butyl 4-[[1-(3-hydroxypropyl)-4-piperidyl]methyl]piperidine-1-carboxylate (1.1 g, 3.23 mmol, 1 eq) in dichloromethane (15 mL) was added TFA (23.03 g, 201.93 mmol, 15 mL, 62.51 eq), and the reaction mixture was stirred at 25° C. for 0.5 h. The mixture was concentrated to afford the title compound (777 mg, crude, trifluoroacetic acid salt) as a yellow oil. LC/MS (ESI) m/z: 241.0 $[M+H]^+$.

Step 3: Preparation of 2-trimethylsilylethyl 4-[[1-(3-hydroxypropyl)-4-piperidyl]methyl]piperidine-1-carboxylate

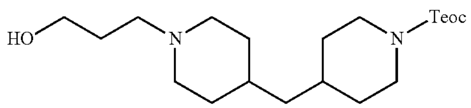

To 3-[4-(4-piperidylmethyl)-1-piperidyl]propan-1-ol (777 mg, 2.19 mmol, 1 eq, TFA salt) in dichloromethane (12 mL) and water (6 mL) were added sodium bicarbonate (1.10 g, 13.15 mmol, 512 μL, 6 eq) and (2,5-dioxopyrrolidin-1-yl) 2-trimethylsilylethyl carbonate (682 mg, 2.63 mmol, 1.2 eq), and the reaction mixture was stirred at 25° C. for 12 h. The mixture was diluted with water (20 mL) and extracted with dichloromethane (20 mL×3). The combined organic extract was washed with brine (20 mL), dried over anhydrous sodium sulfate, filtered, and concentrated in vacuo. The residue was purified by column chromatography on silica gel (Dichloromethane:Methanol=from 100/1 to 10/1) to afford the title compound (700 mg, 83% yield) as a yellow oil. LC/MS (ESI) m/z: 385.2 $[M+H]^+$.

Step 4: Preparation of tert-butyl 3-[8-fluoro-7-[7-fluoro-3-(methoxymethoxy)-8-(2-triisopropylsilylethynyl)-1-naphthyl]-2-[3-[4-[[1-(2-trimethylsilylethoxycarbonyl)-4-piperidyl]methyl]-1-piperidyl]propoxy]pyrido[4,3-d]pyrimidin-4-yl]-3,8-diazabicyclo[3.2.1]octane-8-carboxylate

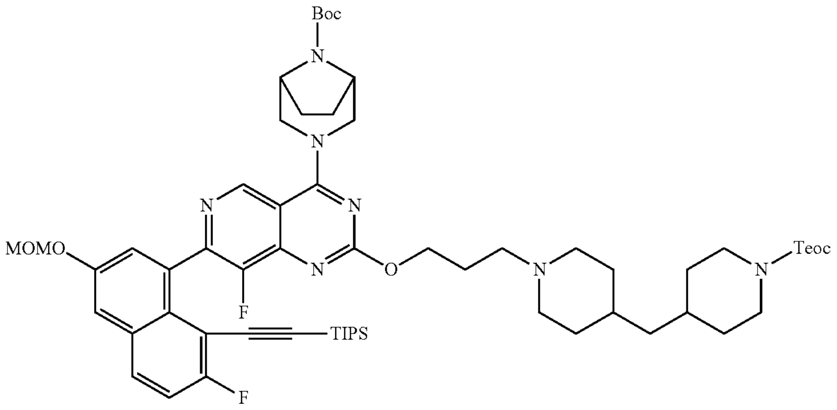

To 2-trimethylsilylethyl 4-[[1-(3-hydroxypropyl)-4-piperidyl]methyl]piperidine-1-carboxylate (600 mg, 1.56 mmol, 1 eq) in tetrahydrofuran (20 mL) was added lithium tert-butoxide (1 M, 2.4 mL, 1.54 eq), and the mixture was stirred at 0° C. for 0.5 h. tert-Butyl 3-[8-fluoro-7-[7-fluoro-3-(methoxymethoxy)-8-(2-triisopropylsilylethynyl)-1-naphthyl]-2-methylsulfonyl-pyrido[4,3-d]pyrimidin-4-yl]-3,8-diazabicyclo[3.2.1]octane-8-carboxylate (1.54 g, 1.87 mmol, 1.2 eq) was then added, and the reaction mixture was stirred for 1 h at 25° C. The reaction was quenched with ammonium chloride solution (20 mL), and the resulting mixture was extracted with ethyl acetate (20 mL×3). The combined organic extract was washed with brine (20 mL), dried over anhydrous sodium sulfate, filtered, and concentrated. The residue was purified by prep-HPLC (column: Phenomenex luna C18 150*40 mm*15 um; mobile phase: [70-100% $CH_3CN$ in water (TFA)]) to afford the title compound (450 mg, 26% yield) as a yellow 10 solid. LC/MS (ESI) m/z: 1126.7 $[M+H]^+$; $^1H$ NMR (400 MHz, $CDCl_3$) δ 9.06 (s, 1H), 7.77-7.51 (m, 1H), 7.33 (m, 1H), 7.34-7.26 (m, 2H), 5.32-5.28 (m, 2H), 4.72 (d, J=7.2 Hz, 1H), 4.63-4.48 (m, 2H), 4.47-4.26 (m, 3H), 4.24-4.15 (m, 5H), 3.80-3.70 (m, 1H), 3.50 (s, 3H), 3.12-2.90 (m, 2H), 2.70-2.60 (m, 2H), 2.55-2.50 (m, 1H), 2.16-2.10 (m, 1H), 2.05-1.95 (m, 4H), 1.65-1.52 (m, 6H), 1.50 (s, 9H), 1.40-1.30 (m, 6H), 1.20-1.10 (m, 2H), 1.05-0.95 (m, 3H), 0.86 (t, J=7.2 Hz, 18H), 0.56-0.53 (m, 3H), 0.07 (s, 9H).

Step 5: Preparation of tert-butyl 3-[7-[8-ethynyl-7-fluoro-3-(methoxymethoxy)-1-naphthyl]-8-fluoro-2-[3-[4-(4-piperidylmethyl)-1-piperidyl]propoxy]pyrido[4,3-d]pyrimidin-4-yl]-3,8-diazabicyclo[3.2.1]octane-8-carboxylate

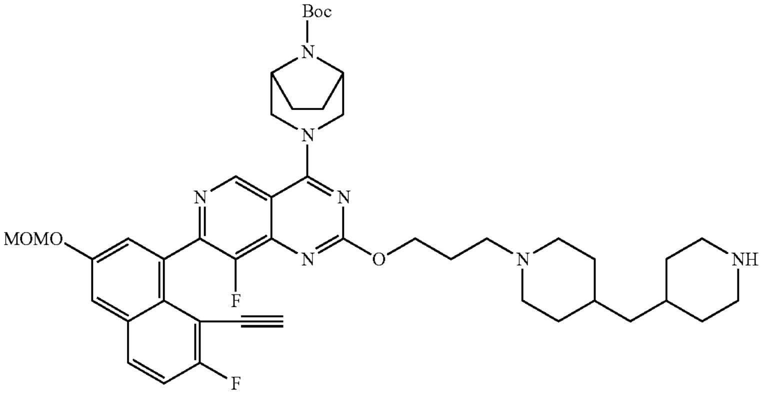

To a solution of tert-butyl 3-[8-fluoro-7-[7-fluoro-3-(methoxymethoxy)-8-(2-triisopropylsilylethynyl)-1-naphthyl]-2-[3-[4-[[1-(2-trimethylsilylethoxycarbonyl)-4-piperidyl]methyl]-1-piperidyl]propoxy]pyrido[4,3-d]pyrimidin-4-yl]-3,8-diazabicyclo[3.2.1]octane-8-carboxylate (540 mg, 0.48 mmol, 1 eq) in dimethylsulfoxide (6 mL) was added cesium fluoride (728 mg, 4.79 mmol, 10 eq) at 25° C., and the reaction mixture was stirred for 2 h at 50° C. mixture was diluted with water (20 mL) and extracted with ethyl acetate (20 mL×3). The combined organic extract was washed with brine (20 mL), dried over anhydrous sodium sulfate, filtered, and concentrated to afford the title compound (390 mg, 98% yield) as a yellow solid. LC/MS (ESI) m/z: 826.4 $[M+H]^+$.

Step 6: Preparation of tert-butyl 3-[2-[3-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

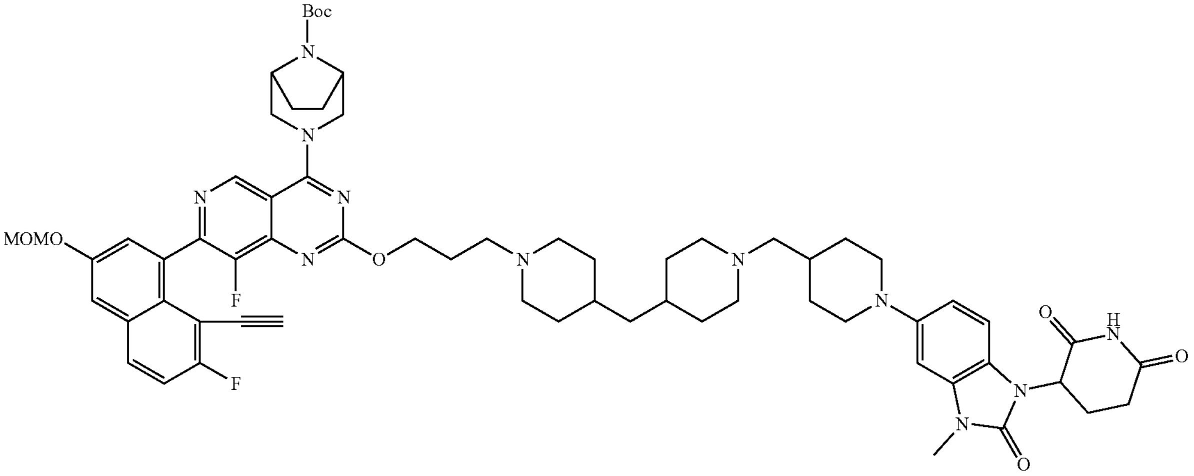

To a solution of tert-butyl 3-[7-[8-ethynyl-7-fluoro-3-(methoxymethoxy)-1-naphthyl]-8-fluoro-2-[3-[4-(4-piperidylmethyl)-1-piperidyl]propoxy]pyrido[4,3-d]pyrimidin-4-yl]-3,8-diazabicyclo[3.2.1]octane-8-carboxylate (340 mg, 0.41 mmol, 1 eq) in dichloromethane (4 mL) and dimethylsulfoxide (4 mL) were added N,N-diisopropylethylamine (106 mg, 0.82 mmol, 143 μL, 2 eq) and 1-[1-(2,6-dioxo-3-piperidyl)-3-methyl-2-oxo-benzimidazol-5-yl]piperidine-4-carbaldehyde (190 mg, 0.41 mmol, 1 eq), and the resulting mixture was stirred at 25° C. for 30 minutes. Sodium triacetoxyborohydride (262 mg, 1.23 mmol, 3 eq) was then added, and the reaction mixture was stirred at 25° C. for 0.5 h. The mixture was poured onto water (20 mL) and extracted with dichloromethane (20 mL×2). The combined organic extracts were washed with brine (20 mL×2), dried over anhydrous sodium sulfate, filtered, and concentrated under reduced pressure. The residue was purified by preparative TLC (Dichloromethane:Methanol=10:1, Rf=0.24) to afford the title compound (290 mg, 60% yield) as a yellow solid. LC/MS (ESI) m/z: 1180.8 $[M+H]^+$.

Step 7: Preparation of 3-[5-[4-[[4-[[1-[3-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxypropyl]-4-piperidyl]methyl]-1-piperidyl]methyl]-1-piperidyl]-3-methyl-2-oxo-benzimidazol-1-yl]piperidine-2,6-dione

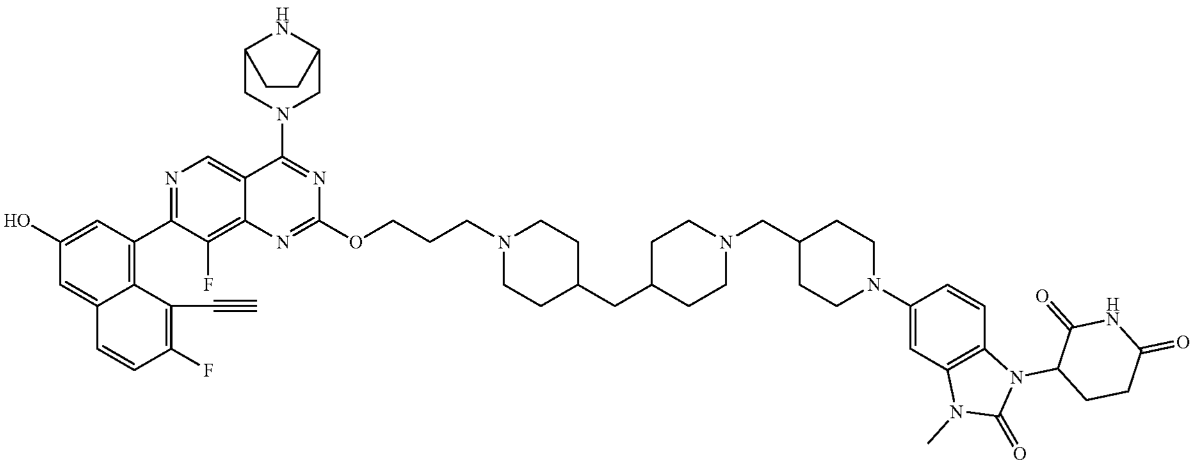 [SMILES: C#Cc1c(F)ccc2cc(O)cc(-c3ncc4c(N5CC6CCC(C5)N6)nc(OCCCN5CCC(CC6CCN(CC7CCN(c8ccc9c(c8)n(C)c(=O)n9C8CCC(=O)NC8=O)CC7)CC6)CC5)nc4c3F)c12]

To a solution of tert-butyl 3-[2-[3-[4-[[1-[[1-[1-(2,6-dioxo-3-piperidyl)-3-methyl-2-oxo-benzimidazol-5-yl]-4-piperidyl]methyl]-4-piperidyl]methyl]-1-piperidyl]propoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (320 mg, 0.27 mmol, 1 eq) in dichloromethane (4 mL) was added hydrochloric acid solution in dioxane (2 M, 4 mL, 29.51 eq), and the reaction mixture was stirred for 0.5 h at 25° C. The mixture was concentrated, and the resulting residue was purified by prep-HPLC {column: YMC-Actus Triart C18 150*30 mm*7 um; mobile phase: [5-35% $CH_3CN$ in water(FA)]} to afford the title compound (194.1 mg, 62% yield, formic acid salt) as a yellow solid. LC/MS (ESI) m/z: 1036.5 $[M+H]^+$; $^1H$ NMR (400 MHz, DMSO-$d_6$) δ 11.05 (s, 1H), 9.05 (s, 1H), 8.22 (s, 2H), 7.97 (dd, J=9.2, 6.0 Hz, 1H), 7.45 (t, J=9.2 Hz, 1H), 7.39 (d, J=2.0 Hz, 1H), 7.18 (d, J=2.0 Hz, 1H), 6.92 (d, J=8.8 Hz, 1H), 6.80 (d, J=2.0 Hz, 1H), 6.64-6.58 (m, 1H), 5.32-5.24 (m, 1H), 4.54-4.48 (m, 1H), 4.40-4.35 (m, 3H), 3.93 (s, 1H), 3.73-3.72 (m, 2H), 3.67-3.63 (m, 2H), 3.59-3.53 (m, 3H), 3.29 (s, 3H), 3.00-2.93 (m, 2H), 2.90-2.83 (m, 3H), 2.73-2.66 (m, 1H), 2.65-2.57 (m, 3H), 2.54 (s, 3H), 2.24 (d, J=6.8 Hz, 2H), 2.09-1.98 (m, 3H), 1.97-1.88 (m, 4H), 1.80-1.70 (m, 6H), 1.65-1.54 (m, 5H), 1.38-1.20 (m, 4H), 1.17-1.05 (m, 6H).

Example 155: Synthesis of 3-[5-[4-[[1-[[1-[[4-(3,8-diazabicyclo[3.2.1]octan-3-yl)-7-(8-ethynyl-7-fluoro-1-naphthyl)-8-fluoro-pyrido[4,3-d]pyrimidin-2-yl]oxymethyl]cyclopropyl]methyl]-4-fluoro-4-piperidyl]methyl]piperazin-1-yl]-3-methyl-2-oxo-benzimidazol-1-yl]piperidine-2,6-dione (Compound 228)

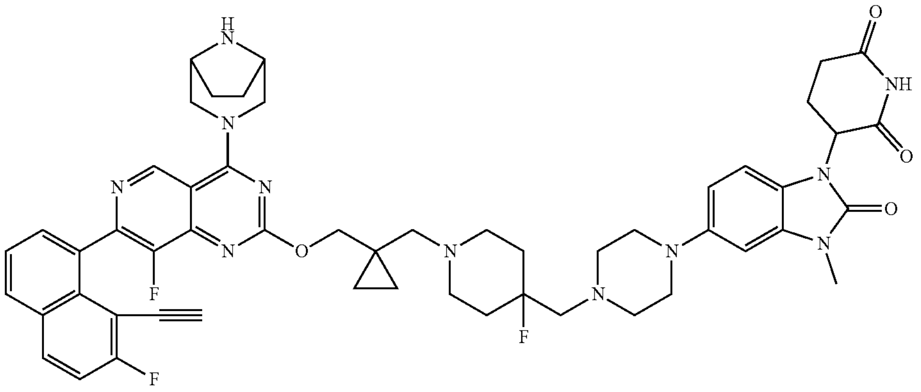 [SMILES: C#Cc1c(F)ccc2cccc(-c3ncc4c(N5CC6CCC(C5)N6)nc(OCC5(CN6CCC(F)(CN7CCN(c8ccc9c(c8)n(C)c(=O)n9C8CCC(=O)NC8=O)CC7)CC6)CC5)nc4c3F)c12]

The title compound was made in an analogous manner to 3-[5-[4-[[3-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-3,9-diazaspiro[5.5]undecan-9-yl]methyl]-1-piperidyl]-3-methyl-2-oxo-benzimidazol-1-yl] piperidine-2,6-dione. (yellow solid, formic acid salt). LC/MS (ESI) m/z: 968.4 $[M+H]^+$. 1H NMR (400 MHz, $CD_3OD$) δ 9.01 (s, 1H), 8.15-7.90 (m, 2H), 7.75-7.48 (m, 2H), 7.35 (dt, J=2.0, 8.8 Hz, 1H), 6.90 (d, J=8.4 Hz, 1H), 6.70 (s, 1H), 6.62 (d, J=8.8 Hz, 1H), 5.22 (dd, J=5.2, 12.4 Hz, 1H), 4.67 (d, J=13.6 Hz, 2H), 4.44 (q, J=11.6 Hz, 2H), 4.01 (s, 2H), 3.84 (t, J=14.0 Hz, 2H), 3.59-3.43 (m, 3H), 3.27-3.23 (m, 2H), 3.16-2.89 (m, 9H), 2.87-2.78 (m, 1H), 2.75-2.58 (m, 6H), 2.57-2.42 (m, 2H), 2.09 (d, J=11.2 Hz, 4H), 2.03-1.88 (m, 5H), 0.86 (s, 2H), 0.74 (s, 2H).

Example 156: Synthesis of 3-[5-[3-[[4-[[1-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-4-piperidyl]methyl]-1-piperidyl]methyl]azetidin-1-yl]-3-methyl-2-oxo-benzimidazol-1-yl]piperidine-2,6-dione (Compound 229)

Step 1: Preparation of 5-fluoro-N-methyl-2-nitro-aniline

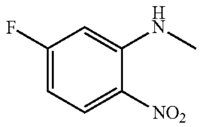

To a mixture of 2,4-difluoro-1-nitro-benzene (20 g, 125.71 mmol, 13.8 mL, 1 eq) and methylamine (16.98 g, 251.43 mmol, 2 eq, hydrochloride) in acetonitrile (200 mL) was added N,N-diisopropylethylamine (64.99 g, 502.86 mmol, 87.6 mL, 4 eq) in one portion at 25° C. under nitrogen. The reaction mixture was stirred at 25° C. for 16 hours. The mixture was cooled to 25° C. and concentrated under reduced pressure at 45° C. The resulting residue was purified by silica gel chromatography (Petroleum ether/Ethyl acetate=10/1, 3/1) to afford the title compound (23 g, crude) as a yellow solid.

Step 2: Preparation of 5-[3-(dimethoxymethyl)azetidin-1-yl]-N-methyl-2-nitro-aniline

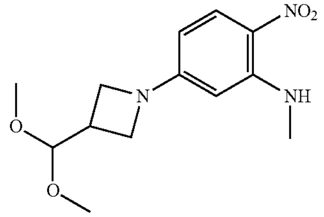 [SMILES: CNc1cc(N2CC(C(OC)OC)C2)ccc1[N+](=O)[O-]]

To a mixture of 3-(dimethoxymethyl)azetidine (17.73 g, 135.18 mmol, 1 eq) and 5-fluoro-N-methyl-2-nitro-aniline (23 g, 135.18 mmol, 1 eq) in dimethyl sulfoxide (200 mL) was added N,N-diisopropylethylamine (52.41 g, 405.55 mmol, 70.6 mL, 3 eq) in one portion at 20° C. under nitrogen. The reaction mixture was stirred at 120° C. for 16 hours. The mixture was poured into ice-water (w/w=1/1) (500 mL) and stirred for 5 minutes. The aqueous phase was extracted with ethyl acetate (300 mL×3). The combined organic extract was washed with brine (300 mL×2), dried with anhydrous sodium sulfate, filtered, and concentrated in vacuum. The residue was purified by silica gel chromatography (Petroleum ether/Ethyl acetate=50/1, 8/1) to afford the title compound (23 g, 60% yield) as a yellow solid. $^1H$ NMR (400 MHz, $CDCl_3$) δ 8.46 (br d, J=2.4 Hz, 1H), 8.08 (d, J=9.6 Hz, 1H), 5.76 (dd, J=2.4, 9.2 Hz, 1H), 5.33 (d, J=2.4 Hz, 1H), 4.62 (d, J=6.8 Hz, 1H), 4.17-4.03 (m, 2H), 3.94-3.87 (m, 2H), 3.42 (s, 6H), 3.15-3.04 (m, 1H), 2.96 (d, J=5.2 Hz, 3H).

Step 3: Preparation of 5-(3-(dimethoxymethyl)azetidin-1-yl)-N1-methylbenzene-1,2-diamine

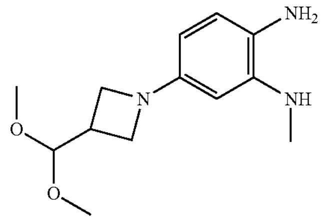

To a solution of 5-[3-(dimethoxymethyl)azetidin-1-yl]-N-methyl-2-nitro-aniline (23 g, 81.76 mmol, 1 eq) in tetrahydrofuran (200 mL) was added Platinum on charcoal (5 g, 5% purity) under nitrogen. The suspension was degassed under vacuum and purged with hydrogen several times. The mixture was stirred under hydrogen (50 psi) at 30° C. for 16 hours. The reaction mixture was filtered, and the filtrate was used into next step directly. LC/MS (ESI) m/z: 252.2 $[M+H]^+$.

Step 4: Preparation of 5-[3-(dimethoxymethyl)azetidin-1-yl]-3-methyl-1H-benzimidazol-2-one

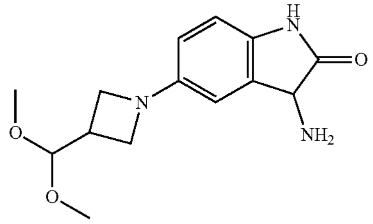 [SMILES: COC(OC)C1CN(c2ccc3c(c2)C(N)C(=O)N3)C1]

To a mixture of 5-(3-(dimethoxymethyl)azetidin-1-yl)-N1-methylbenzene-1,2-diamine (21 g, 83.56 mmol, 1 eq) in tetrahydrofuran (300 mL) was added N'-cyclohexyl-N-[2-(4-methylmorpholin-4-ium-4-yl)ethyl]methanediimine; 4-methylbenzenesulfonate (20.32 g, 125.34 mmol, 1.5 eq) in one portion at 25° C. under nitrogen. The reaction mixture was stirred at 25° C. for 16 hours. The mixture was poured into ice-water (w/w=1/1) (500 mL) and stirred for 5 minutes. The aqueous phase was extracted with ethyl acetate (200 mL×4), and the combined organic extract was washed with brine (200 mL×3), dried with anhydrous sodium sulfate, filtered, and concentrated in vacuum. The residue was purified by silica gel chromatography (Petroleum ether/Ethyl acetate=10/1, 3/1) to afford the title compound (15 g, 64% yield) as a yellow solid. LC/MS (ESI) m/z: 278.1$[M+H]^+$. $^1$H NMR (400 MHz DMSO-$d_6$) δ 10.41 (s, 1H), 6.78 (d, J=8.4 Hz, 1H), 6.21 (d, J=2.0 Hz, 1H), 6.06 (dd, J=2.0, 8.4 Hz, 1H), 4.60 (d, J=7.2 Hz, 1H), 3.81 (t, J=7.6 Hz, 2H), 3.55 (t, J=6.8 Hz, 2H), 3.28 (s, 6H), 3.22 (s, 3H), 3.01-2.90 (m, 1H).

Step 5: Preparation of 3-(5-(3-(dimethoxymethyl)azetidin-1-yl)-3-methyl-2-oxo-2,3-dihydro-1H-benzo[d]imidazol-1-yl)piperidine-2,6-dione

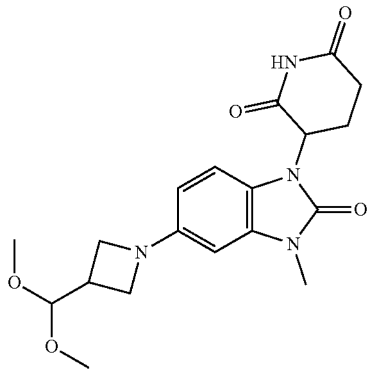 [SMILES: COC(OC)C1CN(c2ccc3c(c2)n(C)c(=O)n3C2CCC(=O)NC2=O)C1]

To a mixture of 5-[3-(dimethoxymethyl)azetidin-1-yl]-3-methyl-1H-benzimidazol-2-one (15 g, 54.09 mmol, 1 eq) in tetrahydrofuran (300 mL) was added sodium hydride (8.65 g, 216.36 mmol, 60% in mineral oil, 4 eq) in portions at 0° C. under nitrogen, and the resulting mixture was stirred at 0° C. for 30 minutes. A solution of 3-bromopiperidine-2,6-dione (31.16 g, 162.27 mmol, 3 eq) in tetrahydrofuran (100 mL) was then added under nitrogen, and the reaction mixture was stirred at 60° C. for 4 hours. The reaction was cooled to 0° C. and quenched by addition of ammonium chloride aqueous solution (500 mL). The aqueous phase was extracted with ethyl acetate (500 mL×2), and the combined organic extract was washed with brine (500 mL×2), dried over anhydrous sodium sulfate, filtered, and concentrated in vacuum. The residue was purified by prep-HPLC (column: Phenomenex luna c18 250 mm×100 mm×10 um; mobile phase: [5-30% $CH_3CN$ in water(TFA)]) to afford the title compound (13.2 g, 62% yield) as a yellow solid. LC/MS (ESI) m/z: 389.0 $[M+H]^+$. $^1$H NMR (400 MHz, $CDCl_3$) δ 8.24-8.06 (m, 1H), 6.57 (d, J=8.4 Hz, 1H), 6.15-5.96 (m, 2H), 5.30-5.18 (m, 1H), 5.10 (dd, J=5.2, 12.8 Hz, 1H), 4.56 (d, J=7.2 Hz, 1H), 3.92-3.81 (m, 2H), 3.70-3.59 (m, 2H), 3.38-3.26 (m, 9H), 3.02-2.90 (m, 1H), 2.89-2.80 (m, 1H), 2.79-2.68 (m, 1H), 2.67-2.54 (m, 1H), 2.13 (dd, J=2.8, 12.8 Hz, 1H).

Step 6: Preparation of 1-[1-(2,6-dioxo-3-piperidyl)-3-methyl-2-oxo-benzimidazol-5-yl]azetidine-3-carbaldehyde

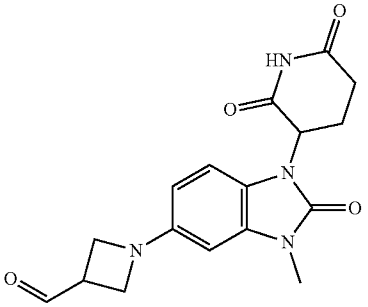 [SMILES: Cn1c(=O)n(C2CCC(=O)NC2=O)c2ccc(N3CC(C=O)C3)cc21]

A mixture of 3-(5-(3-(dimethoxymethyl)azetidin-1-yl)-3-methyl-2-oxo-2,3-dihydro-1H-benzo[d]imidazol-1-yl)piperidine-2,6-dione (500 mg, 1.29 mmol, 1 eq) and trifluoroacetic acid (1.54 g, 13.46 mmol, 1 mL, 10.46 eq) in dichloromethane (1 mL) was stirred at 40° C. for 1 h. The mixture was concentrated under reduced pressure at 40° C. The crude product was triturated with t-butyl methyl ether (50 mL) at 25° C. for 30 minutes to afford the title compound (710 mg, crude, trifluoroacetate) as a white solid. LC/MS (ESI) m/z: 361.0 $[M+H_3O]^+$.

Step 7: Preparation of tert-butyl 4-[[1-[[1-[1-(2,6-dioxo-3-piperidyl)-3-methyl-2-oxo-benzimidazol-5-yl]azetidin-3-yl]methyl]-4-piperidyl]methyl]piperidine-1-carboxylate

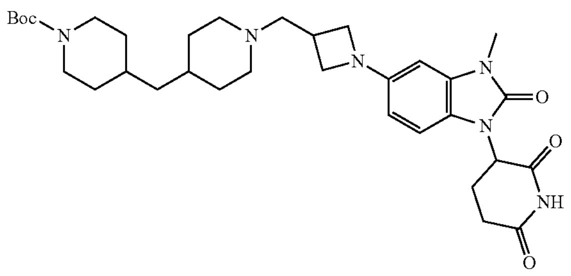 [SMILES: Cn1c(=O)n(C2CCC(=O)NC2=O)c2ccc(N3CC(CN4CCC(CC5CCN(C(=O)OC(C)(C)C)CC5)CC4)C3)cc21]

To a mixture of tert-butyl 4-(4-piperidylmethyl)piperidine-1-carboxylate (600 mg, 1.75 mmol, 1 eq, acetate) and 1-[1-(2,6-dioxo-3-piperidyl)-3-methyl-2-oxo-benzimidazol-5-yl]azetidine-3-carbaldehyde (800 mg, 1.75 mmol, 1 eq, trifluoroacetate) in isopropanol (5 mL) and dichloromethane (15 mL) was added N,N-diisopropylethylamine (680 mg, 5.26 mmol, 0.9 mL, 3 eq) and sodium triacetoxyborohydride (743 mg, 3.51 mmol, 2 eq) in one portion at 20° C. under nitrogen. The reaction mixture was stirred at 20° C. for 16 hours. The mixture was concentrated under reduced pressure at 45° C. The residue was purified by prep-HPLC (column: Phenomenex luna C18 150×40 mm×15 um; mobile phase: [15-45% $CH_3CN$ in water (FA)]) to afford the title compound (930 mg, 87% yield) as a white solid. LC/MS (ESI) m/z: 609.5 $[M+H]^+$.

Step 8: Preparation of 3-[3-methyl-2-oxo-5-[3-[[4-(4-piperidylmethyl)-1-piperidyl]methyl]azetidin-1-yl]benzimidazol-1-yl]piperidine-2,6-dione

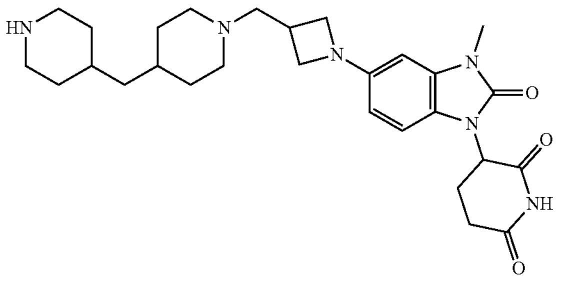 [SMILES: Cn1c(=O)n(C2CCC(=O)NC2=O)c2ccc(N3CC(CN4CCC(CC5CCNCC5)CC4)C3)cc21]

To a mixture of tert-butyl 4-[[1-[[1-[1-(2,6-dioxo-3-piperidyl)-3-methyl-2-oxo-benzimidazol-5-yl]azetidin-3-yl]methyl]-4-piperidyl]methyl]piperidine-1-carboxylate (930 mg, 1.53 mmol, 1 eq) in dichloromethane (4 mL) was added trifluoroacetic acid (3.07 g, 26.92 mmol, 2 mL, 17.62 eq) in one portion at 25° C. The reaction mixture was stirred at 25° C. for 1 hours. The mixture was concentrated under reduced pressure at 45° C. to afford the title compound (950 mg, crude, trifluoroacetate) as a yellow oil. LC/MS (ESI) m/z: 509.4 $[M+H]^+$.

Step 9: Preparation of tert-butyl 3-[2-[[1-[[4-[[1-[[1-[1-(2,6-dioxo-3-piperidyl)-3-methyl-2-oxo-benzimidazol-5-yl]azetidin-3-yl]methyl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate

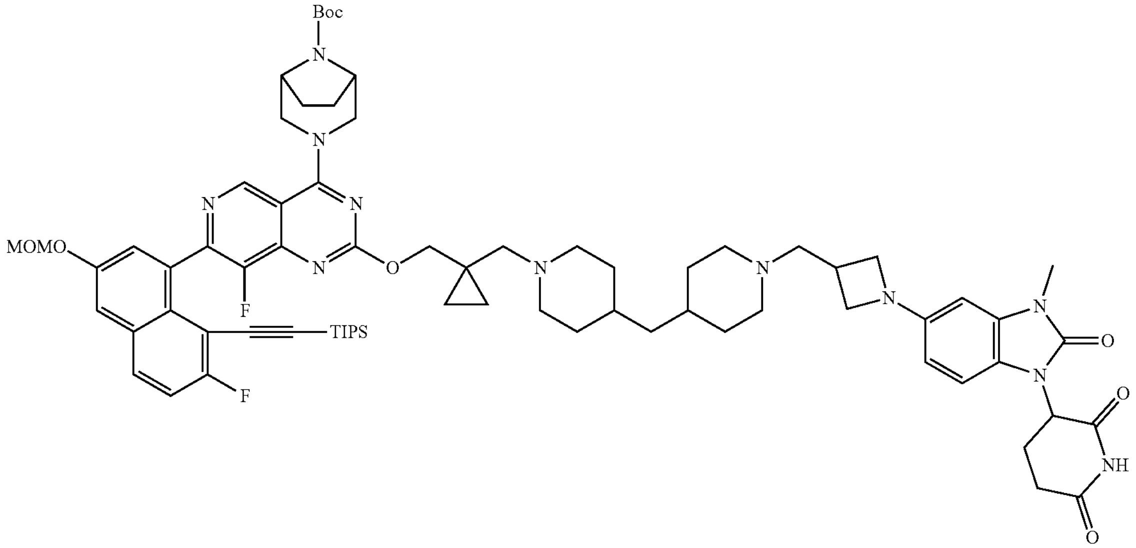

A mixture of 3-[3-methyl-2-oxo-5-[3-[[4-(4-piperidylmethyl)-1-piperidyl]methyl]azetidin-1-yl]benzimidazol-1-yl] piperidine-2,6-dione (950 mg, 1.53 mmol, 1 eq, trifluoroacetate), N,N-diisopropylethylamine (394 mg, 3.05 mmol, 0.5 mL, 2 eq), titanium tetraisopropanolate (650 mg, 2.29 mmol, 0.7 mL, 1.5 eq), and tert-butyl 3-[8-fluoro-7-[7-fluoro-3-(methoxymethoxy)-8-(2-triisopropylsilylethynyl)-1-naphthyl]-2-[(1-formylcyclopropyl)methoxy]pyrido[4,3-d]pyrimidin-4-yl]-3,8-diazabicyclo[3.2.1]octane-8-carboxylate (1.28 g, 1.53 mmol, 1 eq) in dichloromethane (20 mL) and dimethyl sulfoxide (8 mL) was stirred at 45° C. for 10 h, then cooled to 25° C. Sodium triacetoxyborohydride (647 mg, 3.05 mmol, 2 eq) was then added, and the reaction mixture was stirred at 25° C. for 2 hours. The mixture was poured into ice-water (w/w=1/1) (30 mL) and filtered. The filtrate was extracted with dichloromethane (20 mL×3), and the combined organic extract was washed with brine (15 mL×2), dried over anhydrous sodium sulfate, filtered, and concentrated in vacuum. The residue was purified by prep-HPLC (TFA condition; column: Phenomenex luna C18 150×40 mm×15 um; mobile phase: [42-72% $CH_3CN$ in water (TFA)]) to afford the title compound (1.1 g, 54% yield) as a white solid. LC/MS (ESI) m/z: 1334.8 $[M+H]^+$.

Step 10: Preparation of tert-butyl 3-[2-[[1-[[4-[[1-[[1-[1-(2,6-dioxo-3-piperidyl)-3-methyl-2-oxo-benzimidazol-5-yl]azetidin-3-yl]methyl]-4-piperidyl]methyl]-1-piperidyl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate

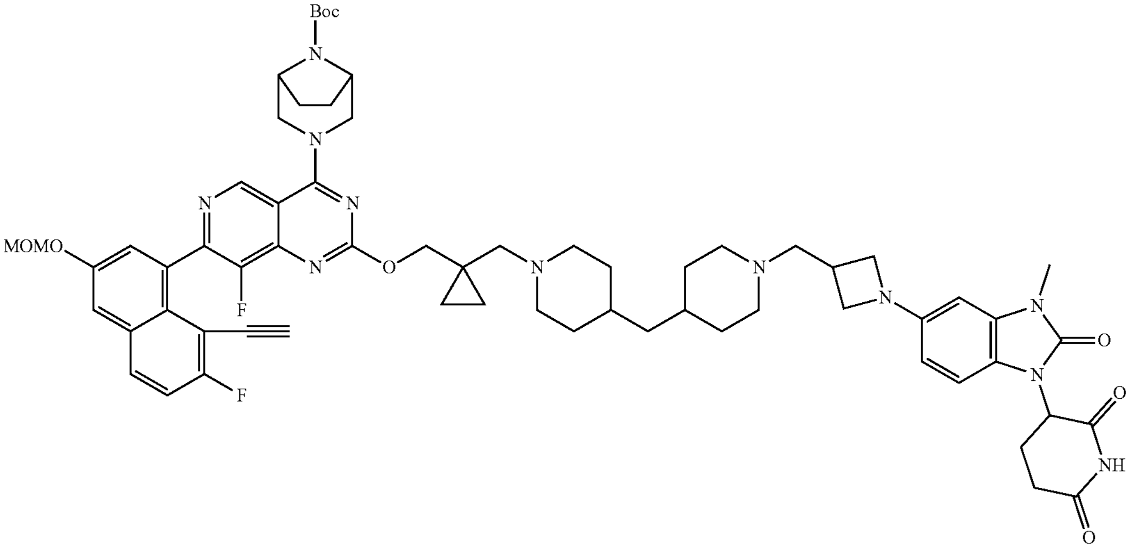

A mixture of tert-butyl 3-[2-[[1-[[4-[[1-[[1-[1-(2,6-dioxo-3-piperidyl)-3-methyl-2-oxo-benzimidazol-5-yl]azetidin-3-yl]methyl]-4-piperidyl]methyl]-1-piperidyl]methyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3,8-diazabicyclo[3.2.1]octane-8-carboxylate (1.1 g, 0.82 mmol, 1 eq) and cesium fluoride (3.76 g, 24.72 mmol, 30 eq) in N,N-dimethylformamide (20 mL) was stirred at 25° C. for 3 h. The mixture was poured into ice-water (w/w=1/1) (50 mL) and stirred for 5 min. The aqueous phase was extracted with ethyl acetate (30 mL×4), and the combined organic extract was washed with brine (20 mL×2), dried over anhydrous sodium sulfate, filtered, and concentrated in vacuum to afford the title compound (890 mg, crude) as a yellow solid. LC/MS (ESI) m/z: 1178.8 $[M+H]^+$.

Step 11: Preparation of 3-[5-[3-[[4-[[1-[[1-[[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]oxymethyl]cyclopropyl]methyl]-4-piperidyl]methyl]-1-piperidyl]methyl]azetidin-1-yl]-3-methyl-2-oxo-benzimidazol-1-yl]piperidine-2,6-dione

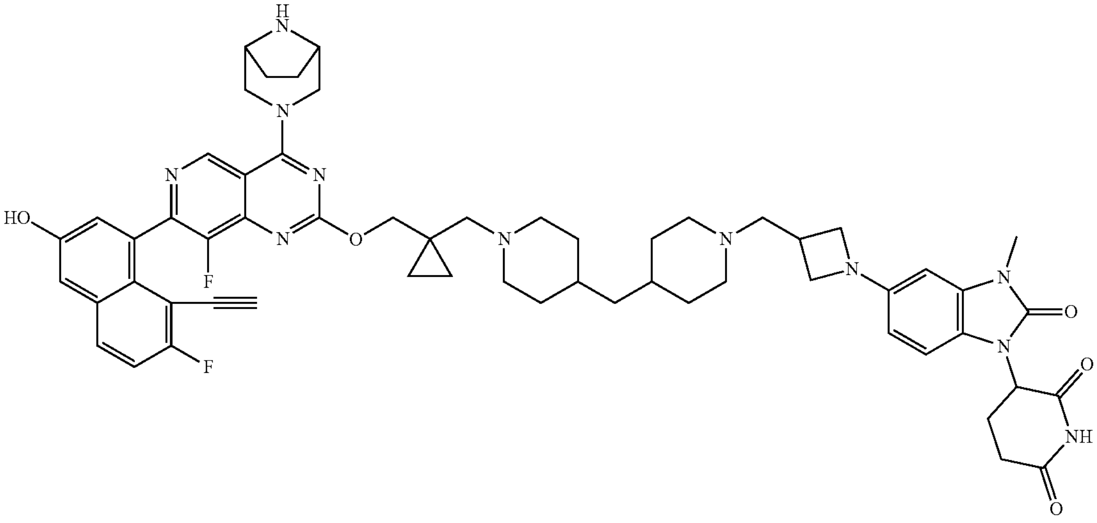 [SMILES: C#Cc1c(F)ccc2cc(O)cc(-c3ncc4c(N5CC6CCC(C5)N6)nc(OCC5(CN6CCC(CC7CCN(CC8CN(c9ccc%10c(c9)n(C)c(=O)n%10C9CCC(=O)NC9=O)C8)CC7)CC6)CC5)nc4c3F)c12]

A mixture of tert-butyl 3-[2-[[1-[[4-[[1-[[1-[1-(2,6-dioxo-3-piperidyl)-3-methyl-2-oxo-benzimidazol-5-yl]azetidin-3-yl]methyl]-4-piperidyl]methyl]-1-piperidyl]methyl]cyclopropyl]methoxy]-7-[8-ethynyl-7-fluoro-3-(methoxymethoxy)-1-naphthyl]-8-fluoro-pyrido[4,3-d]pyrimidin-4-yl]-3,8-diazabicyclo[3.2.1]octane-8-carboxylate (890 mg, 0.76 mmol, 1 eq) and trifluoroacetic acid (4.61 g, 40.39 mmol, 3 mL, 53.47 eq) in dichloromethane (6 mL) was stirred at 25° C. for 15 minutes. The mixture was concentrated under reduced pressure at 45° C., and the residue was adjusted to pH 8 with N,N-diisopropylethylamine. The residue was purified by prep-HPLC (FA condition; column: Phenomenex luna C18 150×25 mm×10 um; mobile phase: [10-30% $CH_3CN$ in water (FA)]) to afford the title compound (134.7 mg, 16% yield, formic acid salt) as a white solid. LC/MS (ESI) m/z: 1034.8 $[M+H]^+$; $^1H$ NMR (400 MHz, DMSO-$d_6$ b: 11.06 (s, 1H), 10.29 (br s, 1H), 9.13 (s, 1H), 8.15 (s, 1H), 8.00 (dd, J=6.0, 9.2 Hz, 1H), 7.48 (t, J=9.2 Hz, 1H), 7.42 (d, J=2.4 Hz, 1H), 7.19 (d, J=2.4 Hz, 1H), 6.93 (d, J=8.4 Hz, 1H), 6.31 (d, J=1.6 Hz, 1H), 6.12 (dd, J=1.6, 8.4 Hz, 1H), 5.37-5.21 (m, 1H), 4.75-4.61 (m, 1H), 4.60-4.47 (m, 1H), 4.34 (br s, 2H), 4.20 (br s, 2H), 4.00 (t, J=7.2 Hz, 2H), 3.94-3.81 (m, 3H), 3.52 (br t, J=6.4 Hz, 2H), 3.40-3.36 (m, 2H), 3.29 (s, 7H), 3.18-3.10 (m, 2H), 2.96-2.75 (m, 4H), 2.71-2.58 (m, 3H), 2.06-1.93 (m, 5H), 1.77 (d, J=12.8 Hz, 4H), 1.61-1.46 (m, 2H), 1.38-1.22 (m, 4H), 1.19-1.07 (m, 2H), 0.91-0.80 (m, 2H), 0.78-0.64 (m, 2H).

Example 157: Synthesis of 3-[5-[4-[[1-[(3R)-1-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]pyrrolidin-3-yl]-4-piperidyl]methyl]-1-piperidyl]-3-methyl-2-oxo-benzimidazol-1-yl]piperidine-2,6-dione (Compound 236)

Step 1: Preparation of tert-butyl (3R)-3-[4-[[1-[1-(2,6-dibenzyloxy-3-pyridyl)-3-methyl-2-oxo-benzimidazol-5-yl]-4-piperidyl]methyl]-1-piperidyl]pyrrolidine-1-carboxylate

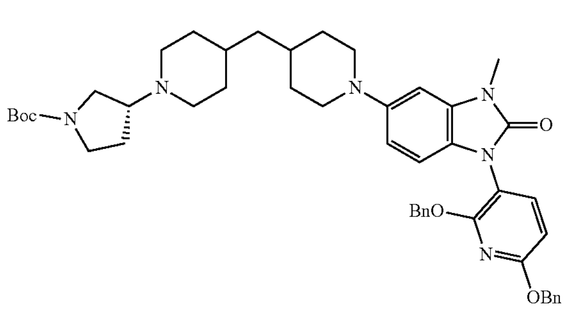 [SMILES: Cn1c(=O)n(-c2ccc(OCc3ccccc3)nc2OCc2ccccc2)c2ccc(N3CCC(CC4CCN([C@@H]5CCN(C(=O)OC(C)(C)C)C5)CC4)CC3)cc21]

To a solution of 5-bromo-1-(2,6-dibenzyloxy-3-pyridyl)-3-methyl-benzimidazol-2-one (500 mg, 0.97 mmol, 1 eq) and tert-butyl (3R)-3-[4-(4-piperidylmethyl)-1-piperidyl]pyrrolidine-1-carboxylate (442 mg, 1.26 mmol, 1.3 eq) in dioxane (20 mL) were added cesium carbonate (946 mg, 2.90 mmol, 3 eq) and methanesulfonato(2-dicyclohexylphosphino-2,6-bis(dimethyl amino)-1,1-biphenyl)(2-amino-1,1-biphenyl-2 (78 mg, 0.09 mmol, 0.1 eq), and the reaction mixture was stirred at 100° C. for 16 h. The mixture was diluted with water (40 mL) and extracted with ethyl acetate (30 mL×3). The combined organic extract was dried over anhydrous sodium sulfate, filtered, and concentrated under vacuum. The crude product was purified by silica gel column chromatography (petroleum ether/ethyl acetate=10/1 to 1/10) to afford the title compound (452 mg, 59% yield) as a brown gum. LC/MS (ESI) m/z: 787.5 $[M+H]^+$.

Step 2: Preparation of (3R)-3-[4-[[1-[1-(2,6-dioxo-3-piperidyl)-3-methyl-2-oxo-benzimidazol-5-yl]-4-piperidyl]methyl]-1-piperidyl]pyrrolidine-1-carboxylate

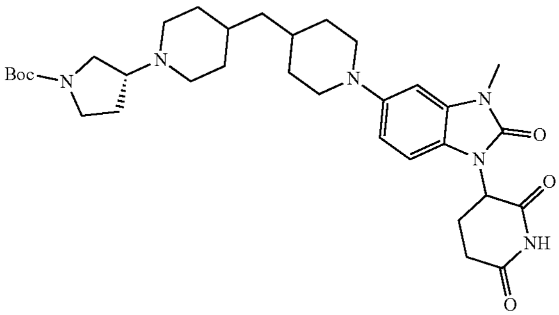 [SMILES: Cn1c(=O)n(C2CCC(=O)NC2=O)c2ccc(N3CCC(CC4CCN([C@@H]5CCN(C(=O)OC(C)(C)C)C5)CC4)CC3)cc21]

To a solution of tert-butyl (3R)-3-[4-[[1-[1-(2,6-dibenzyloxy-3-pyridyl)-3-methyl-2-oxo-benzimidazol-5-yl]-4-piperidyl]methyl]-1-piperidyl]pyrrolidine-1-carboxylate (452 mg, 0.57 mmol, 1 eq) in tetrahydrofuran (20 mL) were added palladium on activated carbon catalyst (150 mg, 10% purity) and palladium hydroxide on activated carbon catalyst (150 mg, 20% purity) under nitrogen atmosphere, and the resulting mixture was degassed and purged with nitrogen for 3 times. The mixture was then stirred at 50° C. for 16 h under hydrogen (50 Psi) atmosphere. The mixture was filtered and concentrated in vacuum to afford the title compound (370 mg, crude) as a black gum. LC/MS (ESI) m/z: 609.4 $[M+H]^+$.

Step 3: Preparation of 3-[3-methyl-2-oxo-5-[4-[[1-[(3R)-pyrrolidin-3-yl]-4-piperidyl]methyl]-1-piperidyl]benzimidazol-1-yl]piperidine-2,6-dione

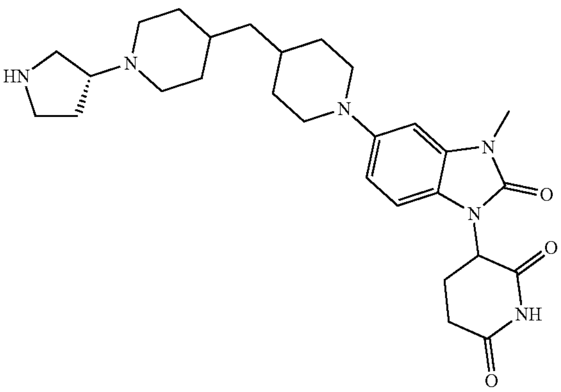 [SMILES: Cn1c(=O)n(C2CCC(=O)NC2=O)c2ccc(N3CCC(CC4CCN([C@@H]5CCNC5)CC4)CC3)cc21]

To tert-butyl (3R)-3-[4-[[1-[1-(2,6-dioxo-3-piperidyl)-3-methyl-2-oxo-benzimidazol-5-yl]-4-piperidyl]methyl]-1-piperidyl]pyrrolidine-1-carboxylate (370 mg, 0.61 mmol, 1 eq) in dichloromethane (8 mL) was added trifluoroacetic acid (4.61 g, 40.39 mmol, 3 mL, 66 eq), and the reaction mixture was stirred at 25° C. for 1 hours. The mixture was filtered and concentrated under vacuum, and the resulting residue was purified by prep-HPLC (column: Waters Atlantis T3 150*30 mm*5 um; mobile phase: [1-20% $CH_3CN$ in water (FA)]) to afford the title compound (113 mg, 0.20 mmol, 33% yield, formic acid salt) as a colorless gum. LC/MS (ESI) m/z: 509.4 $[M+H]^+$.

Step 4: Preparation of 3-[5-[4-[[1-[(3R)-1-[4-(3,8-diazabicyclo[3.2.1]octan-3-yl)-7-(8-ethynyl-7-fluoro-3-hydroxy-1-naphthyl)-8-fluoro-pyrido[4,3-d]pyrimidin-2-yl]pyrrolidin-3-yl]-4-piperidyl]methyl]-1-piperidyl]-3-methyl-2-oxo-benzimidazol-1-yl]piperidine-2,6-dione

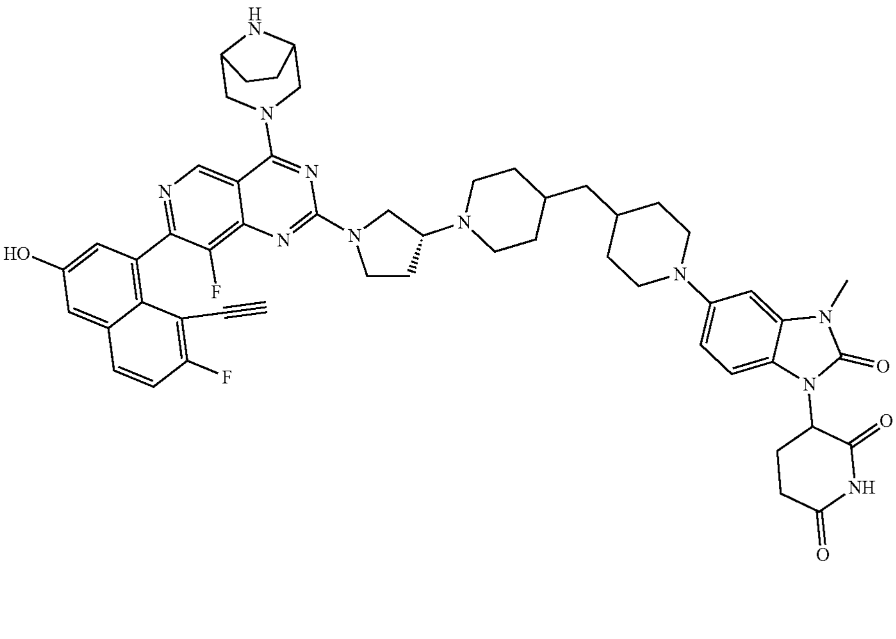 [SMILES: C#Cc1c(F)ccc2cc(O)cc(-c3ncc4c(N5CC6CCC(C5)N6)nc(N5CC[C@@H](N6CCC(CC7CCN(c8ccc9c(c8)n(C)c(=O)n9C8CCC(=O)NC8=O)CC7)CC6)C5)nc4c3F)c12]

The title compound was prepared in an analogous manner to 3-(5-(4-((4-((1-((3R)-1-(4-(3,8-diazabicyclo[3.2.1] octan-3-yl)-7-(8-ethynyl-7-fluoro-3-hydroxynaphthalen-1-yl)-8-fluoropyrido[4,3-d] pyrimidin-2-yl)pyrrolidin-3-yl)piperidin-4-yl)methyl)piperidin-1-yl)methyl)piperidin-1-yl)-3-methyl-2-oxo-2,3-dihydro-1H-benzo[d]imidazol-1-yl) piperidine-2,6-dione. (yellow solid, formic acid salt). LC/MS (ESI) m/z: 950.8 $[M+H]^+$. $^1H$ NMR (400 MHz, DMSO-$d_6$) δ 11.06 (s, 1H), 8.78 (s, 1H), 8.20 (s, 1H), 7.95 (dd, J=6.0, 9.2 Hz, 1H), 7.45 (t, J=8.8 Hz, 1H), 7.36 (d, J=2.4 Hz, 1H), 7.14 (d, J=2.0 Hz, 1H), 6.92 (dd, J=2.4, 8.0 Hz, 1H), 6.81 (s, 1H), 6.68-6.56 (m, 1H), 5.28 (dd, J=3.6, 12.8 Hz, 1H), 4.49-4.36 (m, 1H), 4.28-4.18 (m, 1H), 3.94 (d, J=7.2 Hz, 2H), 3.87-3.72 (m, 2H), 3.63 (s, 2H), 3.59-3.54 (m, 3H), 3.48 (s, 1H), 3.39-3.33 (m, 4H), 3.02-2.94 (m, 1H), 2.90-2.80 (m, 3H), 2.67-2.55 (m, 4H), 2.24-2.12 (m, 1H), 2.05-1.92 (m, 3H), 1.77-1.63 (m, 8H), 1.51-1.33 (m, 2H), 1.29-1.22 (m, 2H), 1.20-1.09 (m, 4H).

Example 158: Library Synthesis

Step 1

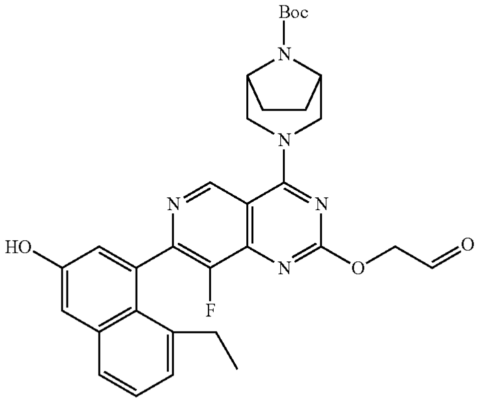 [SMILES: CCc1cccc2cc(O)cc(-c3ncc4c(N5CC6CCC(C5)N6C(=O)OC(C)(C)C)nc(OCC=O)nc4c3F)c12]

To a solution of tert-butyl 3-[2-(2,2-dimethoxyethoxy)-7-[8-ethyl-3-(methoxymethoxy)-1-naphthyl]-8-fluoro-pyrido [4,3-d]pyrimidin-4-yl]-3,8-diazabicyclo[3.2.1]octane-8-carboxylate (295 umol) in acetone (1 mL) was added hydrochloric acid (12 M, 1 mL), the mixture was stirred at 20° C. for 10 min. Then aqueous sodium bicarbonate solution (27 mmol) and di-tert-butyl dicarbonate (354 umol) in THE (3 mL) was added at 20° C. The mixture was stirred at 20° C. for 1 h under nitrogen atmosphere. The reaction was diluted with water (20 mL) and extracted with ethyl acetate (3×20 mL). The combined organic layers were washed with brine (10 mL), dried over anhydrous sodium sulfate, filtered, and concentrated under reduced pressure. The residue was purified by flash silica gel chromatography (55% ethyl acetate/petroleum ether) to afford product.

Step 2

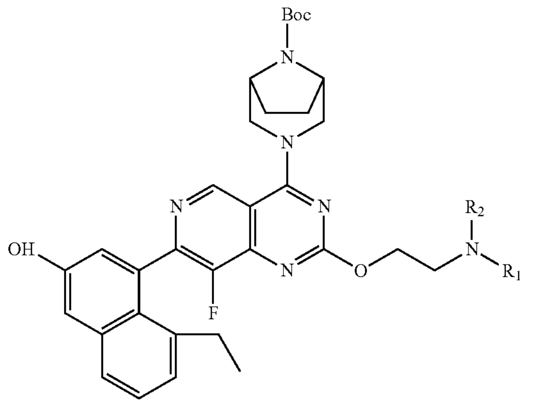

To a solution of tert-butyl 3-[7-(8-ethyl-3-hydroxy-1-naphthyl)-8-fluoro-2-(2-oxoethoxy)pyrido[4,3-d]pyrimidin-4-yl]-3,8-diazabicyclo[3.2.1]octane-8-carboxylate (51 umol) in dichloromethane (1 mL) and isopropyl alcohol (0.1 mL) was added 2-(2,6-dioxo-3-piperidyl)-5-piperazin-1-yl-isoindoline-1,3-dione (54 umol), 2-methylpyridine borane complex (255 umol) and acetic acid (204 umol), the mixture was stirred at 20° C. for 1 h. The reaction mixture was filtered and concentrated. The residue was purified by preparative thin layer chromatography (dichloromethane: methanol=10:1) to afford product.

Step 3

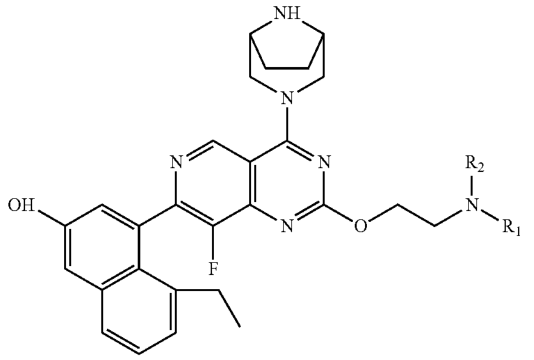

To a solution of tert-butyl 3-[2-[2-[4-[2-(2,6-dioxo-3-piperidyl)-1-oxo-isoindolin-5-yl]-1-piperidyl]ethoxy]-7-(8-ethyl-3-hydroxy-1-naphthyl)-8-fluoro-pyrido[4,3-d]pyrimidin-4-yl]-3,8-diazabicyclo[3.2.1]octane-8-carboxylate (44 umol) in hexafluoroisopropanol (1 mL) was added trifluoroacetic acid (0.2 mL) and stirred at 25° C. for 0.5 h. The reaction mixture was purified by preparative HPLC (Welch Xtimate C18 150×25 mm×5 μm; A: water with 0.225% v/v FA, B: acetonitrile; B %: 20-60; 25 min), lyophilized to afford product.

Compounds 225, 227, 231-233, and 237 were prepared according to the procedure in Example 158.

Characterization data for the compounds of the disclosure is presented below in Table 2.

TABLE 2

| Cmpd | LC/MS | NMR |
|---|---|---|
| 1 | 923.1 | |
| 2 | 937.1 | $^{1}$H NMR (400 MHz, DMSO-$d_6$) δ 10.96 (s, 1H), 9.08 (s, 1H), 8.28 (s, 2H), 7.65 (d, J = 8.0 Hz, 1H), 7.50 (d, J = 8.8 Hz, 1H), 7.36 (t, J = 8.4 Hz, 1H), 7.32-7.23 (m, 1H), 7.14-7.09 (m, 1H), 7.07-7.01 (m, 2H), 6.98-6.94 (m, 1H), 5.06-4.94 (m, 1H), 4.55-4.43 (m, 4H), 4.34-4.14 (m, 3H), 3.44 (br s, 3H), 3.29-3.21 (m, 5H), 3.01-2.81 (m, 4H), 2.75-2.55 (m, 6H), 2.42-2.11 (m, 4H), 2.06-1.92 (m, 3H), 1.82-1.68 (m, 8H), 1.67-1.59 (m, 2H), 1.49-1.37 (m, 1H), 1.20-1.07 (m, 2H), 0.80 (t, J = 7.2 Hz, 3H) |
| 3 | 937.1 | |
| 4 | 941.1 | $^{1}$H NMR (400 MHz, DMSO-$d_6$) δ 11.14 (s, 1H), 9.08 (s, 1H), 8.23 (s, 2H), 7.82 (d, J = 8.4 Hz, 1H), 7.65 (d, J = 8.4 Hz, 1H), 7.36 (t, J = 7.6 Hz, 1H), 7.29-7.22 (m, 3H), 7.11 (d, J = 7.6 Hz, 1H), 6.97-6.93 (m, 1H), 5.13-5.05 (m, 1H), 4.96-4.88 (m, 1H), 4.56-4.44 (m, 4H), 3.92-3.79 (m, 7H), 3.19-3.08 (m, 2H), 2.74-2.65 (m, 1H), 2.68 (br d, J = 5.5 Hz, 4H), 2.46-2.36 (m, 9H), 2.33-2.15 (m, 5H), 2.13-2.09 (m, 3H), 2.06-2.00 (m, 1H), 1.83-1.69 (m, 4H), 0.80 (t, J = 7.6 Hz, 3H) |
| 5 | 976.1 | |
| 6 | 901.1 | |
| 7 | 843.9 | |
| 8 | 926.1 | |
| 10 | 939.1 | |
| 11 | 926.1 | |
| 12 | 924.1 | |
| 13 | 939.1 | |
| 14 | 861.0 | |
| 15 | 915.0 | |
| 16 | 789.9 | |
| 17 | 903.0 | |
| 18 | 926.1 | |
| 19 | 882.0 | |
| 20 | 1008.2 | |
| 21 | 1010.1 | |
| 22 | 979.2 | |
| 25 | 979.2 | |
| 26 | 940.1 | |
| 27 | 896.0 | |
| 28 | 912.8 | $^{1}$H NMR (400 MHz, DMSO-$d_6$) δ: 11.11-11.04 (m, 1H), 9.09 (s, 1H), 8.19 (s, 2H), 7.66 (d, J = 8.0 Hz, 1H), 7.36 (t, J = 7.6 Hz, 1H), 7.28 (d, J = 2.4 Hz, 1H), 7.12 (d, J = 6.4 Hz, 1H), 6.99-6.93 (m, 2H), 6.90-6.83 (m, 2H), 5.34 (dd, J = 5.2, 12.4 Hz, 1H), 4.50-4.39 (m, 4H), 3.67 (s, 1H), 3.63 (s, 1H), 3.61 (s, 3H), 3.45 (s, 1H), 3.11-3.05 (m, 3H), 2.94 (d, J = 9.2 Hz, 3H), 2.90-2.84 (m, 1H), 2.72-2.61 (m, 6H), 2.31-2.10 (m, 3H), 2.05-1.96 (m, 3H), 1.76-1.58 (m, 8H), 1.38-1.27 (m, 3H), 1.20-1.09 (m, 3H), 1.05 (t, J = 6.8 Hz, 2H), 0.82 (t, J = 7.2 Hz, 3H). |
| 31 | 925.1 | |
| 32 | 911.0 | |
| 33 | 911.0 | $^{1}$H NMR (400 MHz, DMSO-$d_6$) δ 11.06 (s, 1H), 9.10 (s, 1H), 8.16 (s, 1H), 7.67 (d, J = 8.0 Hz, 1H), 7.54 (d, J = 8.4 Hz, 1H), 7.36 (t, J = 7.6 Hz, 1H), 7.30-7.26 (m, 1H), 7.15-7.09 (m, 1H), 7.02-6.92 (m, 3H), 6.87-6.81 (m, 1H), 5.06-4.96 (m, 1H), 4.57-4.43 (m, 4H), 3.82-3.63 (m, 9H), 2.93-2.80 (m, 2H), 2.73-2.65 (m, 3H), 2.36-2.11 (m, 5H), 2.07 (s, 4H), 1.88-1.66 (m, 7H), 1.46-1.11 (m, 5H), 0.82 (t, J = 7.6 Hz, 3H) |

TABLE 2-continued

| Cmpd | LC/MS | NMR |
|---|---|---|
| 34 | 812.9 | |
| 35 | 910.2 | $^{1}$H NMR (400 MHz, DMSO-$d_6$) δ 10.98 (s, 1H), 10.45-9.82 (m, 1H), 9.07 (s, 1H), 8.15 (s, 1H), 7.98 (dd, J = 6.0, 9.2 Hz, 1H), 7.57-7.36 (m, 3H), 7.29 (d, J = 7.2 Hz, 1H), 7.19-6.96 (m, 2H), 5.11 (dd, J = 4.8, 13.2 Hz, 1H), 4.66-4.35 (m, 5H), 4.33-4.19 (m, 1H), 3.93 (s, 1H), 3.81 (br s, 2H), 3.71 (br d, J = 14.0 Hz, 2H), 3.04-2.93 (m, 3H), 2.92-2.84 (m, 1H), 2.80-2.63 (m, 7H), 2.14-1.92 (m, 4H), 1.84-1.69 (m, 6H), 1.67-1.59 (m, 2H), 1.56-1.43 (m, 1H), 1.42-1.32 (m, 1H), 1.29-1.19 (m, 2H), 1.19-1.05 (m, 4H) |
| 36 | 798.9 | $^{1}$H NMR (400 MHz, $CD_3OD$) δ 9.11 (s, 1H), 8.49 (s, 1H), 7.72 (s, 1H), 7.68-7.63 (m, 1H), 7.58-7.54 (m, 2H), 7.38 (t, J = 7.6 Hz, 1H), 7.32 (d, J = 2.8 Hz, 1H), 7.20-7.16 (m, 1H), 7.03 (d, J = 2.8 Hz, 1H), 5.20-5.14 (m, 1H), 4.77-4.70 (m, 4H), 4.62-4.60 (m, 2H), 4.52-4.42 (m, 2H), 4.01-3.93 (m, 2H), 3.91-3.79 (m, 2H), 3.60-3.49 (m, 2H), 2.99-2.86 (m, 2H), 2.85-2.74 (m, 3H), 2.59-2.45 (m, 1H), 2.44-2.24 (m, 2H), 2.23-2.15 (m, 1H), 2.09-1.92 (m, 8H), 0.90 (t, J = 7.6 Hz, 3H) |
| 37 | 805.9 | $^{1}$H NMR (400 MHz, $CD_3OD$) δ 9.09 (s, 1H), 8.43 (s, 1H), 7.76 (t, J = 8.8 Hz, 1H), 7.69-7.63 (m, 1H), 7.39 (t, J = 7.6 Hz, 1H), 7.34-7.30 (m, 1H), 7.18 (d, J = 7.6 Hz, 1H), 7.06-7.00 (m, 1H), 6.83 (dd, J = 2.4, 9.2 Hz, 1H), 6.76-6.68 (m, 1H), 4.76-4.62 (m, 6H), 4.19-4.07 (m, 2H), 3.96-3.81 (m, 2H), 3.42-3.36 (m, 4H), 3.00-2.93 (m, 2H), 2.87 (d, J = 5.6 Hz, 5H), 2.76-2.67 (m, 1H), 2.42-2.24 (m, 3H), 2.23-2.04 (m, 5H), 0.89 (s, 1H) |
| 38 | 798.9 | $^{1}$H NMR (400 MHz, $CD_3OD$) δ 9.11 (s, 1H), 8.49 (s, 1H), 7.76-7.74 (d, J = 8.0 Hz, 1H), 7.67-7.65 (d, J = 8.0 Hz, 1H), 7.48 (s, 1H), 7.46-7.41 (m, 1H), 7.41-7.36 (m, 1H), 7.33-7.31 (m, 1H), 7.19-7.15 (m, 1H), 7.03 (t, J = 2.0 Hz, 1H), 5.19-5.13 (m, 1H), 4.82-4.79 (m, 3H), 4.75 (d, J = 7.0 Hz, 2H), 4.49-4.44 (m, 2H), 4.03-3.94 (m, 2H), 3.92-3.78 (m, 2H), 3.57-3.48 (m, 2H), 3.29-3.22 (m, 2H), 2.98-2.85 (m, 2H), 2.84-2.69 (m, 3H), 2.53-2.41 (m, 1H), 2.41-2.24 (m, 2H), 2.23-2.13 (m, 1H), 2.07-1.92 (m, 8H), 0.91 (t, J = 7.4 Hz, 3H) |
| 39 | 799.9 | |
| 40 | 813.9 | |
| 41 | 1007.7 | $^{1}$H NMR (400 MHz, DMSO-$d_6$) δ 10.98 (s, 1H), 10.00 (s, 1H), 9.13 (s, 1H), 8.14 (s, 1H), 7.68 (d, J = 8.4 Hz, 1H), 7.47-7.33 (m, 2H), 7.31-7.25 (m, 2H), 7.17-7.10 (m, 2H), 6.96 (d, J = 2.8 Hz, 1H), 5.15-5.05 (m, 1H), 4.65-4.54 (m, 2H), 4.52-4.37 (m, 3H), 4.33-4.23 (m, 1H), 3.80-3.66 (m, 3H), 3.28-3.20 (m, 3H), 3.15-3.07 (m, 2H), 2.98-2.87 (m, 2H), 2.76-2.65 (m, 3H), 2.62-2.57 (m, 2H), 2.36 (s, 3H), 2.32-2.14 (m, 3H), 2.02-1.92 (m, 3H), 1.78-1.68 (m, 4H), 1.65-1.58 (m, 2H), 1.54-1.42 (m, 2H), 1.34-1.12 (m, 7H), 0.82 (t, J = 7.2 Hz, 3H) |
| 42 | 1007.7 | $^{1}$H NMR (400 MHz, DMSO-$d_6$) δ 10.98 (s, 1H), 9.09 (s, 1H), 8.16 (s, 1H), 8.14 (s, 1H), 7.67 (d, J = 8.4 Hz, 1H), 7.45-7.35 (m, 2H), 7.31-7.25 (m, 2H), 7.17-7.10 (m, 2H), 6.96 (d, J = 2.4 Hz, 1H), 5.15-5.05 (m, 1H), 4.50-4.35 (m, 6H), 4.30-4.25 (m, 1H), 3.72-3.65 (m, 2H), 3.30-3.24 (m, 4H), 2.99- |

TABLE 2-continued

| Cmpd | LC/MS | NMR |
|---|---|---|
| | | 2.83 (m, 6H), 2.75-2.71 (m, 3H), 2.61-2.57 (m, 1H), 2.46-2.42 (m, 1H), 2.29-2.21 (m, 7H), 2.04-1.91 (m, 6H), 1.82-1.74 (m, 2H), 1.63-1.53 (m, 6H), 1.36-1.18 (m, 5H), 1.10-1.04 (m, 6H), 0.81 (t, J = 7.2 Hz, 3H) |
| 43 | 1007.6 | $^1$H NMR (400 MHz, DMSO-$d_6$) δ 10.98 (s, 1H), 9.05 (s, 1H), 8.26-8.20 (m, 2H), 8.00-7.93 (m, 1H), 7.49-7.46 (m, 2H), 7.44-7.41 (m, 2H), 7.39 (d, J = 2.4 Hz, 1H), 7.28 (d, J = 7.2 Hz, 1H), 7.19-7.16 (m, 1H), 7.14 (d, J = 8.0 Hz, 1H), 5.15-5.05 (m, 1H), 4.56-4.48 (m, 1H), 4.47-4.43 (m, 2H), 4.42-4.33 (m, 2H), 4.30-4.22 (m, 1H), 3.93 (s, 1H), 3.77-3.62 (m, 4H), 3.41-3.30 (m, 2H), 3.00-2.80 (m, 5H), 2.75-2.65 (m, 4H), 2.62-2.55 (m, 1H), 2.47-2.42 (m, 2H), 2.25-2.17 (m, 2H), 2.05-1.87 (m, 5H), 1.83-1.66 (m, 7H), 1.65-1.55 (m, 4H), 1.35-1.20 (m, 4H), 1.15-1.00 (m, 6H) |
| 47 | 967.8 | $^1$H NMR (400 MHz, $CD_3OD$) δ 9.14-9.04 (m, 1H), 8.41 (s, 1H), 7.64-7.60 (m, 2H), 7.38-7.36 (m, 1H), 7.28 (d, J = 2.4 Hz, 1H), 7.17-7.13 (m, 1H), 7.07-7.00 (m, 3H), 5.12-5.07 (m, 1H), 4.75-4.51 (m, 6H), 4.44-4.16 (m, 4H), 3.87-3.73 (m, 2H), 3.70-3.36 (m, 10H), 2.95-2.75 (m, 2H), 2.48 (s, 3H), 2.46-1.95 (m, 15H), 1.74 (d, J = 6.9 Hz, 2H), 0.92-0.80 (m, 3H) |
| 48 | 967.8 | $^1$H NMR (400 MHz, $CD_3OD$) δ 9.10 (s, 1H), 8.48 (s, 1H), 7.67-7.59 (m, 2H), 7.37-7.33 (m, 1H), 7.28 (d, J = 2.4 Hz, 1H), 7.15 (t, J = 7.2 Hz, 1H), 7.09-7.00 (m, 3H), 5.15-5.05 (m, 1H), 4.71-4.34 (m, 10H), 4.17-4.16 (m, 1H), 3.86-3.58 (m, 7H), 3.50-3.39 (m, 4H), 2.91-2.73 (m, 2H), 2.43 (s, 3H), 2.41-1.97 (m, 15H), 1.71 (d, J = 7.6 Hz, 2H), 0.92-0.83 (m, 3H) |
| 49 | 967.8 | $^1$H NMR (400 MHz, $CD_3OD$) δ 9.13-8.95 (m, 1H), 8.41 (s, 1H), 7.61 (br d, J = 8.0 Hz, 1H), 7.33 (s, 3H), 7.31-7.26 (m, 1H), 7.23-6.98 (m, 3H), 5.18-5.09 (m, 1H), 4.72 (br d, J = 4.0 Hz, 5H), 4.49 (br d, J = 2.8 Hz, 2H), 4.45-4.33 (m, 2H), 4.32-4.25 (m, 1H), 3.88-3.77 (m, 2H), 3.63 (br s, 2H), 3.55 (br s, 1H), 3.49 (br s, 2H), 3.42-3.37 (m, 1H), 3.09-2.94 (m, 3H), 2.91-2.85 (m, 1H), 2.80-2.72 (m, 1H), 2.58-2.39 (m, 6H), 2.38-2.20 (m, 5H), 2.19-2.06 (m, 7H), 1.80-1.65 (m, 2H), 0.92-0.80 (m, 3H) |
| 50 | 967.9 | $^1$H NMR (400 MHz, $CD_3OD$) δ 9.10 (s, 1H), 8.46 (s, 1H), 7.67-7.59 (m, 2H), 7.38-7.34 (m, 1H), 7.29 (d, J = 2.4 Hz, 1H), 7.15 (t, J = 7.2 Hz, 1H), 7.07-7.05 (m, 2H), 7.01 (d, J = 2.4 Hz, 1H), 5.13-5.08 (m, 1H), 4.81-4.66 (m, 6H), 4.60-4.51 (m, 2H), 4.44-4.31 (m, 3H), 4.19 (s, 1H), 3.97-3.77 (m, 4H), 3.64 (s, 4H), 3.50 (d, J = 5.2 Hz, 1H), 3.13 (s, 3H), 2.98-2.85 (m, 2H), 2.52-1.65 (m, 18H), 0.94-0.77 (m, 3H) |
| 51 | 967.4 | $^1$H NMR (400 MHz, $CD_3OD$) δ 9.15-8.90 (m, 1H), 8.47 (s, 1H), 7.70-7.59 (m, 1H), 7.53-7.27 (m, 4H), 7.26-7.12 (m, 2H), 7.10-6.97 (m, 1H), 5.21-5.09 (m, 1H), 4.75-4.35 (m, 8H), 4.33-4.26 (m, 1H), 3.89-3.38 (m, 10H), 3.11-2.68 (m, 5H), 2.59-2.03 (m, 18H), 1.84-1.62 (m, 2H), 0.94-0.76 (m, 3H) |
| 52 | 967.8 | $^1$H NMR (400 MHz, $CD_3OD$) δ 9.10-9.07 (m, 1H), 7.62 (d, J = 8.4 Hz, 1H), 7.49-7.42 (m, 2H), 7.35 (t, J = 8.0 Hz, 1H), 7.29 (s, 1H), 7.22-7.12 (m, 2H), 7.05-7.00 (m, 1H), 5.18-5.12 (m, 1H), 4.71-4.41 (m, 8H), 4.22 (s, 1H), 3.98 (s, 2H), 3.91-3.81 (m, 2H), 3.64-3.63 (m, 4H), 3.15 (s, 3H), 3.04-2.90 (m, 6H), 2.50-1.94 (m, 18H), 0.91-0.84 (m, 3H) |
| 53 | 967.8 | $^1$H NMR (400 MHz, $CD_3OD$) δ 9.10 (s, 1H), 8.48 (s, 1H), 7.63 (t, J = 8.4 Hz, 2H), 7.38-7.33 (m, 1H), 7.28 (d, J = 1.8 Hz, 1H), 7.15 (t, J = 7.0 Hz, 1H), 7.08-7.00 (m, 3H), 5.16-5.08 (m, 1H), 4.79-4.62 (m, 4H), 4.59-4.48 (m, 2H), 4.44-4.29 (m, 3H), 4.14 (s, 1H), 3.84-3.74 (m, 5H), 3.60-3.64 (m, 4H), 3.41-3.33 (m, 2H), 3.13 (s, 3H), 2.98-2.84 (m, 2H), 2.50-1.81 (m, 18H), 0.93-0.83 (m, 3H) |
| 54 | 967.9 | $^1$H NMR (400 MHz, $CD_3OD$) δ 9.14-9.01 (m, 1H), 8.46 (s, 1H), 7.62 (d, J = 8.4 Hz, 1H), 7.51-7.40 (m, 2H), 7.35 (t, J = 8.0 Hz, 1H), 7.30-7.27 (m, 1H), 7.25-7.10 (m, 2H), 7.05-6.98 (m, 1H), 5.21-5.12 (m, 1H), 4.80-4.71 (m, 2H), 4.66-4.50 (m, 3H), 4.50-4.34 (m, 3H), 4.26-4.13 (m, 1H), 3.97-3.76 (m, 4H), 3.72-3.46 (m, 5H), 3.16-3.10 (m, 3H), 3.09-2.80 (m, 6H), 2.58-1.80 (m, 17H), 0.94-0.79 (m, 3H) |
| 55 | 993.5 | $^1$H NMR (400 MHz, $CD_3OD$) δ 9.10 (s, 1H), 8.49 (s, 2H), 7.64 (d, J = 8.0 Hz, 1H), 7.52-7.42 (m, 2H), 7.37 (t, J = 8.0 Hz, 1H), 7.30 (d, J = 2.8 Hz, 1H), 7.26 (dd, J = 7.2, 1.6 Hz, 1H), 7.17 (d, J = 7.2 Hz, 1H), 7.01 (d, J = 2.8 Hz, 1H), 5.21-5.11 (m, 1H), 4.81-4.77 (m, 2H), 4.75-4.64 (m, 2H), 4.55-4.41 (m, 2H), 4.03-3.93 (m, 2H), 3.91-3.78 (m, 2H), 3.62-3.39 (m, 6H), 3.36-3.32 (m, 2H), 3.07-2.67 (m, 10H), 2.59-2.45 (m, 1H), 2.42-2.13 (m, 3H), 2.09-1.82 (m, 11H), 1.77-1.58 (m, 2H), 1.57-1.36 (m, 6H), 1.33-1.20 (m, 2H), 0.90 (t, J = 7.2 Hz, 3H) |
| 56 | 896.8 | $^1$H NMR (400 MHz, $CD_3OD$) δ 9.11 (s, 1H), 8.34 (s, 2H), 7.64 (d, J = 8.4 Hz, 1H), 7.49-7.34 (m, 3H), 7.30 (d, J = 2.8 Hz, 1H), 7.23 (d, J = 7.2 Hz, 1H), 7.18 (d, J = 7.2 Hz, 1H), 7.01 (d, J = 2.4 Hz, 1H), 5.19-5.12 (m, 1H), 4.80-4.69 (m, 3H), 4.47 (d, J = 4.8 Hz, 2H), 4.03-3.94 (m, 2H), 3.90-3.78 (m, 2H), 3.69-3.58 (m, 2H), 3.53-3.46 (m, 2H), 3.43-3.36 (m, 2H), 3.03-2.86 (m, 3H), 2.84-2.72 (m, 3H), 2.60-2.46 (m, 1H), 2.41-2.23 (m, 2H), 2.21-2.13 (m, 1H), 2.07-1.92 (m, 6H), 1.87-1.69 (m, 3H), 1.59-1.26 (m, 8H), 0.90 (t, J = 7.6 Hz, 3H) |
| 57 | 1007.5 | $^1$H NMR (400 MHz, $CD_3OD$) δ 9.09 (s, 1H), 7.69-7.63 (m, 2H), 7.39-7.30 (m, 4H), 7.17 (d, J = 3.6 Hz, 1H), 7.01 (d, J = 1.6 Hz, 1H), 5.12-5.08 (m, 1H), 4.79-4.69 (m, 5H), 3.95 (s, 2H). 3.87-3.79 (m, 4H), 3.55-3.47 (m, 4H), 3.02-2.82 (m, 7H), 2.77-2.69 (m, 4H), 2.39-2.22 (m, 2H), 2.14-1.92 (m, 13H), 1.64-1.37 (m, 8H), 1.30-1.26 (m, 2H), 0.90 (t, J = 7.2 Hz, 3H) |
| 58 | 953.7 | $^1$H NMR (400 MHz, DMSO-$d_6$) δ 10.95 (s, 1H), 9.08 (s, 1H), 7.66 (d, J = 8.0 Hz, 1H), 7.53 (d, J = 8.8 Hz, 1H), 7.36 (t, J = 7.6 Hz, 1H), 7.28 (d, J = 2.4 Hz, 1H), 7.12 (d, J = 7.2 Hz, 1H), 7.08-7.04 (m, 2H), 6.97 (d, J = 2.4 Hz, 1H), 5.04 (dd, J = 5.2, 13.2 Hz, 1H), 4.49-4.40 (m, 2H), 4.37-4.02 (m, 8H), 3.29 (br s, 9H), 2.95-2.70 (m, 5H), 2.58 (br d, J = 16.0 Hz, 1H), 2.39-2.15 (m, 4H), 2.12-1.88 (m, 3H), 1.80-1.63 (m, 10H), |

TABLE 2-continued

| Cmpd | LC/MS | NMR |
|---|---|---|
| | | 1.56-1.50 (m, 1H), 0.81 (t, J = 7.2 Hz, 3H) |
| 59 | 953.8 | $^1$H NMR (400 MHz, DMSO-d$_6$) δ 10.95 (s, 1H), 9.08 (s, 1H), 7.66 (d, J = 8.4 Hz, 1H), 7.53 (d, J = 8.8 Hz, 1H), 7.36 (t, J = 7.6 Hz, 1H), 7.28 (d, J = 2.4 Hz, 1H), 7.11 (d, J = 7.2 Hz, 1H), 7.08-7.03 (m, 2H), 6.97 (d, J = 2.4 Hz, 1H), 5.04 (dd, J = 5.2, 13.2 Hz, 1H), 4.50-4.40 (m, 2H), 4.36-4.01 (m, 8H), 3.29 (br s, 9H), 3.08-2.63 (m, 5H), 2.58 (br d, J = 16.8 Hz, 1H), 2.47-2.13 (m, 4H), 2.12-1.81 (m, 3H), 1.81-1.62 (m, 10H), 1.56-1.48 (m, 1H), 0.81 (t, J = 7.2 Hz, 3H) |
| 60 | 953.8 | $^1$H NMR (400 MHz, CD$_3$OD) δ 9.18-9.04 (m, 1H), 8.54-8.37 (m, 1H), 7.64 (d, J = 8.0 Hz, 1H), 7.53-7.41 (m, 2H), 7.37 (t, J = 7.6 Hz, 1H), 7.33-7.27 (m, 1H), 7.26-7.13 (m, 2H), 7.09-7.00 (m, 1H), 5.17 (td, J = 4.0, 13.2 Hz, 1H), 4.80-4.66 (m, 4H), 4.60-4.39 (m, 5H), 4.26-4.11 (m, 1H), 3.90-3.75 (m, 4H), 3.66 (d, J = 1.2 Hz, 4H), 3.54-3.47 (m, 1H), 3.17-2.97 (m, 4H), 2.95-2.75 (m, 2H), 2.57-2.31 (m, 4H), 2.26-2.05 (m, 7H), 2.01-1.84 (m, 4H), 1.31 (s, 1H), 0.94-0.85 (m, 3H) |
| 61 | 953.7 | $^1$H NMR (400 MHz, CD3OD) δ 9.16-9.07 (m, 1H), 8.55-8.39 (m, 1H), 7.64 (d, J = 8.4 Hz, 1H), 7.53-7.41 (m, 2H), 7.37 (t, J = 7.6 Hz, 1H), 7.33-7.28 (m, 1H), 7.27-7.11 (m, 2H), 7.08-7.00 (m, 1H), 5.23-5.12 (m, 1H), 4.77-4.65 (m, 4H), 4.59-4.38 (m, 5H), 4.16 (dt, J = 3.6, 7.6 Hz, 1H), 3.87-3.73 (m, 4H), 3.72-3.55 (m, 4H), 3.52-3.45 (m, 1H), 3.18-2.97 (m, 4H), 2.94-2.71 (m, 2H), 2.53-2.29 (m, 4H), 2.24-2.02 (m, 7H), 2.00-1.84 (m, 4H), 1.31 (s, 1H), 0.94-0.85 (m, 3H) |
| 62 | 967.4 | $^1$H NMR (400 MHz, CD$_3$OD) δ 9.09 (s, 1H), 8.50 (s, 1H), 7.69 (dd, J = 8.4, 4.0 Hz, 1H), 7.62 (d, J = 8.0 Hz, 1H), 7.39-7.31 (m, 2H), 7.28 (d, J = 2.4 Hz, 1H), 7.22 (d, J = 8.4 Hz, 1H), 7.18-7.13 (m, 1H), 7.01 (d, J = 2.8 Hz, 1H), 5.11-5.04 (m, 1H), 4.76-4.65 (m, 2H), 4.54-4.47 (m, 2H), 4.44-4.36 (m, 1H), 4.16-4.00 (m, 1H), 3.87-3.55 (m, 9H), 3.52-3.39 (m, 5H), 2.93-2.81 (m, 1H), 2.79-2.68 (m, 2H), 2.44-2.21 (m, 4H), 2.19-1.77 (m, 12H), 0.92-0.85 (m, 3H) |
| 63 | 967.4 | $^1$H NMR (400 MHz, CD$_3$OD) δ 9.10 (s, 1H), 8.49 (s, 1H), 7.69 (dd, J = 8.4, 4.4 Hz, 1H), 7.62 (d, J = 8.0 Hz, 1H), 7.39-7.32 (m, 2H), 7.28 (d, J = 2.8 Hz, 1H), 7.22 (d, J = 8.8 Hz, 1H), 7.16 (t, J = 5.6 Hz, 1H), 7.01 (d, J = 2.4 Hz, 1H), 5.11-5.05 (m, 1H), 4.75-4.66 (m, 2H), 4.56-4.48 (m, 2H), 4.44-4.37 (m, 1H), 4.20-4.04 (m, 1H), 3.89-3.53 (m, 9H), 3.50-3.38 (m, 5H), 2.93-2.81 (m, 1H), 2.78-2.65 (m, 2H), 2.42-2.23 (m, 4H), 2.22-1.78 (m, 12H), 0.93-0.84 (m, 3H) |
| 64 | 967.8 | $^1$H NMR (400 MHz, CD$_3$OD) δ 9.13 (s, 1H), 8.49 (s, 1H), 7.73-7.61 (m, 2H), 7.43 (dd, J = 3.2, 7.2 Hz, 1H), 7.37 (t, J = 7.6 Hz, 1H), 7.33-7.28 (m, 2H), 7.17 (t, J = 6.8 Hz, 1H), 7.03 (s, 1H), 5.11 (dd, J = 5.2, 12.4 Hz, 1H), 4.79 (t, J = 12.0 Hz, 2H), 4.73-4.66 (m, 2H), 4.61-4.52 (m, 2H), 4.46-4.39 (m, 1H), 4.21 (s, 1H), 3.94-3.78 (m, 4H), 3.78-3.64 (m, 4H), 3.51 (d, J = 4.8 Hz, 1H), 3.41-3.35 (m, 1H), 3.31-3.26 (m, 2H), 2.92-2.81 (m, 1H), 2.80-2.65 (m, 2H), 2.48-2.20 (m, 6H), 2.19-1.85 (m, 10H), 0.89 (q, J = 7.6 Hz, 3H) |
| 65 | 967.8 | $^1$H NMR (400 MHz, CD$_3$OD) δ 9.10 (s, 1H), 8.48 (s, 1H), 7.70-7.58 (m, 2H), 7.41 (dd, J = 3.2, 7.2 Hz, 1H), 7.38-7.32 (m, 1H), 7.31-7.26 (m, 2H), 7.15 (t, J = 6.8 Hz, 1H), 7.01 (s, 1H), 5.09 (dd, J = 5.2, 12.4 Hz, 1H), 4.82-4.73 (m, 2H), 4.72-4.65 (m, 2H), 4.60-4.50 (m, 2H), 4.40 (dd, J = 9.2, 12.4 Hz, 1H), 4.24-4.14 (m, 1H), 3.93-3.76 (m, 4H), 3.75-3.62 (m, 4H), 3.49 (d, J = 5.4 Hz, 1H), 3.35 (s, 1H), 3.29-3.25 (m, 2H), 2.91-2.78 (m, 1H), 2.77-2.62 (m, 2H), 2.46-2.18 (m, 6H), 2.17-1.85 (m, 10H), 0.87 (q, J = 7.6 Hz, 3H) |
| 66 | 910.3 | $^1$H NMR (400 MHz, CD$_3$OD) δ 9.11 (s, 1H), 8.47 (s, 1H), 7.67-7.60 (m, 2H), 7.41-7.27 (m, 4H), 7.18 (d, J = 6.8 Hz, 1H), 7.01 (d, J = 2.8 Hz, 1H), 5.09 (dd, J = 5.6, 12.4 Hz, 1H), 4.75 (dd, J = 13.6, 19.2 Hz, 4H), 4.07-3.98 (m, 2H), 3.88 (dd, J = 13.6, 18.4 Hz, 2H), 3.74 (d, J = 12.0 Hz, 2H), 3.63 (d, J = 9.6 Hz, 2H), 3.48 (d, J = 4.4 Hz, 2H), 2.97 (t, J = 12.0 Hz, 2H), 2.91-2.81 (m, 3H), 2.78-2.65 (m, 2H), 2.41-2.23 (m, 2H), 2.13-1.93 (m, 7H), 1.84-1.71 (m, 3H), 1.63-1.41 (m, 5H), 1.29 (t, J = 6.8 Hz, 2H), 0.90 (t, J = 7.2 Hz, 3H) |
| 67 | 910.7 | $^1$H NMR (400 MHz, CD$_3$OD) δ 9.10 (s, 1H), 8.42 (s, 1H), 7.69-7.60 (m, 2H), 7.40-7.34 (m, 1H), 7.31 (dd, J = 2.4, 8.8 Hz, 2H), 7.22-7.14 (m, 2H), 7.01 (d, J = 2.8 Hz, 1H), 5.06 (dd, J = 5.6, 12.4 Hz, 1H), 4.80 (d, J = 5.6 Hz, 2H), 4.70 (d, J = 15.2 Hz, 2H), 4.03 (d, J = 12.8 Hz, 2H), 3.92 (s, 2H), 3.82 (t, J = 14.8 Hz, 2H), 3.58 (d, J = 11.2 Hz, 2H), 3.43 (s, 2H), 3.03-2.80 (m, 5H), 2.79-2.63 (m, 2H), 2.45-2.21 (m, 2H), 2.14-2.05 (m, 1H), 2.03-1.87 (m, 6H), 1.86-1.78 (m, 2H), 1.77-1.63 (m, 2H), 1.52-1.37 (m, 2H), 1.32-1.22 (m, 4H), 0.90 (t, J = 7.2 Hz, 3H) |
| 69 | 1025.7 | $^1$H NMR (400 MHz, DMSO-d$_6$) δ 10.97 (s, 1H), 9.06 (s, 1H), 8.23-8.18 (m, 1H), 8.18-8.14 (m, 1H), 8.01-7.94 (m, 1H), 7.50-7.37 (m, 3H), 7.21-7.10 (m, 2H), 5.06 (dd, J = 5.1, 13.1 Hz, 1H), 4.60-4.41 (m, 6H), 4.35-4.26 (m, 2H), 3.01-2.86 (m, 6H), 2.80-2.71 (m, 4H), 2.63-2.54 (m, 2H), 2.32-2.21 (m, 4H), 2.14-1.94 (m, 6H), 1.86-1.67 (m, 8H), 1.63-1.53 (m, 4H), 1.39-1.24 (m, 4H), 1.19-1.05 (m, 6H). |
| 79 | 1061.2 | $^1$H NMR (400 MHz, DMSO-d6) δ 10.99 (s, 1H), 9.06 (s, 1H), 8.21 (s, 2H), 7.98 (dd, J = 6.0, 9.2 Hz, 1H), 7.52-7.43 (m, 2H), 7.40 (d, J = 2.4 Hz, 1H), 7.20-7.13 (m, 2H), 5.07 (dd, J = 5.2, 13.2 Hz, 1H), 4.56-4.44 (m, 4H), 4.38-4.29 (m, 2H), 3.93 (s, 1H), 3.72-3.62 (m, 4H), 3.54-3.40 (m, 3H), 3.02 (d, J = 10.4 Hz, 2H), 2.95-2.85 (m, 3H), 2.82-2.67 (m, 4H), 2.64-2.56 (m, 1H), 2.46-2.37 (m, 1H), 2.17 (d, J = 6.8 Hz, 2H), 2.07-1.94 (m, 3H), 1.92-1.59 (m, 16H), 1.43-1.37 (m, 4H), 1.32-1.22 (m, 2H) |
| 80 | 1050.3 | |
| 81 | 1041.6 | $^1$H NMR (400 MHz, CD3OD-d4) δ 9.00 (s, 1H), 7.85 (dd, J = 5.6, 9.2 Hz, 1H), 7.66 (d, J = 8.4 Hz, 1H), 7.36-7.16 (m, 4H), 5.12 (dd, J = 5.2, 13.2 Hz, 1H), 4.67-4.54 (m, 4H), 4.50-4.36 (m, 2H), 3.75-3.62 (m, 4H), 3.50-3.43 (m, 2H), 3.36 (s, 1H), 3.08 (dd, J = 1.6, 4.0 Hz, |

TABLE 2-continued

| Cmpd | LC/MS | NMR |
|---|---|---|
| | | 2H), 2.98-2.82 (m, 5H), 2.81-2.70 (m, 3H), 2.57-2.43 (m, 1H), 2.28-2.10 (m, 5H), 1.99 (s, 2H), 1.89-1.67 (m, 10H), 1.65-1.53 (m, 2H), 1.49-1.36 (m, 3H), 1.25 (d, J = 6.8 Hz, 6H) |
| 82 | 1022.2 | |
| 83 | 994.1 | $^1$H NMR (400 MHz, DMSO-d6) δ 11.09 (s, 1H), 9.05 (s, 1H), 8.21 (s, 2H), 7.98 (dd, J = 6.0, 9.2 Hz, 1H), 7.47 (t, J = 9.2 Hz, 1H), 7.40 (d, J = 2.4 Hz, 1H), 7.18 (d, J = 2.4 Hz, 1H), 7.01-6.93 (m, 1H), 6.92-6.83 (m, 2H), 5.35 (br dd, J = 5.6, 12.4 Hz, 1H), 4.54-4.43 (m, 3H), 4.35 (br d, J = 11.6 Hz, 1H), 3.94 (s, 1H), 3.70-3.57 (m, 9H), 3.10 (br d, J = 8.4 Hz, 2H), 2.93-2.83 (m, 1H), 2.76-2.61 (m, 6H), 2.46 (br s, 4H), 2.35 (br s, 4H), 2.26-2.19 (m, 2H), 2.03-1.96 (m, 1H), 1.84-1.76 (m, 2H), 1.71 (br s, 4H), 1.66-1.58 (m, 1H), 1.42 (br s, 8H), 1.35-1.25 (m, 2H) |
| 84 | 1020.2 | |
| 85 | 999.2 | $^1$H NMR (400 MHz, DMSO-d6) δ 10.94 (s, 1H), 9.13 (s, 1H), 8.17 (s, 2H), 7.82-7.70 (m, 1H), 7.50 (d, J = 8.8 Hz, 1H), 7.41-7.30 (m, 2H), 7.09-6.96 (m, 3H), 5.04 (dd, J = 5.2, 13.2 Hz, 1H), 4.62-4.47 (m, 2H), 4.44-4.36 (m, 1H), 4.34-4.25 (m, 2H), 4.23-4.09 (m, 2H), 3.95-3.67 (m, 7H), 3.39-3.23 (m, 2H), 2.96-2.70 (m, 6H), 2.59 (d, J = 16.4 Hz, 1H), 2.43-2.29 (m, 6H), 2.28-2.04 (m, 7H), 1.96-1.88 (m, 2H), 1.85-1.72 (m, 9H), 1.53-1.34 (m, 2H), 1.21-1.09 (m, 2H), 0.77-0.67 (m, 3H) |
| 86 | 1011.2 | $^1$H NMR (400 MHz, DMSO-d6) δ 10.94 (s, 1H), 9.14-9.06 (m, 1H), 8.19 (s, 3H), 7.76 (dd, J = 6.0, 9.2 Hz, 1H), 7.49 (d, J = 9.2 Hz, 1H), 7.39-7.30 (m, 2H), 7.09-6.99 (m, 3H), 5.03 (dd, J = 5.2, 13.2 Hz, 1H), 4.51-4.40 (m, 4H), 4.33-4.28 (m, 1H), 4.16 (s, 1H), 3.85 (br d, J = 12.8 Hz, 4H), 2.96-2.88 (m, 3H), 2.87-2.75 (m, 5H), 2.73-2.66 (m, 2H), 2.61-2.55 (m, 1H), 2.41-2.31 (m, 2H), 2.20-2.08 (m, 3H), 2.06-1.84 (m, 6H), 1.80-1.64 (m, 7H), 1.58 (br d, J = 11.6 Hz, 4H), 1.39-1.21 (m, 3H), 1.20-0.99 (m, 8H), 0.72 (t, J = 7.2 Hz, 3H) |
| 87 | 1007.2 | |
| 88 | 1025.2 | $^1$H NMR (400 MHz, DMSO-d6) δ 10.97 (s, 1H), 9.06 (s, 1H), 8.20 (s, 3H), 8.01-7.92 (m, 1H), 7.51-7.41 (m, 2H), 7.39 (d, J = 2.4 Hz, 1H), 7.21-7.10 (m, 2H), 5.07 (dd, J = 5.2, 13.2 Hz, 1H), 4.59-4.42 (m, 4H), 4.41-4.26 (m, 2H), 3.93 (s, 1H), 3.80-3.64 (m, 4H), 3.47 (d, J = 1.2 Hz, 2H), 2.99-2.82 (m, 5H), 2.80-2.69 (m, 4H), 2.64-2.53 (m, 2H), 2.45-2.30 (m, 2H), 2.23-2.14 (m, 2H), 2.08-1.92 (m, 5H), 1.81-1.69 (m, 6H), 1.64 (t, J = 11.6 Hz, 4H), 1.51 (d, J = 1.6 Hz, 2H), 1.42-1.32 (m, 1H), 1.31-1.22 (m, 2H), 1.21-1.03 (m, 6H) |
| 89 | 925.0 | |
| 90 | 1025.2 | $^1$H NMR (400 MHz, DMSO-d6) δ 10.94 (s, 1H), 8.99 (s, 1H), 8.20 (s, 3H), 7.97 (dd, J = 6.0, 8.8 Hz, 1H), 7.53-7.42 (m, 2H), 7.39 (s, 1H), 7.22-7.08 (m, 1H), 7.07-6.93 (m, 2H), 5.04 (dd, J = 5.2, 13.2 Hz, 1H), 4.36-4.13 (m, 5H), 3.90-3.81 (m, 5H), 3.62 (s, 10H), 2.94-2.75 (m, 6H), 2.64-2.52 (m, 4H), 2.39-2.28 (m, 2H), 2.18-2.08 (m, 4H), 2.02-1.91 (m, 2H), 1.80-1.62 (m, 9H), 1.60-1.34 (m, 7H), 1.25-1.07 (m, 3H) |

TABLE 2-continued

| Cmpd | LC/MS | NMR |
|---|---|---|
| 91 | 1025.2 | |
| 92 | 997.1 | $^1$H NMR (400 MHz, DMSO-d6) δ 10.98 (s, 1H), 9.05 (s, 1H), 8.21 (s, 2H), 7.97 (dd, J = 6.0, 9.2 Hz, 1H), 7.55-7.42 (m, 2H), 7.39 (d, J = 2.4 Hz, 1H), 7.21-7.11 (m, 2H), 5.07 (dd, J = 5.2, 13.2 Hz, 1H), 4.56-4.41 (m, 5H), 4.40-4.23 (m, 3H), 3.94 (s, 1H), 3.73-3.59 (m, 4H), 3.09 (b s, 4H), 2.99-2.86 (m, 3H), 2.71 (t, J = 4.8 Hz, 2H), 2.58 (d, J = 16.8 Hz, 1H), 2.46-2.31 (m, 5H), 2.19 (d, J = 6.8 Hz, 2H), 2.11-1.89 (m, 3H), 1.74 (s, 4H), 1.65 (d, J = 11.2 Hz, 2H), 1.60-1.39 (m, 9H), 1.20-0.99 (m, 2H) |
| 93 | 979.1 | $^1$H NMR (400 MHz, DMSO-d6) δ 10.94 (s, 1H), 9.04 (s, 1H), 8.20 (s, 2H), 7.96 (dd, J = 6.0, 9.2 Hz, 1H), 7.58-7.42 (m, 2H), 7.38 (d, J = 2.4 Hz, 1H), 7.17 (d, J = 2.4 Hz, 1H), 7.07-6.95 (m, 2H), 5.03 (dd, J = 5.2, 13.2 Hz, 1H), 4.50 (d, J = 12.0 Hz, 1H), 4.44 (t, J = 5.6 Hz, 2H), 4.39-4.31 (m, 2H), 4.28 (s, 1H), 4.17 (d, J = 16.8 Hz, 2H), 3.93 (s, 1H), 3.70 (s, 2H), 3.67-3.60 (m, 2H), 3.28 (d, J = 0.8 Hz, 4H), 2.98-2.82 (m, 3H), 2.70 (t, J = 5.2 Hz, 2H), 2.62-2.53 (m, 1H), 2.43-2.26 (m, 5H), 2.21-2.12 (m, 2H), 2.08-1.88 (m, 3H), 1.73 (s, 4H), 1.68-1.59 (m, 2H), 1.48 (d, J = 4.4 Hz, 9H), 1.17-0.94 (m, 2H) |
| 94 | 1050.3 | $^1$H NMR (400 MHz, DMSO-d6) δ 11.06 (s, 1H), 9.06 (s, 1H), 8.16 (s, 2H), 7.97 (dd, J = 6.0, 9.2 Hz, 1H), 7.46 (t, J = 9.2 Hz, 1H), 7.39 (d, J = 2.4 Hz, 1H), 7.17 (d, J = 2.4 Hz, 1H), 7.02-6.91 (m, 1H), 6.90-6.76 (m, 2H), 5.66-5.54 (m, 1H), 5.28 (br dd, J = 5.2, 12.8 Hz, 1H), 4.54 (br d, J = 12.4 Hz, 1H), 4.47 (br t, J = 5.2 Hz, 2H), 4.39 (br d, J = 12.8 Hz, 1H), 3.93 (s, 1H), 3.83 (br s, 2H), 3.71 (br s, 3H), 3.08 (br d, J = 10.4 Hz, 2H), 3.00-2.82 (m, 6H), 2.76-2.70 (m, 2H), 2.69-2.56 (m, 4H), 2.30 (br d, J = 6.0 Hz, 2H), 2.10-1.92 (m, 5H), 1.85-1.72 (m, 6H), 1.69-1.55 (m, 5H), 1.45 (dd, J = 6.8, 10.8 Hz, 6H), 1.37-1.20 (m, 4H), 1.19-1.03 (m, 6H) |
| 95 | 1038.2 | |
| 96 | 1010.1 | |
| 97 | 1021.2 | |
| 98 | 1050.3 | |
| 99 | 950.1 | $^1$H NMR (400 MHz, CD3OD-d4) δ 9.01 (s, 1H), 7.89-7.83 (m, 1H), 7.60 (d, J = 8.4 Hz, 1H), 7.36-7.29 (m, 2H), 7.21 (d, J = 2.4 Hz, 1H), 7.07-7.02 (m, 2H), 5.13-5.07 (m, 1H), 4.63 (br t, J = 13.6 Hz, 3H), 4.51-4.47 (m, 1H), 4.40-4.32 (m, 3H), 3.88 (br d, J = 11.6 Hz, 2H), 3.75-3.65 (m, 4H), 3.37 (s, 1H), 3.23-3.13 (m, 2H), 2.91-2.74 (m, 4H), 2.62-2.39 (m, 3H), 2.18-2.07 (m, 2H), 1.90-1.69 (m, 8H), 1.64-1.53 (m, 1H), 1.51-1.40 (m, 1H), 1.29-1.14 (m, 6H), 0.80-0.71 (m, 2H), 0.56 (br s, 2H) |
| 100 | 1020.2 | $^1$H NMR (400 MHz, CD3OD-d4) δ 9.02 (s, 1H), 7.87-7.85 (m, 1H), 7.62 (dd, J = 2.4, 8.8 Hz, 1H), 7.40-7.26 (m, 2H), 7.21 (t, J = 2.0 Hz, 1H), 7.10-7.00 (m, 2H), 5.09 (d, J = 4.8 Hz, 1H), 4.68-4.54 (m, 4H), 4.48-4.28 (m, 5H), 3.90 (d, J = 12.4 Hz, 2H), 3.77-3.60 (m, 5H), 3.36 (s, 1H), 2.91-2.78 (m, 5H), 2.64-2.43 (m, 9H), 2.29-2.17 (m, 4H), 1.95-1.69 (m, 14H), 1.33-1.22 (m, 2H) |
| 101 | 1026.2 | |
| 102 | 1022.2 | |

TABLE 2-continued

| Cmpd | LC/MS | NMR |
|---|---|---|
| 103 | 916.0 | $^1$H NMR (400 MHz, DMSO-d6) δ 10.98 (s, 1H), 9.06 (s, 1H), 8.12 (s, 1H), 8.01-7.93 (m, 1H), 7.50-7.42 (m, 2H), 7.39 (d, J = 2.4 Hz, 1H), 7.19-7.12 (m, 2H), 7.24-7.17 (m, 1H), 7.07-6.97 (m, 2H), 5.05 (dd, J = 5.2, 9.2 Hz, 1H), 4.56-4.51 (m, 1H), 4.50-4.45 (m, 1H), 4.42-4.35 (m, 2H), 4.33-4.28 (m, 1H), 4.25-4.15 (m, 2H), 3.96-3.93 (m, 1H), 3.79-3.64 (m, 5H), 3.56-3.48 (m, 2H), 3.41-3.26 (m, 4H), 2.96-2.87 (m, 3H), 2.85-2.76 (m, 1H), 2.62-2.55 (m, 1H), 2.44-2.38 (m, 1H), 2.37 (s, 3H), 2.25-2.19 (m, 1H), 1.99-1.86 (m, 5H), 1.77-1.74 (m, 3H), 1.63-1.53 (m, 2H) |
| 104 | 898.0 | |
| 105 | 1038.2 | |
| 106 | 1027.1 | $^1$H NMR (400 MHz, DMSO-d6) δ 10.99 (s, 1H), 9.05 (s, 1H), 8.21 (s, 2H), 7.98 (dd, J = 5.8, 9.2 Hz, 1H), 7.51-7.42 (m, 2H), 7.39 (d, J = 2.4 Hz, 1H), 7.20-7.10 (m, 2H), 5.07 (dd, J = 5.2, 13.2 Hz, 1H), 4.55-4.43 (m, 4H), 4.39-4.27 (m, 3H), 3.94 (s, 1H), 3.76-3.71 (m, 2H), 3.69-3.62 (m, 2H), 3.52-3.44 (m, 2H), 3.39 (s, 2H), 3.16 (s, 2H), 2.97-2.85 (m, 1H), 2.83-2.64 (m, 8H), 2.62-2.54 (m, 1H), 2.44-2.31 (m, 1H), 2.17 (d, J = 6.4 Hz, 3H), 2.08-1.94 (m, 3H), 1.75 (s, 9H), 1.69-1.59 (m, 1H), 1.47-1.32 (m, 4H), 1.31-1.17 (m, 2H) |
| 107 | 1007.2 | |
| 108 | 1006.2 | |
| 109 | 1041.6 | |
| 110 | 1007.2 | $^1$H NMR (400 MHz, DMSO-d6) δ 10.99 (s, 1H), 9.08 (s, 1H), 8.21 (s, 3H), 7.99 (dd, J = 6.0, 9.2 Hz, 1H), 7.47 (t, J = 9.2 Hz, 1H), 7.44-7.37 (m, 2H), 7.25 (dd, J = 2.0, 8.4 Hz, 1H), 7.19 (d, J = 2.4 Hz, 1H), 7.15 (d, J = 1.6 Hz, 1H), 5.10 (dd, J = 5.2, 13.2 Hz, 1H), 4.57 (d, J = 12.4 Hz, 1H), 4.52-4.48 (m, 2H), 4.42 (d, J = 12.4 Hz, 1H), 4.37-4.30 (m, 1H), 4.24-4.17 (m, 1H), 3.95 (s, 1H), 3.90-3.88 (m, 2H), 3.81-3.69 (m, 4H), 3.05-2.87 (m, 5H), 2.82-2.68 (m, 4H), 2.63-2.57 (m, 2H), 2.43-2.29 (m, 4H), 2.13-2.07 (m, 4H), 2.01-1.94 (m, 1H), 1.87-1.71 (m, 7H), 1.63-1.57 (m, 4H), 1.41-1.29 (m, 2H), 1.27-1.04 (m, 8H) |
| 111 | 1008.2 | |
| 112 | 1031.1 | $^1$H NMR (400 MHz, DMSO-d6) δ 10.99 (s, 1H), 9.04 (s, 1H), 8.20 (s, 2H), 7.97 (dd, J = 6.0, 9.2 Hz, 1H), 7.50-7.43 (m, 2H), 7.39 (d, J = 2.4 Hz, 1H), 7.24-7.15 (m, 2H), 5.07 (dd, J = 4.8, 13.2 Hz, 1H), 4.52-4.45 (m, 2H), 4.41-4.29 (m, 3H), 4.24-4.20 (m, 1H), 4.14-4.09 (m, 1H), 3.94 (d, J = 2.0 Hz, 1H), 3.59 (s, 5H), 3.05-2.97 (m, 3H), 2.94 (s, 2H), 2.81-2.73 (m, 4H), 2.60 (d, J = 2.8 Hz, 2H), 2.37-2.31 (m, 5H), 2.24-2.13 (m, 4H), 2.02-1.93 (m, 3H), 1.92-1.85 (m, 3H), 1.78 (d, J = 8.4 Hz, 4H), 1.72-1.65 (m, 4H), 1.45-1.34 (m, 2H) |
| 113 | 1029.6 | |
| 114 | 941.0 | $^1$H NMR (400 MHz, DMSO-d6) δ 10.97-10.89 (m, 1H), 9.02 (t, J = 2.8 Hz, 1H), 8.16 (d, J = 3.2 Hz, 1H), 7.96 (dd, J = 6.0, 9.6 Hz, 1H), 7.52 (d, J = 8.4 Hz, 1H), 7.45 (t, J = 8.8 Hz, 1H), 7.38 (d, J = 2.4 Hz, 1H), 7.16 (d, J = 2.4 Hz, 1H), 7.08-7.00 (m, 2H), 5.06-5.00 (m, 1H), 4.49-4.39 (m, 2H), 4.31 (d, J = 16.8 Hz, 2H), 4.24-4.16 (m, 2H), 4.04 (t, J = 5.2 Hz, 2H), 3.92 (s, 1H), 3.66-3.58 (m, 6H), 3.51 (d, J = 1.6 Hz, 6H), 3.19-3.14 (m, 4H), 2.95-2.83 (m, 2H), 2.60-2.56 (m, 2H), 2.35 (d, J = 4.0 Hz, 1H), 2.02-1.90 (m, 3H), 1.67 (s, 5H), 1.63-1.58 (m, 1H) |
| 115 | 995.1 | $^1$H NMR (400 MHz, DMSO-d6) δ 10.97 (s, 1H), 9.06 (s, 1H), 8.17 (s, 2H), 7.98 (dd, J = 6.0, 9.2Hz, 1H), 7.50-7.37 (m, 3H), 7.32-7.26 (m, 1H), 7.21-7.11 (m, 2H), 5.11 (dd, J = 5.2, 9.2Hz, 1H), 4.61-4.51 (m, 1H), 4.46-4.36 (m, 3H), 4.33-4.24 (m, 2H), 4.16-4.10 (m, 1H), 3.95-3.92 (m, 1H), 3.83 (s, 2H), 3.77-3.69 (m, 2H), 3.40-3.25 (m, 4H), 2.99-2.86 (m, 1H), 2.85-2.78 (m, 1H), 2.75-2.66 (m, 4H), 2.62-2.54 (m, 2H), 2.36 (s, 3H), 2.23-2.16 (m, 3H), 2.11-1.99 (m, 3H), 1.94-1.73 (m, 11H), 1.69-1.60 (m, 1H), 1.48-1.36 (m, 2H), 1.34-1.19 (m, 2H) |
| 116 | 995.1 | |
| 117 | 941.0 | $^1$H NMR (400 MHz, DMSO-d6) δ 10.98 (s, 1H), 9.08-8.97 (m, 1H), 8.17 (s, 1H), 7.97 (dd, J = 5.6, 9.2 Hz, 1H), 7.50-7.40 (m, 2H), 7.39 (d, J = 2.4 Hz, 1H), 7.34 (d, J = 7.6 Hz, 1H), 7.20-7.14 (m, 2H), 5.12 (dd, J = 5.2, 13.2 Hz, 1H), 4.52-4.40 (m, 3H), 4.37-4.27 (m, 2H), 4.26-4.19 (m, 1H), 4.11-4.03 (m, 2H), 3.92 (s, 1H), 3.64 (s, 4H), 3.53 (s, 2H), 3.24-3.22 (m, 2H), 3.16 (d, J = 2.0 Hz, 2H), 3.06-3.00 (m, 4H), 2.92-2.87 (m, 1H), 2.64-2.54 (m, 2H), 2.51-2.51 (m, 3H), 2.45-2.40 (m, 1H), 2.04-1.95 (m, 3H), 1.70 (s, 6H) |
| 118 | 884.0 | $^1$H NMR (400 MHz, DMSO-d6) δ 10.97 (s, 1H), 9.09 (s, 1H), 8.18 (s, 1H), 7.66 (d, J = 8.4 Hz, 1H), 7.45-7.33 (m, 2H), 7.32-7.26 (m, 2H), 7.14 (dd, J = 7.6, 14.4 Hz, 2H), 6.97 (d, J = 2.4 Hz, 1H), 5.10 (dd, J = 5.2, 13.2 Hz, 1H), 4.48-4.36 (m, 4H), 4.33-4.23 (m, 2H), 4.22-4.13 (m, 1H), 3.66 (d, J = 1.2 Hz, 1H), 3.61-3.57 (m, 3H), 3.54-3.47 (m, 5H), 2.95-2.77 (m, 5H), 2.68-2.59 (m, 1H), 2.36 (s, 3H), 2.29-2.17 (m, 3H), 2.01-1.89 (m, 5H), 1.69-1.54 (m, 6H), 0.81 (t, J = 7.6 Hz, 3H) |
| 119 | 987.1 | $^1$H NMR (400 MHz, DMSO-d6) δ 10.98 (s, 1H), 9.08 (s, 1H), 8.14 (s, 2H), 7.98 (dd, J = 5.6, 9.2 Hz, 1H), 7.56-7.43 (m, 2H), 7.40 (d, J = 2.6 Hz, 1H), 7.27-7.13 (m, 2H), 5.07 (dd, J = 4.6, 13.4 Hz, 1H), 4.60 (d, J = 13.2 Hz, 1H), 4.54-4.40 (m, 4H), 4.31 (d, J = 16.8 Hz, 1H), 3.99 (s, 2H), 3.93 (s, 1H), 3.79-3.70 (m, 2H), 3.53-3.40 (m, 3H), 3.04 (s, 4H), 3.00-2.82 (m, 3H), 2.72 (d, J = 12.4 Hz, 3H), 2.65 (s, 1H), 2.62-2.53 (m, 3H), 2.47-2.34 (m, 4H), 1.98 (dd, J = 6.0, 11.2 Hz, 1H), 1.91-1.81 (m, 6H), 1.80-1.71 (m, 2H), 1.68 (s, 3H) |
| 120 | 1015.1 | $^1$H NMR (400 MHz, DMSO-d6) δ 10.99 (s, 1H), 9.07 (s, 1H), 8.15 (s, 2H), 7.98 (dd, J = 6.0, 9.0 Hz, 1H), 7.50-7.44 (m, 2H), 7.40 (d, J = 2.4 Hz, 1H), 7.23-7.15 (m, 2H), 5.07 (dd, J = 5.2, 13.2 Hz, 1H), 4.65-4.36 (m, 6H), 4.31 (d, J = 16.8 Hz, 1H), 3.96-3.87 (m, 4H), 3.74 (t, J = 12.8 Hz, 4H), 3.02 (dd, J = 10.0, 11.2 Hz, 4H), 2.96-2.88 (m, 2H), 2.81 (s, 3H), 2.60 (s, 1H), 2.55 (s, 4H), 2.02-1.88 (m, 4H), 1.87-1.68 (m, 6H), 1.49-1.35 (m, 8H) |

TABLE 2-continued

| Cmpd | LC/MS | NMR |
|---|---|---|
| 121 | 997.1 | $^1H$ NMR (400 MHz, DMSO-d6) δ 11.00 (s, 1H), 9.11 (s, 1H), 8.16 (s, 1H), 7.99 (dd, J = 6.0, 9.2 Hz, 1H), 7.57-7.38 (m, 3H), 7.32 (d, J = 7.6 Hz, 1H), 7.24-7.11 (m, 2H), 5.12 (dd, J = 5.2, 13.2 Hz, 1H), 4.65 (br d, J = 12.8 Hz, 1H), 4.56-4.48 (m, 3H), 4.44 (br d, J = 17.6 Hz, 1H), 4.29 (br d, J = 17.2 Hz, 1H), 4.16 (br s, 2H), 3.95 (s, 1H), 3.83 (br d, J = 13.6 Hz, 2H), 3.45-3.33 (m, 4H), 3.23 (br d, J = 9.2 Hz, 2H), 2.97-2.89 (m, 1H), 2.81 (br d, J = 6.0 Hz, 4H), 2.75 (br d, J = 12.0 Hz, 3H), 2.60 (br d, J = 16.0 Hz, 2H), 2.53 (br d, J = 2.0 Hz, 1H), 2.49-2.34 (m, 4H), 2.05-1.92 (m, 5H), 1.82 (br t, J = 11.6 Hz, 6H), 1.71 (br d, J = 10.0 Hz, 2H), 1.62-1.48 (m, 3H), 1.45-1.26 (m, 4H) |
| 122 | 1013.1 | |
| 123 | 1025.2 | |
| 124 | 1025.2 | $^1H$ NMR (400 MHz, DMSO-d6) δ 11.00 (s, 1H), 9.11 (s, 1H), 8.16 (s, 1H), 7.99 (dd, J = 6.0, 9.2 Hz, 1H), 7.57-7.38 (m, 3H), 7.32 (d, J = 7.6 Hz, 1H), 7.24-7.11 (m, 2H), 5.12 (dd, J = 5.2, 13.2 Hz, 1H), 4.65 (br d, J = 12.8 Hz, 1H), 4.56-4.48 (m, 3H), 4.44 (br d, J = 17.6 Hz, 1H), 4.29 (br d, J = 17.2 Hz, 1H), 4.16 (br s, 2H), 3.95 (s, 1H), 3.83 (br d, J = 13.6 Hz, 2H), 3.45-3.33 (m, 4H), 3.23 (br d, J = 9.2 Hz, 2H), 2.97-2.89 (m, 1H), 2.81 (br d, J = 6.0 Hz, 4H), 2.75 (br d, J = 12.0 Hz, 3H), 2.60 (br d, J = 16.0 Hz, 2H), 2.53 (br d, J = 2.0 Hz, 1H), 2.49-2.34 (m, 4H), 2.05-1.92 (m, 5H), 1.82 (br t, J = 11.6 Hz, 6H), 1.71 (br d, J = 10.0 Hz, 2H), 1.62-1.48 (m, 3H), 1.45-1.26 (m, 4H) |
| 125 | 1025.2 | $^1H$ NMR (400 MHz, DMSO-d6) δ 10.98 (s, 1H), 9.06 (s, 1H), 8.17 (s, 2H), 7.98 (dd, J = 6.0, 9.2 Hz, 1H), 7.52-7.37 (m, 3H), 7.31 (d, J = 7.6 Hz, 1H), 7.22-7.13 (m, 2H), 5.12 (dd, J = 5.2, 13.2 Hz, 1H), 4.56-4.36 (m, 5H), 4.29 (d, J = 17.2 Hz, 1H), 3.93 (s, 1H), 3.78 (s, 3H), 3.71 (d, J = 14.8 Hz, 5H), 3.44 (dd, J = 3.2, 7.6 Hz, 3H), 3.25-3.20 (m, 2H), 3.02-2.91 (m, 5H), 2.87 (d, J = 10.4 Hz, 2H), 2.72 (t, J = 5.8 Hz, 2H), 2.59 (s, 1H), 2.05 (t, J = 10.4 Hz, 4H), 2.00-1.88 (m, 3H), 1.88-1.82 (m, 1H), 1.77 (s, 4H), 1.57 (t, J = 13.2 Hz, 3H), 1.35-1.22 (m, 2H), 1.15-1.03 (m, 5H) |
| 126 | 1007.2 | $^1H$ NMR (400 MHz, CD3OD-d4) δ 9.00 (s, 1H), 7.88-7.84 (m, 1H), 7.45-7.42 (m, 2H), 7.35-7.30 (m, 2H), 7.24-7.21 (m, 2H), 5.16-5.12 (m, 1H), 4.66-4.56 (m, 5H), 4.48-4.47 (m, 2H), 3.73-3.66 (m, 4H), 3.40 (s, 1H), 3.38 (s, 2H), 3.13-3.10 (m, 2H), 3.01-2.99 (m, 2H), 2.92-2.86 (m, 3H), 2.80-2.73 (m, 3H), 2.58-2.50 (m, 1H), 2.34-2.31 (m, 2H), 2.24-2.07 (m, 5H), 1.87-1.72 (m, 10H), 1.48-1.22 (m, 10H) |
| 127 | 969.1 | |
| 128 | 924.1 | $^1H$ NMR (400 MHz, DMSO-d6) δ 10.97 (s, 1H), 9.04 (s, 1H), 8.17-8.15 (m, 1H), 7.97 (dd, J1 = 6.0 Hz, J2 = 9.2 Hz, 1H), 7.51-7.36 (m, 3H), 7.28 (d, J = 7.2 Hz, 1H), 7.20-7.11 (m, 2H), 5.15-5.06 (m, 1H), 4.57-4.20 (m, 8H), 3.92 (s, 1H), 3.65-3.61 (m, 4H), 2.99-2.88 (m, 4H), 2.75-2.65 (m, 6H), 2.06-1.94 (m, 3H), 1.78-1.61 (m, 8H), 1.31-1.06 (m, 10H) |
| 129 | 925.0 | $^1H$ NMR (400 MHz, DMSO-d6) δ 11.08 (s, 1H), 9.05 (s, 1H), 8.18 (s, 2H), 7.97 (dd, J = 6.0, 9.2 Hz, 1H), 7.46 (t, J = 9.2 Hz, 1H), 7.39 (d, J = 2.4 Hz, 1H), 7.17 (d, J = 2.4 Hz, 1H), 6.99-6.92 (m, 1H), 6.90-6.82 (m, 2H), 5.38-5.30 (m, 1H), 4.52-4.42 (m, 3H), 4.39-4.33 (m, 1H), 3.93 (s, 1H), 3.69 (s, 2H), 3.64 (s, 1H), 3.61 (s, 3H), 3.58 (s, 1H), 3.08 (d, J = 9.6 Hz, 2H), 2.96 (d, J = 10.4 Hz, 2H), 2.89-2.83 (m, 1H), 2.74-2.62 (m, 6H), 2.45 (s, 1H), 2.07-1.96 (m, 3H), 1.72 (s, 6H), 1.66-1.59 (m, 2H), 1.50-1.41 (m, 1H), 1.37-1.25 (m, 3H), 1.19-1.06 (m, 4H) |
| 130 | 1025.2 | $^1H$ NMR (400 MHz, DMSO-d6) δ 11.00 (s, 1H), 9.07 (s, 1H), 8.22 (s, 3H), 7.97 (dd, J = 6.0, 9.2 Hz, 1H), 7.46 (t, J = 9.2 Hz, 1H), 7.40 (d, J = 2.4 Hz, 1H), 7.18 (d, J = 2.4 Hz, 1H), 6.99 (dd, J = 2.0, 7.2 Hz, 1H), 6.92 (dd, J = 2.0, 12.0 Hz, 1H), 5.10 (dd, J = 5.2, 13.2 Hz, 3H), 5.00-4.78 (m, 3H), 4.56 (d, J = 12.8 Hz, 1H), 4.51-4.36 (m, 4H), 4.33-4.22 (m, 1H), 3.93 (s, 1H), 3.86 (s, 2H), 3.74 (t, J = 12.4 Hz, 2H), 3.54-3.36 (m, 2H), 3.05-2.94 (m, 2H), 2.89 (d, J = 11.2 Hz, 2H), 2.83-2.68 (m, 4H), 2.63-2.52 (m, 2H), 2.47-2.40 (m, 1H), 2.26 (d, J = 6.4 Hz, 2H), 2.15-1.93 (m, 5H), 1.87-1.68 (m, 6H), 1.60 (d, J = 11.6 Hz, 3H), 1.31 (d, J = 4.0 Hz, 2H), 1.26-1.18 (m, 2H), 1.18-1.02 (m, 5H |
| 131 | 1025.2 | $^1H$ NMR (400 MHz, DMSO-d6) δ 11.00 (s, 1H), 9.79-9.48 (m, 2H), 9.42-9.26 (m, 1H), 9.16 (s, 1H), 8.00 (dd, J = 6.0, 9.2 Hz, 1H), 7.55-7.39 (m, 3H), 7.33 (d, J = 7.6 Hz, 1H), 7.23-7.14 (m, 2H), 5.13 (dd, J = 5.2, 13.2 Hz, 1H), 4.90-4.53 (m, 4H), 4.50-4.38 (m, 1H), 4.35-4.19 (m, 3H), 3.73-3.34 (m, 10H), 3.19-2.87 (m, 7H), 2.84-2.70 (m, 2H), 2.69-2.57 (m, 2H), 2.21-1.71 (m, 16H), 1.71-1.27 (m, 6H) |
| 132 | 979.1 | $^1H$ NMR (400 MHz, DMSO-d6) δ 10.98 (s, 1H), 9.05 (s, 1H), 8.19 (s, 3H), 7.97 (dd, J = 6.0, 9.2 Hz, 1H), 7.52-7.37 (m, 3H), 7.28 (d, J = 7.2 Hz, 1H), 7.20-7.12 (m, 2H), 5.11 (dd, J = 5.2, 13.2 Hz, 1H), 4.51 (d, J = 12.4 Hz, 1H), 4.47-4.43 (m, 2H), 4.41-4.34 (m, 2H), 4.27 (d, J = 17.2 Hz, 2H), 3.93 (s, 1H), 3.70 (s, 2H), 3.64 (s, 2H), 3.40-3.32 (m, 4H), 2.98-2.85 (m, 2H), 2.75-2.68 (m, 4H), 2.58 (d, J = 17.2 Hz, 2H), 2.46-2.43 (m, 2H), 2.35 (s, 4H), 2.22 (d, J = 7.2 Hz, 2H), 2.03-1.94 (m, 1H), 1.79 (d, J = 12.4 Hz, 2H), 1.72 (s, 4H), 1.41 (s, 8H), 1.28-1.19 (m, 2H) |
| 133 | 1022.2 | $^1H$ NMR (400 MHz, DMSO-d6) δ 11.08 (s, 1H), 9.05 (s, 1H), 8.18 (s, 3H), 7.97 (dd, J = 6.0, 9.2 Hz, 1H), 7.46 (t, J = 9.2 Hz, 1H), 7.39 (d, J = 2.4 Hz, 1H), 7.17 (d, J = 2.4 Hz, 1H), 7.02-6.92 (m, 1H), 6.91-6.82 (m, 2H), 5.36-5.31 (m, 1H), 4.51-4.48 (m, 1H), 4.45 (t, J = 5.2 Hz, 2H), 4.36-4.33 (m, 1H), 3.92 (s, 1H), 3.65 (s, 2H), 3.61 (s, 3H), 3.10 (d, J = 8.4 Hz, 4H), 2.97-2.81 (m, 7H), 2.73-2.63 (m, 6H), 2.20 (dd, J = 1.2, 4.0 Hz, 2H), 2.04-1.96 (m, 3H), 1.93-1.85 (m, 2H), 1.81-1.76 (m, 2H), 1.71 (s, 3H), 1.60-1.57 (m, 5H), 1.29 (d, J = 6.4 Hz, 4H), 1.15-1.04 (m, 6H) |
| 134 | 979.1 | |
| 135 | 951.1 | $^1H$ NMR (400 MHz, DMSO-d6) δ 10.97 (s, 1H), 9.11-9.02 (m, 1H), 8.19 (s, 2H), 8.01-7.92 (m, 1H), 7.49-7.37 (m, 3H), 7.31-7.27 (m, 1H), 7.19-7.11 (m, 2H), 5.15-5.06 (m, 1H), 4.51-4.24 (m, |

TABLE 2-continued

| Cmpd | LC/MS | NMR |
|---|---|---|
| | | 7H), 3.90 (d, J = 5.2 Hz, 1H), 3.63 (d, J = 6.0 Hz, 4H), 3.34 (s, 4H), 3.02 (s, 3H), 2.95-2.89 (m, 1H), 2.73-2.55 (m, 7H), 2.43-2.35 (m, 5H), 2.02-1.95 (m, 1H), 1.75 (d, J = 12.4 Hz, 2H), 1.71-1.63 (m, 7H), 1.49-1.41 (m, 1H), 1.30-1.21 (m, 2H) |
| 136 | 1008.2 | $^1$H NMR (400 MHz, DMSO-d6) δ 10.98 (br s, 1H), 9.05 (s, 1H), 8.20 (s, 3H), 7.98 (dd, J = 6.0, 9.2 Hz, 1H), 7.57-7.35 (m, 3H), 7.28 (d, J = 7.6 Hz, 1H), 7.20-7.06 (m, 2H), 5.11 (br dd, J = 5.2, 13.2 Hz, 1H), 4.56-4.41 (m, 3H), 4.40-4.20 (m, 3H), 3.93 (s, 1H), 3.72-3.59 (m, 2H), 3.36 (t, J = 12.0 Hz, 2H), 3.01-2.83 (m, 3H), 2.77-2.65 (m, 4H), 2.58 (br d, J = 17.6 Hz, 4H), 2.49-2.43 (m, 4H), 2.41-2.23 (m, 6H), 2.16 (br d, J = 7.2 Hz, 2H), 2.12-1.93 (m, 5H), 1.83-1.71 (m, 5H), 1.64 (d, J = 11.2 Hz, 3H), 1.38 (s, 1H), 1.34-1.16 (m, 2H), 1.15-0.98 (m, 2H) |
| 137 | 1011.2 | $^1$H NMR (400 MHz, DMSO-d6) δ 10.98 (s, 1H), 9.13 (s, 1H), 8.17 (s, 2H), 7.80-7.72 (m, 1H), 7.42 (t, J = 7.6 Hz, 1H), 7.37-7.32 (m, 2H), 7.29 (d, J = 7.6 Hz, 1H), 7.15 (d, J = 8.0 Hz, 1H), 7.02 (d, J = 2.4 Hz, 1H), 5.15-5.08 (m, 1H), 4.62-4.47 (m, 5H), 4.45-4.39 (m, 1H), 4.31-4.25 (m, 1H), 3.96-3.88 (m, 2H), 2.86-2.72 (m, 3H), 3.42-3.31 (m, 2H), 3.05-2.89 (m, 5H), 2.82-2.76 (m, 2H), 2.74-2.65 (m, 2H), 2.63-2.55 (m, 1H), 2.39-2.30 (m, 3H), 2.19-2.07 (m, 5H), 2.04-1.95 (m, 1H), 1.88-1.72 (m, 7H), 1.66-1.58 (m, 4H), 1.42-1.17 (m, 6H), 1.15-1.05(m, 4H), 0.72 (t, J = 7.2 Hz, 3H) |
| 138 | 1007.2 | |
| 139 | 981.2 | $^1$H NMR (400 MHz, DMSO-d6) δ 11.00-10.96 (m, 1H), 9.10 (s, 1H), 8.15 (s, 2H), 7.67 (d, J = 8.0 Hz, 1H), 7.47-7.34 (m, 2H), 7.31-7.26 (m, 2H), 7.13 (t, J = 7.6 Hz, 2H), 6.96 (d, J = 2.4 Hz, 1H), 5.11 (dd, J = 5.2, 13.2 Hz, 1H), 4.52-4.43 (m, 2H), 4.41-4.35 (m, 2H), 4.31-4.24 (m, 2H), 4.14-4.09 (m, 1H), 3.70 (d, J = 11.6 Hz, 4H), 3.65-3.62 (m, 1H), 3.36 (s, 2H), 3.24 (d, J = 5.6 Hz, 2H), 2.94-2.88 (m, 1H), 2.81-2.77 (m, 1H), 2.73-2.67 (m, 4H), 2.61-2.56 (m, 2H), 2.35 (s, 3H), 2.30-2.23 (m, 2H), 2.22-2.19 (m, 1H), 2.16 (d, J = 7.6 Hz, 2H), 2.04-1.96 (m, 3H), 1.92-1.85 (m, 2H), 1.83-1.76 (m, 4H), 1.74-1.67 (m, 4H), 1.66-1.58 (m, 1H), 1.43-1.34 (m, 2H), 1.29-1.19 (m, 2H), 0.81 (t, J = 7.2 Hz, 3H) |
| 140 | 951.1 | $^1$H NMR (400 MHz, DMSO-d6) δ 11.03-10.96 (m, 1H), 9.06 (s, 1H), 8.19 (s, 2H), 7.98 (dd, J = 6.0, 9.2 Hz, 1H), 7.49-7.42 (m, 2H), 7.40 (d, J = 2.4 Hz, 1H), 7.30 (d, J = 7.6 Hz, 1H), 7.19-7.12 (m, 2H), 5.11 (dd, J = 5.2, 13.2 Hz, 1H), 4.54 (d, J = 12.4 Hz, 1H), 4.45 (d, J = 6.0 Hz, 2H), 4.41-4.37 (m, 2H), 4.29-4.26 (m, 1H), 3.94 (s, 1H), 3.82 (s, 2H), 3.71 (s, 2H), 3.35 (s, 2H), 2.95 (d, J = 6.0 Hz, 8H), 2.88 (d, J = 5.4 Hz, 1H), 2.73-2.70 (m, 2H), 2.61 (s, 2H), 2.56 (s, 1H), 2.46-2.42 (m, 1H), 2.06-1.96 (m, 4H), 1.84 (s, 4H), 1.78 (s, 4H), 1.64 (d, J = 10.8 Hz, 2H), 1.40 (dd, J = 2.4, 7.6 Hz, 1H), 1.20-1.10 (m, 2H) |
| 141 | 840.0 | |
| 142 | 1007.6 | |
| 143 | 1004.2 | |
| 144 | 979.1 | |
| 145 | 907.0 | |
| 146 | 907.0 | |
| 147 | 1004.2 | |
| 148 | 1040.2 | $^1$H NMR (400 MHz, DMSO-d6) δ 11.00-10.90 (m, 1H), 9.06 (s, 1H), 8.18 (s, 2H), 8.01-7.94 (m, 1H), 7.46 (t, J = 8.8 Hz, 1H), 7.39 (d, J = 2.4 Hz, 1H), 7.18 (d, J = 2.1 Hz, 1H), 6.87 (d, J = 7.2 Hz, 1H), 5.02 (dd, J = 5.2, 13.2 Hz, 1H), 4.53 (d, J = 12.8 Hz, 1H), 4.46 (s, 2H), 4.42-4.33 (m, 2H), 4.23 (d, J = 17.2 Hz, 1H), 3.93 (s, 1H), 3.76 (s, 2H), 3.73-3.64 (m, 2H), 3.47 (dd, J = 2.4, 9.2 Hz, 2H), 2.99-2.88 (m, 3H), 2.79-2.65 (m, 5H), 2.63-2.55 (m, 2H), 2.53 (s, 3H), 2.43-2.24 (m, 9H), 2.16 (d, J = 7.2 Hz, 2H), 2.09 (d, J = 7.2 Hz, 2H), 2.06-2.00 (m, 2H), 1.97-1.92 (m, 1H), 1.81-1.72 (m, 6H), 1.65 (d, J = 12.0 Hz, 3H), 1.53-1.41 (m, 1H), 1.30-1.18 (m, 2H), 1.15-1.01 (m, 2H) |
| 149 | 1039.2 | $^1$H NMR (400 MHz, DMSO-d6) δ 10.97 (s, 1H), 9.05 (s, 1H), 8.21 (s, 3H), 7.97 (dd, J = 6.0, 9.2 Hz, 1H), 7.50-7.34 (m, 2H), 7.18 (d, J = 2.4 Hz, 1H), 6.87 (d, J = 7.2 Hz, 1H), 5.02 (dd, J = 4.8, 13.2 Hz, 1H), 4.56-4.33 (m, 5H), 4.22 (d, J = 16.8 Hz, 1H), 3.93 (s, 1H), 3.79-3.60 (m, 4H), 3.47 (dd, J = 3.2, 4.4 Hz, 2H), 3.01-2.81 (m, 5H), 2.79-2.65 (m, 4H), 2.65-2.51 (m, 5H), 2.49-2.31 (m, 3H), 2.25-2.17 (m, 2H), 2.10-1.85 (m, 5H), 1.83-1.64 (m, 7H), 1.59 (d, J = 11.2 Hz, 4H), 1.39-1.19 (m, 4H), 1.16-1.00 (m, 6H) |
| 150 | 983.1 | |
| 151 | 1027.1 | $^1$H NMR (400 MHz, DMSO-d6) δ 10.97 (s, 1H), 9.07 (s, 1H), 8.19 (s, 2H), 7.98 (dd, J = 6.0, 9.2 Hz, 1H), 7.46 (t, J = 9.2 Hz, 1H), 7.40 (d, J = 2.4 Hz, 1H), 7.19 (d, J = 2.4 Hz, 1H), 6.87 (d, J = 7.6 Hz, 1H), 5.02 (dd, J = 5.2, 13.2 Hz, 1H), 4.57 (br d, J = 12.8 Hz, 1H), 4.45-4.33 (m, 3H), 4.30-4.19 (m, 2H), 4.13 (quin, J = 5.6 Hz, 1H), 3.95 (d, J = 2.8 Hz, 1H), 3.89 (br s, 2H), 3.81-3.69 (m, 2H), 3.47 (br d, J = 8.8 Hz, 2H), 3.37-3.22 (m, 2H), 2.96-2.77 (m, 2H), 2.77-2.64 (m, 4H), 2.63-2.54 (m, 1H), 2.52 (s, 3H), 2.47-2.38 (m, 1H), 2.36 (s, 3H), 2.25-2.16 (m, 3H), 2.14-2.02 (m, 2H), 1.99-1.85 (m, 3H), 1.85-1.73 (m, 8H), 1.66 (br s, 2H), 1.50-1.36 (m, 2H), 1.30-1.18 (m, 2H) |
| 152 | 1024.2 | |
| 153 | 1011.1 | $^1$H NMR (400 MHz, DMSO-d6) δ 10.97 (s, 1H), 9.06 (s, 1H), 8.18 (s, 2H), 7.98 (dd, J = 6.0, 9.2 Hz, 1H), 7.46 (t, J = 9.2 Hz, 1H), 7.40 (d, J = 2.4 Hz, 1H), 7.18 (d, J = 2.4 Hz, 1H), 6.88 (d, J = 7.6 Hz, 1H), 5.02 (dd, J = 5.2, 13.2 Hz, 1H), 4.58-4.44 (m, 3H), 4.39 (d, J = 16.8 Hz, 2H), 4.22 (d, J = 16.8 Hz, 1H), 3.94 (s, 1H), 3.81 (s, 2H), 3.72 (t, J = 14.0 Hz, 2H), 3.47 (d, J = 6.4 Hz, 2H), 2.95-2.84 (m, 1H), 2.79-2.69 (m, 4H), 2.61-2.54 (m, 2H), 2.53 (s, 3H), 2.49-2.38 (m, 8H), 2.35-2.19 (m, 3H), 1.99-1.91 (m, 1H), 1.83-1.60 (m, 8H), 1.44 (s, 8H), 1.30-1.20 (m, 2H) |
| 154 | 983.1 | $^1$H NMR (400 MHz, DMSO-d6) δ 10.98 (s, 1H), 10.28 (br s, 1H), 9.13 (s, 1H), 8.14 (s, 1H), 7.99 (dd, J = 6.0, 9.2 Hz, 1H), 7.48 (t, J = 9.2 Hz, 1H), 7.41 (d, J = 2.4 Hz, 1H), 7.18 (d, J = 2.0 Hz, 1H), 6.89 (br d, J = 7.2 Hz, 1H), 5.03 (br |

TABLE 2-continued

| Cmpd | LC/MS | NMR |
|---|---|---|
| | | dd, J = 5.0, 13.2 Hz, 1H), 4.74-4.57 (m, 3H), 4.53 (br d, J = 13.6 Hz, 1H), 4.39 (br d, J = 16.8 Hz, 1H), 4.26-4.14 (m, 3H), 3.95-3.83 (m, 6H), 3.16-2.97 (m, 8H), 2.94-2.85 (m, 1H), 2.61-2.52 (m, 7H), 2.45-2.37 (m, 3H), 1.95 (br d, J = 9.6 Hz, 10H), 1.85-1.67 (m, 3H), 1.46-1.19 (m, 2H) |
| 155 | 953.1 | |
| 156 | 981.1 | |
| 157 | 991.2 | |
| 158 | 914.1 | |
| 159 | 1069.2 | |
| 160 | 1037.2 | $^1$H NMR (400 MHz, DMSO-d6) δ 11.07 (br s, 1H), 9.06 (s, 1H), 8.21 (s, 2H), 8.05-7.92 (m, 1H), 7.47 (t, J = 9.2 Hz, 1H), 7.40 (d, J = 2.4 Hz, 1H), 7.18 (d, J = 2.4 Hz, 1H), 6.92 (d, J = 8.4 Hz, 1H), 6.83-6.77 (m, 1H), 6.62 (dd, J = 2.0, 8.8 Hz, 1H), 5.29 (dd, J = 5.6, 12.8 Hz, 1H), 4.53 (br d, J = 12.4 Hz, 1H), 4.47 (br t, J = 5.2 Hz, 2H), 4.38 (br d, J = 12.4 Hz, 1H), 3.94 (s, 2H), 3.74 (br d, J = 10.0 Hz, 4H), 3.67 (br d, J = 14.4 Hz, 3H), 3.56 (br d, J = 11.6 Hz, 2H), 3.30 (s, 4H), 2.95-2.84 (m, 1H), 2.76 (br s, 2H), 2.63-2.62 (m, 1H), 2.69-2.57 (m, 6H), 2.47 (br s, 3H), 2.40-2.31 (m, 6H), 2.14 (br d, J = 6.8 Hz, 2H), 2.09 (s, 2H), 2.03-1.95 (m, 1H), 1.76 (br s, 6H), 1.65-1.55 (m, 1H), 1.47-1.47 (m, 1H), 1.47 (br d, J = 9.2 Hz, 2H), 1.22 (br d, J = 11.2 Hz, 4H), 0.85 (s, 3H) |
| 161 | 1036.2 | $^1$H NMR (400 MHz, DMSO-$d_6$) δ 11.05 (br s, 1H), 9.05 (s, 1H), 8.21 (s, 2H), 7.97 (dd, J = 6.0, 9.2 Hz, 1H), 7.46 (t, J = 9.2 Hz, 1H), 7.39 (d, J = 2.4 Hz, 1H), 7.17 (d, J = 2.4 Hz, 1H), 6.91 (d, J = 8.8 Hz, 1H), 6.80 (d, J = 2.0 Hz, 1H), 6.61 (dd, J = 2.0, 8.8 Hz, 1H), 5.27 (dd, J = 5.6, 12.8 Hz, 1H), 4.51 (br d, J = 13.2 Hz, 1H), 4.46 (br t, J = 5.6 Hz, 2H), 4.35 (br d, J = 10.8 Hz, 1H), 3.92 (s, 1H), 3.55-3.51 (m, 5H), 3.29 (s, 3H), 2.93-2.84 (m, 1H), 2.79 (br d, J = 11.6 Hz, 2H), 2.73 (br t, J = 5.2 Hz, 2H), 2.70-2.66 (m, 1H), 2.65-2.60 (m, 2H), 2.58 (br d, J = 9.2 Hz, 3H), 2.52 (br s, 2H), 2.42-2.31 (m, 3H), 2.18 (br d, J = 6.8 Hz, 2H), 2.02-1.88 (m, 3H), 1.80-1.69 (m, 6H), 1.60 (br d, J = 12.4 Hz, 3H), 1.43-1.28 (m, 5H), 1.27-1.17 (m, 4H), 1.14 (br d, J = 4.4 Hz, 2H) |
| 162 | 1051.2 | $^1$H NMR (400 MHz, DMSO-$d_6$) δ 11.05 (s, 1H), 9.04 (s, 1H), 8.23 (s, 2H), 7.97 (dd, J = 6.0, 9.2 Hz, 1H), 7.46 (t, J = 9.2 Hz, 1H), 7.39 (d, J = 2.4 Hz, 1H), 7.17 (d, J = 2.4 Hz, 1H), 6.91 (d, J = 8.8 Hz, 1H), 6.80 (d, J = 1.6 Hz, 1H), 6.65-6.57 (m, 1H), 5.28 (dd, J = 5.2, 12.8 Hz, 1H), 4.52-4.46 (m, 1H), 4.38-4.29 (m, 3H), 3.91 (s, 1H), 3.65 (s, 8H), 3.56 (d, J = 12.4 Hz, 5H), 3.29 (s, 3H), 2.89-2.79 (m, 3H), 2.67-2.56 (m, 6H), 2.18 (d, J = 6.8 Hz, 2H), 2.03-1.94 (m, 4H), 1.89 (t, J = 11.2 Hz, 2H), 1.77 (d, J = 11.2 Hz, 2H), 1.72-1.57 (m, 7H), 1.44 (d, J = 4.0 Hz, 1H), 1.28-1.17 (m, 2H), 1.15-1.03 (m, 2H), 0.98 (s, 6H) |
| 163 | 1025.2 | |
| 164 | 967.1 | $^1$H NMR (400 MHz, $CD_3OD$-$d_4$) δ 9.01 (s, 1H), 7.87-7.84 (m, 1H), 7.59-7.56 (m, 1H), 7.35-7.29 (m,2H), 7.21-7.20 (m, 1H), 6.50-6.48 (m, 2H), 5.09-5.05 (m, 1H), 4.65-4.56 (m, 2H), 4.49-4.47 (m, 2H), 4.36-4.34 (m, 2H), 4.25-4.23 (m, 1H), 4.12-4.08 (m, 2H), 3.73-3.61 (m, 6H), 3.48-3.43 (m, 1H), 3.39-3.35 (m, 2H), 3.05-2.99 (m, 2H), 2.92-2.84 (m, 1H), 2.79-2.74 (m, 3H), 2.70-2.67 (m, 2H), 2.52 (s, 3H), 2.46-2.37 (m, 2H), 2.27-2.21 (m, 2H), 2.15-2.00 (m, 3H), 1.92-1.79 (m, 6H), 1.62-1.57 (m, 2H) |
| 165 | 1009.2 | $^1$H NMR (400 MHz, DMSO-$d_6$) δ 10.98-10.91 (m, 1H), 9.06 (s, 1H), 8.16 (s, 2H), 7.98 (dd, J = 6.0, 9.2 Hz, 1H), 7.52-7.44 (m, 2H), 7.40 (d, J = 2.4 Hz, 1H), 7.18 (s, 1H), 7.06-7.00 (m, 2H), 5.07-5.00 (m, 1H), 4.54 (br d, J = 12.8 Hz, 1H), 4.42-4.34 (m, 2H), 4.31 (br d, J = 17.2 Hz, 1H), 4.22-4.12 (m, 3H), 3.94 (s, 1H), 3.86 (br d, J = 12.0 Hz, 2H), 3.79 (br s, 2H), 3.75-3.64 (m, 3H), 3.31-3.26 (m, 2H), 2.98 (br dd, J = 4.0, 10.0 Hz, 1H), 2.92 (td, J = 5.2, 8.0 Hz, 2H), 2.80 (br t, J = 11.6 Hz, 2H), 2.72-2.66 (m, 2H), 2.60 (br s, 1H), 2.37 (br d, J = 5.2 Hz, 1H), 2.21-2.12 (m, 3H), 2.03 (br dd, J = 8.4, 12.0 Hz, 2H), 1.98-1.93 (m, 1H), 1.90-1.84 (m, 2H), 1.82-1.70 (m, 9H), 1.45-1.35 (m, 2H), 1.21-1.12 (m, 2H), 1.03-0.96 (m, 3H) |
| 166 | 1040.2 | $^1$H NMR (400 MHz, DMSO-$d_6$) δ 11.10 (s, 1H), 9.04 (s, 1H), 7.99-7.95 (m, 1H), 7.54-7.35 (m, 2H), 7.17 (d, J = 2.4 Hz, 1H), 6.83 (d, J = 8.4 Hz, 1H), 6.71 (t, J = 8.0 Hz, 1H), 5.37-5.24 (m, 1H), 4.54-4.42 (m, 3H), 4.35 (d, J = 12.0 Hz, 1H), 3.93 (s, 1H), 3.66 (s, 5H), 3.20 (d, J = 10.8 Hz, 4H), 2.97-2.79 (m, 6H), 2.72-2.57 (m, 7H), 2.26 (s, 1H), 2.13 (br d, J = 6.4 Hz, 2H), 2.06-1.96 (m, 3H), 1.88 (t, J = 10.8 Hz, 2H), 1.71 (s, 5H), 1.62 (t, J = 11.8 Hz, 4H), 1.52-1.39 (m, 2H), 1.36-1.21 (m, 3H), 1.19-1.02 (m, 6H) |
| 167 | 1068.2 | $^1$H NMR (400 MHz, $CD_3OD$-$d_4$) δ 9.01 (s, 1H), 7.86 (dd, J = 5.6, 9.2 Hz, 1H), 7.36-7.29 (m, 2H), 7.21 (d, J = 2.4 Hz, 1H), 6.89-6.80 (m, 2H), 5.28 (dd, J = 5.2, 12.4 Hz, 1H), 4.67-4.55 (m, 5H), 3.74-3.64 (m, 4H), 3.37 (s, 1H), 3.14-3.08 (m, 2H), 2.99 (br d, J = 11.2 Hz, 2H), 2.93-2.85 (m, 3H), 2.83-2.75 (m, 2H), 2.74-2.67 (m, 2H), 2.31 (br d, J = 6.4 Hz, 2H), 2.26-2.19 (m, 2H), 2.18-2.10 (m, 2H), 2.09-2.00 (m, 2H), 1.90-1.84 (m, 2H), 1.83-1.77 (m, 6H), 1.73 (br d, J = 13.2 Hz, 2H), 1.69-1.58 (m, 2H), 1.51 (br d, J = 6.8 Hz, 6H), 1.41 (br d, J = 11.6 Hz, 2H), 1.33-1.23 (m, 8H) |
| 168 | 1054.2 | $^1$H NMR (400 MHz, $CD_3OD$-$d_4$) δ 9.02 (d, J = 1.2 Hz, 1H), 7.87 (dd, J = 8.8, 5.6 Hz, 1H), 7.52 (d, J = 8.4 Hz, 1H), 7.37-7.29 (m, 2H), 7.24-7.13 (m, 2H), 5.11 (dd, J = 13.2, 5.2 Hz, 1H), 4.71-4.42 (m, 7H), 3.79-3.64 (m, 4H), 3.63-3.55 (m, 2H), 3.45-3.34 (m, 2H), 2.95-2.73 (m, 5H), 2.61-2.39 (m, 9H), 2.33-2.25 (m, 2H), 2.20-2.11 (m, 3H), 1.94-1.70 (m, 10H), 1.65-1.57 (m, 1H), 1.48-1.32 (m, 2H), 1.29-1.03 (m, 8H) |
| 169 | 1054.2 | $^1$H NMR (400 MHz, $CD_3OD$-$d_4$) δ 9.03 (s, 1H), 7.89-7.86 (m, 1H), 7.54 (d, J = 8.0 Hz, 1H), 7.38-7.31 (m, 2H), 7.25-7.15 (m, 2H), 5.15-5.10 (m, 1H), 4.72-4.56 (m, 5H), 4.54-4.43 (m, 2H), 3.78-3.65 (m, 4H), 3.63-3.57 (m, 2H), 3.38 (s, 1H), 3.18-3.08 (m, 2H), 2.96-2.75 (m, 6H), 2.69-2.59 (m, 2H), 2.55-2.42 (m, 2H), 2.33-2.10 (m, 8H), |

TABLE 2-continued

| Cmpd | LC/MS | NMR |
|---|---|---|
| | | 1.96-1.78 (m, 8H), 1.65-1.54 (m, 2H), 1.40-1.21 (m, 5H), 1.06 (s, 6H) |
| 170 | 1039.2 | $^1$H NMR (400 MHz, $CD_3OD-d_4$) δ 9.01 (s, 1H), 7.86 (dd, J = 5.6, 9.2 Hz, 1H), 7.38-7.29 (m, 2H), 7.21 (d, J = 2.4 Hz, 1H), 6.87 (br d, J = 7.2 Hz, 1H), 5.06 (dd, J = 5.2, 13.2 Hz, 1H), 4.67-4.56 (m, 5H), 4.51-4.30 (m, 3H), 3.76-3.63 (m, 4H), 3.56 (br d, J = 9.2 Hz, 2H), 3.15-3.08 (m, 2H), 3.01 (br d, J = 10.0 Hz, 2H), 2.92-2.85 (m, 3H), 2.81-2.73 (m, 3H), 2.58 (s, 3H), 2.48 (br dd, J = 4.8, 13.2 Hz, 1H), 2.32 (br d, J = 6.4 Hz, 2H), 2.28-2.00 (m, 6H), 1.88-1.70 (m, 10H), 1.42-1.22 (m, 9H) |
| 171 | 998.2 | $^1$H NMR (400 MHz, DMSO-$d_6$) δ 11.06 (s, 1H), 9.11 (s, 1H), 8.20 (s, 3H), 7.76 (dd, J = 6.0, 9.2 Hz, 1H), 7.40-7.30 (m, 2H), 7.01 (d, J = 2.4 Hz, 1H), 6.92 (d, J = 8.8 Hz, 1H), 6.81 (d, J = 2.0 Hz, 1H), 6.62 (dd, J = 2.0, 8.8 Hz, 1H), 5.28 (dd, J = 5.2, 12.8 Hz, 1H), 4.54-4.39 (m, 5H), 3.83-3.62 (m, 5H), 3.56 (d, J = 12.0 Hz, 2H), 3.29 (s, 3H), 2.94-2.83 (m, 1H), 2.78-2.66 (m, 3H), 2.64-2.56 (m, 3H), 2.47 (s, 3H), 2.43-2.31 (m, 5H), 2.24 (d, J = 6.8 Hz, 2H), 2.18-2.09 (m, 1H), 2.02-1.94 (m, 1H), 1.82-1.58 (m, 7H), 1.42 (s, 8H), 1.30-1.15 (m, 3H), 0.72 (t, J = 7.2 Hz, 3H) |
| 172 | 1026.2 | $^1$H NMR (400 MHz, DMSO-$d_6$) δ 11.08 (br s, 1H), 9.13 (s, 1H), 8.26 (s, 3H), 7.77 (dd, J = 6.0, 9.2 Hz, 1H), 7.41-7.30 (m, 2H), 7.03 (d, J = 2.4 Hz, 1H), 6.93 (d, J = 8.8 Hz, 1H), 6.82 (d, J = 2.0 Hz, 1H), 6.62 (dd, J = 2.0, 8.8 Hz, 1H), 5.29 (dd, J = 5.2, 12.8 Hz, 1H), 4.63-4.39 (m, 4H), 3.92-3.66 (m, 4H), 3.57 (br d, J = 11.6 Hz, 2H), 3.03-2.84 (m, 5H), 2.80-2.57 (m, 6H), 2.42-2.26 (m, 3H), 2.21-1.93 (m, 6H), 1.84-1.72 (m, 6H), 1.70-1.55 (m, 5H), 1.40-1.02 (m, 10H), 0.73 (t, J = 7.6 Hz, 3H) |
| 173 | 1023.2 | $^1$H NMR (400 MHz, DMSO-$d_6$) δ 11.05 (s, 1H), 9.05 (s, 1H), 8.21 (s, 2H), 7.97 (dd, J = 6.0, 9.2 Hz, 1H), 7.46 (t, J = 9.2 Hz, 1H), 7.39 (d, J = 2.4 Hz, 1H), 7.18 (d, J = 2.4 Hz, 1H), 6.92 (d, J = 8.8 Hz, 1H), 6.80 (d, J = 2.0 Hz, 1H), 6.62 (dd, J = 2.0, 8.8 Hz, 1H), 5.28 (dd, J = 5.2, 12.8 Hz, 1H), 4.52 (d, J = 12.4 Hz, 1H), 4.45 (t, J = 5.6 Hz, 2H), 4.41-4.34 (m, 1H), 3.92 (s, 1H), 3.77-3.60 (m, 4H), 3.56 (d, J = 11.6 Hz, 2H), 3.30 (s, 3H), 2.95-2.80 (m, 3H), 2.72-2.67 (m, 2H), 2.66-2.54 (m, 4H), 2.49-2.47 (m, 4H), 2.33 (d, J = 1.6 Hz, 4H), 2.22 (d, J = 6.8 Hz, 2H), 2.10 (d, J = 6.8 Hz, 2H), 2.00-1.88 (m, 3H), 1.65 (d, J = 10.4 Hz, 3H), 1.85-1.57 (m, 6H), 1.47 (s, 1H), 1.31-1.18 (m, 2H), 1.15-1.05 (m, 2H) |
| 174 | 1054.2 | $^1$H NMR (400 MHz, DMSO-$d_6$) δ 10.97 (s, 1H), 10.24-10.06 (m, 1H), 9.03 (s, 1H), 7.97 (dd, J = 6.0, 9.2 Hz, 1H), 7.50-7.42 (m, 2H), 7.39 (d, J = 2.4 Hz, 1H), 7.20-7.11 (m, 2H), 5.06 (dd, J = 5.2, 13.2 Hz, 1H), 4.52-4.42 (m, 2H), 4.37-4.26 (m, 4H), 3.91 (s, 1H), 3.66-3.55 (m, 4H), 3.52-3.41 (m, 3H), 2.96-2.71 (m, 6H), 2.61 (br s, 3H), 2.56 (br d, J = 1.6 Hz, 1H), 2.47-2.35 (m, 2H), 2.15 (br d, J = 4.0 Hz, 2H), 2.09-1.93 (m, 5H), 1.92-1.71 (m, 5H), 1.71-1.60 (m, 7H), 1.48-1.38 (m, 1H), 1.30-1.19 (m, 2H), 1.16-1.03 (m, 2H), 0.97 (s, 6H) |
| 175 | 953.1 | $^1$H NMR (400 MHz, DMSO-$d_6$) δ 11.05 (s, 1H), 9.08 (s, 1H), 8.15 (s, 2H), 7.98 (dd, J = 6.0, 9.2 Hz, 1H), 7.47 (t, J = 9.2 Hz, 1H), 7.40 (d, J = 2.4 Hz, 1H), 7.18 (d, J = 2.4 Hz, 1H), 6.94-6.84 (m, 2H), 6.64-6.57 (m, 1H), 5.26 (dd, J = 5.6, 13.1 Hz, 1H), 4.61-4.54 (m, 2H), 4.53-4.46 (m, 2H), 4.42 (d, J = 13.2 Hz, 1H), 3.94 (s, 1H), 3.90 (s, 2H), 3.75 (t, J = 12.4 Hz, 3H), 3.52 (d, J = 11.6 Hz, 4H), 3.01 (s, 3H), 2.90-2.83 (m, 1H), 2.78 (s, 2H), 2.68-2.60 (m, 2H), 2.58 (s, 1H), 2.54 (s, 1H), 2.12 (t, J = 10.8 Hz, 2H), 2.01-1.92 (m, 1H), 1.82 (s, 4H), 1.71 (d, J = 12.4 Hz, 2H), 1.67-1.61 (m, 2H), 1.44 (d, J = 6.8 Hz, 6H), 1.29-1.20 (m, 2H), 1.19-1.08 (m, 4H) |
| 176 | 940.1 | $^1$H NMR (400 MHz, $CD_3OD-d_4$) δ 9.02 (s, 1H), 7.86 (dd, J = 5.6, 9.2 Hz, 1H), 7.36-7.28 (m, 2H), 7.21 (d, J = 2.4 Hz, 1H), 6.98 (d, J = 8.4 Hz, 1H), 6.93 (d, J = 2.0 Hz, 1H), 6.76 (br d, J = 8.8 Hz, 1H), 5.26 (dd, J = 5.6, 12.4 Hz, 1H), 4.68-4.56 (m, 5H), 4.54-4.48 (m, 1H), 3.75-3.65 (m, 4H), 3.49-3.41 (m, 1H), 3.38 (s, 1H), 3.14 (br t, J = 4.0 Hz, 4H), 2.94-2.86 (m, 1H), 2.82-2.74 (m, 2H), 2.71-2.64 (m, 8H), 2.36 (dd, J = 7.6, 12.4 Hz, 1H), 2.17-2.08 (m, 3H), 1.90-1.74 (m, 6H), 1.57-1.51 (m, 6H) |
| 177 | 1033.6 | $^1$H NMR (400 MHz, DMSO-$d_6$) δ 10.99 (s, 1H), 9.12 (s, 1H), 8.18 (s, 2H), 7.76 (dd, J = 6.0, 9.2 Hz, 1H), 7.64 (d, J = 8.0 Hz, 1H), 7.42-7.30 (m, 2H), 7.25 (d, J = 8.4 Hz, 1H), 7.02 (d, J = 2.4 Hz, 1H), 5.09 (dd, J = 5.2, 13.2 Hz, 1H), 4.53 (br t, J = 15.2 Hz, 3H), 4.45-4.35 (m, 3H), 4.32-4.27 (m, 2H), 4.22 (s, 1H), 4.16-4.09 (m, 2H), 3.87 (br d, J = 10.8 Hz, 2H), 3.80 (br d, J = 13.2 Hz, 1H), 3.73 (br d, J = 13.6 Hz, 1H), 3.42-3.31 (m, 3H), 3.26 (br dd, J = 6.0, 9.2 Hz, 1H), 2.96-2.86 (m, 1H), 2.82 (br t, J = 5.2 Hz, 1H), 2.78-2.66 (m, 4H), 2.59 (br d, J = 16.8 Hz, 1H), 2.44 (br dd, J = 4.8, 13.6 Hz, 1H), 2.36 (s, 4H), 2.28-2.18 (m, 3H), 2.16-2.05 (m, 3H), 1.98 (br dd, J = 5.2, 10.4 Hz, 1H), 1.89 (br d, J = 5.2 Hz, 1H), 1.85-1.76 (m, 7H), 1.72-1.59 (m, 1H), 1.51-1.37 (m, 2H), 1.29 (q, J = 10.4 Hz, 2H), 0.72 (t, J = 7.2 Hz, 3H) |
| 178 | 1017.2 | $^1$H NMR (400 MHz, DMSO-$d_6$) δ 10.98 (br s, 1H), 9.11 (s, 1H), 8.21 (s, 1H), 7.76 (dd, J = 6.0, 9.2 Hz, 1H), 7.46 (d, J = 8.0 Hz, 1H), 7.39-7.29 (m, 2H), 7.14 (t, J = 8.0 Hz, 1H), 7.02 (d, J = 2.4 Hz, 1H), 5.07 (br dd, J = 5.2, 13.3 Hz, 1H), 4.47 (br d, J = 16.8 Hz, 3H), 4.41-4.37 (m, 1H), 4.34-4.23 (m, 4H), 4.14-4.10 (m, 1H), 3.80-3.65 (m, 5H), 3.47 (br s, 2H), 3.35-3.19 (m, 2H), 2.98-2.84 (m, 1H), 2.83-2.64 (m, 5H), 2.63-2.55 (m, 1H), 2.48-2.38 (m, 1H), 2.35 (s, 3H), 2.22-2.16 (m, 3H), 2.15-2.10 (m, 1H), 2.05 (br t, J = 9.6 Hz, 2H), 2.00-1.94 (m, 1H), 1.92-1.84 (m, 2H), 1.83-1.63 (m, 8H), 1.49-1.34 (m, 2H), 1.32-1.15 (m, 2H), 0.72 (t, J = 7.6 Hz, 3H) |
| 179 | 1040.3 | $^1$H NMR (400 MHz, DMSO-$d_6$) δ 11.14-10.94 (m, 1H), 9.10 (s, 1H), 8.22 (s, 2H), 7.76 (dd, J = 6.0, 9.2 Hz, 1H), 7.39-7.27 (m, 2H), 7.01 (d, J = 2.4 Hz, 1H), 6.96-6.87 (m, 1H), 6.84-6.75 (m, 1H), 6.67-6.55 (m, 1H), 5.27 (br dd, J = 5.6, 12.8 Hz, 1H), 4.54-4.39 (m, 4H), 3.55 (br d, J = 12.0 Hz, 7H), 3.31- |

TABLE 2-continued

| Cmpd | LC/MS | NMR |
|---|---|---|
| | | 3.27 (m, 3H), 2.95-2.83 (m, 1H), 2.79 (br d, J = 10.8 Hz, 2H), 2.72 (br t, J = 5.6 Hz, 2H), 2.69-2.65 (m, 1H), 2.64-2.54 (m, 5H), 2.52 (br d, J = 2.0 Hz, 2H), 2.42-2.31 (m, 3H), 2.21-2.09 (m, 3H), 2.03-1.88 (m, 3H), 1.76 (br d, J = 12.8 Hz, 2H), 1.72-1.65 (m, 3H), 1.59 (br d, J = 11.2 Hz, 3H), 1.41-1.16 (m, 8H), 1.13 (br d, J = 4.4 Hz, 2H), 0.87 (s, 3H), 0.72 (t, J = 7.6 Hz, 3H) |
| 180 | 1041.2 | $^1$H NMR (400 MHz, DMSO-$d_6$) δ 11.07 (br s, 1H), 9.12 (s, 1H), 8.22 (s, 2H), 7.77 (dd, J = 6.0, 9.2 Hz, 1H), 7.39-7.31 (m, 2H), 7.02 (d, J = 2.4 Hz, 1H), 6.92 (d, J = 8.4 Hz, 1H), 6.81 (d, J = 2.0 Hz, 1H), 6.62 (dd, J = 2.0, 8.8 Hz, 1H), 5.29 (dd, J = 5.2, 12.8 Hz, 1H), 4.55-4.39 (m, 4H), 3.77-3.66 (m, 3H), 3.56 (br d, J = 11.6 Hz, 2H), 3.30 (s, 3H), 3.00-2.67 (m, 2H), 2.55 (s, 4H), 2.47 (br d, J = 4.0 Hz, 7H), 2.41-2.27 (m, 8H), 2.20-2.03 (m, 6H), 2.01-1.94 (m, 1H), 1.79-1.68 (m, 6H), 1.63-1.54 (m, 1H), 1.51-1.42 (m, 2H), 1.22 (br d, J = 8.0 Hz, 4H), 0.85 (s, 3H), 0.73 (t, J = 7.2 Hz, 3H) |
| 181 | 1045.2 | $^1$H NMR (400 MHz, DMSO-$d_6$) δ 11.06 (s, 1H), 9.10 (s, 1H), 8.22-8.17 (m, 2H), 7.76 (dd, J = 6.0, 9.2 Hz, 1H), 7.38-7.31 (m, 2H), 7.02 (d, J = 2.4 Hz, 1H), 6.91 (d, J = 8.8 Hz, 1H), 6.80 (d, J = 2.0 Hz, 1H), 6.61 (dd, J = 2.0, 8.8 Hz, 1H), 5.28 (dd, J = 5.2, 12.8 Hz, 1H), 4.51-4.41 (m, 4H), 3.70-3.60 (m, 5H), 3.56 (d, J = 12.0 Hz, 3H), 3.29 (s, 3H), 2.92-2.83 (m, 1H), 2.76-2.65 (m, 5H), 2.64-2.55 (m, 4H), 2.46 (s, 3H), 2.40 (s, 2H), 2.36-2.28 (m, 6H), 2.13 (d, J = 7.2 Hz, 3H), 2.02-1.94 (m, 1H), 1.82-1.71 (m, 5H), 1.68 (s, 4H), 1.62-1.51 (m, 2H), 1.22 (d, J = 10.0 Hz, 2H), 0.72 (t, J = 7.6 Hz, 3H) |
| 182 | 1044.2 | |
| 183 | 1040.2 | $^1$H NMR (400 MHz, $CD_3OD$-$d_4$) δ 9.01 (s, 1H), 7.88-7.84 (m, 1H), 7.35-7.30 (m, 2H), 7.21-7.20 (m, 1H), 6.99-6.96 (m, 1H), 6.87-6.86 (m, 1H), 6.81-6.78 (m, 1H), 5.30-5.25 (m, 1H), 4.69-4.57 (m, 4H), 3.73-3.67 (m, 4H), 3.58-3.54 (m, 2H), 3.40 (s, 3H), 3.37 (s, 1H), 2.95-2.87 (m, 7H), 2.81-2.75 (m, 2H), 2.70-2.65 (m, 2H), 2.52-2.44 (m, 4H), 2.18-2.09 (m, 3H), 1.90-1.79 (m, 9H), 1.70-1.61 (m, 3H), 1.55-1.46 (m, 1H), 1.39-1.34 (m, 3H), 1.25-1.19 (m, 4H) |
| 184 | 1064.3 | $^1$H NMR (400 MHz, DMSO-$d_6$) δ 11.04 (s, 1H), 10.30-9.99 (m, 1H), 9.03 (s, 1H), 7.97 (dd, J = 6.0, 9.2 Hz, 1H), 7.46 (t, J = 9.2 Hz, 1H), 7.39 (d, J = 2.4 Hz, 1H), 7.17 (s, 1H), 6.95-6.81 (m, 2H), 6.61 (dd, J = 1.6, 8.8 Hz, 1H), 5.25 (dd, J = 5.2, 12.8 Hz, 1H), 4.63-4.53 (m, 1H), 4.52-4.42 (m, 2H), 4.30 (d, J = 12.4 Hz, 1H), 4.16 (dd, J = 6.0, 10.8 Hz, 1H), 3.91 (d, J = 5.2 Hz, 1H), 3.62 (d, J = 11.8 Hz, 1H), 3.58-3.46 (m, 5H), 3.03-2.94 (m, 1H), 2.89-2.74 (m, 5H), 2.65-2.55 (m, 4H), 2.31-2.19 (m, 2H), 2.11 (d, J = 6.8 Hz, 2H), 2.01-1.92 (m, 1H), 1.84-1.72 (m, 4H), 1.68-1.62 (m, 4H), 1.60-1.52 (m, 5H), 1.44 (d, J = 6.8 Hz, 6H), 1.34-1.13 (m, 5H), 1.12-0.96 (m, 9H) |
| 185 | 1039.2 | $^1$H NMR (400 MHz, DMSO-$d_6$) δ 10.97 (s, 1H), 10.49-9.89 (m, 1H), 9.03 (s, 1H), 7.97 (dd, J = 6.0, 9.2 Hz, 1H), 7.50-7.43 (m, 2H), 7.39 (d, J = 2.4 Hz, |

TABLE 2-continued

| Cmpd | LC/MS | NMR |
|---|---|---|
| | | 1H), 7.21-7.09 (m, 2H), 5.06 (dd, J = 5.2, 13.2 Hz, 1H), 4.56-4.42 (m, 3H), 4.30 (d, J = 16.4 Hz, 2H), 4.16 (dd, J = 5.6, 10.4 Hz, 1H), 3.91 (d, J = 5.2 Hz, 1H), 3.62 (d, J = 12.0 Hz, 1H), 3.58-3.51 (m, 3H), 3.47 (s, 2H), 3.01-2.71 (m, 9H), 2.62-2.56 (m, 1H), 2.44-2.34 (m, 1H), 2.25 (q, J = 10.0 Hz, 2H), 2.12 (d, J = 6.8 Hz, 2H), 2.01-1.91 (m, 1H), 1.84-1.74 (m, 4H), 1.69-1.62 ( 5H), 1.56 (d, J = 9.2 Hz, 4H), 1.30-1.20 (m, 4H), 1.10-0.95 (m, 9H) |
| 186 | 985.5 | $^1$H NMR (400 MHz, DMSO-$d_6$) δ 10.98 (s, 1H), 9.03 (s, 1H), 8.21 (s, 1H), 7.97 (dd, J = 6.0, 9.2 Hz, 1H), 7.63 (d, J = 8.4 Hz, 1H), 7.46 (t, J = 8.8 Hz, 1H), 7.39 (d, J = 2.4 Hz, 1H), 7.29-7.21 (m, 1H), 7.17 (d, J = 2.4 Hz, 1H), 5.09 (dd, J = 5.2, 13.6 Hz, 1H), 4.56-4.47 (m, 1H), 4.45-4.36 (m, 1H), 4.34-4.20 (m, 4H), 3.94 (s, 1H), 3.71-3.54 (m, 6H), 3.39-3.34 (m, 2H), 2.94-2.85 (m, 1H), 2.75 2.65 (m, 2H), 2.62-2.56 (m, 1H), 2.47-2.22 (m, 10H), 2.18-2.11 (m, 2H), 2.04-1.93 (m, 1H), 1.84-1.75 (m, 2H), 1.74-1.56 (m, 5H), 1.36-1.18 (m, 2H), 0.69-0.58 (m, 2H), 0.47-0.35 (m, 2H) |
| 187 | 985.5 | |
| 188 | 966.1 | $^1$H NMR (400 MHz, DMSO-$d_6$) δ 11.04 (s, 1H), 9.04 (s, 1H), 8.21 (s, 2H), 7.97 (dd, J = 6.0, 9.2 Hz, 1H), 7.46 (t, J = 9.2 Hz, 1H), 7.39 (d, J = 2.4 Hz, 1H), 7.18 (d, J = 2.4 Hz, 1H), 6.91 (d, J = 8.4 Hz, 1H), 6.80 (d, J = 2.0 Hz, 1H), 6.61 (dd, J = 2.0, 8.8 Hz, 1H), 5.27 (dd, J = 5.2, 12.8 Hz, 1H), 4.53 (d, J = 12.4 Hz, 1H), 4.37-4.27 (m, 3H), 3.93 (s, 1H), 3.69 (s, 5H), 3.61 (d, J = 13.2 Hz, 4H), 3.55 (d, J = 11.6 Hz, 4H), 3.29 (s, 3H), 2.91-2.83 (m, 1H), 2.70-2.64 (m, 1H), 2.62 (d, J = 2.4 Hz, 1H), 2.61-2.55 (m, 2H), 2.36-2.26 (m, 5H), 2.12 (d, J = 7.2 Hz, 2H), 2.02-1.94 (m, 1H), 1.81-1.68 (m, 6H), 1.65-1.53 (m, 1H), 1.27-1.15 (m, 2H), 0.64 (s, 2H), 0.41 (s, 2H) |
| 189 | 966.1 | $^1$H NMR (400 MHz, DMSO-$d_6$) δ 11.06 (s, 1H), 9.03 (s, 1H), 8.20 (s, 1H), 7.97 (dd, J = 6.0, 9.2 Hz, 1H), 7.46 (t, J = 9.6 Hz, 1H), 7.39 (d, J = 2.4 Hz, 1H), 7.17 (d, J = 2.4 Hz, 1H), 6.96-6.90 (m, 1H), 6.83-6.79 (m, 1H), 6.60 (dd, J = 1.6, 8.4 Hz, 1H), 5.28 (dd, J = 5.2, 12.4 Hz, 1H), 4.51 (d, J = 11.6 Hz, 1H), 4.35-4.23 (m, 3H), 3.93 (s, 1H), 3.70-3.58 (m, 5H), 3.29 (s, 3H), 3.08-3.01 (m, 4H), 2.99-2.92 (m, 2H), 2.90-2.84 (m, 1H), 2.72-2.57 (m, 2H), 2.47-2.43 (m, 4H), 2.34-2.29 (m, 2H), 2.13 (d, J = 6.8 Hz, 2H), 2.01-1.94 (m, 1H), 1.92-1.84 (m, 2H), 1.74-1.62 (m, 6H), 1.52-1.44 (m, 1H), 1.12-1.00 (m, 2H), 0.64 (s, 2H), 0.41 (s, 2H) |
| 190 | 984.5 | $^1$H NMR (400 MHz, DMSO-$d_6$) δ 10.97 (s, 1H), 10.56-9.64 (m, 1H), 9.07 (s, 1H), 8.15 (s, 1H), 7.98 (dd, J = 6.0, 9.2 Hz, 1H), 7.64 (d, J = 8.0 Hz, 1H), 7.46 (t, J = 9.2 Hz, 1H), 7.40 (d, J = 2.4 Hz, 1H), 7.24 (d, J = 8.4 Hz, 1H), 7.18 (d, J = 2.4 Hz, 1H), 5.09 (dd, J = 5.2, 13.2 Hz, 1H), 4.59 (d, J = 12.4 Hz, 1H), 4.45-4.36 (m, 2H), 4.33-4.20 (m, 3H), 3.93 (s, 3H), 3.76 (dd, J = 13.2, 17.6 Hz, 2H), 3.13-3.02 (m, 3H), 2.97-2.83 (m, 2H), 2.74-2.66 (m, 2H), 2.63-2.56 (m, 1H), 2.49-2.42 (m, 3H), 2.13-1.94 (m, 3H), 1.85 (s, 4H), 1.76-1.62 (m, |

TABLE 2-continued

| Cmpd | LC/MS | NMR |
|---|---|---|
| | | 4H), 1.55-1.37 (m, 2H), 1.37-1.21 (m, 3H), 1.20-1.06 (m, 4H), 0.69 (s, 2H), 0.49 (s, 2H) |
| 191 | 993.2 | $^1$H NMR (400 MHz, DMSO-$d_6$) δ 11.06 (s, 1H), 10.24 (s, 1H), 9.13 (s, 1H), 8.14 (s, 1H), 8.03-7.95 (m, 1H), 7.47 (t, J = 8.8 Hz, 1H), 7.42-7.39 (m, 1H), 7.20-7.15 (m, 1H), 6.95-6.84 (m, 2H), 6.64-6.57 (m, 1H), 5.32-5.21 (m, 1H), 4.71-4.50 (m, 3H), 4.42-4.30 (m, 2H), 4.23-4.15 (m, 2H), 3.90 (s, 1H), 3.89-3.82 (m, 2H), 3.61-3.45 (m, 4H), 2.94-2.83 (m, 2H), 2.70-2.55 (m, 5H), 2.04-1.90 (m, 6H), 1.88-1.79 (m, 2H), 1.73-1.53 (m, 4H), 1.44 (d, J = 6.8 Hz, 9H), 1.27-1.07 (m, 5H), 0.87-0.63 (m, 4H) |
| 192 | 968.1 | $^1$H NMR (400 MHz, DMSO-$d_6$) δ 10.97 (s, 1H), 9.04 (s, 1H), 8.19 (s, 2H), 7.97 (dd, J = 6.0, 9.2 Hz, 1H), 7.49-7.42 (m, 2H), 7.39 (d, J = 2.4 Hz, 1H), 7.19-7.10 (m, 2H), 5.07 (dd, J = 5.2, 13.2 Hz, 1H), 4.54-4.44 (m, 2H), 4.34-4.26 (m, 4H), 3.95-3.91 (m, 1H), 3.66 (s, 3H), 3.59 (d, J = 12.4 Hz, 2H), 3.45 (s, 3H), 3.00-2.88 (m, 4H), 2.77-2.70 (m, 2H), 2.32 (s, 2H), 2.00-1.93 (m, 1H), 1.91-1.83 (m, 2H), 1.76-1.67 (m, 6H), 1.60 (d, J = 10.8 Hz, 2H), 1.51-1.44 (m, 1H), 1.36-1.18 (m, 4H), 1.16-1.04 (m, 4H), 0.67-0.59 (m, 2H), 0.41 (s, 2H) |
| 193 | 1034.2 | |
| 194 | 1039.2 | |
| 195 | 1064.3 | |
| 196 | 1062.3 | |
| 197 | 1012.1 | |
| 198 | 1040.2 | |
| 199 | 1058.2 | |
| 200 | 1041.2 | |
| 201 | 1046.1 | |
| 202 | 1022.2 | |
| 203 | 1040.2 | |
| 204 | 1035.2 | |
| 205 | 1026.2 | |
| 206 | 1040.2 | |
| 207 | 1014.2 | |
| 208 | 1063.3 | |
| 209 | 1042.2 | |
| 210 | 965.1 | |
| 211 | 1037.2 | |
| 212 | 1054.3 | |
| 213 | 1028.1 | |
| 214 | 1025.2 | |
| 215 | 1007.2 | |
| 216 | 1007.2 | |
| 217 | 1068.2 | |
| 218 | 994.1 | |
| 219 | 1042.6 | |
| 220 | 1013.6 | |
| 221 | 1023.2 | |
| 222 | 1051.2 | |
| 223 | 1026.2 | |
| 224 | 1056.2 | |
| 225 | 985.6 | $^1$H NMR (400 MHz, DMSO-$d_6$) δ 11.10 (s, 1H), 8.19 (s, 1H), 7.96 (dd, J = 6.0, 8.8 Hz, 1H), 7.75 (d, J = 8.8 Hz, 1H), 7.46 (t, J = 8.8 Hz, 1H), 7.36 (d, J = 2.4 Hz, 1H), 7.22 (dd, J = 6.8, 8.4 Hz, 1H), 7.07 (d, J = 2.4 Hz, 1H), 6.84 (d, J = 8.4 Hz, 1H), 6.72 (t, J = 8.0 Hz, 1H), 5.32 (dd, J = 5.2, 12.4 Hz, 1H), 4.48-4.40 (m, 2H), 4.38-4.33 (m, 1H), 4.29-4.24 (m, 1H), 3.86-3.84 (m, 1H), 3.81 (s, 2H), 3.60 (s, 1H), 3.57 (s, 1H), 3.47-3.46 (m, 3H), 3.45-3.43 (m, 1H), 3.23-3.18 (m, 2H), 2.91-2.84 (m, 1H), 2.78-2.71 (m, 2H), 2.69-2.57 |

TABLE 2-continued

| Cmpd | LC/MS | NMR |
|---|---|---|
| | | (m, 4H), 2.49-2.46 (m, 4H), 2.44-2.35 (m, 4H), 2.29-2.22 (m, 2H), 2.04-1.95 (m, 1H), 1.91-1.73 (m, 6H), 1.69-1.56 (m, 1H), 1.52-1.36 (m, 8H), 1.32-1.21 (m, 2H) |
| 227 | 1051.6 | $^1$H NMR (400 MHz, DMSO-$d_6$) δ 11.05 (s, 1H), 8.18 (s, 2H), 7.96 (dd, J = 6.0, 9.2 Hz, 1H), 7.74 (d, J = 8.4 Hz, 1H), 7.46 (t, J = 9.2 Hz, 1H), 7.36 (d, J = 2.4 Hz, 1H), 7.21 (dd, J = 7.2, 8.4 Hz, 1H), 7.07 (d, J = 2.4 Hz, 1H), 6.92 (d, J = 8.8 Hz, 1H), 6.81 (d, J = 2.0 Hz, 1H), 6.62 (dd, J = 2.0, 8.8 Hz, 1H), 5.28 (dd, J = 5.6, 12.8 Hz, 1H), 4.38-4.25 (m, 4H), 3.86 (s, 2H), 3.83 (d, J = 0.8 Hz, 1H), 3.62-3.55 (m, 8H), 3.30 (s, 3H), 2.93-2.84 (m, 3H), 2.73-2.56 (m, 7H), 2.29-2.21 (m, 3H), 2.09-1.93 (m, 6H), 1.91-1.74 (m, 6H), 1.71-1.59 (m, 3H), 1.55-1.40 (m, 1H), 1.31-1.06 (m, 4H), 0.98 (s, 6H) |
| 231 | 1039.5 | $^1$H NMR (400 MHz, DMSO-$d_6$) δ 11.10 (br s, 1H), 8.22 (s, 2H), 7.96 (dd, J = 9.2, 6.0 Hz, 1H), 7.74 (d, J = 8.4 Hz, 1H), 7.45 (t, J = 9.2 Hz, 1H), 7.36 (d, J = 2.4 Hz, 1H), 7.20 (t, J = 7.6 Hz, 1H), 7.07 (d, J = 2.0 Hz, 1H), 6.83 (d, J = 8.4 Hz, 1H), 6.75-6.64 (m, 1H), 5.36-5.26 (m, 1H), 4.47-4.38 (m, 2H), 4.38-4.20 (m, 3H), 3.85 (s, 1H) 3.80-3.70 (m, 2H), 3.55 (d, J = 12.4 Hz, 2H), 3.46 (s, 3H), 3.25-3.15 (m, 2H), 3.00-2.78 (m, 5H), 2.75-2.56 (m, 7H), 2.20-2.10 (m, 2H), 2.08-1.96 (m, 3H), 1.94-1.75 (m, 5H), 1.74-1.57 (m, 6H), 1.54-1.39 (m, 2H), 1.38-1.21 (m, 3H), 1.19-1.02 (m, 5H) |
| 232 | 1039.7 | $^1$H NMR (400 MHz, $CD_3OD$) δ 7.85-7.72 (m, 2H), 7.38-7.18 (m, 3H), 7.08 (d, J = 2.4 Hz, 1H), 6.82 (d, J = 2.4 Hz, 2H), 5.28 (dd, J = 5.6, 12.4 Hz, 1H), 4.68-4.54 (m, 3H), 4.49 (br dd, J = 6.8, 12.0 Hz, 2H), 3.64-3.54 (m, 6H), 3.20 (s, 1H), 3.16-3.03 (m, 2H), 3.00-2.92 (m, 2H), 2.92-2.83 (m, 3H), 2.82-2.64 (m, 4H), 2.29 (br d, J = 6.8 Hz, 2H), 2.25-2.11 (m, 3H), 2.04-1.93 (m, 2H), 1.91-1.77 (m, 6H), 1.69 (br t, J = 9.6 Hz, 5H), 1.48-1.37 (m, 6H), 1.34-1.22 (m, 4H), 1.21-1.14 (m, 2H) |
| 233 | 1021.5 | $^1$H NMR (400 MHz, DMSO-$d_6$) δ 11.05 (s, 1H), 10.16 (s, 1H), 7.96 (dd, J = 6.0, 9.2 Hz, 1H), 7.72 (d, J = 8.4 Hz, 1H), 7.45 (t, J = 9.2 Hz, 1H), 7.35 (d, J = 2.4 Hz, 1H), 7.16 (dd, J = 7.2, 8.4 Hz, 1H), 7.06 (d, J = 2.4 Hz, 1H), 6.91 (d, J = 8.4 Hz, 1H), 6.80 (d, J = 2.0 Hz, 1H), 6.61 (dd, J = 2.0, 8.4 Hz, 1H), 5.27 (dd, J = 5.6, 12.8 Hz, 1H), 4.39 (m, 2H), 4.31-4.15 (m, 2H), 3.84 (s, 1H), 3.60-3.46 (m, 6H), 3.29 (s, 3H), 2.90 (m, J = 10.0 Hz, 3H), 2.76 (m, 2H), 2.69-2.54 (m, 7H), 2.08-1.95 (m, 5H), 1.77-1.55 (m, 12H), 1.50-1.39 (m, 2H), 1.29-1.04 (m, 9H) |
| 234 | 1019.5 | $^1$H NMR (400 MHz, MeOD-$d_4$) δ 9.04 (s, 1H), 8.14-8.06 (m, 2H), 7.68-7.63 (m, 2H), 7.43 (dt, J = 3.6, 9.2 Hz, 1H), 6.98 (dd, J = 2.4, 8.4 Hz, 1H), 6.86 (d, J = 2.0 Hz, 1H), 6.79 (br d, J = 8.8 Hz, 1H), 5.37-5.24 (m, 1H), 4.62 (br t, J = 10.8 Hz, 2H), 4.49-4.41 (m, 1H), 4.35 (br d, J = 11.6 Hz, 1H), 3.76-3.65 (m, 4H), 3.56 (br d, J = 12.0 Hz, 2H), 3.43 (s, 1H), 3.40 (d, J = 1.6 Hz, 3H), 3.16-3.05 (m, 1H), 2.98-2.86 (m, 2H), 2.83-2.73 (m, 3H), 2.71-2.60 (m, 4H), 2.56 (br d, J = 6.8 Hz, 2H), 2.53-2.43 |

TABLE 2-continued

| Cmpd | LC/MS | NMR |
|---|---|---|
| | | (m, 4H), 2.24 (br d, J = 7.2 Hz, 3H), 2.19-2.13 (m, 1H), 2.09-2.03 (m, 1H), 1.99-1.92 (m, 2H), 1.88 (br d, J = 11.2 Hz, 6H), 1.82-1.77 (m, 3H), 1.70-1.63 (m, 1H), 1.47-1.25 (m, 4H), 0.92 (dd, J = 2.8, 7.6 Hz, 1H) |
| 238 | 1022.4 | $^1$H NMR (400 MHz, MeOD-$d_4$) δ 9.05 (s, 1H), 8.19-8.06 (m, 2H), 7.72-7.62 (m, 2H), 7.53 (dd, J = 3.2, 8.0 Hz, 1H), 7.46 (dt, J = 2.0, 9.2 Hz, 1H), 7.17 (dt, J = 3.6, 8.0 Hz, 1H), 5.12 (dd, J = 5.2, 13.4 Hz, 1H), 4.64 (t, J = 11.2 Hz, 2H), 4.58-4.34 (m, 4H), 3.76-3.66 (m, 4H), 3.58 (d, J = 10.8 Hz, 2H), 3.45 (s, 1H), 3.29-3.03 (m, 2H), 2.95-2.88 (m, 2H), 2.83-2.61 (m, 6H), 2.60-2.42 (m, 7H), 2.30-2.22 (m, 3H), 2.21-1.93 (m, 5H), 1.93-1.62 (m, 11H), 1.45-1.34 (m, 2H) |

Example 159: Biological Assays

Reagents

AsPC-1 (CRL-1682) cells were purchased from ATCC and are homozygous for the G12D mutation in KRas. AsPC-1 cells were cultured in GIBCO RPMI-1640 (ThermoFisher Scientific, catalog #61870-036, with Glutamax, no HEPES, no Na Pyruvate) supplemented with 10% FBS (ThermoFisher Scientific, catalog #2060357) and 1× Penicillin-Streptomycin (ThermoFisher Scientific, catalog #15140122, 10000 U/ml, 100×). For degradation assays, 384 well plates were used. Alamar blue was purchased from ThermoFisher Scientific (A50101) and used according to manufacturer instructions. The Nano-Glo® HiBiT Lytic Detection System and Nano-Glo® HiBiT Blotting System were purchased from Promega (#N3050 and #N2410) and used according to manufacturer instructions.

To create the AsPC-1 HiBiT-KRasG12D cell line, CRISPR-Cas9 was used to insert the HiBiT tag onto the N-terminus of one or more of the endogenous KRas alleles. See Schwinn, M. K. et al. (2018) CRISPR-mediated tagging of endogenous proteins with a luminescent peptide, ACS Chem. Biol. 13(2), 467-474. After knock-in of the tag, individual clones were isolated by single cell dilution and screened for HiBiT insertion by PCR. A clone was identified that contained the desired HiBiT-KRasG12D sequence at one allele while the remaining two KRasG12D alleles were untagged. This clone was used in further studies.

HiBiT Degradation Assays (G12D)

AsPC-1 HiBiT-KRasG12D cells were plated at 9000 or 15,000 cells/well in a 384 well plate (Corning #3770). Compounds of the present disclosure and positive controls were diluted in the appropriate cell media and applied to the plated cells resulting in a final concentration titration of 10 μM to 508 μM in 0.5% DMSO. Gambogic acid was used as a positive control for cytotoxicity and titrated from 10 μM to 78 nM. All assays were performed in triplicate. Cells were treated with compounds for 24 hr at 37° C. in an incubator containing 5% $CO_2$. Following treatment, alamar blue was used to determine if any compounds led to a loss in cell viability after 24 hr. The 10× alamar blue reagent was added to a final concentration of 1× as recommended by the manufacturer and cells were returned to the incubator for 4 hr. Plates were then allowed to equilibrate to RT and fluorescence was measured using a Perkin-Elmer EnVision. After completion of the fluorescence read, the liquid from each well was removed and the cells were washed with PBS. The Nano-Glo® HiBiT detection reagent was prepared according to the manufacturer's instructions and added to each well after the PBS wash was removed. Following incubation at room temperature for 45 min, the luminescence was read using the ultra-sensitive luminescence aperture on the Envision instrument.

Data Analysis

Fluorescence values from the alamar blue treatment were normalized to the DMSO-only control for each compound titration. HiBiT luminescence was normalized to the DMSO-only control and the fractional HiBiT signal was plotted versus the log of the PROTAC concentration and fit to a 4-parameter dose-response model to obtain the concentration of the compound that leads to half maximal degradation ($DC_{50}$) as well as the maximum degradation observed ($D_{max}$, conventionally expressed as a percentage of control).

Degradation data is presented below in Table 3.

Table 3. Degradation of KRas-G12D in AsPC-1 cells at 24 h with compounds of the disclosure $DC_{50}$: A, B, C, or D. According to the code, A represents a $DC_{50}$ value 5100.0 nM; B represents a $DC_{50}$ value >100.0 nM and 5250.0 nM; C represents a $DC_{50}$ value >250.0 nM and ≤1000.0 nM; D represents an $DC_{50}$ value >1000 nM.

$D_{max}$: A, B, C, or D. According to the code, A represents a $D_{max}$ value >70%; B represents a $D_{max}$ value >50% and 570%; C represents a $D_{max}$ value >25% and 550%; D represents a $D_{max}$ value ≤25%.

| Compound | KRas Degradation $DC_{50}$ | KRas Degradation $D_{max}$ |
|---|---|---|
| 1 | B | C |
| 2 | A | A |
| 3 | C | B |
| 4 | D | nd* |
| 5 | D | nd* |
| 6 | D | nd* |
| 7 | D | nd* |
| 8 | C | C |
| 9 | C | C |
| 10 | C | C |
| 11 | C | C |
| 12 | D | C |
| 13 | C | C |
| 14 | C | D |
| 15 | C | C |
| 16 | D | nd |
| 17 | C | D |
| 18 | D | D |
| 19 | C | B |
| 20 | B | B |
| 21 | C | C |
| 22 | B | C |
| 23 | C | C |
| 24 | B | C |
| 25 | A | B |
| 26 | C | C |
| 27 | C | C |
| 28 | C | B |
| 29 | C | B |
| 30 | D | C |
| 31 | B | C |
| 32 | C | B |
| 33 | C | B |
| 34 | C | B |
| 35 | B | A |
| 36 | C | C |
| 37 | D | C |
| 38 | B | B |
| 39 | C | D |
| 40 | D | D |

-continued

| Compound | KRas Degradation $DC_{50}$ | KRas Degradation $D_{max}$ |
|---|---|---|
| 41 | D | nd* |
| 42 | D | nd* |
| 43 | A | A |
| 44 | D | nd* |
| 45 | C | C |
| 46 | D | nd* |
| 47 | C | D |
| 48 | D | nd* |
| 49 | D | nd* |
| 50 | A | D |
| 51 | D | nd* |
| 52 | C | D |
| 53 | B | C |
| 54 | C | D |
| 55 | A | B |
| 56 | C | B |
| 57 | B | C |
| 58 | A | B |
| 59 | A | B |
| 60 | B | C |
| 61 | C | B |
| 62 | A | C |
| 63 | C | C |
| 64 | B | C |
| 65 | C | B |
| 66 | C | D |
| 67 | D | C |
| 68 | A | A |
| 69 | A | A |
| 70 | A | A |
| 71 | A | A |
| 72 | A | A |
| 73 | nd* | nd* |
| 74 | A | A |
| 75 | A | B |
| 76 | A | A |
| 77 | A | A |
| 78 | nd* | nd* |
| 79 | A | A |
| 80 | A | A |
| 81 | A | A |
| 82 | A | A |
| 83 | A | A |
| 84 | A | A |
| 85 | A | A |
| 86 | A | A |
| 87 | A | A |
| 88 | A | A |
| 89 | A | A |
| 90 | D | C |
| 91 | A | A |
| 92 | A | A |
| 93 | A | A |
| 94 | A | A |
| 95 | A | A |
| 96 | A | A |
| 97 | D | nd* |
| 98 | A | A |
| 99 | A | A |
| 100 | A | A |
| 101 | A | A |
| 102 | A | A |
| 103 | A | A |
| 104 | A | A |
| 105 | A | D |
| 106 | A | A |
| 107 | D | nd* |
| 108 | A | D |
| 109 | A | A |
| 110 | A | A |
| 111 | A | A |
| 112 | A | A |
| 113 | A | A |
| 114 | A | C |
| 115 | A | A |
| 116 | A | A |

-continued

| Compound | KRas Degradation $DC_{50}$ | KRas Degradation $D_{max}$ |
|---|---|---|
| 117 | C | C |
| 118 | D | B |
| 119 | A | B |
| 120 | A | A |
| 121 | A | A |
| 122 | A | A |
| 123 | A | A |
| 124 | A | A |
| 125 | A | B |
| 126 | A | A |
| 127 | A | B |
| 128 | B | A |
| 129 | A | A |
| 130 | A | A |
| 131 | A | A |
| 132 | A | A |
| 133 | A | A |
| 134 | A | A |
| 135 | C | B |
| 136 | A | A |
| 137 | A | B |
| 138 | A | A |
| 139 | A | A |
| 140 | C | B |
| 141 | D | nd* |
| 142 | A | A |
| 143 | A | B |
| 144 | A | C |
| 145 | B | A |
| 146 | C | B |
| 147 | A | A |
| 148 | A | A |
| 149 | A | A |
| 150 | A | B |
| 151 | A | A |
| 152 | A | B |
| 153 | A | A |
| 154 | A | A |
| 155 | D | nd* |
| 156 | D | nd* |
| 157 | D | nd* |
| 158 | D | D |
| 159 | A | A |
| 160 | A | A |
| 161 | A | A |
| 162 | A | A |
| 163 | A | A |
| 164 | A | A |
| 165 | A | A |
| 166 | A | A |
| 167 | A | B |
| 168 | A | A |
| 169 | A | A |
| 170 | A | A |
| 171 | A | A |
| 172 | A | A |
| 173 | A | A |
| 174 | A | A |
| 175 | A | A |
| 176 | A | A |
| 177 | A | A |
| 178 | A | A |
| 179 | A | A |
| 180 | A | A |
| 181 | A | A |
| 182 | A | A |

-continued

| Compound | KRas Degradation $DC_{50}$ | KRas Degradation $D_{max}$ |
|---|---|---|
| 183 | A | A |
| 184 | A | A |
| 185 | A | A |
| 186 | A | A |
| 187 | A | A |
| 188 | A | A |
| 189 | A | A |
| 190 | A | A |
| 191 | A | A |
| 192 | A | A |
| 193 | A | A |
| 194 | A | A |
| 195 | A | A |
| 196 | A | A |
| 197 | A | A |
| 198 | A | A |
| 199 | A | A |
| 200 | A | A |
| 201 | A | A |
| 202 | A | A |
| 203 | A | A |
| 204 | A | A |
| 205 | A | A |
| 206 | A | A |
| 207 | A | A |
| 208 | A | A |
| 209 | A | A |
| 210 | A | A |
| 211 | A | B |
| 212 | A | A |
| 213 | A | A |
| 214 | A | A |
| 215 | A | A |
| 216 | A | A |
| 217 | A | A |
| 218 | A | A |
| 219 | A | A |
| 220 | A | A |
| 221 | A | A |
| 222 | A | A |
| 223 | A | A |
| 224 | A | A |
| 225 | A | A |
| 226 | A | A |
| 227 | A | B |
| 228 | A | B |
| 229 | A | A |
| 230 | A | B |
| 231 | A | A |
| 232 | A | A |
| 233 | A | A |
| 234 | A | A |
| 235 | A | A |
| 236 | A | A |
| 237 | A | A |
| 238 | A | A |
| 239 | A | A |

*nd = not determined

Example 160: Treatment with Compounds 69 and 102 and Results in Tumor Growth Inhibition In Vivo The effect on tumor growth of treatment with Compound 69 and 102 was assessed in the GP2d (95090714 Millipore Sigma, USA) and LS180 (CL-187 ATCC, USA) colorectal cancer models, and the AsPC-1 (CRL-1682 ATCC, USA), SW1990 (CRL-2172, ATCC, USA), HPAC (CRL-2119 ATCC, USA), and Panc04.03 (CRL-2555 ATCC, USA) pancreatic cancer models. Briefly, cells were grown in HYPER flasks (Corning) and harvested and prepared for implant by preparing a suspension with a final concentration of $25\times10^6$ cells/ml in 50% matrigel (Corning) and 50% phenol red-free media (Gibco DMEM or RPMI-1640, depending on cell line). For Panc04.03, 6-7 week NOD/SCID female mice (GemPharmatech Co. Ltd) were inoculated with 200 μl of the cell suspension (10 million cells/mouse) subcutaneously on the left flank under sterile conditions. For all other cell lines, 6-8 weeks old CB17 SCID female mice (Charles River Laboratories) were inoculated with 200 μl of the cell suspension (5 million cells/mouse) subcutaneously on the left flank under sterile conditions. Studies were initiated when tumors reached an average of approximately 200 $mm^3$. Compound 69 and Compound 102 were prepared in 30% HPbCD in 10 mM citrate buffer, pH 4.0, and dosed intravenously (IV). Tumor growth inhibition (TGI) was calculated using the formula % $TGI=(V_C-V_T)/(V_C-V_0)\times100$ where $V_C$, $V_T$ are the average of control and treated groups at the end of the study, and $V_0$ is the average tumor volume at randomization. Treatment with Compound 69 and Compound 102 resulted in robust TGI in multiple models, including GP2d (FIGS. 7A and 7B), LS180 (FIG. 8), SW1990 (FIGS. 10A and 10B), HPAC (FIG. 11), and Panc04.03 (FIG. 12). More moderate response was observed with Compound 69 in AsPC-1 (FIG. 9A), whereas Compound 102 led to 100% TGI (FIG. 9B). Compound treatment in LS180 resulted in moderate TGI of 30-50% (FIG. 8).

Tumor Lysate Preparation and Western Blot Methods

Cold RIPA buffer was added to frozen tumor pieces at a volume of 1 μl/mg of tumor tissue in a 2 ml tube. A single metal bead (5 mm) was added to each tube and tumors were lysed by rapid shaking in a Tissuelyser for 4 minutes at 24 Hz at 4° C. Beads were removed from tubes and lysates were centrifuged for 15 minutes at 4° C. at 15000 rpm in a benchtop microcentrifuge. The supernatants (lysates) were collected and used to make 1:30 dilutions in RIPA buffer. The concentrated and diluted lysates were frozen at −80° C.

Protein Quantification, BCA assay

The BCA assay was run according to manufacturer's protocol (ThermoFisher) with provided bovine serum albumin (BSA) standard curve (range=2 mg/ml-0.1 mg/ml) in a 96 well plate. The previously prepared 1:30 lysate dilutions were used for the BCA assay and for preparation of gel samples. Plates were read (OD562) using a BioTek Cytation3 plate reader running Gen5 3.11 software. Protein concentration of tumor lysates was determined with GraphPad Prism by interpolating sample ODs with BCA assay standard curve.

SDS-PAGE Gel Samples

Lysates were diluted by combing an appropriate volume of lysate, sample buffer, reducing agent, and ultrapure water. Gel samples were prepared to allow equal volume loading of 8-10 μg of total protein/lane for all tumor samples.

Electrophoresis and Transfer

Gels were loaded with 8 μg of total protein per well on 26 well, 4-12% Bis-Tris gels (ThermoFisher). BioRad Precision Plus molecular weight markers were loaded into lanes 1 and 26 (4 μl per lane). Gels were run in MOPS/SDS running buffer for 65 minutes at 150 volts. Protein was transferred to nitrocellulose membranes using the BioRad Trans Blot Turbo semi-dry system. Transfer conditions were midi gel format at 25 volts, 2.5 amps, for 7 minutes.

Blocking and Antibody Hybridization

Membranes were cut into strips at desired molecular weights and then blocked for 1 hour in 3% BSA/TBS-T. Primary antibodies were diluted as per manufacturer's instructions in 3% BSA/TBS-T and incubated overnight at 4° C. with gentle rocking. Membranes were then washed 5x5 minutes with TBS-T at room temperature. Secondary antibodies were diluted 1:20000 in 3% BSA/TBS-T and incubated at room temperature for 1 hour. Membranes were then washed 5×5 minutes with TBS-T.

Chemiluminescent Development and Densitometry

Membranes were developed for 2 minutes with SuperSignal™ West Femto Maximum Sensitivity Substrate and then imaged with a BioRad ChemiDoc imager running Image Lab software v 5.2.1. Densitometry analysis was done using ImageJ software, all samples were normalized to vinculin loading control and then graphed as a percent of control as compared to vehicle treated tumors.

Reagents for Cell Culture/Implantation

- DMEM—Gibco/ThermoFisher #10566016
- RPMI-1640—Gibco/ThermoFisher #61870036
- DMEM/F12—Gibco/ThermoFisher #10565018
- DMEM (phenol red-free)—Gibco/ThermoFisher #21063029
- RPMI-1640 (phenol red-free) Gibco/ThermoFisher #11835030
- DPBS—Gibco/ThermoFisher #14190144
- Trypsin/EDTA—Gibco/ThermoFisher #25200056
- FBS—Gibco/ThermoFisher #26140079
- Penicillin-Streptomycin (PenStrep)—Gibco/ThermoFisher #15140122
- Human EGF recombinant protein—Gibco/ThermoFisher #PHG0315
- EMEM—ATCC #302003
- RPMI-1640—ATCC #302001
- Hydrocortisone—Millipore Sigma #H0135-1 mg
- Insulin solution, human—Millipore Sigma #19278-5 ml
- ITS supplement—R&D Systems #AR013
- Matrigel—Corning #354234
- HYPER flask—Corning #10034

Reagents for Tumor Western Blots

- RIPA buffer—ThermoFisher #89900
- HALT protease inhibitor—ThermoFisher #78437
- HALT phosphatase inhibitor—Thermofisher #78420
- EDTA, 0.5M—Thermofisher #1861275
- BCA Protein Assay kit—ThermoFisher #23225
- NuPAGE 4×LDS sample buffer—ThermoFisher #NP0007
- Bolt 10×sample reducing agent—Thermofisher #B0009
- NuPAGE 4-12% Bis-Tris Midi gel, 26 well—ThermoFisher #WG1403BX10
- BioRad Precision Plus Dual Color ladder—BioRad #1610374
- Trans-blot midi Nitrocellulose transfer pack—Biorad #1704159
- MOPS/SDS running buffer—Thermofisher #NP0001-02
- SuperSignal™ West Femto—ThermoFisher #34095
- TBS-T (1×TBS with 0.1% tween-20)
- BSA, bovine serum albumin, fraction V—AmericanBio #AB00440-01000
- 5 mm stainless steel bead—Qiagen #69989
- Ras (G12D mutant specific)(D8H7) Rabbit mAb—Cell Signaling Technology #14429S
- Vinculin (E1E9V) XP Rabbit mAb—Cell Signaling Technology #13901S
- Anti-rabbit IgG, HRP-linked Antibody—Cell Signaling Technology #7074P2

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula IVB:

(IVB)

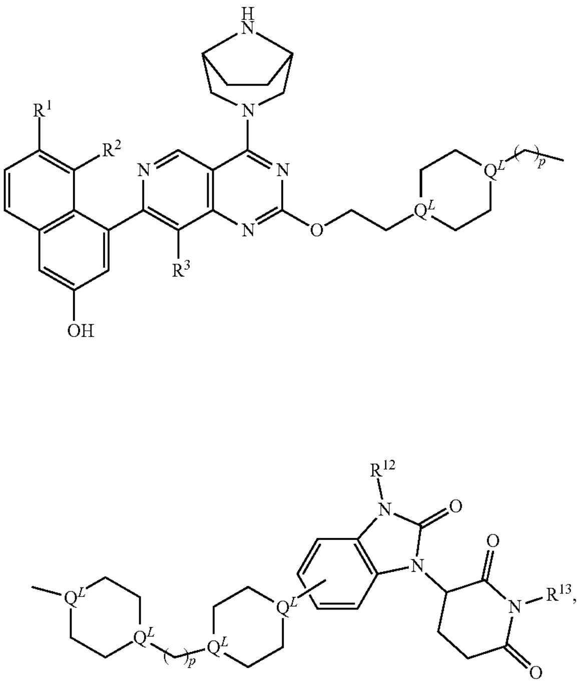

or a pharmaceutically acceptable salt thereof, wherein:

$R^1$ and $R^2$ are each independently selected from H, halo, $C_{1-6}$ alkyl, and $C_{2-6}$ alkynyl;

$R^3$ is selected from H, halo, and CN;

each $Q^L$ is independently $CR^L$ or N;

each $R^L$ is independently H, halo, or CN;

each p is 1, 2, 3, 4, 5, or 6; and $R^{12}$ and $R^{13}$ are each independently selected from H, $C_{1-6}$ alkyl, and $C_{1-6}$ alkoxy.

2. The compound of claim 1, each $R^L$ is independently H or halo.

3. The compound of claim 1, wherein each $Q^L$ is independently CH or N.

4. The compound of claim 1, wherein $R^3$ is halo.

5. The compound of claim 1, wherein each p is 1, 2, 3, or 4.

6. The compound of claim 1, wherein each p is 1, 2, or 3.

7. The compound of claim 1, wherein the compound is selected from:

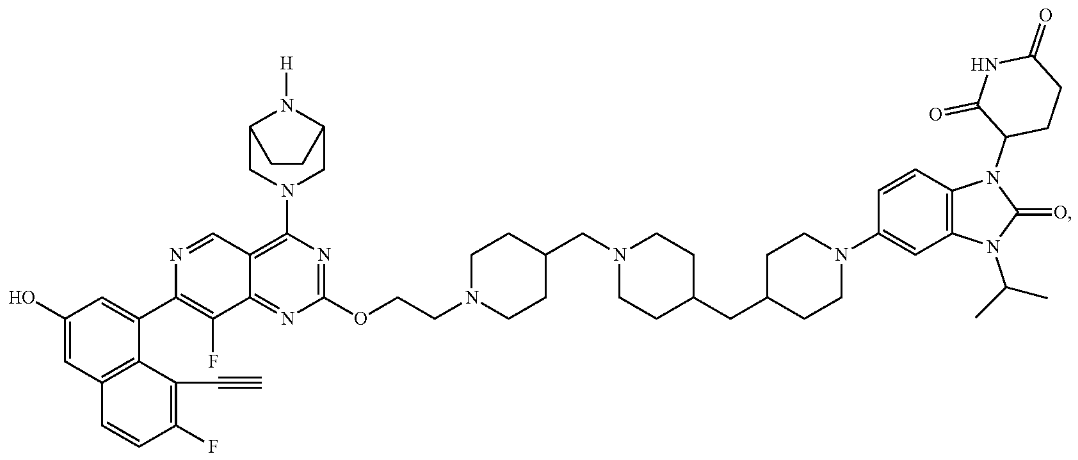
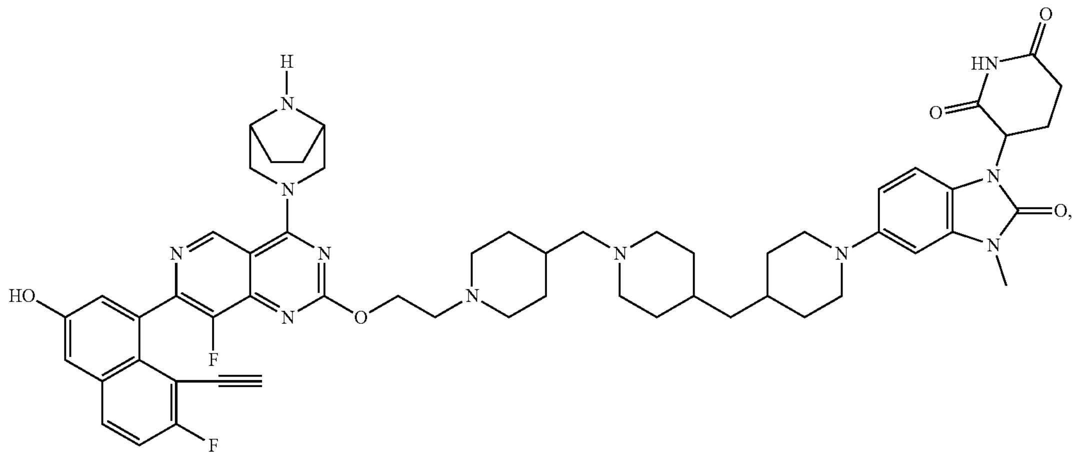
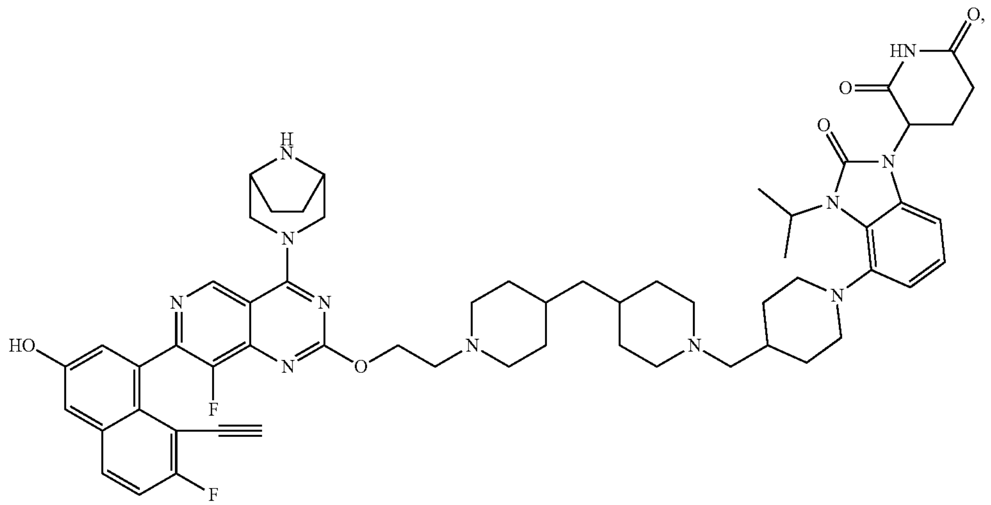

-continued
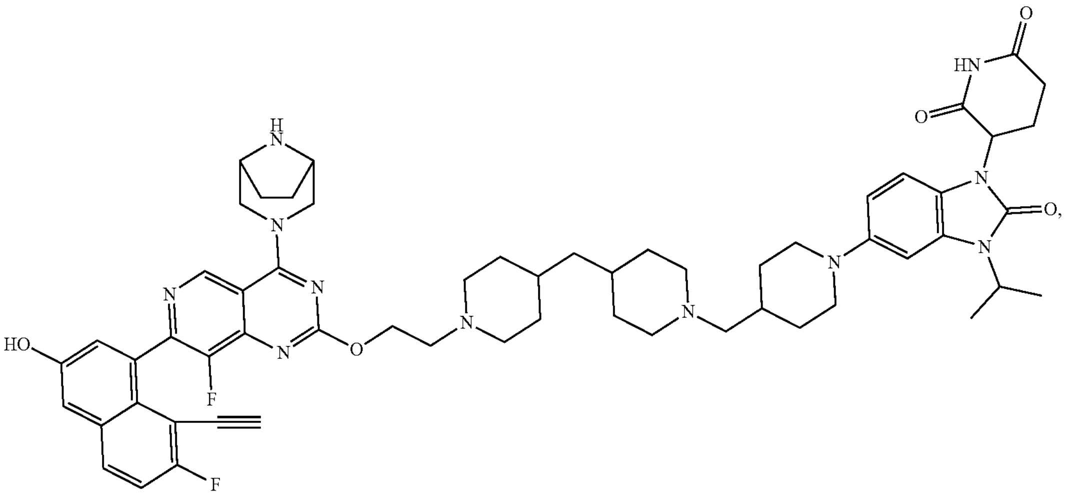
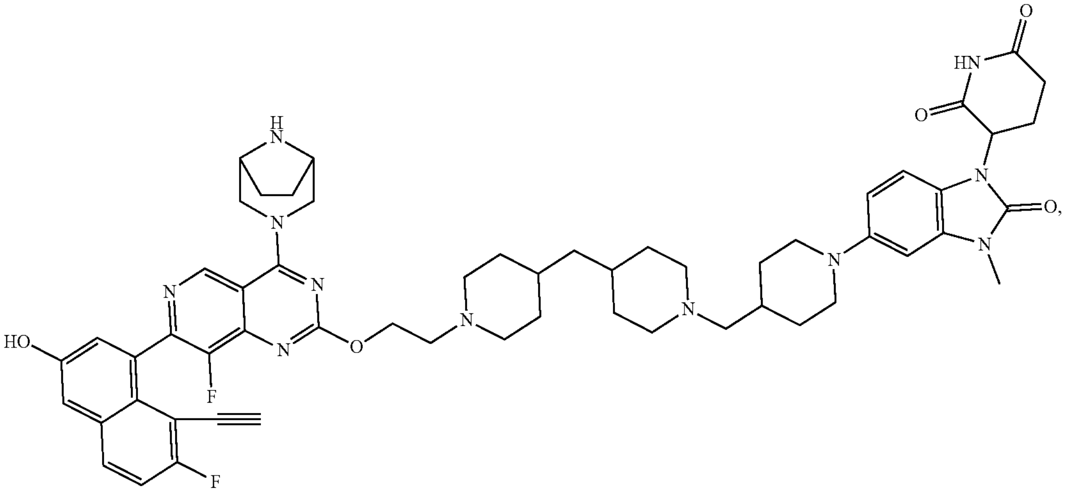
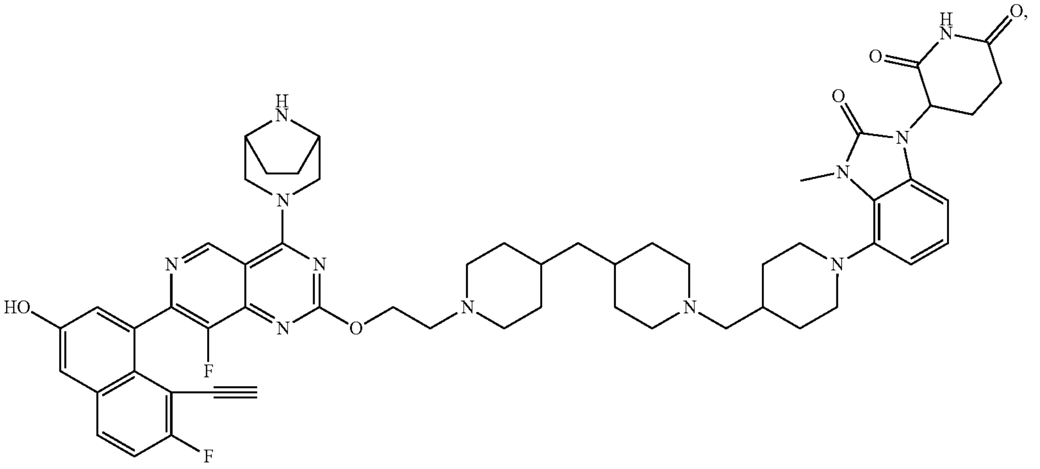

-continued
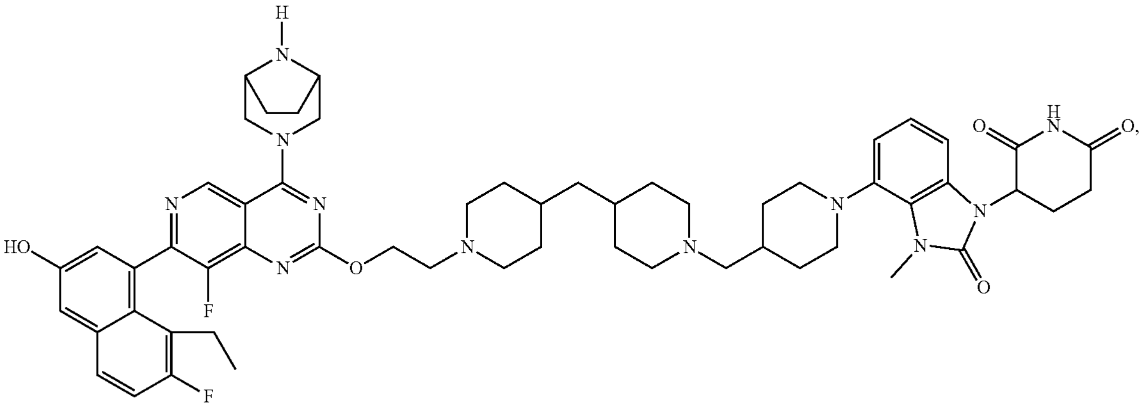
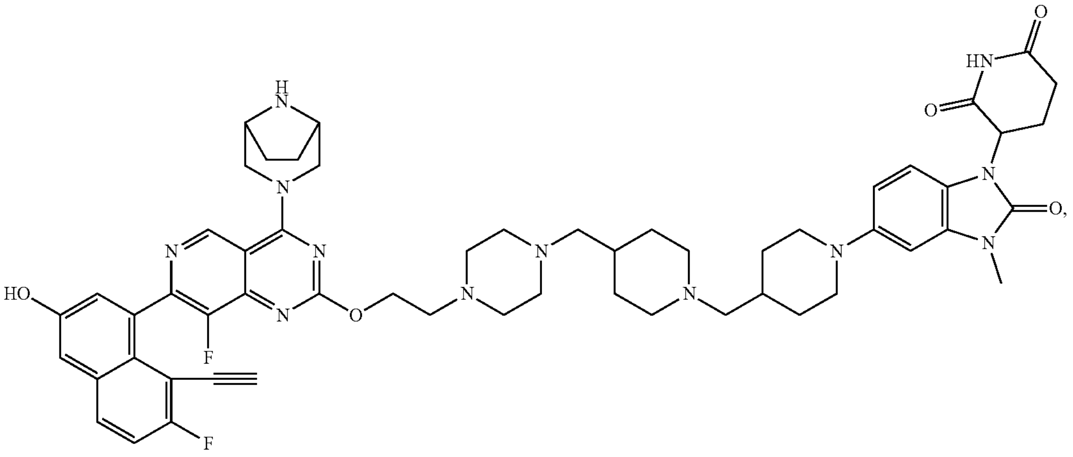
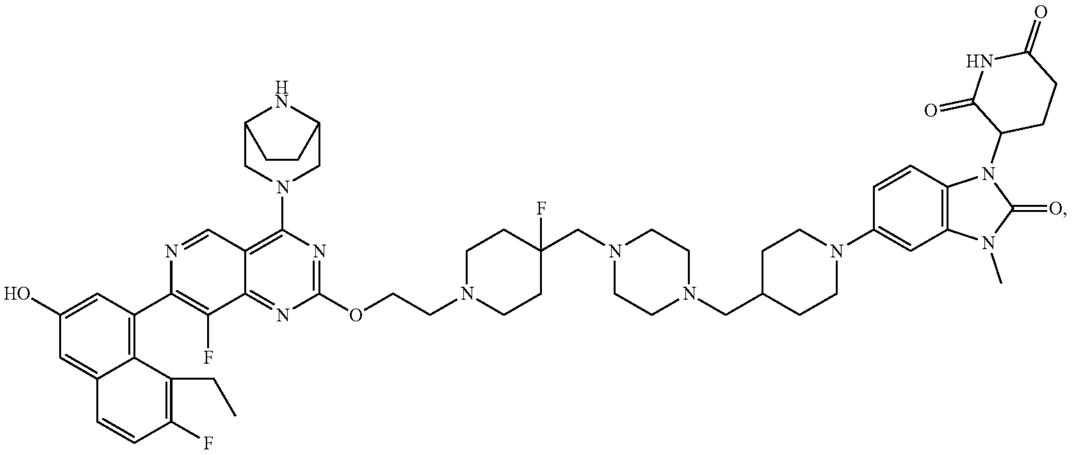

-continued
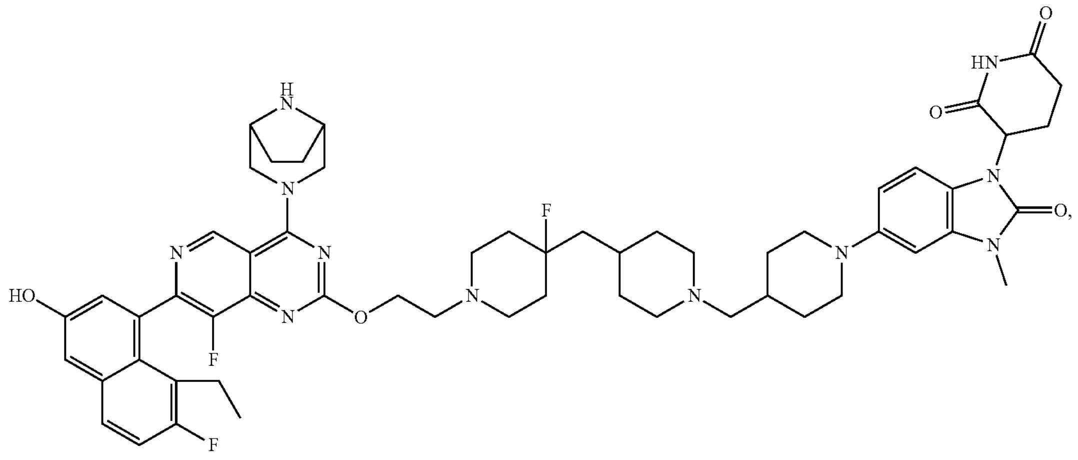
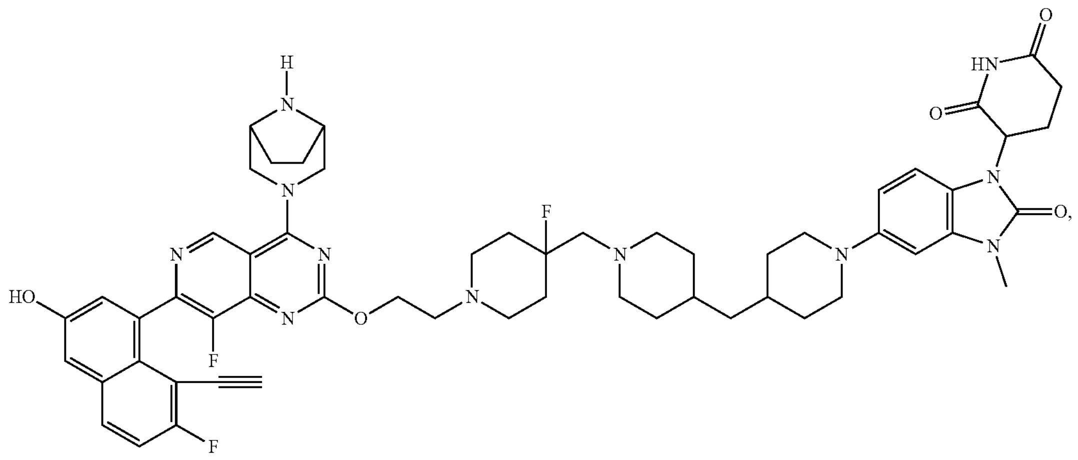
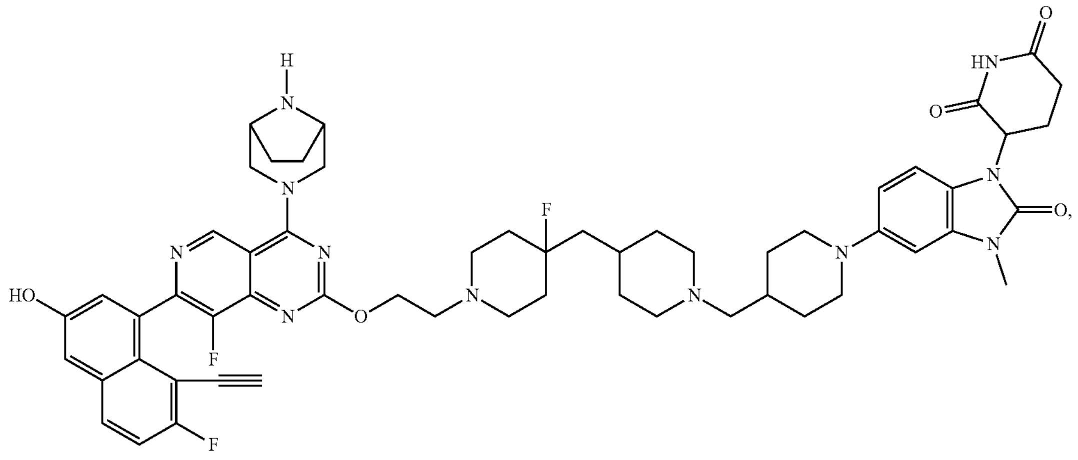

-continued
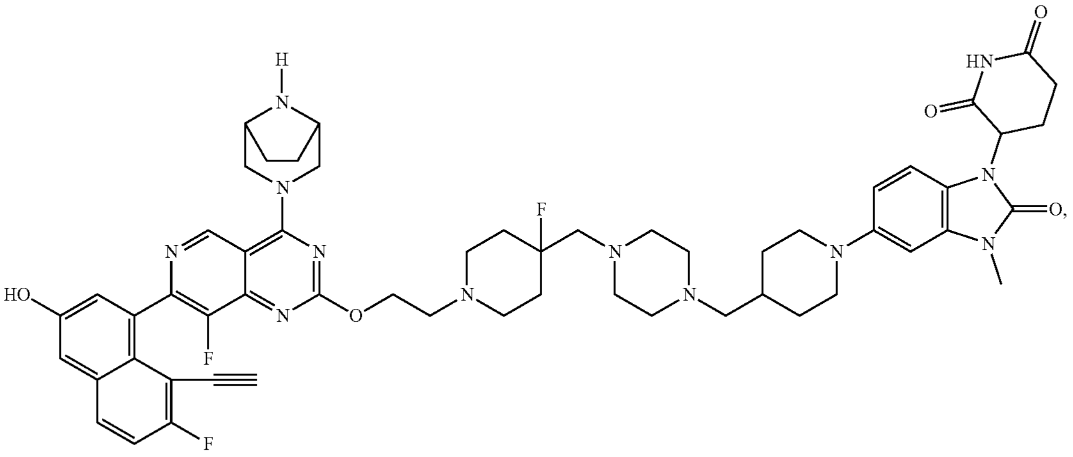
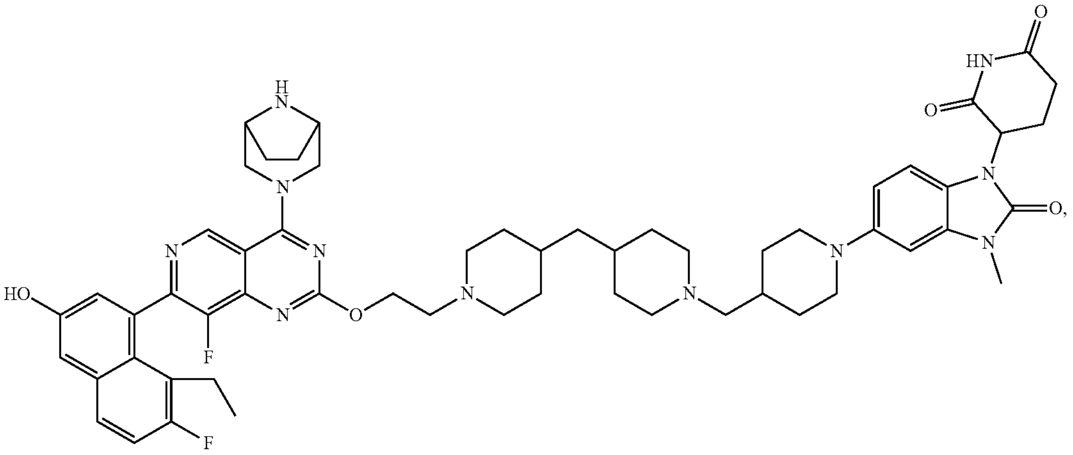
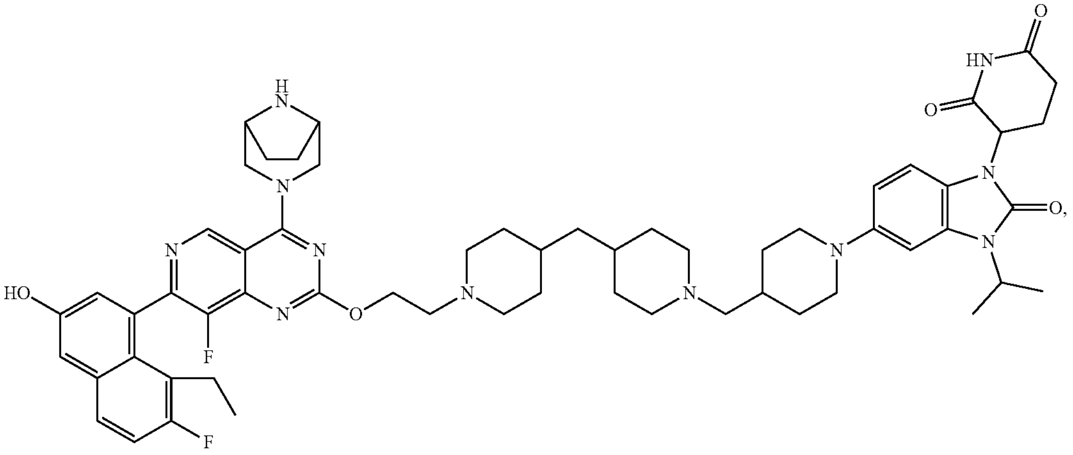

-continued
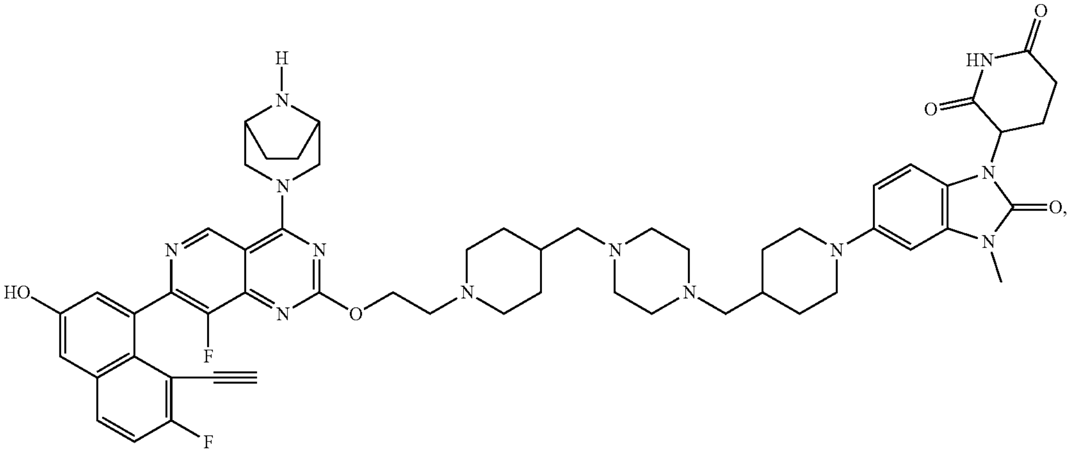
O, and
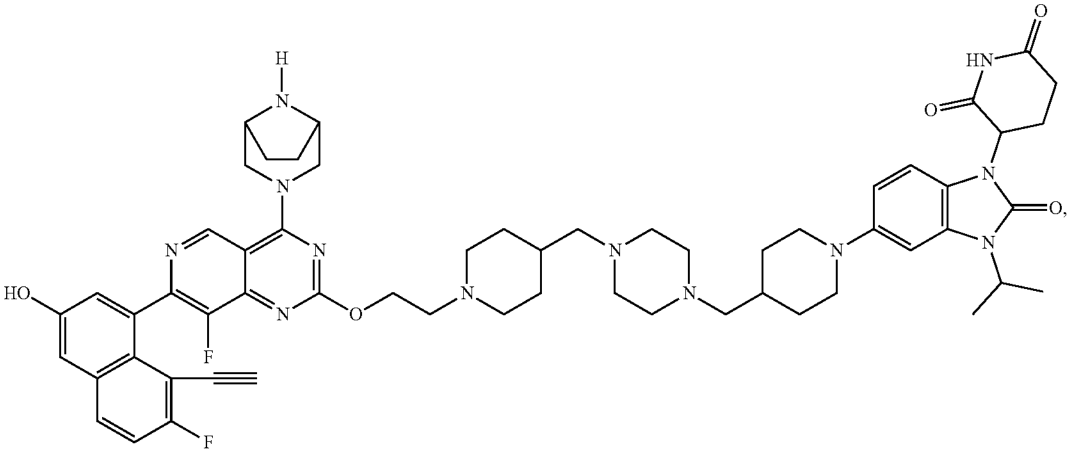
O,
or a pharmaceutically acceptable salt thereof.
8. The compound of claim 1, wherein the compound is selected from:
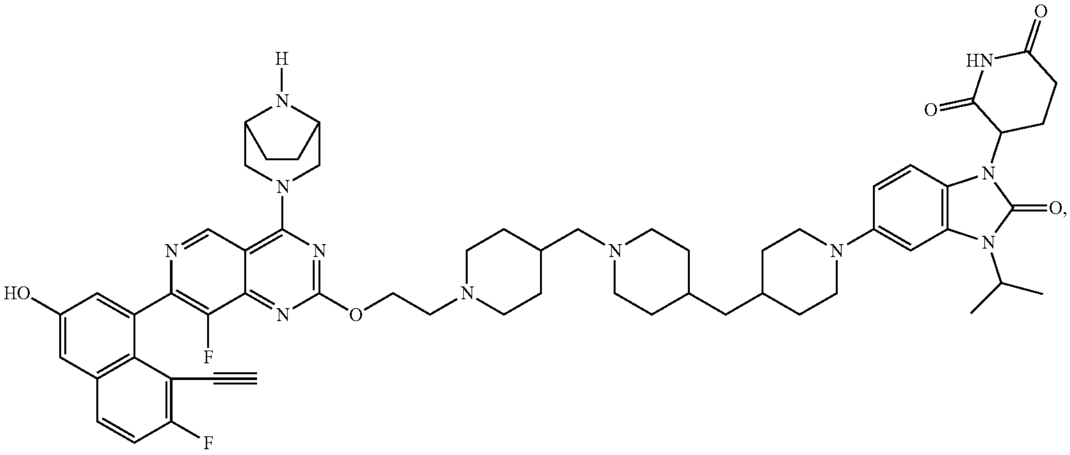
O, -continued
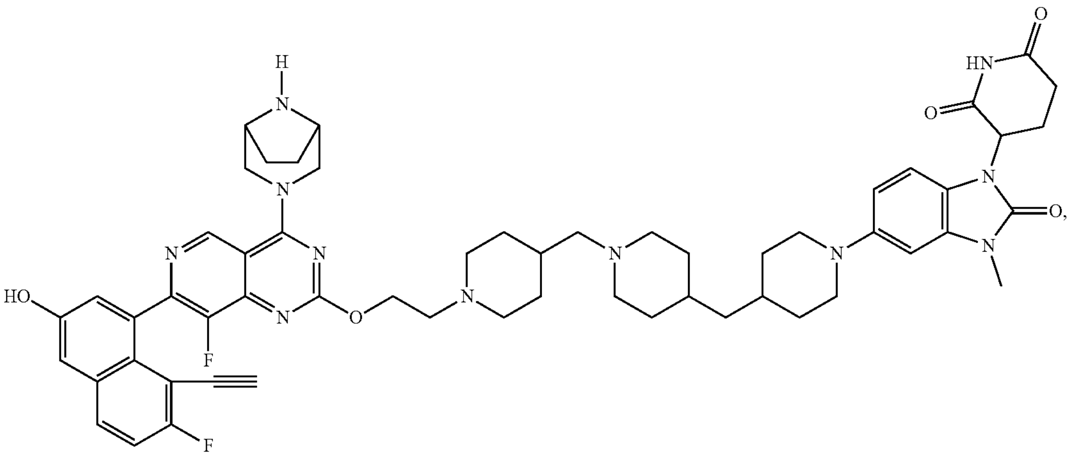
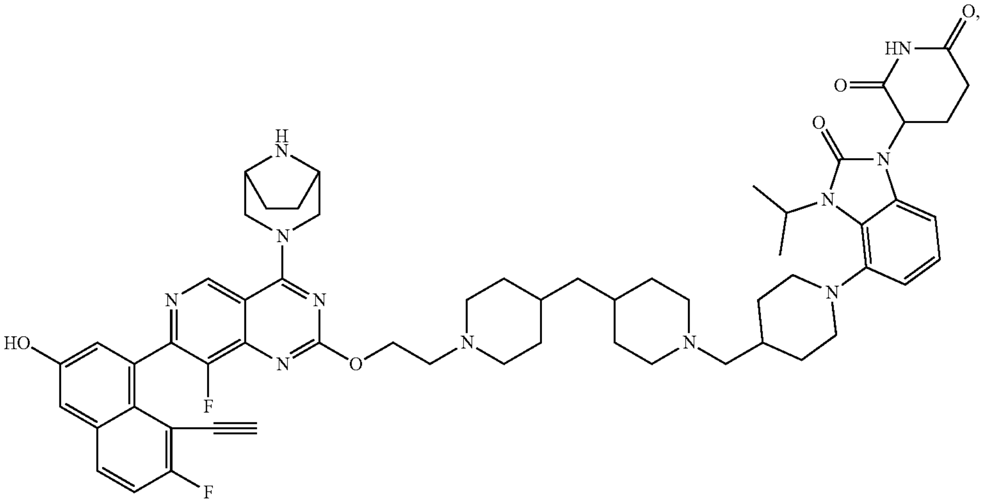
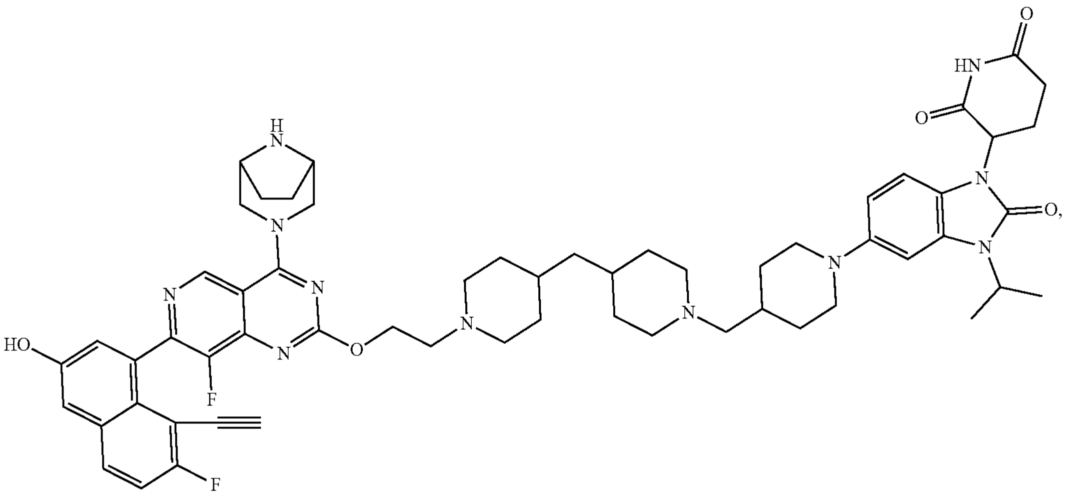

-continued
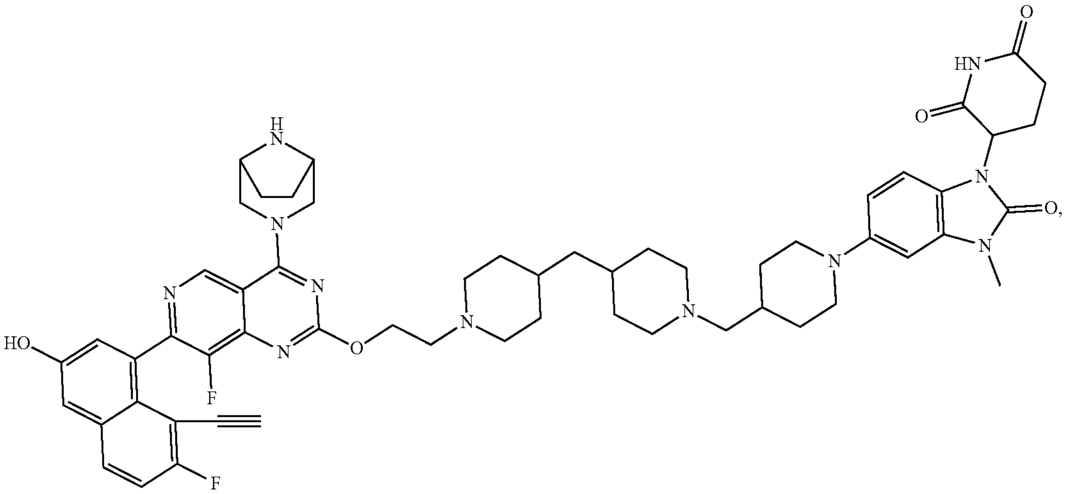
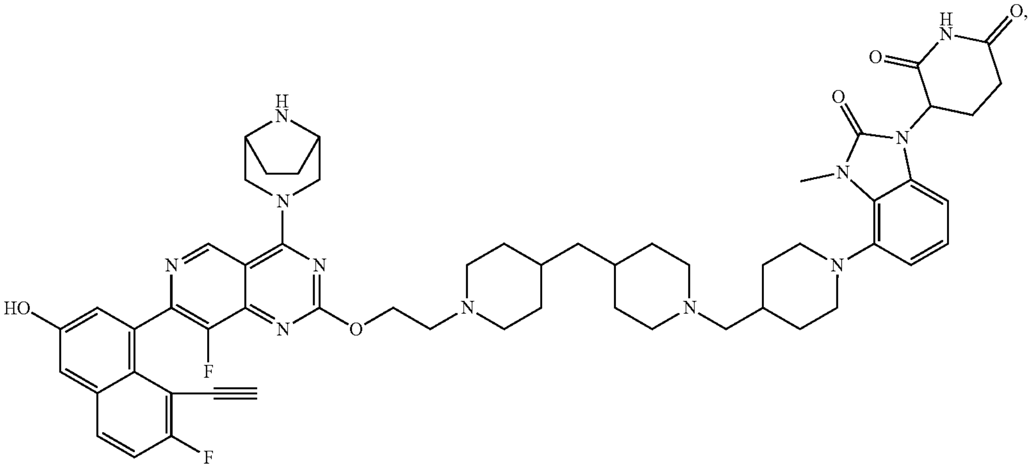
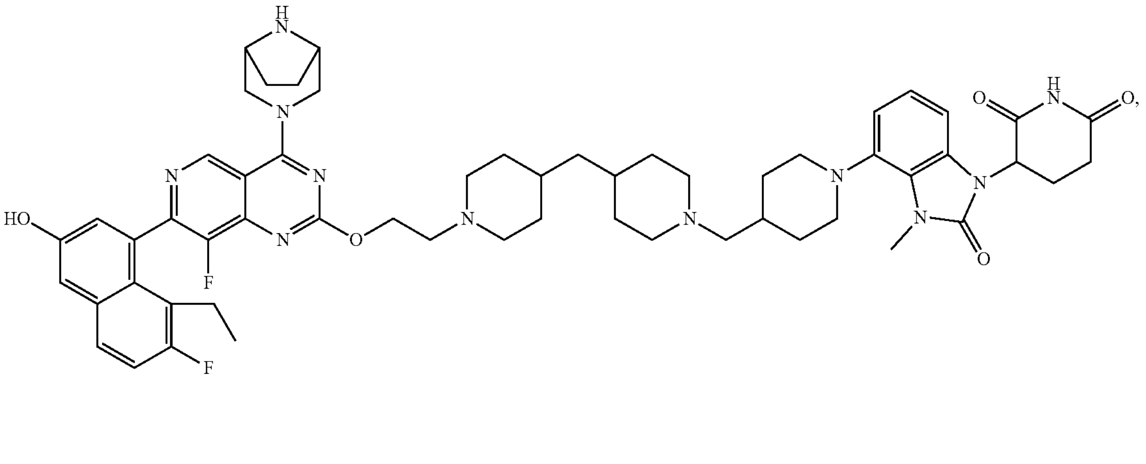

-continued
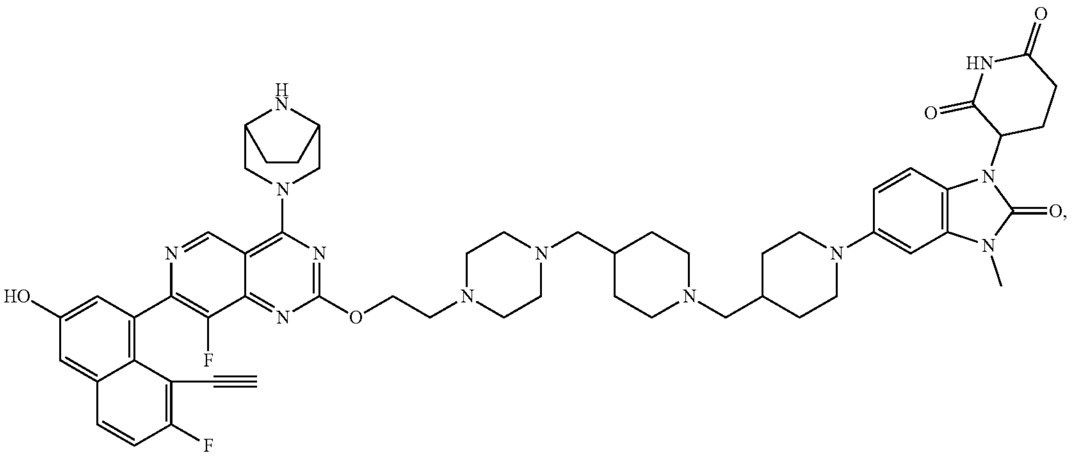
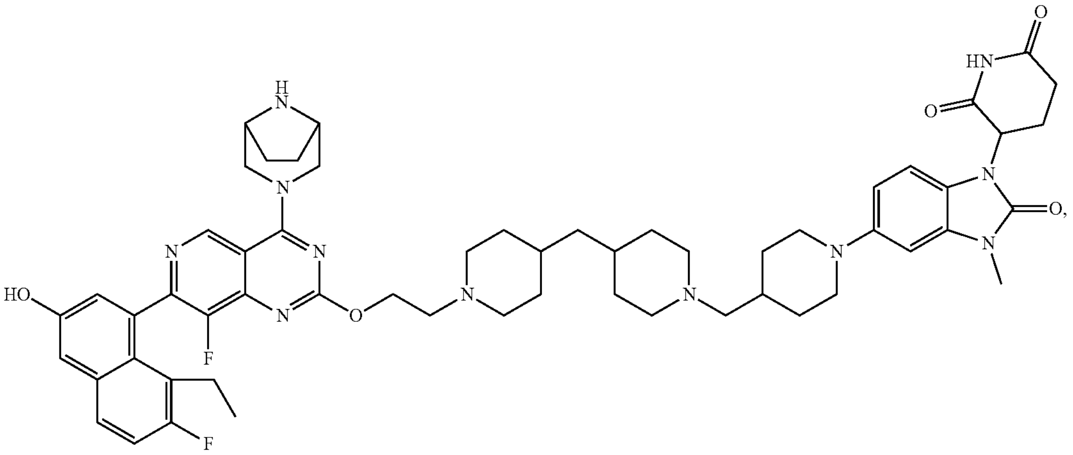
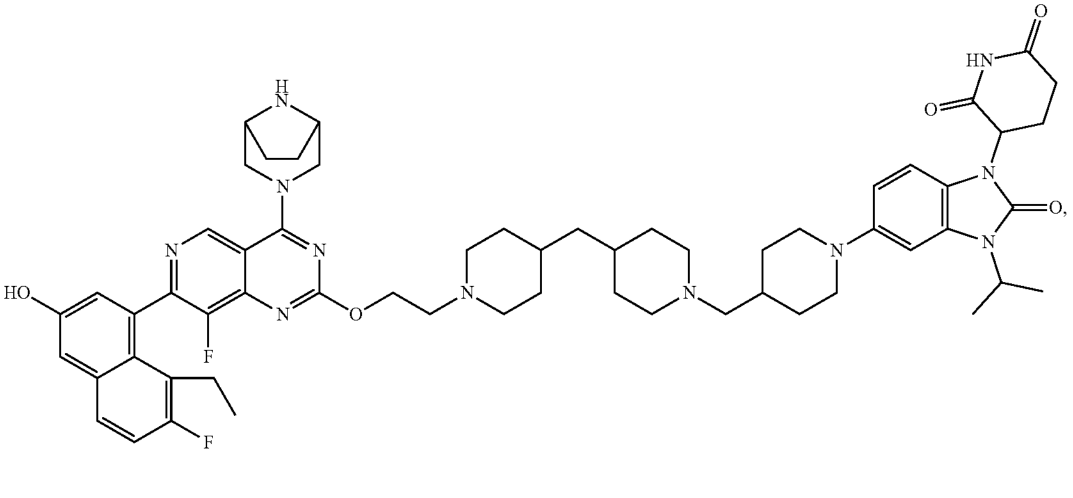

-continued
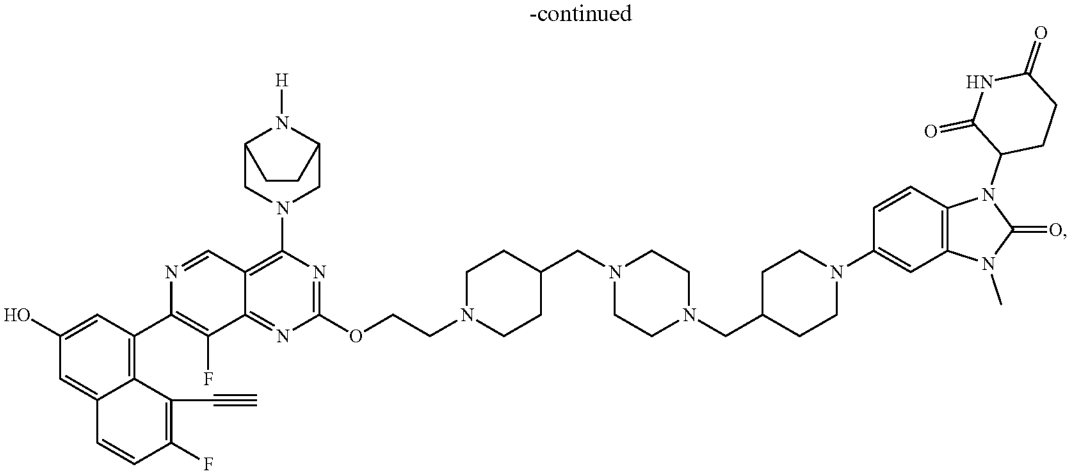
and
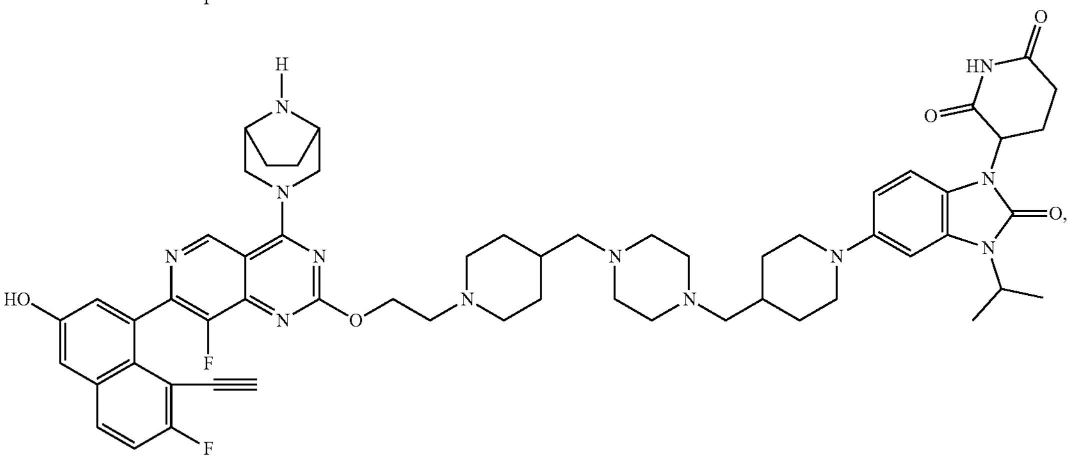
,
or a pharmaceutically acceptable salt thereof.
9. The compound of claim 1 wherein the compound is selected from:
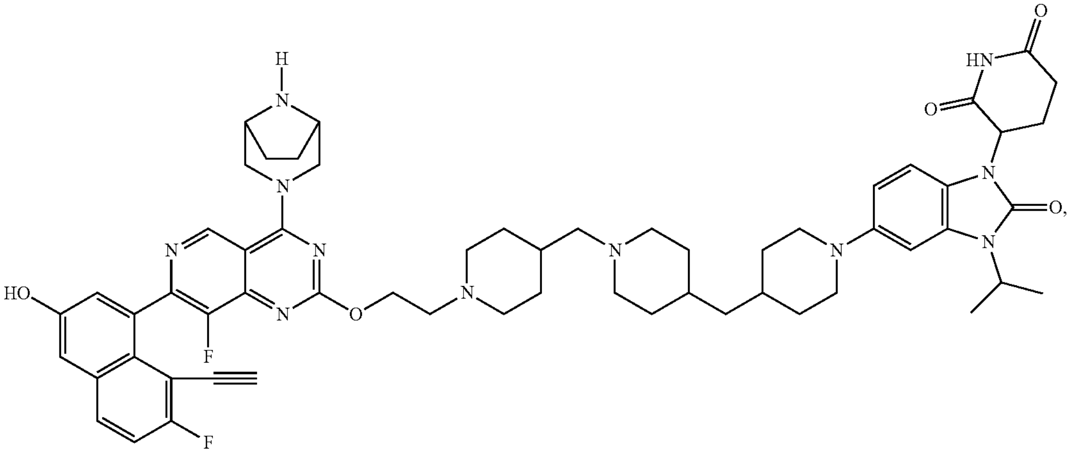
, -continued
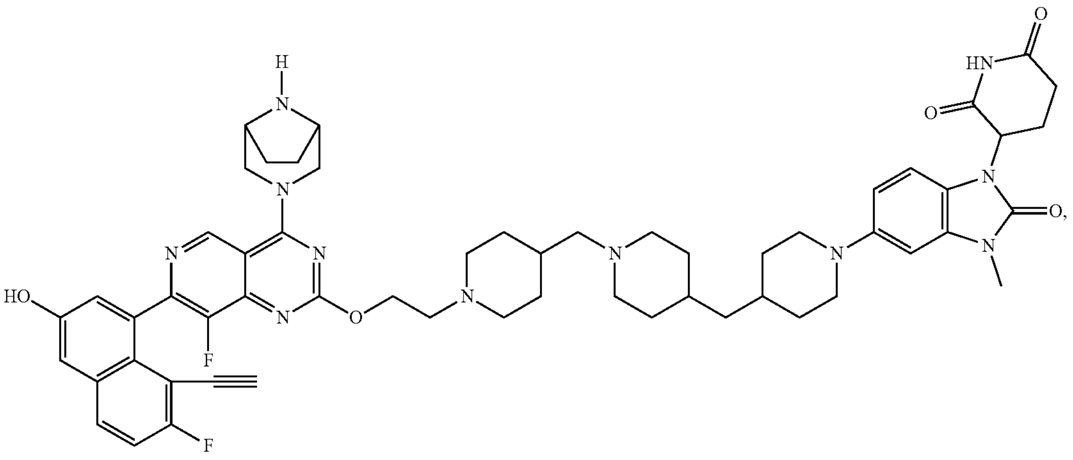
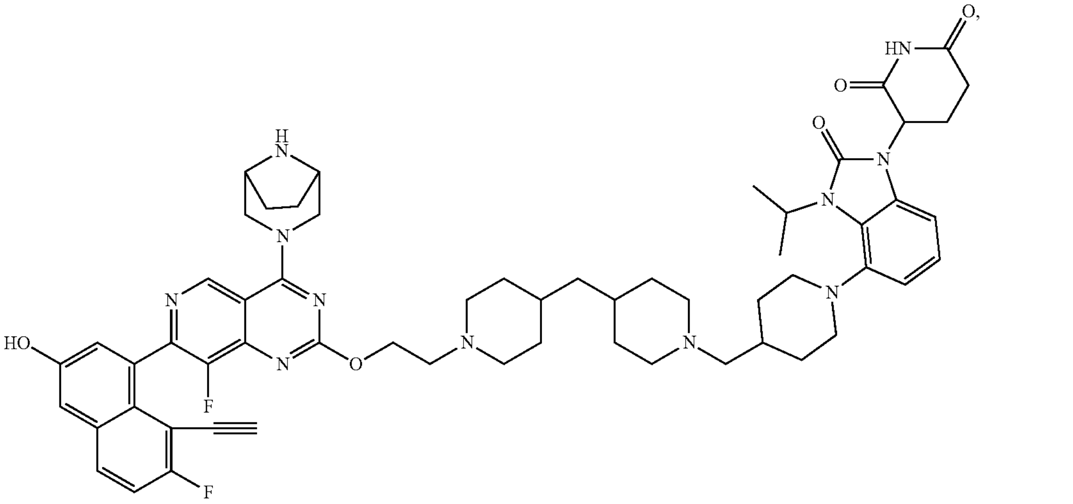
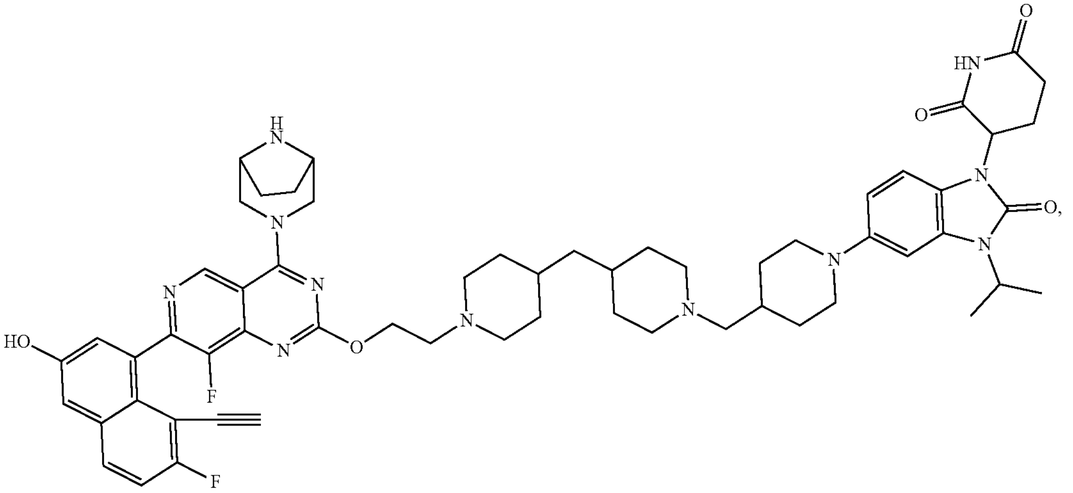

-continued
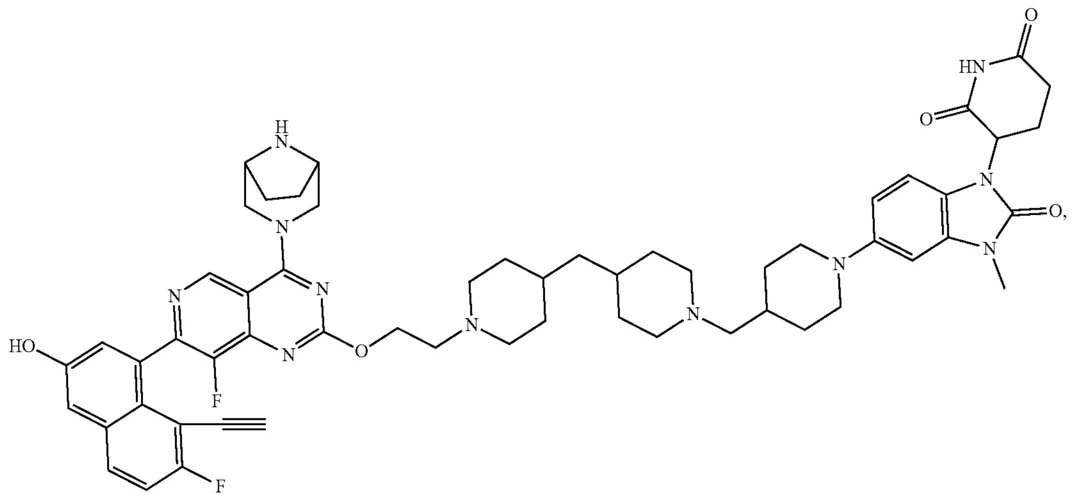
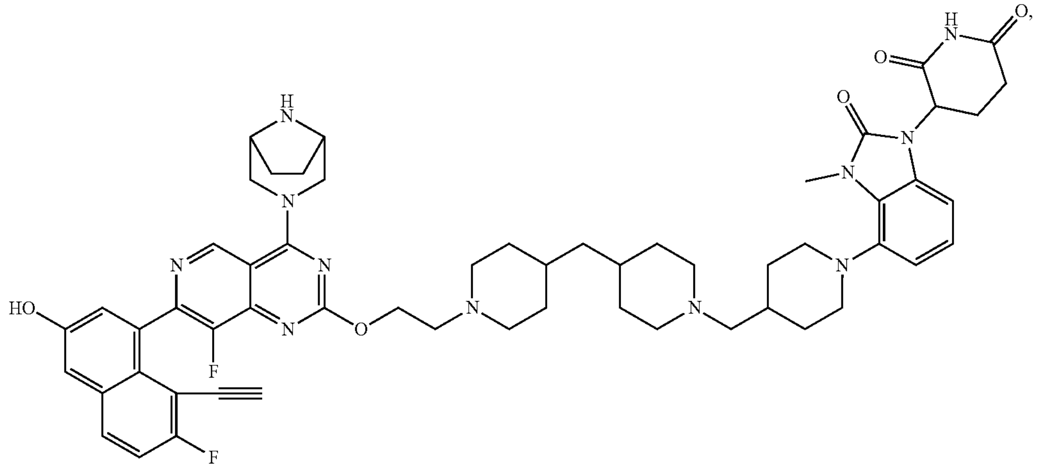
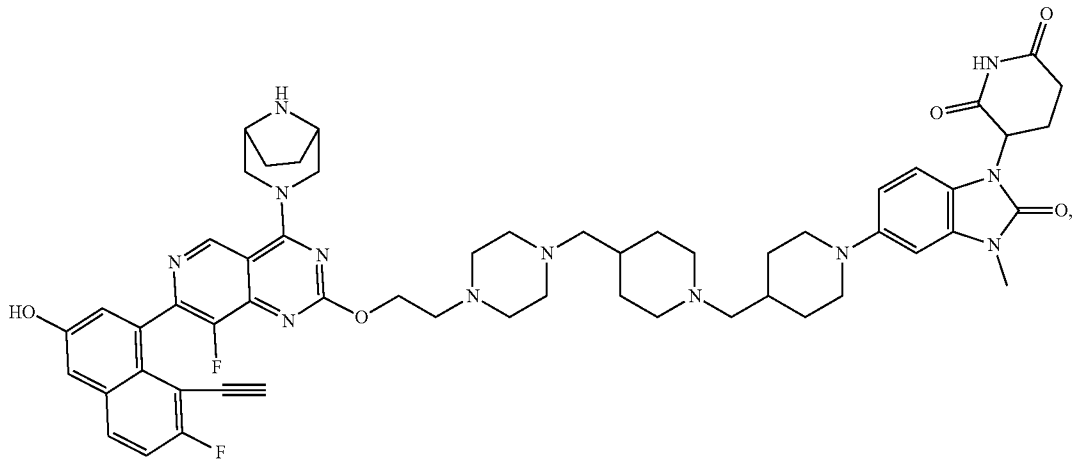

-continued

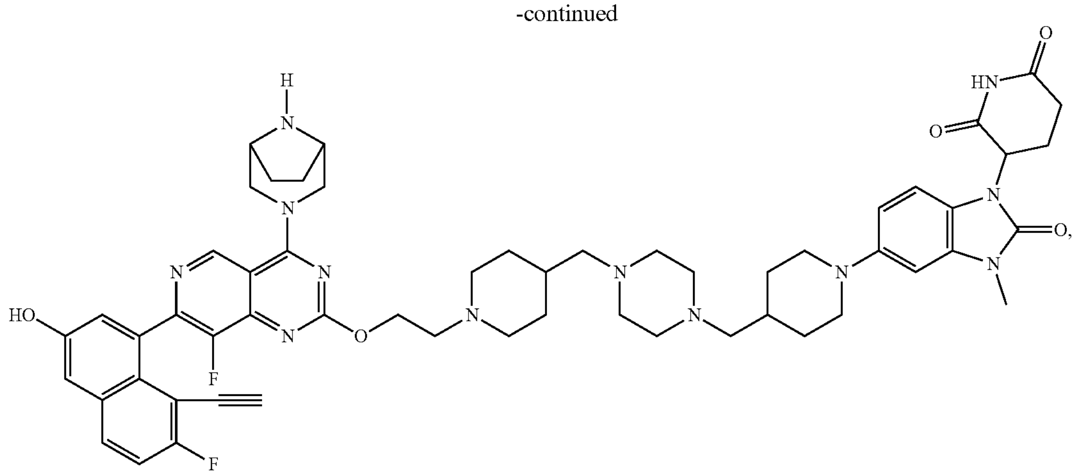

, and

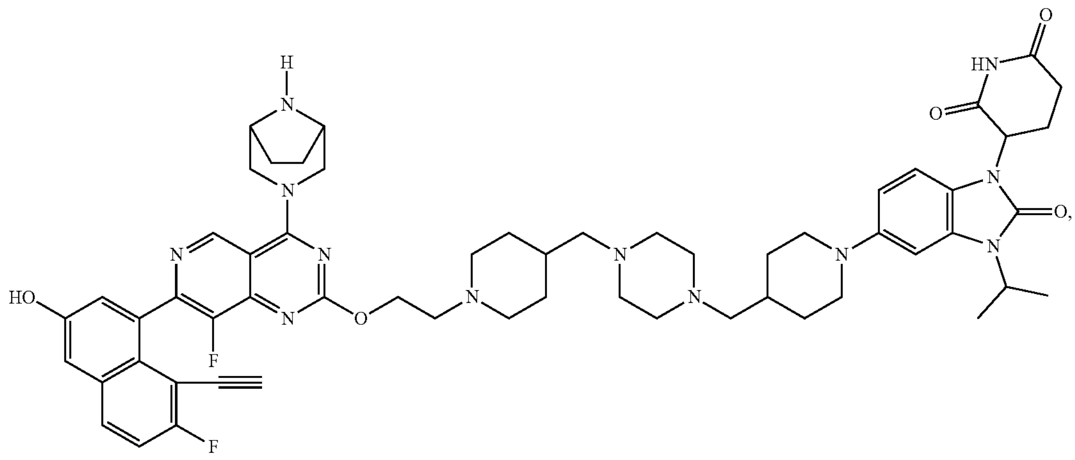

, or a pharmaceutically acceptable salt thereof.

10. A pharmaceutical composition comprising a compound of claim 1 and a pharmaceutically acceptable carrier.

11. A method of treating cancer in a subject comprising administering to the subject an effective amount of a compound according to claim 1, wherein the cancer is characterized by a KRAS G12D mutation.

12. The method of claim 11, wherein the cancer is selected from bladder cancer, bowel cancer, breast cancer, cervical cancer, colon cancer, colorectal cancer, endometrial cancer, esophageal cancer, head cancer, kidney cancer, liver cancer, lung cancer, neck cancer, pancreatic cancer, prostate cancer, stomach cancer, uterine cancer, ovarian cancer, testicular cancer, thyroid cancer, pineal cell tumor, carcinoma, cytoma, ependymoma, ganglioglioma, ganglioneuroma, gliobastoma, glioma, leukemia, lymphoma, medulloblastoma, melanoma, meningioma, myeloma, nephroblastoma, neuroblastoma, neurofibroma, oligodendroglioma peripheral neuroepithelioma, sarcoma, and schwannoma.

13. The method of claim 12, wherein the leukemia is acute lymphoblastic leukemia.

14. A compound of Formula IB-i:

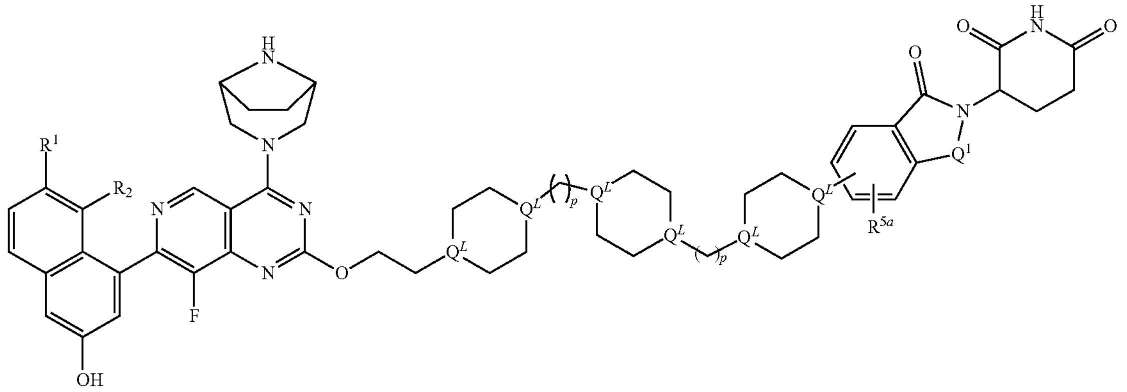

(IB-i)

or a pharmaceutically acceptable salt thereof, wherein:

$Q^1$ is selected from $C(R^{14})_2$, C(O), and $NR^{14}$;

$R^1$ is halo;

$R^2$ is selected from H, halo, $C_{1-6}$ alkyl, $C_{2-6}$ alkenyl, $C_{2-6}$ alkynyl, $C_{1-6}$ alkoxy, and $C_{1-6}$ haloalkyl;

$R^{5a}$ and $R^{14}$ are each independently selected from H, halo, $C_{1-6}$ alkyl, $C_{1-6}$ alkoxy, and $C_{1-6}$ haloalkyl;

each $Q^L$ is independently $CR^L$ or N;

each $R^L$ is independently H, halo, or CN; and each p is independently 1, 2, 3, 4, 5, or 6.

15. The compound of claim 14, wherein $R^2$ is selected from H, $C_{1-6}$ alkyl, and C≡CH.

16. The compound of claim 14, wherein $R^{5a}$ is selected from H, halo, and $C_{1-6}$ alkoxy.

17. The compound of claim 14, wherein $R^{14}$ is H or $C_{1-6}$ alkyl.

18. The compound of claim 14, wherein $Q^1$ is $CH_2$ or C(O).

19. The compound of claim 14, wherein the compound is selected from:

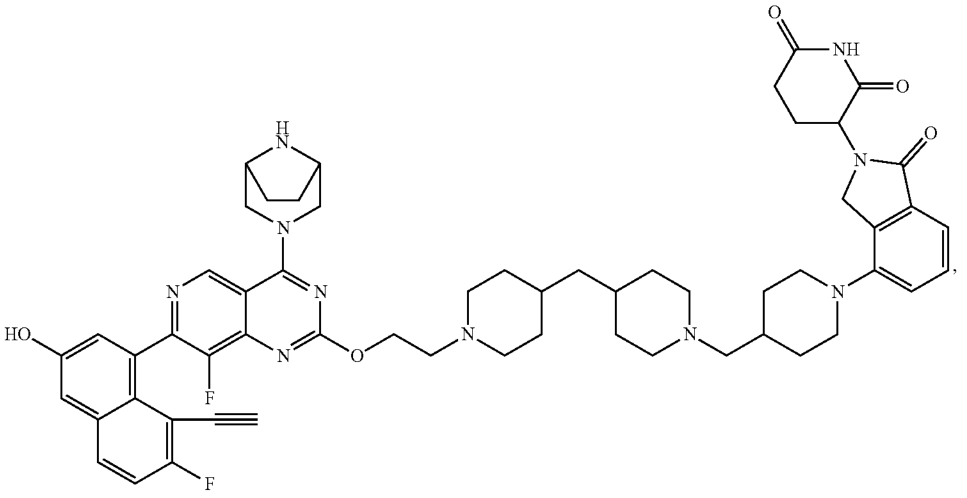 [SMILES: C#Cc1c(F)ccc2cc(O)cc(-c3ncc4c(N5CC6CCC(C5)N6)nc(OCCN5CCC(CC6CCN(CC7CCN(c8cccc9c8CN(C8CCC(=O)NC8=O)C9=O)CC7)CC6)CC5)nc4c3F)c12]

,

-continued
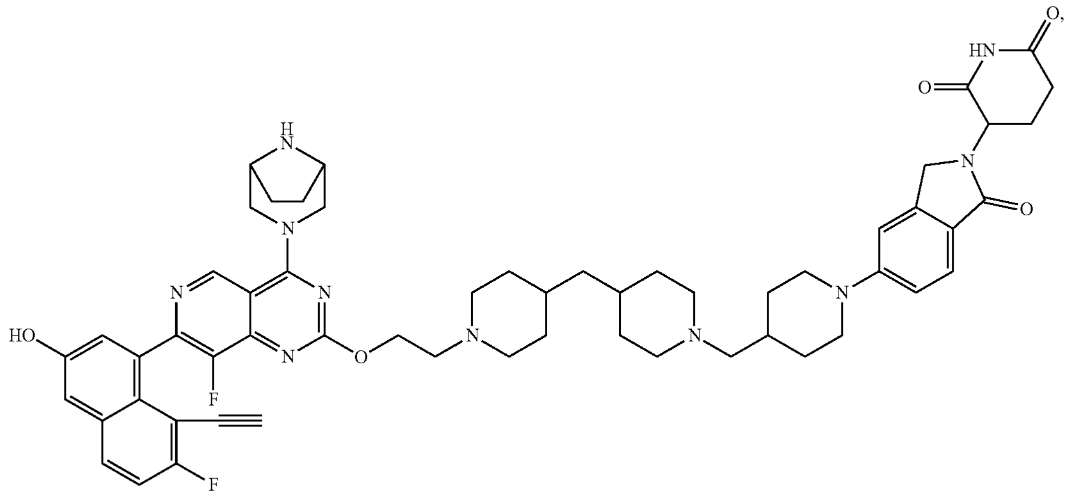
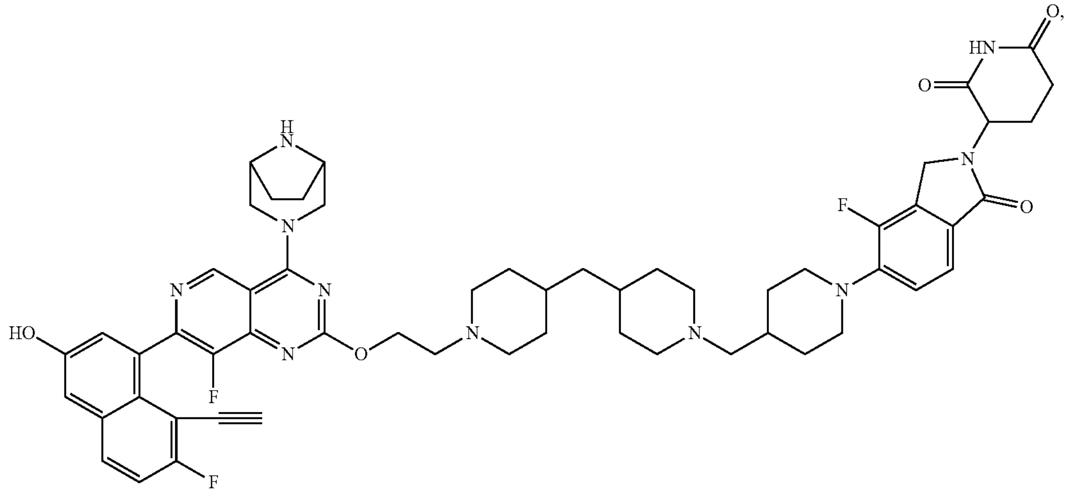
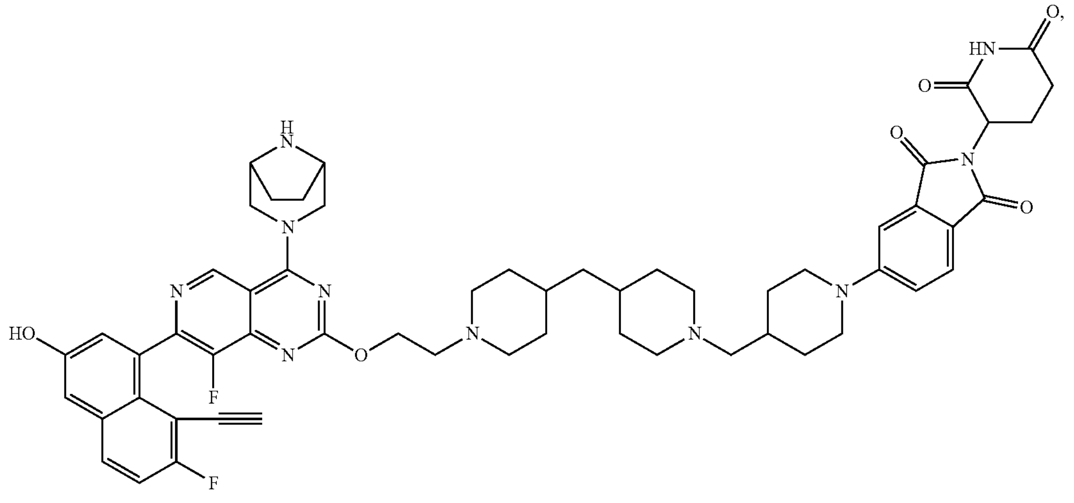

-continued
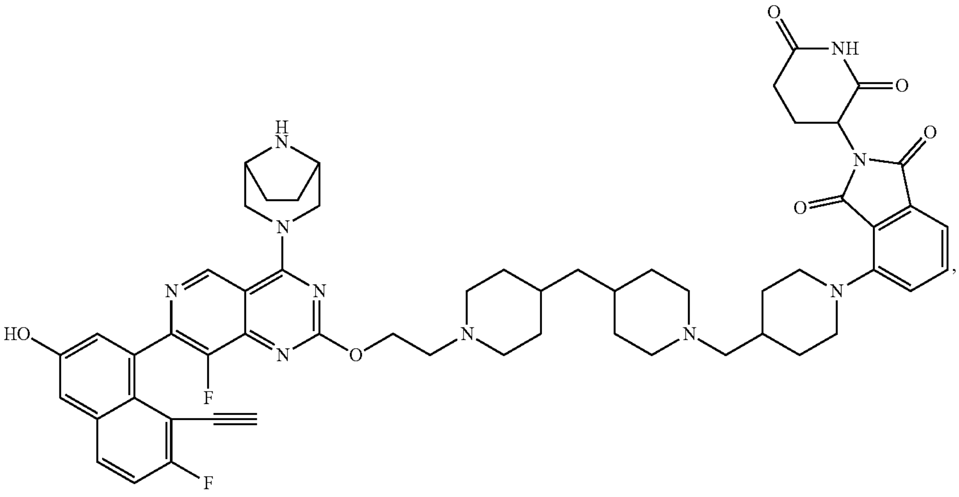
,
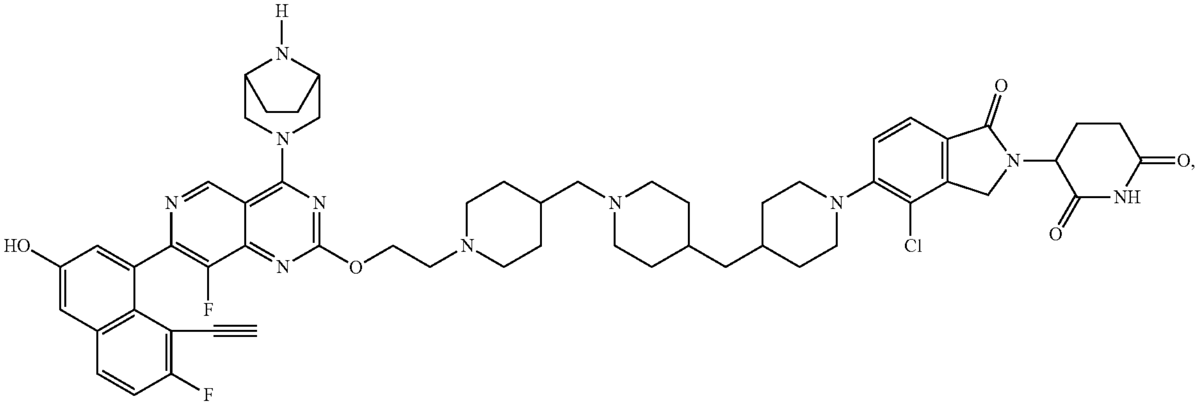
,
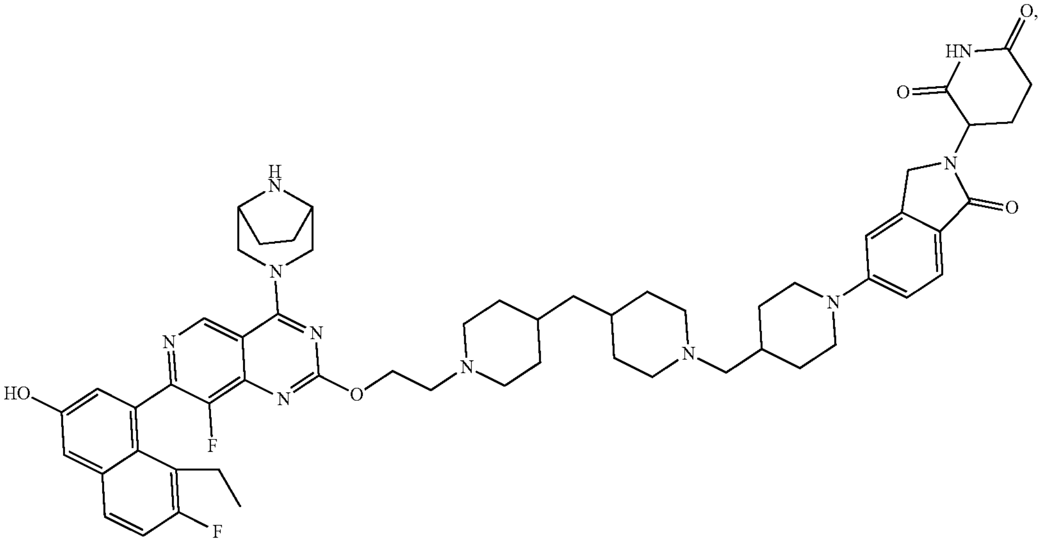
,

-continued
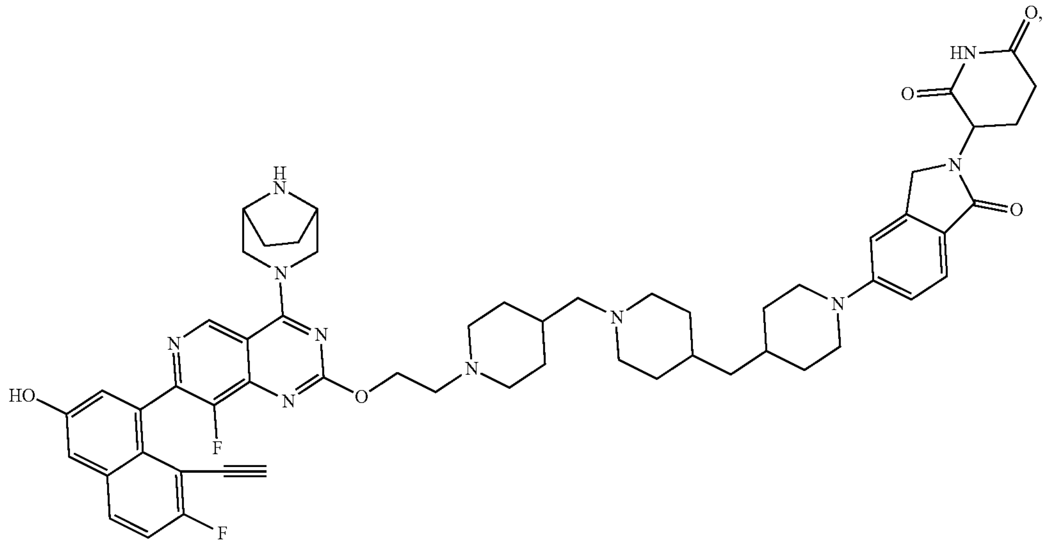
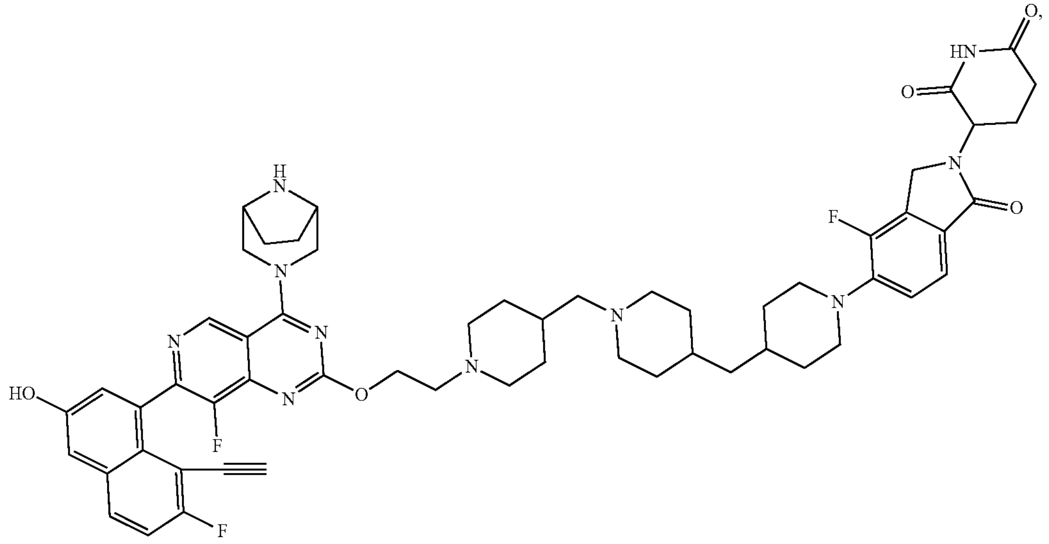
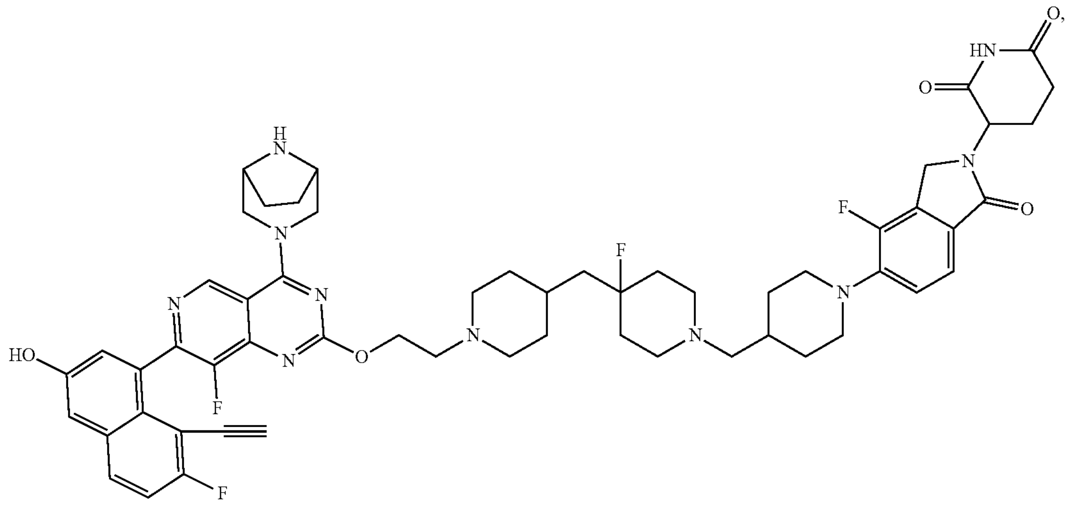

-continued
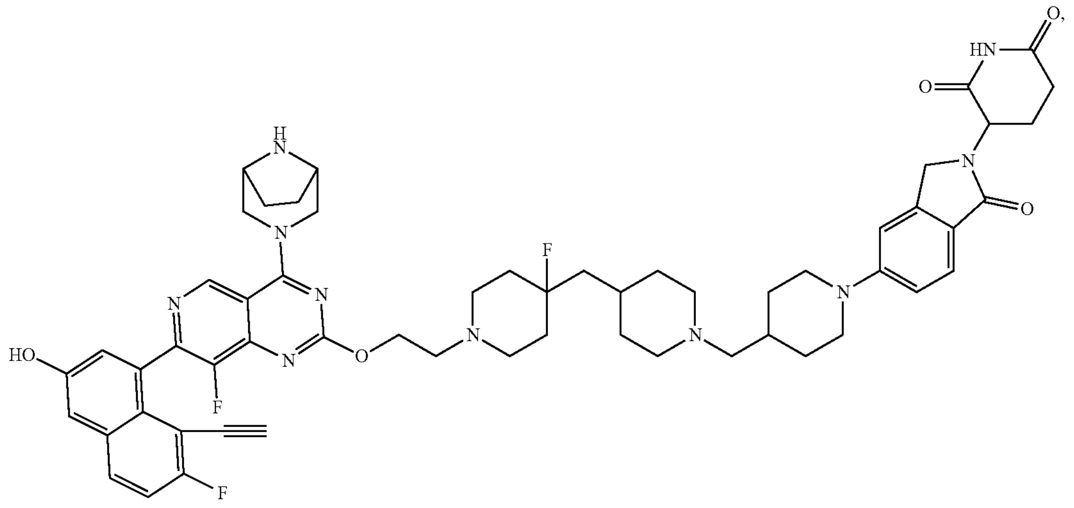
,
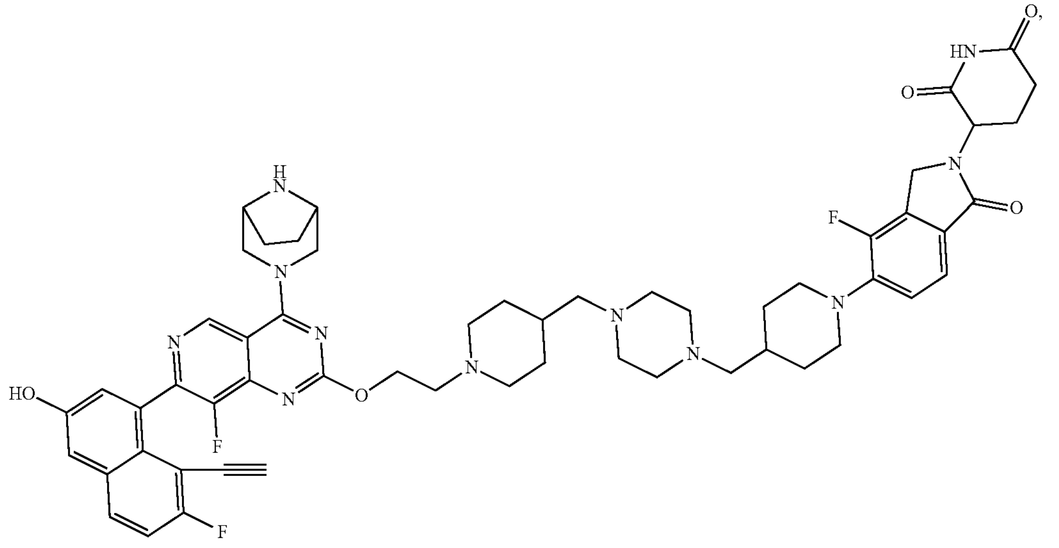
,
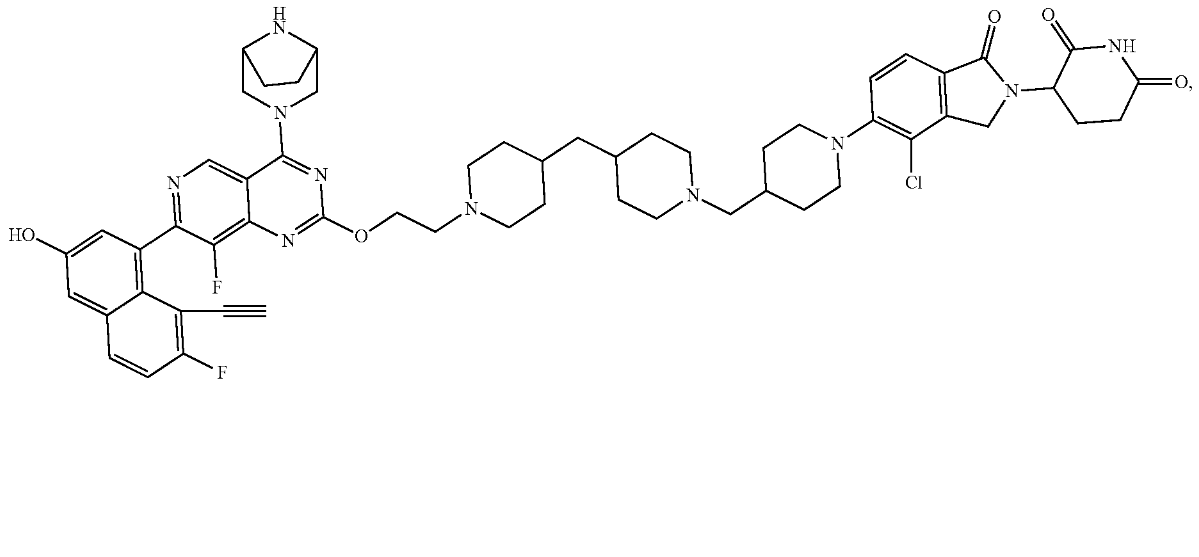
,

-continued
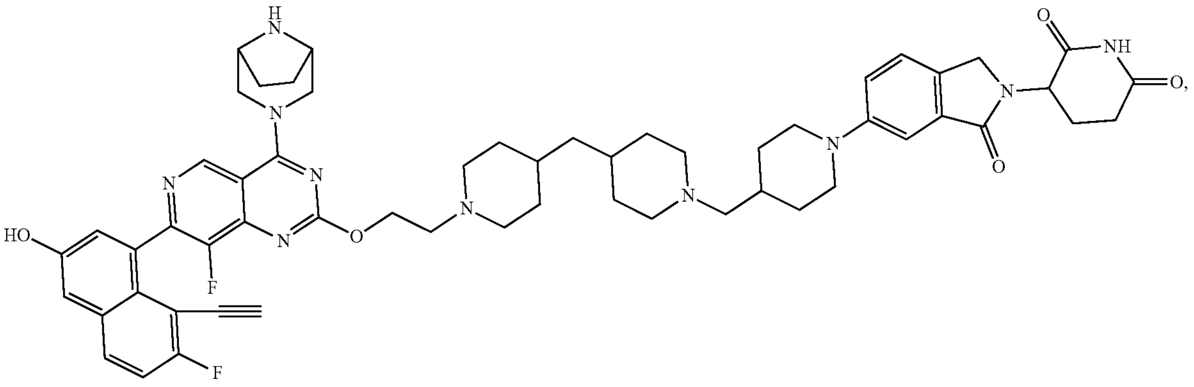
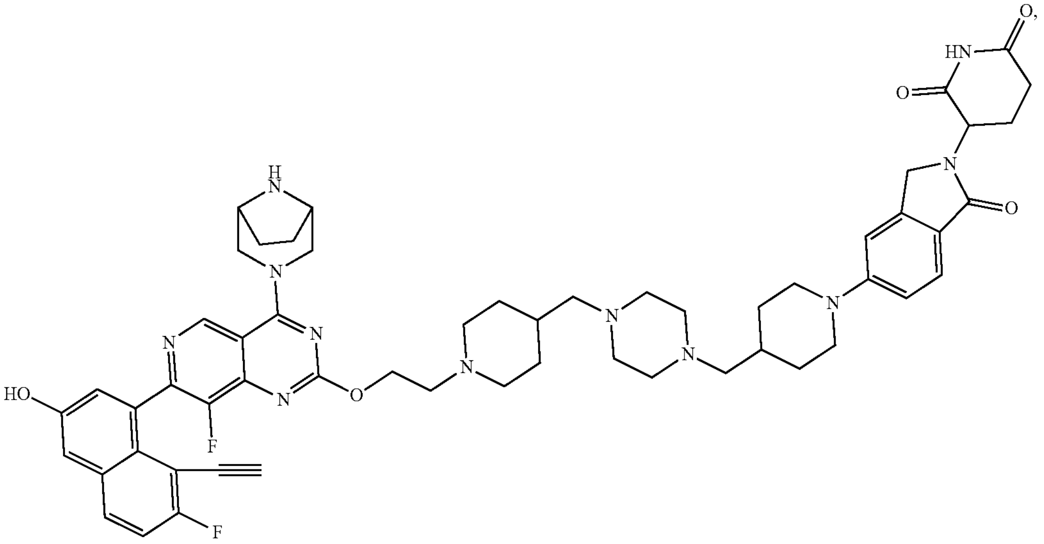
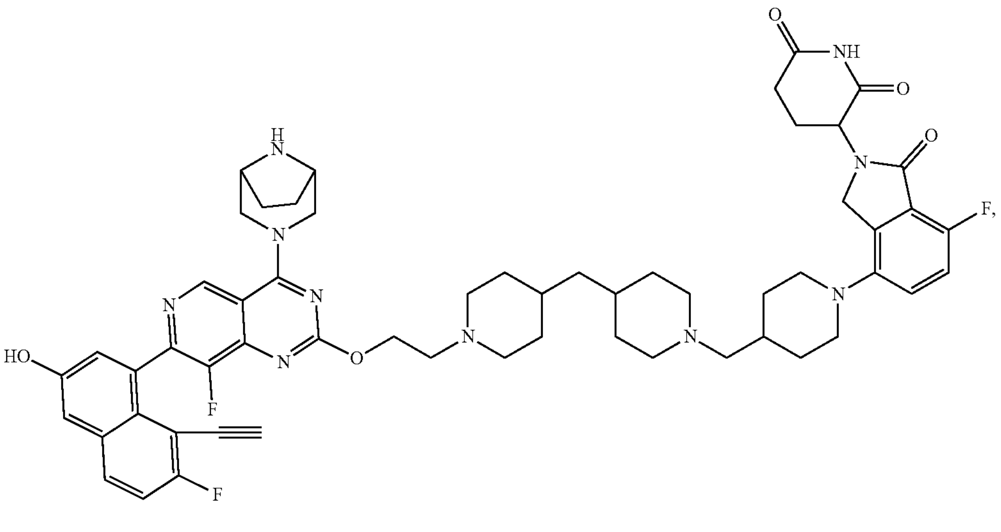

-continued
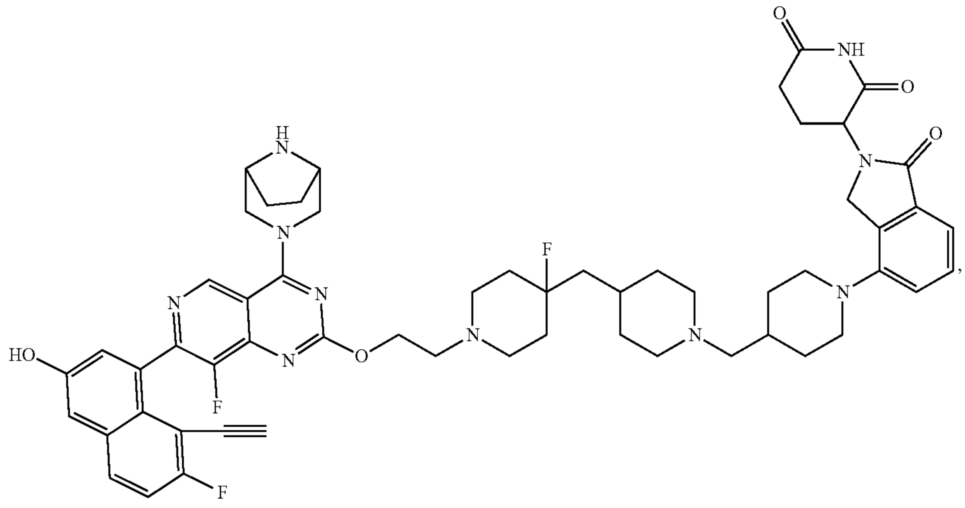
,
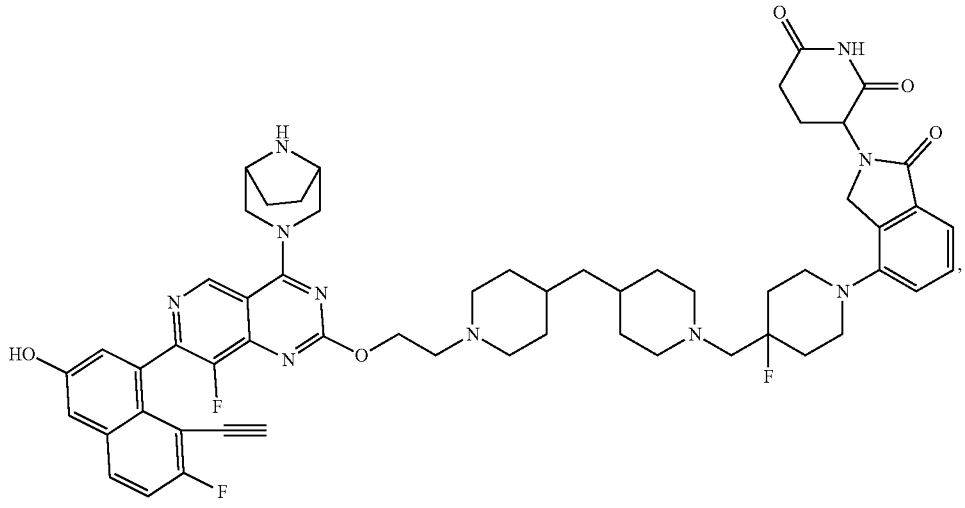
,
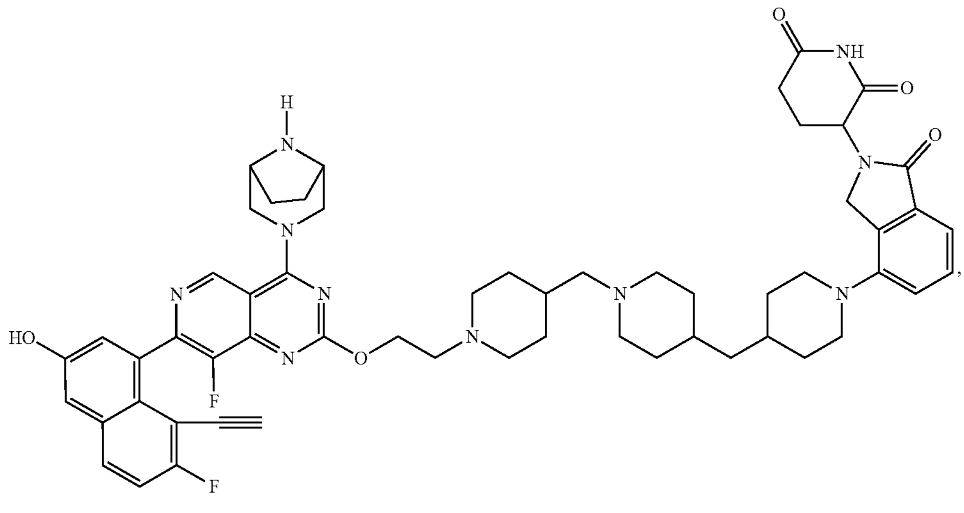
,

-continued
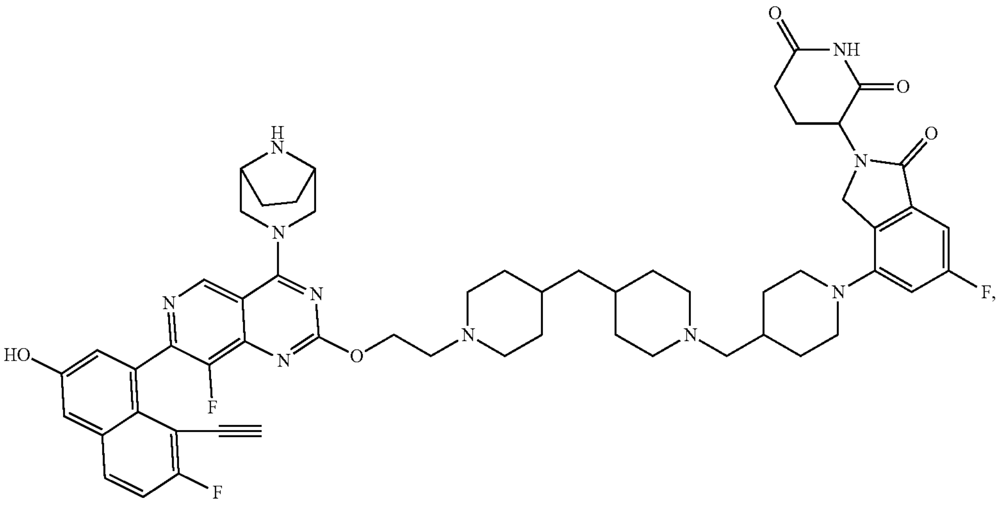
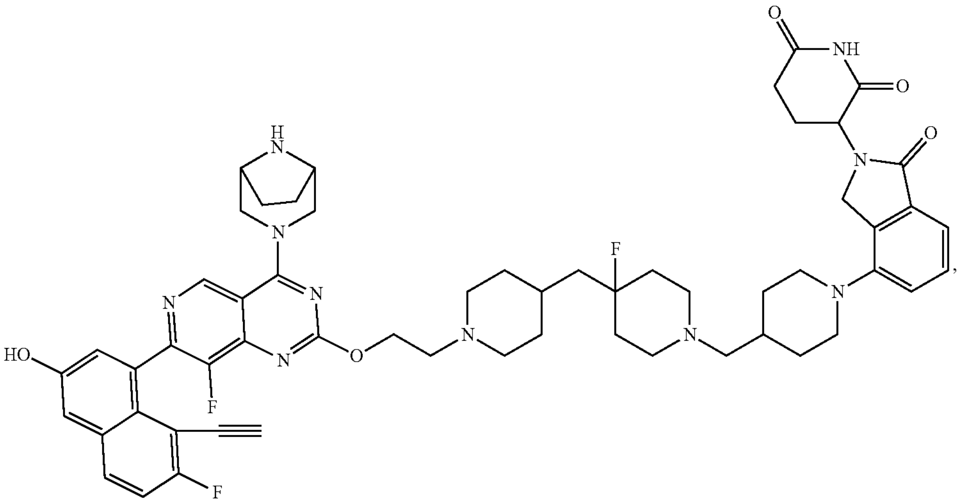
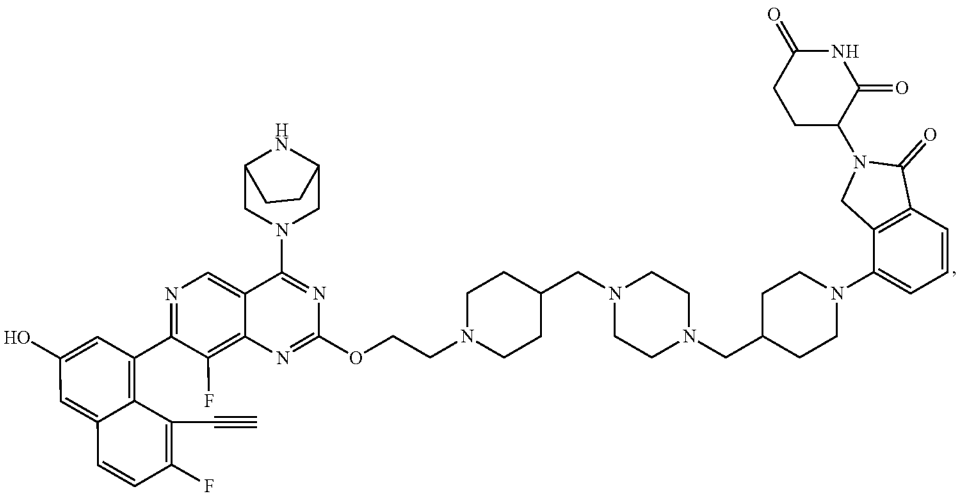

-continued
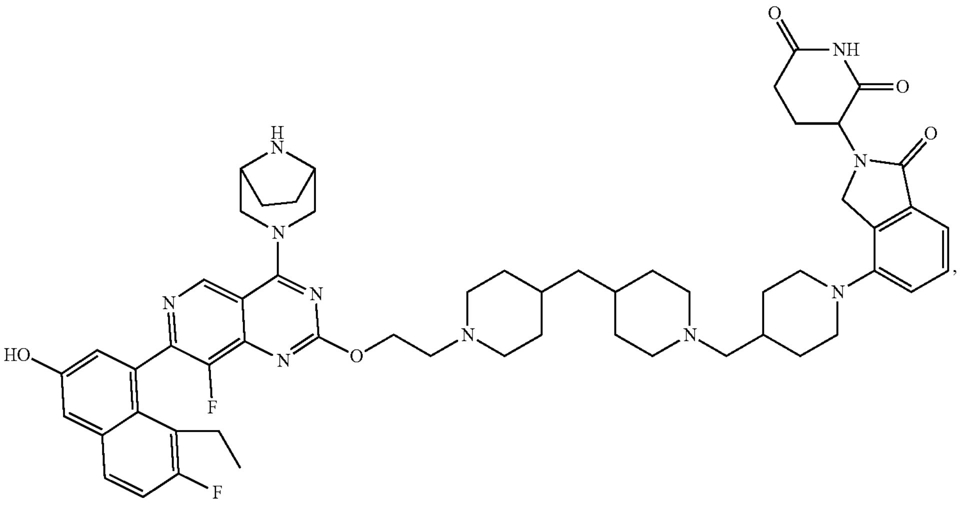
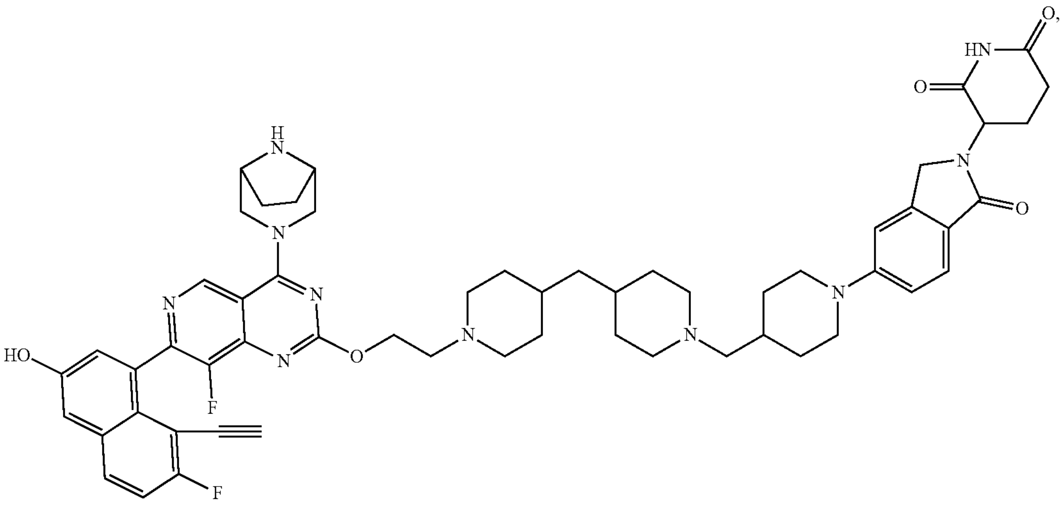
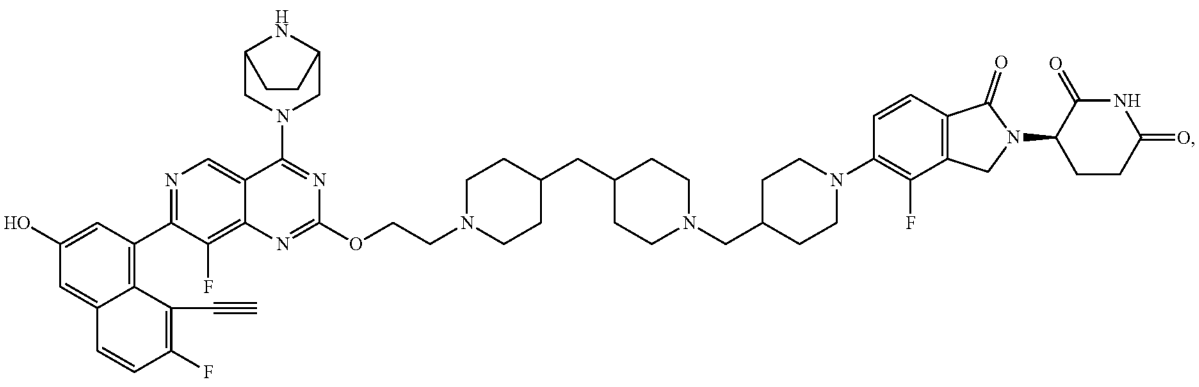

-continued
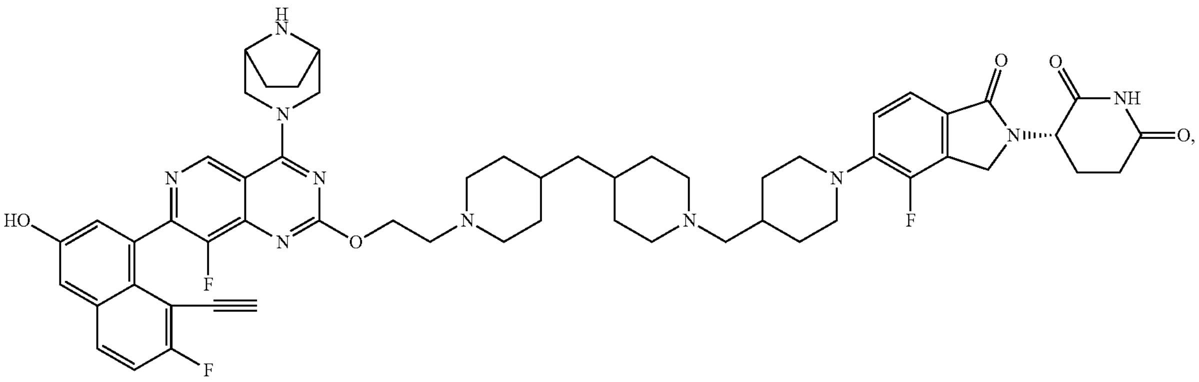
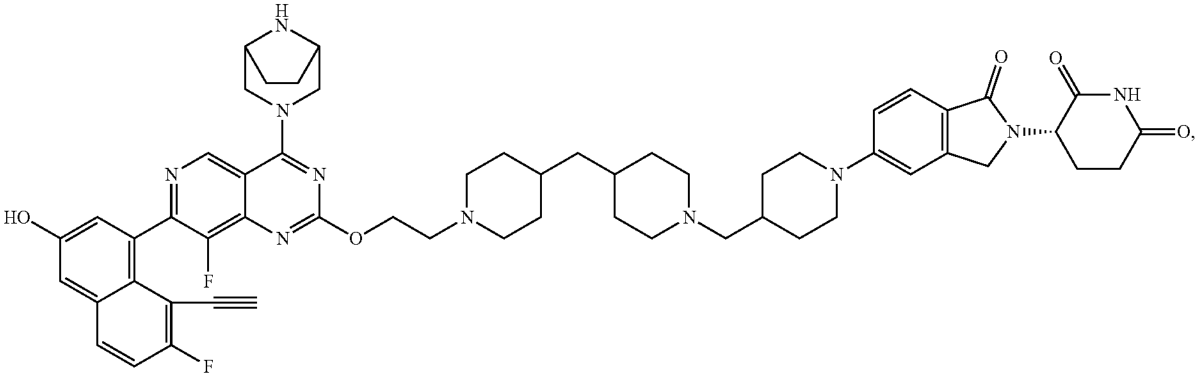
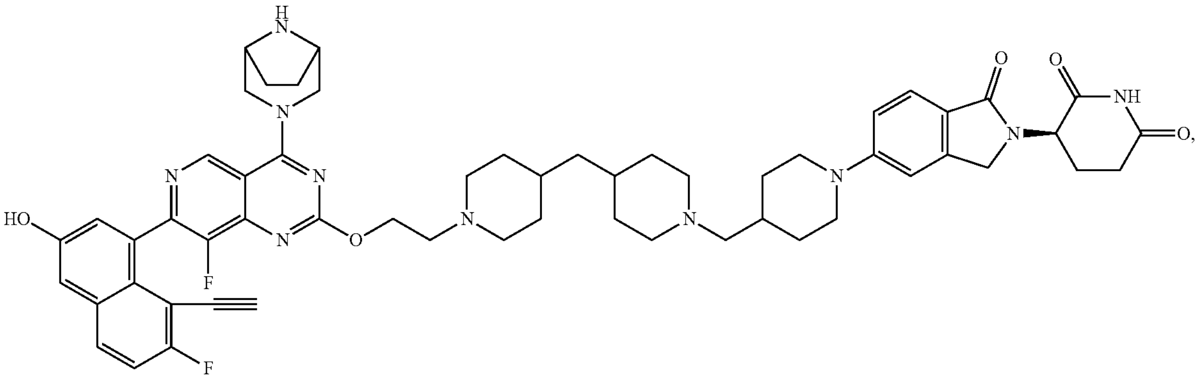
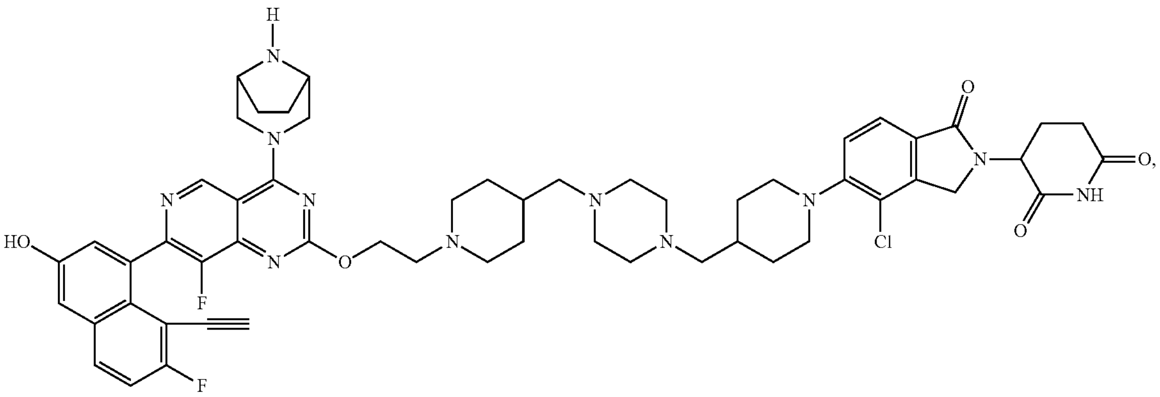
and

-continued
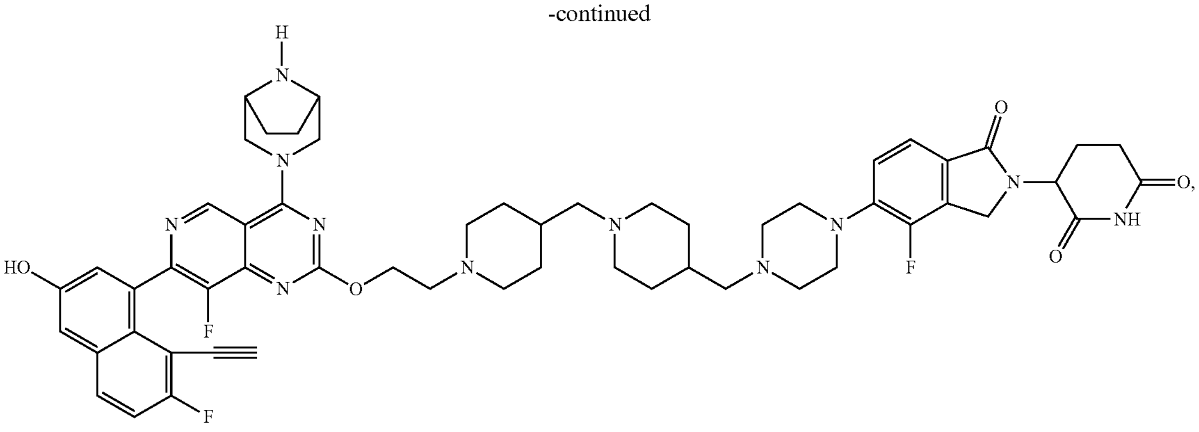
or a pharmaceutically acceptable salt thereof.
20. The compound of claim 14 wherein the compound is selected from:
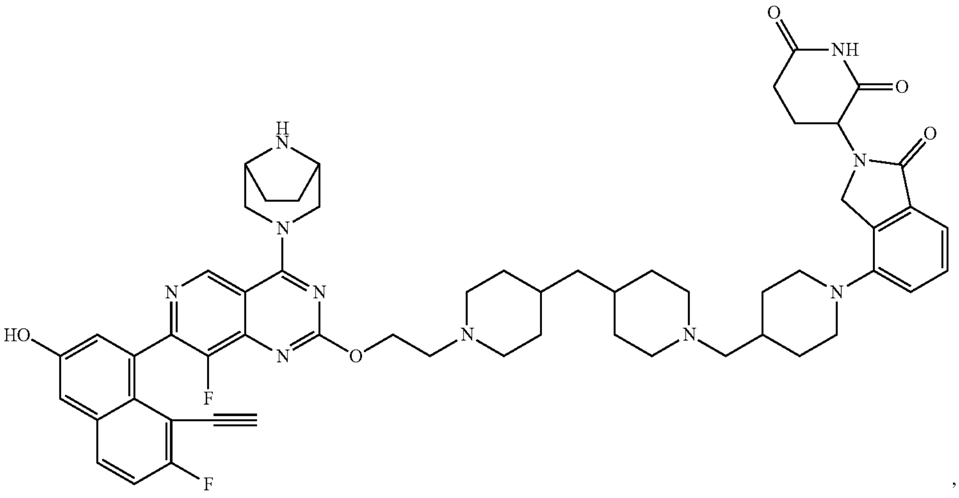
,
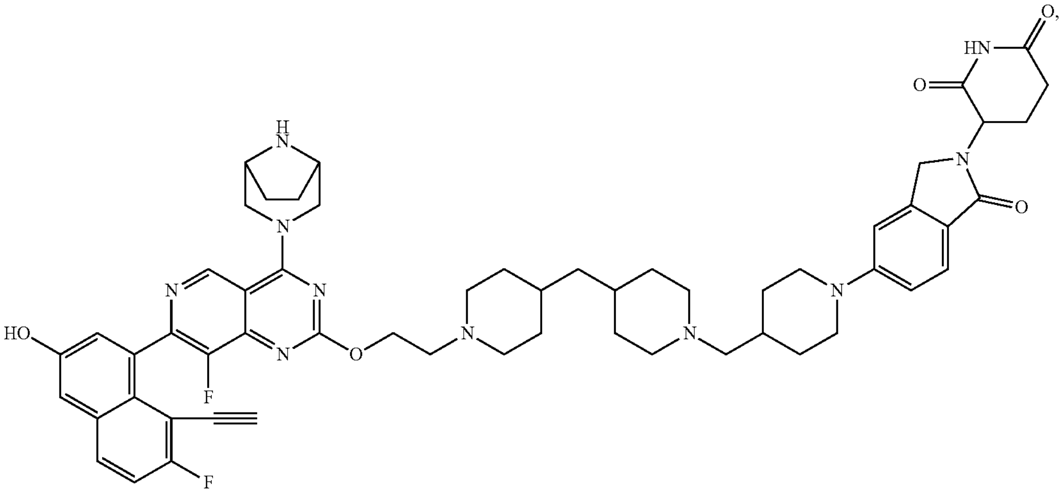

-continued
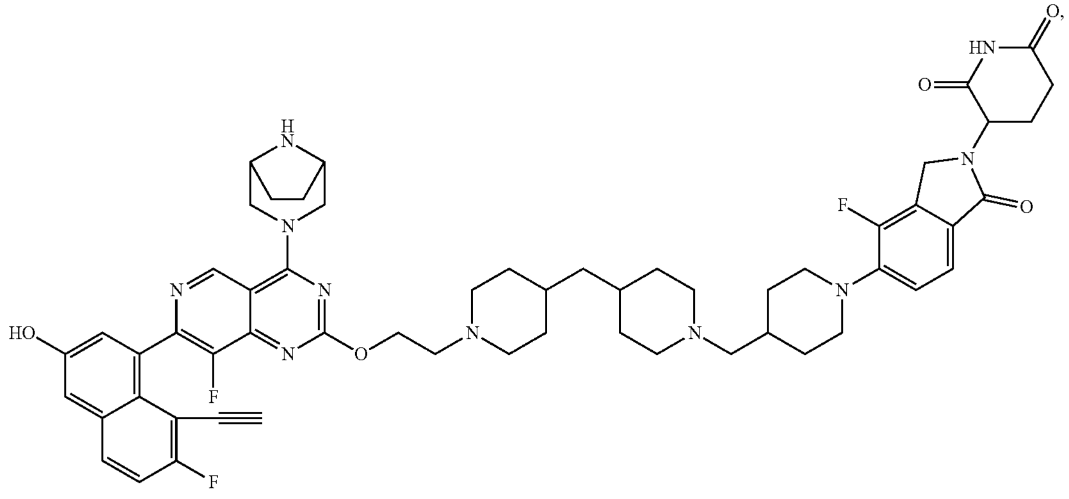
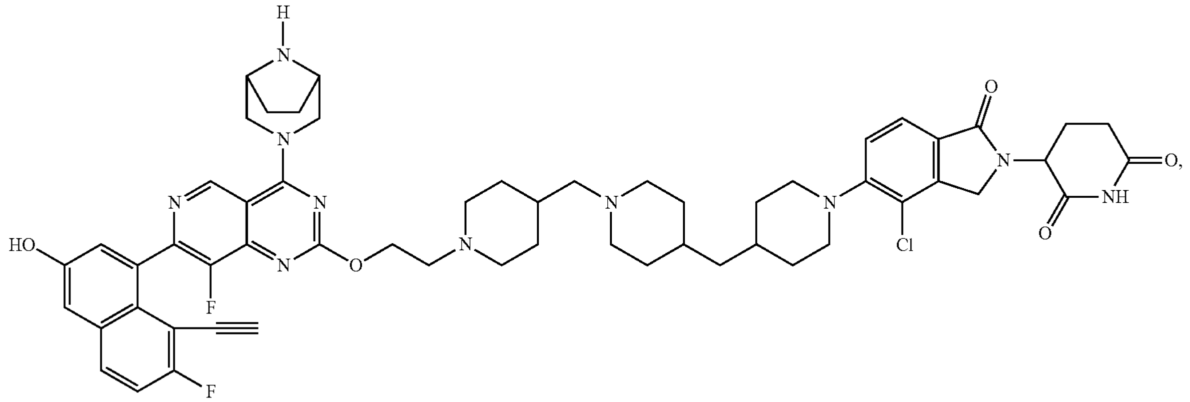
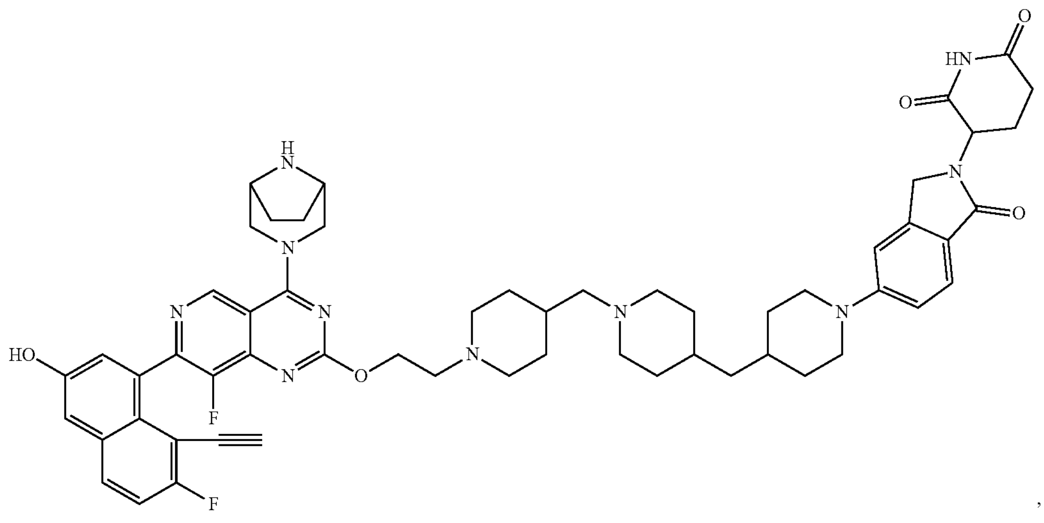
,

-continued
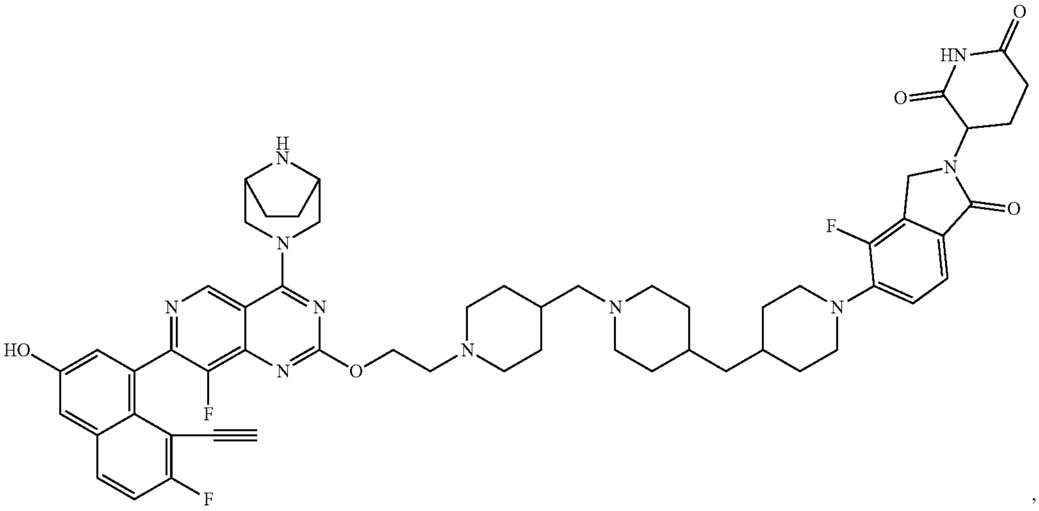
,
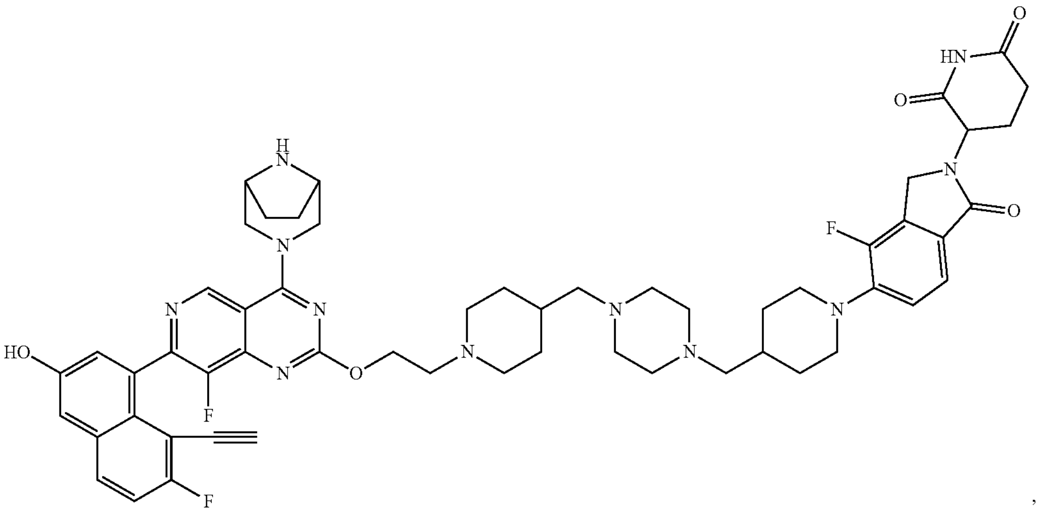
,
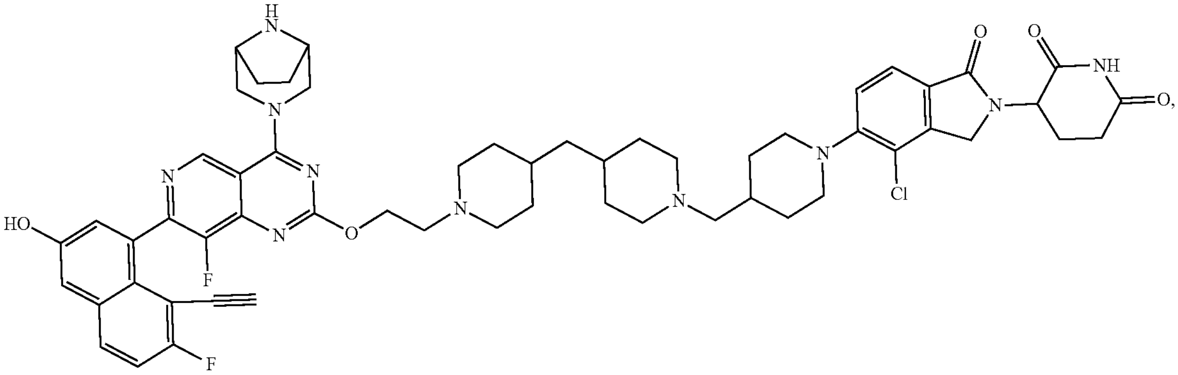
,

-continued
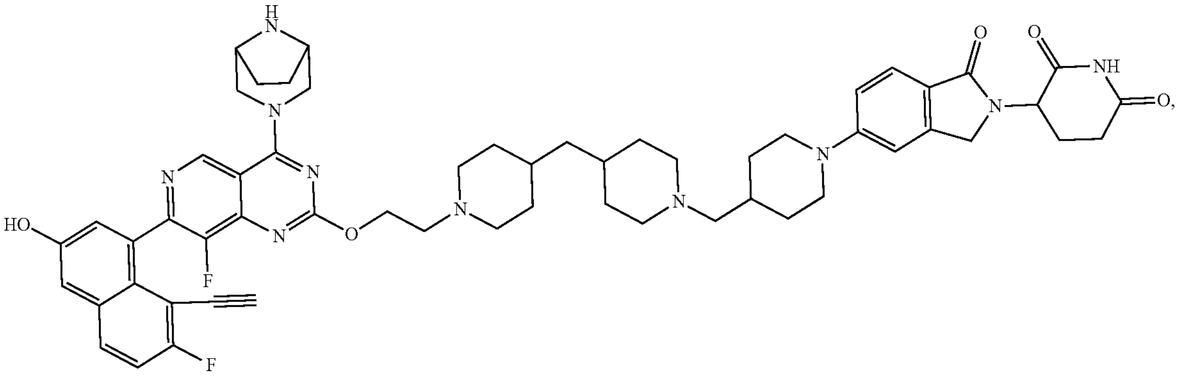
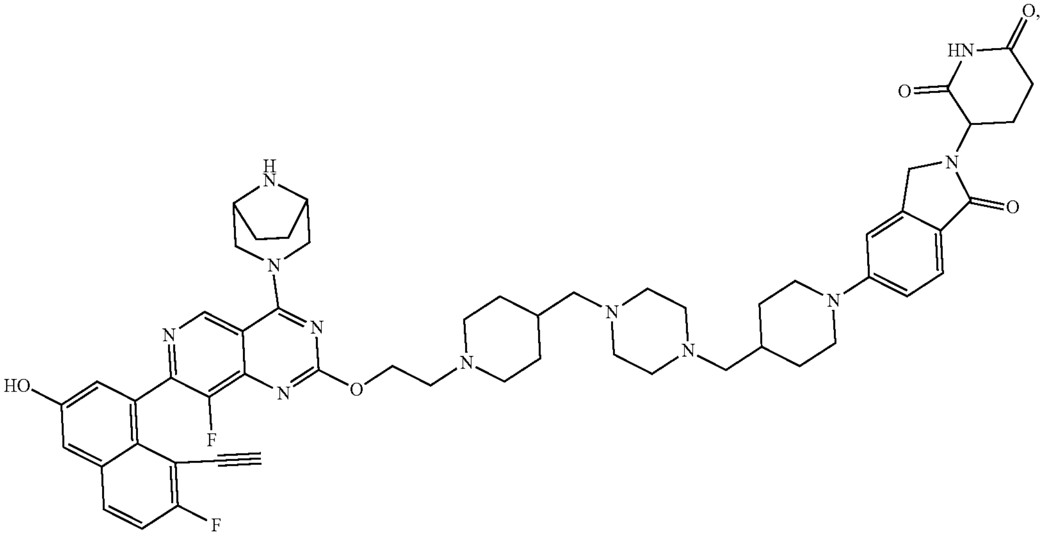
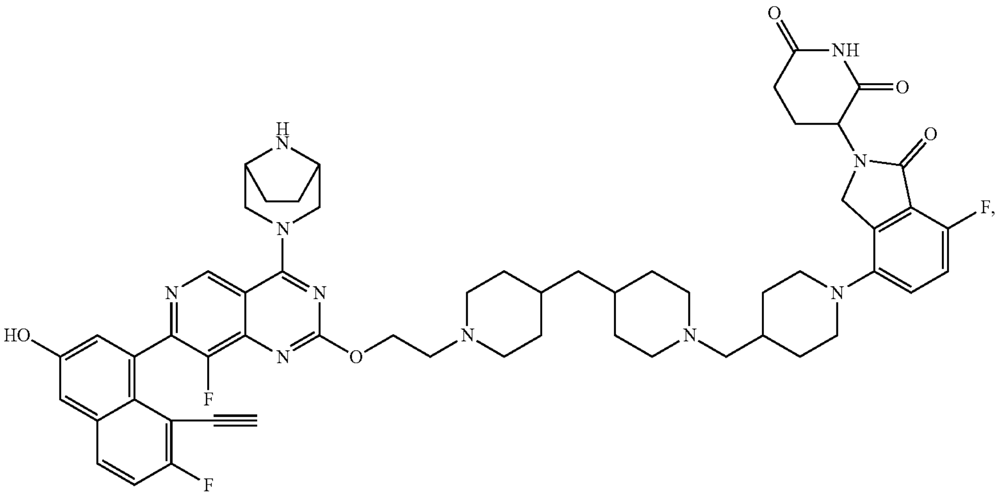

-continued
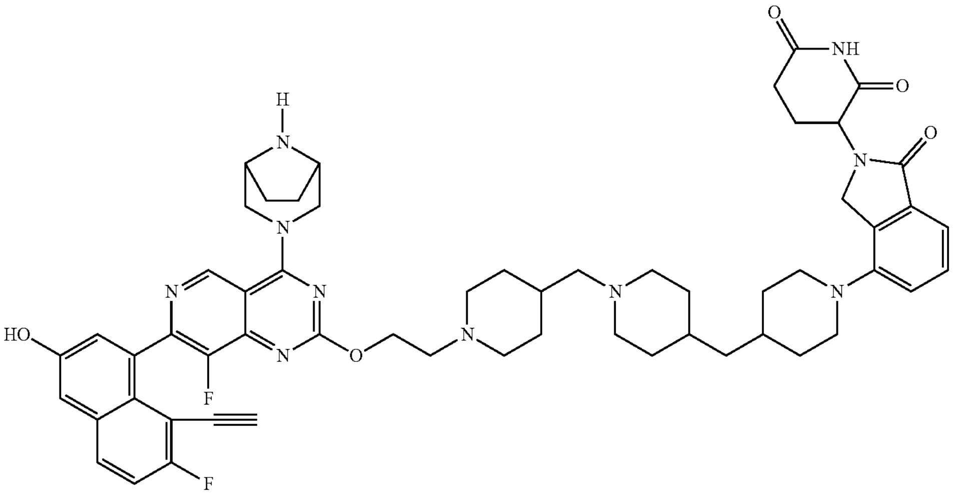
,
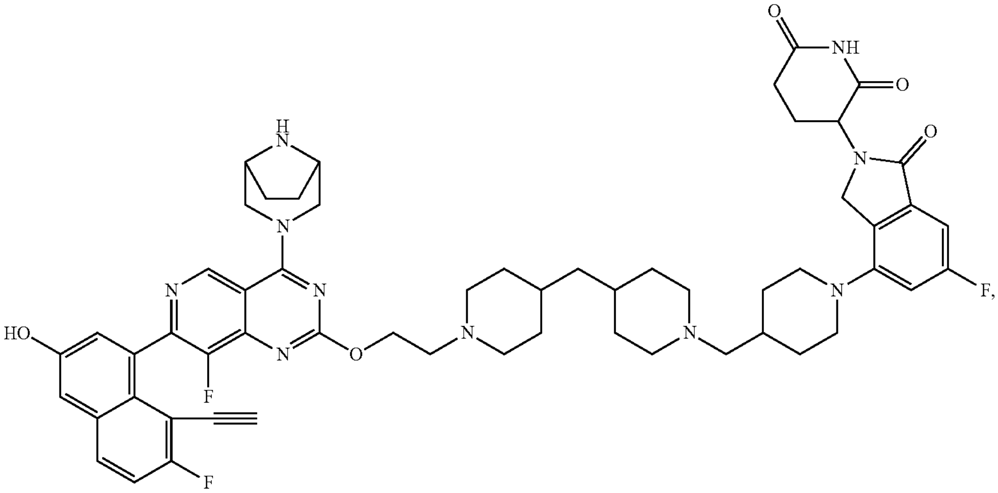
F,
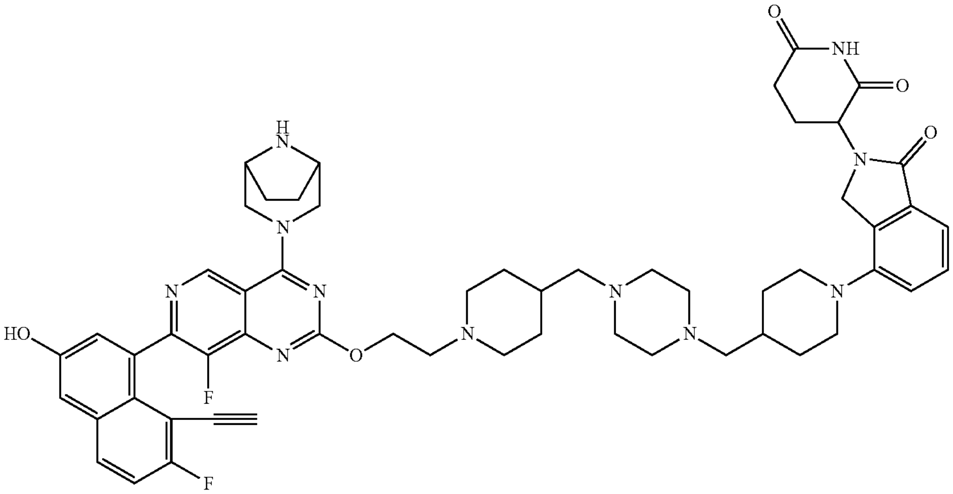
,

-continued
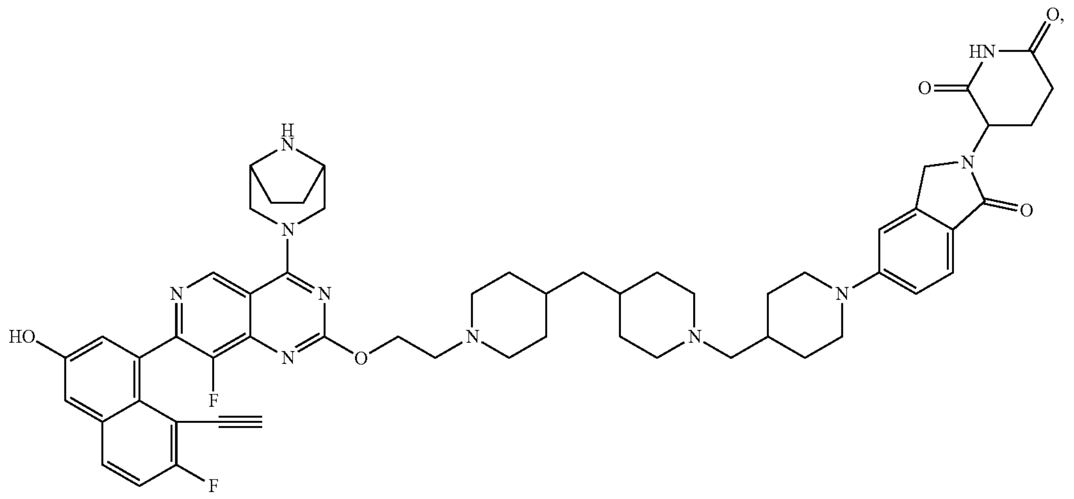
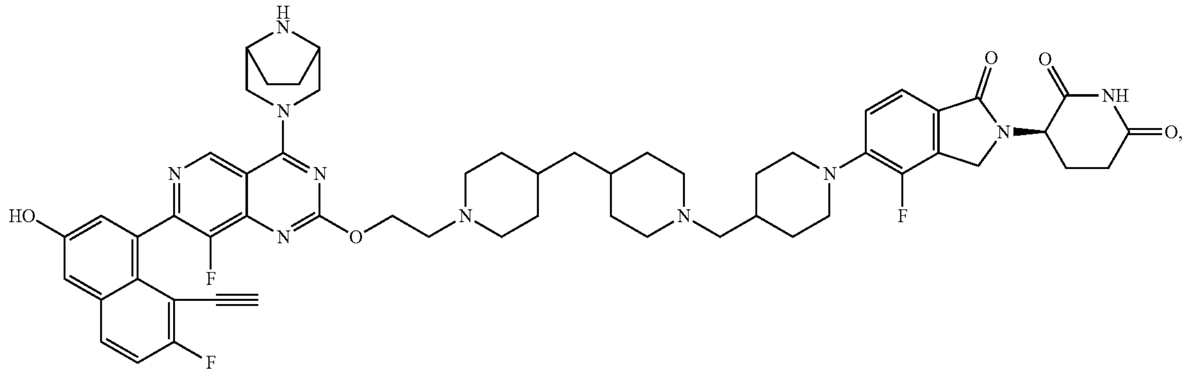
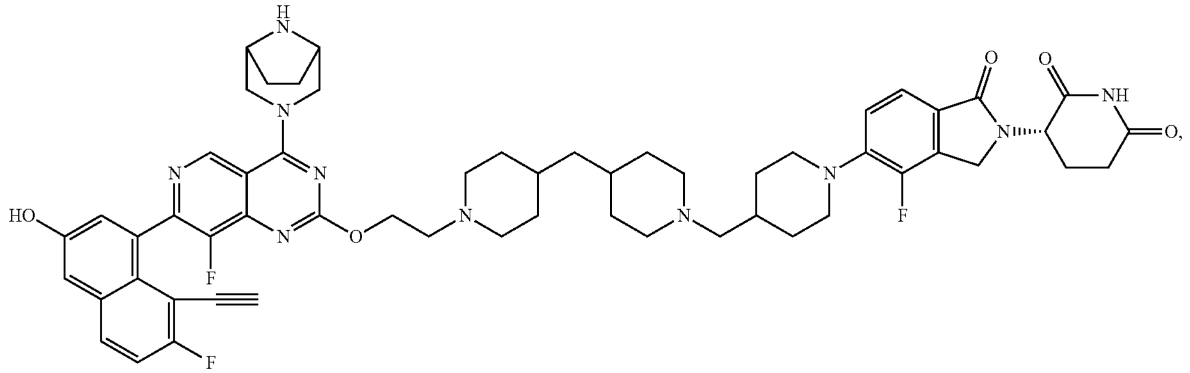
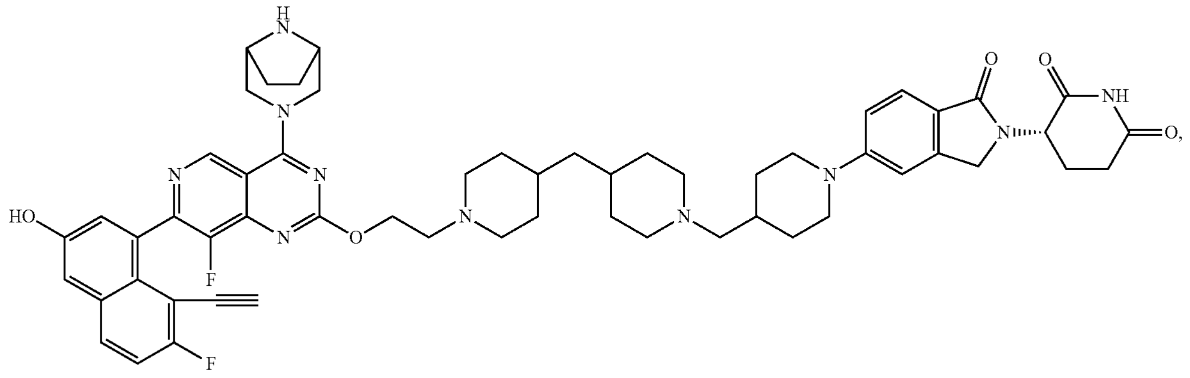

-continued
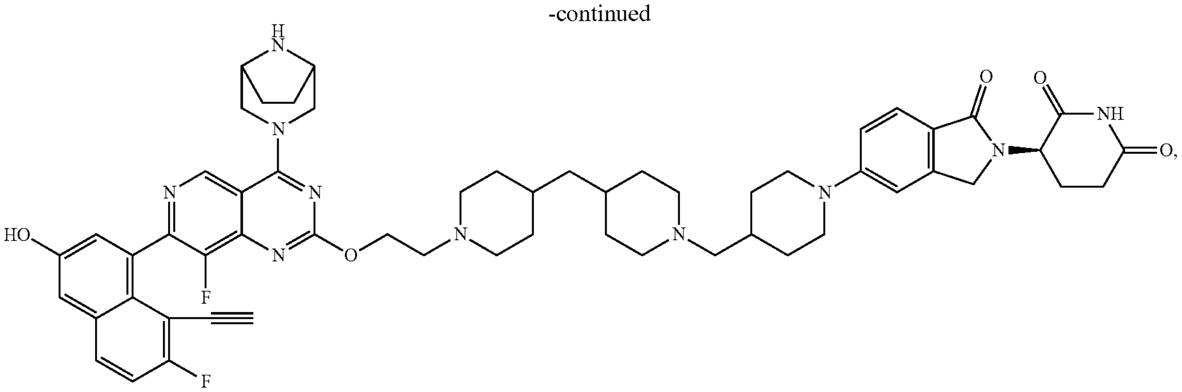
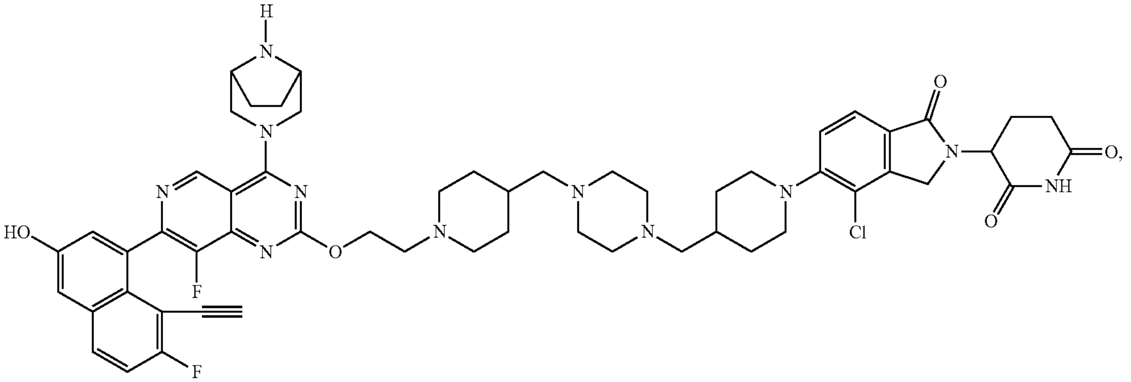
and
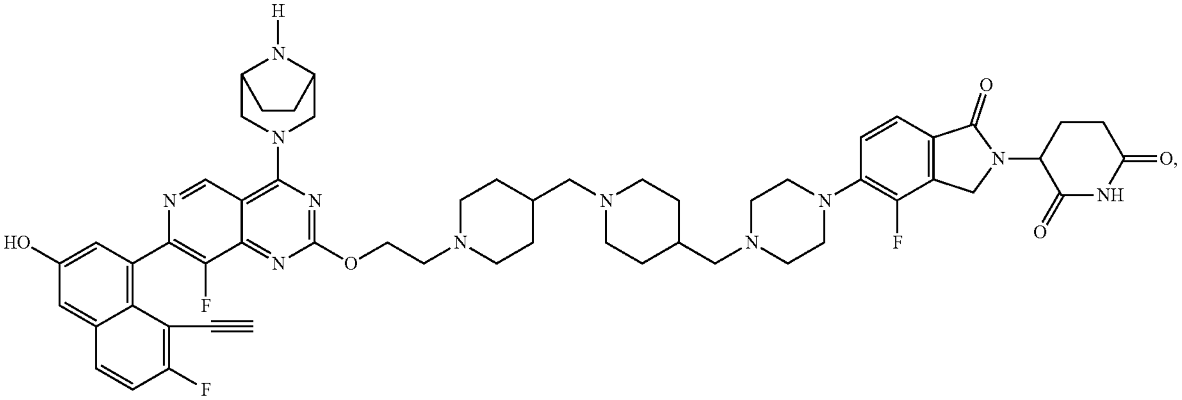 [SMILES: C#Cc1c(F)ccc2cc(O)cc(-c3ncc4c(N5CC6CCC(C5)N6)nc(OCCN5CCC(CN6CCC(CN7CCN(c8ccc9c(c8F)CN(C8CCC(=O)NC8=O)C9=O)CC7)CC6)CC5)nc4c3F)c12]
or a pharmaceutically acceptable salt thereof.
21. The compound of claim 14 wherein the compound is selected from:

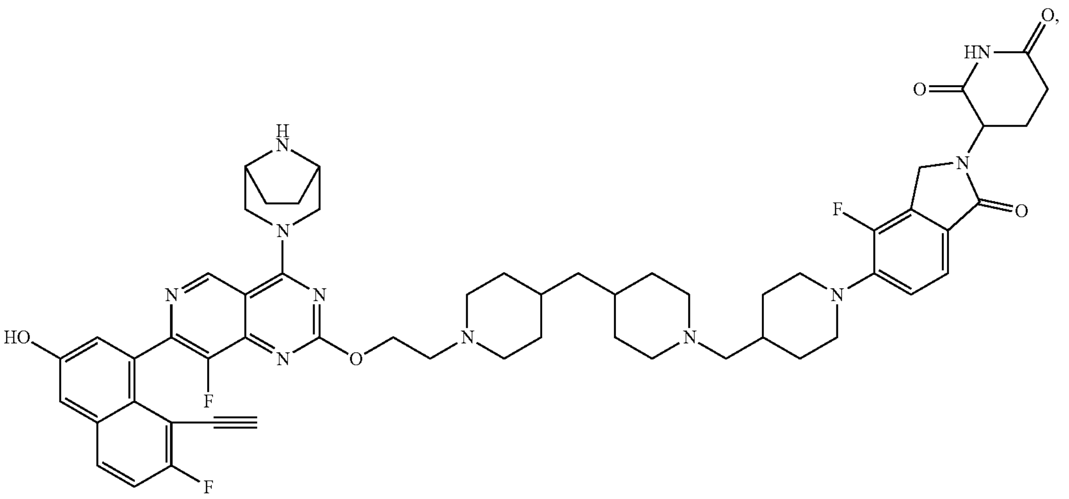
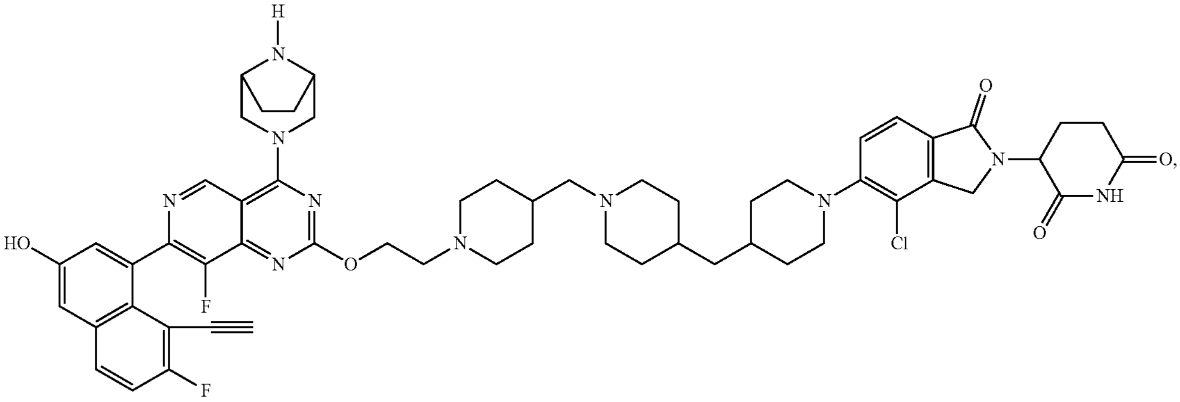
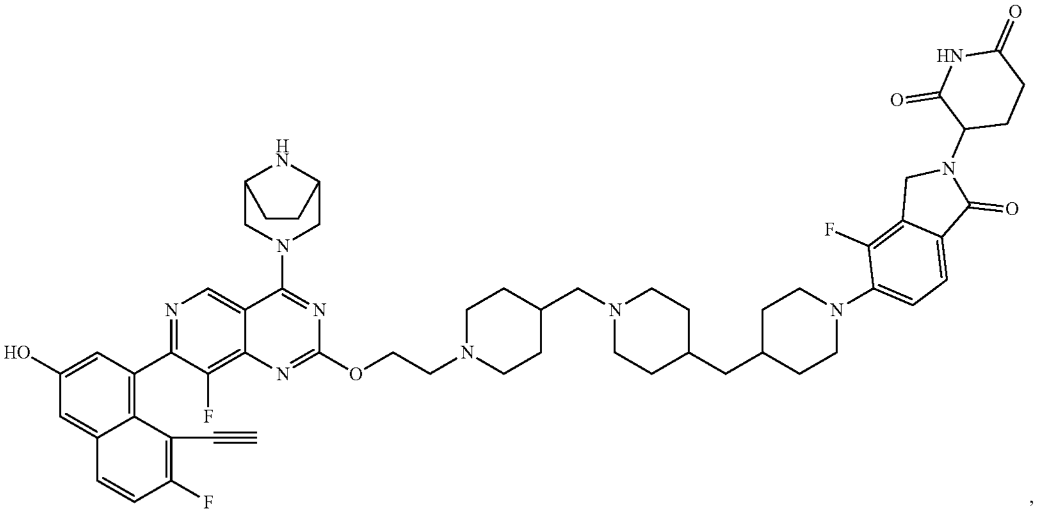
,

-continued
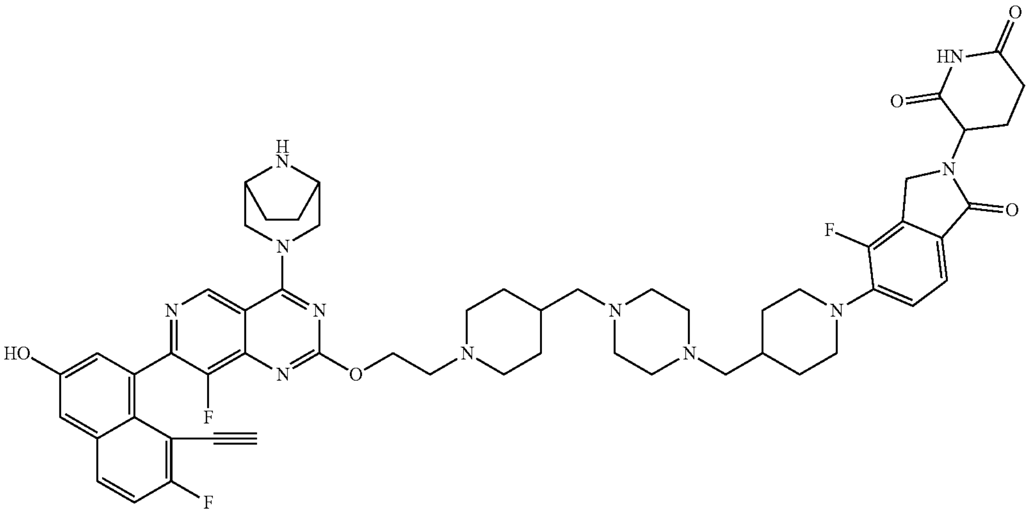
,
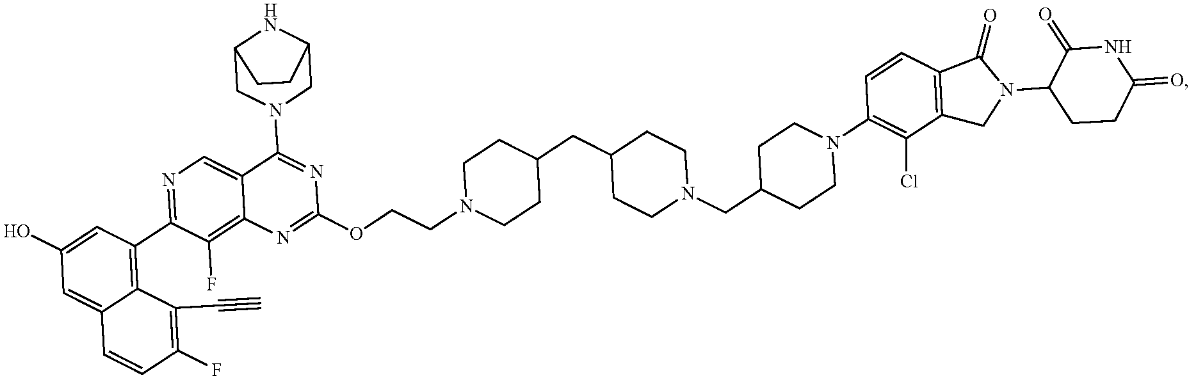
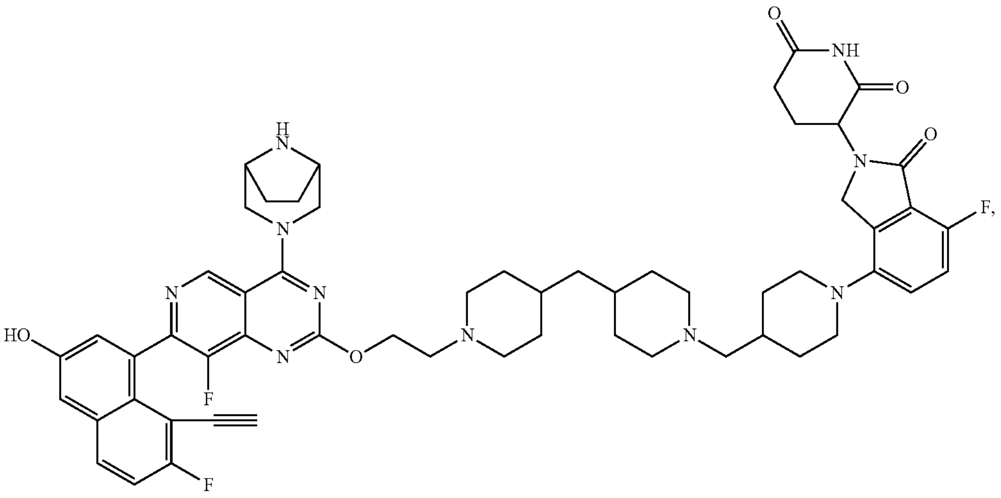

-continued
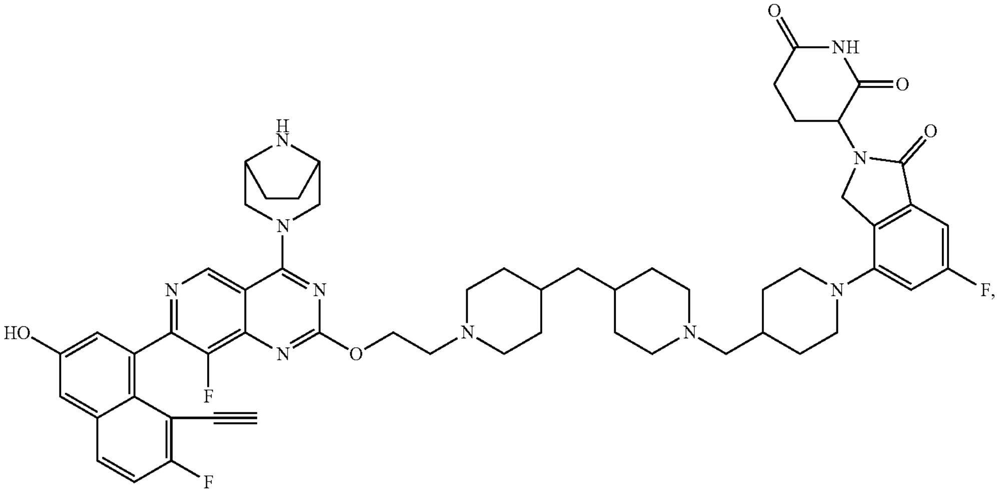
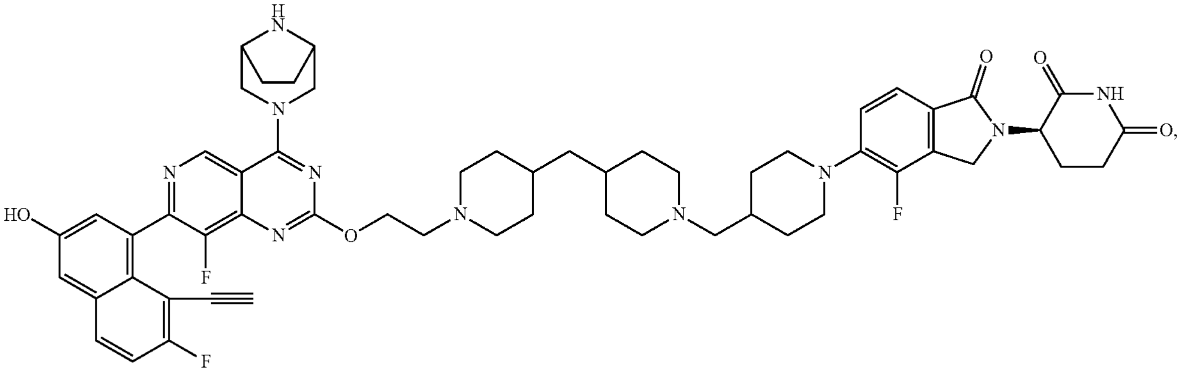
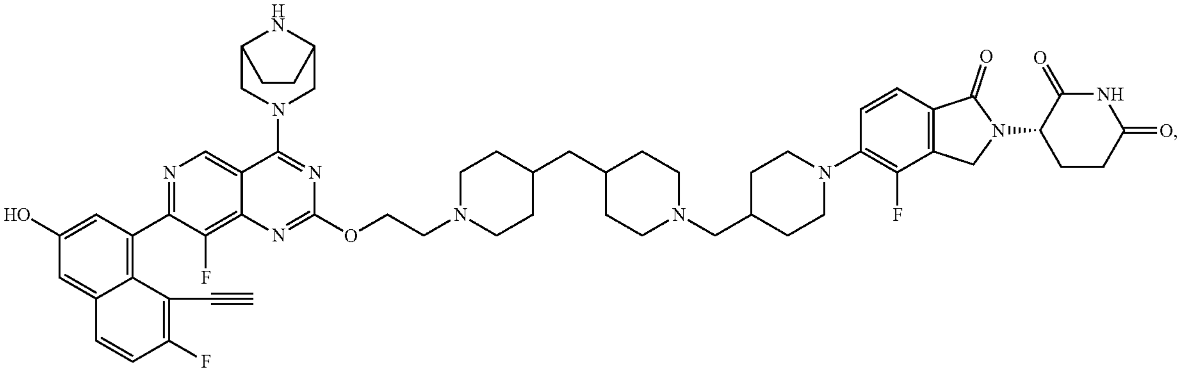
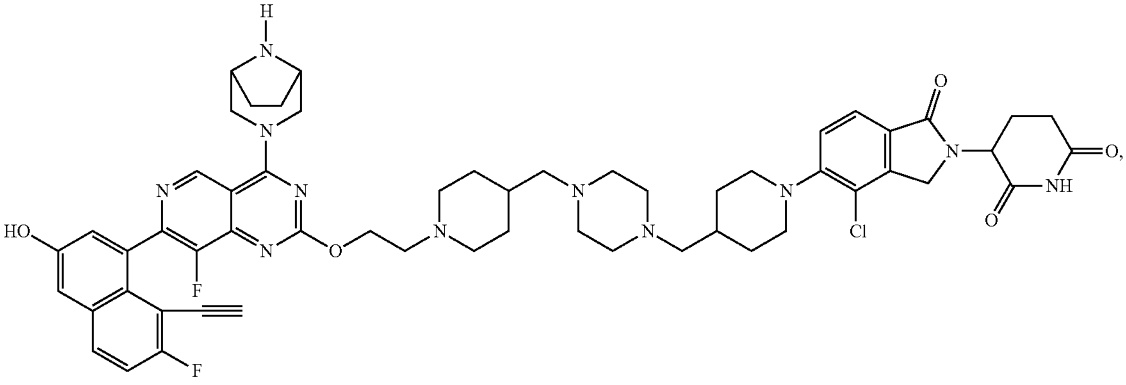
and

-continued

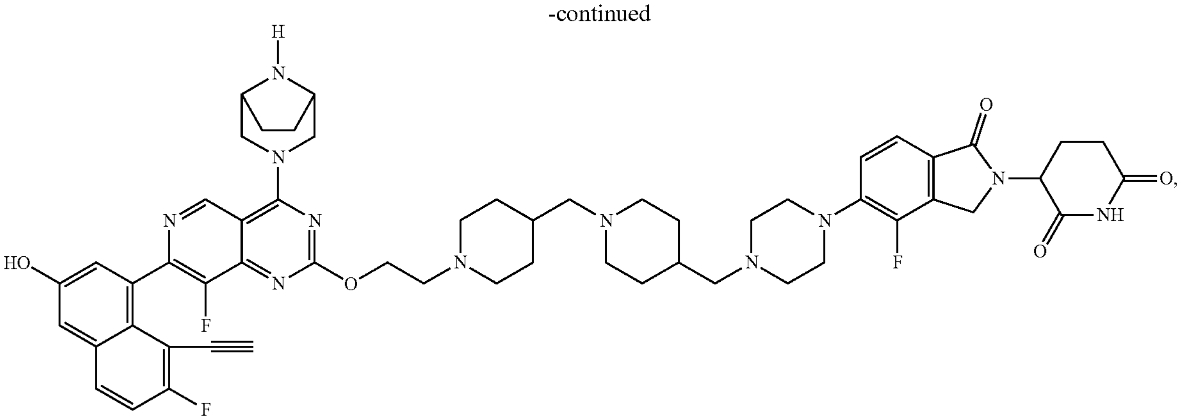

or a pharmaceutically acceptable salt thereof.

22. A pharmaceutical composition comprising a compound of claim 14 and a pharmaceutically acceptable carrier.

23. A method of treating cancer in a subject comprising administering to the subject an effective amount of a compound according to claim 14 wherein the cancer is characterized by a KRAS G12D mutation.

24. The method of claim 23, wherein the cancer is selected from bladder cancer, bowel cancer, breast cancer, cervical cancer, colon cancer, colorectal cancer, endometrial cancer, esophageal cancer, head cancer, kidney cancer, liver cancer, lung cancer, neck cancer, pancreatic cancer, prostate cancer, stomach cancer, uterine cancer, ovarian cancer, testicular cancer, thyroid cancer, pineal cell tumor, carcinoma, cytoma, ependymoma, ganglioglioma, ganglioneuroma, gliobastoma, glioma, leukemia, lymphoma, medulloblastoma, melanoma, meningioma, myeloma, nephroblastoma, neuroblastoma, neurofibroma, oligodendroglioma peripheral neuroepithelioma, sarcoma, and schwannoma.

25. The method of claim 24, wherein the leukemia is acute lymphoblastic leukemia.

26. The compound of claim 1, wherein the compound is selected from:

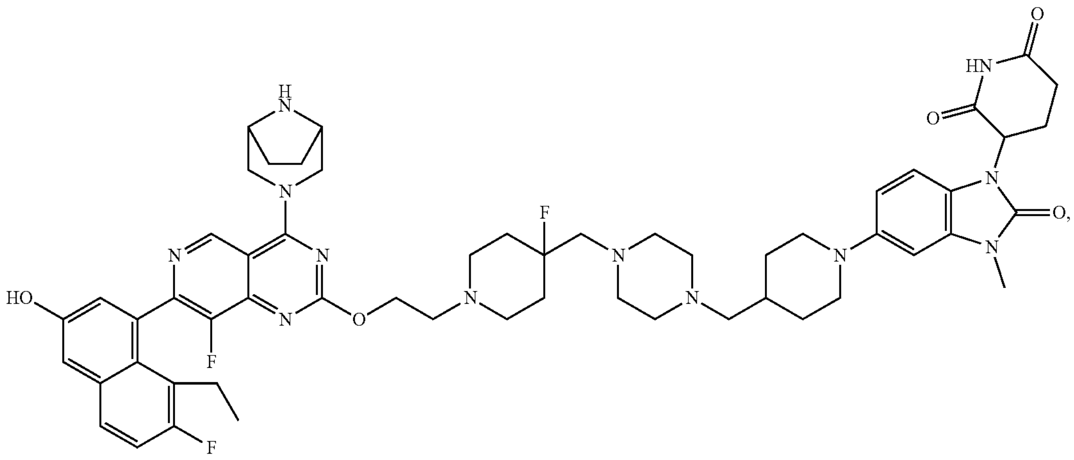

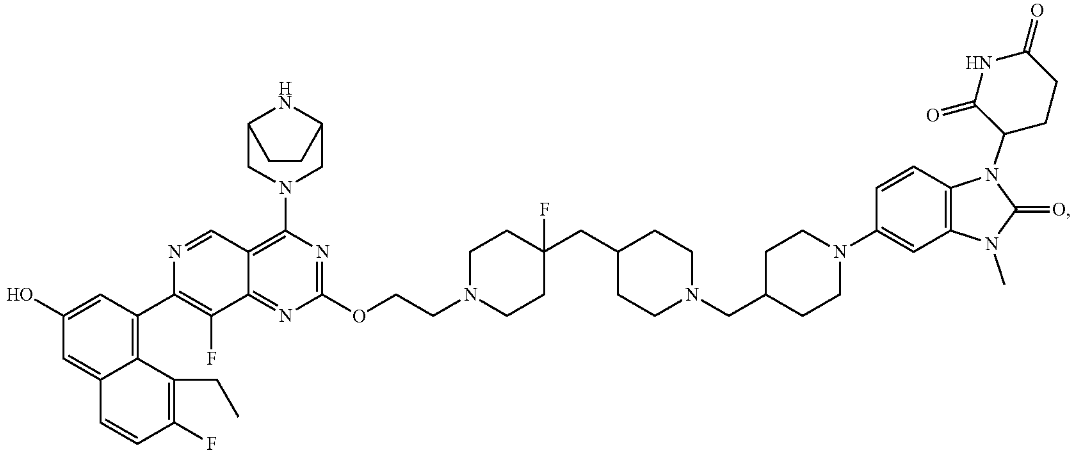

-continued
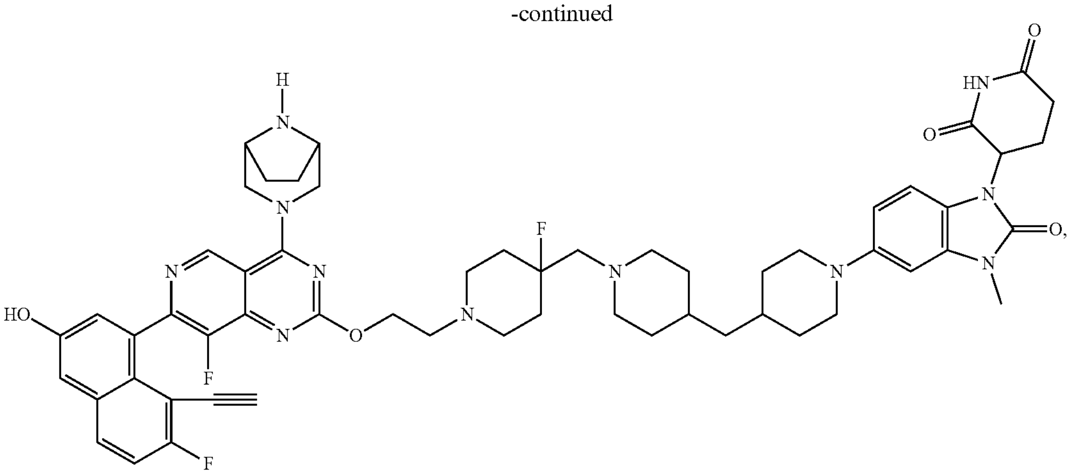
,
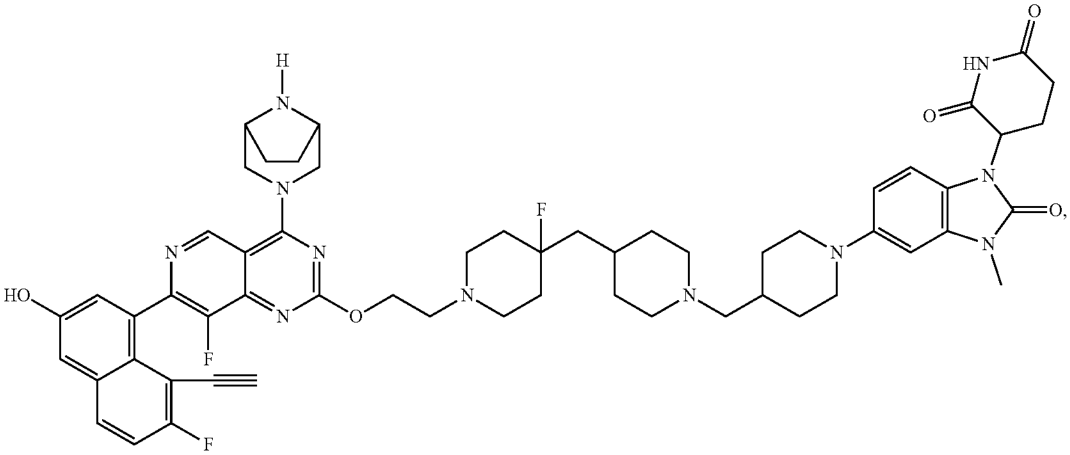
, and
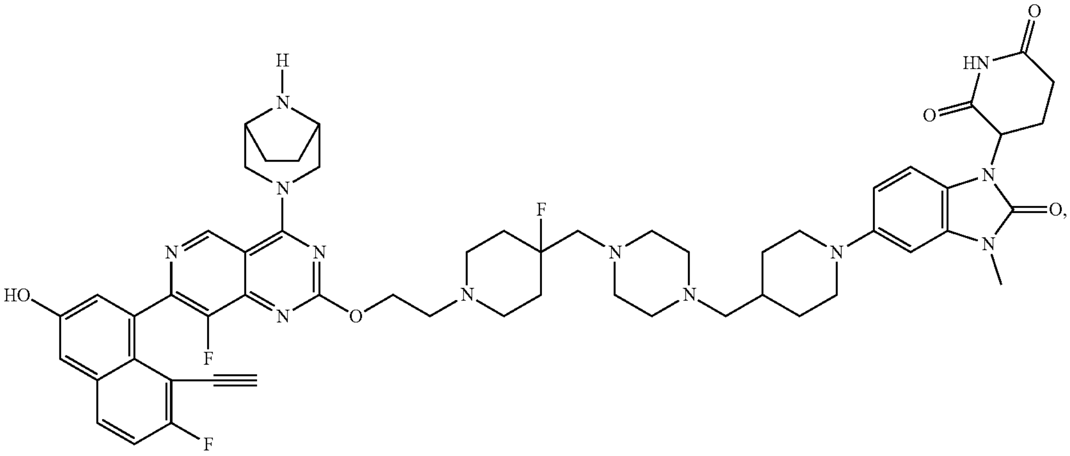
,
or a pharmaceutically acceptable salt thereof.
27. The compound of claim 14, wherein the compound is selected from:

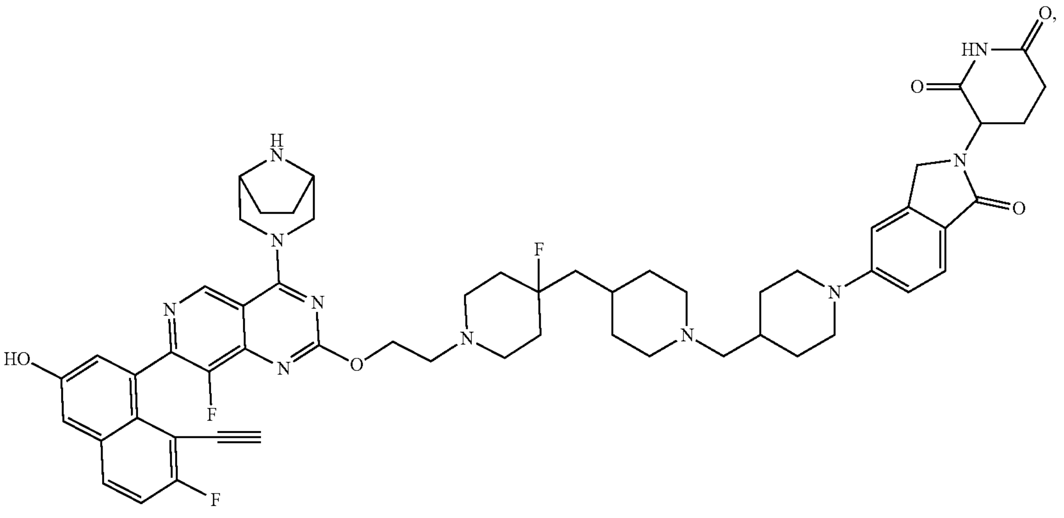
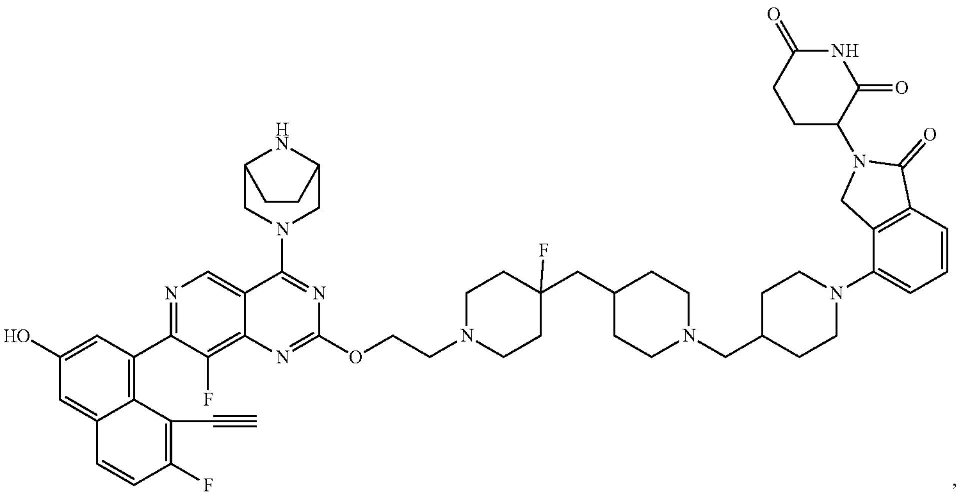
, and
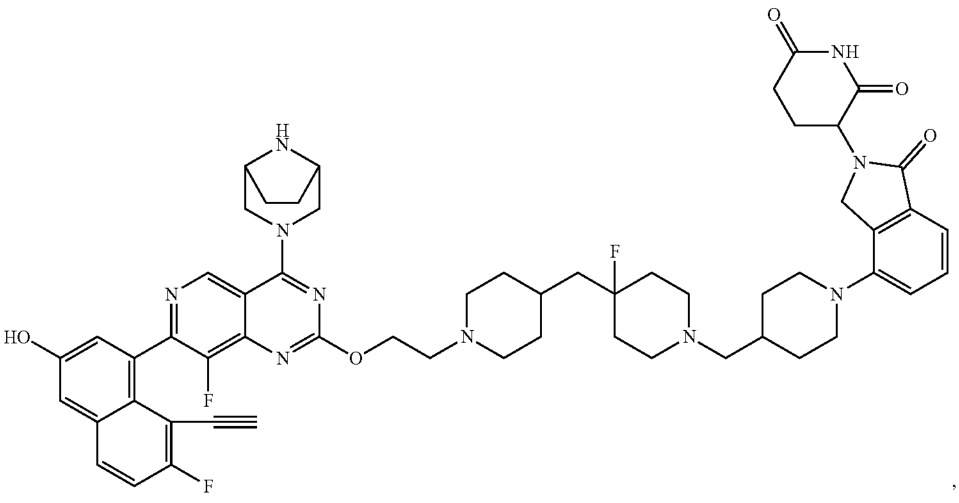
,
or a pharmaceutically acceptable salt thereof.

28. A compound that is:
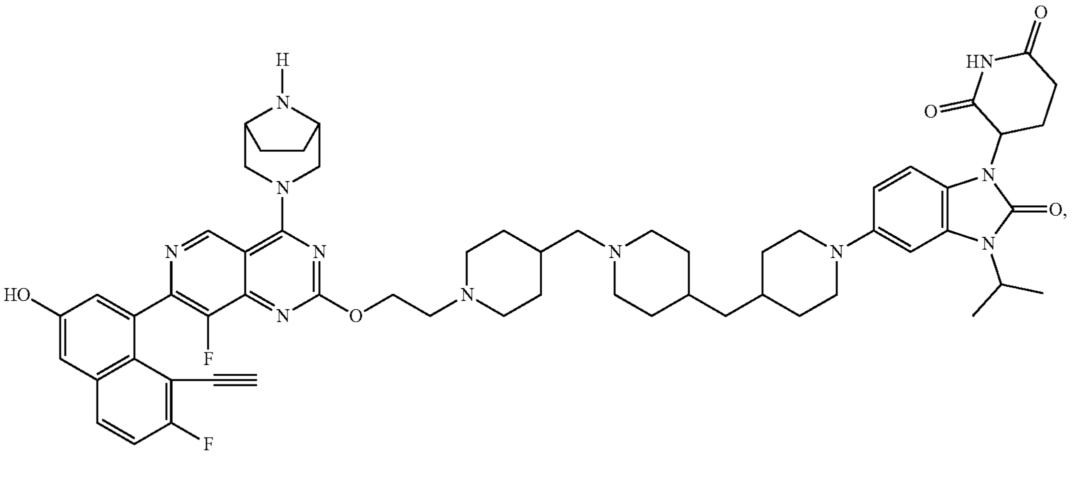 [SMILES: C#Cc1c(F)ccc2cc(O)cc(-c3ncc4c(N5CC6CCC(C5)N6)nc(OCCN5CCC(CN6CCC(CC7CCN(c8ccc9c(c8)n(C(C)C)c(=O)n9C8CCC(=O)NC8=O)CC7)CC6)CC5)nc4c3F)c12]
or a pharmaceutically acceptable salt thereof.
29. A compound that is:
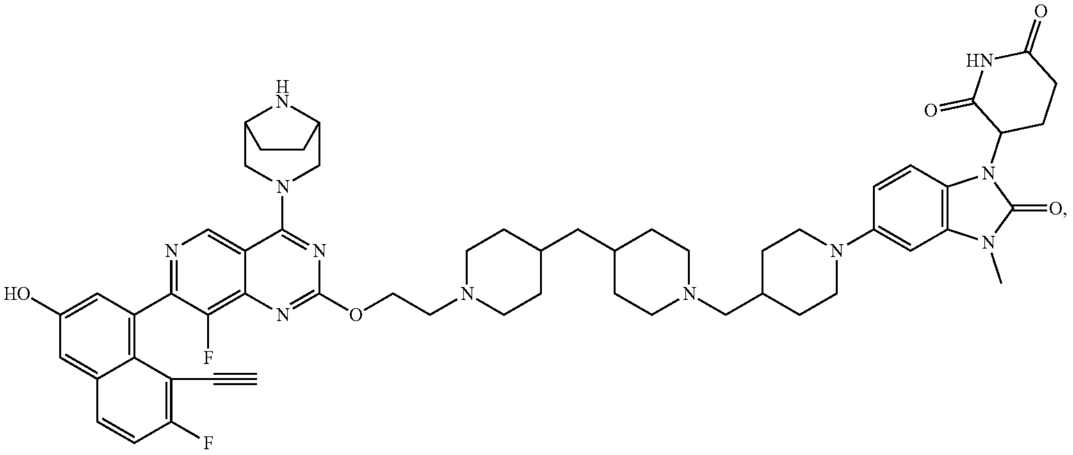 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)n(C)c(=O)n9C8CCC(=O)NC8=O)CC7)CC6)CC5)nc4c3F)c12]
or a pharmaceutically acceptable salt thereof.
30. A compound that is:
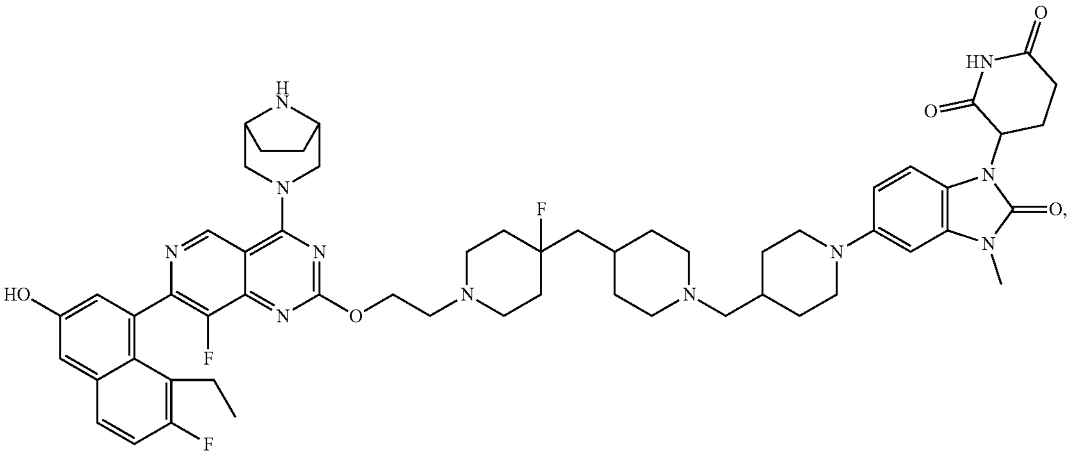 [SMILES: CCc1c(F)ccc2cc(O)cc(-c3ncc4c(N5CC6CCC(C5)N6)nc(OCCN5CCC(F)(CC6CCN(CC7CCN(c8ccc9c(c8)n(C)c(=O)n9C8CCC(=O)NC8=O)CC7)CC6)CC5)nc4c3F)c12]
or a pharmaceutically acceptable salt thereof.

31. A compound that is:
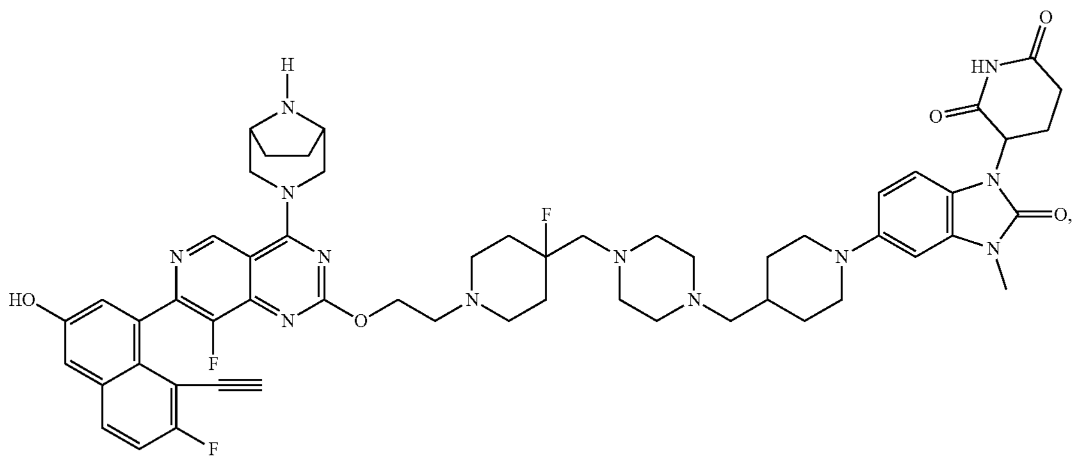 [SMILES: C#Cc1c(F)ccc2cc(O)cc(-c3ncc4c(N5CC6CCC(C5)N6)nc(OCCN5CCC(F)(CN6CCN(CC7CCN(c8ccc9c(c8)n(C)c(=O)n9C8CCC(=O)NC8=O)CC7)CC6)CC5)nc4c3F)c12]
or a pharmaceutically acceptable salt thereof.
32. A compound that is:
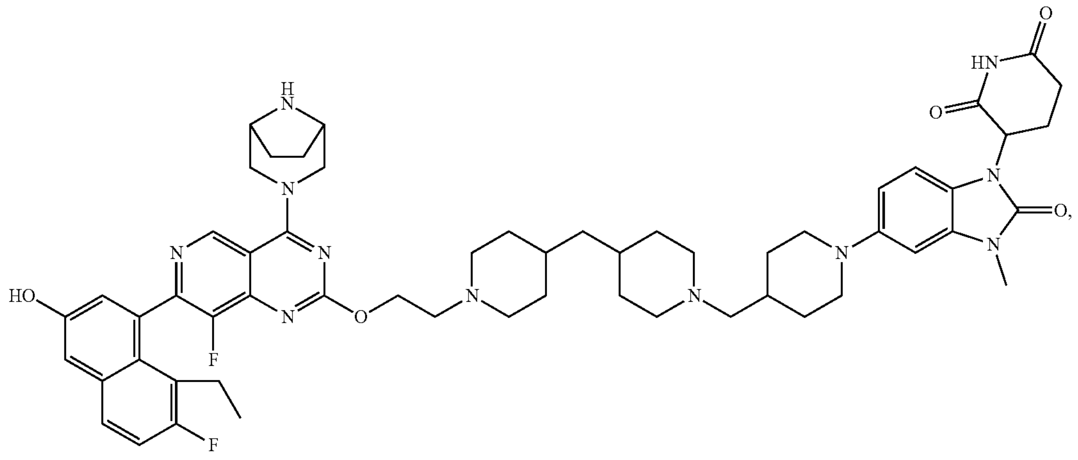 [SMILES: CCc1c(F)ccc2cc(O)cc(-c3ncc4c(N5CC6CCC(C5)N6)nc(OCCN5CCC(CC6CCN(CC7CCN(c8ccc9c(c8)n(C)c(=O)n9C8CCC(=O)NC8=O)CC7)CC6)CC5)nc4c3F)c12]
or a pharmaceutically acceptable salt thereof.
33. A compound that is:
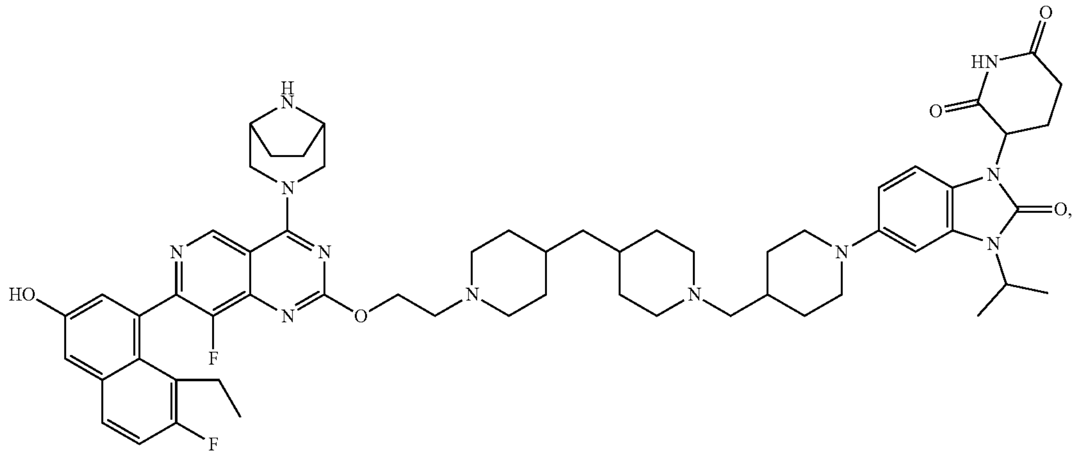 [SMILES: CCc1c(F)ccc2cc(O)cc(-c3ncc4c(N5CC6CCC(C5)N6)nc(OCCN5CCC(CC6CCN(CC7CCN(c8ccc9c(c8)n(C(C)C)c(=O)n9C8CCC(=O)NC8=O)CC7)CC6)CC5)nc4c3F)c12]
or a pharmaceutically acceptable salt thereof.

34. A compound that is:
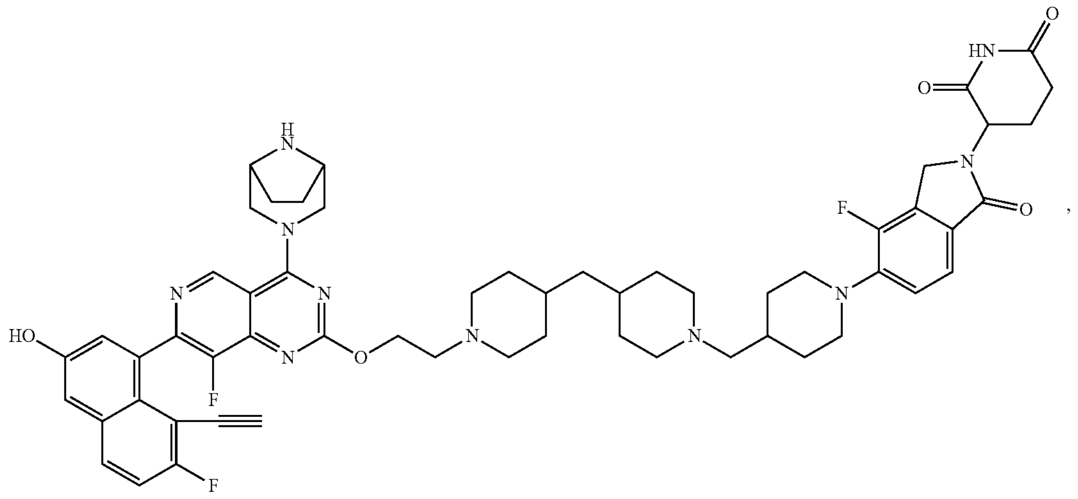 [SMILES: C#Cc1c(F)ccc2cc(O)cc(-c3ncc4c(N5CC6CCC(C5)N6)nc(OCCN5CCC(CC6CCN(CC7CCN(c8ccc9c(c8F)CN(C8CCC(=O)NC8=O)C9=O)CC7)CC6)CC5)nc4c3F)c12 ; ","]
or a pharmaceutically acceptable salt thereof.
35. A compound that is:
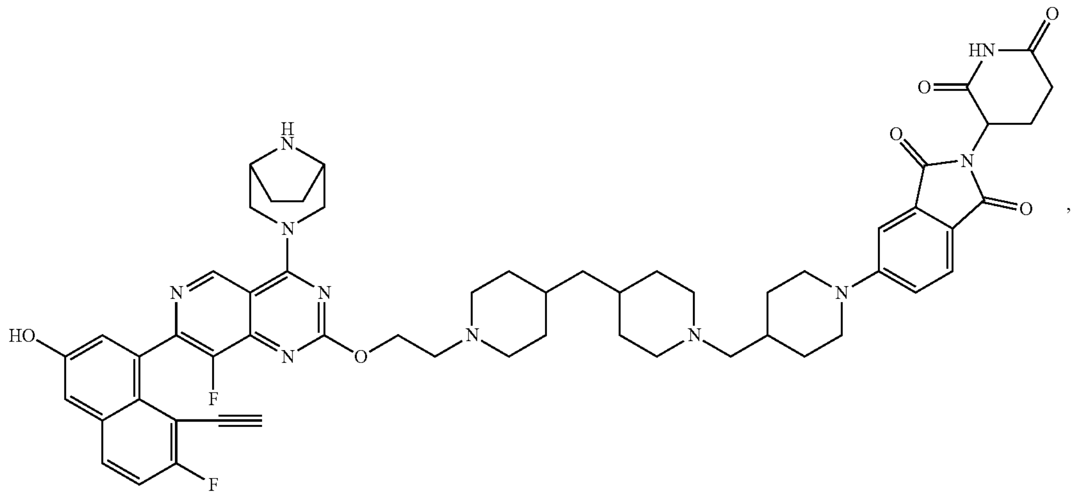 [SMILES: C#Cc1c(F)ccc2cc(O)cc(-c3ncc4c(N5CC6CCC(C5)N6)nc(OCCN5CCC(CC6CCN(CC7CCN(c8ccc9c(c8)C(=O)N(C8CCC(=O)NC8=O)C9=O)CC7)CC6)CC5)nc4c3F)c12 ; ","]
or a pharmaceutically acceptable salt thereof.
36. A compound that is:
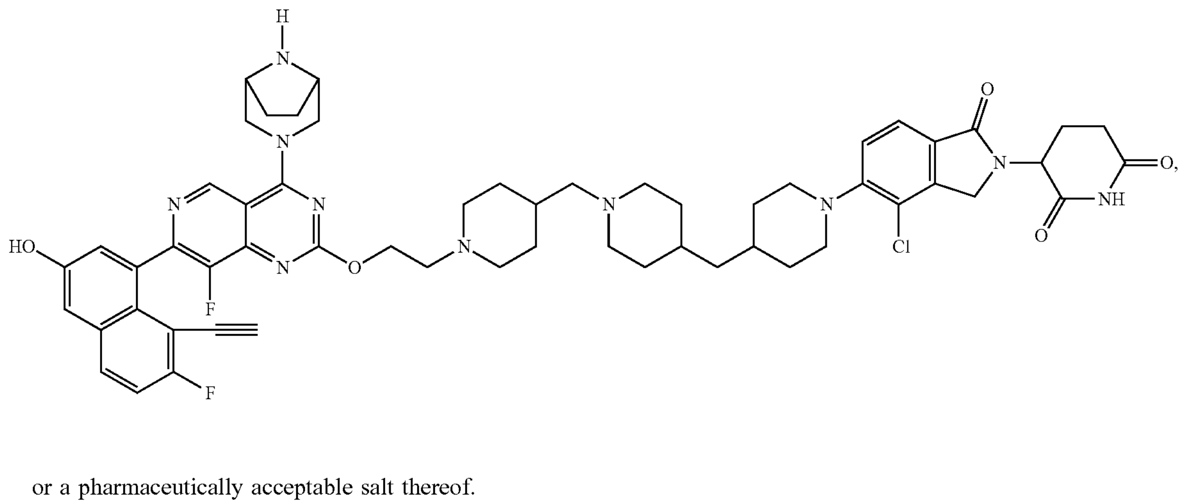
or a pharmaceutically acceptable salt thereof.

37. A compound that is:
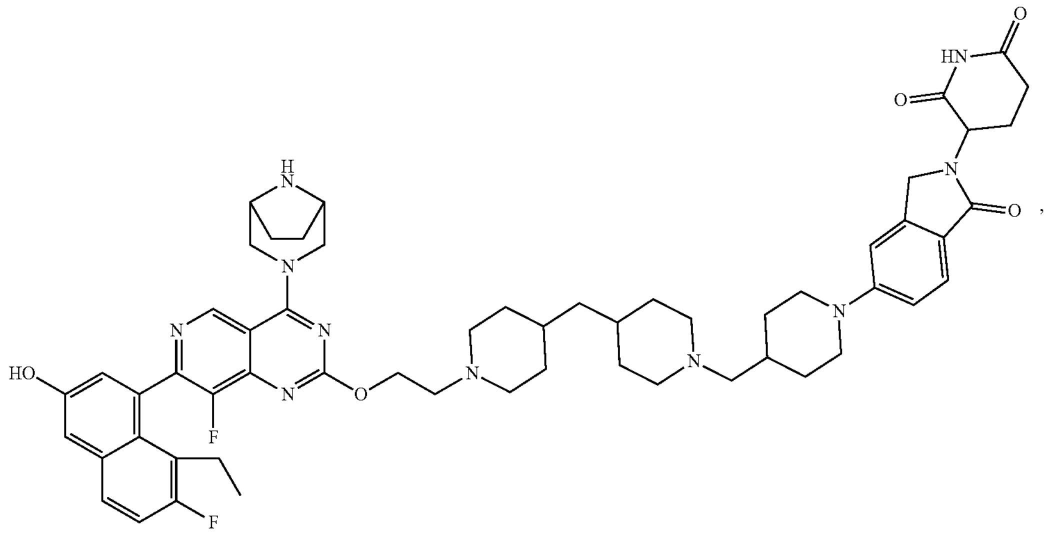 [SMILES: CCc1c(F)ccc2cc(O)cc(-c3ncc4c(N5CC6CCC(C5)N6)nc(OCCN5CCC(CC6CCN(CC7CCN(c8ccc9c(c8)CN(C8CCC(=O)NC8=O)C9=O)CC7)CC6)CC5)nc4c3F)c12 ; ","]
or a pharmaceutically acceptable salt thereof.
38. A compound that is:
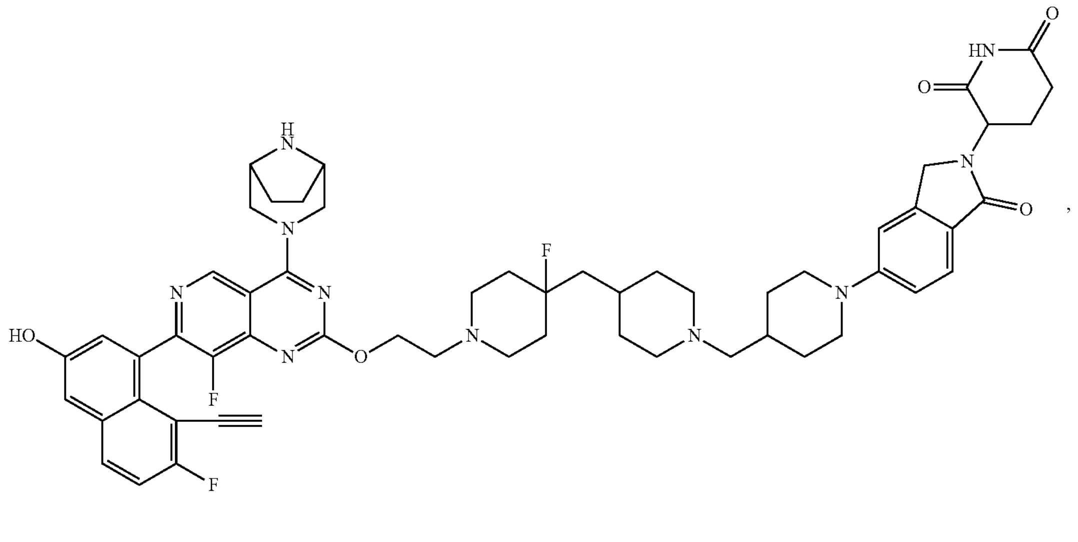 [SMILES: C#Cc1c(F)ccc2cc(O)cc(-c3ncc4c(N5CC6CCC(C5)N6)nc(OCCN5CCC(F)(CC6CCN(CC7CCN(c8ccc9c(c8)CN(C8CCC(=O)NC8=O)C9=O)CC7)CC6)CC5)nc4c3F)c12 ; ","]
or a pharmaceutically acceptable salt thereof.

39. A compound that is:

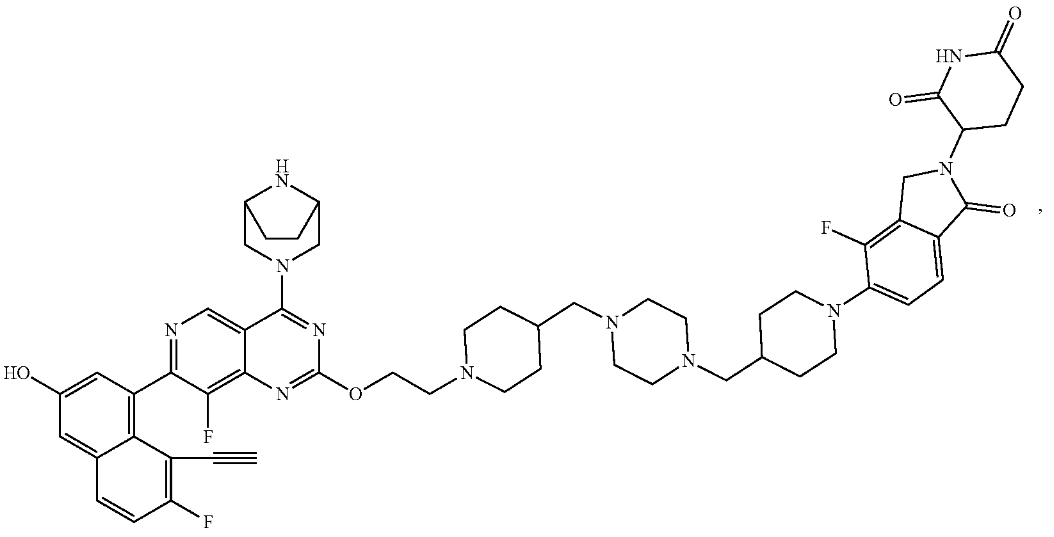 [SMILES: C#Cc1c(F)ccc2cc(O)cc(-c3ncc4c(N5CC6CCC(C5)N6)nc(OCCN5CCC(CN6CCN(CC7CCN(c8ccc9c(c8F)CN(C8CCC(=O)NC8=O)C9=O)CC7)CC6)CC5)nc4c3F)c12 ; ","]

or a pharmaceutically acceptable salt thereof.

40. A compound that is:

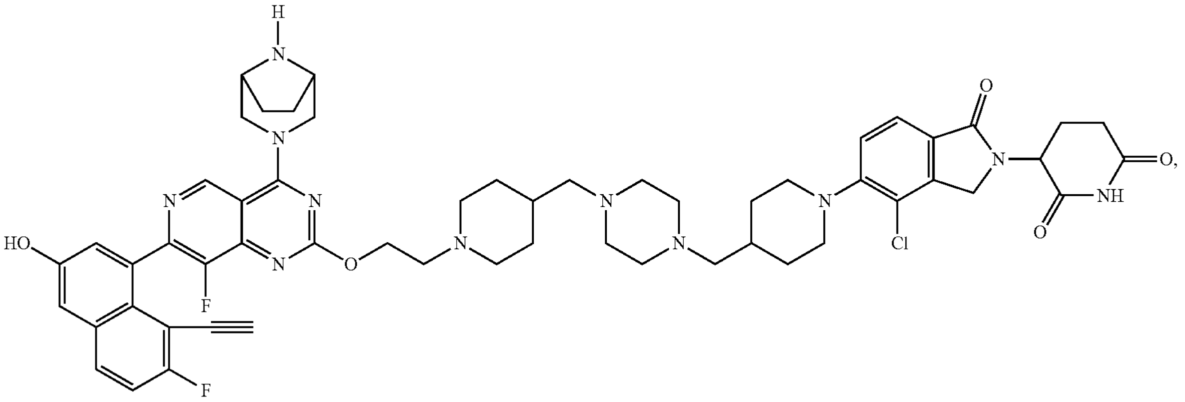 [SMILES: C#Cc1c(F)ccc2cc(O)cc(-c3ncc4c(N5CC6CCC(C5)N6)nc(OCCN5CCC(CN6CCN(CC7CCN(c8ccc9c(c8Cl)CN(C8CCC(=O)NC8=O)C9=O)CC7)CC6)CC5)nc4c3F)c12]

or a pharmaceutically acceptable salt thereof.

41. A pharmaceutical composition comprising a compound of claim 28, and a pharmaceutically acceptable carrier.

42. A method of treating cancer in a subject comprising administering to the subject an effective amount of a compound according to claim 28, wherein the cancer is characterized by a KRAS G12D mutation.

43. A pharmaceutical composition comprising a compound of claim 29, and a pharmaceutically acceptable carrier.

44. A method of treating cancer in a subject comprising administering to the subject an effective amount of a compound according to claim 29, wherein the cancer is characterized by a KRAS G12D mutation.

45. A pharmaceutical composition comprising a compound of claim 30, and a pharmaceutically acceptable carrier.

46. A method of treating cancer in a subject comprising administering to the subject an effective amount of a compound according to claim 30, wherein the cancer is characterized by a KRAS G12D mutation.

47. A pharmaceutical composition comprising a compound of claim 31, and a pharmaceutically acceptable carrier.

48. A method of treating cancer in a subject comprising administering to the subject an effective amount of a compound according to claim 31, wherein the cancer is characterized by a KRAS G12D mutation.

49. A pharmaceutical composition comprising a compound of claim 32, and a pharmaceutically acceptable carrier.

50. A method of treating cancer in a subject comprising administering to the subject an effective amount of a compound according to claim 32, wherein the cancer is characterized by a KRAS G12D mutation.

51. A pharmaceutical composition comprising a compound of claim 33, and a pharmaceutically acceptable carrier.

52. A method of treating cancer in a subject comprising administering to the subject an effective amount of a compound according to claim 33, wherein the cancer is characterized by a KRAS G12D mutation.

53. A pharmaceutical composition comprising a compound of claim 34, and a pharmaceutically acceptable carrier.

54. A method of treating cancer in a subject comprising administering to the subject an effective amount of a compound according to claim 34, wherein the cancer is characterized by a KRAS G12D mutation.

55. A pharmaceutical composition comprising a compound of claim 35, and a pharmaceutically acceptable carrier.

56. A method of treating cancer in a subject comprising administering to the subject an effective amount of a compound according to claim 35, wherein the cancer is characterized by a KRAS G12D mutation.

57. A pharmaceutical composition comprising a compound of claim 36, and a pharmaceutically acceptable carrier.

58. A method of treating cancer in a subject comprising administering to the subject an effective amount of a compound according to claim 36, wherein the cancer is characterized by a KRAS G12D mutation.

59. A pharmaceutical composition comprising a compound of claim 37, and a pharmaceutically acceptable carrier.

60. A method of treating cancer in a subject comprising administering to the subject an effective amount of a compound according to claim 37, wherein the cancer is characterized by a KRAS G12D mutation.

61. A pharmaceutical composition comprising a compound of claim 38, and a pharmaceutically acceptable carrier.

62. A method of treating cancer in a subject comprising administering to the subject an effective amount of a compound according to claim 38, wherein the cancer is characterized by a KRAS G12D mutation.

63. A pharmaceutical composition comprising a compound of claim 39, and a pharmaceutically acceptable carrier.

64. A method of treating cancer in a subject comprising administering to the subject an effective amount of a compound according to claim 39, wherein the cancer is characterized by a KRAS G12D mutation.

65. A pharmaceutical composition comprising a compound of claim 40, and a pharmaceutically acceptable carrier.

66. A method of treating cancer in a subject comprising administering to the subject an effective amount of a compound according to claim 40, wherein the cancer is characterized by a KRAS G12D mutation.

* * * * *